(12) United States Patent
Stadlwieser et al.

(10) Patent No.: US 9,376,442 B2
(45) Date of Patent: *Jun. 28, 2016

(54) METHYLPYRROLOPYRIMIDINE-CARBOXAMIDES

(71) Applicant: Takeda GmbH, Constance (DE)

(72) Inventors: Josef Stadlwieser, Constance (DE); Beate Schmidt, Allensbach (DE); Heiko Bernsmann, Frankfurt (DE); Torsten Dunkern, Juechen Gierath (DE); Ewald Benediktus, Biberach (DE); Andreas Pahl, Ahrensburg (DE); Ragna Hussong, Deisslingen (DE); Olaf Nimz, Constance (DE); Matthias Mueller, Constance (DE); Martin Viertelhaus, Constance (DE)

(73) Assignee: Takeda GmbH, Konstanz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/547,938

(22) Filed: Nov. 19, 2014

(65) Prior Publication Data

US 2015/0073001 A1    Mar. 12, 2015

Related U.S. Application Data

(63) Continuation of application No. 13/390,940, filed as application No. PCT/EP2010/062329 on Aug. 24, 2010, now Pat. No. 8,927,557.

(30) Foreign Application Priority Data

Aug. 26, 2009   (EP) .................................... 09168685

(51) Int. Cl.
A61K 31/519 (2006.01)
C07D 487/04 (2006.01)
A61P 11/00 (2006.01)

(52) U.S. Cl.
CPC .................. *C07D 487/04* (2013.01)

(58) Field of Classification Search
CPC .................................................. C07D 487/04
USPC ...................................... 544/280; 514/265.1
See application file for complete search history.

(56) References Cited

U.S. PATENT DOCUMENTS

| 5,877,190 A | 3/1999 | Dhainaut et al. |
| 2003/0004172 A1 | 1/2003 | Harter et al. |
| 2005/0124623 A1 | 6/2005 | Bender et al. |

FOREIGN PATENT DOCUMENTS

| EP | 1 634 883 A1 | 3/2006 |
| WO | 01/94350 A1 | 12/2001 |
| WO | 2006/049952 A1 | 5/2006 |
| WO | 2008/030119 A1 | 3/2008 |
| WO | 2009/106531 A1 | 9/2009 |

OTHER PUBLICATIONS

P.C. Belanger, et al., "Facile Preparations of 4-Fluororesorcinol", Canadian Journal of Chemistry, 1988, vol. 66, pp. 1479-1482.
H.R. Collard, et al., "Sildenafil Improves Walk Distance in Idiopathic Pulmonary Fibrosis", Chest, 2007, vol. 131, pp. 897-899.
E.J. Corey, et al., "New Methods for the Oxidation of Aldehydes to Carboxylic Acids and Esters", Journal of the American Chemical Society, 1968, vol. 90, pp. 5616-5617.
J. Cortijo, et al., "Roflumilast, a phosphodiesterase 4 inhibitor, alleviates bleomycin-induced lung injury", British Journal of Pharmacology, 2009, vol. 156, pp. 534-544.
T.R. Dunkern, et al., "Inhibition of TGF-β induced lung fibroblast to myofibroblast conversion by phosphodiesterase inhibiting drugs and activators of soluble guanylyl cyclase", European Journal of Pharmacology, 2007, vol. 572, pp. 12-22.
S.D. Erickson, et al., "Potent, selective MCH-1 receptor antagonists", Bioorganic & Medicinal Chemistry Letters, 2008, vol. 18, pp. 1402-1406.
J. Freedman, et al., "The Preparation of 3,4-Dihydro-1-benzoxepin-5(2H)-ones", J. Heterocycl. Chem., 1989, vol. 26, pp. 1547-1554.
A. Gangjee, et al., "Design, Synthesis, and Biological Evaluation of Classical and Nonclassical 2-Amino-4-oxo-5-substituted-6-methylpyrrolo[3,2-d]pyrimidines as Dual Thymidylate Synthase and Dihydrofolate Reductase Inhibitors", J. Med. Chem., 2008, vol. 51, pp. 68-76.

(Continued)

*Primary Examiner* — Susanna Moore
(74) *Attorney, Agent, or Firm* — Nath, Goldberg & Meyer; Joshua B. Goldberg; Scott H. Blackman

(57) ABSTRACT

The compounds of Formula (I),

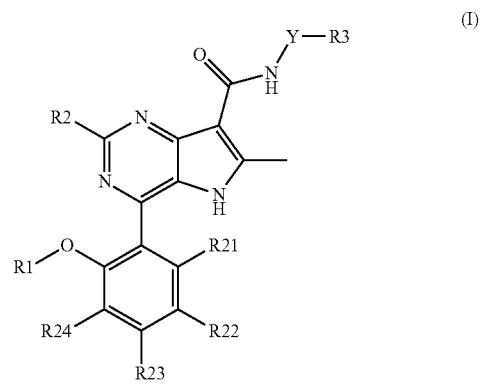

wherein R1, R2, R21, R22, R23, R24, Y and R3 have the meanings as given in the description, the salts thereof, the stereoisomers of the compounds and the salts thereof are effective inhibitors of the type 5 phosphodiesterase and are useful for treating or preventing idiopathic pulmonary lung fibrosis.

10 Claims, No Drawings

(56) References Cited

OTHER PUBLICATIONS

P.G. Gassman, et al., "A General Procedure for the Base-Promoted Hydrolysis of Hindered Esters at Ambient Temperatures", J. Org. Chem., 1977, vol. 42, pp. 918-920.

H.A. Ghofrani, et al., "Sildenafil for Treatment of Lung Fibrosis and Pulmonary Hypertension: a Randomised Controlled Trial", The Lancet, Sep. 2002, vol. 360, pp. 895-900.

A.R. Hemnes, et al., "PDE5A inhibition attenuates bleomycin-induced pulmonary fibrosis and pulmonary hypertension through inhibition of ROS generation and RhoA/Rho kinase activation", Am. Physiol. Lung Cell Mol. Physiol., 2008, vol. 294, pp. 24-33.

J.R. Hwu, et al, "The Trimethylsilyl Cationic Species as a Bulky Proton. Application to Chemoselective Dioxolanation", J. Org. Chem., 1985, vol. 50, pp. 3946-3948.

T. Kohyama, et al. "PDE4 Inhibitors Attenuate Fibroblast Chemotaxis and Contraction of Native Collagen Gels", Am. J. Respir. Cell Mol. Biol., 2002, vol. 26, pp. 694-701.

C. Martin-Chouly, et al., "Modulation of matrix metalloproteinase production from human lung fibroblasts by type 4 phosphodiesterase inhibitors", Life Sciences, 2004, vol. 75, pp. 823-840.

D. Milne, et al., "Dilithiated Aminoalcohols as Homochiral Bases", J. Chem. Soc., Chem. Commun., 1993, pp. 884-886.

J.M. Muchowski, et al., "Protecting Groups for the Pyrrole and Indole Nitrogen Atom. The [2-(Trimethylsilyl)ethoxy] methyl Moiety. Lithiation of 1-[ [ 2-(Trimethylsilypethoxy]methyl]pyrrole", J. Org. Chem., 1984, vol. 49, pp. 203-205.

M. Murata, et al., "Palladium-Catalyzed Borylation of Aryl Halides or Triflates with Dialkoxyborane: A Novel and Facile Synthetic Route to Arylboronates", J. Org. Chem., 2000, vol. 65, pp. 164-168.

M. Murata, et al., "Novel Palladium(0)-Catalyzed Coupling Reaction of Dialkoxyborane with Aryl Halides: Convenient Synthetic Route to Arylboronates", J. Organic Chemistry, 1997, vol. 62, pp. 6458-6459.

W.H. Okamura, et al., "Thermal [1,7]-Sigmatropic Shift of Previtamin D3 to Vitamin D3: Synthesis and Study of Pentadeuterio Derivatives", J. Org. Chem., 1993, vol. 58, pp. 600-610.

B.B. Snider, et al., "Total Synthesis of (±)-Deoxypenostatin A. Approaches to the Syntheses of Penostatins A and B", J. Org. Chem., 2000, vol. 65, pp. 8490-8498.

B. Venugopalan, et al., "Synthesis of 6,7-Dimethoxypyrimido[4,5-b]-indoles as Potential Antihypertensive Agents", J. Heterocyclic. Chem., 1988, vol. 25, pp. 1633-1639.

Y. Yamamoto, et al., "Synthesis of arylboronates via Cp*RuCl-catalyzed cycloaddition of alkynylboronates", Tetrahedron, 2006, vol. 62, pp. 4294-4305.

S. Zhao, et al., "Synthetic Studies Towards a trans-3, 4-Diamine Derivative of Piperidine Mimicking Buspironea", Heterocycles, 1994, vol. 39, No. 1, pp. 163-170.

Mezentseva, et al., Synthesis and Antitumor Activity of Pyrrolo [3,2-d] Pyrimidines' Khimiko-Farmatsevticheskii Zhurnal (Pharmaceutical Chemistry Journal), vol. 25, No. 12, 1991, pp. 19-23, English translation.

Esper, et al., "Evolution of Treatments for Patients with Acute Lung Injury", Expert. Opin. Investig. Drugs, 2005, 14(5), pp. 633-645.

Lee, Denis, "Cirrhosis", www.MedicineNet.com/cirrhosis/article.htm, downloaded Aug. 26, 2012.

Mayo Clinic, "Pulmonary Fibrosis", www.mayoclinic.com/health/pulmonary-fibrosis/DS00927/DSECTION=treatments-anddrugs, downloaded Aug. 26, 2012.

METHYLPYRROLOPYRIMIDINE-CARBOXAMIDES

This application is a continuation application of U.S. Ser. No. 13/390,940, which was filed Feb. 17, 2012 under 35 U.S.C. 371 as the national stage of PCT/EP2010/062329, filed Aug. 24, 2010, which claims priority to EP 09168685.7, filed Aug. 26, 2009.

FIELD OF APPLICATION OF THE PRESENT SUBJECT MATTER

The present subject matter relates to methylpyrrolopyrimidinecarboxamide compounds, processes for their preparation, pharmaceutical compositions comprising said compounds and the use thereof in the treatment or prophylaxis of diseases.

BACKGROUND OF THE INVENTION

Pyrrolopyrimidinecarboxamides are described in WO2009/106531. EP1634883 disclose 2-substituted phenyl-5,7-dihydrocarbyl-3,7-dihydropyrrolo[2,3-d]pyrimidin-4-one derivatives and their use for treatment and/or prevention of sexual dysfunction and other diseases related to phospholipase 5. WO01/94350 disclose 6-phenylpyrrolopyrimidine derivatives as selective cyclic GMP specific phosphodiesterase (PDE 5) inhibitors.

DESCRIPTION OF THE PRESENT SUBJECT MATTER

It has now been found that the methylpyrrolopyrimidinecarboxamide compounds, which are described in detail below, have surprising and advantageous properties.

The present subject matter relates to compounds of formula (I)

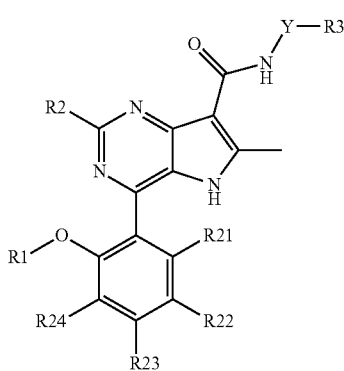

wherein
R1 is —CH$_2$-3-6C-cycloalkyl or 1-4C-alkyl which is optionally substituted by R11,
R11 is 1-4C-alkoxy or hydroxy,
R2 is hydrogen or 1-4C-alkyl
R21 is hydrogen or fluoro,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, —C(O)—NR8R9, halogen, hydroxy or NH$_2$,
R61 is halogen, 1-4C-alkyl or hydroxy,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

1-4C-Alkyl is a straight-chain or branched alkyl group having 1 to 4 carbon atoms. Examples are methyl, ethyl, n-propyl, iso-propyl, n-butyl, iso-butyl, sec-butyl and tert-butyl.

2-4C-Alkyl is a straight-chain or branched alkyl group having 2 to 4 carbon atoms. Examples are ethyl, n-propyl, iso-propyl, n-butyl, iso-butyl, sec-butyl and tert-butyl.

1-4C-Fluoroalkyl is a straight-chain or branched alkyl moiety having 1 to 4 carbon atoms, wherein one or more of the hydrogen atoms of the alkyl moiety are replaced by fluorine. Examples include, but are not limited to, a trifluoromethyl, difluoromethyl, fluoromethyl, perfluoroethyl, 1,1,1-trifluoro-2-fluoroethyl, 1,1,1-trifluoroethyl, 1,1-difluoro-2,2-difluoroethyl, 1,1-difluoro-2-fluoroethyl, 1,1-difluoroethyl, 1-fluoro-2,2-difluoroethyl, 1-fluoro-2-fluoroethyl, 1-fluoroethyl, 2,2-difluoroethyl, 2-fluoroethyl, n-perfluoropropyl, and n-perfluorobutyl group.

1-2C-Fluoroalkyl is a straight-chain or branched alkyl moiety having 1 to 2 carbon atoms, wherein one or more of the hydrogen atoms of the alkyl moiety are replaced by fluorine. Examples include, but are not limited to, a trifluoromethyl, difluoromethyl, fluoromethyl, perfluoroethyl, 1,1,1-trifluoro-2-fluoroethyl, 1,1,1-trifluoroethyl, 1,1-difluoro-2,2-difluoroethyl, 1,1-difluoro-2-fluoroethyl, 1,1-difluoroethyl, 1-fluoro-2,2-difluoroethyl, 1-fluoro-2-fluoroethyl, 1-fluoroethyl, 2,2-difluoroethyl and 2-fluoroethyl group.

Halogen includes fluorine, chlorine, bromine and iodine. In case of R22 and/or R23 and/or R5 and/or R6 and/or R61 being halogen, fluorine is preferred.

3-6C-Cycloalkyl is a cycloalkyl group having 3 to 6 carbon atoms, examples of which include the cyclopropyl, cyclobutyl, cyclopentyl and cyclohexyl group. In case of R3 being 3-6C-cycloalkyl, cyclohexyl and cyclopentyl are preferred.

3-4C-Cycloalkyl is a cycloalkyl group having 3 to 4 carbon atoms, examples of which include the cyclopropyl and cyclobutyl group.

5-6C-Cycloalkyl is a cycloalkyl group having 5 to 6 carbon atoms, examples of which include the cyclopentyl and cyclohexyl group.

1-4C-Alkoxy represents a group which, in addition to the oxygen atom, contains a straight-chain or branched alkyl moiety having 1 to 4 carbon atoms. Examples are methoxy, ethoxy, n-propoxy, iso-propoxy, n-butoxy, iso-butoxy, sec-butoxy and tert-butoxy.

1-2C-Alkoxy represents a group which, in addition to the oxygen atom, contains a straight-chain alkyl moiety having 1 to 2 carbon atoms. Examples are methoxy and ethoxy, 1-4C-Fluoroalkoxy represents a group which, in addition to the oxygen atom, contains a straight-chain or branched alkyl moiety having 1 to 4 carbon atoms, wherein one or more of the hydrogen atoms of the alkyl moiety are replaced by fluorine. Examples include, but are not limited to, a trifluoromethoxy, difluoromethoxy, fluoromethoxy, perfluoroethoxy, 1,1,1-trifluoro-2-fluoroethoxy, 1,1,1-trifluoroethoxy, 1,1-difluoro-2,2-difluoroethoxy, 1,1-difluoro-2-fluoroethoxy, 1,1-difluoroethoxy, 1-fluoro-2,2-difluoroethoxy, 1-fluoro-2-fluoroethoxy, 1-fluoroethoxy, 2,2-difluoroethoxy, 2-fluoroethoxy, n-perfluoropropoxy, and n-perfluorobutoxy group.

The group —C(O)-1-4C-alkyl represents a group which, in addition to the carbonyl group —C(O)—, contains a straight-chain or branched alkyl moiety having 1 to 4 carbon atoms. Examples are methylcarbonyl, ethylcarbonyl, n-propylcarbonyl, iso-propylcarbonyl, n-butylcarbonyl, iso-butylcarbonyl, sec-butylcarbonyl and tert-butylcarbonyl.

The group —C(O)-1-2C-alkyl represents a group which, in addition to the carbonyl group —C(O)—, contains a straight-chain or branched alkyl moiety having 1 to 2 carbon atoms. Examples are methylcarbonyl and ethylcarbonyl.

The group —C(O)-3-6C-cycloalkyl represents a group which, in addition to the carbonyl group —C(O)—, contains a cycloalkyl group having 3 to 6 carbon atoms. Examples are cyclopropylcarbonyl, cyclobutylcarbonyl, cyclopentylcarbonyl and cyclohexylcarbonyl.

The group —C(O)—O-1-4C-alkyl represents a group which, in addition to the oxycarbonyl group —C(O)—O—, contains a straight-chain or branched alkyl moiety having 1 to 4 carbon atoms. Examples are methyloxycarbonyl, ethyloxycarbonyl, n-propyloxycarbonyl, iso-propyloxycarbonyl, n-butyloxycarbonyl, iso-butyloxycarbonyl, sec-butyloxycarbonyl and tert-butyloxycarbonyl.

The 4- to 7-membered saturated heterocyclic ring containing one nitrogen atom and optionally one oxygen atom includes, but is not limited to, azetidinyl, oxazetidinyl, pyrrolidinyl, oxazolidinyl, piperidinyl, morpholinyl, azepanyl and oxazepanyl, in particular azetidinyl, 1,3-oxazetidinyl, pyrrolidinyl, 1,3-oxazolidinyl, piperidinyl, morpholinyl, azepanyl and 1,3-oxazepanyl, preferably azetidin-3-yl, pyrrolidin-3-yl, morpholin-2-yl, piperidin-3-yl and piperidin-4-yl.

The 4- to 6-membered saturated heterocyclic ring containing one nitrogen atom and optionally one oxygen atom includes, but is not limited to, azetidinyl, oxazetidinyl, pyrrolidinyl, oxazolidinyl, piperidinyl and morpholinyl, in particular azetidinyl, 1,3-oxazetidinyl, pyrrolidinyl, 1,3-oxazolidinyl, piperidinyl, morpholinyl, preferably azetidin-3-yl, pyrrolidin-3-yl, morpholin-2-yl, piperidin-3-yl and piperidin-4-yl.

The 5- to 6-membered saturated heterocyclic ring containing one nitrogen atom and optionally one oxygen atom includes, but is not limited to, pyrrolidinyl, oxazolidinyl, piperidinyl and morpholinyl, in particular pyrrolidinyl, 1,3-oxazolidinyl, piperidinyl, morpholinyl, preferably pyrrolidin-3-yl, morpholin-2-yl, piperidin-3-yl and piperidin-4-yl.

In one embodiment, the present subject matter relates to compounds of formula (I), wherein R1 is —CH$_2$-3-6C-cycloalkyl or 1-4C-alkyl which is optionally substituted by R11, R11 is 1-4C-alkoxy or hydroxy, R2 is hydrogen or 1-4C-alkyl R21 is hydrogen or fluoro, R22 is hydrogen, halogen, 1-4C-alkyl, 1-4C-alkoxy, hydroxy, 1-4C-fluoroalkoxy, —C(O)-1-4C-alkyl or 1-4C-fluoroalkyl, or R21 and R22 combine to form a group —O—CH$_2$—O—, R23 is hydrogen, halogen, 1-4C-alkyl, 1-4C-alkoxy, hydroxy or 1-4C-fluoroalkoxy, or R22 and R23 combine to form a group —O—CH$_2$—O—, R24 is hydrogen, Y is —(CH$_2$)$_n$—, n is 0 or 1, R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6, R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, R41 is 1-4C-alkoxy or hydroxy, R42 is 1-4C-alkoxy or hydroxy, R43 is 1-4C-alkoxy or hydroxy, R5 is 1-4C-alkoxy, halogen, 1-4C-alkyl or hydroxy, R6 is —NH—C(O)—R7, —C(O)—NR8R9, halogen, hydroxy or NH$_2$, R7 is hydrogen, 1-4C-alkyl, which is optionally substituted by R71, 3-6C-cycloalkyl, which is optionally substituted by R72, or 1-4C-alkoxy, which is optionally substituted by R73, R71 is 1-4C-alkoxy or hydroxy, R72 is 1-4C-alkoxy or hydroxy, R73 is 1-4C-alkoxy or hydroxy, R8 is hydrogen, R9 is 1-4C-alkyl, which is optionally substituted by R91, or 3-6C-cycloalkyl, which is optionally substituted by R92, R91 is 1-4C-alkoxy or hydroxy, R92 is 1-4C-alkoxy or hydroxy, a salt thereof, or a stereoisomer of the compound or a salt thereof.

In one embodiment, the present subject matter relates to compounds of formula (I), wherein R1 is —CH$_2$-3-4C-cycloalkyl or 2-4C-alkyl which is optionally substituted by R11, R11 is 1-4C-alkoxy or hydroxy, R2 is hydrogen or 1-4C-alkyl R21 is hydrogen or fluoro, R22 is hydrogen, halogen, 1-4C-alkyl, 1-4C-alkoxy, hydroxy, 1-4C-fluoroalkoxy, —C(O)-1-4C-alkyl or 1-4C-fluoroalkyl, or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, halogen, hydroxy or NH$_2$,
R61 is halogen, 1-4C-alkyl or hydroxy,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
a salt thereof, or a stereoisomer of the compound or a salt thereof.

In one embodiment, the present subject matter relates to compounds of formula (I), wherein
R1 is —CH$_2$-3-4C-cycloalkyl or 2-4C-alkyl which is optionally substituted by R11,
R11 is 1-4C-alkoxy or hydroxy,
R2 is hydrogen or 1-4C-alkyl
R21 is hydrogen or fluoro,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, halogen, hydroxy or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl or 2-4C-alkyl,
R2 is hydrogen or 1-4C-alkyl
R21 is hydrogen or fluoro,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy or 1-4C-fluoroalkoxy,
R24 is hydrogen,
Y is —(CH$_2$)$_n$—,
n is 0,
R3 is a 4- to 6-membered saturated heterocyclic ring containing one nitrogen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, halogen, hydroxy or NH$_2$,
R61 is halogen, 1-4C-alkyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl or 2-4C-alkyl,
R2 is hydrogen or 1-4C-alkyl
R21 is hydrogen or fluoro,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy or 1-4C-fluoroalkoxy,
R24 is hydrogen,
Y is —(CH$_2$)$_n$—,
n is 0, R3 is a 4- to 6-membered saturated heterocyclic ring containing one nitrogen atom, said heterocyclic ring being optionally substituted by R4 and/or R5, or a 3-6C-cycloalkyl group substituted by R6, R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43, R41 is 1-4C-alkoxy or hydroxy, R43 is 1-4C-alkoxy or hydroxy, R5 is 1-4C-alkoxy, halogen, 1-4C-alkyl or hydroxy, R6 is —NH—C(O)—R7, halogen, hydroxy or NH$_2$, R7 is hydrogen, 1-4C-alkyl, which is optionally substituted by R71, or 1-4C-alkoxy, which is optionally substituted by R73, R71 is 1-4C-alkoxy or hydroxy, R73 is 1-4C-alkoxy or hydroxy, a salt thereof, or a stereoisomer of the compound or a salt thereof.

In an alternative embodiment, the present subject matter relates to compounds of formula (I), wherein R1 is —CH$_2$-3-4C-cycloalkyl or 2-4C-alkyl, R2 is hydrogen or 1-4C-alkyl R21 is hydrogen or fluoro, R22 is hydrogen, halogen, 1-4C-alkyl, 1-4C-alkoxy, 1-4C-fluoroalkoxy, —C(O)-1-4C-alkyl or 1-4C-fluoroalkyl, or R21 and R22 combine to form a group —O—CH$_2$—O—, R23 is hydrogen, halogen, 1-4C-alkyl, 1-4C-alkoxy or 1-4C-fluoroalkoxy, R24 is hydrogen, Y is —(CH$_2$)$_n$—, n is 0, R3 is a 5- to 6-membered saturated heterocyclic ring containing one nitrogen atom, said heterocyclic ring being optionally substituted by R4 and/or by one or two substituents R5, or a 3-6C-cycloalkyl group substituted by R6 and optionally substituted by R61, R4 is —C(O)-1-4C-alkyl, wherein the 1-4C-alkyl group is optionally substituted by R41, or —C(O)—O-1-4C-alkyl, R41 is 1-4C-alkoxy or hydroxy, if only one substituent R5 is present then R5 is 1-4C-alkoxy, halogen, 1-4C-alkyl or hydroxy, if two substituents R5 are present, these are identical and binding at the same carbon atom and are selected from halogen or 1-4C-alkyl or together with the carbon atom, to which they are bonded, form a spiro-linked cyclopropane ring, R6 is —NH—C(O)—R7, halogen, hydroxy or NH$_2$, R61 is halogen, 1-4C-alkyl or hydroxy, R7 is 1-4C-alkyl, which is optionally substituted by R71, or 1-4C-alkoxy, R71 is 1-4C-alkoxy or hydroxy, a salt thereof, or a stereoisomer of the compound or a salt thereof.

In an alternative embodiment, the present subject matter relates to compounds of formula (I), wherein R1 is —CH$_2$-3-4C-cycloalkyl or 2-4C-alkyl, R2 is hydrogen or 1-4C-alkyl R21 is hydrogen or fluoro, R22 is hydrogen, halogen, 1-4C-alkyl, 1-4C-alkoxy, 1-4C-fluoroalkoxy, —C(O)-1-4C-alkyl or 1-4C-fluoroalkyl, or R21 and R22 combine to form a group —O—CH$_2$—O—, R23 is hydrogen, halogen, 1-4C-alkyl, 1-4C-alkoxy or 1-4C-fluoroalkoxy, R24 is hydrogen, Y is —(CH$_2$)$_n$—, n is 0, R3 is a 5- to 6-membered saturated heterocyclic ring containing one nitrogen atom, said heterocyclic ring being optionally substituted by R4 and/or R5, or a 3-6C-cycloalkyl group substituted by R6, R4 is —C(O)-1-4C-alkyl, wherein the 1-4C-alkyl group is optionally substituted by R41, or —C(O)—O-1-4C-alkyl, R41 is 1-4C-alkoxy or hydroxy, R5 is 1-4C-alkoxy, halogen, 1-4C-alkyl or hydroxy, R6 is —NH—C(O)—R7, hydroxy, halogen or NH$_2$, R7 is 1-4C-alkyl, which is optionally substituted by R71, or 1-4C-alkoxy, R71 is 1-4C-alkoxy or hydroxy, a salt thereof, or a stereoisomer of the compound or a salt thereof.

In an alternative embodiment, the present subject matter relates to compounds of formula (I), wherein R1 is —CH$_2$-3-4C-cycloalkyl, R2 is hydrogen or methyl R21 is hydrogen or fluoro, R22 is hydrogen, halogen, 1-4C-alkyl, 1-2C-alkoxy, 1-4C-fluoroalkoxy, —C(O)-1-2C-alkyl or 1-2C-fluoroalkyl, or R21 and R22 combine to form a group —O—CH$_2$—O—, R23 is hydrogen, halogen, 1-2C-alkoxy, R24 is hydrogen, Y is —(CH$_2$)$_n$—, n is 0, R3 is a 5- to 6-membered saturated heterocyclic ring containing one nitrogen atom, said heterocyclic ring being substituted by R4 at said nitrogen atom and optionally substituted by one or two substituents R5 at said heterocyclic ring, or a cyclohexyl or cyclopentyl group substituted by R6 and optionally substituted by R61, R4 is —C(O)-1-4C-alkyl, wherein the 1-4C-alkyl group is optionally substituted by R41, or —C(O)—O-1-4C-alkyl, R41 is 1-4C-alkoxy or hydroxy, if only one substituent R5 is present then R5 is fluoro, methyl, or hydroxy, if two substituents R5 are present, these are identical and binding at the same carbon atom and are selected from fluoro or methyl or together with the carbon atom, to which they are bonded, form a spiro-linked cyclopropane ring, R6 is —NH—C(O)—R7, fluoro, hydroxy or NH$_2$, R61 is fluoro, methyl or hydroxy, R7 is 1-4C-alkyl, which is optionally substituted by R71, or 1-4C-alkoxy, R71 is 1-4C-alkoxy or hydroxy, a salt thereof, or a stereoisomer of the compound or a salt thereof.

In an alternative embodiment, the present subject matter relates to compounds of formula (I), wherein R1 is —CH$_2$-3-4C-cycloalkyl, R2 is hydrogen, R21 is hydrogen, R22 is hydrogen, halogen, 1-4C-alkyl, 1-2C-alkoxy 1-4C-fluoroalkoxy, —C(O)-1-2C-alkyl or 1-2C-fluoroalkyl, or R21 and R22 combine to form a group —O—CH$_2$—O—, R23 is hydrogen, halogen, 1-2C-alkoxy, R24 is hydrogen, Y is —(CH$_2$)$_n$—, n is 0, R3 is a 5- to 6-membered saturated heterocyclic ring containing one nitrogen atom, said heterocyclic ring being substituted by R4 at said nitrogen atom, or a cyclohexyl or cyclopentyl group substituted by R6, R4 is —C(O)-1-4C-alkyl, wherein the 1-4C-alkyl group is optionally substituted by R41, or —C(O)—O-1-4C-alkyl, R41 is 1-4C-alkoxy or hydroxy, R6 is —NH—C(O)—R7 or hydroxy,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is hydrogen, fluoro, methy, ethyl, isopropyl, methoxy, —C(O)-methyl, fluoromethyl, difluoromethyl or trifluoromethyl,
or R21 and R22 combine to form a group —O—CH$_2$—O—,
R23 is hydrogen, fluoro, or methoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R6 is —NH—C(O)—R7 or hydroxy,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl,
R2 is hydrogen or 1-4C-alkyl,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen, 1-4C-alkyl or 1-4C-alkoxy,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or by one substituent R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, halogen, hydroxy or NH$_2$,
R61 is halogen, 1-4C-alkyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl,
R2 is hydrogen or 1-4C-alkyl,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen or 1-4C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being optionally substituted by R4 and/or by one substituent R5, or a 5-6C-cycloalkyl group substituted by R6 and optionally substituted by R61,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is halogen, 1-4C-alkyl or hydroxy,
R6 is —NH—C(O)—R7, hydroxy or NH$_2$,
R61 is halogen or 1-4C-alkyl,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen or 1-4C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being optionally substituted by R4 and/or by one substituent R5, or a 5-6C-cycloalkyl group substituted by R6 and optionally substituted by R61,
R4 is —C(O)-1-4C-alkyl, wherein the 1-4C-alkyl group is optionally substituted by R41,
R41 is 1-4C-alkoxy or hydroxy,
R5 is halogen, hydroxy or 1-4C-alkyl,
R6 is —NH—C(O)—R7,
R61 is halogen or 1-4C-alkyl,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is hydrogen, fluoro, methyl, methoxy, —C(O)-methyl, difluoromethyl or trifluoromethyl,
or R21 and R22 combine to form a group —O—CH$_2$—O—,
R23 is hydrogen, fluoro or methoxy,
R24 is hydrogen,
Y is —(CH$_2$)$_n$—,
n is 0, R3 is a 5- to 6-membered saturated heterocyclic ring containing one nitrogen atom, said heterocyclic ring being substituted by R4 at said nitrogen atom and optionally substituted by one substituent R5 at said heterocyclic ring, or a cyclohexyl or cyclopentyl group substituted by R6 and optionally substituted by R61,
R4 is —C(O)-1-4C-alkyl, wherein the 1-4C-alkyl group is optionally substituted by R41,
R5 is fluoro, hydroxy or methyl,
R6 is —NH—C(O)—R7,
R61 is fluoro or methyl,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is hydrogen, fluoro, methyl, methoxy, —C(O)-methyl, difluoromethyl or trifluoromethyl,
or R21 and R22 combine to form a group —O—CH$_2$—O—,
R23 is hydrogen, fluoro or methoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and optionally substituted by one substituent R5 at said heterocyclic ring, or a cyclohexyl or cyclopentyl group substituted by R6 and optionally substituted by R61,
R4 is —C(O)-1-4C-alkyl, wherein the 1-4C-alkyl group is optionally substituted by R41,
R41 is methoxy or hydroxy,
R5 is fluoro, hydroxy or methyl,
R6 is —NH—C(O)—R7,
R61 is fluoro or methyl,
R7 is methyl or ethyl, which are optionally substituted by R71, or ethoxy,
R71 is methoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl,
R2 is hydrogen,
R21 is hydrogen or fluoro,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl,
or R21 and R22 combine to form a group —O—CH$_2$—O—,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, —C(O)—NR8R9, halogen, hydroxy or NH$_2$,
R61 is halogen, 1-4C-alkyl or hydroxy,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen or fluoro,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, halogen, hydroxy or NH$_2$,
R61 is halogen, 1-4C-alkyl or hydroxy,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy, a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen or fluoro,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, halogen, hydroxy or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen or halogen,
R22 is hydrogen, halogen, 1-4C-alkyl or 1-4C-fluoroalkyl,
R23 is hydrogen,
R24 is hydrogen,
Y is —(CH$_2$)$_n$—,
n is 0,
R3 is a 4- to 7-membered saturated heterocyclic ring containing one nitrogen atom, said heterocyclic ring being optionally substituted by R4 and/or by one or two substituents R5, or a 3-6C-cycloalkyl group substituted by R6 and optionally substituted by R61,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, halogen, hydroxy or NH$_2$,
R61 is halogen, 1-4C-alkyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen or fluoro,
R22 is hydrogen, halogen, 1-4C-alkyl or 1-4C-fluoroalkyl,
R23 is hydrogen,
R24 is hydrogen,
Y is —(CH$_2$)$_n$—,
n is 0,
R3 is a 4- to 6-membered saturated heterocyclic ring containing one nitrogen atom, said heterocyclic ring being optionally substituted by R4 and/or by one or two substituents R5, or a 3-6C-cycloalkyl group substituted by R6 and optionally substituted by R61,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is methoxy, fluoro, methyl or hydroxy,
if two substituents R5 are present, these are identical and binding at the same carbon atom and are selected from fluoro or methyl or together with the carbon atom, to which they are bonded, form a spiro-linked cyclopropane ring,
R6 is —NH—C(O)—R7, fluoro, hydroxy or NH$_2$,
R61 is fluoro, methyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen or fluoro,
R22 is hydrogen, halogen, 1-4C-alkyl or 1-4C-fluoroalkyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being optionally substituted by R4 and/or by one or two substituents R5, or a cyclohexyl or cyclopentyl group substituted by R6 and optionally substituted by R61,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is methoxy, fluoro, methyl or hydroxy,
if two substituents R5 are present, these are identical and binding at the same carbon atom and are selected from fluoro or methyl or together with the carbon atom, to which they are bonded, form a spiro-linked cyclopropane ring, R6 is —NH—C(O)—R7, fluoro, hydroxy or NH$_2$,
R61 is fluoro, methyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen or fluoro,
R22 is hydrogen, halogen, 1-4C-alkyl or 1-4C-fluoroalkyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is hydrogen, fluoro, methyl, ethyl, isopropyl, fluoromethyl, difluoromethyl or trifluoromethyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and optionally substituted by one or two substituents R5 at said heterocyclic ring, or a cyclohexyl or cyclopentyl group substituted by R6 and optionally substituted by R61,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is methoxy, fluoro, methyl or hydroxy,
if two substituents R5 are present, these are identical and binding at the same carbon atom and are selected from fluoro or methyl or together with the carbon atom, to which they are bonded, form a spiro-linked cyclopropane ring, R6 is —NH—C(O)—R7, fluoro, hydroxy or NH$_2$,
R61 is fluoro, methyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 is halogen, 1-4C-alkyl or 1-4C-fluoroalkyl,
R23 is hydrogen,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or by one substituent R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, halogen, hydroxy or NH$_2$,
R61 is halogen, 1-4C-alkyl or hydroxy,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 is halogen, 1-4C-alkyl or 1-4C-fluoroalkyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being optionally substituted by R4 and/or by one substituent R5, or a 5-6C-cycloalkyl group substituted by R6 and optionally substituted by R61,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is halogen, 1-4C-alkyl or hydroxy,
R6 is —NH—C(O)—R7, hydroxy or NH$_2$,
R61 is halogen or 1-4C-alkyl,
R7 is 1-4C-alkyl, which is optionally substituted by R71, or 1-4C-alkoxy, R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is halogen, 1-4C-alkyl or 1-4C-fluoroalkyl,
R23 is hydrogen,
R24 is hydrogen,
Y is —(CH$_2$)$_n$—,
n is 0,
R3 is a 5-6C-cycloalkyl group substituted by R6 and optionally substituted by R61,
R6 is —NH—C(O)—R7, hydroxy or NH$_2$,
R61 is halogen or 1-4C-alkyl,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is fluoro, methyl, difluoromethyl or trifluoromethyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and optionally substituted by one substituent R5 at said heterocyclic ring, or a 5-6C-cycloalkyl group substituted by
R6 and optionally substituted by R61,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is halogen, 1-4C-alkyl or hydroxy,
R6 is —NH—C(O)—R7, hydroxy or NH$_2$,
R61 is halogen or 1-4C-alkyl,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is fluoro, methyl, difluoromethyl or trifluoromethyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and optionally substituted by one substituent R5 at said heterocyclic ring, or a cyclohexyl or cyclopentyl group substituted by R6 and optionally substituted by R61,
R4 is —C(O)-1-4C-alkyl, wherein the 1-4C-alkyl group is optionally substituted by R41,
R41 is 1-4C-alkoxy or hydroxy,
R5 is halogen or 1-4C-alkyl,
R6 is —NH—C(O)—R7,
R61 is halogen or 1-4C-alkyl,
R7 is 1-4C-alkyl, which is optionally substituted by R71, or 1-4C-alkoxy,
R71 is 1-4C-alkoxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is fluoro, methyl, difluoromethyl or trifluoromethyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and optionally substituted by one substituent R5 at said heterocyclic ring, or a cyclohexyl or cyclopentyl group substituted by R6 and optionally substituted by R61,
R4 is —C(O)-1-4C-alkyl, wherein the 1-4C-alkyl group is optionally substituted by R41,
R41 is 1-4C-alkoxy,
R5 is fluoro or methyl,
R6 is —NH—C(O)—R7,
R61 is fluoro or methyl,
R7 is methyl or ethyl, which are optionally substituted by R71, or ethoxy,
R71 is methoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl,
R2 is hydrogen or 1-4C-alkyl,
R21 is hydrogen,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy, hydroxy or 1-4C-fluoroalkoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring, R6 is —NH—C(O)—R7, —C(O)—NR8R9, halogen, hydroxy or NH$_2$,
R61 is halogen, 1-4C-alkyl or hydroxy,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy, hydroxy or 1-4C-fluoroalkoxy,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, halogen, hydroxy or NH$_2$,
R61 is halogen, 1-4C-alkyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy, hydroxy or 1-4C-fluoroalkoxy,
R24 is hydrogen,
Y is —(CH$_2$)$_n$—,
n is 0,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen or 1-4C-alkoxy,
R24 is hydrogen,
Y is —(CH$_2$)$_n$—,
n is 0,
R3 is a 4- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is hydrogen, fluoro, methyl, ethyl, isopropyl, methoxy, ethoxy, —C(O)-1-2C-alkyl, fluoromethyl, difluoromethyl or trifluoromethyl,
or R21 and R22 combine to form a group —O—CH$_2$—O—,
R23 is hydrogen, fluoro or methoxy
R24 is hydrogen,
Y is —(CH$_2$)$_n$—,
n is 0,
R3 is a 4- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl,
R2 is hydrogen or 1-4C-alkyl,
R21 is hydrogen,
R22 is hydrogen, fluoro, methyl or methoxy,
R23 is hydrogen, fluoro or methoxy
R24 is hydrogen,
Y is —(CH$_2$)$_n$—,
n is 0 or 1,
R3 is a 5- to 6-membered saturated heterocyclic ring containing one nitrogen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, —C(O)—NR8R9, hydroxy or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or methyl,
R21 is hydrogen,
R22 is hydrogen, fluoro, methyl or methoxy,
R23 is hydrogen, fluoro or methoxy
R24 is hydrogen,
Y is —(CH$_2$)$_n$—,
n is 0,
R3 is a 5- to 6-membered saturated heterocyclic ring containing one nitrogen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is methoxy, fluoro, methyl or hydroxy,
R6 is —NH—C(O)—R7, hydroxy or NH$_2$,
R7 is 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen or methyl,
R21 is hydrogen,
R22 is hydrogen, fluoro, methyl or methoxy,
R23 is hydrogen, fluoro or methoxy
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7, hydroxy or NH$_2$,
R7 is 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen
R21 is hydrogen,
R22 is hydrogen, fluoro, methyl or methoxy,
R23 is hydrogen, fluoro or methoxy
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and optionally substituted by one or two substituents R5 at said heterocyclic ring, or a cyclohexyl or cyclopentyl group substituted by R6 and optionally substituted by R61,
R4 is —C(O)—H, —C(O)-1-4C-alkyl, wherein the 1-4C-alkyl group is optionally substituted by R41, or —C(O)—O-1-4C-alkyl,
R41 is 1-4C-alkoxy or hydroxy,
if only one substituent R5 is present then
R5 is fluoro, methyl or hydroxy,
if two substituents R5 are present, these are identical and binding at the same carbon atom and are selected from fluoro or methyl or together with the carbon atom, to which they are bonded, form a spiro-linked cyclopropane ring, R6 is —NH—C(O)—R7, fluoro, hydroxy or NH$_2$,
R61 is fluoro, methyl or hydroxy,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen
R21 is hydrogen,
R22 is hydrogen, fluoro, methyl or methoxy,
R23 is hydrogen, fluoro or methoxy
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and optionally substituted by one substituent R5 at said heterocyclic ring, or a cyclohexyl or cyclopentyl group substituted by R6 and optionally substituted by R61,
R4 is —C(O)—H, —C(O)-1-4C-alkyl, wherein the 1-4C-alkyl group is optionally substituted by R41, or —C(O)—O-1-4C-alkyl,
R41 is 1-4C-alkoxy or hydroxy,
R5 is fluoro, methyl or hydroxy,
R6 is —NH—C(O)—R7, fluoro, hydroxy or NH$_2$,
R61 is fluoro, methyl or hydroxy,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen
R21 is hydrogen,
R22 is hydrogen, fluoro, methyl or methoxy,
R23 is hydrogen, fluoro or methoxy
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and optionally substituted by one substituent R5 at said heterocyclic ring, or a cyclohexyl or cyclopentyl group substituted by R6 and optionally substituted by R61,
R4 is —C(O)—H, —C(O)-1-4C-alkyl, wherein the 1-4C-alkyl group is optionally substituted by R41, or —C(O)—O-1-4C-alkyl,
R41 is 1-4C-alkoxy or hydroxy,
R5 is fluoro, methyl or hydroxy,
R6 is —NH—C(O)—R7,
R61 is fluoro or methyl,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is hydrogen,
R23 is fluoro
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, —C(O)—NR8R9, halogen, hydroxy or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen or 1-4C-alkyl,
R21 is hydrogen,
R22 is hydrogen,
R23 is fluoro
R24 is hydrogen,
Y is —(CH$_2$)$_n$—,
n is 0,
R3 is a 4- to 7-membered saturated heterocyclic ring containing one nitrogen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, halogen, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein R1 is —CH$_2$-3-4C-cycloalkyl,
R2 is hydrogen or methyl,
R21 is hydrogen,
R22 is hydrogen,
R23 is fluoro
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7, fluoro, hydroxy or NH$_2$,
R7 is 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is hydrogen,
R23 is fluoro
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7, fluoro, hydroxy or NH$_2$,
R7 is 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is hydrogen,
R23 is fluoro
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41,
R41 is 1-4C-alkoxy or hydroxy,
R6 is —NH—C(O)—R7 or hydroxy,
R7 is 1-4C-alkyl, which is optionally substituted by R71,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is hydrogen,
R23 is fluoro
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl or cyclopentyl group substituted by R6,
R4 is —C(O)-1-4C-alkyl, wherein the 1-4C-alkyl group is optionally substituted by R41,
R41 is 1-4C-alkoxy or hydroxy,
R5 is hydroxy,
R6 is —NH—C(O)—R7,
R7 is 1-4C-alkyl, which is optionally substituted by R71,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is fluoro
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, —C(O)—NR8R9, halogen, hydroxy or NH$_2$,
R61 is halogen, 1-4C-alkyl or hydroxy, R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is fluoro
R23 is hydrogen,
R24 is hydrogen,
Y is —(CH$_2$)$_n$—,
n is 0,
R3 is a 4- to 7-membered saturated heterocyclic ring containing one nitrogen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, halogen, hydroxy or NH$_2$,
R61 is halogen, 1-4C-alkyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R21 is hydrogen,
R2 is hydrogen or 1-4C-alkyl,
R22 is fluoro
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7 or hydroxy,
R7 is 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is fluoro
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R6 is —NH—C(O)—R7 or hydroxy,
R7 is 1-4C-alkyl, which is optionally substituted by R71, or 1-4C-alkoxy
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is fluoro
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is hydroxy,
R6 is —NH—C(O)—R7,
R7 is 1-4C-alkyl, which is optionally substituted by R71, or 1-4C-alkoxy
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is methoxy R23 is fluoro,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, —C(O)—NR8R9, hydroxy or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is methoxy
R23 is fluoro,
R24 is hydrogen,
Y is —(CH$_2$)$_n$—,
n is 0,
R3 is a 4- to 7-membered saturated heterocyclic ring containing one nitrogen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen or 1-4C-alkyl,
R21 is hydrogen,
R22 is methoxy
R23 is fluoro,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is methoxy
R23 is fluoro,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, or —C(O)—O-1-4C-alkyl,
R6 is —NH—C(O)—R7 or hydroxy,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is methyl,
R23 is fluoro,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, R41 is 1-4C-alkoxy or hydroxy,
R42 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, —C(O)—NR8R9, hydroxy or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is methyl,
R23 is fluoro,
R24 is hydrogen,
Y is —(CH$_2$)$_n$—,
n is 0,
R3 is a 4- to 7-membered saturated heterocyclic ring containing one nitrogen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is methyl,
R23 is fluoro,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is methyl,
R23 is fluoro,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41,
R41 is 1-4C-alkoxy or hydroxy,
R6 is —NH—C(O)—R7 or hydroxy,
R7 is 1-4C-alkyl, which is optionally substituted by R71,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is fluoro,
R23 is methoxy,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, —C(O)—NR8R9, hydroxy or NH$_2$,
R7 is hydrogen, 1-4C-alkyl, which is optionally substituted by R71, 3-6C-cycloalkyl, which is optionally substituted by R72, or 1-4C-alkoxy, which is optionally substituted by R73, R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is fluoro,
R23 is methoxy,
R24 is hydrogen,
Y is —(CH$_2$)$_n$—,
n is 0,
R3 is a 4- to 7-membered saturated heterocyclic ring containing one nitrogen atom, said heterocyclic ring being optionally substituted by R4 and/or R5, or a 3-6C-cycloalkyl group substituted by R6,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is fluoro,
R23 is methoxy,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 is fluoro,
R23 is methoxy,
R23 is hydrogen,
R24 is hydrogen,
Y is —(CH$_2$)$_n$—,
n is 0,
R3 is a 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R6 is —NH—C(O)—R7 or hydroxy,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is 1-4C-alkyl
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, —C(O)—NR8R9, halogen, hydroxy or NH$_2$,
R61 is halogen, 1-4C-alkyl or hydroxy,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen, R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is methyl, ethyl or isopropyl,
R23 is hydrogen,
R24 is hydrogen,
Y is —(CH$_2$)$_n$—,
n is 0,
R3 is a 4- to 7-membered saturated heterocyclic ring containing one nitrogen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43, R41 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, halogen, hydroxy or NH$_2$,
R61 is halogen, 1-4C-alkyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is methyl, ethyl or isopropyl,
R23 is hydrogen,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 is methyl, ethyl or isopropyl,
R23 is hydrogen,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 and/or R5 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is methoxy, fluoro, methyl or hydroxy,
R6 is —NH—C(O)—R7 or hydroxy,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 is 1-4C-alkyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl or cyclopentyl group substituted by R6 and optionally substituted by R61,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, halogen, 1-4C-alkyl or hydroxy,
R6 is —NH—C(O)—R7, halogen, hydroxy or NH$_2$,
R61 is halogen, 1-4C-alkyl or hydroxy,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is methyl, ethyl or isopropyl,
R23 is hydrogen,
R24 is hydrogen,
Y is —(CH$_2$)$_n$—, n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is hydroxy,
R6 is —NH—C(O)—R7 or hydroxy,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is methyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is hydroxy,
R6 is —NH—C(O)—R7 or hydroxy,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is 1-4C-fluoroalkyl,
R23 is hydrogen,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, —C(O)—NR8R9, halogen, hydroxy or NH$_2$,
R61 is halogen, 1-4C-alkyl or hydroxy,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is fluoromethyl, difluoromethyl or trifluoromethyl,
R23 is hydrogen,
R24 is hydrogen,
Y is —(CH$_2$)$_n$—,
n is 0 or 1,
R3 is a 4- to 7-membered saturated heterocyclic ring containing one nitrogen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, —C(O)—NR8R9, halogen, hydroxy or NH$_2$,
R61 is halogen, 1-4C-alkyl or hydroxy,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy, R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is fluoromethyl, difluoromethyl or trifluoromethyl,
R23 is hydrogen,
R24 is hydrogen,
Y is —(CH$_2$)$_n$—,
n is 0,
R3 is a 4- to 7-membered saturated heterocyclic ring containing one nitrogen atom, said heterocyclic ring being optionally substituted by R4 and/or by one or two substituents R5, or a 3-6C-cycloalkyl group substituted by R6 and optionally substituted by R61,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is methoxy, fluoro, methyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, hydroxy or NH$_2$,
R61 is fluoro, methyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is fluoromethyl, difluoromethyl or trifluoromethyl,
R23 is hydrogen,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R6 is —NH—C(O)—R7, hydroxy or NH$_2$,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 trifluoromethyl,
R23 is hydrogen,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R6 is —NH—C(O)—R7 or hydroxy,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is 1-4C-fluoroalkyl,
R23 is hydrogen,
R24 is hydrogen,
Y is —(CH$_2$)$_n$—,
n is 0,
R3 is a 5- to 6-membered saturated heterocyclic ring containing one nitrogen atom, said heterocyclic ring being optionally substituted by R4 and/or by one substituent R5, or a 5-6C-cycloalkyl group substituted by R6 and optionally substituted by R61,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is halogen, 1-4C-alkyl or hydroxy,
R6 is —NH—C(O)—R7, hydroxy or NH$_2$,
R61 is halogen, 1-4C-alkyl or hydroxy,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is fluoromethyl, difluoromethyl or trifluoromethyl,
R23 is hydrogen,
R24 is hydrogen,
Y is —(CH$_2$)$_n$—,
n is 0, R3 is a 5- to 6-membered saturated heterocyclic ring containing one nitrogen atom, said heterocyclic ring being optionally substituted by R4 and/or by one substituent R5, or a 5-6C-cycloalkyl group substituted by R6 and optionally substituted by R61,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is halogen, 1-4C-alkyl or hydroxy,
R6 is —NH—C(O)—R7, hydroxy or $NH_2$,
R61 is halogen, 1-4C-alkyl or hydroxy,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —$CH_2$-3-6C-cycloalkyl,
R2 is hydrogen,
R21 is hydrogen,
R22 is difluoromethyl,
R23 is hydrogen,
R24 is hydrogen,
Y is —$(CH_2)_n$—,
n is 0,
R3 is a 5- to 6-membered saturated heterocyclic ring containing one nitrogen atom, said heterocyclic ring being optionally substituted by R4 and/or by one substituent R5, or a 5-6C-cycloalkyl group substituted by R6 and optionally substituted by R61,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is halogen, 1-4C-alkyl or hydroxy,
R6 is —NH—C(O)—R7, hydroxy or $NH_2$,
R61 is halogen, 1-4C-alkyl or hydroxy,
R7 is 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —$CH_2$-3-4C-cycloalkyl,
R2 is hydrogen,
R21 is hydrogen,
R22 is difluoromethyl,
R23 is hydrogen,
R24 is hydrogen,
Y is —$(CH_2)_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl or cyclopentyl group substituted by R6 and optionally substituted by R61,
R4 is —C(O)-1-4C-alkyl, wherein the 1-4C-alkyl group is optionally substituted by R41,
R41 is 1-4C-alkoxy,
R5 is halogen or 1-4C-alkyl,
R6 is —NH—C(O)—R7,
R61 is halogen or 1-4C-alkyl,
R7 is 1-4C-alkyl, which is optionally substituted by R71, or 1-4C-alkoxy,
R71 is 1-4C-alkoxy,
a salt thereof, or a stereoisomer of the compound or a salt thereof.

In an alternative embodiment, the present subject matter relates to compounds of formula (I), wherein
R1 is —$CH_2$-3-4C-cycloalkyl,
R2 is hydrogen,
R21 is hydrogen,
R22 is difluoromethyl,
R23 is hydrogen,
R24 is hydrogen,
Y is —$(CH_2)_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl or cyclopentyl group substituted by R6 and optionally substituted by R61,
R4 is —C(O)-1-4C-alkyl, wherein the 1-4C-alkyl group is optionally substituted by R41,
R41 is 1-4C-alkoxy,
R5 is fluoro or methyl,
R6 is —NH—C(O)—R7,
R61 is fluoro or methyl,
R7 is 1-4C-alkyl, which is optionally substituted by R71, or 1-4C-alkoxy,
R71 is 1-4C-alkoxy,
a salt thereof, or a stereoisomer of the compound or a salt thereof.

In an alternative embodiment, the present subject matter relates to compounds of formula (I), wherein
R1 is —$CH_2$-3-4C-cycloalkyl,
R2 is hydrogen,
R21 is hydrogen,
R22 is difluoromethyl,
R23 is hydrogen,
R24 is hydrogen,
Y is —$(CH_2)_n$—,
n is 0,
R3 is a 5- to 6-membered saturated heterocyclic ring containing one nitrogen atom, said heterocyclic ring being substituted by R4 at said nitrogen atom and said heterocyclic ring being optionally substituted by R5, or a cyclohexyl or cyclopentyl group substituted by R6 and optionally substituted by R61,
R4 is —C(O)-1-4C-alkyl, wherein the 1-4C-alkyl group is optionally substituted by R41,
R41 is 1-4C-alkoxy,
R5 is fluoro or methyl,
R6 is —NH—C(O)—R7,
R61 is fluoro or methyl,
R7 is methyl or ethyl, which are optionally substituted by R71, or ethoxy,
R71 is methoxy,
a salt thereof, or a stereoisomer of the compound or a salt thereof.

In an alternative embodiment, the present subject matter relates to compounds of formula (I), wherein
R1 is —$CH_2$-3-4C-cycloalkyl,
R2 is hydrogen,
R21 is hydrogen,
R22 is 1-4C-fluoroalkyl,
R23 is hydrogen,
R24 is hydrogen,
Y is —$(CH_2)_n$—,
n is 0, R3 is a 5-6C-cycloalkyl group substituted by R6 and optionally substituted by R61,
R6 is —NH—C(O)—R7,
R61 is halogen or 1-4C-alkyl,
R7 is 1-4C-alkyl, which is optionally substituted by R71,
R71 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is difluoromethyl or trifluoromethyl,
R23 is hydrogen,
R24 is hydrogen,
Y is —(CH$_2$)$_n$—,
n is 0,
R3 is a cyclohexyl group substituted by R6 and optionally substituted by R61,
R6 is —NH—C(O)—R7,
R61 is fluoro or methyl,
R7 is methyl or ethyl, which are optionally substituted by R71,
R71 is methoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is difluoromethyl,
R23 is hydrogen,
R24 is hydrogen,
Y is —(CH$_2$)$_n$—,
n is 0,
R3 is a cyclohexyl group substituted by R6 and optionally substituted by R61,
R6 is —NH—C(O)—R7,
R61 is fluoro or methyl,
R7 is methyl or ethyl, which are optionally substituted by R71,
R71 is methoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl which is optionally substituted by R11,
R11 is 1-4C-alkoxy or hydroxy,
R2 is hydrogen or 1-4C-alkyl,
R21 is hydrogen,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 6-membered saturated heterocyclic ring containing one nitrogen atom, said heterocyclic ring being optionally substituted by R4 and/or by one or two substituents R5,
R4 is —C(O)—H, —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43,
R41 is 1-4C-alkoxy or hydroxy,
R42 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl,
R2 is hydrogen or 1-4C-alkyl,
R21 is hydrogen,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 5- to 6-membered saturated heterocyclic ring containing one nitrogen atom, said heterocyclic ring being optionally substituted by R4 and/or by one or two substituents R5,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is methoxy, fluoro, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is hydrogen, halogen, 1-4C-alkyl, 1-4C-alkoxy, hydroxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0,
R3 is a 6-membered saturated heterocyclic ring containing one nitrogen atom, said heterocyclic ring being substituted by R4 at said nitrogen atom, R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy or 1-4C-fluoroalkoxy,
R24 is hydrogen,
Y is —(CH$_2$)$_n$—,
n is 0,
R3 is a 5-membered saturated heterocyclic ring containing one nitrogen atom, said heterocyclic ring being substituted by R4 at said nitrogen atom,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy,
R24 is hydrogen,
Y is —(CH$_2$)$_n$—,
n is 0,
R3 is a 5-membered saturated heterocyclic ring containing one nitrogen atom, said heterocyclic ring being substituted by R4 at said nitrogen atom and/or R5,
R4 is —C(O)—H, —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, halogen, 1-4C-alkyl or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and/or said heterocyclic ring being optionally substituted by R5,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
R5 is 1-4C-alkoxy, halogen, 1-4C-alkyl or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom and/or said heterocyclic ring being optionally substituted by R5,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is halogen or 1-4C-alkyl,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy,
R24 is hydrogen,
Y is —(CH$_2$)$_n$—, n is 0,
R3 is a 6-membered saturated heterocyclic ring containing one nitrogen atom, said heterocyclic ring being substituted by R4 at said nitrogen atom and/or said heterocyclic ring being optionally substituted by R5,
R4 is —C(O)-1-4C-alkyl, wherein the 1-4C-alkyl group is optionally substituted by R41, or —C(O)—O-1-4C-alkyl,
R41 is 1-4C-alkoxy or hydroxy,
R5 is halogen or 1-4C-alkyl,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl which is optionally substituted by R11,
R11 is 1-4C-alkoxy or hydroxy,
R2 is hydrogen or 1-4C-alkyl,
R21 is hydrogen,
R22 is hydrogen, halogen, 1-4C-alkyl, 1-4C-alkoxy, hydroxy, 1-4C-fluoroalkoxy or —C(O)-1-4C-alkyl, 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 3-6C-cycloalkyl group substituted by R6 and optionally substituted by R61,
R6 is —NH—C(O)—R7, —C(O)—NR8R9, halogen, hydroxy or NH$_2$,
R61 is halogen, 1-4C-alkyl or hydroxy,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl which is optionally substituted by R11,
R11 is 1-4C-alkoxy or hydroxy,
R2 is hydrogen or 1-4C-alkyl,
R21 is hydrogen,
R22 is hydrogen, halogen, 1-4C-alkyl, 1-4C-alkoxy, hydroxy, 1-4C-fluoroalkoxy or —C(O)-1-4C-alkyl, 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a cyclohexyl or cyclopentyl group substituted by R6 and optionally substituted by R61,
R6 is —NH—C(O)—R7, —C(O)—NR8R9, halogen, hydroxy or NH$_2$,
R61 is halogen, 1-4C-alkyl or hydroxy,
R7 is hydrogen, 1-4C-alkyl, which is optionally substituted by R71, 3-6C-cycloalkyl, which is optionally substituted by R72, or 1-4C-alkoxy, which is optionally substituted by R73,
R71 is 1-4C-alkoxy or hydroxy,
R72 is 1-4C-alkoxy or hydroxy,
R73 is 1-4C-alkoxy or hydroxy,
R8 is hydrogen,
R9 is 1-4C-alkyl, which is optionally substituted by R91, or 3-6C-cycloalkyl, which is optionally substituted by R92,
R91 is 1-4C-alkoxy or hydroxy,
R92 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is hydrogen, halogen, 1-4C-alkyl, 1-4C-alkoxy, hydroxy, 1-4C-fluoroalkoxy or —C(O)-1-4C-alkyl, 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
R24 is hydrogen,
Y is —(CH$_2$)$_n$—,
n is 0,
R3 is a 3-6C-cycloalkyl group substituted by R6 and optionally substituted by R61,
R6 is —NH—C(O)—R7, halogen, hydroxy or NH$_2$,
R61 is halogen, 1-4C-alkyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen or 1-4C-alkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy or 1-4C-fluoroalkoxy,
R24 is hydrogen,
Y is —(CH$_2$)$_n$—,
n is 0,
R3 is a cyclohexyl or cyclopentyl group substituted by R6 and optionally substituted by R61,
R6 is —NH—C(O)—R7, hydroxy or NH$_2$,
R61 is halogen, 1-4C-alkyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy,
R24 is hydrogen,
Y is —(CH$_2$)$_n$—,
n is 0,
R3 is a 3-6C-cycloalkyl group substituted by R6,
R6 is —NH—C(O)—R7 or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl,
R2 is hydrogen,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy,
R24 is hydrogen,
Y is —(CH$_2$)$_n$—,
n is 0,
R3 is a cyclohexyl or cyclopentyl group substituted by R6,
R6 is —NH—C(O)—R7 or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-4C-cycloalkyl,
R2 is hydrogen,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy,
R24 is hydrogen,
Y is —(CH$_2$)$_n$—,
n is 0,
R3 is a cyclohexyl or cyclopentyl group substituted by R6 and optionally substituted by R61,
R6 is —NH—C(O)—R7,
R61 is halogen or 1-4C-alkyl,
R7 is 1-4C-alkyl, which is optionally substituted by R71, or 1-4C-alkoxy,
R71 is 1-4C-alkoxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl which is optionally substituted by R11,
R11 is 1-4C-alkoxy or hydroxy,
R2 is hydrogen or 1-4C-alkyl,
R21 is hydrogen,
R22 is hydrogen, halogen, 1-4C-alkyl, 1-4C-alkoxy, hydroxy, 1-4C-fluoroalkoxy or —C(O)-1-4C-alkyl, 1-4C-fluoroalkyl,
or R21 and R22 combine to form a group —O—CH$_2$—O—,
R23 is hydrogen, halogen, 1-4C-alkyl, 1-4C-alkoxy, hydroxy or 1-4C-fluoroalkoxy,
or R22 and R23 combine to form a group —O—CH$_2$—O—,
R24 is hydrogen,
Y is —(CH$_2$)$_n$—,
n is 0 or 1,
R3 is a 4- to 7-membered saturated heterocyclic ring containing one nitrogen atom and optionally one oxygen atom, said heterocyclic ring being optionally substituted by R4 and/or by one or two substituents R5, or a 3-6C-cycloalkyl group substituted by R6 and optionally substituted by R61,
R4 is —C(O)-1-4C-alkyl, wherein the 1-4C-alkyl group is optionally substituted by R41, or —C(O)—O-1-4C-alkyl, wherein the 1-4C-alkyl group is optionally substituted by R43,
R41 is 1-4C-alkoxy or hydroxy,
R43 is 1-4C-alkoxy or hydroxy,
if only one substituent R5 is present then
R5 is 1-4C-alkoxy, halogen, 1-4C-alkyl or hydroxy,
if two substituents R5 are present, these are identical and binding at the same carbon atom and are selected from halogen or 1-4C-alkyl or together with the carbon atom, to which they are bonded, form a spiro-linked cyclopropane ring,
R6 is —NH—C(O)—R7, halogen, hydroxy or NH$_2$,
R61 is halogen, 1-4C-alkyl or hydroxy,
R7 is hydrogen, 1-4C-alkyl, which is optionally substituted by R71, or 1-4C-alkoxy, which is optionally substituted by R73,
R71 is 1-4C-alkoxy or hydroxy,
R73 is 1-4C-alkoxy or hydroxy,
a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl which is optionally substituted by R11,
R11 is 1-4C-alkoxy or hydroxy,
R2 is hydrogen or 1-4C-alkyl,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy or 1-4C-fluoroalkoxy,
R24 is hydrogen,
Y is —(CH$_2$)$_n$—,
n is 0 or 1,
R3 is a 5- to 6-membered saturated heterocyclic ring containing one nitrogen atom, said heterocyclic ring being optionally substituted by R4 and/or R5, or a cyclohexyl or cyclopentyl group substituted by R6,
R4 is —C(O)-1-4C-alkyl, wherein the 1-4C-alkyl group is optionally substituted by R41,
R41 is 1-4C-alkoxy or hydroxy,
R5 is 1-4C-alkoxy, halogen, 1-4C-alkyl or hydroxy,
R6 is —NH—C(O)—R7 or hydroxy,
R7 is hydrogen, 1-4C-alkyl, which is optionally substituted by R71, or 1-4C-alkoxy,
R71 is 1-4C-alkoxy or hydroxy, a salt thereof, or a stereoisomer of the compound or a salt thereof.

In an alternative embodiment, the present subject matter relates to compounds of formula (I), wherein
R1 is —CH$_2$-3-6C-cycloalkyl or 1-4C-alkyl,
R2 is hydrogen,
R21 is hydrogen,
R22 is hydrogen, halogen, 1-4C-alkyl, 1-4C-alkoxy, 1-4C-fluoroalkoxy, —C(O)-1-4C-alkyl or 1-4C-fluoroalkyl,
or R21 and R22 combine to form a group —O—CH$_2$—O—,
R23 is hydrogen, halogen, 1-4C-alkyl, 1-4C-alkoxy,
R24 is hydrogen,
Y is —(CH$_2$)$_n$—,
n is 0,
R3 is a 5- to 6-membered saturated heterocyclic ring containing one nitrogen atom, said heterocyclic ring being substituted by R4 at said nitrogen atom, or a cyclohexyl or cyclopentyl group substituted by R6,
R4 is —C(O)-1-4C-alkyl, wherein the 1-4C-alkyl group is optionally substituted by R41,
R41 is 1-4C-alkoxy or hydroxy,
R6 is —NH—C(O)—R7 or hydroxy,
R7 is hydrogen, 1-4C-alkyl, which is optionally substituted by R71, or 1-4C-alkoxy,
R71 is 1-4C-alkoxy or hydroxy,
a salt thereof, or a stereoisomer of the compound or a salt thereof.

In an alternative embodiment, the present subject matter relates to compounds of formula (I) or salts thereof, wherein R1 is —CH$_2$-3-6C-cycloalkyl or 1-4C-alkyl, R2, R21, R22, R23, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R1 is —CH$_2$-3-6C-cycloalkyl, R2, R21, R22, R23, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R1 is —CH$_2$-3-4C-cycloalkyl, R2, R21, R22, R23, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R2 is hydrogen, R1, R21, R22, R23, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R2 is methyl, R1, R21, R22, R23, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R21 is hydrogen, R1, R2, R22, R23, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R21 is fluoro, R1, R2, R22, R23, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R22 is hydrogen, halogen, 1-4C-alkyl, 1-4C-alkoxy, —C(O)-1-4C-alkyl, 1-4C-fluoroalkyl, or R21 and R22 combine to form a group —O—CH$_2$—O—, R1, R11, R2, R21, R23, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R22 is hydrogen, fluoro, methy, ethyl, isopropyl, methoxy, —C(O)-methyl, fluoromethyl, difluoromethyl, trifluoromethyl, or R21 and R22 combine to form a group —O—CH$_2$—O—, R1, R11, R2, R21, R23, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R22 is fluoro, methyl, difluoromethyl or trifluoromethyl, R1, R11, R2, R21, R23, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R23 is hydrogen, halogen, or 1-4C-alkoxy, R1, R11, R2, R21, R22, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R23 is hydrogen, fluoro, or methoxy, R1, R11, R2, R21, R22, R24, Y, n, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein n is 0, R1, R11, R2, R21, R22, R23, R24, Y, R3, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R3 is a 5- to 6-membered saturated heterocyclic ring containing one nitrogen atom, said heterocyclic ring being substituted by R4 at said nitrogen atom and optionally substituted by one or two substituents R5 at said heterocyclic ring, or a cyclohexyl or cyclopentyl group substituted by R6 and optionally substituted by R61, R1, R11, R2, R21, R22, R23, R24, Y, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R3 is a 5- to 6-membered saturated heterocyclic ring containing one nitrogen atom, said heterocyclic ring being substituted by R4 at said nitrogen atom and optionally substituted by one substituent R5 at said heterocyclic ring, or a cyclohexyl or cyclopentyl group substituted by R6 and optionally substituted by R61, R1, R11, R2, R21, R22, R23, R24, Y, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R3 is a 5- to 6-membered saturated heterocyclic ring containing one nitrogen atom, said heterocyclic ring being substituted by R4 at said nitrogen atom, or a cyclohexyl or cyclopentyl group substituted by R6, R1, R11, R2, R21, R22, R23, R24, Y, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R3 is piperidine substituted by R4 at the nitrogen atom and optionally substituted by one or two substituents R5 at said piperidine ring, or a cyclohexyl or cyclopentyl group substituted by R6 and optionally substituted by R61, R1, R11, R2, R21, R22, R23, R24, Y, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R3 is piperidine substituted by R4 at the nitrogen atom, or a cyclohexyl or cyclopentyl group substituted by R6, R1, R11, R2, R21, R22, R23, R24, Y, R4, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R4 is —C(O)-1-4C-alkyl, wherein the 1-4C-alkyl group is optionally substituted by R41, R1, R11, R2, R21, R22, R23, R24, Y, R3, R41, R42, R43, R5, R6, R61, R7, R71, R72, R73, R8, R9, R91 and R92 are as described above or below.

In an alternative embodiment, the present subject matter relates to compounds of formula (I) or salts thereof, wherein R5 is hydroxy, R1, R11, R21, R2, R22, R23, R24, Y, R3, R4, R41, R42, R43, R6, R61, R7, R71, R72, R73, R8, R9, R91 and R92 are as described above or below.

In an alternative embodiment, the present subject matter relates to compounds of formula (I) or salts thereof, wherein R5 is fluoro, R1, R11, R21, R2, R22, R23, R24, Y, R3, R4, R41, R42, R43, R6, R61, R7, R71, R72, R73, R8, R9, R91 and R92 are as described above or below.

In an alternative embodiment, the present subject matter relates to compounds of formula (I) or salts thereof, wherein R5 is hydroxy or fluoro, R1, R11, R21, R2, R22, R23, R24, Y, R3, R4, R41, R42, R43, R6, R61, R7, R71, R72, R73, R8, R9, R91 and R92 are as described above or below.

In an alternative embodiment, the present subject matter relates to compounds of formula (I) or salts thereof, wherein R5 is methyl, R1, R11, R21, R2, R22, R23, R24, Y, R3, R4, R41, R42, R43, R6, R61, R7, R71, R72, R73, R8, R9, R91 and R92 are as described above or below.

In an alternative embodiment, the present subject matter relates to compounds of formula (I) or salts thereof, wherein two substituents R5 are present, these are identical and binding at the same carbon atom and are fluoro, R1, R11, R21, R2, R22, R23, R24, Y, R3, R4, R41, R42, R43, R6, R61, R7, R71, R72, R73, R8, R9, R91 and R92 are as described above or below.

In an alternative embodiment, the present subject matter relates to compounds of formula (I) or salts thereof, wherein two substituents R5 are present, these are identical and binding at the same carbon atom and are methyl, R1, R11, R21, R2, R22, R23, R24, Y, R3, R4, R41, R42, R43, R6, R61, R7, R71, R72, R73, R8, R9, R91 and R92 are as described above or below.

In an alternative embodiment, the present subject matter relates to compounds of formula (I) or salts thereof, wherein two substituents R5 are present and together with the carbon atom, to which they are bonded, form a spiro-linked cyclopropane ring, R1, R11, R21, R2, R22, R23, R24, Y, R3, R4, R41, R42, R43, R6, R61, R7, R71, R72, R73, R8, R9, R91 and R92 are as described above or below.

In an alternative embodiment, the present subject matter relates to compounds of formula (I) or salts thereof, wherein R5 is halogen or 1-4C-alkyl, R1, R11, R21, R2, R22, R23, R24, Y, R3, R4, R41, R42, R43, R6, R61, R7, R71, R72, R73, R8, R9, R91 and R92 are as described above or below.

In an alternative embodiment, the present subject matter relates to compounds of formula (I) or salts thereof, wherein R5 is fluoro or methyl, R1, R11, R21, R2, R22, R23, R24, Y, R3, R4, R41, R42, R43, R6, R61, R7, R71, R72, R73, R8, R9, R91 and R92 are as described above or below.

In an alternative embodiment, the present subject matter relates to compounds of formula (I) or salts thereof, wherein R6 is —NH—C(O)—R7, halogen, hydroxy or NH₂, R1, R11, R2, R21, R22, R23, R24, Y, R3, R4, R41, R42, R43, R5, R61, R7, R71, R72 and R73 are as described above or below.

In an alternative embodiment, the present subject matter relates to compounds of formula (I) or salts thereof, wherein R6 is —NH—C(O)—R7, hydroxy or NH₂, R1, R11, R2, R21, R22, R23, R24, Y, R3, R4, R41, R42, R43, R5, R61, R7, R71, R72 and R73 are as described above or below.

In an alternative embodiment, the present subject matter relates to compounds of formula (I) or salts thereof, wherein R6 is —NH—C(O)—R7 or NH₂, R1, R11, R2, R21, R22, R23, R24, Y, R3, R4, R41, R42, R43, R5, R61, R7, R71, R72 and R73 are as described above or below.

In an alternative embodiment, the present subject matter relates to compounds of formula (I) or salts thereof, wherein R6 is —NH—C(O)—R7 or hydroxy, R1, R11, R2, R21, R22, R23, R24, Y, R3, R4, R41, R42, R43, R5, R61, R7, R71, R72 and R73 are as described above or below.

In an alternative embodiment, the present subject matter relates to compounds of formula (I) or salts thereof, wherein R6 is —NH—C(O)—R7, R1, R11, R2, R21, R22, R23, R24, Y, R3, R4, R41, R42, R43, R5, R61, R7, R71, R72 and R73 are as described above or below.

In an alternative embodiment, the present subject matter relates to compounds of formula (I) or salts thereof, wherein R6 is hydroxy, R1, R11, R2, R21, R22, R23, R24, Y, R3, R4, R41, R42, R43, R5 and R61 are as described above or below.

In an alternative embodiment, the present subject matter relates to compounds of formula (I) or salts thereof, wherein R6 is halogen R1, R11, R2, R21, R22, R23, R24, Y, R3, R4, R41, R42, R43, R5, and R61 are as described above or below.

In an alternative embodiment, the present subject matter relates to compounds of formula (I) or salts thereof, wherein R61 is halogen R1, R11, R2, R21, R22, R23, R24, Y, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R61 is fluoro R1, R11, R2, R21, R22, R23, R24, Y, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R61 is 1-4C-alkyl R1, R11, R2, R21, R22, R23, R24, Y, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R61 is methyl R1, R11, R2, R21, R22, R23, R24, Y, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R61 is halogen or 1-4C-alkyl, R1, R11, R2, R21, R22, R23, R24, Y, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R61 is fluoro or methyl, R1, R11, R2, R21, R22, R23, R24, Y, R3, R4, R41, R42, R43, R5, R6, R7, R71, R72, R73, R8, R9, R91 and R92 are as described above or below.

In an alternative embodiment, the present subject matter relates to compounds of formula (I) or salts thereof, wherein R7 is 1-4C-alkyl, which is optionally substituted by R71, or 1-4C-alkoxy, R1, R11, R21, R2, R22, R23, R24, Y, R3, R4, R41, R42, R43, R5, R6, R61, R71, R8, R9, R91 and R92 are as described above or below.

In an alternative embodiment, the present subject matter relates to compounds of formula (I) or salts thereof, wherein R1 is —CH$_2$-3-4C-cycloalkyl, n is 0, R2 is hydrogen, R3 is a 5- to 6-membered saturated heterocyclic ring containing one nitrogen atom, said heterocyclic ring being substituted by R4 at said nitrogen atom and optionally substituted by one or two substituents R5 at said heterocyclic ring, or a cyclohexyl or cyclopentyl group substituted by R6 and optionally substituted by R61, R4 is —C(O)-1-4C-alkyl, wherein the 1-4C-alkyl group is optionally substituted by R41, R6 is —NH—C(O)—R7 or hydroxy, R7 is 1-4C-alkyl, which is optionally substituted by R71, or 1-4C-alkoxy, R21, R22, R23, R24, Y, R41 R5, R61 and R71 are as described above or below.

In an alternative embodiment, the present subject matter relates to compounds of formula (I) or salts thereof, wherein R1 is —CH$_2$-3-4C-cycloalkyl, n is 0, R2 is hydrogen, R3 is a 5- to 6-membered saturated heterocyclic ring containing one nitrogen atom, said heterocyclic ring being substituted by R4 at said nitrogen atom and optionally substituted by one substituent R5 at said heterocyclic ring, or a cyclohexyl or cyclopentyl group substituted by R6 and optionally substituted by R61, R4 is —C(O)-1-4C-alkyl, wherein the 1-4C-alkyl group is optionally substituted by R41, R6 is —NH—C(O)—R7, R7 is 1-4C-alkyl, which is optionally substituted by R71, or 1-4C-alkoxy, R21, R22, R23, R24, Y, R41 R5, R61 and R71 are as described above or below.

In an alternative embodiment, the present subject matter relates to compounds of formula (I) or salts thereof, wherein R1 is —CH$_2$-3-4C-cycloalkyl, n is 0, R2 is hydrogen, R3 is a 5- to 6-membered saturated heterocyclic ring containing one nitrogen atom, said heterocyclic ring being substituted by R4 at said nitrogen atom, or a cyclohexyl or cyclopentyl group substituted by R6, R4 is —C(O)-1-4C-alkyl, wherein the 1-4C-alkyl group is optionally substituted by R41, R6 is —NH—C(O)—R7 or hydroxy, R7 is 1-4C-alkyl, which is optionally substituted by R71, or 1-4C-alkoxy, R21, R22, R23, R24, Y, R41 and R71 are as described above or below.

In an alternative embodiment, the present subject matter relates to compounds of formula (I) or salts thereof, wherein R1 is —CH$_2$-3-4C-cycloalkyl, n is 0, R2 is hydrogen, R3 is a 5- to 6-membered saturated heterocyclic ring containing one nitrogen atom, said heterocyclic ring being substituted by R4 at said nitrogen atom, or a cyclohexyl or cyclopentyl group substituted by R6, R4 is —C(O)-1-4C-alkyl, wherein the 1-4C-alkyl group is optionally substituted by R41, R6 is —NH—C(O)—R7, R7 is 1-4C-alkyl, which is optionally substituted by R71, or 1-4C-alkoxy, R21, R22, R23, R24, Y, R41 and R71 are as described above or below.

In an alternative embodiment, the present subject matter relates to compounds of formula (I), selected from N-(1-Acetylpiperidin-4-yl)-4-[5-(cyclopropylmethoxy)-1,3-benzodioxol-4-yl]-6-methyl-5H-pyrrolo[3,2-d]pyrimidine-7-carboxamide; 4-[5-(Cyclopropylmethoxy)-1,3-benzodioxol-4-yl]-6-methyl-N-(1-propionylpiperidin-4-yl)-5H-pyrrolo[3,2-d]pyrimidine-7-carboxamide; 4-[5-(Cyclopropylmethoxy)-1,3-benzodioxol-4-yl]-N-[1-(methoxyacetyl)piperidin-4-yl]-6-methyl-5H-pyrrolo[3,2-d]pyrimidine-7-carboxamide; Ethyl 4-[({4-[5-(cyclopropylmethoxy)-1,3-benzodioxol-4-yl]-6-methyl-5H-pyrrolo[3,2-d]pyrimidin-7-yl}carbonyl)amino]piperidine-1-carboxylate; N-(trans-4-acetamidocyclohexyl)-4-[5-(cyclopropylmethoxy)-1,3-benzodioxol-4-yl]-6-methyl-5H-pyrrolo[3,2-d]pyrimidine-7-carboxamide; 4-[5-(Cyclopropylmethoxy)-1,3-benzodioxol-4-yl]-6-methyl-N-[trans-4-(propionylamino)cyclohexyl]-5H-pyrrolo[3,2-d]pyrimidine-7-carboxamide; 4-[5-(Cyclopropylmethoxy)-1,3-benzodioxol-4-yl]-N-{trans-4-[(methoxyacetyl)amino]cyclohexyl}-6-methyl-5H-pyrrolo[3,2-d]pyrimidine-7-carboxamide; Ethyl {trans-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; N-(cis-4-acetamidocyclohexyl)-4-[5-(cyclopropylmethoxy)-1,3-benzodioxol-4-yl]-6-methyl-5H-pyrrolo[3,2-d]pyrimidine-7-carboxamide; 4-[5-(Cyclopropylmethoxy)-1,3-benzodioxol-4-yl]-6-methyl-N-[cis-4-(propionylamino)cyclohexyl]-5H-pyrrolo[3,2-d]pyrimidine-7-carboxamide; 4-[5-(Cyclopropylmethoxy)-1,3-benzodioxol-4-yl]-N-{cis-4-[(methoxyacetyl)amino]cyclohexyl}-6-methyl-5H-pyrrolo[3,2-d]pyrimidine-7-carboxamide; Ethyl {cis-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; N-[(3R)-1-acetylpyrrolidin-3-yl]-4-[5-(cyclopropylmethoxy)-1,3-benzodioxol-4-yl]-6-methyl-5H-pyrrolo[3,2-d]pyrimidine-7-carboxamide; 4-[5-(Cyclopropylmethoxy)-1,3-benzodioxol-4-yl]-6-methyl-N-[(3R)-1-propionylpyrrolidin-3-yl]-5H-pyrrolo[3,2-d]pyrimidine-7-carboxamide; 4-[5-(Cyclopropylmethoxy)-1,3-benzodioxol-4-yl]-N-[(3R)-1-(methoxyacetyl)pyrrolidin-3-yl]-6-methyl-5H-pyrrolo[3,2-d]pyrimidine-7-carboxamide; N-[(3R*,4R*)-1-acetyl-4-hydroxypyrrolidin-3-yl]-4-[5-(cyclopropylmethoxy)-1,3-benzodioxol-4-yl]-6-methyl-5H-pyrrolo[3,2-d]pyrimidine-7-carboxamide; 4-[5-(Cyclopropylmethoxy)-1,3-benzodioxol-4-yl]-N-[(3R*,4R*)-4-hydroxy-1-propionylpyrrolidin-3-yl]-6-methyl-5H-pyrrolo[3,2-d]pyrimidine-7-carboxamide; 4-[5-(Cyclopropylmethoxy)-1,3-benzodioxol-4-yl]-N-[(3R*,4R*)-4-hydroxy-1-(methoxyacetyl)pyrrolidin-3-yl]-6-methyl-5H-pyrrolo[3,2-d]pyrimidine-7-carboxamide; N-(1-acetylpiperidin-4-yl)-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-6-methyl-N-(1-propionylpiperidin-4-yl)-5H-pyrrolo[3,2-d]pyrimidine-7-carboxamide; 4-[2-(Cyclopropylmethoxy)-4-fluorophenyl]-N-[1-(methoxyacetyl)piperidin-4-yl]-6-methyl-5H-pyrrolo[3,2-d]pyrimidine-7-carboxamide; N-(trans-4-acetamidocyclohexyl)-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-6-methyl-N-[trans-4-(propionylamino)cyclohexyl]-5H-pyrrolo[3,2-d]pyrimidine-7-carboxamide; 4-[2-(Cyclopropylmethoxy)-4-fluorophenyl]-N-{trans-4-[(methoxyacetyl)amino]cyclohexyl}-6-methyl-5H-pyrrolo[3,2-d]pyrimidine-7-carboxamide; N-(cis-4-acetamidocyclohexyl)-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-6-methyl-N-[cis-4-(propionylamino)cyclohexyl]-5H-pyrrolo[3,2-d]pyrimidine-7-carboxamide; 4-[2-(Cyclopropylmethoxy)-4-fluorophenyl]-N-{cis-4-[(methoxyacetyl)amino]cyclohexyl}-6-methyl-5H-pyrrolo[3,2-d]pyrimidine-7-carboxamide; N-[(3R)-1-acetylpyrrolidin-3-yl]-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-6-methyl-N-[(3R)-1-propanoylpyrrolidin-3-yl]-5H-pyrrolo[3,2-d]pyrimidine-7-carboxamide; 4-[2-(Cyclopropylmethoxy)-

4-fluorophenyl]-N-[(3R)-1-(methoxyacetyl)pyrrolidin-3-yl]-6-methyl-5H-pyrrolo[3,2-d]pyrimidine-7-carboxamide; N-[(3R*,4R*)-1-acetyl-4-hydroxypyrrolidin-3-yl]-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-N-[(3R*,4R*)-4-hydroxy-1-propanoylpyrrolidin-3-yl]-6-methyl-5H-pyrrolo[3,2-d]pyrimidine-7-carboxamide; 4-[2-(Cyclopropylmethoxy)-4-fluorophenyl]-N-[(3R*,4R*)-4-hydroxy-1-(methoxyacetyl)pyrrolidin-3-yl]-6-methyl-5H-pyrrolo[3,2-d]pyrimidine-7-carboxamide; N-[(3S*,4S*)-1-acetyl-3-hydroxypiperidin-4-yl]-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-N-[(3S*,4S*)-3-hydroxy-1-propanoylpiperidin-4-yl]-6-methyl-5H-pyrrolo[3,2-d]pyrimidine-7-carboxamide; 4-[2-(Cyclopropylmethoxy)-4-fluorophenyl]-N-[(3S*,4S*)-3-hydroxy-1-(methoxyacetyl)piperidin-4-yl]-6-methyl-5H-pyrrolo[3,2-d]pyrimidine-7-carboxamide; 4-(2-Cyclopropylmethoxy-5-fluoro-phenyl)-6-methyl-5H-pyrrolo[3,2-d]pyrimidine-7-carboxylic acid (1-acetyl-piperidin-4-yl)-amide; 4-[2-(cyclopropylmethoxy)-5-fluorophenyl]-6-methyl-N-(1-propionylpiperidin-4-yl)-5H-pyrrolo[3,2-d]pyrimidine-7-carboxamide; 4-(2-Cyclopropylmethoxy-5-fluoro-phenyl)-6-methyl-5H-pyrrolo[3,2-d]pyrimidine-7-carboxylic acid [1-(2-methoxy-acetyl)-piperidin-4-yl]-amide; Ethyl 4-[({-4-[2-(cyclopropylmethoxy)-5-fluorophenyl]-6-methyl-5H-pyrrolo[3,2-d]pyrimidin-7-yl}carbonyl)amino]piperidine-1-carboxylate; N-(trans-4-acetamidocyclohexyl)-4-[2-(cyclopropylmethoxy)-5-fluorophenyl]-6-methyl-5H-pyrrolo[3,2-d]pyrimidine-7-carboxamide; 4-[2-(Cyclopropylmethoxy)-5-fluorophenyl]-6-methyl-N-[trans-4-(propionylamino)cyclohexyl]-5H-pyrrolo[3,2-d]pyrimidine-7-carboxamide; 4-[2-(Cyclopropylmethoxy)-5-fluorophenyl]-N-{trans-4-[(methoxyacetyl)amino]cyclohexyl}-6-methyl-5H-pyrrolo[3,2-d]pyrimidine-7-carboxamide; Ethyl {trans-4-[({4-[2-(cyclopropylmethoxy)-5-fluorophenyl]-6-methyl-5H-pyrrolo[3,2-d]-pyrimidin-7-yl}carbonyl)amino]cyclohexyl}carbamate; N-(cis-4-acetamidocyclohexyl)-4-[2-(cyclopropylmethoxy)-5-fluorophenyl]-6-methyl-5H-pyrrolo[3,2-d]pyrimidine-7-carboxamide; N-[(3R)-1-acetylpyrrolidin-3-yl]-4-[2-(cyclopropylmethoxy)-5-fluorophenyl]-6-methyl-5H-pyrrolo[3,2-d]pyrimidine-7-carboxamide; 4-[2-(Cyclopropylmethoxy)-5-fluorophenyl]-6-methyl-N-[(3R)-1-propanoylpyrrolidin-3-yl]-5H-pyrrolo[3,2-d]pyrimidine-7-carboxamide; 4-[2-(Cyclopropylmethoxy)-5-fluorophenyl]-N-[(3R)-1-(methoxyacetyl)pyrrolidin-3-yl]-6-methyl-5H-pyrrolo[3,2-d]pyrimidine-7-carboxamide; N-[(3R*,4R*)-1-acetyl-3-hydroxypiperidin-4-yl]-4-[2-(cyclopropylmethoxy)-5-fluorophenyl]-6-methyl-5H-pyrrolo[3,2-d]pyrimidine-7-carboxamide; 4-[2-(Cyclopropylmethoxy)-5-fluorophenyl]-N-[(3R*,4R*)-3-hydroxy-1-propanoylpiperidin-4-yl]-6-methyl-5H-pyrrolo[3,2-d]pyrimidine-7-carboxamide; 4-[2-(Cyclopropylmethoxy)-5-fluorophenyl]-N-[(3R*,4R*)-3-hydroxy-1-(methoxyacetyl)piperidin-4-yl]-6-methyl-5H-pyrrolo[3,2-d]pyrimidine-7-carboxamide; N-(1-acetylpiperidin-4-yl)-4-(2-ethoxy-5-fluorophenyl)-6-methyl-5H-pyrrolo[3,2-d]pyrimidine-7-carboxamide; 4-(2-Ethoxy-5-fluorophenyl)-6-methyl-N-(1-propanoylpiperidin-4-yl)-5H-pyrrolo[3,2-d]pyrimidine-7-carboxamide; 4-(2-Ethoxy-5-fluorophenyl)-N-[1-(methoxyacetyl)piperidin-4-yl]-6-methyl-5H-pyrrolo[3,2-d]pyrimidine-7-carboxamide; N-(1-acetylpiperidin-4-yl)-4-[2-(cyclopropylmethoxy)-4-methoxyphenyl]-6-methyl-5H-pyrrolo[3,2-d]pyrimidine-7-carboxamide; 4-[2-(Cyclopropylmethoxy)-4-methoxyphenyl]-6-methyl-N-(1-propionylpiperidin-4-yl)-5H-pyrrolo[3,2-d]pyrimidine-7-carboxamide; 4-[2-(Cyclopropylmethoxy)-4-methoxyphenyl]-N-[1-(methoxyacetyl)piperidin-4-yl]-6-methyl-5H-pyrrolo[3,2-d]pyrimidine-7-carboxamide; N-(trans-4-acetamidocyclohexyl)-4-[2-(cyclopropylmethoxy)-4-methoxyphenyl]-6-methyl-5H-pyrrolo[3,2-d]pyrimidine-7-carboxamide; N-(cis-4-acetamidocyclohexyl)-4-[2-(cyclopropylmethoxy)-4-methoxyphenyl]-6-methyl-5H-pyrrolo[3,2-d]pyrimidine-7-carboxamide; N-[(3R)-1-acetylpyrrolidin-3-yl]-4-[2-(cyclopropylmethoxy)-4-methoxyphenyl]-6-methyl-5H-pyrrolo[3,2-d]pyrimidine-7-carboxamide; 4-[2-(Cyclopropylmethoxy)-4-methoxyphenyl]-6-methyl-N-[(3R)-1-propionylpyrrolidin-3-yl]-5H-pyrrolo[3,2-d]pyrimidine-7-carboxamide; 4-[2-(Cyclopropylmethoxy)-4-methoxyphenyl]-N-[(3R)-1-(methoxyacetyl)pyrrolidin-3-yl]-6-methyl-5H-pyrrolo[3,2-d]pyrimidine-7-carboxamide; N-[(3R*,4R*)-1-acetyl-4-hydroxypyrrolidin-3-yl]-4-[2-(cyclopropylmethoxy)-4-methoxyphenyl]-6-methyl-5H-pyrrolo[3,2-d]pyrimidine-7-carboxamide; 4-[2-(Cyclopropylmethoxy)-4-methoxyphenyl]-N-[(3R*,4R*)-4-hydroxy-1-propionylpyrrolidin-3-yl]-6-methyl-5H-pyrrolo[3,2-d]pyrimidine-7-carboxamide; 4-[2-(Cyclopropylmethoxy)-4-methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide; N-(1-acetylpiperidin-4-yl)-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-6-methyl-N-(1-propionylpiperidin-4-yl)-5H-pyrrolo[3,2-d]pyrimidine-7-carboxamide; 4-[2-(Cyclopropylmethoxy)-5-methoxyphenyl]-N-[1-(methoxyacetyl)piperidin-4-yl]-6-methyl-5H-pyrrolo[3,2-d]pyrimidine-7-carboxamide; N-(trans-4-acetamidocyclohexyl)-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-6-methyl-N-[trans-4-(propionylamino)cyclohexyl]-5H-pyrrolo[3,2-d]pyrimidine-7-carboxamide; 4-[2-(Cyclopropylmethoxy)-5-methoxyphenyl]-N-{trans-4-[(methoxyacetyl)amino]cyclohexyl}-6-methyl-5H-pyrrolo[3,2-d]pyrimidine-7-carboxamide; N-(cis-4-acetamidocyclohexyl)-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-6-methyl-N-[cis-4-(propionylamino)cyclohexyl]-5H-pyrrolo[3,2-d]pyrimidine-7-carboxamide; 4-[2-(Cyclopropylmethoxy)-5-methoxyphenyl]-N-{cis-4-[(methoxyacetyl)amino]cyclohexyl}-6-methyl-5H-pyrrolo[3,2-d]pyrimidine-7-carboxamide; N-[(3R)-1-acetylpyrrolidin-3-yl]-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-6-methyl-N-[(3R)-1-propionylpyrrolidin-3-yl]-5H-pyrrolo[3,2-d]pyrimidine-7-carboxamide; 4-[2-(Cyclopropylmethoxy)-5-methoxyphenyl]-N-[(3R)-1-(methoxyacetyl)pyrrolidin-3-yl]-6-methyl-5H-pyrrolo[3,2-d]pyrimidine-7-carboxamide; N-[(3R*,4R*)-1-acetyl-3-hydroxypiperidin-4-yl]-4-[2-(cyclopropylmethoxy)-5-methoxyphenyl]-6-methyl-5H-pyrrolo[3,2-d]pyrimidine- 7-carboxamide; 4-[2-(Cyclopropylmethoxy)-5-methoxyphenyl]-N-[(3R*,4R*)-3-hydroxy-1-propanoylpiperidin-4-yl]-6-methyl-5H-pyrrolo[3,2-d]pyrimidine-7-carboxamide; 4-[2-(Cyclopropylmethoxy)-5-methoxyphenyl]-N-[(3R*,4R*)-3-hydroxy-1-(methoxyacetyl)piperidin-4-yl]-6-methyl-5H-pyrrolo[3,2-d]pyrimidine-7-carboxamide; N-(1-Acetylpiperidin-4-yl)-4-[2-(cyclopropylmethoxy)-5-methylphenyl]-6-methyl-5H-pyrrolo[3,2-d]pyrimidine-7-carboxamide; 4-[2-(Cyclopropylmethoxy)-5-methylphenyl]-6-methyl-N-(1-propanoylpiperidin-4-yl)-5H-pyrrolo[3,2-d]pyrimidine-7-carboxamide; 4-[2-(cyclopropylmethoxy)-5-methylphenyl]-N-[1-(methoxyacetyl)piperidin-4-yl]-6-methyl-5H-pyrrolo[3,2-d]pyrimidine-7-carboxamide; N-[trans-4-(acetylamino)cyclohexyl]-4-[2-(cyclopropylmethoxy)-5-methylphenyl]-6-methyl-5H-pyrrolo[3,2-d]pyrimidine-7-carboxamide; 4-[2-(Cyclopropylmethoxy)-5-methylphenyl]-6-methyl-N-[trans-4-(propanoylamino)cyclohexyl]-5H-pyrrolo[3,2-d]pyrimidine-7-carboxamide; 4-[2-(Cyclopropylmethoxy)-5-methylphenyl]-N-{trans-4-[(methoxyacetyl)amino]cyclohexyl}-6-methyl-5H-pyrrolo[3,2-d]pyrimidine-7-carboxamide; N-[cis-4-(acetylamino)cyclohexyl]-4-[2-(cyclopropylmethoxy)-5-methylphenyl]-6-methyl-5H-pyrrolo[3,2-d]pyrimidine-7-carboxamide; 4-[2-(Cyclopropylmethoxy)-5-methylphenyl]-6-methyl-N-[cis-4-(propanoylamino)cyclohexyl]-5H-pyrrolo[3,2-d]pyrimidine-7-carboxamide; 4-[2-(Cyclopropylmethoxy)-5-methylphenyl]-N-{cis-4-[(methoxyacetyl)amino]cyclohexyl}-6-methyl-5H-pyrrolo[3,2-d]pyrimidine-7-carboxamide; N-(1-Acetylpiperidin-4-yl)-4-[2-(cyclopropylmethoxy)-5-(trifluoromethyl)phenyl]-6-methyl-5H-pyrrolo[3,2-d]pyrimidine-7-carboxamide; 4-[2-(Cyclopropylmethoxy)-5-(trifluoromethyl)phenyl]-6-methyl-N-(1-propanoylpiperidin-4-yl)-5H-pyrrolo[3,2-d]pyrimidine-7-carboxamide; 4-[2-(Cyclopropylmethoxy)-5-(trifluoromethyl)phenyl]-N-[1-(methoxyacetyl)piperidin-4-yl]-6-methyl-5H-pyrrolo[3,2-d]pyrimidine-7-carboxamide; N-[trans-4-(acetylamino)cyclohexyl]-4-[2-(cyclopropylmethoxy)-5-(trifluoromethyl)phenyl]-6-methyl-5H-pyrrolo[3,2-d]pyrimidine-7-carboxamide; 4-[2-(cyclopropylmethoxy)-5-(trifluoromethyl)phenyl]-6-methyl-N-[trans-4-(propanoylamino)cyclohexyl]-5H-pyrrolo[3,2-d]pyrimidine-7-carboxamide; 4-[2-(Cyclopropylmethoxy)-5-(trifluoromethyl)phenyl]-N-{trans-4-[(methoxyacetyl)amino]cyclohexyl}-6-methyl-5H-pyrrolo[3,2-d]pyrimidine-7-carboxamide; N-[cis-4-(acetylamino)cyclohexyl]-4-[2-(cyclopropylmethoxy)-5-(trifluoromethyl)phenyl]-6-methyl-5H-pyrrolo[3,2-d]pyrimidine-7-carboxamide; 4-[2-(Cyclopropylmethoxy)-5-(trifluoromethyl)phenyl]-6-methyl-N-[cis-4-(propanoylamino)cyclohexyl]-5H-pyrrolo[3,2-d]pyrimidine-7-carboxamide; 4-[2-(Cyclopropylmethoxy)-5-(trifluoromethyl)phenyl]-N-{cis-4-[(methoxyacetyl)amino]cyclohexyl}-6-methyl-5H-pyrrolo[3,2-d]pyrimidine-7-carboxamide; N-(1-acetylpiperidin-4-yl)-4-[2-ethoxy-5-(trifluoromethyl)phenyl]-6-methyl-5H-pyrrolo[3,2-d]pyrimidine-7-carboxamide; 4-[2-Ethoxy-5-(trifluoromethyl)phenyl]-6-methyl-N-(1-propanoylpiperidin-4-yl)-5H-pyrrolo[3,2-d]pyrimidine-7-carboxamide; 4-[2-Ethoxy-5-(trifluoromethyl)phenyl]-N-[1-(methoxyacetyl)piperidin-4-yl]-6-methyl-5H-pyrrolo[3,2-d]pyrimidine-7-carboxamide; N-(1-Acetylpiperidin-4-yl)-4-[2-(cyclopropylmethoxy)-4-fluoro-5-methoxyphenyl]-6-methyl-5H-pyrrolo[3,2-d]pyrimidine-7-carboxamide; 4-[2-(cyclopropylmethoxy)-4-fluoro-5-methoxyphenyl]-6-methyl-N-(1-propionylpiperidin-4-yl)-5H-pyrrolo[3,2-d]pyrimidine-7-carboxamide; 4-[2-(Cyclopropylmethoxy)-4-fluoro-5-methoxyphenyl]-N-[1-(methoxyacetyl)piperidin-4-yl]-6-methyl-5H-pyrrolo[3,2-d]pyrimidine-7-carboxamide; Ethyl 4-[({4-[2-(cyclopropylmethoxy)-4-fluoro-5-methoxyphenyl]-6-methyl-5H-pyrrolo[3,2-d]pyrimidin-7-yl}carbonyl)amino]piperidine-1-carboxylate; N-(trans-4-Acetamidocyclohexyl)-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-6-methyl-N-[trans-4-(propionylamino)cyclohexyl]-5H-pyrrolo[3,2-d]pyrimidine-7-carboxamide; 4-[2-(Cyclopropylmethoxy)-4-fluoro-5-methoxyphenyl]-N-{trans-4-[(methoxyacetyl)amino]cyclohexyl}-6-methyl-5H-pyrrolo[3,2-d]pyrimidine-7-carboxamide; Ethyl {trans-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate; N-(cis-4-Acetamidocyclohexyl)-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-6-methyl-N-[cis-4-(propionylamino)cyclohexyl]-5H-pyrrolo[3,2-d]pyrimidine-7-carboxamide; 4-[2-(Cyclopropylmethoxy)-4-fluoro-5-methoxyphenyl]-N-{cis-4-[(methoxyacetyl)amino]cyclohexyl}-6-methyl-5H-pyrrolo[3,2-d]pyrimidine-7-carboxamide; N-[(3R*,4R*)-1-Acetyl-3-hydroxypiperidin-4-yl]-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-N-[(3R*,4R*)-3-hydroxy-1-propionylpiperidin-4-yl]-6-methyl-5H-pyrrolo[3,2-d]pyrimidine-7-carboxamide; 4-[2-(cyclopropylmethoxy)-4-fluoro-5-methoxyphenyl]-N-[(3R*,4R*)-3-hydroxy-1-(methoxyacetyl)piperidin-4-yl]-6-methyl-5H-pyrrolo[3,2-d]pyrimidine-7-carboxamide; N-[(3S*,4S*)-1-Acetyl-4-hydroxypiperidin-3-yl]-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-N-[(3S*,4S*)-4-hydroxy-1-propionylpiperidin-3-yl]-6-methyl-5H-pyrrolo[3,2-d]pyrimidine-7-carboxamide; 4-[2-(cyclopropylmethoxy)-4-fluoro-5-methoxyphenyl]-N-[(3S*,4S*)-4-hydroxy-1-(methoxyacetyl)piperidin-3-yl]-6-methyl-5H-pyrrolo[3,2-d]pyrimidine-7-carboxamide; N-(1-Acetylpiperidin-4-yl)-4-[2-(cyclopropylmethoxy)-4-fluoro-5-methylphenyl]-6-methyl-5H-pyrrolo[3,2-d]pyrimidine-7-carboxamide; 4-[2-(Cyclopropylmethoxy)-4-fluoro-5-methylphenyl]-6-methyl-N-(1-propanoylpiperidin-4-yl)-5H-pyrrolo[3,2-d]pyrimidine-7-carboxamide; 4-[2-(Cyclopropylmethoxy)-4-fluoro-5-methylphenyl]-N-[1-(methoxyacetyl)piperidin-4-yl]-6-methyl-5H-pyrrolo[3,2-d]pyrimidine-7-carboxamide; N-[trans-4-(Acetylamino)cyclohexyl]-4-[2-(cyclopropylmethoxy)-4-fluoro-5-methylphenyl]-6-methyl-5H-pyrrolo[3,2-d]pyrimidine-7-carboxamide; 4-[2-(Cyclopropylmethoxy)-4-fluoro-5-methylphenyl]-6-methyl-N-[trans-4-(propanoylamino)cyclohexyl]-5H-pyrrolo[3,2-d]pyrimidine-7-carboxamide; 4-[2-(Cyclopropylmethoxy)-4-fluoro-5-methylphenyl]-N-{trans-4-[(methoxyacetyl)amino]cyclohexyl}-6-methyl-5H-pyrrolo[3,2-d]pyrimidine-7-carboxamide; N-[cis-4-(Acetylamino)cyclohexyl]-4-[2-(cyclopropylmethoxy)-4-fluoro-5-methylphenyl]-6-methyl-5H-pyrrolo[3,2-d]pyrimidine-7-carboxamide; 4-[2-(Cyclopropylmethoxy)-4-fluoro-5- methylphenyl]-6-methyl-N-[cis-4-(propanoylamino) cyclohexyl]-5H-pyrrolo[3,2-d]pyrimidine-7-carboxamide; 4-[2-(Cyclopropylmethoxy)-4-fluoro-5-methylphenyl]-N-{cis-4-[(methoxyacetyl)amino]cyclohexyl}-6-methyl-5H-pyrrolo[3,2-d]pyrimidine-7-carboxamide; N-[(3R*,4R*)-1-Acetyl-3-hydroxypiperidin-4-yl]-4-[2-(cyclopropylmethoxy)-4-fluoro-5-methylphenyl]-6-methyl-5H-pyrrolo[3,2-d]pyrimidine-7-carboxamide; 4-[2-(cyclopropylmethoxy)-4-fluoro-5-methylphenyl]-N-[(3R*,4R*)-3-hydroxy-1-propanoylpiperidin-4-yl]-6-methyl-5H-pyrrolo[3,2-d]pyrimidine-7-carboxamide; 4-[2-(Cyclopropylmethoxy)-4-fluoro-5-methylphenyl]-N-[(3R*,4R*)-3-hydroxy-1-(methoxyacetyl)piperidin-4-yl]-6-methyl-5H-pyrrolo[3,2-d]pyrimidine-7-carboxamide; N-(1-Acetylpiperidin-4-yl)-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-6-methyl-N-(1-propionylpiperidin-4-yl)-5H-pyrrolo[3,2-d]pyrimidine-7-carboxamide; 4-[2-(Cyclopropylmethoxy)-5-fluoro-4-methoxyphenyl]-N-[1-(methoxyacetyl)piperidin-4-yl]-6-methyl-5H-pyrrolo[3,2-d]pyrimidine-7-carboxamide; Ethyl 4-[({4-[2-(cyclopropylmethoxy)-5-fluoro-4-methoxyphenyl]-6-methyl-5H-pyrrolo[3,2-d]pyrimidin-7-yl}carbonyl)amino]piperidine-1-carboxylate; N-(trans-4-Acetamidocyclohexyl)-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-6-methyl-N-[trans-4-(propionylamino)cyclohexyl]-5H-pyrrolo[3,2-d]pyrimidine-7-carboxamide; 4-[2-(Cyclopropylmethoxy)-5-fluoro-4-methoxyphenyl]-N-{trans-4-[(methoxyacetyl)amino]cyclohexyl}-6-methyl-5H-pyrrolo[3,2-d]pyrimidine-7-carboxamide; N-(cis-4-Acetamidocyclohexyl)-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-6-methyl-N-[cis-4-(propionylamino)cyclohexyl]-5H-pyrrolo[3,2-d]pyrimidine-7-carboxamide; 4-[2-(Cyclopropylmethoxy)-5-fluoro-4-methoxyphenyl]-N-{cis-4-[(methoxyacetyl)amino]cyclohexyl}-6-methyl-5H-pyrrolo[3,2-d]pyrimidine-7-carboxamide; Ethyl {cis-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate; N-[(3R*,4R*)-1-Acetyl-3-hydroxypiperidin-4-yl]-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-N-[(3R*,4R*)-3-hydroxy-1-propanoylpiperidin-4-yl]-6-methyl-5H-pyrrolo[3,2-d]pyrimidine-7-carboxamide; 4-[2-(Cyclopropylmethoxy)-5-fluoro-4-methoxyphenyl]-N-[(3R*,4R*)-3-hydroxy-1-(methoxyacetyl)piperidin-4-yl]-6-methyl-5H-pyrrolo[3,2-d]pyrimidine-7-carboxamide; N-(1-Acetylpiperidin-4-yl)-4-[2-(cyclopropylmethoxy)-5-ethylphenyl]-6-methyl-5H-pyrrolo[3,2-d]pyrimidine-7-carboxamide; 4-[2-(Cyclopropylmethoxy)-5-ethylphenyl]-6-methyl-N-(1-propanoylpiperidin-4-yl)-5H-pyrrolo[3,2-d]pyrimidine-7-carboxamide; 4-[2-(Cyclopropylmethoxy)-5-ethylphenyl]-N-[1-(methoxyacetyl)piperidin-4-yl]-6-methyl-5H-pyrrolo[3,2-d]pyrimidine-7-carboxamide; N-[trans-4-(Acetylamino)cyclohexyl]-4-[2-(cyclopropylmethoxy)-5-ethylphenyl]-6-methyl-5H-pyrrolo[3,2-d]pyrimidine-7-carboxamide; 4-[2-(Cyclopropylmethoxy)-5-ethylphenyl]-6-methyl-N-[trans-4-(propanoylamino)cyclohexyl]-5H-pyrrolo[3,2-d]pyrimidine-7-carboxamide; 4-[2-(Cyclopropylmethoxy)-5-ethylphenyl]-N-{trans-4-[(methoxyacetyl)amino]cyclohexyl}-6-methyl-5H-pyrrolo[3,2-d]pyrimidine-7-carboxamide; N-[cis-4-(Acetylamino)cyclohexyl]-4-[2-(cyclopropylmethoxy)-5-ethylphenyl]-6-methyl-5H-pyrrolo[3,2-d]pyrimidine-7-carboxamide; 4-[2-(Cyclopropylmethoxy)-5-ethylphenyl]-6-methyl-N-[cis-4-(propanoylamino)cyclohexyl]-5H-pyrrolo[3,2-d]pyrimidine-7-carboxamide; 4-[2-(Cyclopropylmethoxy)-5-ethylphenyl]-N-{cis-4-[(methoxyacetyl)amino]cyclohexyl}-6-methyl-5H-pyrrolo[3,2-d]pyrimidine-7-carboxamide; N-[(3R*,4R*)-1-Acetyl-4-hydroxypyrrolidin-3-yl]-4-[2-(cyclopropylmethoxy)-5-ethylphenyl]-6-methyl-5H-pyrrolo[3,2-d]pyrimidine-7-carboxamide; 4-[2-(Cyclopropylmethoxy)-5-ethylphenyl]-N-[(3R*,4R*)-4-hydroxy-1-propanoylpyrrolidin-3-yl]-6-methyl-5H-pyrrolo[3,2-d]pyrimidine-7-carboxamide; 4-[2-(Cyclopropylmethoxy)-5-ethylphenyl]-N-[(3R*,4R*)-4-hydroxy-1-(methoxyacetyl)pyrrolidin-3-yl]-6-methyl-5H-pyrrolo[3,2-d]pyrimidine-7-carboxamide; N-(1-Acetylpiperidin-4-yl)-4-[2-(cyclopropylmethoxy)-5-(propan-2-yl)phenyl]-6-methyl-5H-pyrrolo[3,2-d]pyrimidine-7-carboxamide; 4-[2-(Cyclopropylmethoxy)-5-(propan-2-yl)phenyl]-N-[1-(methoxyacetyl)piperidin-4-yl]-6-methyl-5H-pyrrolo[3,2-d]pyrimidine-7-carboxamide; N-[trans-4-(Acetylamino)cyclohexyl]-4-[2-(cyclopropylmethoxy)-5-(propan-2-yl)phenyl]-6-methyl-5H-pyrrolo[3,2-d]pyrimidine-7-carboxamide; 4-[2-(Cyclopropylmethoxy)-5-(propan-2-yl)phenyl]-N-{trans-4-[(methoxyacetyl)amino]cyclohexyl}-6-methyl-5H-pyrrolo[3,2-d]pyrimidine-7-carboxamide; N-[cis-4-(Acetylamino)cyclohexyl]-4-[2-(cyclopropylmethoxy)-5-(propan-2-yl)phenyl]-6-methyl-5H-pyrrolo[3,2-d]pyrimidine-7-carboxamide; 4-[2-(Cyclopropylmethoxy)-5-(propan-2-yl)phenyl]-N-{cis-4-[(methoxyacetyl)amino]cyclohexyl}-6-methyl-5H-pyrrolo[3,2-d]pyrimidine-7-carboxamide; 4-[5-Acetyl-2-(cyclopropylmethoxy)phenyl]-N-(1-acetylpiperidin-4-yl)-6-methyl-5H-pyrrolo[3,2-d]pyrimidine-7-carboxamide; 4-[5-Acetyl-2-(cyclopropylmethoxy)phenyl]-6-methyl-N-(1-propanoylpiperidin-4-yl)-5H-pyrrolo[3,2-d]pyrimidine-7-carboxamide; 4-[5-Acetyl-2-(cyclopropylmethoxy)phenyl]-N-[1-(methoxyacetyl)piperidin-4-yl]-6-methyl-5H-pyrrolo[3,2-d]pyrimidine-7-carboxamide; N-[trans-4-(Acetylamino)cyclohexyl]-4-[5-acetyl-2-(cyclopropylmethoxy)phenyl]-6-methyl-5H-pyrrolo[3,2-d]pyrimidine-7-carboxamide; 4-[5-Acetyl-2-(cyclopropylmethoxy)phenyl]-6-methyl-N-[trans-4-(propanoylamino)cyclohexyl]-5H-pyrrolo[3,2-d]pyrimidine-7-carboxamide; 4-[5-Acetyl-2-(cyclopropylmethoxy)phenyl]-N-{trans-4-[(methoxyacetyl)amino]cyclohexyl}-6-methyl-5H-pyrrolo[3,2-d]pyrimidine-7-carboxamide; 4-[2-(Cyclopropylmethoxy)-4-fluoro-5-methoxyphenyl]-N-[1-(methoxyacetyl)piperidin-4-yl]-2,6-dimethyl-5H-pyrrolo[3,2-d]pyrimidine-7-carboxamide; 4-[2-(Cyclopropylmethoxy)-4-fluoro-5-methoxyphenyl]-2,6-dimethyl-N-(1-propanoylpiperidin-4-yl)-5H-pyrrolo[3,2-d]pyrimidine-7-carboxamide; N-(1-Acetylpiperidin-4-yl)-4-[2-(cyclopropylmethoxy)-4-fluoro-5-methoxyphenyl]-2,6-dimethyl-5-pyrrolo[3,2-d]pyrimidine-7-carboxamide; N-(1-Acetyl piperidin-4-yl)-4-[2-(cyclopropylmethoxy)-5-fluoro-4-methoxyphenyl]-2,6-dimethyl-5H-pyrrolo[3,2-d]pyrimidine-7-carboxamide; 4-[2-(Cyclopropylmethoxy)-5-methyl phenyl]-N-[1-(methoxyacetyl)piperidin-4-yl]-2,6-dimethyl-5-pyrrolo[3,2-d]pyrimidine-7-carboxamide; 4-[2-(Cyclopropylmethoxy)-5-methylphenyl]-2,6-dimethyl-N-(1-propanoyl piperidin-4-yl)-5H-pyrrolo[3,2-d]pyrimidine-7-carboxamide; N-(1-Acetylpiperidin-4-yl)-4-[2-(cyclopropylmethoxy)-5-methyl phen yl]-2,6-dimethyl-5H-pyrrolo[3,2-d]pyrimidine-7-carboxamide; N-[(3R)-1-Acetylpyrrolidin-3-yl]-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-6-methyl-N-[(3R)-1-propionylpyrrolidin-3-yl]-5H-pyrrolo[3,2-d]pyrimidine-7-carboxamide; 4-[2-(Cyclopropylmethoxy)-4-fluoro-5-methoxyphenyl]-N-[(3R)-1-(methoxyacetyl)pyrrolidin-3-yl]-6-methyl-5H-pyrrolo[3,2-d]pyrimidine-7-carboxamide; Ethyl (3R)-3-[({4-[2-(cyclopropylmethoxy)-4-fluoro-5-methoxyphenyl]-6-methyl-5H-pyrrolo[3,2-d]pyrimidin-7-yl}carbonyl)amino]pyrrolidine-1-carboxylate; N-[(3R*,4R*)-1-Acetyl-4-hydroxypyrrolidin-3-yl]-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-N-[(3R*,4R*)-4-hydroxy-1-propionylpyrrolidin-3-yl]-6-methyl-5H-pyrrolo[3,2-d]pyrimidine-7-carboxamide; 4-[2-(Cyclopropylmethoxy)-4-fluoro-5-methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide; N-[(3R)-1-Acetylpyrrolidin-3-yl]-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-6-methyl-N-[(3R)-1-propionylpyrrolidin-3-yl]-5H-pyrrolo[3,2-d]pyrimidine-7-carboxamide; 4-[2-(Cyclopropylmethoxy)-5-fluoro-4-methoxyphenyl]-N-[(3R)-1-(methoxyacetyl)pyrrolidin-3-yl]-6-methyl-5H-pyrrolo[3,2-d]pyrimidine-7-carboxamide; N-[(3R*,4R*)-1-Acetyl-4-hydroxypyrrolidin-3-yl]-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-N-[(3R*,4R*)-4-hydroxy-1-propionylpyrrolidin-3-yl]-6-methyl-5H-pyrrolo[3,2-d]pyrimidine-7-carboxamide; 4-[2-(Cyclopropylmethoxy)-5-fluoro-4-methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide; N-[(3R*,4R*)-1-Acetyl-4-hydroxypyrrolidin-3-yl]-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-N-[(3R*,4R*)-4-hydroxy-1-propionylpyrrolidin-3-yl]-6-methyl-5H-pyrrolo[3,2-d]pyrimidine-7-carboxamide; 4-[2-(Cyclopropylmethoxy)-5-methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide; 4-[5-(Cyclopropylmethoxy)-1,3-benzodioxol-4-yl]-N-(1-glycoloylpiperidin-4-yl)-6-methyl-5H-pyrrolo[3,2-d]pyrimidine-7-carboxamide; 4-[5-(Cyclopropylmethoxy)-1,3-benzodioxol-4-yl]-N-{1-[(2S)-2-hydroxypropanoyl]piperidin-4-yl}-6-methyl-5H-pyrrolo[3,2-d]pyrimidine-7-carboxamide; 4-[5-(Cyclopropylmethoxy)-1,3-benzodioxol-4-yl]-N-[trans-4-(glycoloylamino)cyclohexyl]-6-methyl-5H-pyrrolo[3,2-d]pyrimidine-7-carboxamide; 4-[5-(Cyclopropylmethoxy)-1,3-benzodioxol-4-yl]-N-(trans-4-{[(2S)-2-hydroxypropanoyl]amino}cyclohexyl)-6-methyl-5H-pyrrolo[3,2-d]pyrimidine-7-carboxamide; 4-[5-(Cyclopropylmethoxy)-1,3-benzodioxol-4-yl]-N-[cis-4-(glycoloylamino)cyclohexyl]-6-methyl-5H-pyrrolo[3,2-d]pyrimidine-7-carboxamide; 4-[5-(Cyclopropylmethoxy)-1,3-benzodioxol-4-yl]-N-(cis-4-{[(2S)-2-hydroxypropanoyl]amino}cyclohexyl)-6-methyl-5H-pyrrolo[3,2-d]pyrimidine-7-carboxamide; 4-[5-(Cyclopropylmethoxy)-1,3-benzodioxol-4-yl]-N-[(3R)-1-glycoloylpyrrolidin-3-yl]-6-methyl-5H-pyrrolo[3,2-d]pyrimidine-7-carboxamide; 4-[5-(Cyclopropylmethoxy)-1,3-benzodioxol-4-yl]-N-{(3R)-1-[(2S)-2-hydroxypropanoyl]pyrrolidin-3-yl}-6-methyl-5H-pyrrolo[3,2-d]pyrimidine-7-carboxamide 4-[5-(Cyclopropylmethoxy)-1,3-benzodioxol-4-yl]-N-[(3R*,4R*)-1-glycoloyl-4-hydroxypyrrolidin-3-yl]-6-methyl-5H-pyrrolo[3,2-d]pyrimidine-7-carboxamide; 4-[5-(Cyclopropylmethoxy)-1,3-benzodioxol-4-yl]-N-{(3R,4R)-4-hydroxy-1-[(2S)-2-hydroxypropanoyl]pyrrolidin-3-yl}-6-methyl-5H-pyrrolo[3,2-d]pyrimidine-7-carboxamide; 4-[5-(cyclopropylmethoxy)-1,3-benzodioxol-4-yl]-N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-4-fluorophenyl]-N-(1-glycoloylpiperidin-4-yl)-6-methyl-5H-pyrrolo[3,2-d]pyrimidine-7-carboxamide; 4-[2-(Cyclopropylmethoxy)-4-fluorophenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluorophenyl]-N-[trans-4-(glycoloylamino)cyclohexyl]-6-methyl-5H-pyrrolo[3,2-d]pyrimidine-7-carboxamide; 4-[2-(Cyclopropylmethoxy)-4-fluorophenyl]-N-(trans-4-{[(2S)-2-hydroxypropanoyl]amino}cyclohexyl)-6-methyl-5H-pyrrolo[3,2-d]pyrimidine-7-carboxamide; 4-[2-(cyclopropylmethoxy)-4-fluorophenyl]-N-[cis-4-(glycoloylamino)cyclohexyl]-6-methyl-5H-pyrrolo[3,2-d]pyrimidine-7-carboxamide; 4-[2-(Cyclopropylmethoxy)-4-fluorophenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-fluorophenyl]-N-[(3R)-1-(hydroxyacetyppyrrolidin-3-yl]-6-methyl-5H-pyrrolo[3,2-d]pyrimidine-7-carboxamide; 4-[2-(cyclopropylmethoxy)-4-fluorophenyl]-N-{(3R)-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-4-fluorophenyl]-N-[(3R*,4R*)-4-hydroxy-1-(hydroxyacetyppyrrolidin-3-yl]-6-methyl-5H-pyrrolo[3,2-d]pyrimidine-7-carboxamide; 4-[2-(Cyclopropylmethoxy)-4-fluorophenyl]-N-{(3R,4R)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-4-fluorophenyl]-N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-4-fluorophenyl]-N-[(3S*,4S*)-3-hydroxy-1-(hydroxyacetyppiperidin-4-yl]-6-methyl-5H-pyrrolo[3,2-d]pyrimidine-7-carboxamide; 4-[2-(Cyclopropylmethoxy)-4-fluorophenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluorophenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide; 4-(2-Cyclopropylmethoxy-5-fluoro-phenyl)-6-methyl-5H-pyrrolo[3,2-d]pyrimidine-7-carboxylic acid [1-(2-hydroxy-acetyl)-piperidin-4-yl]amide; 4-(2-Cyclopropylmethoxy-5-fluoro-phenyl)-6-methyl-5H-pyrrolo[3, 2-d]pyrimidine-7-carboxylic acid [1-((S)-2-hydroxy-propionyl)-piperidin-4-yl]-amide; 4-[2-(Cyclopropylmethoxy)-5-fluorophenyl]-N-[trans-4-(glycoloylamino)cyclohexyl]-6-methyl-5H-pyrrolo[3,2-d]pyrimidine-7-carboxamide; 4-[2-(Cyclopropylmethoxy)-5-fluorophenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-fluorophenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-fluorophenyl]-N-[(3R)-1-(hydroxyacetyppyrrolidin-3-yl]-6-methyl-5H-pyrrolo[3,2-d]pyrimidine-7-carboxamide; 4-[2-(Cyclopropylmethoxy)-5-fluorophenyl]-N-{(3R)-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-fluorophenyl]-N-[(3R*,4R*)-3-hydroxy-1-(hydroxyacetyl)piperidin-4-yl]-6-methyl-5H-pyrrolo[3,2-d]pyrimidine-7-carboxamide; 4-[2-(cyclopropylmethoxy)-5-fluorophenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide; 4-[2-(cyclopropylmethoxy)-5-fluorophenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide; 4-(2-Ethoxy-5-fluorophenyl)-N-[1-(hydroxyacetyl)piperidin-4-yl]-6-methyl-5H-pyrrolo[3,2-d]pyrimidine-7-carboxamide; 4-(2-Ethoxy-5-fluorophenyl)-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-methoxyphenyl]-N-(1-glycoloylpiperidin-4-yl)-6-methyl-5H-pyrrolo[3,2-d]pyrimidine-7-carboxamide; 4-[2-(Cyclopropylmethoxy)-4-methoxyphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-methoxyphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-methoxyphenyl]-N-[(3R)-1-glycoloylpyrrolidin-3-yl]-6-methyl-5H-pyrrolo[3,2-d]pyrimidine-7-carboxamide; 4-[2-(Cyclopropylmethoxy)-4-methoxyphenyl]-N-{(3R)-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-4-methoxyphenyl]-N-[(3R*,4R*)-1-glycoloyl-4-hydroxypyrrolidin-3-yl]-6-methyl-5H-pyrrolo[3,2-d]pyrimidine-7-carboxamide; 4-[2-(cyclopropylmethoxy)-4-methoxyphenyl]-N-{(3R,4R)-4-hydroxy-1-[(2S)-2-hydroxypropanoyl]pyrrolidin-3-yl}-6-methyl-5H-pyrrolo[3,2-d]pyrimidine-7-carboxamide; 4-[2-(cyclopropylmethoxy)-4-methoxyphenyl]-N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-methoxyphenyl]-N-(1-glycoloylpiperidin-4-yl)-6-methyl-5H-pyrrolo[3,2-d]pyrimidine-7-carboxamide; 4-[2-(Cyclopropylmethoxy)-5-methoxyphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-methoxyphenyl]-N-[trans-4-(glycoloylamino)cyclohexyl]-6-methyl-5H-pyrrolo[3,2-d]pyrimidine-7-carboxamide; 4-[2-(Cyclopropylmethoxy)-5-methoxyphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-methoxyphenyl]-N-[cis-4-(glycoloylamino)cyclohexyl]-6-methyl-5H-pyrrolo[3,2-d]pyrimidine-7-carboxamide; 4-[2-(cyclopropylmethoxy)-5-methoxyphenyl]-N-(cis-4-{[(2S)-2-hydroxypropanoyl]amino}cyclohexyl)-6-methyl-5H-pyrrolo[3,2-d]pyrimidine-7-carboxamide; 4-[2-(cyclopropylmethoxy)-5-methoxyphenyl]-N-[(3R)-1-glycoloylpyrrolidin-3-yl]-6-methyl-5H-pyrrolo[3,2-d]pyrimidine-7-carboxamide; 4-[2-(cyclopropylmethoxy)-5-methoxyphenyl]-N-{(3R)-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-methoxyphenyl]-N-[(3R*,4R*)-3-hydroxy-1-(hydroxyacetyl)piperidin-4-yl]-6-methyl-5H-pyrrolo[3,2-d]pyrimidine-7-carboxamide; 4-[2-(Cyclopropylmethoxy)-5-methoxyphenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-methoxyphenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-methylphenyl]-N-[1-(hydroxyacetyl)piperidin-4-yl]-6-methyl-5H-pyrrolo[3,2-d]pyrimidine-7-carboxamide; 4-[2-(Cyclopropylmethoxy)-5-methylphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-methylphenyl]-N-{trans-4-[(hydroxyacetyl)amino]cyclohexyl}-6-methyl-5H-pyrrolo[3,2-d]pyrimidine-7-carboxamide; 4-[2-(Cyclopropylmethoxy)-5-methylphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-methylphenyl]-N-{cis-4-[(hydroxyacetyl)amino]cyclohexyl}-6-methyl-5H-pyrrolo[3,2-d]pyrimidine-7-carboxamide; 4-[2-(Cyclopropylmethoxy)-5-methylphenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-(trifluoromethyl)phenyl]-N-[1-(hydroxyacetyl)piperidin-4-yl]-6-methyl-5H-pyrrolo[3,2-d]pyrimidine-7-carboxamide; 4-[2-(Cyclopropylmethoxy)-5-(trifluoromethyl)phenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-(trifluoromethyl)phenyl]-N-{trans-4-[(hydroxyacetyl)amino]cyclohexyl}-6-methyl-5H-pyrrolo[3,2-d]pyrimidine-7-carboxamide; 4-[2-(Cyclopropylmethoxy)-5-(trifluoromethyl)phenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-(trifluoromethyl)phenyl]-N-{cis-4-[(hydroxyacetyl)amino]cyclohexyl}-6-methyl-5H-pyrrolo[3,2-d]pyrimidine-7-carboxamide; 4-[2-(Cyclopropylmethoxy)-5-(trifluoromethyl)phenyl]-N-(cis-4-{[(2S)-2-hydroxypropanoyl]amino}cyclohexyl)-6-methyl-5H-pyrrolo[3,2-d]pyrimidine-7-carboxamide; 4-[2-Ethoxy-5-(trifluoromethyl)phenyl]-N-[1-(hydroxyacetyl)piperidin-4-yl]-6-methyl-5H-pyrrolo[3,2-d]pyrimidine-7-carboxamide; 4-[2-Ethoxy-5-(trifluoromethyl)phenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methoxyphenyl]-N-(1-glycoloylpiperidin-4-yl)-6-methyl-5H-pyrrolo[3,2-d]pyrimidine-7-carboxamide; 4-[2-(Cyclopropylmethoxy)-4-fluoro-5-methoxyphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methoxyphenyl]-N-

[trans-4-(glycoloylamino)cyclohexyl]-6-methyl-5H-pyrrolo[3,2-d]pyrimidine-7-carboxamide; 4-[2-(Cyclopropylmethoxy)-4-fluoro-5-methoxyphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-fluoro-5-methoxyphenyl]-N-[cis-4-(glycoloylamino)cyclohexyl]-6-methyl-5H-pyrrolo[3,2-d]pyrimidine-7-carboxamide; 4-[2-(Cyclopropylmethoxy)-4-fluoro-5-methoxyphenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-fluoro-5-methoxyphenyl]-N-[3R*,4R*)-1-glycoloyl-3-hydroxypiperidin-4-yl]-6-methyl-5H-pyrrolo[3,2-d]pyrimidine-7-carboxamide; 4-[2-(Cyclopropylmethoxy)-4-fluoro-5-methoxyphenyl]-N-{(rac.-3R,4R)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methoxyphenyl]-N-{(rac.-3S,4S)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methoxyphenyl]-N-[(3S*,4S*)-1-glycoloyl-4-hydroxypiperidin-3-yl]-6-methyl-5H-pyrrolo[3,2-d]pyrimidine-7-carboxamide; 4-[2-(Cyclopropylmethoxy)-4-fluoro-5-methoxyphenyl]-N-{(rac.-3S,4S)-4-hydroxy-1-[(2S)-2-hydroxypropanoyl]piperidin-3-yl}-6-methyl-5H-pyrrolo[3,2-d]pyrimidine-7-carboxamide; 4-[2-(Cyclopropylmethoxy)-4-fluoro-5-methoxyphenyl]-N-{(rac.-3R,4R)-4-hydroxy-1-[(2S)-2-hydroxypropanoyl]piperidin-3-yl}-6-methyl-5H-pyrrolo[3,2-d]pyrimidine-7-carboxamide; 4-[2-(Cyclopropylmethoxy)-4-fluoro-5-methyl phenyl]-N-[1-(hydroxyacetyl)piperidin-4-yl]-6-methyl-5H-pyrrolo[3,2-d]pyrimidine-7-carboxamide; 4-[2-(Cyclopropylmethoxy)-4-fluoro-5-methylphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methyl phenyl]-N-{trans-4-[(hydroxyacetyl)amino]cyclohexyl}-6-methyl-5H-pyrrolo[3,2-d]pyrimidine-7-carboxamide; 4-[2-(Cyclopropylmethoxy)-4-fluoro-5-methylphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-fluoro-5-methylphenyl]-N-{cis-4-[(hydroxyacetyl)amino]cyclohexyl}-6-methyl-5H-pyrrolo[3,2-d]pyrimidine-7-carboxamide; 4-[2-(Cyclopropylmethoxy)-4-fluoro-5-methyl phenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-fluoro-5-methylphenyl]-N-[(3R*,4R*)-3-hydroxy-1-(hydroxyacetyl)piperidin-4-yl]-6-methyl-5H-pyrrolo[3,2-d]pyrimidine-7-carboxamide; 4-[2-(Cyclopropylmethoxy)-4-fluoro-5-methylphenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methylphenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-fluoro-4-methoxyphenyl]-N-(1-glycoloylpiperidin-4-yl)-6-methyl-5H-pyrrolo[3,2-d]pyrimidine-7-carboxamide 4-[2-(Cyclopropylmethoxy)-5-fluoro-4-methoxyphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-fluoro-4-methoxyphenyl]-N-[trans-4-(glycoloylamino)cyclohexyl]-6-methyl-5H-pyrrolo[3,2-d]pyrimidine-7-carboxamide; 4-[2-(Cyclopropylmethoxy)-5-fluoro-4-methoxyphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cycloploymethoxy)-5-fluoro-4-methoxyphenyl]-N-[cis-4-(glycoloylamino)cyclohexyl]-6-methyl-5H-pyrrolo[3,2-d]pyrimidine-7-carboxamide; 4-[2-(Cyclopropylmethoxy)-5-fluoro-4-methoxyphenyl]-N-(cis-4-{[(2S)-2-hydroxypropanoyl]amino}cyclohexyl)-6-methyl-5H-pyrrolo[3,2-d]pyrimidine-7-carboxamide; 4-[2-(cyclopropylmethoxy)-5-fluoro-4-methoxyphenyl]-N-[(3R*,4R*)-3-hydroxy-1-(hydroxyacetyl)piperidin-4-yl]-6-methyl-5H-pyrrolo[3,2-d]pyrimidine-7-carboxamide; 4-[2-(Cyclopropylmethoxy)-5-fluoro-4-methoxyphenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-fluoro-4-methoxyphenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-ethylphenyl]-N-[1-(hydroxyacetyppiperidin-4-yl]-6-methyl-5H-pyrrolo[3,2-d]pyrimidine-7-carboxamide; 4-[2-(Cyclopropylmethoxy)-5-ethylphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-ethylphenyl]-N-{trans-4-[(hydroxyacetyl)amino]cyclohexyl}-6-methyl-5H-pyrrolo[3,2-d]pyrimidine-7-carboxamide; 4-[2-(Cyclopropylmethoxy)-5-ethylphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-ethylphenyl]-N-{cis-4-[(hydroxyacetyl)amino]cyclohexyl}-6-methyl-5H-pyrrolo[3,2-d]pyrimidine-7-carboxamide; 4-[2-(Cyclopropylmethoxy)-5-ethylphenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-ethylphenyl]-N-[(3R*,4R*)-4-hydroxy-1-(hydroxyacetyppyrrolidin-3-yl]-6-methyl-5H-pyrrolo[3,2-d]pyrimidine-7-carboxamide; 4-[2-(cyclopropylmethoxy)-5-ethylphenyl]-N-{(3R,4R)-4-hydroxy-1-[(2S)-2-hydroxypropanoyl]pyrrolidin-3-yl}-6-methyl-5H-pyrrolo[3,2-d]pyrimidine-7-carboxamide; 4-[2-(cyclopropylmethoxy)-5-ethylphenyl]-N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-(propan-2-yl)phenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-(propan-2-yl)phenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-(propan-2-yl)phenyl]-N-(cis-4-{[(2S)-2-hydroxypropanoyl]amino}cyclohexyl)-6-methyl-5H-pyrrolo[3,2-d]pyrimidine-7-carboxamide; 4-[5-Acetyl-2-(cyclopropylmethoxy)phenyl]-N-[1-(hydroxyacetyppiperidin-4-yl]-6-methyl-5H-pyrrolo[3,2-d]pyrimidine-7-carboxamide; 4-[5-Acetyl-2-(cyclopropylmethoxy)phenyl]-N-{1-[(2S)-2-hydroxypropanoyl]piperidin-4-yl}-6-methyl-5H-pyrrolo[3,2-d]pyrimidine-7-carboxamide; 4-[5-Acetyl-2-(cyclopropylmethoxy)phenyl]-N-{trans-4-[(hydroxyacetyl)amino]cyclohexyl}-6-methyl-5H-pyrrolo[3,2-d]pyrimidine-7-carboxamide; 4-[5-Acetyl-2-(cyclopropylmethoxy)phenyl]-N-(trans-4-{[(2S)-2-hydroxypropanoyl]amino}cyclohexyl)-6-methyl-5H-pyrrolo[3,2-d]pyrimidine-7-carboxamide; 4-[2-

(Cyclopropylmethoxy)-5-methylphenyl]-N-[1-(hydroxyacetyl)piperidin-4-yl]-2,6-dimethyl-5H-pyrrolo[3,2-d]pyrimidine-7-carboxamide; 4-[2-(Cyclopropylmethoxy)-5-methylphenyl]-N-{1-[(2S)-2-hydroxypropanoyl]piperidin-4-yl}-2,6-dimethyl-5H-pyrrolo[3,2-d]pyrimidine-7-carboxamide; 4-[2-(Cyclopropylmethoxy)-5-fluoro-4-methoxyphenyl]-N-{1-[(2S)-2-hydroxypropanoyl]piperidin-4-yl}-2,6-dimethyl-5H-pyrrolo[3,2-d]pyrimidine-7-carboxamide; 4-[2-(Cyclopropylmethoxy)-4-fluoro-5-methoxyphenyl]-N-[1-(hydroxyacetyl)piperidin-4-yl]-2,6-dimethyl-5H-pyrrolo[3,2-d]pyrimidine-7-carboxamide; 4-[2-(Cyclopropylmethoxy)-4-fluoro-5-methoxyphenyl]-N-{1-[(2S)-2-hydroxypropanoyl]piperidin-4-yl}-2,6-dimethyl-5H-pyrrolo[3,2-d]pyrimidine-7-carboxamide; 4-[2-(Cyclopropylmethoxy)-5-methylphenyl]-N-[(1S,2S)-2-hydroxycyclopentyl]-6-methyl-5H-pyrrolo[3,2-d]pyrimidine-7-carboxamide; 4-[2-(Cyclopropylmethoxy)-5-methylphenyl]-N-[(1S,2R)-2-hydroxycyclopentyl]-6-methyl-5H-pyrrolo[3,2-d]pyrimidine-7-carboxamide; 4-[2-(Cyclopropylmethoxy)-5-methylphenyl]-N-[(1R,2R)-2-hydroxycyclopentyl]-6-methyl-5H-pyrrolo[3,2-d]pyrimidine-7-carboxamide; 4-[2-(Cyclopropylmethoxy)-4-fluoro-5-methoxyphenyl]-N-[(3R)-1-glycoloylpyrrolidin-3-yl]-6-methyl-5H-pyrrolo[3,2-d]pyrimidine-7-carboxamide; 4-[2-(Cyclopropylmethoxy)-4-fluoro-5-methoxyphenyl]-N-{(3R)-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-4-fluoro-5-methoxyphenyl]-N-[(3R*,4R*)-1-glycoloyl-4-hydroxypyrrolidin-3-yl]-6-methyl-5H-pyrrolo[3,2-d]pyrimidine-7-carboxamide; 4-[2-(Cyclopropylmethoxy)-4-fluoro-5-methoxyphenyl]-N-{(3R*,4R*)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-fluoro-4-methoxyphenyl]-N-[(3R)-1-glycoloylpyrrolidin-3-yl]-6-methyl-5H-pyrrolo[3,2-d]pyrimidine-7-carboxamide; 4-[2-(Cyclopropylmethoxy)-5-fluoro-4-methoxyphenyl]-N-{(3R)-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-fluoro-4-methoxyphenyl]-N-[(3R*,4R*)-1-glycoloyl-4-hydroxypyrrolidin-3-yl]-6-methyl-5H-pyrrolo[3,2-d]pyrimidine-7-carboxamide; 4-[2-(Cyclopropylmethoxy)-5-fluoro-4-methoxyphenyl]-N-{(3R*,4R*)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-methoxyphenyl]-N-[(3R*,4R*)-1-glycoloyl-4-hydroxypyrrolidin-3-yl]-6-methyl-5H-pyrrolo[3,2-d]pyrimidine-7-carboxamide; 4-[2-(Cyclopropylmethoxy)-5-methoxyphenyl]-N-{(3R*,4R*)-4-hydroxy-1-[(2S)-2-hydroxypropanoyl]pyrrolidin-3-yl}-6-methyl-5H-pyrrolo[3,2-d]pyrimidine-7-carboxamide; tert-Butyl 4-[({4-[5-(cyclopropylmethoxy)-1,3-benzodioxol-4-yl]-6-methyl-5H-pyrrolo[3,2-d]pyrimidin-7-yl}carbonyl)amino]piperidine-1-carboxylate; tert-Butyl {trans-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; tert-Butyl {cis-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; tert-Butyl (3R)-3-[({4-[5-(cyclopropylmethoxy)-1,3-benzodioxol-4-yl]-6-methyl-5H-pyrrolo[3,2-d]pyrimidin-7-yl}carbonyl)amino]pyrrolidine-1-carboxylate; tert-Butyl (3R*,4R*)-3-[({4-[5-(cyclopropylmethoxy)-1,3-benzodioxol-4-yl]-6-methyl-5H-pyrrolo[3,2-d]pyrimidin-7-yl}carbonyl)amino]-4-hydroxypyrrolidine-1-carboxylate; tert-Butyl 4-[({4-[2-(cyclopropylmethoxy)-4-fluorophenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-4-fluorophenyl]-6-methyl-5H-pyrrolo[3,2-d]pyrimidin-7-yl}carbonyl)amino]cyclohexyl}carbamate; Tert-butyl {cis-4-[({4-[2-(cyclopropylmethoxy)-4-fluorophenyl]-6-methyl-5H-pyrrolo[3,2-d]pyrimidin-7-yl}carbonyl)amino]cyclohexyl}carbamate; tert-Butyl (3R)-3-[({4-[2-(cyclopropylmethoxy)-4-fluorophenyl]-6-methyl-5H-pyrrolo[3,2-d]pyrimidin-7-yl}carbonyl)amino]pyrrolidine-1-carboxylate; tert-Butyl (3R*,4R*)-3-[({4-[2-(cyclopropylmethoxy)-4-fluorophenyl]-6-methyl-5H-pyrrolo[3,2-d]pyrimidin-7-yl}carbonyl)amino]-4-hydroxypyrrolidine-1-carboxylate; Tert-butyl (3S*,4S*)-4-[({4-[2-(cyclopropylmethoxy)-4-fluorophenyl]-6-methyl-5H-pyrrolo[3,2-d]pyrimidin-7-yl}carbonyl)amino]-3-hydroxypiperidine-1-carboxylate; tert-Butyl 4-({1-[4-(2-cyclopropylmethoxy-5-fluoro-phenyl)-6-methyl-5H-pyrrolo[3,2-d]pyrimidin-7-yl]-methanoyl}-amino)-piperidine-1-carboxylate; tert-Butyl {trans-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate; tert-Butyl (3R)-3-[({4-[2-(cyclopropylmethoxy)-5-fluorophenyl]-6-methyl-5H-pyrrolo[3,2-d]pyrimidin-7-yl}carbonyl)amino]pyrrolidine-1-carboxylate; tert-Butyl (3R*,4R*)-4-[({4-[2-(cyclopropylmethoxy)-5-fluorophenyl]-6-methyl-5H-pyrrolo[3,2-d]pyrimidin-7-yl}carbonyl)amino]-3-hydroxypiperidine-1-carboxylate; tert-Butyl 4-({[4-(2-ethoxy-5-fluorophenyl)-6-methyl-5H-pyrrolo[3,2-d]pyrimidin-7-yl}carbonyl]amino)piperidine-1-carboxylate; tert-butyl 4-[({4-[2-(cyclopropylmethoxy)-4-methoxyphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-4-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-4-methoxyphenyl]-6-methyl-5H-pyrrolo[3,2-d]pyrimidin-7-yl}carbonyl)amino]cyclohexyl}carbamate; tert-Butyl (3R)-3-[({4-[2-(cyclopropylmethoxy)-4-methoxyphenyl]-6-methyl-5H-pyrrolo[3,2-d]pyrimidin-7-yl}carbonyl)amino]pyrrolidine-1-carboxylate; tert-Butyl (3R*,4R*)-3-[({4-[2-(cyclopropylmethoxy)-4-methoxyphenyl]-6-methyl-5H-pyrrolo[3,2-d]pyrimidin-7-yl}carbonyl)amino]-4-hydroxypyrrolidine-1-carboxylate; tert-Butyl 4-[({4-[2-(cyclopropylmethoxy)-5-methoxyphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-methoxyphenyl]-6-methyl-5H-pyrrolo[3,2-d]pyrimidin-7-yl}carbonyl)amino]cyclohexyl}carbamate; tert-Butyl (3R)-3-[({4-[2-(cyclopropylmethoxy)-5-methoxyphenyl]-6-methyl-5H-pyrrolo[3,2-d]pyrimidin-7-yl}carbonyl)amino]pyrrolidine-1-carboxylate; tert-Butyl (3R*,4R*)-4-[({4-[2-(cyclopropylmethoxy)-5-methoxyphenyl]-6-methyl-5H-pyrrolo[3,2-d]pyrimidin-7-yl}carbonyl)amino]-3-hydroxypiperidine-1-carboxylate; tert-Butyl 4-[({4-[2-

(cyclopropylmethoxy)-5-methylphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-methylphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-methylphenyl]-6-methyl-5H-pyrrolo[3,2-d]pyrimidin-7-yl}carbonyl)amino]cyclohexyl}carbamate; tert-Butyl 4-[({4-[2-(cyclopropylmethoxy)-5-(trifluoromethyl)phenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-(trifluoromethyl)phenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-(trifluoromethyl)phenyl]-6-methyl-5H-pyrrolo[3,2-d]pyrimidin-7-yl}carbonyl)amino]cyclohexyl}carbamate; tert-Butyl 4-[({4-[2-ethoxy-5-(trifluoromethyl)phenyl]-6-methyl-5H-pyrrolo[3,2-d]pyrimidin-7-yl}carbonyl)amino]piperidine-1-carboxylate; tert-Butyl 4-[({4-[2-(cyclopropylmethoxy)-4-fluoro-5-methoxyphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate; tert-Butyl (3R*,4R*)-4-[({4-[2-(cyclopropylmethoxy)-4-fluoro-5-methoxyphenyl]-6-methyl-5H-pyrrolo[3,2-d]pyrimidin-7-yl}carbonyl)amino]-3-hydroxypiperidine-1-carboxylate; tert-Butyl (3S*,4S*)-3-[({4-[2-(cyclopropylmethoxy)-4-fluoro-5-methoxyphenyl]-6-methyl-5H-pyrrolo[3,2-d]pyrimidin-7-yl}carbonyl)amino]-4-hydroxypiperidine-1-carboxylate; tert-Butyl 4-[({4-[2-(cyclopropylmethoxy)-4-fluoro-5-methylphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-4-fluoro-5-methylphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-4-fluoro-5-methylphenyl]-6-methyl-5H-pyrrolo[3,2-d]pyrimidin-7-yl}carbonyl)amino]cyclohexyl}carbamate; tert-Butyl (3R*,4R*)-4-[({4-[2-(cyclopropylmethoxy)-4-fluoro-5-methylphenyl]-6-methyl-5H-pyrrolo[3,2-d]pyrimidin-7-yl}carbonyl)amino]-3-hydroxypiperidine-1-carboxylate; tert-Butyl 4-[({4-[2-(cyclopropylmethoxy)-5-fluoro-4-methoxyphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate; tert-Butyl (3R*,4R*)-4-[({4-[2-(cyclopropylmethoxy)-5-fluoro-4-methoxyphenyl]-6-methyl-5H-pyrrolo[3,2-d]pyrimidin-7-yl}carbonyl)amino]-3-hydroxypiperidine-1-carboxylate; tert-butyl 4-[({4-[2-(cyclopropylmethoxy)-5-ethylphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-ethylphenyl]-6-methyl-5H-pyrrolo[3,2-d]pyrimidin-7-yl}carbonyl)amino]cyclohexyl}carbamate; tert-butyl {cis-4-[({4-[2-(cyclopropylmethoxy)-5-ethylphenyl]-6-methyl-5H-pyrrolo[3,2-d]pyrimidin-7-yl}carbonyl)amino]cyclohexyl}carbamate; tert-Butyl (3R*,4R*)-3-[({4-[2-(cyclopropylmethoxy)-5-ethylphenyl]-6-methyl-5H-pyrrolo[3,2-d]pyrimidin-7-yl}carbonyl)amino]-4-hydroxypyrrolidine-1-carboxylate; tert-Butyl 4-[({4-[2-(cyclopropylmethoxy)-5-(propan-2-yl)phenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-(propan-2-yl)phenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-(propan-2-yl)phenyl]-6-methyl-5H-pyrrolo[3,2-d]pyrimidin-7-yl}carbonyl)amino]cyclohexyl}carbamate; tert-Butyl 4-[({4-[2-(cyclopropylmethoxy)-5-(2-methyl-1,3-dioxolan-2-yl)phenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-(2-methyl-1,3-dioxolan-2-yl)phenyl]-6-methyl-5H-pyrrolo[3,2-d]pyrimidin-7-yl}carbonyl)amino]cyclohexyl}carbamate; tert-Butyl 4-[({4-[2-(cyclopropylmethoxy)-5-methylphenyl]-2,6-dimethyl-5H-pyrrolo[3,2-d]pyrimidin-7-yl}carbonyl)amino]piperidine-1-carboxylate; tert-Butyl 4-[({4-[2-(cyclopropylmethoxy)-5-fluoro-4-methoxyphenyl]-2,6-dimethyl-5H-pyrrolo[3,2-d]pyrimidin-7-yl}carbonyl)amino]piperidine-1-carboxylate; tert-Butyl 4[({4-[2-(cyclopropylmethoxy)-4-fluoro-5-methoxyphenyl]-2,6-dimethyl-5H-pyrrolo[3,2-d]pyrimidin-7-yl}carbonyl)amino]piperidine-1-carboxylate;

a salt thereof, or a stereoisomer of the compound or a salt thereof.

In an alternative embodiment, the present subject matter relates to compounds of formula (I), selected from N-(1-Acetylpiperidin-4-yl)-4-[5-(cyclopropylmethoxy)-1,3-benzodioxol-4-yl]-6-methyl-5H-pyrrolo[3,2-d]pyrimidine-7-carboxamide; 4-[5-(Cyclopropylmethoxy)-1,3-benzodioxol-4-yl]-6-methyl-N-(1-propionylpiperidin-4-yl)-5H-pyrrolo[3,2-d]pyrimidine-7-carboxamide; 4-[5-(Cyclopropylmethoxy)-1,3-benzodioxol-4-yl]-N-[1-(methoxyacetyl)piperidin-4-yl]-6-methyl-5H-pyrrolo[3,2-d]pyrimidine-7-carboxamide; Ethyl 4-[({4-[5-(cyclopropylmethoxy)-1,3-benzodioxol-4-yl]-6-methyl-5H-pyrrolo[3,2-d]pyrimidin-7-yl}carbonyl)amino]piperidine-1-carboxylate; N-(trans-4-acetamidocyclohexyl)-4-[5-(cyclopropylmethoxy)-1,3-benzodioxol-4-yl]-6-methyl-5H-pyrrolo[3,2-d]pyrimidine-7-carboxamide; 4-[5-(Cyclopropylmethoxy)-1,3-benzodioxol-4-yl]-6-methyl-N-[trans-4-(propionylamino)cyclohexyl]-5H-pyrrolo[3,2-d]pyrimidine-7-carboxamide; 4-[5-(Cyclopropylmethoxy)-1,3-benzodioxol-4-yl]-N-{trans-4-[(methoxyacetyl)amino]cyclohexyl}-6-methyl-5H-pyrrolo[3,2-d]pyrimidine-7-carboxamide; Ethyl {trans-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; N-(cis-4-acetamidocyclohexyl)-4-[5-(cyclopropylmethoxy)-1,3-benzodioxol-4-yl]-6-methyl-5H-pyrrolo[3,2-d]pyrimidine-7-carboxamide; 4-[5-(Cyclopropylmethoxy)-1,3-benzodioxol-4-yl]-6-methyl-N-[cis-4-(propionylamino)cyclohexyl]-5H-pyrrolo[3,2-d]pyrimidine-7-carboxamide; 4-[5-(Cyclopropylmethoxy)-1,3-benzodioxol-4-yl]-N-{cis-4-[(methoxyacetyl)amino]cyclohexyl}-6-methyl-5H-pyrrolo[3,2-d]pyrimidine-7-carboxamide; Ethyl {cis-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; N-[(3R)-1-acetylpyrrolidin-3-yl]-4-[5-(cyclopropylmethoxy)-1,3-benzodioxol-4-yl]-6-methyl- 5H-pyrrolo[3,2-d]pyrimidine-7-carboxamide; 4-[5-(Cyclopropylmethoxy)-1,3-benzodioxol-4-yl]-6-methyl-N-[(3R)-1-propionylpyrrolidin-3-yl]-5H-pyrrolo[3,2-d]pyrimidine-7-carboxamide; 4-[5-(Cyclopropylmethoxy)-1,3-benzodioxol-4-yl]-N-[(3R)-1-(methoxyacetyl)pyrrolidin-3-yl]-6-methyl-5H-pyrrolo[3,2-d]pyrimidine-7-carboxamide; N-[(3R*,4R*)-1-acetyl-4-hydroxypyrrolidin-3-yl]-4-[5-(cyclopropylmethoxy)-1,3-benzodioxol-4-yl]-6-methyl-5H-pyrrolo[3,2-d]pyrimidine-7-carboxamide; 4-[5-(Cyclopropylmethoxy)-1,3-benzodioxol-4-yl]-N-[(3R*,4R*)-4-hydroxy-1-propionylpyrrolidin-3-yl]-6-methyl-5H-pyrrolo[3,2-d]pyrimidine-7-carboxamide; 4-[5-(Cyclopropylmethoxy)-1,3-benzodioxol-4-yl]-N-[(3R*,4R*)-4-hydroxy-1-(methoxyacetyl)pyrrolidin-3-yl]-6-methyl-5H-pyrrolo[3,2-d]pyrimidine-7-carboxamide; N-(1-acetylpiperidin-4-yl)-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-6-methyl-N-(1-propionylpiperidin-4-yl)-5H-pyrrolo[3,2-d]pyrimidine-7-carboxamide; 4-[2-(Cyclopropylmethoxy)-4-fluorophenyl]-N-[1-(methoxyacetyl)piperidin-4-yl]-6-methyl-5H-pyrrolo[3,2-d]pyrimidine-7-carboxamide; N-(trans-4-acetamidocyclohexyl)-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-6-methyl-N-[trans-4-(propionylamino)cyclohexyl]-5H-pyrrolo[3,2-d]pyrimidine-7-carboxamide; 4-[2-(Cyclopropylmethoxy)-4-fluorophenyl]-N-{trans-4-[(methoxyacetyl)amino]cyclohexyl}-6-methyl-5H-pyrrolo[3,2-d]pyrimidine-7-carboxamide; N-(cis-4-acetamidocyclohexyl)-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-6-methyl-N-[cis-4-(propionylamino)cyclohexyl]-5H-pyrrolo[3,2-d]pyrimidine-7-carboxamide; 4-[2-(Cyclopropylmethoxy)-4-fluorophenyl]-N-{cis-4-[(methoxyacetyl)amino]cyclohexyl}-6-methyl-5H-pyrrolo[3,2-d]pyrimidine-7-carboxamide; N-[(3R)-1-acetylpyrrolidin-3-yl]-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-6-methyl-N-[(3R)-1-propanoylpyrrolidin-3-yl]-5H-pyrrolo[3,2-d]pyrimidine-7-carboxamide; 4-[2-(Cyclopropylmethoxy)-4-fluorophenyl]-N-[(3R)-1-(methoxyacetyl)pyrrolidin-3-yl]-6-methyl-5H-pyrrolo[3,2-d]pyrimidine-7-carboxamide; N-[(3R*,4R*)-1-acetyl-4-hydroxypyrrolidin-3-yl]-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-N-[(3R*,4R*)-4-hydroxy-1-propanoylpyrrolidin-3-yl]-6-methyl-5H-pyrrolo[3,2-d]pyrimidine-7-carboxamide; 4-[2-(Cyclopropylmethoxy)-4-fluorophenyl]-N-[(3R*,4R*)-4-hydroxy-1-(methoxyacetyl)pyrrolidin-3-yl]-6-methyl-5H-pyrrolo[3,2-d]pyrimidine-7-carboxamide; N-[(3S*,4S*)-1-acetyl-3-hydroxypiperidin-4-yl]-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-N-[(3S*,4S*)-3-hydroxy-1-propanoylpiperidin-4-yl]-6-methyl-5H-pyrrolo[3,2-d]pyrimidine-7-carboxamide; 4-[2-(Cyclopropylmethoxy)-4-fluorophenyl]-N-[(3S*,4S*)-3-hydroxy-1-(methoxyacetyl)piperidin-4-yl]-6-methyl-5H-pyrrolo[3,2-d]pyrimidine-7-carboxamide; 4-(2-Cyclopropylmethoxy-5-fluoro-phenyl)-6-methyl-5H-pyrrolo[3,2-d]pyrimidine-7-carboxylic acid (1-acetyl-piperidin-4-yl)-amide; 4-[2-(cyclopropylmethoxy)-5-fluorophenyl]-6-methyl-N-(1-propionylpiperidin-4-yl)-5H-pyrrolo[3,2-d]pyrimidine-7-carboxamide; 4-(2-Cyclopropylmethoxy-5-fluoro-phenyl)-6-methyl-5H-pyrrolo[3,2-d]pyrimidine-7-carboxylic acid [1-(2-methoxy-acetyl)-piperidin-4-yl]-amide; Ethyl 4-[({4-[2-(cyclopropylmethoxy)-5-fluorophenyl]-6-methyl-5H-pyrrolo[3,2-d]pyrimidin-7-yl}carbonyl)amino]piperidine-1-carboxylate; N-(trans-4-acetamidocyclohexyl)-4-[2-(cyclopropylmethoxy)-5-fluorophenyl]-6-methyl-5H-pyrrolo[3,2-d]pyrimidine-7-carboxamide; 4-[2-(Cyclopropylmethoxy)-5-fluorophenyl]-6-methyl-N-[trans-4-(propionylamino)cyclohexyl]-5H-pyrrolo[3,2-d]pyrimidine-7-carboxamide; 4-[2-(Cyclopropylmethoxy)-5-fluorophenyl]-N-{trans-4-[(methoxyacetyl)amino]cyclohexyl}-6-methyl-5H-pyrrolo[3,2-d]pyrimidine-7-carboxamide; Ethyl {trans-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate; N-(cis-4-acetamidocyclohexyl)-4-[2-(cyclopropylmethoxy)-5-fluorophenyl]-6-methyl-5H-pyrrolo[3,2-d]pyrimidine-7-carboxamide; N-[(3R)-1-acetylpyrrolidin-3-yl]-4-[2-(cyclopropylmethoxy)-5-fluorophenyl]-6-methyl-5H-pyrrolo[3,2-d]pyrimidine-7-carboxamide; 4-[2-(Cyclopropylmethoxy)-5-fluorophenyl]-6-methyl-N-[(3R)-1-propanoylpyrrolidin-3-yl]-5H-pyrrolo[3,2-d]pyrimidine-7-carboxamide; 4-[2-(Cyclopropylmethoxy)-5-fluorophenyl]-N-[(3R)-1-(methoxyacetyl)pyrrolidin-3-yl]-6-methyl-5H-pyrrolo[3,2-d]pyrimidine-7-carboxamide; N-[(3R*,4R*)-1-acetyl-3-hydroxypiperidin-4-yl]-4-[2-(cyclopropylmethoxy)-5-fluorophenyl]-6-methyl-5H-pyrrolo[3,2-d]pyrimidine-7-carboxamide; 4-[2-(Cyclopropylmethoxy)-5-fluorophenyl]-N-[(3R*,4R*)-3-hydroxy-1-propanoylpiperidin-4-yl]-6-methyl-5H-pyrrolo[3,2-d]pyrimidine-7-carboxamide; 4-[2-(Cyclopropylmethoxy)-5-fluorophenyl]-N-[(3R*,4R*)-3-hydroxy-1-(methoxyacetyl)piperidin-4-yl]-6-methyl-5H-pyrrolo[3,2-d]pyrimidine-7-carboxamide; N-(1-acetylpiperidin-4-yl)-4-(2-ethoxy-5-fluorophenyl)-6-methyl-5H-pyrrolo[3,2-d]pyrimidine-7-carboxamide; 4-(2-Ethoxy-5-fluorophenyl)-6-methyl-N-(1-propanoylpiperidin-4-yl)-5H-pyrrolo[3,2-d]pyrimidine-7-carboxamide; 4-(2-Ethoxy-5-fluorophenyl)-N-[1-(methoxyacetyl)piperidin-4-yl]-6-methyl-5H-pyrrolo[3,2-d]pyrimidine-7-carboxamide; N-(1-acetylpiperidin-4-yl)-4-[2-(cyclopropylmethoxy)-4-methoxyphenyl]-6-methyl-5H-pyrrolo[3,2-d]pyrimidine-7-carboxamide; 4-[2-(Cyclopropylmethoxy)-4-methoxyphenyl]-6-methyl-N-(1-propionylpiperidin-4-yl)-5H-pyrrolo[3,2-d]pyrimidine-7-carboxamide; 4-[2-(Cyclopropylmethoxy)-4-methoxyphenyl]-N-[1-(methoxyacetyl)piperidin-4-yl]-6-methyl-5H-pyrrolo[3,2-d]pyrimidine-7-carboxamide; N-(trans-4-acetamidocyclohexyl)-4-[2-(cyclopropylmethoxy)-4-methoxyphenyl]-6-methyl-5H-pyrrolo[3,2-d]pyrimidine-7-carboxamide; N-(cis-4-acetamidocyclohexyl)-4-[2-(cyclopropylmethoxy)-4-methoxyphenyl]-6-methyl-5H-pyrrolo[3,2-d]pyrimidine-7-carboxamide; N-[(3R)-1-acetylpyrrolidin-3-yl]-4-[2-(cyclopropylmethoxy)-4-methoxyphenyl]-6-methyl-5H-pyrrolo[3,2-d]pyrimidine-7-carboxamide; 4-[2-(Cyclopropylmethoxy)-4-methoxyphenyl]-6-methyl-N-[(3R)-1-propionylpyrrolidin-3-yl]-5H-pyrrolo[3,2-d]pyrimidine-7-carboxamide; 4-[2-(Cyclopropylmethoxy)-4-methoxyphenyl]-N-[(3R)-1-(methoxyacetyl)pyrrolidin-3-yl]-6-methyl-5H-pyrrolo[3,2-d]pyrimidine-7-carboxamide; N-[(3R*,4R*)-1-acetyl-4-hydroxypyrrolidin-3-yl]-4-[2-(cyclopropylmethoxy)-4-methoxyphenyl]-6-methyl-5H-pyrrolo[3,2-d]pyrimidine-7-carboxamide; 4-[2-(Cyclopropylmethoxy)-4-methoxyphenyl]-N-[(3R*,4R*)-4-hydroxy-1-propionylpyrrolidin-3-yl]-6-methyl-5H-pyrrolo[3,2-d]pyrimidine-7-carboxamide; 4-[2-(Cyclopropylmethoxy)-4- methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide; N-(1-acetylpiperidin-4-yl)-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-6-methyl-N-(1-propionylpiperidin-4-yl)-5H-pyrrolo[3,2-d]pyrimidine-7-carboxamide; 4-[2-(Cyclopropylmethoxy)-5-methoxyphenyl]-N-[1-(methoxyacetyl)piperidin-4-yl]-6-methyl-5H-pyrrolo[3,2-d]pyrimidine-7-carboxamide; N-(trans-4-acetamidocyclohexyl)-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-6-methyl-N-[trans-4-(propionylamino)cyclohexyl]-5H-pyrrolo[3,2-d]pyrimidine-7-carboxamide; 4-[2-(Cyclopropylmethoxy)-5-methoxyphenyl]-N-{trans-4-[(methoxyacetyl)amino]cyclohexyl}-6-methyl-5H-pyrrolo[3,2-d]pyrimidine-7-carboxamide; N-(cis-4-acetamidocyclohexyl)-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-6-methyl-N-[cis-4-(propionylamino)cyclohexyl]-5H-pyrrolo[3,2-d]pyrimidine-7-carboxamide; 4-[2-(Cyclopropylmethoxy)-5-methoxyphenyl]-N-{cis-4-[(methoxyacetyl)amino]cyclohexyl}-6-methyl-5H-pyrrolo[3,2-d]pyrimidine-7-carboxamide; N-[(3R)-1-acetylpyrrolidin-3-yl]-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-6-methyl-N-[(3R)-1-propionylpyrrolidin-3-yl]-5H-pyrrolo[3,2-d]pyrimidine-7-carboxamide; 4-[2-(Cyclopropylmethoxy)-5-methoxyphenyl]-N-[(3R)-1-(methoxyacetyl)pyrrolidin-3-yl]-6-methyl-5H-pyrrolo[3,2-d]pyrimidine-7-carboxamide; N-[(3R*,4R*)-1-acetyl-3-hydroxypiperidin-4-yl]-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-N-[(3R*,4R*)-3-hydroxy-1-propanoylpiperidin-4-yl]-6-methyl-5H-pyrrolo[3,2-d]pyrimidine-7-carboxamide; 4-[2-(Cyclopropylmethoxy)-5-methoxyphenyl]-N-[(3R*,4R*)-3-hydroxy-1-(methoxyacetyl)piperidin-4-yl]-6-methyl-5H-pyrrolo[3,2-d]pyrimidine-7-carboxamide; N-(1-Acetylpiperidin-4-yl)-4-[2-(cyclopropylmethoxy)-5-methylphenyl]-6-methyl-5H-pyrrolo[3,2-d]pyrimidine-7-carboxamide; 4-[2-(Cyclopropylmethoxy)-5-methylphenyl]-6-methyl-N-(1-propanoylpiperidin-4-yl)-5H-pyrrolo[3,2-d]pyrimidine-7-carboxamide; 4-[2-(cyclopropylmethoxy)-5-methylphenyl]-N-[1-(methoxyacetyl)piperidin-4-yl]-6-methyl-5H-pyrrolo[3,2-d]pyrimidine-7-carboxamide; N-[trans-4-(acetylamino)cyclohexyl]-4-[2-(cyclopropylmethoxy)-5-methylphenyl]-6-methyl-5H-pyrrolo[3,2-d]pyrimidine-7-carboxamide; 4-[2-(Cyclopropylmethoxy)-5-methylphenyl]-6-methyl-N-[trans-4-(propanoylamino)cyclohexyl]-5H-pyrrolo[3,2-d]pyrimidine-7-carboxamide; 4-[2-(Cyclopropylmethoxy)-5-methylphenyl]-N-{trans-4-[(methoxyacetyl)amino]cyclohexyl}-6-methyl-5H-pyrrolo[3,2-d]pyrimidine-7-carboxamide; N-[cis-4-(acetylamino)cyclohexyl]-4-[2-(cyclopropylmethoxy)-5-methylphenyl]-6-methyl-5H-pyrrolo[3,2-d]pyrimidine-7-carboxamide; 4-[2-(Cyclopropylmethoxy)-5-methylphenyl]-6-methyl-N-[cis-4-(propanoylamino)cyclohexyl]-5H-pyrrolo[3,2-d]pyrimidine-7-carboxamide; 4-[2-(Cyclopropylmethoxy)-5-methylphenyl]-N-{cis-4-[(methoxyacetyl)amino]cyclohexyl}-6-methyl-5H-pyrrolo[3,2-d]pyrimidine-7-carboxamide; N-(1-Acetylpiperidin-4-yl)-4-[2-(cyclopropylmethoxy)-5-(trifluoromethyl)phenyl]-6-methyl-5H-pyrrolo[3,2-d]pyrimidine-7-carboxamide; 4-[2-(Cyclopropylmethoxy)-5-(trifluoromethyl)phenyl]-6-methyl-N-(1-propanoylpiperidin-4-yl)-5H-pyrrolo[3,2-d]pyrimidine-7-carboxamide; 4-[2-(Cyclopropylmethoxy)-5-(trifluoromethyl)phenyl]-N-[1-(methoxyacetyl)piperidin-4-yl]-6-methyl-5H-pyrrolo[3,2-d]pyrimidine-7-carboxamide; N-[trans-4-(acetylamino)cyclohexyl]-4-[2-(cyclopropylmethoxy)-5-(trifluoromethyl)phenyl]-6-methyl-5H-pyrrolo[3,2-d]pyrimidine-7-carboxamide; 4-[2-(cyclopropylmethoxy)-5-(trifluoromethyl)phenyl]-6-methyl-N-[trans-4-(propanoylamino)cyclohexyl]-5H-pyrrolo[3,2-d]pyrimidine-7-carboxamide; 4-[2-(Cyclopropylmethoxy)-5-(trifluoromethyl)phenyl]-N-{trans-4-[(methoxyacetyl)amino]cyclohexyl}-6-methyl-5H-pyrrolo[3,2-d]pyrimidine-7-carboxamide; N-[cis-4-(acetylamino)cyclohexyl]-4-[2-(cyclopropylmethoxy)-5-(trifluoromethyl)phenyl]-6-methyl-5H-pyrrolo[3,2-d]pyrimidine-7-carboxamide; 4-[2-(Cyclopropylmethoxy)-5-(trifluoromethyl)phenyl]-6-methyl-N-[cis-4-(propanoylamino)cyclohexyl]-5H-pyrrolo[3,2-d]pyrimidine-7-carboxamide; 4-[2-(Cyclopropylmethoxy)-5-(trifluoromethyl)phenyl]-N-{cis-4-[(methoxyacetyl)amino]cyclohexyl}-6-methyl-5H-pyrrolo[3,2-d]pyrimidine-7-carboxamide; N-(1-acetylpiperidin-4-yl)-4-[2-ethoxy-5-(trifluoromethyl)phenyl]-6-methyl-5H-pyrrolo[3,2-d]pyrimidine-7-carboxamide; 4-[2-Ethoxy-5-(trifluoromethyl)phenyl]-6-methyl-N-(1-propanoylpiperidin-4-yl)-5H-pyrrolo[3,2-d]pyrimidine-7-carboxamide; 4-[2-Ethoxy-5-(trifluoromethyl)phenyl]-N-[1-(methoxyacetyl)piperidin-4-yl]-6-methyl-5H-pyrrolo[3,2-d]pyrimidine-7-carboxamide; N-(1-Acetylpiperidin-4-yl)-4-[2-(cyclopropylmethoxy)-4-fluoro-5-methoxyphenyl]-6-methyl-5H-pyrrolo[3,2-d]pyrimidine-7-carboxamide; 4-[2-(cyclopropylmethoxy)-4-fluoro-5-methoxyphenyl]-6-methyl-N-(1-propionylpiperidin-4-yl)-5H-pyrrolo[3,2-d]pyrimidine-7-carboxamide; 4-[2-(Cyclopropylmethoxy)-4-fluoro-5-methoxyphenyl]-N-[1-(methoxyacetyl)piperidin-4-yl]-6-methyl-5H-pyrrolo[3,2-d]pyrimidine-7-carboxamide; Ethyl 4-[({4-[2-(cyclopropylmethoxy)-4-fluoro-5-methoxyphenyl]-6-methyl-5H-pyrrolo[3,2-d]pyrimidin-7-yl}carbonyl)amino]piperidine-1-carboxylate; N-(trans-4-Acetamidocyclohexyl)-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-6-methyl-N-[trans-4-(propionylamino)cyclohexyl]-5H-pyrrolo[3,2-d]pyrimidine-7-carboxamide; 4-[2-(Cyclopropylmethoxy)-4-fluoro-5-methoxyphenyl]-N-{trans-4-[(methoxyacetyl)amino]cyclohexyl}-6-methyl-5H-pyrrolo[3,2-d]pyrimidine-7-carboxamide; Ethyl {trans-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate; N-(cis-4-Acetamidocyclohexyl)-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-6-methyl-N-[cis-4-(propionylamino)cyclohexyl]-5H-pyrrolo[3,2-d]pyrimidine-7-carboxamide; 4-[2-(Cyclopropylmethoxy)-4-fluoro-5-methoxyphenyl]-N-{cis-4-[(methoxyacetyl)amino]cyclohexyl}-6-methyl-5H-pyrrolo[3,2-d]pyrimidine-7-carboxamide; N-[(3R*,4R*)-1-Acetyl-3-hydroxypiperidin-4-yl]-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-N-[(3R*,4R*)-3-hydroxy-1-propionylpiperidin-4-yl]-6-methyl-5H-pyrrolo[3,2-d]pyrimidine-7-carboxamide; 4-[2-(cyclopropylmethoxy)-4-fluoro-5-methoxyphenyl]-N-

[(3R*,4R*)-3-hydroxy-1-(methoxyacetyl)piperidin-4-yl]-6-methyl-5H-pyrrolo[3,2-d]pyrimidine-7-carboxamide; N-[(3S*,4S*)-1-Acetyl-4-hydroxypiperidin-3-yl]-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-N-[(3S*,4S*)-4-hydroxy-1-propionylpiperidin-3-yl]-6-methyl-5H-pyrrolo[3,2-d]pyrimidine-7-carboxamide; 4-[2-(cyclopropylmethoxy)-4-fluoro-5-methoxyphenyl]-N-[(3S*,4S*)-4-hydroxy-1-(methoxyacetyl)piperidin-3-yl]-6-methyl-5H-pyrrolo[3,2-d]pyrimidine-7-carboxamide; N-(1-Acetylpiperidin-4-yl)-4-[2-(cyclopropylmethoxy)-4-fluoro-5-methylphenyl]-6-methyl-5H-pyrrolo[3,2-d]pyrimidine-7-carboxamide; 4-[2-(Cyclopropylmethoxy)-4-fluoro-5-methylphenyl]-6-methyl-N-(1-propanoylpiperidin-4-yl)-5H-pyrrolo[3,2-d]pyrimidine-7-carboxamide; 4-[2-(Cyclopropylmethoxy)-4-fluoro-5-methylphenyl]-N-[1-(methoxyacetyl)piperidin-4-yl]-6-methyl-5H-pyrrolo[3,2-d]pyrimidine-7-carboxamide; N-[trans-4-(Acetylamino)cyclohexyl]-4-[2-(cyclopropylmethoxy)-4-fluoro-5-methylphenyl]-6-methyl-5H-pyrrolo[3,2-d]pyrimidine-7-carboxamide; 4-[2-(Cyclopropylmethoxy)-4-fluoro-5-methylphenyl]-6-methyl-N-[trans-4-(propanoylamino)cyclohexyl]-5H-pyrrolo[3,2-d]pyrimidine-7-carboxamide; 4-[2-(Cyclopropylmethoxy)-4-fluoro-5-methylphenyl]-N-{trans-4-[(methoxyacetyl)amino]cyclohexyl}-6-methyl-5H-pyrrolo[3,2-d]pyrimidine-7-carboxamide; N-[cis-4-(Acetylamino)cyclohexyl]-4-[2-(cyclopropylmethoxy)-4-fluoro-5-methylphenyl]-6-methyl-5H-pyrrolo[3,2-d]pyrimidine-7-carboxamide; 4-[2-(Cyclopropylmethoxy)-4-fluoro-5-methylphenyl]-6-methyl-N-[cis-4-(propanoylamino)cyclohexyl]-5H-pyrrolo[3,2-d]pyrimidine-7-carboxamide; 4-[2-(Cyclopropylmethoxy)-4-fluoro-5-methylphenyl]-N-{cis-4-[(methoxyacetyl)amino]cyclohexyl}-6-methyl-5H-pyrrolo[3,2-d]pyrimidine-7-carboxamide; N-[(3R*,4R*)-1-Acetyl-3-hydroxypiperidin-4-yl]-4-[2-(cyclopropylmethoxy)-4-fluoro-5-methylphenyl]-6-methyl-5H-pyrrolo[3,2-d]pyrimidine-7-carboxamide; 4-[2-(cyclopropylmethoxy)-4-fluoro-5-methylphenyl]-N-[(3R*,4R*)-3-hydroxy-1-propanoylpiperidin-4-yl]-6-methyl-5H-pyrrolo[3,2-d]pyrimidine-7-carboxamide; 4-[2-(Cyclopropylmethoxy)-4-fluoro-5-methylphenyl]-N-[(3R*,4R*)-3-hydroxy-1-(methoxyacetyl)piperidin-4-yl]-6-methyl-5H-pyrrolo[3,2-d]pyrimidine-7-carboxamide; N-(1-Acetylpiperidin-4-yl)-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-6-methyl-N-(1-propionylpiperidin-4-yl)-5H-pyrrolo[3,2-d]pyrimidine-7-carboxamide; 4-[2-(Cyclopropylmethoxy)-5-fluoro-4-methoxyphenyl]-N-[1-(methoxyacetyl)piperidin-4-yl]-6-methyl-5H-pyrrolo[3,2-d]pyrimidine-7-carboxamide; Ethyl 4-[({4-[2-(cyclopropylmethoxy)-5-fluoro-4-methoxyphenyl]-6-methyl-5H-pyrrolo[3,2-d]pyrimidin-7-yl}carbonyl)amino]piperidine-1-carboxylate; N-(trans-4-Acetamidocyclohexyl)-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-6-methyl-N-[trans-4-(propionylamino)cyclohexyl]-5H-pyrrolo[3,2-d]pyrimidine-7-carboxamide; 4-[2-(Cyclopropylmethoxy)-5-fluoro-4-methoxyphenyl]-N-{trans-4-[(methoxyacetyl)amino]cyclohexyl}-6-methyl-5H-pyrrolo[3,2-d]pyrimidine-7-carboxamide; N-(cis-4-Acetamidocyclohexyl)-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-6-methyl-N-[cis-4-(propionylamino)cyclohexyl]-5H-pyrrolo[3,2-d]pyrimidine-7-carboxamide; 4-[2-(Cyclopropylmethoxy)-5-fluoro-4-methoxyphenyl]-N-{cis-4-[(methoxyacetyl)amino]cyclohexyl}-6-methyl-5H-pyrrolo[3,2-d]pyrimidine-7-carboxamide; Ethyl {cis-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate; N-[(3R*,4R*)-1-Acetyl-3-hydroxypiperidin-4-yl]-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-N-[(3R*,4R*)-3-hydroxy-1-propanoylpiperidin-4-yl]-6-methyl-5H-pyrrolo[3,2-d]pyrimidine-7-carboxamide; 4-[2-(Cyclopropylmethoxy)-5-fluoro-4-methoxyphenyl]-N-[(3R*,4R*)-3-hydroxy-1-(methoxyacetyl)piperidin-4-yl]-6-methyl-5H-pyrrolo[3,2-d]pyrimidine-7-carboxamide; N-(1-Acetylpiperidin-4-yl)-4-[2-(cyclopropylmethoxy)-5-ethylphenyl]-6-methyl-5H-pyrrolo[3,2-d]pyrimidine-7-carboxamide; 4-[2-(Cyclopropylmethoxy)-5-ethylphenyl]-6-methyl-N-(1-propanoylpiperidin-4-yl)-5H-pyrrolo[3,2-d]pyrimidine-7-carboxamide; 4-[2-(Cyclopropylmethoxy)-5-ethylphenyl]-N-[1-(methoxyacetyl)piperidin-4-yl]-6-methyl-5H-pyrrolo[3,2-d]pyrimidine-7-carboxamide; N-[trans-4-(Acetylamino)cyclohexyl]-4-[2-(cyclopropylmethoxy)-5-ethylphenyl]-6-methyl-5H-pyrrolo[3,2-d]pyrimidine-7-carboxamide; 4-[2-(Cyclopropylmethoxy)-5-ethylphenyl]-6-methyl-N-[trans-4-(propanoylamino)cyclohexyl]-5H-pyrrolo[3,2-d]pyrimidine-7-carboxamide; 4-[2-(Cyclopropylmethoxy)-5-ethylphenyl]-N-{trans-4-[(methoxyacetyl)amino]cyclohexyl}-6-methyl-5H-pyrrolo[3,2-d]pyrimidine-7-carboxamide; N-[cis-4-(Acetylamino)cyclohexyl]-4-[2-(cyclopropylmethoxy)-5-ethylphenyl]-6-methyl-5H-pyrrolo[3,2-d]pyrimidine-7-carboxamide; 4-[2-(Cyclopropylmethoxy)-5-ethylphenyl]-6-methyl-N-[cis-4-(propanoylamino)cyclohexyl]-5H-pyrrolo[3,2-d]pyrimidine-7-carboxamide; 4-[2-(Cyclopropylmethoxy)-5-ethylphenyl]-N-{cis-4-[(methoxyacetyl)amino]cyclohexyl}-6-methyl-5H-pyrrolo[3,2-d]pyrimidine-7-carboxamide; N-[(3R*,4R*)-1-Acetyl-4-hydroxypyrrolidin-3-yl]-4-[2-(cyclopropylmethoxy)-5-ethylphenyl]-6-methyl-5H-pyrrolo[3,2-d]pyrimidine-7-carboxamide; 4-[2-(Cyclopropylmethoxy)-5-ethylphenyl]-N-[(3R*,4R*)-4-hydroxy-1-propanoylpyrrolidin-3-yl]-6-methyl-5H-pyrrolo[3,2-d]pyrimidine-7-carboxamide; 4-[2-(Cyclopropylmethoxy)-5-ethylphenyl]-N-[(3R*,4R*)-4-hydroxy-1-(methoxyacetyl)pyrrolidin-3-yl]-6-methyl-5H-pyrrolo[3,2-d]pyrimidine-7-carboxamide; N-(1-Acetylpiperidin-4-yl)-4-[2-(cyclopropylmethoxy)-5-(propan-2-yl)phenyl]-6-methyl-5H-pyrrolo[3,2-d]pyrimidine-7-carboxamide; 4-[2-(Cyclopropylmethoxy)-5-(propan-2-yl)phenyl]-N-[1-(methoxyacetyl)piperidin-4-yl]-6-methyl-5H-pyrrolo[3,2-d]pyrimidine-7-carboxamide; N-[trans-4-(Acetylamino)cyclohexyl]-4-[2-(cyclopropylmethoxy)-5-(propan-2-yl)phenyl]-6-methyl-5H-pyrrolo[3,2-d]pyrimidine-7-carboxamide; 4-[2-(Cyclopropylmethoxy)-5-(propan-2-yl)phenyl]-N-{trans-4-[(methoxyacetyl)amino]cyclohexyl}-6-methyl-5H-pyrrolo[3,2-d]pyrimidine-7-carboxamide; N-[cis-4-(Acetylamino)cyclohexyl]-4-[2-(cyclopropylmethoxy)-5-(propan-2-yl)phenyl]-6-methyl-5H-pyrrolo[3,2-d]pyrimidine-7-carboxamide; 4-[2-(Cyclopropylmethoxy)-5-(propan-2-yl)phenyl]-N-{cis-4-[(methoxyacetyl)amino]cyclohexyl}-6-methyl-5H-pyrrolo[3,2-d]pyrimidine-7-carboxamide; 4-[5-Acetyl-2-(cyclopropylmethoxy)phenyl]-N-(1-acetylpiperidin-4-yl)-6-methyl-5H-pyrrolo[3,2-d]pyrimidine-7-carboxamide; 4-[5-Acetyl-2-

(cyclopropylmethoxy)phenyl]-6-methyl-N-(1-propanoylpiperidin-4-yl)-5H-pyrrolo[3,2-d]pyrimidine-7-carboxamide; 4-[5-Acetyl-2-(cyclopropylmethoxy)phenyl]-N-[1-(methoxyacetyl)piperidin-4-yl]-6-methyl-5H-pyrrolo[3,2-d]pyrimidine-7-carboxamide; N-[trans-4-(Acetylamino)cyclohexyl]-4-[5-acetyl-2-(cyclopropylmethoxy)phenyl]-6-methyl-5H-pyrrolo[3,2-d]pyrimidine-7-carboxamide; 4-[5-Acetyl-2-(cyclopropylmethoxy)phenyl]-6-methyl-N-[trans-4-(propanoylamino)cyclohexyl]-5H-pyrrolo[3,2-d]pyrimidine-7-carboxamide; 4-[5-Acetyl-2-(cyclopropylmethoxy)phenyl]-N-{trans-4-[(methoxyacetyl)amino]cyclohexyl}-6-methyl-5H-pyrrolo[3,2-d]pyrimidine-7-carboxamide; 4-[2-(Cyclopropylmethoxy)-4-fluoro-5-methoxyphenyl]-N-[1-(methoxyacetyl)piperidin-4-yl]-2,6-dimethyl-5H-pyrrolo[3,2-d]pyrimidine-7-carboxamide; 4-[2-(Cyclopropylmethoxy)-4-fluoro-5-methoxyphenyl]-2,6-dimethyl-N-(1-propanoylpiperidin-4-yl)-5H-pyrrolo[3,2-d]pyrimidine-7-carboxamide; N-(1-Acetylpiperidin-4-yl)-4-[2-(cyclopropylmethoxy)-4-fluoro-5-methoxyphenyl]-2,6-dimethyl-5H-pyrrolo[3,2-d]pyrimidine-7-carboxamide; N-(1-Acetylpiperidin-4-yl)-4-[2-(cyclopropylmethoxy)-5-fluoro-4-methoxyphenyl]-2,6-dimethyl-5H-pyrrolo[3,2-d]pyrimidine-7-carboxamide; 4-[2-(Cyclopropylmethoxy)-5-methylphenyl]-N-[1-(methoxyacetyl)piperidin-4-yl]-2,6-dimethyl-5H-pyrrolo[3,2-d]pyrimidine-7-carboxamide; 4-[2-(Cyclopropylmethoxy)-5-methylphenyl]-2,6-dimethyl-N-(1-propanoylpiperidin-4-yl)-5H-pyrrolo[3,2-d]pyrimidine-7-carboxamide; N-(1-Acetylpiperidin-4-yl)-4-[2-(cyclopropylmethoxy)-5-methylphenyl]-2,6-dimethyl-5H-pyrrolo[3,2-d]pyrimidine-7-carboxamide; N-[(3R)-1-Acetylpyrrolidin-3-yl]-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-6-methyl-N-[(3R)-1-propionylpyrrolidin-3-yl]-5H-pyrrolo[3,2-d]pyrimidine-7-carboxamide; 4-[2-(Cyclopropylmethoxy)-4-fluoro-5-methoxyphenyl]-N-[(3R)-1-(methoxyacetyl)pyrrolidin-3-yl]-6-methyl-5H-pyrrolo[3,2-d]pyrimidine-7-carboxamide; Ethyl (3R)-3-[({4-[2-(cyclopropylmethoxy)-4-fluoro-5-methoxyphenyl]-6-methyl-5H-pyrrolo[3,2-d]pyrimidin-7-yl}carbonyl)amino]pyrrolidine-1-carboxylate; N-[(3R*,4R*)-1-Acetyl-4-hydroxypyrrolidin-3-yl]-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-N-[(3R*,4R*)-4-hydroxy-1-propionylpyrrolidin-3-yl]-6-methyl-5H-pyrrolo[3,2-d]pyrimidine-7-carboxamide; 4-[2-(Cyclopropylmethoxy)-4-fluoro-5-methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide; N-[(3R)-1-Acetylpyrrolidin-3-yl]-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-6-methyl-N-[(3R)-1-propionylpyrrolidin-3-yl]-5H-pyrrolo[3,2-d]pyrimidine-7-carboxamide; 4-[2-(Cyclopropylmethoxy)-5-fluoro-4-methoxyphenyl]-N-[(3R)-1-(methoxyacetyl)pyrrolidin-3-yl]-6-methyl-5H-pyrrolo[3,2-d]pyrimidine-7-carboxamide; N-[(3R*,4R*)-1-Acetyl-4-hydroxypyrrolidin-3-yl]-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-N-[(3R*,4R*)-4-hydroxy-1-propionylpyrrolidin-3-yl]-6-methyl-5H-pyrrolo[3,2-d]pyrimidine-7-carboxamide; 4-[2-(Cyclopropylmethoxy)-5-fluoro-4-methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide; N-[(3R*,4R*)-1-Acetyl-4-hydroxypyrrolidin-3-yl]-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-N-[(3R*,4R*)-4-hydroxy-1-propionylpyrrolidin-3-yl]-6-methyl-5H-pyrrolo[3,2-d]pyrimidine-7-carboxamide; 4-[2-(Cyclopropylmethoxy)-5-methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide; 4-[5-(Cyclopropylmethoxy)-1,3-benzodioxol-4-yl]-N-(1-glycoloylpiperidin-4-yl)-6-methyl-5H-pyrrolo[3,2-d]pyrimidine-7-carboxamide; 4-[5-(Cyclopropylmethoxy)-1,3-benzodioxol-4-yl]-N-{1-[(2S)-2-hydroxypropanoyl]piperidin-4-yl}-6-methyl-5H-pyrrolo[3,2-d]pyrimidine-7-carboxamide; 4-[5-(Cyclopropylmethoxy)-1,3-benzodioxol-4-yl]-N-[trans-4-(glycoloylamino)cyclohexyl]-6-methyl-5H-pyrrolo[3,2-d]pyrimidine-7-carboxamide; 4-[5-(cyclopropylmethoxy)-1,3-benzodioxol-4-yl]-N-(trans-4-{[(2S)-2-hydroxypropanoyl]amino}cyclohexyl)-6-methyl-5H-pyrrolo[3,2-d]pyrimidine-7-carboxamide; 4-[5-(Cyclopropylmethoxy)-1,3-benzodioxol-4-yl]-N-[cis-4-(glycoloylamino)cyclohexyl]-6-methyl-5H-pyrrolo[3,2-d]pyrimidine-7-carboxamide; 4-[5-(Cyclopropylmethoxy)-1,3-benzodioxol-4-yl]-N-(cis-4-{[(2S)-2-hydroxypropanoyl]amino}cyclohexyl)-6-methyl-5H-pyrrolo[3,2-d]pyrimidine-7-carboxamide; 4-[5-(Cyclopropylmethoxy)-1,3-benzodioxol-4-yl]-N-[(3R)-1-glycoloylpyrrolidin-3-yl]-6-methyl-5H-pyrrolo[3,2-d]pyrimidine-7-carboxamide; 4-[5-(Cyclopropylmethoxy)-1,3-benzodioxol-4-yl]-N-{(3R)-1-[(2S)-2-hydroxypropanoyl]pyrrolidin-3-yl}-6-methyl-5H-pyrrolo[3,2-d]pyrimidine-7-carboxamide 4-[5-(Cyclopropylmethoxy)-1,3-benzodioxol-4-yl]-N-[(3R*,4R*)-1-glycoloyl-4-hydroxypyrrolidin-3-yl]-6-methyl-5H-pyrrolo[3,2-d]pyrimidine-7-carboxamide; 4-[5-(Cyclopropylmethoxy)-1,3-benzodioxol-4-yl]-N-{(3R,4R)-4-hydroxy-1-[(2S)-2-hydroxypropanoyl]pyrrolidin-3-yl}-6-methyl-5H-pyrrolo[3,2-d]pyrimidine-7-carboxamide; 4-[5-(cyclopropylmethoxy)-1,3-benzodioxol-4-yl]-N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-4-fluorophenyl]-N-(1-glycoloylpiperidin-4-yl)-6-methyl-5H-pyrrolo[3,2-d]pyrimidine-7-carboxamide; 4-[2-(Cyclopropylmethoxy)-4-fluorophenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluorophenyl]-N-[trans-4-(glycoloylamino)cyclohexyl]-6-methyl-5H-pyrrolo[3,2-d]pyrimidine-7-carboxamide; 4-[2-(Cyclopropylmethoxy)-4-fluorophenyl]-N-(trans-4-{[(2S)-2-hydroxypropanoyl]amino}cyclohexyl)-6-methyl-5H-pyrrolo[3,2-d]pyrimidine-7-carboxamide; 4-[2-(cyclopropylmethoxy)-4-fluorophenyl]-N-[cis-4-(glycoloylamino)cyclohexyl]-6-methyl-5H-pyrrolo[3,2-d]pyrimidine-7-carboxamide; 4-[2-(Cyclopropylmethoxy)-4-fluorophenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-fluorophenyl]-N-[(3R)-1-(hydroxyacetyppyrrolidin-3-yl]-6-methyl-5H-pyrrolo[3,2-d]pyrimidine-7-carboxamide; 4-[2-(cyclopropylmethoxy)-4-fluorophenyl]-N-{(3R)-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-4-fluorophenyl]-N-[(3R*,4R*)-4-hydroxy-1-(hydroxyacetyppyrrolidin-3-yl]-6-methyl-5H-pyrrolo[3,2-d]pyrimidine-7-carboxamide; 4-[2-(Cyclopropylmethoxy)-4-fluorophenyl]-N-{(3R,4R)-4-hydroxy-1-[(2S)-2-hydroxypropanoyl]pyrrolidin-3-yl}-6-methyl-5H-pyrrolo[3,2-d]pyrimidine-7-carboxamide; 4-[2-

(Cyclopropylmethoxy)-4-fluorophenyl]-N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-4-fluorophenyl]-N-[(3S*,4S*)-3-hydroxy-1-(hydroxyacetyppiperidin-4-yl]-6-methyl-5H-pyrrolo[3,2-d]pyrimidine-7-carboxamide; 4-[2-(Cyclopropylmethoxy)-4-fluorophenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluorophenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide; 4-(2-Cyclopropylmethoxy-5-fluoro-phenyl)-6-methyl-5H-pyrrolo[3,2-d]pyrimidine-7-carboxylic acid [1-(2-hydroxy-acetyl)-piperidin-4-yl]-amide; 4-(2-Cyclopropylmethoxy-5-fluoro-phenyl)-6-methyl-5H-pyrrolo[3,2-d]pyrimidine-7-carboxylic acid [1-((S)-2-hydroxy-propionyl)-piperidin-4-yl]-amide; 4-[2-(Cyclopropylmethoxy)-5-fluorophenyl]-N-[trans-4-(glycoloylamino)cyclohexyl]-6-methyl-5H-pyrrolo[3,2-d]pyrimidine-7-carboxamide; 4-[2-(Cyclopropylmethoxy)-5-fluorophenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-fluorophenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-fluorophenyl]-N-[(3R)-1-(hydroxyacetyppyrrolidin-3-yl]-6-methyl-5H-pyrrolo[3,2-d]pyrimidine-7-carboxamide; 4-[2-(Cyclopropylmethoxy)-5-fluorophenyl]-N-{(3R)-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-fluorophenyl]-N-[(3R*,4R*)-3-hydroxy-1-(hydroxyacetyppiperidin-4-yl]-6-methyl-5H-pyrrolo[3,2-d]pyrimidine-7-carboxamide; 4-[2-(cyclopropylmethoxy)-5-fluorophenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide; 4-[2-(cyclopropylmethoxy)-5-fluorophenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide; 4-(2-Ethoxy-5-fluorophenyl)-N-[1-(hydroxyacetyl)piperidin-4-yl]-6-methyl-5H-pyrrolo[3,2-d]pyrimidine-7-carboxamide; 4-(2-Ethoxy-5-fluorophenyl)-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-methoxyphenyl]-N-(1-glycoloylpiperidin-4-yl)-6-methyl-5H-pyrrolo[3,2-d]pyrimidine-7-carboxamide; 4-[2-(Cyclopropylmethoxy)-4-methoxyphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-methoxyphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-methoxyphenyl]-N-[(3R)-1-glycoloylpyrrolidin-3-yl]-6-methyl-5H-pyrrolo[3,2-d]pyrimidine-7-carboxamide; 4-[2-(Cyclopropylmethoxy)-4-methoxyphenyl]-N-{(3R)-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-4-methoxyphenyl]-N-[(3R*,4R*)-1-glycoloyl-4-hydroxypyrrolidin-3-yl]-6-methyl-5H-pyrrolo[3,2-d]pyrimidine-7-carboxamide; 4-[2-(cyclopropylmethoxy)-4-methoxyphenyl]-N-{(3R,4R)-4-hydroxy-1-[(2S)-2-hydroxypropanoyl]pyrrolidin-3-yl}-6-methyl-5H-pyrrolo[3,2-d]pyrimidine-7-carboxamide; 4-[2-(cyclopropylmethoxy)-4-methoxyphenyl]-N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-methoxyphenyl]-N-(1-glycoloylpiperidin-4-yl)-6-methyl-5H-pyrrolo[3,2-d]pyrimidine-7-carboxamide; 4-[2-(Cyclopropylmethoxy)-5-methoxyphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-methoxyphenyl]-N-[trans-4-(glycoloylamino)cyclohexyl]-6-methyl-5H-pyrrolo[3,2-d]pyrimidine-7-carboxamide; 4-[2-(Cyclopropylmethoxy)-5-methoxyphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-methoxyphenyl]-N-[cis-4-(glycoloylamino)cyclohexyl]-6-methyl-5H-pyrrolo[3,2-d]pyrimidine-7-carboxamide; 4-[2-(cyclopropylmethoxy)-5-methoxyphenyl]-N-(cis-4-{[(2S)-2-hydroxypropanoyl]amino}cyclohexyl)-6-methyl-5H-pyrrolo[3,2-d]pyrimidine-7-carboxamide; 4-[2-(cyclopropylmethoxy)-5-methoxyphenyl]-N-[(3R)-1-glycoloylpyrrolidin-3-yl]-6-methyl-5H-pyrrolo[3,2-d]pyrimidine-7-carboxamide; 4-[2-(cyclopropylmethoxy)-5-methoxyphenyl]-N-[(3R)-1-[(2S)-2-hydroxypropanoyl]pyrrolidin-3-yl]-6-methyl-5H-pyrrolo[3,2-d]pyrimidine-7-carboxamide; 4-[2-(Cyclopropylmethoxy)-5-methoxyphenyl]-N-[(3R*,4R*)-3-hydroxy-1-(hydroxyacetyppiperidin-4-yl]-6-methyl-5H-pyrrolo[3,2-d]pyrimidine-7-carboxamide; 4-[2-(Cyclopropylmethoxy)-5-methoxyphenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-methoxyphenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-methylphenyl]-N-[1-(hydroxyacetyppiperidin-4-yl]-6-methyl-5H-pyrrolo[3,2-d]pyrimidine-7-carboxamide; 4-[2-(Cyclopropylmethoxy)-5-methylphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-methylphenyl]-N-{trans-4-[(hydroxyacetyl)amino]cyclohexyl}-6-methyl-5H-pyrrolo[3,2-d]pyrimidine-7-carboxamide; 4-[2-(Cyclopropylmethoxy)-5-methylphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-methylphenyl]-N-{cis-4-[(hydroxyacetyl)amino]cyclohexyl}-6-methyl-5H-pyrrolo[3,2-d]pyrimidine-7-carboxamide; 4-[2-(Cyclopropylmethoxy)-5-methylphenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-(trifluoromethyl)phenyl]-N-[1-(hydroxyacetyppiperidin-4-yl]-6-methyl-5H-pyrrolo[3,2-d]pyrimidine-7-carboxamide; 4-[2-(Cyclopropylmethoxy)-5-(trifluoromethyl)phenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-(trifluoromethyl)phenyl]-N-{trans-4-[(hydroxyacetyl)amino]cyclohexyl}-6-methyl-5H-pyrrolo[3,2-d]pyrimidine-7-carboxamide; 4-[2-(Cyclopropylmethoxy)-5-(trifluoromethyl)phenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-(trifluoromethyl)phenyl]-N-{cis-4-[(hydroxyacetyl)amino]cyclohexyl}-6-methyl-5H-pyrrolo[3,2-d]pyrimidine-7-carboxamide; 4-[2-(Cyclopropylmethoxy)-5-(trifluoromethyl)phenyl]-N-(cis-4-{[(2S)-2-hydroxypropanoyl]amino}cyclohexyl)-6-methyl-5H-pyrrolo[3,2-d]pyrimidine-7-carboxamide; 4-[2-

Ethoxy-5-(trifluoromethyl)phenyl]-N-[1-(hydroxyacetyl)piperidin-4-yl]-6-methyl-5H-pyrrolo[3,2-d]pyrimidine-7-carboxamide; 4-[2-Ethoxy-5-(trifluoromethyl)phenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methoxyphenyl]-N-(1-glycoloylpiperidin-4-yl)-6-methyl-5H-pyrrolo[3,2-d]pyrimidine-7-carboxamide; 4-[2-(Cyclopropylmethoxy)-4-fluoro-5-methoxyphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methoxyphenyl]-N-[trans-4-(glycoloylamino)cyclohexyl]-6-methyl-5H-pyrrolo[3,2-d]pyrimidine-7-carboxamide; 4-[2-(Cyclopropylmethoxy)-4-fluoro-5-methoxyphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-fluoro-5-methoxyphenyl]-N-[cis-4-(glycoloylamino)cyclohexyl]-6-methyl-5H-pyrrolo[3,2-d]pyrimidine-7-carboxamide; 4-[2-(Cyclopropylmethoxy)-4-fluoro-5-methoxyphenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-fluoro-5-methoxyphenyl]-N-[(3R*,4R*)-1-glycoloyl-3-hydroxypiperidin-4-yl]-6-methyl-5H-pyrrolo[3,2-d]pyrimidine-7-carboxamide; 4-[2-(Cyclopropylmethoxy)-4-fluoro-5-methoxyphenyl]-N-{(rac.-3R,4R)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methoxyphenyl]-N-{(rac.-3S,4S)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methoxyphenyl]-N-[cis-4-glycoloyl-4-hydroxypiperidin-3-yl]-6-methyl-5H-pyrrolo[3,2-d]pyrimidine-7-carboxamide; 4-[2-(Cyclopropylmethoxy)-4-fluoro-5-methoxyphenyl]-N-{(rac.-3S,4S)-4-hydroxy-1-[(2S)-2-hydroxypropanoyl]piperidin-3-yl}-6-methyl-5H-pyrrolo[3,2-d]pyrimidine-7-carboxamide; 4-[2-(Cyclopropylmethoxy)-4-fluoro-5-methoxyphenyl]-N-{(rac.-3R,4R)-4-hydroxy-1-[(2S)-2-hydroxypropanoyl]piperidin-3-yl}-6-methyl-5H-pyrrolo[3,2-d]pyrimidine-7-carboxamide; 4-[2-(Cyclopropylmethoxy)-4-fluoro-5-methyl phenyl]-N-[1-(hydroxyacetyl)piperidin-4-yl]-6-methyl-5H-pyrrolo[3,2-d]pyrimidine-7-carboxamide; 4-[2-(Cyclopropylmethoxy)-4-fluoro-5-methylphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methyl phenyl]-N-{trans-4-[(hydroxyacetyl)amino]cyclohexyl}-6-methyl-5H-pyrrolo[3,2-d]pyrimidine-7-carboxamide; 4-[2-(Cyclopropylmethoxy)-4-fluoro-5-methylphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-fluoro-5-methylphenyl]-N-{cis-4-[(hydroxyacetyl)amino]cyclohexyl}-6-methyl-5H-pyrrolo[3,2-d]pyrimidine-7-carboxamide; 4-[2-(Cyclopropylmethoxy)-4-fluoro-5-methyl phenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-4-fluoro-5-methylphenyl]-N-[(3R*,4R*)-3-hydroxy-1-(hydroxyacetyl)piperidin-4-yl]-6-methyl-5H-pyrrolo[3,2-d]pyrimidine-7-carboxamide; 4-[2-(Cyclopropylmethoxy)-4-fluoro-5-methylphenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-4-fluoro-5-methylphenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-fluoro-4-methoxyphenyl]-N-(1-glycoloylpiperidin-4-yl)-6-methyl-5H-pyrrolo[3,2-d]pyrimidine-7-carboxamide-4-[2-(Cyclopropylmethoxy)-5-fluoro-4-methoxyphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-fluoro-4-methoxyphenyl]-N-[trans-4-(glycoloylamino)cyclohexyl]-6-methyl-5H-pyrrolo[3,2-d]pyrimidine-7-carboxamide; 4-[2-(Cyclopropylmethoxy)-5-fluoro-4-methoxyphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-fluoro-4-methoxyphenyl]-N-[cis-4-(glycoloylamino)cyclohexyl]-6-methyl-5H-pyrrolo[3,2-d]pyrimidine-7-carboxamide; 4-[2-(Cyclopropylmethoxy)-5-fluoro-4-methoxyphenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-fluoro-4-methoxyphenyl]-N-[(3R*,4R*)-3-hydroxy-1-(hydroxyacetyl)piperidin-4-yl]-6-methyl-5H-pyrrolo[3,2-d]pyrimidine-7-carboxamide; 4-[2-(Cyclopropylmethoxy)-5-fluoro-4-methoxyphenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-fluoro-4-methoxyphenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-ethylphenyl]-N-[1-(hydroxyacetyl)piperidin-4-yl]-6-methyl-5H-pyrrolo[3,2-d]pyrimidine-7-carboxamide; 4-[2-(Cyclopropylmethoxy)-5-ethylphenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-ethyl phenyl]-N-{trans-4-[(hydroxyacetyl)amino]cyclohexyl}-6-methyl-5-pyrrolo[3,2-d]pyrimidine-7-carboxamide; 4-[2-(Cyclopropylmethoxy)-5-ethylphenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-ethylphenyl]-N-{cis-4-[(hydroxyacetyl)amino]cyclohexyl}-6-methyl-5H-pyrrolo[3,2-d]pyrimidine-7-carboxamide; 4-[2-(Cyclopropylmethoxy)-5-ethylphenyl]-N-(cis-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-ethylphenyl]-N-[(3R*,4R*)-4-hydroxy-1-(hydroxyacetyl)pyrrolidin-3-yl]-6-methyl-5H-pyrrolo[3,2-d]pyrimidine-7-carboxamide; 4-[2-(cyclopropylmethoxy)-5-ethylphenyl]-N-{(3R,4R)-4-hydroxy-1-[(2S)-2-hydroxypropanoyl]pyrrolidin-3-yl}-6-methyl-5H-pyrrolo[3,2-d]pyrimidine-7-carboxamide; 4-[2-(cyclopropylmethoxy)-5-ethylphenyl]-N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-(propan-2-yl)phenyl]-N-{1-[(2S)-2-hydroxypropanoyl]piperidin-4-yl}-6-methyl-5H-pyrrolo[3,2-d]pyrimidine-7-carboxamide; 4-[2-(Cyclopropylmethoxy)-5-(propan-2-yl)phenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-(propan-2-yl)phenyl]-N-(cis-4-{[(2S)-2-hydroxypropanoyl]amino}cyclohexyl)-6-methyl-5H-pyrrolo[3,2-d]pyrimidine-7-carboxamide; 4-[5-Acetyl-2-(cyclopropylmethoxy)phenyl]-N-[1-(hydroxyacetyppiperidin-4-yl]-6-methyl-5H-pyrrolo[3,2-d]pyrimidine-7-carboxamide; 4-[5-Acetyl-2-

(cyclopropylmethoxy)phenyl]-N-{1-[(2S)-2-hydroxypropanoyl]piperidin-4-yl}-6-methyl-5H-pyrrolo[3,2-d]pyrimidine-7-carboxamide; 4-[5-Acetyl-2-(cyclopropylmethoxy)phenyl]-N-{trans-4-[(hydroxyacetyl)amino]cyclohexyl}-6-methyl-5H-pyrrolo[3,2-d]pyrimidine-7-carboxamide; 4-[5-Acetyl-2-(cyclopropylmethoxy)phenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-methylphenyl]-N-[1-(hydroxyacetyl)piperidin-4-yl]-2,6-dimethyl-5H-pyrrolo[3,2-d]pyrimidine-7-carboxamide; 4-[2-(Cyclopropylmethoxy)-5-methylphenyl]-N-{1-[(2S)-2-hydroxypropanoyl]piperidin-4-yl}-2,6-dimethyl-5H-pyrrolo[3,2-d]pyrimidine-7-carboxamide; 4-[2-(Cyclopropylmethoxy)-5-fluoro-4-methoxyphenyl]-N-{1-[(2S)-2-hydroxypropanoyl]piperidin-4-yl}-2,6-dimethyl-5H-pyrrolo[3,2-d]pyrimidine-7-carboxamide; 4-[2-(Cyclopropylmethoxy)-4-fluoro-5-methoxyphenyl]-N-[1-(hydroxyacetyppiperidin-4-yl]-2,6-dimethyl-5H-pyrrolo[3,2-d]pyrimidine-7-carboxamide; 4-[2-(Cyclopropylmethoxy)-4-fluoro-5-methoxyphenyl]-N-{1-[(2S)-2-hydroxypropanoyl]piperidin-4-yl}-2,6-dimethyl-5H-pyrrolo[3,2-d]pyrimidine-7-carboxamide; 4-[2-(Cyclopropylmethoxy)-5-methylphenyl]-N-[(1S,2S)-2-hydroxycyclopentyl]-6-methyl-5H-pyrrolo[3,2-d]pyrimidine-7-carboxamide; 4-[2-(Cyclopropylmethoxy)-5-methylphenyl]-N-[(1S,2R)-2-hydroxycyclopentyl]-6-methyl-5H-pyrrolo[3,2-d]pyrimidine-7-carboxamide; 4-[2-(Cyclopropylmethoxy)-5-methylphenyl]-N-[(1R,2R)-2-hydroxycyclopentyl]-6-methyl-5H-pyrrolo[3,2-d]pyrimidine-7-carboxamide; 4-[2-(Cyclopropylmethoxy)-4-fluoro-5-methoxyphenyl]-N-[(3R)-1-glycoloylpyrrolidin-3-yl]-6-methyl-5H-pyrrolo[3,2-d]pyrimidine-7-carboxamide; 4-[2-(Cyclopropylmethoxy)-4-fluoro-5-methoxyphenyl]-N-{(3R)-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-4-fluoro-5-methoxyphenyl]-N-[(3R*,4R*)-1-glycoloyl-4-hydroxypyrrolidin-3-yl]-6-methyl-5H-pyrrolo[3,2-d]pyrimidine-7-carboxamide; 4-[2-(Cyclopropylmethoxy)-4-fluoro-5-methoxyphenyl]-N-{(3R*,4R*)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-fluoro-4-methoxyphenyl]-N-[(3R)-1-glycoloylpyrrolidin-3-yl]-6-methyl-5H-pyrrolo[3,2-d]pyrimidine-7-carboxamide; 4-[2-(Cyclopropylmethoxy)-5-fluoro-4-methoxyphenyl]-N-{(3R)-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-fluoro-4-methoxyphenyl]-N-[(3R*,4R*)-1-glycoloyl-4-hydroxypyrrolidin-3-yl]-6-methyl-5H-pyrrolo[3,2-d]pyrimidine-7-carboxamide; 4-[2-(Cyclopropylmethoxy)-5-fluoro-4-methoxyphenyl]-N-{(3R*,4R*)-4-hydroxy-1-[(2S)-2-hydroxypropanoyl]pyrrolidin-3-yl}-6-methyl-5H-pyrrolo[3,2-d]pyrimidine-7-carboxamide; 4-[2-(Cyclopropylmethoxy)-5-methoxyphenyl]-N-[(3R*,4R*)-1-glycoloyl-4-hydroxypyrrolidin-3-yl]-6-methyl-5H-pyrrolo[3,2-d]pyrimidine-7-carboxamide; 4-[2-(Cyclopropylmethoxy)-5-methoxyphenyl]-N-{(3R*,4R*)-4-hydroxy-1-[(2S)-2-hydroxypropanoyl]pyrrolidin-3-yl}-6-methyl-5H-pyrrolo[3,2-d]pyrimidine-7-carboxamide; tert-Butyl 4-[({4-[5-(cyclopropylmethoxy)-1,3-benzodioxol-4-yl]-6-methyl-5H-pyrrolo[3,2-d]pyrimidin-7-yl}carbonyl)amino]piperidine-1-carboxylate; tert-Butyl {trans-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; tert-Butyl {cis-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; tert-Butyl (3R)-3-[({4-[5-(cyclopropylmethoxy)-1,3-benzodioxol-4-yl]-6-methyl-5H-pyrrolo[3,2-d]pyrimidin-7-yl}carbonyl)amino]pyrrolidine-1-carboxylate; tert-Butyl (3R*,4R*)-3-[({4-[5-(cyclopropylmethoxy)-1,3-benzodioxol-4-yl]-6-methyl-5H-pyrrolo[3,2-d]pyrimidin-7-yl}carbonyl)amino]-4-hydroxypyrrolidine-1-carboxylate; tert-Butyl 4-[({4-[2-(cyclopropylmethoxy)-4-fluorophenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-4-fluorophenyl]-6-methyl-5H-pyrrolo[3,2-d]pyrimidin-7-yl}carbonyl)amino]cyclohexyl}carbamate; Tert-butyl {cis-4-[({4-[2-(cyclopropylmethoxy)-4-fluorophenyl]-6-methyl-5H-pyrrolo[3,2-d]pyrimidin-7-yl}carbonyl)amino]cyclohexyl}carbamate; tert-Butyl (3R)-3-[({4-[2-(cyclopropylmethoxy)-4-fluorophenyl]-6-methyl-5H-pyrrolo[3,2-d]pyrimidin-7-yl}carbonyl)amino]pyrrolidine-1-carboxylate; tert-Butyl (3R*,4R*)-3-[({4-[2-(cyclopropylmethoxy)-4-fluorophenyl]-6-methyl-5H-pyrrolo[3,2-d]pyrimidin-7-yl}carbonyl)amino]-4-hydroxypyrrolidine-1-carboxylate; Tert-butyl (3S*,4S*)-4-[({4-[2-(cyclopropylmethoxy)-4-fluorophenyl]-6-methyl-5H-pyrrolo[3,2-d]pyrimidin-7-yl}carbonyl)amino]-3-hydroxypiperidine-1-carboxylate; tert-Butyl 4-({1-[4-(2-cyclopropylmethoxy-5-fluoro-phenyl)-6-methyl-5H-pyrrolo[3,2-d]pyrimidin-7-yl]-methanoyl}-amino)-piperidine-1-carboxylate; tert-Butyl {trans-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate; tert-Butyl (3R)-3-[({4-[2-(cyclopropylmethoxy)-5-fluorophenyl]-6-methyl-5H-pyrrolo[3,2-d]pyrimidin-7-yl}carbonyl)amino]pyrrolidine-1-carboxylate; tert-Butyl (3R*,4R*)-4-[({4-[2-(cyclopropylmethoxy)-5-fluorophenyl]-6-methyl-5H-pyrrolo[3,2-d]pyrimidin-7-yl}carbonyl)amino]-3-hydroxypiperidine-1-carboxylate; tert-Butyl 4-({[4-(2-ethoxy-5-fluorophenyl)-6-methyl-5H-pyrrolo[3,2-d]pyrimidin-7-yl}carbonyl]amino)piperidine-1-carboxylate; tert-butyl 4-[({4-[2-(cyclopropylmethoxy)-4-methoxyphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-4-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-4-methoxyphenyl]-6-methyl-5H-pyrrolo[3,2-d]pyrimidin-7-yl}carbonyl)amino]cyclohexyl}carbamate; tert-Butyl (3R)-3-[({4-[2-(cyclopropylmethoxy)-4-methoxyphenyl]-6-methyl-5H-pyrrolo[3,2-d]pyrimidin-7-yl}carbonyl)amino]pyrrolidine-1-carboxylate; tert-Butyl (3R*,4R*)-3-[({4-[2-(cyclopropylmethoxy)-4-methoxyphenyl]-6-methyl-5H-pyrrolo[3,2-d]pyrimidin-7-yl}carbonyl)amino]-4-hydroxypyrrolidine-1-carboxylate; tert-Butyl 4-[({4-[2-(cyclopropylmethoxy)-5-methoxyphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-methoxyphenyl]-6-methyl-5H-pyrrolo[3,2-d]pyrimidin-7-yl]carbonyl)amino}cyclohexyl}carbamate; tert-Butyl (3R)-3-[({4-[2-

(cyclopropylmethoxy)-5-methoxyphenyl]-6-methyl-5H-pyrrolo[3,2-d]pyrimidin-7-yl}carbonyl)amino]pyrrolidine-1-carboxylate; tert-Butyl (3R*,4R*)-4-[({4-[2-(cyclopropylmethoxy)-5-methoxyphenyl]-6-methyl-5H-pyrrolo[3,2-d]pyrimidin-7-yl}carbonyl)amino]-3-hydroxypiperidine-1-carboxylate; tert-Butyl 4-[({4-[2-(cyclopropylmethoxy)-5-methylphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-methylphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-methylphenyl]-6-methyl-5H-pyrrolo[3,2-d]pyrimidin-7-yl}carbonyl)amino]cyclohexyl}carbamate; tert-Butyl 4-[({4-[2-(cyclopropylmethoxy)-5-(trifluoromethyl)phenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-(trifluoromethyl)phenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-(trifluoromethyl)phenyl]-6-methyl-5H-pyrrolo[3,2-d]pyrimidin-7-yl}carbonyl)amino]cyclohexyl}carbamate; tert-Butyl 4-[({4-[2-ethoxy-5-(trifluoromethyl)phenyl]-6-methyl-5H-pyrrolo[3,2-d]pyrimidin-7-yl}carbonyl)amino]piperidine-1-carboxylate; tert-Butyl 4-[({4-[2-(cyclopropylmethoxy)-4-fluoro-5-methoxyphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate; tert-Butyl (3R*,4R*)-4-[({4-[2-(cyclopropylmethoxy)-4-fluoro-5-methoxyphenyl]-6-methyl-5H-pyrrolo[3,2-d]pyrimidin-7-yl}carbonyl)amino]-3-hydroxypiperidine-1-carboxylate; tert-Butyl (3S*,4S*)-3-[({4-[2-(cyclopropylmethoxy)-4-fluoro-5-methoxyphenyl]-6-methyl-5H-pyrrolo[3,2-d]pyrimidin-7-yl}carbonyl)amino]-4-hydroxypiperidine-1-carboxylate; tert-Butyl 4-[({4-[2-(cyclopropylmethoxy)-4-fluoro-5-methylphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-4-fluoro-5-methylphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-4-fluoro-5-methylphenyl]-6-methyl-5H-pyrrolo[3,2-d]pyrimidin-7-yl}carbonyl)amino]cyclohexyl}carbamate; tert-Butyl (3R*,4R*)-4-[({4-[2-(cyclopropylmethoxy)-4-fluoro-5-methylphenyl]-6-methyl-5H-pyrrolo[3,2-d]pyrimidin-7-yl}carbonyl)amino]-3-hydroxypiperidine-1-carboxylate; tert-Butyl 4-[({4-[2-(cyclopropylmethoxy)-5-fluoro-4-methoxyphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate; tert-Butyl (3R*,4R*)-4-[({4-[2-(cyclopropylmethoxy)-5-fluoro-4-methoxyphenyl]-6-methyl-5H-pyrrolo[3,2-d]pyrimidin-7-yl}carbonyl)amino]-3-hydroxypiperidine-1-carboxylate; tert-butyl 4-[({4-[2-(cyclopropylmethoxy)-5-ethylphenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-ethylphenyl]-6-methyl-5H-pyrrolo[3,2-d]pyrimidin-7-yl}carbonyl)amino]cyclohexyl}carbamate; tert-butyl {cis-4-[({4-[2-(cyclopropylmethoxy)-5-ethylphenyl]-6-methyl-5H-pyrrolo[3,2-d]pyrimidin-7-yl}carbonyl)amino]cyclohexyl}carbamate; tert-Butyl (3R*,4R*)-3-[({4-[2-(cyclopropylmethoxy)-5-ethylphenyl]-6-methyl-5H-pyrrolo[3,2-d]pyrimidin-7-yl}carbonyl)amino]-4-hydroxypyrrolidine-1-carboxylate; tert-Butyl 4-[({4-[2-(cyclopropylmethoxy)-5-(propan-2-yl)phenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-(propan-2-yl)phenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-(propan-2-yl)phenyl]-6-methyl-5H-pyrrolo[3,2-d]pyrimidin-7-yl}carbonyl)amino]cyclohexyl}carbamate; tert-Butyl 4-[({4-[2-(cyclopropylmethoxy)-5-(2-methyl-1,3-dioxolan-2-yl)phenyl]-6-methyl-5H-pyrrolo[3,2-d]pyrimidin-7-yl}carbonyl)amino]piperidine-1-carboxylate; tert-Butyl {trans-4-[({4-[2-(cyclopropylmethoxy)-5-(2-methyl-1,3-dioxolan-2-yl)phenyl]-6-methyl-5H-pyrrolo[3,2-d]pyrimidin-7-yl}carbonyl)amino]cyclohexyl}carbamate; tert-Butyl 4-[({4-[2-(cyclopropylmethoxy)-5-methylphenyl]-2,6-dimethyl-5H-pyrrolo[3,2-d]pyrimidin-7-yl}carbonyl)amino]piperidine-1-carboxylate; tert-Butyl 4-[({4-[2-(cyclopropylmethoxy)-5-fluoro-4-methoxyphenyl]-2,6-dimethyl-5H-pyrrolo[3,2-d]pyrimidin-7-yl}carbonyl)amino]piperidine-1-carboxylate; tert-Butyl 4-[({4-[2-(cyclopropylmethoxy)-4-fluoro-5-methoxyphenyl]-2,6-dimethyl-5H-pyrrolo[3,2-d]pyrimidin-7-yl}carbonyl)amino]piperidine-1-carboxylate; N-(1-Acetylpiperidin-4-yl)-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-(1-propanoylpiperidin-4-yl)-5H-pyrrolo[3,2-d]pyrimidine-7-carboxamide; 4-[2-(Cyclopropylmethoxy)-5-(difluoromethyl)phenyl]-N-[1-(methoxyacetyl)piperidin-4-yl]-6-methyl-5H-pyrrolo[3,2-d]pyrimidine-7-carboxamide; N-[trans-4-(Acetylamino)cyclohexyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-[trans-4-(propanoylamino)cyclohexyl]-5$^H$-pyrrolo[3,2-d]pyrimidine-7-carboxamide; 4-[2-(Cyclopropylmethoxy)-5-(difluoromethyl)phenyl]-N-{trans-4-[(methoxyacetyl)amino]cyclohexyl}-6-methyl-5H-pyrrolo[3,2-d]pyrimidine-7-carboxamide; N-[(3S,5S)-1-Acetyl-5-methylpyrrolidin-3-yl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-[(3S,5S)-5-methyl-1-propanoylpyrrolidin-3-yl]-5H-pyrrolo[3,2-d]pyrimidine-7-carboxamide; 4-[2-(Cyclopropylmethoxy)-5-(difluoromethyl)phenyl]-N-[(3S,5S)-1-(methoxyacetyl)-5-methylpyrrolidin-3-yl]-6-methyl-5H-pyrrolo[3,2-d]pyrimidine-7-carboxamide; N-[(1S,3S)-3-(Acetylamino)cyclopentyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-[(1S,3S)-3-(propanoylamino)cyclopentyl]-5H-pyrrolo[3,2-d]pyrimidine-7-carboxamide; 4-[2-(Cyclopropylmethoxy)-5-(difluoromethyl)phenyl]-N-{(1S,3S)-3-[(methoxyacetyl)amino]cyclopentyl}-6-methyl-5H-pyrrolo[3,2-d]pyrimidine-7-carboxamide; N-[(1R*,2R*,4R*)-4-(Acetylamino)-2-fluorocyclopentyl]-4-[2-(cyclopropylmethoxy)-5-(difluoromethyl)phenyl]-6-methyl-5H-pyrrolo[3,2-d]pyrimidine-7-carboxamide; 4-[2-

(Cyclopropylmethoxy)-5-(difluoromethyl)phenyl]-N-[(1R*,2R*,4R*)-2-fluoro-4-(propanoylamino)cyclopentyl]-6-methyl-5H-pyrrolo[3,2-d]pyrimidine-7-carboxamide; 4-[2-(Cyclopropylmethoxy)-5-(difluoromethyl)phenyl]-N-{(1R*,2R*,4R*)-2-fluoro-4-[(methoxyacetyl)amino]cyclopentyl}-6-methyl-5H-pyrrolo[3,2-d]pyrimidine-7-carboxamide; N-[(1S*,2S*,4S*)-4-(Acetylamino)-2-methylcyclohexyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-[(1S*,2S*,4S*)-2-methyl-4-(propanoylamino)cyclohexyl]-5H-pyrrolo[3,2-d]pyrimidine-7-carboxamide; 4-[2-(Cyclopropylmethoxy)-5-(difluoromethyl)phenyl]-N-{(1S*,2S*,4S*)-4-[(methoxyacetyl)amino]-2-methylcyclohexyl}-6-methyl-5H-pyrrolo[3,2-d]pyrimidine-7-carboxamide; N-[(1R*,2R*,4R*)-4-(Acetylamino)-2-fluorocyclohexyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-N-[(1R*,2R*,4R*)-2-fluoro-4-(propanoylamino)cyclohexyl]-6-methyl-5H-pyrrolo[3,2-d]pyrimidine-7-carboxamide; 4-[2-(Cyclopropylmethoxy)-5-(difluoromethyl)phenyl]-N-{(1R*,2R*,4R*)-2-fluoro-4-[(methoxyacetyl)amino]cyclohexyl}-6-methyl-5H-pyrrolo[3,2-d]pyrimidine-7-carboxamide; N-[(1S*,3S*,4S*)-4-(Acetylamino)-3-methylcyclohexyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-[(1S*,3S*,4S*)-3-methyl-4-(propanoylamino)cyclohexyl]-5H-pyrrolo[3,2-d]pyrimidine-7-carboxamide; 4-[2-(Cyclopropylmethoxy)-5-(difluoromethyl)phenyl]-N-{(1S*,3S*,4S*)-4-[(methoxyacetyl)amino]-3-methylcyclohexyl}-6-methyl-5H-pyrrolo[3,2-d]pyrimidine-7-carboxamide; N-[(1S*,3S*,4S*)-4-(Acetylamino)-3-fluorocyclohexyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-N-[(1S*,3S*,4S*)-3-fluoro-4-(propanoylamino)cyclohexyl]-6-methyl-5H-pyrrolo[3,2-d]pyrimidine-7-carboxamide; 4-[2-(Cyclopropylmethoxy)-5-(difluoromethyl)phenyl]-N-{(1S*,3S*,4S*)-3-fluoro-4-[(methoxyacetyl)amino]cyclohexyl}-6-methyl-5H-pyrrolo[3,2-d]pyrimidine-7-carboxamide; N-[(1R*,3S*,4S*)-3-(Acetylamino)-4-methylcyclopentyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-[(1R*,3S*,4S*)-3-methyl-4-(propanoylamino)cyclopentyl]-5H-pyrrolo[3,2-d]pyrimidine-7-carboxamide; 4-[2-(Cyclopropylmethoxy)-5-(difluoromethyl)phenyl]-N-{(1R*,3S*,4S*)-3-[(methoxyacetyl)amino]-4-methylcyclopentyl}-6-methyl-5H-pyrrolo[3,2-d]pyrimidine-7-carboxamide; N-[(1R*,2R*,4S*)-4-(acetylamino)-2-methylcyclopentyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-[(1R*,2R*,4S*)-2-methyl-4-(propanoylamino)cyclopentyl]-5H-pyrrolo[3,2-d]pyrimidine-7-carboxamide; 4-[2-(Cyclopropylmethoxy)-5-(difluoromethyl)phenyl]-N-{(1R*,2R*,4S*)-4-[(methoxyacetyl)amino]-2-methylcyclopentyl}-6-methyl-5H-pyrrolo[3,2-d]pyrimidine-7-carboxamide; N-[(1S*,3S*,4S*)-3-(Acetylamino)-4-fluorocyclopentyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-N-[(1S*,3S*,4S*)-3-fluoro-4-(propanoylamino)cyclopentyl]-6-methyl-5H-pyrrolo[3,2-d]pyrimidine-7-carboxamide; 4-[2-(cyclopropylmethoxy)-5-(difluoromethyl)phenyl]-N-{(1S*,3S*,4S*)-3-fluoro-4-[(methoxyacetyl)amino]cyclopentyl}-6-methyl-5H-pyrrolo[3,2-d]pyrimidine-7-carboxamide; N-[(1S*,2R*,4S*)-4-(Acetylamino)-2-fluorocyclohexyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-N-[(1S*,2R*,4S*)-2-fluoro-4-(propanoylamino)cyclohexyl]-6-methyl-5H-pyrrolo[3,2-d]pyrimidine-7-carboxamide; 4-[2-(Cyclopropylmethoxy)-5-(difluoromethyl)phenyl]-N-{(1S*,2R*,4S*)-2-fluoro-4-[(methoxyacetyl)amino]cyclohexyl}-6-methyl-5H-pyrrolo[3,2-d]pyrimidine-7-carboxamide;

a salt thereof, or a stereoisomer of the compound or a salt thereof.

It is to be understood that the present subject matter covers all combinations of substituent groups referred to hereinabove. In particular, the present subject matter covers all combinations of alternative or preferred groups described hereinabove.

Salts of the compounds according to the present subject matter and the stereoisomers thereof include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, gluconates including D-gluconates and L-gluconates, glucuronates including D-glucuronates and L-glucuronates, benzoates, 2-(4-hydroxybenzoyl)benzoates, butyrates, salicylates, sulfosalicylates, maleates, laurates, malates including L-malates and D-malates, lactates including L-lactates and D-lactates, fumarates, succinates, oxalates, tartarates including L-tartarates, D-tartarates and meso-tartarates, stearates, benzenesulfonates (besilates), toluenesulfonates (tosilates), methanesulfonates (mesilates), laurylsulfonates, 3-hydroxy-2-naphthoates, lactobionates (salts of 4-O-beta-D-galactopyranosyl-D-gluconic acid), galactarates, embonates and ascorbates.

Examples of salts with bases include, but are not limited to, lithium, sodium, potassium, calcium, aluminum, magnesium, titanium, ammonium, meglumine and guanidinium salts.

The salts include water-insoluble and, particularly, water-soluble salts.

The compounds according to the present subject matter, the salts thereof, the stereoisomers of the compounds and the salts thereof may contain, e.g. when isolated in crystalline form, varying amounts of solvents. Included within the scope of the present subject matter are, therefore, all solvates of the compounds of formula (I), the salts thereof, the stereoisomers of the compounds and the salts thereof. Hydrates are a preferred example of said solvates.

Some of the compounds of formula 1, salts thereof, stereoisomers thereof or salts of the latter may exist in different crystalline forms (polymorphs), which are within the scope of the invention. The obtained solids of the compounds of formula 1, salts thereof, stereoisomers thereof or salts of the latter are re-crystalised in different crystalline forms (polymorphs) with solvents or mixtures of the solvents selected from water, methanol, ethanol, isopropanol, n-butanol, dichloromethane, tert-butylmethylether, acetonitril, dioxan, methylethylketon, aceton, glycole, ethylene glycol, methylisobutylketon, The compounds according to the present subject matter and the salts thereof include stereoisomers.

Examples of stereoisomers include, but are not limited to, compounds of formula (I) wherein R3 is a 3-6C-cycloalkyl group substituted by R6. Stereoisomers of one exemplified compound of formula (I) wherein R3 is a 3-6C-cycloalkyl group substituted by R6 are shown below (cis/trans stereoisomers), wherein the trans stereoisomer (S1) is preferred:

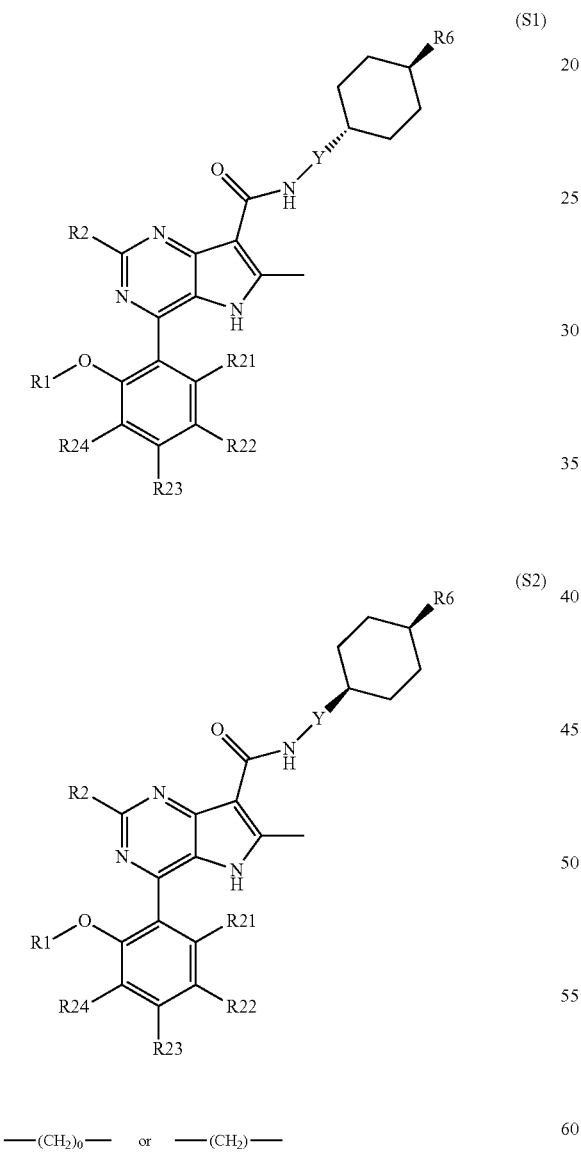

Y = ——(CH₂)₀—— or ——(CH₂)——

Furthermore the present subject matter includes the pure (R,R)-isomers, (R,S)-isomers, (S,R)-isomers and (S,S)-isomers, and mixtures of two or more thereof in any ratio. An example of said isomers is shown below:

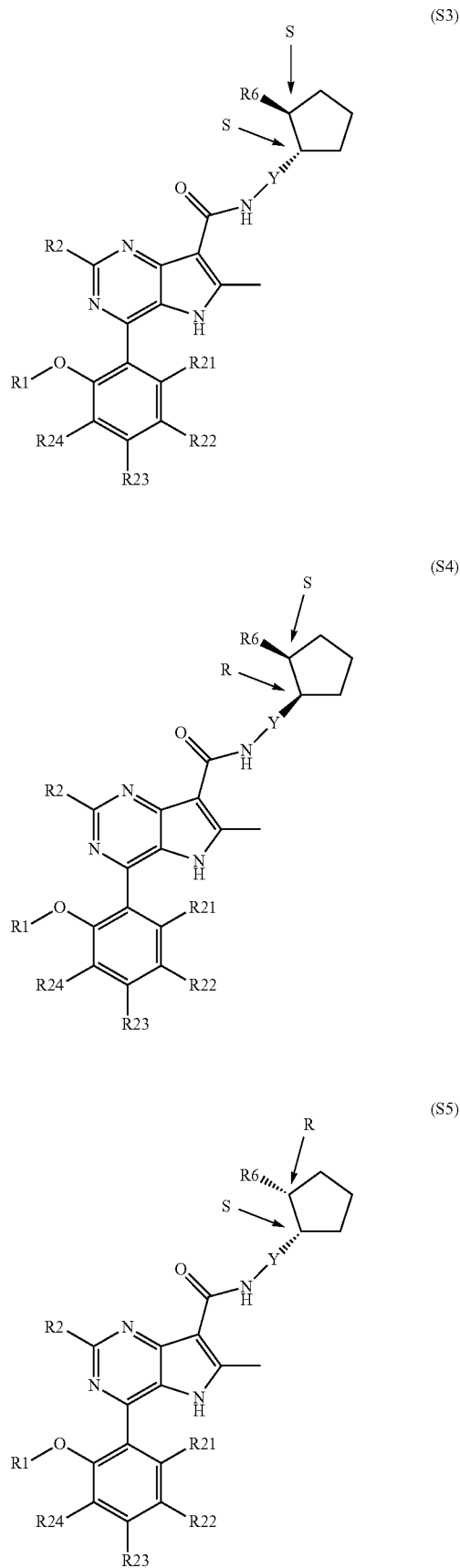

-continued

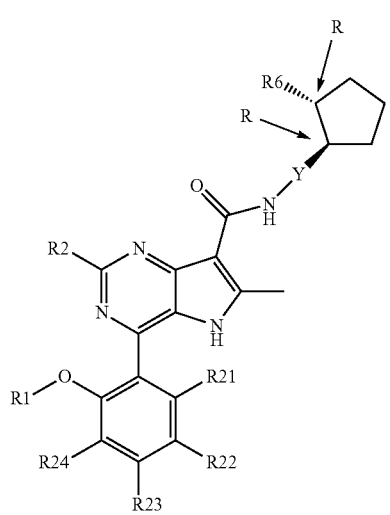

(S6)

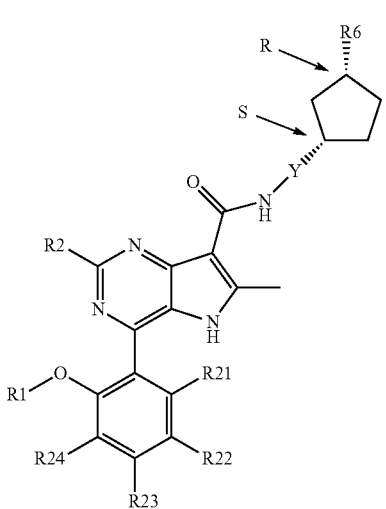

(S9)

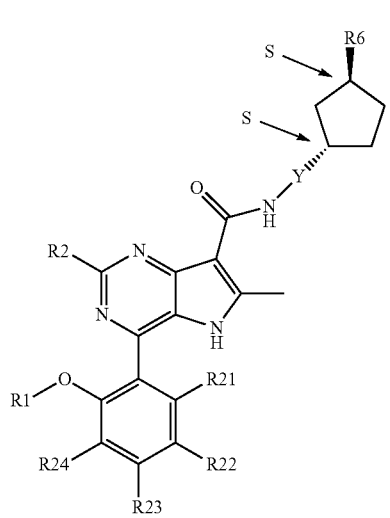

(S7)

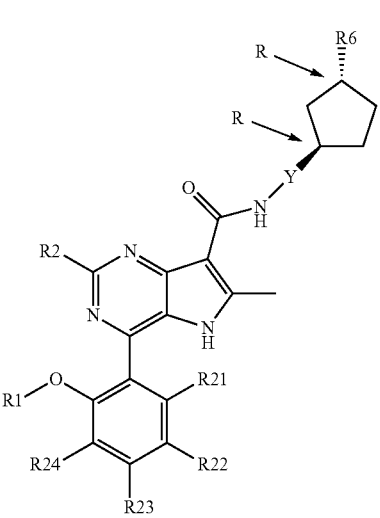

(S10)

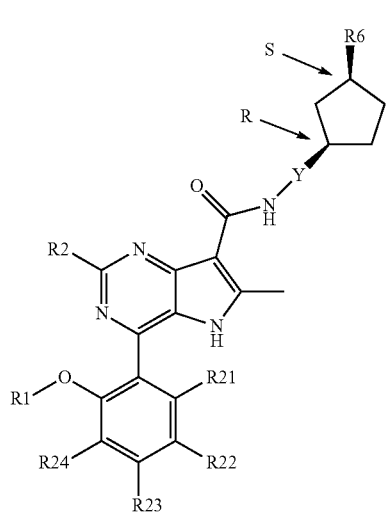

(S8)

Y = —(CH₂)₀— or —(CH₂)—

Examples of stereoisomers include, but are not limited to, compounds of formula (I) wherein R3 is a 3-6C-cycloalkyl group substituted by R6 and optionally substituted by R61. Stereoisomers of one exemplified compound of formula (I) wherein R3 is a 3-6C-cycloalkyl group substituted by R6 and optionally substituted by R61 includes the pure (S,S,S)-isomers, (S,S,R)-isomers, (S,R,S)-isomers and (S,R,R)-isomers, (R,R,R)-isomers, (R,R,S)-isomers, (R,S,S)-isomers and (R,S,R)-isomers and mixtures of two or more thereof in any ratio, wherein the stereoisomers (S11), (S13), (S15) and (S18) and mixtures of two or more thereof in any ratio are preferred. An example of said isomers is shown below:

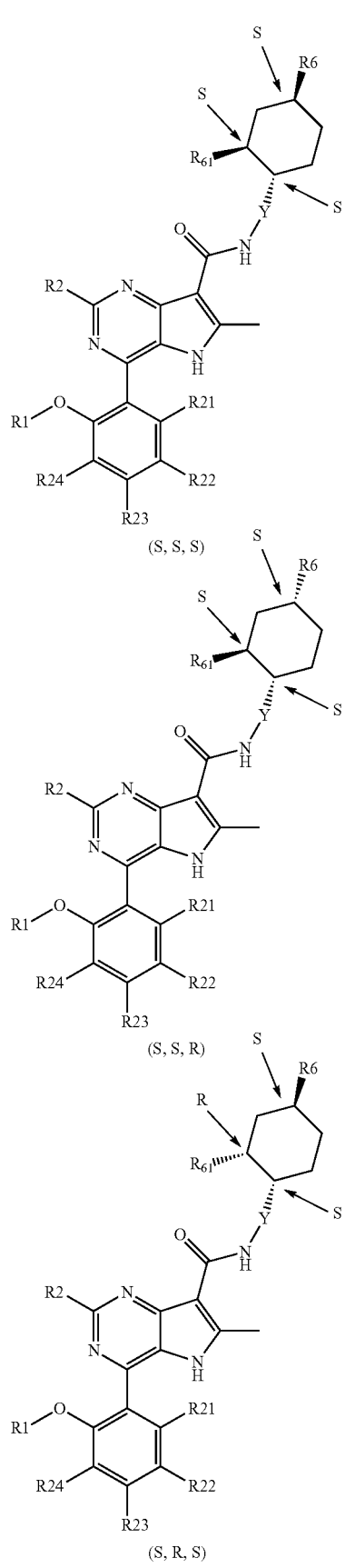
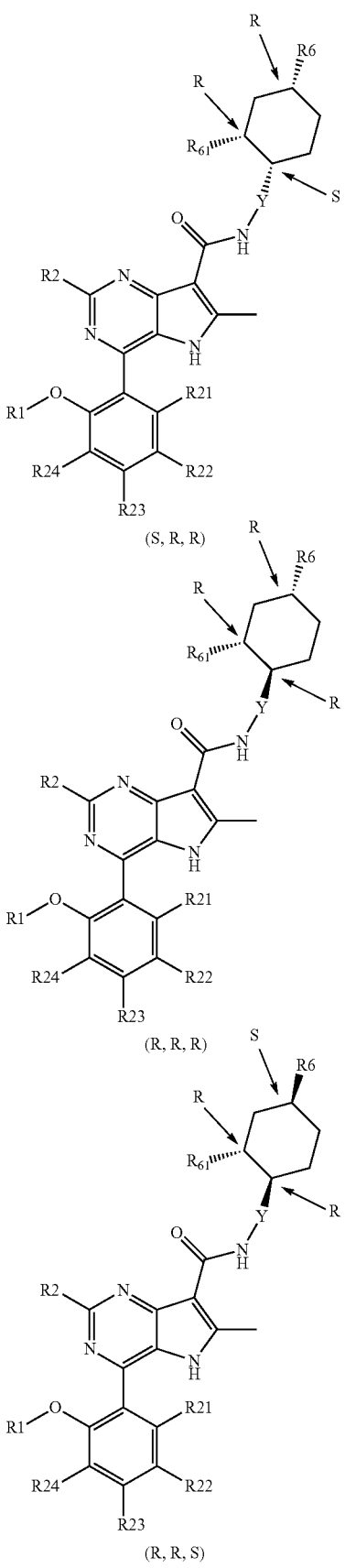

-continued

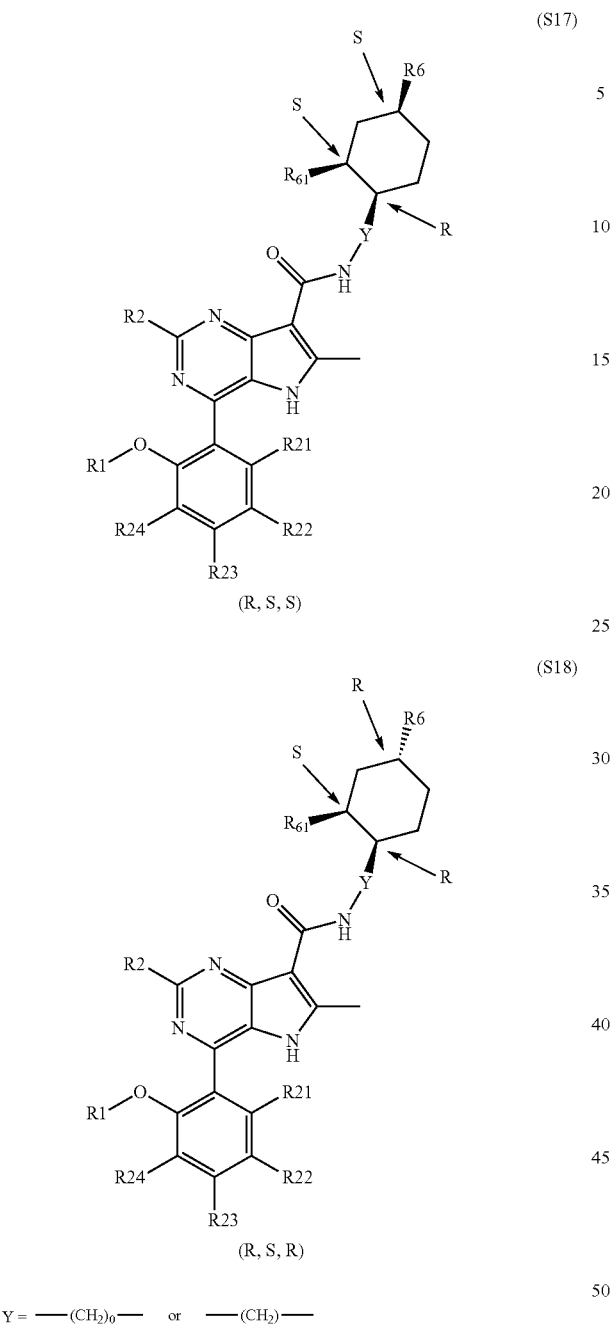

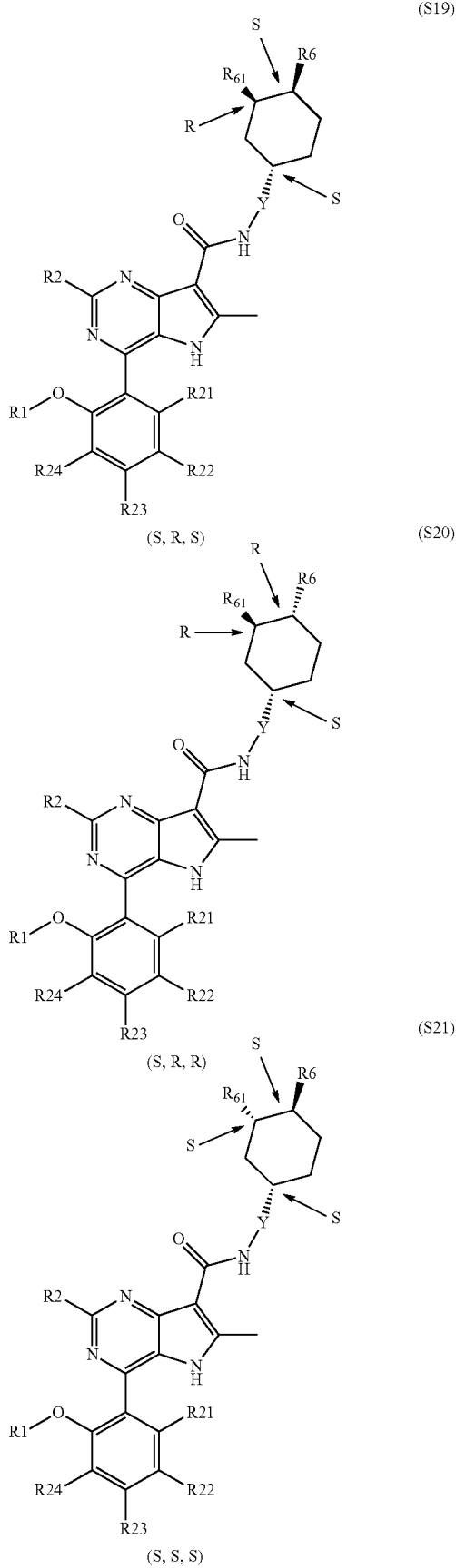

Y = —(CH₂)₀— or —(CH₂)—

Furthermore examples of stereoisomers include, but are not limited to, compounds of formula (I) wherein R3 is a 3-6C-cycloalkyl group substituted by R6 and optionally substituted by R61. Stereoisomers of one exemplified compound of formula (I) wherein R3 is a 3-6C-cycloalkyl group substituted by R6 and optionally substituted by R61 includes the pure (S,S,S)-isomers, (S,S,R)-isomers, (S,R,S)-isomers and (S,R,R)-isomers, (R,R,R)-isomers, (R,R,S)-isomers, (R,S,S)-isomers and (R,S,R)-isomers and mixtures of two or more thereof in any ratio, wherein the stereoisomers (S19), (S21), (S23) and (S26) and mixtures of two or more thereof in any ratio are preferred. An example of said isomers is shown below:

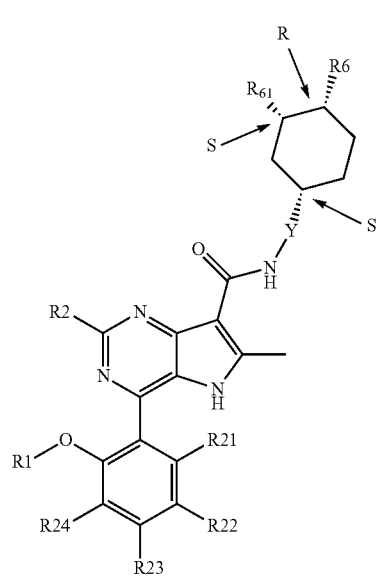
(S22)

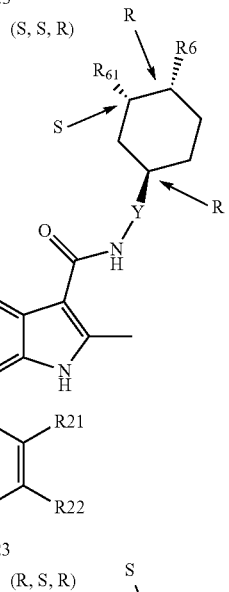
(S23)

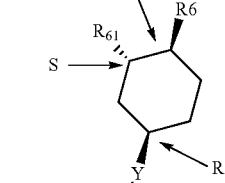
(S24)

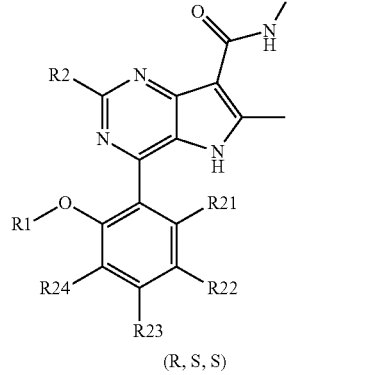
(R, S, S)

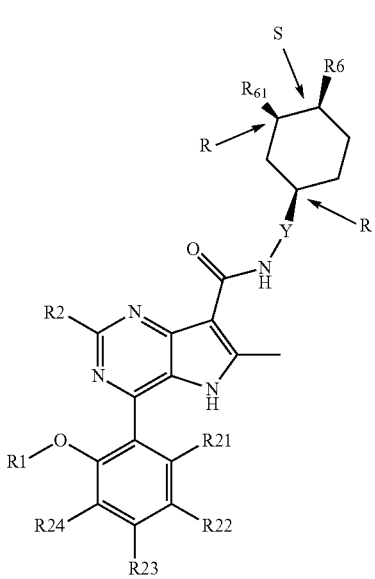
(S25)

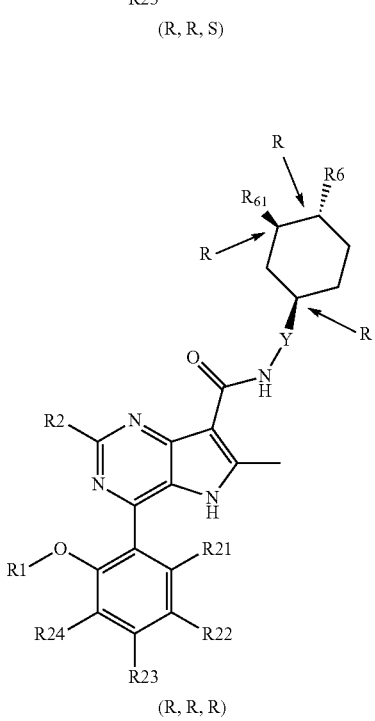
(S26)

Y = —(CH₂)₀— or —(CH₂)—

Further examples of stereoisomers include, but are not limited to, compounds of formula (I) wherein R3 is a 4- to 7-membered saturated heterocyclic ring containing one nitrogen atom and optionally one oxygen atom, said heterocyclic ring being optionally substituted by R4 and wherein said heterocyclic ring contains a stereogenic center. Stereoisomers of an exemplified compound of formula (I) wherein R3 is a 4- to 7-membered saturated heterocyclic ring containing one nitrogen atom, said heterocyclic ring being optionally substituted by R4 and said heterocyclic ring containing a stereogenic center are shown below:

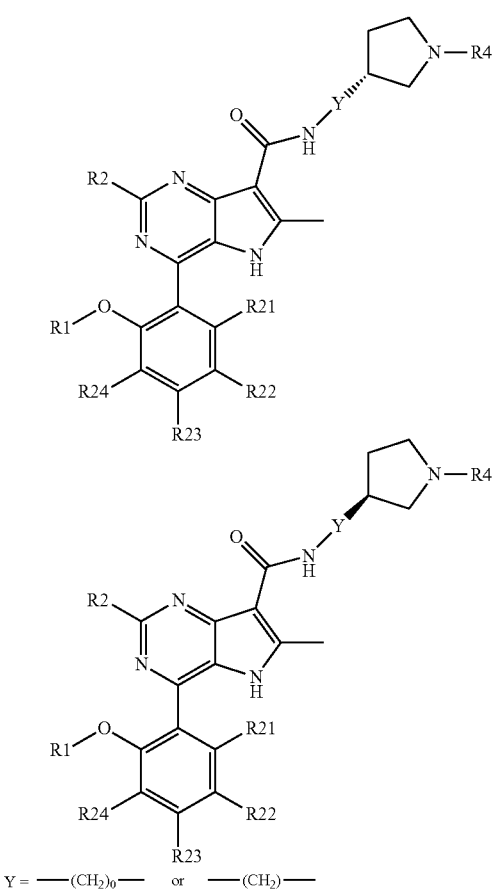

(S27)

(S28)

Y = ——(CH$_2$)$_0$—— or ——(CH$_2$)——

Further examples of stereoisomers include, but are not limited to, compounds of formula (I) wherein R3 is a 4- to 7-membered saturated heterocyclic ring containing one nitrogen atom and optionally one oxygen atom, said heterocyclic ring being optionally substituted by R4 and/or by two substituents R5 and wherein said heterocyclic ring contains a stereogenic center. Stereoisomers of an exemplified compound of formula (I) wherein R3 is a 4- to 7-membered saturated heterocyclic ring containing one nitrogen atom, said heterocyclic ring being optionally substituted by R4 and/or by two substituents R5 and said heterocyclic ring containing a stereogenic center are shown below:

-continued

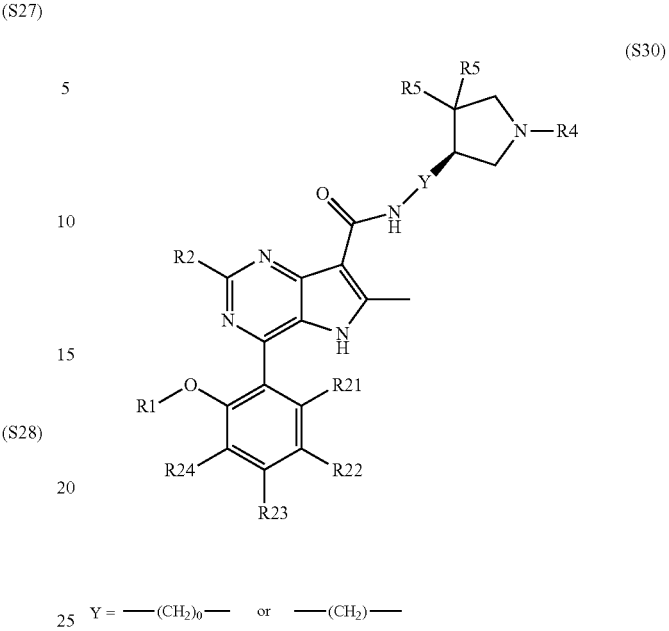

(S30)

Y = ——(CH$_2$)$_0$—— or ——(CH$_2$)——

Further examples of stereoisomers include, but are not limited to, compounds of formula (I) wherein R3 is a 4- to 7-membered saturated heterocyclic ring containing one nitrogen atom and optionally one oxygen atom, said heterocyclic ring being optionally substituted by R4 and/or R5 and wherein said heterocyclic ring contains stereogenic centers. The present subject matter includes the pure (R,R)-isomers, (R,S)-isomers, (S,R)-isomers and (S,S)-isomers, and mixtures of two or more thereof in any ratio. An example of said isomers is shown below:

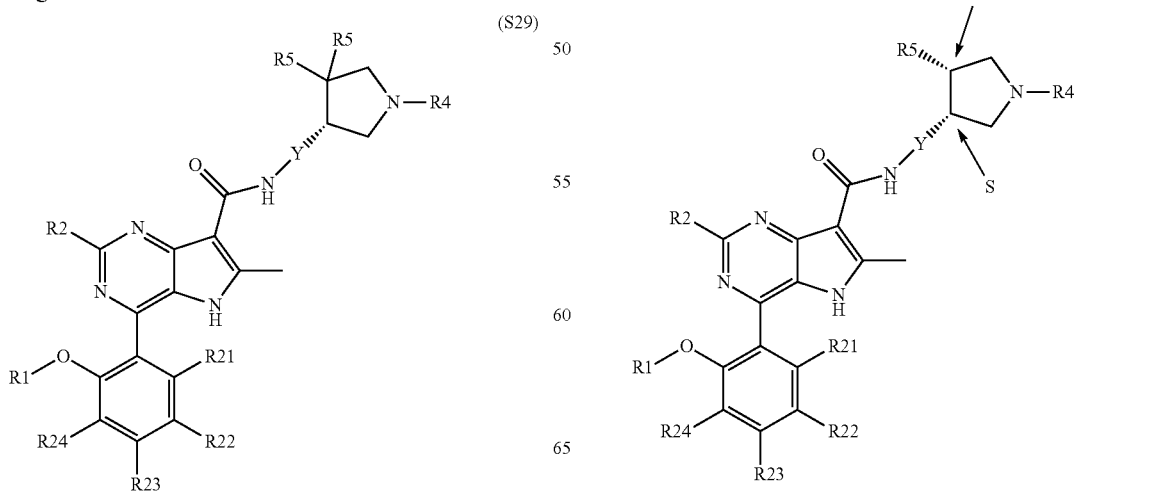

(S29)

(S31)

-continued
(S32)
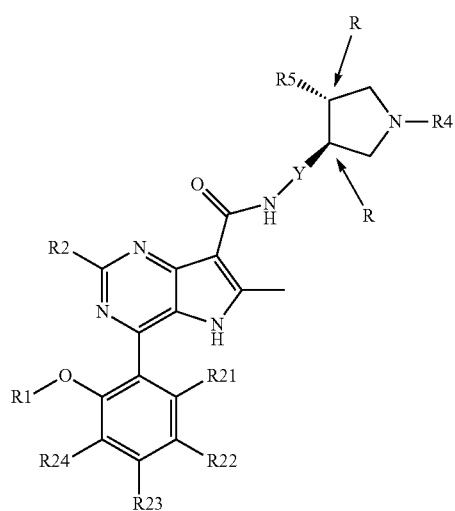
(S33)
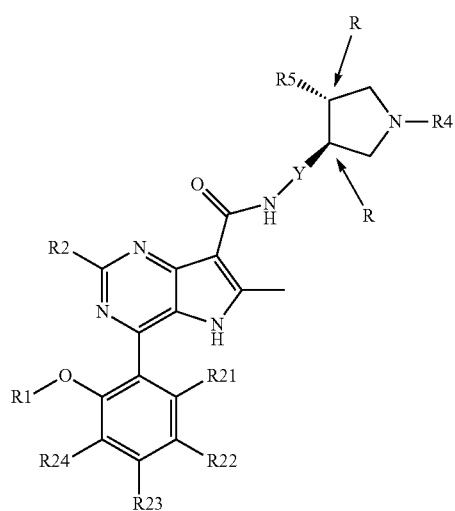
(S34)
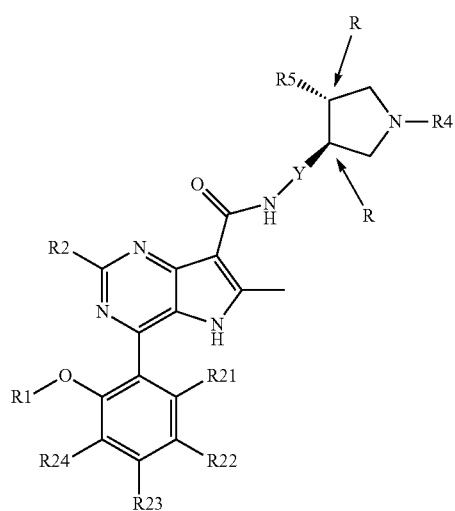
Y = —(CH₂)₀—
Furthermore the present subject matter includes the pure (R,R)-isomers, (R,S)-isomers, (S,R)-isomers and (S,S)-isomers, and mixtures of two or more thereof in any ratio. An example of said isomers is shown below:
(S35)
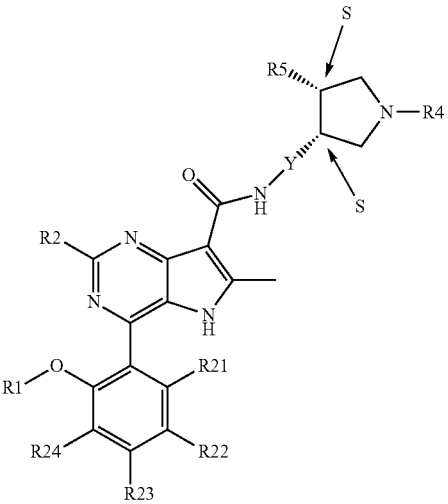
(S36)
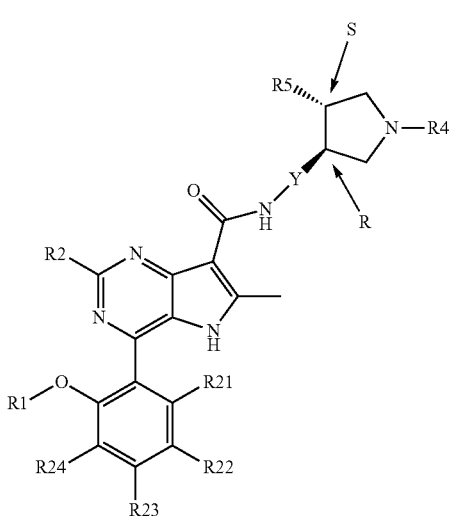
(S37)
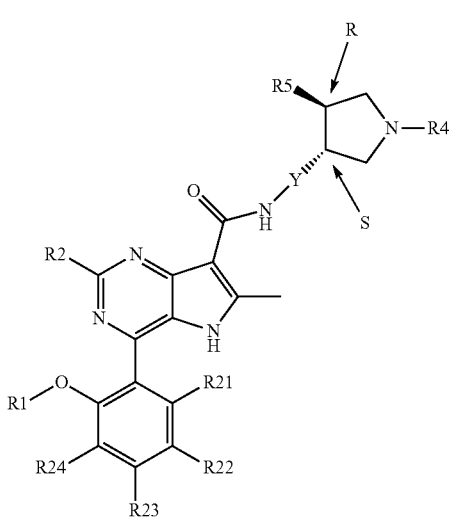

(S38)
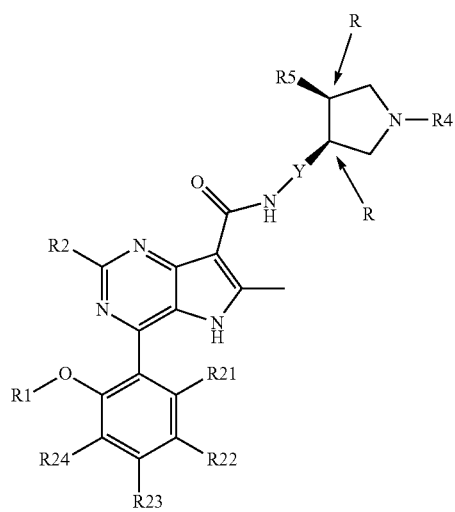

Y = —(CH₂)—

Furthermore the present subject matter includes the pure (R,R)-isomers, (R,S)-isomers, (S,R)-isomers and (S,S)-isomers, and mixtures of two or more thereof in any ratio. An example of said isomers is shown below:

(S39)
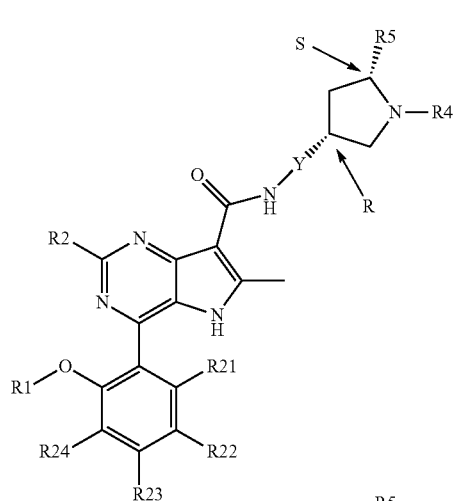

(S40)
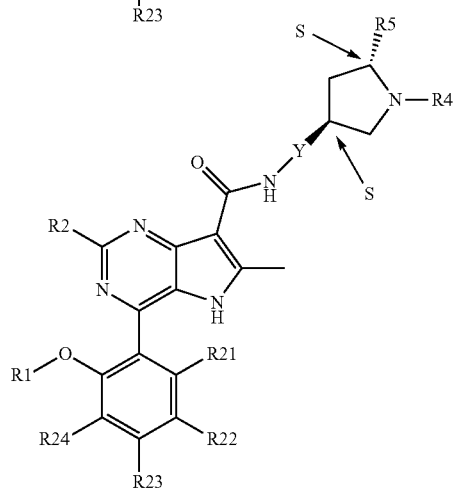

(S41)
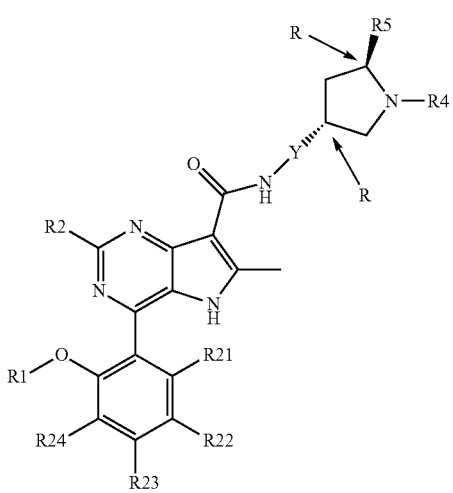

(S42)
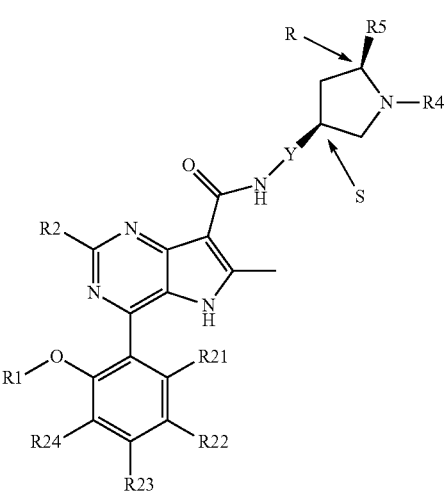

Y = —(CH₂)₀—

Furthermore the present subject matter includes the pure (R,R)-isomers, (R,S)-isomers, (S,R)-isomers and (S,S)-isomers, and mixtures of two or more thereof in any ratio. An example of said isomers is shown below:

(S43)
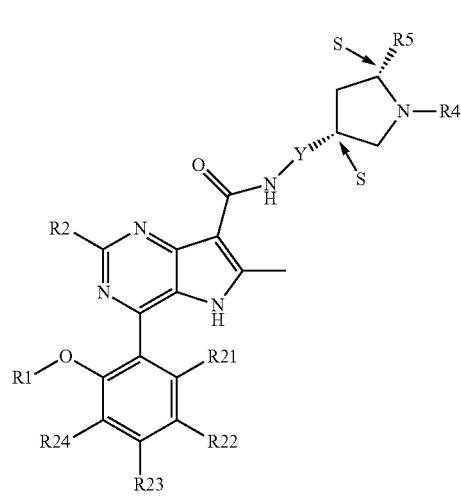

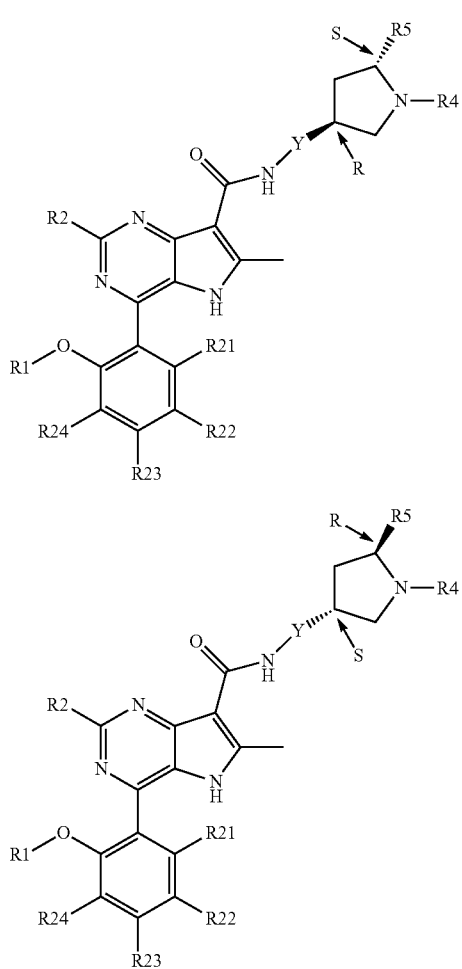

(S44)

(S45)

(S46)

Y = —(CH₂)—

Stereoisomers of a further exemplified compound of formula (I) wherein R3 is a 4- to 7-membered saturated heterocyclic ring containing one nitrogen atom, said heterocyclic ring being optionally substituted by R4 and said heterocyclic ring containing a stereogenic center are shown below:

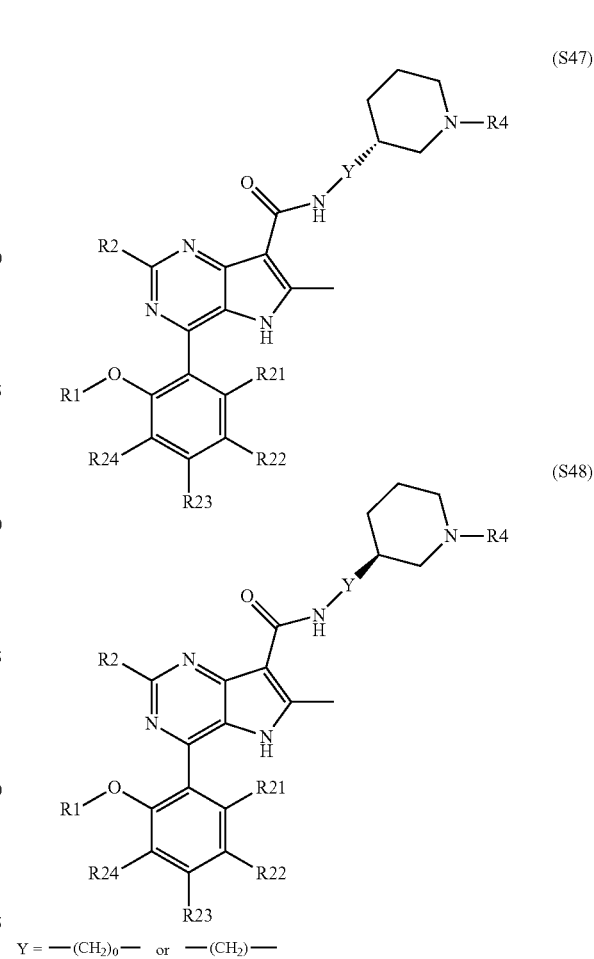

(S47)

(S48)

Y = —(CH₂)₀— or —(CH₂)—

Stereoisomers of a further exemplified compound of formula (I) wherein R3 is a 4- to 7-membered saturated heterocyclic ring containing one nitrogen atom, said heterocyclic ring being optionally substituted by R4 and/or R5 and said heterocyclic ring containing stereogenic centers. The present subject matter includes the pure (R,R)-isomers, (R,S)-isomers, (S,R)-isomers and (S,S)-isomers, and mixtures of two or more thereof in any ratio. An example of said isomers is shown below:

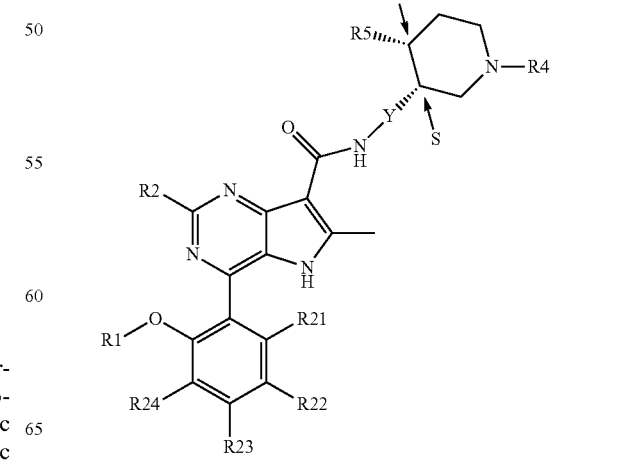

(S49)

-continued
(S50)
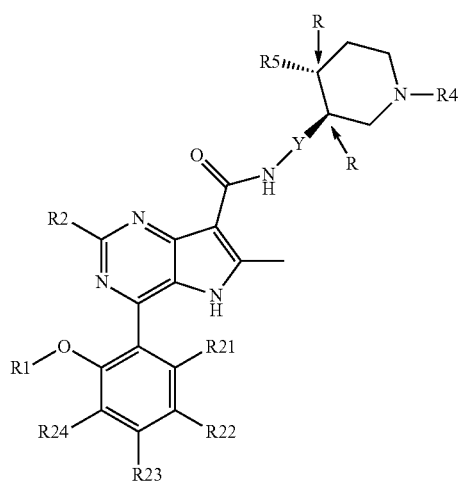
(S51)
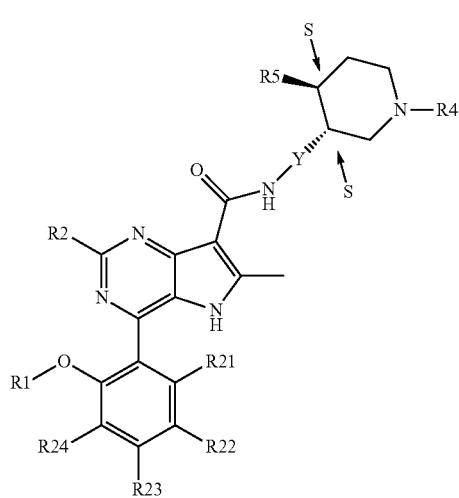
(S52)
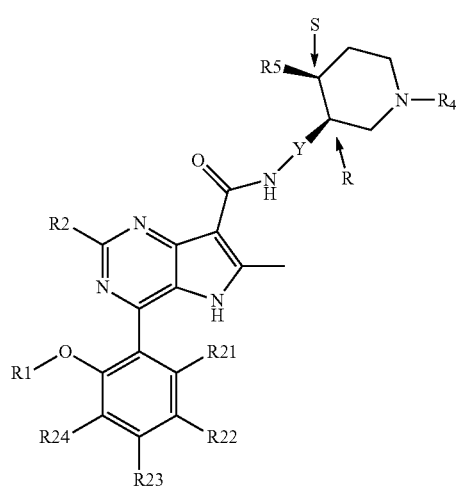
Y = —(CH₂)₀— or —(CH₂)—
Furthermore, the present subject matter includes the pure (R,R)-isomers, (R,S)-isomers, (S,R)-isomers and (S,S)-isomers, and mixtures of two or more thereof in any ratio. An example of said isomers is shown below:
(S53)
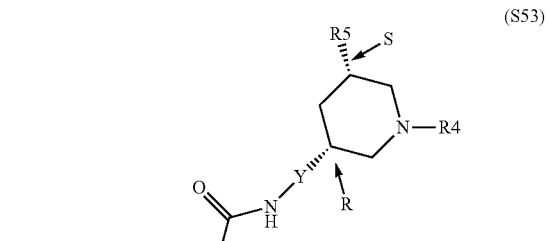
(S54)
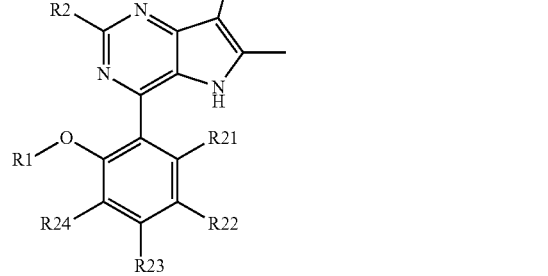
(S55)
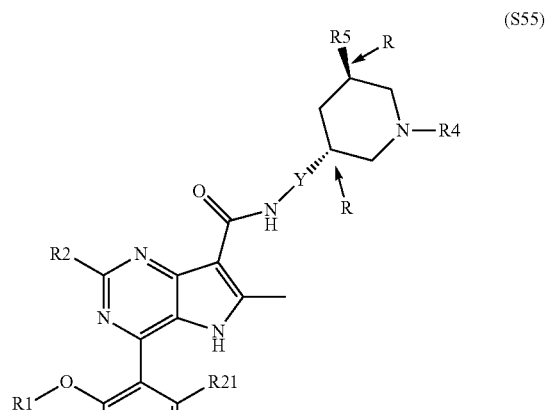

(S56)
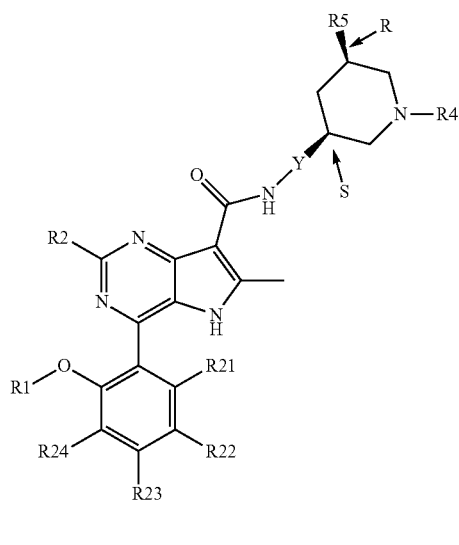
(S57)
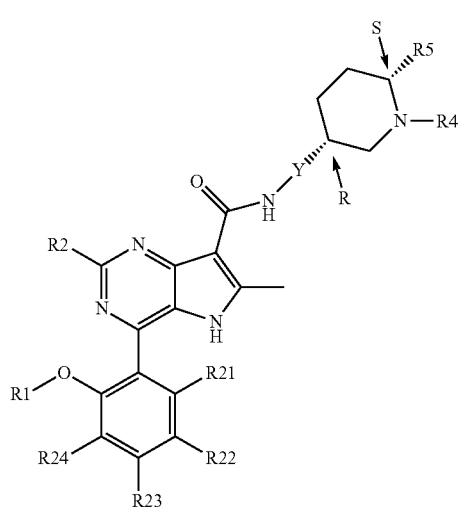
(S58)
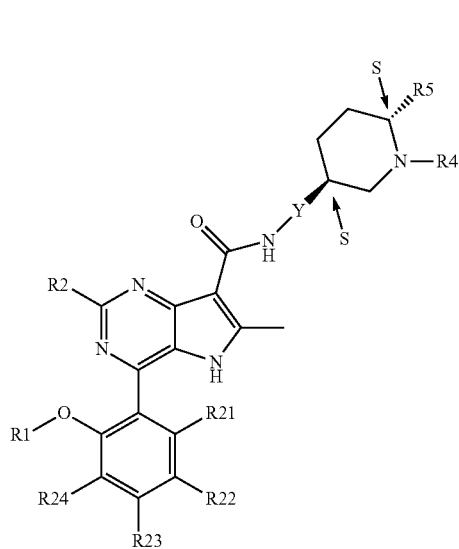
(S59)
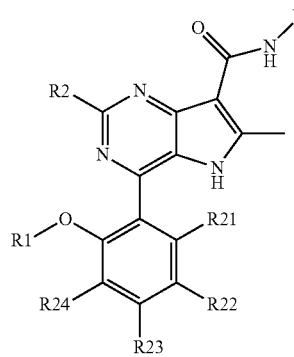
(S60)
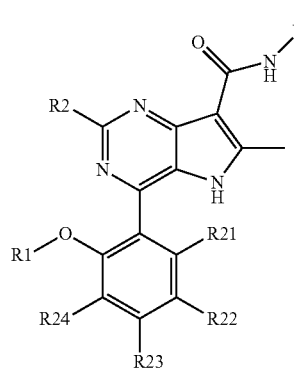
Y = —(CH$_2$)$_0$—
Furthermore, the present subject matter includes the pure (R,R)-isomers, (R,S)-isomers, (S,R)-isomers and (S,S)-isomers, and mixtures of two or more thereof in any ratio. An example of said isomers is shown below:
(S61)
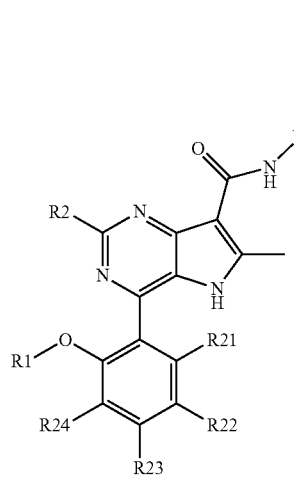

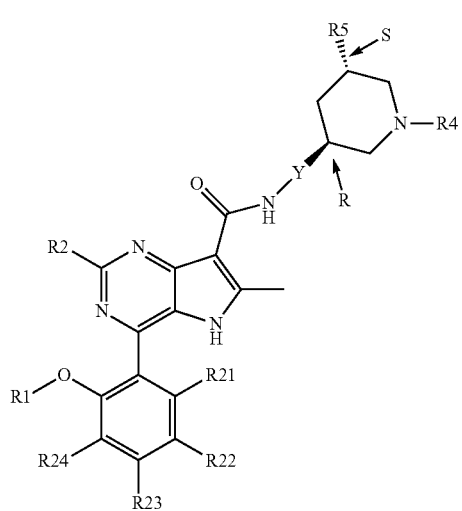
(S62)
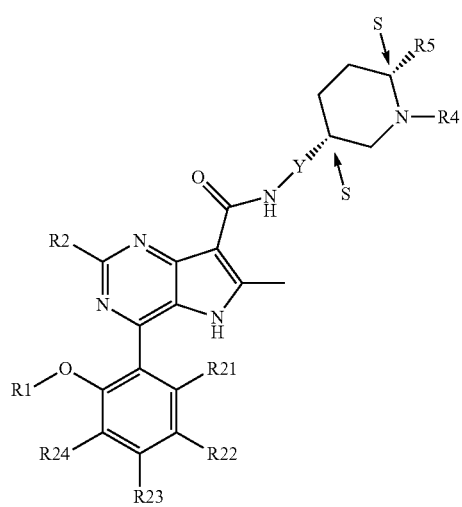
(S65)
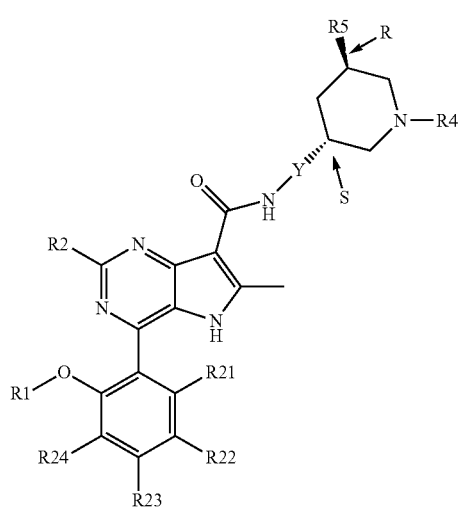
(S63)
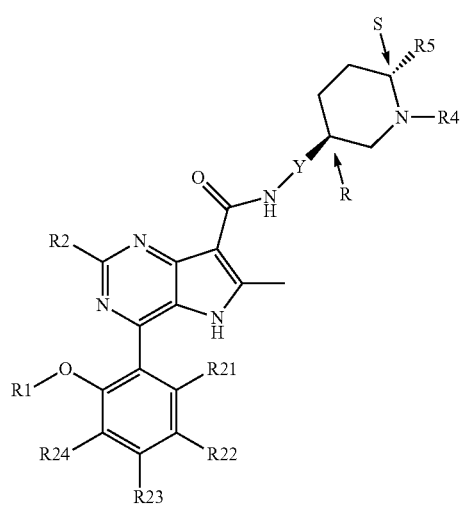
(S66)
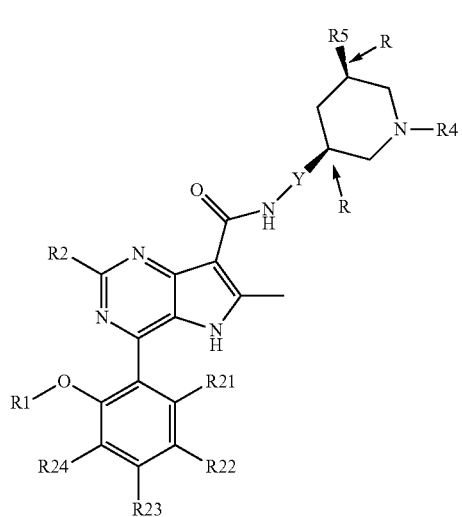
(S64)
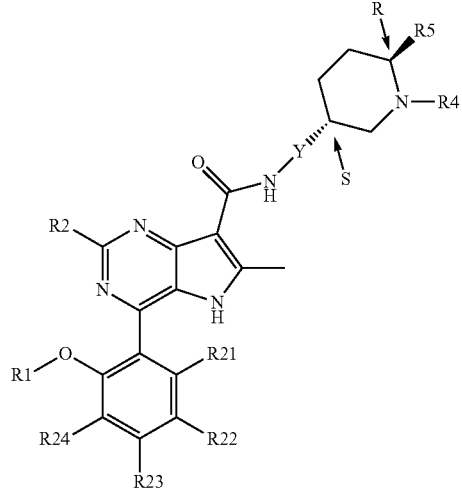
(S67)

(S68)
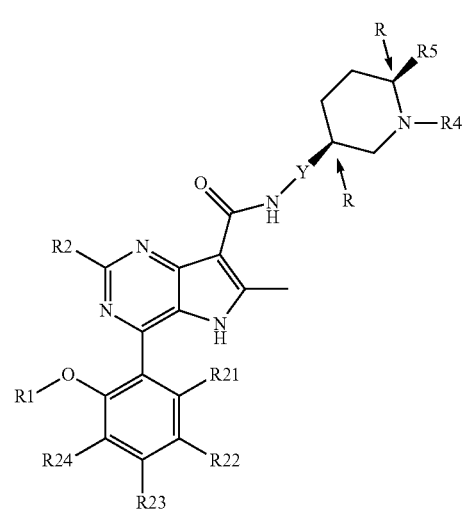
Y = —(CH₂)—

Furthermore, the present subject matter includes the pure (R,R)-isomers, (R,S)-isomers, (S,R)-isomers and (S,S)-isomers, and mixtures of two or more thereof in any ratio. An example of said isomers is shown below:

(S69)
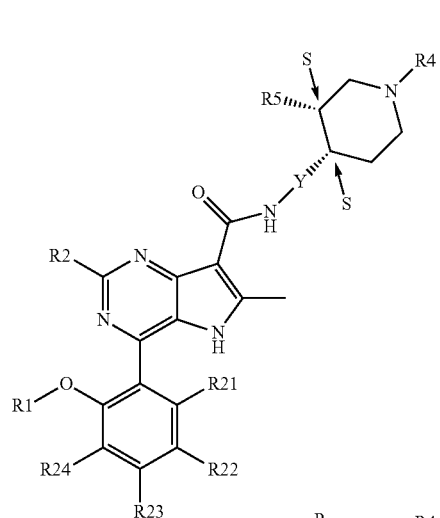

(S70)
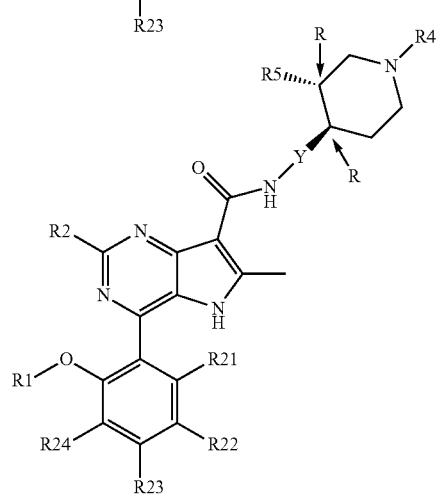

(S71)
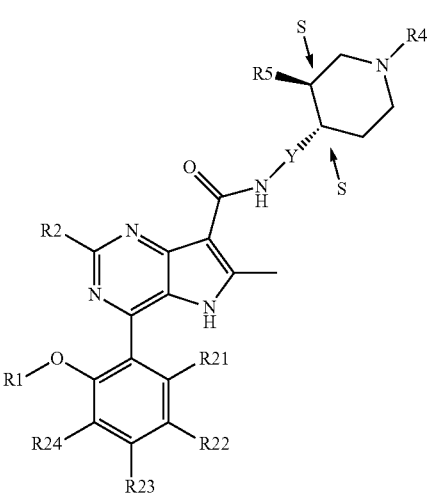

(S72)
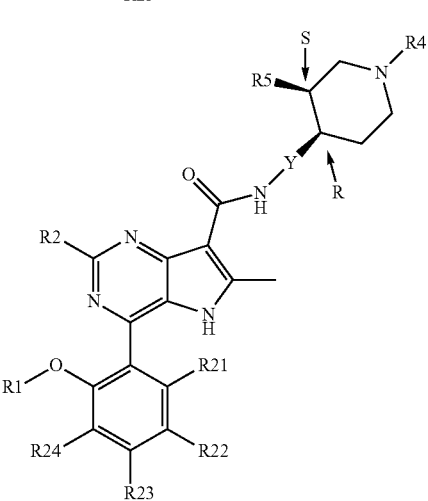

Y = —(CH₂)₀—

Furthermore, the present subject matter includes the pure (R,R)-isomers, (R,S)-isomers, (S,R)-isomers and (S,S)-isomers, and mixtures of two or more thereof in any ratio. An example of said isomers is shown below:

(S73)
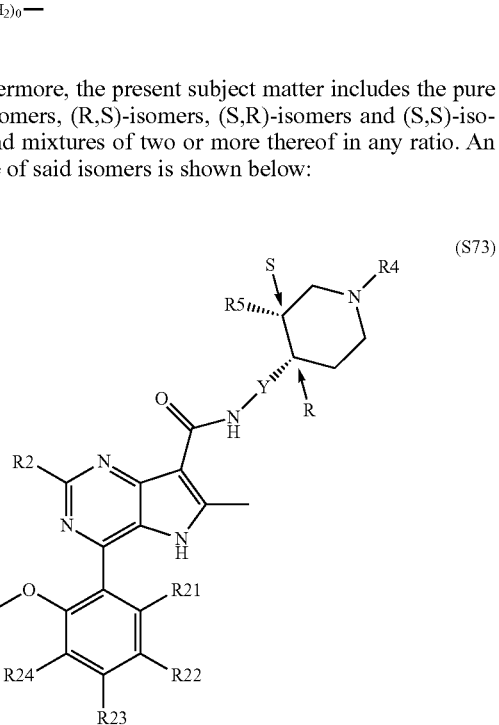

(S74)

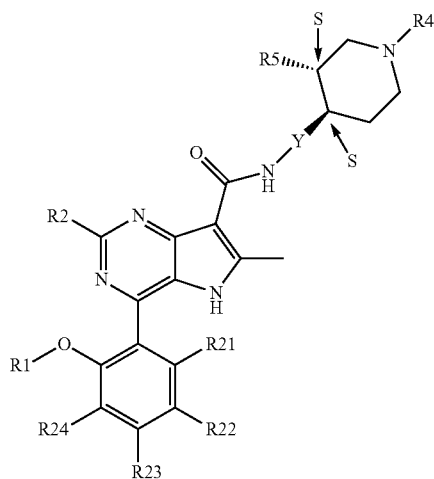

(S75)

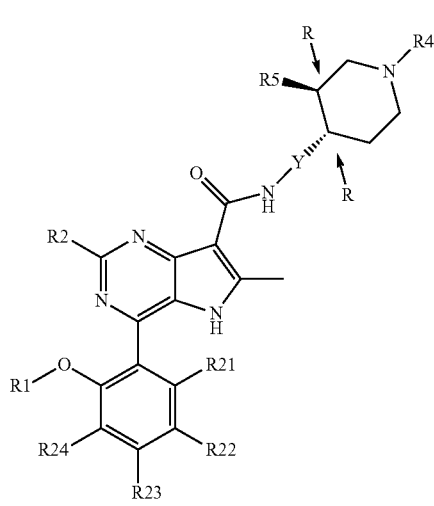

(S76)

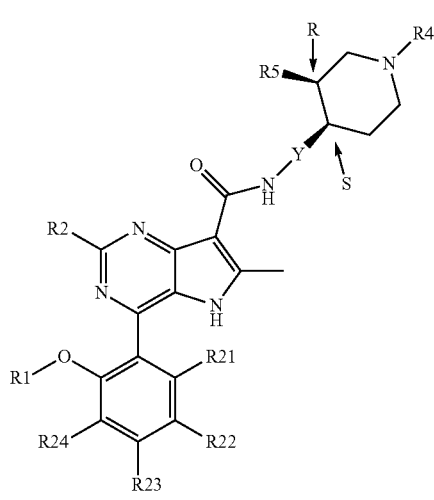

(S76)

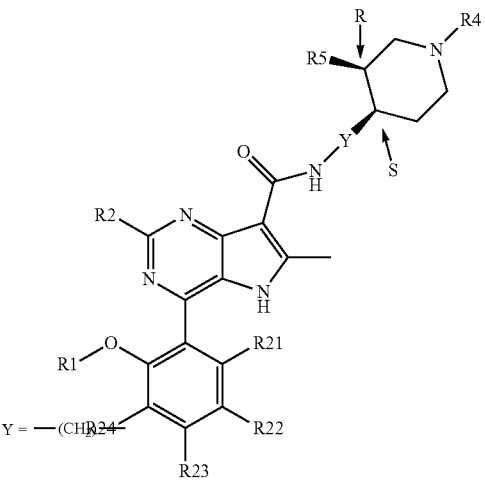

Y = —(CH₂)—

Further examples of stereoisomers include, but are not limited to, compounds of formula (I) wherein R4 is a group having a stereogenic center, such as a group —C(O)—CH(CH₃)—OH. Further examples of stereoisomers include, but are not limited to, compounds of formula (I) wherein R6 is a group having a stereogenic center, such as a group —NH—C(O)—CH(CH₃)—OCH₃.

Each of said stereogenic centers may have the absolute configuration R or the absolute configuration S (according to the rules of Cahn, Ingold and Prelog).

The present subject matter relates to the pure stereoisomers and to mixtures of the stereoisomers independent of the ratio, including the racemates. Accordingly, the present subject matter relates to the pure (cis)-isomers, the pure (trans)-isomers, and mixtures thereof, the pure (R)-isomers, the pure (S)-isomers, and mixtures thereof, the pure (RS)-isomers, the pure (SS)-isomers, the pure (SR)-isomers, the pure (RR)-isomers, and mixtures of two or more thereof in any ratio.

Furthermore, the present subject matter includes the pure (trans,R)-isomers, (trans,S)-isomers, (cis,R)-isomers and (cis,S)-isomers, and mixtures of two or more thereof in any ratio, wherein the stereoisomers (S77) and (S78) and mixtures of two or more thereof in any ratio are preferred. An example of said isomers is shown below:

(S77)

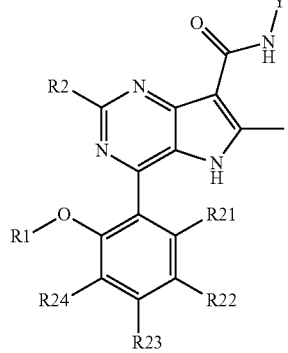

(trans, S)

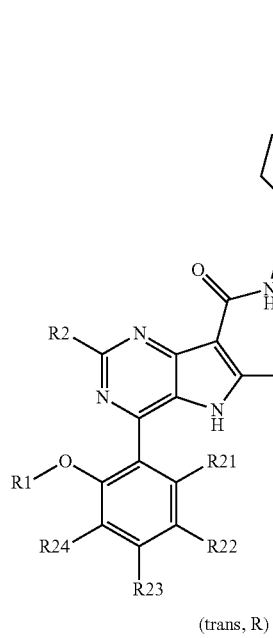
(S78)
(trans, R)
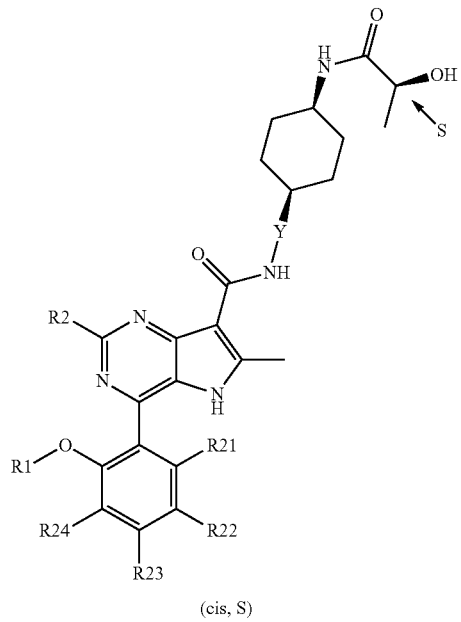
(S79)
(cis, S)
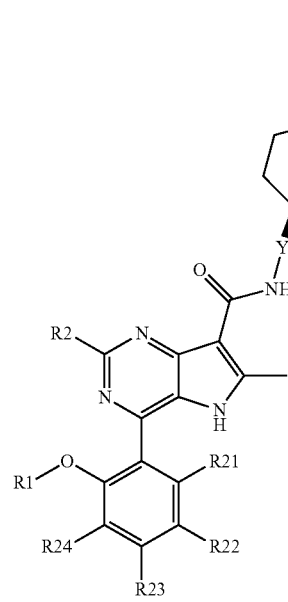
(S80)
(cis, R)
Y = —(CH₂)₀— or —(CH₂)—
Furthermore, the present subject matter includes the pure (R,R)-isomers, (R,S)-isomers, (S,R)-isomers and (S,S)-isomers, and mixtures of two or more thereof in any ratio. An example of said isomers is shown below:
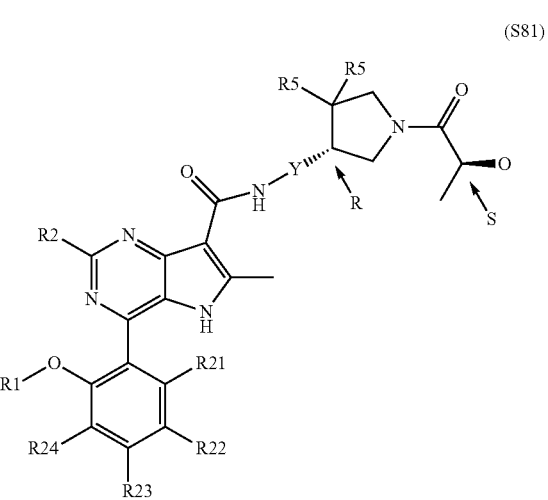
(S81)

-continued
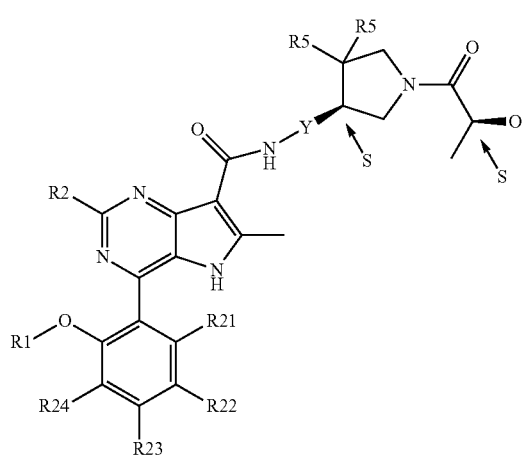
(S82)
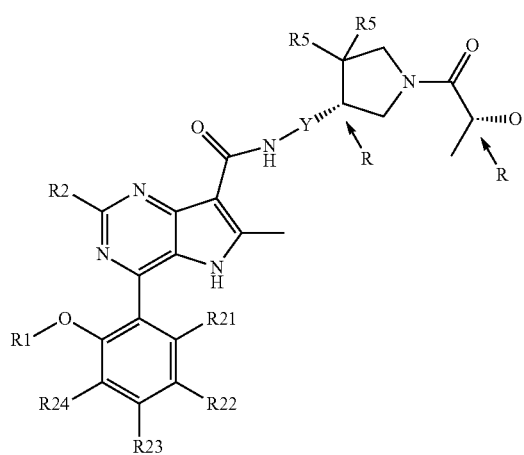
(S83)
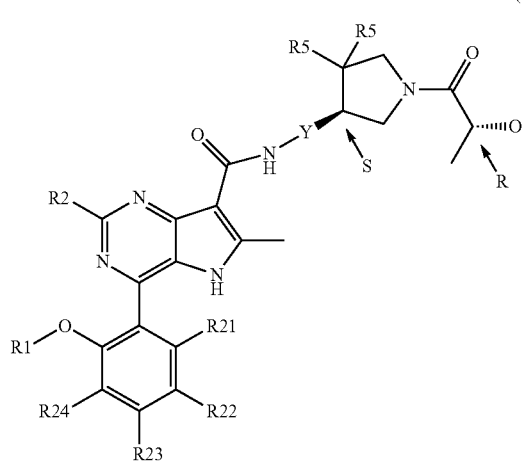
(S84)
Y = —(CH$_2$)$_0$—
Furthermore, the present subject matter includes the pure (R,R)-isomers, (R,S)-isomers, (S,R)-isomers and (S,S)-isomers, and mixtures of two or more thereof in any ratio. An example of said isomers is shown below:
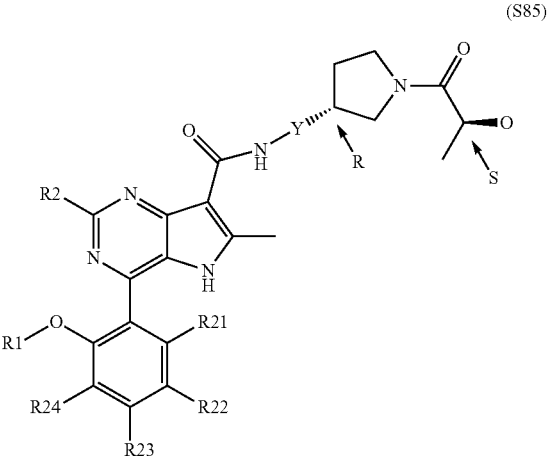
(S85)
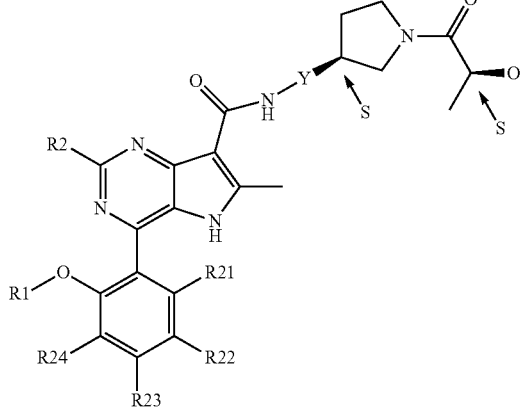
(S86)
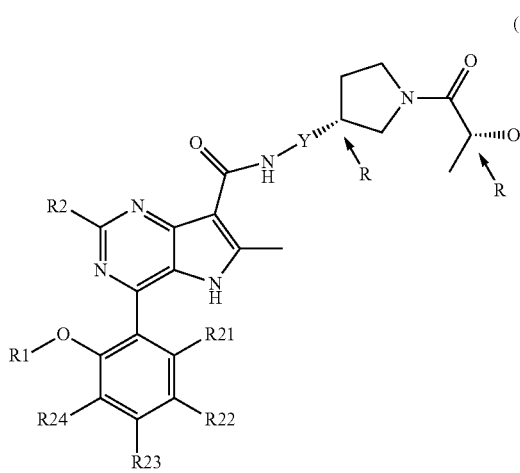
(S87)

(S88)
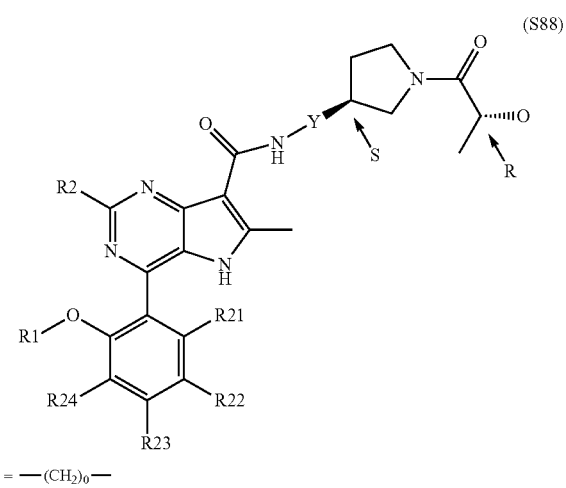

Y = —(CH₂)₀—

Furthermore, the present subject matter includes the pure (R,R)-isomers, (R,S)-isomers, (S,R)-isomers and (S,S)-isomers, and mixtures of two or more thereof in any ratio. An example of said isomers is shown below:

(S89)
(S90)
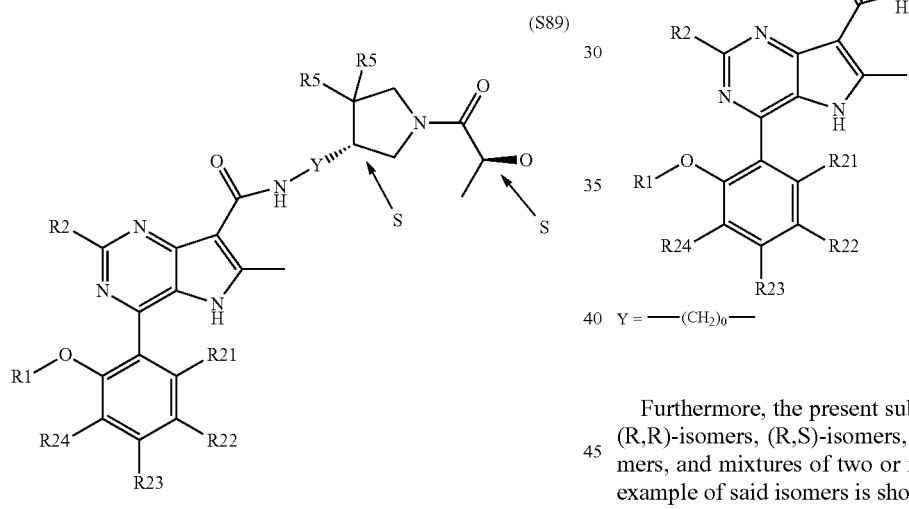

(S91)
(S92)
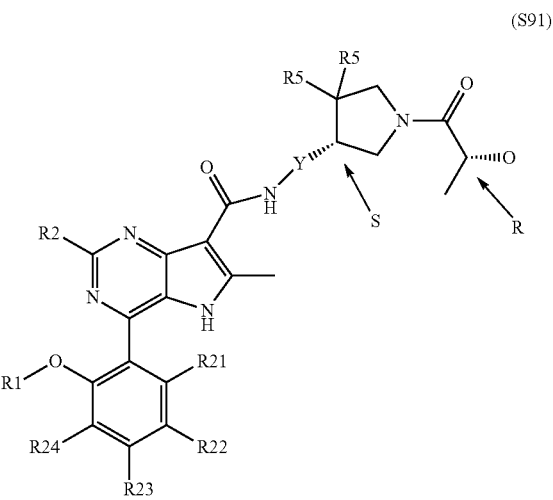

Y = —(CH₂)₀—

Furthermore, the present subject matter includes the pure (R,R)-isomers, (R,S)-isomers, (S,R)-isomers and (S,S)-isomers, and mixtures of two or more thereof in any ratio. An example of said isomers is shown below:

(S93)
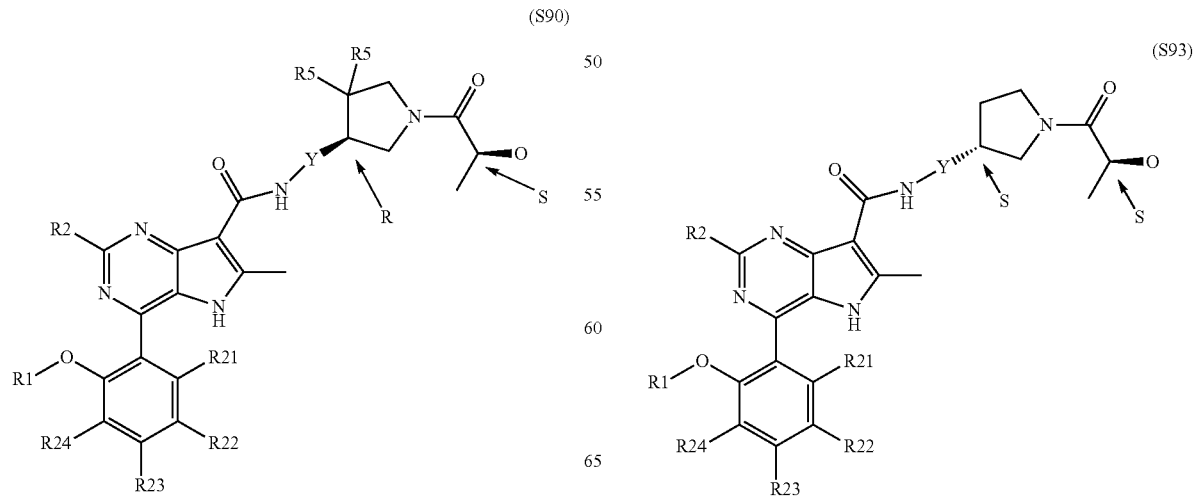

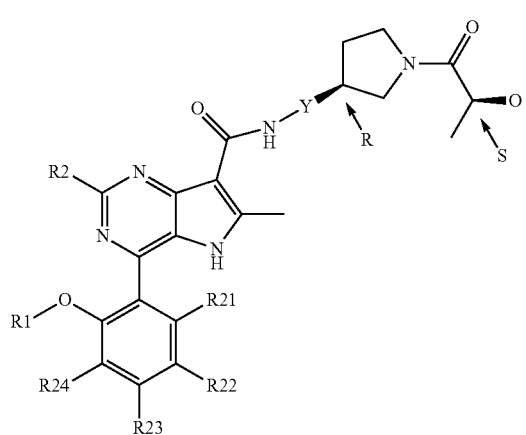
(S94)
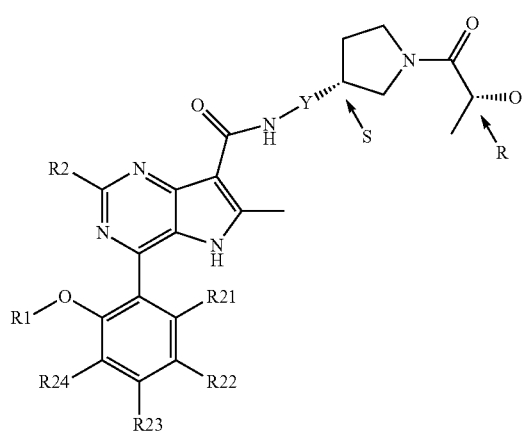
(S95)
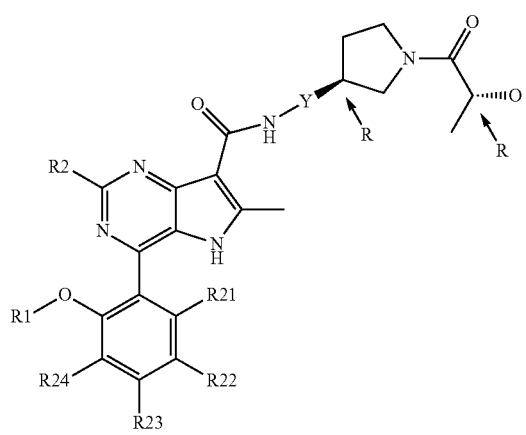
(S96)
Y = —(CH₂)—
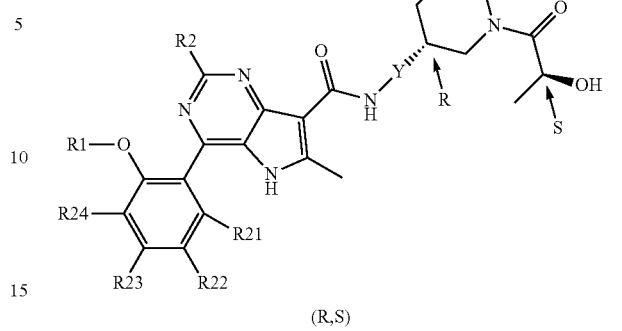
(S97) (R,S)
(S98) (S,S)
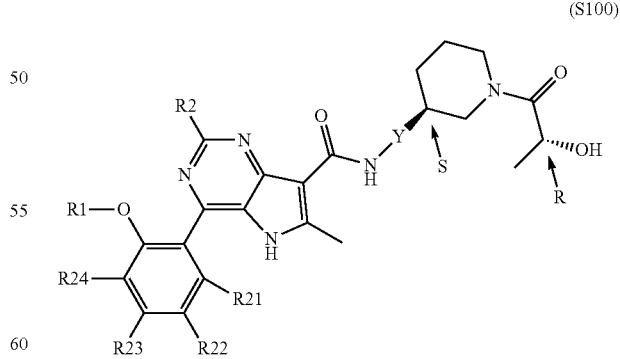
(S99) (R,R)
(S100) (S,R)
Y = —(CH₂)₀—
Furthermore, the present subject matter includes the pure (R,R)-isomers, (R,S)-isomers, (S,R)-isomers and (S,S)-isomers, and mixtures of two or more thereof in any ratio. An example of said isomers is shown below:
Furthermore, the present subject matter includes the pure (R,R)-isomers, (R,S)-isomers, (S,R)-isomers and (S,S)-isomers, and mixtures of two or more thereof in any ratio. An example of said isomers is shown below:
Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:
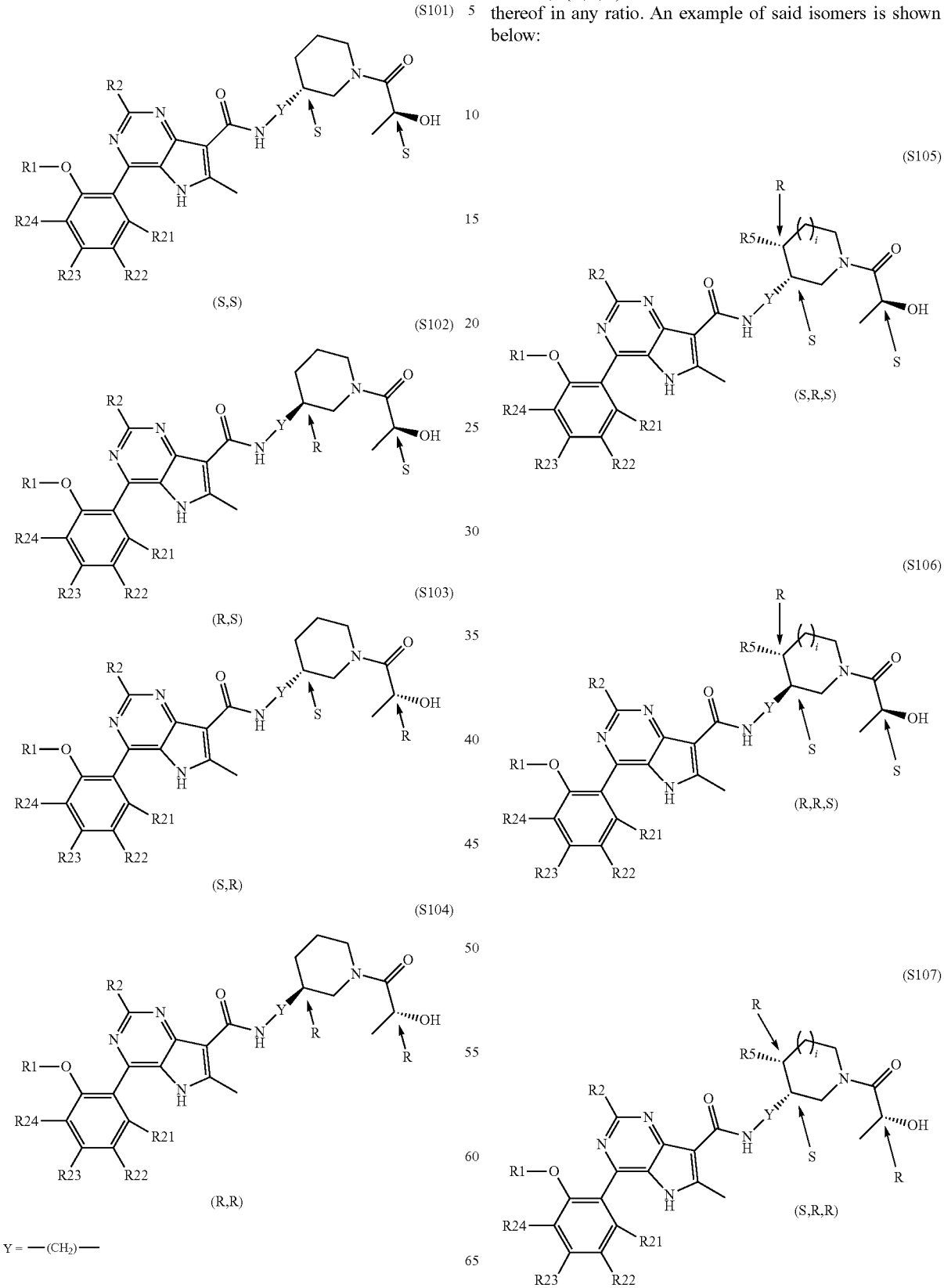

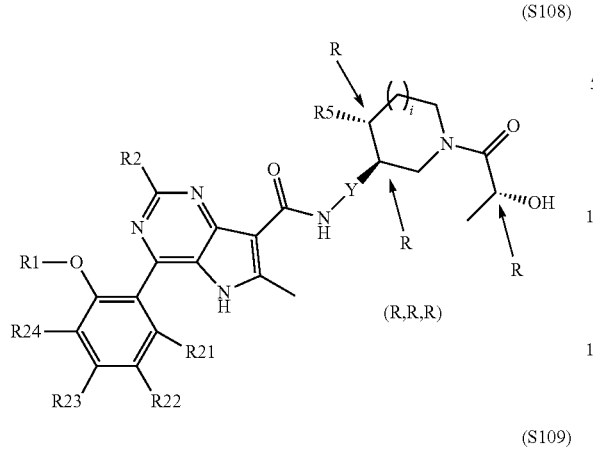
(S108) (R,R,R)
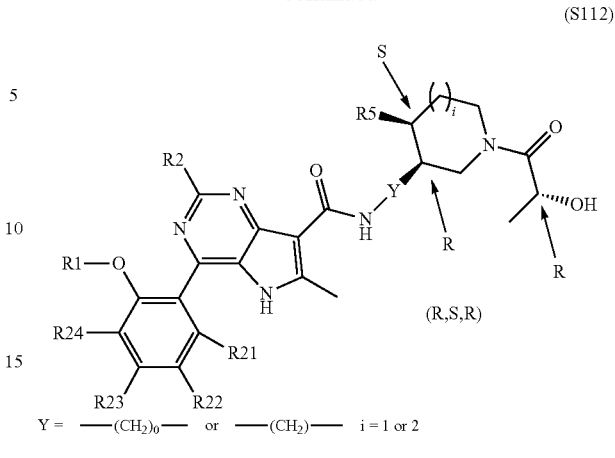
(S112) (R,S,R)
Y = —(CH₂)₀— or —(CH₂)— i = 1 or 2
Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:
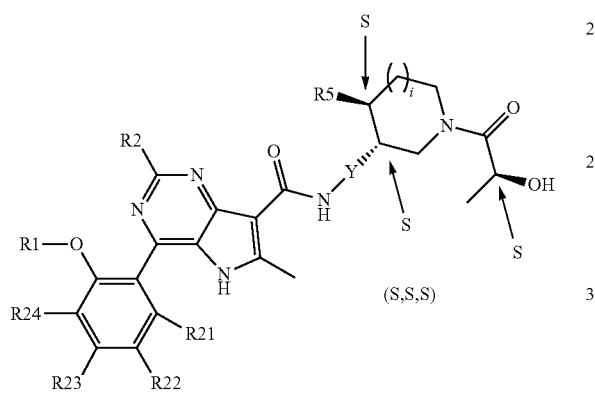
(S109) (S,S,S)
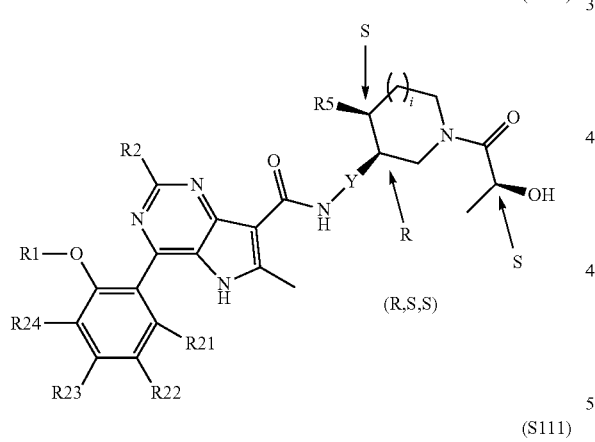
(S110) (R,S,S)
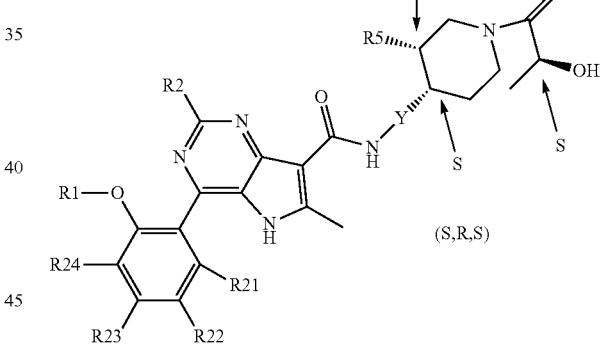
(S113) (S,R,S)
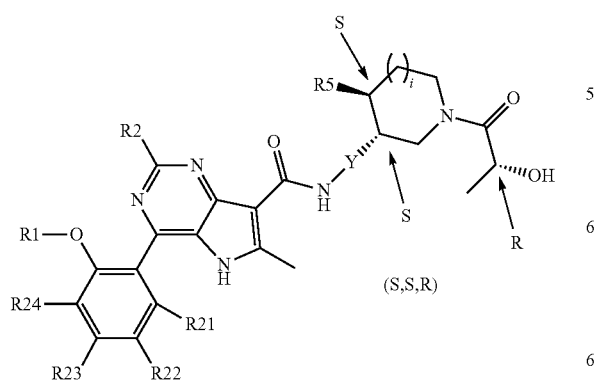
(S111) (S,S,R)
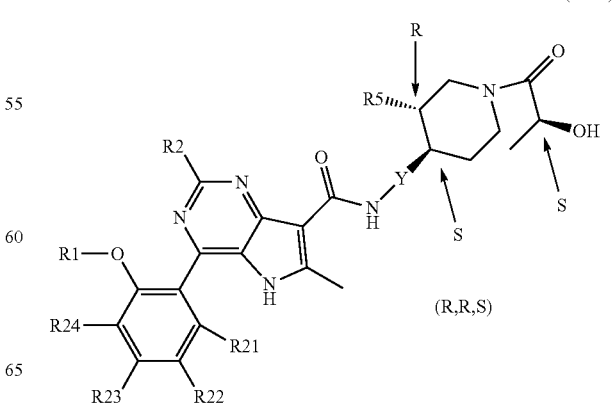
(S114) (R,R,S)

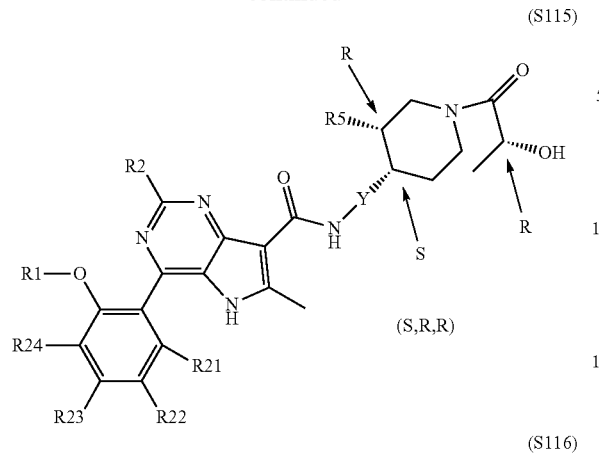
(S115) (S,R,R)
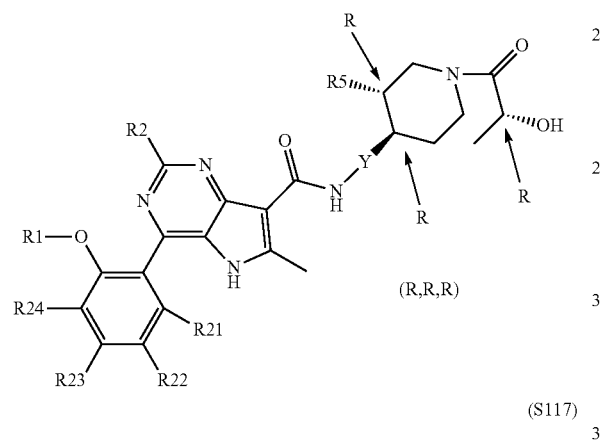
(S116) (R,R,R)
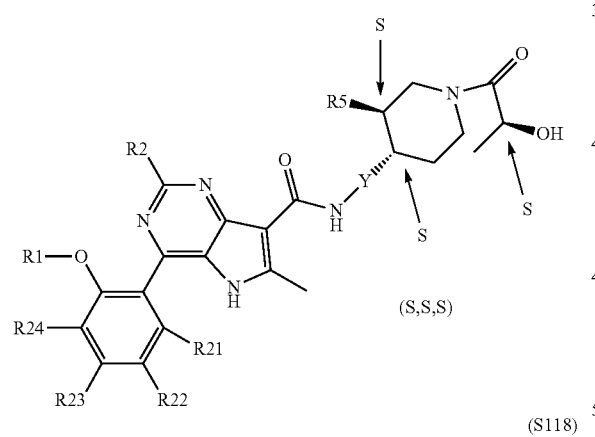
(S117) (S,S,S)
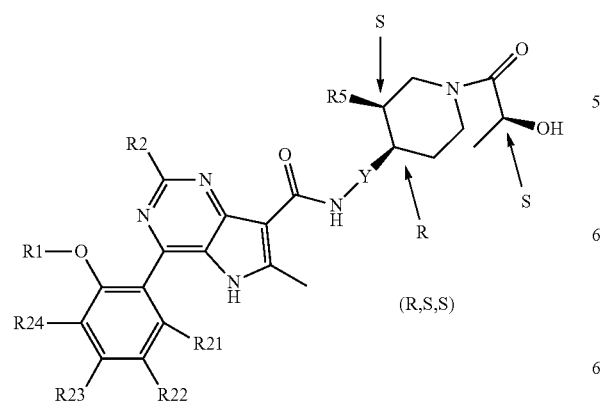
(S118) (R,S,S)
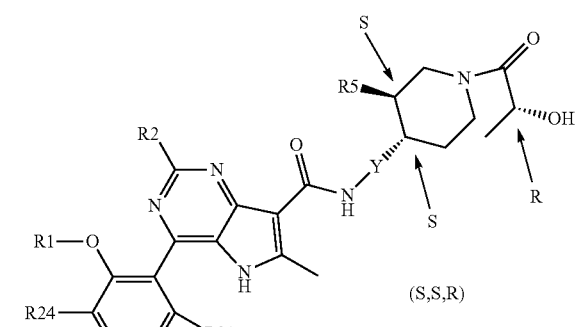
(S119) (S,S,R)
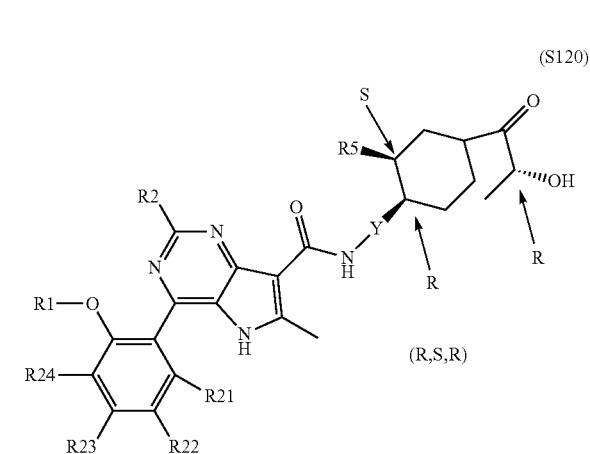
(S120) (R,S,R)
Y = —(CH$_2$)$_0$—
Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:
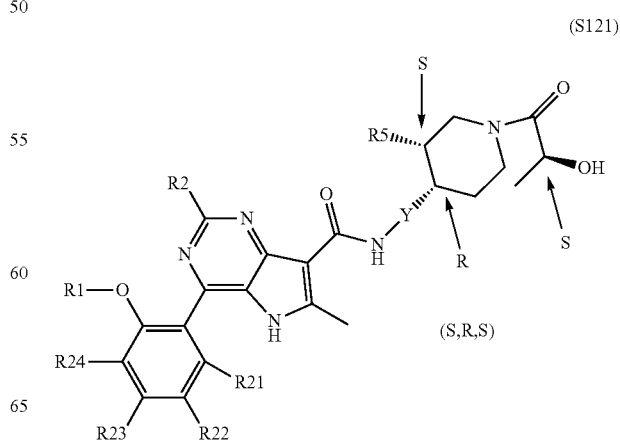
(S121) (S,R,S)

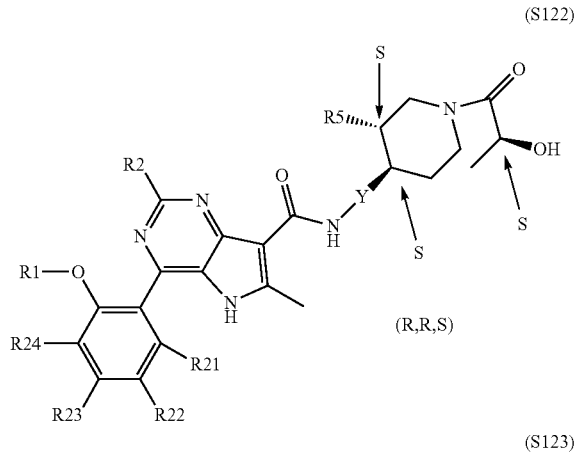
(S122) (R,R,S)
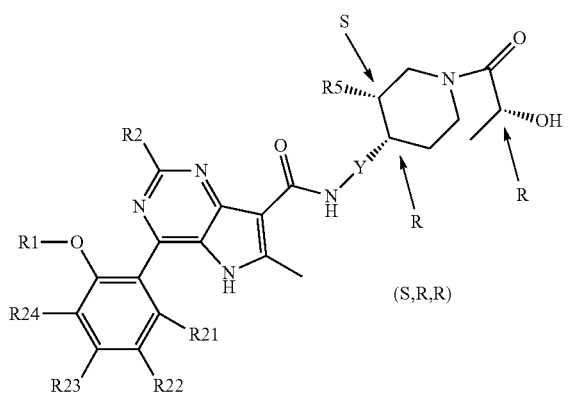
(S123) (S,R,R)
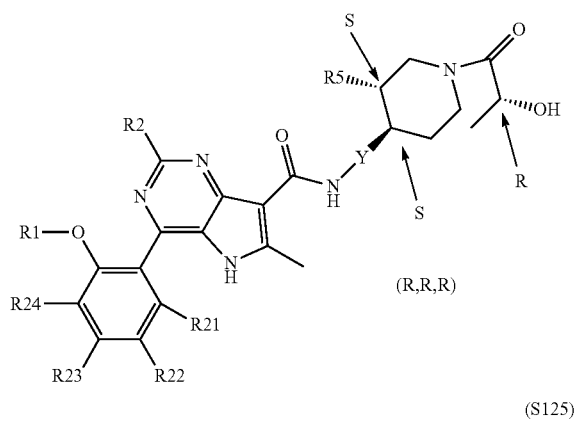
(S124) (R,R,R)
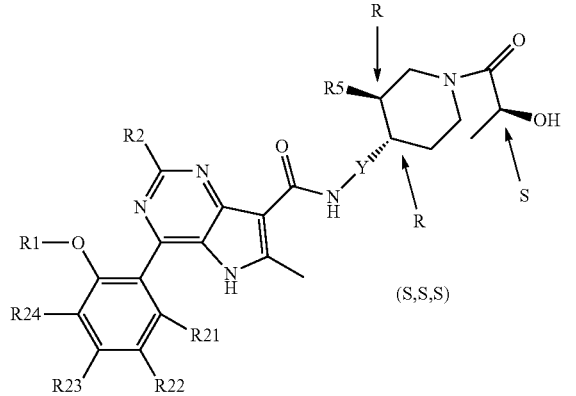
(S125) (S,S,S)
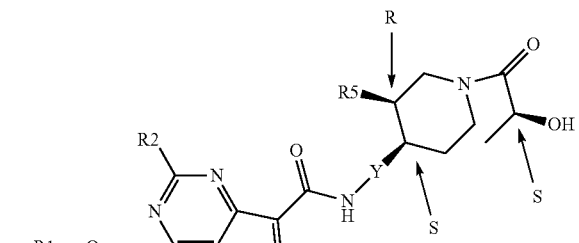
(S126) (R,S,S)
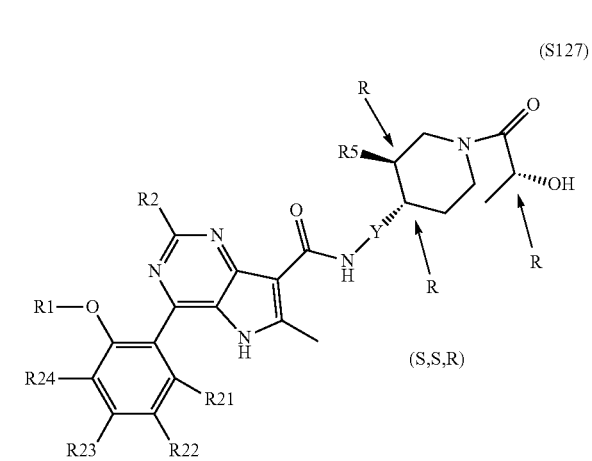
(S127) (S,S,R)
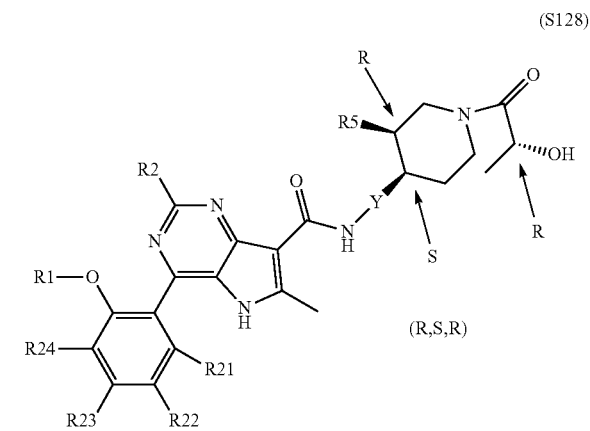
(S128) (R,S,R)
Y = —(CH$_2$)—
Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:

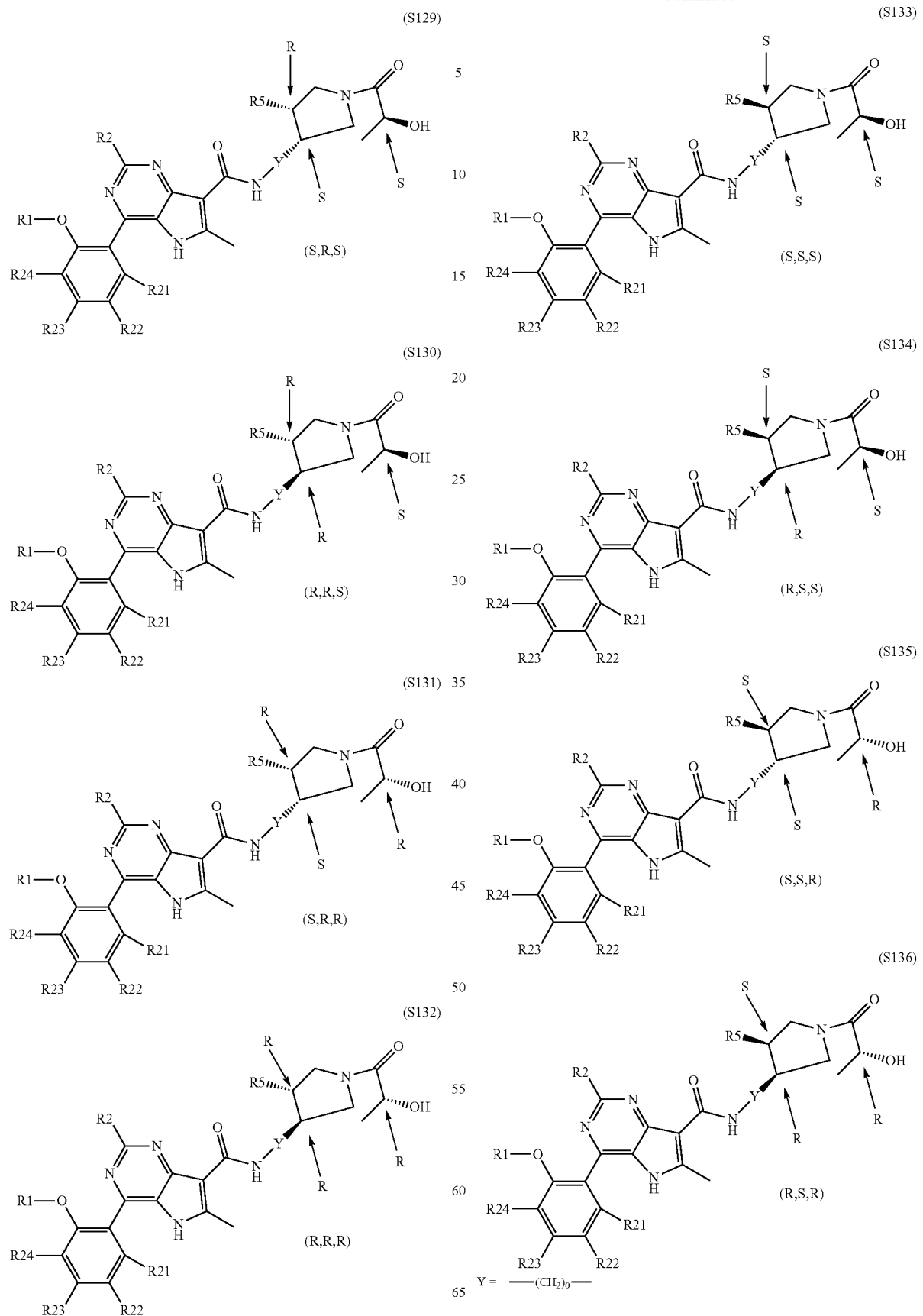

Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:
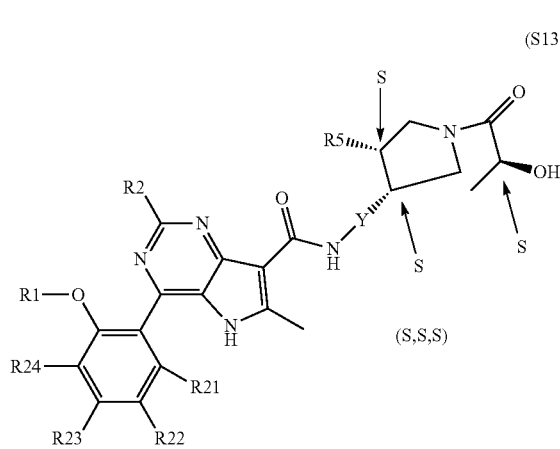
(S137) (S,S,S)
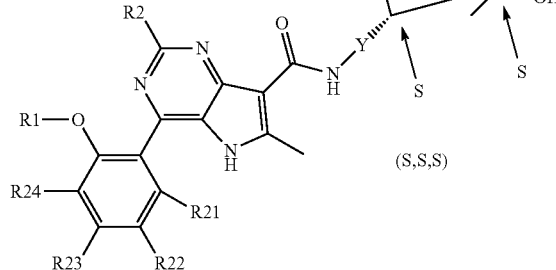
(S138) (R,S,S)
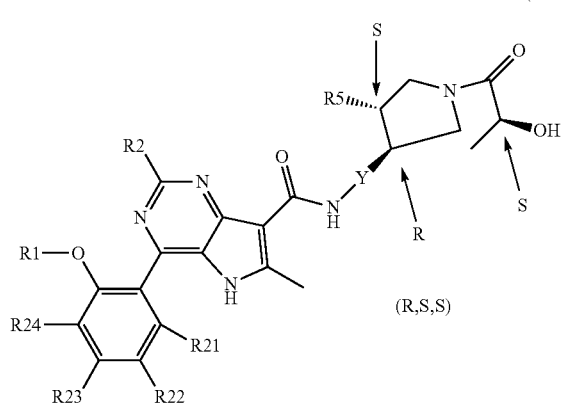
(S139) (S,S,R)
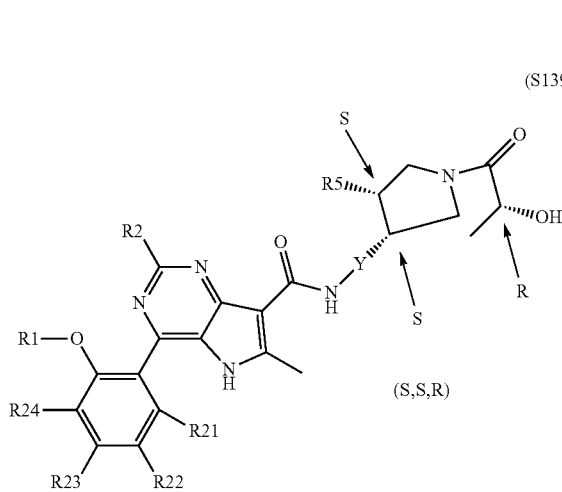
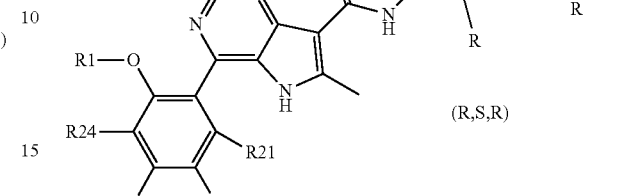
(S140) (R,S,R)
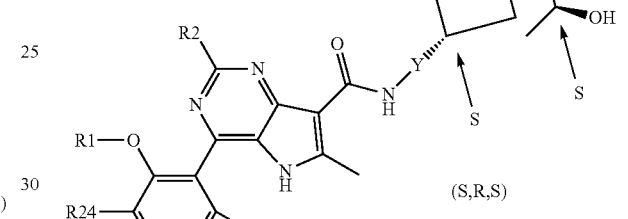
(S141) (S,R,S)
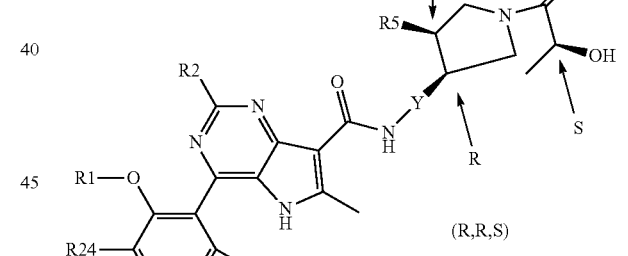
(S142) (R,R,S)
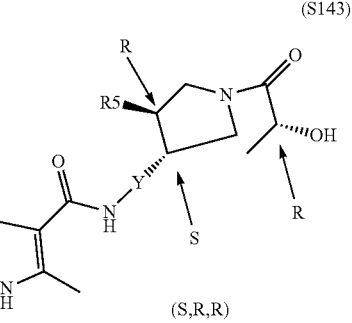
(S143) (S,R,R)

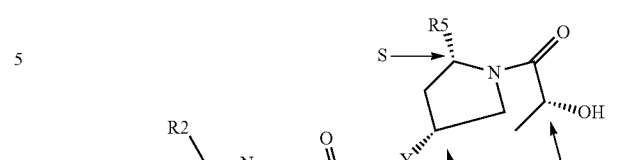
(S147)
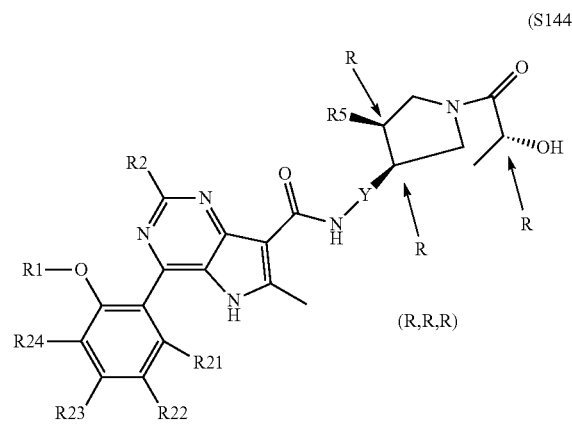
(S144)
Y = ―(CH₂)―
Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:
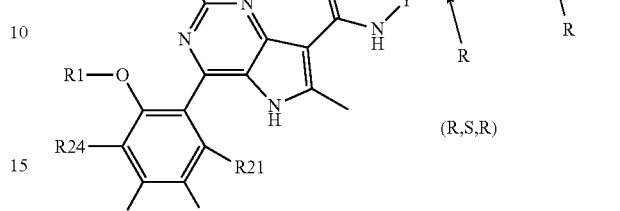
(S148)
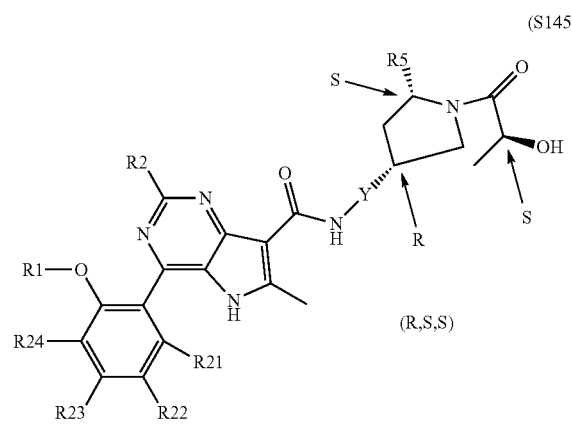
(S145)
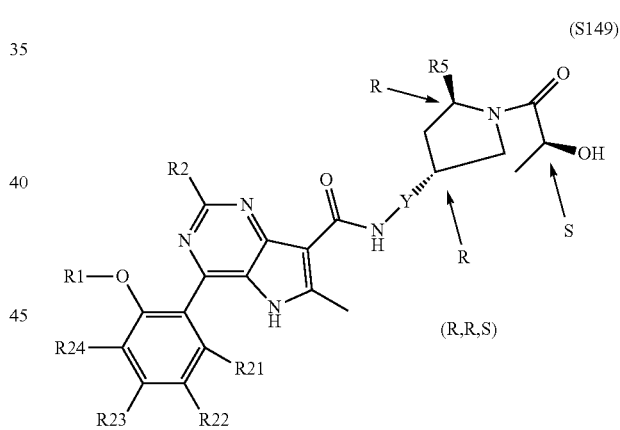
(S149)
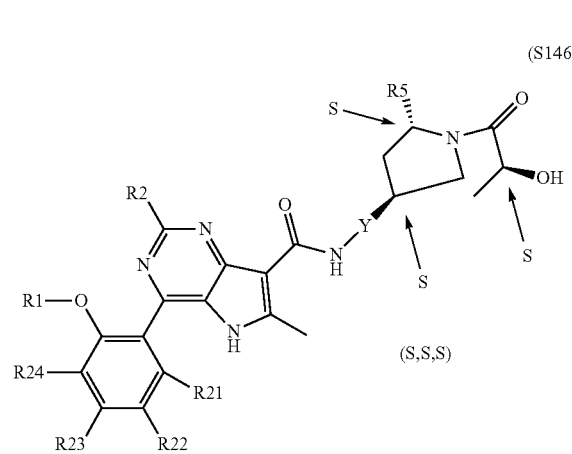
(S146)
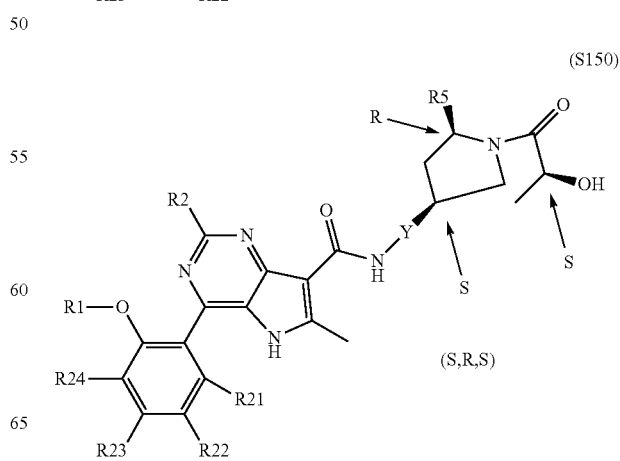
(S150)

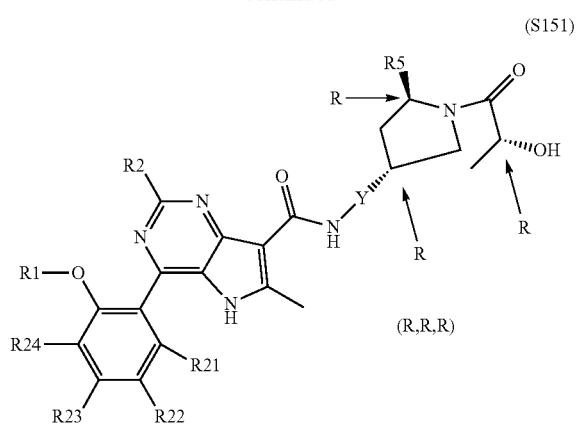
(S151) (R,R,R)
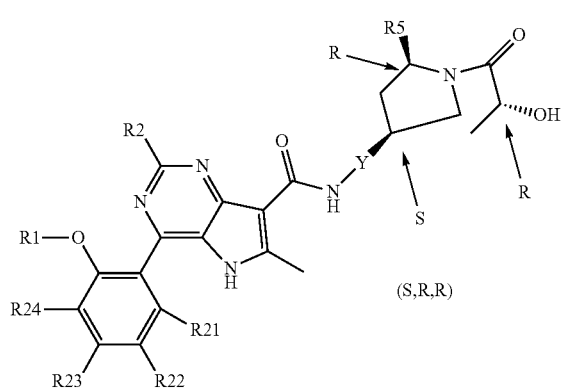
(S152) (S,R,R)
Y = —(CH₂)₀—
Furthermore, the present subject matter includes the pure (S,R,S)-isomers, (R,R,S)-isomers, (S,R,R)-isomers, (R,R,R)-isomers, (S,S,S)-isomers, (R,S,S)-isomers and (S,S,R)-isomers, (R,S,R)-isomers and mixtures of two or more thereof in any ratio. An example of said isomers is shown below:
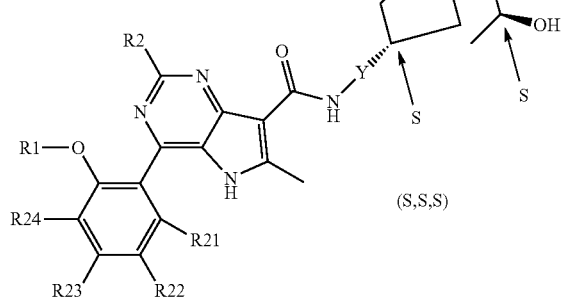
(S153) (S,S,S)
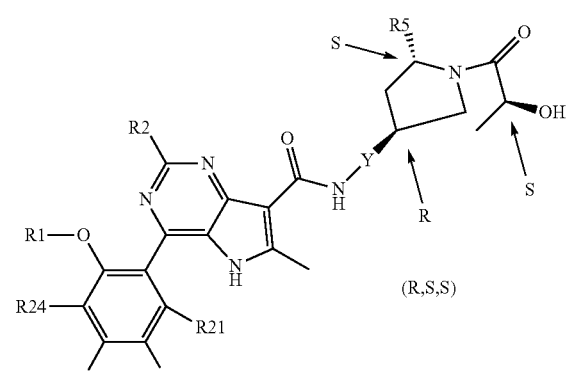
(S154) (R,S,S)
(S155) (S,S,R)
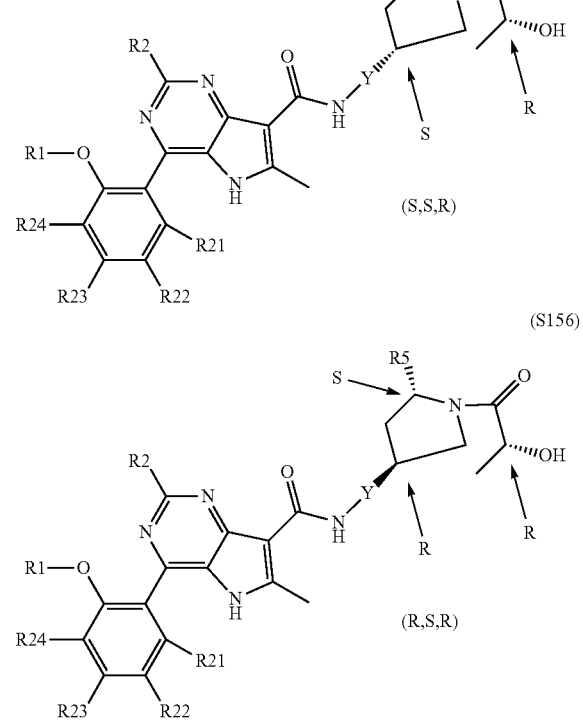
(S156) (R,S,R)
(S157) (S,R,S)

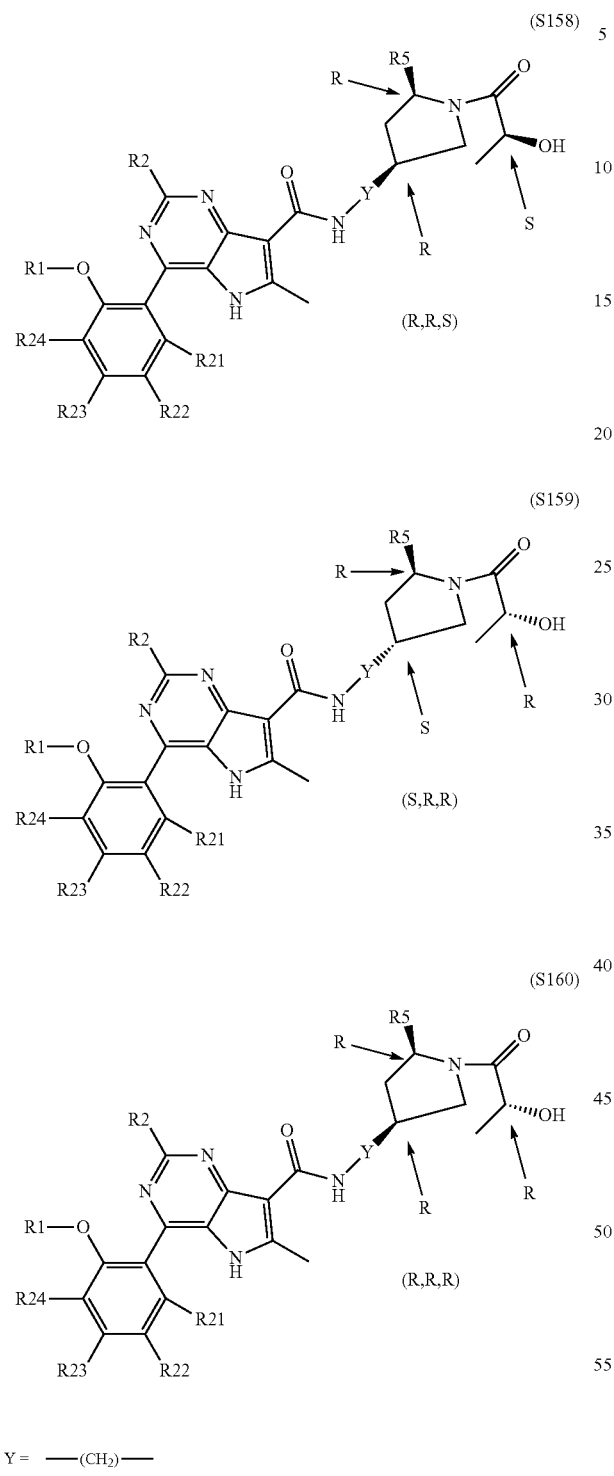

Y = —(CH₂)—

Furthermore, the present subject matter includes the pure (S,S,S,S)-isomers, (S,S,S,R)-isomers, (R,S,S,S)-isomers and (R,S,S,R)-isomers, (S,R,S,S)-isomers, (S,R,S,R)-isomers, (R,R,S,S)-isomers, (R,R,S,R)-isomers, (S,S,R,S)-isomers, (S,S,R,R)-isomers, (R,S,R,S)-isomers, (R,S,R,R)-isomers, (S,R,R,S)-isomers, (S,R,R,R)-isomers, (R,R,R,S)-isomers and (R,R,R,R)-isomers and mixtures of two or more thereof in any ratio, wherein the stereoisomers (S161), (S162), (S165), (S166), (S171), (S172), (S175) and (S176) and mixtures of two or more thereof in any ratio are preferred. An example of said isomers is shown below:

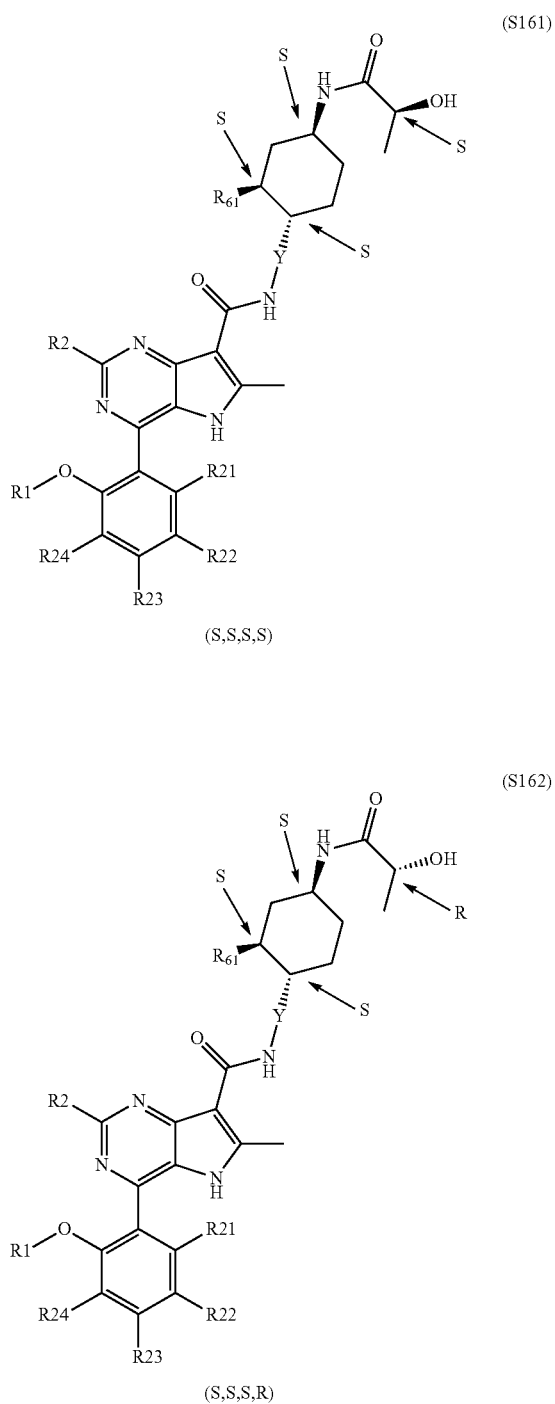

145
-continued
(S163)
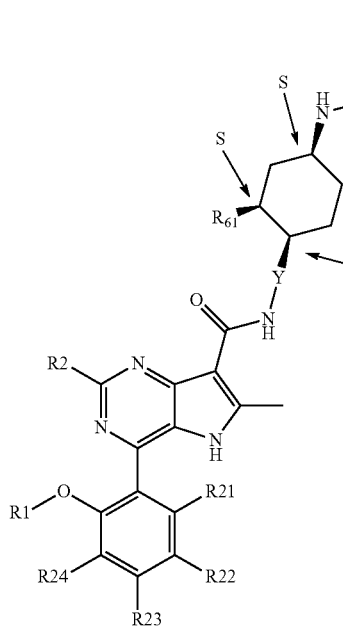
(R,S,S,S)
(S164)
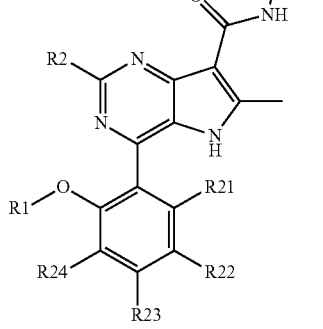
(R,S,S,R)
146
-continued
(S165)
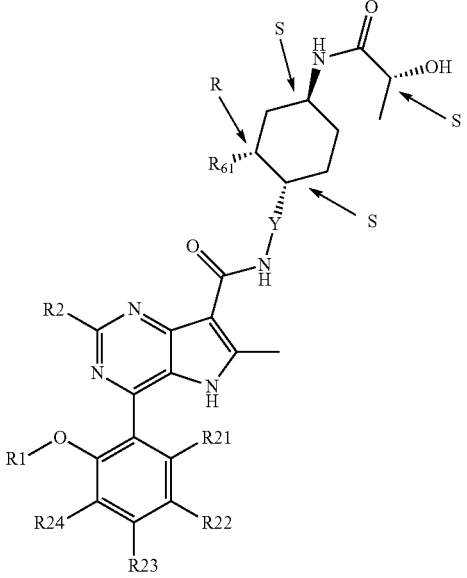
(S,R,S,S)
(S166)
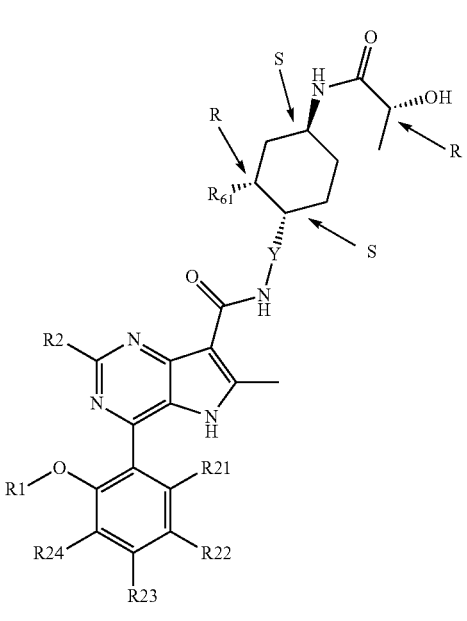
(S,R,S,R)

147
-continued
(S167)
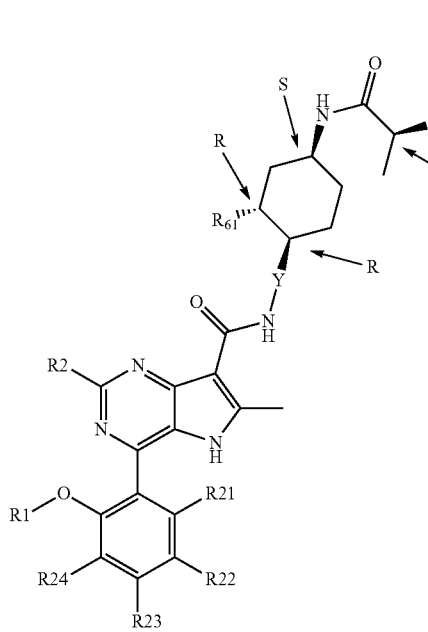
(R,R,S,S)
(S168)
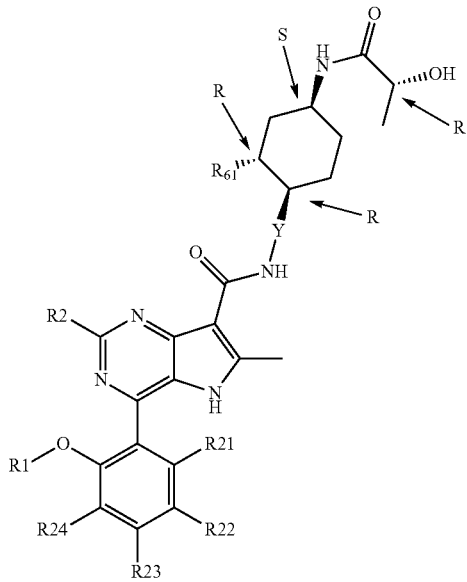
(R,R,S,R)
148
-continued
(S169)
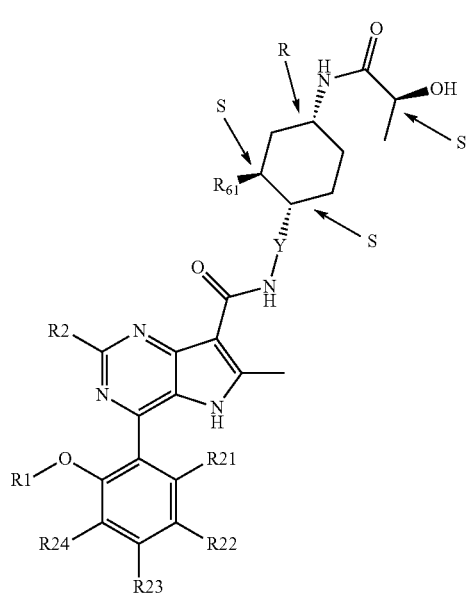
(S,S,R,S)
(S170)
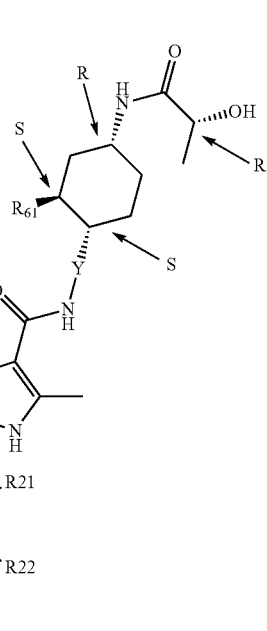
(S,S,R,R)

149
-continued
(S171)
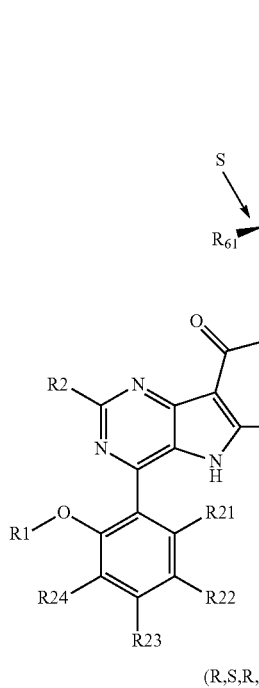
(R,S,R,S)
(S172)
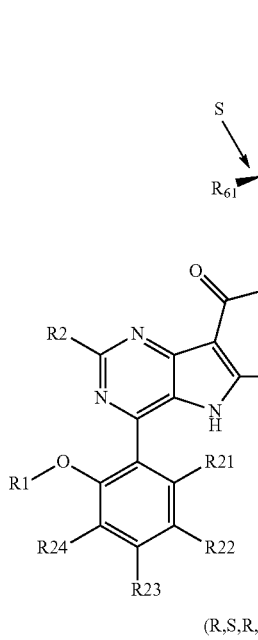
(R,S,R,R)
150
-continued
(S173)
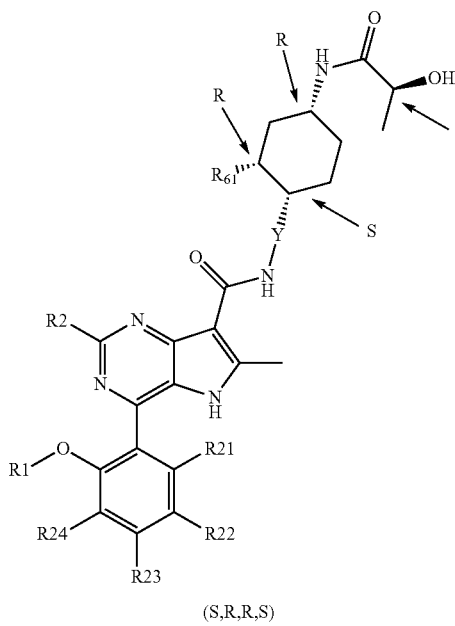
(S,R,R,S)
(S174)
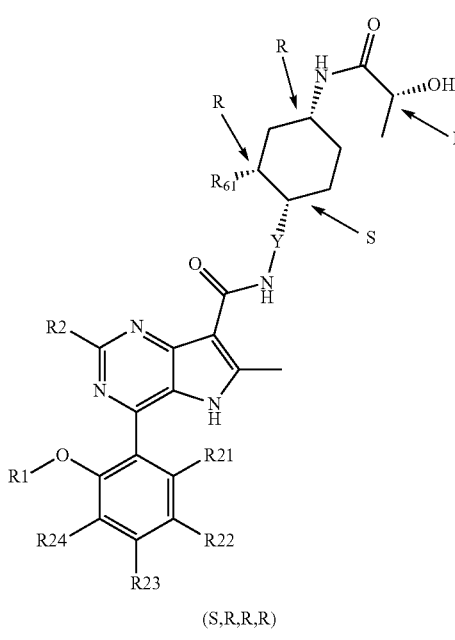
(S,R,R,R)

-continued

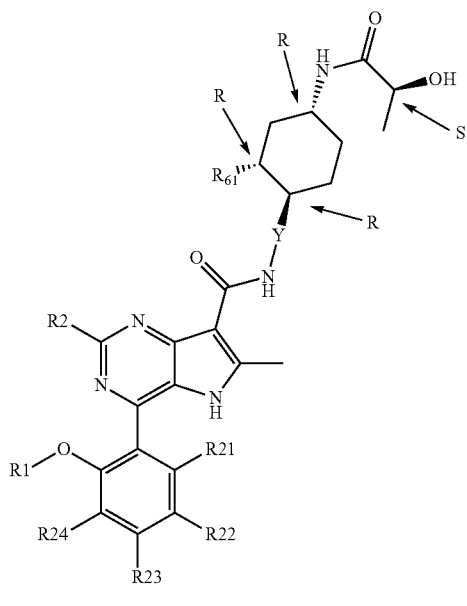

(S175)
(R,R,R,S)

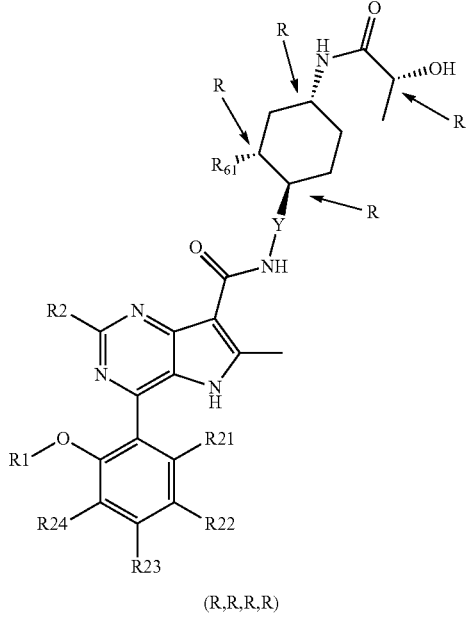

(S176)
(R,R,R,R)

Y = —(CH₂)₀—

Furthermore, the present subject matter includes the pure (S,S,S,S)-isomers, (S,S,S,R)-isomers, (R,S,S,S)-isomers and (R,S,S,R)-isomers, (S,R,S,S)-isomers, (S,R,S,R)-isomers, (R,R,S,S)-isomers, (R,R,S,R)-isomers, (S,S,R,S)-isomers, (S,S,R,R)-isomers, (R,S,R,S)-isomers, (R,S,R,R)-isomers, (S,R,R,S)-isomers, (S,R,R,R)-isomers, (R,R,R,S)-isomers and (R,R,R,R)-isomers and mixtures of two or more thereof in any ratio, wherein the stereoisomers (S177), (S178), (S181), (S182), (S187), (S188), (S191) and (S192) and mixtures of two or more thereof in any ratio are preferred. An example of said isomers is shown below:

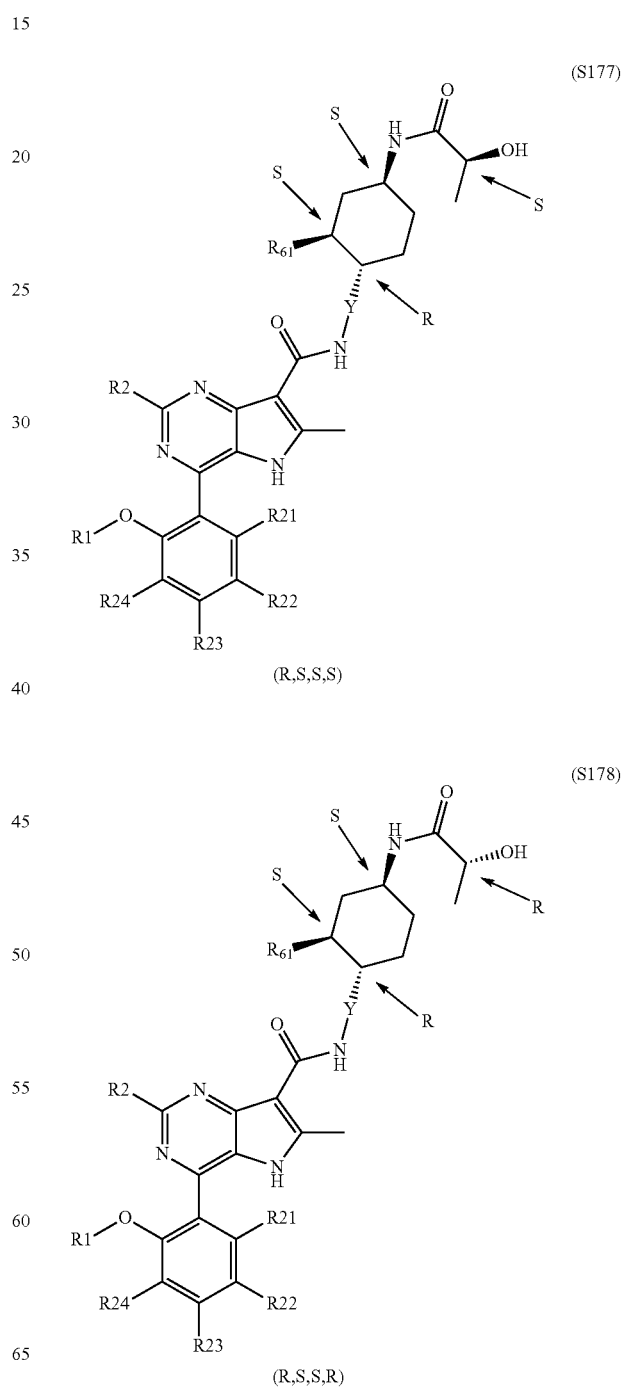

153
-continued
(S179)
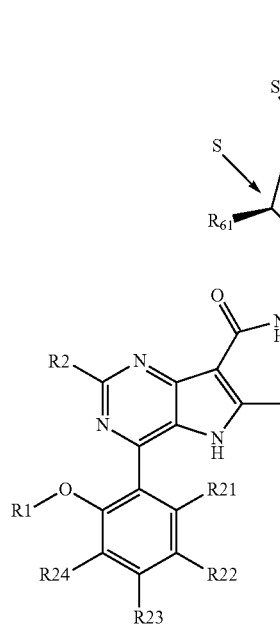
(S,S,S,S)
(S180)
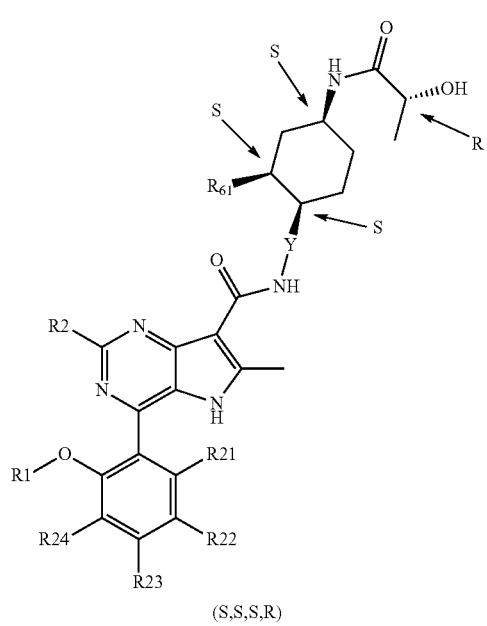
(S,S,S,R)
154
-continued
(S181)
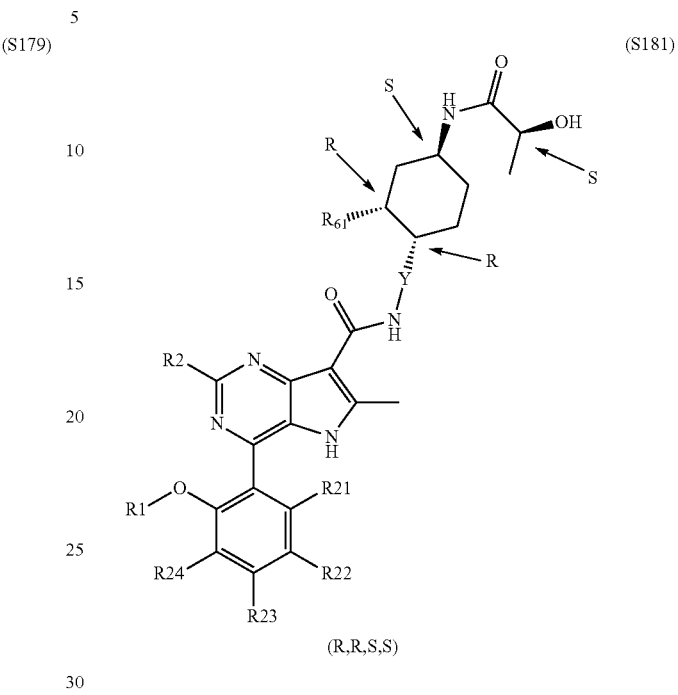
(R,R,S,S)
(S182)
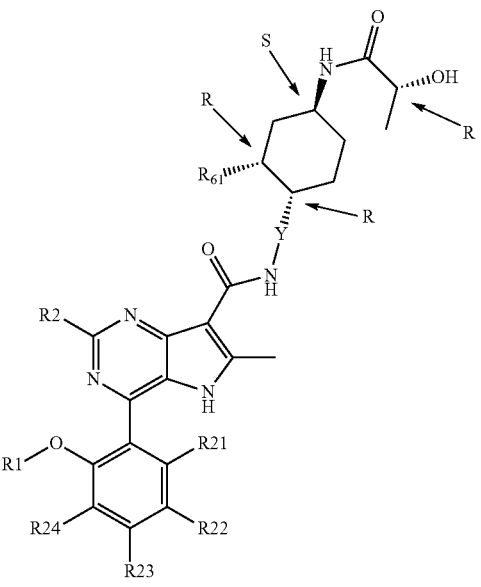
(R,R,S,R)

155
-continued
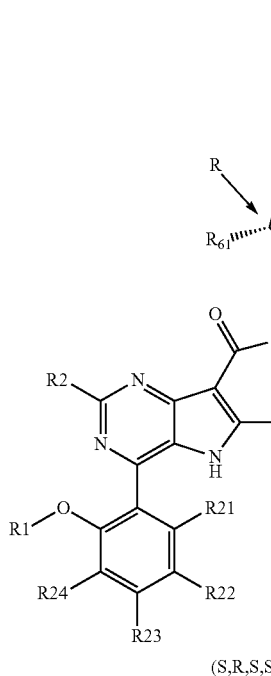
(S183)
(S,R,S,S)
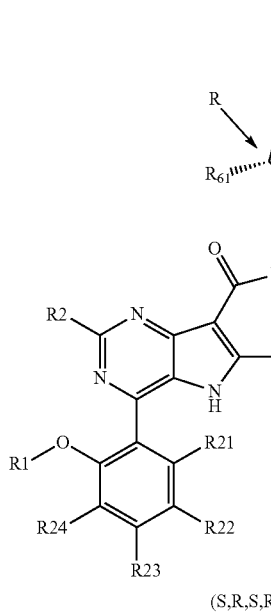
(S184)
(S,R,S,R)
156
-continued
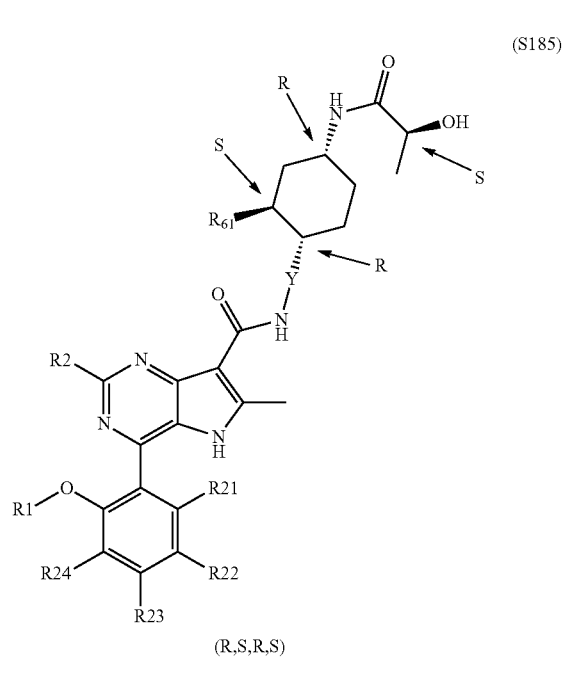
(S185)
(R,S,R,S)
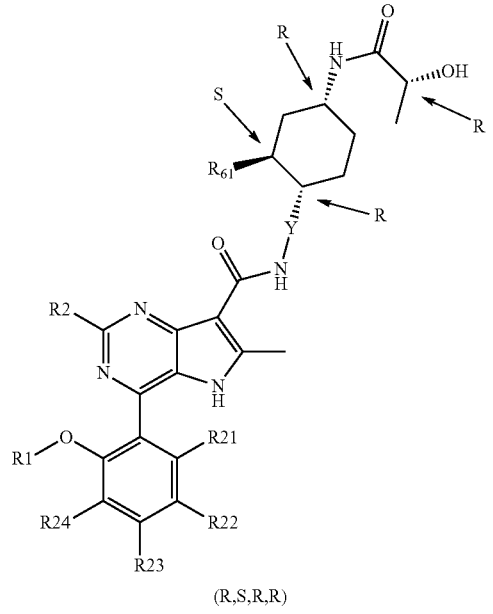
(S186)
(R,S,R,R)

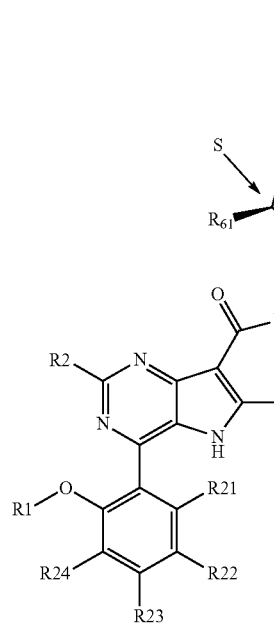
(S187)
(S,S,R,S)
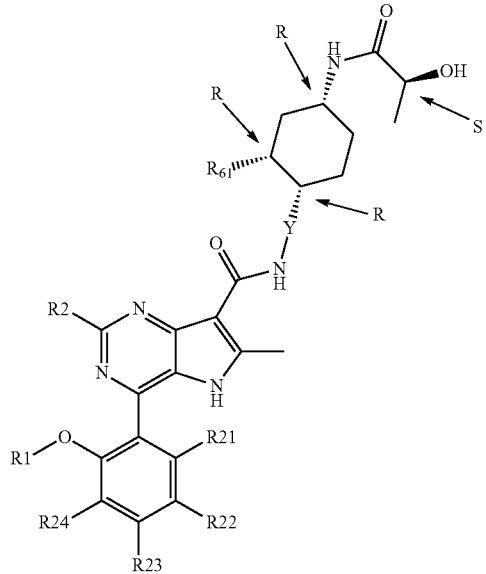
(S189)
(R,R,R,S)
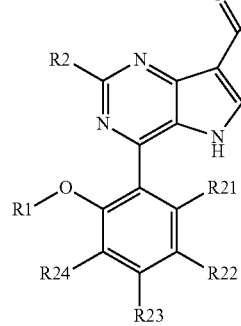
(S188)
(S,S,R,R)
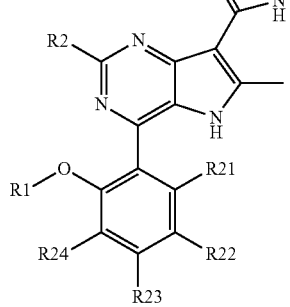
(S190)
(R,R,R,R)

-continued

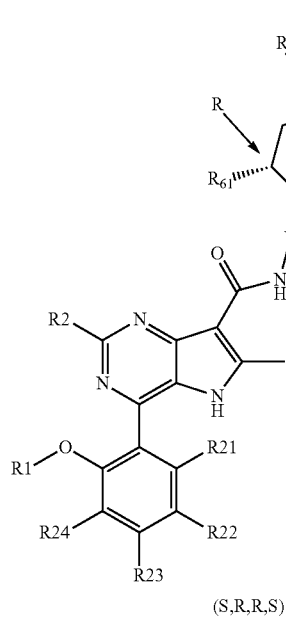

(S,R,R,S)

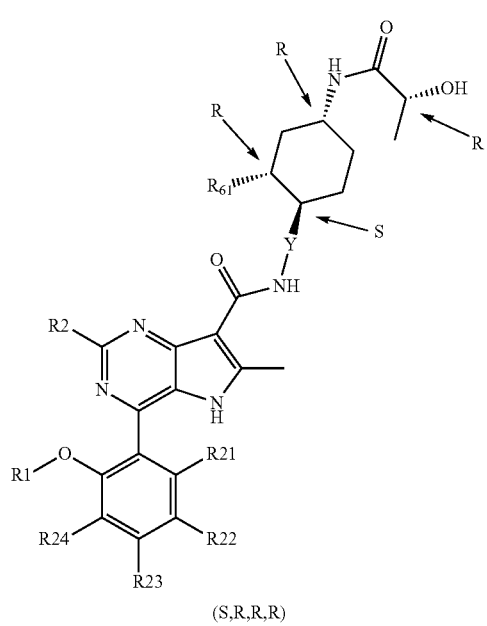

(S,R,R,R)

Y = —(CH₂)—

Furthermore, the present subject matter includes the pure (S,S,S,S)-isomers, (S,S,S,R)-isomers, (R,S,S,S)-isomers and (R,S,S,R)-isomers, (S,R,S,S)-isomers, (S,R,S,R)-isomers, (R,R,S,S)-isomers, (R,R,S,R)-isomers, (S,S,R,S)-isomers, (S,S,R,R)-isomers, (R,S,R,S)-isomers, (R,S,R,R)-isomers, (S,R,R,S)-isomers, (S,R,R,R)-isomers, (R,R,R,S)-isomers and (R,R,R,R)-isomers and mixtures of two or more thereof in any ratio, wherein the stereoisomers (S193), (S194), (S197), (S198), (S203), (S204), (S207) and (S208) and mixtures of two or more thereof in any ratio are preferred. An example of said isomers is shown below:

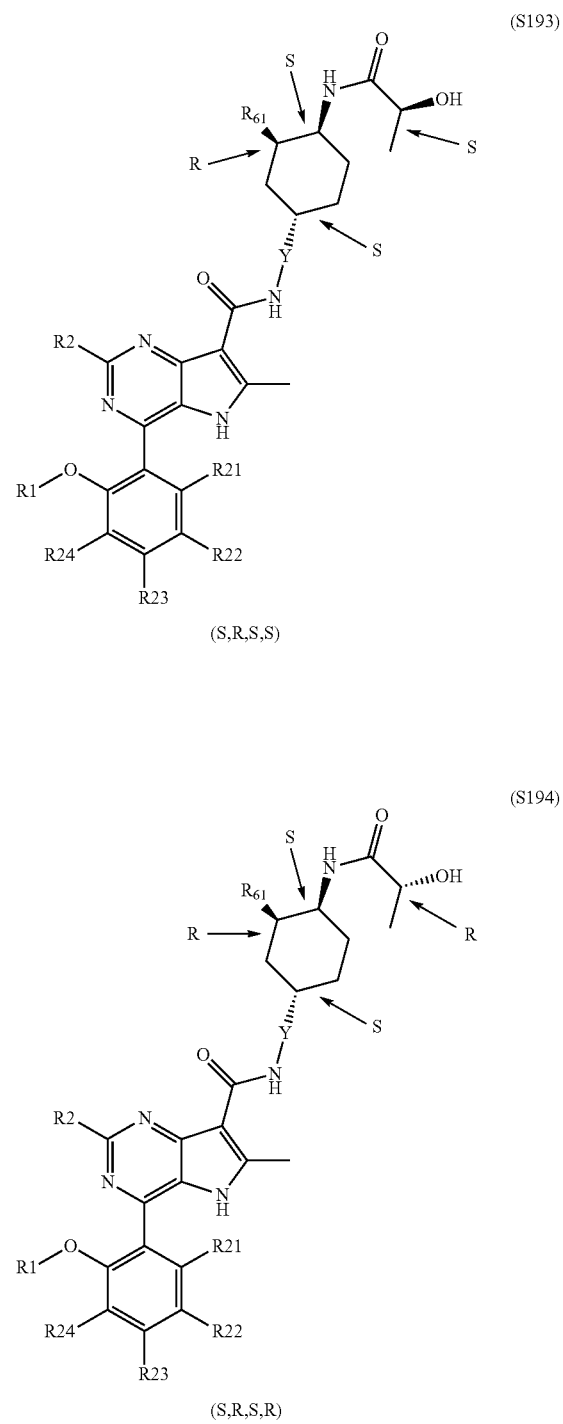

161
-continued
162
-continued
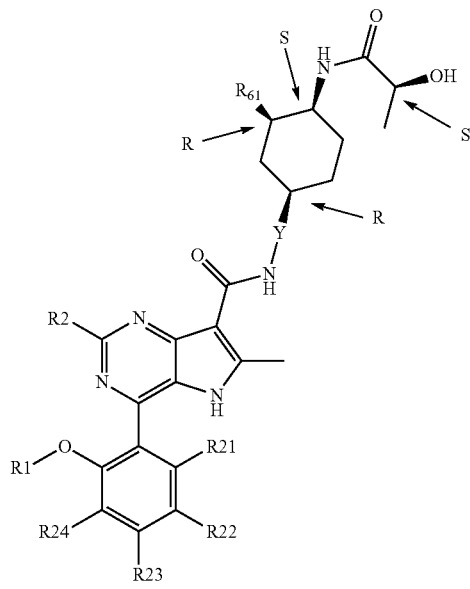
(S195)
(R,R,S,S)
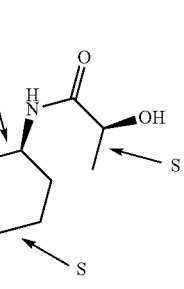
(S197)
(S,S,S,S)
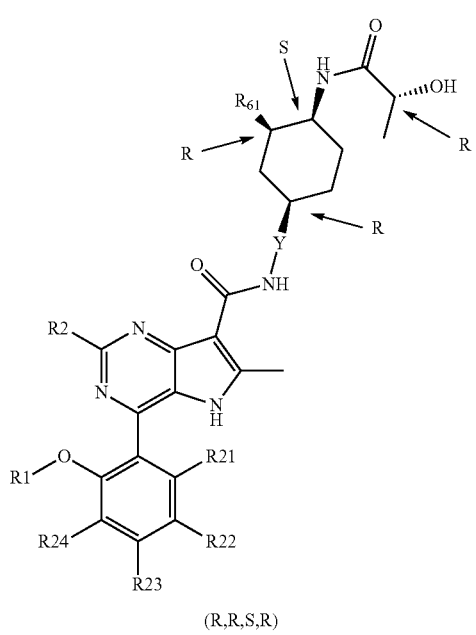
(S196)
(R,R,S,R)
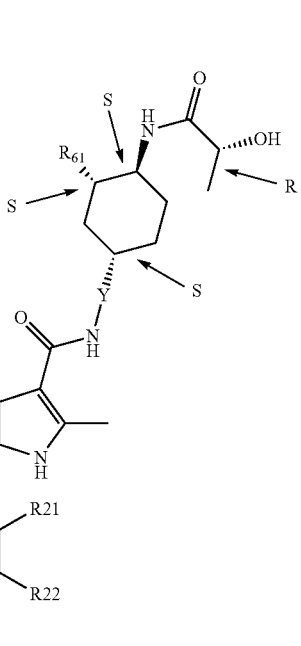
(S198)
(S,S,S,R)

163
-continued
(S199)
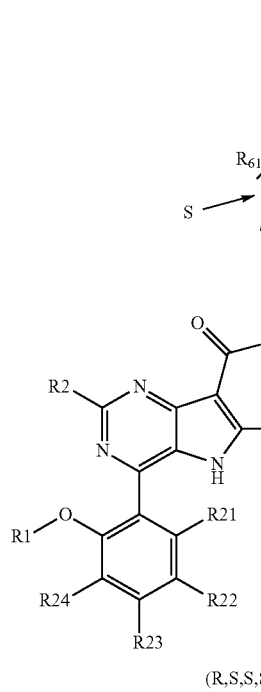
(R,S,S,S)
(S200)
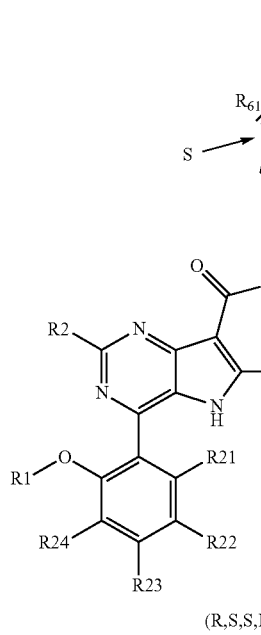
(R,S,S,R)
164
-continued
(S201)
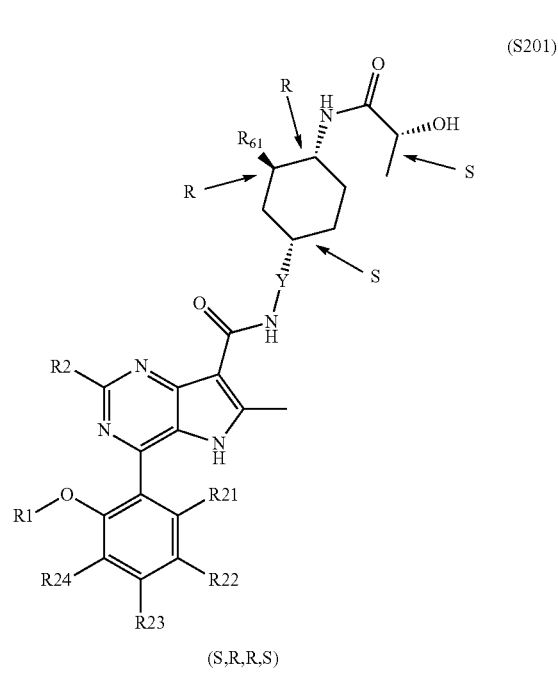
(S,R,R,S)
(S202)
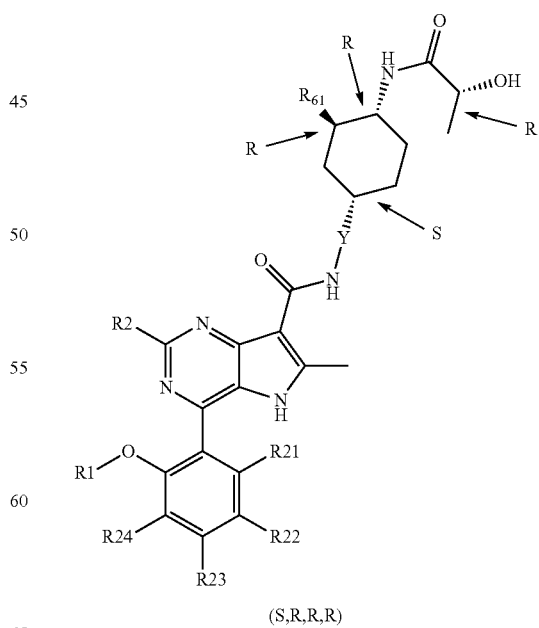
(S,R,R,R)

(S203)
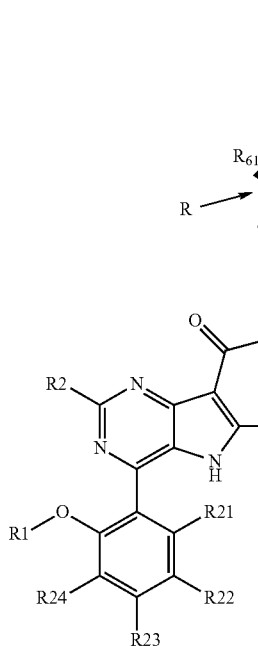
(R,R,R,S)
(S205)
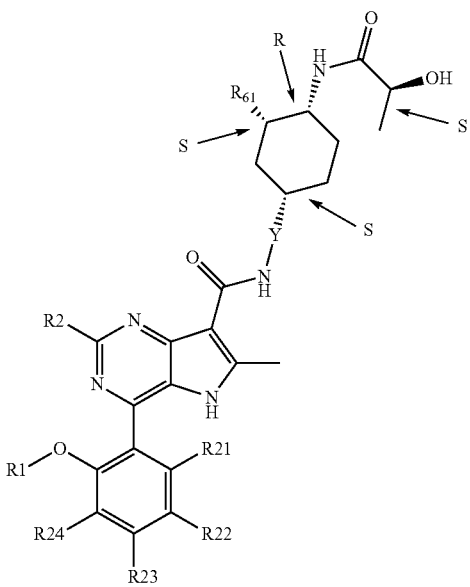
(S,S,R,S)
(S204)
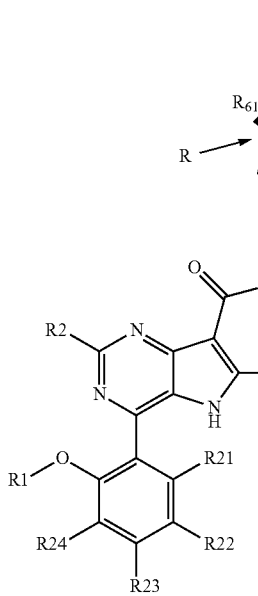
(R,R,R,R)
(S206)
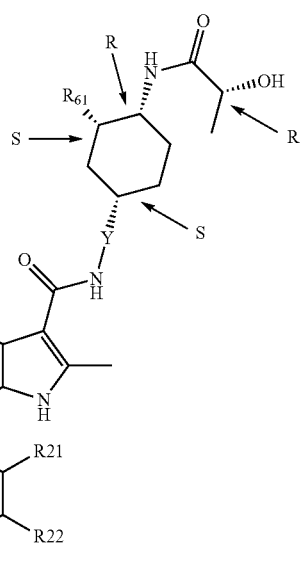
(S,S,R,R)

-continued

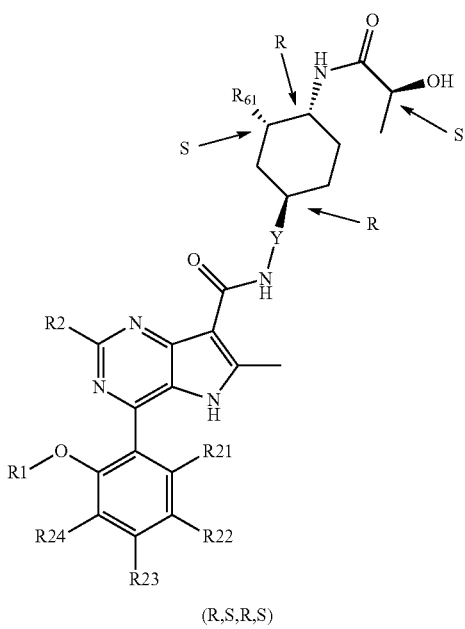

(S207)

(R,S,R,S)

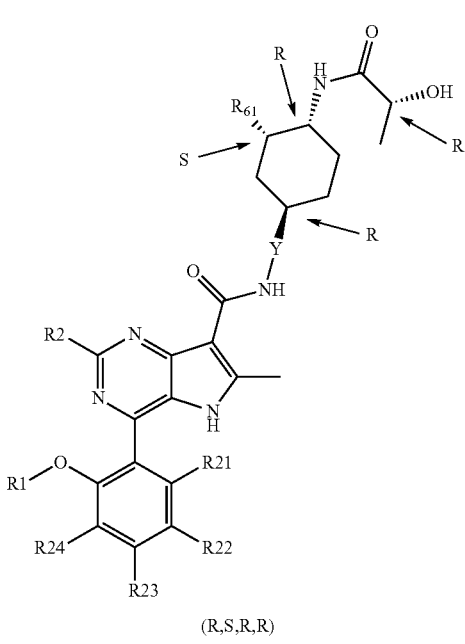

(S208)

(R,S,R,R)

Y = —(CH₂)₀— or —(CH₂)—

Furthermore, derivatives of the compounds according to the present subject matter, the salts thereof, the stereoisomers of the compounds and the salts thereof which are converted into compounds according to the present subject matter, the salts thereof, the stereoisomers of the compounds or the salts thereof in a biological system (bioprecursors or pro-drugs) are covered by the present subject matter. Said biological system is e.g. a mammalian organism, particularly a human subject. The bioprecursor is, for example, converted into the compounds according to the present subject matter, the salts thereof, the stereoisomers of the compounds or the salts thereof by metabolic processes.

The compounds according to the invention can be prepared as follows.

Reaction scheme 1

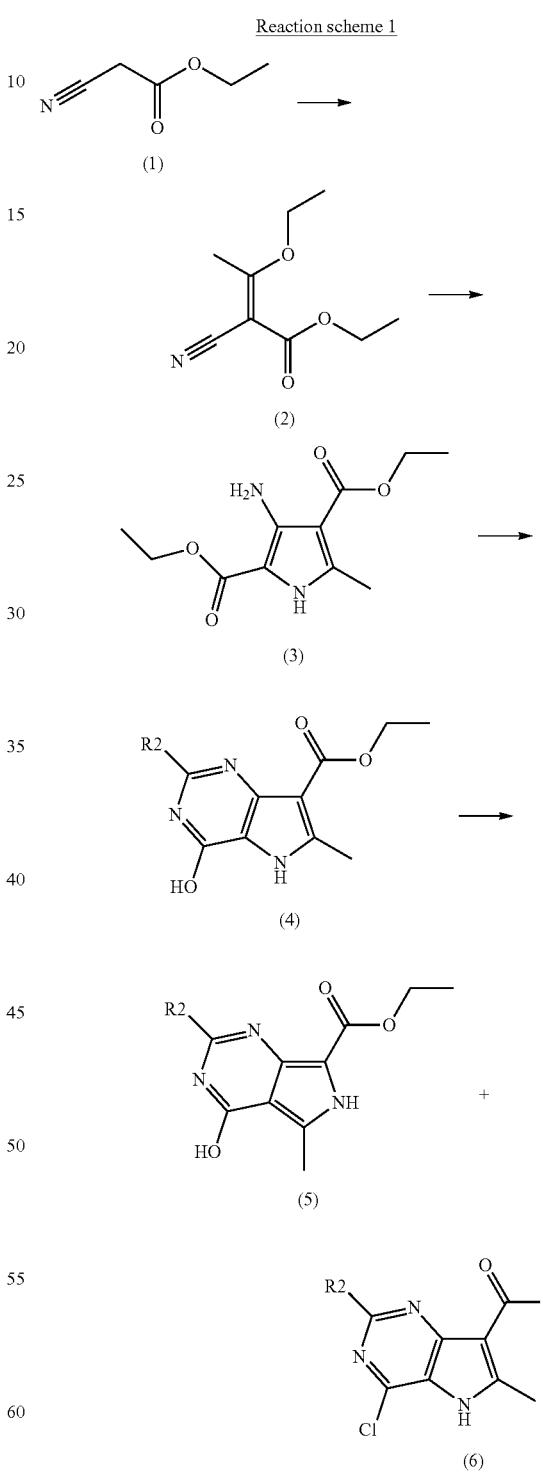

The compound of formula (6) wherein R2 is hydrogen can be obtained as shown in reaction scheme 1 according to the procedures described in US 2005/0124623A1.

Reaction scheme 2

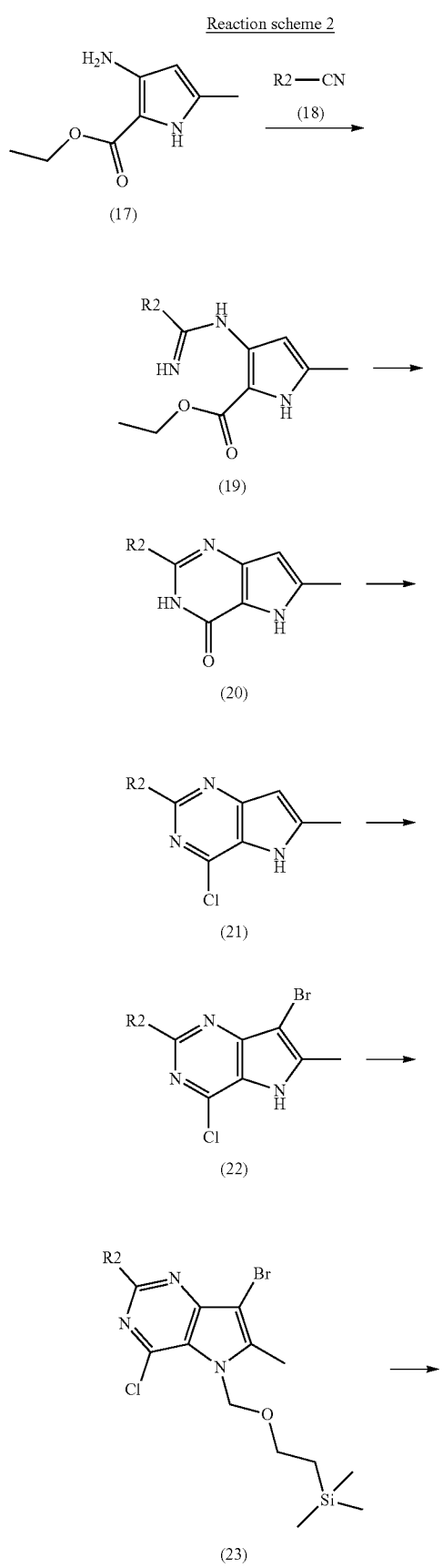

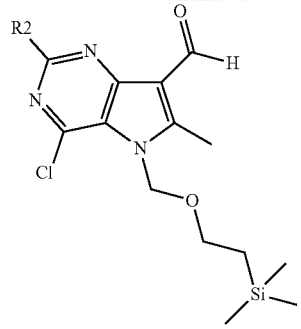

(24)

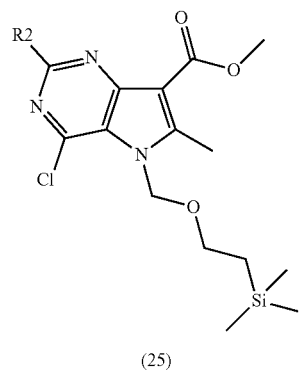

(25)

As shown in reaction scheme 2 synthesis of the compound of formula (25), wherein R2 is methyl may start from the literature known compound of formula (17) [Gangjee, A.; Li, W.; Yang, J.; Kisliuk, R. L.; J. Med. Chem. 2008, 51, 68] by reaction with a nitril of formula (18) in the presence of an acid (preferentially hydrochloric acid) under anhydrous conditions and cyclization of the obtained compound of formula (19) or its salt to the compound of formula (20) wherein R2 is methyl according to the procedures as for example described in Venugopalan, B.; Desai, P. D.; Souza, N.J.; J. Heterocyclic Chem. 1988, 25, 1633. Subsequent reaction of the compound of formula (20) with either neat $POCl_3$ or a solution of $POCl_3$ in an inert organic solvent (preferentially acetonitril) at reflux temperature for 2 h to 24 h and reaction of the obtained compound of formula (21) with for example bromine or N-bromosuccinimide in an organic solvent such as dichloromethane (DCM) at a temperature of from −40 to 20° C. for 0.5 to 4 h gives the compounds of formula (22). The compound of formula (22) thus obtained can then be protected by reaction with a base such as sodium hydride and (2-chloromethoxy-ethyl)-trimethyl-silane in a organic solvent such as dimethoxyethane, dimethylformamide or dimethylsulfoxide at a temperature of from 0° C. to 25° C. for 1 h to 24 h as for example described in Muchowski, J. M.; Solas, D. R.; J. Org: Chem. 1984, 49, 203 to a compound of formula (23).

In an additional step a solution of the compound of formula (23) in an organic solvent, such as tetrahydrofurane can be reacted with n-BuLi (n-butyl lithium) in an organic solvent, such as hexane, at a temperature of −78° C. for 0.5 to 3 h. Subsequently, dimethylformamide (DMF) is added and the reaction is performed at a temperature of from −78 to 0° C. for 0.5 to 3 h, as for example described in WO2008/30119 to yield the compound of formula (24).

Finally a solution of the compound of formula (24) in methanol is treated with $MnO_2$ in the presence of potassium cyanide at ambient temperature for 4 h to 24 h as for example described in Corey, E. J.; Gilman, N. W.; Ganem, B. E.; J. Am. Chem. Soc. 1968, 90, 5616 to give the compound of formula (25).

Reaction scheme 3

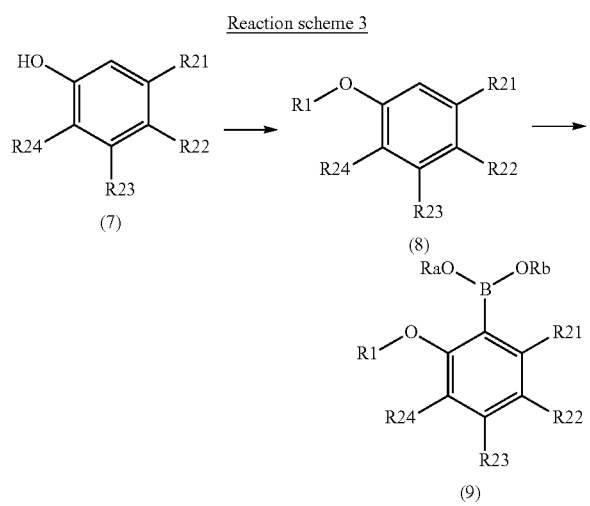

As shown in reaction scheme 3, synthesis of a boronic acid derivative of formula (9) may start from phenols of formula (7) wherein R21, R22, R23 and R24 have the above defined meanings. The phenols of formula (7) are commercially available or can be prepared by methods known to a person skilled in the art. In a first step R1, which has the above defined meaning, may be introduced by alkylation. The alkylation is for example carried out by suspending sodium hydride in an organic solvent, such as dimethylethane (DME) or dimethylsulfoxide (DMSO) or a mixture thereof, adding a solution of compound (7) in an organic solvent, such as DME, at a temperature in the range of from 0 to 40° C., then adding a compound R1-halogen, preferably R1-Br or R1-I, and reacting the mixture at a temperature of from 20 to 80° C. for 1 to 48 h to give a compound of formula (8). In a second step, directed ortho-metalation followed by reaction with a boron electrophile leads to the compounds of formula (9) wherein R1, R21, R22, R23 and R24 have the above defined meanings, and Ra and Rb represent 1-4C-alkyl or hydrogen, preferably Ra and Rb combine to form a straight-chain or branched alkylene group having 2 to 8 carbon atoms, for example without limitation —C(CH$_3$)$_2$—C(CH$_3$)$_2$—. In particular, a solution of compound (8) in an organic solvent, such as tetrahydrofuran (THF), can be reacted with n-butyl lithium (n-BuLi) in an organic solvent, such as hexane, at a temperature of from −78 to 0° C. for 0.5 to 4 h. Subsequently, for example commercially available 2-iso-propoxy-4,4,5,5-tetramethyl-[1,3,2]dioxaborolane is added and the reaction is performed at a temperature of from −78 to 0° C. for 0.5 to 3 h to yield a compound of formula (9).

Reaction scheme 4

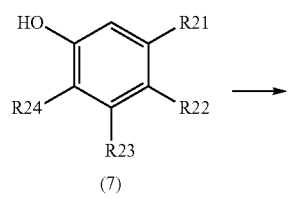

An alternative preparation of compounds of formula (9) is shown in reaction scheme 4. The preparation may start from phenols of formula (7), wherein R21, R22, R23 and R24 have the above or below defined meanings and which are commercially available or can be prepared by methods known to a person skilled in the art or as for example described in Yamamoto, Y.; Hattori, K.; Ishii, J.-I.; Nishiyama, H. Tetrahedron, 2006, 62, 4294. The phenols of formula (7) are for example reacted with bromine or N-bromosuccinimide in an organic solvent such as dichloromethane (DCM) at a temperature of from −40 to 20° C. for 0.5 to 4 h to give compounds of formula (10). In a second step R1, which has the above defined meaning, may be introduced by alkylation. The alkylation is for example carried out by suspending sodium hydride in an organic solvent, such as dimethylethane (DME) or dimethylsulfoxide (DMSO) or a mixture thereof, adding a solution of compound (10) in an organic solvent, such as DME, at a temperature in the range of from 0 to 40° C., then adding a compound R1-halogen, preferably R1-Br or R1-I, and reacting the mixture at a temperature of from 20 to 80° C. for 1 to 48 h leading to compounds of formula (II). In case R22 is difluoromethyl a compound of formula 11, wherein R21, R23, R24 and R1 have the above defined meanings and R22 is CH=O is reacted in an additional step with a fluorinating agent, such as tris(2-methoxyethyl)aminosulfurtrifluoride, in an organic solvent, such as dichloromethane, at elevated temperatures preferably under microwave heating. In a next step, halogen-lithium exchange followed by reaction with a boron electrophile yields the compounds of formula (9), wherein R1, R21, R22, R23 and R24 have the above defined meanings, and Ra and Rb represent 1-4C-alkyl or hydrogen, preferably Ra and Rb combine to form a straight-chain or branched alkylene group having 2 to 8 carbon atoms, for example without limitation —C(CH$_3$)$_2$—C(CH$_3$)$_2$—. In particular, a solution of compound (II) in an organic solvent, such as tert-butylmethylether, can be reacted with n-BuLi (n-butyl lithium) in an organic solvent, such as hexane, at a temperature of from −78 to 0° C. for 0.5 to 3 h. Subsequently, for example commercially available 2-iso-propoxy-4,4,5,5-tetramethyl-[1,3,2]dioxaborolane is added and the reaction is performed at a temperature of from −78 to 0° C. for 0.5 to 3 h to yield a compound of formula (9). Compounds of formula (9), wherein R22 is 1-4C-alkyl-1,3-dioxolane and R1, R21, R23, R24, Ra and Rb have the above defined meanings can be also prepared starting from phenols of formula (7), wherein R22 is —C(O)-1-4C-alkyl and R1, R21, R23 and R24 have the above defined meanings, by acetalisation of compound (II), wherein R22 is —C(O)-1-4C-alkyl and R1, R21, R23 and R24 have the above defined meanings before the halogen-lithium exchange reaction as described above is followed. The acetalisation can be performed by methods known to a person skilled in the art for example by reacting compound (II) in an organic solvent, such as dichloromethane with 1,2-bis(trimethylsilyloxy)-ethane in the presence of a catalytic amount of trimethylsilyl trifluoro-methane sulfonate at a temperature of from 0° C. to 25° C. for 1 to 4 h as for example described in Hwu, J. R.; Wetzel, J. M.; J. Org. Chem. 1985, 50, 3946.

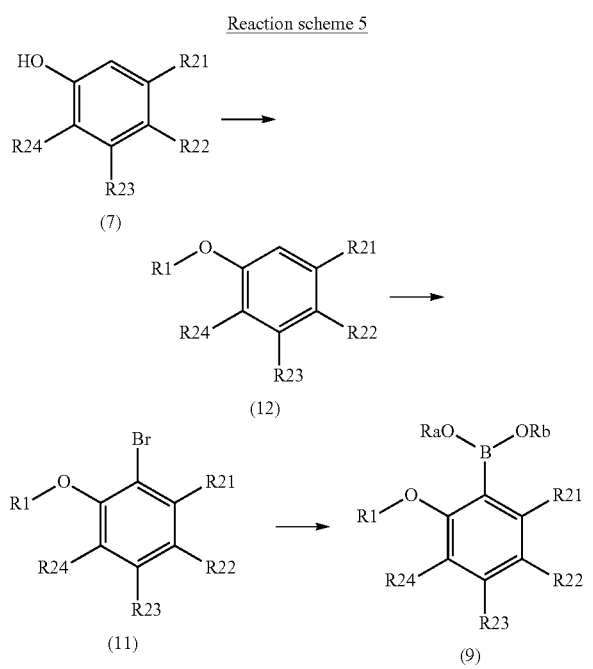

According to a further alternative preparation method shown in reaction scheme 5, synthesis of boronic acid derivatives of formula (9) may start from phenols of formula (7) wherein R21, R22, R23 and R24 have the above defined meanings and which are commercially available or can be prepared by methods known to a person skilled in the art. In a first step R1, which has the above defined meaning, is introduced by alkylation. The alkylation is for example carried out by suspending sodium hydride in an organic solvent, such as dimethylethane (DME) or dimethylsulfoxide (DMSO) or a mixture thereof, adding a solution of compound (7) in an organic solvent, such as DME, at a temperature in the range of from 0 to 40° C., then adding a compound R1-halogen, preferably R1-Br or R1-I, and reacting the mixture at a temperature of from 20 to 80° C. for 1 to 48 h to give a compound of formula (12). In a second step, compound (II) may be prepared for example from compound (12) by reaction with N-bromosuccinimide in an organic solvent, such as dimethylformamide, at a temperature of from 0 to 60° C. for 0.5 to 5 h. In a third step, halogen-lithium exchange followed by reaction with a boron electrophile yields the compounds of formula (9), wherein R1, R21, R22, R23 and R24 have the above defined meanings, and Ra and Rb represent 1-4C-alkyl or hydrogen, preferably Ra and Rb combine to form a straight-chain or branched alkylene group having 2 to 8 carbon atoms, for example without limitation —C(CH$_3$)$_2$—C(CH$_3$)$_2$—. In particular, a solution of compound (II) in an organic solvent, such as tert-butylmethylether, can be reacted with n-BuLi (n-butyl lithium) in an organic solvent, such as hexane, at a temperature of from −78 to 0° C. for 0.5 to 3 h. Subsequently, for example commercially available 2-iso-propoxy-4,4,5,5-tetramethyl-[1,3,2]dioxaborolane is added and the reaction is performed at a temperature of from −78 to 0° C. for 0.5 to 3 h to yield a compound of formula (9). Alternatively, compounds of formula (9) may be synthesized from compounds of formula (II) and an appropriate boron compound, such as bis(pinacolato)diboron, in the presence of a Pd catalyst, such as 1,1'-bis(diphenyl-phosphino)ferrocene palladium-(II)-chloride, and a base, such as potassium acetate, in an organic solvent, such as dioxane, at a temperature of from 20 to 100° C. for 1 to 24 h. The Pd catalyzed preparation of boronic acid derivatives is, for example, described in Murata et al, J Org Chem 2000, 65, 164 and J Org Chem 1997, 62, 6458.

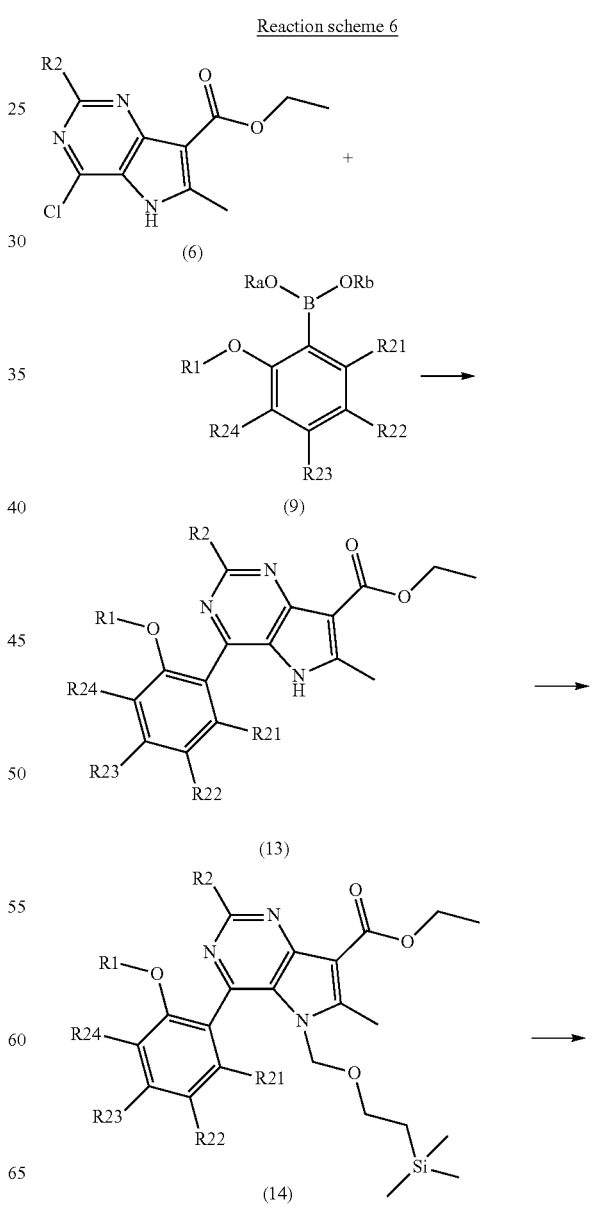

-continued

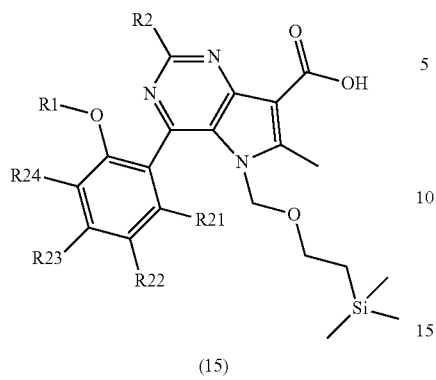

(15)

Reaction scheme 6 illustrates the synthesis of compounds of formula (15) wherein R2 is hydrogen and R1, R21, R22, R23 and R24 have the above defined meanings. In a first step, compound (6) prepared according to reaction scheme 1 can be reacted with a compound of formula (9) prepared according to any of reaction schemes 3, 4 or 5, wherein R1, R21, R22, R23, R24, Ra and Rb have the above defined meanings, to obtain a compound of formula (13). In particular, the compound of formula (6), a base, such as $K_2CO_3$, $Cs_2CO_3$ or $K_3PO_4$, a solvent, such as dimethoxyethane, dioxane or dimethylformamide, a compound of formula (9) and a Pd catalyst, such as $PdCl_2(PCy_3)_2$ (Cy=cyclohexyl), are preferably heated at a temperature in the range of from 60 to 120° C. for 1 to 16 h. The compound of formula (13) thus obtained can then be protected by reaction with a base such as sodium hydride and (2-chloromethoxy-ethyl)-trimethyl-silane in a organic solvent such as dimethoxyethane, dimethylformamide or dimethylsulfoxide at a temperature of from 0° C. to 25° C. for 1 h to 24 h as for example described in Muchowski, J. M.; Solas, D. R.; J. Org: Chem. 1984, 49, 203 to a compound of formula (14). The compound of formula (14) is reacted with an alkali hydroxide, such as LiOH, in a solvent, preferably a mixture of an organic solvent, such as dioxane, and water, at a temperature in the range of from 20 to 100° C. for 1 to 48 h to yield a compound of formula (15).

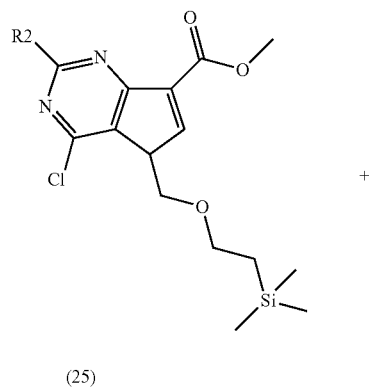

(25)

-continued

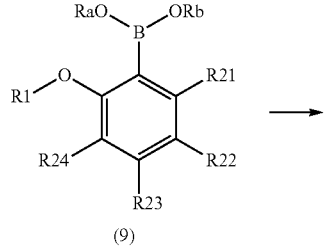

(9)

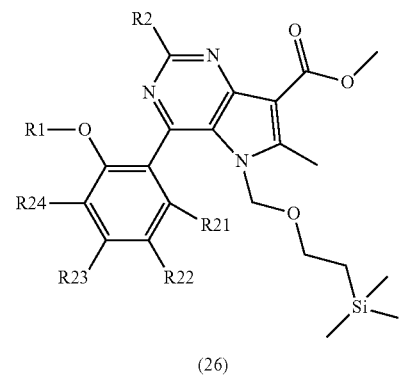

(26)

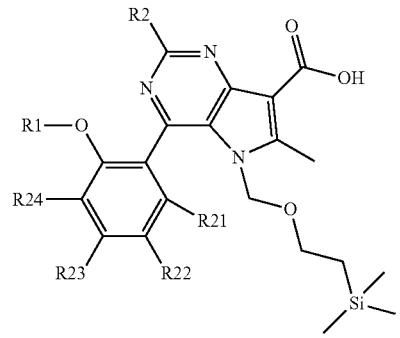

(15)

Reaction scheme 7 illustrates the synthesis of compounds of formula (15) wherein R2 is methyl and R1, R2, R21, R22, R23 and R24 have the above defined meanings. In a first step, compound (25) prepared according to reaction scheme 2 can be reacted with a compound of formula (9) prepared according to any of reaction schemes 3, 4 or 5, wherein R1, R21, R22, R23, R24, Ra and Rb have the above defined meanings, to obtain a compound of formula (26). In particular, the compound of formula (25), a base, such as $K_2CO_3$, $Cs_2CO_3$ or $K_3PO_4$, a solvent, such as dimethoxyethane, dioxane or dimethylformamide, a compound of formula (9) and a Pd catalyst, such as $PdCl_2(PCy_3)_2$ (Cy=cyclohexyl), are preferably heated at a temperature in the range of from 60 to 120° C. for 1 to 16 h. The compound of formula (26) thus obtained is reacted with an alkali hydroxide, such as LiOH, in a solvent, preferably a mixture of an organic solvent, such as dioxane, and water, at a temperature in the range of from 20 to 100° C. for 1 to 48 h to yield a compound of formula (15).

Reaction scheme 8

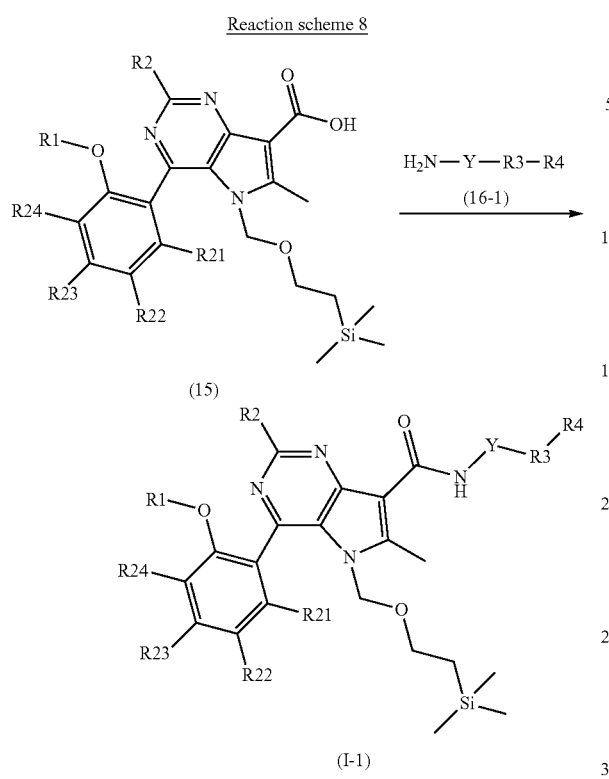

As shown in reaction scheme 8, starting from compounds of formula (15) prepared according to any of reaction schemes 6 or 7, compounds of formula (I-1), wherein R1, R2, R21, R22, R23, R24 and Y have the above defined meanings and R3 is a 4- to 7-membered saturated heterocyclic ring containing one nitrogen atom and optionally one oxygen atom, said heterocyclic ring being substituted by R4 and optionally substituted by one or two substituents R5, wherein R5 has the above defined meaning and R4 being —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, with R41, R42 and R43 having the above defined meanings, can be prepared by reaction with compounds of formula (16-1), wherein Y has the above defined meaning and R3 is a 4- to 7-membered saturated heterocyclic ring containing one nitrogen atom and optionally one oxygen atom, said heterocyclic ring being substituted by R4 and optionally substituted by one or two substituents R5, wherein R5 has the above defined meaning and R4 being —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, with R41, R42 and R43 having the above defined meanings, under standard amide bond forming conditions. The compounds of formula (16-1) are commercially available or can be prepared by methods known to a person skilled in the art or as described in reaction scheme 16. In particular, a dehydrating agent, such as 1-(3-dimethylaminopropyl)-3-ethylcarbodiimide hydrochloride, a base, such as triethylamine, and a catalyst, such as 1-hydroxybenzotriazole, can be added to a compound of formula (15) which is preferably dissolved or suspended in an organic solvent, e.g. dichloromethane. After stirring the mixture e.g. for 0.3 to 2 h, preferably at ambient temperature (e.g. 20 to 25° C.), a compound of formula (16-1) can be added and the reaction is preferably performed at ambient temperature (e.g. 20 to 25° C.) for 1 to 48 h to yield the compound of formula (I-1).

Reaction scheme 9

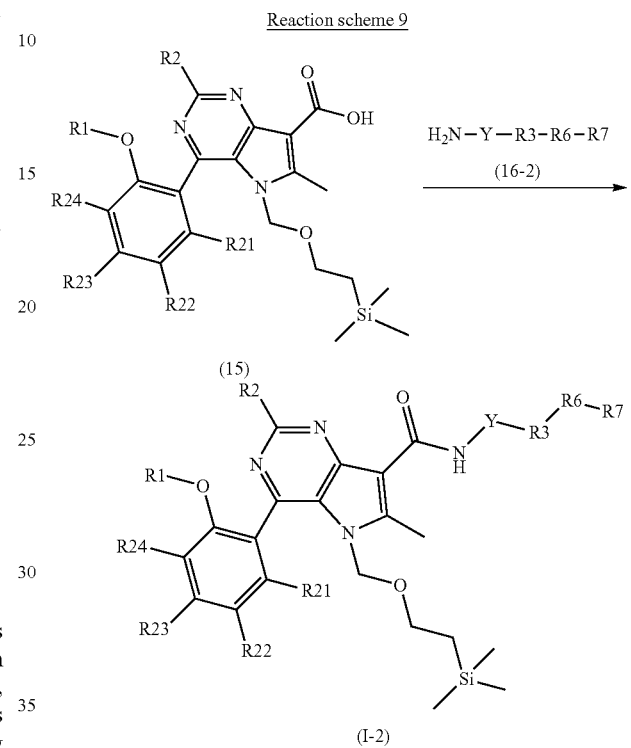

As shown in reaction scheme 9, compounds of formula (I-2), wherein R1, R2, R21, R22, R23, R24 and Y have the above defined meanings and R3 is a 3-6C-cycloalkyl group substituted by R6 and optionally substituted by R61, with R6 being —NH—C(O)—R7 and R7 being 1-4C-alkyl, which is optionally substituted by R71, 3-6C-cycloalkyl, which is optionally substituted by R72, or 1-4C-alkoxy, which is optionally substituted by R73, with R61, R71, R72 and R73 having the above defined meanings can be synthesized by reaction of compounds of formula (15) prepared according to any of reaction schemes 6 or 7, with compounds of formula (16-2), wherein Y has the above defined meaning and R3 is a 3-6C-cycloalkyl group substituted by R6 and optionally substituted by R61, with R6 being —NH—C(O)—R7 and R7 being 1-4C-alkyl, which is optionally substituted by R71, 3-6C-cycloalkyl, which is optionally substituted by R72, or 1-4C-alkoxy, which is optionally substituted by R73, with R61, R71, R72 and R73 having the above defined meanings. The compounds of formula (16-2) are commercially available or can be prepared by methods known to a person skilled in the art or can be prepared by methods described in the experimental part (see C11, CC22, C33 and C44). In particular, a dehydrating agent, such as 1-(3-dimethylaminopropyl)-3-ethylcarbodiimide hydrochloride, a base, such as triethylamine, and a catalyst, such as 1-hydroxybenzotriazole, can be added to a compound of formula (15) which is preferably dissolved or suspended in an organic solvent, such as dichloromethane. After stirring the mixture e.g. for 0.3 to 2 h preferably at ambient temperature (e.g. 20 to 25° C.), a compound of formula (16-2) can be added and the reaction is preferably performed at ambient temperature (e.g. 20 to 25° C.) for 1 to 48 h to yield the compound of formula (I-2).

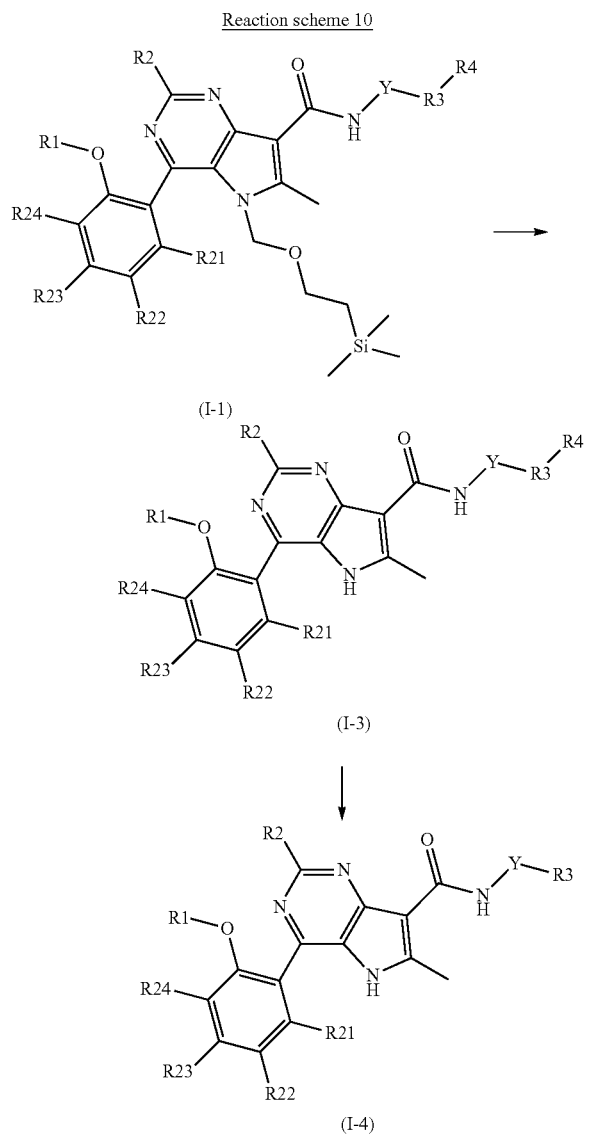

Compounds of formula (I-1), wherein R1, R2, R21, R22, R23, R24 and Y have the above defined meanings and R3 is a 4- to 7-membered saturated heterocyclic ring containing one nitrogen atom and optionally one oxygen atom, said heterocyclic ring being substituted by R4 and optionally substituted by one or two substituents R5, wherein R5 has the above defined meaning and R4 being —C(O)—O—C(CH₃)₃, prepared according to reaction scheme 8 can be deprotected and converted into compounds of formula (I-4), wherein R1, R2, R21, R22, R23, R24 and Y have the above defined meanings and R3 is a 4- to 7-membered saturated heterocyclic ring containing one nitrogen atom and optionally one oxygen atom, said heterocyclic ring being optionally substituted by one or two substituents R5, wherein R5 has the above defined meaning. In particular, compounds of formula (I-1) are deprotected by methods known to a person skilled in the art for example by reaction with tetrabutylammonium fluoride and 1,2-diamino-ethane in an organic solvent like tetrahydrofurane as for example described in Muchowski, J. M.; Solas, D. R.; J. Org: Chem. 1984, 49, 203.

In the following step HCl preferably dissolved in an organic solvent, such as dioxane, can be added to the compound of formula (I-3) which is preferably dissolved in an organic solvent, such as an alcohol, e.g. 2-propanol. The reaction mixture is then preferably heated at 40 to 80° C. for 1 to 4 h to yield the hydrochloride of the compound of formula (I-4). The compound of formula (I-4) can be prepared from said hydrochloride as known to a person skilled in the art, such as by treatment with a base, e.g. aqueous potassium carbonate or aqueous ammonia.

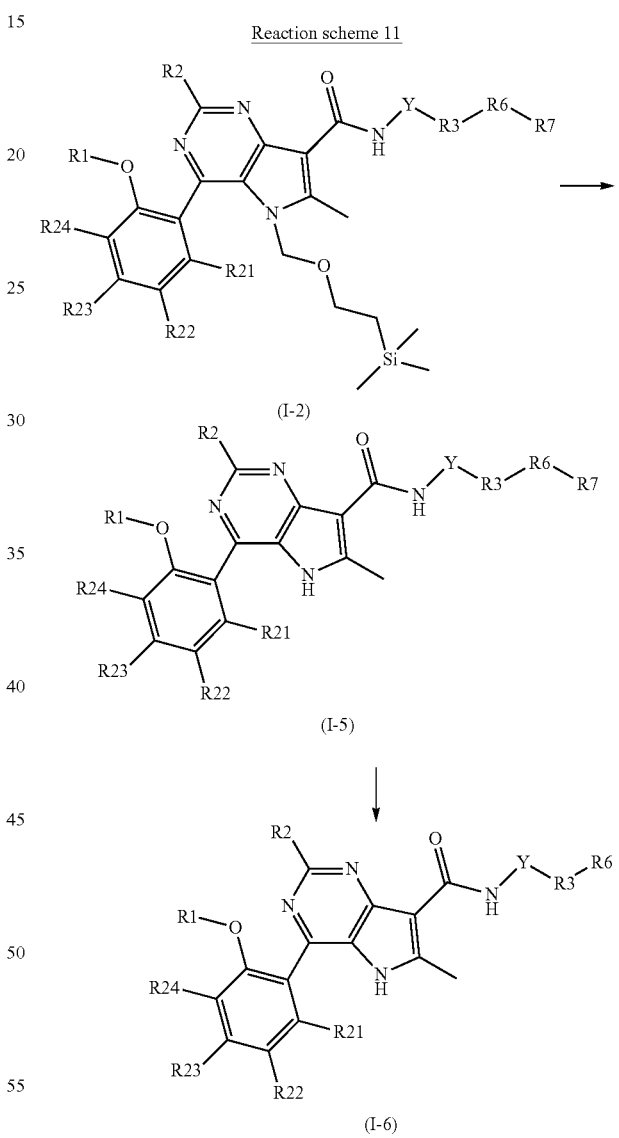

Compounds of formula (I-2), wherein R1, R2, R21, R22, R23, R24 and Y have the above defined meanings and R3 is a 3-6C-cycloalkyl group substituted by R6 and optionally substituted by R61 with R6 being —NH—C(O)—R7 and R7 being —O—C(CH₃)₃ and R61 has the above defined meaning prepared according to reaction scheme 9 can be deprotected and converted into compounds of formula (I-6), wherein R1, R2, R21, R22, R23, R24 and Y have the above defined meanings and R3 is a 3-6C-cycloalkyl group substituted by R6 and optionally substituted by R61 with R6 being —NH$_2$ as shown in reaction scheme 11 and R61 has the above defined meaning. In particular, compounds of formula (I-2) are deprotected by methods known to a person skilled in the art for example by reaction with tetrabutylammonium fluoride and 1,2-diamino-ethane in an organic solvent like tetrahydrofurane as for example described in Muchowski, J. M.; Solas, D. R.; J. Org: Chem. 1984, 49, 203.

In the following step HCl preferably dissolved in an organic solvent, such as dioxane, can be added to the compound of formula (I-5) which is preferably dissolved in an organic solvent, such as an alcohol, e.g. 2-propanol. The reaction mixture is then preferably heated at 40 to 80° C. for 1 to 4 h to yield the hydrochloride of the compound of formula (I-6). The compound of formula (I-6) can be prepared from said hydrochloride as known to a person skilled in the art, such as by treatment with a base, e.g. aqueous potassium carbonate or aqueous ammonia.

Compounds of formula (I-2), wherein R1, R2, R21, R22, R23, R24 and Y have the above defined meanings and R3 is a 3-6C-cycloalkyl group substituted by R6 and optionally substituted by R61 with R6 being hydroxy and R61 has the above defined meaning, prepared according to reaction scheme 9 can be deprotected and converted into compounds of formula (I-5), wherein R1, R2, R21, R22, R23, R24 and Y have the above defined meanings and R3 is a 3-6C-cycloalkyl group substituted by R6 and optionally substituted by R61 with R6 being hydroxy as shown in reaction scheme 11 and R61 has the above defined meaning. In particular, compounds of formula (I-2) are deprotected by methods known to a person skilled in the art for example by reaction with tetrabutylammonium fluoride and 1,2-diamino-ethane in an organic solvent like tetrahydrofurane as for example described in Muchowski, J. M.; Solas, D. R.; J. Org: Chem. 1984, 49, 203.

Reaction scheme 11a:
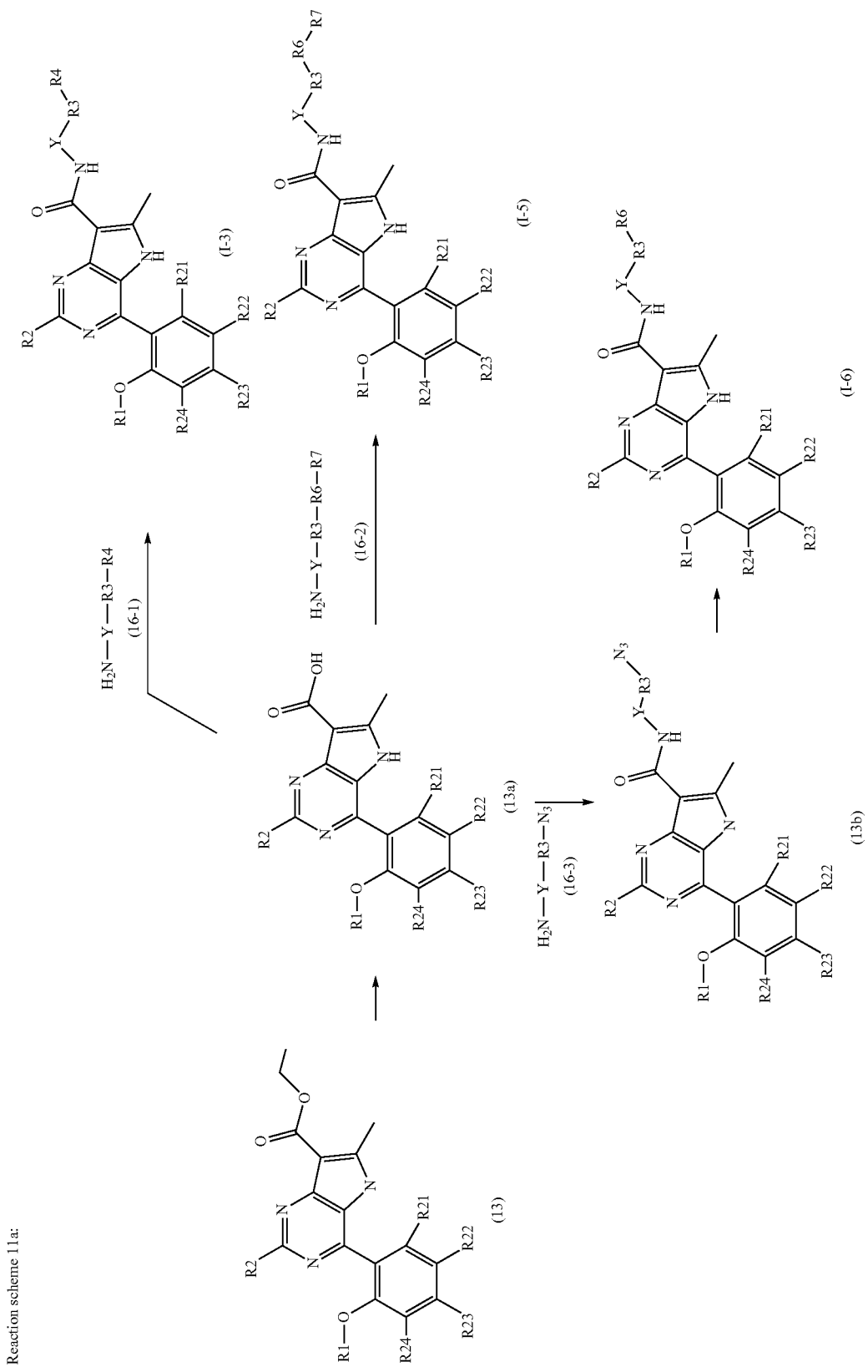

An alternative synthesis of compounds of formula (I-3), wherein R1, R2, R21, R22, R23, R24 and Y have the above defined meanings and R3 is a 4- to 7-membered saturated heterocyclic ring containing one nitrogen atom and optionally one oxygen atom, said heterocyclic ring being substituted by R4 and optionally substituted by one or two substituents R5, wherein R5 has the above defined meaning and R4 being —C(O)—O—C(CH₃)₃, and compounds of formula (I-5), wherein R1, R2, R21, R22, R23, R24 and Y have the above defined meanings and R3 is a 3-6C-cycloalkyl group substituted by R6 and optionally substituted by R61 with R6 being —NH—C(O)—R7 and R7 being —O—C(CH₃)₃ and R61 has the above defined meaning, and compounds of formula (I-6), wherein R1, R2, R21, R22, R23, R24 and Y have the above defined meanings and R3 is a 3-6C-cycloalkyl group substituted by R6 and optionally substituted by R61 with R6 being —NH₂ and R61 has the above defined meaning, is shown in reaction scheme 11a.

A compound of formula (13) prepared according to reaction scheme 6, wherein R1, R2, R21, R22, R23 and R24 have the above defined meanings is transformed into a compound of formula (13a) by reacting with an alkali metal hydroxid preferably KOH (generated from potassium tert-butoxyde and water) in an organic solvent preferably tert-BuOH. A comparable reaction is, for example described in Gassman, P. G.; Schenk, W. N. *J. Org. Chem.* 1977, 42, 918.

A compound of formula (13a) can be reacted with a compound of formula (16-1), which are commercially available or can be prepared by methods known to a person skilled in the art or as described in reaction scheme 16, a compound of formula (16-2), which are commercially available or can be prepared by methods known to a person skilled in the art or can be prepared by methods described in the experimental part (see 011, CC22, C33 and C44), or a compound of (16-3), which are commercially available or can be prepared by methods known to a person skilled in the art or can be prepared by methods described in the experimental part (see C12, C23, C34 and C45). In particular, a dehydrating agent, such as 1-(3-dimethylaminopropyl)-3-ethylcarbodiimide hydrochloride, a base, such as triethylamine, and a catalyst, such as 1-hydroxybenzotriazole, can be added to a compound of formula (13) which is preferably dissolved or suspended in an organic solvent, such as dichloromethane. After stirring the mixture e.g. for 0.3 to 2 h preferably at ambient temperature (e.g. 20 to 25° C.), a compound of formula (16-1), a compound of formula (16-2) or a compound of formula (16-3) can be added and the reaction is preferably performed at ambient temperature (e.g. 20 to 25° C.) for 1 to 48 h to yield a corresponding compound of formula (I-3), a compound of formula (I-5) or a compound of formula (13b). A compound of formula (I-6) can be obtained by pressure hydrogenation, such as 10 to 30 bar, of a compound of formula (13b) preferably at ambient temperature, such as 20 to 25° C., in the presence of a catalyst, such as Pd on carbon or Pd(OH)₂ on carbon, in an organic solvent such as methanol.

Reaction scheme 12

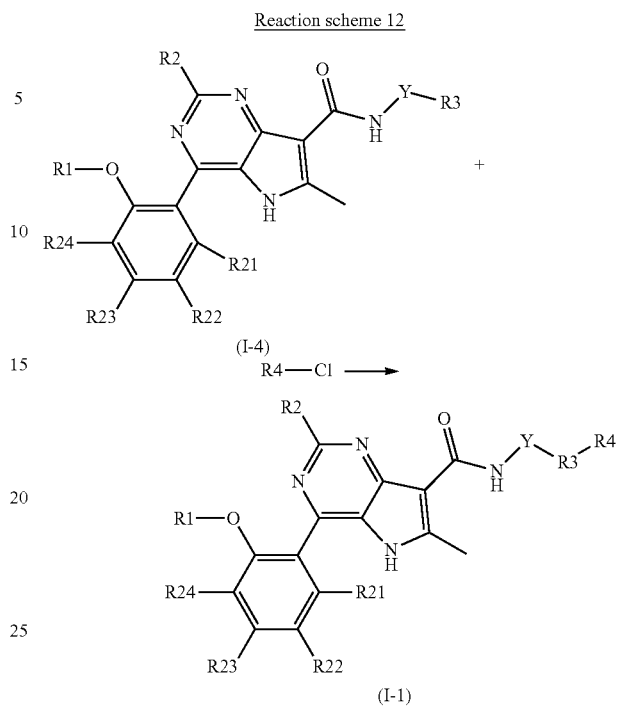

Alternatively, as shown in reaction scheme 12, compounds of formula (I-1), wherein R1, R2, R21, R22, R23, R24 and Y have the above defined meanings and R3 is a 4- to 7-membered saturated heterocyclic ring containing one nitrogen atom and optionally one oxygen atom, said heterocyclic ring being substituted by R4 and optionally substituted by one or two substituents R5, wherein R5 has the above defined meaning and R4 being —C(O)-1-4C-alkyl, wherein the 1-4C-alkyl group is optionally substituted by R41, —C(O)-3-6C-cycloalkyl, wherein the 3-6C-cycloalkyl group is optionally substituted by R42, or —C(O)—O-1-4C-alkyl, wherein the 1-4C-alkyl group is optionally substituted by R43, and R41, R42 and R43 are as defined above, may be prepared from compounds of formula (I-4), wherein R1, R21, R22, R23, R24 and Y have the above defined meanings and R3 is a 4- to 7-membered saturated heterocyclic ring containing one nitrogen atom and optionally one oxygen atom, said heterocyclic ring being optionally substituted by one or two substituents R5, wherein R5 has the above defined meaning, prepared according to reaction scheme 10. In particular, a compound R4-Cl can be added to the compound of formula (I-4) which is preferably dissolved in an organic solvent, such as dichloromethane, in the presence of a base, such as diazabicycloundecene (DBU). The compound of formula R4-Cl is commercially available or can be prepared by methods known to a person skilled in the art. The addition is preferably carried out at a temperature of from 0 to 20° C. After complete addition, the reaction is preferably continued at ambient temperature (e.g. 20 to 25° C.) for 1 to 24 h. In case R41, R42 or R43 represent hydroxy, it is known to a person skilled in the art that the hydroxy group is preferably to be protected by a suitable protecting group, such as an acetate group or a silyl protective group, e.g. a tert-butyl-dimethylsilyl group or a tert-butyl-diphenylsilyl group. Said protective groups can be removed by methods known to a person skilled in the art with or without prior isolation of the protected intermediate (i.e. the compound of formula (I-1) in its protected form).

Reaction scheme 13

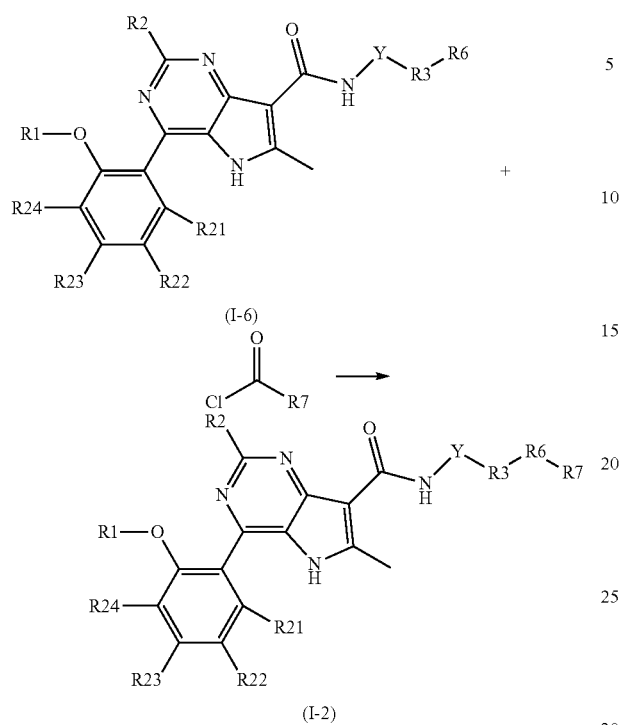

Reaction scheme 14

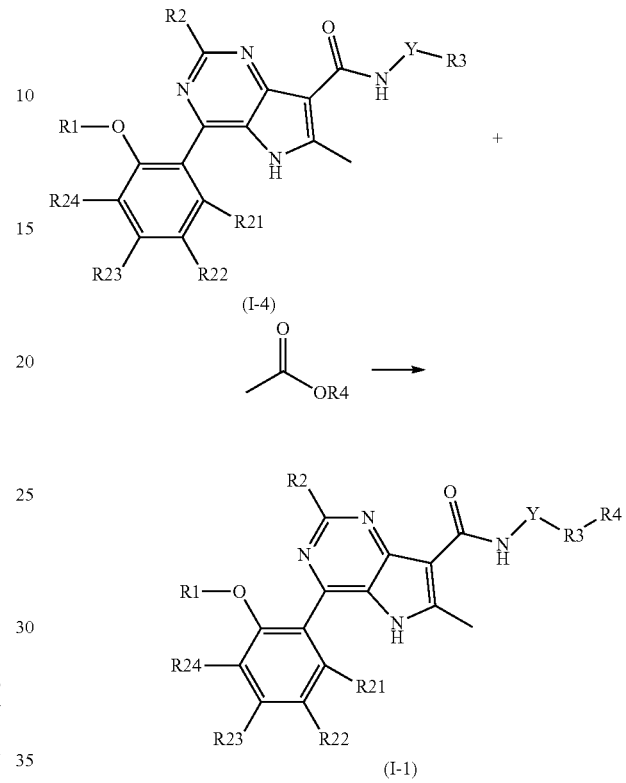

Alternatively, as shown in reaction scheme 13, compounds of formula (I-2), wherein R1, R2, R21, R22, R23, R24 and Y have the above defined meanings and R3 is a 3-6C-cycloalkyl group substituted by R6 and optionally substituted by R61, with R6 being —NH—C(O)—R7, with R7 being 1-4C-alkyl, which is optionally substituted by R71, 3-6C-cycloalkyl, which is optionally substituted by R72, or 1-4C-alkoxy, which is optionally substituted by R73, and R61, R71, R72 and R73 are as defined above, may be prepared from compounds of formula (I-6), wherein R1, R21, R22, R23, R24 and Y have the above defined meanings and R3 is a 3-6C-cycloalkyl group substituted by R6 and optionally substituted by R61 with R6 being NH₂ prepared according to reaction scheme 11 and R61 has the above defined meanings. In particular, a compound R7-C(O)—Cl can be added to the compound of formula (I-6) which is preferably dissolved in an organic solvent, such as dichloromethane, in the presence of a base, such as diazabicycloundecene (DBU). The compound of formula R7-C(O)—Cl is commercially available or can be prepared by methods known to a person skilled in the art. The addition is preferably carried out at a temperature of from 0 to 20° C. After complete addition, the reaction is preferably continued at ambient temperature (e.g. 20 to 25° C.) for 1 to 24 h to yield the compound of formula (I-2). In case R71, R72 or R73 represent hydroxy, it is known to a person skilled in the art that the hydroxy group is preferably to be protected by a suitable protecting group, such as an acetate group or a silyl protective group, e.g. a tert-butyl-dimethylsilyl group or tert-butyl-diphenylsilyl group. Said protective groups can be removed by methods known to a person skilled in the art with or without prior isolation of the protected intermediate (i.e. the compound of formula (I-2) in its protected form).

As shown in reaction scheme 14, compounds of formula (I-1), wherein R1, R2, R21, R22, R23, R24 and Y have the above defined meanings and R3 is a 4- to 7-membered saturated heterocyclic ring containing one nitrogen atom and optionally one oxygen atom, said heterocyclic ring being substituted by R4 and optionally substituted by one or two substituents R5, wherein R5 has the above defined meaning and R4 being —C(O)—H can be prepared from compounds of formula (I-4), wherein R1, R2, R21, R22, R23, R24 and Y have the above defined meanings and R3 is a 4- to 7-membered saturated heterocyclic ring containing one nitrogen atom and optionally one oxygen atom, said heterocyclic ring being optionally substituted by one or two substituents R5, wherein R5 has the above defined meaning, prepared according to reaction scheme 10. In particular, the compound R4-O—C(O)—CH₃, which can be prepared by methods known to a person skilled in the art, can be added to the compound of formula (I-4) which is preferably dissolved in an organic solvent, such as dichloromethane, in the presence of a base, such as diazabicycloundecene (DBU). The addition is preferably carried out at a temperature of from 0 to 20° C. After completion of addition, the reaction is preferably continued at ambient temperature (e.g. 20 to 25° C.) for 1 to 24 h to yield the compound of formula (I-1).

Reaction scheme 15

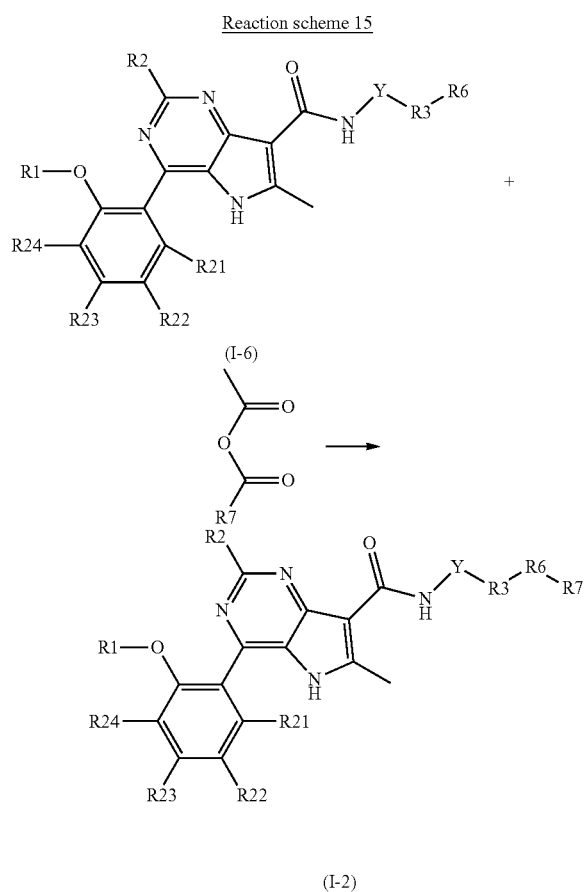

As shown in reaction scheme 15, compounds of formula (I-2), wherein R1, R2, R21, R22, R23, R24 and Y have the above defined meanings and R3 is a 3-6C-cycloalkyl group substituted by R6 and optionally substituted by R61 with R6 being —NH—C(O)—R7 with R7 being hydrogen and R61 has the above defined meaning can be prepared from compounds of formula (I-6), wherein R1, R2, R21, R22, R23, R24 and Y have the above defined meanings and R3 is a 3-6C-cycloalkyl group substituted by R6 and optionally substituted by R61 with R6 being —NH$_2$, obtained according to reaction scheme 11. In particular, the compound R7-C(O)—O—C(O)—CH$_3$ with R7 being hydrogen, which can be prepared by methods known to a person skilled in the art, can be added to the compound of formula (I-6) which is preferably dissolved in an organic solvent, such as dichloromethane, in the presence of a base, such as diazabicycloundecene (DBU). The addition is preferably carried out at a temperature of from 0 to 20° C. After completion of addition, the reaction is preferably continued at ambient temperature (e.g. 20 to 25° C.) for 1 to 24 h to yield a compound of formula (I-2).

Reaction Scheme 16

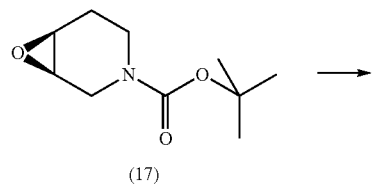

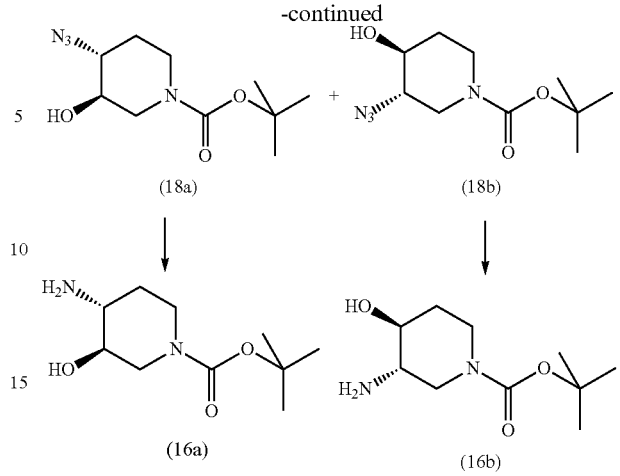

As shown in reaction scheme 16, compounds of formula (16a) or (16b) can be prepared from known compounds (18a) or (18b) [Zhao, S.; Ghosh, A.; D'Andrea, S. V.; Freeman, P.; VonVoigtlander, P. F.; Carter, D. B.; Smith, M. W.; Heterocycles, 1994, 39, 163 and Erickson, S. D.; Banner, B.; Berthel, S.; Conde-Knape, K.; Falicioni, F.; Hakimi, L; Hennessy, B.; Kester, R. F.; Kim, K.; Ma, Ch.; McComas, W.; Mennona, F.; Mischke, S.; Orzechowski, L.; Qian, Y.; Salari, H.; Tengi, J.; Thakkar, K.; Taub, R.; Tilley, J. W.; Wang, H.; Bioorg. Med. Chem. Lett. 2008, 18, 1402] by methods known to a person skilled in the art for example by catalytic hydrogenation in an organic solvent like ethanol or methanol in the presence of a precious metal catalyst like palladium on carbon or platinum oxide at a temperature of from 20 to 50° C. and at standard atmospheric pressure (101,325 kPa) to 1050 kPa for 1 h to 48 h.

It is known to the person skilled in the art that, if there are a number of reactive centers on a starting or intermediate compound, it may be necessary to block one or more reactive centers temporarily by protective groups in order to allow a reaction to proceed specifically at the desired reaction center.

The compounds according to the present subject matter are isolated and purified in a manner known per se, e.g. by distilling off the solvent in vacuo and recrystallizing the residue obtained from a suitable solvent or subjecting them to one of the customary purification methods, such as column chromatography on a suitable support material.

Salts of the compounds of formula (I) and the stereoisomers thereof can be obtained by dissolving the free compound in a suitable solvent (for example a ketone such as acetone, methylethylketone or methylisobutylketone, an ether such as diethyl ether, tetrahydrofurane or dioxane, a chlorinated hydrocarbon such as methylene chloride or chloroform, a low molecular weight aliphatic alcohol such as methanol, ethanol or isopropanol, a low molecular weight aliphatic ester such as ethyl acetate or isopropyl acetate, or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the compounds of formula (I) and the salts thereof can be obtained e.g. by asymmetric synthesis, by using chiral starting compounds in synthesis and/or by splitting up enantiomeric and diasteriomeric mixtures obtained in synthesis. Preferably, the pure diastereomeric and pure enantiomeric compounds of the present subject matter are obtainable by using chiral starting compounds in synthesis and/or by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

All patents, patent applications, publications, test methods and other materials cited herein are incorporated by reference in their entireties.

The following examples illustrate the present subject matter in greater detail, without restricting it. Further compounds according to the present subject matter, of which the preparation is not explicitly described, can be prepared in an analogous way.

The compounds, salts and stereoisomers which are mentioned in the examples, and the salts of the compounds which are mentioned in the examples, and the stereoisomers of the compounds mentioned in the examples, the stereoisomers of the salts which are mentioned in the examples and the stereoisomers of the salts of the compounds which are mentioned in the examples represent preferred embodiments of the present subject matter.

EXAMPLES

The following abbreviations are used: min: minutes, h: hour(s), DCM: dichloromethane, DCE: dichloroethane, THF: tetrahydrofuran, EA: ethyl acetate, sesamol: 3,4-methylenedioxyphenol, brine: saturated sodium chloride solution, DBU: 1,8-diazabicyclo[5.4.0]undec-7-en, Huenigs base: N-ethyl-diisopropylamine, mp.: melting point, bp: boiling point, RT: room temperature (20 to 25° C.), ambient temperature: 20 to 25° C., TLC: thin layer chromatography, GC-MS (EI): gas chromatography coupled to mass spectrometry with electron impact ionization, MS (ESI): mass spectrometry with electron spray ionization, HR-MM (ESI): high resolution mass spectrometry with electron spray ionization, $^1$H-NMR: $^1$H nuclear magnetic resonance spectroscopy (chemical shifts are reported as ppm against tetramethylsilane as internal standard, coupling constants J are reported in Hz). Epimers and/or racemates are marked herein with a "*" in the chemical name at the corresponding stereogenic center.

Example A1

(E/Z)-2-Cyano-3-ethoxy-but-2-enoic acid ethyl ester

A round bottom flask equipped with a magnetic stirring bar, a short Vigreux-Column and a condenser is charged with commercially available triethyl ortho acetate (973.4 g; 6.0 mol), commercially available cyano-acetic acid ethyl ester (452.5 g; 4.0 mol) and commercially available acetic anhydride (816.7 g; 8.0 mol). The stirred reaction mixture is heated to about 100° C. and the formed ethyl acetate is removed by distillation. As the reaction progressed the temperature is gradually raised to 150° C.

The reaction mixture is cooled to ambient temperature. The semisolid crude is distilled in high vacuum. The fraction boiling between 110° C. and 120° C. ($4 \times 10^{-3}$ mbar) is collected and redistilled to yield the title compound as pale yellow solid.

GC-MS (EI): m/z=183 (M$^+$); 127 (100%).

$^1$H-NMR (300 MHz, DMSO-d$_6$): 4.35 (qu, J=7.0, 2H); 4.15 (qu, J=7.1, 2H); 2.63 (s, 3H); 1.29 (t, J=7.0, 3H); 1.22 (t, J=7.1, 3H).

Example A2

3-Amino-5-methyl-1H-pyrrole-2,4-dicarboxylic acid diethyl ester

A reaction flask equipped with a mechanic stirrer, a dropping funnel, a reflux condenser and a nitrogen bubbler is charged with dry EtOH (700 mL), (E/Z)-2-cyano-3-ethoxy-but-2-enoic acid ethyl ester from example 1 (128.25 g; 0.70 mol) and commercially available 2-amino-malonic acid diethyl ester hydrochloride (148.15 g; 0.70 mol). To the well-stirred reaction mixture NaOEt (~21% solution in EtOH; 1150 mL; ~2.45 mol) is added within 15 min (slightly exothermic). After complete addition the reaction mixture is heated to gentle reflux under an atmosphere of nitrogen and mechanical stirring for 18 hours.

The reaction mixture is cooled to ambient temperature and neutralized to pH=7 by slow addition of a sufficient amount of 1M citric acid. EtOH is removed under reduced pressure at 50° C. (rotavapour). The residual solid is distributed between water (1500 mL) and dichloromethane (500 mL). The organic layer is separated. The aqueous layer is extracted with dichloromethane (2×500 ml). The combined organic layers are dried over MgSO$_4$ in the presence of decolorizing charcoal. The solution is filtered through a plug of neutral alumina (act. 2-3) followed by filtration through a plug of silica. The solvent is removed under reduced pressure until the product starts to precipitate. Precipitation of the product is completed by addition of cyclohexane (1000 ml) and cooling to 0° C. for three hours. The solid is collected by suction filtration, washed with several portions of hexane and dried in vacuum at 50° C. over night to yield the title compound as off-white solid.

MS (ESI): m/z=241 (MH$^+$, 100%).

$^1$H-NMR (300 MHz, DMSO-d$_6$): 11.26 (br.s, 1H, —NH); 5.62 (br.s, 2H, —NH$_2$); 4.20 (qu, J=7.1, 2H); 4.18 (qu, J=7.1, 2H); 2.34 (s, 3H); 1.27 (t, J=7.1, 3H); 1.26 (t, J=7.1, 3H).

Example A3

Ethyl-4-hydroxy-6-methyl-5H-pyrrolo[3,2-d]pyrimidine-7-carboxylate

A reaction flask equipped with a mechanical stirrer, a reflux condenser and a nitrogen bubbler is charged with EtOH (5000 mL), 3-amino-5-methyl-1H-pyrrole-2,4-dicarboxylic acid diethyl ester from example A2 (565.57 g; 2.50 mol) and formamidine acetate (1041.10 g; 10.00 mol). The well-stirred reaction mixture is heated to gentle reflux for five days under an atmosphere of nitrogen.

The reaction mixture is cooled to ambient temperature. The precipitated crude is collected by suction filtration, washed with several small portions of EtOH and sucked dry for one hour. The solid is suspended in water (2500 mL), stirred for two hours at ambient temperature, collected by suction filtration, ished with several small portions of water and sucked dry for one hour. The solid is again suspended in EtOH (2500 mL). The suspension is stirred for three hours at ambient temperature. The solid is collected by suction filtration, washed with several small portions of EtOH, sucked dry for one hour and finally dried in vacuum at 50° C. over night to yield the title compound 7 containing 15 mol % of isomer 8 as off-white solid.

The mixture of 7 and 8 (50.0 g, 0.23 mol) is suspended in EtOH (1000 mL). The stirred suspension is refluxed for one hour, filtered while still hot and washed with several small portions of boiling EtOH. The remaining solid is resuspended in EtOH (500 mL). The stirred suspension is refluxed for one hour, filtered while still hot, washed with several small portions of boiling EtOH and dried in vacuum at 50° C. over night to deliver the title compound as colorless solid.

MS (ESI): m/z=222 (MH$^+$, 100%).
$^1$H-NMR (300 MHz, DMSO-$d_6$): 12.56 (s, 1H, —NH); 12.04 (s, 1H, —OH); 7.88 (s, 1H); 4.24 (qu, J=6.9, 2H); 2.55 (s, 3H); 1.28 (t, J=6.9, 3H).

Pure isomer 8 is obtained as colorless solid from the evaporated filtrates after crystallization from EtOH.

MS (ESI): m/z=222 (MH$^+$, 100%).
$^1$H-NMR (300 MHz, DMSO-$d_6$): 12.64 (s, 1H, —NH); 11.41 (s, 1H, —OH); 7.77 (s, 1H); 4.28 (qu, J=7.1, 2H); 2.56 (s, 3H); 1.30 (t, J=7.1, 3H).

Example A4

Ethyl-4-chloro-6-methyl-5H-pyrrolo[3,2-d]pyrimidine-7-carboxylate

A reaction flask, equipped with a mechanic stirrer, a reflux condenser and a nitrogen bubbler is charged with POCl$_3$ (1200 mL). Ethyl 4-hydroxy-6-methyl-5H-pyrrolo[3,2-d]pyrimidine-7-carboxylate from example A3 (207.19 g; 1.00 mol) is added in several portions. The carefully stirred suspension is heated to gentle reflux for five hours.

The resulting dark solution is cooled to ambient temperature. POCK is removed by distillation under reduced pressure until the precipitated crude product prevented further stirring. Remaining POCl$_3$ is removed by repeated co-distillation with dry toluene (3×1000 mL). Finally the resulting solid is suspended in toluene and stirred at ambient temperature under an atmosphere of nitrogen over night. The dark precipitate is collected by suction filtration, ished with several small portions of toluene and diethyl ether, and sucked dry under an atmosphere of nitrogen.

The dry solid is suspended in ice cold water (1000 mL). The pH of the well-stirred suspension is adjusted to 8 by careful addition of 2M KHCO$_3$-solution. The suspension is stirred for several hours until pH stayed at 8.0 (from time to time the pH has to be readjusted to 8.0 by addition of 2M KHCO$_3$-solution). The product is isolated by suction filtration, washed with several small portions of water and sucked dry for two hours.

For further purification the product is suspended in acetonitrile (1000 mL). The suspension is stirred at 60° C. for one hour and at ambient temperature for one additional hour. The product is collected by suction filtration washed with several small portions of acetonitril and sucked dry for one hour. A second crop of product is obtained from the mother liquor after concentration under reduced pressure. The solids are combined and dried in vacuum at 50° C. over night to yield the title compound as off-white solid.

MS (ESI): m/z=240 (MH$^+$); 226 (100%); 212.
$^1$H-NMR (300 MHz, DMSO-$d_6$): 12.76 (br.s, 1H, —NH); 8.64 (s, 1H); 4.29 (qu, J=7.1, 2H); 1.32 (t, J=7.1, 3H).

Example A.5

Ethyl 3-(ethanimidoylamino)-5-methyl-1H-pyrrole-2-carboxylate hydrochloride

Ethyl-3-amino-5-methyl-1H-pyrrole-2-carboxylate (58.87 g; 0.35 mol) prepared according to literature [Gangjee A.; Li W.; Yang J.; Kisliuk R. L.; J. Med. Chem. 2008, 51, 68] is suspended in acetonitrile (1750 mL). To the suspension is added dropwise 4M HCl in dioxane (473 mL; 1.89 mol) within 15 minutes. After complete addition the reaction mixture is heated to 50° C. for 18 hours. The reaction mixture is cooled to 10° C., the solid is collected by suction filtration and washed with cold acetonitrile (400 mL). A second crop of product is obtained from the mother liquor after concentration under reduced pressure. The residue is collected with t-butylmethyl-ether. After the suction filtration the solids are combined and dried in vacuum at 50° C. to yield the title compound as off-white solid.

MS (ESI): m/z=210 (MH$^+$)
$^1$H-NMR (300 MHz, DMSO-$d_6$): 11.96 (s, 1H, —NH); 10.93 (s, 1H, —NH); 9.45 (s, 1H, —NH); 8.22 (s, 1H, —NH); 5.92 (m, 1H); 4.19 (qu, J=7.1, 2H); 2.29 (s, 3H); 2.23 (s, 3H); 1.26 (t, J=7.1, 3H).

Example A.6

2,6-Dimethyl-3,5-dihydro-4H-pyrrolo[3,2-d]pyrimidin-4-one

A reaction flask equipped with a mechanical stirrer and a reflux condenser is charged with EtOH (900 mL), Ethyl-3-(ethanimidoylamino)-5-methyl-1H-pyrrole-2-carboxylate hydrochloride from example A5 (82.79 g; 0.34 mol) and 6M NaOH (226 mL; 1.36 mol). The well-stirred reaction mixture is heated to gentle reflux for 4 hours and is cooled to ambient temperature. The resulting solution is diluted with water (1000 mL) and the pH is adjusted to 6.5 by carefully addition of 2M citric acid. The precipitate is collected by suction filtration, washed with several portions of water and dried in vacuum at 50° C. to yield the title compound as off-white solid.

MS (ESI): m/z=164 (MH$^+$)
$^1$H-NMR (300 MHz, DMSO-$d_6$): 11.63 (s, 1H, —NH); 11.58 (s, 1H, —OH); 5.98 (m, 1H); 2.29 (s, 3H); 2.26 (s, 3H).

Example A.7

4-Chloro-2,6-dimethyl-5H-pyrrolo[3,2-d]pyrimidine 2,6-Dimethyl-3,5-dihydro-4H-pyrrolo[3,2-d]pyrimidin-4-one from example A6 (87.00 g; 0.53 mol) is suspended in dry acetonitrile (870 mL). After addition of $POCl_3$ (122 mL; 1.33 mol) the stirred reaction mixture is heated to gentle reflux for 18 hours.

The volatiles are removed by destillation under reduced pressure. The residue is diluted with ice cold water (1500 mL) and the well-stirred suspension is adjusted to pH=8 by addition of 5M KOH. The suspension is stirred for several hours until pH stayed at 8.0. (from time to time the pH has to be readjusted to 8.0 by addition of 5M KOH). The solid is isolated by suction filtration, dissolved in dichloromethane, dried over $MgSO_4$ and filtered through a plug of neutral alumina (act. 2-3). The solvent is removed under reduced pressure. The product is resuspended in tert-butylmethylether, filtered and dried in vacuum at 50° C. over night to yield the title compound as off-white solid.

MS (ESI): m/z=182 (MH$^+$)
$^1$H-NMR (300 MHz, DMSO-d$_6$): 11.99 (s, 1H, —NH); 6.33 (m, 1H); 2.57 (s, 3H); 2.48 (s, 3H).

Example A.8

7-Bromo-4-chloro-2,6-dimethyl-5H-pyrrolo[3,2-d]pyrimidine

4-Chloro-2,6-dimethyl-5H-pyrrolo[3,2-d]pyrimidine from example A7 (10.90 g; 60.00 mmol) is dissolved in dichloromethane (120 mL). The stirred mixture is cooled to 10° C. Br$_2$ (3.08 mL; 60.00 mmol) dissolved in dichloromethane (20 mL) is added dropwise within 25 minutes. The resulting precipitate is collected by suction filtration, suspended in Na$_2$SO$_3$ (5% solution) (100 mL) and is stirred for 30 minutes at ambient temperature. After filtratrion the product is dissolved in acetonitrile (1000 mL), refluxed for one hour and filtered while still hot. The solvent is removed under reduced pressure until the product starts to precipitate. Precipitation of the product is completed by addition of cyclohexane and cooling to 0° C. for several hours. The solid is collected by suction filtration, washed with cyclohexane and dried in vacuum at 50° C. over night to yield the title compound as a white solid.

MS (ESI): m/z=262 (MH$^+$)
$^1$H-NMR (300 MHz, DMSO-d$_6$): 12.61 (s, 1H, —NH); 2.62 (s, 3H); 2.48 (s, 3H).

Example A.9

7-Bromo-4-chloro-2,6-dimethyl-5-{[2-(trimethylsilyl)ethoxy]methyl}-5H-pyrrolo[3,2-d]pyrimidine Sodium hydride (1.82 g; 45.60 mmol; 60% in oil, washed with hexane), is suspended in dry DMF (125 mL) and dry DMSO (25 mL). To the stirring suspension 7-Bromo-4-chloro-2,6-dimethyl-5H-pyrrolo[3,2-d]pyrimidine from example A8 (10.00 g; 38.00 mmol) dissolved in dry DMF (125 mL) is added dropwise within 30 minutes at ambient temperature. After complete addition the reaction mixture is stirred for one hour at ambient temperature. To the resulting solution 2-(trimethylsilyl)ethoxymethylchloride (8.74 mL; 49.40 mmol) is added dropwise and the reaction mixture is stirred for one hour at ambient temperature. After diluting with water/ice and dichloromethane, the organic layer is separated and the aqueous layer is extracted with dichloromethane (2×400 mL). The combined organic layers are dried over MgSO$_4$ and filtered through a plug of neutral alumina (act. 2-3). The solvent is removed under reduced pressure and the residue is purified by column chromatography on silica gel (cyclohexane:ethylacetate/9:1) affording the title compound as a white solid.

MS (ESI): m/z=392 (MH$^+$)
$^1$H-NMR (300 MHz, DMSO-d$_6$): 5.81 (s, 2H); 3.57 (t, J=7.9, 2H); 2.63 (s, 3H); 2.58 (s, 3H); 0.83 (m, 2H); −0.09 (s, 9H).

Example A.10

4-Chloro-2,6-dimethyl-5-{[2-(trimethylsilyl)ethoxy]methyl}-5H-pyrrolo[3,2-d]pyrimidine-7-carbaldehyde 7-Bromo-4-chloro-2,6-dimethyl-5-{[2-(trimethylsilyl)ethoxy]methyl}-5H-pyrrolo[3,2-d]pyrimidine from example A9 (12.41 g; 31.76 mmol) is dissolved in dry tetrahydrofurane (100 mL). At −78° C. n-butyllithium (12.7 mL; 31.76 mmol; 2.5M solution in n-hexane) is syringed into the stirred reaction mixture. After 30 min DMF (12.4 mL; 158.80 mmol) is added via syringe and the mixture is stirred for additional 2 hours at −78° C. and for 30 minutes at 0° C. The reaction is quenched by addition of 1M citric acid (32 mL) and brine (32 mL). After diluting with tert-butylmethylether the aqueous layer is separated and extracted with tert-butylmethylether (3×50 mL). The combined organic layers are dried over MgSO$_4$ and the solvent is removed under reduced pressure. The residue is purified by column chromatography on silica gel (cyclohexane:ethylacetate/7:3) affording the title compound as a white solid.

MS (ESI): m/z=340 (MH$^+$)
$^1$H-NMR (300 MHz, DMSO-d$_6$): 10.35 (s, 1H); 5.85 (s, 1H); 3.61 (t. J=7.9, 2H); 2.87 (s, 3H); 2.67 (s, 3H); 0.85 (m, 2H); −0.08 (s, 9H).

Example A.11

Methyl 4-chloro-2,6-dimethyl-5-{[2-(trimethylsilyl)ethoxy]methyl}-5H-pyrrolo[3,2-d]pyrimidine-7-carboxylate To a well stirred mixture of 4-chloro-2,6-dimethyl-5-{[2-(trimethylsilyl)ethoxy]methyl}-5H-pyrrolo[3,2-d]pyrimidine-7-carbaldehyde from example A10 (9.49 g; 27.90 mmol), MeOH (50 mL), KCN (6.00 g; 92.10 mmol) and MnO$_2$ (35.60 g, 383.30 mmol) acetic acid (1.68 g; 27.90 mmol) is added at ambient temperature. After 4 hours the dark mixture is filtered through Celite and the solvent is removed under reduced pressure. The residue is purified by column chromatography on silica gel (cyclohexane:ethylacetate/9:1) affording the title compound as an pale yellow oil.

MS (ESI): m/z=370 (MH$^+$)
$^1$H-NMR (300 MHz, DMSO-d$_6$): 5.85 (s, 2H); 3.84 (s, 3H); 3.59 (t, J=7.9, 2H); 2.84 (s, 3H); 2.64 (s, 3H); 0.84 (m, 2H); −0.09 (s, 9H).

Example B.a1

2-Bromo-5-fluoro-4-methoxy-phenol

3-Fluoro-4-methoxy-phenol (21.32 g; 0.15 mol) prepared according to literature [Freedman, J.; Stewart, K. T.; J. Heterocycl. Chem. 1989, 26, 1547-1554] is dissolved in dry dichloromethane (300 mL). The well stirred reaction mixture is cooled to −15° C. (ice/salt). A solution of bromine (23.97 g; 0.15 mol) in dry dichloromethane (75 mL) is dropped into the reaction mixture. After complete addition stirring is continued for one hour. Water (150 mL) containing sodium sulfite (3.0 g) is added to the reaction mixture. Stirring is continued at ambient temperature for 30 min. The organic layer is separated, washed with water (100 mL) and dried over $MgSO_4$ in the presence of decolorizing charcoal. After filtration the solvent is completely removed under reduced pressure. The residue is crystallized from tert-butylmethylether/hexane to yield the title compound as a colorless solid.

GC-MS (EI): m/z=222, 220 (M$^+$); 207, 205 (M$^+$-CH$_3$, 100%); 179, 177.

$^1$H-NMR (300 MHz, DMSO-d$_6$): 10.06 (s, 1H, —OH); 7.28 (d, J=9.2, 1H); 6.81 (d, J=12.6, 1H); 3.76 (s, 3H).

The following compounds are obtained analogously to the procedure described in above example B.a1.

Example B.a2

2-Bromo-4-fluoro-5-methoxy-phenol

Starting from 4-fluoro-3-methoxy-phenol prepared according to literature [Belanger, P. C.; Lau, C. K.; Williams, H. W. R.; Dufresne, C.; Scheigetz, J. Can. J. Chem. 1988, 66, 1479-1482] the title compound is obtained as colorless solid.

GC-MS (EI): m/z=222, 220 (M$^+$, 100%); 207, 205 (M-CH$_3^+$); 179, 177.

$^1$H-NMR (300 MHz, CDCl$_3$): 7.16 (d, J=10.2, 1H); 6.67 (d, J=7.7, 1H); 5.29 (s, 1H, —OH); 3.85 (s, 3H)

Example B.a3

2-Bromo-5-fluoro-4-methylphenol

Starting from commercially available 3-fluoro-4-methylphenol the title compound is obtained as colorless solid.

GC-MS (EI): m/z=206, 204 (M$^+$); 125 (100%).

$^1$H-NMR (300 MHz, DMSO-d$_6$): 10.38 (br.s, 1H, —OH); 7.39 (d, J=8.2, 1H); 6.70 (d, J=11.1, 1H); 2.11 (s, 3H).

Example B.a4

1-(3-Bromo-4-hydroxy-phenyl)-ethanone

Starting from commercially available 1-(4-hydroxy-phenyl)-ethanone the title compound is obtained as colorless solid.

GC-MS (EI): m/z=214, 212 (M$^+$); 199, 197 (100%).

$^1$H-NMR (300 MHz, DMSO-d$_6$): 11.19 (s, 1H, —OH); 8.06 (d, J=2.2, 1H); 7.82 (dd, J=8.4, 2.2, 1H); 7.03 (d, J=8.4, 1H); 2.49 (s, 3H).

Example B.a5

2-Bromo-4-ethyl-phenol

Starting from commercially available 4-ethyl-phenol the title compound is obtained as colorless oil after short path distillation at 10 mbar.

GC-MS (EI): m/z=202, 200 (M$^+$); 187, 195 (100%).

$^1$H-NMR (300 MHz, DMSO-d$_6$): 9.88 (s, 1H, —OH); 7.29 (d, J=2.0, 1H); 7.00 (dd, J=8.2, 2.0, 1H); 6.85 (d, J=8.2, 1H); 2.49 (qu, J=7.7, 2H); 1.12 (t, J=7.7, 3H).

Example B.a6

2-bromo-4-isopropyl-phenol

Starting from commercially available 4-isopropyl-phenol the title compound is obtained as colorless oil after short path distillation at 10 mbar.

GC-MS (EI): m/z=216, 214 (M$^+$); 201, 199; 120 (100%).

$^1$H-NMR (300 MHz, DMSO-d$_6$): 9.88 (s, 1H, —OH); 7.30 (d, J=2.2, 1H); 7.04 (dd, J=8.4, 2.2, 1H); 6.86 (d, J=8.4, 1H); 2.78 (sept, J=6.9, 1H); 1.14 (d, J=6.9, 6H).

Example B.b1

5-Cyclopropylmethoxy-benzo[1,3]dioxole

Sodium hydride (60 wt % dispersion in mineral oil; 11.0 g; 275.0 mmol) is freed from oil by washing with hexane (2×50 mL) and suspended in dry DME (375 mL) and dry DMSO (37.5 mL). Under an atmosphere of nitrogen a solution of commercially available sesamol (3,4-methylenedioxy-phenol) (34.53 g; 250.0 mmol) in dry DME (250 mL) is dropped into the well-stirred suspension at a rate to keep the internal temperature below 40° C. After complete addition stirring is continued at ambient temperature for one hour.

Neat commercially available bromomethyl-cyclopropane (37.13 g; 275.0 mmol) is added in one portion and the reaction mixture is stirred at 80° C. over night. Ice-cold water (125 mL) is drop wise added and the reaction mixture is stirred for 30 min at ambient temperature. After addition of brine (125 mL) the organic layer is separated and concentrated in vacuo. The aqueous layer is extracted with tert-butylmethylether (3×200 mL). All organic phases are combined, washed with brine (200 mL), dried over $MgSO_4$ and filtered through a plug of neutral alumina containing 5 wt % of water. The product is completely eluted with several portions of tert-butylmethylether. The solvent is removed under reduced pressure. The remaining crude product is purified by short path distillation at 3×10$^{-3}$ mbar (117° C.) to give the title compound as colorless oil that solidifies at ambient temperature.

GC-MS (EI): m/z=192 (M$^+$); 138 (M$^+$-C$_4$H$_6$, 100%).

$^1$H-NMR (200 MHz, DMSO-d$_6$): 6.77 (d, J=8.5, 1H); 6.59 (d, J=2.5, 1H); 6.32 (dd, J=8.5, 2.5, 1H); 5.93 (s, 2H); 3.71 (d, J=6.9, 2H); 1.15 (m, 1H); 0.53 (m, 2H); 0.27 (m, 2H).

The following compounds are obtained analogously to the procedure described in above example B.b1.

Example B.b2

1-Bromo-2-cyclopropylmethoxy-4-fluoro-benzene

Starting from commercially available 2-bromo-5-fluoro-phenol and commercially available bromomethyl-cyclopropane the title compound is obtained as colorless oil after distillation at 5×10$^3$ mbar.

GC-MS (EI): m/z=244, 246 (M$^+$); 190, 192 (M$^+$-C4H6); 55 (100%).

$^1$H-NMR (300 MHz, DMSO-d$_6$): 7.58 (dd, J=8.7, 6.4, 1H); 7.02 (dd, J=11.2, 2.8, 1H); 6.75 (ddd, J=8.7, 2.8, 1H); 3.93 (d, J=6.8, 2H); 1.24 (m, 1H); 0.56 (m, 2H); 0.38 (m, 2H).

Example B.b3

1-Bromo-2-cyclopropylmethoxy-5-fluoro-benzene

Starting from commercially available 2-bromo-4-fluoro-phenol and commercially available bromomethyl-cyclopropane the title compound is obtained as colorless oil after distillation at 5×10$^{-3}$ mbar.

GC-MS (EI): m/z=244, 246 (M$^+$); 190, 192; (M$^+$-C$_4$H$_6$); 55 (100%).
$^1$H-NMR (400 MHz, DMSO-d$_6$): 7.52 (dd, J$_1$=8.2, J$_2$=3.1, 1H); 7.19 (ddd, J$_1$=9.1, J$_2$=8.2, J$_3$=3.1, 1H); 7.10 (dd, J1=9.1, J2=5.0, 1H); 3.89 (d, J=6.8, 2H); 1.22 (m, 2H); 0.57 (m, 2H); 0.35 (m, 2H).

Example B.b5

1-Bromo-2-cyclopropylmethoxy-4-methoxy-benzene

Starting from commercially available 2-bromo-5-methoxy-phenol and bromomethyl-cyclopropane the title compound is obtained as colorless solid.
GC-MS (EI): m/z=258, 256 (M$^+$).
$^1$H-NMR (200 MHz, DMSO-d$_6$): 7.41 (d, J=7.9, 1H); 6.48 (dd, J1=7.9, J2=2.2, 1H); 6.45 (d, J=2.2, 1H); 3.87 (d, J=5.6, 2H); 3.76 (s, 3H); 1.26 (m, 1H); 0.63 (m, 2H); 0.36 (m, 2H).

Example B.b6

1-Bromo-2-cyclopropylmethoxy-5-methoxy-benzene

Starting from commercially available 2-bromo-4-methoxy-phenol and bromomethyl-cyclopropane the title compound is obtained as colorless oil after distillation at 5×10$^{-3}$ mbar.
GC-MS (EI): m/z=256, 258 (M$^+$); 202, 204 (100%).
$^1$H-NMR (200 MHz, CDCl$_3$): 7.11 (d, J=2.8, 1H); 6.86 (d, J=8.9, 1H); 6.78 (dd, J1=8.9, J2=2.8, 1H); 3.82 (d, J=6.8, 2H); 3.75 (s, 3H); 1.16 (m, 1H); 0.51 (m, 2H); 0.44 (m, 2H).

Example B.b7

2-Bromo-1-cyclopropylmethoxy-4-methyl-benzene

Starting from commercially available 2-bromo-4-methyl-phenol and bromomethyl-cyclopropane the title compound is obtained as colorless oil after distillation at 5×10$^{-3}$ mbar.
GC-MS (EI): m/z=242, 240 (M$^+$); 188, 186 (M$^+$-C$_4$H$_6$); 107; 80, 78; 55 (100%).
$^1$H-NMR (300 MHz, DMSO-d$_6$): 7.38 (dd, J=2.2, 0.7, 1H); 7.10 (ddd, J=8.4, 2.2, 0.7, 1H); 6.96 (d, J=8.4, 1H); 3.86 (d, J=6.8, 2H); 2.22 (s, 3H); 1.21 (m, 1H); 0.56 (m, 2H); 0.33 (m, 2H).

Example B.b8

2-Bromo-1-cyclopropylmethoxy-4-trifluoromethyl-benzene

Starting from commercially available 2-bromo-4-trifluoromethyl-phenol and bromomethyl-cyclopropane the title compound is obtained as colorless oil after distillation at 5×10$^{-3}$ mbar.
GC-MS (EI): m/z=296, 294 (M$^+$); 268, 266; 242, 240 (M$^+$-C$_4$H$_6$); 132; 55 (100%).
$^1$H-NMR (300 MHz, DMSO-d$_6$): 7.93 (dd, J=2.3, 0.5, 1H); 7.70 (ddd, J=8.8, 2.3, 0.5, 1H); 7.26 (d, J=8.8, 1H); 4.03 (d, J=6.9, 2H); 1.27 (m, 1H); 0.60 (m, 2H); 0.38 (m, 2H).

Example B.b9

2-Bromo-1-ethoxy-4-trifluoromethyl-benzene

Starting from commercially available 2-bromo-4-trifluoromethyl-phenol and ethyliodide the title compound is obtained as colorless oil after distillation at 5×10$^{-3}$ mbar.

GC-MS (EI): m/z=270, 268 (M$^+$); 242, 240 (M$^+$-C$_2$H$_4$, 100%); 132.
$^1$H-NMR (300 MHz, DMSO-d$_6$): 7.93 (dd, J=2.3, 0.7, 1H); 7/1 (ddd, J=8.8, 2.3, 0.7, 1H); 7.27 (d, J=8.8, 1H); 4.21 (qu, J=6.9, 2H); 1.38 (t, J=6.9, 3H).

Example B.b10

1-Bromo-2-cyclopropylmethoxy-4-fluoro-5-methoxy-benzene

Starting from 2-bromo-5-fluoro-4-methoxy-phenol (example B.a1) and commercially available bromomethyl-cyclopropane the title compound is obtained as colorless solid.
GC-MS (EI): m/z=276, 274 (M$^+$); 222, 220 (M$^+$-C$_4$H$_6$, 100%); 206, 204.
$^1$H-NMR (400 MHz, DMSO-d$_6$): 7.38 (d, J=9.2, 1H); 7.13 (d, J=13.1, 1H); 3.85 (d, J=6.9, 2H); 3.80 (s, 3H); 1.20 (m, 1H); 0.57 (m, 2H); 0.33 (m, 2H).

Example B.b11

1-Bromo-2-cyclopropylmethoxy-4-fluoro-5-methyl-benzene

Starting from 2-bromo-5-fluoro-4-methyl-phenol (example B.a3) and commercially available bromomethyl-cyclopropane the title compound is obtained as colorless oil after distillation at 5×10$^{-3}$ mbar.
GC-MS (EI): m/z=260, 258 (M$^+$); 206, 204 (M$^+$-C$_4$H$_6$); 179; 125; 96; 55 (100%).
$^1$H-NMR (400 MHz, DMSO-d$_6$): 7.49 (d, J=8.2, 1H); 6.97 (d, J=11.7, 1H); 3.89 (d, J=6.9, 2H); 2.14 (d, J=1.8, 3H); 1.22 (m, 1H); 0.57 (m, 2H); 0.34 (m, 2H).

Example B.b12

1-Bromo-2-cyclopropylmethoxy-5-fluoro-4-methoxy-benzene

Starting from 2-bromo-4-fluoro-5-methoxy-phenol (example B.a2) and commercially available bromomethyl-cyclopropane the title compound is obtained as colorless solid.
GC-MS (EI): m/z=276, 274 (M$^+$); 222, 220 (M$^+$-C$_4$H$_6$, 100%).
$^1$H-NMR (400 MHz, DMSO-d$_6$): 7.48 (d, J=10.8, 1H); 6.90 (d, J=7.9, 1H); 3.93 (d, J=6.8, 2H); 3.85 (s, 3H); 1.24 (m, 1H); 0.58 (m, 2H); 0.36 (m, 2H).

Example B.b13

1-(3-Bromo-4-cyclopropylmethoxy-phenyl)-ethanone

Starting from 1-(3-bromo-4-hydroxy-phenyl)-ethanone (example B.a4) and commercially available bromomethyl-cyclopropane the title compound is obtained as colorless solid.
GC-MS (EI): m/z=270, 268 (M$^+$); 242, 240; 216, 214 (M$^+$-C$_4$H$_6$); 201, 199; 55 (100%).
$^1$H-NMR (400 MHz, DMSO-d$_6$): 8.11 (d, J=2.1, 1H); 7.94 (dd, J=8.7, 2.1, 1H); 7.19 (d, J=8.7, 1H); 4.03 (d, J=6.9, 2H); 2.53 (s, 3H); 1.27 (m, 1H); 0.60 (m, 2H); 0.38 (m, 2H).

Example B.b14

2-[3-Bromo-4-(cyclopropylmethoxy)phenyl]-2-methyl-1,3-dioxolane

A solution of 1-(3-bromo-4-cyclopropylmethoxy-phenyl)-ethanone from example B.b13 (14.0 g; 52.0 mmol) in dry dichloromethane (250 mL) was cooled in an ice-bath before addition of trimethylsilyl trifluoro-methane sulfonate (0.23 g; 1.04 mmol) and dropwise addition of 1,2-bis(trimethylsilyloxy)-ethane (13.15 g; 62.4 mmol). The reaction mixture was stirred for two hours, extracted with 1M aqueous $NaHCO_3$ (100 mL) and dried over $MgSO_4$. The crude is purified by column chromatography on silica gel (ethyl acetate/cyclohexane-9:1) to yield the title compound as pale yellow oil.

GC-MS (EI): m/z=314, 314 ($M^+$); 299, 297 ($M^+$-$CH_3$, 100%); 245, 243 ($M^+$-$CH_3$, —$C_4H_6$); 201, 199; 87; 55.

$^1$H-NMR (400 MHz, DMSO-$d_6$): 7.53 (d, J=2.2, 1H); 7.33 (dd, J=8.6, 2.2, 1H); 7.05 (d, J=8.6, 1H); 3.96 (m, 2H); 3.91 (d, J=6.9, 2H); 3.69 (m, 2H); 1.53 (s, 3H); 1.23 (m, 1H); 0.58 (m, 2H); 0.35 (m, 2H).

Example B.b15

1-Bromo-2-cyclopropylmethoxy-5-ethyl-benzene

Starting from 2-bromo-4-ethyl-phenol (example B.a5) and commercially available bromomethyl-cyclopropane the title compound is obtained as colorless oil after distillation at 10 mbar.

GC-MS (EI): m/z=256, 254 ($M^+$); 228, 226 ($M^+$-$C_2H_4$); 202, 200 ($M^+$-$C_4H_6$); 187, 185 ($M^+$-$C_4H_6$, —$CH_3$); 55 (100%).

$^1$H-NMR (300 MHz, DMSO-$d_6$): 7.39 (d, J=2.0, 1H); 7.13 (dd, J=8.4, 2.0, 1H); 6.98 (d, J=8.4, 1H); 3.87 (d, J=6.8, 2H); 3.53 (qu, J=7.7, 2H); 1.22 (m, 1H); 1.13 (t, J=7.7, 3H); 0.56 (m, 2H); 0.33 (m, 2H).

Example B.b16

2-Bromo-1-cyclopropylmethoxy-4-(propan-2-yl)benzene

Starting from 2-bromo-4-isopropyl-phenol (example B.a6) and commercially available bromomethyl-cyclopropane the title compound is obtained as colorless solid after short path distillation at $2\times10^{-3}$ mbar.

GC-MS (EI): m/z=270, 268 ($M^+$); 201, 199; 120; 91; 55 (100%).

$^1$H-NMR (300 MHz, DMSO-$d_6$): 7.41 (d, J=2.2, 1H); 7.17 (dd, J=8.4, 2.2, 1H); 6.99 (d, J=8.4, 1H); 3.87 (d, J=6.8, 2H); 2.38 (sept, J=6.9, 1H); 1.22 (m, 1H); 1.16 (d, J=6.9, 6H); 0.56 (m, 2H); 0.34 (m, 2H).

Example B.b17

3-Bromo-4-(cyclopropylmethoxy)benzaldehyde

A well stirred mixture of commercially available 3-bromo-4-hydroxy-benzaldehyde (40.2 g; 220 mmol), anhydrous $K_2CO_3$ (30.4 g; 220 mmol) and commercially available bromomethyl-cyclopropane (32.4 g; 240 mmol) in dry DMF (200 mL) is heated to 60° C. over night. The reaction mixture is filtered, concentrated under reduced pressure, diluted with water and extracted with tert. BuOMe. The combined organic extracts are washed with brine, dried over $Mg_2SO_4$ and concentrated under reduced pressure. The residue is chromatographed on silica gel (cyclohexane/AcOEt 100:0 to 85:15) to yield 47.5 g of the title compound as pale yellow oil.

$^1$H-NMR (300 MHz, DMSO-$d_6$): 9.85 8s, 1H); 8.10 (d, J=2.0, 1H); 7.89 (dd, J=8.6, 2.0, 1H); 7.28 (d, J=8.6, 1H); 4.06 (d, J=6.9, 2H); 1.28 (m, 1H); 0.61 (m, 2H); 0.39 (m, 2H).

Example B.b18

2-Bromo-1-(cyclopropylmethoxy)-4-(difluoromethyl)benzene

A pressure vial is charged with dichloromethane (10.0 mL), 3-bromo-4-cyclopropylmethoxybenzaldehyde (example B.b17; 2.55 g; 10.0 mmol) and commercially available bis(2-methoxyethyl)aminosulfurtrifluoride (5.53 g; 25.0 mmol). After capping the reaction mixture was heated in a microwave oven to 70° C. for 15 min. and slowly poured into a well stirred ice cold 2M $NaHCO_3$ solution (50 mL.). After extraction with dichloromethane the combined organic layers are dried over $MgSO_4$ and concentrated under reduced pressure. The residue is chromatographed on silica gel (hexane/AcOEt:90:10 to 80:20) to yield 2.3 g of the title compound as pale yellow oil. $^1$H-NMR (300 MHz, DMSO-$d_6$): 7.77 (~t, J=0.9, 1H); 7.54 (~dt, J=8.6, 0.9, 1H); 7.20 (d, J=8.6, 1H); 6.95 (t, J=55.9, 1H); 3.98 (d, J 0 6.9, 2H); 1.26 (m, 1H), 0.59 (m, 2H); 0.37 (m, 2H).

Example B.c1

5-Cyclopropylmethoxy-4-(4,4,5,5-tetramethyl-[1,3,2]dioxaborolan-2-yl)benzo[1,3]dioxole The reaction is performed in flame-dried glassware under an atmosphere of argon.

A stirred solution of 5-cyclopropylmethoxy-benzo[1,3]dioxole from example B.b1 (38.44 g; 200.0 mmol) in dry THF (500 mL) is cooled to −40° C. before n-butyl lithium (138.0 mL; 1.6M solution in hexane; 220 mmol) is slowly added via syringe. After complete addition, stirring is continued at −40° C. for two hours. At −78° C. neat 2-iso-propoxy-4,4,5,5-tetramethyl-[1,3,2]dioxaborolane (40.95 g; 220.0 mmol) is added via syringe and stirring is continued at −78° C. for two hours.

At −15° C. the reaction mixture is quenched with saturated $NH_4Cl$-solution (200 mL) and stirred at ambient temperature for 30 min. The organic layer is separated and concentrated under reduced pressure. The aqueous layer is extracted with tert.-butylmethylether (3×200 mL). All organic phases are combined, washed with saturated NaCl-solution (200 mL), dried over $MgSO_4$ and filtered through a plug of neutral alumina containing 5 wt % of water. The product is completely eluted with several small portions of tert. butylmethylether.

The solvent is removed under reduced pressure. The crude is treated with ice-cold methanol (50 mL) to deliver the title compound as colorless solid.

GC-MS (EI): m/z=318 ($M^+$); 264 ($M^+$-$C_4H_6$); 207; 164 (100%).

$^1$H-NMR (200 MHz, DMSO-$d_6$): 6.78 (d, J=8.4, 1H); 6.29 (d, J=8.4; 1H); 5.92 (s, 2H); 3.71 (d, J=6.3, 2H); 1.29 (s, 12H); 1.14 (m, 1H); 0.50 (m, 2H); 0.34 (m, 2H).

Example B.c2

2-(2-Cyclopropylmethoxy-4-fluoro-5-methoxy-phenyl)-4,4,5,5-tetramethyl-[1,3,2]dioxaborolane The reaction is performed in flame-dried glassware under an atmosphere of argon.

A stirred solution of 1-bromo-2-cyclopropylmethoxy-4-fluoro-5-methoxy-benzene from example B.b10 (27.51 g; 0.10 mol) in dry tert. butylmethylether (500 mL) is cooled to −20° C. before addition of n-butyl lithium (1.6M in hexane;

68.8 mL; 0.11 mol) via syringe. After complete addition stirring is continued for one hour. Neat 2-iso-propoxy-4,4,5,5-tetramethyl-[1,3,2]dioxaborolane is added via syringe into the reaction mixture at −40° C. After 30 min the reaction is quenched with 1M citric acid (200 mL) at 0° C. and stirred for one hour at ambient temperature. The organic layer is separated. The aqueous layer is extracted with tert.-butylmethylether (100 mL). The combined organic layers are washed with brine (200 mL) dried over MgSO$_4$ and filtered through a plug of neutral alumina containing 5 wt % of water. The product is completely eluted with several small portions of tert.-butylmethylether. The solvent is removed under reduced pressure. The crude is purified by short path distillation at 3×10$^{-3}$ mbar (160° C.) to give the title compound as a colorless oil that solidifies at ambient temperature.

GC-MS (EI): m/z=322 (M$^+$, 100%); 211, 168.

$^1$H-NMR (300 MHz, DMSO-d$_6$): 7.14 (d, J=10.5, 1H); 6.91 (d, J=13.6, 1H); 3.81 (d, J=6.0, 2H); 3.77 (s, 3H); 1.28 (s, 12H); 1.16 (m, 1H); 0.48 (m, 2H); 0.38 (m, 2H).

The following compounds are obtained analogously to the procedure described in above example B.c2.

Example B.c3

2-(2-Cyclopropylmethoxy-4-fluoro-phenyl)-4,4,5,5-tetramethyl-[1,3,2]dioxaborolane Starting from 1-bromo-2-cyclopropylmethoxy-4-fluorobenzene (example B.b2) the title compound is obtained as colorless solid after short bath distillation at 3×10$^{-3}$ mbar (130° C.).

GC-MS (EI): m/z=292 (M$^+$); 181, 55 (100%).

$^1$H-NMR (300 MHz, DMSO-d$_6$): 7.48 (dd, J1=J2=8.0, 1H); 6.80 (dd, J1=12.0, J2=2.2, 1H); 6.71 (ddd, J1=8.4, J2=8.0, J3=2.2, 1H); 3.89 (d, J=5.8, 2H); 1.27 (s, 12H); 1.17 (m, 1H); 0.51 (m, 2H); 0.46 (m, 2H).

Example B.c4

2-(2-Cyclopropylmethoxy-5-fluoro-phenyl)-4,4,5,5-tetramethyl-[1,3,2]dioxaborolane Starting from 1-bromo-2-cyclopropylmethoxy-5-fluorobenzene (example B.b3) the title compound is obtained as colorless solid after short bath distillation at 3×10$^{-3}$ mbar (100° C.).

GC-MS (EI): m/z=292 (M$^+$); 181 (100%); 55.

$^1$H-NMR (300 MHz, DMSO-d$_6$): 7.22-7.13 (m, 2H); 6.95 (dd, J1=8.9, J2=4.2, 1H); 3.85 (d, J=6.4, 2H); 1.28 (s, 12H); 1.17 (m, 1H); 0.52 (m, 2H); 0.46 (m, 2H).

Example B.c6

2-(2-Cyclopropylmethoxy-4-methoxy-phenyl)-4,4,5,5-tetramethyl-[1,3,2]dioxaborolane Starting from 1-bromo-2-cyclopropylmethoxy-4-methoxy-benzene (example B.b5) the title compound is prepared as colorless solid after crystallization from hexane.

GC-MS (EI): m/z=304 (M$^+$); 276; 250; 193; 164 (100%); 150.

$^1$H-NMR (200 MHz, DMSO-d$_6$): 7.41 (d, J=7.9, 1H); 6.48 (dd, J$_1$=7.9, J$_2$=2.2, 1H); 6.45 (d, J=2.2, 1H); 3.87 (d, J=5.6, 2H); 3.75 (s, 3H); 1.25 (s, 12H); 1.16 (m, 1H); 0.49 (m, 2H); 0.44 (m, 2H).

Example B.c7

2-(2-Cyclopropylmethoxy-5-methoxy-phenyl)-4,4,5,5-tetramethyl-[1,3,2]dioxaborolane Starting from 1-bromo-2-cyclopropylmethoxy-5-methoxy-benzene (example B.b6) the title compound is obtained as colorless oil after short bath distillation at 3×10$^{-3}$ mbar (160° C.).

GC-MS (EI): m/z=304 (M$^+$); 276; 250; 193 (100%); 150.

$^1$H-NMR (200 MHz, CDCl$_3$): 7.15 (d, J=3.1, 1H); 6.90 (dd, J$_1$=9.0, J$_2$=3.1, 1H); 6.81 (d, J=9.0, 1H); 3.80 (d, J=6.3, 2H); 3.78 (s, 3H); 1.35 (s, 12H); 1.17 (m, 1H); 0.55 (m, 2H); 0.38 (m, 2H).

Example B.c8

2-(2-Cyclopropylmethoxy-5-methyl-phenyl)-4,4,5,5-tetramethyl-[1,3,2]dioxaborolane Starting from 1-bromo-2-cyclopropylmethoxy-5-methyl-benzene (example B.b7) the title compound is obtained as colorless solid.

GC-MS (EI): m/z=288 (M$^+$); 177 (100%).

$^1$H-NMR 400 MHz, DMSO-d$_6$): 7.26 (d, J=2.1, 1H); 7.16 (dd, J=8.3, 2.1, 1H); 6.81 (d, J=8.3, 1H); 3.81 (d, J=5.9, 2H); 2.21 (s, 3H); 1.27 (s, 12H); 1.15 (m, 1H); 0.47 (m, 2H); 0.40 (m, 2H).

Example B.c9

2-(2-Cyclopropylmethoxy-5-trifluoromethyl-phenyl)-4,4,5,5-tetramethyl-[1,3,2]dioxaborolane Starting from 2-bromo-1-cyclopropylmethoxy-4-trifluoromethyl-benzene (example B.b8) the title compound is obtained as colorless solid.

GC-MS (EI): m/z=342 (M$^+$); 231 (100%).

$^1$H-NMR 300 MHz, DMSO-d$_6$): 7.74 (ddd, J=8.8, 2.6, 0.7, 1H); 7.69 (d, J=2.6, 1H); 7.12 (d, J=8.8, 1H); 3.98 (d, J=5.8, 2H); 1.30 (s, 12H); 1.20 (m, 1H); 0.59 (m, 2H); 0.43 (m, 2H).

Example B.c10

2-(2-Ethoxy-5-trifluoromethyl-phenyl)-4,4,5,5-tetramethyl-[1,3,2]dioxaborolane

Starting from 2-bromo-1-ethoxy-4-trifluoromethyl-benzene (example B.b9) the title compound is obtained as colorless solid GC-MS (EI): m/z=316 (NC); 216 (100%).

$^1$H-NMR 300 MHz, DMSO-d$_6$): 7.75 (ddd, J=8.8, 2.4, 0.6, 1H); 7.70 (d, J=2.4, 1H); 7.13 (d, J=8.8, 1H); 4.09 (qu, J=6.9, 2H); 1.33 (t, j=6.9, 3H); 1.29 (s, 12H).

Example B.c11

2-(2-Cyclopropylmethoxy-4-fluoro-5-methyl-phenyl)-4,4,5,5-tetramethyl-[1,3,2]dioxaborolane Starting from 1-bromo-2-cyclopropylmethoxy-4-fluoro-5-methyl-benzene (example B.b11) the title compound is obtained as colorless oil.

GC-MS (EI): m/z=306 (M$^+$); 195 (100%); 55.

$^1$H-NMR (300 MHz, DMSO-d$_6$): 7.35 (dd, J=10.0, 0.5, 1H); 6.76 (d, J=12.4, 1H); 3.85 (d, J=5.8, 2H); 2.13 (d, J=0.5, 3H); 1.27 (s, 12H); 1.15 (m, 1H); 0.49 (m, 2H); 0.41 (m, 2H).

Example B.c12

2-(2-Cyclopropylmethoxy-5-fluoro-4-methoxy-phenyl)-4,4,5,5-tetramethyl-[1,3,2]dioxaborolane Starting from 1-bromo-2-cyclopropylmethoxy-5-fluoro-4-methoxy-benzene (example B.b12) the title compound is obtained as colorless solid after crystallization from methanol.

GC-MS (EI): m/z=322 (M$^+$); 211; 182; 168 (100%); 55.
$^1$H-NMR (300 MHz, DMSO-d$_6$): 7.15 (d, J=11.7, 1H); 6.73 (d, J=7.0, 1H); 3.88 (d, J=6.0, 2H); 3.85 (s, 3H); 1.26 (s, 12H); 1.16 (m, 1H); 0.50 (m, 2H); 0.30 (m, 2H).

Example B.c13

2-[2-(Cyclopropylmethoxy)-5-(2-methyl-1,3-dioxolan-2-yl)phenyl]-4,4,5,5-tetramethyl-1,3,2-dioxaborolane Starting from 2-[3-bromo-4-(cyclopropylmethoxy)phenyl]-2-methyl-1,3-dioxolane (example B.b14) the title compound is obtained as colorless solid.

GC-MS (EI): m/z=360 (M$^+$); 345 (100%).
$^1$H-NMR (300 MHz, DMSO-d$_6$): 7.49 (d, J=2.5, 1H); 7.40 (dd, J=8.6, 2.5, 1H); 6.89 (d, J=8.6, 1H); 3.95 (m, 2H); 3.86 (d, J=5.7, 2H); 3.67 (m, 2H); 1.50 (s, 3H); 1.28 (s, 12H); 1.17 (m, 1H); 0.48 (m, 2H); 0.41 (m, 2H).

Example B.c14

2-(2-Cyclopropylmethoxy-5-ethyl-phenyl)-4,4,5,5-tetramethyl-[1,3,2]dioxaborolane Starting from 1-bromo-2-cyclopropylmethoxy-5-ethyl-benzene (example B.b15) the title compound is obtained as pale yellow oil.

GC-MS (EI): m/z=302 (M$^+$); 274; 191 (100%); 55.
$^1$H-NMR (300 MHz, DMSO-d$_6$): 7.27 (d, J=2.0, 1H); 7.20 (dd, J=8.4, 2.0, 1H); 6.83 (d, J=8.4, 1H); 3.82 (d, J=5.8, 2H); 2.50 (qu, J=7.7, 2H); 1.28 (s, 12H); 1.13 (t, J=7.7, 3H); 1.12 (m, 1H); 0.48 (m, 2H); 0.39 (m, 2H).

Example B.c15

2-[2-(Cyclopropylmethoxy)-5-(propan-2-yl)phenyl]-4,4,5,5-tetramethyl-1,3,2-dioxaborolane Starting from 2-bromo-1-cyclopropylmethoxy-4-(propan-2-yl)benzene (example B.b16) the title compound is obtained as colorless solid.

GC-MS (EI): m/z=316 (M$^+$); 301; 288; 247; 205; 147 (100%); 103; 83; 55.
$^1$H-NMR (300 MHz, DMSO-d$_6$): 7.29 (d, J=2.4, 1H); 7.23 (dd, J=8.4, 2.2, 1H); 6.84 (d, J=8.4, 1H); 3.82 (d, J=5.9, 2H); 2.81 (sept, J=6.9, 1H); 1.28 (s, 12H); 1.15 (d, J=6.9, 6H & m, 1H); 0.48 (m, 2H); 0.40 (m, 2H).

Example B.c16

2-[2-(Cyclopropylmethoxy)-5-(difluoromethyl)phenyl]-4,4,5,5-tetramethyl-1,3,2-dioxaborolane 2-Bromo-1-cyclopropylmethoxy-4-difluoromethyl-benzene (example B.b18; 24.35 g; 87.9 mmol) is dissolved in dry tert. BuOMe (440 mL). n-BuLi (1.6M in hexane; 60.0 mL; 96.0 mmol) is slowly syringed into the well stirred reaction mixture at −40° C. After one hour commercially available 2-isopropoxy-4,4,5,5-tetramethyl-1,3,2-dioxaborolane (17.86 g; 96.0 mmol) is added at −40° C. followed by stirring at 0° C. for one additional hour. The reaction mixture is quenched by addition of 2M aqueous citric acid (90.0 mL). The organic layer is separated, washed with brine, dried over Mg$_2$SO$_4$ and filtered through a pad of neutral alumina (act.2-3). The solvent is removed under reduced pressure to yield 28.1 g of the title compound as pale yellow oil.

Caution:
The Compound Tends to Vigorously Decompose when Heated Above 80° C.
$^1$H-NMR (300 MHz, DMSO-d$_6$): 7.63 (~t, J=1.1, 1H); 7.58 (~dt, J=8.4, 1.1, 1H); 7.05 (d, J=8.4, 1H); 6.95 (t, J=56.2, 1H); 3.94 (d, J=5.8, 2H); 1.29 (s, 12H); 1.19 (m, 1H), 0.51 (m, 2H); 0.43 (m, 2H).

Example C1 tert-Butyl-(3R*,4R*)-4-azido-3-hydroxy-piperidine-1-carboxylate (23f) and tert-butyl-(3S*,4S*)-3-azido-4-hydroxy-piperidine-1-carboxylate (23g)

A mixture of tert-butyl 7-oxa-3-azabicyclo[4.1.0]heptane-3-carboxylate (60 g, 0.30 mol), prepared according to literature [Zhao, S.; Ghosh, A.; D'Andrea, S. V.; Freeman, P.; VonVoigtlander, P. F.; Carter, D. B.; Smith, M. W.; Heterocycles, 1994, 39, 163], sodium azide (25.4 g, 0.39 mol) and ammonium chloride (21 g, 0.39 mol) in ethanol (150 mL) and water (150 mL) is heated to gentle reflux overnight. Ethanol is evaporated in vacuo. The residue is distributed between dichloromethane and water. The aqueous layer is separated and extracted with dichloromethane. The combined organic layer is washed with water and brine, dried over Na$_2$SO$_4$ and concentrated in vacuo to obtain, 67.3 g of the crude as a 4:1 mixture 23f and 23g according to $^1$H-NMR in agreement with literature data [Erickson, S. D.; Banner, B.; Berthel, S.; Conde-Knape, K.; Falicioni, F.; Hakimi, I.; Hennessy, B.; Kester, R. F.; Kim, K.; Ma, Ch.; McComas, W.; Mennona, F.; Mischke, S.; Orzechowski, L.; Qian, Y.; Salari, H.; Tengi, J.; Thakkar, K.; Taub, R.; Tilley, J. W.; Wang, H.; Bioorg. Med. Chem. Lett. 2008, 18, 1402].

Separation by column chromatography on silica gel (heptane:ethyl acetate—4:1) yields faster eluting 23f, slower eluting 23g and un-separated 23f and 23g.

tert-Butyl-(3R*,4R*)-4-azido-3-hydroxy-piperidine-1-carboxylate (23f)

MS (ESI): m/z=217 (MH$^+$, 100%).
$^1$H-NMR (400 MHz, CDCl$_3$): 4.12 (m, 1H); 3.95 (br.m, 1H); 3.50 (m, 1H); 3.38 (m, 1H); 2.89 (m, 1H); 2.78 (m, 1H); 2.71-2.32 (m 1H); 2.00 (m, 1H); 1.52 (m, 1H); 1.44 (s, 9H).

tert-Butyl-(3S*,4S*)-3-azido-4-hydroxy-piperidine-1-carboxylate (23g)

MS (ESI): m/z=217 (MH$^+$, 100%).
$^1$H-NMR (400 MHz, CDCl$_3$): 4.23 (m, 1H); 4.00 (m, 1H); 3.54 (m, 1H); 3.30 (m, 1H); 2.82 (m, 1H); 2.66 (m, 1H); 2.24 (m, 1H); 1.97 (m, 1H); 1.59 (m, 1H); 1.46 (s, 9H).

Example C2 tert-Butyl (3R*,4R*)-4-amino-3-hydroxy-piperidine-1-carboxylate (21f)

(3S*,4S*)-tert-butyl 4-azido-3-hydroxypiperidine-1-carboxylate from example C1 (47 g, 194 mmol) is dissolved in methanol (1200 mL) under nitrogen. Palladium hydroxide (20% on carbon; 4.7 g) is added. The atmosphere is changed to hydrogen and the stirred reaction mixture is hydrogenated at room temperature and 70 psi for 72 hours. The mixture is filtered through celite. The filtrate is evaporated. The residue is recrystallized from $CH_2Cl_2$ with a small amount of MeOH to obtain the title compound as a white solid.

HR-MS (ESI): m/z=217.1539 ([MH]$^+$, $C_{10}H_{21}N_2O_3^+$, calc. 217.1547).

Example C3 tert-Btyl (3S*,4S*)-3-Amino-4-hydroxy-piperidine-1-carboxylate (21g)

Following the procedure outlined in above example C2 starting from (3S*,4S*)-3-azido-4-hydroxypiperidine-1-carboxylic acid tert-butyl ester (example C1) the title compound is obtained as white solid.

HR-MS (ESI): m/z=217.1541 ([MH]$^+$, $C_{10}H_{21}N_2O_3^+$, calc. 217.1547).

Example C4

(1R,3S)-3-[(tert-Butoxycarbonyl)amino]cyclopentyl methanesulfonate

Methansulfonyl chloride (8.2 g; 72.0 mmol) is slowly added to an ice cold solution of commercially available tert-butyl [(1S,3R)-3-hydroxycyclopentyl]carbamate (12.1 g; 60.0 mmol) and 2,6-lutidine (9.6 g; 90.0 mmol) in dry dichloromethane (300 mL). The stirred reaction mixture is allowed to warm to ambient temperature over night. The reaction mixture is extracted with water, ice cold 1N HCl, half saturated brine, and dried over $MgSO_4$. After filtration through a pad of neural alumina (act. 2-3) the solvent is removed under reduced pressure to yield the crude title compound as yellow oil that is processed without additional purification.

Example C5 tert-Butyl [(1S,3S)-3-azidocyclopentyl]carbamate

Crude product from example C4 is dissolved in dry DMF (180 mL). After addition of sodium azide (11.7 g; 180.0 mmol) the reaction mixture is stirred for three days at 60° C. After filtration the reaction mixture is concentrated under reduced pressure, diluted with dichloromethane, extracted with water, half saturated brine and dried over $MgSO_4$. After column chromatography on silica gel (cyclohexane/AcOEt—9:1) 11.8 g of the title compound is obtained as pale yellow oil.

$^1$H-NMR (300 MHz, DMSO-d$_6$): 6.90 (d, J=6.2, 1H, —NH); 4.11 (m, 1H); 3.88 (m, 1H); 2.08-1.77 (m, 3H); 1.70 (m, 1H); 1.60-1.31 (m, 2H & s, 9H).

Example C6 tert-Butyl [(1S,3S)-3-aminocyclopentyl]carbamate hydrochloride tert-Butyl [(1S,3S)-3-azidocyclopentyl]carbamate (example C5; 11.3 g; 50.0 mmol) is dissolved in MeOH (250 mL) and pressure hydrogenated over Pd(OH)$_2$ (20% on charcoal; 0.45 g) at 20 bar and ambient temperature over night. After filtration through a pad of celite the solvent is removed under reduced pressure. The residue is dissolved in tert.-BuOMe (250 mL) cooled to 0° C. and treated with HCl (4N in dioxane; 13.5 mL). The precipitate is collected by suction filtration, washed with several small portions of tert.-BuOMe and dried under reduced pressure to yield 11.1 g of the title compound as off-white solid.

$^1$H-NMR (300 MHz, DMSO-d$_6$): 8.26-7.08 (br.s, 3H, —NH$_3^+$); 6.95 (d, J=6.9, 1H, —NH); 3.95 (m, 1H); 3.52 (m, 1H); 1.98 (m, 2H); 1.77 (m, 2H); 1.43 (m, 2H); 1.38 (s, 9H).

Example C7 tert-Butyl [(1R*,3S*,4R*)-4-(benzyloxy)-3-methyl-cyclohexyl]carbamate

Known (1R*,2S*,4R*)-4-azido-2-methylcyclohexyl benzyl ether (12.0 g; 48.9 mmol) [Aicher, T.; Chicarelli, M. J.; Hinklin, R. J.; Tian, H.; Wallace, O. B.; Chen, Z.; Mabry, T. E.; McCowan, J. R.; Snyder, N. J.; Winneroski, L. L.; Allen, J. G.; WO 2006/049952 (2009)] is dissolved in MeOH (500.0 mL) and pressure hydrogenated over Pd (10% on charcoal; 1.2 g) at 20 bar and ambient temperature for two hours. The catalyst is removed by filtration through a pad of celite. The filtrate is concentrated under reduced pressure. The residue is dissolved in dioxane (100 mL). After addition of 2N NaOH (25.0 mL; 50.0 mmol) and di tert-butyl dicarbonate (11.4 g; 51.3 mmol) the mixture is stirred for one hour at ambient temperature and concentrated under reduced pressure. After addition of water and extraction with tert-BuOMe the organic layer is dried over $MgSO_4$. The solvent is removed under reduced pressure and the residue is chromatographed on silica gel (cyclohexane/AcOEt—9:1) to yield 14.4 g of the title compound as colourless oil.

$^1$H-NMR (300 MHz, CDCl$_3$): 7.35-7.21 (m, 5H); 4.59 (d, J=12.1, 1H); 4.36 (d, J=12.1, 1H & br.s, 1H, —NH); 3.55-3.35 (m, 2H); 2.08 (m, 1H); 1.79-1.57 (m, 3H); 1.44 (s, 9H); 1.42-1.21 (m, 3H); 0.99 (d, J=6.6, 3H).

Example C8 tert-Butyl [(1R*,3R*,4S*)-4-hydroxy-3-methylcyclohexyl]carbamate tert-Butyl [(1R*,3S*,4R*)-4-(benzyloxy)-3-methylcyclohexyl]carbamate (example C7; 14.0 g; 43.8 mmol) dissolved in MeOH (440 mL) is pressure hydrogenated over Pd (10% on charcoal; 1.4 g) at 50 bar and ambient temperature for 72 hours. The catalyst is removed by filtration through a pad of celite. The filtrate is concentrated under reduced pressure. The residue is chromatographed on silica gel (cyclohexane/AcOEt—70:30 to 50:50) to yield 8.5 g of the tile compound as colourless oil.

$^1$H-NMR (300 MHz, CDCl$_3$): 4.42 (br.s, 1H, —NH); 3.76 (m, 1H); 3.46 (m, 1H); 1.89 (m, 1H); 1.80-1.33 (m, 6H); 1.45 (s, 9H); 1.23 (m, 1H); 0.98 (d, J=6.8, 3H).

Example C9

(1S*,2R*,4R*)-4-[(tert-Butoxycarbonyl)amino]-2-methylcyclohexyl methanesulfonate Starting from tert-butyl [(1R*,3R*,4S*)-4-hydroxy-3-methylcyclohexyl]carbamate (example C8; 10.2 g; 44.3 mmol) and following the procedure as described in example C4 12.3 g of the title compound is obtained as colourless oil after column chromatography on silica gel (cyclohexane/AcOEt—70:30).

¹H-NMR (300 MHz, CDCl₃): 4.74 (br.s, 1H); 4.42 (br.s, 1H, —NH); 3.51 (m, 1H); 3.01 (s, 3H); 2.24 (m, 1H); 1.93-1.56 (m, 4H); 1.44 (s, 9H & m, 1H); 1.20 (m, 1H); 1.03 (d, J=6.6, 3H).

Example C10 tert-Butyl [(1R*,3R*,4R*)-4-azido-3-methylcyclohexyl]carbamate

Starting from (1S*,2R*,4R*)-4-[(tert-butoxycarbonyl)amino]-2-methylcyclohexyl methanesulfonate (example C9; 2.4 g; 7.8 mmol) and following the procedure as described in example C5 1.4 g of the title compound is obtained as colourless solid after column chromatography on silica gel (cyclohexane/AcOEt—95:05 to 85:15).

¹H-NMR (300 MHz, CDCl₃): 4.35 (br.s, 1H, —NH); 3.46 (m, 1H); 2.78 2.78 (m, 1H); 2.18-1.95 (m, 3H); 1.63-1.33 (s, 9H & m, 2H); 1.17 (m, 1H); 1.03 (d, J=6.6, 3H); 0.90 (m, 1H).

Example C11 tert-Butyl [(1R*,3R*,4R*)-4-amino-3-methylcyclohexyl]carbamate tert-Butyl [(1R*,3R*,4R*)-4-azido-3-methylcyclohexyl]carbamate (example 010; 1.2 g; 4.7 mmol) is dissolved in MeOH (20.0 mL) and pressure hydrogenated over Pd (10% on charcoal; 0.1 g) at 20 bar and ambient temperature over night. After filtration through a pad of celite the solvent is removed under reduced pressure to yield 1.0 g of the title compound as off-white solid.

¹H-NMR (300 MHz, CDCl₃, MeOH-d₄): 3.41 (m, 1H); 2.20 (m, 1H); 2.03-1.81 (m, 3H); 1.44 (s, 9H); 1.34-1.07 (m, 3H); 0.98 (d, J=6.6, 3H); 0.91 (m, 1H).

HR-MS (ESI): m/z=229.1899 ([MH]⁺, C₁₂H₂₅N₂O₂⁺, calc. 229.1911).

Example C12

(1R*,3R*,4R*)-4-Azido-3-methylcyclohexanamine hydrochloride tert-Butyl [(1R*,3R*,4R*)-4-azido-3-methylcyclohexyl]carbamate (example C10; 2.5 g; 10.0 mmol) is dissolved in THF (25.0 mL). After addition of HCl (4M solution in dioxane; 10.0 mL; 40.0 mmol) the reaction mixture is stirred at ambient temperature over night and gently refluxed for additional 6 hours. tert-BuOMe is added at ambient temperature, the precipitated product is collected by suction filtration, washed with several small portions of tert-BuOMe and dried under reduced pressure to yield 1.8 g of the title compound as colourless solid.

¹H-NMR (400 MHz, MeOH-d₄): 3.16 (m, 1H); 2.95 (m, 1H); 2.19 (m, 1H); 2.11 (m, 1H); 2.03 (m, 1H); 1.60-1.44 (m, 3H); 1.23 (m, 1H); 1.10 (d, J=6.5, 3H).

HR-MS (ESI): m/z=155.1284 ([MH]⁺, C₇H₁₅N₄⁺, calc. 155.1291).

Example C13 tert-Butyl(diphenyl)({4-[(trimethylsilyl)oxy]cyclohex-3-en-1-yl}oxy)silane

Trimethylsilyl trifluoromethanesulfonate (45.0 g; 198.8 mmol) is dropped into a solution of known 4{[tert-butyl(diphenyl)silyl]oxy}cyclohexanone [Okamura, W. H.; Elnagar, H. Y.; Ruther, M.; Dobreff, S. *J. Org. Chem.* 1993, 58, 600] (58.4 g, 165.5 mmol) and triethylamine (55.4 mL; 397.6 mmol) in dichloromethane (500 mL) at −78° C. under an atmosphere of nitrogen. After one hour the reaction mixture is allowed to warm to 0° C. and quenched with saturated NaHCO₃-solution (120 mL). The organic layer is separated, dried over MgSO₄ and concentrated under reduced pressure. A 1:1-mixture of tert-BuOMe and hexane is added to the biphasic residue. The organic layer is separated, washed with saturated NaHCO₃-solution and dried over MgSO₄. The solvent is removed under reduced pressure to deliver 69.0 g of the title compound as colourless oil.

¹H-NMR (300 MHz, CDCl₃): 7.64 (m, 4H); 7.45-7.32 (m, 6H); 4.64 (m, 1H); 3.93 (m, 1H); 2.23-2.05 (m, 3H); 1.99-1.85 (m, 1H); 1.81-1.62 (m, 2H); 1.05 (s, 9H); 0.16 (s, 9H).

Example C14

(2S*,4R*)-4-{[tert-Butyl(diphenyl)silyl]oxy}-2-fluorocyclohexanone and (2R*,4R*)-4-{[tert-butyl(diphenyl)silyl]oxy}-2-fluorocyclohexanone To a stirred solution of tert-butyl(diphenyl)({4-[(trimethylsilyl)oxy]cyclohex-3-en-1-yl}oxy)silane (example C13; 69.0 g; 162 mmol) in dry acetonitrile (750 mL) Selectfluor 0 (68.6 g; 184 mmol) is added in small portions at 5° C. After complete addition the reaction mixture is stirred at ambient temperature over night. Saturated NaHCO₃-solution (200 mL) is added, the precipitate is removed by filtration and the filtrate is concentrated under reduced pressure. The residue is distributed between tert-BuOMe and saturated NaHCO₃-solution. The organic layer is separated, washed with brine and dried over MgSO₄. The solvent is removed under reduced pressure. The residue is chromatographed on silica gel (cyclohexane/AcOEt—10:0 to 9:1) to deliver 44.9 g of (2S*,4R*)-4-{[tert-butyl(diphenyl)silyl]oxy}-2-fluorocyclohexanone as white solid ¹H-NMR (300 MHz, CDCl₃): 7.67 (m, 4H); 7.50-7.34 (m, 6H); 5.41 (ddd, J=48.7, 12.2, 6.8, 1H); 4.33 (m, 1H); 2.93 (td, J=13.9, 6.0, 1H); 2.56-2.34 (m, 2H); 2.05-1.93 (m, 1H); 1.81 (m, 1H); 1.69 (tdd, J=13.9, 4.6, 2.4, 1H); 1.12 (s, 9H) and 9.3 g of (2R*,4R*)-4-{[tert-butyl(diphenyl)silyl]oxy}-2-fluorocyclohexanone as white solid ¹H-NMR (300 MHz, CDCl₃): 7.68 (m, 4H); 7.49-7.36 (m, 6H); 4.68 (ddd, J=48.0, 12.4, 7.3, 1H); 4.08 (m, 1H); 2.54 (m, 1H); 2.40 (m, 1H); 2.16-1.96 (m, 3H); 1.89-1.73 (m, 1H); 1.06 (s, 9H).

Example C15

(1R*,2S*,4R*)-4-{[tert-Butyl(diphenyl)silyl]oxy}-2-fluorocyclohexanol

L-Selectride® (1M in THF; 69.0 mL; 69.0 mm0l) is dropped into a stirred solution of (2S*,4R*)-4-{[tert-butyl(diphenyl)silyl]oxy}-2-fluorocyclohexanone (example C14; 23.3 g; 62.8 mmol) in dry THF (230 mL) at −15° C. The reaction mixture is stirred over night and cooled to 0° C. before careful addition of ice cold water (100 mL), followed by dropwise addition of H₂O₂ (30% solution in water; 39.0 mL). After 30 min. saturated Na₂SO₃-solution (80 mL) is dropwise added at 0° C. tert-BuOMe (300 mL) is added, the organic layer is separated and concentrated under reduced pressure. The aqueous layer is extracted with tert-BuOMe. All combined organic phases are washed with brine and dried over MgSO₄. The solvent is removed under reduced pressure.

The residue is chromatographed on silica gel (cyclohexane/AcOEt—10:0 to 9:1) to yield 15.5 g of the title compound as colourless liquid.

$^1$H-NMR (300 MHz, DMSO-$d_6$): 7.59 (m, 4H); 7.44 (m, 6H); 4.77 (d, J=4.7, 1H, —OH); 4.70 (tdd, J=49.5, 7.1, 2.7, 1H); 3.97 (m, 1H); 3.70 (m, 1H); 1.98 (m, 1H); 1.75-1.53 (m, 3H); 1.40 (m, 2H); 1.01 (s, 9H).

Example C16

(1R*,2S*,4R*)-4-{[tert-Butyl(diphenyl)silyl]oxy}-2-fluorocyclohexyl methane sulfonate Starting from (1R*,2S*,4R*)-4-{[tert-butyl(diphenyl)silyl]oxy}-2-fluorocyclohexanol (example C15; 10.4 g; 27.8 mmol) and following the procedure as described in example C4 12.2 g of the title compound is obtained as pale yellow oil after column chromatography on silica gel (cyclohexane/AcOEt—90:10 to 80:20).

$^1$H-NMR (300 MHz, CDCl$_3$): 7.62 (m, 4H); 7.43 (m, 6H); 5.16-4.91 (m, 2H); 4.20 (m, 1H); 3.02 (s, 3H); 2.17-1.84 (m, 4H); 1.69 (m, 1H); 1.49 (m, 1H); 1.07 (s, 9H).

Example C17

{[(1R*,3S*,4S*)-4-Azido-3-fluorocyclohexyl]oxy}tert-butyl)diphenylsilane

Starting from (1R*,2S*,4R*)-4-{[tert-butyl(diphenyl)silyl]oxy}-2-fluorocyclohexyl methanesulfonate (example C16; 12.1 g; 26.8 mmol) and following the procedure as described in example C5, 9.4 g of the title compound is obtained as colourless oil after column chromatography on silica gel (cyclohexane/AcOEt—95:05).

$^1$H-NMR (300 MHz, CDCl$_3$): 7.63 (m, 4H); 7.39 (m, 6H); 4.84 (dm, J=50.3, 1H); 4.15 (m, 1H); 3.45 (m, 1H); 2.16 (m, 1H); 1.99-1.75 (m, 2H); 1.65 (m, 1H); 1.49 (m, 1H); 1.33 (m, 1H); 1.07 (s, 9H).

Example C18 tert-Butyl [(1S*,2S*,4R*)-4-{[tert-butyl(diphenyl)silyl]oxy}-2-fluorocyclohexyl]carbamate Starting from {[(1R*,3S*,4S*)-4-azido-3-fluorocyclohexyl]oxy}(tert-butyl)diphenylsilane (example C17; 9.4 g; 23.6 mmol) and following the procedure as described in example C7, 8.7 g of the title compound is obtained as colourless solid after column chromatography on silica gel (cyclohexane/AcOEt—95:05).

$^1$H-NMR (300 MHz, DMSO-$d_6$): 7.60 (m, 4H); 7.46 (m, 6H); 7.11 (d, J=8.4, 1H, —NH); 4.73 (tdd, J=50.4, 10.4, 4.6, 1H); 4.09 (m, 1H); 3.44 (m, 1H); 1.98 (m, 1H); 1.76 (m, 1H); 1.67-1.46 (m, 3H); 1.39 (s, 9H & m, 1H); 1.03 (s, 9H).

Example C19 tert-Butyl [(1S*,2S*,4R*)-2-fluoro-4-hydroxycyclohexyl]carbamate

Tetrabutylammoniumfluoride trihydrate (11.9 g; 36.7 mmol) is added to a solution of tert-butyl [(1S*,2S*,4R*)-4-{[tert-butyl(diphenyl)silyl]oxy}-2-fluorocyclohexyl]carbamate (example C18; 8.7 g; 18.3 mmol). The reaction mixture is stirred over night at ambient temperature. The solvent is removed under reduced pressure. The residue is chromatographed on silica gel (cyclohexane/AcOEt—60:40 to 40:60) to yield 4.2 g of the title compound as colourless oil.

$^1$H-NMR (300 MHz, DMSO-$d_6$): 6.91 (d, J=8.0, 1H, —NH); 4.57 (d, J=2.7, 1H, —OH); 4.56 (dm, J=50.4, 1H); 3.94 (m, 1H); 3.41 (m, 1H); 2.03 (m, 1H); 1.64-1.50 (m, 4H); 1.50-1.32 (s, 9H & m, 1H).

Example C20

(1R*,3S*,4S*)-4-[(tert-Butoxycarbonyl)amino]-3-fluorocyclohexyl methane sulfonate Starting from tert-butyl [(1S*,2S*,4R*)-2-fluoro-4-hydroxycyclohexyl]carbamate (example C19; 5.9 g; 25.5 mmol) and following the procedure as described in example C4, 6.6 g of the title compound is obtained as colourless solid after chromatography on silica gel (cyclohexane/AcOEt—60:40 to 50:50)

$^1$H-NMR (300 MHz, CDCl$_3$): 5.05 (m, 1H); 4.61 (br.s, 1H, —NH & dm, J=48.9, 1H); 3.72 (m, 1H); 3.02 (s, 3H); 2.40 (m, 1H); 2.09 (m, 1H); 1.96 (m, 2H); 1.79 (m, 1H); 1.64 (m, 1H); 1.45 (s, 9H).

Example C21 tert-Butyl [(1S*,2S*,4S*)-4-azido-2-fluorocyclohexyl]carbamate

Starting from (1R*,3S*,4S*)-4-[(tert-butoxycarbonyl)amino]-3-fluorocyclohexyl methanesulfonate (example C20; 5.3 g; 17.0 mmol) and following the procedure as described in example C5, 4.0 g of the title compound is obtained as colourless solid after chromatography on silica gel (cyclohexane/AcOEt—60:40).

$^1$H-NMR (300 MHz, CDCl$_3$): 4.45 (br.s, 1H, —NH); 4.25 (dm, J=49.7, 1H); 3.55 (m, 1H); 3.35 (m, 1H); 2.46 (m, 1H); 2.21 (m, 1H); 1.99 (m, 1H); 1.64 (m, 1H); 1.45 (s, 9H & m, 1H); 1.23 (m, 1H).

Example C22 tert-Butyl [(1S*,2S*,4S*)-4-amino-2-fluorocyclohexyl]carbamate

Starting from tert-butyl [(1S*,2S*,4S*)-4-azido-2-fluorocyclohexyl]carbamate (example C21; 2.0 g; 7.7 mmol) and following the procedure as described in example C11 yields 1.7 g of the title compound as colourless solid.

HR-MS (ESI): m/z=233.1651 ([MH]$^+$, $C_{11}H_{22}FN_2O_2^+$, calc. 233.1659).

Example C23

(1S*,2S*,4S*)-4-Azido-2-fluorocyclohexanamine hydrochloride

Starting from tert-butyl [(1S*,2S*,4S*)-4-azido-2-fluorocyclohexyl]carbamate (example C21; 1.9 g; 7.5 mmol) and following the procedure as described in example C12 yields 1.4 g of the title compound as colourless solid.

HR-MS (ESI): m/z=159.1038 ([MH]$^+$, $C_6H_{13}FN_4^+$, calc. 159.1040).

Example C24

(1S*,2S*,4S*)-4-(Benzyloxy)-2-methylcyclopentanol

A stirred suspension of CuCN (8.9 g; 100.0 mmol) in dry THF (100.0 mL) is cooled to −78° C. before addition of MeLi (1.6M solution in Et$_2$O; 125.0 mL; 200.0 mmol). The mixture is allowed to warm to ambient temperature and re-cooled to −78° C. before dropwise addition of a solution of known cis-3-(benzyloxy)-6-oxabicyclo[3.1.0]hexane (9.5 g; 50.0 mmol) [Snider, B. B.; Liu, T. *J. Org. Chem.* 2000, 65, 8490; Milne, D.; Murphy, P. J. *J. Chem. Soc. Chemical Communication* 1993, 884] in dry THF (100 mL) followed by dropwise addition of BF$_3$ etherate (6.8 mL; 55.0 mmol). The cooled reaction mixture is stirred over night, allowed to warm to 0° C. and quenched with saturated NH$_4$Cl-solution containing 10% (v/v) of 25% aqueous NH$_4$OH-solution (250 mL). The organic layer is separated and concentrated under reduced pressure. The aqueous layer is extracted with tert-BuOMe. All organic phases are combined, washed with brine, dried over MgSO$_4$ and concentrated under reduced pressure. The residue is chromatographed on silica gel (cyclohexane/tert-BuOMe—80:20 to 50:50) to yield 7.6 g of the title compound as pale yellow oil.

$^1$H-NMR (300 MHz, DMSO-d$_6$): 7.31 (m, 5H); 4.62 (d, J=5.3, 1H, —OH); 4.38 (s, 2H); 3.87 (m, 1H); 3.39 (m, 1H); 2.26 (m, 1H); 1.84 (m, 2H); 1.47 (m, 1H); 1.30 (m, 1H); 0.93 (d, J=6.2, 3H).

Example C25

(1R*,2S*,4S*)-4-(Benzyloxy)-2-methylcyclopentyl 3-nitrobenzoate

To an ice-cold stirred solution of (1S*,2S*,4S*)-4-(benzyloxy)-2-methylcyclopentanol (example C24; 7.5 g; 36.5 mmol), 3-nirobenzoic acid (18.4 g; 110.0 mmol) and triphenylphoshine (23.0 g; 87.6 mmol) diethyl azodicarboxylate (40% solution in toluene; 38.1 g; 87.6 mmol) is dropwise added. The reaction mixture is stirred at ambient temperature for two hours and concentrated under reduced pressure. The residue is chromatographed on silica gel (cyclohexane/tert-BuOMe—100:0 to 80:20) to yield 11.5 g of the title compound as pale yellow oil.

$^1$H-NMR (300 MHz, DMSO-d$_6$): 8.61 (~s, 1H); 8.49 (m, 1H); 8.37 (m, 1H); 7.84 (t, J=8.0, 1H); 7.33 (m, 5H); 5.41 (m, 1H); 4.44 (d, J=1.5, 2H); 4.20 (m, 1H); 2.43 (m, 1H); 2.18 (m, 2H); 2.00 (m, 1H); 1.73 (m, 1H); 1.00 (d, J=6.7, 3H).

Example C26

(1R*,2S*,4S*)-4-(Benzyloxy)-2-methylcyclopentanol

To a solution of (1R*,2S*,4S*)-4-(benzyloxy)-2-methylcyclopentyl 3-nitrobenzoate (example 25; 11.5 g; 32.5 mmol) in THF (80.0 mL) and MeOH (40.0 mL) LiOH (1.17 g; 48.7 mmol) dissolved in water (40.0 mL) is added. The reaction mixture is stirred at ambient temperature for one hour and concentrated under reduced pressure. The residue is diluted with water and extracted with dichloromethane. The organic layer is dried over MgSO$_4$, and concentrated under reduced pressure. The residue is chromatographed on silica gel (cyclohexane/tert-BuOMe—80:20 to 50:50) to yield 5.9 g of the title compound as pale yellow oil.

$^1$H-NMR (300 MHz, DMSO-d$_6$): 7.30 (m, 5H); 4.37 (s, 2H); 4.28 (d, J=4.2, 1H, —OH); 4.07 (m, 1H); 3.97 (m, 1H); 2.08-1.86 (m, 2H); 1.84-1.68 (m, 2H); 1.54 (m, 1H); 0.90 (d, J=6.8, 3H).

Example C27

(1R*,2S*,4S*)-4-(Benzyloxy)-2-methylcyclopentyl methanesulfonate

Starting from (1R*,2S*,4S*)-4-(benzyloxy)-2-methylcyclopentanol (example C26; 5.9 g; 28.4 mmol) and following the procedure as described in example C4, 7.5 g of the title compound is obtained as pale yellow oil after column chromatography on silica gel (cyclohexane/tert-BuOMe—90:10 to 65:35).

$^1$H-NMR (300 MHz, DMSO-d$_6$): 7.32 (m, 5H); 5.02 (m, 1H); 4.40 (d, J=2.2, 2H); 4.14 (m, 1H); 3.14 (s, 3H); 2.39-2.24 (m, 2H); 2.08 (m, 1H); 1.91 (m, 1H); 1.52 (m, 1H); 0.99 (d, J=6.7, 3H).

Example C28

(1S*,2S*,4S*)-1-Azido-4-(benzyloxy)-2-methylcyclopentane

Starting from (1R*,2S*,4S*)-4-(benzyloxy)-2-methylcyclopentyl methanesulfonate (example C27; 7.4 g; 26.5 mmol) and following the procedure as described in example C5, 5.6 g of the title compound is obtained as pale yellow oil after column chromatography on silica gel (cyclohexane/tert-BuOMe—90:10 to 65:35).

$^1$H-NMR (300 MHz, DMSO-d$_6$): 7.32 (m, 5H); 4.41 (s, 2H); 3.97 (m, 1H); 3.38 (m, 1H); 2.40 (m, 1H); 2.11-1.90 (m, 2H); 1.65 (m, 1H); 1.39 (m, 1H); 1.02 (d, J=6.4, 3H).

Example C29 tert-Butyl [(1S*,2S*,4S*)-4-(benzyloxy)-2-methylcyclopentyl]carbamate

Starting from (1S*,2S*,4S*)-1-azido-4-(benzyloxy)-2-methylcyclopentane (example C28; 4.9 g; 24.0 mmol) and following the procedure as described in example C7, 5.5 g of the title compound is obtained as pale yellow oil after column chromatography on silica gel (cyclohexane/tert-BuOMe—95:05 to 70:30).

$^1$H-NMR (300 MHz, DMSO-d$_6$): 7.31 (m, 5H); 6.74 (d, J=8.2, 1H, —NH); 4.37 (s, 2H); 3.90 (m, 1H); 3.26 (m, 1H); 2.27 (m, 1H); 1.87 (m, 2H); 1.46 (m, 1H); 1.37 (s, 9H & m, 1H); 0.90 (d, J=6.0, 3H).

Example C30 tert-Butyl [(1S*,2S*,4S*)-4-hydroxy-2-methylcyclopentyl]carbamate

Starting from tert-butyl [(1S*,2S*,4S*)-4-(benzyloxy)-2-methylcyclopentyl]carbamate (example C29; 5.4 g; 18.1 mmol) and following the procedure as described in example C8, 3.9 g of the title compound is obtained as pale yellow oil.

$^1$H-NMR (300 MHz, DMSO-d$_6$): 6.64 (d, J=8.0, 1H, —NH); 4.47 (d, J=4.0, 1H, —OH); 4.03 (m, 1H); 3.21 (m, 1H); 2.15 (m, 1H); 1.89 (m, 1H); 1.64 (m, 1H); 1.37 (s, 9H); 1.31 (m, 2H); 0.89 (d, J=6.6, 3H).

Example C31

(1S*,3S*,4S*)-3-[(tert-Butoxycarbonyl)amino]-4-methylcyclopentyl methanesulfonate Starting from tert-butyl [(1S*,2S*,4S*)-4-hydroxy-2-methylcyclopentyl]carbamate (example C30; 3.9 g; 18.0 mmol) and following the procedure as described in example C4, 4.8 g of the title compound is obtained as colourless solid after column chromatography on silica gel (cyclohexane/tert-BuOMe—90:10 to 60:40).

¹H-NMR (300 MHz, DMSO-d₆): 6.89 (d, J=7.9, 1H, —NH); 4.99 (m, 1H); 3.29 (m, 1H); 3.12 (s, 3H); 2.45 (m, 1H); 2.09-1.84 (m, 2H); 1.69-1.50 (m, 2H); 1.38 (s, 9H); 0.93 (d, J=6.2, 3H).

Example C32 tert-Butyl [(1S*,2S*,4R*)-4-azido-2-methylcyclopentyl]carbamate

Starting from (1S*,3S*,4S*)-3-[(tert-butoxycarbonyl)amino]-4-methylcyclopentyl methanesulfonate (example C31; 4.8 g; 16.0 mmol) and following the procedure as described in example C5, 3.7 g of the title compound is obtained as colourless oil after column chromatography on silica gel (cyclohexane/tert-BuOMe—90:10 to 80:20).

¹H-NMR (300 MHz, DMSO-d₆): 6.82 (d, J=8.0, 1H, —NH); 4.03 (m, 1H); 3.42 (m, 1H); 2.22 (m, 1H); 1.87 (m, 1H); 1.79-1.64 (m, 2H); 1.38 (s, 9H); 1.15 (m, 1H); 0.96 (d, J=6.2, 3H).

Example C33 tert-Butyl [(1S*,2S*,4R*)-4-amino-2-methylcyclopentyl]carbamate

Starting from tert-butyl [(1S*,2S*,4R*)-4-azido-2-methylcyclopentyl]carbamate (example C32; 1.6 g; 6.8 mmol) and following the procedure as described in example C11, 1.4 g of the title compound is obtained as colourless oil.

¹H-NMR (300 MHz, DMSO-d₆): 6.64 (d, J=7.7, 1H, —NH); 3.45 (m, 1H); 3.29 (br.s, 2H, —NH₂); 3.21 (m, 1H); 1.99 (m, 1H); 1.71-1.50 (m, 3H); 1.37 (s, 9H); 0.93 (d, J=6.6, 3H); 0.83 (m, 1H).

Example C34

(1S*,2S*,4R*)-4-Azido-2-methylcyclopentanamine hydrochloride

Starting from tert-butyl [(1S*,2S*,4R*)-4-azido-2-methylcyclopentyl]carbamate (example C32; 3.6 g; 15.0 mmol) and following the procedure as described in example C12, 2.4 g of the title compound is obtained as colourless solid.

¹H-NMR (300 MHz, DMSO-d₆): 8.27 (br.s, 3H, NH₃⁺); 4.20 (m, 1H); 3.12 (m, 1H); 2.29 (m, 1H); 2.13-1.94 (m, 3H); 1.26 (m, 1H); 1.10 (d, J=6.8, 3H).

HR-MS (ESI): m/z=141.1136 ([MH]⁺, C₆H₁₃N₄⁺, calc. 141.1135)

Example C35

(1S*,2S*,4R*)-4-(Benzyloxy)-2-fluorocyclopentanol

A stirred mixture of known cis-3-(benzyloxy)-6-oxabicyclo[3.1.0]hexane (6.1 g; 32.1 mmol) [Snider, B. B.; Liu, T. *J. Org. Chem.* 2000, 65, 8490; Milne, D.; Murphy, P. J. *J. Chem. Soc. Chemical Communication* 1993, 884] and tetrabutylammonium dihydrogen trifluoride (16.3 g; 54.1 mmol) is heated to 150° C. over night. The mixture is diluted with AcOEt and extracted with sat. NaHCO₃-solution. The organic layer is dried over MgSO₄ and concentrated under reduced pressure. The residue is chromatographed on silica gel (cyclohexane/AcOEt—10:0 to 80:29) to yield 5.5 g of the title compound as pale yellow oil.

¹H-NMR (300 MHz, DMSO-d₆): 7.32 (m, 5H); 5.13 (d, J=4.6, 1H, —OH); 4.81 (dm, J=53.1, 1H); 4.43 (s, 2H); 4.11-3.93 (m, 2H); 2.32 (m, 1H); 2.18-1.88 (m, 2H); 1.51 (m, 1H).

Example C36

(1S*,2R*,4S*)-4-(Benzyloxy)-2-fluorocyclopentyl 3-nitrobenzoate

Starting from (1S*,2S*,4R*)-4-(Benzyloxy)-2-fluorocyclopentanol (example C35; 6.5 g; 30.9 mmol) and following the procedure as described in example C25, 7.3 g of the title compound is obtained as pale yellow oil.

¹H-NMR (300 MHz, DMSO-d₆): 8.63 (m, 1H); 8.52 (m, 1H); 8.39 (m, 1H); 7.86 (t, J=8.0, 1H); 7.40-7.24 (m, 5H); 5.50-5.21 (m, 2H); 4.48 (s, 2H); 4.30 (m, 1H); 2.46-2.04 (m, 4H).

Example C37

(1S*,2R*,4S*)-4-(Benzyloxy)-2-fluorocyclopentanol

Starting from (1S*,2R*,4S*)-4-(Benzyloxy)-2-fluorocyclopentyl 3-nitrobenzoate (example C36; 7.3 g; 20.0 mmol) and following the procedure as described in example C26, 3.8 g of the title compound is obtained as colourless oil.

¹H-NMR (300 MHz, DMSO-d₆): 7.31 (m, 5H); 4.91 (d, J=5.8, 1H, —OH); 4.83 (dm, J=54.7, 1H); 4.39 (s, 2H); 4.18-3.99 (m, 2H); 2.20 (m, 1H); 2.00-1.75 (m, 3H).

Example C38

(1S*,2R*,4S*)-4-(Benzyloxy)-2-fluorocyclopentyl methanesulfonate

Starting from (1S*,2R*,4S*)-4-(benzyloxy)-2-fluorocyclopentanol (example C37; 3.8 g; 17.9 mmol) and following the procedure as described in example C4, 5.1 g of the title compound is obtained as pale yellow oil.

¹H-NMR (300 MHz, DMSO-d₆): 7.33 (m, 5H); 5.32-5.01 (m, 2H); 4.43 (d, J=1.8, 2H); 4.22 (m, 1H); 3.24 (s, 3H); 2.40-1.91 (m, 4H).

Example C39

(1S*,3R*,4R*)-3-Azido-4-fluorocyclopentyl benzyl ether

Starting from (1S*,2R*,4S*)-4-(Benzyloxy)-2-fluorocyclopentyl methanesulfonate (example C38; 5.1 g; 17.7 mmol) and following the procedure as described in example C5, 3.5 g of the title compound is obtained as colourless oil.

¹H-NMR (300 MHz, DMSO-d₆): 7.32 (m, 5H); 5.03 (dm, J=53.1, 1H); 4.44 (s, 2H); 4.22-4.07 (m, 2H); 2.44 (m, 1H); 2.16 (m, 1H); 2.08 (m, 1H); 1.72 (m, 1H).

Example C40 tert-Butyl [(1R*,2R*,4S*)-4-(benzyloxy)-2-fluorocyclopentyl]carbamate

Starting from (1S*,3R*,4R*)-3-azido-4-fluorocyclopentyl benzyl ether (example C39; 4.5 g; 19.0 mmol) and following the procedure as described in example C7, 5.2 g of the title compound is obtained as colourless solid.

¹H-NMR (300 MHz, DMSO-d₆): 7.32 (m, 5H); 6.95 (br.d, J=6.8, 1H, —NH); 4.87 (dm, J=53.3, 1H); 4.43 (s, 2H); 4.05 (m, 1H); 3.83 (m, 1H); 2.32 (m, 1H); 2.18-1.89 (m, 2H); 1.53 (m, 1H); 1.38 (s, 9H).

Example C41 tert-Butyl [(1R*,2R*,4S*)-2-fluoro-4-hydroxycyclopentyl]carbamate

Starting from tert-butyl [(1R*,2R*,4S*)-4-(benzyloxy)-2-fluorocyclopentyl]carbamate (example C40; 5.2 g; 16.9 mmol) and following the procedure as described in example C8, 3.5 g of the title compound is obtained as colourless solid.

¹H-NMR (300 MHz, DMSO-d₆): 6.86 (br.d, J=7.1, 1H, —NH); 4.86 (d, J=3.7, 1H, —OH); 4.84 (dm; J=53.1, 1H); 4.15 (m, 1H); 3.79 (m, 1H); 2.19 (m, 1H); 2.07-1.71 (m, 2H); 1.38 (s, 9H & m, 1H).

Example C42

(1S*,3R*,4R*)-3-[(tert-Butoxycarbonyl)amino]-4-fluorocyclopentyl methanesulfonate Starting from tert-butyl [(1R*,2R*,4S*)-2-fluoro-4-hydroxycyclopentyl]carbamate (example C41; 3.5 g; 16.0 mmol) and following the procedure as described in example C4, 4.4 g of the title compound is obtained as colourless solid.

¹H-NMR (300 MHz, DMSO-d₆): 7.13 (br.d, J=6.6, 1H, —NH); 5.09 (m, 1H); 4.93 (dm; J=52.8, 1H); 3.87 (m, 1H); 3.18 (s, 3H); 2.52 (m, 1H); 2.38-2.10 (m, 2H); 1.74 (m, 1H); 1.39 (s, 9H).

Example C43 tert-Butyl [(1R*,2R*,4R*)-4-azido-2-fluorocyclopentyl]carbamate

Starting from (1S*,3R*,4R*)-3-[(tert-butoxycarbonyl)amino]-4-fluorocyclopentyl methanesulfonate (example C42; 4.4 g; 14.8 mmol) and following the procedure as described in example C5, 3.5 g of the title compound is obtained as colourless solid.

¹H-NMR (300 MHz, DMSO-d₆): 7.07 (br.d, J=5.8, 1H, —NH); 4.85 (dm; J=52.8, 1H); 4.20 (m, 1H); 3.98 (m, 1H); 2.36 (m, 1H); 1.97 (m, 1H); 1.92-1.73 (m, 2H); 1.39 (s, 9H).

Example C44 tert-Butyl [(1R*,2R*,4R*)-4-amino-2-fluorocyclopentyl]carbamate

Starting from tert-butyl [(1R*,2R*,4R*)-4-azido-2-fluorocyclopentyl]carbamate (example C43; 1.7 g; 7.0 mmol) and following the procedure as described in example C11, 1.5 g of the title compound is obtained as colourless solid.

¹H-NMR (300 MHz, DMSO-d₆, MeOH-d₄): 4.76 (dm; J=52.8, 1H); 4.04 (m, 1H); 3.31 (m, 1H); 2.23 (m, 1H); 1.67 (m, 2H); 1.48 (m, 1H); 1.39 (s, 9H).

HR-MS (ESI): m/z=219.1495 ([MH]⁺, $C_{10}H_{20}FN_2O_2^+$, calc. 219.1503).

Example C45

(1R*,2R*,4R*)-4-Azido-2-fluorocyclopentanamine hydrochloride

Starting from tert-butyl [(1R*,2R*,4R*)-4-azido-2-fluorocyclopentyl]carbamate (example C43; 1.8 g; 7.5 mmol) and following the procedure as described in example C12, 1.3 g of the title compound is obtained as colourless solid.

¹H-NMR (300 MHz, DMSO-d₆): 8.54 (br.s, 3H, NH₃⁺); 5.19 (dm; J=52.4, 1H); 4.34 (m, 1H); 3.75 (m, 1H); 2.49 (m, 1H); 2.17 (m, 1H); 2.06-1.88 (m, 2H).

HR-MS (ESI): m/z=145.0888 ([MH]⁺, $C_5H_{10}FN_4^+$, calc. 145.0884).

Example C46

(1S*,2R*,4R*)-4-{[tert-Butyl(diphenyl)silyl]oxy}-2-fluorocyclohexanol

Starting from ((2R*,4R*)-4-{[tert-butyl(diphenyl)silyl]oxy}-2-fluorocyclohexanone (example C14; 18.7 g; 50.4 mmol) and following the procedure as described in example C15 17.9 g of the title compound is obtained as colourless oil after column chromatography on silica gel (cyclohexane/AcOEt—100:0 to 85:15).

¹H-NMR (300 MHz, CDCl₃): 7.67 (m, 4H); 7.38 (m, 6H); 4.31 (dddd, J=47.1, 10.7, 4.8, 2.9, 1H); 3.94 (m, 1H); 3.61 (m, 1H); 2.14-1.67 (m, 4H & 1H, —OH); 2.92 (m, 1H); 1.20 (m, 1H); 1.05 (s, 9H).

Example C47

(1R*,2R*,4R*)-4-{[tert-Butyl(diphenyl)silyl]oxy}-2-fluorocyclohexyl 3-nitrobenzoate Starting from (1S*,2R*,4R*)-4-{[tert-butyl(diphenyl)silyl]oxy}-2-fluorocyclohexanol (example C46; 17.8 g; 47.9 mmol) and following the procedure as described in example C25 15.8 g of the title compound is obtained as pale yellow oil after column chromatography on silica gel (cyclohexane/AcOEt—100:0 to 85:15).

¹H-NMR (300 MHz, DMSO-d₆): 8.60 (m, 1H); 8.49 (m, 1H); 8.34 (m, 1H); 7.83 (t, J=8.2, 1H); 7.64 (m, 4H); 7.46 (m, 6H); 5.09 (m, 1H); 4.65 (dm, J=50.6, 1H); 3.87 (m, 1H); 2.24 (m, 1H); 1.97 (m, 1H); 1.87-1.50 (m, 3H); 1.35 (m, 1H); 1.02 (s, 9H).

Example C48

(1R*,2R*,4R*)-4-{[tert-Butyl(diphenyl)silyl]oxy}-2-fluorocyclohexanol

Starting from (1R*,2R*,4R*)-4-{[tert-butyl(diphenyl)silyl]oxy}-2-fluorocyclohexyl 3-nitrobenzoate (example C47; 15.8 g; 30.3 mmol) and following the procedure as described in example C26 10.9 g of the title compound is obtained as colourless oil after column chromatography on silica gel (cyclohexane/AcOEt—100:0 to 85:15).

¹H-NMR (300 MHz, DMSO-d₆): 7.61 (m, 4H); 7.45 (m, 6H); 4.97 (d, J=4.7, 1H, —OH); 4.01 (dm, J=50.4, 1H); 3.71 (m, 1H); 3.40 (m, 1H); 2.09 (m, 1H); 1.67 (m, 2H); 1.53 (m, 1H); 1.37 (m, 1H); 1.00 (s, 9H & m, 1H).

Example C49

(1R*,2R*,4R*)-4-{[tert-Butyl(diphenyl)silyl]oxy}-2-fluorocyclohexyl methanesulfonate Starting from (1R*,2R*,4R*)-4-{[tert-butyl(diphenyl)silyl]oxy}-2-fluorocyclohexanol (example C48; 13.1 g; 35.2 mmol) and following the procedure as described in example C4 14.8 g of the title compound is obtained as pale yellow oil after column chromatography on silica gel (cyclohexane/AcOEt—100:0 to 80:20).

¹H-NMR (400 MHz, DMSO-d₆): 7.62 (m, 4H); 7.45 (m, 6H); 4.63 (m, 1H); 4.45 (dm, J=50.3, 1H); 3.83 (m, 1H); 3.13 (s, 3H); 2.19 (m, 1H); 1.97 (m, 1H); 1.72 (m, 2H); 1.51 (m, 1H); 1.35 (m, 1H); 1.00 (s, 9H).

Example C50

{[(1R*,3R*,4S*)-4-Azido-3-fluorocyclohexyl]oxy}tert-butyl)diphenylsilane

Starting from (1R*,2R*,4R*)-4-{[tert-butyl(diphenyl)silyl]oxy}-2-fluorocyclohexyl methanesulfonate (example C49; 14.7 g; 32.7 mmol) and following the procedure as described in example C5 10.2 g of the title compound is obtained as colourless oil after column chromatography on silica gel (cyclohexane/AcOEt—100:0 to 95:05).

¹H-NMR (300 MHz, CDCl₃): 7.66 (m, 4H); 7.39 (m, 6H); 4.41 (dm, J=46.4, 1H); 3.79 (m, 1H); 3.60 (m, 1H); 2.13-1.81 (m, 3H); 1.71-1.46 (m, 2H); 1.22 (m, 1H); 1.05 (s, 9H).

Example C51 tert-Butyl [(1S*,2R*,4R*)-4-{[tert-butyl(diphenyl)silyl]oxy}-2-fluorocyclohexyl]carbamate Starting from {[(1R*,3R*,4S*)-4-azido-3-fluorocyclohexyl]oxy}(tert-butyl)diphenylsilane (example C50; 10.1 g; 25.6 mmol) and following the procedure as described in example C7 10.5 g of the title compound is obtained as colourless solid after column chromatography on silica gel (cyclohexane/AcOEt—100:0 to 95:05).

¹H-NMR (300 MHz, CDCl₃): 7.66 (m, 4H); 7.39 (m, 6H); 4.92 (br.s, 1H, —NH); 4.64 (dm, J=46.7, 1H); 3.89 (m, 1H); 3.66 (m, 1H); 2.08 (m, 2H); 1.87-1.37 (m, 4H); 1.45 (s, 9H); 1.06 (s, 9H).

Example C52 tert-Butyl [(1R*,2S*,4S*)-2-fluoro-4-hydroxycyclohexyl]carbamate

Starting from tert-butyl [(1S*,2R*,4R*)-4-{[tert-butyl(diphenyl)silyl]oxy}-2-fluorocyclohexyl]carbamate (example C51; 10.4 g; 22.0 mmol) and following the procedure as described in example C19 4.5 g of the title compound is obtained as colourless oil after column chromatography on silica gel (cyclohexane/AcOEt—50:50).

¹H-NMR (300 MHz, CDCl₃): 4.89 (dm, J=48.9, 1H); 4.87 (br.s, 1H, —NH); 3.97 (m, 1H); 3.66 (m, 1H); 2.31 (m, 1H); 2.19 (m, 1H); 2.01-1.80 (m, 2H); 1.78-1.54 (m, 2H & 1H, —OH); 1.45 (s, 9H).

Example C53

(1S*,3S*,4R*)-4-[(tert-Butoxycarbonyl)amino]-3-fluorocyclohexyl methanesulfonate Starting from tert-butyl [(1R*,2S*,4S*)-2-fluoro-4-hydroxycyclohexyl]carbamate (example C52; 4.4 g; 18.7 mmol) and following the procedure as described in example C4 5.1 g of the title compound is obtained as pale yellow solid after column chromatography on silica gel (cyclohexane/AcOEt—50:50).

¹H-NMR (300 MHz, CDCl₃): 4.97 (m, 1H); 4.88 (br.s, 1H, —NH); 4.80 (dm, J=48.9, 1H); 3.68 (m, 1H); 3.03 (s, 3H); 2.56 (m, 1H); 2.19 (m, 1H); 2.01-1.63 (m, 4H); 1.45 (s, 9H).

Example C54 tert-Butyl [(1R*,2S*,4R*)-4-azido-2-fluorocyclohexyl]carbamate

Starting from (1S*,3S*,4R*)-4-[(tert-butoxycarbonyl)amino]-3-fluorocyclohexyl methanesulfonate (example C53; 5.0 g; 16.1 mmol) and following the procedure as described in example C5 3.0 g of the title compound is obtained as colourless solid after column chromatography on silica gel (cyclohexane/tert-BuOMe—80:20).

¹H-NMR (300 MHz, CDCl₃): 4.86 (dm, J=49.5, 1H); 4.77 (br.s, 1H, —NH); 3.75-3.51 (m, 2H); 2.38 (m, 1H); 2.08 (m, 1H); 1.90 (m, 1H); 1.70-1.37 (m, 3H); 1.44 (m, 9H).

Example C55 tert-Butyl [(1R*,2S*,4R*)-4-amino-2-fluorocyclohexyl]carbamate

Starting from tert-butyl [(1R*,2S*,4R*)-4-azido-2-fluorocyclohexyl]carbamate (example C54; 0.72 g; 2.8 mmol) and following the procedure as described in example C11 0.65 g of the title compound is obtained as off-white solid.

HR-MS (ESI): m/z=233.1665 ([MH]⁺, $C_{11}H_{22}FN_2O_2^+$, calc. 233.1660).

Example C56

(1R*,2S*,4R*)-4-Azido-2-fluorocyclohexanamine hydrochloride

Starting from tert-butyl [(1R*,2S*,4R*)-4-azido-2-fluorocyclohexyl]carbamate (example C54; 1.29 g; 5.0 mmol) and following the procedure as described in example C12 0.92 g of the title compound is obtained as off-white solid.

HR-MS (ESI): m/z=159.1036 ([MH]⁺, $C_6H_{12}FN_4^+$, calc. 159.1041).

Example D.a1

Ethyl 4-(5-cyclopropylmethoxy-benzo[1,3]dioxol-4-yl)-6-methyl-5H-pyrrolo[3,2-d]pyrimidine-7-carboxylate Ethyl-4-chloro-6-methyl-5H-pyrrolo[3,2-d]pyrimidine-7-carboxylate from example A4 (11.98 g; 50.0 mmol), dioxane (200 mL) and Cs₂CO₃ (2M aqueous solution; 75.0 mL; 150.0 mmol) is heated to 80° C. under nitrogen before addition of Pd(OAc)₂ (247 mg; 1.1 mmol) and tricyclohexylphosphine (617 mg; 2.2 mmol). After 30 min a solution of 5-cyclopropylmethoxy-4-(4,4,5,5-tetramethyl-[1,3,2]dioxaborolan-2-yl)-benzo[1,3]dioxole from example B.c1 (17.50 g; 55.0 mmol) in dioxane (50.0 mL) is added and the reaction mixture is heated to 100° C. until the starting material is consumed according to LC-MS.

The cooled reaction mixture is diluted with water (250 mL) and acidified to pH=6 by carefule addition of 2M aqueous citric acid. The precipitated crude is filtered, dissolved in dioxane and filtered through a short column of neutral alumina containing 5 wt % of water. The column is rinsed with several portions of dioxane. The filtrate is concentrated under reduced pressure and the product is collected with tert-butyl methyl ether to yield the title compound as off-white solid.

MS (ESI): m/z=396 (MH⁺, 100%); 382.

¹H-NMR (300 MHz, DMSO-$d_6$): 12.09 (br.s, 1H, —NH); 8.92 (s, 1H); 7.00 (d, J=8.6, 1H); 6.55 (d, J=8.6, 1H); 5.99 (s, 2H); 4.31 (qu, J=7.1, 2H); 3.75 (d, J=6.7, 2H); 2.72 (s, 3H); 1.33 (t, J=7.1, 3H); 0.88 (m, 1H); 0.30 (m, 2H); 0.11 (m, 2H).

The following compounds were prepared analogously to the procedure described in above example D.a1.

Example D.a2

Ethyl 4-(2-cyclopropylmethoxy-4-fluoro-phenyl)-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-(2-cyclopropylmethoxy-4-fluoro-phenyl)-4,4,5,5-tetramethyl-[1,3,2]dioxaborolane (example B.c3) the title compound is obtained as off-white solid.

MS (ESI): m/z=392 (MNa⁺); 370 (MH⁺); 356 (100%); 314; 302.

¹H-NMR (400 MHz, DMSO-$d_6$): 11.89 (br.s, 1H, —NH); 9.19 (s, 1H); 7.64 (dd, J=8.4, 7.4, 1H); 7.08 (dd, J=11.6, 2.1, 1H); 6.95 (ddd; J=8.4, 8.4, 2.1, 1H); 4.31 (qu, J=6.9, 2H); 3.90 (d, J=6.9, 2H); 2.74 (s, 3H); 1.34 (t, J=6.9, 3H); 0.94 (m, 1H); 0.38 (m, 2H); 0.24 (m, 2H).

Example D.a3

Ethyl 4-(2-Cyclopropylmethoxy-5-fluoro-phenyl)-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-(2-cyclopropylmethoxy-5-fluoro-phenyl)-4,4,5,5-tetramethyl-[1,3,2]dioxaborolane (example B.c4) the title compound is obtained as off-white solid.

MS (ESI): m/z=424 (MH⁺, 100%); 356.

¹H-NMR (300 MHz, DMSO-$d_6$): 11.92 (br.s, 1H, —NH); 8.96 (s, 1H); 7.41 (dd, J=9.0, 3.2, 1H); 7.37 (ddd, J=9.1, 8.3, 3.2, 1H); 7.18 (dd, J=9.1, 4.4, 1H); 4.32 (qu, J=7.1, 2H); 3.87 (d, J=6.9, 2H); 2.74 (s, 3H); 1.34 (t, J=7.1, 3H); 0.93 (m, 1H); 0.36 (m, 2H); 0.21 (m, 2H).

Example D.a4

Ethyl 4-(2-ethoxy-5-fluorophenyl)-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and commercially available 2-ethoxy-5-fluoro-phenyl-boronic acid the title compound is obtained as pale yellow solid.

MS (ESI): m/z=344 (MH⁺, 100%).

¹H-NMR (300 MHz, DMSO-$d_6$): 11.95 (s, 1H, —NH); 8.95 (s, 1H); 7.41 (ddd, J=8.9, 8.9, 3.3, 1H); 7.37 (dd, J=8.2, 3.3, 1H); 7.22 (dd, J=8.9, 4.4, 1H); 4.31 (qu, J=7.1, 2H); 4.08 (qu, J=6.9, 2H); 2.74 (s, 3H); 1.34 (t, J=7.1, 3H); 1.10 (t, J=6.9, 3H).

Example D.a5

Ethyl 4-(2-cyclopropylmethoxy-4-methoxy-phenyl)-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-(2-cyclopropylmethoxy-4-methoxy-phenyl)-4,4,5,5-tetramethyl-[1,3,2]dioxaborolane (example B.c6) the title compound is obtained as off-white solid.

MS (ESI): m/z=404 (MNa⁺); 382 (MH⁺, 100%); 368; 314.

¹H-NMR (300 MHz, DMSO-$d_6$): 11.76 (br.s, 1H, —NH); 8.90 (s, 1H); 7.56 (d, J=8.4, 1H); 6.71 (dd, J=8.4, 2.2, 2H); 6.68 (d, J=2.2, 1H); 4.30 (qu, J=7.0, 2H); 3.90 (d, J=6.9, 2H); 3.85 (s, 3H); 2.73 (s, 3H); 1.33 (t, J=7.1, 3H); 0.95 (m, 1H); 0.37 (m, 2H); 0.25 (m, 2H).

Example D.a6

Ethyl 4-(2-cyclopropylmethoxy-5-methoxy-phenyl)-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-(2-cyclopropylmethoxy-5-methoxy-phenyl)-4,4,5,5-tetramethyl-[1,3,2]dioxaborolane (example B.c7) the title compound is obtained as yellow solid.

MS (ESI): m/z=404 (MNa⁺); 382 (MH⁺, 100%); 368; 298.

¹H-NMR (300 MHz, DMSO-$d_6$): 11.84 (br.s, 1H, —NH); 8.94 (s, 1H); 7.15 (t, J=1.8, 1H); 7.09 (d, J=1.8, 2H); 4.31 (qu, J=7.1, 2H); 3.81 (d, J=6.9, 2H); 3.76 (s, 3H); 2.73 (s, 3H); 1.34 (t, J=7.1, 3H); 0.91 (m, 1H); 0.34 (m, 2H); 0.18 (m, 2H).

Example D.a7

Ethyl 4-[2-(cyclopropylmethoxy)-5-methylphenyl]-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-(2-cyclopropylmethoxy-5-methyl-phenyl)-4,4,5,5-tetramethyl-[1,3,2]dioxaborolane (example B.c8) the title compound is obtained as pale yellow solid.

MS (ESI): m/z=366 (MH⁺, 100%).

¹H-NMR (300 MHz, DMSO-$d_6$): 11.82 (s, 1H, —NH); 8.93 (s, 1H); 7.41 (d, J=2.1, 1H); 7.32 (dd, J=8.4, 2.1, 1H); 7.05 (d, J=8.4, 1H); 4.31 (qu, J=7.1, 2H); 3.85 (d, J=6.8, 2H); 2.72 (s, 3H); 2.33 (s, 3H); 1.34 (t, J=7.1, 3H); 0.93 (m, 1H); 0.35 (m, 2H); 0.21 (m, 2H).

Example D.a8

Ethyl 4-[2-(cyclopropylmethoxy)-5-(trifluoromethyl)phenyl]-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-(2-Cyclopropylmethoxy-5-trifluoromethyl-phenyl)-4,4,5,5-tetramethyl-[1,3,2]dioxaborolane (example B.c9) the title compound is obtained as off-white solid.

MS (ESI): m/z=420 (MH⁺, 100%).

¹H-NMR (300 MHz, DMSO-$d_6$): 11.98 (s, 1H, —NH); 8.98 (s, 1H); 7.93-7.85 (m, 2H); 7.37 (m, 1H); 4.32 (qu, J=7.1, 2H); 3.99 (d, J=6.9, 2H); 2.74 (s, 3H); 1.34 (t, J=7.1, 3H); 0.89 (m, 1H); 0.39 (m, 2H); 0.26 (m, 2H).

Example D.a9

Ethyl 4-[2-ethoxy-5-(trifluoromethyl)phenyl]-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-(2-Ethoxy-5- trifluoromethyl-phenyl)-4,4,5,5-tetramethyl-[1,3,2]diox-aborolane (example B.c10) the title compound is obtained as off-white solid.

MS (ESI): m/z=394 (MH$^+$, 100%).

$^1$H-NMR (300 MHz, DMSO-d$_6$): 12.01 (s, 1H, —NH); 8.97 (s, 1H); 7.91 (dd, J=8.9, 2.1, 1H); 7.89 (d, J=2.1, 1H); 7.41 (d, J=8.9, 1H); 4.32 (qu, J=7.1, 2H); 4.20 (qu, J=6.9, 2H); 2.74 (s, 3H); 1.34 (t, J=7.1, 3H); 1.15 (t, J=6.9, 3H).

Example D.a10

Ethyl 4-(2-cyclopropylmethoxy-4-fluoro-5-methoxy-phenyl)-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-(2-Cyclopropylmethoxy-4-fluoro-5-methoxy-phenyl)-4,4,5,5-tetramethyl-[1,3,2]dioxaborolane (example B.c2) the title compound is obtained as off-white solid.

MS (ESI): m/z=422 (MNa$^+$, 100%); 400 (MH$^+$); 368; 316.

$^1$H-NMR (300 MHz, DMSO-d$_6$): 11.84 (br.s, 1H, —NH); 8.95 (s, 1H); 7.37 (d, J=9.8, 1H); 7.17 (d, J=13.5, 1H); 4.31 (qu, J=7.1, 2H); 3.84 (s, 3H); 3.83 (d, J=6.9, 2H); 2.74 (s, 3H); 1.34 (t, J=7.1, 3H); 0.92 (m, 1H); 0.36 (m, 2H); 0.19 (m, 2H).

Example D.a11

Ethyl 4-[2-(cyclopropylmethoxy)-4-fluoro-5-methylphenyl]-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-(2-cyclopropylmethoxy-4-fluoro-5-methyl-phenyl)-4,4,5,5-tetramethyl-[1,3,2]dioxaborolane (example B.c11) the title compound is obtained as pale yellow solid.

MS (ESI): m/z=384 (MH$^+$, 100%).

$^1$H-NMR (300 MHz, DMSO-d$_6$): 11.83 (s, 1H, —NH); 8.92 (s, 1H); 7.52 (d, J=9.7, 1H); 7.03 (d, J=12.2, 1H); 4.31 (qu, J=7.1, 2H); 3.87 (d, J=6.9, 2H); 2.73 (s, 3H); 2.24 (d, J=1.3, 3H); 1.34 (t, J=7.1, 3H); 0.94 (m, 1H); 0.37 (m, 2H); 0.22 (m, 2H).

Example D.a12

Ethyl 4-(2-cyclopropylmethoxy-5-fluoro-4-methoxy-phenyl)-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-(2-cyclopropylmethoxy-5-fluoro-4-methoxy-phenyl)-4,4,5,5-tetramethyl-[1,3,2]dioxaborolane (example B.c12) the title compound is obtained as pale yellow solid.

MS (ESI): m/z=422 (MNa$^+$); 400 (MH$^+$, 100%); 386; 331.

$^1$H-NMR (300 MHz, DMSO-d$_6$): 11.81 (br.s, 1H, —NH); 8.91 (s, 1H); 7.45 (d, J=11.8, 1H); 6.92 (d, J=7.3, 1H); 4.31 (qu, J=7.1, 2H); 3.96 (s, 3H); 3.93 (d, J=7.0, 2H); 2.74 (s, 3H); 1.33 (t, J=7.1, 3H); 0.94 (m, 1H); 0.38 (m, 2H); 0.23 (m, 2H).

Example D.a13

Ethyl 4-[2-(cyclopropylmethoxy)-5-(2-methyl-1,3-dioxolan-2-yl)phenyl]-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-[2-(cyclopropylmethoxy)-5-(2-methyl-1,3-dioxolan-2-yl)phenyl]-4,4,5,5-tetramethyl-1,3,2-dioxaborolane (example B.c13) the title compound is obtained as off-white solid.

MS (ESI): m/z=438 (MH$^+$, 100%).

$^1$H-NMR (300 MHz, DMSO-d$_6$): 11.87 (s, 1H, —NH); 8.95 (s, 1H); 7.63 (d, J=2.4, 1H); 7.54 (dd, J=8.6, 2.4, 1H); 7.14 (d, J=8.6, 1H); 4.31 (qu, J=7.1, 2H); 3.99 (m, 2H); 3.90 (d, J=6.9. 2H); 3.71 (m, 2H); 2.73 (s, 3H); 1.58 (s, 3H); 1.34 (t, J=7.1, 3H); 0.95 (m, 1H); 0.37 (m, 2H); 0.24 (m, 2H).

Example D.a14

Ethyl 4-[2-(cyclopropylmethoxy)-5-ethylphenyl]-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-(2-cyclopropylmethoxy-5-ethyl-phenyl)-4,4,5,5-tetramethyl-[1,3,2]dioxaborolane (example B.c14) the title compound is obtained as pale yellow solid.

MS (ESI): m/z=380 (MH$^+$, 100%).

$^1$H-NMR (300 MHz, DMSO-d$_6$): 11.83 (s, 1H, —NH); 8.94 (s, 1H); 7.43 (d, J=2.4, 1H); 7.35 (dd, J=8.4, 2.4, 1H); 7.07 (d, J=8.4, 1H); 4.31 (qu, J=7.1, 2H); 3.86 (d, J=6.9, 2H); 2.73 (s, 3H); 2.63 (qu, J=7.5, 2H); 1.34 (t, J=7.1, 3H); 1.18 (t, J=7.5, 3H); 0.93 (m, 1H); 0.35 (m, 2H); 0.21 (m, 2H).

Example D.a15

Ethyl 4-[2-(cyclopropylmethoxy)-5-(propan-2-yl)phenyl]-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-[2-(cyclopropylmethoxy)-5-(propan-2-yl)phenyl]-4,4,5,5-tetramethyl-1,3,2-dioxaborolane (example B.c15) the title compound is obtained as off white solid.

MS (ESI): m/z=394 (MH$^+$, 100%).

$^1$H-NMR (300 MHz, DMSO-d$_6$): 11.84 (s, 1H, —NH); 8.94 (s, 1H); 7.45 (d, J=2.4, 1H); 7.39 (dd, J=8.6, 2.4, 1H); 7.08 (d; J=8.6, 1H); 4.31 (qu, J=7.1, 2H); 3.86 (d, J=6.9, 2H); 2.94 (sept, J=6.9, 1H); 2.73 (s, 3H); 1.34 (t, J=7.1, 3H); 1.22 (d, J=6.9, 6H); 0.93 (m, 1H); 0.35 (m, 2H); 0.21 (m, 2H).

Example D.a16

Methyl 4-[2-(cyclopropylmethoxy)-5-methylphenyl]-2,6-dimethyl-5-{[2-(trimethylsilyl)ethoxy]methyl}-5H-pyrrolo[3,2-d]pyrimidine-7-carboxylate Starting from methyl 4-chloro-2,6-dimethyl-5-{[2-(trimethylsilyl)ethoxy]methyl}-5H-pyrrolo[3,2-d]pyrimidine-7-carboxylate (example A.11) and 2-(2-cyclopropylmethoxy-5-methyl-phenyl)-4,4,5,5-tetramethyl-[1,3,2]dioxaborolane (example B.c8) the title compound is obtained as off white solid.

MS (ESI): m/z=496 (MH$^+$, 100%)

$^1$H-NMR (300 MHz, DMSO-d$_6$): 7.31 (dd, J=8.4, 2.0, 1H); 7.23 (d, J=2-0, 1H); 7.03 (d, J=8.4, 1H); 5.38 (d, J=11.0, 1H); 4.98 (d, J=11.0, 1H); 3.85 (s, 3H); 3.79 (dd, J=10.4, 6.6, 1H);

3.75 (dd, J=10.4, 6.9, 1H); 2.87 (m, 2H); 2.78 (s, 3H); 2.67 (s, 3H); 2.31 (s, 3H); 0.87 (m, 1H); 0.52 (m, 2H); 0.30 (m, 2H); 0.03 (m, 2H); −0.17 (s, 9H).

Example D.a17

Methyl 4-[2-(cyclopropylmethoxy)-5-fluoro-4-methoxyphenyl]-2,6-dimethyl-5-{[2-(trimethylsilyl)ethoxy]methyl}-5H-pyrrolo[3,2-d]pyrimidine-7-carboxylate Starting from methyl 4-chloro-2,6-dimethyl-5-{[2-(trimethylsilyl)ethoxy]methyl}-5H-pyrrolo[3,2-d]pyrimidine-7-carboxylate (example A.11) and 2-(2-cyclopropylmethoxy-5-fluoro-4-methoxyphenyl)-4,4,5,5-tetramethyl-[1,3,2]dioxaborolane (example B.c15) the title compound is obtained as off white solid.

MS (ESI): 530 (MH$^+$, 100%)

$^1$H-NMR (300 MHz, DMSO-$d_6$): 7.29 (d, J=11.5, 1H); 6.92 (d, J=7.3, 1H), 5.43 (d, J=11.0, 1H); 5.03 (d, J=11.0, 1H); 3.95 (s, 3H); 3.85 (s, 3H); 3.83 (m, 2H); 2.95 (m, 2H); 2.80 (s, 3H); 2.67 (s, 3H); 0.88 (m, 1H); 0.55 (m, 2H); 0.31 (m, 2H); 0.04 (m, 2H); −0.17 (s, 9H).

Example D.a18

Methyl 4-[2-(cyclopropylmethoxy)-4-fluoro-5-methoxyphenyl]-2,6-dimethyl-5-{[2-(trimethylsilyl)ethoxy]methyl}-5H-pyrrolo[3,2-d]pyrimidine-7-carboxylate Starting from methyl 4-chloro-2,6-dimethyl-5-{[2-(trimethylsilyl)ethoxy]methyl}-5H-pyrrolo[3,2-d]pyrimidine-7-carboxylate (example A.11) and 2-(2-cyclopropylmethoxy-4-fluoro-5-methoxyphenyl)-4,4,5,5-tetramethyl-[1,3,2]dioxaborolane e (example B.c2) the title compound is obtained as off white solid.

MS (ESI): m/z=530 (MH$^+$, 100%).

$^1$H-NMR (300 MHz, DMSO-$d_6$): 7.23 (d, J=9.9, 1H); 7.16 (d, J=13.1, 1H); 5.36 (d, J=10.9, 1H); 4.97 (d, J=10.9, 1H); 3.85 (s, 3H); 3.81 (s, 3H); 3.79 (dd, J=10.2, 6.4, 1H); 3.72 (dd, J=10.2, 6.9, 1H); 3.04-2.87 (m, 2H); 2.79 (s, 3H); 2.68 (s, 3H); 0.86 (m, 1H); 0.57 (m, 2H); 0.30 (m, 2H); 0.01 (m, 2H); −0.15 (s, 9H).

Example D.a19

Ethyl 4-[2-(cyclopropylmethoxy)-5-(difluoromethyl)phenyl]-6-methyl-5H-pyrrolo[3,2-d]pyrimidine-7-carboxylate Starting from ethyl 4-chloro-6-methyl-5H-pyrrolo[3,2-d]pyrimidine-7-carboxylate (example A4) and 2-[2-(cyclopropylmethoxy)-5-(difluoromethyl)phenyl]-4,4,5,5-tetramethyl-1,3,2-dioxaborolane (example B.c16) the title compound is obtained as off-white solid.

$^1$H-NMR (300 MHz, DMSO-$d_6$): 11.93 (s, 1H, —NH); 8.97 (s, 1H); 7.81 (d, J=2.1, 1H); 7.74 (dd, J=8.8, 2.1, 1H); 7.30 (d, J=8.8, 1H); 7.08 (t, J=55.9, 1H); 4.32 (qu, J=7.1, 2H); 3.96 (d, J=6.9, 2H); 2.74 (s, 3H); 1.34 (t, J=7.1, 3H); 0.97 (m, 1H); 0.38 (m, 2H); 0.25 (m, 2H).

Example D.b1

Ethyl 4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidine-7-carboxylate Sodium hydride (1.77 g; ~60% dispersion in oil) is washed with hexane (2×25) and suspended in dry DMF (150 mL) and dry DMSO (50 mL). Ethyl 4-(5-cyclopropylmethoxy-benzo[1,3]dioxol-4-yl)-6-methyl-5H-pyrrolo[3,2-d]pyrimidine-7-carboxylate from example D.a1 (14.55 g; 36.8 mmol) is added st the well stirred suspension in several small portions. After complete addition the reaction mixture is stirred for one hour at 60° C. and cooled to 10° C. before slow addition of (2-chloromethoxyethyl)-trimethyl-silane (7.98 g; 47.8 mmol). After stirring over night at ambient temperature the mixture is poured on ice-cold water and repeatedly extracted with dichloromethane. The combined organic layer is dried over MgSO$_4$, The solvent is evaporated. The crued product is purified by column chromatography on silica gel (ethylacetate/cyclohexane—1:1) to yield the title compound as pale yellow viscous oil.

MS (ESI): m/z=526 (MH$^+$, 100%).

$^1$H-NMR (300 MHz, DMSO-$d_6$): 8.99 (s, 1H); 7.00 (d, J=8.6, 1H); 6.56 (d, J=8.6, 1H); 6.02 (d, J=0.6, 1H); 5.92 (d, J=0.6, 1H); 5.39 (d, J=10.9, 1H); 5.13 (d, J=10.9, 1H); 4.35 (qu, J=7.1, 2H); 3.76 (dd, J=10.2, 6.6, 1H); 3.67 (dd, J=10.2, 6.8, 1H); 3.01 (m, 2H); 2.82 (s, 3H); 1.35 (t, J=7.1, 3H); 0.86 (m, 1H); 0.62 (m, 2H); 0.29 (m, 2H); 0.00 (m, 2H); −0.13 (s, 9H).

The following compounds were prepared analogously to the procedure described in above example D.b1.

Example D.b2

Ethyl 4-[2-(cyclopropylmethoxy)-4-fluorophenyl]-6-methyl-5-{[2-(trimethylsilyl)ethoxy]methyl}-5H-pyrrolo[3,2-d]pyrimidine-7-carboxylate Starting from 4-(2-Cyclopropylmethoxy-4-fluoro-phenyl)-6-methyl-5H-pyrrolo[3,2-d]pyrimidine-7-carboxylic acid ethyl ester (example D.a2) and commercially available (2-chloromethoxy-ethyl)trimethyl-silane the title compound is prepared as pale yellow viscous oil.

MS (ESI): m/z=500 (MH$^+$, 100%).

$^1$H-NMR (300 MHz, DMSO-$d_6$): 8.97 (s, 1H); 7.49 (dd, J=8.4, 6.9, 1H); 7.09 (dd, J=11.3, 2.4, 1H); 6.97 (ddd, J=8.4, 8.4, 2.4, 1H); 6.41 (d, J=10.9, 1H); 4.99 (d, J=10.9, 1H); 4.35 (qu, J=7.1, 2H); 3.89 (dd, J=10.3, 6.5, 1H); 3.80 (dd, J=10.3, 7.0, 1H); 2.93 (m, 2H); 2.82 (s, 3H); 1.35 (t, J=7.1, 3H); 0.91 (m, 1H); 0.56 (dd, J=9.5, 6.9, 2H); 0.33 (m, 2H): 0.06 (m, 2H); −0.16 (s, 9H).

Example D.b3

Ethyl 4-[2-(cyclopropylmethoxy)-5-fluorophenyl]-6-methyl-5-{[2-(trimethylsilyl)ethoxy]methyl}-5H-pyrrolo[3,2-d]pyrimidine-7-carboxylate Starting from ethyl 4-(2-cyclopropylmethoxy-5-fluorophenyl)-6-methyl-5H-pyrrolo[3,2-d]pyrimidine-7-carboxylate (example D.a3) and commercially available (2-chloromethoxy-ethyl)-trimethyl-silane the title compound is prepared as pale yellow viscous oil.

MS (ESI): m/z=500 (MK).

$^1$H-NMR (300 MHz, DMSO-$d_6$): 8.99 (s, 1H); 7.38 (ddd, J=9.1, 8.4, 3.2, 1H); 7.30 (dd, J=8.6, 3.2, 1H); 7.19 (dd, J=9.1, 4.4, 1H); 5.42 (d, J=10.9, 1H); 5.00 (d, J=10.9, 1H); 4.35 (qu, J=7.1, 2H); 3.83 (dd, J=10.4, 6.6, 1H); 3.76 (dd, J=10.4, 6.9, 1H); 2.94 (m, 2H); 2.82 (s, 3H); 1.35 (t, J=7.1, 3H); 0.88 (m, 1H); 0.56 (m, 2H); 0.31 (m, 2H); 0.03 (m, 2H); −0.15 (s, 9H).

Example D.b4

Ethyl 4-(2-ethoxy-5-fluorophenyl)-6-methyl-5-{[2-(trimethylsilyl)ethoxy]methyl}-5H-pyrrolo[3,2-d]pyrimidine-7-carboxylate Starting from ethyl 4-(2-ethoxy-5-fluorophenyl)-6-methyl-5H-pyrrolo[3,2-d]pyrimidine-7-carboxylate (example D.a4) and commercially available (2-chloromethoxy-ethyl)-trimethyl-silane the title compound is obtained as yellow viscous oil.

MS (ESI): m/z=474 (MH$^+$, 100%).
$^1$H-NMR (300 MHz, DMSO-d$_6$): 8.98 (s, 1H); 7.39 (ddd, J=9.1, 8.8, 3.3, 1H); 7.29 (dd, J=8.6, 3.3, 1H); 7.20 (dd, J=9.1, 4.4, 1H); 5.40 (d, J=11.0, 1H); 4.98 (d, J=11.0, 1H); 4.35 (qu, J=7.1, 2H); 3.99 (qu, J=6.9, 2H); 2.99-2.88 (m, 2H); 2.82 (s, 3H); 1.35 (t, J=7.1, 3H); 1.01 (t, J=6.9, 3H); 0.57 (m, 2H); −0.15 (s, 9H).

Example D.b5

Ethyl 4-[2-(cyclopropylmethoxy)-4-methoxyphenyl]-6-methyl-5-{[2-(trimethylsilyl)ethoxy]methyl}-5H-pyrrolo[3,2-d]pyrimidine-7-carboxylate Starting from ethyl 4-(2-cyclopropylmethoxy-4-methoxyphenyl)-6-methyl-5H-pyrrolo[3,2-d]pyrimidine-7-carboxylate (example D.a5) and commercially available (2-chloromethoxy-ethyl)trimethyl-silane the title compound is obtained as yellow viscous oil.

MS (ESI): m/z=512 (MH$^+$, 100%).
$^1$H-NMR (300 MHz, DMSO-d$_6$): 8.94 (s, 1H); 7.40 (d, J=8.4, 1H); 6.72 (dd, J=8.4, 2.2, 2H); 6.69 (d, J=2.2, 1H); 5.46 (d, J=10.9, 1H); 5.06 (d, J=10.9, 1H); 4.35 (qu, J=7.0, 2H); 3.88 (dd, J=10.2, 5.5, 1H); 3.85 (s, 3H); 3.77 (dd, J=10.2, 6.9, 1H); 2.91 (t, J=8.0, 2H); 2.82 (s, 3H); 1.35 (t, J=7.0, 3H); 0.88 (m, 1H); 0.52 (m, 2H); 0.32 (m, 2H); 0.06 (m, 2H); −0.18 (s, 9H).

Example D.b6

Ethyl 4-[2-(cyclopropylmethoxy)-5-methoxyphenyl]-6-methyl-5-{[2-(trimethylsilyl)ethoxy]methyl}-5H-pyrrolo[3,2-d]pyrimidine-7-carboxylate Starting from ethyl 4-(2-cyclopropylmethoxy-5-methoxyphenyl)-6-methyl-5H-pyrrolo[3,2-d]pyrimidine-7-carboxylate (example D.a6) and commercially available (2-chloromethoxy-ethyl)trimethyl-silane the title compound is obtained as yellow viscous oil.

MS (ESI): m/z=512 (MH$^+$, 100%).
$^1$H-NMR (300 MHz, DMSO-d$_6$): 8.98 (s, 1H); 7.10 (d, J=1.5, 2H); 7.01 (t, J=1.5, 1H); 5.42 (d, J=11.0, 1H); 5.04 (d, J=11.0, 1H); 4.35 (qu, J=7.1, 2H); 3.76 (s, 3H & dd, J=10.2, 6.5, 1H); 3.70 (dd, J=10.2, 6.9, 1H); 2.92 (m, 2H); 2.82 (s, 3H); 1.35 (t, J=7.1, 3H); 0.85 (m, 1H); 0.54 (m, 2H); 0.29 (m, 2H); 0.00 (m, 2H); −0.18 (s, 9H).

Example D.b7

Ethyl 4-[2-(cyclopropylmethoxy)-5-methylphenyl]-6-methyl-5-{[2-(trimethylsilyl)ethoxy]methyl}-5H-pyrrolo[3,2-d]pyrimidine-7-carboxylate Starting from ethyl 4-[2-(cyclopropylmethoxy)-5-methylphenyl]-6-methyl-5H-pyrrolo[3,2-d]pyrimidine-7-carboxylate (example D.a7) and commercially available (2-chloromethoxy-ethyl)trimethyl-silane the title compound is obtained as yellow viscous oil.

MS (ESI): m/z=496 (MH$^+$, 100%).
$^1$H-NMR (400 MHz, DMSO-d$_6$): 8.97 (s, 1H); 7.33 (dd, J=8.5, 2.0, 1H); 7.26 (d, J=2.0, 1H); 7.05 (d, J=8.5, 1H); 5.43 (d, J=11.0, 1H); 5.03 (d, J=11.0, 1H); 4.35 (qu, J=7.1, 2H); 3.81 (dd, J=10.2, 6.5, 1H); 3.74 (dd, J=10.2, 6.9, 1H); 2.89 (m, 2H); 2.81 (s, 3H); 2.32 (s, 3H); 1.35 (t, J=7.1, 3H); 0.88 (m, 1H); 0.55 (m, 2H); 0.31 (m, 2H); 0.03 (m, 2H); −0.17 (s, 9H).

Example D.b8

Ethyl 4-[2-(cyclopropylmethoxy)-5-(trifluoromethyl)phenyl]-6-methyl-5-{[2-(trimethylsilyl)ethoxy]methyl}-5H-pyrrolo[3,2-d]pyrimidine-7-carboxylate Starting from ethyl 4-[2-(cyclopropylmethoxy)-5-(trifluoromethyl)phenyl]-6-methyl-5H-pyrrolo[3,2-d]pyrimidine-7-carboxylate (example D.a8) and commercially available (2-chloromethoxy-ethyl)trimethyl-silane the title compound is obtained as yellow viscous oil.

MS (ESI): m/z=550 (MH$^+$, 100%).
$^1$H-NMR (400 MHz, DMSO-d$_6$): 9.01 (s, 1H); 7.90 (dd, J=8.8, 2.1, 1H); 7.77 (d, J=2.1, 1H); 7.38 (d, J=8.8, 1H); 5.40 (d, J=10.9, 1H); 4.96 (d, J=10.9, 1H); 4.36 (qu, J=7.1, 2H); 3.98 (dd, J=10.4, 6.6, 1H); 3.91 (dd, J=10.4, 7.1, 1H); 2.92 (t, J=8.2, 2H); 2.83 (s, 3H); 1.36 (t, J=7.1, 3H); 0.94 (m, 1H); 0.51 (m, 2H); 0.35 (m, 2H); 0.10 (m, 2H); −0.18 (s, 9H).

Example D.b9

Ethyl 4-[2-ethoxy-5-(trifluoromethyl)phenyl]-6-methyl-5-{[2-(trimethylsilyl)ethoxy]methyl}-5H-pyrrolo[3,2-d]pyrimidine-7-carboxylate Starting from ethyl 4-[2-ethoxy-5-(trifluoromethyl)phenyl]-6-methyl-5H-pyrrolo[3,2-d]pyrimidine-7-carboxylate (example D.a9) and commercially available (2-chloromethoxy-ethyl)-trimethyl-silane the title compound is obtained as yellow viscous oil.

MS (ESI): m/z=524 (MH$^+$, 100%).
$^1$H-NMR (300 MHz, DMSO-d$_6$): 9.00 (s, 1H); 7.91 (dd, J=8.8, 2.2, 1H); 7.76 (d, J=2.2, 1H); 7.40 (d, J=8.8, 1H); 5.38 (d, J=10.9, 1H); 4.94 (d, J=10.9, 1H); 4.30 (qu, J=7.1, 2H); 4.17-4.08 (m, 2H); 2.93 (t, J=8.3, 2H); 2.83 (s, 3H); 1.35 (t, J=7.1, 3H); 1.07 (t, J=7.0, 3H); 0.59-0.45 (m, 2H); −0.18 (s, 9H).

Example D.b10

Ethyl 4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidine-7-carboxylate Starting from 4-(2-cyclopropylmethoxy-4-fluoro-5-methoxy-phenyl)-6-methyl-5H-pyrrolo[3,2-d]pyrimidine-7-carboxylic acid ethyl ester (example D.a10) and commercially available (2-chloromethoxy-ethyl)-trimethyl-silane the title compound is obtained as yellow viscous oil.

MS (ESI): m/z=552 (MNa$^+$); 530 (MH$^+$, 100%).
$^1$H-NMR (300 MHz, DMSO-d$_6$): 8.98 (s, 1H); 7.27 (d, J=9.7, 1H); 7.18 (d, J=13.3, 1H); 5.41 (d, J=10.9, 1H); 5.03 (d, J=11.0, 1H); 4.35 (qu, J=7.1, 2H); 3.82 (s, 3H); 3.80 (dd, J=10.4, 6.7, 1H); 3.74 (dd, J=10.4, 7.0, 1H); 2.97 (m, 2H); 2.82 (s, 3H); 1.35 (t, J=7.1, 3H); 0.87 (m, 1H); 0.56 (m, 2H); 0.31 (m, 2H); 0.02 (m, 2H); −0.15 (s, 9H).

Example D.b11

Ethyl 4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidine-7-carboxylate Starting from ethyl 4-[2-(cyclopropylmethoxy)-4-fluoro-5-methylphenyl]-6-methyl-5H-pyrrolo[3,2-d]pyrimidine-7-carboxylate (example D.a11) and commercially available (2-chloromethoxy-ethyl)trimethyl-silane the title compound is obtained as yellow solid.
MS (ESI): m/z=514 (MH$^+$, 100%).
$^1$H-NMR (300 MHz, DMSO-d$_6$): 8.96 (s, 1H); 7.37 (d, J=8.9, 1H); 7.05 (d, J=12.1, 1H); 5.43 (d, J=11.0, 1H); 5.02 (d, J=11.0, 1H); 4.35 (qu, J=7.1, 2H); 3.85 (dd, J=10.4, 6.6, 1H); 3.77 (dd, J=10.4, 7.1, 1H); 2.94 (m, 2H); 2.82 (s, 3H); 2.23 (d, J=1.3, 3H); 1.35 (t, J=7.1, 3H); 0.89 (m, 1H); 0.54 (m, 2H); 0.33 (m, 2H); 0.06 (m, 2H); −0.16 (s, 9H).

Example D.b12

Ethyl 4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidine-7-carboxylate Starting from ethyl 4-(2-cyclopropylmethoxy-5-fluoro-4-methoxy-phenyl)-6-methyl-5H-pyrrolo[3,2-d]pyrimidine-7-carboxylate (example D.a12) and commercially available (2-chloromethoxy-ethyl)trimethyl-silane the title compound is obtained as yellow viscous oil.
MS (ESI): m/z=552 (MNa$^+$, 100%); 530 (MH$^+$); 458 (MH$^+$-C$_3$H$_8$Si).
$^1$H-NMR (300 MHz, DMSO-d$_6$): 8.95 (s, 1H); 7.30 (d, J=11.5, 1H); 6.92 (d, J=7.3, 1H); 5.46 (d, J=11.1, 1H); 5.06 (d, J=11.1, 1H); 4.34 (qu, J=7.1, 2H); 3.94 (s, 3H); 3.87 (dd, J=10.2, 6.6, 1H); 3.80 (dd, J=10.2, 7.0, 1H); 2.95 (m, 2H); 2.81 (s, 3H); 1.34 (t, J=7.1, 3H); 0.87 (m, 1H); 0.54 (m, 2H); 0.31 (m, 2H); 0.03 (m, 2H); −0.18 (s, 9H).

Example D.b13

Ethyl 4-[2-(cyclopropylmethoxy)-5-(2-methyl-1,3-dioxolan-2-yl)phenyl]-6-methyl-5-{[2-(trimethylsilyl)ethoxy]methyl}-5H-pyrrolo[3,2-d]pyrimidine-7-carboxylate Starting from ethyl 4-[2-(cyclopropylmethoxy)-5-(2-methyl-1,3-dioxolan-2-yl)phenyl]-6-methyl-5H-pyrrolo[3,2-d]pyrimidine-7-carboxylate (example D.a13) and commercially available (2-chloromethoxy-ethyl)-trimethyl-silane the title compound is obtained as yellow viscous oil.
MS (ESI): m/z=568 (MH$^+$, 100%).

Example D.b14

Ethyl 4-[2-(cyclopropylmethoxy)-5-ethylphenyl]-6-methyl-5-{[2-(trimethylsilyl)ethoxy]methyl}-5H-pyrrolo[3,2-d]pyrimidine-7-carboxylate Starting from ethyl 4-[2-(cyclopropylmethoxy)-5-ethylphenyl]-6-methyl-5H-pyrrolo[3,2-d]pyrimidine-7-carboxylate (example D.a14) and commercially available (2-chloromethoxy-ethyl)-trimethyl-silane the title compound is obtained as yellow viscous oil.
MS (ESI): m/z=510 (MH$^+$, 100%).
$^1$H-NMR (300 MHz, DMSO-d$_6$): 8.97 (s, 1H); 7.41 (dd, J=8.6, 2.2, 1H); 7.29 (d, J=2.2, 1H); 7.08 (d, J=8.6, 1H); 5.42 (d, J=10.9, 1H); 5.03 (d, J=10.9, 1H); 4.35 (qu, J=7.1, 2H); 3.84 (dd, J=10.2, 6.4, 1H); 3.74 (dd, J=10.2, 6.8, 1H); 2.89 (m, 2H); 2.81 (s, 3H); 2.62 (qu, J=7.5, 2H); 1.34 (t, J=7.1, 3H); 1.20 (t, J=7.5, 3H); 0.93 (m, 1H); 0.52 (m, 2H); 0.32 (m, 2H); 0.04 (m, 2H); −0.18 (s, 9H).

Example D.b15

Ethyl 4-[2-(cyclopropylmethoxy)-5-(propan-2-yl)phenyl]-6-methyl-5-{[2-(trimethylsilyl)ethoxy]methyl}-5H-pyrrolo[3,2-d]pyrimidine-7-carboxylate Starting from ethyl 4-[2-(cyclopropylmethoxy)-5-(propan-2-yl)phenyl]-6-methyl-5H-pyrrolo[3,2-d]pyrimidine-7-carboxylate (example D.a15) and commercially available (2-chloromethoxy-ethyl)trimethyl-silane the title compound is obtained as yellow viscous oil.
MS (ESI): m/z=524 (MH$^+$, 100%).
$^1$H-NMR (300 MHz, DMSO-d$_6$): 8.97 (s, 1H); 7.39 (dd, J=8.6, 2.4, 1H); 7.32 (d, J=2.4, 1H); 7.08 (d; J=8.6, 1H); 5.41 (d, J=10.9, 1H); 5.04 (d, J=10.9, 1H); 4.35 (qu, J=7.1, 2H); 3.82 (dd, J=10.2, 6.6, 1H); 3.74 (dd, J=10.2, 6.8, 1H); 2.98-2.84 (m, 3H); 2.82 (s, 3H); 1.36 (t, J=7.1, 3H); 1.23 (dd, J=6.9, 2.2, 6H); 0.89 (m, 1H); 0.51 (m, 2H); 0.31 (m, 2H); 0.04 (m, 2H); −0.19 (s, 9H).

Example D.c1

4-[5-(Cyclopropylmethoxy)-1,3-benzodioxol-4-yl]-6-methyl-5-{[2-(trimethylsilyl)ethoxy]methyl}-5H-pyrrolo[3,2-d]pyrimidine-7-carboxylic acid Ethyl 4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidine-7-carboxylate from example D.b1 (15.28 g; 29.0 mmol) is dissolved in 1,4-dioxane (150 mL) and aqueous LiOH (prepared from 1.04 g; 43.5 mmol; and 75 mL of water). The stirred reaction mixture is heated to 80° C. until the starting material is consumed according to LC-MS. The mixture is concentrated under reduced pressure, and diluted with water. The product is precipitated by addition of 2M citric acid to adjust pH to 5, isolated by suction filtration, washed with several small portions of water and dried in high vacuo at 40° C. to yield 13.55 g of the title compound as pale yellow solid.
MS (ESI): m/z=498 (MH$^+$, 100%).
$^1$H-NMR (300 MHz, DMSO-d$_6$): 8.93 (s, 1H); 7.00 (d, J=8.6, 1H); 6.56 (d, J=8.6, 1H); 6.02 (d, J=0.6, 1H); 5.91 (d, J=0.6, 1H); 5.37 (d, J=11.0, 1H); 5.11 (d, J=11.0, 1H); 3.76 (dd, J=10.2, 6.6, 2H); 3.68 (dd, J=10.2, 6.8, 1H); 3.01 (m, 2H); 2.84 (s, 3H); 0.87 (m, 1H); 0.61 (m, 2H); 0.29 (m, 2H); 0.00 (m, 2H); −0.13 (s, 9H).

The following compounds were prepared analogously to the procedure described in above example D.c1.

Example D.c2

4-[2-(Cyclopropylmethoxy)-4-fluorophenyl]-6-methyl-5-{[2-(trimethylsilyl)ethoxy]methyl}-5H-pyrrolo[3,2-d]pyrimidine-7-carboxylic acid Starting from ethyl 4-[2-(cyclopropylmethoxy)-4-fluorophenyl]-6-methyl-5-{[2-(trimethylsilyl)ethoxy]methyl}-5H-pyrrolo[3,2-d]pyrimidine-7-carboxylate (example D.b2) the title compound is obtained as pale yellow solid.

MS (ESI): m/z=472 (MH+, 100%).
¹H-NMR (300 MHz, DMSO-d₆): 8.70 (s, 1H); 7.46 (dd, J=8.4, 6.9, 1H); 7.08 (dd, J=11.5, 2.4, 1H); 6.95 (ddd, J=8.4, 8.4, 2.4, 1H); 5.32 (d, J=10.9, 1H); 4.93 (d, J=10.9, 1H); 3.89 (dd, J=10.3, 6.6, 1H); 3.79 (dd, J=10.3, 6.9, 1H); 2.90 (m, 2H); 2.89 (s, 3H); 0.91 (m, 1H); 0.54 (dd, J=8.2, 7.8, 2H); 0.32 (m, 2H): 0.06 (m, 2H); −0.16 (s, 9H).

Example D.c3

4-[2-(Cyclopropylmethoxy)-5-fluorophenyl]-6-methyl-5-{[2-(trimethylsilyl)ethoxy]methyl}-5H-pyrrolo[3,2-d]pyrimidine-7-carboxylic acid Starting from ethyl 4-[2-(cyclopropylmethoxy)-5-fluorophenyl]-6-methyl-5-{[2-(trimethylsilyl)ethoxy]methyl}-5H-pyrrolo[3,2-d]pyrimidine-7-carboxylate (example D.b3) the title compound is obtained as yellow foam.
MS (ESI): m/z=472 (MH+).
¹H-NMR (300 MHz, DMSO-d₆): 8.77 (s, 1H); 7.36 (ddd, J=9.1, 8.9, 3.3, 1H); 7.27 (dd, J=8.6, 3.3, 1H); 7.18 (dd, J=9.1, 4.4, 1H); 5.35 (d, J=10.9, 1H); 4.94 (d, J=10.9, 1H); 3.83 (dd, J=10.2, 6.6, 1H); 3.76 (dd, J=10.2, 6.9, 1H); 2.92 (m, 2H); 2.88 (s, 3H); 0.88 (m, 1H); 0.56 (m, 2H); 0.30 (m, 2H); 0.03 (m, 2H); −0.16 (s, 9H).

Example D.c4

4-(2-ethoxy-5-fluorophenyl)-6-methyl-5-{[2-(trimethylsilyl)ethoxy]methyl}-5H-pyrrolo[3,2-d]pyrimidine-7-carboxylic acid Starting from ethyl 4-(2-ethoxy-5-fluorophenyl)-6-methyl-5-{[2-(trimethylsilyl)ethoxy]methyl}-5H-pyrrolo[3,2-d]pyrimidine-7-carboxylate (example D.b4) the title compound is obtained as pale yellow solid.
MS (ESI): m/z=446 (MH+, 100%).
¹H-NMR (300 MHz, DMSO-d₆, MeOH-d₄): 8.78 (s, 1H); 7.37 (ddd, J=9.1, 8.9, 3.3, 1H); 7.27 (dd, J=8.8, 3.3, 1H); 7.19 (dd, J=9.1, 4.4, 1H); 5.33 (d, J=11.0, 1H); 4.94 (d, J=11.0, 1H); 3.99 (qu, J=6.9, 2H); 3.01-2.86 (m, 2H); 2.87 (s, 3H); 1.02 (t, J=6.9, 3H); 0.57 (m, 2H); −0.15 (s, 9H).

Example D.c5

4-[2-(cyclopropylmethoxy)-4-methoxyphenyl]-6-methyl-5-{[2-(trimethylsilyl)ethoxy]methyl}-5H-pyrrolo[3,2-d]pyrimidine-7-carboxylic acid Starting from ethyl 4-[2-(cyclopropylmethoxy)-4-methoxyphenyl]-6-methyl-5-{[2-(trimethylsilyl)ethoxy]methyl}-5H-pyrrolo[3,2-d]pyrimidine-7-carboxylate (example D.b5) the title compound is obtained as yellow foam.
MS (ESI): m/z=484 (MH+, 100%).
¹H-NMR (300 MHz, DMSO-d₆): 12.35 (br.s, 1H, CO₂H); 8.92 (s, 1H); 7.40 (d, J=8.4, 1H); 6.72 (dd, J=8.4, 2.2, 2H); 6.69 (d, J=2.2, 1H); 5.46 (d, J=10.9, 1H); 5.06 (d, J=10.9, 1H); 3.87 (dd, J=10.2, 6.4, 1H); 3.85 (s, 3H); 3.78 (dd, J=10.2, 6.9, 1H); 2.91 (t, J=8.0, 2H); 2.82 (s, 3H); 0.89 (m, 1H); 0.52 (m, 2H); 0.32 (m, 2H); 0.06 (m, 2H); −0.18 (s, 9H).

Example D.c6

4-[2-(cyclopropylmethoxy)-5-methoxyphenyl]-6-methyl-5-{[2-(trimethylsilyl)ethoxy]methyl}-5H-pyrrolo[3,2-d]pyrimidine-7-carboxylic acid Starting from ethyl 4-[2-(cyclopropylmethoxy)-5-methoxyphenyl]-6-methyl-5-{[2-(trimethylsilyl)ethoxy]methyl}-5H-pyrrolo[3,2-d]pyrimidine-7-carboxylate (example D.b6) the title compound is obtained as yellow foam.
MS (ESI): m/z=484 (MH+, 100%).

Example D.c7

4-[2-(Cyclopropylmethoxy)-5-methylphenyl]-6-methyl-5-{[2-(trimethylsilyl)ethoxy]methyl}-5H-pyrrolo[3,2-d]pyrimidine-7-carboxylic acid Starting from ethyl 4-[2-(cyclopropylmethoxy)-5-methylphenyl]-6-methyl-5-{[2-(trimethylsilyl)ethoxy]methyl}-5H-pyrrolo[3,2-d]pyrimidine-7-carboxylate (example D.b7) the title compound is obtained as yellow solid.
¹H-NMR (400 MHz, DMSO-d₆): 12.35 (br.s, 1H, CO₂H); 8.96 (s, 1H); 7.33 (dd, J=8.6, 2.0, 1H); 7.27 (d, J=2.0, 1H); 7.06 (d, J=8.6, 1H); 5.43 (d, J=11.0, 1H); 5.03 (d, J=11.0, 1H); 3.82 (dd, J=10.3, 6.5, 1H); 3.75 (dd, J=10.2, 6.9, 1H); 2.89 (m, 2H); 2.83 (s, 3H); 2.32 (s, 3H); 0.89 (m, 1H); 0.52 (m, 2H); 0.31 (m, 2H); 0.04 (m, 2H); −0.17 (s, 9H).

Example D.c8

4-[2-(Cyclopropylmethoxy)-5-(trifluoromethyl)phenyl]-6-methyl-5-{[2-(trimethylsilyl)ethoxy]methyl}-5H-pyrrolo[3,2-d]pyrimidine-7-carboxylic acid Starting from ethyl 4-[2-(cyclopropylmethoxy)-5-(trifluoromethyl)phenyl]-6-methyl-5-{[2-(trimethylsilyl)ethoxy]methyl}-5H-pyrrolo[3,2-d]pyrimidine-7-carboxylate (example D.b8) the title compound is obtained as pale yellow solid.
MS (ESI): m/z=522 (MH+, 100%).
¹H-NMR (400 MHz, DMSO-d₆): 8.91 (s, 1H); 7.90 (dd, J=8.8, 2.1, 1H); 7.76 (d, J=2.1, 1H); 7.38 (d, J=8.8, 1H); 5.37 (d, J=11.0, 1H); 4.94 (d, J=11.0, 1H); 3.98 (dd, J=10.5, 6.6, 1H); 3.91 (dd, J=10.5, 7.0, 1H); 2.91 (t, J=8.2, 2H); 2.86 (s, 3H); 0.95 (m, 1H); 0.51 (m, 2H); 0.35 (m, 2H); 0.10 (m, 2H); −0.18 (s, 9H).

Example D.c9

4-[2-ethoxy-5-(trifluoromethyl)phenyl]-6-methyl-5-{[2-(trimethylsilyl)ethoxy]methyl}-5H-pyrrolo[3,2-d]pyrimidine-7-carboxylic acid Starting from ethyl 4-[2-ethoxy-5-(trifluoromethyl)phenyl]-6-methyl-5-{[2-(trimethylsilyl)ethoxy]methyl}-5H-pyrrolo[3,2-d]pyrimidine-7-carboxylate (example D.b9) the title compound is obtaines as pale yellow solid.
MS (ESI): m/z=496 (MH+, 100%).
¹H-NMR (300 MHz, DMSO-d₆, MeOH-d₄): 8.75 (s, 1H); 7.90 (dd, J=8.8, 2.2, 1H); 7.74 (d, J=2.2, 1H); 7.39 (d, J=8.8, 1H); 5.30 (d, J=11.0, 1H); 4.89 (d, J=11.0, 1H); 4.18-4.06 (m, 2H); 2.90 (t, J=8.6, 2H); 2.89 (s, 3H); 1.08 (t, J=7.0, 3H); 0.52 (m, 2H); −0.18 (s, 9H).

Example D.c10

4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidine-7-carboxylic acid Starting from ethyl 4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidine-7-carboxylate (example D.b10) the title compound is obtained as yellow foam.

MS (ESI): m/z=524 (MNa⁺); 502 (MH⁺, 100%).
¹H-NMR (300 MHz, DMSO-d₆): 12.38 (br.s, 1H, —CO₂H); 8.98 (s, 1H); 7.28 (d, J=9.7, 1H); 7.19 (d, J=13.1, 1H); 5.42 (d, J=10.9, 1H); 5.03 (d, J=10.9, 1H); 3.82 (s, 3H); 3.81 (dd, J=10.3, 6.6, 1H); 3.73 (dd, J=10.3, 7.0, 1H); 3.05-2.89 (m, 2H); 2.83 (s, 3H); 0.87 (m, 1H); 0.56 (m, 2H); 0.31 (m, 2H); 0.02 (m, 2H); −0.15 (s, 9H).

Example D.c11

4-[2-(Cyclopropylmethoxy)-4-fluoro-5-methylphenyl]-6-methyl-5-{[2-(trimethylsilyl)ethoxy]methyl}-5H-pyrrolo[3,2-d]pyrimidine-7-carboxylic acid Starting from ethyl 4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidine-7-carboxylate (example D.b11) the title compound is obtained as pale yellow solid.
MS (ESI): m/z=514 (MH⁺, 100%).
¹H-NMR (300 MHz, DMSO-d₆): 8.96 (s, 1H); 7.37 (d, J=8.9, 1H); 7.05 (d, J=12.1, 1H); 5.43 (d, J=11.0, 1H); 5.02 (d, J=11.0, 1H); 4.35 (qu, J=7.1, 2H); 3.85 (dd, J=10.4, 6.6, 1H); 3.77 (dd, J=10.4, 7.1, 1H); 2.94 (m, 2H); 2.82 (s, 3H); 2.23 (d, J=1.3, 3H); 1.35 (t, J=7.1, 3H); 0.89 (m, 1H); 0.54 (m, 2H); 0.33 (m, 2H); 0.06 (m, 2H); −0.16 (s, 9H).

Example D.c12

4-[2-(Cyclopropylmethoxy)-5-fluoro-4-methoxyphenyl]-6-methyl-5-{[2-(trimethylsilyl)ethoxy]methyl}-5H-pyrrolo[3,2-d]pyrimidine-7-carboxylic acid Starting from ethyl 4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidine-7-carboxylate (example D.b12) the title compound is obtained as yellow foam.
MS (ESI): m/z=552 (MNa⁺, 100%); 530 (MH⁺); 458 (MH⁺-C₃H₈Si).
¹H-NMR (300 MHz, DMSO-d₆): 8.95 (s, 1H); 7.30 (d, J=11.5, 1H); 6.92 (d, J=7.3, 1H); 5.46 (d, J=11.1, 1H); 5.06 (d, J=11.1, 1H); 4.34 (qu, J=7.1, 2H); 3.94 (s, 3H); 3.87 (dd, J=10.2, 6.6, 1H); 3.80 (dd, J=10.2, 7.0, 1H); 2.95 (m, 2H); 2.81 (s, 3H); 1.34 (t, J=7.1, 3H); 0.87 (m, 1H); 0.54 (m, 2H); 0.31 (m, 2H); 0.03 (m, 2H); −0.18 (s, 9H).

Example D.c13

4-[2-(cyclopropylmethoxy)-5-(2-methyl-1,3-dioxolan-2-yl)phenyl]-6-methyl-5-{[2-(trimethylsilyl)ethoxy]methyl}-5H-pyrrolo[3,2-d]pyrimidine-7-carboxylic acid Starting from ethyl 4-[2-(cyclopropylmethoxy)-5-(2-methyl-1,3-dioxolan-2-yl)phenyl]-6-methyl-5-{[2-(trimethylsilyl)ethoxy]methyl}-5H-pyrrolo[3,2-d]pyrimidine-7-carboxylate (example D.b13) the title compound is obtained as yellow foam.
MS (ESI): m/z=540 (MH⁺, 100%).
¹H-NMR (300 MHz, DMSO-d₆): 8.93 (s, 1H); 7.56 (dd, J=8.8, 2.4, 1H); 7.49 (d, J=2.4, 1H); 7.14 (d, J=8.8, 1H); 5.38 (d, J=11.1, 1H); 5.03 (d, J=11.1, 1H); 4.00 (m, 2H); 3.86 (dd, J=10.2, 6.4, 1H); 3.78 (dd, J=10.2, 6.9, 1H); 3.73 (dd, J=10.2, 7.0, 2H); 2.89 (m, 2H); 2.84 (s, 3H); 1.59 (s, 3H); 0.91 (m, 1H); 0.50 (m, 2H); 0.32 (m, 2H); 0.06 (m, 2H); −0.20 (s, 9H).

Example D.c14

4-[2-(Cyclopropylmethoxy)-5-ethylphenyl]-6-methyl-5-{[2-(trimethylsilyl)ethoxy]methyl}-5H-pyrrolo[3,2-d]pyrimidine-7-carboxyli c acid Starting from ethyl 4-[2-(cyclopropylmethoxy)-5-ethylphenyl]-6-methyl-5-{[2-(trimethylsilyl)ethoxy]methyl}-5H-pyrrolo[3,2-d]pyrimidine-7-carboxylate (example D.b14) the title compound is obtained as pale yellow solid.
MS (ESI): m/z=510 (MH⁺, 100%).
¹H-NMR (300 MHz, DMSO-d₆): 8.97 (s, 1H); 7.41 (dd, J=8.6, 2.2, 1H); 7.29 (d, J=2.2, 1H); 7.08 (d, J=8.6, 1H); 5.42 (d, J=10.9, 1H); 5.03 (d, J=10.9, 1H); 4.35 (qu, J=7.1, 2H); 3.84 (dd, J=10.2, 6.4, 1H); 3.74 (dd, J=10.2, 6.8, 1H); 2.89 (m, 2H); 2.81 (s, 3H); 2.62 (qu, J=7.5, 2H); 1.34 (t, J=7.1, 3H); 1.20 (t, J=7.5, 3H); 0.93 (m, 1H); 0.52 (m, 2H); 0.32 (m, 2H); 0.04 (m, 2H); −0.18 (s, 9H).

Example D.c15

4-[2-(cyclopropylmethoxy)-5-(propan-2-yl)phenyl]-6-methyl-5-{[2-(trimethylsilyl)ethoxy]methyl}-5H-pyrrolo[3,2-d]pyrimidine-7-carboxylic acid Starting from ethyl 4-[2-(cyclopropylmethoxy)-5-(propan-2-yl)phenyl]-6-methyl-5-{[2-(trimethylsilyl)ethoxy]methyl}-5H-pyrrolo[3,2-d]pyrimidine-7-carboxylate (example D.b15) the title compound is obtained as yellow foam.
MS (ESI): m/z=496 (MH⁺, 100%).

Example D.c16

4-[2-(Cyclopropylmethoxy)-5-methylphenyl]-2,6-dimethyl-5-{[2-(trimethylsilyl)ethoxy]methyl}-5H-pyrrolo[3,2-d]pyrimidine-7-carboxylic acid Starting from methyl 4-[2-(cyclopropylmethoxy)-5-methylphenyl]-2,6-dimethyl-5-{[2-(trimethylsilyl)ethoxy]methyl}-5H-pyrrolo[3,2-d]pyrimidine-7-carboxylate (example D.a16) the title compound is obtained as pale yellow foam.
MS (ESI): m/z=482 (MH⁺, 100%)
¹H-NMR (300 MHz, DMSO-d₆): 12.32 (br.s, 1H, —CO₂H); 7.33 (dd, J=8.4, 1.8, 1H); 7.24 (d, J=1.8, 1H); 7.05 (d, J=8.4, 1H); 5.42 (d, J=11.0, 1H); 5.01 (d, J=11.0, 1H); 3.80 (dd, J=10.2, 6.6, 1H); 3.76 (dd, J=10.2, 6.9, 1H); 2.89 (m, 2H); 2.81 (s, 3H); 2.70 (s, 3H); 2.32 (s, 3H); 0.89 (m, 1H); 0.52 (m, 2H); 0.31 (m, 2H); 0.05 (m, 2H); −0.17 (s, 9H).

Example D.c17

4-[2-(Cyclopropylmethoxy)-5-fluoro-4-methoxyphenyl]-2,6-dimethyl-5-{[2-(trimethylsilyl)ethoxy]methyl}-5H-pyrrolo[3,2-d]pyrimidine-7-carboxylic acid Starting from methyl 4-[2-(cyclopropylmethoxy)-5-fluoro-4-methoxyphenyl]-2,6-dimethyl-5-{[2-(trimethylsilyl)ethoxy]methyl}-5H-pyrrolo[3,2-d]pyrimidine-7-carboxylate (example D.a17) the title compound is obtained as pale yellow foam
MS (ESI): 516 (MW, 100%)
¹H-NMR (300 MHz, DMSO-d₆): 12.32 (br.s, 1H, —CO₂H); 7.30 (d, J=11.3, 1H); 6.93 (d, J=7.3, 1H), 5.46 (d, J=11.1, 1H); 5.05 (d, J=11.1, 1H); 3.95 (s, 3H); 3.85 (m, 2H); 2.96 (m, 2H); 2.82 (s, 3H); 2.70 (s, 3H); 0.89 (m, 1H); 0.55 (m, 2H); 0.33 (m, 2H); 0.06 (m, 2H); −0.17 (s, 9H).

Example D.c18

4-[2-(Cyclopropylmethoxy)-4-fluoro-5-methoxyphenyl]-2,6-dimethyl-5-{[2-(trimethylsilyl)ethoxy]methyl}-5H-pyrrolo[3,2-d]pyrimidine-7-carboxylic acid Starting from methyl 4-[2-(cyclopropylmethoxy)-4-fluoro-5-methoxyphenyl]-2,6-dimethyl-5-{[2-(trimethylsilyl)ethoxy]methyl}-5H-pyrrolo[3,2-d]pyrimidine-7-carboxylate (example D.a18) the title compound is obtained as pale yellow foam MS (ESI): m/z=516 (MH$^+$, 100%).
$^1$H-NMR (300 MHz, DMSO-d$_6$): 7.25 (d, J=9.7, 1H); 7.17 (d, J=13.1, 1H); 5.38 (d, J=10.8, 1H); 5.01 (d, J=10.8, 1H); 3.82 (s, 3H); 3.80 (dd, J=10.4, 6.6, 1H); 3.73 (dd, J=10.4, 7.0, 1H); 3.06-2.90 (m, 2H); 2.82 (s, 3H); 2.72 (s, 3H); 0.88 (m, 1H); 0.57 (m, 2H); 0.33 (m, 2H); 0.04 (m, 2H); −0.15 (s, 9H).

Example D.d1 tert-Butyl 4-{[(4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidin-7-yl)carbonyl]amino}piperidine-1-carboxylate 4-[5-(Cyclopropylmethoxy)-1,3-benzodioxol-4-yl]-6-methyl-5-{[2-(trimethylsilyl)ethoxy]methyl}-5H-pyrrolo[3,2-d]pyrimidine-7-carboxylic acid from example D.c1 (3.98 g; 8.0 mmol), triethylamine (2.43 g; 24.0 mmol) and HOBt (1.08 g; 8.0 mmol) is stirred in dry dichloromethane (40 mL) for 30 min, before addition of EDC (1.84 g; 9.6 mmol). The reaction mixture is stirred for one hour at ambient temperature. After addition of tert-butyl 4-amino-piperidine-1-carboxylate hydrochloride (2.27 g; 9.6 mmol) the reaction mixture is stirred at ambient temperature until the starting material is consumed according to LC-MS and chromatographed on silica gel (ethylacetate/cyclohexane 1:1) to yield the title compound as colorless foam.

MS (ESI): m/z=680 (MH$^+$, 100%).
$^1$H-NMR (300 MHz, DMSO-d$_6$): 9.02 (d, J=7.2, 1H, —NH); 9.01 (s, 1H); 7.01 (d, J=8.4, 1H); 6.57 (d, J=8.4, 1H); 6.07 (s, 1H); 5.92 (s, 1H); 5.39 (d, J=11.0, 1H); 5.12 (d, J=11.0, 1H); 4.06 (m, 1H); 3.85 (m, 2H); 3.76 (dd, J=10.2, 6.5, 1H); 3.68 (dd, J=10.2, 6.9, 1H); 3.13-2.94 (m, 4H); 2.91 (s, 3H); 1.93 (m, 2H); 1.46 (m, 2H); 1.42 (s, 9H); 0.86 (m, 1H); 0.61 (m, 2H); 0.29 (m, 2H); 0.01 (m, 2H); −0.13 (s, 9H).

The following compounds were prepared analogously to the procedure described in above example D.d1.

Example D.d2 tert-Butyl (trans-4-{[(4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[5-(yyclopropylmethoxy)-1,3-benzodioxol-4-yl]-6-methyl-5-{[2-(trimethylsilyl)ethoxy]methyl}-5H-pyrrolo[3,2-d]pyrimidine-7-carboxylic acid (example D.c1) and commercially available tert-butyl trans-(4-amino-cyclohexyl)-carbamate the title compound is obtained as pale yellow viscous oil. The compound is further processed without characterisation.

Example D.d3 tert-Butyl (cis-4-{[(4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[5-(yyclopropylmethoxy)-1,3-benzodioxol-4-yl]-6-methyl-5-{[2-(trimethylsilyl)ethoxy]methyl}-5H-pyrrolo[3,2-d]pyrimidine-7-carboxylic acid (example D.c1) and commercially available tert-butyl cis-(4-amino-cyclohexyl)-carbamate the title compound is obtained as pale yellow viscous oil. The compound is further processed without characterisation.

Example D.d4 tert-Butyl (3R)-3-{[(4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidin-7-yl)carbonyl]amino}pyrrolidine-1-carboxylate Starting from 4-[5-(yyclopropylmethoxy)-1,3-benzodioxol-4-yl]-6-methyl-5-{[2-(trimethylsilyl)ethoxy]methyl}-5H-pyrrolo[3,2-d]pyrimidine-7-carboxylic acid (example D.c1) and commercially available tert-butyl (R)-3-amino-pyrrolidine-1-carboxylate the title compound is obtained as pale yellow foam.

MS (ESI): m/z=666 (MH$^+$, 100%).
$^1$H-NMR (300 MHz, DMSO-d$_6$): 9.13 (d, J=6.8, 1H, —NH); 8.99 (s, 1H); 7.01 (d, J=8.6, 1H); 6.57 (d, J=8.6, 1H); 6.02 (d, J=0.6, 1H); 5.92 (d, J=0.6, 1H); 5.40 (d, J=10.9, 1H); 5.12 (d, J=10.9, 1H); 4.50 (m, 1H); 3.76 (dd, J=10.2, 6.6, 1H); 3.67 (dd, J=10.2, 6.9, 1H); 3.61 (m, 1H); 3.43 (m, 2H); 3.25 (m, 1H); 3.00 (m, 2H); 2.91 (s, 3H); 2.22 (m, 1H); 1.96 (m, 1H); 1.41 (s, 9H); 0.86 (m, 1H); 0.61 (m, 2H); 0.29 (m, 2H); 0.01 (m, 2H); −0.14 (s, 9H).

Example D.d5 tert-Butyl (3R*,4R*)-3-{[(4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidin-7-yl)carbonyl]amino}-4-hydroxypyrrolidine-1-carboxylate Starting from 4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidine-7-carboxylic acid (example D.c1) and commercially available tert-butyl (3R*,4R*)-3-amino-4-hydroxy-pyrrolidine-1-carboxylate the title compound is obtained as pale yellow foam.

MS (ESI): m/z=682 (MH$^+$, 100%).
$^1$H-NMR (300 MHz, DMSO-d$_6$): 9.06 (br.s, 1H, —NH); 8.97 (s, 1H); 7.02 (d, J=8.6, 1H); 6.57 (d, J=8.6, 1H); 6.02 (s, 1H); 5.92 (s, 1H); 5.48 (d, J=3.8, 1H, —OH); 5.40 (d, J=11.0, 1H); 5.12 (d, J=11.0, 1H); 4.24 (m, 2H); 3.76 (dd, J=10.2, 6.6, 1H); 3.67 (dd, J=10.2, 6.9, 1H & m, 1H); 3.56 (m, 1H); 3.23 (m, 2H); 3.09-2.92 (m, 2H); 2.91 (s, 3H); 1.43 (s, 9H); 0.86 (m, 1H); 0.61 (m, 2H); 0.29 (m, 2H); 0.01 (m, 2H); −0.13 (s, 9H).

Example D.d6 tert-Butyl 4-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-4-fluorophenyl]-6-methyl-5-{[2-(trimethylsilyl)ethoxy]methyl}-5H- pyrrolo[3,2-d]pyrimidine-7-carboxylic acid (example D.c2) and commercially available tert-butyl 4-amino-piperidine-1-carboxylate the title compound is obtained as pale yellow viscous oil.

MS (ESI): m/z=654 (MH$^+$, 100%).

$^1$H-NMR (300 MHz, DMSO-d$_6$): 9.07 (d, J=7.7, 1H, —NH); 8.99 (s, 1H); 7.49 (dd, J=8.4, 6.8, 1H); 7.10 (dd, J=11.3, 2.4, 1H); 6.97 (ddd, J=8.4, 8.4, 2.4, 1H); 5.41 (d, J=11.1, 1H); 4.98 (d, J=11.1, 1H); 4.08 (m, 1H); 3.90 (dd, J=10.2, 6.6, 1H); 3.81 (dd, J=10.2, 7.1, 1H); 3.92-3.78 (m, 2H); 3.06 (m, 2H); 2.92 (m, 2H); 2.91 (s, 3H); 1.93 (m, 2H); 1.45 (m, 2H); 1.42 (s, 9H); 0.91 (m, 1H); 0.54 (dd, J=9.1, 7.3, 2H); 0.34 (m, 2H): 0.08 (m, 2H); −0.16 (s, 9H).

Example D.d7

Tert-butyl (trans-4-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-4-fluorophenyl]-6-methyl-5-{[2-(trimethylsilyl)ethoxy]methyl}-5H-pyrrolo[3,2-d]pyrimidine-7-carboxylic acid (example D.c2) and commercially available tert-butyl trans-(4-amino-cyclohexyl)-carbamate the title compound is obtained as pale yellow viscous oil.

MS (ESI): m/z=668 (MH$^+$, 100%).

$^1$H-NMR (300 MHz, DMSO-d$_6$): 8.99 (s, 1H); 8.90 (d, J=7.7, 1H, —NH); 7.49 (dd, 8.4, 6.9, 1H); 7.10 (dd, 11.3, 2.2, 1H); 6.97 (ddd, 8.4, 8.4, 2.2, 1H); 6.72 (d, J=7.9, 1H, —NH); 5.40 (d, J=11.1, 1H); 4.98 (d, J=11.1, 1H); 3.90 (dd, J=10.2, 6.6, 1H); 3.80 (dd, J=10.2, 7.1, 1H); 3.79 (m, 1H); 3.29 (m, 1H); 2.92 (m, 2H); 2.90 (s, 3H); 2.00 (m, 2H); 1.85 (m, 2H); 1.39 (s, 9H); 1.36 (m, 4H); 0.91 (m, 1H); 0.54 (m, 2H); 0.33 (m, 2H); 0.07 (m, 2H); −0.16 (s 9H).

Example D.d8 tert-Butyl (cis-4-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-4-fluorophenyl]-6-methyl-5-{[2-(trimethylsilyl)ethoxy]methyl}-5H-pyrrolo[3,2-d]pyrimidine-7-carboxylic acid (example D.c2) and commercially available tert-butyl cis-(4-amino-cyclohexyl)-carbamate the title compound is obtained as pale yellow viscous oil.

MS (ESI): m/z=668 (MH$^+$, 100%).

$^1$H-NMR (300 MHz, DMSO-d$_6$): 9.29 (d, J=7.7, 1H, —NH); 9.04 (s, 1H); 7.50 (dd, 8.4, 6.7, 1H); 7.12 (dd, 11.5, 2.4, 1H); 6.97 (ddd, 8.4, 8.4, 2.4, 1H & br.s, 1H, —NH); 5.42 (d, J=10.9, 1H); 4.98 (d, J=10.9, 1H); 4.07 (m, 1H); 3.85 (dd, J=10.4, 6.6, 1H); 3.80 (dd, J=10.4, 7.1, 1H); 3.42 (m, 1H); 2.91 (m, 2H & s, 3H); 1.88-1.48 (m, 8H); 1.40 (s, 9H); 0.92 (m, 1H); 0.54 (dd, J=9.1, 7.1, 2H); 0.35 (m, 2H); 0.09 (m, 2H); −0.16 (s 9H).

Example D.d9

Tert-butyl (3R)-3-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}pyrrolidine-1-carboxylate Starting from 4-[2-(cyclopropylmethoxy)-4-fluorophenyl]-6-methyl-5-{[2-(trimethylsilyl)ethoxy]methyl}-5H-pyrrolo[3,2-d]pyrimidine-7-carboxylic acid (example D.c2) and commercially available tert-butyl (R)-3-amino-pyrrolidine-1-carboxylate the title compound is obtained as pale yellow viscous oil.

MS (ESI): m/z=640 (MH$^+$, 100%).

$^1$H-NMR (300 MHz, DMSO-d$_6$): 9.17 (d, J=6.7, 1H, —NH); 8.98 (s, 1H); 7.50 (dd, J=8.4, 6.9, 1H); 7.10 (dd, J=11.3, 2.4, 1H); 6.97 (ddd, J=8.4, 8.4, 2.4, 1H); 5.42 (d, J=11.0, 1H); 4.99 (d, J=11.0, 1H); 4.50 (m, 1H); 3.90 (dd, J=10.2, 6.4, 1H); 3.80 (dd, J=10.2, 7.1, 1H); 3.62 (m, 1H); 3.43 (m, 2H); 3.27 (m, 1H); 2.92 (m, 2H); 2.91 (s. 3H); 2.22 (m, 1H); 1.96 (m, 1H); 1.41 (s, 9H); 0.91 (m, 1H); 0.54 (dd, J=9.1, 7.3, 2H); 0.33 (m, 2H); 0.07 (m, 2H); −0.16 (s, 9H).

Example D.d10 tert-Butyl (3r,4r)-3-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}-4-hydroxypyrrolidine-1-carboxylate Starting from 4-[2-(cyclopropylmethoxy)-4-fluorophenyl]-6-methyl-5-{[2-(trimethylsilyl)ethoxy]methyl}-5H-pyrrolo[3,2-d]pyrimidine-7-carboxylic acid (example D.c2) and commercially available tert-butyl (3R*,4R*)-3-amino-4-hydroxy-pyrrolidine-1-carboxylate the title compound is obtained as pale yellow viscous oil.

MS (ESI): m/z=656 (MH$^+$, 100%).

$^1$H-NMR (300 MHz, DMSO-d$_6$): 9.11 (br.s, 1H, —NH); 8.95 (s, 1H); 7.50 (dd, J=8.4, 6.9, 1H); 7.10 (dd, J=11.5, 2.4, 1H); 6.97 (ddd, J=8.4, 8.4, 2.4, 1H); 5.48 (d, J=5.5, 1H, —OH); 5.42 (d, J=11.1, 1H); 4.99 (d, J=11.1, 1H); 4.26 (m, 1H); 4.20 (m, 1H); 3.90 (dd, J=10.2, 6.6, 1H); 3.80 (dd, J=10.2, 6.9, 1H); 3.68 (m, 1H); 3.56 (m, 1H); 3.25 (m, 2H); 2.94 (m, 2H); 2.91 (s, 3H); 1.43 (s, 9H); 0.90 (m, 1H); 0.54 (m, 2H); 0.34 (m, 2H); 0.08 (m, 2H), −0.16 (s, 9H).

Example D.d11 tert-Butyl (3S*,4S*)-4-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate Starting from 4-[2-(cyclopropylmethoxy)-4-fluorophenyl]-6-methyl-5-{[2-(trimethylsilyl)ethoxy]methyl}-5H-pyrrolo[3,2-d]pyrimidine-7-carboxylic acid (example D.c2) and tert-butyl (3R*,4R*)-4-amino-3-hydroxy-piperidine-1-carboxylate (example C2) the title compound is obtained as pale yellow viscous oil.

MS (ESI): m/z=670 (MH$^+$, 100%).

$^1$H-NMR (300 MHz, DMSO-d$_6$): 9.11 (d, J=7.5, 1H, —NH); 8.99 (s, 1H); 7.50 (dd, J=8.4, 7.1, 1H); 7.11 (dd, J=11.3, 2.4, 1H); 6.98 (ddd, J=8.4, 8.4, 2.4, 1H); 5.42 (d, J=11.0, 1H); 5.26 (t, J=5.1, 1H, —OH); 4.99 (d, J=11.0, 1H); 3.99-3.75 (m, 5H); 3.45 (m, 1H); 3.27 (m, 1H); 3.06-2.88 (m, 3H); 2.92 (s. 3H); 2.79 (m, 1H); 2.07 (m, 1H); 1.43 (s, 9H & m, 1H); 0.92 (m, 1H); 0.55 (m, 2H); 0.35 (m, 2H); 0.10 (m, 2H); −0.15 (s, 9H).

Example D.d12 tert-Butyl (4-{[(4-[2-(cyclopropylmethoxy)-5-fluorophenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-fluorophenyl]-6-methyl-5-{[2-(trimethylsilyl)ethoxy]methyl}-5H- pyrrolo[3,2-d]pyrimidine-7-carboxylic acid (example D.c3) and commercially available tert-butyl 4-amino-piperidine-1-carboxylate the title compound is obtained as pale yellow viscous oil.

MS (ESI): m/z=654 (MH$^+$).
$^1$H-NMR (300 MHz, DMSO-d$_6$): 9.05 (d, J=7.7, 1H, —NH); 9.01 (s, 1H); 7.39 (ddd, J=9.1, 8.8, 3.1, 1H); 7.30 (dd, J=8.6, 3.1, 1H); 7.20 (dd, J=9.1, 4.4, 1H); 5.42 (d, J=11.0, 1H); 4.99 (d, J=11.0, 1H); 4.08 (m, 1H); 3.84 (dd, J=10.4, 6.6, 1H); 3.83 (m, 2H); 3.77 (dd, J=10.4, 7.1, 1H); 3.06 (m, 2H); 2.94 (m, 2H); 2.92 (s, 3H); 1.93 (m, 2H); 1.45 (m, 2H); 1.42 (s, 9H); 0.88 (m, 1H); 0.55 (m, 2H); 0.32 (m, 2H); 0.04 (m, 2H); −0.15 (s, 9H).

Example D.d13 tert-Butyl (trans-4-{[(4-[2-(cyclopropylmethoxy)-5-fluorophenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-fluorophenyl]-6-methyl-5-{[2-(trimethylsilyl)ethoxy]methyl}-5H-pyrrolo[3,2-d]pyrimidine-7-carboxylic acid (example D.c3) and commercially available tert-butyl trans-(4-amino-cyclohexyl)-carbamate the title compound is obtained as pale yellow viscous oil.

MS (ESI): m/z=668 (MH$^+$).
$^1$H-NMR (300 MHz, DMSO-d$_6$): 9.01 (s, 1H); 8.89 (d, J=7.9, 1H, —NH); 7.38 (ddd, J=9.1, 8.4, 3.3, 1H); 7.30 (dd, J=8.6, 3.3, 1H); 7.20 (dd, J=9.1, 4.4, 1H); 6.73 (d, J=7.1, 1H, —NH); 5.42 (d, J=11.0, 1H); 4.99 (d, J=11.0, 1H); 3.84 (dd, J=10.2, 6.6, 1H); 3.76 (dd, J=10.2, 6.9, 1H & m, 1H); 3.28 (m, 1H); 2.93 (m, 2H); 2.91 (s, 3H); 2.01 (m, 2H); 1.85 (m, 2H); 1.39 (s, 9H); 1.34 (m, 4H); 0.88 (m, 1H); 0.55 (m, 2H); 0.31 (m, 2H); 0.04 (m, 2H); −0.16 (s, 9H).

Example D.d14 tert-Butyl (4-{[(4-[2-(cyclopropylmethoxy)-5-fluorophenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-fluorophenyl]-6-methyl-5-{[2-(trimethylsilyl)ethoxy]methyl}-5H-pyrrolo[3,2-d]pyrimidine-7-carboxylic acid (example D.c3) and commercially available tert-butyl cis-(4-amino-cyclohexyl)-carbamate the title compound is obtained as pale yellow viscous oil.

MS (ESI): m/z=668 (MH$^+$).
$^1$H-NMR (300 MHz, DMSO-d$_6$): 9.26 (d, J=7.9, 1H, —NH); 9.05 (s, 1H); 7.39 (ddd, J=9.1, 8.7, 3.1, 1H); 7.30 (dd, J=8.7, 3.1, 1H); 7.20 (dd, J=9.1, 4.4, 1H); 6.92 (m, 1H, —NH); 5.42 (d, J=11.1, 1H); 4.99 (d, J=11.1, 1H); 4.07 (m, 1H); 3.85 (dd, J=10.4, 6.6, 1H); 3.77 (dd, J=10.4, 7.0, 1H); 3.43 (m, 1H); 2.94 (m, 2H); 2.92 (s, 3H); 1.85-1.52 (m, 8H); 1.40 (s, 9H); 0.87 (m, 1H); 0.56 (m, 2H); 0.32 (m, 2H); 0.05 (m, 2H); −0.15 (s, 9H).

Example D.d15 tert-butyl (3R,4R)-4-{[(4-[2-(cyclopropylmethoxy)-5-fluorophenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate Starting from 4-[2-(cyclopropylmethoxy)-5-fluorophenyl]-6-methyl-5-{[2-(trimethylsilyl)ethoxy]methyl}-5H-pyrrolo[3,2-d]pyrimidine-7-carboxylic acid (example D.c3) and commercially available tert-butyl (R)-3-amino-pyrrolidine-1-carboxylate the title compound is obtained as pale yellow viscous oil.

MS (ESI): m/z=640 (MH$^+$, 100%).
$^1$H-NMR (300 MHz, DMSO-d$_6$): 9.16 (d, J=6.8, 1H, —NH); 8.99 (s, 1H); 7.39 (ddd, J=9.1, 8.4, 3.3, 1H); 7.30 (ddd, J=8.6, 3.3, 1.1, 1H); 7.20 (dd, J=9.1, 4.4, 1H); 5.43 (d, J=10.9, 1H); 4.99 (d, J=10.9, 1H); 4.50 (m, 1H); 3.84 (dd, J=10.2, 6.6, 1H); 3.76 (d, J=10.2, 7.0, 1H); 3.62 (m, 1H); 3.43 (m, 2H); 3.27 (m, 1H); 2.94 (m, 2H); 2.92 (s, 3H); 2.21 (m, 1H); 1.96 (m, 1H); 1.42 (s, 9H); 0.88 (m, 1H); 0.56 (dd, J=9.1, 7.2, 2H); 0.31 (m, 2H); 0.04 (m, 2H); −0.16 (s, 9H).

Example D.d16 tert-Butyl (3R*,4R*)-4-{[(4-[2-(cyclopropylmethoxy)-5-fluorophenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate Starting from 4-[2-(cyclopropylmethoxy)-5-fluorophenyl]-6-methyl-5-{[2-(trimethylsilyl)ethoxy]methyl}-5H-pyrrolo[3,2-d]pyrimidine-7-carboxylic acid (example D.c3) and tert-butyl (3R*,4R*)-4-amino-3-hydroxy-piperidine-1-carboxylate (example C2) the title compound is obtained as pale yellow viscous oil.

MS (ESI): m/z=670 (MH$^+$, 100%).
$^1$H-NMR (300 MHz, DMSO-d$_6$): 9.10 (d, J=7.5, 1H, —NH); 9.01 (s, 1H); 7.39 (ddd, J=8.9, 8.9, 3.3, 1H); 7.30 (ddd, J=8.4, 3.1, 0.7, 1H); 7.20 (dd, J=8.9, 4.4, 1H); 5.43 (d, J=11.1, 1H); 5.24 (dd, J=5.1, 5.1, 1H, —OH); 4.99 (d, J=11.1, 1H); 4.02-3.71 (m, 5H); 3.45 (m, 1H); 3.00-2.88 (m, 3H); 2.92 (s, 3H); 2.78 (m, 1H); 2.07 (m, 1H); 1.42 (s, 9H & m, 1H); 0.89 (m, 1H); 0.56 (m, 2H); 0.32 (m, 2H); 0.06 (m, 2H), −0.15 (s, 9H).

Example D.d17 tert-Bbutyl 4-({[4-(2-ethoxy-5-fluorophenyl)-6-methyl-5-{[2-(trimethylsilyl)ethoxy]methyl}-5H-pyrrolo[3,2-d]pyrimidin-7-yl]carbonyl}amino)piperidine-1-carboxylate Starting from 4-(2-ethoxy-5-fluorophenyl)-6-methyl-5-{[2-(trimethylsilyl)ethoxy]methyl}-5H-pyrrolo[3,2-d]pyrimidine-7-carboxylic acid (example D.c4) and commercially available tert-butyl 4-amino-piperidine-1-carboxylate the title compound is obtained as pale yellow foam.

MS (ESI): m/z=628 (MH$^+$, 100%).
$^1$H-NMR (300 MHz, DMSO-d$_6$, MeOH-d$_4$): 9.05 (d, J=7.5, 1H, —NH); 9.00 (s, 1H); 7.40 (ddd, J=9.1, 8.9, 3.3, 1H); 7.30 (dd, J=8.6, 3.3, 1H); 7.21 (dd, J=9.1, 4.4, 1H); 5.41 (d, J=11.0, 1H); 4.98 (d, J=11.0, 1H); 4.08 (m, 1H); 3.99 (qu, J=7.1, 2H); 3.85 (m, 2H); 3.06 (m, 2H); 2.94 (m, 2H); 2.91 (s, 3H); 1.93 (m, 2H); 1.42 (s, 9H &m, 2H); 1.02 (t, J=7.1, 3H); 0.56 (m, 2H); −0.15 (s, 9H).

Example D.d18 tert-Butyl 4-{[(4-[2-(cyclopropylmethoxy)-4-methoxyphenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-4-methoxyphenyl]-6-methyl-5-{[2-(trimethylsilyl)ethoxy]methyl}-5H- pyrrolo[3,2-d]pyrimidine-7-carboxylic acid (example D.c5) and commercially available tert-butyl 4-amino-piperidine-1-carboxylate the title compound is obtained as pale yellow foam.

MS (ESI): m/z=666 (MH$^+$, 100%).

$^1$H-NMR (300 MHz, DMSO-d$_6$): 9.09 (d, J=7.5, 1H, —NH); 8.96 (s, 1H); 7.41 (d, J=8.4, 1H); 6.73 (dd, J=8.4, 2.2, 2H); 6.70 (d, J=2.2, 1H); 5.46 (d, J=10.9, 1H); 5.05 (d, J=10.9, 1H); 4.06 (m, 1H); 3.87 (dd, J=10.2, 6.6, 1H); 3.85 (s, 3H); 3.83 (m, 2H); 3.78 (dd, J=10.2, 7.1, 1H); 3.08 (m, 2H); 2.91 (s, 3H & m, 2H); 1.93 (m, 2H); 1.45 (m, 2H); 1.42 (s, 9H); 0.89 (m, 1H); 0.51 (m, 2H); 0.33 (m, 2H); 0.07 (m, 2H); −0.18 (s, 9H).

Example D.d19 tert-Butyl (trans-4-{[(4-[2-(cyclopropylmethoxy)-4-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-4-methoxyphenyl]-6-methyl-5-{[2-(trimethylsilyl)ethoxy]methyl}-5H-pyrrolo[3,2-d]pyrimidine-7-carboxylic acid (example D.c5) and commercially available tert-butyl trans-(4-amino-cyclohexyl)-carbamate the title compound is obtained as colorless foam.

MS (ESI): m/z=680 (MH$^+$, 100%).

$^1$H-NMR (300 MHz, DMSO-d$_6$): 8.96 (s, 1H); 8.93 (d, J=7.9, 1H, —NH); 7.41 (d, J=8.4, 1H); 6.73 (dd, J=8.4, 2.2, 2H); 6.70 (d, J=2.2, 1H & br.s, 1H, —NH); 5.46 (d, J=11.1, 1H); 5.05 (d, J=11.1, 1H); 3.87 (dd, J=10.2, 6.4, 1H); 3.85 (s, 3H); 3.77 (dd, J=10.2, 7.0, 1H & m, 1H); 3.28 (m, 1H); 2.90 (s, 3H & m, 2H); 2.00 (m, 2H); 1.85 (m, 2H); 1.39 (s, 9H); 1.36 (m, 4H); 0.89 (m, 1H); 0.51 (m, 2H); 0.33 (m, 2H); 0.07 (m, 2H); −0.18 (s, 9H).

Example D.d20 tert-Butyl (cis-4-{[(4-[2-(cyclopropylmethoxy)-4-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-4-methoxyphenyl]-6-methyl-5-{[2-(trimethylsilyl)ethoxy]methyl}-5H-pyrrolo[3,2-d]pyrimidine-7-carboxylic acid (example D.c5) and commercially available tert-butyl cis-(4-amino-cyclohexyl)-carbamate the title compound is obtained as colorless foam.

MS (ESI): m/z=680 (MH$^+$, 100%).

$^1$H-NMR (300 MHz, DMSO-d$_6$): 9.29 (d, J=7.7, 1H, —NH); 9.01 (s, 1H); 7.41 (d, J=8.4, 1H); 6.92 (br.s, 1H, —NH); 6.73 (dd, J=8.4, 2.2, 2H); 6.70 (d, J=2.2, 1H); 5.46 (d, J=10.9, 1H); 5.06 (d, J=10.9, 1H); 4.07 (m, 1H); 3.88 (dd, J=10.2, 6.6, 1H); 3.85 (s, 3H); 3.78 (dd, J=10.2, 7.1, 1H); 3.43 (m, 1H); 2.91 (s, 3H & m, 2H); 1.86-1.53 (m, 8H); 1.40 (s, 9H); 0.90 (m, 1H); 0.51 (m, 2H); 0.34 (m, 2H); 0.08 (m, 2H); −0.18 (s, 9H).

Example D.d21 tert-Butyl (3R)-3-{[(4-[2-(cyclopropylmethoxy)-4-methoxyphenyl]-6-methyl-5-{[2-(trimethylsilyl)ethoxy]methyl}-5H-pyrrolo[3,2-d]pyrimidin-7-yl)carbonyl]amino}pyrrolidine-1-carboxylate Starting from 4-[2-(cyclopropylmethoxy)-4-methoxyphenyl]-6-methyl-5-{[2-(trimethylsilyl)ethoxy]methyl}-5H-pyrrolo[3,2-d]pyrimidine-7-carboxylic acid (example D.c5) and commercially available tert-butyl (R)-3-amino-pyrrolidine-1-carboxylate the title compound is obtained as colorless foam.

MS (ESI): m/z=652 (MH$^+$, 100%).

$^1$H-NMR (300 MHz, DMSO-d$_6$): 9.20 (d, J=6.8, 1H, —NH); 8.95 (s, 1H); 7.41 (d, J=8.4, 1H); 6.73 (dd, J=8.4, 2.2, 2H); 6.69 (d, J=2.2, 1H); 5.47 (d, J=11.1, 1H); 5.06 (d, J=11.1, 1H); 4.50 (m, 1H); 3.87 (dd, J=10.2, 6.6, 1H); 3.85 (s, 3H); 3.78 (dd, J=10.2, 7.1, 1H); 3.62 (m, 1H); 3.43 (m, 2H); 3.25 (m, 1H); 2.91 (s, 3H & m, 2H); 2.22 (m, 1H); 1.96 (m, 1H); 1.41 (s, 9H); 0.88 (m, 1H); 0.51 (m, 2H); 0.33 (m, 2H); 0.07 (m, 2H); −0.17 (s, 9H).

Example D.d22 tert-Butyl (3R,4R)-3-([({4-[2-(cyclopropylmethoxy)-4-methoxyphenyl]-6-methyl-5-{[2-(trimethylsilyl)ethoxy]methyl}-5H-pyrrolo[3,2-d]pyrimidin-7-yl)carbonyl]amino}-4-hydroxypyrrolidine-1-carboxylate Starting from 4-[2-(cyclopropylmethoxy)-4-methoxyphenyl]-6-methyl-5-{[2-(trimethylsilyl)ethoxy]methyl}-5H-pyrrolo[3,2-d]pyrimidine-7-carboxylic acid (example D.c5) and commercially available tert-butyl (3R*,4R*)-3-amino-4-hydroxy-pyrrolidine-1-carboxylate the title compound is obtained as colorless foam.

MS (ESI): m/z=668 (MH$^+$, 100%).

$^1$H-NMR (300 MHz, DMSO-d$_6$): 9.13 (br.s, 1H, —NH); 8.92 (s, 1H); 7.41 (d, J=8.4, 1H); 6.73 (dd, J=8.4, 2.2, 2H); 6.70 (d, J=2.2, 1H); 5.48 (d, J=6.2, 1H); 5.47 (d, J=11.0, 1H); 5.06 (d, J=11.0, 1H); 4.26 (m, 1H); 4.20 (m, 1H); 3.87 (dd, J=10.4, 6.6, 1H); 3.85 (s, 3H); 3.77 (dd, J=10.4, 7.3, 1H); 3.68 (m, 1H); 3.55 (m, 1H); 3.24 (m, 2H); 2.91 (s, 3H & m, 2H); 1.43 (s, 9H); 0.89 (m, 1H); 0.51 (m, 2H); 0.33 (m, 2H); 0.07 (m, 2H); −0.18 (s, 9H).

Example D.d23 tert-Butyl 4-{[(4-[2-(cyclopropylmethoxy)-5-methoxyphenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-5-methoxyphenyl]-6-methyl-5-{[2-(trimethylsilyl)ethoxy]methyl}-5H-pyrrolo[3,2-d]pyrimidine-7-carboxylic acid (example D.c6) and commercially available tert-butyl 4-amino-piperidine-1-carboxylate the title compound is obtained as colorless foam.

MS (ESI): m/z=666 (MH$^+$, 100%).

$^1$H-NMR (300 MHz, DMSO-d$_6$): 9.07 (d, J=7.7, 1H, —NH); 9.00 (s, 1H); 7.11 (d, J=1.6, 2H); 7.02 (t, J=1.6, 1H); 5.42 (d, J=10.9, 1H); 5.04 (d, J=10.9, 1H); 4.08 (m, 1H); 3.85 (m, 2H); 3.77 (dd, J=10.2, 6.6, 1H); 3.76 (s, 3H); 3.70 (dd, J=10.2, 6.9, 1H); 3.06 (m, 2H); 2.91 (s, 3H & m, 2H); 1.93 (m, 2H); 1.46 (m, 2H); 1.42 (s, 9H); 0.86 (m, 1H); 0.53 (m, 2H); 0.30 (m, 2H); 0.01 (m, 2H); −0.17 (s, 9H).

Example D.d24 tert-Butyl (trans-4-{[(4-[2-(cyclopropylmethoxy)-5-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-methoxyphenyl]-6-methyl-5-{[2-(trimethylsilyl)ethoxy]methyl}-5H- pyrrolo[3,2-d]pyrimidine-7-carboxylic acid (example D.c6) and commercially available tert-butyl trans-(4-amino-cyclohexyl)-carbamate the title compound is obtained as colorless solid.

MS (ESI): m/z=680 (MH$^+$, 100%).

$^1$H-NMR (300 MHz, DMSO-d$_6$): 9.00 (s, 1H); 8.91 (d, J=7.7, 1H, —NH); 7.11 (d, J=1.6, 2H); 7.02 (t, J=1.6, 1H); 6.72 (d, J=7.5, 1H, —NH); 5.41 (d, J=11.0, 1H); 5.03 (d, J=11.0, 1H); 3.77 (dd, J=10.2, 6.6, 1H); 3.76 (s, 3H & m, 1H); 3.70 (dd, J=10.2, 6.9, 1H); 3.29 (m, 1H); 2.90 (s, 3H & m, 2H); 2.01 (m, 2H); 1.86 (m, 2H); 1.39 (s, 9H); 1.34 (m, 4H); 0.85 (m, 1H); 0.53 (m, 2H); 0.24 (m, 2H); 0.01 (m, 2H); −0.17 (s, 9H).

Example D.d25 tert-Butyl (cis-4-{[(4-[2-(cyclopropylmethoxy)-5-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-methoxyphenyl]-6-methyl-5-{[2-(trimethylsilyl)ethoxy]methyl}-5H-pyrrolo[3,2-d]pyrimidine-7-carboxylic acid (example D.c6) and commercially available tert-butyl cis-(4-amino-cyclohexyl)-carbamate the title compound is obtained as colorless foam.

MS (ESI): m/z=680 (MH$^+$, 100%).

$^1$H-NMR (300 MHz, DMSO-d$_6$): 9.27 (d, J=7.7, 1H, —NH); 9.04 (s, 1H); 7.11 (d, J=1.6, 2H); 7.02 (t, J=1.6, 1H); 6.92 (~br.d, 1H, —NH); 5.41 (d, J=11.0, 1H); 5.03 (d, J=11.0, 1H); 4.07 (m, 2H); 3.78 (dd, J=10.2, 6.6, 1H); 3.76 (s, 3H); 3.71 (dd, J=10.2, 6.9, 1H); 3.43 (m, 1H); 2.91 (s, 3H & m, 2H); 1.85-1.52 (m, 8H); 1.40 (s, 9H); 0.86 (m, 1H); 0.54 (m, 2H); 0.31 (m, 2H); 0.02 (m, 2H); −0.17 (s, 9H).

Example D.d26 tert-butyl (3R)-3-{[(4-[2-(cyclopropylmethoxy)-5-methoxyphenyl]-6-methyl-5-{[2-(trimethylsilyl)ethoxy]methyl}-5H-pyrrolo[3,2-d]pyrimidin-7-yl)carbonyl]amino}pyrrolidine-1-carboxylate Starting from 4-[2-(cyclopropylmethoxy)-5-methoxyphenyl]-6-methyl-5-{[2-(trimethylsilyl)ethoxy]methyl}-5H-pyrrolo[3,2-d]pyrimidine-7-carboxylic acid (example D.c6) and commercially available tert-butyl (R)-3-amino-pyrrolidine-1-carboxylate the title compound is obtained as colorless foam.

MS (ESI): m/z=652 (MH$^+$, 100%).

$^1$H-NMR (300 MHz, DMSO-d$_6$): 9.18 (d, J=6.8, 1H, —NH); 8.98 (s, 1H); 7.11 (d, J=1.8, 2H); 7.02 (t, J=1.8, 1H); 5.43 (d, J=10.9, 1H); 5.03 (d, J=10.9, 1H); 4.50 (m, 1H); 3.76 (dd, J=10.4, 6.6, 1H & s, 3H); 3.70 (dd, J=10.4, 6.9, 1H); 3.62 (m, 1H); 3.43 (m, 2H); 3.26 (m, 1H); 2.91 (s, 3H & m, 2H); 2.21 (m, 1H); 1.96 (m, 1H); 1.41 (s, 9H); 0.85 (m, 1H); 0.53 (m, 2H); 0.29 (m, 2H); 0.01 (m, 2H); −0.17 (s, 9H).

Example D.d27 tert-Butyl (3R,4R)-4-[({4-[2-(cyclopropylmethoxy)-5-methoxyphenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate Starting from 4-[2-(cyclopropylmethoxy)-5-methoxyphenyl]-6-methyl-5-{[2-(trimethylsilyl)ethoxy]methyl}-5H-pyrrolo[3,2-d]pyrimidine-7-carboxylic acid (example D.c6) and: tert-butyl (3R*,4R*)-4-amino-3-hydroxy-piperidine-1-carboxylate (Example C2) the title compound is obtained as pale yellow foam.

MS (ESI): m/z=682 (MH$^+$, 100%).

$^1$H-NMR (300 MHz, DMSO-d$_6$): 9.11 (d, J=7.3, 1H, —NH); 8.99 (s, 1H); 7.11 (d, J=1.6, 2H); 7.02 (t, J=1.6, 1H); 5.43 (d, J=10.9, 1H); 5.24 (t, J=4.9, 1H, —OH); 5.04 (d, J=10.9, 1H); 3.99-3.66 (m, 5H); 3.76 (s, 3H); 3.45 (m, 1H); 2.91 (s, 3H & m, 1H); 2.79 (m, 1H); 2.07 (m, 1H); 1.42 (s, 9H & m, 1H); 0.86 (m, 1H); 0.53 (m, 2H); 0.30 (m, 2H); 0.02 (m, 2H); −0.17 (s, 9H).

Example D.d28

Tert-butyl 4-{[(4-[2-(cyclopropylmethoxy)-5-methylphenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-5-methylphenyl]-6-methyl-5-{[2-(trimethylsilyl)ethoxy]methyl}-5H-pyrrolo[3,2-d]pyrimidine-7-carboxylic acid (example D.c7) and commercially available tert-butyl 4-amino-piperidine-1-carboxylate the title compound is obtained as pale yellow viscous oil.

MS (ESI): m/z=650 (MH$^+$, 100%).

$^1$H-NMR (300 MHz, DMSO-d$_6$): 9.08 (d, J=7.7, 1H, —NH); 8.98 (s, 1H); 7.34 (dd, J=8.4, 2.0, 1H); 7.26 (d, J=2.0, 1H); 7.07 (d, J=8.4, 1H); 5.43 (d, J=11.0, 1H); 5.02 (d, J=11.0, 1H); 4.08 (m, 1H); 3.87 (m, 2H); 3.82 (dd, J=10.4, 6.6, 1H); 3.75 (dd, J=10.4, 7.0, 1H); 3.06 (m, 2H); 2.93-2.86 (m, 2H); 2.90 (s, 3H); 2.32 (s, 3H); 1.93 (m, 2H); 1.46 (m, 2H); 1.43 (s, 9H); 0.88 (m, 1H); 0.52 (m, 2H); 0.31 (m, 2H); 0.05 (m, 2H); −0.17 (s, 9H).

Example D.d29 tert-Butyl (trans-4-{[(4-[2-(cyclopropylmethoxy)-5-methylphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-methylphenyl]-6-methyl-5-{[2-(trimethylsilyl)ethoxy]methyl}-5H-pyrrolo[3,2-d]pyrimidine-7-carboxylic acid (example D.c7) and commercially available tert-butyl trans-(4-amino-cyclohexyl)-carbamate the title compound is obtained as colorless solid.

MS (ESI): m/z=664 (MH$^+$, 100%).

$^1$H-NMR (300 MHz, DMSO-d$_6$): $^1$H-NMR (400 MHz, DMSO-d$_6$): 8.98 (s, 1H); 8.92 (d, J=7.7, 1H, —NH); 7.34 (dd, J=8.4, 2.0, 1H); 7.27 (d, J=2.0, 1H); 7.07 (d, J=8.4, 1H); 6.72 (d, J=6.6, 1H, —NH); 5.42 (d, J=11.0, 1H); 5.02 (d, J=11.0, 1H); 3.81 (dd, J=10.3, 6.5, 1H); 3.78 (m, 1H); 3.74 (dd, J=10.2, 7.0, 1H); 3.28 (m, 1H); 2.90 (s, 3H); 2.88 (m, 2H); 2.32 (s, 3H); 2.00 (m, 2H); 1.86 (m, 2H); 1.39 (s, 9H); 1.36 (m, 4H); 0.88 (m, 1H); 0.51 (m, 2H); 0.31 (m, 2H); 0.04 (m, 2H); −0.18 (s, 9H).

Example D.d30

Tert-butyl (cis-4-{[(4-[2-(cyclopropylmethoxy)-5-methylphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-methylphenyl]-6-methyl-5-{[2-(trimethylsilyl)ethoxy]methyl}-5H- pyrrolo[3,2-d]pyrimidine-7-carboxylic acid (example D.c7) and commercially available tert-butyl cis-(4-amino-cyclohexyl)-carbamate the title compound is obtained as colorless foam.

MS (ESI): m/z=664 (MH+, 100%).
$^1$H-NMR (300 MHz, DMSO-d$_6$): 9.31 (d, J=7.7, 1H, —NH); 9.03 (s, 1H); 7.34 (dd, J=8.4, 2.0, 1H); 7.27 (d, J=2.0, 1H); 7.07 (d, J=8.4, 1H); 6.89 (br.s, 1H, —NH); 5.42 (d, J=11.0, 1H); 5.04 (d, J=11.0, 1H); 4.09 (m, 1H); 3.83 (dd, J=10.2, 6.6, 1H); 3.75 (dd, J=10.2, 6.9, 1H); 3.44 (m, 1H); 2.91 (s, 3H); 2.90 (m, 2H); 2.33 (s, 3H); 1.86-1.55 (m, 8H); 1.41 (s, 9H); 0.90 (m, 1H); 0.53 (m, 2H); 0.33 (m, 2H); 0.06 (m, 2H); −0.17 (s, 9H).

Example D.d31 tert-Butyl 4-{[(4-[2-(cyclopropylmethoxy)-5-(trifluoromethyl)phenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-5-(trifluoromethyl)phenyl]-6-methyl-5-{[2-(trimethylsilyl)ethoxy]methyl}-5H-pyrrolo[3,2-d]pyrimidine-7-carboxylic acid (example D.c8) and commercially available tert-butyl 4-amino-piperidine-1-carboxylate the title compound is obtained as colorless foam.

MS (ESI): m/z=704 (MH+, 100%).
$^1$H-NMR (400 MHz, DMSO-d$_6$): 9.05 (d, J=7.6, 1H, —NH); 9.03 (s, 1H); 7.91 (dd, J=8.8, 2.1, 1H); 7.77 (d, J=2.1, 1H); 7.39 (d, J=8.8, 1H); 5.40 (d, J=11.0, 1H); 4.95 (d, J=11.0, 1H); 4.08 (m, 1H); 3.98 (dd, J=10.4, 6.6, 1H); 3.91 (dd, J=10.4, 7.1, 1H); 3.85 (m, 2H); 3.06 (m, 2H); 2.92 (s, 3H & t, J=8.2, 2H); 1.94 (m, 2H); 1.47 (m, 2H); 1.42 (s, 9H); 0.95 (m, 1H); 0.50 (m, 2H); 0.35 (m, 2H); 0.11 (m, 2H); −0.19 (s, 9H).

Example D.d32 tert-Butyl (trans-4-{[(4-[2-(cyclopropylmethoxy)-5-(trifluoromethyl)phenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-(trifluoromethyl)phenyl]-6-methyl-5-{[2-(trimethylsilyl)ethoxy]methyl}-5H-pyrrolo[3,2-d]pyrimidine-7-carboxylic acid (example D.c8) and commercially available tert-butyl trans-(4-amino-cyclohexyl)-carbamate the title compound is obtained as colorless foam.

MS (ESI): m/z=718 (MH+, 100%).
$^1$H-NMR (400 MHz, DMSO-d$_6$): 9.03 (s, 1H); 8.89 (d, J=7.7, 1H, —NH); 7.90 (dd, J=8.8, 2.1, 1H); 7.77 (d, J=2.1, 1H); 7.39 (d, J=8.8, 1H); 6.72 (d, J=7.9, 1H, —NH); 5.40 (d, J=11.0, 1H); 4.94 (d, J=11.0, 1H); 3.98 (dd, J=10.5, 6.6, 1H); 3.91 (dd, J=10.5, 7.1, 1H); 3.78 (m, 1H); 3.29 (m, 1H); 2.91 (s, 3H & t, J=8.0, 2H); 2.01 (m, 2H); 1.85 (m, 2H); 1.39 (s, 9H); 1.35 (m, 4H); 0.94 (m, 1H); 0.50 (m, 2H); 0.35 (m, 2H); 0.11 (m, 2H); −0.19 (s, 9H).

Example D.d33 tert-Butyl (cis-4-{[(4-[2-(cyclopropylmethoxy)-5-(trifluoromethyl)phenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-(trifluoromethyl)phenyl]-6-methyl-5-{[2-(trimethylsilyl)ethoxy]methyl}-5H-pyrrolo[3,2-d]pyrimidine-7-carboxylic acid (example D.c8) and commercially available tert-butyl cis-(4-amino-cyclohexyl)-carbamate the title compound is obtained as colorless foam.

MS (ESI): m/z=718 (MH+, 100%).
$^1$H-NMR (400 MHz, DMSO-d$_6$): 9.26 (d, J=7.7, 1H, —NH); 9.07 (s, 1H); 7.91 (dd, J=8.8, 2.1, 1H); 7.78 (d, J=2.1, 1H); 7.40 (d, J=8.8, 1H); 6.93 (br.s, 1H, —NH); 5.40 (d, J=10.9, 1H); 4.94 (d, J=10.9, 1H); 4.08 (m, 1H); 3.99 (dd, J=10.2, 6.7, 1H); 3.92 (dd, J=10.2, 7.1, 1H); 3.43 (m, 1H); 2.92 (s, 3H & t, J=8.1, 2H); 1.86-1.51 (m, 8H); 1.40 (s, 9H); 0.95 (m, 1H); 0.50 (m, 2H); 0.36 (m, 2H); 0.12 (m, 2H); −0.19 (s, 9H).

Example D.d34 tert-Butyl 4-{[(4-[2-ethoxy-5-(trifluoromethyl)phenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-ethoxy-5-(trifluoromethyl)phenyl]-6-methyl-5-{[2-(trimethylsilyl)ethoxy]methyl}-5H-pyrrolo[3,2-d]pyrimidine-7-carboxylic acid (example D.c9) and commercially available tert-butyl 4-amino-piperidine-1-carboxylate the title compound is obtained as pale yellow foam.

MS (ESI): m/z=678 (MH+, 100%).
$^1$H-NMR (300 MHz, DMSO-d$_6$): 9.08 (d, J=7.7, 1H, —NH); 9.05 (s, 1H); 7.96 (dd, J=8.8, 2.2, 1H); 7.80 (d, J=2.2, 1H); 7.74 (d, J=8.8, 1H); 5.41 (d, J=11.0, 1H); 4.97 (d, J=11.0, 1H); 4.22-4.04 (m, 2H & m, 1H); 3.88 (m, 2H); 3.09 (m, 2H); 2.95 (s, 3H & m, 2H); 1.97 (m, 2H); 1.50 (m, 2H); 1.46 (s, 9H); 1.11 (t, J=7.0, 3H); 0.55 (m, 2H); −0.15 (s, 9H).

Example D.d35 tert-Butyl 4-{[(4-[2-cyclopropylmethoxy-4-fluoro-5-methoxyphenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidine-7-carboxylic acid (example D.c10) and commercially available tert-butyl 4-amino-piperidine-1-carboxylate the title compound is obtained as colorless foam.

MS (ESI): m/z=684 (MH+, 100%); 628 (MH+-C$_4$H$_8$)
$^1$H-NMR (300 MHz, DMSO-d$_6$): 9.06 (d, J=7.5, 1H, —NH); 9.00 (s, 1H); 7.27 (d, J=9.7, 1H); 7.19 (d, J=13.1, 1H); 5.42 (d, J=10.9, 1H); 5.03 (d, J=10.9, 1H); 4.08 (m, 1H); 3.87 (m, 2H); 3.82 (s, 3H); 3.80 (dd, J=10.3, 6.7, 1H); 3.75 (dd, J=10.3, 7.1, 1H); 3.06 (m, 2H); 3.03-2.88 (m, 2H); 2.91 (s, 3H); 1.93 (m, 2H); 1.46 (m, 2H); 1.42 (s, 9H); 0.87 (m, 1H); 0.55 (m, 2H); 0.31 (m, 2H); 0.04 (m, 2H); −0.16 (s, 9H).

Example D.d36 tert-Butyl (trans-4-{[(4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidine-7-carboxylic acid (example D.c10) and commercially available tert-butyl trans-(4-amino-cyclohexyl)-carbamate the title compound is obtained as colorless foam.

MS (ESI): m/z=698 (MH⁺, 100%).

$^1$H-NMR (300 MHz, DMSO-$d_6$): 9.00 (s, 1H); 8.90 (d, J=7.7, 1H); 7.27 (d, J=9.7, 1H); 7.19 (d, J=13.3, 1H); 6.72 (d, J=7.5, 1H, —NH); 5.41 (d, J=10.9, 1H); 5.03 (d, J=10.9, 1H); 3.82 (s, 3H & m, 1H); 3.80 (dd, J=10.4, 6.7, 1H); 3.72 (dd, J=10.4, 7.0, 1H); 3.29 (m, 1H); 3.03-2.88 (m, 2H); 2.91 (s, 3H); 2.00 (m, 2H); 1.85 (m, 2H); 1.39 (s, 9H); 1.36 (m, 4H); 0.86 (m, 1H); 0.55 (m, 2H); 0.31 (m, 2H); 0.03 (m, 2H); −0.16 (s, 9H).

Example D.d37 tert-Butyl (cis-4-{[(4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidine-7-carboxylic acid (example D.c10) and commercially available tert-butyl cis-(4-amino-cyclohexyl)-carbamate the title compound is obtained as colorless foam.

MS (ESI): m/z=698 (MH⁺, 100%); 642 (MH⁺-$C_4H_8$).

$^1$H-NMR (300 MHz, DMSO-$d_6$): 9.26 (d, J=7.8, 1H, —NH); 9.04 (s, 1H); 7.27 (d, J=9.5, 1H); 7.19 (d, J=13.3, 1H); 6.91 (br.s, 1H, —NH); 5.42 (d, J=10.9, 1H); 5.02 (d, J=10.9, 1H); 4.07 (m, 1H); 3.82 (s, 3H); 3.81 (dd, J=10.2, 6.7, 1H); 3.73 (dd, J=10.2, 7.0, 1H); 3.43 (m, 1H); 3.04-2.89 (m, 2H); 2.92 (s, 3H); 1.87-1.51 (m, 8H); 1.40 (s, 9H); 0.88 (m, 1H); 0.55 (m, 2H); 0.32 (m, 2H); 0.04 (m, 2H); −0.16 (s, 9H).

Example D.d38 tert-Butyl (3R*,4R*)-4-{[(4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate Starting from 4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidine-7-carboxylic acid (example D.c10) and tert-butyl (3R*,4R*)-4-amino-3-hydroxypiperidine-1-carboxylate (example C2) the title compound is obtained as pale yellow viscous oil.

MS (ESI): m/z=700 (MH⁺, 100%); 644 (MH⁺-$C_4H_8$)

$^1$H-NMR (300 MHz, DMSO-$d_6$): 9.12 (d, J=7.3, 1H, —NH); 9.01 (s, 1H); 7.28 (dd, J=9.7, 1.4, 1H); 7.20 (d, J=12.6, 1H); 5.44 (d, J=10.9, 1H); 5.27 (dd, J=4.9, 4.2, 1H, —OH); 5.02 (d, J=10.9, 1H); 3.99-3.68 (m, 5H); 3.82 (s, 3H); 3.44 (m, 1H); 3.03-2.86 (m, 3H); 2.92 (s, 3H); 2.79 (m, 1H); 2.07 (m, 1H); 1.42 (s, 9H & m, 1H); 0.87 (m, 1H); 0.55 (m, 2H); 0.32 (m, 2H); 0.05 (m, 2H); −0.16 (s, 9H).

Example D.d39 tert-Butyl (3S*,4S*)-3-{[(4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidin-7-yl)carbonyl]amino}-4-hydroxypiperidine-1-carboxylate Starting from 4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidine-7-carboxylic acid (example D.c10) and tert-butyl (3S*,4S*)-3-amino-4-hydroxypiperidine-1-carboxylate (Example C3) the title compound is obtained as pale yellow viscous oil.

MS (ESI): m/z=700 (MH⁺, 100%); 644 (MH⁺-$C_4H_8$)—

Example D.d40 tert-Butyl 4-{[(4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidine-7-carboxylic acid (example D.c11) and commercially available tert-butyl 4-amino-piperidine-1-carboxylate the title compound is obtained as pale yellow foam.

MS (ESI): m/z=668 (MH⁺, 100%).

$^1$H-NMR (300 MHz, DMSO-$d_6$): 9.07 (d, J=7.7, 1H, —NH); 8.98 (s, 1H); 7.38 (d, J=9.3, 1H); 7.06 (d, J=12.1, 1H); 5.43 (d, J=11.0, 1H); 5.01 (d, J=11.0, 1H); 4.08 (m, 1H); 3.86 (m, 2H & dd, J=10.8, 6.6, 1H); 3.77 (dd, J=10.8, 7.1, 1H); 3.06 (m, 2H); 2.94 (m, 2H); 2.91 (s, 3H); 2.24 (d, J=1.3, 3H); 1.93 (m, 2H); 1.45 (m, 2H); 1.42 (s, 9H); 0.90 (m, 1H); 0.53 (m, 2H); 0.33 (m, 2H); 0.07 (m, 2H); −0.17 (s, 9H).

Example D.d41 tert-Butyl (trans-4-{[(4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidine-7-carboxylic acid (example D.c11) and commercially available tert-butyl trans-(4-amino-cyclohexyl)-carbamate the title compound is obtained as pale yellow foam.

MS (ESI): m/z=682 (MH⁺, 100%).

$^1$H-NMR (300 MHz, DMSO-$d_6$): 8.98 (s, 1H); 8.91 (d, J=7.9, 1H, —NH); 7.38 (d, J=8.8, 1H); 7.05 (d, J=11.9, 1H); 6.72 (br.d, J=7.9, 1H, —NH); 5.42 (d, J=10.9, 1H); 5.00 (d, J=10.9, 1H); 3.86 (m, J=10.2, 6.6, 1H); 3.76 (m, 1H & dd, J=10.2, 7.1, 1H); 3.29 (m, 1H); 2.94 (m, 2H); 2.92 (m, 2H); 2.90 (s, 3H); 2.23 (d, J=1.1, 3H); 2.00 (m, 2H); 1.85 (m, 2H); 1.39 (s, 9H); 1.34 (m, 4H); 0.89 (m, 1H); 0.53 (m, 2H); 0.32 (m, 2H); 0.06 (m, 2H); −0.17 (s, 9H).

Example D.d42 tert-Butyl (cis-4-{[(4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidine-7-carboxylic acid (example D.c11) and commercially available tert-butyl cis-(4-amino-cyclohexyl)-carbamate the title compound is obtained as pale yellow foam.

MS (ESI): m/z=682 (MH⁺, 100%).

$^1$H-NMR (300 MHz, DMSO-$d_6$): 9.28 (d, J=7.7, 1H, —NH); 9.03 (s, 1H); 7.39 (d, J=8.9, 1H); 7.06 (d, J=11.9, 1H);

6.91 (br.s, 1H, —NH); 5.43 (d, J=11.1, 1H); 5.01 (d, J=11.1, 1H); 4.07 (m, 1H); 3.87 (dd, J=10.4, 6.6, 1H); 3.77 (dd, J=10.4, 7.1, 1H); 3.43 (m, 1H); 2.94 (m, 2H); 2.91 (s, 3H); 2.24 (d, J=1.3, 3H); 1.86-1.51 (m, 8H); 1.40 (s, 9H); 0.90 (m, 1H); 0.53 (m, 2H); 0.34 (m, 2H); 0.07 (m, 2H); −0.16 (s, 9H).

Example D.d43 tert-Butyl (3R,4R)-4-{[(4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate Starting from 4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidine-7-carboxylic acid (example D.c11) and tert-butyl (3R*,4R*)-4-amino-3-hydroxypiperidine-1-carboxylate (example C2) the title compound is obtained as pale yellow foam.
MS (ESI): m/z=684 (MH$^+$, 100%).
$^1$H-NMR (300 MHz, DMSO-d$_6$): 9.11 (d, J=7.3, 1H, —NH); 8.98 (s, 1H); 7.39 (d, J=8.9, 1H); 7.06 (d, J=11.9, 1H); 5.44 (d, J=11.0, 1H); 5.24 (dd, J=4.9, 3.7, 1H, —OH); 5.02 (d, J=11.0 1H); 4.00-3.37 (m, 3H); 3.86 (ddd, J=10.4, 7.9, 1.1, 1H); 3.77 (ddd, J=10.4, 7.1, 2.7, 1H); 3.45 (m, 1H); 2.98 (m, 1H); 2.93 (m, 2H); 2.92 (s, 3H); 2.79 (m, 1H); 2.24 (s, 3H); 2.07 (m, 1H); 1.42 (s, 9H); 1.38 (m, 1H); 0.90 (m, 1H); 0.54 (m, 2H); 0.34 (m, 2H); 0.07 (m, 2H); −0.16 (s, 9H).

Example D.d44 tert-Butyl 4-{[(4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidine-7-carboxylic acid (example D.c12) and commercially available tert-butyl 4-amino-piperidine-1-carboxylate the title compound is obtained as pale yellow foam.
MS (ESI): m/z=684 (MH$^+$, 100%); 628 (MH$^+$-C$_4$H$_8$).
$^1$H-NMR (300 MHz, DMSO-d$_6$): 9.07 (d, J=7.7, 1H, —NH); 8.98 (s, 1H); 7.32 (d, J=11.3, 1H); 6.94 (d, J=7.3, 1H); 5.47 (d, J=11.1, 1H); 5.07 (d, J=11.1, 1H); 4.07 (m, 1H); 3.96 (s, 3H); 3.92-3.79 (m, 4H); 3.06 (m, 2H); 2.95 (m, 2H); 2.92 (s, 3H); 1.93 (m, 2H); 1.45 (m, 2H); 1.41 (s, 9H); 0.88 (m, 1H); 0.54 (m, 2H); 0.33 (m, 2H); 0.06 (m, 2H); −0.17 (s, 9H).

Example D.d45 tert-butyl (trans-4-{[(4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidine-7-carboxylic acid (example D.c12) and commercially available tert-butyl trans-(4-amino-cyclohexyl)-carbamate the title compound is obtained as pale yellow foam.

MS (ESI): m/z=698 (MH$^+$, 100%); 642 (MH$^+$-C$_4$H$_8$).
$^1$H-NMR (300 MHz, DMSO-d$_6$): 8.98 (s, 1H); 8.91 (d, J=7.7, 1H, —NH); 7.32 (d, J=11.3, 1H); 6.94 (d, J=7.3, 1H); 6.72 (d, J=7.5, 1H, —NH); 5.47 (d, J=10.9 1H); 5.06 (d, J=10.9, 1H); 3.96 (s, 3H); 3.89 (dd, J=10.2, 6.6, 1H); 3.81 (dd, J=10.2, 7.1, 1H); 3.77 (m, 2H); 2.94 (m, 2H); 2.91 (s, 3H); 2.00 (m, 2H); 1.85 (m, 2H); 1.39 (s, 9H); 1.36 (m, 4H); 0.88 (m, 1H); 0.54 (m, 2H); 0.32 (m, 2H); 0.05 (m, 2H); −0.18 (s, 9H).

Example D.d46 tert-Butyl (cis-4-{[(4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidine-7-carboxylic acid (example D.c12) and commercially available tert-butyl cis-(4-amino-cyclohexyl)-carbamate the title compound is obtained as colorless foam.
MS (ESI): m/z=698 (MH$^+$, 100%); 642 (MH$^+$-C$_4$H$_8$).
$^1$H-NMR (300 MHz, DMSO-d$_6$): 9.27 (s, 1H, —NH); 9.02 (s, 1H); 7.32 (d, J=11.3, 1H); 6.91 (d, J=7.3, 1H); 6.91 (br.s, 1H, —NH); 5.47 (d, J=11.1 1H); 5.07 (d, J=11.1, 1H); 4.07 (m, 1H); 3.96 (s, 3H); 3.90 (dd, J=10.3, 6.6, 1H); 3.82 (dd, J=10.3, 6.9, 1H); 3.43 (m, 1H); 3.05 (m, 2H); 2.92 (s, 3H); 1.77 (m, 2H); 1.64 (m, 6H); 1.40 (s, 9H); 0.89 (m, 1H); 0.54 (m, 2H); 0.33 (m, 2H); 0.07 (m, 2H); −0.17 (s, 9H).

Example D.d47 tert-Butyl (3R*,4R*)-4-{[(4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate Starting from 4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidine-7-carboxylic acid (example D.c12) and tert-butyl (3R*,4R*)-4-amino-3-hydroxypiperidine-1-carboxylate (Example C2) the title compound is obtained as pale yellow foam.
MS (ESI): m/z=700 (MH$^+$, 100%).
$^1$H-NMR (300 MHz, DMSO-d$_6$): 9.12 (d, J=7.7, 1H, —NH); [8.98 (s), 8.96 (s), 1H)]; 7.34 (d, J=11.5, 1H); 6.94 (d, J=7.3, 1H); [5.50 (d, J=11.0), 5.49 (d, J=11.0), 1H)]; 5.27 (t, J=4.9, 1H, —OH); 5.07 (d, J=11.0, 1H); 3.96 (s, 3H); 3.95-3.75 (m, 5H); 3.44 (m, 1H); 2.93 (s, 3H & m, 3H); 2.79 (m, 1H); 2.07 (m, 1H); 1.42 (s, 9H & m, 1H); 0.88 (m, 1H); 0.54 (m, 2H); 0.33 (m, 2H); 0.06 (m, 2H); −0.17 (s, 9H).

Example D.d48 tert-Butyl 4-{[(4-[2-(cyclopropylmethoxy)-5-ethylphenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-5-ethylphenyl]-6-methyl-5-{[2-(trimethylsilyl)ethoxy]methyl}-5H-pyrrolo[3,2-d]pyrimidine-7-carboxylic acid (example D.c14) and commercially available tert-butyl 4-amino-piperidine-1-carboxylate the title compound is obtained as pale yellow viscous oil.

MS (ESI): m/z=664 (MH+, 100%).

¹H-NMR (300 MHz, DMSO-d₆): 9.08 (d, J=7.5, 1H, —NH); 8.99 (s, 1H); 7.37 (dd, J=8.6, 2.2, 1H); 7.29 (d, J=2.2, 1H); 7.08 (d, J=8.6, 1H); 5.42 (d, J=11.1, 1H); 5.03 (d, J=11.1, 1H); 4.08 (m, 1H); 3.87 (m, 2H); 3.82 (dd, J=10.2, 6.6, 1H); 3.75 (dd, J=10.2, 6.9. 1H); 3.06 (m, 2H); 2.94-2.82 (m, 2H); 2.91 (s, 3H); 2.63 (qu, J=7.6, 2H); 1.94 (m, 2H); 1.46 (m, 2H); 1.40 (s, 9H); 1.20 (t, J=7.6, 3H); 0.89 (m, 1H); 0.51 (m, 2H); 0.32 (m, 2H); 0.05 (m, 2H); −0.19 (s, 9H).

Example D.d49 tert-Butyl (trans-4-{[(4-[2-(cyclopropylmethoxy)-5-ethylphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-ethylphenyl]-6-methyl-5-{[2-(trimethylsilyl)ethoxy]methyl}-5H-pyrrolo[3,2-d]pyrimidine-7-carboxylic acid (example D.c14) and commercially available tert-butyl trans-(4-amino-cyclohexyl)-carbamate the title compound is obtained as pale yellow foam.

MS (ESI): m/z=678 (MH+, 100%).

¹H-NMR (300 MHz, DMSO-d₆): 8.99 (s, 1H); 8.92 (d, J=7.3, 1H, —NH); 7.37 (dd, J=8.6, 2.2, 1H); 7.29 (d, J=2.2, 1H); 7.08 (d, J=8.6, 1H); 6.72 (d, J=8.1, 1H, —NH); 5.42 (d, J=10.9, 1H); 5.02 (d, J=10.9, 1H); 3.82 (dd, J=10.2, 6.6, 1H); 3.74 (dd, J=10.2, 6.9. 1H & m, 1H); 3.27 (m, 1H); 2.90 (s, 3H); 2.88 (t, J=8.2, 2H); 2.63 (qu, J=7.5, 2H); 2.00 (m, 2H); 1.85 (m, 2H); 1.40 (s, 9H); 1.37 (m, 4H); 1.20 (t, J=7.6, 3H); 0.88 (m, 1H); 0.50 (m, 2H); 0.31 (m, 2H); 0.04 (m, 2H); −0.19 (s, 9H).

Example D.d50 tert-butyl (cis-4-{[(4-[2-(cyclopropylmethoxy)-5-ethylphenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-ethylphenyl]-6-methyl-5-{[2-(trimethylsilyl)ethoxy]methyl}-5H-pyrrolo[3,2-d]pyrimidine-7-carboxylic acid (example D.c14) and commercially available tert-butyl cis-(4-amino-cyclohexyl)-carbamate the title compound is obtained as pale yellow foam.

MS (ESI): m/z=678 (MH+, 100%).

¹H-NMR (300 MHz, DMSO-d₆): ¹H 9.28 (d, J=7.9, 1H, —NH); 9.03 (s, 1H); 7.35 (dd, J=8.6, 2.2, 1H); 7.30 (d, J=2.2, 1H); 7.09 (d, J=8.6, 1H); 6.92 (br.d, J~7.2, 1H, —NH); 5.42 (d, J=11.1, 1H); 5.03 (d, J=11.1, 1H); 4.07 (m, 1H); 3.83 (dd, J=10.2, 6.4, 1H); 3.75 (dd, J=10.2, 6.9. 1H & m, 1H); 3.43 (m, 1H); 2.91 (s, 3H); 2.89 (m, 2H); 2.64 (qu, J=7.5, 2H); 1.86-1.51 (m, 8H); 1.40 (s, 9H); 1.20 (t, J=7.5, 3H); 0.90 (m, 1H); 0.51 (m, 2H); 0.33 (m, 2H); 0.06 (m, 2H); −0.18 (s, 9H).

Example D.d51 tert-Butyl (3R*,4R*)-3-{[(4-[2-(cyclopropylmethoxy)-5-ethylphenyl]-6-methyl-5-{[2-(trimethylsilyl)ethoxy]methyl}-5H-pyrrolo[3,2-d]pyrimidin-7-yl)carbonyl]amino}-4-hydroxypyrrolidine-1-carboxylate Starting from 4-[2-(cyclopropylmethoxy)-5-ethylphenyl]-6-methyl-5-{[2-(trimethylsilyl)ethoxy]methyl}-5H-pyrrolo[3,2-d]pyrimidine-7-carboxylic acid (example D.c14) and commercially available tert-butyl (3R*,4R*)-3-amino-4-hydroxy-pyrrolidine-1-carboxylate the title compound is obtained as pale yellow viscous oil.

MS (ESI): m/z=666 (MH+, 100%).

¹H-NMR (300 MHz, DMSO-d₆): 9.13 (br.s, 1H, —NH); 8.95 (s, 1H); 7.37 (dd, J=8.6, 2.4, 1H); 7.29 (d, J=2.4, 1H); 7.09 (d, J=8.6, 1H); 5.48 (d, J=3.8, 1H, —OH); 5.43 (d, J=10.9, 1H); 5.03 (d, J=10.9, 1H); 4.27 (m, 1H); 4.21 (m, 1H); 3.83 (d, J=10.2, 6.6, 1H); 3.74 (dd, J=10.2, 7.1, 0.9, 1H); 3.69 (m, 1H); 3.56 (m, 1H); 3.24 (m, 2H); 2.91 (s, 3H); 2.88 (m, 2H); 2.63 (qu, J=7.5, 2H); 1.40 (s, 9H); 1.20 (t, J=7.5, 3H); 0.87 (m, 1H); 0.50 (m, 2H); 0.32 (m, 2H); 0.05 (m, 2H); −0.18 (s, 9H).

Example D.d52 tert-Butyl 4-{[(4-[2-(cyclopropylmethoxy)-5-(propan-2-yl)phenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-5-(propan-2-yl)phenyl]-6-methyl-5-{[2-(trimethylsilyl)ethoxy]methyl}-5H-pyrrolo[3,2-d]pyrimidine-7-carboxylic acid (example D.c15) and commercially available tert-butyl 4-amino-piperidine-1-carboxylate the title compound is obtained as pale yellow viscous oil.

MS (ESI): m/z=678 (MH+, 100%).

¹H-NMR (300 MHz, DMSO-d₆): 9.08 (d, J=7.7, 1H, —NH); 8.99 (s, 1H); 7.40 (dd, J=8.6, 2.2, 1H); 7.32 (d, J=2.2, 1H); 7.09 (d; J=8.6, 1H); 5.42 (d, J=10.9, 1H); 5.04 (d, J=10.9, 1H); 4.08 (m, 1H); 3.90-3.79 (m, 3H); 3.75 (dd, J=10.2, 6.9, 1H); 3.06 (m, 2H); 2.98-2.82 (m, 3H); 2.91 (s, 3H); 1.93 (m, 2H); 1.47 (m, 2H); 1.40 (s, 9H); 1.22 (dd, J=6.9, 2.2, 6H); 0.89 (m, 1H); 0.50 (m, 2H); 0.32 (m, 2H); 0.05 (m, 2H); −0.19 (s, 9H).

Example D.d53 tert-Butyl (trans-4-{[(4-[2-(cyclopropylmethoxy)-5-(propan-2-yl)phenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-(propan-2-yl)phenyl]-6-methyl-5-{[2-(trimethylsilyl)ethoxy]methyl}-5H-pyrrolo[3,2-d]pyrimidine-7-carboxylic acid (example D.c15) and commercially available tert-butyl trans-(4-amino-cyclohexyl)-carbamate the title compound is obtained as pale yellow viscous oil.

MS (ESI): m/z=692 (MH+, 100%).

¹H-NMR (300 MHz, DMSO-d₆): 8.99 (s, 1H); 8.92 (d, J=7.7, 1H, —NH); 7.40 (dd, J=8.6, 2.4, 1H); 7.32 (d, J=2.4, 1H); 7.09 (d; J=8.6, 1H); 6.72 (br.d, J~8.6, 1H, —NH); 5.41 (d, J=11.0, 1H); 5.03 (d, J=11.0, 1H); 3.82 (dd, J=10.2, 6.6, 1H); 3.74 (dd, J=10.2, 6.9, 1H &m, 2H); 3.27 (m, 1H); 2.99-2.80 (sept, J=6.9, 1H & m, 2H); 2.90 (s, 3H); 2.01 (m, 2H); 1.86 (m, 2H); 1.39 (s, 9H); 1.37 (m, 4H); 1.22 (dd, J=6.9, 2.4, 6H); 0.89 (m, 1H); 0.49 (m, 2H); 0.32 (m, 2H); 0.05 (m, 2H); −0.19 (s, 9H).

Example D.d54 tert-Butyl (cis-4-{[(4-[2-(cyclopropylmethoxy)-5-(propan-2-yl)phenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-(propan-2-yl)phenyl]-6-methyl-5-{[2-(trimethylsilyl)ethoxy]methyl}-

5H-pyrrolo[3,2-d]pyrimidine-7-carboxylic acid (example D.c15) and commercially available tert-butyl cis-(4-amino-cyclohexyl)-carbamate the title compound is obtained as pale yellow viscous oil.

MS (ESI): m/z=692 (MH+, 100%).

$^1$H-NMR (300 MHz, DMSO-$d_6$): 9.28 (d, J=7.9, 1H, —NH); 9.03 (s, 1H); 7.41 (dd, J=8.6, 2.4, 1H); 7.33 (d, J=2.4, 1H); 7.09 (d; J=8.6, 1H); 6.92 (br.d, J~6.9, 1H, —NH); 5.41 (d, J=11.0, 1H); 5.04 (d, J=11.0, 1H); 4.07 (m, 1H); 3.83 (dd, J=10.4, 6.6, 1H); 3.75 (dd, J=10.4, 6.9, 1H); 3.43 (m, 1H); 2.91 (s, 3H & m, 2H & sept, J=6.9, 1H); 1.85-1.53 (m, 8H); 1.40 (s, 9H); 1.24 (dd, J=6.9, 2.4, 6H); 0.90 (m, 1H); 0.51 (m, 2H); 0.33 (m, 2H); 0.06 (m, 2H); −0.19 (s, 9H).

Example D.d55 tert-Butyl 4-{[(4-[2-(cyclopropylmethoxy)-5-(2-methyl-1,3-dioxolan-2-yl)phenyl]-6-methyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-5-(2-methyl-1,3-dioxolan-2-yl)phenyl]-6-methyl-5-{[2-(trimethylsilyl)ethoxy]methyl}-5H-pyrrolo[3,2-d]pyrimidine-7-carboxylic acid (example D.c13) and commercially available tert-butyl 4-amino-piperidine-1-carboxylate the title compound is obtained as pale yellow viscous oil.

MS (ESI): m/z=722 (MH+, 100%).

$^1$H-NMR (400 MHz, DMSO-$d_6$): 9.08 (d, J=7.6, 1H, —NH); 9.00 (s, 1H); 7.57 (dd, J=8.7, 2.3, 1H); 7.50 (d, J=2.3, 1H); 7.15 (d, J=8.7, 1H); 5.40 (d, J=11.0, 1H); 5.04 (d, J=11.0, 1H); 4.09 (m, 1H); 4.00 (m, 2H); 3.90-3.70 (m, 6H); 3.06 (m, 2H); 2.97-2.83 (s, 3H & m, 2H); 1.99 (s, 3H); 1.94 (m, 2H); 1.46 (m, 2H); 1.43 (s, 9H); 0.90 (m, 1H); 0.49 (m, 2H); 0.33 (m, 2H); 0.07 (m, 2H); −0.20 (s, 9H).

Example D.d56 tert-Butyl (trans-4-{[(4-[2-(cyclopropylmethoxy)-5-(2-methyl-1,3-dioxolan-2-yl)phenyl]-6-methyl-5-{[2-(trimethylsilyl)ethoxy]methyl}-5H-pyrrolo[3,2-d]pyrimidin-7-yl)carbonyl]amino}cyclohexyl)carbamate Starting from 4-[2-(cyclopropylmethoxy)-5-(2-methyl-1,3-dioxolan-2-yl)phenyl]-6-methyl-5-{[2-(trimethylsilyl)ethoxy]methyl}-5H-pyrrolo[3,2-d]pyrimidine-7-carboxylic acid (example D.c13) and commercially available tert-butyl trans-(4-amino-cyclohexyl)-carbamate the title compound is obtained as pale yellow viscous oil.

MS (ESI): m/z=736 (MH+, 100%).

$^1$H-NMR (400 MHz, DMSO-$d_6$): 9.00 (s, 1H); 8.93 (d, J=7.6, 1H, —NH); 7.56 (dd, J=8.7, 2.3, 1H); 7.50 (d, J=2.3, 1H); 7.15 (d, J=8.7, 1H); 6.72 (br.d, J~7.5, 1H, —NH); 5.40 (d, J=11.1, 1H); 5.03 (d, J=11.1, 1H); 4.00 (m, 2H); 3.86 (dd, J=10.2, 6.6, 1H); 3.78 (dd. J=10.2, 6.9, 1H); 3.73 (m, 2H & m, 1H); 3.27 (m, 1H); 2.97-2.82 (m, 2H); 2.91 (s, 3H); 2.01 (m, 2H); 1.99 (s, 3H); 1.86 (m, 2H); 1.39 (s, 9H); 1.34 (m, 4H); 0.90 (m, 1H); 0.49 (m, 2H); 0.33 (m, 2H); 0.06 (m, 2H); −0.20 (s, 9H).

Example D.d57 tert-Butyl 4-{[(4-[2-(cyclopropylmethoxy)-5-methylphenyl]-2,6-dimethyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-5-methylphenyl]-2,6-dimethyl-5-{[2-(trimethylsilyl)ethoxy]methyl}-5H-pyrrolo[3,2-d]pyrimidine-7-carboxylic acid (example D.c16) and commercially available tert-butyl 4-amino-piperidine-1-carboxylate the title compound is obtained as pale yellow viscous oil.

MS (ESI): m/z=664 (MH+, 100%)

$^1$H-NMR (300 MHz, DMSO-$d_6$): 9.31 (d, J=7.5, 1H, —NH); 7.32 (dd, J=8.4, 2.0, 1H); 7.22 (d, J=2.0, 1H); 7.04 (d, J=8.4, 1H); 5.39 (d, J=11.0, 1H); 4.98 (d, J=11.0, 1H); 4.15-4.01 (m, 1H); 3.87-3.69 (m, 4H); 3.12 (m, 2H); 2.87 (m, 5H); 2.71 (s, 3H); 2.32 (s, 3H); 1.99-1.87 (m, 2H); 1.46 (m, 2H); 1.43 (s, 9H); 0.89 (m, 1H); 0.51 (m, 2H); 0.32 (m, 2H); 0.05 (m, 2H); −0.17 (s, 9H).

Example D.d58 tert-Butyl 4-{[(4-[2-(cyclopropylmethoxy)-5-fluoro-4-methoxyphenyl]-2,6-dimethyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-5-fluoro-4-methoxyphenyl]-2,6-dimethyl-5-{[2-(trimethylsilyl)ethoxy]methyl}-5H-pyrrolo[3,2-d]pyrimidine-7-carboxylic acid (example D.c17) and commercially available tert-butyl 4-amino-piperidine-1-carboxylate the title compound is obtained as colorless foam.

MS (ESI): 698 (MH+, 100%)

$^1$H-NMR (300 MHz, DMSO-$d_6$): 9.30 (d, J=7.5, 1H, —NH); 7.28 (d, J=11.3, 1H); 6.93 (d, J=7.3, 1H), 5.43 (d, J=11.0, 1H); 5.02 (d, J=11.0, 1H); 4.13-4.00 (m, 1H); 3.95 (s, 3H); 3.93-3.74 (m, 4H); 3.12 (m, 2H); 2.94 (m, 2H); 2.89 (s, 3H); 2.71 (s, 3H); 1.98-1.86 (m, 2H); 1.47 (m, 2H); 1.42 (s, 9H); 0.88 (m, 1H); 0.54 (m, 2H); 0.33 (m, 2H); 0.07 (m, 2H); −0.17 (s, 9H).

Example D.d59 tert-Butyl 4-{[(4-[2-(cyclopropylmethoxy)-4-fluoro-5-methoxyphenyl]-2,6-dimethyl-5-{[2-(trimethylsilyl)ethoxy]methyl}-5H-pyrrolo[3,2-d]pyrimidin-7-yl)carbonyl]amino}piperidine-1-carboxylate Starting from 4-[2-(cyclopropylmethoxy)-4-fluoro-5-methoxyphenyl]-2,6-dimethyl-5-{[2-(trimethylsilyl)ethoxy]methyl}-5H-pyrrolo[3,2-d]pyrimidine-7-carboxylic acid (example D.c18) and commercially available tert-butyl 4-amino-piperidine-1-carboxylate the title compound is obtained as colorless foam.

MS (ESI): m/z=698 (MH+, 100%).

$^1$H-NMR (300 MHz, DMSO-$d_6$): 9.29 (d, J=7.5, 1H, —NH); 7.22 (d, J=9.9, 1H); 7.17 (d, J=13.3, 1H); 5.36 (d, J=10.9, 1H); 4.97 (d, J=10.9, 1H); 4.07 (m, 1H); 3.81 (s, 3H & dd, J=10.4, 6.6, 1H & m, 2H); 3.72 (dd, J=10.4, 7.1, 1H); 3.12 (m, 2H); 3.04-2.90 (m, 2H); 2.88 (s, 3H); 2.72 (s, 3H); 1.93 (m, 2H); 1.47 (m, 2H); 1.40 (s, 9H); 0.87 (m, 1H); 0.56 (m, 2H); 0.32 (m, 2H); 0.04 (m, 2H); −0.15 (s, 9H).

Example D.d60

4-[2-(Cyclopropylmethoxy)-5-methylphenyl]-N-[(1S,2S)-2-hydroxycyclopentyl]-6-methyl-5-{[2-(trimethylsilyl)ethoxy]methyl}-5H-pyrrolo[3,2-d]pyrimidine-7-carboxamide Starting from 4-[2-(cyclopropylmethoxy)-4-fluoro-5-methoxyphenyl]-2,6-dimethyl-5-{[2-(trimethylsilyl)ethoxy]methyl}-5H-pyrrolo[3,2-d]pyrimidine-7-carboxylic acid (example D.c18) and commercially available (1S,2S)-2-amino-cyclopentanol the title compound is obtained as colorless foam.

MS (ESI): m/z=551 (MH$^+$, 100%).

$^1$H-NMR (300 MHz, DMSO-d$_6$): 9.04 (d, J=7.1, 1H, —NH); 8.98 (s, 1H); 7.34 (dd, J=8.6, 2.0, 1H); 7.27 (d, J=2.0, 1H); 7.06 (d, J=8.6, 1H); 5.43 (d, J=11.0, 1H); 5.02 (d, J=11.0, 1H); 4.91 (dd, J=4.2, 1.3, 1H; —OH); 4.09 (m, 1H); 4.00 (m, 1H); 3.82 (dd, J=10.2, 6.6, 1H); 3.74 (dd, J=10.2, 6.9, 1H); 2.91 (s, 3H); 2.88 (t, J=7.8, 2H); 2.32 (s, 3H); 2.12 (m, 1H); 1.91 (m, 1H); 1.74 (m, 2H); 1.54 (m, 2H); 0.88 (m, 1H); 0.52 (m, 2H); 0.32 (m, 2H); 0.04 (m, 2H); −0.17 (s, 9H).

Example D.d61

4-[2-(Cyclopropylmethoxy)-5-methylphenyl]-N-[(1S,2R)-2-hydroxycyclopentyl]-6-methyl-5-{[2-(trimethylsilyl)ethoxy]methyl}-5H-pyrrolo[3,2-d]pyrimidine-7-carboxamide Starting from 4-[2-(cyclopropylmethoxy)-4-fluoro-5-methoxyphenyl]-2,6-dimethyl-5-{[2-(trimethylsilyl)ethoxy]methyl}-5H-pyrrolo[3,2-d]pyrimidine-7-carboxylic acid (example D.c18) and commercially available (1R,2S)-2-amino-cyclopentanol the title compound is obtained as colorless foam.

MS (ESI): m/z=551 (MH$^+$, 100%).

$^1$H-NMR (300 MHz, DMSO-d$_6$): 9.26 (d, J=7.9, 1H, —NH); 8.96 (s, 1H); 7.34 (dd, J=8.4, 1.8, 1H); 7.28 (d, J=1.8, 1H); 7.06 (d, J=8.4, 1H); 5.43 (d, J=11.1, 1H); 5.02 (d, J=11.1, 1H); 4.92 (dd, J=4.0, 3.8, 1H; —OH); 4.17 (m, 1H); 4.04 (m, 1H); 3.82 (ddd, J=10.4, 6.6, 1.5, 1H); 3.74 (ddd, J=10.4, 6.9, 2.2, 1H); 2.92 (s, 3H); 2.88 (t, J=7.9, 2H); 2.32 (s, 3H); 2.03-1.73 (m, 3H); 1.71-1.47 (m, 3H); 0.88 (m, 1H); 0.52 (m, 2H); 0.31 (m, 2H); 0.05 (m, 2H); −0.17 (s, 9H).

Example D.d62

4-[2-(Cyclopropylmethoxy)-5-methylphenyl]-N-[(1R,2R)-2-hydroxycyclopentyl]-6-methyl-5-{[2-(trimethylsilyl)ethoxy]methyl}-5H-pyrrolo[3,2-d]pyrimidine-7-carboxamide Starting from 4-[2-(cyclopropylmethoxy)-4-fluoro-5-methoxyphenyl]-2,6-dimethyl-5-{[2-(trimethylsilyl)ethoxy]methyl}-5H-pyrrolo[3,2-d]pyrimidine-7-carboxylic acid (example D.c18) and commercially available (1R,2R)-2-amino-cyclopentanol the title compound is obtained as colorless foam.

MS (ESI): m/z=551 (MH$^+$, 100%).

$^1$H-NMR (300 MHz, DMSO-d$_6$): 9.04 (d, J=7.1, 1H, —NH); 8.98 (s, 1H); 7.34 (dd, J=8.6, 2.0, 1H); 7.27 (d, J=2.0, 1H); 7.06 (d, J=8.6, 1H); 5.43 (d, J=11.0, 1H); 5.02 (d, J=11.0, 1H); 4.91 (dd, J=4.2, 1.3, 1H; —OH); 4.09 (m, 1H); 4.00 (m, 1H); 3.82 (dd, J=10.2, 6.6, 1H); 3.74 (dd, J=10.2, 6.9, 1H); 2.91 (s, 3H); 2.88 (t, J=7.8, 2H); 2.32 (s, 3H); 2.12 (m, 1H); 1.91 (m, 1H); 1.74 (m, 2H); 1.54 (m, 2H); 0.88 (m, 1H); 0.52 (m, 2H); 0.32 (m, 2H); 0.04 (m, 2H); −0.17 (s, 9H).

Example D.e1 tert-Butyl 4-[({4-[5-(cyclopropylmethoxy)-1,3-benzodioxol-4-yl]-6-methyl-5H-pyrrolo[3,2-d]pyrimidin-7-yl}carbonyl)amino]piperidine-1-carboxylate A solution of tert-butyl 4-{[(4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidin-7-yl)carbonyl]amino}piperidine-1-carboxylate from example D.d1 (3.74 g; 5.5 mmol), tetrabutylammonium fluoride trihydrate (5.21 g; 16.5 mmol) and ethane-1,2-diamine (0.50 g; 8.25 mmol) in tetrahydrofurane (40 mL) is heated to gentle reflux until the starting material is completely consumed according to LC-MS. The crude is purified by column chromatography on silica gel (ethyl acetate/cyclohexane—1:1 to 2:1) to yield the title compound as colorless solid.

MS (ESI): m/z=550 (MH$^+$, 100%).

$^1$H-NMR (300 MHz, DMSO-d$_6$): 11.99 (s, 1H, —NH); 8.93 (s, 1H); 8.74 (d, J=7.7, 1H, —NH); 7.00 (d, J=8.6, 1H); 6.56 (d, J=8.6, 1H); 6.00 (s, 2H); 4.04 (m, 1H); 3.85 (m, 2H); 3.76 (d, J=6.8, 2H); 3.05 (m, 2H); 2.76 (s, 3H); 1.92 (m, 2H); 1.44 (m, 2H); 1.42 (s, 9H); 0.87 (m, 1H); 0.30 (m, 2H); 0.12 (m, 2H).

The following compounds were prepared analogously to the procedure described in above example D.e1

Example D.e2 tert-Butyl {trans-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate Starting from tert-butyl (trans-4-{[(4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d2) the title compound is obtained as colorless solid.

MS (ESI): m/z=564 (MH$^+$, 100%).

$^1$H-NMR (300 MHz, DMSO-d$_6$): 11.96 (s, 1H, —NH); 8.93 (s, 1H); 8.58 (d, J=7.7, 1H, —NH); 7.00 (d, J=8.6, 1H); 6.71 (br.d, J~7.7, 1H, —NH); 6.55 (d, J=8.6, 1H); 6.00 (s, 2H); 3.76 (d, J=6.8, 2H & m, 1H); 3.27 (m, 1H); 2.76 (s, 3H); 1.99 (m, 2H); 1.84 (m, 2H); 1.39 (s, 9H); 1.34 (m, 4H); 0.88 (m, 1H); 0.30 (m, 2H); 0.12 (m, 2H).

Example D.e3 tert-Butyl {cis-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate Starting from tert-butyl (cis-4-{[(4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d3) the title compound is obtained as colorless solid.

MS (ESI): m/z=694 (MH$^+$, 100%).

$^1$H-NMR (300 MHz, DMSO-d$_6$): 9.23 (d, J=7.8, 1H, —NH); 9.05 (s, 1H); 7.02 (d, J=8.6, 1H); 6.91 (br.d, J~6.4, 1H, —NH); 6.57 (d, J=8.6, 1H); 6.03 (d, J=0.6, 1H); 5.92 (d, J=0.6, 1H); 5.39 (d, J=10.8, 1H); 5.12 (d, J=10.8, 1H); 4.07 (m, 1H); 3.76 (dd, J=10.2, 6.6, 2H); 3.68 (dd, J=10.2, 6.9, 1H); 3.34 (m, 1H); 3.01 (m, 2H); 2.92 (s, 3H); 1.86-1.51 (m, 8H); 1.40 (s, 9H); 0.87 (m, 1H); 0.61 (m, 2H); 0.30 (m, 2H); 0.02 (m, 2H); −0.13 (s, 9H).

Example D.e4 tert-Butyl (3R)-3-[({4-[5-(cyclopropylmethoxy)-1,3-benzodioxol-4-yl]-6-methyl-5H-pyrrolo[3,2-d]pyrimidin-7-yl}carbonyl)amino]pyrrolidine-1-carboxylate Starting from tert-butyl (3R)-3-{[(4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidin-7-yl)carbonyl]amino}pyrrolidine-1-carboxylate (example D.d4) the title compound is obtained as colorless solid.

MS (ESI): m/z=536 (MH⁺, 100%).

¹H-NMR (300 MHz, DMSO-d₆): 12.03 (s, 1H, —NH); 8.92 (s, 1H); 8.85 (d, J=6.8, 1H, —NH); 7.00 (d, J=8.6, 1H); 6.56 (d, J=8.6, 1H); 6.00 (s, 2H); 4.49 (m, 1H); 3.76 (d, 6.8, 2H); 3.61 (m, 1H); 3.42 (m, 2H); 3.22 (m, 1H); 2.77 (s, 3H); 2.20 (m, 1H); 1.95 (m, 1H); 1.42 (s, 9H); 0.88 (m, 1H); 0.30 (m, 2H); 0.12 (m, 2H).

Example D.e5 tert-Butyl (3R*,4R*)-3-[({4-[5-(cyclopropylmethoxy)-1,3-benzodioxol-4-yl]-6-methyl-5H-pyrrolo[3,2-d]pyrimidin-7-yl}carbonyl)amino]-4-hydroxypyrrolidine-1-carboxylate Starting from tert-butyl (3R*,4R*)-3-{[(4-[5-(cyclopropylmethoxy)-1,3-benzodioxol-4-yl]-6-methyl-5-{[2-(trimethylsilyl)ethoxy]methyl}-5H-pyrrolo[3,2-d]pyrimidin-7-yl)carbonyl]amino}-4-hydroxypyrrolidine-1-carboxylate (example D.d5) the title compound is obtained as pale yellow viscous oil.

MS (ESI): m/z=552 (MH⁺, 100%).

¹H-NMR (300 MHz, DMSO-d₆): 12.05 (br.s, 1H, —NH); 8.89 (s, 1H); 8.79 (br.s, 1H, —NH); 7.01 (d, J=8.6, 1H); 6.56 (d, J=8.6, 1H); 6.00 (s, 2H); 5.47 (d, J=3.8, 1H, —OH); 4.21 (m, 2H); 3.76 (d, J=6.8, 2H); 3.68 (m, 1H); 3.55 (m, 1H); 3.26 (m, 2H); 2.77 (s, 3H); 1.43 (s, 9H); 0.86 (m, 1H); 0.31 (m, 2H); 0.12 (m, 2H).

Example D.e6 tert-Butyl 4-[({4-[2-(cyclopropylmethoxy)-4-fluorophenyl]-6-methyl-5H-pyrrolo[3,2-d]pyrimidin-7-yl}carbonyl)amino]piperidine-1-carboxylate Starting from tert-butyl 4-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d6) the title compound is obtained as pale yellow foam.

MS (ESI): m/z=524 (MH⁺, 100%).

¹H-NMR (300 MHz, DMSO-d₆): 11.79 (s, 1H, —NH); 8.94 (s. 1H); 8.80 (d, J=7.7, 1H, —NH); 7.66 (dd, J=8.4, 6.9, 1H); 7.08 (dd, J=11.5, 2.4, 1H); 6.96 (ddd, J=8.4, 8.4, 2.4, 1H); 4.05 (m, 1H); 3.91 (d, J=6.9, 2H); 3.85 (m, 2H); 3.05 (m, 2H); 2.78 (s, 3H); 1.92 (m, 2H); 1.42 (m, 2H & s, 9H); 0.96 (m, 1H); 0.38 (m, 2H): 0.25 (m, 2H).

Example D.e7 tert-Butyl {trans-4-[({4-[2-(cyclopropylmethoxy)-4-fluorophenyl]-6-methyl-5H-pyrrolo[3,2-d]pyrimidin-7-yl}carbonyl)amino]cyclohexyl}carbamate Starting from tert-butyl (trans-4-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d7) the title compound is obtained as pale yellow foam.

MS (ESI): m/z=538 (MH⁺, 100%).

¹H-NMR (300 MHz, DMSO-d₆): 11.80 (s, 1H, —NH); 8.95 (s, 1H); 8.64 (d, J=7.7, 1H, —NH); 7.66 (dd, 8.4, 6.9, 1H); 7.09 (dd, 11.3, 2.4, 1H); 6.96 (ddd, 8.4, 8.4, 2.4, 1H); 6.77 (d, J=7.7, 1H, —NH); 3.90 (d, J=6.9, 2H); 3.76 (m, 1H); 3.31 (m, 1H); 2.77 (s, 3H); 1.98 (m, 2H); 1.85 (m, 2H); 1.39 (s, 9H); 1.33 (m, 4H); 0.95 (m, 1H); 0.38 (m, 2H); 0.26 (m, 2H).

Example D.e8

Tert-butyl {cis-4-[({4-[2-(cyclopropylmethoxy)-4-fluorophenyl]-6-methyl-5H-pyrrolo[3,2-d]pyrimidin-7-yl}carbonyl)amino]cyclohexyl}carbamate Starting from tert-butyl (cis-4-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d8) the title compound is obtained as colorless viscous oil.

MS (ESI): m/z=538 (MH⁺, 100%).

¹H-NMR (300 MHz, DMSO-d₆): 11.76 (s, 1H, —NH); 8.98 (s, 1H); 8.97 (d, J=6.6, 1H, —NH); 7.66 (dd, 8.5, 7.1, 1H); 7.09 (dd, 11.6, 2.3, 1H); 6.96 (ddd, 8.5, 8.5, 2.3, 1H); 6.92 (br.s, 1H, —NH); 4.04 (m, 1H); 3.91 (d, J=7.0, 2H); 3.43 (m, 1H); 2.78 (s, 3H); 1.85-1.54 (m, 8H); 1.40 (s, 9H); 0.96 (m, 1H); 0.38 (m, 2H); 0.26 (m, 2H).

Example D.e9 tert-Butyl (3R)-3-[({4-[2-(cyclopropylmethoxy)-4-fluorophenyl]-6-methyl-5H-pyrrolo[3,2-d]pyrimidin-7-yl}carbonyl)amino]pyrrolidine-1-carboxylate Starting from tert-butyl (3R)-3-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}pyrrolidine-1-carboxylate (example D.d9) the title compound is obtained as pale yellow foam.

MS (ESI): m/z=510 (MH⁺, 100%).

¹H-NMR (300 MHz, DMSO-d₆): 11.83 (s, 1H, —NH); 8.93 (s, 1H); 8.91 (d, J=6.7, 1H, —NH); 7.66 (dd, J=8.4, 6.9, 1H); 7.08 (dd, J=11.5, 2.4, 1H); 6.96 (ddd, J=8.4, 8.4, 2.4, 1H); 4.49 (m, 1H); 3.91 (d, J=6.9, 2H); 3.62 (m, 1H); 3.43 (m, 2H); 3.23 (m, 1H); 2.79 (s. 3H); 2.21 (m, 1H); 1.94 (m, 1H); 1.42 (s, 9H); 0.96 (m, 1H); 0.38 (m, 2H); 0.25 (m, 2H).

Example D.e10 tert-Butyl (3R*,4R*)-3-[({4-[2-(cyclopropylmethoxy)-4-fluorophenyl]-6-methyl-5H-pyrrolo[3,2-d]pyrimidin-7-yl}carbonyl)amino]-4-hydroxypyrrolidine-1-carboxylate Starting from tert-butyl (3R*,4S*)-3-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}-4-hydroxypyrrolidine-1-carboxylate (example D.d10) the title compound is obtained as pale yellow foam.

MS (ESI): m/z=526 (MH⁺, 100%).

¹H-NMR (300 MHz, DMSO-d₆): 11.85 (s, 1H, —NH); 8.91 (s, 1H); 8.84 (br.s, 1H, —NH); 7.66 (dd, J=8.4, 6.9, 1H); 7.08 (dd, J=11.7, 2.4, 1H); 6.96 (ddd, J=8.4, 8.4, 2.4, 1H); 5.47 (d, J=3.8, 1H, —OH); 4.26 (m, 1H); 4.19 (m, 1H); 3.91 (d, 7.1, 2H); 3.68 (m, 1H); 3.55 (m, 1H); 3.25 (m, 2H); 2.79 (s. 3H); 1.43 (s, 9H); 0.96 (m, 1H); 0.38 (m, 2H); 0.25 (m, 2H).

Example D.e11

Tert-butyl (3S*,4S*)-4-[({4-[2-(cyclopropyl-methoxy)-4-fluorophenyl]-6-methyl-5H-pyrrolo[3,2-d]pyrimidin-7-yl}carbonyl)amino]-3-hydroxypiperidine-1-carboxylate Starting from tert-butyl (3S*,4S*)-4-{[(4-[2-(cyclopropylmethoxy)-4-fluorophenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate (example D.d11) the title compound is obtained as colorless solid.

MS (ESI): m/z=540 (MH+, 100%).

$^1$H-NMR (300 MHz, DMSO-d$_6$): 11.79 8s, 1H, —NH); 8.94 (s, 1H); 8.84 (d, J=7.3, 1H, —NH); 7.65 (dd, J=8.6, 6.9, 1H); 7.08 (dd, J=11.7, 2.4, 1H); 6.96 (ddd, J=8.6, 8.6, 2.4, 1H); 5.24 (d, J=4.9, 1H, —OH); 3.98-3.74 (m, 3H); 3.91 (d, J=6.9, 2H, —NH; 3.43 (m, 1H); 2.98 (m, 1H); 2.78 (s. 3H); 2.06 (m, 1H); 1.42 (s, 9H & m, 1H); 0.96 (m, 1H); 0.38 (m, 2H); 0.25 (m, 2H).

Example D.e12 tert-Butyl 4-({1-[4-(2-cyclopropylmethoxy-5-fluorophenyl)-6-methyl-5H-pyrrolo[3,2-d]pyrimidin-7-yl]-methanoyl}-amino)-piperidine-1-carboxylate Starting from tert-butyl (4-{[(4-[2-(cyclopropylmethoxy)-5-fluorophenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d12) the title compound is obtained as pale yellow foam.

MS (ESI): m/z=524 (MH+, 100%).

$^1$H-NMR (300 MHz, DMSO-d$_6$): 11.83 (s, 1H, —NH); 8.97 (s, 1H); 8.79 (d, J=7.6, 1H, —NH); 7.43 (dd, J=9.0, 3.2, 1H); 7.37 (ddd, J=9.1, 8.3, 3.2, 1H); 7.19 (dd, J=9.1, 4.4, 1H); 4.07 (m, 1H); 3.87 (d, J=6.9, 2H); 3.84 (m, 2H); 3.05 (m, 2H); 2.79 (s, 3H); 1.92 (m, 2H); 1.42 (s, 9H & m, 2H); 0.94 (m, 1H); 0.36 (m, 2H); 0.23 (m, 2H).

Example D.e13 tert-Butyl {trans-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate Starting from tert-butyl (trans-4-{[(4-[2-(cyclopropylmethoxy)-5-fluorophenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d13) the title compound is obtained as pale yellow viscous oil.

MS (ESI): m/z=538 (MH+).

$^1$H-NMR (300 MHz, DMSO-d$_6$): 11.81 (br.s, 1H, —NH); 8.97 (s, 1H); 8.62 (d, J=7.8, 1H, —NH); 7.42 (dd, J=8.9, 3.1, 1H); 7.36 (ddd, J=9.0, 8.6, 3.1, 1H); 7.18 (dd, J=9.0, 4.4, 1H); 6.72 (d, J=7.5, 1H, —NH); 3.87 (d, J=6.9, 2H); 3.82-3.70 (m, 2H); 2.78 (s, 3H); 1.98 (m, 2H); 1.85 (m, 2H); 1.39 (s, 9H); 1.35 (m, 4H); 0.93 (m, 1H); 0.36 (m, 2H); 0.22 (m, 2H).

Example D.e14 tert-Butyl {cis-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate Starting from tert-butyl (4-{[(4-[2-(cyclopropylmethoxy)-5-fluorophenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d14) the title compound is obtained as colorless solid.

MS (ESI): m/z=538 (MH+).

$^1$H-NMR (300 MHz, DMSO-d$_6$): 11.81 (br.s, 1H, —NH); 9.00 (s, 1H); 8.96 (d, J=7.7, 1H, —NH); 7.43 (dd, J=8.9, 3.3, 1H); 7.38 (ddd, J=8.9, 8.2, 3.3, 1H); 7.19 (dd, J=8.9, 4.4, 1H); 6.92 (br.s, 1H, —NH); 4.04 (m, 1H); 3.88 (d, J=6.9, 2H); 3.42 (m, 1H); 2.79 (s, 3H); 1.85-1.53 (m, 8H); 1.40 (s, 9H); 0.94 (m, 1H); 0.36 (m, 2H); 0.23 (m, 2H).

Example D.e15 tert-Butyl (3R)-3-[({4-[2-(cyclopropylmethoxy)-5-fluorophenyl]-6-methyl-5H-pyrrolo[3,2-d]pyrimidin-7-yl}carbonyl)amino]pyrrolidine-1-carboxylate Starting from tert-butyl (3R)-3-{[(4-[2-(cyclopropylmethoxy)-5-fluorophenyl]-6-methyl-5-{[2-(trimethylsilyl)ethoxy]methyl}-5H-pyrrolo[3,2-d]pyrimidin-7-yl)carbonyl]amino}pyrrolidine-1-carboxylate (example D.d15) the title compound is obtained as pale yellow foam.

MS (ESI): m/z=510 (MH+, 100%).

$^1$H-NMR (300 MHz, DMSO-d$_6$): 11.87 (s, 1H, —NH); 8.95 (s, 1H); 8.89 (d, J=6.8, 1H, —NH); 7.42 (dd, J=8.9, 3.3, 1H); 7.38 (ddd, J=9.1, 8.4, 3.3, 1H); 7.19 (dd, J=9.1, 4.4, 1H); 4.49 (m, 1H); 3.87 (d, J=6.9, 2H); 3.62 (m, 1H); 3.42 (m, 2H); 3.22 (m, 1H); 2.79 (s, 3H); 2.20 (m, 1H); 1.94 (m, 1H); 1.42 (s, 9H); 0.93 (m, 1H); 0.36 (m, 2H); 0.22 (m, 2H).

Example D.e16 tert-Butyl (3R*,4R*)-4-[({4-[2-(cyclopropylmethoxy)-5-fluorophenyl]-6-methyl-5H-pyrrolo[3,2-d]pyrimidin-7-yl}carbonyl)amino]-3-hydroxypiperidine-1-carboxylate Starting from tert-butyl (3R*,4R*)-4-{[(4-[2-(cyclopropylmethoxy)-5-fluorophenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate (example D.d16) the title compound is obtained as colorless solid.

MS (ESI): m/z=540 (MH+, 100%).

$^1$H-NMR (300 MHz, DMSO-d$_6$): 11.83 (s, 1H, —NH); 8.97 (s, 1H); 8.83 (d, J=7.5, 1H, —NH); 7.42 (ddd, J=9.1, 8.9, 3.3, 1H); 7.36 (dd, J=8.2, 3.2, 1H); 7.19 (dd, J=9.1, 4.4, 1H); 5.24 (d, J=4.9, 1H, —OH); 3.99-3.74 (m, 3H); 3.87 (d, J=6.8, 2H); 3.43 (m, 1H); 2.98 (m, 1H); 2.79 (s, 3H & m, 1H); 2.06 (m, 1H); 1.42 (s, 9H & m, 1H); 0.94 (m, 1H); 0.36 (m, 2H); 0.22 (m, 2H).

Example D.e17 tert-Butyl 4-[({4-(2-ethoxy-5-fluorophenyl)-6-methyl-5H-pyrrolo[3,2-d]-pyrimidin-7-yl]carbonyl}amino)piperidine-1-carboxylate Starting from tert-butyl 4-({[4-(2-ethoxy-5-fluorophenyl)-6-methyl-5-{[2-(trimethylsilyl)ethoxy]methyl}-5H-pyrrolo[3,2-d]pyrimidin-7-yl]carbonyl}amino)piperidine-1-carboxylate (example D.d17) the title compound is obtained as colorless solid.

MS (ESI): m/z=498 (MH+, 100%).

$^1$H-NMR (300 MHz, DMSO-d$_6$, MeOH-d$_4$): 11.87 (br.s, 1H, —NH); 8.96 (s, 1H); 8.78 (d, J=7.7, 1H, —NH); 7.43 (ddd, J=9.1, 8.9, 3.3, 1H); 7.38 (dd, J=8.2, 3.3, 1H); 7.22 (dd, J=9.1, 4.4, 1H); 4.08 (qu, J=6.9, 2H & m, 1H); 3.85 (m, 2H); 3.05 (m, 2H); 2.78 (s, 3H); 1.92 (m, 2H); 1.42 (s, 9H & m, 2H); 1.11 (t, J=6.9, 3H).

Example D.e18 tert-butyl 4-[({4-[2-(cyclopropylmethoxy)-4-methoxyphenyl]-6-methyl-5H-pyrrolo[3,2-d]pyrimidin-7-yl}carbonyl)amino]piperidine-1-carboxylate Starting from tert-butyl 4-{[(4-[2-(cyclopropylmethoxy)-4-methoxyphenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d18) the title compound is obtained as pale yellow foam.
MS (ESI): m/z=
$^1$H-NMR (300 MHz, DMSO-d$_6$):

Example D.e19 tert-Butyl {trans-4-[({4-[2-(cyclopropylmethoxy)-4-methoxyphenyl]-6-methyl-5H-pyrrolo[3,2-d]pyrimidin-7-yl}carbonyl)amino]cyclohexyl}carbamate Starting from tert-butyl (trans-4-{[(4-[2-(cyclopropylmethoxy)-4-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d19) the title compound is obtained as colorless solid.
MS (ESI): m/z=550 (MH$^+$, 100%).
$^1$H-NMR (300 MHz, DMSO-d$_6$): 11.64 (s, 1H, —NH); 8.91 (s, 1H); 8.66 (d, J=7.7, 1H, —NH); 7.58 (d, J=8.4, 1H); 6.72 (dd, J=8.4, 2.2, 1H); 6.68 (d, J=2.2, 1H & br.s, 1H, —NH); 3.90 (d, J=6.9, 2H); 3.85 (s, 3H); 3.76 (m, 1H); 3.28 (m, 1H); 2.77 (s, 3H); 1.99 (m, 2H); 1.85 (m, 2H); 1.39 (s, 9H); 1.37-1.21 (m, 4H); 0.95 (m, 1H); 0.37 (m, 2H); 0.26 (m, 2H).

Example D.e20 tert-Butyl {cis-4-[({4-[2-(cyclopropylmethoxy)-4-methoxyphenyl]-6-methyl-5H-pyrrolo[3,2-d]pyrimidin-7-yl}carbonyl)amino]cyclohexyl}carbamate Starting from tert-butyl (cis-4-{[(4-[2-(cyclopropylmethoxy)-4-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d20) the title compound is obtained as colorless solid.
MS (ESI): m/z=550 (MH$^+$, 100%).
$^1$H-NMR (300 MHz, DMSO-d$_6$): 11.64 (s, 1H, —NH); 8.99 (d, J=7.9, 1H, —NH); 8.94 (s, 1H); 7.59 (d, J=8.4, 1H); 6.92 (br.s, 1H, —NH); 6.72 (dd, J=8.4, 2.2, 1H); 6.69 (d, J=2.2, 1H); 4.03 (m, 1H); 3.91 (d, J=6.9, 2H); 3.86 (s, 3H); 3.43 (m, 1H); 2.77 (s, 3H); 1.84-1.54 (m, 8H); 1.40 (s, 9H); 0.96 (m, 1H); 0.38 (m, 2H); 0.27 (m, 2H).

Example D.e21 tert-Butyl (3R)-3-[({4-[2-(cyclopropylmethoxy)-4-methoxyphenyl]-6-methyl-5H-pyrrolo[3,2-d]pyrimidin-7-yl}carbonyl)amino]pyrrolidine-1-carboxylate Starting from tert-butyl (3R)-3-{[(4-[2-(cyclopropylmethoxy)-4-methoxyphenyl]-6-methyl-5-{[2-(trimethylsilyl)ethoxy]methyl}-5H-pyrrolo[3,2-d]pyrimidin-7-yl)carbonyl]amino}pyrrolidine-1-carboxylate (example D.d21) the title compound is obtained as pale yellow solid.
MS (ESI): m/z=522 (MH$^+$, 100%).
$^1$H-NMR (300 MHz, DMSO-d$_6$): 11.71 (s, 1H, —NH); 8.93 (d, J=6.8, 1H, —NH); 8.89 (s, 1H); 7.59 (d, J=8.4, 1H); 6.72 (dd, J=8.4, 2.2, 1H); 6.69 (d, J=2.2, 1H); 4.48 (m, 1H); 3.91 (d, J=6.9, 2H); 3.86 (s, 3H); 3.61 (m, 1H); 3.43 (m, 2H); 3.22 (m, 1H); 2.78 (s, 3H); 2.21 (m, 1H); 1.93 (m, 1H); 1.42 (s, 9H); 0.96 (m, 1H); 0.38 (m, 2H); 0.26 (m, 2H).

Example D.e22 tert-Butyl (3R*,4R*)-3-[({4-[2-(cyclopropylmethoxy)-4-methoxyphenyl]-6-methyl-5H-pyrrolo[3,2-d]pyrimidin-7-yl}carbonyl)amino]-4-hydroxy-pyrrolidine-1-carboxylate Starting from tert-butyl (3R*,4R*)-3-{[(4-[2-(cyclopropylmethoxy)-4-methoxyphenyl]-6-methyl-5-{[2-(trimethylsilyl)ethoxy]methyl}-5H-pyrrolo[3,2-d]pyrimidin-7-yl)carbonyl]amino}-4-hydroxypyrrolidine-1-carboxylate (example D.d22) the title compound is obtained as colorless solid.
MS (ESI): m/z=538 (MH$^+$, 100%).
$^1$H-NMR (300 MHz, DMSO-d$_6$): 11.73 (br.s, 1H, —NH); 8.87 (s, 1H & br.s, 1H, —NH); 7.59 (d, J=8.4, 1H); 6.72 (dd, J=8.4, 2.2, 1H); 6.69 (d, J=2.2, 1H); 5.46 (d, J=3.8, 1H, —OH); 4.25 (m, 1H); 3.90 (d, J=6.9, 2H); 3.86 (s, 3H); 3.68 (m, 1H); 3.54 (m, 1H); 3.23 (m, 2H); 2.78 (s, 3H); 1.43 (s, 9H); 0.96 (m, 1H); 0.38 (m, 2H); 0.26 (m, 2H).

Example D.e23 tert-Butyl 4-[({4-[2-(cyclopropylmethoxy)-5-methoxyphenyl]-6-methyl-5H-pyrrolo[3,2-d]pyrimidin-7-yl}carbonyl)amino]piperidine-1-carboxylate Starting from tert-butyl 4-{[(4-[2-(cyclopropylmethoxy)-5-methoxyphenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d23) the title compound is obtained as colorless viscous oil.
MS (ESI): m/z=536 (MH$^+$, 100%).
$^1$H-NMR (300 MHz, DMSO-d$_6$): 11.76 (s, 1H, —NH); 8.96 (s, 1H); 8.80 (d, J=7.7, 1H, —NH); 7.17 (t, J=1.8, 1H); 7.11 (d, J=1.8, 2H); 4.07 (m, 1H); 3.87 (m, 2H); 3.82 (d, J=6.8, 2H); 3.77 (s, 3H); 3.05 (m, 2H); 2.78 (s, 3H); 1.92 (m, 2H); 1.42 (s, 9H & m, 2H); 0.92 (m, 1H); 0.34 (m, 2H); 0.19 (m, 2H).

Example D.e24 tert-Butyl {trans-4-[({4-[2-(cyclopropylmethoxy)-5-methoxyphenyl]-6-methyl-5H-pyrrolo[3,2-d]pyrimidin-7-yl}carbonyl)amino]cyclohexyl}carbamate Starting from tert-butyl (trans-4-{[(4-[2-(cyclopropylmethoxy)-5-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d24) the title compound is obtained as colorless foam.
MS (ESI): m/z=450 (MH$^+$, 100%).
$^1$H-NMR (300 MHz, DMSO-d$_6$): 12.07 (s, 1H, —NH); 9.01 (s, 1H); 8.59 (d, J=7.9, 1H, —NH); 8.03 (br.d, J~4.8, 3H, —NH$_3^+$); 7.20 (t, J=1.8, 1H); 7.14 (d, J=1.8, 2H); 3.84 (d, J=6.9, 2H & m, 1H); 3.78 (s, 3H); 3.09 (m, 1H); 2.80 (s, 3H); 2.04 (m, 4H); 1.47 (m, 4H); 0.92 (m, 1H); 0.34 (m, 2H); 0.19 (m, 2H).

Example D.e25 tert-Butyl {cis-4-[({4-[2-(cyclopropylmethoxy)-5-methoxyphenyl]-6-methyl-5H-pyrrolo[3,2-d]pyrimidin-7-yl}carbonyl)amino]cyclohexyl}carbamate Starting from tert-butyl (cis-4-{[(4-[2-(cyclopropylmethoxy)-5-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d25) the title compound is obtained as colorless foam.
MS (ESI): m/z=549 (MH+, 100%).
$^1$H-NMR (300 MHz, DMSO-d$_6$): 11.73 (s, 1H, —NH); 8.99 (s, 1H); 8.97 (d, J=7.9, 1H, —NH); 7.18 (t, J=1.8, 1H); 7.11 (d, J=1.8, 2H); 6.92 (br.d, J~7.1, 1H, —NH); 4.03 (m, 1H); 3.83 (d, J=6.9, 2H); 3.77 (s, 3H); 3.43 (m, 1H); 2.78 (s, 3H); 1.85-1.52 (m, 8H); 1.40 (s, 9H); 0.92 (m, 1H); 0.35 (m, 2H); 0.20 (m, 2H).

Example D.e26 tert-Butyl (3R)-3-[({4-[2-(cyclopropylmethoxy)-5-methoxyphenyl]-6-methyl-5H-pyrrolo[3,2-d]pyrimidin-7-yl}carbonyl)amino]pyrrolidine-1-carboxylate Starting from tert-butyl (3R)-3-{[(4-[2-(cyclopropylmethoxy)-5-methoxyphenyl]-6-methyl-5-{[2-(trimethylsilyl)ethoxy]methyl}-5H-pyrrolo[3,2-d]pyrimidin-7-yl)carbonyl]amino}pyrrolidine-1-carboxylate (example D.d26) the title compound is obtained as colorless viscous oil.
MS (ESI): m/z=522 (MH+, 100%).
$^1$H-NMR (300 MHz, DMSO-d$_6$): 11.80 (s, 1H, —NH); 8.94 (s, 1H); 8.91 (d, J=6.8, 1H, —NH); 7.18 (t, J=1.6, 2H); 7.11 (d, J=1.6, 1H); 4.49 (m, 1H); 3.82 (d, J=6.9, 2H); 3.77 (s, 2H); 3.62 (m, 1H); 3.42 (m, 2H); 3.22 (m, 1H); 2.78 (s, 3H); 2.21 (m, 1H); 1.94 (m, 1H); 1.42 (s, 9H); 0.92 (m, 1H); 0.34 (m, 2H); 0.19 (m, 2H).

Example D.e27 tert-Butyl (3R*,4R*)-4-[({4-[2-(cyclopropylmethoxy)-5-methoxyphenyl]-6-methyl-5H-pyrrolo[3,2-d]pyrimidin-7-yl}carbonyl)amino]-3-hydroxypiperidine-1-carboxylate Starting from tert-butyl (3R*,4R*)-4-{[(4-[2-(cyclopropylmethoxy)-5-methoxyphenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate (example D.d27) the title compound is obtained as colorless viscous oil.
MS (ESI): m/z=552 (MH+, 100%).
$^1$H-NMR (300 MHz, DMSO-d$_6$): 11.76 (s, 1H); 8.95 (s, 1H); 8.85 (d, J=7.3, 1H, —NH); 7.18 (t, J=1.6, 1H); 7.11 (d, J=1.6, 2H); 5.24 (d, J=4.9, 1H, —OH); 3.98-3.79 (m, 3H); 3.82 (d, J=6.8, 2H); 3.77 (s, 3H); 3.43 (m, 1H); 2.98 (m, 1H); 2.78 (s, 3H & m, 1H); 2.06 (m, 1H); 1.42 (s, 9H); 1.38 (m, 1H); 0.92 (m, 1H); 0.35 (m, 2H); 0.20 (m, 2H).

Example D.e28 tert-Butyl 4-[({4-[2-(cyclopropylmethoxy)-5-methylphenyl]-6-methyl-5H-pyrrolo[3,2-d]pyrimidin-7-yl}carbonyl)amino]piperidine-1-carboxylate Starting from tert-butyl 4-{[(4-[2-(cyclopropylmethoxy)-5-methylphenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d28) the title compound is obtained as pale yellow foam.
MS (ESI): m/z=520 (MH+, 100%).
$^1$H-NMR (400 MHz, DMSO-d$_6$): 11.73 (s, 1H, —NH); 8.94 (s, 1H); 8.82 (d, J=7.7, 1H, —NH); 7.43 (d, J=2.2, 1H); 7.33 (dd, J=8.6, 2.0, 1H); 7.06 (d, J=8.6, 1H); 4.06 (m, 1H); 3.86 (d, J=6.9, 2H & m, 2H); 3.05 (m, 2H); 2.78 (s, 3H); 2.33 (s, 3H); 1.92 (m, 2H); 1.43 (s, 9H & m, 2H); 0.94 (m, 1H); 0.35 (m, 2H); 0.22 (m, 2H).

Example D.e29 tert-Butyl {trans-4-[({4-[2-(cyclopropylmethoxy)-5-methylphenyl]-6-methyl-5H-pyrrolo[3,2-d]pyrimidin-7-yl}carbonyl)amino]cyclohexyl}carbamate Starting from tert-butyl (trans-4-{[(4-[2-(cyclopropylmethoxy)-5-methylphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d29) the title compound is obtained as colorless solid.
MS (ESI): m/z=534 (MH+, 100%).
$^1$H-NMR (300 MHz, DMSO-d$_6$): 11.71 (s, 1H, —NH); 8.94 (s, 1H); 8.65 (d, J=7.7, 1H, —NH); 7.43 (d, J=2.2, 1H); 7.32 (dd, J=8.6, 2.0, 1H); 7.05 (d, J=8.6, 1H); 6.72 (d, J=7.1, 1H, —NH); 3.85 (d, J=6.9, 2H); 3.76 (m, 1H); 3.30 (m, 1H); 2.77 (s, 3H); 2.33 (s, 3H); 1.99 (m, 2H); 1.85 (m, 2H); 1.39 (s, 9H); 1.33 (m, 4H); 0.94 (m, 1H); 0.35 (m, 2H); 0.22 (m, 2H).

Example D.e30 tert-Butyl {cis-4-[({4-[2-(cyclopropylmethoxy)-5-methylphenyl]-6-methyl-5H-pyrrolo[3,2-d]pyrimidin-7-yl}carbonyl)amino]cyclohexyl}carbamate Starting from tert-butyl (cis-4-{[(4-[2-(cyclopropylmethoxy)-5-methylphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d30) the title compound is obtained as colorless solid.
MS (ESI): m/z=534 (MH+, 100%).
$^1$H-NMR (300 MHz, DMSO-d$_6$): 11.73 (s, 1H, —NH); 9.00 (d, J=9.3, 1H, —NH); 8.98 (s, 1H); 7.43 (d, J=2.1, 1H); 7.33 (dd, J=8.4, 2.1, 1H); 7.06 (d, J=8.4, 1H); 6.97 (d, J=7.7, 1H, —NH); 4.03 (m, 1H); 3.86 (d, J=6.9, 2H); 3.42 (m, 1H); 2.78 (s, 3H); 2.32 (s, 3H); 1.81-1.51 (m, 8H); 1.40 (s, 9H); 0.94 (m, 1H); 0.37 (m, 2H); 0.23 (m, 2H).

Example D.e31 tert-Butyl 4-[({4-[2-(cyclopropylmethoxy)-5-(trifluoromethyl)phenyl]-6-methyl-5H-pyrrolo[3,2-d]pyrimidin-7-yl}carbonyl)amino]piperidine-1-carboxylate Starting from tert-butyl 4-{[(4-[2-(cyclopropylmethoxy)-5-(trifluoromethyl)phenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d31) the title compound is obtained as pale yellow viscous oil.
MS (ESI): m/z=574 (MH+, 100%).
$^1$H-NMR (300 MHz, DMSO-d$_6$): 11.90 (s, 1H, —NH); 8.99 (s, 1H); 8.79 (d, J=7.7, 1H, —NH); 7.91 (d, J=2.0, 1H); 7.89 (dd, J=8.8, 2.0, 1H); 7.38 (d, J=8.8, 1H); 4.05 (m, 1H);

4.00 (d, J=6.9, 2H); 3.85 (m, 2H); 3.05 (m, 2H); 2.79 (s, 3H); 1.93 (m, 2H); 1.45 (m, 2H); 1.43 (s, 9H); 0.98 (m, 1H); 0.39 (m, 2H); 0.27 (m, 2H).

Example D.e32 tert-Butyl {trans-4-[({4-[2-(cyclopropylmethoxy)-5-(trifluoromethyl)phenyl]-6-methyl-5H-pyrrolo[3,2-d]pyrimidin-7-yl}carbonyl)amino]cyclohexyl}carbamate Starting from tert-butyl (trans-4-{[(4-[2-(cyclopropylmethoxy)-5-(trifluoromethyl)phenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d32) the title compound is obtained as pale yellow solid.

Alternatively, following the procedure as described for example D.d1 the title compound is prepared from 4-[2-(cyclopropylmethoxy)-5-(trifluoromethyl)phenyl]-6-methyl-5H-pyrrolo[3,2-d]pyrimidine-7-carboxylic acid (example D.g2) and commercially available tert-butyl trans-(4-amino-cyclohexyl)carbamate.

MS (ESI): m/z=588 (MH$^+$, 100%).

$^1$H-NMR (300 MHz, DMSO-d$_6$): 11.87 (s, 1H, —NH); 8.99 (s, 1H); 8.62 (d, J=7.7, 1H, —NH); 7.91 (d, J=2.0, 1H); 7.89 (dd, J=8.6, 2.0, 1H); 7.38 (d, J=8.6, 1H); 6.72 (d, J=7.2, 1H, —NH); 4.00 (d, J=7.0, 2H); 3.76 (m, 1H); 3.29 (m, 1H); 2.78 (s, 3H); 2.00 (m, 2H); 1.85 (m, 2H); 1.39 (s, 9H); 1.36 (m, 4H); 0.98 (m, 1H); 0.39 (m, 2H); 0.27 (m, 2H).

Example D.e33 tert-Butyl {cis-4-[({4-[2-(cyclopropyl methoxy)-5-(trifluoromethyl)phenyl]-6-methyl-5H-pyrrolo[3,2-d]pyrimidin-7-yl}carbonyl)amino]cyclohexyl}carbamate Starting from tert-Butyl (cis-4-{[(4-[2-(cyclopropylmethoxy)-5-(trifluoromethyl)phenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d33) the title compound is obtained as colorless solid.

MS (ESI): m/z=588 (MH$^+$, 100%).

$^1$H-NMR (300 MHz, DMSO-d$_6$): 11.87 (s, 1H, —NH); 9.03 (s, 1H); 8.96 (d, J=7.7, 1H, —NH); 7.91 (d, J=2.1, 1H); 7.89 (dd, J=8.5, 2.1, 1H); 7.38 (d, J=8.5, 1H); 6.92 (br.s, 1H, —NH); 4.06 (m, 1H); 4.00 (d, J=6.9, 2H); 3.43 (m, 1H); 2.79 (s, 3H); 1.84-1.54 (m, 8H); 1.40 (s, 9H); 0.99 (m, 1H); 0.40 (m, 2H); 0.28 (m, 2H).

Example D.e34 tert-Butyl 4-[({4-[2-ethoxy-5-(trifluoromethyl)phenyl]-6-methyl-5H-pyrrolo[3,2-d]pyrimidin-7-yl}carbonyl)amino]piperidine-1-carboxylate Starting from tert-butyl 4-{[(4-[2-ethoxy-5-(trifluoromethyl)phenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d34) the title compound is obtained as colorless solid.

MS (ESI): m/z=548 (MH$^+$, 100%).

$^1$H-NMR (300 MHz, DMSO-d$_6$): 11.92 (s, 1H, —NH); 8.98 (s, 1H); 8.78 (d, J=7.7, 1H); 7.92 (d, J=2.2, 1H); 7.90 (dd, J=9.5, 2.2, 1H); 7.42 (d, J=9.5, 1H); 4.21 (qu, J=7.0, 2H); 4.06 (m, 1H); 3.85 (m, 2H); 3.05 (m, 2H); 2.79 (s, 3H); 1.97 (m, 2H); 1.92 (m, 2H); 1.42 (s, 9H & m, 2H); 1.15 (t, J=7.0, 3H).

Example D.e35 tert-Butyl 4-[({4-[2-(cyclopropylmethoxy)-4-fluoro-5-methoxyphenyl]-6-methyl-5H-pyrrolo[3,2-d]pyrimidin-7-yl}carbonyl)amino]piperidine-1-carboxylate Starting from tert-butyl 4-{[(4-[2-cyclopropylmethoxy-4-fluoro-5-methoxyphenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d35) the title compound is obtained as pale yellow viscous oil.

MS (ESI): m/z=554 (MH$^+$, 100%); 498 (MH$^+$-C$_4$H$_8$); 454 (MH$^+$-C$_5$H$_8$O$_2$).

$^1$H-NMR (300 MHz, DMSO-d$_6$): 11.78 (s, 1H, —NH); 8.96 (s, 1H); 8.79 (d, J=7.8, 1H, —NH); 7.39 (d, J=9.8, 1H); 7.18 (d, J=13.5, 1H); 4.04 (m, 1H); 3.87 (m, 2H); 3.84 (s, 3H & d, J=6.9, 2H); 3.05 (m, 2H); 2.78 (s, 3H); 1.93 (m, 2H); 1.42 (s, 9H & m, 1H); 1.29 (m, 1H); 0.93 (m, 1H); 0.36 (m, 2H); 0.21 (m, 2H).

Example D.e36 tert-Butyl {trans-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate Starting from tert-butyl (trans-4-{[(4-[2-cyclopropylmethoxy)-4-fluoro-5-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d36) the title compound is obtained as colorless solid.

MS (ESI): m/z=568 (MH$^+$, 100%); 512 (MH$^+$-C$_4$H$_8$)

$^1$H-NMR (300 MHz, DMSO-d$_6$): 11.73 (s, 1H, —NH); 8.96 (s, 1H); 8.64 (d, J=7.9, 1H, —NH); 7.39 (d, J=9.9, 1H); 7.18 (d, J=13.3, 1H); 6.72 (d, J=7.7, 1H, —NH); 3.84 (s, 3H & d, J=6.8, 2H); 3.76 (m, 1H); 3.27 (m, 1H); 2.78 (s, 3H); 1.99 (m, 2H); 1.85 (m, 2H); 1.39 (s, 9H); 1.35 (m, 4H); 0.93 (m, 1H); 0.36 (m, 2H); 0.21 (m, 2H).

Example D.e37 tert-Butyl {cis-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate Starting from tert-butyl (cis-4-{[(4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d37) the title compound is obtained as colorless solid.

MS (ESI): m/z=568 (MH$^+$, 100%); 512 (MH$^+$-C$_4$H$_8$); 468 (MH$^+$-C$_5$H$_8$O$_2$).

$^1$H-NMR (300 MHz, DMSO-d$_6$): 11.73 (s, 1H, —NH); 8.99 (s, 1H); 8.96 (d, J=7.7, 1H, —NH); 7.39 (d, J=9.9, 1H); 7.19 (d, J=13.3, 1H); 6.91 (br.s, 1H, —NH); 4.03 (m, 1H);

3.85 (s, 3H); 3.84 (d, J=6.8, 2H); 3.43 (m, 1H); 2.78 (s, 3H); 1.77 (m, 2H); 1.64 (m, 6H); 1.40 (s, 9H); 0.93 (m, 1H); 0.36 (m, 2H); 0.21 (m, 2H).

Example D.e38 tert-Butyl (3R*,4R*)-4-[({4-[2-(cyclopropyl-methoxy)-4-fluoro-5-methoxyphenyl]-6-methyl-5H-pyrrolo[3,2-d]pyrimidin-7-yl}carbonyl)amino]-3-hydroxypiperidine-1-carboxylate Starting from tert-butyl (3R*,4R*)-4-{[(4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate (example D.d38) the title compound is obtained as pale yellow viscous oil.

MS (ESI): m/z=570 (MH$^+$, 100%).

$^1$H-NMR (300 MHz, DMSO-d$_6$): 11.75 (s, 1H, —NH); 8.96 (s, 1H); 8.84 (d, J=7.3, 1H, —NH); 7.40 (d, J=9.9, 1H); 7.18 (d, J=13.3, 1H); 5.24 (d, J=4.9, 1H, —OH); 3.99-3.73 (m, 3H); 3.84 (s, 3H & d, J=6.8, 2H); 3.43 (m, 1H); 2.98 (m, 1H); 2.79 (s, 3H & m, 1H); 2.06 (m, 1H); 1.42 (s, 9H); 1.37 (m, 1H); 0.93 (m, 1H); 0.36 (m, 2H); 0.21 (m, 2H).

Example D.e39 tert-Butyl (3S*,4S*)-3-[({4-[2-(cyclopropyl-methoxy)-4-fluoro-5-methoxyphenyl]-6-methyl-5H-pyrrolo[3,2-d]pyrimidin-7-yl}carbonyl)amino]-4-hydroxypiperidine-1-carboxylate Starting from tert-butyl (3S*,4S*)-3-{[(4-[2-(cyclopropylmethoxy)-4-fluoro-5-methoxyphenyl]-6-methyl-5-{[2-(trimethylsilyl)ethoxy]methyl}-5H-pyrrolo[3,2-d]pyrimidin-7-yl)carbonyl]amino}-4-hydroxypiperidine-1-carboxylate (example D.d39) the title compound is obtained as colorless solid.

MS (ESI): m/z=570 (MH$^+$, 100%).

$^1$H-NMR (300 MHz, DMSO-d$_6$): 11.76 (s, 1H, —NH); 8.92 (s, 1H); 8.86 (d, J=7.5, 1H, —NH); 7.40 (d, J=9.9, 1H); 7.18 (d, J=13.3, 1H); 5.09 (d, J=4.6, 1H, —OH); 3.84 (s, 3H & d, J=6.8, 2H & m, 3H); 3.69 (m, 1H); 3.53 (m, 1H); 3.31 (m, 1H); 2.79 (s, 3H); 1.90 (m, 1H); 1.47 (m, 1H); 1.31 (br.s, 9H); 0.92 (m, 1H); 0.36 (m, 2H); 0.20 (m, 2H).

Example D.e40 tert-Butyl 4-[({4-[2-(cyclopropylmethoxy)-4-fluoro-5-methylphenyl]-6-methyl-5H-pyrrolo[3,2-d]pyrimidin-7-yl}carbonyl)amino]piperidine-1-carboxylate Starting from tert-butyl 4-{[(4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d40) the title compound is obtained as colorless solid.

MS (ESI): m/z=538 (MH$^+$, 100%).

$^1$H-NMR (300 MHz, DMSO-d$_6$): 11.74 (s, 1H, —NH); 8.93 (s, 1H); 8.80 (d, J=7.7, 1H, —NH); 7.54 (d, J=9.1, 1H); 7.03 (d, J=12.2, 1H); 4.06 (m, 1H); 3.87 (d, J=6.9, 2H); 3.84 (m, 2H); 3.05 (m, 2H); 2.78 (s, 3H); 2.25 (d, J=1.1, 3H); 1.92 (m, 2H); 1.42 (s, 9H & m, 2H); 0.95 (m, 1H); 0.37 (m, 2H); 0.24 (m, 2H).

Example D.e41 tert-Butyl {trans-4-[({4-[2-(cyclopropylmethoxy)-4-fluoro-5-methylphenyl]-6-methyl-5H-pyrrolo[3,2-d]pyrimidin-7-yl}carbonyl)amino]cyclohexyl}carbamate Starting from tert-butyl (trans-4-{[(4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d41) the title compound is obtained as pale yellow foam.

MS (ESI): m/z=552 (MH$^+$, 100%).

$^1$H-NMR (300 MHz, DMSO-d$_6$): 11.72 (s, 1H, —NH); 8.93 (s, 1H); 8.63 (d, J=7.7, 1H, —NH); 7.54 (dd, J=9.1, 0.6, 1H); 7.03 (d, J=11.9, 1H); 6.72 (d, J=6.9, 1H, —NH); 3.87 (d, J=6.9, 2H); 3.76 (m, 1H); 3.29 (m, 1H); 2.77 (s, 3H); 2.25 (d, J=1.1, 3H); 1.99 (m, 2H); 1.86 (m, 2H); 1.39 (s, 9H); 1.35 (m, 4H); 0.95 (m, 1H); 0.37 (m, 2H); 0.23 (m, 2H).

Example D.e42 tert-Butyl {cis-4-[({4-[2-(cyclopropyl methoxy)-4-fluoro-5-methylphenyl]-6-methyl-5H-pyrrolo[3,2-d]pyrimidin-7-yl}carbonyl)amino]cyclohexyl}carbamate Starting from tert-butyl (cis-4-{[(4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d42) the title compound is obtained as colorless viscous oil.

MS (ESI): m/z=552 (MH$^+$, 100%).

$^1$H-NMR (300 MHz, DMSO-d$_6$): 11.72 (s, 1H, —NH); 8.97 (s, 1H & d, J=7.7, 1H, —NH); 7.54 (d, J=9.7, 1H); 7.03 (d, J=12.2, 1H); 6.92 (br.s, 1H, —NH); 4.04 (m, 1H); 3.88 (d, J=6.9, 2H); 3.43 (m, 1H); 2.78 (s, 3H); 2.25 (d, J=1.1, 3H); 1.81-1.52 (m, 8H); 1.40 (s, 9H); 0.95 (m, 1H); 0.37 (m, 2H); 0.24 (m, 2H).

Example D.e43 tert-Butyl (3R*,4R*)-4-[({4-[2-(cyclopropylmethoxy)-4-fluoro-5-methylphenyl]-6-methyl-5H-pyrrolo[3,2-d]pyrimidin-7-yl}carbonyl)amino]-3-hydroxypiperidine-1-carboxylate Starting from tert-butyl (3R*,4R*)-4-{[(4-[2-(cyclopropylmethoxy)-4-fluoro-5-methylphenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate (example D.d43) the title compound is obtained as colorless foam.

MS (ESI): m/z=554 (MH$^+$, 100%).

$^1$H-NMR (300 MHz, DMSO-d$_6$): 11.74 (s, 1H, —NH); 8.93 (s, 1H); 8.84 (d, J=7.3, 1H, —NH); 7.54 (d, J=9.1, 1H); 7.03 (d, J=12.0, 1H); 5.23 (d, J=5.1, 1H, —OH); 3.99-3.74 (m, 3H); 3.87 (d, J=6.9, 2H); 3.43 (m, 1H); 2.98 (m, 1H); 2.81 (m, 1H); 2.78 (s, 3H); 2.25 (d, J=1.1, 3H); 2.06 (m, 1H); 1.42 (s, 9H); 1.37 (m, 1H); 0.94 (m, 1H); 0.37 (m, 2H); 0.24 (m, 2H).

Example D.e44 tert-Butyl 4-[({4-[2-(cyclopropylmethoxy)-5-fluoro-4-methoxyphenyl]-6-methyl-5H-pyrrolo[3,2-d]pyrimidin-7-yl}carbonyl)amino]piperidine-1-carboxylate Starting from tert-butyl 4-{[(4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d44) the title compound is obtained as pale yellow viscous oil.

MS (ESI): m/z=554 (MH$^+$, 100%); 498 (MH$^+$-C$_4$H$_8$); 454 (MH+-C$_5$H$_8$O).

$^1$H-NMR (300 MHz, DMSO-d$_6$): 11.72 (s, 1H, —NH); 8.92 (s, 1H); 8.81 (d, J=7.7, 1H, —NH); 7.47 (d, J=11.9, 1H); 6.92 (d, J=7.3, 1H); 4.05 (m, 1H); 3.97 (s, 3H); 3.94 (d, J=6.9, 2H); 3.84 (m, 2H); 3.05 (m, 2H); 2.98 (s, 3H); 1.92 (m, 2H); 1.42 (s, 9H & m, 2H); 0.96 (m, 1H); 0.38 (m, 2H); 0.25 (m, 2H).

Example D.e45 tert-Butyl {trans-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate Starting from (example D.d45) the title compound is obtained as colorless foam. The compound is further processed without characterisation.

Example D.e46 tert-Butyl {cis-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate Starting from tert-butyl (cis-4-{[(4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d46) the title compound is obtained as colorless foam.

MS (ESI): m/z=568 (MH$^+$, 100%); 512 (MH$^+$-C$_4$H$_8$); 468 (MH$^+$-C$_5$H$_8$O$_2$).

$^1$H-NMR (300 MHz, DMSO-d$_6$): 11.69 (s, 1H, —NH); 8.98 (d, J=7.8, 1H, —NH); 8.96 (s, 1H); 7.47 (d, J=11.9, 1H); 6.93 (d, J=7.1, 1H); 6.92 (br.s, 1H, —NH); 4.04 (m, 1H); 3.97 (s, 3H); 3.94 (d, J=6.9, 2H); 3.43 (m, 1H); 2.79 (s, 3H); 1.76 (m, 2H); 1.64 (m, 6H); 1.40 (s, 9H); 0.96 (m, 1H); 0.39 (m, 2H); 0.25 (m, 2H).

Example D.e47 tert-Butyl (3R*,4R*)-4-[({4-[2-(cyclopropylmethoxy)-5-fluoro-4-methoxyphenyl]-6-methyl-5H-pyrrolo[3,2-d]pyrimidin-7-yl}carbonyl)amino]-3-hydroxypiperidine-1-carboxylate Starting from tert-butyl (3R*,4R*)-4-{[(4-[2-(cyclopropylmethoxy)-5-fluoro-4-methoxyphenyl]-6-methyl-5-{[2-(trimethylsilyl)ethoxy]methyl}-5H-pyrrolo[3,2-d]pyrimidin-7-yl)carbonyl]amino}-3-hydroxypiperidine-1-carboxylate (example D.d47) the title compound is obtained as pale yellow foam.

MS (ESI): m/z=570 (MH$^+$, 100%).

$^1$H-NMR (300 MHz, DMSO-d$_6$): 11.72 (s, 1H, —NH); 8.92 (s, 1H); 8.85 (d, J=7.3, 1H, —NH); 7.42 (d, J=11.9, 1H); 6.92 (d, J=7.3, 1H); 5.23 (d, J=4.9, 1H, —OH); 3.97 (s, 3H); 3.94 (d, J=6.9, 2H & m, 2H); 3.82 (m, 1H); 3.43 (m, 1H); 2.99 (m, 1H); 2.79 (s, 3H & m, 1H); 2.06 (m, 1H); 1.42 (s, 9H & m, 1H); 0.96 (m, 1H); 0.38 (m, 2H); 0.25 (m, 2H).

Example D.e48 tert-butyl 4-[({4-[2-(cyclopropylmethoxy)-5-ethylphenyl]-6-methyl-5H-pyrrolo[3,2-d]pyrimidin-7-yl}carbonyl)amino]piperidine-1-carboxylate Starting from tert-butyl 4-{[(4-[2-(cyclopropylmethoxy)-5-ethylphenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d48) the title compound is obtained as pale yellow foam.

MS (ESI): m/z=534 (MH$^+$, 100%).

$^1$H-NMR (300 MHz, DMSO-d$_6$): 11.75 (s, 1H, —NH); 8.95 (s, 1H); 8.82 (d, J=7.7, 1H, —NH); 7.45 (d, J=2.4, 1H); 7.36 (dd, J=8.4, 2.4, 1H); 7.08 (d, J=8.4, 1H); 4.06 (m, 1H); 3.86 (d, J=6.8, 2H); 3.84 (m, 2H); 3.05 (m, 2H); 2.78 (s, 3H); 2.64 (qu, J=7.6, 2H); 1.93 (m, 2H); 1.45 (m, 2H); 1.43 (s, 9H); 1.18 (t, J=7.6, 3H); 0.94 (m, 1H); 0.36 (m, 2H); 0.23 (m, 2H).

Example D.e49 tert-Butyl {trans-4-[({4-[2-(cyclopropylmethoxy)-5-ethylphenyl]-6-methyl-5H-pyrrolo[3,2-d]pyrimidin-7-yl}carbonyl)amino]cyclohexyl}carbamate Starting from tert-butyl (trans-4-{[(4-[2-(cyclopropylmethoxy)-5-ethylphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d49) the title compound is obtained as pale yellow foam.

MS (ESI): m/z=548 (MH$^+$, 100%).

$^1$H-NMR (300 MHz, DMSO-d$_6$): 11.72 (s, 1H, —NH); 8.95 (s, 1H); 8.65 (d, J=7.7, 1H, —NH); 7.45 (d, J=2.4, 1H); 7.35 (dd, J=8.4, 2.4, 1H); 7.07 (d, J=8.4, 1H); 6.72 (d, J=7.3, 1H, —NH); 3.86 (d, J=6.8, 2H); 3.75 (m, 1H); 3.27 (m, 1H); 2.77 (s, 3H); 2.63 (qu, J=7.5, 2H); 2.00 (m, 2H); 1.85 (m, 2H); 1.39 (s, 9H); 1.34 (m, 4H); 1.17 (t, J=7.6, 3H); 0.94 (m, 1H); 0.35 (m, 2H); 0.22 (m, 2H).

Example D.e50 tert-butyl {cis-4-[({4-[2-(cyclopropylmethoxy)-5-ethylphenyl]-6-methyl-5H-pyrrolo[3,2-d]pyrimidin-7-yl}carbonyl)amino]cyclohexyl}carbamate Starting from tert-butyl (cis-4-{[(4-[2-(cyclopropylmethoxy)-5-ethylphenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d50) the title compound is obtained as colorless solid.

MS (ESI): m/z=548 (MH$^+$, 100%).

$^1$H-NMR (300 MHz, DMSO-d$_6$): 11.72 (s, 1H, —NH); 8.98 (s, 1H & d, J=7.1, 1H, —NH); 7.45 (d, J=2.4, 1H); 7.36 (dd, J=8.4, 2.4, 1H); 7.08 (d, J=8.6, 1H); 6.93 (br.s, 1H, —NH); 4.04 (m, 1H); 3.87 (d, J=6.8, 2H); 3.43 (m, 1H); 2.78

(s, 3H); 2.64 (qu, J=7.5, 2H); 1.85-1.54 (m, 8H); 1.40 (s, 9H); 1.19 (t, J=7.5, 3H); 0.94 (m, 1H); 0.36 (m, 2H); 0.23 (m, 2H).

Example D.e51 tert-Butyl (3R*,4R*)-3-[({4-[2-(cyclopropyl-methoxy)-5-ethylphenyl]-6-methyl-5H-pyrrolo[3,2-d]pyrimidin-7-yl}carbonyl)amino]-4-hydroxypyrrolidine-1-carboxylate Starting from tert-butyl (3R*,4R*)-3-{[(4-[2-(cyclopropylmethoxy)-5-ethylphenyl]-6-methyl-5-{[2-(trimethylsilyl)ethoxy]methyl}-5H-pyrrolo[3,2-d]pyrimidin-7-yl)carbonyl]amino}-4-hydroxypyrrolidine-1-carboxylate (example D.d51) the title compound is obtained as pale yellow viscous oil.

MS (ESI): m/z=536 (MH$^+$, 100%).
$^1$H-NMR (300 MHz, DMSO-d$_6$): 11.80 (s, 1H, —NH); 8.91 (s, 1H); 8.85 (br.s, 1H, —NH); 7.45 (d, J=2.4, 1H); 7.36 (dd, J=8.4, 2.4, 1H); 7.08 (d, J=8.4, 1H); 5.47 (d, J=3.8, 1H, —OH); 4.25 (m, 1H); 4.19 (m, 1H); 3.86 (d, J=6.8, 2H); 3.68 (m, 1H); 3.55 (m, 1H); 3.22 (m, 2H); 2.78 (s, 3H); 2.63 (qu, J=7.6, 2H); 1.43 (s, 9H); 1.18 (t, J=7.6, 3H); 0.94 (m, 1H); 0.36 (m, 2H); 0.23 (m, 2H).

Example D.e52 tert-Butyl 4-[({4-[2-(cyclopropylmethoxy)-5-(propan-2-yl)phenyl]-6-methyl-5H-pyrrolo[3,2-d]pyrimidin-7-yl}carbonyl)amino]piperidine-1-carboxylate Starting from tert-butyl 4-{[(4-[2-(cyclopropylmethoxy)-5-(propan-2-yl)phenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d52) the title compound is obtained as pale yellow viscous oil.

MS (ESI): m/z=548 (MH$^+$, 100%).
$^1$H-NMR (300 MHz, DMSO-d$_6$): 11.75 (s, 1H, —NH); 8.95 (s, 1H); 8.81 (d, J=7.7, 1H, —NH); 7.47 (d, J=2.4, 1H); 7.39 (dd, J=8.6, 2.4, 1H); 7.08 (d; J=8.6, 1H); 4.06 (m, 1H); 3.87 (d, J=6.8, 2H & m, 2H); 3.05 (m, 2H); 2.94 (sept, J=6.9, 1H); 2.77 (s, 3H); 1.92 (m, 2H); 1.45 (m, 2H); 1.43 (s, 9H); 1.22 (d, J=6.9, 6H); 0.94 (m, 1H); 0.36 (m, 2H); 0.23 (m, 2H).

Example D.e53 tert-Butyl {trans-4-[({4-[2-(cyclopropylmethoxy)-5-(propan-2-yl)phenyl]-6-methyl-5H-pyrrolo[3,2-d]pyrimidin-7-yl}carbonyl)amino]cyclohexyl}carbamate Starting from tert-butyl (trans-4-{[(4-[2-(cyclopropylmethoxy)-5-(propan-2-yl)phenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d53) the title compound is obtained as pale yellow viscous oil.

MS (ESI): m/z=692 (MH$^+$, 100%).
$^1$H-NMR (300 MHz, DMSO-d$_6$): 8.99 (s, 1H); 8.92 (d, J=7.7, 1H, —NH); 7.40 (dd, J=8.6, 2.4, 1H); 7.32 (d, J=2.4, 1H); 7.09 (d; J=8.6, 1H); 6.72 (br.d, J~8.6, 1H, —NH); 5.41 (d, J=11.0, 1H); 5.03 (d, J=11.0, 1H); 3.82 (dd, J=10.2, 6.6, 1H); 3.74 (dd, J=10.2, 6.9, 1H &m, 2H); 3.27 (m, 1H); 2.99-2.80 (sept, J=6.9, 1H & m, 2H); 2.90 (s, 3H); 2.01 (m, 2H); 1.86 (m, 2H); 1.39 (s, 9H); 1.37 (m, 4H); 1.22 (dd, J=6.9, 2.4, 6H); 0.89 (m, 1H); 0.49 (m, 2H); 0.32 (m, 2H); 0.05 (m, 2H); −0.19 (s, 9H).

Example D.e54 tert-Butyl {cis-4-[({4-[2-(cyclopropylmethoxy)-5-(propan-2-yl)phenyl]-6-methyl-5H-pyrrolo[3,2-d]pyrimidin-7-yl}carbonyl)amino]cyclohexyl}carbamate Starting from tert-butyl (cis-4-{[(4-[2-(cyclopropylmethoxy)-5-(propan-2-yl)phenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d54) the title compound is obtained as pale yellow viscous oil.

MS (ESI): m/z=562 (MH$^+$, 100%).
$^1$H-NMR (300 MHz, DMSO-d$_6$): 11.72 (s, 1H, —NH); 8.99 (s, 1H); 8.98 (d, J=7.1, 1H, —NH); 7.47 (d, J=2.4, 1H); 7.40 (dd, J=8.6, 2.4, 1H); 7.09 (d; J=8.6, 1H); 6.82 (br.d, J~6.0, 1H, —NH); 4.04 (m, 1H); 3.87 (d, J=6.8, 2H); 3.43 (m, 1H); 2.95 (sept, J=6.9, 1H); 2.77 (s, 3H); 1.85-1.52 (m, 8H); 1.40 (s, 9H); 1.22 (d, J=6.9, 6H); 0.94 (m, 1H); 0.36 (m, 2H); 0.23 (m, 2H).

Example D.e55 tert-Butyl 4-[({4-[2-(cyclopropylmethoxy)-5-(2-methyl-1,3-dioxolan-2-yl)phenyl]-6-methyl-5H-pyrrolo[3,2-d]pyrimidin-7-yl}carbonyl)amino]piperidine-1-carboxylate Starting from tert-butyl 4-{[(4-[2-(cyclopropylmethoxy)-5-(2-methyl-1,3-dioxolan-2-yl)phenyl]-6-methyl-5-{[2-(trimethylsilyl)ethoxy]methyl}-5H-pyrrolo[3,2-d]pyrimidin-7-yl)carbonyl]amino}piperidine-1-carboxylate (example D.d55) the title compound is obtained as pale yellow viscous oil.

MS (ESI): m/z=722 (MH$^+$, 100%).
$^1$H-NMR (400 MHz, DMSO-d$_6$): 9.08 (d, J=7.6, 1H, —NH); 9.00 (s, 1H); 7.57 (dd, J=8.7, 2.3, 1H); 7.50 (d, J=2.3, 1H); 7.15 (d, J=8.7, 1H); 5.40 (d, J=11.0, 1H); 5.04 (d, J=11.0, 1H); 4.09 (m, 1H); 4.00 (m, 2H); 3.90-3.70 (m, 6H); 3.06 (m, 2H); 2.97-2.83 (s, 3H & m, 2H); 1.99 (s, 3H); 1.94 (m, 2H); 1.46 (m, 2H); 1.43 (s, 9H); 0.90 (m, 1H); 0.49 (m, 2H); 0.33 (m, 2H); 0.07 (m, 2H); −0.20 (s, 9H).

Example D.e56 tert-Butyl {trans-4-[({4-[2-(cyclopropylmethoxy)-5-(2-methyl-1,3-dioxolan-2-yl)phenyl]-6-methyl-5H-pyrrolo[3,2-d]pyrimidin-7-yl}carbonyl)amino]cyclohexyl}carbamate Starting from tert-butyl (trans-4-{[(4-[2-(cyclopropylmethoxy)-5-(2-methyl-1,3-dioxolan-2-yl)phenyl]-6-methyl-5-{[2-(trimethylsilyl)ethoxy]methyl}-5H-pyrrolo[3,2-d]pyrimidin-7-yl)carbonyl]amino}cyclohexyl)carbamate (example D.d56) the title compound is obtained as pale yellow viscous oil.

MS (ESI): m/z=606 (MH$^+$, 100%).
$^1$H-NMR (400 MHz, DMSO-d$_6$): 11.75 (s, 1H, —NH); 8.97 (s, 1H); 8.65 (d, J=7.7, 1H, —NH); 7.66 (d, J=2.4, 1H); 7.55 (dd, J=8.7, 2.4, 1H); 7.14 (d, J=8.7, 1H); 6.72 (br.d, J~7.3, 1H, —NH); 3.99 (m, 2H); 3.90 (d, J=6.9, 2H); 3.76 (m, 1H); 3.71 (m, 2H); 3.27 (m, 1H); 2.77 (s, 3H); 2.01 (m, 2H);

1.99 (s, 3H); 1.86 (m, 2H); 1.39 (s, 9H); 1.34 (m, 4H); 0.95 (m, 1H); 0.37 (m, 2H); 0.24 (m, 2H).

Example D.e57 tert-Butyl 4-[({4-[2-(cyclopropylmethoxy)-5-methylphenyl]-2,6-dimethyl-5H-pyrrolo[3,2-d]pyrimidin-7-yl}carbonyl)amino]piperidine-1-carboxylate Starting from tert-butyl 4-{[(4-[2-(cyclopropylmethoxy)-5-methylphenyl]-2,6-dimethyl-5-{[2-(trimethylsilyl)ethoxy]methyl}-5H-pyrrolo[3,2-d]pyrimidin-7-yl)carbonyl]amino}piperidine-1-carboxylate (example D.d57) the title compound is obtained as colorless solid.

MS (ESI): m/z=534 (MH$^+$, 100%).

$^1$H-NMR (300 MHz, DMSO-d$_6$): 11.58 (s, 1H, —NH); 9.04 (d, J=7.7, 1H, —NH); 7.38 (d, J=2.2, 1H); 7.31 (dd, J=8.4, 2.2, 1H); 7.04 (d, J=8.4, 1H); 4.13-3.99 (m, 1H); 3.89-3.74 (m, 4H); 3.12 (m, 2H); 2.74 (s, 3H); 2.72 (s, 3H); 2.32 (s, 3H); 1.97-1.86 (m, 2H); 1.48 (m, 2H); 1.43 (s, 9H); 0.93 (m, 1H); 0.35 (m, 2H); 0.22 (m, 2H).

Example D.e58 tert-Butyl 4-[({4-[2-(cyclopropylmethoxy)-5-fluoro-4-methoxyphenyl]-2,6-dimethyl-5H-pyrrolo[3,2-d]pyrimidin-7-yl}carbonyl)amino]piperidine-1-carboxylate Starting from tert-butyl 4-{[(4-[2-(cyclopropylmethoxy)-5-fluoro-4-methoxyphenyl]-2,6-dimethyl-5-{[2-(trimethylsilyl)ethoxy]methyl}-5H-pyrrolo[3,2-d]pyrimidin-7-yl)carbonyl]amino}piperidine-1-carboxylate (example D.d58) the title compound is obtained as colorless foam.

MS (ESI): 568 (MH$^+$, 100%).

$^1$H-NMR (300 MHz, DMSO-d$_6$): 11.56 (s, 1H, —NH); 9.04 (d, J=7.7, 1H, —NH); 7.43 (d, J=11.7, 1H); 6.91 (d, J=7.3, 1H); 4.06 (m, 1H); 3.96 (s, 3H); 3.93 (d, J=6.9, 2H); 3.87-3.73 (m, 2H); 3.12 (m, 2H); 2.75 (s, 3H); 2.71 (s, 3); 1.98-1.85 (m, 2H); 1.46 (m, 2H); 1.42 (s, 9H); 0.95 (m, 1H); 0.38 (m, 2H); 0.24 (m, 2H).

Example D.e59 tert-Butyl 4-[({4-[2-(cyclopropylmethoxy)-4-fluoro-5-methoxyphenyl]-2,6-dimethyl-5H-pyrrolo[3,2-d]pyrimidin-7-yl}carbonyl)amino]piperidine-1-carboxylate Starting from tert-butyl 4-{[(4-[2-(cyclopropylmethoxy)-4-fluoro-5-methoxyphenyl]-2,6-dimethyl-5-{[2-(trimethylsilyl)ethoxy]methyl}-5H-pyrrolo[3,2-d]pyrimidin-7-yl)carbonyl]amino}piperidine-1-carboxylate (example D.d59) the title compound is obtained as colorless foam.

MS (ESI): m/z=568 (MH$^+$, 100%).

$^1$H-NMR (300 MHz, DMSO-d$_6$): 11.60 (s, 1H, —NH); 9.02 (d, J=7.7, 1H, —NH); 7.33 (d, J=9.9, 1H); 7.16 (d, J=13.3, 1H); 4.05 (m, 1H); 3.84 (s, 3H); 3.82 (d, J=6.8, 2H); 3.78 (m, 2H); 3.12 (m, 2H); 2.74 (s, 3H); 2.73 (s, 3H); 1.99-1.86 (m, 2H); 1.47 (m, 2H); 1.42 (s, 9H); 0.92 (m, 1H); 0.35 (m, 2H); 0.20 (m, 2H).

The following compounds were prepared analogously to the procedure described in above example D.d1

Example D.e60 tert.-Butyl 4-[({4-[2-(cyclopropylmethoxy)-5-(difluoromethyl)phenyl]-6-methyl-5H-pyrrolo[3,2-d]pyrimidin-7-yl}carbonyl)amino]piperidine-1-carboxylate Starting from 4-[2-(cyclopropylmethoxy)-5-(difluoromethyl)phenyl]-6-methyl-5H-pyrrolo[3,2d]-pyrimidine-7-carboxylic acid (example D.g1) and commercially available tert-butyl 4-aminopiperidine-1-carboxylate the title compound is obtained as pale yellow foam.

MS (ESI): m/z=556 (MH$^+$, 100%).

$^1$H-NMR (300 MHz, DMSO-d$_6$): 11.85 (s, 1H, —NH); 8.98 (s, 1H); 8.80 (d, J=7.7, 1H, —NH); 7.83 (d, J=2.0, 1H); 7.74 (dd, J=8.8, 2.0, 1H); 7.31 (d, J=8.8, 1H); 7.08 (t, J=56.0, 1H); 4.07 (m, 1H); 3.96 (d, J=6.9, 2H); 3.91-3.79 (m, 2H); 3.05 (m, 2H); 2.79 (s, 3H); 1.93 (m, 2H); 1.43 (s, 9H & m, 2H); 0.97 (m, 1H); 0.38 (m, 2H); 0.26 (m, 2H).

Example D.e61 tert-Butyl {trans-4-[({4-[2-(cyclopropylmethoxy)-5-(difluoromethyl)phenyl]-6-methyl-5H-pyrrolo[3,2-d]pyrimidin-7-yl}carbonyl)amino]cyclohexyl}carbamate Starting from 4-[2-(cyclopropylmethoxy)-5-(difluoromethyl)phenyl]-6-methyl-5H-pyrrolo[3,2-d]pyrimidine-7-carboxylic acid (example D.g1) and commercially available tert-butyl trans-(4-aminocyclohexyl)-carbamate the title compound is obtained as pale yellow foam.

MS (ESI): m/z=570 (MH$^+$, 100%).

$^1$H-NMR (300 MHz, DMSO-d$_6$): 11.82 (s, 1H, —NH); 8.98 (s, 1H); 8.64 (d, J=7.9, 1H, —NH); 7.82 (d, J=2.0, 1H); 7.74 (dd, J=8.6, 2.0, 1H); 7.31 (d, J=8.6, 1H); 7.08 (t, J=56.0, 1H); 6.72 (br.d, J=8.2, 1H, —NH); 3.96 (d, J=6.9, 2H); 3.76 (m, 1H); 3.29 (m, 1H); 2.78 (s, 3H); 1.98 (m, 2H); 1.85 (m, 2H); 1.39 (s, 9H); 1.36 (m, 4H); 0.97 (m, 1H); 0.37 (m, 2H); 0.26 (m, 2H).

Example D.e62 tert-Butyl {(1S*,2S*,4S*)-4-[({4-[2-(cyclopropylmethoxy)-5-(difluoromethyl)phenyl]-6-methyl-5H-pyrrolo[3,2-d]pyrimidin-7-yl}carbonyl)amino]-2-fluorocyclohexyl}carbamate Starting from 4-[2-(cyclopropylmethoxy)-5-(difluoromethyl)phenyl]-6-methyl-5H-pyrrolo[3,2-d]pyrimidine-7-carboxylic acid (example D.g1) and tert-butyl [(1S*,2S*,4S*)-4-amino-2-fluorocyclohexyl]carbamate (example C22) the title compound is obtained as pale yellow foam.

MS (ESI): m/z=588 (MH$^+$, 100%).

$^1$H-NMR (300 MHz, DMSO-d$_6$): 11.85 (s, 1H, —NH); 8.99 (s, 1H); 8.73 (d, J=7.7, 1H, —NH); 7.83 (d, J=2.0, 1H); 7.74 (dd, J=8.6, 2.0, 1H); 7.31 (d, J=8.6, 1H); 7.08 (t, J=56.0, 1H); 6.93 (br.s, 1H, —NH); 4.41 (m, 1H); 3.96 (d, J=6.9, 2H); 3.90 (m, 1H); 3.51 (m, 1H); 2.78 (s, 3H); 2.41 (m, 1H);

1.99-1.77 (m, 2H); 1.65 (m, 1H); 1.40 (s, 9H & m, 2H); 0.97 (m, 1H); 0.38 (m, 2H); 0.26 (m, 2H).

Example D.e63 tert-Butyl {(1S*,3S*,4S*)-4-[({4-[2-(cyclopropyl-methoxy)-5-(difluoromethyl)phenyl]-6-methyl-5H-pyrrolo[3,2-d]pyrimidin-7-yl}carbonyl)amino]-3-methylcyclohexyl}carbamate Starting from 4-[2-(cyclopropylmethoxy)-5-(difluoromethyl)phenyl]-6-methyl-5H-pyrrolo[3,2-d]pyrimidine-7-carboxylic acid (example D.g1) and tert-butyl [(1R*,3R*,4R*)-4-amino-3-methylcyclohexyl]carbamate (example C11) the title compound is obtained as pale yellow foam.

MS (ESI): m/z=584 (MH$^+$, 100%).

$^1$H-NMR (300 MHz, DMSO-d$_6$): 11.87 (s, 1H, —NH); 8.99 (s, 1H); 8.58 (d, J=8.6, 1H, —NH); 7.83 (s, 1H); 7.75 (d, J=8.8, 1H); 7.31 (d, J=8.8, 1H); 7.09 (t, J=56.2, 1H); 6.78 (d, J=7.7, 1H, —NH); 3.96 (d, J=6.8, 2H); 3.49 (m, 1H); 3.35 (m, 1H); 2.79 (s, 3H); 2.03-1.75 (m, 4H); 1.58 (m, 1H); 1.391 (s, 9H); 1.38-1.21 (m, 1H); 1.06 (m, 1H); 0.99 (m, 1H); 0.94 (d, J=6.4, 3H); 0.39 (m, 2H); 0.28 (m, 2H).

Example D.e64 tert-Butyl {(1S,3S)-3-[({4-[2-(cyclopropylmethoxy)-5-(difluoromethyl)phenyl]-6-methyl-5H-pyrrolo[3,2-d]pyrimidin-7-yl}carbonyl)amino]cyclopentyl}carbamate Starting from 4-[2-(cyclopropylmethoxy)-5-(difluoromethyl)phenyl]-6-methyl-5H-pyrrolo[3,2-d]pyrimidine-7-carboxylic acid (example D.g1) and tert-butyl [(1S,3S)-3-aminocyclopentyl]carbamate hydrochloride (example C6) the title compound is obtained as pale yellow foam.

MS (ESI): m/z=556 (MH$^+$, 100%).

$^1$H-NMR (300 MHz, DMSO-d$_6$): 11.82 (s, 1H, —NH); 8.98 (s, 1H); 8.75 (d, J=7.3, 1H, —NH); 7.83 (t, J=1.1, 1H); 7.74 (td, J=8.7, 1.1, 1H); 7.31 (d, J=8.7, 1H); 7.08 (t, J=56.0, 1H); 6.95 (br.d, J~5.5, 1H, —NH); 4.42 (m, 1H); 3.98 (m, 1H); 3.96 (d, J=7.1, 2H); 2.78 (s, 3H); 2.20-1.98 (m, 2H); 1.84 (m, 2H); 1.49 (m, 2H); 1.40 (s, 9H); 0.97 (m, 1H); 0.38 (m, 2H); 0.26 (m, 2H).

Example D.e65

N-[(1S*,3S*,4S*)-4-Azido-3-methylcyclohexyl]-4-[2-(cyclopropylmethoxy)-5-(difluoromethyl)phenyl]-6-methyl-5H-pyrrolo[3,2-d]pyrimidine-7-carboxamide Starting from 4-[2-(cyclopropylmethoxy)-5-(difluoromethyl)phenyl]-6-methyl-5H-pyrrolo[3,2-d]pyrimidine-7-carboxylic acid (example D.g1) and (1R*,3R*,4R*)-4-azido-3-methylcyclohexanamine hydrochloride (example C12) the title compound is obtained as pale yellow foam.

MS (ESI): m/z=510 (MH$^+$, 100%).

$^1$H-NMR (300 MHz, DMSO-d$_6$): 11.87 (s, 1H, —NH); 8.98 (s, 1H); 8.65 (d, J=8.4, 1H, —NH); 7.83 (s, 1H); 7.75 (d, J=8.6, 1H); 7.31 (d, J=8.6, 1H); 7.09 (t, J=55.8, 1H); 3.96 (d, J=7.1, 2H); 3.88 (m, 1H); 3.12 (m, 1H); 2.78 (s, 3H); 2.13-1.99 (m, 3H); 1.62-1.37 (m, 3H); 1.21 (m, 1H); 1.02 (d, J=6.5, 3H); 0.97 (m, 1H); 0.38 (m, 2H); 0.27 (m, 2H).

Example D.e66 tert-Butyl (2S,4S)-4-[({4-[2-(cyclopropylmethoxy)-5-(difluoromethyl)phenyl]-6-methyl-5H-pyrrolo[3,2-d]pyrimidin-7-yl}carbonyl)amino]-2-methylpyrrolidine-1-carboxylate Starting from 4-[2-(cyclopropylmethoxy)-5-(difluoromethyl)phenyl]-6-methyl-5H-pyrrolo[3,2-d]pyrimidine-7-carboxylic acid (example D.g1) and commercially available tert-butyl (2S,4S)-4-amino-2-methylpyrrolidine-1-carboxylate the title compound is obtained as pale yellow foam.

MS (ESI): m/z=557 (MH$^+$, 100%).

$^1$H-NMR (400 MHz, DMSO-d$_6$): 11.88 (s, 1H, —NH); 8.94 (s, 1H); 8.87 (d, J=6.2, 1H, —NH); 7.83 (s, 1H); 7.74 (d, J=8.7, 1H); 7.31 (d, J=8.7, 1H); 7.08 (t, J=56.0, 1H); 4.55 (m, 1H); 3.96 (d, J=7.0, 2H & m, 1H); 3.61 (m, 1H); 3.29 (m, 1H); 2.79 (s, 3H); 2.14 (m, 1H); 1.92 (m, 1H); 1.41 (s, 9H); 1.23 (d, J=5.6, 3H); 0.97 (m, 1H); 0.38 (m, 2H); 0.26 (m, 2H).

Example D.e67

N-[(1R*,2R*,4R*)-4-Azido-2-fluorocyclohexyl]-4-[2-(cyclopropylmethoxy)-5-(difluoromethyl)phenyl]-6-methyl-5H-pyrrolo[3,2-d]pyrimidine-7-carboxamide Starting from 4-[2-(cyclopropylmethoxy)-5-(difluoromethyl)phenyl]-6-methyl-5H-pyrrolo[3,2-d]pyrimidine-7-carboxylic acid (example D.g1) and (1S*,2S*,4S*)-4-azido-2-fluorocyclohexanamine hydrochloride (example C23) the title compound is obtained as pale yellow foam.

MS (ESI): m/z=514 (MH$^+$, 100%).

$^1$H-NMR (300 MHz, DMSO-d$_6$): 11.89 (s, 1H, —NH); 8.99 (s, 1H); 8.80 (d, J=8.2, 1H, —NH); 7.83 (t, J=1.0, 1H); 7.75 (td, J=8.6, 1.0, 1H); 7.31 (d, J=8.6, 1H); 7.09 (t, J=56.0, 1H); 4.69 (tdd, J=49.9, 10.0, 4.5, 1H); 4.11 (m, 1H); 3.96 (d, J=6.9, 2H); 3.69 (m, 1H); 2.79 (s, 3H); 2.43 (m, 1H); 2.06 (m, 1H); 1.95 (m, 1H); 1.68 (m, 1H); 1.50 (m, 2H); 0.98 (m, 1H); 0.39 (m, 2H); 0.26 (m, 2H).

Example D.e68 tert-Butyl {(1S*,2S*,4R*)-4-[({4-[2-(cyclopropyl-methoxy)-5-(difluoromethyl)phenyl]-6-methyl-5H-pyrrolo[3,2-d]pyrimidin-7-yl}carbonyl)amino]-2-methylcyclopentyl}carbamate Starting from 4-[2-(cyclopropylmethoxy)-5-(difluoromethyl)phenyl]-6-methyl-5H-pyrrolo[3,2-d]pyrimidine-7-carboxylic acid (example D.g1) and tert-butyl [(1S*,2S*,4R*)-4-amino-2-methylcyclopentyl]carbamate (example C33) the title compound is obtained as pale yellow foam.

MS (ESI): m/z=570 (MH$^+$, 100%).

$^1$H-NMR (300 MHz, DMSO-d$_6$): 11.83 (s, 1H, —NH); 8.99 (s, 1H); 8.78 (d, J=7.5, 1H, —NH); 7.83 (d, J=1.1, 1H); 7.74 (dd, J=8.7, 1.1, 1H); 7.31 (d, J=8.7, 1H); 7.09 (t, J=56.0, 1H); 6.87 (d, J=8.2, 1H, —NH); 4.37 (m, 1H); 3.97 (d, J=6.9, 2H); 3.55 (m, 1H); 2.78 (s, 3H); 2.30 (m, 1H); 1.95-172 (m,

3H); 1.40 (s, 9H); 1.20 (m, 1H); 1.04 (d, J=6.6, 3H); 0.98 (m, 1H); 0.39 (m, 2H); 0.27 (m, 2H).

Example D.e69

N-[(1R*,2R*,4S*)-4-Azido-2-methylcyclopentyl]-4-[2-(cyclopropylmethoxy)-5-(difluoromethyl)phenyl]-6-methyl-5H-pyrrolo[3,2-d]pyrimidine-7-carboxamide Starting from 4-[2-(cyclopropylmethoxy)-5-(difluoromethyl)phenyl]-6-methyl-5H-pyrrolo[3,2-d]pyrimidine-7-carboxylic acid (example D.g1) and (1S*,2S*,4R*)-4-azido-2-methylcyclopentanamine hydrochloride (example C34) the title compound is obtained as pale yellow foam.

MS (ESI): m/z=496 (MH+, 100%).

$^1$H-NMR (300 MHz, DMSO-d$_6$): 11.86 (s, 1H, —NH); 8.98 (s, 1H); 8.74 (d, J=7.9, 1H, —NH); 7.83 (dd, J=0.9, 0.9, 1H); 7.74 (ddd, J=8.7, 0.9, 0.9, 1H); 7.31 (d, J=8.7, 1H); 7.08 (t, J=56.0, 1H); 4.20 (m, 1H); 4.04 (m, 1H); 3.96 (d, J=7.1, 2H); 2.79 (s, 3H); 2.39 (m, 1H); 2.13 (m, 1H); 2.03-1.83 (m, 2H); 1.31 (m, 1H); 1.09 (d, J=7.1, 3H); 0.98 (m, 1H); 0.39 (m, 2H); 0.27 (m, 2H).

Example D.e70 tert-Butyl {(1S*,2S*,4S*)-4-[({4-[2-(cyclopropylmethoxy)-5-(difluoromethyl)phenyl]-6-methyl-5H-pyrrolo[3,2-d]pyrimidin-7-yl}carbonyl)amino]-2-fluorocyclopentyl}carbamate Starting from 4-[2-(cyclopropylmethoxy)-5-(difluoromethyl)phenyl]-6-methyl-5H-pyrrolo[3,2-d]pyrimidine-7-carboxylic acid (example D.g1) and tert-butyl [(1R*,2R*,4R*)-4-amino-2-fluorocyclopentyl]carbamate (example C44) the title compound is obtained as pale yellow foam.

MS (ESI): m/z=574 (MH+, 100%).

$^1$H-NMR (300 MHz, DMSO-d$_6$): 11.84 (s, 1H, —NH); 8.97 (s, 1H); 8.90 (d, J=7.5, 1H, —NH); 7.83 (~s, 1H); 7.74 (~d, J=8.6, 1H); 7.31 (d, J=8.6, 1H); 7.14 (br.d, J~5.1, 1H, —NH); 7.08 (t, J=55.9, 1H); 4.93 (dm, J=52.2, 1H); 4.60 (m, 1H); 4.09 (m, 1H); 3.96 (d, J=6.9, 2H); 2.79 (s, 3H); 2.44 (m, 1H); 2.03 (m, 2H); 1.83 (m, 1H); 1.41 (s, 9H); 0.98 (m, 1H); 0.38 (m, 2H); 0.26 (m, 2H).

Example D.e71

N-[(1R*,2R*,4R*)-4-azido-2-fluorocyclopentyl]-4-[2-(cyclopropylmethoxy)-5-(difluoromethyl)phenyl]-6-methyl-5H-pyrrolo[3,2-d]pyrimidine-7-carboxamide Starting from 4-[2-(cyclopropylmethoxy)-5-(difluoromethyl)phenyl]-6-methyl-5H-pyrrolo[3,2-d]pyrimidine-7-carboxylic acid (example D.g1) and (1R*,2R*,4R*)-4-azido-2-fluorocyclopentanamine hydrochloride (example C45) the title compound is obtained as pale yellow foam.

MS (ESI): m/z=500 (MH+, 100%).

$^1$H-NMR (300 MHz, DMSO-d$_6$): 11.90 (s, 1H, —NH); 8.99 (s, 1H); 8.85 (d, J=7.5, 1H, —NH); 7.83 (~s, 1H); 7.74 (~d, J=8.7, 1H); 7.31 (d, J=8.7, 1H); 7.08 (t, J=56.0, 1H); 5.16 (dm, J=53.7, 1H); 4.59 (m, 1H); 4.37 (m, 1H); 3.96 (d, J=7.1, 2H); 2.79 (s, 3H); 2.67-2.47 (m, 1H); 2.26-1.86 (m, 3H); 0.97 (m, 1H); 0.38 (m, 2H); 0.26 (m, 2H).

Example D.e72 tert-Butyl {(1S*,2R*,4S*)-4-[({4-[2-(cyclopropylmethoxy)-5-(difluoromethyl)phenyl]-6-methyl-5H-pyrrolo[3,2-d]pyrimidin-7-yl}carbonyl)amino]-2-fluorocyclohexyl}carbamate Starting from 4-[2-(cyclopropylmethoxy)-5-(difluoromethyl)phenyl]-6-methyl-5H-pyrrolo[3,2-d]pyrimidine-7-carboxylic acid (example D.g1) and tert-butyl [(1R*,2S*,4R*)-4-amino-2-fluorocyclohexyl]carbamate (example C55) the title compound is obtained as pale yellow foam.

HR-MS (ESI): m/z=588.2797 ([MH]+, C$_{30}$H$_{37}$F$_3$N$_5$O$_4^+$, calc. 588.2792).

$^1$H-NMR (400 MHz, DMSO-d$_6$): 11.88 (s, 1H, —NH); 8.99 (s, 1H); 8.63 (d, J=7.9, 1H, —NH); 7.83 (s, 1H); 7.75 (d, J=8.7, 1H); 7.31 (d, J=8.7, 1H); 7.09 (t, J=55.8, 1H); 6.97 (d, J=7.7, 1H); 4.86 (~d, J=50.3, 1H); 4.12 (m, 1H); 3.96 (d, J=7.1, 2H); 3.55 (m, 1H); 2.79 (s, 3H); 2.30 (m, 1H); 1.99 (m, 1H); 1.85-1.60 (m, 3H); 1.55 (m, 1H); 1.41 (s, 9H); 0.95 (m, 1H); 0.39 (m, 2H); 0.27 (m, 2H).

Example D.e73

N-[(1S*,2R*,4S*)-4-Azido-2-fluorocyclohexyl]-4-[2-(cyclopropylmethoxy)-5-(difluoromethyl)phenyl]-6-methyl-5H-pyrrolo[3,2-d]pyrimidine-7-carboxamide Starting from 4-[2-(cyclopropylmethoxy)-5-(difluoromethyl)phenyl]-6-methyl-5H-pyrrolo[3,2-d]pyrimidine-7-carboxylic acid (example D.g1) and (1R*,2S*,4R*)-4-azido-2-fluorocyclohexanamine hydrochloride (example C56) the title compound is obtained as pale yellow foam.

HR-MS (ESI): m/z=514.2176 ([MH]+, C$_{25}$H$_{27}$F$_3$N$_7$O$_2^+$, calc. 514.2173).

$^1$H-NMR (400 MHz, DMSO-d$_6$): 11.92 (s, 1H, —NH); 8.99 (s, 1H); 8.98 (d, J=6.9, 1H, —NH); 7.84 (~s, 1H); 7.75 (~d, J=8.7, 1H); 7.32 (d, J=8.7, 1H); 7.09 (t, J=56.0, 1H); 4.99 (~d, J=50.1, 1H); 4.20 (dm, J=31.9, 1H); 3.97 (d, J=7.0, 2H); 3.77 (m, 1H); 2.80 (s, 3H); 2.33 (m, 1H); 2.05 (m, 1H); 1.96-1.67 (m, 3H); 1.59 (m, 1H); 0.98 (m, 1H); 0.39 (m, 2H); 0.28 (m, 2H).

Example D.f1

4-[5-(Cyclopropylmethoxy)-1,3-benzodioxol-4-yl]-6-methyl-N-piperidin-4-yl-5H-pyrrolo[3,2-d]pyrimidine-7-carboxamide hydrochloride tert-Butyl 4-[({4-[5-(cyclopropylmethoxy)-1,3-benzodioxol-4-yl]-6-methyl-5H-pyrrolo[3,2-d]pyrimidin-7-yl}carbonyl)amino]piperidine-1-carboxylate from example D.e1 (2.72 g; 4.95 mmol) is dissolved in dry 2-propanol (50 mL). After addition of 4M HCl in dioxane (5.0 mL) the stirred reaction mixture is heated to 80° C. for two hours. At ambient temperature tert.-butyl methyl ether (100 mL) is added. The precipitated product is isolated by suction filtration, washed with several portions of tert.-butyl methyl ether and dried in high vacuo at 40° C. to yield the title compound as yellow solid.

MS (ESI): m/z=450 (MH+, 100%).

$^1$H-NMR (300 MHz, DMSO-d$_6$): 12.38 (s, 1H, —NH); 9.03 (s, 1H); 9.00 (br.s, 2H, —NH$_2^+$); 8.66 (d, J=7.5, 1H,

—NH); 7.04 (d, J=8.6, 1H); 6.58 (d, J=8.6, 1H); 6.03 (s, 2H); 4.15 (m, 1H); 3.78 (d, J=6.8, 2H); 3.31 (m, 2H); 3.08 (m, 2H); 2.80 (s, 3H); 2.13 (m, 2H); 1.79 (m, 2H); 0.90 (m, 1H); 0.32 (m, 2H); 0.15 (m, 2H).

The following compounds were prepared analogously to the procedure described in above example D.f1.

Example D.f2

N-(trans-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride Starting from tert-butyl {trans-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate (example D.e2) the title compound is obtained as yellow solid.

MS (ESI): m/z=464 (MH$^+$, 100%).

$^1$H-NMR (300 MHz, DMSO-d$_6$): 12.27 (s, 1H, —NH); 8.98 (s, 1H); 8.54 (d, J=7.9, 1H, —NH); 8.04 (br.d, J~4.8, 3H, —NH$_3^+$); 7.04 (d, J=8.6, 1H); 6.57 (d, J=8.6, 1H); 6.02 (s, 2H); 3.80 (m, 1H); 3.77 (d, J=6.8, 2H); 3.09 (m, 1H); 2.79 (s, 3H); 2.04 (m, 4H); 1.47 (m, 4H); 0.89 (m, 1H); 0.31 (m, 2H); 0.14 (m, 2H).

Example D.f3

N-(cis-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride Starting from tert-butyl {cis-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate (example D.e3) the title compound is obtained as yellow solid.

MS (ESI): m/z=464 (MH$^+$, 100%).

$^1$H-NMR (300 MHz, DMSO-d$_6$): 12.40 (s, 1H, —NH); 9.10 (s, 1H); 8.91 (d, J=7.5, 1H, —NH); 8.15 (br.s, 3H, —NH$_3^+$); 7.05 (d, J=8.6, 1H); 6.58 (d, J=8.6, 1H); 6.04 (s, 2H); 4.12 (m, 1H); 3.79 (d, J=6.8, 2H); 3.17 (m, 1H); 2.81 (s, 3H); 1.96-1.64 (m, 8H); 0.91 (m, 1H); 0.33 (m, 2H); 0.16 (m, 2H).

Example D.f4

4-[5-(cyclopropylmethoxy)-1,3-benzodioxol-4-yl]-6-methyl-N-[(3R)pyrrolidin-3-yl]-5H-pyrrolo[3,2-d]pyrimidine-7-carboxamide hydrochloride Starting from tert-butyl (3R)-3-[({4-[5-(cyclopropylmethoxy)-1,3-benzodioxol-4-yl]-6-methyl-5H-pyrrolo[3,2-d]pyrimidin-7-yl}carbonyl)amino]pyrrolidine-1-carboxylate (example D.e4) the title compound is obtained as yellow solid.

MS (ESI): m/z=436 (MH$^+$, 100%).

$^1$H-NMR (300 MHz, DMSO-d$_6$): 12.39 (s, 1H, —NH); 9.32 (br.s, 2H, —NH$_2^+$); 9.02 (s, 1H); 8.80 (d, J=6.8, 1H, —NH); 7.04 (d, J=8.6, 1H); 6.58 (d, J=8.6, 1H); 6.03 (s, 2H); 4.63 (m, 1H); 3.78 (d, 6.8, 2H); 3.52 (m, 1H); 3.39 (m, 1H); 3.26 (m, 1H); 3.17 (m, 1H); 2.79 (s, 3H); 2.34 (m, 1H); 2.01 (m, 1H); 0.89 (m, 1H); 0.31 (m, 2H); 0.14 (m, 2H).

Example D.f5

4-[5-(cyclopropylmethoxy)-1,3-benzodioxol-4-yl]-N-[(3R*,4R*)-4-hydroxypyrrolidin-3-yl]-6-methyl-5H-pyrrolo[3,2-d]pyrimidine-7-carboxamide hydrochloride Starting from tert-butyl (3R*,4R*)-3-[({4-[5-(cyclopropylmethoxy)-1,3-benzodioxol-4-yl]-6-methyl-5H-pyrrolo[3,2-d]pyrimidin-7-yl}carbonyl)amino]-4-hydroxypyrrolidine-1-carboxylate (example D.e5) the title compound is obtained as yellow solid.

MS (ESI): m/z=452 (MH$^+$, 100%).

$^1$H-NMR (300 MHz, DMSO-d$_6$, MeOH-d$_4$): 9.04 (s, 1H); 7.05 (d, J=8.6, 1H); 6.60 (d, J=8.6, 1H); 6.04 (s, 2H); 4.43 (m, 2H); 3.79 (d, J=6.9, 2H); 3.67 (m, 1H); 3.47 (m, 1H); 3.33 (m, 1H); 3.20 (m, 1H); 2.81 (s, 3H); 0.91 (m, 1H); 0.33 (m, 2H); 0.16 (m, 2H).

Example D.f6

4-[2-(Cyclopropylmethoxy)-4-fluorophenyl]-6-methyl-N-piperidin-4-yl-5H-pyrrolo[3,2-d]pyrimidine-7-carboxamide hydrochloride Starting from tert-butyl 4-[({4-[2-(cyclopropylmethoxy)-4-fluorophenyl]-6-methyl-5H-pyrrolo[3,2-d]pyrimidin-7-yl}carbonyl)amino]piperidine-1-carboxylate (example D.e6) the title compound is obtained as yellow solid.

MS (ESI): m/z=424 (MH$^+$, 100%).

$^1$H-NMR (300 MHz, DMSO-d$_6$): 12.15 (s, 1H, —NH); 9.03 (s. 1H); 8.99 (br.s, 2H, —NH$_2^+$); 8.71 (d, J=7.7, 1H, —NH); 7.68 (dd, J=8.4, 6.9, 1H); 7.12 (dd, J=11.7, 2.4, 1H); 6.99 (ddd, J=8.4, 8.4, 2.4, 1H); 4.15 (m, 1H); 3.93 (d, J=7.1, 2H); 3.31 (m, 2H); 3.07 (m, 2H); 2.80 (s, 3H); 2.13 (m, 2H); 1.79 (m, 2H); 0.96 (m, 1H); 0.38 (m, 2H): 0.26 (m, 2H).

Example D.f7

N-(trans-4-aminocyclohexyl)-4-[2-(cyclopropylmethoxy)-4-fluorophenyl]-6-methyl-5H-pyrrolo[3,2-d]pyrimidine-7-carboxamide hydrochloride Starting from tert-butyl {trans-4-[({4-[2-(cyclopropylmethoxy)-4-fluorophenyl]-6-methyl-5H-pyrrolo[3,2-d]pyrimidin-7-yl}carbonyl)amino]cyclohexyl}carbamate (example D.e7) the title compound is obtained as yellow solid.

MS (ESI): m/z=438 (MH$^+$, 100%).

$^1$H-NMR (300 MHz, DMSO-d$_6$): 12.18 (s, 1H, —NH); 9.00 (s, 1H); 8.56 (d, J=7.8, 1H, —NH); 8.10 (br.s, 3H, —NH$_3^+$); 7.68 (dd, 8.4, 6.9, 1H); 7.12 (dd, 11.7, 2.4, 1H); 7.00 (ddd, 8.4, 8.4, 2.4, 1H); 3.93 (d, J=6.9, 2H); 3.81 (m, 1H); 3.08 (m, 1H); 2.81 (s, 3H); 2.04 (m, 4H); 1.47 (m, 4H); 0.96 (m, 1H); 0.38 (m, 2H); 0.26 (m, 2H).

Example D.f8

N-(cis-4-aminocyclohexyl)-4-[2-(cyclopropylmethoxy)-4-fluorophenyl]-6-methyl-5H-pyrrolo[3,2-d]pyrimidine-7-carboxamide hydrochloride Starting from tert-butyl {cis-4-[({4-[2-(cyclopropylmethoxy)-4-fluorophenyl]-6-methyl-5H-pyrrolo[3,2-d]pyrimidin-7-yl}carbonyl)amino]cyclohexyl}carbamate (example D.e8) the title compound is obtained as yellow solid.

MS (ESI): m/z=438 (MH+, 100%).

$^1$H-NMR (300 MHz, DMSO-$d_6$): 12.15 (s, 1H, —NH); 9.09 (s, 1H); 8.97 (d, J=7.5, 1H, —NH); 8.14 (br.s, 3H, —NH$_3^+$); 7.69 (dd, 8.6, 6.9, 1H); 7.12 (dd, 11.7, 2.4, 1H); 7.00 (ddd, 8.6, 8.6, 2.4, 1H); 4.13 (m, 1H); 3.93 (d, J=7.1, 2H); 3.18 (m, 1H); 2.81 (s, 3H); 1.87 (m, 4H); 1.74 (m, 4H); 0.97 (m, 1H); 0.38 (m, 2H); 0.26 (m, 2H).

Example D.f9

4-[2-(Cyclopropylmethoxy)-4-fluorophenyl]-6-methyl-N-[(3R)-pyrrolidin-3-yl]-5H-pyrrolo[3,2-d]pyrimidine-7-carboxamide hydrochloride Starting from tert-butyl (3R)-3-[({4-[2-(cyclopropylmethoxy)-4-fluorophenyl]-6-methyl-5H-pyrrolo[3,2-d]pyrimidin-7-yl}carbonyl)amino]pyrrolidine-1-carboxylate (example D.e9) the title compound is obtained as yellow solid.

MS (ESI): m/z=410 (MH+, 100%).

$^1$H-NMR (300 MHz, DMSO-$d_6$): 12.15 (s, 1H, —NH); 9.31 (br.s, 2H, —NH$_2^+$); 9.01 (s, 1H); 8.85 (d, J=6.6, 1H, —NH); 7.68 (dd, J=8.4, 6.9, 1H); 7.11 (dd, J=11.7, 2.4, 1H); 6.99 (ddd, J=8.4, 8.4, 2.4, 1H); 4.63 (m, 1H); 3.93 (d, J=7.1, 2H); 3.51 (m, 1H); 3.39 (m, 1H); 3.27 (m, 1H); 3.16 (m, 1H); 2.80 (s. 3H); 2.35 (m, 1H); 2.01 (m, 1H); 0.96 (m, 1H); 0.38 (m, 2H); 0.25 (m, 2H).

Example D.f10

4-[2-(Cyclopropylmethoxy)-4-fluorophenyl]-N-[(3R*,4R*)-4-hydroxypyrrolidin-3-yl]-6-methyl-5H-pyrrolo[3,2-d]pyrimidine-7-carboxamide hydrochloride Starting from tert-butyl (3R*,4R*)-3-[({4-[2-(cyclopropylmethoxy)-4-fluorophenyl]-6-methyl-5H-pyrrolo[3,2-d]pyrimidin-7-yl}carbonyl)amino]-4-hydroxypyrrolidine-1-carboxylate (example De10) the title compound is obtained as yellow solid.

MS (ESI): m/z=426 (MH+, 100%).

$^1$H-NMR (300 MHz, DMSO-$d_6$): 12.07 (s, 1H, —NH); 9.42 (br.s, 2H, —NH$_2^+$); 8.99 (s, 1H); 8.85 (d, J=6.0, 1H, —NH); 7.68 (dd, J=8.4, 6.9, 1H); 7.11 (dd, J=11.7, 2.4, 1H); 6.98 (ddd, J=8.4, 8.4, 2.4, 1H); 4.53-4.34 (m, 2H); 3.92 (d, 7.1, 2H); 3.63 (m, 1H); 3.43 (m, 1H); 3.27 (m, 1H); 3.16 (m, 1H); 2.80 (s. 3H); 0.95 (m, 1H); 0.37 (m, 2H); 0.26 (m, 2H).

Example D.f11

4-[2-(Cyclopropylmethoxy)-4-fluorophenyl]-N-[(3R*,4S*)-3-hydroxypiperidin-4-yl]-6-methyl-5H-pyrrolo[3,2-d]pyrimidine-7-carboxamide hydrochloride Starting from tert-butyl (3S*,4S*)-4-[({4-[2-(cyclopropylmethoxy)-4-fluorophenyl]-6-methyl-5H-pyrrolo[3,2-d]pyrimidin-7-yl}carbonyl)amino]-3-hydroxypiperidine-1-carboxylate (example D.e11) the title compound is obtained as yellow solid.

MS (ESI): m/z=440 (MH+, 100%).

$^1$H-NMR (300 MHz, DMSO-$d_6$): 12.20 (s, 1H, —NH); [9.37 (br. s), 9.04 (br. s), 2H, —NH$_2^+$]; 9.04 (s, 1H); 8.78 (d, J=7.3, 1H, —NH); 7.69 (dd, J=8.6, 6.9, 1H); 7.12 (dd, J=11.7, 2.4, 1H); 7.00 (ddd, 8.6, 8.6, 2.4, 1H); 4.02 (m, 1H); 3.93 (d, 7.1, 2H); 3.63 (m, 1H); 3.88 (m, 1H); 3.26 (m, 2H); 3.05 (m, 1H); 2.86 (m, 1H); 2.82 (s. 3H); 2.24 (m, 1H); 1.76 (m, 1H); 0.97 (m, 1H); 0.38 (m, 2H); 0.27 (m, 2H).

Example D.f12

4-(2-Cyclopropylmethoxy-5-fluoro-phenyl)-6-methyl-5H-pyrrolo[3,2-d]pyrimidine-7-carboxylic acid piperidin-4-ylamide hydrochloride Starting from tert-butyl 4-({1-[4-(2-Cyclopropylmethoxy-5-fluoro-phenyl)-6-methyl-5H-pyrrolo[3,2-d]-pyrimidin-7-yl]-methanoyl}-amino)-piperidine-1-carboxylate (example D.e12) the title compound is obtained as yellow solid.

MS (ESI): m/z=424 (MH+, 100%).

$^1$H-NMR (300 MHz, DMSO-$d_6$): 12.03 (br.s, 1H, —NH); 9.02 (s, 1H); 8.78 (br.s, 2H, —NH$_2^+$); 8.75 (d, J=6.5, 1H, —NH); 7.44 (dd, J=9.0, 3.2, 1H); 7.40 (ddd, J=9.1, 8.2, 3.2, 1H); 7.20 (dd, J=9.1, 4.4, 1H); 4.15 (m, 1H); 3.88 (d, J=7.0, 2H); 3.32 (m, 2H); 3.08 (m, 2H); 2.80 (s, 3H); 2.13 (m, 2H); 1.78 (m, 2H); 0.94 (m, 1H); 0.36 (m, 2H); 0.23 (m, 2H).

Example D.f13

N-(trans-4-aminocyclohexyl)-4-[2-(cyclopropylmethoxy)-5-fluorophenyl]-6-methyl-5H-pyrrolo[3,2-d]pyrimidine-7-carboxamide hydrochloride Starting from tert-butyl {trans-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate (example D.e13) the title compound is obtained as yellow solid.

MS (ESI): m/z=438 (MH+, 100%).

$^1$H-NMR (300 MHz, DMSO-$d_6$): 12.04 (s, 1H, —NH); 8.99 (s, 1H); 8.60 (d, J=7.9, 1H, —NH); 8.07 (br.s, 3H, —NH$_3^+$); 7.44 (dd, J=8.4, 3.2, 1H); 7.39 (ddd, J=8.9, 8.3, 3.2, 1H); 7.20 (dd, J=8.9, 4.3, 1H); 3.88 (d, J=7.1, 2H); 3.81 (m, 1H); 3.09 (m, 1H); 2.80 (s, 3H); 2.04 (m, 4H); 1.47 (m, 4H); 0.94 (m, 1H); 0.36 (m, 2H); 0.23 (m, 2H).

Example D.f14

N-(cis-4-aminocyclohexyl)-4-[2-(cyclopropylmethoxy)-5-fluorophenyl]-6-methyl-5H-pyrrolo[3,2-d]pyrimidine-7-carboxamide hydrochloride Starting from tert-butyl {cis-4-[({4-[2-(cyclopropylmethoxy)-5-fluorophenyl]-6-methyl-5H-pyrrolo[3,2-d]-pyrimidin-7-yl}carbonyl)amino]cyclohexyl}carbamate (example D.e14) the title compound is obtained as yellow solid.

MS (ESI): m/z=438 (MH+, 100%).

$^1$H-NMR (300 MHz, DMSO-$d_6$): 12.10 (br.s, 1H, —NH); 9.08 (s, 1H); 8.98 (d, J=7.5, 1H, —NH); 8.15 (br.s, 3H, —NH$_3^+$); 7.46 (dd, J=8.9, 3.3, 1H); 7.41 (ddd, J=8.9, 8.6, 3.3, 1H); 7.21 (dd, J=9.1, 4.4, 1H); 4.12 (m, 1H); 3.89 (d, J=6.9, 2H); 3.18 (m, 1H); 2.81 (s, 3H); 1.95-1.67 (m, 8H); 0.95 (m, 1H); 0.36 (m, 2H); 0.23 (m, 2H).

Example D.f15

4-[2-(cyclopropylmethoxy)-5-fluorophenyl]-6-methyl-N-[(3R)-pyrrolidin-3-yl]-5H-pyrrolo[3,2-d]pyrimidine-7-carboxamide hydrochloride Starting from tert-butyl (3R)-3-[({4-[2-(cyclopropylmethoxy)-5-fluorophenyl]-6-methyl-5H-pyrrolo[3,2-d]pyrimidin-7-yl}carbonyl)amino]pyrrolidine-1-carboxylate (example D.e15) the title compound is obtained as yellow solid.

MS (ESI): m/z=410 (MH+, 100%).

¹H-NMR (300 MHz, DMSO-d₆): 12.15 (s, 1H, —NH); 9.34 (br.s, 2H, —NH₂⁺); 9.02 (s, 1H); 8.86 (d, J=6.6, 1H, —NH); 7.46 (dd, J=8.9, 3.2, 1H); 7.41 (ddd, J=9.1, 8.4, 3.2, 1H); 7.21 (dd, J=9.1, 4.4, 1H); 4.64 (m, 1H); 3.89 (d, J=6.9, 2H); 3.50 (m, 1H); 3.39 (m, 1H); 3.27 (m, 1H); 3.16 (m, 1H); 2.81 (s, 3H); 2.35 (m, 1H); 2.01 (m, 1H); 0.94 (m, 1H); 0.35 (m, 2H); 0.23 (m, 2H).

Example D.f16

4-[2-(cyclopropylmethoxy)-5-fluorophenyl]-N-[(3R*,4R*)-3-hydroxypiperidin-4-yl]-6-methyl-5H-pyrrolo[3,2-d]pyrimidine-7-carboxamide hydrochloride Starting from tert-butyl (3R*,4R*)-4-[({4-[2-(cyclopropylmethoxy)-5-fluorophenyl]-6-methyl-5H-pyrrolo[3,2-d]pyrimidin-7-yl}carbonyl)amino]-3-hydroxypiperidine-1-carboxylate (example D.e16) the title compound is obtained as yellow solid.

MS (ESI): m/z=440 (MH+, 100%).

¹H-NMR (300 MHz, DMSO-d₆, MeOH-d₄): 9.05 (s, 1H); 7.46 (ddd, J=9.1, 8.8, 3.1, 1H); 7.40 (dd, J=8.2, 3.1, 1H); 7.22 (dd, J=9.1, 4.4, 1H); 4.03 (m, 1H); 3.90 (d, J=6.9, 2H & m, 1H); 3.30 (m, 1H); 3.25 (m, 1H); 3.09 (m, 1H); 2.90 (m, 1H); 2.82 (s, 3H); 2.27 (m, 1H); 1.76 (m, 1H); 0.95 (m, 1H); 0.37 (m, 2H); 0.24 (m, 2H).

Example D.f17

4-(2-Ethoxy-5-fluorophenyl)-6-methyl-N-(piperidin-4-yl)-5H-pyrrolo[3,2-d]pyrimidine-7-carboxamide hydrochloride Starting from tert-butyl 4-({[4-(2-ethoxy-5-fluorophenyl)-6-methyl-5H-pyrrolo[3,2-d]pyrimidin-7-yl]carbonyl}amino)piperidine-1-carboxylate (example D.e17) the title compound is obtained as yellow solid.

MS (ESI): m/z=398 (MH+, 100%).

¹H-NMR (300 MHz, DMSO-d₆): 12.11 (br.s, 1H, —NH); 9.02 (s, 1H); 8.96 (br.s, 2H, —NH₂⁺); 8.72 (d, J=7.5, 1H, —NH); 7.45 (ddd, J=9.1, 8.9, 3.3, 1H); 7.41 (dd, J=8.2, 3.3, 1H); 7.24 (dd, J=9.1, 4.4, 1H); 4.14 (m, 1H); 4.08 (qu, J=6.9, 2H); 3.31 (m, 2H); 3.08 (m, 2H); 2.80 (s, 3H); 2.12 (m, 2H); 1.78 (m, 2H); 1.11 (t, J=6.9, 3H).

Example D.f18

4-[2-(Cyclopropylmethoxy)-4-methoxyphenyl]-6-methyl-N-piperidin-4-yl-5H-pyrrolo[3,2-d]pyrimidine-7-carboxamide hydrochloride Starting from tert-butyl 4-[({4-[2-(cyclopropylmethoxy)-4-methoxyphenyl]-6-methyl-5H-pyrrolo[3,2-d]pyrimidin-7-yl}carbonyl)amino]piperidine-1-carboxylate (example D.e18) the title compound is obtained as yellow solid.

MS (ESI): m/z=436 (MH+, 100%).

¹H-NMR (300 MHz, DMSO-d₆): 12.28 (br.s, 1H, —NH); 9.04 (s, 1H); 8.98 (br.s, 2H, —NH₂⁺); 8.66 (d, J=7.5, 1H, —NH); 7.62 (d, J=8.4, 1H); 6.77 (dd, J=8.4, 2.2, 2H); 6.73 (d, J=2.2, 1H); 4.03 (m, 1H); 3.93 (d, J=6.9, 2H); 3.88 (s, 3H); 3.31 (m, 2H); 3.08 (m, 2H); 2.82 (s, 3H); 2.12 (m, 2H); 1.79 (m, 2H); 0.97 (m, 1H); 0.39 (m, 2H); 0.27 (m, 2H).

Example D.f19

N-(trans-4-aminocyclohexyl)-4-[2-(cyclopropylmethoxy)-4-methoxyphenyl]-6-methyl-5H-pyrrolo[3,2-d]pyrimidine-7-carboxamide hydrochloride Starting from tert-butyl {trans-4-[({4-[2-(cyclopropylmethoxy)-4-methoxyphenyl]-6-methyl-5H-pyrrolo[3,2-d]pyrimidin-7-yl}carbonyl)amino]cyclohexyl}carbamate (example De1 9) the title compound is obtained as yellow solid.

MS (ESI): m/z=450 (MH+, 100%).

¹H-NMR (300 MHz, DMSO-d₆): 12.39 (s, 1H, —NH); 9.03 (s, 1H); 8.48 (d, J=7.7, 1H, —NH); 8.11 (br.d, J~4.2, 3H, —NH₃⁺); 7.62 (d, J=8.4, 1H); 6.78 (dd, J=8.4, 2.2, 1H); 6.74 (d, J=2.2, 1H); 3.94 (d, J=6.9, 2H); 3.88 (s, 3H); 3.81 (m, 1H); 3.08 (m, 1H); 2.83 (s, 3H); 2.04 (m, 4H); 1.47 (m, 4H); 0.97 (m, 1H); 0.39 (m, 2H); 0.27 (m, 2H).

Example D.f20

N-(cis-4-aminocyclohexyl)-4-[2-(cyclopropylmethoxy)-4-methoxyphenyl]-6-methyl-5H-pyrrolo[3,2-d]pyrimidine-7-carboxamide hydrochloride Starting from tert-butyl {cis-4-[({4-[2-(cyclopropylmethoxy)-4-methoxyphenyl]-6-methyl-5H-pyrrolo[3,2-d]pyrimidin-7-yl}carbonyl)amino]cyclohexyl}carbamate (example D.e20) the title compound is obtained as yellow solid.

MS (ESI): m/z=450 (MH+, 100%).

¹H-NMR (300 MHz, DMSO-d₆): 12.35 (br.s, 1H, —NH); 9.14 (s, 1H); 8.94 (d, J=7.7, 1H, —NH); 8.19 (br.s, 3H, —NH₃⁺); 7.63 (d, J=8.4, 1H); 6.78 (dd, J=8.4, 2.2, 2H); 6.75 (d, J=2.2, 1H); 4.14 (m, 1H); 3.94 (d, J=6.9, 2H); 3.88 (s, 3H); 3.18 (m, 1H); 2.83 (s, 3H); 1.96-1.66 (m, 8H); 0.98 (m, 1H); 0.39 (m, 2H); 0.28 (m, 2H).

Example D.f21

4-[2-(Cyclopropylmethoxy)-4-methoxyphenyl]-6-methyl-N-[(3R)-pyrrolidin-3-yl]-5H-pyrrolo[3,2-d]pyrimidine-7-carboxamide hydrochloride Starting from tert-butyl (3R)-3-[({4-[2-(cyclopropylmethoxy)-4-methoxyphenyl]-6-methyl-5H-pyrrolo[3,2-d]pyrimidin-7-yl}carbonyl)amino]pyrrolidine-1-carboxylate (example D.e21) the title compound is obtained as yellow solid.

MS (ESI): m/z=422 (MH+, 100%).

¹H-NMR (300 MHz, DMSO-d₆): 12.28 (br.s, 1H, —NH); 9.31 (br.s, 2H, —NH₂⁺); 9.02 (s, 1H); 8.81 (d, J=6.8, 1H, —NH); 7.63 (d, J=8.4, 1H); 6.77 (dd, J=8.4, 2.2, 2H); 6.73 (d, J=2.2, 1H); 4.63 (m, 1H); 3.93 (d, J=7.1, 2H); 3.88 (s, 3H); 3.51 (m, 1H); 3.39 (m, 1H); 3.27 (m, 1H); 3.16 (m, 1H); 2.82 (s, 3H); 2.35 (m, 1H); 2.01 (m, 1H); 0.97 (m, 1H); 0.38 (m, 2H); 0.27 (m, 2H).

Example D.f22

4-[2-(cyclopropylmethoxy)-4-methoxyphenyl]-N-[(3R*,4R*)-4-hydroxypyrrolidin-3-yl]-6-methyl-5H-pyrrolo[3,2-d]pyrimidine-7-carboxamide hydrochloride Starting from tert-butyl (3R*,4R*)-3-[({4-[2-(cyclopropylmethoxy)-4-methoxyphenyl]-6-methyl-5H-pyrrolo[3,2-d]

pyrimidin-7-yl}carbonyl)amino]-4-hydroxypyrrolidine-1-carboxylate (example D.e22) the title compound is obtained as yellow solid.

MS (ESI): m/z=438 (MH$^+$, 100%).

$^1$H-NMR (300 MHz, DMSO-d$_6$): 12.36 (br.s, 1H, —NH); [9.64 (br.s, 1H), 9.48 (br.s, 1H), —NH$_2^+$]; 9.01 (s, 1H); 8.78 (d, J=6.2, 1H, —NH); 7.63 (d, J=8.4, 1H); 6.77 (dd, J=8.4, 2.2, 2H); 6.74 (d, J=2.2, 1H); 4.39 (m, 2H); 3.94 (d, J=6.9, 2H); 3.88 (s, 3H); 3.63 (m, 1H); 3.43 (m, 1H); 3.26 (m, 1H); 3.15 (m, 1H); 2.82 (s, 3H); 0.97 (m, 1H); 0.38 (m, 2H); 0.27 (m, 2H).

Example D.f23

4-[2-(Cyclopropylmethoxy)-5-methoxyphenyl]-6-methyl-N-piperidin-4-yl-5H-pyrrolo[3,2-d]pyrimidine-7-carboxamide hydrochloride Starting from tert-butyl 4-[({4-[2-(cyclopropylmethoxy)-5-methoxyphenyl]-6-methyl-5H-pyrrolo[3,2-d]pyrimidin-7-yl}carbonyl)amino]piperidine-1-carboxylate (example D.e23) the title compound is obtained as yellow solid.

MS (ESI): m/z=436 (MH$^+$, 100%).

$^1$H-NMR (300 MHz, DMSO-d$_6$): 12.12 (s, 1H, —NH); 9.04 (s, 1H); 8.94 (br.s, 2H, —NH$_2^+$); 8.72 (d, J=7.5, 1H, —NH); 7.20 (t, J=1.6, 1H); 7.15 (d, J=1.6, 1H); 4.16 (m, 1H); 3.84 (d, J=6.8, 2H); 3.78 (s, 3H); 3.31 (m, 2H); 3.08 (m, 2H); 2.81 (s, 3H); 2.13 (m, 2H); 1.79 (m, 2H); 0.93 (m, 1H); 0.35 (m, 2H); 0.20 (m, 2H).

Example D.f24

N-(trans-4-aminocyclohexyl)-4-[2-(cyclopropylmethoxy)-5-methoxyphenyl]-6-methyl-5H-pyrrolo[3,2-d]pyrimidine-7-carboxamide hydrochloride Starting from tert-butyl {trans-4-[({4-[2-(cyclopropylmethoxy)-5-methoxyphenyl]-6-methyl-5H-pyrrolo[3,2-d]pyrimidin-7-yl}carbonyl)amino]cyclohexyl}carbamate (example D.e24) the title compound is obtained as yellow solid.

MS (ESI): m/z=450 (MH$^+$, 100%).

$^1$H-NMR (300 MHz, DMSO-d$_6$): 12.07 (s, 1H, —NH); 9.01 (s, 1H); 8.59 (d, J=7.9, 1H, —NH); 8.03 (br.d, J~4.8, 3H, —NH$_3^+$); 7.20 (t, J=1.8, 1H); 7.14 (d, J=1.8, 2H); 3.84 (d, J=6.9, 2H & m, 1H); 3.78 (s, 3H); 3.09 (m, 1H); 2.80 (s, 3H); 2.04 (m, 4H); 1.47 (m, 4H); 0.92 (m, 1H); 0.34 (m, 2H); 0.19 (m, 2H).

Example D.f25

N-(cis-4-aminocyclohexyl)-4-[2-(cyclopropylmethoxy)-5-methoxyphenyl]-6-methyl-5H-pyrrolo[3,2-d]pyrimidine-7-carboxamide hydrochloride Starting from tert-butyl {cis-4-[({4-[2-(cyclopropylmethoxy)-5-methoxyphenyl]-6-methyl-5H-pyrrolo[3,2-d]pyrimidin-7-yl}carbonyl)amino]cyclohexyl}carbamate (example D.e25) the title compound is obtained as yellow solid.

MS (ESI): m/z=450 (MH$^+$, 100%).

$^1$H-NMR (300 MHz, DMSO-d$_6$): 12.15 (br.s, 1H, —NH); 9.11 (s, 1H); 8.96 (d, J=7.5, 1H, —NH); 8.13 (br.s, 3H, —NH$_3^+$); 7.22 (t, J=1.6, 1H); 7.15 (d, J=1.6, 2H); 4.13 (m, 1H); 3.85 (d, J=6.9, 2H); 3.78 (s, 3H); 3.18 (m, 1H); 2.82 (s, 3H); 1.95-1.67 (m, 8H); 0.93 (m, 1H); 0.35 (m, 2H); 0.21 (m, 2H).

Example D.f26

4-[2-(Cyclopropylmethoxy)-5-methoxyphenyl]-6-methyl-N-[(3R)-pyrrolidin-3-yl]-5H-pyrrolo[3,2-d]pyrimidine-7-carboxamide hydrochloride Starting from tert-butyl (3R)-3-[({4-[2-(cyclopropylmethoxy)-5-methoxyphenyl]-6-methyl-5H-pyrrolo[3,2-d]pyrimidin-7-yl}carbonyl)amino]pyrrolidine-1-carboxylate (example D.e26) the title compound is obtained as yellow solid.

MS (ESI): m/z=422 (MH$^+$, 100%).

$^1$H-NMR (300 MHz, DMSO-d$_6$, MeOH-d$_4$): 9.07 (s, 1H); 7.24 (dd, J=2.2, 0.9, 2H); 7.17 (d, J=2.2, 1H); 7.16 (d, J=0.9, 1H); 4.64 (m, 1H); 3.85 (d, J=6.9, 2H); 3.78 (s, 2H); 3.53 (m, 1H); 3.44 (m, 1H); 3.29 (m, 1H); 3.22 (m, 1H); 2.83 (s, 3H); 2.37 (m, 1H); 2.04 (m, 1H); 0.93 (m, 1H); 0.35 (m, 2H); 0.21 (m, 2H).

Example D.f27

4-[2-(cyclopropylmethoxy)-5-methoxyphenyl]-N-[(3R*,4R*)-3-hydroxypiperidin-4-yl]-6-methyl-5H-pyrrolo[3,2-d]pyrimidine-7-carboxamide hydrochloride Starting from tert-butyl (3R*,4R*)-4-[({4-[2-(cyclopropylmethoxy)-5-methoxyphenyl]-6-methyl-5H-pyrrolo[3,2-d]pyrimidin-7-yl}carbonyl)amino]-3-hydroxypiperidine-1-carboxylate (example D.e27) the title compound is obtained as yellow solid.

MS (ESI): m/z=452 (MH$^+$, 100%).

$^1$H-NMR (300 MHz, DMSO-d$_6$, MeOH-d$_4$): 9.09 (s, 1H); 7.24 (s, 1H); 7.18 (s, 2H); 4.04 (m, 1H); 3.93 (m, 1H); 3.86 (d, J=6.8, 2H); 3.80 (m, 3H); 3.32 (m, 1H); 3.25 (m, 1H); 3.09 (m, 1H); 2.90 (m, 1H); 2.84 (s, 3H); 2.27 (m, 1H); 1.77 (m, 1H); 0.94 (m, 1H); 0.36 (m, 2H); 0.22 (m, 2H).

Example D.f28

4-[2-(Cyclopropylmethoxy)-5-methylphenyl]-6-methyl-N-(piperidin-4-yl)-5H-pyrrolo[3,2-d]pyrimidine-7-carboxamide hydrochloride Starting from tert-butyl 4-[({4-[2-(cyclopropylmethoxy)-5-methylphenyl]-6-methyl-5H-pyrrolo[3,2-d]pyrimidin-7-yl}carbonyl)amino]piperidine-1-carboxylate (example D.e28) the title compound is obtained as yellow solid.

MS (ESI): m/z=420 (MH$^+$, 100%).

$^1$H-NMR (300 MHz, DMSO-d$_6$): 12.25 (br.s, 1H, —NH); 9.11 (br.s, 2H, —NH$_2^+$); 9.06 (s, 1H); 7.47 (d, J=2.1, 1H); 7.39 (dd, J=8.4, 2.1, 1H); 7.10 (d, J=8.6, 1H); 4.12 (m, 1H); 3.88 (d, J=6.9, 2H); 3.31 (m, 2H); 3.08 (m, 2H); 2.81 (s, 3H); 2.34 (s, 3H); 2.13 (m, 2H); 1.79 (m, 2H); 0.93 (m, 1H); 0.36 (m, 2H); 0.25 (m, 2H).

Example D.f29

N-(Trans-4-aminocyclohexyl)-4-[2-(cyclopropylmethoxy)-5-methylphenyl]-6-methyl-5H-pyrrolo[3,2-d]pyrimidine-7-carboxamide hydrochloride Starting from tert-butyl {trans-4-[({4-[2-(cyclopropylmethoxy)-5-methylphenyl]-6-methyl-5H-pyrrolo[3,2-d]pyrimidin-7-yl}carbonyl)amino]cyclohexyl}carbamate (example D.e29) the title compound is obtained as yellow solid.

MS (ESI): m/z=434 (MH+, 100%).

¹H-NMR (300 MHz, DMSO-d₆): 12.25 (br.s, 1H, —NH); 9.03 (s, 1H); 8.55 (d, J=7.9, 1H, —NH); 8.09 (br.d, J=4.2, 3H, —NH₃⁺); 7.46 (d, J=2.1, 1H); 7.39 (dd, J=8.4, 2.1, 1H); 7.11 (d, J=8.6, 1H); 3.88 (d, J=6.9, 2H); 3.82 (m, 1H); 3.09 (m, 1H); 2.81 (s, 3H); 2.34 (s, 3H); 2.04 (m, 4H); 1.47 (m, 4H); 0.93 (m, 1H); 0.36 (m, 2H); 0.24 (m, 2H).

Example D.f30

N-(Cis-4-aminocyclohexyl)-4-[2-(cyclopropylmethoxy)-5-methylphenyl]-6-methyl-5H-pyrrolo[3,2-d]pyrimidine-7-carboxamide hydrochloride Starting from tert-butyl {cis-4-[({4-[2-(cyclopropylmethoxy)-5-methylphenyl]-6-methyl-5H-pyrrolo[3,2-d]pyrimidin-7-yl}carbonyl)amino]cyclohexyl}carbamate (example D.e30) the title compound is obtained as yellow solid.

MS (ESI): m/z=534 (MH+, 100%).

¹H-NMR (300 MHz, DMSO-d₆): 11.73 (s, 1H, —NH); 9.00 (d, J=9.3, 1H, —NH); 8.98 (s, 1H); 7.43 (d, J=2.1, 1H); 7.33 (dd, J=8.4, 2.1, 1H); 7.06 (d, J=8.4, 1H); 6.97 (d, J=7.7, 1H, —NH); 4.03 (m, 1H); 3.86 (d, J=6.9, 2H); 3.42 (m, 1H); 2.78 (s, 3H); 2.32 (s, 3H); 1.81-1.51 (m, 8H); 1.40 (s, 9H); 0.94 (m, 1H); 0.37 (m, 2H); 0.23 (m, 2H).

Example D.f31

4-[2-(Cyclopropylmethoxy)-5-(trifluoromethyl)phenyl]-6-methyl-N-(piperidin-4-yl)-5H-pyrrolo[3,2-d]pyrimidine-7-carboxamide hydrochloride Starting tert-butyl 4-[({4-[2-(cyclopropylmethoxy)-5-(trifluoromethyl)phenyl]-6-methyl-5H-pyrrolo[3,2-d]pyrimidin-7-yl}carbonyl)amino]piperidine-1-carboxylate from (example D.e31) the title compound is obtained as yellow solid.

MS (ESI): m/z=474 (MH+, 100%).

¹H-NMR (300 MHz, DMSO-d₆): 12.11 (s, 1H, —NH); 9.04 (s, 1H); 8.98 (br.s, 2H, —NH₂⁺); 8.75 (d, J=7.5, 1H, —NH); 7.93 (d, J=2.0, 1H); 7.91 (dd, J=8.8, 2.0, 1H); 7.39 (d, J=8.8, 1H); 4.16 (m, 1H); 4.01 (d, J=6.9, 2H); 3.32 (m, 2H); 3.08 (m, 2H); 2.80 (s, 3H); 2.13 (m, 2H); 1.79 (m, 2H); 0.98 (m, 1H); 0.39 (m, 2H); 0.27 (m, 2H).

Example D.f32

N-(trans-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride Starting from tert-butyl {trans-4-[({4-[2-(cyclopropylmethoxy)-5-(trifluoromethyl)phenyl]-6-methyl-5H-pyrrolo[3,2-d]pyrimidin-7-yl}carbonyl)amino]cyclohexyl}carbamate (example D.e32) the title compound is obtained as yellow solid.

MS (ESI): m/z=488 (MH+, 100%).

¹H-NMR (300 MHz, DMSO-d₆): 12.08 (s, 1H, —NH); 9.01 (s, 1H); 8.61 (d, J=8.6, 1H, —NH); 8.07 (br.s, 3H, —NH₃⁺); 7.92 (d, J=2.0, 1H); 7.91 (dd, J=8.8, 2.0, 1H); 7.39 (d, J=8.8, 1H); 4.01 (d, J=7.0, 2H); 3.81 (m, 2H); 3.09 (m, 2H); 2.80 (s, 3H); 2.04 (m, 4H); 1.48 (m, 4H); 0.98 (m, 1H); 0.39 (m, 2H); 0.27 (m, 2H).

Example D.f33

N-(cis-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride Starting from tert-butyl {cis-4-[({4-[2-(cyclopropylmethoxy)-5-(trifluoromethyl)phenyl]-6-methyl-5H-pyrrolo[3,2-d]pyrimidin-7-yl}carbonyl)amino]cyclohexyl}carbamate (example D.e33) the title compound is obtained as yellow solid.

MS (ESI): m/z=488 (MH+, 100%).

¹H-NMR (400 MHz, DMSO-d₆): 12.04 (s, 1H, —NH); 9.08 (s, 1H); 8.98 (d, J=7.3, 1H, —NH); 7.99 (br.s, 3H, —NH₃⁺); 7.94 (d, J=2.1, 1H); 7.92 (dd, J=8.7, 2.1, 1H); 7.40 (d, J=8.7, 1H); 4.13 (m, 1H); 4.02 (d, J=6.9, 2H); 3.20 (m, 1H); 2.82 (s, 3H); 1.89 (m, 4H); 1.75 (m, 4H); 0.99 (m, 1H); 0.41 (m, 2H); 0.29 (m, 2H).

Example D.f34

4-[2-Ethoxy-5-(trifluoromethyl)phenyl]-6-methyl-N-(piperidin-4-yl)-5H-pyrrolo[3,2-d]pyrimidine-7-carboxamide hydrochloride Starting from tert-butyl 4-[({4-[2-ethoxy-5-(trifluoromethyl)phenyl]-6-methyl-5H-pyrrolo[3,2-d]-pyrimidin-7-yl}carbonyl)amino]piperidine-1-carboxylate (example D.e34) the title compound is obtained as yellow solid.

MS (ESI): m/z=448 (MH+, 100%).

¹H-NMR (300 MHz, DMSO-d₆): 12.15 (br.s, 1H, —NH); 9.04 (s, 1H); 8.99 (br.s, 2H, —NH₂⁺); 8.73 (d, J=7.1, 1H, —NH); 7.93 (d, J=2.2, 1H); 7.92 (dd, J=9.5, 2.2, 1H); 7.43 (d, J=9.5, 1H); 4.22 (qu, J=6.9, 2H); 4.17 (m, 1H); 3.31 (m, 2H); 3.08 (m, 2H); 2.80 (s, 3H); 2.13 (m, 2H); 1.79 (m, 2H); 1.16 (t, J=6.9, 3H).

Example D.f35

4-[2-(cyclopropylmethoxy)-4-fluoro-5-methoxyphenyl]-6-methyl-N-piperidin-4-yl-5H-pyrrolo[3,2-d]pyrimidine-7-carboxamide hydrochloride Starting from tert-butyl 4-[({4-[2-(cyclopropylmethoxy)-4-fluoro-5-methoxyphenyl]-6-methyl-5H-pyrrolo[3,2-d]pyrimidin-7-yl}carbonyl)amino]piperidine-1-carboxylate (example D.e35) the title compound is obtained as yellow solid.

MS (ESI): m/z=454 (MH+, 100%).

¹H-NMR (300 MHz, DMSO-d₆): 12.11 (s, 1H, —NH); 9.04 (s, 1H); 8.96 (br.s, 3H, NH₂⁺); 8.72 (d, J=6.9, 1H, —NH); 7.43 (d, J=9.9, 1H); 7.22 (d, J=13.3, 1H); 4.15 (m, 1H); 3.86 (d, J=6.9, 2H); 3.85 (s, 3H); 3.31 (m, 2H); 3.08 (m, 2H); 2.81 (s, 3H); 2.13 (m, 2H); 1.79 (m, 2H); 0.93 (m, 1H); 0.36 (m, 2H); 0.22 (m, 2H).

Example D.f36

N-(trans-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride Starting from tert-butyl {trans-4-[({4-[2-(cyclopropylmethoxy)-4-fluoro-5-methoxyphenyl]-6-methyl-5H-pyrrolo

[3,2-d]pyrimidin-7-yl}carbonyl)amino]cyclohexyl}carbamate (example D.e36) the title compound is obtained as yellow solid.

MS (ESI): m/z=468 (MH+, 100%).

$^1$H-NMR (300 MHz, DMSO-$d_6$): 12.15 (s, 1H, —NH); 9.02 (s, 1H); 8.56 (d, J=7.7, 1H, —NH); 8.09 (br.s, 3H, NH$_3^+$); 7.43 (d, J=9.7, 1H); 7.22 (d, J=13.5, 1H); 3.86 (d, J=6.9, 2H); 3.85 (s, 3H); 3.79 (m, 1H); 3.08 (m, 1H); 2.81 (s, 3H); 2.04 (m, 4H); 1.47 (m, 4H); 0.92 (m, 1H); 0.36 (m, 2H); 0.22 (m, 2H).

Example D.f37

N-(cis-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride Starting from tert-butyl {cis-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate (example D.e37) the title compound is obtained as yellow solid.

MS (ESI): m/z=468 (MH+, 100%).

$^1$H-NMR (300 MHz, DMSO-$d_6$): 12.19 (s, 1H, —NH); 9.12 (s, 1H); 8.95 (d, J=7.5, 1H, —NH); 8.18 (br.s, 3H, NH$_3^+$); 7.45 (d, J=9.7, 1H); 7.23 (d, J=13.5, 1H); 4.14 (m, 1H); 3.87 (d, J=6.9, 2H); 3.86 (s, 3H); 3.17 (m, 1H); 2.82 (s, 3H); 1.81 (m, 8H); 0.94 (m, 1H); 0.37 (m, 2H); 0.23 (m, 2H).

Example D.f38

4-[2-(Cyclopropylmethoxy)-4-fluoro-5-methoxyphenyl]-N-[(3R*,4R*)-3-hydroxypiperidin-4-yl]-6-methyl-5H-pyrrolo[3,2-d]pyrimidine-7-carboxamide hydrochloride Starting from tert-butyl (3R*,4R*)-4-[({4-[2-(cyclopropylmethoxy)-4-fluoro-5-methoxyphenyl]-6-methyl-5H-pyrrolo[3,2-d]pyrimidin-7-yl}carbonyl)amino]-3-hydroxypiperidine-1-carboxylate (example D.e38) the title compound is obtained as yellow solid.

MS (ESI): m/z=470 (MH+, 100%).

$^1$H-NMR (300 MHz, DMSO-$d_6$, MeOH-$d_4$): 9.08 (s, 1H); 7.47 (d, J=9.9, 1H); 7.24 (d, J=13.3, 1H); 4.05 (m, 1H); 3.87 (s, 3H & d, J=6.9, 2H & m, 1H); 3.29 (m, 2H); 3.11 (m, 1H); 2.92 (m, 1H); 2.84 (s, 3H); 2.28 (m, 1H); 1.76 (m, 1H); 0.95 (m, 1H); 0.38 (m, 2H); 0.25 (m, 2H).

Example D.f39

4-[2-(Cyclopropylmethoxy)-4-fluoro-5-methoxyphenyl]-N-[(3S*,4S*)-4-hydroxypiperidin-3-yl]-6-methyl-5H-pyrrolo[3,2-d]pyrimidine-7-carboxamide hydrochloride Starting from tert-butyl (3S*,4S*)-3-[({4-[2-(cyclopropylmethoxy)-4-fluoro-5-methoxyphenyl]-6-methyl-5H-pyrrolo[3,2-d]pyrimidin-7-yl}carbonyl)amino]-4-hydroxypiperidine-1-carboxylate (example D.e39) the title compound is obtained as yellow solid.

MS (ESI): m/z=470 (MH+, 100%).

$^1$H-NMR (300 MHz, DMSO-$d_6$, MeOH-$d_4$): 9.05 (s, 1H); 7.45 (d, J=9.7, 1H); 7.23 (d, J=13.3, 1H); 4.08 (m, 1H); 3.86 (s, 3H & d, J=6.8, 2H & m, 1H); 3.50 (m, 1H); 3.30 (m, 1H); 3.00 (m, 1H); 2.83 (s, 3H); 2.10 (m, 1H); 1.73 (m, 1H); 0.94 (m, 1H); 0.37 (m, 2H); 0.24 (m, 2H).

Example D.f40

4-[2-(cyclopropylmethoxy)-4-fluoro-5-methylphenyl]-6-methyl-N-(piperidin-4-yl)-5H-pyrrolo[3,2-d]pyrimidine-7-carboxamide hydrochloride Starting from tert-butyl 4-[({4-[2-(cyclopropylmethoxy)-4-fluoro-5-methylphenyl]-6-methyl-5H-pyrrolo[3,2-d]pyrimidin-7-yl}carbonyl)amino]piperidine-1-carboxylate (example D.e40) the title compound is obtained as yellow solid.

MS (ESI): m/z=438/(MW, 100%).

$^1$H-NMR (300 MHz, DMSO-$d_6$): 12.32 (s, 1H, —NH); 9.10 (br.s, 2H, —NH$_2^+$); 9.06 (s, 1H); 8.66 (d, J=7.5, 1H, —NH); 7.58 (d, J=8.9, 1H); 7.09 (d, J=12.1, 1H); 4.14 (m, 1H); 3.90 (d, J=7.1, 2H); 3.31 (m, 2H); 3.07 (m, 2H); 2.82 (s, 3H); 2.26 (d, J=0.9, 3H); 2.13 (m, 1H); 1.80 (m, 2H); 0.96 (m, 1H); 0.37 (m, 2H); 0.24 (m, 2H).

Example D.f41

N-(trans-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride Starting from tert-butyl {trans-4-[({4-[2-(cyclopropylmethoxy)-4-fluoro-5-methylphenyl]-6-methyl-5H-pyrrolo[3,2-d]pyrimidin-7-yl}carbonyl)amino]cyclohexyl}carbamate (example D.e41) the title compound is obtained as yellow solid.

MS (ESI): m/z=452 (MH+, 100%).

$^1$H-NMR (300 MHz, DMSO-$d_6$): 11.97 (s, 1H, —NH); 8.96 (s, 1H); 8.66 (d, J=7.9, 1H, —NH); 7.98 (br.d, J~4.6, 3H, —NH$_3^+$); 7.55 (dd, J=9.1, 0.6, 1H); 7.06 (d, J=12.0, 1H); 3.88 (d, J=7.1, 2H); 3.82 (m, 1H); 3.09 (m, 1H); 2.79 (s, 3H); 2.25 (d, J=1.1, 3H); 2.04 (m, 4H); 1.47 (m, 4H); 0.95 (m, 1H); 0.37 (m, 2H); 0.24 (m, 2H).

Example D.f42

N-(cis-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride Starting from tert-butyl {cis-4-[({4-[2-(cyclopropylmethoxy)-4-fluoro-5-methylphenyl]-6-methyl-5H-pyrrolo[3,2-d]pyrimidin-7-yl}carbonyl)amino]cyclohexyl}carbamate (example D.e42) the title compound is obtained as yellow solid.

MS (ESI): m/z=452 (MH+, 100%).

$^1$H-NMR (300 MHz, DMSO-$d_6$): 12.20 (br.s, 1H, —NH); 9.10 (s, 1H); 8.96 (d, J=7.5, 1H, —NH); 8.16 (br.s, 3H, —NH$_3^+$); 7.58 (dd, J=8.9, 0.6, 1H); 7.08 (d, J=12.1, 1H); 4.13 (m, 1H); 3.90 (d, J=6.9, 2H); 3.17 (m, 1H); 2.82 (s, 3H); 2.26 (d, J=1.1, 3H); 1.93-1.56 (m, 8H); 0.96 (m, 1H); 0.38 (m, 2H); 0.25 (m, 2H).

Example D.f43

4-[2-(Cyclopropylmethoxy)-4-fluoro-5-methylphenyl]-N-[(3R*,4R*)-3-hydroxypiperidin-4-yl]-6-methyl-5H-pyrrolo[3,2-d]pyrimidine-7-carboxamide hydrochloride Starting from tert-butyl (3R*,4R*)-4-[({4-[2-(cyclopropylmethoxy)-4-fluoro-5-methylphenyl]-6-methyl-5H-pyrrolo

[3,2-d]pyrimidin-7-yl}carbonyl)amino]-3-hydroxypiperidine-1-carboxylate (example D.e43) the title compound is obtained as yellow solid.

MS (ESI): m/z=454 (MH⁺, 100%).

¹H-NMR (300 MHz, DMSO-d₆): 12.51 (s, 1H, —NH); [9.62 (br.m, 1H), 9.18 (br.m, 1H), —NH₂⁺]; 9.06 (s, 1H); 8.70 (d, J=7.1, 1H, —NH); 7.60 (d, J=8.9, 1H); 7.10 (d, J=12.0, 1H); 4.01 (m, 1H); 3.91 (d, J=7.1, 2H & m, 1H); 3.26 (m, 2H); 3.04 (m, 2H); 2.84 (s, 3H & m, 1H); 2.26 (s, 3H); 2.23 (m, 1H); 1.78 (m, 1H); 0.97 (m, 1H); 0.38 (m, 2H); 0.26 (m, 2H).

Example D.f44

4-[2-(Cyclopropylmethoxy)-5-fluoro-4-methoxyphenyl]-6-methyl-N-piperidin-4-yl-5H-pyrrolo[3,2-d]pyrimidine-7-carboxamide hydrochloride Starting from tert-butyl 4-[({4-[2-(cyclopropylmethoxy)-5-fluoro-4-methoxyphenyl]-6-methyl-5H-pyrrolo[3,2-d]pyrimidin-7-yl}carbonyl)amino]piperidine-1-carboxylate (example D.e44) the title compound is obtained as yellow solid.

MS (ESI): m/z=454 (MH⁺, 100%).

¹H-NMR (300 MHz, DMSO-d₆): 12.27 (br.s, 1H, —NH); 9.10 (br.s, 2H, —NH₂⁺); 9.04 (s, 1H); 8.67 (d, J=7.5, 1H, —NH); 7.53 (d, J=11.9, 1H); 6.96 (d, J=7.3, 1H); 4.15 (m, 1H); 3.99 (s, 3H); 3.97 (d, J=6.9, 2H); 3.31 (m, 2H); 3.07 (m, 2H); 2.82 (s, 3H); 2.13 (m, 2H); 1.80 (m, 2H); 0.97 (m, 1H); 0.39 (m, 2H); 0.26 (m, 2H).

Example D.f45

N-(trans-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride Starting from tert-butyl {trans-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate (example D.e45) the title compound is obtained as yellow solid.

MS (ESI): m/z=468 (MH⁺, 100%).

¹H-NMR (300 MHz, DMSO-d₆): 12.32 (br.s, 1H, —NH); 9.01 (s, 1H); 8.51 (d, J=7.7, 1H, —NH); 8.18 (br.d, J=4.6, 3H, —NH₃⁺); 7.54 (d, J=11.7, 1H); 6.96 (d, J=7.3, 1H); 3.99 (s, 3H); 3.97 (d, J=7.4, 2H); 3.81 (m, 1H); 3.07 (m, 1H); 2.83 (s, 3H); 2.05 (m, 4H); 1.48 (m, 4H); 0.97 (m, 1H); 0.39 (m, 2H); 0.27 (m, 2H).

Example D.f46

N-(cis-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride Starting from tert-butyl {cis-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate (example D.e46) the title compound is obtained as yellow solid.

MS (ESI): m/z=468 (MH⁺, 100%).

¹H-NMR (300 MHz, DMSO-d₆): 12.36 (br.s, 1H, —NH); 9.14 (s, 1H); 8.94 (d, J=77, 1H, —NH); 8.25 (br.s, 3H, —NH₃⁺); 7.55 (d, J=11.7, 1H); 6.97 (d, J=7.3, 1H); 4.14 (m, 1H); 3.99 (s, 3H); 3.97 (d, J=7.1, 2H); 3.16 (m, 1H); 2.84 (s, 3H); 1.86 (m, 4H); 1.74 (m, 4H); 0.98 (m, 1H); 0.39 (m, 2H); 0.27 (m, 2H).

Example D.f47

4-[2-(Cyclopropylmethoxy)-5-fluoro-4-methoxyphenyl]-N-[(3R*,4R*)-3-hydroxypiperidin-4-yl]-6-methyl-5H-pyrrolo[3,2-d]pyrimidine-7-carboxamide hydrochloride Starting from tert-butyl (3R*,4R*)-4-[({4-[2-(cyclopropylmethoxy)-5-fluoro-4-methoxyphenyl]-6-methyl-5H-pyrrolo[3,2-d]pyrimidin-7-yl}carbonyl)amino]-3-hydroxypiperidine-1-carboxylate (example D.e47) the title compound is obtained as yellow solid.

MS (ESI): m/z=470 (MH⁺, 100%).

¹H-NMR (300 MHz, DMSO-d₆, MeOH-d₄): 9.04 (s, 1H); 7.54 (d, J=11.9, 1H); 6.96 (d, J=7.3, 1H); 4.02 (m, 1H); 3.99 (s, 3H); 3.94 (d, J=6.9, 2H); 3.88 (m, 1H); 3.29 (m, 2H); 3.10 (m, 1H); 2.93 (m, 1H); 2.84 (s, 3H); 2.29 (m, 1H); 1.78 (m, 1H); 0.98 (m, 1H); 0.40 (m, 2H); 0.27 (m, 2H).

Example D.f48

4-[2-(cyclopropylmethoxy)-5-ethylphenyl]-6-methyl-N-(piperidin-4-yl)-5H-pyrrolo[3,2-d]pyrimidine-7-carboxamide hydrochloride Starting from tert-butyl 4-[({4-[2-(cyclopropylmethoxy)-5-ethylphenyl]-6-methyl-5H-pyrrolo[3,2-d]pyrimidin-7-yl}carbonyl)amino]piperidine-1-carboxylate (example D.e48) the title compound is obtained as yellow solid.

MS (ESI): m/z=434 (MH⁺, 100%).

¹H-NMR (300 MHz, DMSO-d₆): 12.22 (s, 1H, —NH); 9.06 (s, 1H); 9.00 (br.s, 2H, —NH₂⁺); 8.69 (d, J=7.5, 1H, —NH); 7.48 (d, J=2.2, 1H); 7.42 (dd, J=8.6, 2.2, 1H); 7.12 (d, J=8.6, 1H); 4.16 (m, 1H); 3.89 (d, J=6.9, 2H); 3.31 (m, 2H); 3.08 (m, 2H); 2.81 (s, 3H); 2.65 (qu, J=7.5, 2H); 2.13 (m, 2H); 1.79 (m, 2H); 1.20 (t, J=7.5, 3H); 0.95 (m, 1H); 0.36 (m, 2H); 0.24 (m, 2H).

Example D.f49

N-(trans-4-aminocyclohexyl)-4-[2-(cyclopropylmethoxy)-5-ethylphenyl]-6-methyl-5H-pyrrolo[3,2-d]pyrimidine-7-carboxamide Starting from tert-butyl {trans-4-[({4-[2-(cyclopropylmethoxy)-5-ethylphenyl]-6-methyl-5H-pyrrolo[3,2-d]pyrimidin-7-yl}carbonyl)amino]cyclohexyl}carbamate (example D.e49) the title compound is obtained as yellow solid.

MS (ESI): m/z=448 (MH⁺, 100%).

¹H-NMR (300 MHz, DMSO-d₆): 12.21 (s, 1H, —NH); 9.02 (s, 1H); 8.55 (d, J=7.7, 1H, —NH); 8.09 (br.s, 3H, —NH₃⁺); 7.48 (d, J=2.2, 1H); 7.42 (dd, J=8.6, 2.2, 1H); 7.12 (d, J=8.6, 1H); 3.89 (d, J=6.9, 2H); 3.81 (m, 1H); 3.08 (m, 1H); 3.08 (m, 2H); 2.81 (s, 3H); 2.64 (qu, J=7.5, 2H); 2.05 (m, 4H); 1.48 (m, 4H); 1.20 (t, J=7.5, 3H); 0.95 (m, 1H); 0.36 (m, 2H); 0.23 (m, 2H).

Example D.f50

N-(cis-4-aminocyclohexyl)-4-[2-(cyclopropylmethoxy)-5-ethylphenyl]-6-methyl-5H-pyrrolo[3,2-d]pyrimidine-7-carboxamide hydrochloride Starting from tert-butyl {cis-4-[({4-[2-(cyclopropylmethoxy)-5-ethylphenyl]-6-methyl-5H-pyrrolo[3,2-d]pyrimidin-7-yl}carbonyl)amino]cyclohexyl}carbamate (example D.e50) the title compound is obtained as yellow solid.
MS (ESI): m/z=448 (MH+, 100%).
1H-NMR (300 MHz, DMSO-d6): 12.18 (br.s, 1H, —NH); 9.11 (s, 1H); 8.96 (d, J=7.7, 1H, —NH); 8.15 (br.s, 3H, —NH3+); 7.48 (d, J=2.2, 1H); 7.42 (dd, J=8.6, 2.2, 1H); 7.13 (d, J=8.6, 1H); 4.13 (m, 1H); 3.89 (d, J=6.8, 2H); 3.18 (m, 1H); 3.08 (m, 1H); 2.82 (s, 3H); 2.65 (qu, J=7.5, 2H); 1.96-1.66 (m, 8H); 1.20 (t, J=7.5, 3H); 0.95 (m, 1H); 0.37 (m, 2H); 0.24 (m, 2H).

Example D.f51

4-[2-(Cyclopropylmethoxy)-5-ethylphenyl]-N-[(3R*, 4R*)-4-hydroxypyrrolidin-3-yl]-6-methyl-5H-pyrrolo[3,2-d]pyrimidine-7-carboxamide hydrochloride Starting from tert-butyl (3R*,4R*)-3-[({4-[2-(cyclopropylmethoxy)-5-ethylphenyl]-6-methyl-5H-pyrrolo[3,2-d]pyrimidin-7-yl}carbonyl)amino]-4-hydroxypyrrolidine-1-carboxylate (example D.e51) the title compound is obtained as yellow solid.
MS (ESI): m/z=436 (MH+, 100%).

Example D.f52

4-[2-(Cyclopropylmethoxy)-5-(propan-2-yl)phenyl]-6-methyl-N-(piperidin-4-yl)-5H-pyrrolo[3,2-d]pyrimidine-7-carboxamide hydrochloride Starting from tert-butyl 4-[({4-[2-(cyclopropylmethoxy)-5-(propan-2-yl)phenyl]-6-methyl-5H-pyrrolo[3,2-d]pyrimidin-7-yl}carbonyl)amino]piperidine-1-carboxylate (example D.e52) the title compound is obtained as yellow solid.
MS (ESI): m/z=548 (MH+, 100%).
1H-NMR (300 MHz, DMSO-d6): 11.75 (s, 1H, —NH); 8.95 (s, 1H); 8.81 (d, J=7.7, 1H, —NH); 7.47 (d, J=2.4, 1H); 7.39 (dd, J=8.6, 2.4, 1H); 7.08 (d; J=8.6, 1H); 4.06 (m, 1H); 3.87 (d, J=6.8, 2H & m, 2H); 3.05 (m, 2H); 2.94 (sept, J=6.9, 1H); 2.77 (s, 3H); 1.92 (m, 2H); 1.45 (m, 2H); 1.43 (s, 9H); 1.22 (d, J=6.9, 6H); 0.94 (m, 1H); 0.36 (m, 2H); 0.23 (m, 2H).

Example D.f53

N-(trans-4-Aminocyclohexyl)-4-[2-(cyclopropylmethoxy)-5-(propan-2-yl)phenyl]-6-methyl-5H-pyrrolo[3,2-d]pyrimidine-7-carboxamide hydrochloride Starting from tert-butyl {trans-4-[({4-[2-(cyclopropylmethoxy)-5-(propan-2-yl)phenyl]-6-methyl-5H-pyrrolo[3,2-d]pyrimidin-7-yl}carbonyl)amino]cyclohexyl}carbamate (example D.e53) the title compound is obtained as yellow solid.
MS (ESI): m/z=462 (MH+, 100%).
1H-NMR (300 MHz, DMSO-d6): 12.15 (br.s, 1H, —NH); 9.02 (s, 1H); 8.56 (d, J=7.9, 1H, —NH); 8.06 (br.d, J~4.0, 3H, —NH3+); 7.49 (d, J=2.4, 1H); 7.45 (dd, J=8.6, 2.4, 1H); 7.12 (d; J=8.6, 1H); 3.89 (d, J=6.9, 2H); 3.81 (m, 1H); 3.10 (m, 1H); 2.95 (sept, J=6.9, 1H); 2.80 (s, 3H); 2.04 (m, 4H); 1.47 (m, 4H); 1.22 (d, J=6.9, 6H); 0.94 (m, 1H); 0.36 (m, 2H); 0.23 (m, 2H).

Example D.f54

N-(cis-4-Aminocyclohexyl)-4-[2-(cyclopropylmethoxy)-5-(propan-2-yl)phenyl]-6-methyl-5H-pyrrolo[3,2-d]pyrimidine-7-carboxamide hydrochloride Starting from tert-butyl {cis-4-[({4-[2-(cyclopropylmethoxy)-5-(propan-2-yl)phenyl]-6-methyl-5H-pyrrolo[3,2-d]pyrimidin-7-yl}carbonyl)amino]cyclohexyl}carbamate (example D.e54) the title compound is obtained as yellow solid.
MS (ESI): m/z=462 (MH+, 100%).
1H-NMR (300 MHz, DMSO-d6): 12.28 (br.s, 1H, —NH); 9.15 (s, 1H); 8.95 (d, J=7.7, 1H, —NH); 8.19 (br.s, 3H, NH3+); 7.51 (d, J=2.4, 1H); 7.47 (dd, J=8.6, 2.4, 1H); 7.14 (d; J=8.6, 1H); 4.14 (m, 1H); 3.90 (d, J=6.9, 2H); 3.18 (m, 1H); 2.96 (sept, J=6.9, 1H); 2.82 (s, 3H); 1.96-1.66 (m, 8H); 1.23 (d, J=6.9, 6H); 0.95 (m, 1H); 0.37 (m, 2H); 0.24 (m, 2H).

Example D.f55

4-[5-Acetyl-2-(cyclopropylmethoxy)phenyl]-6-methyl-N-(piperidin-4-yl)-5H-pyrrolo[3,2-d]pyrimidine-7-carboxamide hydrochloride tert-Butyl 4-[({4-[2-(cyclopropylmethoxy)-5-(2-methyl-1,3-dioxolan-2-yl)phenyl]-6-methyl-5H-pyrrolo[3,2-d]pyrimidin-7-yl}carbonyl)amino]piperidine-1-carboxylate from example D.e55 (1.77 g; 2.99 mmol) is dissolved in dry acetone (30 mL). After addition of 4M HCl in dioxane (3 mL) the stirred mixture is gently refluxed until the starting material is consumed according to LC-MS. At ambient temperature the product is precipitated by addition of tert.-butyl methyl ether, isolated by suction filtration, washed with several portions of tert.-butyl methyl ether and dried in high vacuo at 40° C. to yield 1.40 g of the title compound as pale yellow solid.
MS (ESI): m/z=448 (MH+, 100%).
1H-NMR (400 MHz, DMSO-d6): 12.18 (s, 1H, —NH); 9.06 (s, 1H); 8.99 (br.s, 2H, —NH2+); 8.73 (d, J=7.5, 1H, —NH); 8.23 (d, J=2.3, 1H); 8.17 (dd, J=8.8, 2.3, 1H); 7.32 (d, J=8.8, 1H); 4.10 (m, 1H); 4.02 (d, J=7.1, 2H); 3.31 (m, 2H); 3.08 (m, 2H); 2.81 (s, 3H); 2.59 (s, 3H); 2.13 (m, 2H); 1.80 (m, 2H); 0.99 (m, 1H); 0.39 (m, 2H); 0.29 (m, 2H).

Example D.f56

4-[5-Acetyl-2-(cyclopropylmethoxy)phenyl]-N-(trans-4-aminocyclohexyl)-6-methyl-5H-pyrrolo[3,2-d]pyrimidine-7-carboxamide hydrochloride Starting from tert-butyl {trans-4-[({4-[2-(cyclopropylmethoxy)-5-(2-methyl-1,3-dioxolan-2-yl)phenyl]-6-methyl-5H-pyrrolo[3,2-d]pyrimidin-7-yl}carbonyl)amino]cyclohexyl}carbamate (example D.e56) and following the procedure as described for above example D.f55 the title compound is obtained as yellow solid.
MS (ESI): m/z=462 (MH+, 100%).
1H-NMR (400 MHz, DMSO-d6): 12.15 (s, 1H, —NH); 9.03 (s, 1H); 8.60 (d, J=7.7, 1H, —NH); 8.23 (d, J=2.2, 1H); 8.17 (dd, J=8.8, 2.2, 1H); 8.08 (br.s, 3H, —NH3+); 7.31 (d, J=8.8, 1H); 4.02 (d, J=6.9, 2H); 3.80 (m, 1H); 3.09 (m, 1H); 2.81 (s, 3H); 2.59 (s, 3H); 2.05 (m, 4H); 1.48 (m, 4H); 0.99 (m, 1H); 0.39 (m, 2H); 0.28 (m, 2H).

Example D.f57

4-[2-(Cyclopropylmethoxy)-5-methylphenyl]-2,6-dimethyl-N-(piperidin-4-yl)-5H-pyrrolo[3,2-d]pyrimidine-7-carboxamide hydrochloride Starting from tert-butyl 4-[({4-[2-(cyclopropylmethoxy)-5-methylphenyl]-2,6-dimethyl-5H-pyrrolo[3,2-d]pyrimidin-7-yl}carbonyl)amino]piperidine-1-carboxylate (example D.e57) the title compound is obtained as colorless solid.

MS (ESI): m/z=434 (MH+, 100%)
¹H-NMR (300 MHz, DMSO-d₆, MeOH-d₄): 7.49 (d, J=2.0, 1H); 7.45 (dd, J=8.6, 2.0, 1H); 7.15 (d, J=8.6, 1H); 4.22-4.08 (m, 1H); 3.90 (d, J=6.9, 2H); 3.35-3.22 (m, 2H); 3.16-3.00 (m, 2H); 2.87 (s, 3H); 2.83 (s, 3H); 2.35 (s, 3H); 2.20-2.07 (m, 2H); 1.83 (m, 2H); 0.96 (m, 1H); 0.38 (m, 2H); 0.26 (m, 2H).

Example D.f58

4-[2-(Cyclopropylmethoxy)-5-fluoro-4-methoxyphenyl]-2,6-dimethyl-N-(piperidin-4-yl)-5H-pyrrolo[3,2-d]pyrimidine-7-carboxamide hydrochloride Starting from tert-butyl 4-[({4-[2-(cyclopropylmethoxy)-5-fluoro-4-methoxyphenyl]-2,6-dimethyl-5H-pyrrolo[3,2-d]pyrimidin-7-yl}carbonyl)amino]piperidine-1-carboxylate (example D.e58) the title compound is obtained as colorless solid.
MS (ESI): 468 (MH+, 100%)
¹H-NMR (300 MHz, DMSO-d₆, MeOH-d₄): 7.60 (d, J=11.7, 1H); 6.98 (d, J=7.1, 1H); 4.21-4.07 (m, 1H); 4.03-3.94 (m, 5H); 3.34-3.22 (m, 2H); 3.18-3.00 (m, 1H); 2.86 (s, 3H); 2.83 (s, 3H); 2.19-2.08 (m, 2H); 1.91-1.74 (m, 2H); 0.98 (m, 1H); 0.40 (m, 2H); 0.28 (m, 2H).

Example D.f59

4-[2-(Cyclopropylmethoxy)-4-fluoro-5-methoxyphenyl]-2,6-dimethyl-N-(piperidin-4-yl)-5H-pyrrolo[3,2-d]pyrimidine-7-carboxamide hydrochloride Starting from tert-butyl 4-[({4-[2-(cyclopropylmethoxy)-4-fluoro-5-methoxyphenyl]-2,6-dimethyl-5H-pyrrolo[3,2-d]pyrimidin-7-yl}carbonyl)amino]piperidine-1-carboxylate (example D.e59) the title compound is obtained as colorless solid.
MS (ESI): m/z=468 (MH+, 100%).
¹H-NMR (300 MHz, DMSO-d₆, MeOH-d₄): 7.49 (d, J=9.5, 1H); 7.27 (d, J=13.3, 1H); 4.16 (m, 1H); 3.88 (s, 3H & d, J=6.9, 2H); 3.35 (m, 1H); 3.30 (m, 1H); 3.14 (m, 2H); 2.86 (s, 3H); 2.83 (s, 3H); 2.15 (m, 2H); 1.81 (m, 2H); 0.95 (m, 1H); 0.39 (m, 2H); 0.23 (m, 2H).

Example D.f60

4-[2-(Cyclopropylmethoxy)-5-(difluoromethyl)phenyl]-6-methyl-N-(piperidin-4-yl)-5H-pyrrolo[3,2-d]pyrimidine-7-carboxamide hydrochloride Starting from tert.-butyl 4-[({4-[2-(cyclopropylmethoxy)-5-(difluoromethyl)phenyl]-6-methyl-5H-pyrrolo[3,2-d]pyrimidin-7-yl}carbonyl)amino]piperidine-1-carboxylate (example D.e60) the title compound is obtained as colorless solid.
HR-MS (ESI): m/z=456.2210 ([MH]+, $C_{24}H_{28}F_2N_5O_2^+$, calc. 456.2206).

Example D.f61

N-(trans-4-Aminocyclohexyl)-4-[2-(cyclopropylmethoxy)-5-(difluoromethyl)phenyl]-6-methyl-5H-pyrrolo[3,2-d]pyrimidine-7-carboxamide hydrochloride Starting from tert-butyl {trans-4-[({4-[2-(cyclopropylmethoxy)-5-(difluoromethyl)phenyl]-6-methyl-5H-pyrrolo[3,2-d]pyrimidin-7-yl}carbonyl)amino]cyclohexyl}carbamate (example D.e61) the title compound is obtained as colorless solid.
HR-MS (ESI): m/z=470.2347 ([MH]+, $C_{25}H_{30}F_2N_5O_2^+$, calc. 470.2362).

Example D.f62

N-[(1S*,3S*,4S*)-4-Amino-3-fluorocyclohexyl]-4-[2-(cyclopropylmethoxy)-5-(difluoromethyl)phenyl]-6-methyl-5H-pyrrolo[3,2-d]pyrimidine-7-carboxamide hydrochloride Starting from tert-butyl {(1S*,2S*,4S*)-4-[({4-[2-(cyclopropylmethoxy)-5-(difluoromethyl)phenyl]-6-methyl-5H-pyrrolo[3,2-d]pyrimidin-7-yl}carbonyl)amino]-2-fluorocyclohexyl}carbamate (example D.e62) the title compound is obtained as colorless solid.
MS (ESI): m/z=488 (MH+, 100%).
¹H-NMR (300 MHz, DMSO-d₆): 12.11 (s, 1H, —NH); 9.01 (s, 1H); 8.71 (d, J=7.9, 1H, —NH); 8.45 (br.d, J~3.1, 3H, —NH₃+); 7.84 (d, J=2.0, 1H); 7.76 (dd, J=8.8, 2.0, 1H); 7.33 (d, J=8.8, 1H); 7.09 (t, J=55.9, 1H); 4.76 (m, 1H); 4.01 (m, 1H); 3.97 (d, J=7.1, 2H); 3.33 (m, 1H); 2.81 (s, 3H); 2.46 (m, 1H); 2.10 (m, 1H); 2.00 (m, 1H); 1.77 (m, 1H); 1.54 (m, 2H); 0.98 (m, 1H); 0.38 (m, 2H); 0.27 (m, 2H).

Example D.f63

N-[(1S*,2S*,4S*)-4-Amino-2-methylcyclohexyl]-4-[2-(cyclopropylmethoxy)-5-(difluoromethyl)phenyl]-6-methyl-5H-pyrrolo[3,2-d]pyrimidine-7-carboxamide hydrochloride Starting from tert-butyl {(1S*,3S*,4S*)-4-[({4-[2-(cyclopropylmethoxy)-5-(difluoromethyl)phenyl]-6-methyl-5H-pyrrolo[3,2-d]pyrimidin-7-yl}carbonyl)amino]-3-methylcyclohexyl}carbamate (example D.e63) the title compound is obtained as colorless solid.
¹H-NMR (300 MHz, DMSO-d₆): 12.00 (s, 1H, —NH); 9.00 (s, 1H); 8.59 (d, J=8.6, 1H, —NH); 7.98 (br.s, 3H, —NH₃+); 7.82 (s, 1H); 7.76 (d, J=8.7, 1H); 7.32 (d, J=8.7, 1H); 7.10 (t, J=55.8, 1H); 3.97 (d, J=6.9, 2H); 3.56 (m, 1H); 3.16 (m, 1H); 2.80 (s, 3H); 2.01 (m, 3H); 1.69 (m, 1H); 1.45 (m, 2H); 1.24 (m, 1H); 0.98 (m, 1H & d, J=6.4, 3H); 0.39 (m, 2H); 0.28 (m, 2H).

Example D.f64

N-[(1S,3S)-3-Aminocyclopentyl]-4-[2-(cyclopropylmethoxy)-5-(difluoromethyl)phenyl]-6-methyl-5H-pyrrolo[3,2-d]pyrimidine-7-carboxamide hydrochloride Starting from tert-butyl {(1S,3S)-3-[({4-[2-(cyclopropylmethoxy)-5-(difluoromethyl)phenyl]-6-methyl-5H-pyrrolo[3,2-d]pyrimidin-7-yl}carbonyl)amino]cyclopentyl}carbamate (example D.e64) the title compound is obtained as colorless solid.

HR-MS (ESI): m/z=456.2218 ([MH]$^+$, $C_{24}H_{28}F_2N_5O_2^+$, calc. 456.2206).

Example D.f66

4-[2-(Cyclopropylmethoxy)-5-(difluoromethyl)phenyl]-6-methyl-N-[(3S,5S)-5-methylpyrrolidin-3-yl]-5H-pyrrolo[3,2-d]pyrimidine-7-carboxamide hydrochloride Starting from tert-butyl (2S,4S)-4-[({4-[2-(cyclopropylmethoxy)-5-(difluoromethyl)phenyl]-6-methyl-5H-pyrrolo[3,2-d]pyrimidin-7-yl}carbonyl)amino]-2-methylpyrrolidine-1-carboxylate (example D.e66) the title compound is obtained as colorless solid.

HR-MS (ESI): m/z=456.2210 ([MH]$^+$, $C_{24}H_{28}F_2N_5O_2^+$, calc. 456.2206).

Example D.f68

N-[(1R*,3S*,4S*)-3-amino-4-methylcyclopentyl]-4-[2-(cyclopropylmethoxy)-5-(difluoromethyl)phenyl]-6-methyl-5H-pyrrolo[3,2-d]pyrimidine-7-carboxamide hydrochloride Starting from tert-butyl {(1S*,2S*,4R*)-4-[({4-[2-(cyclopropylmethoxy)-5-(difluoromethyl)phenyl]-6-methyl-5H-pyrrolo[3,2-d]pyrimidin-7-yl}carbonyl)amino]-2-methylcyclopentyl}carbamate (example D.e68) the title compound is obtained as colorless solid.

HR-MS (ESI): m/z=470.2363 ([MH]$^+$, $C_{25}H_{30}F_2N_5O_2^+$, calc. 470.2362).

Example D.f70

N-[(1S*,3S*,4S*)-3-Amino-4-fluorocyclopentyl]-4-[2-(cyclopropylmethoxy)-5-(difluoromethyl)phenyl]-6-methyl-5H-pyrrolo[3,2-d]pyrimidine-7-carboxamide hydrochloride Starting from tert-butyl {(1S*,2S*,4S*)-4-[({4-[2-(cyclopropylmethoxy)-5-(difluoromethyl)phenyl]-6-methyl-5H-pyrrolo[3,2-d]pyrimidin-7-yl}carbonyl)amino]-2-fluorocyclopentyl}carbamate (example D.e70) the title compound is obtained as colorless solid.

HR-MS (ESI): m/z=474.2117 ([MH]$^+$, $C_{24}H_{27}F_3N_5O_2^+$, calc. 474.2111).

Example D.f72

N-[(1S*,3R*,4S*)-4-amino-3-fluorocyclohexyl]-4-[2-(cyclopropylmethoxy)-5-(difluoromethyl)phenyl]-6-methyl-5H-pyrrolo[3,2-d]pyrimidine-7-carboxamide hydrochloride Starting from tert-butyl {(1S*,2R*,4S*)-4-[({4-[2-(cyclopropylmethoxy)-5-(difluoromethyl)phenyl]-6-methyl-5H-pyrrolo[3,2-d]pyrimidin-7-yl}carbonyl)amino]-2-fluorocyclohexyl}carbamate (example D.e72) the title compound is obtained as colorless solid.

HR-MS (ESI): m/z=488.2271 ([MH]$^+$, $C_{25}H_{29}F_3N_5O_2^+$, calc. 488.2268).

Example D.f65

N-[(1S*,3S*,4S*)-4-Amino-3-methylcyclohexyl]-4-[2-(cyclopropylmethoxy)-5-(difluoromethyl)phenyl]-6-methyl-5H-pyrrolo[3,2-d]pyrimidine-7-carboxamide hydrochloride N-[(1S*,3S*,4S*)-4-azido-3-methylcyclohexyl]-4-[2-(cyclopropylmethoxy)-5-(difluoromethyl)phenyl]-6-methyl-5H-pyrrolo[3,2-d]pyrimidine-7-carboxamide (example D.e65; 1.3 g; 2.6 mmol) is dissolved in MeOH (25 mL) and pressure hydrogenated over Pd(OH)$_2$ (20% on charcoal; 70.0 mg) at 20 bar and ambient temperature over night. After filtration through a pad of celite the solvent is removed under reduced pressure. The residual amine is dissolved in dioxane (5 mL). At ice bath temperature HCl (4M in dioxane; 0.7 mL) is added followed by tert-BuOMe (10 mL). The precipitate is collected by suction filtration, washed with several small portions of tert-BuOMe and dried under reduced pressure to yield 1.3 g of the title compound as pale yellow solid.

HR-MS (ESI): m/z=484.2525 ([MH]$^+$, $C_{26}H_{32}F_2N_5O_2^+$, calc. 484.2519).

The following compounds were prepared analogously to the procedure described in the above example D.f65. The compounds were obtained after pressure hydrogenation and removal of the catalyst and solvent.

Example D.f67

N-[(1R*,2R*,4R*)-4-Amino-2-fluorocyclohexyl]-4-[2-(cyclopropylmethoxy)-5-(difluoromethyl)phenyl]-6-methyl-5H-pyrrolo[3,2-d]pyrimidine-7-carboxamide Starting from N-[(1R*,2R*,4R*)-4-azido-2-fluorocyclohexyl]-4-[2-(cyclopropylmethoxy)-5-(difluoromethyl)phenyl]-6-methyl-5H-pyrrolo[3,2-d]pyrimidine-7-carboxamide (example D.e67) the title compound (free base) is obtained as colorless solid.

HR-MS (ESI): m/z=488.2265 ([MH]$^+$, $C_{25}H_{29}F_3N_5O_2^+$, calc. 488.2268).

Example D.f69

N-[(1R*,2R*,4S*)-4-amino-2-methylcyclopentyl]-4-[2-(cyclopropylmethoxy)-5-(difluoromethyl)phenyl]-6-methyl-5H-pyrrolo[3,2-d]pyrimidine-7-carboxamide Starting from N-[(1R*,2R*,4S*)-4-azido-2-methylcyclopentyl]-4-[2-(cyclopropylmethoxy)-5-(difluoromethyl)phenyl]-6-methyl-5H-pyrrolo[3,2-d]pyrimidine-7-carboxamide (example D.e69) the title compound (free base) is obtained as colorless solid.

HR-MS (ESI): m/z=470.2369 ([MH]$^+$, $C_{25}H_{30}F_2N_5O_2^+$, calc. 470.2363).

Example D.f71

N-[(1R*,2R*,4R*)-4-Amino-2-fluorocyclopentyl]-4-[2-(cyclopropylmethoxy)-5-(difluoromethyl)phenyl]-6-methyl-5H-pyrrolo[3,2-d]pyrimidine-7-carboxamide Starting from N-[(1R*,2R*,4R*)-4-azido-2-fluorocyclopentyl]-4-[2-(cyclopropylmethoxy)-5-(difluoromethyl)phenyl]-6-methyl-5H-pyrrolo[3,2-d]pyrimidine-7-carboxamide (example D.e71) the title compound is obtained as colorless solid.

HR-MS (ESI): m/z=474.2115 VFW, $C_{24}H_{27}F_3N_5O_2^+$, calc. 474.2111).

Example D.f73

N-[(1S*,2R*,4S*)-4-Amino-2-fluorocyclohexyl]-4-[2-(cyclopropylmethoxy)-5-(difluoromethyl)phenyl]-6-methyl-5H-pyrrolo[3,2-d]pyrimidine-7-carboxamide Starting from N-[(1S*,2R*,4S*)-4-azido-2-fluorocyclohexyl]-4-[2-(cyclopropylmethoxy)-5-(difluoromethyl)phenyl]-6-methyl-5H-pyrrolo[3,2-d]pyrimidine-7-carboxamide (example D.e73) the title compound is obtained as colorless solid.

HR-MS (ESI): m/z=488.2265 ([MH]$^+$, $C_{25}H_{29}F_3N_5O_2^+$, calc. 488.2268).

Example D.g1

4-[2-(Cyclopropylmethoxy)-5-(difluoromethyl)phenyl]-6-methyl-5H-pyrrolo[3,2-d]pyrimidine-7-carboxylic acid Ethyl 4-[2-(cyclopropylmethoxy)-5-(difluoromethyl)phenyl]-6-methyl-5H-pyrrolo[3,2-d]pyrimidine-7-carboxylate (example D.a19; 52.73 g; 131.4 mmol) is dissolved in tert. BuOH (500.0 mL) and water (5.0 mL). After addition of commercially available KOtBu (73.70 g; 656.8 mmol) the reaction mixture is stirred at 100° C. over night and cooled to ambient temperature. Water (1500 mL) is added and pH is adjusted to 6.0 by careful addition of 2M aqueous citric acid. The precipitated product is filtered washed with several portions of water and dried under reduced pressure to yield 45.3 g of the title compound as off-white solid.

$^1$H-NMR (300 MHz, DMSO-d$_6$): 12.22-11.77 (br.s, 2H, —NH, —CO$_2$H); 8.96 (s, 1H); 7.82 (d, J=2.0, 1H); 7.74 (dd, J=8.6, 2.0, 1H); 7.31 (d, J=8.6, 1H); 7.08 (t, J=56.0, 1H); 3.96 (d, J=6.9, 2H); 2.74 (s, 3H); 0.98 (m, 1H); 0.39 (m, 2H); 0.26 (m, 2H).

Example D.g2

4-[2-(Cyclopropylmethoxy)-5-(trifluoromethyl)phenyl]-6-methyl-5H-pyrrolo[3,2-d]pyrimidine-7-carboxylic acid Starting from ethyl 4-[2-(cyclopropylmethoxy)-5-(trifluoromethyl)phenyl]-6-methyl-5H-pyrrolo[3,2-d]pyrimidine-7-carboxylate (example D.a8) and following the procedure as described in example D.g1 the title compound is obtained as off-white solid.

$^1$H-NMR (300 MHz, DMSO-d$_6$/MeOH-d$_4$): 8.95 (s, 1H); 7.89 (d, J=2.1, 1H); 7.88 (dd, J=8.4, 2.1, 1H); 7.37 (d, J=8.4, 1H); 4.00 (d, J=7.1, 2H); 2.74 (s, 3H); 1.00 (m, 1H); 0.40 (m, 2H); 0.27 (m, 2H).

Example E1

N-(1-Acetylpiperidin-4-yl)-4-[5-(cyclopropylmethoxy)-1,3-benzodioxol-4-yl]-6-methyl-5H-pyrrolo[3,2-d]pyrimidine-7-carboxamide 4-[5-(Cyclopropylmethoxy)-1,3-benzodioxol-4-yl]-6-methyl-N-piperidin-4-yl-5H-pyrrolo[3,2-d]pyrimidine-7-carboxamide hydrochloride from example D.f1 (486 mg; 1.0 mmol) and DBU (2.5 mmol) is dissolved in dry dichloromethane (5 mL). Acetyl chloride (1.1 mmol) is syringed into the reaction mixture at ice bath temperature. After addition the mixture is stirred at ambient temperature over night. Methanol (1 mL) is added and stirring is continued for two hours. The volatiles are evaporated. The residue is purified by reversed phase preparative HPLC. The collected product fraction is freeze-dried to yield the title compound as colorless solid.

MS (ESI): m/z=492 (MH$^+$, 100%).

$^1$H-NMR (300 MHz, DMSO-d$_6$): 12.00 (s, 1H, —NH); 8.93 (s, 1H); 8.76 (d, J=7.8, 1H, —NH); 7.00 (d, J=8.6, 1H); 6.56 (d, J=8.6, 1H); 6.00 (s, 2H); 4.23-4.04 (m, 2H); 3.80 (m, 1H); 3.76 (d, J=6.8, 2H); 3.28 (m, 1H); 2.95 (m, 1H); 2.77 (s, 3H); 2.04 (s, 3H); 1.95 (m, 2H); 1.54 (m, 1H); 1.38 (m, 1H); 0.88 (m, 1H); 0.31 (m, 2H); 0.13 (m, 2H).

The following compounds are prepared analogously to the procedure described in above example E1.

Example E2

4-[5-(Cyclopropylmethoxy)-1,3-benzodioxol-4-yl]-6-methyl-N-(1-propionylpiperidin-4-yl)-5H-pyrrolo[3,2-d]pyrimidine-7-carboxamide Starting from 4-[5-(cyclopropylmethoxy)-1,3-benzodioxol-4-yl]-6-methyl-N-piperidin-4-yl-5H-pyrrolo[3,2-d]pyrimidine-7-carboxamide hydrochloride (example D.f1) and commercially available propionyl chloride the title compound is obtained as colorless solid.

MS (ESI): m/z=506 (MH$^+$, 100%).

$^1$H-NMR (300 MHz, DMSO-d$_6$): 12.00 (s, 1H, —NH); 8.93 (s, 1H); 8.75 (d, J=7.7, 1H, —NH); 7.00 (d, J=8.6, 1H); 6.56 (d, J=8.6, 1H); 6.00 (s, 2H); 4.25-4.03 (m, 2H); 3.79 (m, 1H); 3.76 (d, J=6.8, 2H); 3.25 (m, 1H); 2.95 (m, 1H); 2.77 (s, 3H); 2.36 (qu, J=7.5, 2H); 1.96 (m, 2H); 1.52 (m, 1H); 1.39 (m, 1H); 1.01 (t, J=7.5, 3H); 0.88 (m, 1H); 0.31 (m, 2H); 0.13 (m, 2H).

Example E3

4-[5-(Cyclopropylmethoxy)-1,3-benzodioxol-4-yl]-N-[1-(methoxyacetyl)piperidin-4-yl]-6-methyl-5H-pyrrolo[3,2-d]pyrimidine-7-carboxamide Starting from 4-[5-(cyclopropylmethoxy)-1,3-benzodioxol-4-yl]-6-methyl-N-piperidin-4-yl-5H-pyrrolo[3,2-d]pyrimidine-7-carboxamide hydrochloride (example D.f1) and commercially available methoxy-acetyl chloride the title compound is obtained as colorless solid.

MS (ESI): m/z=522 (MH$^+$, 100%).

$^1$H-NMR (300 MHz, DMSO-d$_6$): 12.00 (s, 1H, —NH); 8.93 (s, 1H); 8.75 (d, J=7.7, 1H, —NH); 7.00 (d, J=8.6, 1H); 6.55 (d, J=8.6, 1H); 6.00 (s, 2H); 422-4.03 (m, 2H); 4.12 (d, J=1.8, 2H); 3.76 (d, J=6.8, 2H); 3.73 (m, 1H); 3.31 (s, 3H); 3.22 (m, 1H); 2.98 (m, 1H); 2.77 (s, 3H); 1.97 (m, 2H); 1.54 (m, 1H); 1.41 (m, 1H); 0.88 (m, 1H); 0.31 (m, 2H); 0.13 (m, 2H).

Example E4

Ethyl 4-[({4-[5-(cyclopropylmethoxy)-1,3-benzodioxol-4-yl]-6-methyl-5H-pyrrolo[3,2-d]pyrimidin-7-yl}carbonyl)amino]piperidine-1-carboxylate Starting from 4-[5-(cyclopropylmethoxy)-1,3-benzodioxol-4-yl]-6-methyl-N-piperidin-4-yl-5H-pyrrolo[3,2-d]

pyrimidine-7-carboxamide hydrochloride (example D.f1) and commercially available ethyl chloroformate the title compound is obtained as colorless solid.

MS (ESI): m/z=522 (MH+, 100%).

$^1$H-NMR (300 MHz, DMSO-d$_6$): 11.99 (s, 1H, —NH); 8.93 (s, 1H); 8.75 (d, J=7.7, 1H, —NH); 7.00 (d, J=8.6, 1H); 6.56 (d, J=8.6, 1H); 6.00 (s, 2H); 4.06 (m, 1H & qu, J=7.1, 2H); 3.88 (m, 2H); 3.76 (d, J=6.8, 2H); 3.11 (m, 2H); 2.77 (s, 3H); 1.94 (m, 2H); 1.46 (m, 2H); 1.20 (t, J=7.1, 3H); 0.88 (m, 1H); 0.31 (m, 2H); 0.13 (m, 2H).

Example E5

N-(trans-4-acetamidocyclohexyl)-4-[5-(cyclopropylmethoxy)-1,3-benzodioxol-4-yl]-6-methyl-5H-pyrrolo[3,2-d]pyrimidine-7-carboxamide Starting from N-(trans-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride (example D.f2) and commercially available acetyl chloride the title compound is obtained as colorless solid.

MS (ESI): m/z=506 (MH+, 100%).

$^1$H-NMR (300 MHz, DMSO-d$_6$): 11.97 (s, 1H, —NH); 8.93 (s, 1H); 8.59 (d, J=7.7, 1H, —NH); 7.72 (d, J=7.9, 1H, —NH); 7.00 (d, J=8.6, 1H); 6.55 (d, J=8.6, 1H); 6.00 (s, 2H); 3.80 (m, 1H); 3.76 (d, J=6.8, 2H); 3.58 (m, 1H); 2.76 (s, 3H); 2.00 (m, 2H); 1.86 (m, 2H); 1.79 (s, 3H); 1.35 (m, 4H); 0.88 (m, 1H); 0.31 (m, 2H); 0.13 (m, 2H).

Example E6

4-[5-(Cyclopropylmethoxy)-1,3-benzodioxol-4-yl]-6-methyl-N-[trans-4-(propionylamino)cyclohexyl]-5H-pyrrolo[3,2-d]pyrimidine-7-carboxamide Starting from N-(trans-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride (example D.f2) and commercially available propionyl chloride the title compound is obtained as colorless solid.

MS (ESI): m/z=520 (MH+, 100%).

$^1$H-NMR (300 MHz, DMSO-d$_6$): 11.97 (s, 1H, —NH); 8.93 (s, 1H); 8.60 (d, J=7.7, 1H, —NH); 7.62 (d, J=7.9, 1H, —NH); 7.00 (d, J=8.6, 1H); 6.56 (d, J=8.6, 1H); 6.00 (s, 2H); 3.79 (m, 1H); 3.76 (d, J=6.8, 2H); 3.59 (m, 1H); 2.76 (s, 3H); 2.05 (qu, J=7.6, 2H); 2.01 (m, 2H); 1.86 (m, 2H); 1.35 (m, 4H); 0.99 (t, J=7.6, 3H); 0.88 (m, 1H); 0.30 (m, 2H); 0.12 (m, 2H).

Example E7

4-[5-(Cyclopropylmethoxy)-1,3-benzodioxol-4-yl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride (example D.f2) and commercially available methoxy-acetyl chloride the title compound is obtained as colorless solid.

MS (ESI): m/z=536 (MH+, 100%).

$^1$H-NMR (300 MHz, DMSO-d$_6$): 11.97 (s, 1H, —NH); 8.93 (s, 1H); 8.59 (d, J=7.7, 1H, —NH); 7.57 (d, J=8.2, 1H, —NH); 7.00 (d, J=8.6, 1H); 6.56 (d, J=8.6, 1H); 6.00 (s, 2H); 3.78 (m, 1H & s, 2H); 3.76 (d, J=6.8, 2H); 3.68 (m, 2H); 3.31 (s, 3H); 2.76 (s, 3H); 2.01 (m, 2H); 1.82 (m, 2H); 1.43 (m, 4H); 0.88 (m, 1H); 0.30 (m, 2H); 0.12 (m, 2H).

Example E8

Ethyl {trans-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate Starting from N-(trans-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride (example D.f2) and commercially available ethyl chloroformate the title compound is obtained as colorless solid.

MS (ESI): m/z=536 (MH+, 100%).

$^1$H-NMR (300 MHz, DMSO-d$_6$): 11.97 (s, 1H, —NH); 8.93 (s, 1H); 8.59 (d, J=7.7, 1H, —NH); 7.00 (d, J=6.8, 1H & d, J=8.6, 1H, —NH); 6.56 (d, J=8.6, 1H); 6.00 (s, 2H); 3.98 (qu, J=6.9, 2H); 3.94 (m, 1H); 3.76 (m, 1H & d, J=6.8, 2H); 3.33 (m, 1H); 2.76 (s, 3H); 2.00 (m, 2H); 1.87 (m, 2H); 1.35 (m, 4H); 1.16 (t, J=6.9, 3H); 0.88 (m, 1H); 0.30 (m, 2H); 0.12 (m, 2H).

Example E9

N-(cis-4-acetamidocyclohexyl)-4-[5-(cyclopropylmethoxy)-1,3-benzodioxol-4-yl]-6-methyl-5H-pyrrolo[3,2-d]pyrimidine-7-carboxamide Starting from N-(cis-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride (example D.f3) and commercially available acetyl chloride the title compound is obtained as colorless solid.

MS (ESI): m/z=506 (MH+, 100%).

$^1$H-NMR (300 MHz, DMSO-d$_6$): 11.98 (s, 1H, —NH); 8.96 (s, 1H); 8.87 (d, J=7.5, 1H, —NH); 7.84 (d, J=7.3, 1H, —NH); 7.01 (d, J=8.6, 1H); 6.56 (d, J=8.6, 1H); 6.00 (s, 2H); 4.01 (m, 1H); 3.77 (m, 1H & d, J=6.8, 2H); 2.77 (s, 3H); 1.83 (s, 3H); 1.82-1.51 (m, 8H); 0.88 (m, 1H); 0.31 (m, 2H); 0.13 (m, 2H).

Example E10

4-[5-(Cyclopropylmethoxy)-1,3-benzodioxol-4-yl]-6-methyl-N-[cis-4-(propionylamino)cyclohexyl]-5H-pyrrolo[3,2-d]pyrimidine-7-carboxamide Starting from N-(cis-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride (example D.f3) and commercially available propionyl chloride the title compound is obtained as colorless solid.

MS (ESI): m/z=520 (MH+, 100%).

$^1$H-NMR (300 MHz, DMSO-d$_6$): 11.98 (s, 1H, —NH); 8.96 (s, 1H); 8.87 (d, J=7.5, 1H, —NH); 7.75 (d, J=7.5, 1H, —NH); 7.01 (d, J=8.6, 1H); 6.56 (d, J=8.6, 1H); 6.00 (s, 2H); 4.01 (m, 1H); 3.76 (m, 1H & d, J=6.8, 2H); 2.77 (s, 3H); 2.11 (qu, J=7.5, 2H); 1.87-1.50 (m, 8H); 1.00 (t, J=7.6, 3H); 0.88 (m, 1H); 0.31 (m, 2H); 0.13 (m, 2H).

Example E11

4-[5-(Cyclopropylmethoxy)-1,3-benzodioxol-4-yl]-N-{cis-4-[(methoxyacetyl)amino]cyclohexyl}-6-methyl-5H-pyrrolo[3,2-d]pyrimidine-7-carboxamide Starting from N-(cis-4-aminocyclohexyl)-4-[5-(cyclopropylmethoxy)-1,3-benzodioxol-4-yl]-6-methyl-5H-pyrrolo

[3,2-d]pyrimidine-7-carboxamide hydrochloride (example D.f3) and commercially available methoxy-acetyl chloride the title compound is obtained as colorless solid.

MS (ESI): m/z=536 (MH$^+$, 100%).

$^1$H-NMR (300 MHz, DMSO-d$_6$): 11.98 (s, 1H, —NH); 8.97 (s, 1H); 8.91 (d, J=7.3, 1H, —NH); 7.67 (d, J=7.9, 1H, —NH); 7.01 (d, J=8.6, 1H); 6.56 (d, J=8.6, 1H); 6.00 (s, 2H); 4.04 (m, 1H); 3.81 (s, 2H); 3.76 (m, 1H & d, J=6.8, 2H); 3.31 (s, 3H); 2.77 (s, 3H); 1.87-1.57 (m, 8H); 0.89 (m, 1H); 0.31 (m, 2H); 0.13 (m, 2H).

Example E12

Ethyl {cis-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate Starting from N-(cis-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride (example D.f3) and commercially available ethyl chloroformate the title compound is obtained as colorless solid.

MS (ESI): m/z=536 (MH$^+$, 100%).

$^1$H-NMR (300 MHz, DMSO-d$_6$): 11.97 (s, 1H, —NH); 8.96 (s, 1H); 8.91 (d, J=7.9, 1H, —NH); 7.20 (br.d, J~6.2, 1H, —NH); 7.01 (d, J=8.6, 1H); 6.56 (d, J=8.6, 1H); 6.00 (s, 2H); 3.99 (m, 1H & qu, J=7.1, 2H); 3.76 (d, J=6.8, 2H); 3.48 (m, 1H); 2.77 (s, 3H); 1.85-1.54 (m, 8H); 1.17 (t, J=7.1, 3H); 0.89 (m, 1H); 0.31 (m, 2H); 0.13 (m, 2H).

Example E13

N-[(3R)-1-acetylpyrrolidin-3-yl]-4-[5-(cyclopropylmethoxy)-1,3-benzodioxol-4-yl]-6-methyl-5H-pyrrolo[3,2-d]pyrimidine-7-carboxamide Starting from 4-[5-(cyclopropylmethoxy)-1,3-benzodioxol-4-yl]-6-methyl-N-[(3R)-pyrrolidin-3-yl]-5H-pyrrolo[3,2-d]pyrimidine-7-carboxamide hydrochloride (example D.f4) and commercially available acetyl chloride the title compound is obtained as colorless solid.

MS (ESI): m/z=478 (MH$^+$, 100%).

$^1$H-NMR (400 MHz, DMSO-d$_6$): 12.03 (s, 1H, —NH); 8.93 (s, 1H); [8.88 (d, J=7.0), 8.85 (d, 6.7), 1H, —NH]; 7.00 (d, J=8.6, 1H); 6.56 (d, J=8.6, 1H); 6.00 (s, 2H); [4.59 (m), 4.49 (m), 1H]; [3.84 (m), 3.68-3.58 (m), 2H]; 3.76 (d, J=6.7, 2H); 3.56-3.27 (m, 2H); [2.78 (s), 2.77 (s), 3H]; 2.34-2.16 (m, 1H); 2.08-1.87 (m, 1H); [1.98 (s), 1.96 (s), 3H]; 0.88 (m, 1H); 0.31 (m, 2H); 0.12 (m, 2H).

Example E14

4-[5-(Cyclopropylmethoxy)-1,3-benzodioxol-4-yl]-6-methyl-N-[(3R)-1-propionylpyrrolidin-3-yl]-5H-pyrrolo[3,2-d]pyrimidine-7-carboxamide Starting from 4-[5-(cyclopropylmethoxy)-1,3-benzodioxol-4-yl]-6-methyl-N-[(3R)-pyrrolidin-3-yl]-5H-pyrrolo[3,2-d]pyrimidine-7-carboxamide hydrochloride (example D.f4) and commercially available propionyl chloride the title compound is obtained as colorless solid.

MS (ESI): m/z=492 (MH$^+$, 100%).

$^1$H-NMR (400 MHz, DMSO-d$_6$): 12.03 (s, 1H, —NH); 8.92 (s, 1H); [8.88 (d, J=7.0), 8.85 (d, 6.7), 1H, —NH]; 7.01 (d, J=8.6, 1H); 6.56 (d, J=8.6, 1H); 6.00 (s, 2H); [4.59 (m), 4.49 (m), 1H]; [3.82 (m), 3.69-3.57 (m), 2H]; 3.76 (d, J=6.7, 2H); 3.55-3.26 (m, 2H); [2.78 (s), 2.77 (s), 3H]; 2.34-2.16 (m, 1H); [2.29 (qu, J=7.5), 2.25 (qu, J=7.5), 2H]; [2.03 (m), 1.92 (m), 1H]; [1.01 (t, J=7.5), 0.99 (t, J=7.5), 3H]; 0.88 (m, 1H); 0.31 (m, 2H); 0.12 (m, 2H).

Example E15

4-[5-(Cyclopropylmethoxy)-1,3-benzodioxol-4-yl]-N-[(3R)-1-(methoxyacetyl)pyrrolidin-3-yl]-6-methyl-5H-pyrrolo[3,2-d]pyrimidine-7-carboxamide Starting from 4-[5-(cyclopropylmethoxy)-1,3-benzodioxol-4-yl]-6-methyl-N-[(3R)-pyrrolidin-3-yl]-5H-pyrrolo[3,2-d]pyrimidine-7-carboxamide hydrochloride (example D.f4) and commercially available methoxy-acetyl chloride the title compound is obtained as colorless solid.

MS (ESI): m/z=508 (MH$^+$, 100%).

$^1$H-NMR (400 MHz, DMSO-d$_6$): 12.03 (s, 1H, —NH); [8.93 (s), 8.92 (s), 1H]; [8.87 (d, J=7.2), 8.85 (d, 6.9), 1H, —NH]; 7.00 (d, J=8.6, 1H); 6.56 (d, J=8.6, 1H); 6.00 (s, 2H); [4.59 (m), 4.49 (m), 1H]; [4.06 (d, J=6.6), 4.01 (d, J=2.2), 2H]; [3.80 (m), 3.68 (m), 1H]; 3.76 (d, J=6.7, 2H); 3.63-3.42 (m, 2H); 3.39-3.26 (m, 1H); [3.32 (s), 3.30 (s), 3H]; 2.77 (s, 3H); 2.34-2.15 (m, 1H); [2.03 (m), 1.91 (m), 1H]; 0.88 (m, 1H); 0.30 (m, 2H); 0.12 (m, 2H).

Example E16

N-[(3R*,4R*)-1-acetyl-4-hydroxypyrrolidin-3-yl]-4-[5-(cyclopropylmethoxy)-1,3-benzodioxol-4-yl]-6-methyl-5H-pyrrolo[3,2-d]pyrimidine-7-carboxamide Starting from 4-[5-(cyclopropylmethoxy)-1,3-benzodioxol-4-yl]-N-[(3R*,4R*)-4-hydroxypyrrolidin-3-yl]-6-methyl-5H-pyrrolo[3,2-d]pyrimidine-7-carboxamide hydrochloride (example D.f5) and commercially available acetyl chloride the title compound is obtained as colorless solid.

HR-MS (ESI): m/z=494.2040 ([MH]$^+$, C$_{25}$H$_{28}$N$_5$O$_6$$^+$, calc. 494.2034).

Example E17

4-[5-(Cyclopropylmethoxy)-1,3-benzodioxol-4-yl]-N-[(3R*,4R*)-4-hydroxy-1-propionylpyrrolidin-3-yl]-6-methyl-5H-pyrrolo[3,2-d]pyrimidine-7-carboxamide Starting from 4-[5-(cyclopropylmethoxy)-1,3-benzodioxol-4-yl]-N-[(3R*,4R*)-4-hydroxypyrrolidin-3-yl]-6-methyl-5H-pyrrolo[3,2-d]pyrimidine-7-carboxamide hydrochloride (example D.f5) and commercially available propionyl chloride the title compound is obtained as colorless solid.

HR-MS (ESI): m/z=508.2191 ([MH]$^+$, C$_{26}$H$_{30}$N$_5$O$_6$$^+$, calc. 508.2191).

Example E18

4-[5-(Cyclopropylmethoxy)-1,3-benzodioxol-4-yl]-N-[(3R*,4R*)-4-hydroxy-1-(methoxyacetyl)pyrrolidin-3-yl]-6-methyl-5H-pyrrolo[3,2-d]pyrimidine-7-carboxamide Starting from 4-[5-(cyclopropylmethoxy)-1,3-benzodioxol-4-yl]-N-[(3R*,4R*)-4-hydroxypyrrolidin-3-yl]-6-methyl-5H-pyrrolo[3,2-d]pyrimidine-7-carboxamide hydrochloride (example D.f5) and commercially available methoxy-acetyl chloride the title compound is obtained as colorless solid.

HR-MS (ESI): m/z=524.2140 ([MH]$^+$, $C_{26}H_{30}N_5O_7^+$, calc. 524.2140).

Example E19

N-(1-acetylpiperidin-4-yl)-4-[2-(cyclopropyl-methoxy)-4-fluorophenyl]-6-methyl-5H-pyrrolo[3,2-d]pyrimidine-7-carboxamide Starting from 4-[2-(cyclopropylmethoxy)-4-fluorophenyl]-6-methyl-N-piperidin-4-yl-5H-pyrrolo[3,2-d]pyrimidine-7-carboxamide hydrochloride (example D.f6) and commercially available acetyl chloride the title compound is obtained as colorless solid.

MS (ESI): m/z=466 (MH$^+$, 100%).
$^1$H-NMR (300 MHz, DMSO-d$_6$): 11.80 (s, 1H, —NH); 8.94 (s. 1H); 8.81 (d, J=7.7, 1H, —NH); 7.66 (dd, J=8.4, 6.9, 1H); 7.08 (dd, J=11.7, 2.4, 1H); 6.96 (ddd, J=8.4, 8.4, 2.4, 1H); 4.23-4.04 (m, 2H); 3.91 (d, J=6.9, 2H); 3.78 (m, 1H); 3.28 (m, 1H); 2.95 (m, 1H); 2.79 (s, 3H); 2.04 (s, 3H); 1.95 (m, 2H); 1.54 (m, 1H); 1.38 (m, 1H); 0.96 (m, 1H); 0.38 (m, 2H): 0.25 (m, 2H).

Example E20

4-[2-(Cyclopropylmethoxy)-4-fluorophenyl]-6-methyl-N-(1-propionylpiperidin-4-yl)-5H-pyrrolo[3,2-d]pyrimidine-7-carboxamide Starting from 4-[2-(cyclopropylmethoxy)-4-fluorophenyl]-6-methyl-N-piperidin-4-yl-5H-pyrrolo[3,2-d]pyrimidine-7-carboxamide hydrochloride (example D.f6) and commercially available propionyl chloride the title compound is obtained as colorless solid.

MS (ESI): m/z=480 (MH$^+$, 100%).
$^1$H-NMR (300 MHz, DMSO-d$_6$): 11.80 (s, 1H, —NH); 8.94 (s. 1H); 8.81 (d, J=7.7, 1H, —NH); 7.66 (dd, J=8.6, 7.1, 1H); 7.08 (dd, J=11.7, 2.4, 1H); 6.96 (ddd, J=8.6, 8.6, 2.4, 1H); 4.26-4.04 (m, 2H); 3.91 (d, J=6.9, 2H); 3.81 (m, 1H); 3.25 (m, 1H); 2.96 (m, 1H); 2.78 (s, 3H); 2.36 (qu, J=7.5, 3H); 1.95 (m, 2H); 1.51 (m, 1H); 1.38 (m, 1H); 1.01 (t, J=7.5, 3H); 0.96 (m, 1H); 0.38 (m, 2H): 0.25 (m, 2H).

Example E21

4-[2-(Cyclopropylmethoxy)-4-fluorophenyl]-N-[1-(methoxyacetyl)piperidin-4-yl]-6-methyl-5H-pyrrolo[3,2-d]pyrimidine-7-carboxamide Starting from 4-[2-(cyclopropylmethoxy)-4-fluorophenyl]-6-methyl-N-piperidin-4-yl-5H-pyrrolo[3,2-d]pyrimidine-7-carboxamide hydrochloride (example D.f6) and commercially available methoxyacetyl chloride the title compound is obtained as colorless solid.

MS (ESI): m/z=496 (MH$^+$, 100%).
$^1$H-NMR (300 MHz, DMSO-d$_6$): 11.80 (s, 1H, —NH); 8.94 (s. 1H); 8.81 (d, J=7.7, 1H, —NH); 7.66 (dd, J=8.6, 7.1, 1H); 7.09 (dd, J=11.7, 2.4, 1H); 6.96 (ddd, J=8.6, 8.6, 2.4, 1H); 4.24-4.04 (m, 2H); 4.12 (d, J=1.6, 2H); 3.91 (d, J=7.1, 2H); 3.75 (m, 1H); 3.31 (s, 3H); 3.24 (m, 1H); 2.98 (m, 1H); 2.78 (s, 3H); 1.96 (m, 2H); 1.54 (m, 1H); 1.41 (m, 1H); 0.96 (m, 1H); 0.38 (m, 2H): 0.25 (m, 2H).

Example E22

N-(trans-4-acetamidocyclohexyl)-4-[2-(cyclopropyl-methoxy)-4-fluorophenyl]-6-methyl-5H-pyrrolo[3,2-d]pyrimidine-7-carboxamide Starting from N-(trans-4-aminocyclohexyl)-4-[2-(cyclopropylmethoxy)-4-fluorophenyl]-6-methyl-5H-pyrrolo[3,2-d]pyrimidine-7-carboxamide hydrochloride (example D.f7) and commercially available acetyl chloride the title compound is obtained as colorless solid.

MS (ESI): m/z=480 (MH$^+$, 100%).
$^1$H-NMR (300 MHz, DMSO-d$_6$): 11.77 (s, 1H, —NH); 8.94 (s, 1H); 8.65 (d, J=7.9, 1H, —NH); 7.72 (d, J=7.7, 1H, —NH); 7.66 (dd, 8.4, 7.1, 1H); 7.08 (dd, 11.7, 2.4, 1H); 6.96 (ddd, 8.4, 8.4, 2.4, 1H); 3.91 (d, J=6.9, 2H); 3.80 (m, 1H); 3.58 (m, 1H); 2.78 (s, 3H); 2.00 (m, 2H); 1.86 (m, 2H); 1.79 (s, 3H); 1.35 (m, 4H); 0.96 (m, 1H); 0.38 (m, 2H); 0.25 (m, 2H).

Example E23

4-[2-(Cyclopropylmethoxy)-4-fluorophenyl]-6-methyl-N-[trans-4-(propionylamino)cyclohexyl]-5H-pyrrolo[3,2-d]pyrimidine-7-carboxamide Starting from N-(trans-4-aminocyclohexyl)-4-[2-(cyclopropylmethoxy)-4-fluorophenyl]-6-methyl-5H-pyrrolo[3,2-d]pyrimidine-7-carboxamide hydrochloride (example D.f7) and commercially available propionyl chloride the title compound is obtained as colorless solid.

MS (ESI): m/z=494 (MH$^+$, 100%).
$^1$H-NMR (300 MHz, DMSO-d$_6$): 11.77 (s, 1H, —NH); 8.94 (s, 1H); 8.65 (d, J=7.7, 1H, —NH); 7.65 (dd, 8.4, 7.1, 1H); 7.62 (d, J=7.6, 1H, —NH); 7.08 (dd, 11.7, 2.4, 1H); 6.96 (ddd, 8.4, 8.4, 2.4, 1H); 3.91 (d, J=6.9, 2H); 3.80 (m, 1H); 3.59 (m, 1H); 2.78 (s, 3H); 2.06 (qu, J=7.5, 2H); 2.01 (m, 2H); 1.86 (m, 2H); 1.35 (m, 4H); 0.99 (t, J=7.5, 3H); 0.96 (m, 1H); 0.38 (m, 2H); 0.25 (m, 2H).

Example E24

4-[2-(Cyclopropylmethoxy)-4-fluorophenyl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-4-fluorophenyl]-6-methyl-5H-pyrrolo[3,2-d]pyrimidine-7-carboxamide hydrochloride (example D.f7) and commercially available methoxy-acetyl chloride the title compound is obtained as colorless solid.

MS (ESI): m/z=510 (MH$^+$, 100%).
$^1$H-NMR (300 MHz, DMSO-d$_6$): 11.77 (s, 1H, —NH); 8.94 (s, 1H); 8.64 (d, J=7.9, 1H, —NH); 7.66 (dd, 8.4, 6.9, 1H); 7.57 (d, J=8.4, 1H, —NH); 7.08 (dd, 11.7, 2.4, 1H); 6.96 (ddd, 8.4, 8.4, 2.4, 1H); 3.91 (d, J=6.9, 2H); 3.78 (s, 2H & m, 1H); 3.68 (m, 1H); 3.31 (s, 3H); 2.78 (s, 3H); 2.01 (m, 2H); 1.82 (m, 2H); 1.43 (m, 4H); 0.96 (m, 1H); 0.38 (m, 2H); 0.25 (m, 2H).

Example E25

N-(cis-4-acetamidocyclohexyl)-4-[2-(cyclopropyl-methoxy)-4-fluorophenyl]-6-methyl-5H-pyrrolo[3,2-d]pyrimidine-7-carboxamide Starting from N-(cis-4-aminocyclohexyl)-4-[2-(cyclopropylmethoxy)-4-fluorophenyl]-6-methyl-5H-pyrrolo[3,2-d]

pyrimidine-7-carboxamide hydrochloride (example D.f8) and commercially available acetyl chloride the title compound is obtained as colorless solid.

MS (ESI): m/z=480 (MH+, 100%).

$^1$H-NMR (300 MHz, DMSO-d$_6$): 11.78 (s, 1H, —NH); 8.97 (s, 1H); 8.93 (d, J=7.5, 1H, —NH); 7.84 (d, J=7.7, 1H, —NH); 7.66 (dd, 8.4, 7.1, 1H); 7.09 (dd, 11.7, 2.4, 1H); 6.96 (ddd, 8.4, 8.4, 2.4, 1H); 4.02 (m, 1H); 3.91 (d, J=7.1, 2H); 3.75 (m, 1H); 2.79 (s, 3H); 1.84 (s, 3H); 1.84-1.51 (m, 8H); 0.96 (m, 1H); 0.38 (m, 2H); 0.25 (m, 2H).

Example E26

4-[2-(Cyclopropylmethoxy)-4-fluorophenyl]-6-methyl-N-[cis-4-(propionylamino)cyclohexyl]-5H-pyrrolo[3,2-d]pyrimidine-7-carboxamide Starting from N-(cis-4-aminocyclohexyl)-4-[2-(cyclopropylmethoxy)-4-fluorophenyl]-6-methyl-5H-pyrrolo[3,2-d]pyrimidine-7-carboxamide hydrochloride (example D.f8) and commercially available propionyl chloride the title compound is obtained as colorless solid.

MS (ESI): m/z=494 (MH+, 100%).

$^1$H-NMR (300 MHz, DMSO-d$_6$): 11.78 (s, 1H, —NH); 8.97 (s, 1H); 8.93 (d, J=7.7, 1H, —NH); 7.75 (d, J=7.7, 1H, —NH); 7.66 (dd, 8.4, 6.9, 1H); 7.09 (dd, 11.7, 2.4, 1H); 6.96 (ddd, 8.4, 8.4, 2.4, 1H); 4.02 (m, 1H); 3.92 (d, J=7.1, 2H); 3.75 (m, 1H); 2.79 (s, 3H); 2.11 (qu, J=7.5, 2H); 1.84-1.51 (m, 8H); 1.00 (t, J=7.5, 3H); 0.96 (m, 1H); 0.38 (m, 2H); 0.25 (m, 2H).

Example E27

4-[2-(Cyclopropylmethoxy)-4-fluorophenyl]-N-{cis-4-[(methoxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-4-fluorophenyl]-6-methyl-5H-pyrrolo[3,2-d]pyrimidine-7-carboxamide hydrochloride (example D.f8) and commercially available methoxy-acetyl chloride the title compound is obtained as colorless solid.

MS (ESI): m/z=510 (MH+, 100%).

$^1$H-NMR (300 MHz, DMSO-d$_6$): 11.78 (s, 1H, —NH); 8.98 (s, 1H); 8.96 (d, J=7.5, 1H, —NH); 7.67 (d, J=7.6, 1H, —NH); 7.66 (dd, 8.4, 6.9, 1H); 7.09 (dd, 11.5, 2.4, 1H); 6.96 (ddd, 8.4, 8.4, 2.4, 1H); 4.05 (m, 1H); 3.91 (d, J=7.1, 2H); 3.82 (s, 2H); 3.79 (m, 1H); 3.31 (s, 3H); 2.79 (s, 3H); 1.86-1.58 (m, 8H); 0.96 (m, 1H); 0.38 (m, 2H); 0.25 (m, 2H).

Example E28

N-[(3R)-1-acetylpyrrolidin-3-yl]-4-[2-(cyclopropylmethoxy)-4-fluorophenyl]-6-methyl-5H-pyrrolo[3,2-d]pyrimidine-7-carboxamide Starting from 4-[2-(cyclopropylmethoxy)-4-fluorophenyl]-6-methyl-N-[(3R)-pyrrolidin-3-yl]-5H-pyrrolo[3,2-d]pyrimidine-7-carboxamide hydrochloride (example D.f9) and commercially available acetyl chloride the title compound is obtained as colorless solid.

MS (ESI): m/z=452 (MH+, 100%).

$^1$H-NMR (300 MHz, DMSO-d$_6$): 11.83 (s, 1H, —NH); 8.94 (s, 1H); [8.93 (d, J=6.8), 8.90 (d, J=6.9), 1H, —NH]; 7.66 (ddd, J=8.4, 7.1, 1.1, 1H); 7.09 (dd, J=11.5, 2.4, 1H); 6.96 (ddd, J=8.4, 8.4, 2.4, 1H); [4.59 (m), 4.49 (m), 1H]; 3.91 (d, J=7.1, 2H); [3.84 (m), 3.69-3.58 (m), 2H]; 3.56-3.27 (m, 2H); [2.79 (s), 2.78 (s), 3H]; 2.35-2.16 (m, 1H); 2.08-1.86 (m, 1H); [1.98 (s), 1.96 (s), 3H]; 0.95 (m, 1H); 0.38 (m, 2H); 0.25 (m, 2H).

Example E29

4-[2-(Cyclopropylmethoxy)-4-fluorophenyl]-6-methyl-N-[(3R)-1-propanoylpyrrolidin-3-yl]-5H-pyrrolo[3,2-d]pyrimidine-7-carboxamide Starting from 4-[2-(cyclopropylmethoxy)-4-fluorophenyl]-6-methyl-N-[(3R)-pyrrolidin-3-yl]-5H-pyrrolo[3,2-d]pyrimidine-7-carboxamide hydrochloride (example D.f9) and commercially available propionyl chloride the title compound is obtained as colorless solid.

MS (ESI): m/z=466 (MH+, 100%).

$^1$H-NMR (300 MHz, DMSO-d$_6$): 11.83 (s, 1H, —NH); [8.93 (d, J=7.1), 8.90 (d, J=6.8), 1H, —NH]; [8.93 (s), 8.92 (s), 1H]; 7.66 (ddd, J=8.4, 7.1, 0.7, 1H); 7.08 (dd, J=11.7, 2.4, 1H); 6.96 (ddd, J=8.4, 8.4, 2.4, 1H); [4.59 (m), 4.49 (m), 1H]; 3.91 (d, J=7.1, 2H); [3.82 (m), 3.70-3.58 (m), 2H]; 3.55-3.27 (m, 2H); [2.79 (s), 2.78 (s), 3H]; 2.34-2.15 (m, 1H); [2.29 (qu, J=7.5), 2.25 (qu, J=7.5), 2H]; 2.08-1.86 (m, 1H); [1.01 (t, J=7.5), 0.99 (t, J=7.5), 3H]; 0.95 (m, 1H); 0.38 (m, 2H); 0.25 (m, 2H).

Example E30

4-[2-(Cyclopropylmethoxy)-4-fluorophenyl]-N-[(3R)-1-(methoxyacetyl)pyrrolidin-3-yl]-6-methyl-5H-pyrrolo[3,2-d]pyrimidine-7-carboxamide Starting from 4-[2-(cyclopropylmethoxy)-4-fluorophenyl]-6-methyl-N-[(3R)-pyrrolidin-3-yl]-5H-pyrrolo[3,2-d]pyrimidine-7-carboxamide hydrochloride (example D.f9) and commercially available methoxy-acetyl chloride the title compound is obtained as colorless solid.

MS (ESI): m/z=482 (MH+, 100%).

$^1$H-NMR (300 MHz, DMSO-d$_6$): 11.83 (s, 1H, —NH); [8.94 (s), 8.93 (s), 1H]; [8.92 (d, J=7.1), 8.90 (d, J=6.8), 1H, —NH]; 7.66 (ddd, J=8.4, 6.9, 0.7, 1H); 7.09 (dd, J=11.5, 2.4, 1H); 6.96 (ddd, J=8.4, 8.4, 2.4, 1H); [4.59 (m), 4.49 (m), 1H]; [4.06 (d, J=4.0), 4.01 (d, J=1.1), 2H]; 3.91 (d, J=6.9, 2H); [3.79 (m), 3.68 (m), 1H]; 3.62-3.42 (m, 2H); 3.38-3.27 (m, 1H); [3.32 (s), 3.29 (s), 3H]; 2.79 (s, 3H); 2.33-2.15 (m, 1H); [2.03 (m), 1.91 (m), 1H]; 0.95 (m, 1H); 0.38 (m, 2H); 0.25 (m, 2H).

Example E31

N-[(3R*,4R*)-1-acetyl-4-hydroxypyrrolidin-3-yl]-4-[2-(cyclopropylmethoxy)-4-fluorophenyl]-6-methyl-5H-pyrrolo[3,2-d]pyrimidine-7-carboxamide Starting from 4-[2-(cyclopropylmethoxy)-4-fluorophenyl]-N-[(3R*,4R*)-4-hydroxypyrrolidin-3-yl]-6-methyl-5H-pyrrolo[3,2-d]pyrimidine-7-carboxamide hydrochloride (example D.f10) and commercially available acetyl chloride the title compound is obtained as colorless solid.

MS (ESI): m/z=468 (MH+, 100%).

$^1$H-NMR (300 MHz, DMSO-d$_6$): 11.84 (s, 1H, —NH); 8.93 (s, 1H); [8.88 (d, J=7.2), 8.83 (d, J=6.6), 1H, —NH]; 7.65 (dd, J=8.4, 7.1, 1H); 7.09 (dd, J=11.7, 2.0, 1H); 6.96 (ddd, J=8.4, 8.4, 2.0, 1H); [5.56 (d, J=3.2), 5.48 (d, J=3.9), 1H, —OH]; [4.36 (m), 4.19 (m), 1H]; 4.27 (m, 1H); 3.91 (d, 7.2, 2H); [3.76 (m), 3.69 (m), 3.58 (m), 3.45 (m), 2H]; 3.41-

3.27 (m, 2H); 2.79 (s. 3H); [1.99 (s), 1.98 (s), 3H]; 0.95 (m, 1H); 0.38 (m, 2H); 0.25 (m, 2H).

Example E32

4-[2-(Cyclopropylmethoxy)-4-fluorophenyl]-N-[(3R*,4R*)-4-hydroxy-1-propanoylpyrrolidin-3-yl]-6-methyl-5H-pyrrolo[3,2-d]pyrimidine-7-carboxamide Starting from 4-[2-(cyclopropylmethoxy)-4-fluorophenyl]-N-[(3R*,4R*)-4-hydroxypyrrolidin-3-yl]-6-methyl-5H-pyrrolo[3,2-d]pyrimidine-7-carboxamide hydrochloride (example D.f10) and commercially available propionyl chloride the title compound is obtained as colorless solid.

MS (ESI): m/z=482 (MH$^+$, 100%). 1H-NMR (300 MHz, DMSO-d$_6$): 11.84 (s, 1H, —NH); 8.91 (s, 1H); [8.88 (d, J=7.1), 8.82 (d, J=6.8), 1H, —NH]; 7.65 (dd, J=8.4, 7.1, 1H); 7.09 (dd, J=11.7, 2.4, 1H); 6.96 (ddd, J=8.4, 8.4, 2.4, 1H); [5.55 (d, J=3.8), 5.47 (d, J=4.0), 1H, —OH]; [4.36 (m), 4.19 (m), 1H]; 4.27 (m, 1H); 3.91 (d, 6.9, 2H); [3.86 (m), 3.59 (m), 1H]; 3.72 (m, 1H); 3.49-3.27 (m, 2H); 2.78 (s. 3H); [2.28 (qu, J=7.5), 2.27 (qu, J=7.5), 2H]; [1.03 (t, J=7.5), 1.01 (t, J=7.5), 3H]; 0.95 (m, 1H); 0.38 (m, 2H); 0.25 (m, 2H).

Example E33

4-[2-(Cyclopropylmethoxy)-4-fluorophenyl]-N-[(3R*,4R*)-4-hydroxy-1-(methoxyacetyl)pyrrolidin-3-yl]-6-methyl-5H-pyrrolo[3,2-d]pyrimidine-7-carboxamide Starting from 4-[2-(cyclopropylmethoxy)-4-fluorophenyl]-N-[(3R*,4R*)-4-hydroxypyrrolidin-3-yl]-6-methyl-5H-pyrrolo[3,2-d]pyrimidine-7-carboxamide hydrochloride (example D.f10) and commercially available methoxy-acetyl chloride the title compound is obtained as colorless solid.

MS (ESI): m/z=498 (MH$^+$, 100%).

$^1$H-NMR (300 MHz, DMSO-d$_6$): 11.85 (s, 1H, —NH); [8.91 (s), 8.90 (s), 1H]; [8.87 (d, J=7.1), 8.83 (d, J=6.6), 1H, —NH]; 7.65 (dd, J=8.4, 7.3, 1H); 7.09 (dd, J=11.7, 2.4, 1H); 6.96 (ddd, J=8.4, 8.4, 2.4, 1H); [5.56 (d, J=3.8), 5.50 (d, J=4.0), 1H, —OH]; [4.36 (m), 4.19 (m), 1H]; 4.27 (m, 1H); [4.09 (dd, J=14.6, 3.5) 4.02 (d, J=14.6) 2H]; 3.91 (d, 6.9, 2H); [3.85 (m), 3.62 (m), 1H]; 3.73 (m, 1H); 3.49-3.27 (m, 2H); [3.34 (s), 3.32 (s), 3H]; 2.78 (s. 3H); 0.95 (m, 2H); 0.25 (m, 2H).

Example E34

N-[(3S*,4S*)-1-acetyl-3-hydroxypiperidin-4-yl]-4-[2-(cyclopropylmethoxy)-4-fluorophenyl]-6-methyl-5H-pyrrolo[3,2-d]pyrimidine-7-carboxamide Starting from 4-[2-(cyclopropylmethoxy)-4-fluorophenyl]-N-[(3R*,4S*)-3-hydroxypiperidin-4-yl]-6-methyl-5H-pyrrolo[3,2-d]pyrimidine-7-carboxamide hydrochloride (example D.f11) and commercially available acetyl chloride the title compound is obtained as colorless solid.

HR-MS (ESI): m/z=482.2196 ([MH]$^+$, C$_{25}$H$_{29}$FN$_5$O$_4^+$, calc. 482.2198).

Example E35

4-[2-(Cyclopropylmethoxy)-4-fluorophenyl]-N-[(3S*,4S*)-3-hydroxy-1-propanoylpiperidin-4-yl]-6-methyl-5H-pyrrolo[3,2-d]pyrimidine-7-carboxamide Starting from 4-[2-(cyclopropylmethoxy)-4-fluorophenyl]-N-[(3R*,4S*)-3-hydroxypiperidin-4-yl]-6-methyl-5H-pyrrolo[3,2-d]pyrimidine-7-carboxamide hydrochloride (example D.f11) and commercially available propionyl chloride the title compound is obtained as colorless solid.

HR-MS (ESI): m/z=496.2345 ([MH]$^+$, C$_{26}$H$_{31}$FN$_5$O$_4^+$, calc. 496.2355).

Example E36

4-[2-(Cyclopropylmethoxy)-4-fluorophenyl]-N-[(3S*,4S*)-3-hydroxy-1-(methoxyacetyl)piperidin-4-yl]-6-methyl-5H-pyrrolo[3,2-d]pyrimidine-7-carboxamide Starting from 4-[2-(cyclopropylmethoxy)-4-fluorophenyl]-N-[(3R*,4S*)-3-hydroxypiperidin-4-yl]-6-methyl-5H-pyrrolo[3,2-d]pyrimidine-7-carboxamide hydrochloride (example D.f11) and commercially available methoxy-acetyl chloride the title compound is obtained as colorless solid.

HR-MS (ESI): m/z=512.2288 ([MH]$^+$, C$_{26}$H$_{31}$FN$_5$O$_5^+$, calc. 512.2304).

Example E37

4-(2-Cyclopropylmethoxy-5-fluoro-phenyl)-6-methyl-5H-pyrrolo[3,2-d]pyrimidine-7-carboxylic acid (1-acetyl-piperidin-4-yl)-amide Starting from 4-(2-cyclopropylmethoxy-5-fluoro-phenyl)-6-methyl-5H-pyrrolo[3,2-d]pyrimidine-7-carboxylic acid piperidin-4-ylamide hydrochloride (example D.f12) and commercially acetyl chloride the title compound is obtained as colorless solid.

MS (ESI): m/z=466 (MH$^+$, 100%), 356, 302.

$^1$H-NMR (300 MHz, DMSO-d$_6$): 11.84 (br.s, 1H, —NH); 8.96 (s, 1H); 8.80 (d, J=7.7, 1H, —NH); 7.43 (dd, J=9.0, 3.3, 1H); 7.37 (ddd, J=9.1, 8.3, 3.3, 1H); 7.19 (dd, J=9.1, 4.4, 1H); 4.22-4.06 (m, 2H); 3.87 (d, J=6.9, 2H); 3.78 (m, 1H); 3.27 (m, 1H); 2.95 (m, 1H); 2.79 (s, 3H); 2.04 (s, 3H); 1.96 (m, 2H); 1.54 (m, 1H); 1.39 (m, 1H); 0.94 (m, 1H); 0.36 (m, 2H); 0.22 (m, 2H).

Example E38

4-[2-(cyclopropylmethoxy)-5-fluorophenyl]-6-methyl-N-(1-propionylpiperidin-4-yl)-5H-pyrrolo[3,2-d]pyrimidine-7-carboxamide Starting from 4-(2-cyclopropylmethoxy-5-fluoro-phenyl)-6-methyl-5H-pyrrolo[3,2-d]pyrimidine-7-carboxylic acid piperidin-4-ylamide hydrochloride (example D.f12) and commercially propionyl chloride the title compound is obtained as colorless solid.

MS (ESI): m/z=480 (MH$^+$, 100%).

$^1$H-NMR (300 MHz, DMSO-d$_6$): 11.84 (s, 1H, —NH); 8.96 (s, 1H); 8.80 (d, J=7.7, 1H, —NH); 7.42 (dd, J=9.0, 3.2, 1H); 7.36 (ddd, J=9.1, 8.3, 3.2, 1H); 7.19 (dd, J=9.1, 4.4, 1H); 4.25-4.04 (m, 2H); 3.87 (d, J=6.9, 2H); 3.81 (m, 1H); 3.27 (m, 1H); 2.96 (m, 1H); 2.79 (s, 3H); 2.36 (qu, J=7.5, 2H); 1.96 (m, 2H); 1.52 (m, 1H); 1.39 (m, 1H); 1.01 (t, J=7.5, 3H); 0.94 (m, 1H); 0.36 (m, 2H); 0.22 (m, 2H).

Example E39

4-(2-Cyclopropylmethoxy-5-fluoro-phenyl)-6-methyl-5H-pyrrolo[3,2-d]pyrimidine-7-carboxylic acid [1-(2-methoxy-acetyl)-piperidin-4-yl]-amide Starting from 4-(2-cyclopropylmethoxy-5-fluoro-phenyl)-6-methyl-5H-pyrrolo[3,2-d]pyrimidine-7-carboxylic acid piperidin-4-ylamide hydrochloride (example D.f12) and commercially methoxyacetyl chloride the title compound is obtained as colorless solid.

MS (ESI): m/z=496 (MH+, 100%), 356, 302.

$^1$H-NMR (300 MHz, DMSO-d$_6$): 11.84 (br.s, 1H, —NH); 8.96 (s, 1H); 8.80 (d, J=77, 1H, —NH); 7.43 (dd, J=9.0, 3.3, 1H); 7.37 (ddd, J=9.1, 8.3, 3.3, 1H); 7.19 (dd, J=9.1, 4.4, 1H); 4.23-4.07 (m, 2H); 4.12 (d, J=1.6, 2H); 3.87 (d, J=6.9, 2H); 3.75 (m, 1H); 3.31 (s, 3H); 3.22 (m, 1H); 2.98 (m, 1H); 2.79 (s, 3H); 1.97 (m, 2H); 1.54 (m, 1H); 1.41 (m, 1H); 0.87 (m, 1H); 0.36 (m, 2H); 0.22 (m, 2H).

Example E40

Ethyl 4-[({4-[2-(cyclopropylmethoxy)-5-fluorophenyl]-6-methyl-5H-pyrrolo[3,2-d]pyrimidin-7-yl}carbonyl)amino]piperidine-1-carboxylate Starting from 4-(2-cyclopropylmethoxy-5-fluoro-phenyl)-6-methyl-5H-pyrrolo[3,2-d]pyrimidine-7-carboxylic acid piperidin-4-ylamide hydrochloride (example D.f12) and commercially ethyl chloroformate the title compound is obtained as colorless solid.

MS (ESI): m/z=496 (MH+, 100%).

$^1$H-NMR (300 MHz, DMSO-d$_6$): 11.84 (s, 1H, —NH); 8.97 (s, 1H); 8.80 (d, J=7.7, 1H, —NH); 7.42 (dd, J=9.1, 3.3, 1H); 7.37 (ddd, J=9.1, 8.2, 3.3, 1H); 7.19 (dd, J=9.1, 4.4, 1H); 4.06 (qu, J=7.2, 2H & m, 1H); 3.87 (d, J=6.9, 2H & m, 2H); 3.11 (m, 2H); 2.79 (s, 3H); 1.94 (m, 2H); 1.46 (m, 2H); 1.20 (t, J=7.2, 3H); 0.94 (m, 1H); 0.36 (m, 2H); 0.22 (m, 2H).

Example E41

N-(trans-4-acetamidocyclohexyl)-4-[2-(cyclopropylmethoxy)-5-fluorophenyl]-6-methyl-5H-pyrrolo[3,2-d]pyrimidine-7-carboxamide Starting from N-(trans-4-aminocyclohexyl)-4-[2-(cyclopropylmethoxy)-5-fluorophenyl]-6-methyl-5H-pyrrolo[3,2-d]pyrimidine-7-carboxamide hydrochloride (example D.f13) and commercially acetyl chloride the title compound is obtained as colorless solid.

MS (ESI): m/z=480 (MH+, 100%).

$^1$H-NMR (300 MHz, DMSO-d$_6$): 11.81 (s, 1H, —NH); 8.97 (s, 1H); 8.67 (d, J=7.7, 1H, —NH); 7.72 (d, J=7.7, 1H, —NH); 7.42 (d, J=8.9, 3.2, 1H); 7.36 (ddd, J=9.1, 8.4, 3.2, 1H); 7.18 (dd, J=9.1, 4.4, 1H); 3.87 (d, J=6.9, 2H); 3.80 (m, 1H); 3.58 (m, 1H); 2.78 (s, 3H); 2.00 (m, 2H); 1.86 (m, 2H); 1.79 (s, 3H); 1.35 (m, 4H); 0.94 (m, 1H); 0.36 (m, 2H); 0.23 (m, 2H).

Example E42

4-[2-(Cyclopropylmethoxy)-5-fluorophenyl]-6-methyl-N-[trans-4-(propionylamino)cyclohexyl]-5H-pyrrolo[3,2-d]pyrimidine-7-carboxamide Starting from N-(trans-4-aminocyclohexyl)-4-[2-(cyclopropylmethoxy)-5-fluorophenyl]-6-methyl-5H-pyrrolo[3,2-d]pyrimidine-7-carboxamide hydrochloride (example D.f13) and commercially propionyl chloride the title compound is obtained as colorless solid.

MS (ESI): m/z=494 (MH+, 100%).

$^1$H-NMR (300 MHz, DMSO-d$_6$): 11.81 (s, 1H, —NH); 8.97 (s, 1H); 8.64 (d, J=7.7, 1H, —NH); 7.62 (d, J=7.7, 1H, —NH); 7.42 (dd, J=8.9, 3.3, 1H); 7.36 (ddd, J=9.1, 8.2, 3.3, 1H); 7.18 (dd, J=9.1, 4.4, 1H); 3.87 (d, J=6.9, 2H); 3.80 (m, 1H); 3.60 (m, 1H); 2.78 (s, 3H); 2.06 (m, 2H); 1.86 (m, 2H); 1.79 (s, 3H); 1.35 (m, 4H); 0.94 (m, 1H); 0.36 (m, 2H); 0.23 (m, 2H).

Example E43

4-[2-(Cyclopropylmethoxy)-5-fluorophenyl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-5-fluorophenyl]-6-methyl-5H-pyrrolo[3,2-d]pyrimidine-7-carboxamide hydrochloride (example D.f13) and commercially methoxyacetyl chloride the title compound is obtained as colorless solid.

MS (ESI): m/z=510 (MH+, 100%).

$^1$H-NMR (300 MHz, DMSO-d$_6$): 11.81 (s, 1H, —NH); 8.97 (s, 1H); 8.63 (d, J=7.7, 1H, —NH); 7.57 (d, J=8.2, 1H, —NH); 7.42 (dd, J=8.9, 3.3, 1H); 7.36 (ddd, J=8.9, 8.2, 3.3, 1H); 7.18 (dd, J=8.9, 4.4, 1H); 3.87 (d, J=6.9, 2H); 3.78 (s, 2H & m, 1H); 3.69 (m, 1H); 3.31 (s, 3H); 2.78 (s, 3H); 2.01 (m, 2H); 1.82 (m, 2H); 1.43 (m, 4H); 0.94 (m, 1H); 0.36 (m, 2H); 0.22 (m, 2H).

Example E44

Ethyl {trans-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate Starting from N-(trans-4-aminocyclohexyl)-4-[2-(cyclopropylmethoxy)-5-fluorophenyl]-6-methyl-5H-pyrrolo[3,2-d]pyrimidine-7-carboxamide hydrochloride (example D.f13) and commercially ethyl chloroformate the title compound is obtained as colorless solid.

MS (ESI): m/z=510 (MH+, 100%).

$^1$H-NMR (300 MHz, DMSO-d$_6$): 11.81 (s, 1H, —NH); 8.96 (s, 1H); 8.63 (d, J=7.7, 1H, —NH); 7.42 (dd, J=8.9, 3.3, 1H); 7.36 (ddd, J=9.1, 8.3, 3.3, 1H); 7.18 (dd, J=9.1, 4.4, 1H); 7.01 (d, J=7.3, 1H, —NH); 3.98 (qu, J=7.1, 2H); 3.87 (d, J=6.9, 2H); 3.77 (m, 1H); 3.34 (m, 1H); 2.78 (s, 3H); 2.00 (m, 2H); 1.87 (m, 2H); 1.36 (m, 4H); 1.16 (d, J=6.7, 3H); 0.94 (m, 1H); 0.36 (m, 2H); 0.22 (m, 2H).

Example E45

N-(cis-4-acetamidocyclohexyl)-4-[2-(cyclopropylmethoxy)-5-fluorophenyl]-6-methyl-5H-pyrrolo[3,2-d]pyrimidine-7-carboxamide Starting from N-(cis-4-aminocyclohexyl)-4-[2-(cyclopropylmethoxy)-5-fluorophenyl]-6-methyl-5H-pyrrolo[3,2-d]pyrimidine-7-carboxamide hydrochloride (example D.f14) and commercially acetyl chloride the title compound is obtained as colorless solid.

MS (ESI): m/z=480 (MH+, 100%).

$^1$H-NMR (300 MHz, DMSO-d$_6$): 11.83 (s, 1H, —NH); 9.00 (s, 1H); 8.92 (d, J=7.5, 1H, —NH); 7.85 (d, J=7.7, 1H, —NH); 7.43 (dd, J=8.9, 3.3, 1H); 7.38 (ddd, J=8.9, 8.2, 3.3, 1H); 7.19 (dd, J=8.9, 4.4, 1H); 4.03 (m, 1H); 3.88 (d, J=6.8, 2H); 3.75 (m, 1H); 2.79 (s, 3H); 1.84 (s, 3H); 1.82-1.52 (m, 8H); 0.94 (m, 1H); 0.37 (m, 2H); 0.23 (m, 2H).

Example E46

N-[(3R)-1-acetylpyrrolidin-3-yl]-4-[2-(cyclopropylmethoxy)-5-fluorophenyl]-6-methyl-5H-pyrrolo[3,2-d]pyrimidine-7-carboxamide Starting from 4-[2-(cyclopropylmethoxy)-5-fluorophenyl]-6-methyl-N-[(3R)-pyrrolidin-3-yl]-5H-pyrrolo[3,2-d]pyrimidine-7-carboxamide hydrochloride (example D.f15) and commercially acetyl chloride the title compound is obtained as colorless solid.

MS (ESI): m/z=452 (MH+, 100%).

$^1$H-NMR (300 MHz, DMSO-$d_6$): 11.88 (s, 1H, —NH); 8.97 (s, 1H); [8.93 (d, J=6.9), 8.89 (d, J=6.9), 1H, —NH]; 7.43 (dd, J=8.9, 3.2, 1H); 7.38 (ddd, J=9.0, 8.6, 3.2, 1H); 7.19 (dd, J=9.0, 4.4, 1H); [4.59 (m), 4.49 (m), 1H]; 3.88 (d, J=6.9, 2H); [3.84 (m), 3.65 (m), 1H]; 3.62 (m, 1H); 3.55-3.26 (m, 2H); [2.80 (s); 2.79 (s), 3H]; 2.35-2.16 (m, 1H); 2.09-1.87 (m, 1H); [1.98 (s), 1.96 (s), 3H]; 0.94 (m, 1H); 0.36 (m, 2H); 0.22 (m, 2H).

Example E47

4-[2-(Cyclopropylmethoxy)-5-fluorophenyl]-6-methyl-N-[(3R)-1-propanoylpyrrolidin-3-yl]-5H-pyrrolo[3,2-d]pyrimidine-7-carboxamide Starting from 4-[2-(cyclopropylmethoxy)-5-fluorophenyl]-6-methyl-N-[(3R)-pyrrolidin-3-yl]-5H-pyrrolo[3,2-d]pyrimidine-7-carboxamide hydrochloride (example D.f15) and commercially propionyl chloride the title compound is obtained as colorless solid.

MS (ESI): m/z=466 (MH+, 100%).

$^1$H-NMR (300 MHz, DMSO-$d_6$): 11.87 (s, 1H, —NH); 8.96 (s, 1H); [8.92 (d, J=7.1), 8.89 (d, J=6.8), 1H, —NH]; 7.42 (dd, J=8.9, 3.3, 1H); 7.38 (ddd, J=9.1, 8.4, 3.3, 1H); 7.19 (dd, J=9.1, 4.4, 1H); [4.59 (m), 4.49 (m), 1H]; 3.87 (d, J=6.9, 2H); [3.82 (m), 3.66 (m), 1H]; 3.61 (m, 1H); 3.55-3.26 (m, 2H); [2.80 (s); 2.79 (s), 3H]; 2.34-2.15 (m, 1H); [2.29 (qu, J=7.5), 2.25 (qu, J=7.5), 2H]; [2.03 (m), 1.92 (m), 1H]; [1.01 (t, J=7.5), 1.00 (t, J=7.5), 3H]; 0.93 (m, 1H); 0.36 (m, 2H); 0.22 (m, 2H).

Example E48

4-[2-(Cyclopropylmethoxy)-5-fluorophenyl]-N-[(3R)-1-(methoxyacetyl)pyrrolidin-3-yl]-6-methyl-5H-pyrrolo[3,2-d]pyrimidine-7-carboxamide Starting from 4-[2-(cyclopropylmethoxy)-5-fluorophenyl]-6-methyl-N-[(3R)-pyrrolidin-3-yl]-5H-pyrrolo[3,2-d]pyrimidine-7-carboxamide hydrochloride (example D.f15) and commercially methoxyacetyl chloride the title compound is obtained as colorless solid.

MS (ESI): m/z=482 (MH+, 100%).

$^1$H-NMR (300 MHz, DMSO-$d_6$): 11.88 (s, 1H, —NH); 8.96 (s, 1H); [8.91 (d, J=7.1), 8.89 (d, J=6.8), 1H, —NH]; 7.42 (ddd, J=8.9, 3.3, 0.6, 1H); 7.38 (ddd, J=9.1, 8.4, 3.3, 1H); 7.19 (dd, J=9.1, 4.4, 1H); [4.59 (m), 4.50 (m), 1H]; [4.06 (d, J=4.0), 4.01 (d, J=1.1), 2H]; 3.87 (d, J=6.9, 2H); [3.80 (m), 3.68 (m), 1H]; 3.63-3.42 (m, 2H); 3.36 (m, 1H); [3.32 (s), 3.30 (s), 3H]; 2.79 (s, 3H); 2.34-2.13 (m, 1H); [2.03 (m), 1.92 (m), 1H]; 0.93 (m, 1H); 0.36 (m, 2H); 0.22 (m, 2H).

Example E49

N-[(3R*,4R*)-1-acetyl-3-hydroxypiperidin-4-yl]-4-[2-(cyclopropylmethoxy)-5-fluorophenyl]-6-methyl-5H-pyrrolo[3,2-d]pyrimidine-7-carboxamide Starting from 4-[2-(cyclopropylmethoxy)-5-fluorophenyl]-N-[(3R*,4R*)-3-hydroxypiperidin-4-yl]-6-methyl-5H-pyrrolo[3,2-d]pyrimidine-7-carboxamide hydrochloride (example D.f16) and commercially acetyl chloride the title compound is obtained as colorless solid.

HR-MS (ESI): m/z=482.2199 ([MH]+, $C_{25}H_{29}FN_5O_4^+$, calc. 482.2198).

Example E50

4-[2-(Cyclopropylmethoxy)-5-fluorophenyl]-N-[(3R*,4R*)-3-hydroxy-1-propanoylpiperidin-4-yl]-6-methyl-5H-pyrrolo[3,2-d]pyrimidine-7-carboxamide Starting from 4-[2-(cyclopropylmethoxy)-5-fluorophenyl]-N-[(3R*,4R*)-3-hydroxypiperidin-4-yl]-6-methyl-5H-pyrrolo[3,2-d]pyrimidine-7-carboxamide hydrochloride (example D.f16) and commercially propionyl chloride the title compound is obtained as colorless solid.

HR-MS (ESI): m/z=496.2359 ([MH]+, $C_{26}H_{31}FN_5O_4^+$, calc. 496.2355).

Example E51

4-[2-(Cyclopropylmethoxy)-5-fluorophenyl]-N-[(3R*,4R*)-3-hydroxy-1-(methoxyacetyl)piperidin-4-yl]-6-methyl-5H-pyrrolo[3,2-d]pyrimidine-7-carboxamide Starting from 4-[2-(cyclopropylmethoxy)-5-fluorophenyl]-N-[(3R*,4R*)-3-hydroxypiperidin-4-yl]-6-methyl-5H-pyrrolo[3,2-d]pyrimidine-7-carboxamide hydrochloride (example D.f16) and commercially methoxy-acetyl chloride the title compound is obtained as colorless solid.

HR-MS (ESI): m/z=512.2294 ([MH]+, $C_{26}H_{31}FN_5O_5^+$, calc. 512.2304).

Example E52

N-(1-acetylpiperidin-4-yl)-4-(2-ethoxy-5-fluorophenyl)-6-methyl-5H-pyrrolo[3,2-d]pyrimidine-7-carboxamide Starting from 4-(2-ethoxy-5-fluorophenyl)-6-methyl-N-(piperidin-4-yl)-5H-pyrrolo[3,2-d]pyrimidine-7-carboxamide (example D.f17) and commercially acetyl chloride the title compound is obtained as colorless solid.

MS (ESI): m/z=440 (MH+, 100%).

$^1$H-NMR (300 MHz, DMSO-$d_6$): 11.87 (s, 1H, —NH); 8.95 (s, 1H); 8.79 (d, J=7.7, 1H, —NH); 7.42 (ddd, J=9.1, 8.9, 3.2, 1H); 7.38 (dd, J=8.2, 3.2, 1H); 7.22 (dd, J=9.1, 4.4, 1H); 4.22-4.06 (m, 2H); 4.08 (qu, J=7.0, 2H); 3.78 (m, 1H); 3.27 (m, 1H); 2.95 (m, 2H); 2.79 (s, 3H); 2.04 (s, 3H); 1.95 (m, 2H); 1.54 (m, 1H); 1.38 (m, 1H); 1.10 (t, J=7.0, 3H).

Example E53

4-(2-Ethoxy-5-fluorophenyl)-6-methyl-N-(1-propanoylpiperidin-4-yl)-5H-pyrrolo[3,2-d]pyrimidine-7-carboxamide Starting from 4-(2-ethoxy-5-fluorophenyl)-6-methyl-N-(piperidin-4-yl)-5H-pyrrolo[3,2-d]pyrimidine-7-carboxamide (example D.f17) and commercially propionyl chloride the title compound is obtained as colorless solid.

MS (ESI): m/z=454 (MH+, 100%).

¹H-NMR (300 MHz, DMSO-d₆, MeOH-d₄): 11.87 (s, 1H, —NH); 8.95 (s, 1H); 8.79 (d, J=7.7, 1H, —NH); 7.42 (ddd, J=9.1, 8.9, 3.2, 1H); 7.38 (dd, J=8.2, 3.2, 1H); 7.22 (dd, J=9.1, 4.4, 1H); 4.25-4.03 (m, 2H); 4.08 (qu, J=6.9, 2H); 3.81 (m, 1H); 3.25 (m, 1H); 2.96 (m, 2H); 2.78 (s, 3H); 2.36 (qu, J=7.3, 2H); 1.95 (m, 2H); 1.52 (m, 1H); 1.38 (m, 1H); 1.11 (t, J=6.9, 3H); 1.01 (t, J=7.3, 3H).

Example E54

4-(2-Ethoxy-5-fluorophenyl)-N-[1-(methoxyacetyl) piperidin-4-yl]-6-methyl-5H-pyrrolo[3,2-d]pyrimidine-7-carboxamide Starting from 4-(2-ethoxy-5-fluorophenyl)-6-methyl-N-(piperidin-4-yl)-5H-pyrrolo[3,2-d]pyrimidine-7-carboxamide (example D.f17) and commercially methoxy-acetyl chloride the title compound is obtained as colorless solid.

MS (ESI): m/z=470 (MH+, 100%).

¹H-NMR (300 MHz, DMSO-d₆): 11.87 (s, 1H, —NH); 8.95 (s, 1H); 8.79 (d, J=7.7, 1H, —NH); 7.42 (ddd, J=9.1, 8.9, 3.2, 1H); 7.38 (dd, J=8.3, 3.2, 1H); 7.22 (dd, J=9.1, 4.4, 1H); 4.21-4.06 (m, 2H); 4.12 (d, J=3.0, 2H); 4.08 (qu, J=7.0, 2H); 3.75 (m, 1H); 3.31 (s, 3H); 3.22 (m, 1H); 2.98 (m, 1H); 2.78 (s, 3H); 1.97 (m, 2H); 1.53 (m, 1H); 1.41 (m, 1H); 1.11 (t, J=6.9, 3H).

Example E55

N-(1-acetylpiperidin-4-yl)-4-[2-(cyclopropylmethoxy)-4-methoxyphenyl]-6-methyl-5H-pyrrolo[3,2-d]pyrimidine-7-carboxamide Starting from 4-[2-(cyclopropylmethoxy)-4-methoxyphenyl]-6-methyl-N-piperidin-4-yl-5H-pyrrolo[3,2-d]pyrimidine-7-carboxamide hydrochloride (example D.f18) and commercially acetyl chloride the title compound is obtained as colorless solid.

MS (ESI): m/z=478 (MH+, 100%).

¹H-NMR (300 MHz, DMSO-d₆): 11.68 (s, 1H, —NH); 8.90 (s, 1H); 8.84 (d, J=7.7, 1H, —NH); 7.59 (d, J=8.4, 1H); 6.72 (dd, J=8.4, 2.2, 1H); 6.69 (d, J=2.2, 1H); 4.21-4.04 (m, 2H); 3.91 (d, J=6.9, 2H); 3.86 (s, 3H); 3.78 (m, 1H); 3.27 (m, 1H); 2.95 (m, 1H); 2.78 (s, 3H); 2.04 (s, 3H); 1.95 (m, 2H); 1.54 (m, 1H); 1.38 (m, 1H); 0.96 (m, 1H); 0.38 (m, 2H); 0.26 (m, 2H).

Example E56

4-[2-(Cyclopropylmethoxy)-4-methoxyphenyl]-6-methyl-N-(1-propionylpiperidin-4-yl)-5H-pyrrolo[3,2-d]pyrimidine-7-carboxamide Starting from 4-[2-(cyclopropylmethoxy)-4-methoxyphenyl]-6-methyl-N-piperidin-4-yl-5H-pyrrolo[3,2-d]pyrimidine-7-carboxamide hydrochloride (example D.f18) and commercially propionyl chloride the title compound is obtained as colorless solid.

MS (ESI): m/z=492 (MH+, 100%).

¹H-NMR (300 MHz, DMSO-d₆): 11.68 (s, 1H, —NH); 8.90 (s, 1H); 8.84 (d, J=7.8, 1H, —NH); 7.59 (d, J=8.4, 1H); 6.72 (dd, J=8.4, 2.2, 1H); 6.69 (d, J=2.2, 1H); 4.25-4.03 (m, 2H); 3.90 (d, J=6.9, 2H); 3.86 (s, 3H); 3.81 (m, 1H); 3.25 (m, 1H); 2.96 (m, 1H); 2.78 (s, 3H); 2.36 (qu, J=7.3, 2H); 1.95 (m, 2H); 1.51 (m, 1H); 1.38 (m, 1H); 1.01 (t, J=7.3, 3H); 0.96 (m, 1H); 0.38 (m, 2H); 0.26 (m, 2H).

Example E57

4-[2-(Cyclopropylmethoxy)-4-methoxyphenyl]-N-[1-(methoxyacetyl)piperidin-4-yl]-6-methyl-5H-pyrrolo[3,2-d]pyrimidine-7-carboxamide Starting from 4-[2-(cyclopropylmethoxy)-4-methoxyphenyl]-6-methyl-N-piperidin-4-yl-5H-pyrrolo[3,2-d]pyrimidine-7-carboxamide hydrochloride (example D.f18) and commercially methoxyacetyl chloride the title compound is obtained as colorless solid.

MS (ESI): m/z=508 (MH+, 100%).

¹H-NMR (300 MHz, DMSO-d₆): 11.68 (s, 1H, —NH); 8.90 (s, 1H); 8.84 (d, J=7.7, 1H, —NH); 7.59 (d, J=8.4, 1H); 6.72 (dd, J=8.4, 2.2, 2H); 6.69 (d, J=2.2, 1H); 4.21-4.06 (m, 2H); 4.12 (d, J=1.5, 2H); 3.90 (d, J=6.8, 2H); 3.86 (s, 3H); 3.75 (m, 1H); 3.31 (s, 3H); 3.22 (m, 1H); 2.99 (m, 1H); 2.78 (s, 3H); 1.96 (m, 2H); 1.53 (m, 1H); 1.41 (m, 1H); 0.96 (m, 1H); 0.38 (m, 2H); 0.26 (m, 2H).

Example E58

N-(trans-4-acetamidocyclohexyl)-4-[2-(cyclopropylmethoxy)-4-methoxyphenyl]-6-methyl-5H-pyrrolo[3,2-d]pyrimidine-7-carboxamide Starting from N-(trans-4-aminocyclohexyl)-4-[2-(cyclopropylmethoxy)-4-methoxyphenyl]-6-methyl-5H-pyrrolo[3,2-d]pyrimidine-7-carboxamide hydrochloride (example D.f19) and commercially acetyl chloride the title compound is obtained as colorless solid.

MS (ESI): m/z=492 (MH+, 100%).

¹H-NMR (300 MHz, DMSO-d₆): 11.66 (s, 1H, —NH); 8.91 (s, 1H); 8.67 (d, J=7.9, 1H, —NH); 7.72 (d, J=7.9, 1H, —NH); 7.58 (d, J=8.4, 1H); 6.72 (dd, J=8.4, 2.2, 1H); 6.68 (d, J=2.2, 1H); 3.90 (d, J=6.9, 2H); 3.86 (s, 3H); 3.80 (m, 1H); 3.58 (m, 1H); 2.77 (s, 3H); 2.00 (m, 2H); 1.86 (m, 2H); 1.79 (s, 3H); 1.35 (m, 4H); 0.96 (m, 1H); 0.38 (m, 2H); 0.26 (m, 2H).

Example E59

N-(cis-4-acetamidocyclohexyl)-4-[2-(cyclopropylmethoxy)-4-methoxyphenyl]-6-methyl-5H-pyrrolo[3,2-d]pyrimidine-7-carboxamide Starting from N-(cis-4-aminocyclohexyl)-4-[2-(cyclopropylmethoxy)-4-methoxyphenyl]-6-methyl-5H-pyrrolo[3,2-d]pyrimidine-7-carboxamide hydrochloride (example D.f20) and commercially acetyl chloride the title compound is obtained as colorless solid.

MS (ESI): m/z=492 (MH+, 100%).

¹H-NMR (300 MHz, DMSO-d₆): 11.66 (s, 1H, —NH); 8.95 (d, J=6.9, 1H, —NH); 8.94 (s, 1H); 7.84 (d, J=7.5, 1H, —NH); 7.59 (d, J=8.4, 1H); 6.72 (dd, J=8.4, 2.2, 2H); 6.69 (d, J=2.2, 1H); 4.02 (m, 1H); 3.91 (d, J=6.8, 2H); 3.86 (s, 3H); 3.75 (m, 1H); 2.78 (s, 3H); 1.84 (s, 3H); 1.81-1.51 (m, 8H); 0.96 (m, 1H); 0.38 (m, 2H); 0.27 (m, 2H).

Example E60

N-[(3R)-1-acetylpyrrolidin-3-yl]-4-[2-(cyclopropylmethoxy)-4-methoxyphenyl]-6-methyl-5H-pyrrolo[3,2-d]pyrimidine-7-carboxamide Starting from 4-[2-(cyclopropylmethoxy)-4-methoxyphenyl]-6-methyl-N-[(3R)-pyrrolidin-3-yl]-5H-pyrrolo[3,2-d]

pyrimidine-7-carboxamide hydrochloride (example D.f21) and commercially acetyl chloride the title compound is obtained as colorless solid.

MS (ESI): m/z=464 (MH+, 100%).
$^1$H-NMR (300 MHz, DMSO-$d_6$): 11.72 (br.s, 1H, —NH); [8.96 (d, J=6.8), 8.93 (d, J=6.8), 1H, —NH]; 8.91 (s, 1H); 7.59 (dd, J=8.4, 0.9, 1H); 6.72 (dd, J=8.4, 2.2, 1H); 6.69 (d, J=2.2, 1H); [4.58 (m), 4.49 (m), 1H]; 3.90 (d, J=6.9, 2H); 3.86 (s, 3H); [3.83 (m), 3.65 (m), 1H]; 3.62 (m, 1H); 3.55-3.27 (m, 2H); [2.78 (s), 2.77 (s), 3H]; 2.34-2.15 (m 1H); 2.08-1.86 (m, 1H); [1.98 (s), 1.96 (s), 3H]; 0.95 (m, 1H); 0.38 (m, 2H); 0.26 (m, 2H).

Example E61

4-[2-(Cyclopropylmethoxy)-4-methoxyphenyl]-6-methyl-N-[(3R)-1-propionylpyrrolidin-3-yl]-5H-pyrrolo[3,2-d]pyrimidine-7-carboxamide Starting from 4-[2-(cyclopropylmethoxy)-4-methoxyphenyl]-6-methyl-N-[(3R)-pyrrolidin-3-yl]-5H-pyrrolo[3,2-d]pyrimidine-7-carboxamide hydrochloride (example D.f21) and commercially propionyl chloride the title compound is obtained as colorless solid.

MS (ESI): m/z=478 (MH+, 100%).
$^1$H-NMR (300 MHz, DMSO-$d_6$): 11.71 (br.s, 1H, —NH); [8.96 (d, J=6.8), 8.93 (d, J=6.8), 1H, —NH]; [8.90 (s), 8.89 (s), 1H]; 7.59 (dd, J=8.4, 0.7, 1H); 6.72 (dd, J=8.4, 2.2, 1H); 6.69 (d, J=2.2, 1H); [4.58 (m), 4.48 (m), 1H]; 3.90 (d, J=6.9, 2H); 3.86 (s, 3H); [3.81 (m), 3.67 (m), 1H]; 3.60 (m, 1H); 3.55-3.26 (m, 2H); [2.79 (s), 2.78 (s), 3H]; 2.34-2.15 (m 1H); [2.28 (qu, J=7.5), 2.25 (qu, J=7.5), 2H]; [2.03 (m), 1.91 (m), 1H]; [1.01 (t, J=7.5), 0.99 (t, J=7.5), 3H]; 0.95 (m, 1H); 0.37 (m, 2H); 0.26 (m, 2H).

Example E62

4-[2-(Cyclopropylmethoxy)-4-methoxyphenyl]-N-[(3R)-1-(methoxyacetyl)pyrrolidin-3-yl]-6-methyl-5H-pyrrolo[3,2-d]pyrimidine-7-carboxamide Starting from 4-[2-(cyclopropylmethoxy)-4-methoxyphenyl]-6-methyl-N-[(3R)-pyrrolidin-3-yl]-5H-pyrrolo[3,2-d]pyrimidine-7-carboxamide hydrochloride (example D.f21) and commercially methoxyacetyl chloride the title compound is obtained as colorless solid.

MS (ESI): m/z=494 (MH+, 100%).
$^1$H-NMR (300 MHz, DMSO-$d_6$): 11.71 (br.s, 1H, —NH); [8.95 (d, J=6.8), 8.93 (d, J=6.8), 1H, —NH]; [8.90 (s), 8.89 (s), 1H]; 7.59 (dd, J=8.4, 0.7, 1H); 6.72 (dd, J=8.4, 2.2, 1H); 6.69 (d, J=2.2, 1H); [4.58 (m), 4.49 (m), 1H]; [4.06 (d, J=3.8), 4.01 (d, J=1.1), 2H]; 3.90 (d, J=6.9, 2H); 3.86 (s, 3H); [3.79 (m), 3.68 (m), 1H]; 3.62-3.42 (m, 2H); 3.38-327 (m, 1H); [3.32 (s), 3.29 (s), 3H]; 2.78 (s, 3H); 2.33-2.14 (m 1H); [2.03 (m), 1.90 (m), 1H]; 0.95 (m, 1H); 0.37 (m, 2H); 0.26 (m, 2H).

Example E63

N-[(3R*,4R*)-1-acetyl-4-hydroxypyrrolidin-3-yl]-4-[2-(cyclopropylmethoxy)-4-methoxyphenyl]-6-methyl-5H-pyrrolo[3,2-d]pyrimidine-7-carboxamide Starting from 4-[2-(cyclopropylmethoxy)-4-methoxyphenyl]-N-[(3R*,4R*)-4-hydroxypyrrolidin-3-yl]-6-methyl-5H-pyrrolo[3,2-d]pyrimidine-7-carboxamide hydrochloride (example D.f22) and commercially acetyl chloride the title compound is obtained as colorless solid.

MS (ESI): m/z=480 (MH+, 100%).
$^1$H-NMR (300 MHz, DMSO-$d_6$): 11.74 (br.s, 1H, —NH); [8.91 (d, J=7.1), 8.85 (d, J=6.8), 1H, —NH]; 8.89 (s, 1H); 7.59 (dd, J=8.4, 0.7, 1H); 6.72 (dd, J=8.4, 2.2, 1H); 6.69 (d, J=2.2, 1H); 5.50 (br.s, 1H, —OH); [4.35 (m), 4.19 (m), 1H]; 4.27 (m, 1H); 3.90 (d, J=6.9, 2H); 3.86 (s, 3H); 3.79-3.65 (m, 1H); 3.62-3.53 (m, 1H); 3.48-3.32 (m, 2H); 2.78 (s, 3H); [1.99 (s); 1.98 (s), 3H]; 0.95 (m, 1H); 0.38 (m, 2H); 0.26 (m, 2H).

Example E64

4-[2-(Cyclopropylmethoxy)-4-methoxyphenyl]-N-[(3R*,4R*)-4-hydroxy-1-propionylpyrrolidin-3-yl]-6-methyl-5H-pyrrolo[3,2-d]pyrimidine-7-carboxamide Starting from 4-[2-(cyclopropylmethoxy)-4-methoxyphenyl]-N-[(3R*,4R*)-4-hydroxypyrrolidin-3-yl]-6-methyl-5H-pyrrolo[3,2-d]pyrimidine-7-carboxamide hydrochloride (example D.f22) and commercially propionyl chloride the title compound is obtained as colorless solid.

MS (ESI): m/z=494 (MH+, 100%).
$^1$H-NMR (300 MHz, DMSO-$d_6$): 11.73 (br.s, 1H, —NH); [8.90 (d, J=7.1), 8.85 (d, J=6.6), 1H, —NH]; 8.87 (s, 1H); 7.58 (d, J=8.4, 1H); 6.72 (dd, J=8.4, 2.2, 1H); 6.69 (d, J=2.2, 1H); [5.54 (br. s), 5.46 (br. s), 1H, —OH]; [4.35 (m), 4.18 (m), 1H]; 4.27 (m, 1H); 3.91 (d, J=7.1, 2H); 3.86 (s, 3H); 3.79-3.66 (m, 1H); 3.63-3.55 (m, 1H); 3.48-3.32 (m, 2H); 2.78 (s, 3H); [2.28 (qu, J=7.5), 2.27 (qu, J=7.5), 2H]; [1.03 (d, J=7.5); 1.01 (d, J=7.5), 3H]; 0.95 (m, 1H); 0.37 (m, 2H); 0.26 (m, 2H).

Example E65

4-[2-(Cyclopropylmethoxy)-4-methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide Starting from 4-[2-(cyclopropylmethoxy)-4-methoxyphenyl]-N-[(3R*,4R*)-4-hydroxypyrrolidin-3-yl]-6-methyl-5H-pyrrolo[3,2-d]pyrimidine-7-carboxamide hydrochloride (example D.f22) and commercially available methoxy-acetyl chloride the title compound is obtained as colorless solid.

MS (ESI): m/z=510 (MH+, 100%).
$^1$H-NMR (300 MHz, DMSO-$d_6$): 11.74 (br.s, 1H, —NH); [8.90 (d, J=7.1), 8.85 (d, J=6.6), 1H, —NH]; [8.87 (s), 8.86 (s), 1H]; 7.58 (d, J=8.4, 1H); 6.72 (dd, J=8.4, 2.2, 1H); 6.69 (d, J=2.2, 1H); 5.68-5.36 (br.s, 1H, —OH); [4.36 (m), 4.19 (m), 1H]; 4.27 (m, 1H); [4.09 (dd, J=14.6, 3.5), 4.01 [d, J=14.6), 2H]; 3.90 (d, J=6.9, 2H); 3.86 (s, 3H); 3.78-3.68 (m, 1H); 3.66-3.58 (m, 1H); 3.48-3.32 (m, 2H); [3.33 (s), 3.31 (s), 3H]; 2.78 (s, 3H); 0.95 (m, 1H); 0.37 (m, 2H); 0.26 (m, 2H).

Example E66

N-(1-acetylpiperidin-4-yl)-4-[2-(cyclopropylmethoxy)-5-methoxyphenyl]-6-methyl-5H-pyrrolo[3,2-d]pyrimidine-7-carboxamide Starting from 4-[2-(cyclopropylmethoxy)-5-methoxyphenyl]-6-methyl-N-piperidin-4-yl-5H-pyrrolo[3,2-d]pyrimidine-7-carboxamide hydrochloride (example D.f23) and commercially available acetyl chloride the title compound is obtained as colorless solid.

MS (ESI): m/z=478 (MH+, 100%).
¹H-NMR (300 MHz, DMSO-d₆): 11.77 (s, 1H, —NH); 8.95 (s, 1H); 8.82 (d, J=7.7, 1H, —NH); 7.18 (t, J=1.8, 1H); 7.11 (d, J=1.8, 2H); 4.22-3.93 (m, 2H); 3.82 (d, J=6.8, 2H); 3.77 (s, 3H & m, 1H); 3.27 (m, 1H); 2.95 (m, 1H); 2.79 (s, 3H); 2.04 (s, 3H); 1.95 (m, 2H); 1.54 (m, 1H); 1.39 (m, 1H); 0.92 (m, 1H); 0.34 (m, 2H); 0.19 (m, 2H).

Example E67

4-[2-(Cyclopropylmethoxy)-5-methoxyphenyl]-6-methyl-N-(1-propionylpiperidin-4-yl)-5H-pyrrolo[3,2-d]pyrimidine-7-carboxamide Starting from 4-[2-(cyclopropylmethoxy)-5-methoxyphenyl]-6-methyl-N-piperidin-4-yl-5H-pyrrolo[3,2-d]pyrimidine-7-carboxamide hydrochloride (example D.f23) and commercially available propionyl chloride the title compound is obtained as colorless solid.
MS (ESI): m/z=492 (MH+, 100%).
¹H-NMR (300 MHz, DMSO-d₆): 11.76 (s, 1H, —NH); 8.95 (s, 1H); 8.82 (d, J=7.7, 1H, —NH); 7.17 (t, J=1.8, 1H); 7.11 (d, J=1.8, 1H); 4.25-4.05 (m, 2H); 3.82 (d, J=6.9, 2H); 3.79 (m, 1H); 3.77 (s, 3H); 3.25 (m, 1H); 2.96 (m, 1H); 2.79 (s, 3H); 2.36 (qu, J=7.5, 2H); 1.96 (m, 2H); 1.52 (m, 1H); 1.38 (m, 1H); 1.01 (t, J=7.5, 3H); 0.92 (m, 1H); 0.34 (m, 2H); 0.20 (m, 2H).

Example E68

4-[2-(Cyclopropylmethoxy)-5-methoxyphenyl]-N-[1-(methoxyacetyl)piperidin-4-yl]-6-methyl-5H-pyrrolo[3,2-d]pyrimidine-7-carboxamide Starting from 4-[2-(cyclopropylmethoxy)-5-methoxyphenyl]-6-methyl-N-piperidin-4-yl-5H-pyrrolo[3,2-d]pyrimidine-7-carboxamide hydrochloride (example D.f23) and commercially available methoxy-acetyl chloride the title compound is obtained as colorless solid.
MS (ESI): m/z=508 (MH+, 100%).
¹H-NMR (300 MHz, DMSO-d₆): 11.77 (s, 1H, —NH); 8.95 (s, 1H); 8.82 (d, J=7.7, 1H, —NH); 7.17 (t, J=1.8, 1H); 7.11 (d, J=1.8, 2H); 4.21-4.06 (m, 2H); 4.12 (d, J=1.6, 2H); 3.82 (d, J=6.8, 2H); 3.77 (s, 3H); 3.73 (m, 1H); 3.31 (s, 3H); 3.22 (m, 1H); 2.98 (m, 1H); 2.79 (s, 3H); 1.97 (m, 2H); 1.54 (m, 1H); 1.41 (m, 1H); 0.92 (m, 1H); 0.34 (m, 2H); 0.20 (m, 2H).

Example E69

N-(trans-4-acetamidocyclohexyl)-4-[2-(cyclopropylmethoxy)-5-methoxyphenyl]-6-methyl-5H-pyrrolo[3,2-d]pyrimidine-7-carboxamide Starting from N-(trans-4-aminocyclohexyl)-4-[2-(cyclopropylmethoxy)-5-methoxyphenyl]-6-methyl-5H-pyrrolo[3,2-d]pyrimidine-7-carboxamide hydrochloride (example D.f24) and commercially available acetyl chloride the title compound is obtained as colorless solid.
MS (ESI): m/z=492 (MH+, 100%).
¹H-NMR (300 MHz, DMSO-d₆): 11.74 (s, 1H, —NH); 8.96 (s, 1H); 8.65 (d, J=7.7, 1H, —NH); 7.72 (d, J=7.7, 1H, —NH); 7.17 (t, J=1.8, 1H); 7.10 (d, J=1.8, 2H); 3.82 (d, J=6.8, 2H); 3.77 (s, 3H & m, 1H); 3.59 (m, 1H); 2.78 (s, 3H); 2.01 (m, 2H); 1.86 (m, 2H); 1.79 (s, 3H); 1.35 (m, 4H); 0.92 (m, 1H); 0.34 (m, 2H); 0.19 (m, 2H).

Example E70

4-[2-(Cyclopropylmethoxy)-5-methoxyphenyl]-6-methyl-N-[trans-4-(propionylamino)cyclohexyl]-5H-pyrrolo[3,2-d]pyrimidine-7-carboxamide Starting from N-(trans-4-aminocyclohexyl)-4-[2-(cyclopropylmethoxy)-5-methoxyphenyl]-6-methyl-5H-pyrrolo[3,2-d]pyrimidine-7-carboxamide hydrochloride (example D.f24) and commercially available propionyl chloride the title compound is obtained as colorless solid.
MS (ESI): m/z=506 (MH+, 100%).
¹H-NMR (300 MHz, DMSO-d₆): 11.74 (s, 1H, —NH); 8.96 (s, 1H); 8.66 (d, J=7.7, 1H, —NH); 7.62 (d, J=7.7, 1H, —NH); 7.17 (t, J=1.8, 1H); 7.10 (d, J=1.8, 2H); 3.82 (d, J=6.8, 2H); 3.79 (m, 1H); 3.77 (s, 3H); 3.59 (m, 1H); 2.78 (s, 3H); 2.06 (qu, J=7.5, 2H); 2.01 (m, 2H); 1.86 (m, 2H); 1.35 (m, 4H); 0.99 (t, J=7.5, 3H); 0.92 (m, 1H); 0.34 (m, 2H); 0.19 (m, 2H).

Example E71

4-[2-(Cyclopropylmethoxy)-5-methoxyphenyl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-5-methoxyphenyl]-6-methyl-5H-pyrrolo[3,2-d]pyrimidine-7-carboxamide hydrochloride (example D.f24) and commercially available methoxy-acetyl chloride the title compound is obtained as colorless solid.
MS (ESI): m/z=522 (MH+, 100%).
¹H-NMR (300 MHz, DMSO-d₆): 11.74 (s, 1H, —NH); 8.96 (s, 1H); 8.65 (d, J=7.7, 1H, —NH); 7.57 (d, J=8.2, 1H, —NH); 7.17 (t, J=1.8, 1H); 7.10 (d, J=1.8, 2H); 3.82 (d, J=6.8, 2H); 3.78 (s, 2H); 3.77 (s, 3H & m, 1H); 3.69 (m, 1H); 3.31 (s, 3H); 2.78 (s, 3H); 2.01 (m, 2H); 1.82 (m, 2H); 1.43 (m, 4H); 0.92 (m, 1H); 0.34 (m, 2H); 0.19 (m, 2H).

Example E72

N-(cis-4-acetamidocyclohexyl)-4-[2-(cyclopropylmethoxy)-5-methoxyphenyl]-6-methyl-5H-pyrrolo[3,2-d]pyrimidine-7-carboxamide Starting from N-(cis-4-aminocyclohexyl)-4-[2-(cyclopropylmethoxy)-5-methoxyphenyl]-6-methyl-5H-pyrrolo[3,2-d]pyrimidine-7-carboxamide hydrochloride (example D.f25) and commercially available acetyl chloride the title compound is obtained as colorless solid.
MS (ESI): m/z=492 (MH+, 100%).
¹H-NMR (300 MHz, DMSO-d₆): 11.76 (s, 1H, —NH); 8.99 (s, 1H); 8.93 (d, J=7.5, 1H, —NH); 7.85 (d, J=7.3, 1H, —NH); 7.18 (t, J=1.8, 1H); 7.11 (d, J=1.8, 2H); 4.02 (m, 1H); 3.83 (d, J=6.8, 2H); 3.77 (s, 3H); 3.75 (m, 1H); 2.79 (s, 3H); 1.84 (s, 3H); 1.81-1.52 (m, 8H); 0.92 (m, 1H); 0.35 (m, 2H); 0.20 (m, 2H).

Example E73

4-[2-(Cyclopropylmethoxy)-5-methoxyphenyl]-6-methyl-N-[cis-4-(propionylamino)cyclohexyl]-5H-pyrrolo[3,2-d]pyrimidine-7-carboxamide Starting from N-(cis-4-aminocyclohexyl)-4-[2-(cyclopropylmethoxy)-5-methoxyphenyl]-6-methyl-5H-pyrrolo[3,2-d]pyrimidine-7-carboxamide hydrochloride (example D.f25)

and commercially available propionyl chloride the title compound is obtained as colorless solid.

MS (ESI): m/z=506 (MH+, 100%).

$^1$H-NMR (300 MHz, DMSO-$d_6$): 11.76 (s, 1H, —NH); 8.99 (s, 1H); 8.92 (d, J=7.7, 1H, —NH); 7.75 (d, J=7.7, 1H, —NH); 7.18 (t, J=1.8, 1H); 7.11 (d, J=1.8, 2H); 4.02 (m, 1H); 3.83 (d, J=6.9, 2H); 3.77 (s, 3H); 3.75 (m, 1H); 2.79 (s, 3H); 2.11 (qu, J=7.5, 2H); 1.86-1.50 (m, 8H); 1.00 (t, J=7.5, 3H); 0.92 (m, 1H); 0.35 (m, 2H); 0.20 (m, 2H).

Example E74

4-[2-(Cyclopropylmethoxy)-5-methoxyphenyl]-N-{cis-4-[(methoxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-5-methoxyphenyl]-6-methyl-5H-pyrrolo[3,2-d]pyrimidine-7-carboxamide hydrochloride (example D.f25) and commercially available methoxy-acetyl chloride the title compound is obtained as colorless solid.

MS (ESI): m/z=522 (MH+, 100%).

$^1$H-NMR (300 MHz, DMSO-$d_6$): 11.75 (s, 1H, —NH); 8.99 (s, 1H); 8.96 (d, J=7.5, 1H, —NH); 7.67 (d, J=7.7, 1H, —NH); 7.18 (t, J=1.8, 1H); 7.11 (d, J=1.8, 2H); 4.05 (m, 1H); 3.83 (d, J=6.7, 2H); 3.80 (s, 2H & m, 1H); 3.77 (s, 3H); 3.31 (s, 3H); 2.79 (s, 3H); 1.87-1.58 (m, 8H); 0.92 (m, 1H); 0.35 (m, 2H); 0.20 (m, 2H).

Example E75

N-[(3R)-1-acetylpyrrolidin-3-yl]-4-[2-(cyclopropylmethoxy)-5-methoxyphenyl]-6-methyl-5H-pyrrolo[3,2-d]pyrimidine-7-carboxamide Starting from 4-[2-(cyclopropylmethoxy)-5-methoxyphenyl]-6-methyl-N-[(3R)-pyrrolidin-3-yl]-5H-pyrrolo[3,2-d]pyrimidine-7-carboxamide hydrochloride (example D.f26) and commercially available acetyl chloride the title compound is obtained as colorless solid.

HR-MS (ESI): m/z=464.2290 ([MH]+, $C_{25}H_{30}N_5O_4^+$, calc. 464.2292).

Example E76

4-[2-(Cyclopropylmethoxy)-5-methoxyphenyl]-6-methyl-N-[(3R)-1-propionylpyrrolidin-3-yl]-5H-pyrrolo[3,2-d]pyrimidine-7-carboxamide Starting from 4-[2-(cyclopropylmethoxy)-5-methoxyphenyl]-6-methyl-N-[(3R)-pyrrolidin-3-yl]-5H-pyrrolo[3,2-d]pyrimidine-7-carboxamide hydrochloride (example D.f26) and commercially available propionyl chloride the title compound is obtained as colorless solid.

HR-MS (ESI): m/z=478.2450 ([MH]+, $C_{26}H_{32}N_5O_4^+$, calc. 478.2449).

Example E77

4-[2-(Cyclopropylmethoxy)-5-methoxyphenyl]-N-[(3R)-1-(methoxyacetyl)pyrrolidin-3-yl]-6-methyl-5H-pyrrolo[3,2-d]pyrimidine-7-carboxamide Starting from 4-[2-(cyclopropylmethoxy)-5-methoxyphenyl]-6-methyl-N-[(3R)-pyrrolidin-3-yl]-5H-pyrrolo[3,2-d]pyrimidine-7-carboxamide hydrochloride (example D.f26) and commercially available methoxy-acetyl chloride the title compound is obtained as colorless solid.

HR-MS (ESI): m/z=494.2393 ([MH]+, $C_{26}H_{32}N_5O_5^+$, calc. 494.2398).

Example E78

N-[(3R*,4R*)-1-acetyl-3-hydroxypiperidin-4-yl]-4-[2-(cyclopropylmethoxy)-5-methoxyphenyl]-6-methyl-5H-pyrrolo[3,2-d]pyrimidine-7-carboxamide Starting from 4-[2-(cyclopropylmethoxy)-5-methoxyphenyl]-N-[(3R*,4R*)-3-hydroxypiperidin-4-yl]-6-methyl-5H-pyrrolo[3,2-d]pyrimidine-7-carboxamide hydrochloride (example D.f27) and commercially available acetyl chloride the title compound is obtained as colorless solid.

HR-MS (ESI): m/z=494.2405 ([MH]+, $C_{26}H_{32}N_5O_5^+$, calc. 494.2398).

Example E79

4-[2-(Cyclopropylmethoxy)-5-methoxyphenyl]-N-[(3R*,4R*)-3-hydroxy-1-propanoylpiperidin-4-yl]-6-methyl-5H-pyrrolo[3,2-d]pyrimidine-7-carboxamide Starting from 4-[2-(cyclopropylmethoxy)-5-methoxyphenyl]-N-[(3R*,4R*)-3-hydroxypiperidin-4-yl]-6-methyl-5H-pyrrolo[3,2-d]pyrimidine-7-carboxamide hydrochloride (example D.f27) and commercially available propionyl chloride the title compound is obtained as colorless solid.

HR-MS (ESI): m/z=508.2551 ([MH]+, $C_{27}H_{34}N_5O_5^+$, calc. 508.2554).

Example E80

4-[2-(Cyclopropylmethoxy)-5-methoxyphenyl]-N-[(3R*,4R*)-3-hydroxy-1-(methoxyacetyl)piperidin-4-yl]-6-methyl-5H-pyrrolo[3,2-d]pyrimidine-7-carboxamide Starting from 4-[2-(cyclopropylmethoxy)-5-methoxyphenyl]-N-[(3R*,4R*)-3-hydroxypiperidin-4-yl]-6-methyl-5H-pyrrolo[3,2-d]pyrimidine-7-carboxamide hydrochloride (example D.f27) and commercially available methoxy-acetyl chloride the title compound is obtained as colorless solid.

HR-MS (ESI): m/z=524.2501 ([MH]+, $C_{27}H_{34}N_5O_6^+$, calc. 524.2504).

Example E81

N-(1-Acetylpiperidin-4-yl)-4-[2-(cyclopropylmethoxy)-5-methyl phenyl]-6-methyl-5H-pyrrolo[3,2-d]pyrimidine-7-carboxamide Starting from 4-[2-(cyclopropylmethoxy)-5-methylphenyl]-6-methyl-N-(piperidin-4-yl)-5H-pyrrolo[3,2-d]pyrimidine-7-carboxamide hydrochloride (example D.f28) and commercially available acetyl chloride the title compound is obtained as colorless solid.

MS (ESI): m/z=420 (MH+, 100%).

$^1$H-NMR (300 MHz, DMSO-$d_6$): 12.25 (br.s, 1H, —NH); 9.11 (br.s, 2H, —NH$_2^+$); 9.06 (s, 1H); 7.47 (d, J=2.1, 1H); 7.39 (dd, J=8.4, 2.1, 1H); 7.10 (d, J=8.6, 1H); 4.12 (m, 1H); 3.88 (d, J=6.9, 2H); 3.31 (m, 2H); 3.08 (m, 2H); 2.81 (s, 3H); 2.34 (s, 3H); 2.13 (m, 2H); 1.79 (m, 2H); 0.93 (m, 1H); 0.36 (m, 2H); 0.25 (m, 2H).

Example E82

4-[2-(Cyclopropylmethoxy)-5-methylphenyl]-6-methyl-N-(1-propanoylpiperidin-4-yl)-5H-pyrrolo[3,2-d]pyrimidine-7-carboxamide Starting from 4-[2-(cyclopropylmethoxy)-5-methylphenyl]-6-methyl-N-(piperidin-4-yl)-5H-pyrrolo[3,2-d]pyrimidine-7-carboxamide hydrochloride (example D.f28) and commercially available propionyl chloride the title compound is obtained as colorless solid.

MS (ESI): m/z=476 (MH$^+$, 100%).
$^1$H-NMR (300 MHz, DMSO-d$_6$): 11.68 (br.s, 1H, —NH); 8.93 (s, 1H); 8.82 (d, J=7.7, 1H, —NH); 7.43 (d, J=1.8, 1H); 7.32 (dd, J=8.4, 1.8, 1H); 7.05 (d, J=8.4, 1H); 4.26-4.05 (m, 2H); 3.86 (d, J=6.9, 2H); 3.81 (m, 1H); 3.25 (m, 1H); 2.96 (m, 1H); 2.78 (s, 3H); 2.36 (qu, J=7.3, 2H); 2.33 (s, 3H); 1.96 (m, 2H); 1.51 (m, 1H); 1.39 (m, 1H); 1.01 (t, J=7.3, 3H); 0.94 (m, 1H); 0.35 (m, 2H); 0.22 (m, 2H).

Example E83

4-[2-(cyclopropylmethoxy)-5-methylphenyl]-N-[1-(methoxyacetyl)piperidin-4-yl]-6-methyl-5H-pyrrolo[3,2-d]pyrimidine-7-carboxamide Starting from 4-[2-(cyclopropylmethoxy)-5-methylphenyl]-6-methyl-N-(piperidin-4-yl)-5H-pyrrolo[3,2-d]pyrimidine-7-carboxamide hydrochloride (example D.f28) and commercially available methoxyacetyl chloride the title compound is obtained as colorless solid.

MS (ESI): m/z=492 (MH$^+$, 100%).
$^1$H-NMR (300 MHz, DMSO-d$_6$): 11.67 (br.s, 1H, —NH); 8.92 (s, 1H); 8.83 (d, J=7.7, 1H, —NH); 7.42 (d, J=1.8, 1H); 7.32 (dd, J=8.4, 1.8, 1H); 7.06 (d, J=8.4, 1H); 4.23-4.04 (m, 2H); 4.12 (d, J=1.8, 2H); 3.86 (d, J=6.8, 2H); 3.75 (m, 1H); 3.31 (s, 3H); 3.22 (m, 1H); 2.99 (m, 1H); 2.77 (s, 3H); 2.33 (s, 3H); 1.97 (m, 2H); 1.53 (m, 1H); 1.40 (m, 1H); 0.94 (m, 1H); 0.35 (m, 2H); 0.22 (m, 2H).

Example E84

N-[trans-4-(acetylamino)cyclohexyl]-4-[2-(cyclopropylmethoxy)-5-methylphenyl]-6-methyl-5H-pyrrolo[3,2-d]pyrimidine-7-carboxamide Starting from N-(trans-4-aminocyclohexyl)-4-[2-(cyclopropylmethoxy)-5-methylphenyl]-6-methyl-5H-pyrrolo[3,2-d]pyrimidine-7-carboxamide hydrochloride (example D.f29) and commercially available acetyl chloride the title compound is obtained as colorless solid.

MS (ESI): m/z=434 (MH$^+$, 100%).
$^1$H-NMR (300 MHz, DMSO-d$_6$): 12.25 (br.s, 1H, —NH); 9.03 (s, 1H); 8.55 (d, J=7.9, 1H, —NH); 8.09 (br.d, J=4.2, 3H, NH$_3^+$); 7.46 (d, J=2.1, 1H); 7.39 (dd, J=8.4, 2.1, 1H); 7.11 (d, J=8.6, 1H); 3.88 (d, J=6.9, 2H); 3.82 (m, 1H); 3.09 (m, 1H); 2.81 (s, 3H); 2.34 (s, 3H); 2.04 (m, 4H); 1.47 (m, 4H); 0.93 (m, 1H); 0.36 (m, 2H); 0.24 (m, 2H).

Example E85

4-[2-(Cyclopropylmethoxy)-5-methylphenyl]-6-methyl-N-[trans-4-(propanoylamino)cyclohexyl]-5H-pyrrolo[3,2-d]pyrimidine-7-carboxamide Starting from N-(trans-4-aminocyclohexyl)-4-[2-(cyclopropylmethoxy)-5-methylphenyl]-6-methyl-5H-pyrrolo[3,2-d]pyrimidine-7-carboxamide hydrochloride (example D.f29) and commercially available propionyl chloride the title compound is obtained as colorless solid.

MS (ESI): m/z=490 (MH$^+$, 100%).
$^1$H-NMR (300 MHz, DMSO-d$_6$): 11.71 (s, 1H, —NH); 8.94 (s, 1H); 8.67 (d, J=7.7, 1H, —NH); 7.62 (d, J=7.9, 1H, —NH); 7.43 (d, J=2.0, 1H); 7.32 (dd, J=8.4, 2.0, 1H); 7.06 (d, J=8.4, 1H); 3.86 (d, J=6.9, 2H); 3.80 (m, 1H); 3.59 (m, 1H); 2.77 (s, 3H); 2.33 (s, 3H); 2.05 (qu, J=7.5, 2H); 2.01 (m, 2H); 1.86 (m, 2H); 1.35 (m, 4H); 0.99 (t, J=7.5, 3H); 0.94 (m, 1H); 0.35 (m, 2H); 0.22 (m, 2H).

Example E86

4-[2-(Cyclopropylmethoxy)-5-methylphenyl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-5-methylphenyl]-6-methyl-5H-pyrrolo[3,2-d]pyrimidine-7-carboxamide hydrochloride (example D.f29) and commercially available methoxy-acetyl chloride the title compound is obtained as colorless solid.

MS (ESI): m/z=506 (MH$^+$, 100%).
$^1$H-NMR (300 MHz, DMSO-d$_6$): 11.71 (s, 1H, —NH); 8.94 (s, 1H); 8.66 (d, J=7.7, 1H, —NH); 7.57 (d, J=8.4, 1H, —NH); 7.43 (d, J=2.1, 1H); 7.32 (dd, J=8.4, 2.1, 1H); 7.06 (d, J=8.4, 1H); 5.40 (t, J=5.9, 1H, —OH); 3.86 (d, J=6.9, 2H); 3.78 (s, 2H & m, 1H); 3.69 (m, 1H); 3.31 (s, 3H); 2.77 (s, 3H); 2.33 (s, 3H); 2.01 (m, 2H); 1.82 (m, 2H); 1.34 (m, 4H); 0.94 (m, 1H); 0.35 (m, 2H); 0.22 (m, 2H).

Example E87

N-[cis-4-(acetylamino)cyclohexyl]-4-[2-(cyclopropylmethoxy)-5-methylphenyl]-6-methyl-5H-pyrrolo[3,2-d]pyrimidine-7-carboxamide Starting from N-(cis-4-aminocyclohexyl)-4-[2-(cyclopropylmethoxy)-5-methylphenyl]-6-methyl-5H-pyrrolo[3,2-d]pyrimidine-7-carboxamide hydrochloride (example D.f30) and commercially available acetyl chloride the title compound is obtained as colorless solid.

MS (ESI): m/z=476 (MH$^+$, 100%).
$^1$H-NMR (300 MHz, DMSO-d$_6$): 11.72 (s, 1H, —NH); 8.97 (s, 1H); 8.94 (d, J=7.7, 1H, —NH); 7.85 (d, J=7.7, 1H, —NH); 7.44 (d, J=1.8, 1H); 7.33 (dd, J=8.4, 1.8, 1H); 7.06 (d, J=8.4, 1H); 4.02 (m, 1H); 3.86 (d, J=6.9, 2H); 3.75 (m, 1H); 2.78 (s, 3H); 2.33 (s, 3H); 1.84 (s, 3H); 1.81-1.51 (m, 8H); 0.94 (m, 1H); 0.36 (m, 2H); 0.22 (m, 2H).

Example E88

4-[2-(Cyclopropylmethoxy)-5-methylphenyl]-6-methyl-N-[cis-4-(propanoylamino)cyclohexyl]-5H-pyrrolo[3,2-d]pyrimidine-7-carboxamide Starting from N-(cis-4-aminocyclohexyl)-4-[2-(cyclopropylmethoxy)-5-methylphenyl]-6-methyl-5H-pyrrolo[3,2-d]pyrimidine-7-carboxamide hydrochloride (example D.f30) and commercially available propionyl chloride the title compound is obtained as colorless solid.

MS (ESI): m/z=490 (MH$^+$, 100%).
$^1$H-NMR (300 MHz, DMSO-d$_6$): 11.72 (s, 1H, —NH); 8.97 (s, 1H); 8.94 (d, J=7.5, 1H, —NH); 7.75 (d, J=7.7, 1H, —NH); 7.44 (d, J=1.8, 1H); 7.33 (dd, J=8.4, 1.8, 1H); 7.06 (d, J=8.4, 1H); 4.02 (m, 1H); 3.86 (d, J=6.9, 2H); 3.75 (m, 1H);

2.78 (s, 3H); 2.33 (s, 3H); 2.11 (qu, J=7.7, 2H); 1.83-1.53 (m, 8H); 1.00 (t, J=7.7, 3H); 0.94 (m, 1H); 0.36 (m, 2H); 0.22 (m, 2H).

Example E89

4-[2-(Cyclopropylmethoxy)-5-methylphenyl]-N-{cis-4-[(methoxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-5-methylphenyl]-6-methyl-5H-pyrrolo[3,2-d]pyrimidine-7-carboxamide hydrochloride (example D.f30) and commercially available methoxy-acetyl chloride the title compound is obtained as colorless solid.
MS (ESI): m/z=506 (MH$^+$, 100%).
$^1$H-NMR (300 MHz, DMSO-d$_6$): 11.72 (s, 1H, —NH); 8.97 (s, 1H & d, J=7.5, 1H, —NH); 7.67 (d, J=7.7, 1H, —NH); 7.44 (d, J=2.1, 1H); 7.33 (dd, J=8.4, 2.1, 1H); 7.06 (d, J=8.4, 1H); 4.05 (m, 1H); 3.86 (d, J=6.9, 2H); 3.82 (s, 2H); 3.79 (m, 1H); 3.31 (s, 3H); 2.78 (s, 3H); 2.33 (s, 3H); 1.84-1.61 (m, 8H); 0.94 (m, 1H); 0.36 (m, 2H); 0.22 (m, 2H).

Example E90

N-(1-Acetylpiperidin-4-yl)-4-[2-(cyclopropylmethoxy)-5-(trifluoromethyl)phenyl]-6-methyl-5H-pyrrolo[3,2-d]pyrimidine-7-carboxamide Starting from 4-[2-(cyclopropylmethoxy)-5-(trifluoromethyl)phenyl]-6-methyl-N-(piperidin-4-yl)-5H-pyrrolo[3,2-d]pyrimidine-7-carboxamide hydrochloride (example D.f31) and commercially available acetyl chloride the title compound is obtained as colorless solid.
MS (ESI): m/z=516 (MH$^+$, 100%).
$^1$H-NMR (300 MHz, DMSO-d$_6$): 11.90 (s, 1H, —NH); 8.99 (s, 1H); 8.80 (d, J=7.9, 1H, —NH); 7.91 (d, J=2.0, 1H); 7.89 (dd, J=8.8, 2.0, 1H); 7.38 (d, J=8.8, 1H); 4.23-4.05 (m, 2H); 4.00 (d, J=7.0, 2H); 3.79 (m, 1H); 3.28 (m, 1H); 2.95 (m, 1H); 2.80 (s, 3H); 2.04 (s, 3H); 1.96 (m, 2H); 1.55 (m, 1H); 1.39 (m, 1H); 0.99 (m, 1H); 0.39 (m, 2H); 0.27 (m, 2H).

Example E91

4-[2-(Cyclopropylmethoxy)-5-(trifluoromethyl)phenyl]-6-methyl-N-(1-propanoylpiperidin-4-yl)-5H-pyrrolo[3,2-d]pyrimidine-7-carboxamide Starting from 4-[2-(cyclopropylmethoxy)-5-(trifluoromethyl)phenyl]-6-methyl-N-(piperidin-4-yl)-5H-pyrrolo[3,2-d]pyrimidine-7-carboxamide hydrochloride (example D.f31) and commercially available propionyl chloride the title compound is obtained as colorless solid.
MS (ESI): m/z=530 (MH$^+$, 100%).
$^1$H-NMR (300 MHz, DMSO-d$_6$): 11.90 (s, 1H, —NH); 8.99 (s, 1H); 8.80 (d, J=7.7, 1H, —NH); 7.91 (d, J=2.0, 1H); 7.89 (dd, J=8.8, 2.0, 1H); 7.38 (d, J=8.8, 1H); 4.26-4.06 (m, 2H); 4.00 (d, J=6.9, 2H); 3.82 (m, 1H); 3.28 (m, 1H); 2.96 (m, 1H); 2.79 (s, 3H); 2.36 (qu, J=7.4, 2H); 1.96 (m, 2H); 1.52 (m, 1H); 1.39 (m, 1H); 1.01 (t, J=7.4, 3H); 0.99 (m, 1H); 0.39 (m, 2H); 0.27 (m, 2H).

Example E92

4-[2-(Cyclopropylmethoxy)-5-(trifluoromethyl)phenyl]-N-[1-(methoxyacetyl)piperidin-4-yl]-6-methyl-5H-pyrrolo[3,2-d]pyrimidine-7-carboxamide Starting from 4-[2-(cyclopropylmethoxy)-5-(trifluoromethyl)phenyl]-6-methyl-N-(piperidin-4-yl)-5H-pyrrolo[3,2-d]pyrimidine-7-carboxamide hydrochloride (example D.f31) and commercially available methoxy-methyl chloride the title compound is obtained as colorless solid.
MS (ESI): m/z=546 (MH$^+$, 100%).
$^1$H-NMR (300 MHz, DMSO-d$_6$): 11.90 (s, 1H, —NH); 8.99 (s, 1H); 8.80 (d, J=7.7, 1H, —NH); 7.91 (d, J=2.0, 1H); 7.89 (dd, J=8.8, 2.0, 1H); 7.38 (d, J=8.8, 1H); 4.24-4.06 (m, 2H); 4.12 (s, 2H); 4.00 (d, J=6.9, 2H); 3.75 (m, 1H); 3.31 (s, 3H); 3.23 (m, 1H); 2.99 (m, 1H); 2.79 (s, 3H); 1.97 (m, 2H); 1.54 (m, 1H); 1.41 (m, 1H); 0.98 (m, 1H); 0.39 (m, 2H); 0.27 (m, 2H).

Example E93

N-[trans-4-(acetylamino)cyclohexyl]-4-[2-(cyclopropylmethoxy)-5-(trifluoromethyl)phenyl]-6-methyl-5H-pyrrolo[3,2-d]pyrimidine-7-carboxamide Starting from N-(trans-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride (example D.f32) and commercially available acetyl chloride the title compound is obtained as colorless solid.
MS (ESI): m/z=530 (MH$^+$, 100%).
$^1$H-NMR (300 MHz, DMSO-d$_6$): 11.87 (s, 1H, —NH); 8.99 (s, 1H); 8.64 (d, J=7.7, 1H, —NH); 7.91 (d, J=2.0, 1H); 7.89 (dd, J=8.8, 2.0, 1H); 7.72 (d, J=7.7, 1H, —NH); 7.38 (d, J=8.8, 1H); 4.00 (d, J=6.9, 2H); 3.81 (m, 1H); 3.59 (m, 1H); 2.79 (s, 3H); 2.01 (m, 2H); 1.86 (m, 2H); 1.79 (s, 3H); 1.36 (m, 4H); 0.98 (m, 1H); 0.39 (m, 2H); 0.27 (m, 2H).

Example E94

4-[2-(cyclopropylmethoxy)-5-(trifluoromethyl)phenyl]-6-methyl-N-[trans-4-(propanoylamino)cyclohexyl]-5H-pyrrolo[3,2-d]pyrimidine-7-carboxamide Starting from N-(trans-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride (example D.f32) and commercially available propionyl chloride the title compound is obtained as colorless solid. Alternative the above obtained solid is re-crystalised from ethylene glycol/water mixture (5/1).
MS (ESI): m/z=544 (MH$^+$, 100%).
$^1$H-NMR (300 MHz, DMSO-d$_6$): 11.87 (s, 1H, —NH); 8.99 (s, 1H); 8.64 (d, J=7.7, 1H, —NH); 7.90 (d, J=2.0, 1H); 7.89 (dd, J=8.8, 2.0, 1H); 7.63 (d, J=7.8, 1H, —NH); 7.38 (d, J=8.8, 1H); 3.99 (d, J=6.9, 2H); 3.80 (m, 1H); 3.59 (m, 1H); 2.79 (s, 3H); 2.06 (qu, J=7.5, 2H); 2.01 (m, 2H); 1.86 (m, 2H); 1.36 (m, 4H); 0.98 (t, J=7.5, 3H & m, 1H); 0.39 (m, 2H); 0.27 (m, 2H).

Example E95

4-[2-(Cyclopropylmethoxy)-5-(trifluoromethyl)phenyl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride (example D.f32) and commercially available methoxy-acetyl chloride the title compound is obtained as colorless solid.

MS (ESI): m/z=560 (MH⁺, 100%).
¹H-NMR (300 MHz, DMSO-d₆): 11.87 (s, 1H, —NH); 8.99 (s, 1H); 8.63 (d, J=7.7, 1H, —NH); 7.91 (d, J=2.0, 1H); 7.89 (dd, J=8.8, 2.0, 1H); 7.57 (d, J=8.2, 1H, —NH); 7.38 (d, J=8.8, 1H); 4.00 (d, J=7.0, 2H); 3.78 (s, 2H & m, 1H); 3.70 (m, 1H); 3.31 (s, 3H); 2.79 (s, 3H); 2.01 (m, 2H); 1.82 (m, 2H); 1.44 (m, 4H); 0.98 (m, 1H); 0.39 (m, 2H); 0.27 (m, 2H).

Example E96

N-[cis-4-(acetylamino)cyclohexyl]-4-[2-(cyclopropylmethoxy)-5-(trifluoromethyl)phenyl]-6-methyl-5H-pyrrolo[3,2-d]pyrimidine-7-carboxamide Starting from N-(cis-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride (example D.f33) and commercially available acetyl chloride the title compound is obtained as colorless solid.
MS (ESI): m/z=530 (MH⁺, 100%).
¹H-NMR (400 MHz, DMSO-d₆): 11.88 (br.s, 1H, —NH); 9.02 (s, 1H); 8.92 (d, J=7.5, 1H, —NH); 7.91 (s, 1H); 7.88 (d, J=8.2, 1H); 7.85 (d, J=7.6, 1H, —NH); 7.38 (d, J=8.2, 1H); 4.04 (m, 1H); 4.00 (d, J=6.9, 2H); 3.75 (m, 1H); 2.80 (s, 3H); 1.84 (s, 3H); 1.81-1.52 (m, 8H); 0.99 (m, 1H); 0.40 (m, 2H); 0.28 (m, 2H).

Example E97

4-[2-(Cyclopropylmethoxy)-5-(trifluoromethyl)phenyl]-6-methyl-N-[cis-4-(propanoylamino)cyclohexyl]-5H-pyrrolo[3,2-d]pyrimidine-7-carboxamide Starting from N-(cis-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride (example D.f33) and commercially available propionyl chloride the title compound is obtained as colorless solid.
MS (ESI): m/z=544 (MH⁺, 100%).
¹H-NMR (400 MHz, DMSO-d₆): 11.88 (br.s, 1H, —NH); 9.01 (s, 1H); 8.92 (d, J=7.3, 1H, —NH); 7.91 (s, 1H); 7.89 (d, J=8.7, 1H); 7.79 (d, J=7.6, 1H, —NH); 7.38 (d, J=8.7, 1H); 4.03 (m, 1H); 4.00 (d, J=7.0, 2H); 3.75 (m, 1H); 2.79 (s, 3H); 2.12 (qu, J=7.6, 2H); 1.83-1.52 (m, 8H); 1.00 (t, J=7.6, 3H); 0.98 (m, 1H); 0.40 (m, 2H); 0.28 (m, 2H).

Example E98

4-[2-(Cyclopropylmethoxy)-5-(trifluoromethyl)phenyl]-N-{cis-4-[(methoxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride (example D.f33) and commercially available methoxy-acetyl chloride the title compound is obtained as colorless solid.
MS (ESI): m/z=560 (MH⁺, 100%).
¹H-NMR (400 MHz, DMSO-d₆): 11.91 (s, 1H, —NH); 9.03 (s, 1H); 8.96 (d, J=7.3, 1H, —NH); 7.91 (s, 1H); 7.90 (d, J=8.8, 1H); 7.72 (d, J=7.8, 1H, —NH); 7.39 (d, J=8.8, 1H); 4.06 (m, 1H); 4.00 (d, J=7.0, 2H); 3.82 (s, 2H); 3.79 (m, 1H); 3.31 (s, 3H); 2.80 (s, 3H); 1.85-1.60 (m, 8H); 0.98 (m, 1H); 0.40 (m, 2H); 0.28 (m, 2H).

Example E99

N-(1-acetylpiperidin-4-yl)-4-[2-ethoxy-5-(trifluoromethyl)phenyl]-6-methyl-5H-pyrrolo[3,2-d]pyrimidine-7-carboxamide Starting from 4-[2-ethoxy-5-(trifluoromethyl)phenyl]-6-methyl-N-(piperidin-4-yl)-5H-pyrrolo[3,2-d]pyrimidine-7-carboxamide hydrochloride (example D.f34) and commercially available acetyl chloride the title compound is obtained as colorless solid.
MS (ESI): m/z=490 (MH⁺, 100%).
¹H-NMR (400 MHz, DMSO-d₆): 11.92 (br.s, 1H, —NH); 8.98 (s, 1H); 8.79 (d, J=7.7, 1H, —NH); 7.92 (d, J=2.2, 1H); 7.91 (dd, J=9.4, 2.2, 1H); 7.43 (d, J=9.4, 1H); 4.21 (qu, J=7.0, 2H); 4.18-4.07 (m, 2H); 3.78 (m, 1H); 3.28 (m, 1H); 2.95 (m, 1H); 2.79 (s, 3H); 2.04 (s, 3H); 1.96 (m, 2H); 1.54 (m, 1H); 1.39 (m, 1H); 1.16 (t, J=7.0, 3H).

Example E100

4-[2-Ethoxy-5-(trifluoromethyl)phenyl]-6-methyl-N-(1-propanoylpiperidin-4-yl)-5H-pyrrolo[3,2-d]pyrimidine-7-carboxamide Starting from 4-[2-ethoxy-5-(trifluoromethyl)phenyl]-6-methyl-N-(piperidin-4-yl)-5H-pyrrolo[3,2-d]pyrimidine-7-carboxamide hydrochloride (example D.f34) and commercially available propionyl chloride the title compound is obtained as colorless solid.
MS (ESI): m/z=504 (MH⁺, 100%).
¹H-NMR (400 MHz, DMSO-d₆): 11.93 (br.s, 1H, —NH); 8.98 (s, 1H); 8.79 (d, J=7.7, 1H, —NH); 7.92 (d, J=2.2, 1H); 7.91 (dd, J=9.4, 2.2, 1H); 7.42 (d, J=9.4, 1H); 4.21 (qu, J=7.0, 2H); 4.17-4.07 (m, 2H); 3.82 (m, 1H); 3.26 (m, 1H); 2.96 (m, 1H); 2.79 (s, 3H); 2.36 (qu, J=7.1, 2H); 1.96 (m, 2H); 1.52 (m, 1H); 1.38 (m, 1H); 1.16 (t, J=7.0, 3H); 1.01 (t, J=7.1, 3H).

Example E101

4-[2-Ethoxy-5-(trifluoromethyl)phenyl]-N-[1-(methoxyacetyl)piperidin-4-yl]-6-methyl-5H-pyrrolo[3,2-d]pyrimidine-7-carboxamide Starting from 4-[2-ethoxy-5-(trifluoromethyl)phenyl]-6-methyl-N-(piperidin-4-yl)-5H-pyrrolo[3,2-d]pyrimidine-7-carboxamide hydrochloride (example D.f34) and commercially available methoxyacetyl chloride the title compound is obtained as colorless solid.
MS (ESI): m/z=520 (MH⁺, 100%).
¹H-NMR (400 MHz, DMSO-d₆): 11.93 (br.s, 1H, —NH); 8.98 (s, 1H); 8.79 (d, J=7.7, 1H, —NH); 7.92 (d, J=2.2, 1H); 7.91 (dd, J=9.5, 2.2, 1H); 7.42 (d, J=9.5, 1H); 4.21 (qu, J=7.0, 2H); 4.17-4.06 (m, 2H); 4.12 (d, J=2.8, 2H); 3.75 (m, 1H); 3.31 (s, 3H); 3.23 (m, 1H); 2.99 (m, 1H); 2.79 (s, 3H); 1.97 (m, 2H); 1.54 (m, 1H); 1.41 (m, 1H); 1.16 (t, J=7.0, 3H).

Example E102

N-(1-Acetylpiperidin-4-yl)-4-[2-(cyclopropylmethoxy)-4-fluoro-5-methoxyphenyl]-6-methyl-5H-pyrrolo[3,2-d]pyrimidine-7-carboxamide Starting from 4-[2-(cyclopropylmethoxy)-4-fluoro-5-methoxyphenyl]-6-methyl-N-piperidin-4-yl-5H-pyrrolo[3,2-d]pyrimidine-7-carboxamide hydrochloride (example D.f35) and commercially available acetyl chloride the title compound is obtained as colorless solid.

MS (ESI): m/z=496 (MH+, 100%).

$^1$H-NMR (300 MHz, 11.76 (s, 1H, —NH); 8.95 (s, 1H); 8.81 (d, J=7.7, 1H, —NH); 7.39 (d, J=9.9, 1H); 7.18 (d, J=13.3, 1H); 4.23-4.05 (m, 2H); 3.84 (s, 3H & d, J=6.8, 2H); 3.78 (m, 1H); 3.28 (m, 1H); 2.95 (m, 1H); 2.79 (s, 3H); 2.04 (s, 3H); 1.96 (m, 2H); 1.54 (m, 1H); 1.38 (m, 1H); 0.93 (m, 1H); 0.36 (m, 2H); 0.21 (m, 2H).

Example E103

4-[2-(cyclopropylmethoxy)-4-fluoro-5-methoxyphenyl]-6-methyl-N-(1-propionylpiperidin-4-yl)-5H-pyrrolo[3,2-d]pyrimidine-7-carboxamide Starting from 4-[2-(cyclopropylmethoxy)-4-fluoro-5-methoxyphenyl]-6-methyl-N-piperidin-4-yl-5H-pyrrolo[3,2-d]pyrimidine-7-carboxamide hydrochloride (example D.f35) and commercially available propionyl chloride the title compound is obtained as colorless solid.

MS (ESI): m/z=510 (MH+, 100%).

$^1$H-NMR (300 MHz, DMSO-d$_6$): 11.76 (s, 1H, —NH); 8.95 (s, 1H); 8.81 (d, J=7.7, 1H, —NH); 7.39 (d, J=9.9, 1H); 7.18 (d, J=13.3, 1H); 4.25-4.05 (m, 2H); 3.84 (s, 3H & d, J=6.8, 2H); 3.79 (m, 1H); 3.26 (m, 1H); 2.96 (m, 1H); 2.79 (s, 3H); 2.36 (qu J=7.4, 2H); 1.96 (m, 2H); 1.52 (m, 1H); 1.38 (m, 1H); 1.01 (t, J=7.4, 3H); 0.93 (m, 1H); 0.36 (m, 2H); 0.21 (m, 2H).

Example E104

4-[2-(Cyclopropylmethoxy)-4-fluoro-5-methoxyphenyl]-N-[1-(methoxyacetyl)piperidin-4-yl]-6-methyl-5H-pyrrolo[3,2-d]pyrimidine-7-carboxamide Starting from 4-[2-(cyclopropylmethoxy)-4-fluoro-5-methoxyphenyl]-6-methyl-N-piperidin-4-yl-5H-pyrrolo[3,2-d]pyrimidine-7-carboxamide hydrochloride (example D.f35) and commercially available methoxy-acetyl chloride the title compound is obtained as colorless solid.

MS (ESI): m/z=526 (MH+, 100%).

$^1$H-NMR (300 MHz, DMSO-d$_6$): 11.76 (s, 1H, —NH); 8.96 (s, 1H); 8.81 (d, J=7.7, 1H, —NH); 7.39 (d, J=9.9, 1H); 7.18 (d, J=13.3, 1H); 4.22-4.05 (m, 2H); 4.11 (s, 2H); 3.84 (s, 3H & d, J=6.9, 2H); 3.75 (m, 1H); 3.24 (m, 1H); 2.98 (m, 1H); 2.79 (s, 3H); 1.97 (m, 2H); 1.54 (m, 1H); 1.41 (m, 1H); 0.93 (m, 1H); 0.36 (m, 2H); 0.21 (m, 2H).

Example E105

Ethyl 4-[({4-[2-(cyclopropylmethoxy)-4-fluoro-5-methoxyphenyl]-6-methyl-5H-pyrrolo[3,2-d]pyrimidin-7-yl}carbonyl)amino]piperidine-1-carboxylate Starting from 4-[2-(cyclopropylmethoxy)-4-fluoro-5-methoxyphenyl]-6-methyl-N-piperidin-4-yl-5H-pyrrolo[3,2-d]pyrimidine-7-carboxamide hydrochloride (example D.f35) and commercially available ethyl chloroformate the title compound is obtained as colorless solid.

MS (ESI): m/z=526 (MH+, 100%).

$^1$H-NMR (300 MHz, DMSO-d$_6$): 11.76 (s, 1H, —NH); 8.96 (s, 1H); 8.80 (d, J=7.7, 1H, —NH); 7.39 (d, J=9.9, 1H); 7.18 (d, J=13.3, 1H); 4.06 (qu, J=7.1, 2H & m, 1H); 3.88 (m, 2H); 3.84 (s, 3H & d, J=6.8, 2H); 3.11 (m, 2H); 2.78 (s, 3H); 1.94 (m, 2H); 1.46 (m, 1H); 1.20 (t, J=7.1, 3H); 0.93 (m, 1H); 0.36 (m, 2H); 0.21 (m, 2H).

Example E106

N-(trans-4-Acetamidocyclohexyl)-4-[2-(cyclopropylmethoxy)-4-fluoro-5-methoxyphenyl]-6-methyl-5H-pyrrolo[3,2-d]pyrimidine-7-carboxamide Starting from N-(trans-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride (example D.f36) and commercially available acetyl chloride the title compound is obtained as colorless solid.

MS (ESI): m/z=510 (MH+, 100%).

$^1$H-NMR (300 MHz, DMSO-d$_6$): 11.73 (s, 1H, —NH); 8.96 (s, 1H); 8.65 (s, J=7.7, 1H, —NH); 7.72 (d, J=7.7, 1H, —NH); 7.40 (d, J=9.9, 1H); 7.18 (d, J=13.3, 1H); 3.84 (s, 3H & d, J=6.8, 2H); 3.80 (m, 1H); 3.58 (m, 1H); 2.78 (s, 3H); 2.01 (m, 2H); 1.86 (m, 2H); 1.79 (s, 3H); 1.35 (m, 4H); 0.93 (m, 1H); 0.36 (m, 2H); 0.21 (m, 2H).

Example E107

4-[2-(Cyclopropylmethoxy)-4-fluoro-5-methoxyphenyl]-6-methyl-N-[trans-4-(propionylamino)cyclohexyl]-5H-pyrrolo[3,2-d]pyrimidine-7-carboxamide Starting from N-(trans-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride (example D.f36) and commercially available propionyl chloride the title compound is obtained as colorless solid.

MS (ESI): m/z=524 (MH+, 100%).

$^1$H-NMR (300 MHz, DMSO-d$_6$): 11.74 (s, 1H, —NH); 8.96 (s, 1H); 8.65 (d, J=7.7, 1H, —NH); 7.62 (d, J=7.7, 1H, —NH); 7.39 (d, J=9.9, 1H); 7.18 (d, J=13.3, 1H); 3.84 (s, 3H & d, J=6.8, 2H); 3.80 (m, 1H); 3.59 (m, 1H); 2.78 (s, 3H); 2.06 (qu, J=7.6, 2H); 2.01 (m, 2H); 1.86 (m, 2H); 1.35 (m, 4H); 0.99 (t, J=7.6, 3H); 0.93 (m, 1H); 0.36 (m, 2H); 0.21 (m, 2H).

Example E108

4-[2-(Cyclopropylmethoxy)-4-fluoro-5-methoxyphenyl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride (example D.f36) and commercially available methoxy-acetyl chloride the title compound is obtained as colorless solid.

MS (ESI): m/z=540 (MH+, 100%).

$^1$H-NMR (300 MHz, DMSO-d$_6$): 11.74 (s, 1H, —NH); 8.96 (s, 1H); 8.64 (s, J=7.7, 1H, —NH); 7.56 (d, J=8.2, 1H, —NH); 7.39 (d, J=9.9, 1H); 7.18 (d, J=13.3, 1H); 3.84 (s, 3H); 3.83 (d, J=6.8, 2H); 3.78 (s, 2H & m, 1H); 3.69 (m, 1H); 3.31 (s, 3H); 2.78 (s, 3H); 2.01 (m, 2H); 1.82 (m, 2H); 1.43 (m, 4H); 0.93 (m, 1H); 0.36 (m, 2H); 0.21 (m, 2H).

Example E109

Ethyl {trans-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate Starting from N-(trans-4-aminocyclohexyl)-4-[2-(cyclopropylmethoxy)-4-fluoro-5-methoxyphenyl]-6-methyl-5H- pyrrolo[3,2-d]pyrimidine-7-carboxamide hydrochloride (example D.f36) and commercially available ethyl chloroformate the title compound is obtained as colorless solid.

MS (ESI): m/z=540 (MH+, 100%).

$^{1}$H-NMR (300 MHz, DMSO-d$_{6}$): 11.73 (s, 1H, —NH); 8.96 (s, 1H); 8.64 (d, J=7.7, 1H, —NH); 7.39 (d, J=9.9, 1H); 7.18 (d, J=13.3, 1H); 7.01 (d, J=7.1, 1H, —NH); 3.98 (qu, J=7.0, 2H); 3.84 (s, 3H & d, J=6.8, 2H); 3.76 (m, 1H); 3.33 (m, 1H); 2.78 (s, 3H); 2.00 (m, 2H); 1.87 (m, 2H); 1.36 (m, 4H); 1.16 (t, J=7.0, 3H); 0.93 (m, 1H); 0.36 (m, 2H); 0.21 (m, 2H).

Example E110

N-(cis-4-Acetamidocyclohexyl)-4-[2-(cyclopropylmethoxy)-4-fluoro-5-methoxyphenyl]-6-methyl-5H-pyrrolo[3,2-d]pyrimidine-7-carboxamide Starting from N-(cis-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride (example D.f37) and commercially available acetyl chloride chloride the title compound is obtained as colorless solid.

MS (ESI): m/z=510 (MH+, 100%).

$^{1}$H-NMR (300 MHz, DMSO-d$_{6}$): 11.75 (s, 1H, —NH); 8.99 (s, 1H); 8.91 (d, J=7.5, 1H, —NH); 7.84 (d, J=7.3, 1H, —NH); 7.40 (d, J=9.9, 1H); 7.18 (d, J=13.3, 1H); 4.02 (m, 1H); 3.85 (s, 3H & d, J=6.7, 2H); 3.75 (m, 1H); 2.79 (s, 3H); 1.84 (s, 3H); 1.82-1.51 (m, 8H); 0.93 (m, 1H); 0.36 (m, 2H); 0.21 (m, 2H).

Example E111

4-[2-(Cyclopropylmethoxy)-4-fluoro-5-methoxyphenyl]-6-methyl-N-[cis-4-(propionylamino)cyclohexyl]-5H-pyrrolo[3,2-d]pyrimidine-7-carboxamide Starting from N-(cis-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride (example D.f37) and commercially available propionyl chloride the title compound is obtained as colorless solid.

MS (ESI): m/z=524 (MH+, 100%).

$^{1}$H-NMR (300 MHz, DMSO-d$_{6}$): 11.75 (s, 1H, —NH); 8.99 (s, 1H); 8.91 (d, J=7.5, 1H, —NH); 7.75 (d, J=7.3, 1H, —NH); 7.40 (d, J=9.9, 1H); 7.19 (d, J=13.3, 1H); 4.02 (m, 1H); 3.85 (s, 3H & d, J=6.9, 2H); 3.75 (m, 1H); 2.79 (s, 3H); 2.11 (qu, J=7.7, 2H); 1.85-1.51 (m, 8H); 1.00 (t, J=7.7, 3H); 0.93 (m, 1H); 0.36 (m, 2H); 0.21 (m, 2H).

Example E112

4-[2-(Cyclopropylmethoxy)-4-fluoro-5-methoxyphenyl]-N-{cis-4-[(methoxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride (example D.f37) and commercially available mehoxy-acetyl chloride the title compound is obtained as colorless solid.

MS (ESI): m/z=540 (MH+, 100 To)

$^{1}$H-NMR (300 MHz, DMSO-d$_{6}$): 11.74 (s, 1H, —NH); 8.99 (s, 1H); 8.95 (d, J=7.3, 1H, —NH); 7.66 (d, J=7.7, 1H, —NH); 7.39 (d, J=9.7, 1H); 7.19 (d, J=13.5, 1H); 4.05 (m, 1H); 3.85 (s, 3H & d, J=6.9, 2H); 3.82 (s, 2H); 3.79 (m, 1H); 3.29 (s, 3H); 2.79 (s, 3H); 1.86-1.58 (m, 8H); 0.93 (m, 1H); 0.36 (m, 2H); 0.21 (m, 2H).

Example E113

N-[(3R*,4R*)-1-Acetyl-3-hydroxypiperidin-4-yl]-4-[2-(cyclopropylmethoxy)-4-fluoro-5-methoxyphenyl]-6-methyl-5H-pyrrolo[3,2-d]pyrimidine-7-carboxamide Starting from 4-[2-(cyclopropylmethoxy)-4-fluoro-5-methoxyphenyl]-N-[(3R*,4R*)-3-hydroxypiperidin-4-yl]-6-methyl-5H-pyrrolo[3,2-d]pyrimidine-7-carboxamide hydrochloride (example D.f38) and commercially available acetyl chloride the title compound is obtained as colorless solid.

HR-MS (ESI): m/z=512.2310 ([MH]+, $C_{26}H_{31}FN_5O_4^+$, calc. 512.2304).

Example E114

4-[2-(Cyclopropylmethoxy)-4-fluoro-5-methoxyphenyl]-N-[(3R*,4R*)-3-hydroxy-1-propionylpiperidin-4-yl]-6-methyl-5H-pyrrolo[3,2-d]pyrimidine-7-carboxamide Starting from 4-[2-(cyclopropylmethoxy)-4-fluoro-5-methoxyphenyl]-N-[(3R*,4R*)-3-hydroxypiperidin-4-yl]-6-methyl-5H-pyrrolo[3,2-d]pyrimidine-7-carboxamide hydrochloride (example D.f38) and commercially available propionyl chloride the title compound is obtained as colorless solid.

HR-MS (ESI): m/z=526.2462 ([MH]+, $C_{27}H_{33}FN_5O_4^+$, calc. 526.2460).

Example E115

4-[2-(cyclopropylmethoxy)-4-fluoro-5-methoxyphenyl]-N-[(3R*,4R*)-3-hydroxy-1-(methoxyacetyl)piperidin-4-yl]-6-methyl-5H-pyrrolo[3,2-d]pyrimidine-7-carboxamide Starting from 4-[2-(cyclopropylmethoxy)-4-fluoro-5-methoxyphenyl]-N-[(3R*,4R*)-3-hydroxypiperidin-4-yl]-6-methyl-5H-pyrrolo[3,2-d]pyrimidine-7-carboxamide hydrochloride (example D.f38) and commercially available methoxy-acetyl chloride the title compound is obtained as colorless solid.

HR-MS (ESI): m/z=542.2399 ([MH]+, $C_{27}H_{33}FN_5O_6^+$, calc. 542.2409).

Example E116

N-[(3S*,4S*)-1-Acetyl-4-hydroxypiperidin-3-yl]-4-[2-(cyclopropylmethoxy)-4-fluoro-5-methoxyphenyl]-6-methyl-5H-pyrrolo[3,2-d]pyrimidine-7-carboxamide Starting from 4-[2-(cyclopropylmethoxy)-4-fluoro-5-methoxyphenyl]-N-[(3S*,4S*)-4-hydroxypiperidin-3-yl]-6-methyl-5H-pyrrolo[3,2-d]pyrimidine-7-carboxamide hydrochloride (example D.f39) and commercially available acetyl chloride the title compound is obtained as colorless solid.

HR-MS (ESI): m/z=512.2302 ([MH]+, $C_{26}H_{31}FN_5O_4^+$, calc. 512.2304).

Example E117

4-[2-(Cyclopropylmethoxy)-4-fluoro-5-methoxyphenyl]-N-[(3S*,4S*)-4-hydroxy-1-propionylpiperidin-3-yl]-6-methyl-5H-pyrrolo[3,2-d]pyrimidine-7-carboxamide Starting from 4-[2-(cyclopropylmethoxy)-4-fluoro-5-methoxyphenyl]-N-[(3S*,4S*)-4-hydroxypiperidin-3-yl]-6-methyl-5H-pyrrolo[3,2-d]pyrimidine-7-carboxamide hydrochloride (example D.f39) and commercially available propionyl chloride the title compound is obtained as colorless solid.

HR-MS (ESI): m/z=526.2462 ([MH]$^+$, $C_{27}H_{33}FN_5O_4^+$, calc. 526.2460).

Example E118

4-[2-(cyclopropylmethoxy)-4-fluoro-5-methoxyphenyl]-N-[(3S*,4S*)-4-hydroxy-1-(methoxyacetyl)piperidin-3-yl]-6-methyl-5H-pyrrolo[3,2-d]pyrimidine-7-carboxamide Starting from 4-[2-(cyclopropylmethoxy)-4-fluoro-5-methoxyphenyl]-N-[(3S*,4S*)-4-hydroxypiperidin-3-yl]-6-methyl-5H-pyrrolo[3,2-d]pyrimidine-7-carboxamide hydrochloride (example D.f39) and commercially available methoxy-acetyl chloride the title compound is obtained as colorless solid.

HR-MS (ESI): m/z=542.2401 ([MH]$^+$, $C_{27}H_{33}FN_5O_6^+$, calc. 542.2409).

Example E119

N-(1-Acetylpiperidin-4-yl)-4-[2-(cyclopropylmethoxy)-4-fluoro-5-methylphenyl]-6-methyl-5H-pyrrolo[3,2-d]pyrimidine-7-carboxamide Starting from 4-[2-(cyclopropylmethoxy)-4-fluoro-5-methylphenyl]-6-methyl-N-(piperidin-4-yl)-5H-pyrrolo[3,2-d]pyrimidine-7-carboxamide hydrochloride (example D.f40) and commercially available acetyl chloride the title compound is obtained as colorless solid.

MS (ESI): m/z=554 (MH$^+$, 100%).

$^1$H-NMR (300 MHz, DMSO-$d_6$): 11.75 (s, 1H, —NH); 8.93 (s, 1H); 8.82 (d, J=7.7, 1H, —NH); 7.54 (d, J=9.1, 1H); 7.04 (d, J=12.0, 1H); 4.22-4.05 (m, 2H); 3.87 (d, J=6.9, 2H); 3.78 (m, 1H); 3.28 (m, 1H); 2.95 (m, 1H); 2.78 (s, 3H); 2.25 (d, J=1.1, 3H); 2.04 (s, 3H); 1.95 (m, 2H); 1.54 (m, 1H); 1.38 (m, 1H); 0.95 (m, 1H); 0.37 (m, 2H); 0.24 (m, 2H).

Example E120

4-[2-(Cyclopropylmethoxy)-4-fluoro-5-methylphenyl]-6-methyl-N-(1-propanoylpiperidin-4-yl)-5H-pyrrolo[3,2-d]pyrimidine-7-carboxamide Starting from 4-[2-(cyclopropylmethoxy)-4-fluoro-5-methylphenyl]-6-methyl-N-(piperidin-4-yl)-5H-pyrrolo[3,2-d]pyrimidine-7-carboxamide hydrochloride (example D.f40) and commercially available propionyl chloride the title compound is obtained as colorless solid.

MS (ESI): m/z=494 (MH$^+$, 100%).

$^1$H-NMR (300 MHz, DMSO-$d_6$): 11.75 (s, 1H, —NH); 8.93 (s, 1H); 8.81 (d, J=7.9, 1H, —NH); 7.54 (d, J=9.1, 1H); 7.04 (d, J=12.0, 1H); 4.25-4.05 (m, 2H); 3.87 (d, J=6.9, 2H); 3.81 (m, 1H); 3.26 (m, 1H); 2.96 (m, 1H); 2.78 (s, 3H); 2.36 (qu, J=7.5, 2H); 2.24 (d, J=1.1, 3H); 1.95 (m, 2H); 1.51 (m, 1H); 1.38 (m, 1H); 1.01 (t, J=7.5, 3H); 0.95 (m, 1H); 0.37 (m, 2H); 0.24 (m, 2H).

Example E121

4-[2-(Cyclopropylmethoxy)-4-fluoro-5-methylphenyl]-N-[1-(methoxyacetyl)piperidin-4-yl]-6-methyl-5H-pyrrolo[3,2-d]pyrimidine-7-carboxamide Starting from 4-[2-(cyclopropylmethoxy)-4-fluoro-5-methylphenyl]-6-methyl-N-(piperidin-4-yl)-5H-pyrrolo[3,2-d]pyrimidine-7-carboxamide hydrochloride (example D.f40) and commercially available methoxy-acetyl chloride the title compound is obtained as colorless solid.

MS (ESI): m/z=510 (MH$^+$, 100%).

$^1$H-NMR (300 MHz, DMSO-$d_6$): 11.75 (s, 1H, —NH); 8.93 (s, 1H); 8.81 (d, J=7.7, 1H, —NH); 7.54 (d, J=9.1, 1H); 7.04 (d, J=12.0, 1H); 4.22-4.06 (m, 2H); 4.12 (d, J=1.6, 2H); 3.87 (d, J=6.9, 2H); 3.75 (m, 1H); 3.31 (s, 3H); 3.22 (m, 1H); 2.98 (m, 1H); 2.78 (s, 3H); 2.24 (d, J=1.1, 3H); 1.96 (m, 2H); 1.53 (m, 1H); 1.41 (m, 1H); 0.95 (m, 1H); 0.37 (m, 2H); 0.24 (m, 2H).

Example E122

N-[trans-4-(Acetylamino)cyclohexyl]-4-[2-(cyclopropylmethoxy)-4-fluoro-5-methylphenyl]-6-methyl-5H-pyrrolo[3,2-d]pyrimidine-7-carboxamide Starting from N-(trans-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride (example D.f41) and commercially available acetyl chloride the title compound is obtained as colorless solid.

MS (ESI): m/z=494 (MH$^+$, 100%).

$^1$H-NMR (300 MHz, DMSO-$d_6$): 11.72 (s, 1H, —NH); 8.93 (s, 1H); 8.65 (d, J=7.7, 1H, —NH); 7.72 (d, J=7.7, 1H, —NH); 7.54 (d, J=9.1, 1H); 7.03 (d, J=12.0, 1H); 3.87 (d, J=6.9, 2H); 3.80 (m, 1H); 3.58 (m, 1H); 2.77 (s, 3H); 2.25 (d, J=1.1, 3H); 2.00 (m, 2H); 1.86 (m, 2H); 1.79 (s, 3H); 1.35 (m, 4H); 0.95 (m, 1H); 0.37 (m, 2H); 0.24 (m, 2H).

Example E123

4-[2-(Cyclopropylmethoxy)-4-fluoro-5-methylphenyl]-6-methyl-N-[trans-4-(propanoylamino)cyclohexyl]-5H-pyrrolo[3,2-d]pyrimidine-7-carboxamide Starting from N-(trans-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride (example D.f41) and commercially available propionyl chloride the title compound is obtained as colorless solid.

MS (ESI): m/z=508 (MH$^+$, 100%).

$^1$H-NMR (300 MHz, DMSO-$d_6$): 11.72 (s, 1H, —NH); 8.93 (s, 1H); 8.65 (d, J=7.7, 1H, —NH); 7.62 (d, J=7.7, 1H, —NH); 7.54 (d, J=9.1, 1H); 7.03 (d, J=12.0, 1H); 3.87 (d, J=6.9, 2H); 3.80 (m, 1H); 3.59 (m, 1H); 2.77 (s, 3H); 2.25 (d, J=0.9, 3H); 2.05 (qu, J=7.7, 2H); 2.01 (m, 2H); 1.85 (m, 2H); 1.35 (m, 4H); 0.99 (t, J=7.7, 3H); 0.95 (m, 1H); 0.37 (m, 2H); 0.24 (m, 2H).

Example E124

4-[2-(Cyclopropylmethoxy)-4-fluoro-5-methylphenyl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride (example D.f41) and commercially available methoxy-acetyl chloride the title compound is obtained as colorless solid.

MS (ESI): m/z=524 (MH$^+$, 100%).
$^1$H-NMR (300 MHz, DMSO-d$_6$): 11.72 (s, 1H, —NH); 8.93 (s, 1H); 8.64 (d, J=7.7, 1H, —NH); 7.57 (d, J=7.7, 1H, —NH); 7.54 (d, J=9.1, 1H); 7.03 (d, J=12.0, 1H); 3.87 (d, J=6.9, 2H); 3.78 (m, 1H & s, 2H); 3.68 (m, 1H); 3.31 (s, 3H); 2.77 (s, 3H); 2.25 (d, J=1.1, 3H); 2.01 (m, 2H); 1.82 (m, 2H); 1.43 (m, 4H); 0.95 (m, 1H); 0.37 (m, 2H); 0.24 (m, 2H).

Example E125

N-[cis-4-(Acetylamino)cyclohexyl]-4-[2-(cyclopropylmethoxy)-4-fluoro-5-methylphenyl]-6-methyl-5H-pyrrolo[3,2-d]pyrimidine-7-carboxamide Starting from N-(cis-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride (example D.f42) and commercially available acetyl chloride the title compound is obtained as colorless solid.

MS (ESI): m/z=494 (MH$^+$, 100%).
$^1$H-NMR (300 MHz, DMSO-d$_6$): 11.73 (s, 1H, —NH); 8.96 (s, 1H); 8.93 (d, J=7.7, 1H, —NH); 7.84 (d, J=7.7, 1H, —NH); 7.54 (d, J=9.1, 1H); 7.04 (d, J=12.0, 1H); 4.03 (m, 1H); 3.88 (d, J=6.9, 2H); 3.75 (m, 1H); 2.78 (s, 3H); 2.25 (d, J=1.1, 3H); 1.84 (s, 3H); 1.84-1.51 (m, 8H); 0.95 (m, 1H); 0.37 (m, 2H); 0.24 (m, 2H).

Example E126

4-[2-(Cyclopropylmethoxy)-4-fluoro-5-methylphenyl]-6-methyl-N-[cis-4-(propanoylamino)cyclohexyl]-5H-pyrrolo[3,2-d]pyrimidine-7-carboxamide Starting from N-(cis-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride (example D.f42) and commercially available propionyl chloride the title compound is obtained as colorless solid.

MS (ESI): m/z=508 (MH$^+$, 100%).
$^1$H-NMR (300 MHz, DMSO-d$_6$): 11.73 (s, 1H, —NH); 8.96 (s, 1H); 8.93 (d, J=7.5, 1H, —NH); 7.75 (d, J=7.5, 1H, —NH); 7.54 (d, J=9.1, 1H); 7.04 (d, J=12.2, 1H); 4.03 (m, 1H); 3.88 (d, J=7.1, 2H); 3.75 (m, 1H); 2.78 (s, 3H); 2.25 (d, J=1.1, 3H); 2.11 (qu, J=7.5, 2H); 1.84-1.51 (m, 8H); 1.00 (t, J=7.5, 3H); 0.95 (m, 1H); 0.37 (m, 2H); 0.24 (m, 2H).

Example E127

4-[2-(Cyclopropylmethoxy)-4-fluoro-5-methylphenyl]-N-{cis-4-[(methoxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride (example D.f42) and commercially available methoxy-acetyl chloride the title compound is obtained as colorless solid.

MS (ESI): m/z=524 (MH$^+$, 100%).
$^1$H-NMR (300 MHz, DMSO-d$_6$): 11.73 (s, 1H, —NH); 8.97 (s, 1H); 8.96 (d, J=7.8, 1H, —NH); 7.66 (d, J=7.8, 1H, —NH); 7.54 (d, J=9.1, 1H); 7.04 (d, J=12.2, 1H); 4.05 (m, 1H); 3.88 (d, J=6.9, 2H); 3.82 (s, 2H); 3.79 (m, 1H); 3.31 (s 3H); 2.78 (s, 3H); 2.25 (d, J=1.1, 3H); 1.86-1.59 (m, 8H); 0.95 (m, 1H); 0.37 (m, 2H); 0.24 (m, 2H).

Example E128

N-[(3R*,4R*)-1-Acetyl-3-hydroxypiperidin-4-yl]-4-[2-(cyclopropylmethoxy)-4-fluoro-5-methylphenyl]-6-methyl-5H-pyrrolo[3,2-d]pyrimidine-7-carboxamide Starting from 4-[2-(cyclopropylmethoxy)-4-fluoro-5-methylphenyl]-N-[(3R*,4R*)-3-hydroxypiperidin-4-yl]-6-methyl-5H-pyrrolo[3,2-d]pyrimidine-7-carboxamide hydrochloride (example D.f43) and commercially available acetyl chloride the title compound is obtained as colorless solid.

HR-MS (ESI): m/z=496.2373 ([MH]$^+$, C$_{26}$H$_{31}$FN$_5$O$_4^+$, calc. 496.2355).

Example E129

4-[2-(cyclopropylmethoxy)-4-fluoro-5-methylphenyl]-N-[(3R*,4R*)-3-hydroxy-1-propanoylpiperidin-4-yl]-6-methyl-5H-pyrrolo[3,2-d]pyrimidine-7-carboxamide Starting from 4-[2-(cyclopropylmethoxy)-4-fluoro-5-methylphenyl]-N-[(3R*,4R*)-3-hydroxypiperidin-4-yl]-6-methyl-5H-pyrrolo[3,2-d]pyrimidine-7-carboxamide hydrochloride (example D.f43) and commercially available propionyl chloride the title compound is obtained as colorless solid.

HR-MS (ESI): m/z=510.2534 ([MH]$^+$, C$_{27}$H$_{33}$FN$_5$O$_4^+$, calc. 510.2511).

Example E130

4-[2-(Cyclopropylmethoxy)-4-fluoro-5-methylphenyl]-N-[(3R*,4R*)-3-hydroxy-1-(methoxyacetyl)piperidin-4-yl]-6-methyl-5H-pyrrolo[3,2-d]pyrimidine-7-carboxamide Starting from 4-[2-(cyclopropylmethoxy)-4-fluoro-5-methylphenyl]-N-[(3R*,4R*)-3-hydroxypiperidin-4-yl]-6-methyl-5H-pyrrolo[3,2-d]pyrimidine-7-carboxamide hydrochloride (example D.f43) and commercially available methoxy-acetyl chloride the title compound is obtained as colorless solid.

HR-MS (ESI): m/z=526.2474 ([MH]$^+$, C$_{27}$H$_{33}$FN$_5$O$_5^+$, calc. 526.2460).

Example E131

N-(1-Acetylpiperidin-4-yl)-4-[2-(cyclopropylmethoxy)-5-fluoro-4-methoxyphenyl]-6-methyl-5H-pyrrolo[3,2-d]pyrimidine-7-carboxamide Starting from 4-[2-(cyclopropylmethoxy)-5-fluoro-4-methoxyphenyl]-6-methyl-N-piperidin-4-yl-5H-pyrrolo[3,2-d]pyrimidine-7-carboxamide hydrochloride (example D.f44) and commercially available acetyl chloride the title compound is obtained as colorless solid.

MS (ESI): m/z=496 (MH+, 100%).

$^1$H-NMR (300 MHz, DMSO-d$_6$): 11.73 (br.s, 1H, —NH); 8.92 (s, 1H); 8.82 (d, J=7.7, 1H, —NH); 7.47 (d, J=11.9, 1H); 6.93 (d, J=7.3, 1H); 4.22-4.04 (m, 2H); 3.97 (s, 3H); 3.94 (d, J=6.9, 2H); 3.78 (m, 1H); 3.27 (m, 1H); 2.95 (m, 1H); 2.79 (s, 3H); 2.04 (s, 3H); 1.95 (m, 2H); 1.54 (m, 1H); 1.38 (m, 1H); 0.96 (m, 1H); 0.38 (m, 2H); 0.25 (m, 2H).

Example E132

4-[2-(Cyclopropylmethoxy)-5-fluoro-4-methoxyphenyl]-6-methyl-N-(1-propionylpiperidin-4-yl)-5H-pyrrolo[3,2-d]pyrimidine-7-carboxamide Starting from 4-[2-(cyclopropylmethoxy)-5-fluoro-4-methoxyphenyl]-6-methyl-N-piperidin-4-yl-5H-pyrrolo[3,2-d]pyrimidine-7-carboxamide hydrochloride (example D.f44) and commercially available propionyl chloride the title compound is obtained as colorless solid.

MS (ESI): m/z=510 (MH+, 100%).

$^1$H-NMR (300 MHz, DMSO-d$_6$): 11.72 (br.s, 1H, —NH); 8.91 (s, 1H); 8.82 (d, J=7.7, 1H, —NH); 7.47 (d, J=11.9, 1H); 6.92 (d, J=7.3, 1H); 4.19 (m, 1H); 4.12 (m, 1H); 3.97 (s, 3H); 3.94 (d, J=6.9, 2H); 3.81 (m, 1H); 3.25 (m, 1H); 2.96 (m, 1H); 2.79 (s, 3H); 2.36 (qu, J=7.3, 2H); 1.95 (m, 2H); 1.51 (m, 1H); 1.38 (m, 1H); 1.01 (t, J=7.3, 3H); 0.96 (m, 1H); 0.38 (m, 2H); 0.25 (m, 2H).

Example E133

4-[2-(Cyclopropylmethoxy)-5-fluoro-4-methoxyphenyl]-N-[1-(methoxyacetyl)piperidin-4-yl]-6-methyl-5H-pyrrolo[3,2-d]pyrimidine-7-carboxamide Starting from 4-[2-(cyclopropylmethoxy)-5-fluoro-4-methoxyphenyl]-6-methyl-N-piperidin-4-yl-5H-pyrrolo[3,2-d]pyrimidine-7-carboxamide hydrochloride (example D.f44) and commercially available methoxy-acetyl chloride the title compound is obtained as colorless solid.

MS (ESI): m/z=526 (MH+, 100%).

$^1$H-NMR (300 MHz, DMSO-d$_6$): 11.73 (br.s, 1H, —NH); 8.92 (s, 1H); 8.82 (d, J=77, 1H, —NH); 7.47 (d, J=11.9, 1H); 6.92 (d, J=7.3, 1H); 4.22-4.06 (s, 2H & m, 2H); 3.97 (s, 3H); 3.94 (d, J=6.9, 2H); 3.75 (m, 1H); 3.31 (m, 1H); 3.22 (m, 1H); 2.98 (m, 1H); 2.79 (s, 3H); 1.96 (m, 2H); 1.53 (m, 1H); 1.40 (m, 1H); 0.96 (m, 1H); 0.38 (m, 2H); 0.25 (m, 2H).

Example E134

Ethyl 4-[({4-[2-(cyclopropylmethoxy)-5-fluoro-4-methoxyphenyl]-6-methyl-5H-pyrrolo[3,2-d]pyrimidin-7-yl}carbonyl)amino]piperidine-1-carboxylate Starting from 4-[2-(cyclopropylmethoxy)-5-fluoro-4-methoxyphenyl]-6-methyl-N-piperidin-4-yl-5H-pyrrolo[3,2-d]pyrimidine-7-carboxamide hydrochloride (example D.f44) and commercially available ethyl chloroformate the title compound is obtained as colorless solid.

MS (ESI): m/z=526 (MH+, 100%).

$^1$H-NMR (300 MHz, DMSO-d$_6$): 11.72 (br.s, 1H, —NH); 8.92 (s, 1H); 8.82 (d, J=7.7, 1H, —NH); 7.47 (d, J=11.9, 1H); 6.93 (d, J=7.3, 1H); 4.06 (qu, J=7.1, 2H & m, 3H); 3.97 (s, 3H); 3.94 (d, J=7.1, 2H); 3.88 (m, 2H); 3.11 (m, 2H); 2.79 (s, 3H); 1.94 (m, 2H); 1.45 (m, 1H); 1.20 (t, J=7.1, 3H); 0.96 (m, 1H); 0.39 (m, 2H); 0.25 (m, 2H).

Example E135

N-(trans-4-Acetamidocyclohexyl)-4-[2-(cyclopropylmethoxy)-5-fluoro-4-methoxyphenyl]-6-methyl-5H-pyrrolo[3,2-d]pyrimidine-7-carboxamide Starting from N-(trans-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride (example D.f45) and commercially available acetyl chloride the title compound is obtained as colorless solid.

MS (ESI): m/z=468 (MH+, 100%).

$^1$H-NMR (300 MHz, DMSO-d$_6$): 12.32 (br.s, 1H, —NH); 9.01 (s, 1H); 8.51 (d, J=7.7, 1H, —NH); 8.18 (br.d, J=4.6, 3H, NH$_3$+); 7.54 (d, J=11.7, 1H); 6.96 (d, J=7.3, 1H); 3.99 (s, 3H); 3.97 (d, J=7.4, 2H); 3.81 (m, 1H); 3.07 (m, 1H); 2.83 (s, 3H); 2.05 (m, 4H); 1.48 (m, 4H); 0.97 (m, 1H); 0.39 (m, 2H); 0.27 (m, 2H).

Example E136

4-[2-(Cyclopropylmethoxy)-5-fluoro-4-methoxyphenyl]-6-methyl-N-[trans-4-(propionylamino)cyclohexyl]-5H-pyrrolo[3,2-d]pyrimidine-7-carboxamide Starting from N-(trans-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride (example D.f45) and commercially available propionyl chloride the title compound is obtained as colorless solid.

MS (ESI): m/z=524 (MH+, 100%).

$^1$H-NMR (300 MHz, DMSO-d$_6$): 11.70 (s, 1H, —NH); 8.92 (s, 1H); 8.66 (d, J=7.7, 1H, —NH); 7.62 (d, J=7.7, 1H, —NH); 7.47 (d, J=11.8, 1H); 6.92 (d, J=7.5, 1H); 3.97 (s, 3H); 3.94 (d, J=6.9, 2H); 3.80 (m, 1H); 3.59 (m, 1H); 2.78 (s, 3H); 2.05 (qu, J=7.7, 2H); 2.00 (m, 2H); 1.86 (m, 2H); 1.35 (m, 4H); 0.99 (t, J=7.7, 3H); 0.96 (m, 1H); 0.38 (m, 2H); 0.25 (m, 2H).

Example E137

4-[2-(Cyclopropylmethoxy)-5-fluoro-4-methoxyphenyl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride (example D.f45) and commercially available methoxy-acetyl chloride the title compound is obtained as colorless solid.

MS (ESI): m/z=540 (MH+, 100%).

$^1$H-NMR (300 MHz, DMSO-d$_6$): 11.70 (s, 1H, —NH); 8.92 (s, 1H); 8.65 (d, J=7.7, 1H, —NH); 7.56 (d, J=8.2, 1H, —NH); 7.47 (d, J=11.7, 1H); 6.92 (d, J=7.3, 1H); 3.97 (s, 3H); 3.94 (d, J=6.9, 2H); 3.78 (s, 2H & m, 1H); 3.69 (m, 1H); 3.31 (s, 3H); 2.78 (s, 3H); 2.01 (m, 2H); 1.82 (m, 2H); 1.43 (m, 4H); 0.96 (m, 1H); 0.38 (m, 2H); 0.25 (m, 2H).

Example E138

N-(cis-4-Acetamidocyclohexyl)-4-[2-(cyclopropylmethoxy)-5-fluoro-4-methoxyphenyl]-6-methyl-5H-pyrrolo[3,2-d]pyrimidine-7-carboxamide Starting from N-(cis-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride (example D.f46) and commercially available acetyl chloride the title compound is obtained as colorless solid.

MS (ESI): m/z=510 (MH$^+$, 100%).

$^1$H-NMR (300 MHz, DMSO-d$_6$): 11.71 (s, 1H, —NH); 8.95 (s, 1H); 8.94 (d, J=7.7, 1H, —NH); 7.84 (d, J=7.5, 1H, —NH); 7.48 (d, J=11.9, 1H); 6.93 (d, J=7.3, 1H); 4.02 (m, 1H); 3.97 (s, 3H); 3.95 (d, J=6.9, 2H); 3.75 (m, 1H); 2.79 (s, 3H); 1.84 (s, 3H); 1.80-1.52 (m, 8H); 0.96 (m, 1H); 0.39 (m, 2H); 0.25 (m, 2H).

Example E139

4-[2-(Cyclopropylmethoxy)-5-fluoro-4-methoxyphenyl]-6-methyl-N-[cis-4-(propionylamino)cyclohexyl]-5H-pyrrolo[3,2-d]pyrimidine-7-carboxamide Starting from N-(cis-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride (example D.f46) and commercially available propionyl chloride the title compound is obtained as colorless solid.

MS (ESI): m/z=524 (MH$^+$, 100%).

$^1$H-NMR (300 MHz, DMSO-d$_6$): 11.71 (s, 1H, —NH); 8.95 (s, 1H); 8.93 (d, J=7.7, 1H, —NH); 7.75 (d, J=7.5, 1H, —NH); 7.47 (d, J=11.9, 1H); 6.93 (d, J=7.3, 1H); 4.02 (m, 1H); 3.97 (s, 3H); 3.94 (d, J=6.9, 2H); 3.75 (m, 1H); 2.79 (s, 3H); 2.11 (qu, J=7.6, 2H); 1.83-1.52 (m, 8H); 1.00 (t, J=7.6, 1H); 0.96 (m, 1H); 0.39 (m, 2H); 0.25 (m, 2H).

Example E140

4-[2-(Cyclopropylmethoxy)-5-fluoro-4-methoxyphenyl]-N-{cis-4-[(methoxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride (example D.f46) and commercially available methoxy-acetyl chloride the title compound is obtained as colorless solid.

MS (ESI): m/z=540 (MH$^+$, 100%).

$^1$H-NMR (300 MHz, DMSO-d$_6$): 11.70 (s, 1H, —NH); 8.97 (d, J=7.7, 1H, —NH); 8.96 (s, 1H); 7.67 (d, J=7.7, 1H, —NH); 7.47 (d, J=11.9, 1H); 6.93 (d, J=7.3, 1H); 4.05 (m, 1H); 3.97 (s, 3H); 3.94 (d, J=7.1, 2H); 3.82 (s, 2H); 3.79 (m, 1H); 3.31 (s, 3H); 2.79 (s, 3H); 1.85-1.59 (m, 8H); 0.96 (m, 1H); 0.39 (m, 2H); 0.25 (m, 2H).

Example E141

Ethyl {cis-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate Starting from N-(cis-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride (example D.f46) and commercially available ethyl chloroformate the title compound is obtained as colorless solid.

MS (ESI): m/z=540 (MH$^+$, 100%).

$^1$H-NMR (300 MHz, DMSO-d$_6$): 11.69 (s, 1H, —NH); 8.98 (d, J=7.7, 1H, —NH); 8.95 (s, 1H); 7.47 (d, J=11.9, 1H); 7.21 (br.d, J=6.0, 1H, —NH); 6.93 (d, J=7.3, 1H); 4.03 (m, 1H); 3.99 (qu, J=7.1, 2H); 3.97 (s, 3H); 3.94 (d, J=7.1, 2H); 3.48 (m, 1H); 2.78 (s, 3H); 1.85-1.54 (m, 8H); 1.17 (t, J=7.1, 3H); 0.96 (m, 1H); 0.39 (m, 2H); 0.25 (m, 2H).

Example E142

N-[(3R*,4R*)-1-Acetyl-3-hydroxypiperidin-4-yl]-4-[2-(cyclopropylmethoxy)-5-fluoro-4-methoxyphenyl]-6-methyl-5H-pyrrolo[3,2-d]pyrimidine-7-carboxamide Starting from 4-[2-(cyclopropylmethoxy)-5-fluoro-4-methoxyphenyl]-N-[(3R*,4R*)-3-hydroxypiperidin-4-yl]-6-methyl-5H-pyrrolo[3,2-d]pyrimidine-7-carboxamide hydrochloride (example D.f47) and commercially available acetyl chloride the title compound is obtained as colorless solid.

HR-MS (ESI): m/z=512.2301 ([MH]$^+$, C$_{26}$H$_{31}$FN$_5$O$_5^+$, calc. 512.2304).

Example E143

4-[2-(Cyclopropylmethoxy)-5-fluoro-4-methoxyphenyl]-N-[(3R*,4R*)-3-hydroxy-1-propanoylpiperidin-4-yl]-6-methyl-5H-pyrrolo[3,2-d]pyrimidine-7-carboxamide Starting from 4-[2-(cyclopropylmethoxy)-5-fluoro-4-methoxyphenyl]-N-[(3R*,4R*)-3-hydroxypiperidin-4-yl]-6-methyl-5H-pyrrolo[3,2-d]pyrimidine-7-carboxamide hydrochloride (example D.f47) and commercially available propionyl chloride the title compound is obtained as colorless solid.

HR-MS (ESI): m/z=HR_MS (ESI): m/z=526.2454 ([MH]$^+$, C$_{27}$H$_{33}$FN$_5$O$_5^+$, calc. 526.2460).

Example E144

4-[2-(Cyclopropylmethoxy)-5-fluoro-4-methoxyphenyl]-N-[(3R*,4R*)-3-hydroxy-1-(methoxyacetyl)piperidin-4-yl]-6-methyl-5H-pyrrolo[3,2-d]pyrimidine-7-carboxamide Starting from 4-[2-(cyclopropylmethoxy)-5-fluoro-4-methoxyphenyl]-N-[(3R*,4R*)-3-hydroxypiperidin-4-yl]-6-methyl-5H-pyrrolo[3,2-d]pyrimidine-7-carboxamide hydrochloride (example D.f47) and commercially available methoxy-acetyl chloride the title compound is obtained as colorless solid.

HR-MS (ESI): m/z=542.2398 ([MH]$^+$, C$_{27}$H$_{33}$FN$_5$O$_6^+$, calc. 542.2409).

Example E145

N-(1-Acetylpiperidin-4-yl)-4-[2-(cyclopropylmethoxy)-5-ethylphenyl]-6-methyl-5H-pyrrolo[3,2-d]pyrimidine-7-carboxamide Starting from 4-[2-(cyclopropylmethoxy)-5-ethylphenyl]-6-methyl-N-(piperidin-4-yl)-5H-pyrrolo[3,2-d]pyrimidine-7-carboxamide hydrochloride (example D.f48) and commercially available acetyl chloride the title compound is obtained as colorless solid.

MS (ESI): m/z=476 (MH$^+$, 100%).

$^1$H-NMR (300 MHz, DMSO-d$_6$): 11.76 (s, 1H, —NH); 8.95 (s, 1H); 8.83 (d, J=7.7, 1H, —NH); 7.45 (d, J=2.2, 1H); 7.36 (dd, J=8.6, 2.2, 1H); 7.08 (d, J=8.6, 1H); 4.22-4.04 (m, 2H); 3.87 (d, J=6.9, 2H); 3.78 (m, 1H); 3.28 (m, 1H); 2.95 (m,

1H); 2.78 (s, 3H); 2.64 (qu, J=7.5, 2H); 2.04 (s, 3H); 1.96 (m, 2H); 1.54 (m, 1H); 1.39 (m, 1H); 1.18 (t, J=7.5, 3H); 0.94 (m, 1H); 0.36 (m, 2H); 0.25 (m, 2H).

Example E146

4-[2-(Cyclopropylmethoxy)-5-ethylphenyl]-6-methyl-N-(1-propanoylpiperidin-4-yl)-5H-pyrrolo[3,2-d]pyrimidine-7-carboxamide Starting from 4-[2-(cyclopropylmethoxy)-5-ethylphenyl]-6-methyl-N-(piperidin-4-yl)-5H-pyrrolo[3,2-d]pyrimidine-7-carboxamide hydrochloride (example D.f48) and commercially available propionyl chloride the title compound is obtained as colorless solid.

MS (ESI): m/z=490 (MH+, 100%).

$^1$H-NMR (300 MHz, DMSO-$d_6$): 11.76 (s, 1H, —NH); 8.94 (s, 1H); 8.82 (d, J=7.7, 1H, —NH); 7.45 (d, J=2.4, 1H); 7.36 (dd, J=8.6, 2.4, 1H); 7.08 (d, J=8.6, 1H); 4.25-4.04 (m, 2H); 3.87 (d, J=6.9, 2H); 3.82 (m, 1H); 3.25 (m, 1H); 2.97 (m, 1H); 2.78 (s, 3H); 2.64 (qu, J=7.5, 2H); 2.36 (qu, J=7.5, 2H); 1.96 (m, 2H); 1.52 (m, 1H); 1.38 (m, 1H); 1.18 (t, J=7.5, 3H); 1.01 (t, J=7.5, 3H); 0.94 (m, 1H); 0.36 (m, 2H); 0.23 (m, 2H).

Example E147

4-[2-(Cyclopropylmethoxy)-5-ethylphenyl]-N-[1-(methoxyacetyl)piperidin-4-yl]-6-methyl-5H-pyrrolo[3,2-d]pyrimidine-7-carboxamide Starting from 4-[2-(cyclopropylmethoxy)-5-ethylphenyl]-6-methyl-N-(piperidin-4-yl)-5H-pyrrolo[3,2-d]pyrimidine-7-carboxamide hydrochloride (example D.f48) and commercially available methoxyacetyl chloride the title compound is obtained as colorless solid.

MS (ESI): m/z=506 (MH+, 100%).

$^1$H-NMR (300 MHz, DMSO-$d_6$): 11.76 (s, 1H, —NH); 8.95 (s, 1H); 8.82 (d, J=7.7, 1H, —NH); 7.45 (d, J=2.4, 1H); 7.36 (dd, J=8.6, 2.4, 1H); 7.08 (d, J=8.6, 1H); 4.22-4.04 (m, 2H); 4.12 (d, J=1.6, 2H); 3.87 (d, J=6.9, 2H); 3.75 (m, 1H); 3.31 (s, 3H); 3.22 (m, 1H); 2.99 (m, 1H); 2.78 (s, 3H); 2.64 (qu, J=7.5, 2H); 1.96 (m, 2H); 1.54 (m, 1H); 1.41 (m, 1H); 1.18 (t, J=7.5, 3H); 0.94 (m, 1H); 0.36 (m, 2H); 0.23 (m, 2H).

Example E148

N-[trans-4-(Acetylamino)cyclohexyl]-4-[2-(cyclopropylmethoxy)-5-ethylphenyl]-6-methyl-5H-pyrrolo[3,2-d]pyrimidine-7-carboxamide Starting from N-(trans-4-aminocyclohexyl)-4-[2-(cyclopropylmethoxy)-5-ethylphenyl]-6-methyl-5H-pyrrolo[3,2-d]pyrimidine-7-carboxamide hydrochloride (example D.f49) and commercially available acetylchloride the title compound is obtained as colorless solid.

MS (ESI): m/z=490 (MH+, 100%).

$^1$H-NMR (300 MHz, DMSO-$d_6$): 11.72 (s, 1H, —NH); 8.95 (s, 1H); 8.66 (d, J=7.7, 1H, —NH); 7.72 (d, J=7.7, 1H, —NH); 7.45 (d, J=2.2, 1H); 7.35 (dd, J=8.6, 2.2, 1H); 7.08 (d, J=8.6, 1H); 3.86 (d, J=6.9, 2H); 3.80 (m, 1H); 3.58 (m, 1H); 2.77 (s, 3H); 2.64 (qu, J=7.5, 2H); 2.00 (m, 2H); 1.87 (m, 2H); 1.79 (s, 3H); 1.35 (m, 4H); 1.18 (t, J=7.5, 3H); 0.94 (m, 1H); 0.36 (m, 2H); 0.22 (m, 2H).

Example E149

4-[2-(Cyclopropylmethoxy)-5-ethylphenyl]-6-methyl-N-[trans-4-(propanoylamino)cyclohexyl]-5H-pyrrolo[3,2-d]pyrimidine-7-carboxamide Starting from N-(trans-4-aminocyclohexyl)-4-[2-(cyclopropylmethoxy)-5-ethylphenyl]-6-methyl-5H-pyrrolo[3,2-d]pyrimidine-7-carboxamide hydrochloride (example D.f49) and commercially available propionyl chloride the title compound is obtained as colorless solid.

MS (ESI): m/z=504 (MH+, 100%).

$^1$H-NMR (300 MHz, DMSO-$d_6$): 11.72 (s, 1H, —NH); 8.95 (s, 1H); 8.67 (d, J=7.7, 1H, —NH); 7.62 (d, J=7.7, 1H, —NH); 7.45 (d, J=2.2, 1H); 7.36 (dd, J=8.6, 2.2, 1H); 7.08 (d, J=8.6, 1H); 3.86 (d, J=6.9, 2H); 3.80 (m, 1H); 3.58 (m, 1H); 2.77 (s, 3H); 2.64 (qu, J=7.5, 2H); 2.06 (qu, J=7.7, 2H); 2.01 (m, 2H); 1.86 (m, 2H); 1.35 (m, 4H); 1.18 (t, J=7.5, 3H); 0.99 (t, J=7.5, 3H); 0.94 (m, 1H); 0.36 (m, 2H); 0.22 (m, 2H).

Example E150

4-[2-(Cyclopropylmethoxy)-5-ethylphenyl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-5-ethylphenyl]-6-methyl-5H-pyrrolo[3,2-d]pyrimidine-7-carboxamide hydrochloride (example D.f49) and commercially available methoxy-acetyl chloride the title compound is obtained as colorless solid.

MS (ESI): m/z=504 (MH+, 100%).

$^1$H-NMR (300 MHz, DMSO-$d_6$): 11.86 (br.s, 1H, —NH); 8.93 (s, 1H); 8.66 (d, J=7.7, 1H, —NH); 7.57 (d, J=8.2, 1H, —NH); 7.44 (d, J=2.4, 1H); 7.35 (dd, J=8.6, 2.4, 1H); 7.07 (d, J=8.6, 1H); 3.86 (d, J=6.9, 2H); 3.78 (s, 2H & m, 1H); 3.69 (m, 1H); 3.31 (s, 3H); 2.77 (s, 3H); 2.63 (qu, J=7.5, 2H); 2.01 (m, 2H); 1.82 (m, 2H); 1.43 (m, 4H); 1.18 (t, J=7.5, 3H); 0.94 (m, 1H); 0.35 (m, 2H); 0.22 (m, 2H).

Example E151

N-[cis-4-(Acetylamino)cyclohexyl]-4-[2-(cyclopropylmethoxy)-5-ethylphenyl]-6-methyl-5H-pyrrolo[3,2-d]pyrimidine-7-carboxamide Starting from N-(cis-4-aminocyclohexyl)-4-[2-(cyclopropylmethoxy)-5-ethylphenyl]-6-methyl-5H-pyrrolo[3,2-d]pyrimidine-7-carboxamide hydrochloride (example D.f50) and commercially available acetyl chloride the title compound is obtained as colorless solid.

MS (ESI): m/z=490 (MH+, 100%).

$^1$H-NMR (300 MHz, DMSO-$d_6$): 11.73 (s, 1H, —NH); 8.98 (s, 1H); 8.94 (d, J=7.7, 1H, —NH); 7.85 (d, J=7.5, 1H, —NH); 7.45 (d, J=2.4, 1H); 7.36 (dd, J=8.6, 2.4, 1H); 7.08 (d, J=8.6, 1H); 4.03 (m, 1H); 3.87 (d, J=6.9, 2H); 3.75 (m, 1H); 2.78 (s, 3H); 2.64 (qu, J=7.5, 2H); 1.84 (s, 3H); 1.82-1.51 (m, 8H); 1.19 (t, J=7.5, 3H); 0.94 (m, 1H); 0.36 (m, 2H); 0.23 (m, 2H).

Example E152

4-[2-(Cyclopropylmethoxy)-5-ethylphenyl]-6-methyl-N-[cis-4-(propanoylamino)cyclohexyl]-5H-pyrrolo[3,2-d]pyrimidine-7-carboxamide Starting from N-(cis-4-aminocyclohexyl)-4-[2-(cyclopropylmethoxy)-5-ethylphenyl]-6-methyl-5H-pyrrolo[3,2-d]

pyrimidine-7-carboxamide hydrochloride (example D.f50) and commercially available propionyl chloride the title compound is obtained as colorless solid.

MS (ESI): m/z=504 (MH$^+$, 100%).

$^1$H-NMR (300 MHz, DMSO-d$_6$): 11.73 (s, 1H, —NH); 8.98 (s, 1H); 8.94 (d, J=7.5, 1H, —NH); 7.75 (d, J=7.5, 1H, —NH); 7.45 (d, J=2.2, 1H); 7.36 (dd, J=8.6, 2.2, 1H); 7.08 (d, J=8.6, 1H); 4.02 (m, 1H); 3.87 (d, J=6.8, 2H); 3.75 (m, 1H); 2.78 (s, 3H); 2.64 (qu, J=7.5, 2H); 2.11 (qu, J=7.5, 2H); 1.89-1.52 (m, 8H); 1.19 (t, J=7.5, 3H); 1.00 (t, J=7.5, 3H); 0.94 (m, 1H); 0.36 (m, 2H); 0.23 (m, 2H).

Example E153

4-[2-(Cyclopropylmethoxy)-5-ethylphenyl]-N-{cis-4-[(methoxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-5-ethylphenyl]-6-methyl-5H-pyrrolo[3,2-d]pyrimidine-7-carboxamide hydrochloride (example D.f50) and commercially available methoxy-acetyl chloride the title compound is obtained as colorless solid.

MS (ESI): m/z=504 (MH$^+$, 100%).

$^1$H-NMR (300 MHz, DMSO-d$_6$): 11.73 (s, 1H, —NH); 8.98 (s, 1H); 8.97 (d, J=7.5, 1H, —NH); 7.67 (d, J=7.5, 1H, —NH); 7.45 (d, J=2.2, 1H); 7.36 (dd, J=8.6, 2.2, 1H); 7.08 (d, J=8.6, 1H); 4.06 (m, 1H); 3.87 (d, J=6.8, 2H); 3.82 (s, 2H); 3.79 (m, 1H); 3.31 (s, 3H); 2.78 (s, 3H); 2.64 (qu, J=7.6, 2H); 1.89-1.55 (m, 8H); 1.19 (t, J=7.6, 3H); 0.94 (m, 1H); 0.36 (m, 2H); 0.23 (m, 2H).

Example E154

N-[(3R*,4R*)-1-Acetyl-4-hydroxypyrrolidin-3-yl]-4-[2-(cyclopropylmethoxy)-5-ethylphenyl]-6-methyl-5H-pyrrolo[3,2-d]pyrimidine-7-carboxamide Starting from 4-[2-(cyclopropylmethoxy)-5-ethylphenyl]-N-[(3R*,4R*)-4-hydroxypyrrolidin-3-yl]-6-methyl-5H-pyrrolo[3,2-d]pyrimidine-7-carboxamide hydrochloride (example D.f51) and commercially available acetyl chloride the title compound is obtained as colorless solid.

MS (ESI): m/z=478 (MH$^+$, 100%).

$^1$H-NMR (300 MHz, DMSO-d$_6$): 11.80 (s, 1H, —NH); 8.93 (s, 1H); [8.90 (d, J=7.1), 8.84 (d, J=6.6), 1H, —NH]; 7.45 (d, J=2.4, 1H); 7.36 (dd, J=8.4, 2.4, 1H); 7.08 (d, J=8.4, 1H); [5.56 (d, J=3.8), 5.48 (J=4.0), 1H, —OH]; [4.36 (m), 4.19 (m), 1H]; 4.27 (m, 1H); 3.86 (d, J=6.9, 2H); 3.80-3.65 (m, 1H); [3.58 (m), 3.45 (m), 1H]; 3.41-3.27 (m, 2H); [2.78 (s), 2.77 (s), 3H]; 2.63 (qu, J=7.6, 2H); [1.99 (s)-1.98 (s), 3H]; 1.18 (t, J=7.6, 3H); 0.94 (m, 1H); 0.36 (m, 2H); 0.23 (m, 2H).

Example E155

4-[2-(Cyclopropylmethoxy)-5-ethylphenyl]-N-[(3R*,4R*)-4-hydroxy-1-propanoylpyrrolidin-3-yl]-6-methyl-5H-pyrrolo[3,2-d]pyrimidine-7-carboxamide Starting from 4-[2-(cyclopropylmethoxy)-5-ethylphenyl]-N-[(3R*,4R*)-4-hydroxypyrrolidin-3-yl]-6-methyl-5H-pyrrolo[3,2-d]pyrimidine-7-carboxamide hydrochloride (example D.f51) and commercially available propionyl chloride the title compound is obtained as colorless solid.

MS (ESI): m/z=492 (MH$^+$, 100%).

$^1$H-NMR (300 MHz, DMSO-d$_6$): 11.79 (s, 1H, —NH); 8.91 (s, 1H); [8.88 (d, J=7.1), 8.84 (d, J=6.6), 1H, —NH]; 7.44 (d, J=2.4, 1H); 7.36 (dd, J=8.6, 2.4, 1H); 7.08 (d, J=8.6, 1H); [5.55 (d, J=3.7), 5.47 (d, J=3.9), 1H, —OH]; [4.36 (m), 4.19 (m), 1H]; 4.27 (m, 1H); 3.86 (d, J=6.8, 2H); 3.73 (m, 1H); [3.59 (m), 3.45 (m), 1H]; 3.42-3.27 (m, 2H); 2.78 (s, 3H); 2.63 (qu, J=7.6, 2H); [2.29 (qu, J=7.5), 2.28 (qu, J=7.5), 2H]; 1.18 (t, J=7.6, 3H); [1.03 (t, J=7.5), 1.01 (t, J=7.5), 3H]; 0.93 (m, 1H); 0.35 (m, 2H); 0.22 (m, 2H).

Example E156

4-[2-(Cyclopropylmethoxy)-5-ethylphenyl]-N-[(3R*,4R*)-4-hydroxy-1-(methoxyacetyl)pyrrolidin-3-yl]-6-methyl-5H-pyrrolo[3,2-d]pyrimidine-7-carboxamide Starting from 4-[2-(cyclopropylmethoxy)-5-ethylphenyl]-N-[(3R*,4R*)-4-hydroxypyrrolidin-3-yl]-6-methyl-5H-pyrrolo[3,2-d]pyrimidine-7-carboxamide hydrochloride (example D.f51) and commercially available methoxy-acetyl chloride the title compound is obtained as colorless solid.

MS (ESI): m/z=508 (MH$^+$, 100%).

$^1$H-NMR (300 MHz, DMSO-d$_6$): 11.77 (s, 1H, —NH); [8.91 (s), 8.90 (s), 1H]; [8.88 (d, J=7.1), 8.84 (d, J=6.6), 1H, —NH]; 7.44 (d, J=2.4, 1H); 7.36 (dd, J=8.4, 2.4, 1H); 7.08 (d, J=8.4, 1H); [5.57 (d, J=3.7), 5.50 (d, J=3.9), 1H, —OH]; [4.36 (m), 4.19 (m), 1H]; 4.27 (m, 1H); [4.07 (d, J=3.5), 4.04 (s), 2H]; 3.86 (d, J=6.9, 2H); 3.73 (m, 1H); [3.62 (m), 3.46 (m), 1H]; 3.44-3.27 (m, 2H); [3.34 (s), 3.32 (s), 3H]; 2.78 (s, 3H); 2.63 (qu, J=7.6, 2H); 1.18 (t, J=7.6, 3H); 0.93 (m, 1H); 0.35 (m, 2H); 0.22 (m, 2H).

Example E157

N-(1-Acetylpiperidin-4-yl)-4-[2-(cyclopropylmethoxy)-5-(propan-2-yl)phenyl]-6-methyl-5H-pyrrolo[3,2-d]pyrimidine-7-carboxamide Starting from 4-[2-(cyclopropylmethoxy)-5-(propan-2-yl)phenyl]-6-methyl-N-(piperidin-4-yl)-5H-pyrrolo[3,2-d]pyrimidine-7-carboxamide hydrochloride (example D.f52) and commercially available acetyl chloride the title compound is obtained as colorless solid.

MS (ESI): m/z=490 (MH$^+$, 100%).

$^1$H-NMR (300 MHz, DMSO-d$_6$): 11.76 (s, 1H, —NH); 8.95 (s, 1H); 8.83 (d, J=7.7, 1H, —NH); 7.47 (d, J=2.4, 1H); 7.39 (dd, J=8.6, 2.4, 1H); 7.09 (d; J=8.6, 1H); 4.23-4.05 (m, 2H); 3.87 (d, J=6.9, 2H); 3.78 (m, 1H); 3.28 (m, 1H); 2.94 (m, 1H & sept J=6.9, 1H); 2.78 (s, 3H); 2.04 (s, 3H); 1.96 (m, 2H); 1.54 (m, 1H); 1.39 (m, 1H); 1.22 (d, J=6.9, 6H); 0.94 (m, 1H); 0.36 (m, 2H); 0.23 (m, 2H).

Example E158

4-[2-(Cyclopropylmethoxy)-5-(propan-2-yl)phenyl]-N-[1-(methoxyacetyl)piperidin-4-yl]-6-methyl-5H-pyrrolo[3,2-d]pyrimidine-7-carboxamide Starting from 4-[2-(cyclopropylmethoxy)-5-(propan-2-yl)phenyl]-6-methyl-N-(piperidin-4-yl)-5–/– pyrrolo[3,2-d]pyrimidine-7-carboxamide hydrochloride (example D.f52) and commercially available methoxy-acetyl chloride the title compound is obtained as colorless solid.

MS (ESI): m/z=520 (MH$^+$, 100%).

$^1$H-NMR (300 MHz, DMSO-d$_6$): 11.76 (s, 1H, —NH); 8.95 (s, 1H); 8.82 (d, J=7.9, 1H, —NH); 7.47 (d, J=2.4, 1H); 7.39 (dd, J=8.6, 2.4, 1H); 7.09 (d; J=8.6, 1H); 4.21-4.05 (m, 2H); 4.12 (d, J=1.6, 2H); 3.87 (d, J=6.9, 2H); 3.75 (m, 1H);

3.31 (s, 3H); 3.22 (m, 1H); 2.94 (m, 1H & sept, J=6.9, 1H); 2.78 (s, 3H); 1.96 (m, 2H); 1.54 (m, 1H); 1.41 (m, 1H); 1.22 (d, J=6.9, 6H); 0.94 (m, 1H); 0.36 (m, 2H); 0.23 (m, 2H).

Example E159

N-[trans-4-(Acetylamino)cyclohexyl]-4-[2-(cyclopropylmethoxy)-5-(propan-2-yl)phenyl]-6-methyl-5H-pyrrolo[3,2-d]pyrimidine-7-carboxamide Starting from N-(trans-4-aminocyclohexyl)-4-[2-(cyclopropylmethoxy)-5-(propan-2-yl)phenyl]-6-methyl-5H-pyrrolo[3,2-d]pyrimidine-7-carboxamide hydrochloride (example D.f53) and commercially available acetyl chloride the title compound is obtained as colorless solid.

MS (ESI): m/z=504 (MH$^+$, 100%).

$^1$H-NMR (300 MHz, DMSO-d$_6$): 11.73 (s, 1H, —NH); 8.96 (s, 1H); 8.66 (d, J=7.7, 1H, —NH); 7.72 (d, J=7.7, 1H, —NH); 7.47 (d, J=2.4, 1H); 7.39 (dd, J=8.6, 2.4, 1H); 7.08 (d; J=8.6, 1H); 3.87 (d, J=6.9, 2H); 3.80 (m, 1H); 3.58 (m, 1H); 2.94 (sept, J=6.9, 1H); 2.77 (s, 3H); 2.01 (m, 2H); 1.87 (m, 2H); 1.79 (s, 3H); 1.35 (m, 4H); 1.22 (d, J=6.9, 6H); 0.94 (m, 1H); 0.36 (m, 2H); 0.22 (m, 2H).

Example E160

4-[2-(Cyclopropylmethoxy)-5-(propan-2-yl)phenyl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-5-(propan-2-yl)phenyl]-6-methyl-5H-pyrrolo[3,2-d]pyrimidine-7-carboxamide hydrochloride (example D.f53) and commercially available methoxy-acetyl chloride the title compound is obtained as colorless solid.

MS (ESI): m/z=534 (MH$^+$, 100%).

$^1$H-NMR (300 MHz, DMSO-d$_6$): 11.73 (s, 1H, —NH); 8.95 (s, 1H); 8.66 (d, J=7.7, 1H, —NH); 7.57 (d, J=8.2, 1H, —NH); 7.47 (d, J=2.4, 1H); 7.39 (dd, J=8.6, 2.4, 1H); 7.08 (d; J=8.6, 1H); 3.87 (d, J=6.9, 2H); 3.78 (s, 2H & m, 1H); 3.69 (m, 1H); 3.31 (s, 3H); 2.94 (sept, J=6.9, 1H); 2.77 (s, 3H); 2.01 (m, 2H); 1.82 (m, 2H); 1.43 (m, 4H); 1.22 (d, J=6.9, 6H); 0.94 (m, 1H); 0.36 (m, 2H); 0.22 (m, 2H).

Example E161

N-[cis-4-(Acetylamino)cyclohexyl]-4-[2-(cyclopropylmethoxy)-5-(propan-2-yl)phenyl]-6-methyl-5H-pyrrolo[3,2-d]pyrimidine-7-carboxamide Starting from N-(cis-4-aminocyclohexyl)-4-[2-(cyclopropylmethoxy)-5-(propan-2-yl)phenyl]-6-methyl-5H-pyrrolo[3,2-d]pyrimidine-7-carboxamide hydrochloride (example D.f54) and commercially available acetyl chloride the title compound is obtained as colorless solid.

MS (ESI): m/z=504 (MH$^+$, 100%).

$^1$H-NMR (300 MHz, DMSO-d$_6$): 11.74 (s, 1H, —NH); 8.98 (s, 1H); 8.93 (d, J=7.5, 1H, —NH); 7.85 (d, J=7.7, 1H, —NH); 7.47 (d, J=2.4, 1H); 7.40 (dd, J=8.6, 2.4, 1H); 7.09 (d; J=8.6, 1H); 4.02 (m, 1H); 3.87 (d, J=6.9, 2H); 3.75 (m, 1H); 2.94 (sept, J=6.8, 1H); 2.78 (s, 3H); 1.84 (s, 3H); 1.81-1.51 (m, 8H); 1.22 (d, J=6.8, 6H); 0.94 (m, 1H); 0.36 (m, 2H); 0.23 (m, 2H).

Example E162

4-[2-(Cyclopropylmethoxy)-5-(propan-2-yl)phenyl]-N-{cis-4-[(methoxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-5-(propan-2-yl)phenyl]-6-methyl-5H-pyrrolo[3,2-d]pyrimidine-7-carboxamide hydrochloride (example D.f54) and commercially available methoxy-acetyl chloride the title compound is obtained as colorless solid.

MS (ESI): m/z=534 (MH$^+$, 100%).

$^1$H-NMR (300 MHz, DMSO-d$_6$): 11.73 (s, 1H, —NH); 8.99 (s, 1H); 8.97 (d, J=7.3, 1H, —NH); 7.67 (d, J=7.7, 1H, —NH); 7.47 (d, J=2.4, 1H); 7.40 (dd, J=8.6, 2.4, 1H); 7.09 (d; J=8.6, 1H); 4.06 (m, 1H); 3.86 (d, J=6.9, 2H); 3.82 (s, 2H); 3.79 (m, 1H); 3.31 (s, 3H); 2.95 (sept, J=6.9, 1H); 2.78 (s, 3H); 1.86-1.61 (m, 8H); 1.22 (d, J=6.9, 6H); 0.94 (m, 1H); 0.36 (m, 2H); 0.24 (m, 2H).

Example E163

4-[5-Acetyl-2-(cyclopropylmethoxy)phenyl-]-N-(1-acetylpiperidin-4-yl)-6-methyl-5H-pyrrolo[3,2-d]pyrimidine-7-carboxamide Starting from 4-[5-acetyl-2-(cyclopropylmethoxy)phenyl]-6-methyl-N-(piperidin-4-yl)-5H-pyrrolo[3,2-d]pyrimidine-7-carboxamide hydrochloride (example D.f55) and commercially available acetyl chloride the title compound is obtained as colorless solid.

MS (ESI): m/z=490 (MH$^+$, 100%).

$^1$H-NMR (400 MHz, DMSO-d$_6$): 11.88 (s, 1H, —NH); 8.99 (s, 1H); 8.92 (d, J=7.7, 1H, —NH); 8.21 (d, J=2.3, 1H); 8.15 (dd, J=8.8, 2.3, 1H); 7.30 (d, J=8.8, 1H); 4.22-4.07 (m, 2H); 4.01 (d, J=7.1, 2H); 3.79 (m, 1H); 3.28 (m, 1H); 2.95 (m, 1H); 2.79 (s, 3H); 2.58 (s, 3H); 2.04 (s, 3H); 1.96 (m, 2H); 1.55 (m, 1H); 1.40 (m, 1H); 0.99 (m, 1H); 0.39 (m, 2H); 0.28 (m, 2H).

Example E164

4-[5-Acetyl-2-(cyclopropylmethoxy)phenyl]-6-methyl-N-(1-propanoylpiperidin-4-yl)-5H-pyrrolo[3,2-d]pyrimidine-7-carboxamide Starting from 4-[5-acetyl-2-(cyclopropylmethoxy)phenyl]-6-methyl-N-(piperidin-4-yl)-5H-pyrrolo[3,2-d]pyrimidine-7-carboxamide hydrochloride (example D.f55) and commercially available propionyl chloride the title compound is obtained as colorless solid.

MS (ESI): m/z=504 (MH$^+$, 100%).

$^1$H-NMR (400 MHz, DMSO-d$_6$): 11.88 (s, 1H, —NH); 8.99 (s, 1H); 8.81 (d, J=7.7, 1H, —NH); 8.21 (d, J=2.2, 1H); 8.15 (dd, J=8.8, 2.2, 1H); 7.30 (d, J=8.8, 1H); 4.20 (m, 1H); 4.13 (m, 1H); 4.01 (d, J=7.0, 2H); 3.82 (m, 1H); 3.27 (m, 1H); 2.96 (m, 1H); 2.79 (s, 3H); 2.58 (s, 3H); 2.36 (dqu, J=7.5, 1.3, 2H); 1.96 (m, 2H); 1.53 (m, 1H); 1.39 (m, 1H); 1.01 (t, J=7.5, 3H); 0.99 (m, 1H); 0.39 (m, 2H); 0.28 (m, 2H).

Example E165

4-[5-Acetyl-2-(cyclopropylmethoxy)phenyl]-N-[1-(methoxyacetyl)piperidin-4-yl]-6-methyl-5H-pyrrolo[3,2-d]pyrimidine-7-carboxamide Starting from 4-[5-acetyl-2-(cyclopropylmethoxy)phenyl]-6-methyl-N-(piperidin-4-yl)-5H-pyrrolo[3,2-d]pyrimidine-7-carboxamide hydrochloride (example D.f55) and commercially available methoxyacetyl chloride the title compound is obtained as colorless solid.

MS (ESI): m/z=520 (MH+, 100%).

$^1$H-NMR (400 MHz, DMSO-d$_6$): 11.88 (s, 1H, —NH); 8.99 (s, 1H); 8.81 (d, J=7.7, 1H, —NH); 8.21 (d, J=2.3, 1H); 8.15 (dd, J=8.8, 2.3, 1H); 7.30 (d, J=8.8, 1H); 4.22-4.07 (m, 2H); 4.12 (d, J=3.0, 2H); 4.01 (d, J=7.0, 2H); 3.75 (m, 1H); 3.31 (s, 3H); 3.23 (m, 1H); 2.98 (m, 1H); 2.79 (s, 3H); 2.58 (s, 3H); 1.97 (m, 2H); 1.55 (m, 1H); 1.42 (m, 1H); 0.99 (m, 1H); 0.39 (m, 2H); 0.28 (m, 2H).

Example E166

N-[trans-4-(Acetylamino)cyclohexyl]-4-[5-acetyl-2-(cyclopropylmethoxy)phenyl]-6-methyl-5H-pyrrolo[3,2-d]pyrimidine-7-carboxamide Starting from 4-[5-acetyl-2-(cyclopropylmethoxy)phenyl]-N-(trans-4-aminocyclohexyl)-6-methyl-5H-pyrrolo[3,2-d]pyrimidine-7-carboxamide hydrochloride (example D.f56) and commercially available acetyl chloride the title compound is obtained as colorless solid.

MS (ESI): m/z=504 (MH+, 100%).

$^1$H-NMR (400 MHz, DMSO-d$_6$): 11.23 (br.s, 1H, —NH); 8.97 (s, 1H); 8.65 (d, J=7.7, 1H, —NH); 8.20 (d, J=2.2, 1H); 8.14 (dd, J=8.8, 2.2, 1H); 7.73 (d, J=7.7, 1H, —NH); 7.29 (d, J=8.8, 1H); 4.01 (d, J=7.0, 2H); 3.80 (m, 1H); 3.59 (m, 1H); 2.77 (s, 3H); 2.58 (s, 3H); 2.01 (m, 2H); 1.86 (m, 2H); 1.79 (s, 3H); 1.35 (m, 4H); 0.99 (m, 1H); 0.39 (m, 2H); 0.27 (m, 2H).

Example E167

4-[5-Acetyl-2-(cyclopropylmethoxy)phenyl]-6-methyl-N-[trans-4-(propanoylamino)cyclohexyl]-5H-pyrrolo[3,2-d]pyrimidine-7-carboxamide Starting from 4-[5-acetyl-2-(cyclopropylmethoxy)phenyl]-N-(trans-4-aminocyclohexyl)-6-methyl-5H-pyrrolo[3,2-d]pyrimidine-7-carboxamide hydrochloride (example D.f56) and commercially available propionyl chloride the title compound is obtained as colorless solid.

MS (ESI): m/z=518 (MH+, 100%).

$^1$H-NMR (400 MHz, DMSO-d$_6$): 11.78 (br.s, 1H, —NH); 8.98 (s, 1H); 8.65 (d, J=7.7, 1H, —NH); 8.20 (d, J=2.3, 1H); 8.14 (dd, J=8.9, 2.3, 1H); 7.62 (d, J=7.7, 1H, —NH); 7.29 (d, J=8.9, 1H); 4.01 (d, J=7.0, 2H); 3.80 (m, 1H); 3.59 (m, 1H); 2.78 (s, 3H); 2.58 (s, 3H); 2.05 (qu, J=7.7, 2H); 2.01 (m, 2H); 1.86 (m, 2H); 1.36 (m, 4H); 0.99 (t, J=7.7, 3H & m, 1H); 0.39 (m, 2H); 0.27 (m, 2H).

Example E168

4-[5-Acetyl-2-(cyclopropylmethoxy)phenyl]-N-{trans-4-[(methoxyacetyl)amino]cyclohexyl}-6-methyl-5H-pyrrolo[3,2-d]pyrimidine-7-carboxamide Starting from 4-[5-acetyl-2-(cyclopropylmethoxy)phenyl]-N-(trans-4-aminocyclohexyl)-6-methyl-5H-pyrrolo[3,2-d]pyrimidine-7-carboxamide hydrochloride (example D.f56) and commercially available methoxy-acetyl chloride the title compound is obtained as colorless solid.

MS (ESI): m/z=534 (MH+, 100%).

$^1$H-NMR (400 MHz, DMSO-d$_6$): 11.84 (br.s, 1H, —NH); 8.99 (s, 1H); 8.64 (d, J=7.8, 1H, —NH); 8.21 (d, J=2.3, 1H); 8.14 (dd, J=8.8, 2.3, 1H); 7.57 (d, J=8.2, 1H, —NH); 7.30 (d, J=8.8, 1H); 4.01 (d, J=7.0, 2H); 3.81 (m, 1H); 3.78 (s, 2H); 3.70 (m, 1H); 3.31 (s, 3H); 2.78 (s, 3H); 2.58 (s, 3H); 2.02 (m, 2H); 1.82 (m, 2H); 1.44 (m, 4H); 0.99 (m, 1H); 0.39 (m, 2H); 0.28 (m, 2H).

Example E169

N-(1-Acetylpiperidin-4-yl)-4-[2-(cyclopropylmethoxy)-5-methylphenyl]-2,6-dimethyl-5H-pyrrolo[3,2-d]pyrimidine-7-carboxamide Starting from 4-[2-(cyclopropylmethoxy)-5-methylphenyl]-2,6-dimethyl-N-(piperidin-4-yl)-5H-pyrrolo[3,2-d]pyrimidine-7-carboxamide hydrochloride (example D.f57) and commercially available acetyl chloride the title compound is obtained as colorless solid.

MS (ESI): m/z=476 (MH+, 100%)

$^1$H-NMR (300 MHz, DMSO-d$_6$): 11.59 (s, 1H, —NH); 9.05 (d, J=7.7, 1H, —NH); 7.39 (d, J=1.8, 1H); 7.31 (dd, J=8.4, 1.8, 1H); 7.04 (d, J=8.4, 1H); 4.18-4.03 (m, 2H); 3.85 (d, J=6.9, 2H); 3.77 (m, 1H); 3.40-3.23 (m, 1H); 3.06 (m, 1H); 2.75 (s, 3H); 2.72 (s, 3H); 2.33 (s, 3H); 2.04 (s, 3H); 1.95 (m, 2H); 1.63-1.33 (m, 2H); 0.93 (m, 1H); 0.36 (m, 2H); 0.22 (m, 2H).

Example E170

4-[2-(Cyclopropylmethoxy)-5-methylphenyl]-2,6-dimethyl-N-(1-propanoylpiperidin-4-yl)-5H-pyrrolo[3,2-d]pyrimidine-7-carboxamide Starting from 4-[2-(cyclopropylmethoxy)-5-methylphenyl]-2,6-dimethyl-N-(piperidin-4-yl)-5H-pyrrolo[3,2-d]pyrimidine-7-carboxamide hydrochloride (example D.f57) and commercially available propionyl chloride the title compound is obtained as colorless solid.

MS (ESI): m/z=490 (MH+, 100%)

$^1$H-NMR (300 MHz, DMSO-d$_6$): 11.58 (s, 1H, —NH); 9.05 (d, J=7.7, 1H, —NH); 7.39 (d, J=2.0, 1H); 7.31 (dd, J=8.4, 2.0, 1H); 7.04 (d, J=8.4, 1H); 4.18-4.03 (m, 2H); 3.85 (d, J=6.9, 2H); 3.77 (m, 1H); 3.37-3.22 (m, 1H); 3.07 (m, 1H); 2.75 (s, 3H); 2.72 (s, 3H); 2.36 (qu, J=7.3, 2H); 2.33 (s, 3H); 1.95 (m, 2H); 1.60-1.34 (m, 2H); 1.01 (t, J=7.3, 3H); 0.92 (m, 1H); 0.35 (m, 2H); 0.22 (m, 2H).

Example E171

4-[2-(Cyclopropylmethoxy)-5-methylphenyl]-N-[1-(methoxyacetyl)piperidin-4-yl]-2,6-dimethyl-5H-pyrrolo[3,2-d]pyrimidine-7-carboxamide Starting from 4-[2-(cyclopropylmethoxy)-5-methylphenyl]-2,6-dimethyl-N-(piperidin-4-yl)-5H-pyrrolo[3,2-d]pyrimidine-7-carboxamide hydrochloride (example D.f57) and commercially available available methoxy-acetyl chloride the title compound is obtained as colorless solid.

MS (ESI): m/z=506 (MH+, 100%)

$^1$H-NMR (300 MHz, DMSO-d$_6$): 11.58 (s, 1H, —NH); 9.05 (d, J=7.7, 1H, —NH); 7.39 (d, J=1.8, 1H); 7.31 (dd, J=8.6, 1.8, 1H); 7.04 (d, J=8.6, 1H); 4.20-4.02 (m, 2H); 4.12 (d, J=0.9, 2H); 3.85 (d, J=6.9, 2H); 3.72 (m, 1H); 3.31 (s, 3H); 3.27 (m, 1H); 3.09 (m, 1H); 2.75 (s, 3H); 2.72 (s, 3H); 2.33 (s, 3H); 1.97 (m, 2H); 1.63-1.35 (m, 2H); 0.93 (m, 1H); 0.35 (m, 2H); 0.21 (m, 2H).

Example E172

N-(1-Acetylpiperidin-4-yl)-4-[2-(cyclopropyl-methoxy)-5-fluoro-4-methoxyphenyl]-2,6-dimethyl-5H-pyrrolo[3,2-d]pyrimidine-7-carboxamide Starting from 4-[2-(cyclopropylmethoxy)-5-fluoro-4-methoxyphenyl]-2,6-dimethyl-N-(piperidin-4-yl)-5H-pyrrolo[3,2-d]pyrimidine-7-carboxamide hydrochloride (example D.f58) and commercially available available acetyl chloride the title compound is obtained as colorless solid.

MS (ESI): m/z=510 (MH$^+$, 100%)
$^1$H-NMR (300 MHz, DMSO-d$_6$): 11.56 (s, 1H, —NH); 9.04 (d, J=7.7, 1H, —NH); 7.43 (d, J=11.9, 1H); 6.91 (d, J=7.3, 1H); 4.18-4.03 (m, 2H); 3.96 (s, 3H); 3.93 (d, J=6.9, 2H); 3.81-3.70 (m, 1H); 3.38-3.25 (m, 1H); 3.06 (m, 1H); 2.76 (s, 3H); 2.71 (s, 3H); 2.04 (s, 3H); 1.94 (m, 2H); 1.62-1.33 (m, 2H); 0.95 (m, 1H); 0.39 (m, 2H); 0.25 (m, 2H).

Example E173

N-(1-Acetylpiperidin-4-yl)-4-[2-(cyclopropyl-methoxy)-4-fluoro-5-methoxyphenyl]-2,6-dimethyl-5H-pyrrolo[3,2-d]pyrimidine-7-carboxamide Starting from 4-[2-(cyclopropylmethoxy)-4-fluoro-5-methoxyphenyl]-2,6-dimethyl-N-(piperidin-4-yl)-5H-pyrrolo[3,2-d]pyrimidine-7-carboxamide hydrochloride (example D.f59) and commercially available available acetyl chloride the title compound is obtained as colorless solid.

MS (ESI): m/z=510 (MH$^+$, 100%).
$^1$H-NMR (300 MHz, DMSO-d$_6$): 11.59 (br.s, 1H, —NH); 9.02 (d, J=7.7, 1H, —NH); 7.33 (d, J=9.9, 1H); 7.16 (d, J=13.5, 1H); 4.19-4.03 (m, 2H); 3.84 (s, 3H); 3.82 (d, J=6.8, 2H); 3.76 (m, 2H); 3.34 (m, 1H); 3.05 (m, 1H); 2.75 (s, 3H); 2.73 (s, 3H); 2.04 (s, 3H); 1.95 (m, 2H); 1.54 (m, 1H); 1.41 (m, 1H); 0.92 (m, 1H); 0.35 (m, 2H); 0.19 (m, 2H).

Example E174

4-[2-(Cyclopropylmethoxy)-4-fluoro-5-methoxyphenyl]-2,6-dimethyl-N-(1-propanoylpiperidin-4-yl)-5H-pyrrolo[3,2-d]pyrimidine-7-carboxamide Starting from 4-[2-(cyclopropylmethoxy)-4-fluoro-5-methoxyphenyl]-2,6-dimethyl-N-(piperidin-4-yl)-5H-pyrrolo[3,2-d]pyrimidine-7-carboxamide hydrochloride (example D.f59) and commercially available available propionyl chloride the title compound is obtained as colorless solid.

MS (ESI): m/z=524 (MH$^+$, 100%).
$^1$H-NMR (300 MHz, DMSO-d$_6$): 11.60 (br.s, 1H, —NH); 9.02 (d, J=7.7, 1H, —NH); 7.33 (d, J=9.9, 1H); 7.16 (d, J=13.3, 1H); 4.19-4.03 (m, 2H); 3.84 (s, 3H); 3.83 (d, J=6.8, 2H); 3.77 (m, 2H); 3.28 (m, 1H); 3.07 (m, 1H); 2.75 (s, 3H); 2.73 (s, 3H); 2.36 (qu, J=7.3, 2H); 1.95 (m, 2H); 1.52 (m, 1H); 1.41 (m, 1H); 1.01 (t, J=7.3, 3H); 0.92 (m, 1H); 0.35 (m, 2H); 0.19 (m, 2H).

Example E175

4-[2-(Cyclopropylmethoxy)-4-fluoro-5-methoxyphenyl]-N-[1-(methoxyacetyl)piperidin-4-yl]-2,6-dimethyl-5H-pyrrolo[3,2-d]pyrimidine-7-carboxamide Starting from 4-[2-(cyclopropylmethoxy)-4-fluoro-5-methoxyphenyl]-2,6-dimethyl-N-(piperidin-4-yl)-5H-pyrrolo[3,2-d]pyrimidine-7-carboxamide hydrochloride (example D.f59) and commercially available available methoxyacetyl chloride the title compound is obtained as colorless solid.

MS (ESI): m/z=540 (MH$^+$, 100%).
$^1$H-NMR (300 MHz, DMSO-d$_6$): 11.60 (br.s, 1H, —NH); 9.02 (d, J=7.7, 1H, —NH); 7.33 (d, J=9.9, 1H); 7.16 (d, J=13.5, 1H); 4.20-4.01 (m, 2H); 4.12 (s, 2H); 3.84 (s, 3H); 3.83 (d, J=6.8, 2H); 3.72 (m, 1H); 3.31 (s, 3H); 3.24 (m, 1H); 3.08 (m, 1H); 2.75 (s, 3H); 2.73 (s, 3H); 1.96 (m, 2H); 1.63-1.33 (m, 2H); 0.92 (m, 1H); 0.35 (m, 2H); 0.20 (m, 2H).

Example E176

4-[2-(Cyclopropylmethoxy)-5-methylphenyl]-N-[(1S,2S)-2-hydroxycyclopentyl]-6-methyl-5H-pyrrolo[3,2-d]pyrimidine-7-carboxamide Starting from 4-[2-(cyclopropylmethoxy)-5-methylphenyl]-N-[(1S,2S)-2-hydroxycyclopentyl]-6-methyl-5-{[2-(trimethylsilyl)ethoxy]methyl}-5H-pyrrolo[3,2-d]pyrimidine-7-carboxamide (example D.d60) the title compound is obtained as colorless solid.

MS (ESI): m/z=421 (MH$^+$, 100%).
$^1$H-NMR (300 MHz, DMSO-d$_6$): 11.72 (s, 1H, —NH); 8.94 (s, 1H); 8.78 (d, J=7.1, 1H, —NH); 7.44 (d, J=2.2, 1H); 7.33 (dd, J=8.6, 2.2, 1H); 7.06 (d, J=8.6, 1H); 4.92 (d, J=4.0, 1H; —OH); 4.07 (m, 1H); 3.99 (m, 1H); 3.86 (d, J=6.9, 2H); 2.78 (s, 3H); 2.33 (s, 3H); 2.12 (m, 1H); 1.91 (m, 1H); 1.74 (m, 2H); 1.53 (m, 2H); 0.94 (m, 1H); 0.36 (m, 2H); 0.23 (m, 2H).

Example E177

4-[2-(Cyclopropylmethoxy)-5-methylphenyl]-N-[(1S,2R)-2-hydroxycyclopentyl]-6-methyl-5H-pyrrolo[3,2-d]pyrimidine-7-carboxamide Starting from 4-[2-(cyclopropylmethoxy)-5-methylphenyl]-N-[(1S,2R)-2-hydroxycyclopentyl]-6-methyl-5-{[2-(trimethylsilyl)ethoxy]methyl}-5H-pyrrolo[3,2-d]pyrimidine-7-carboxamide (example D.d61) the title compound is obtained as colorless solid.

MS (ESI): m/z=421 (MH$^+$, 100%).
$^1$H-NMR (300 MHz, DMSO-d$_6$): 11.66 (s, 1H, —NH); 8.99 (d, J=7.1, 1H, —NH); 8.92 (s, 1H); 7.43 (d, J=2.0, 1H); 7.32 (dd, J=8.6, 2.0, 1H); 7.06 (d, J=8.6, 1H); 4.882 (d, J=4.2, 1H; —OH); 4.16 (m, 1H); 4.02 (m, 1H); 3.86 (d, J=6.9, 2H); 2.79 (s, 3H); 2.33 (s, 3H); 2.01-1.73 (m, 3H); 1.70-1.46 (m, 3H); 0.94 (m, 1H); 0.36 (m, 2H); 0.22 (m, 2H).

Example E178

4-[2-(Cyclopropylmethoxy)-5-methylphenyl]-N-[(1R,2R)-2-hydroxycyclopentyl]-6-methyl-5H-pyrrolo[3,2-d]pyrimidine-7-carboxamide Starting from 4-[2-(cyclopropylmethoxy)-5-methylphenyl]-N-[(1R,2R)-2-hydroxycyclopentyl]-6-methyl-5-{[2-(trimethylsilyl)ethoxy]methyl}-5H-pyrrolo[3,2-d]pyrimidine-7-carboxamide (example D.d62) the title compound is obtained as colorless solid.

MS (ESI): m/z=421 (MH$^+$, 100%).
$^1$H-NMR (300 MHz, DMSO-d$_6$): 11.72 (s, 1H, —NH); 8.93 (s, 1H); 8.77 (d, J=7.1, 1H, —NH); 7.44 (d, J=2.2, 1H); 7.32 (dd, J=8.6, 2.2, 1H); 7.05 (d, J=8.6, 1H); 4.92 (d, J=4.0, 1H; —OH); 4.07 (m, 1H); 3.98 (m, 1H); 3.85 (d, J=6.9, 2H);

2.78 (s, 3H); 2.33 (s, 3H); 2.11 (m, 1H); 1.91 (m, 1H); 1.74 (m, 2H); 1.53 (m, 2H); 0.94 (m, 1H); 0.35 (m, 2H); 0.22 (m, 2H).

Example E179

N-[(3R)-1-Acetylpyrrolidin-3-yl]-4-[2-(cyclopropylmethoxy)-4-fluoro-5-methoxyphenyl]-6-methyl-5H-pyrrolo[3,2-d]pyrimidine-7-carboxamide MS (ESI): m/z=482 (MH$^+$, 100%). 1H-NMR (300 MHz, DMSO-d$_6$): 11.69 (s, 1H, —NH); 8.93 (s, 1H); [8.92 (d, J=6.9), 8.89 (d, J=6.7), 1H, —NH]; 7.39 (d, J=9.9, 1H); 7.18 (d, J=13.5, 1H); [4.58 (m), 4.49 (m), 1H]; 3.84 (d, J=6.8, 2H & s, 3H); 3.68-3.57 (m, 1H); 3.55-3.35 (m, 2H); 3.32-3.21 (m, 1H); 2.77 (s, 3H); 2.34-2.16 (m, 1H); [2.04 (m), 1.91 (m), 1H]; [1.98 (s), 1.96 (s), 3H]; 0.93 (m, 1H); 0.35 (m, 2H); 0.20 (m, 2H).

Example E180

4-[2-(Cyclopropylmethoxy)-4-fluoro-5-methoxyphenyl]-6-methyl-N-[(3R)-1-propionylpyrrolidin-3-yl]-5H-pyrrolo[3,2-d]pyrimidine-7-carboxamide MS (ESI): m/z=496 (MH$^+$, 100%). 1H-NMR (300 MHz, DMSO-d$_6$): 11.70 (s, 1H, —NH); 8.93 (s, 1H); [8.92 (d, J=6.9), 8.89 (d, J=6.9), 1H, —NH]; 7.39 (d, J=9.9, 1H); 7.18 (d, J=13.5, 1H); [4.58 (m), 4.49 (m), 1H]; 3.84 (d, J=6.9, 2H & s, 3H); 3.69-3.57 (m, 1H); 3.55-3.42 (m, 1H); 3.40-3.22 (m, 2H); 2.78 (s, 3H); 2.34-2.15 (m, 1H); [2.29 (qu, J=7.4), 2.25 (qu, J=7.4), 2H]; [2.04 (m), 1.91 (m), 1H]; [1.01 (t, J=7.4), 0.99 (t, J=7.4), 3H]; 0.93 (m, 1H); 0.36 (m, 2H); 0.20 (m, 2H).

Example E181

4-[2-(Cyclopropylmethoxy)-4-fluoro-5-methoxyphenyl]-N-[(3R)-1-(methoxyacetyl)pyrrolidin-3-yl]-6-methyl-5H-pyrrolo[3,2-d]pyrimidine-7-carboxamide MS (ESI): m/z=512 (MH$^+$, 100%).
1H-NMR (300 MHz, DMSO-d$_6$): 11.78 (s, 1H, —NH); 8.94 (s, 1H); [8.92 (d, J=7.4), 8.90 (d, J=7.9, 1H, —NH); 7.39 (d, J=9.7, 1H); 7.18 (d, J=13.4, 1H); [4.58 (m), 4.49 (m), 1H]; [4.06 (d, J=4.2), 4.01 (d, J=1.3), 2H]; 3.84 (d, J=6.9, 2H & s, 3H); [3.80 (m), 3.68 (m), 1H]; 3.62-3.43 (m, 2H); 3.36 (m, 1H); 3.32 (s, 3H); 2.78 (s, 3H); 2.33-2.15 (m, 1H); [2.04 (m), 1.90 (m), 1H]; 0.92 (m, 1H); 0.36 (m, 2H); 0.20 (m, 2H).

Example E182

Ethyl (3R)-3-[({4-[2-(cyclopropylmethoxy)-4-fluoro-5-methoxyphenyl]-6-methyl-5H-pyrrolo[3,2-d]pyrimidin-7-yl}carbonyl)amino]pyrrolidine-1-carboxylate MS (ESI): m/z=512 (MH$^+$, 100%). 1H-NMR (300 MHz, DMSO-d$_6$): 11.80 (s, 1H, —NH); 8.95 (s, 1H); 8.91 (d, J=6.7, 1H, —NH); 7.40 (d, J=9.9, 1H); 7.19 (d, J=13.5, 1H); 4.51 (m, 1H); 4.05 (qu, J=6.9, 2H); 3.84 (d, J=6.9, 2H & s, 3H); 3.66 (m, 1H); 3.47 (m, 2H); 3.27 (m, 1H); 2.78 (s, 3H); 2.23 (m, 1H); 1.91 (m, 1H); 1.19 (t, J=6.9, 3H); 0.93 (m, 1H); 0.36 (m, 2H); 0.21 (m, 2H).

Example E183

N-[(3R*,4R*)-1-Acetyl-4-hydroxypyrrolidin-3-yl]-4-[2-(cyclopropylmethoxy)-4-fluoro-5-methoxyphenyl]-6-methyl-5H-pyrrolo[3,2-d]pyrimidine-7-carboxamide MS (ESI): m/z=498 (MH$^+$, 100%).
$^1$H-NMR (300 MHz, DMSO-d$_6$): 11.75 (br.s, 1H, —NH); 8.93 (s, 1H); [8.88 (d, J=7.1), 8.82 (d, J=6.6), 1H, —NH]; 7.39 (d, J=9.9, 1H); 7.18 (d, J=13.5, 1H); [5.56 (d, J=3.8), 5.49 (d, J=4.0), 1H, —OH]; 4.39-4.16 (m, 2H); 3.91 (m, 1H); 3.83 (d, J=6.9, 2H & s, 3H); 3.73 (m, 1H); 3.47-3.22 (m, 2H); 2.78 (s, 3H); [1.99 (s), 1.98 (s), 3H]; 0.92 (m, 1H); 0.36 (m, 2H); 0.21 (m, 2H).

Example E184

4-[2-(Cyclopropylmethoxy)-4-fluoro-5-methoxyphenyl]-N-[(3R*,4R*)-4-hydroxy-1-propionylpyrrolidin-3-yl]-6-methyl-5H-pyrrolo[3,2-d]pyrimidine-7-carboxamide MS (ESI): m/z=512 (MH$^+$, 100%).
$^1$H-NMR (300 MHz, DMSO-d$_6$): 11.69 (br.s, 1H, —NH); 8.90 (s, 1H); [8.87 (d, J=7.1), 8.82 (d, J=6.6), 1H, —NH]; 7.38 (d, J=9.9, 1H); 7.18 (d, J=13.5, 1H); [5.56 (d, J=3.5), 5.47 (d, J=3.8), 1H, —OH]; 4.39-4.14 (m, 2H); 3.88 (m, 1H); 3.84 (d, J=6.9, 2H & s, 3H); 3.72 (m, 1H); 3.63-3.20 (m, 2H); 2.78 (s, 3H); 2.28 (m, 2H); [1.03 (t, J=7.7), 1.01 (t, J=7.5), 3H]; 0.92 (m, 1H); 0.36 (m, 2H); 0.20 (m, 2H).

Example E185

4-[2-(Cyclopropylmethoxy)-4-fluoro-5-methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide MS (ESI): m/z=528 (MH$^+$, 100%)

$^1$H-NMR (300 MHz, DMSO-d$_6$): 11.68 (br.s, 1H, —NH); [8.90 (s), 8.89 (s), 1H]; [8.86 (d, J=7.1), 8.82 (d, J=6.8), 1H, —NH]; 7.38 (d, J=9.9, 1H); 7.18 (d, J=13.3, 1H); [5.57 (d, J=2.4), 5.50 (d, J=3.7), 1H, —OH]; 4.40-4.15 (m, 2H); [4.06 (d, J=3.3), 4.04 (s), 2H]; 3.86 (m, 1H); 3.84 (d, J=6.8, 2H & s, 3H); 3.73 (m, 1H); 3.65-3.22 (m, 2H); [3.33 (s), 3.31 (s), 3H]; 2.77 (s, 3H); 0.92 (m, 1H); 0.36 (m, 2H); 0.20 (m, 2H).

Example E186

N-[(3R)-1-Acetylpyrrolidin-3-yl]-4-[2-(cyclopropylmethoxy)-5-fluoro-4-methoxyphenyl]-6-methyl-5H-pyrrolo[3,2-d]pyrimidine-7-carboxamide MS (ESI): m/z=482 (MH$^+$, 100%).

Example E187

4-[2-(Cyclopropylmethoxy)-5-fluoro-4-methoxyphenyl]-6-methyl-N-[(3R)-1-propionylpyrrolidin-3-yl]-5H-pyrrolo[3,2-d]pyrimidine-7-carboxamide MS (ESI): m/z=496 (MH$^+$, 100%).

Example E188

4-[2-(Cyclopropylmethoxy)-5-fluoro-4-methoxyphenyl]-N-[(3R)-1-(methoxyacetyl)pyrrolidin-3-yl]-6-methyl-5H-pyrrolo[3,2-d]pyrimidine-7-carboxamide MS (ESI): m/z=512 (MH$^+$, 100%).

Example E189

N-[(3R*,4R*)-1-Acetyl-4-hydroxypyrrolidin-3-yl]-4-[2-(cyclopropylmethoxy)-5-fluoro-4-methoxyphenyl]-6-methyl-5H-pyrrolo[3,2-d]pyrimidine-7-carboxamide MS (ESI): m/z=498 (MH$^+$, 100%).

Example E190

4-[2-(Cyclopropylmethoxy)-5-fluoro-4-methoxyphenyl]-N-[(3R*,4R*)-4-hydroxy-1-propionylpyrrolidin-3-yl]-6-methyl-5H-pyrrolo[3,2-d]pyrimidine-7-carboxamide MS (ESI): m/z=512 (MH$^+$, 100%).

Example E191

4-[2-(Cyclopropylmethoxy)-5-fluoro-4-methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide MS (ESI): m/z=528 (MH$^+$, 100%).

Example E192

N-[(3R*,4R*)-1-Acetyl-4-hydroxypyrrolidin-3-yl]-4-[2-(cyclopropylmethoxy)-5-methoxyphenyl]-6-methyl-5H-pyrrolo[3,2-d]pyrimidine-7-carboxamide MS (ESI): m/z=480 (MH$^+$, 100%).

Example E193

4-[2-(Cyclopropylmethoxy)-5-methoxyphenyl]-N-[(3R*,4R*)-4-hydroxy-1-propionylpyrrolidin-3-yl]-6-methyl-5H-pyrrolo[3,2-d]pyrimidine-7-carboxamide MS (ESI): m/z=494 (MH$^+$, 100%).

Example E194

4-[2-(Cyclopropylmethoxy)-5-methoxyphenyl]-N-[(3R*,4R*)-4-hydroxy-1-(methoxyacetyl)pyrrolidin-3-yl]-6-methyl-5H-pyrrolo[3,2-d]pyrimidine-7-carboxamide MS (ESI): m/z=510 (MH$^+$, 100%).

Example E195

N-[(1R*,3S*,4S*)-3-(Acetylamino)-4-methylcyclopentyl]-4-[2-(cyclopropylmethoxy)-5-(difluoromethyl)phenyl]-6-methyl-5H-pyrrolo[3,2-d]pyrimidine-7-carboxamide Starting from N-[(1R*,3S*,4S*)-3-amino-4-methylcyclopentyl]-4-[2-(cyclopropylmethoxy)-5-(difluoromethyl)phenyl]-6-methyl-5H-pyrrolo[3,2-d]pyrimidine-7-carboxamide hydrochloride (example D.f68) and commercially available acetyl chloride the title compound is obtained as colorless solid.

HR-MS (ESI): m/z=512.2463 ([MH]$^+$, $C_{27}H_{32}F_2N_5O_3^+$, calc. 512.2468).

Example E196

4-[2-(Cyclopropylmethoxy)-5-(difluoromethyl)phenyl]-6-methyl-N-[(1R*,3S*,4S*)-3-methyl-4-(propanoylamino)cyclopentyl]-5H-pyrrolo[3,2-d]pyrimidine-7-carboxamide Starting from N-[(1R*,3S*,4S*)-3-amino-4-methylcyclopentyl]-4-[2-(cyclopropylmethoxy)-5-(difluoromethyl)phenyl]-6-methyl-5H-pyrrolo[3,2-d]pyrimidine-7-carboxamide hydrochloride (example D.f68) and commercially available propionyl chloride the title compound is obtained as colorless solid.

HR-MS (ESI): m/z=526.2624 ([MH]$^+$, $C_{28}H_{34}F_2N_5O_3^+$, calc. 526.2624).

Example E197

4-[2-(Cyclopropylmethoxy)-5-(difluoromethyl)phenyl]-N-{(1R*,3S*,4S*)-3-[(methoxyacetyl)amino]-4-methylcyclopentyl}-6-methyl-5H-pyrrolo[3,2-d]pyrimidine-7-carboxamide Starting from N-[(1R*,3S*,4S*)-3-amino-4-methylcyclopentyl]-4-[2-(cyclopropylmethoxy)-5-(difluoromethyl)phenyl]-6-methyl-5H-pyrrolo[3,2-d]pyrimidine-7-carboxamide hydrochloride (example D.f68) and commercially available methoxy-acetyl chloride the title compound is obtained as colorless solid.

HR-MS (ESI): m/z=542.2570 ([MH]$^+$, $C_{28}H_{34}F_2N_5O_4^+$, calc. 542.2573).

Example E198

N-[(1R*,2R*,4S*)-4-(acetylamino)-2-methylcyclopentyl]-4-[2-(cyclopropylmethoxy)-5-(difluoromethyl)phenyl]-6-methyl-5H-pyrrolo[3,2-d]pyrimidine-7-carboxamide Starting from N-[(1R*,2R*,4S*)-4-amino-2-methylcyclopentyl]-4-[2-(cyclopropylmethoxy)-5-(difluoromethyl)phenyl]-6-methyl-5H-pyrrolo[3,2-d]pyrimidine-7-carboxamide (example D.f69) and commercially available acetyl chloride the title compound is obtained as colorless solid.

HR-MS (ESI): m/z=512.2475 VFW, $C_{27}H_{32}F_2N_5O_3^+$, calc. 512.2468).

Example E199

4-[2-(Cyclopropylmethoxy)-5-(difluoromethyl)phenyl]-6-methyl-N-[(1R*,2R*,4S*)-2-methyl-4-(propanoylamino)cyclopentyl]-5H-pyrrolo[3,2-d]pyrimidine-7-carboxamide Starting from N-[(1R*,2R*,4S*)-4-amino-2-methylcyclopentyl]-4-[2-(cyclopropylmethoxy)-5-(difluoromethyl)phenyl]-6-methyl-5H-pyrrolo[3,2-d]pyrimidine-7-carboxamide (example D.f69) and commercially available propionyl chloride the title compound is obtained as colorless solid.
HR-MS (ESI): m/z=526.2622 ([MH]$^+$, $C_{28}H_{34}F_2N_5O_3^+$, calc. 526.2624).

Example E200

4-[2-(Cyclopropylmethoxy)-5-(difluoromethyl)phenyl]-N-{(1R*,2R*,4S*)-4-[(methoxyacetyl)amino]-2-methylcyclopentyl}-6-methyl-5H-pyrrolo[3,2-d]pyrimidine-7-carboxamide Starting from N-[(1R*,2R*,4S*)-4-amino-2-methylcyclopentyl]-4-[2-(cyclopropylmethoxy)-5-(difluoromethyl)phenyl]-6-methyl-5H-pyrrolo[3,2-d]pyrimidine-7-carboxamide (example D.f69) and commercially available methoxy-acetyl chloride the title compound is obtained as colorless solid.
HR-MS (ESI): m/z=542.2575 ([MH]$^+$, $C_{28}H_{34}F_2N_5O_4^+$, calc. 542.2573).

Example E201

N-[(1S*,3S*,4S*)-3-(Acetylamino)-4-fluorocyclopentyl]-4-[2-(cyclopropylmethoxy)-5-(difluoromethyl)phenyl]-6-methyl-5H-pyrrolo[3,2-d]pyrimidine-7-carboxamide Starting from N-[(1S*,3S*,4S*)-3-amino-4-fluorocyclopentyl]-4-[2-(cyclopropylmethoxy)-5-(difluoromethyl)phenyl]-6-methyl-5H-pyrrolo[3,2-d]pyrimidine-7-carboxamide hydrochloride (example D.f70) and commercially available acetyl chloride the title compound is obtained as colorless solid.
HR-MS (ESI): m/z=516.2215 ([MH]$^+$, $C_{26}H_{29}F_3N_5O_3^+$, calc. 516.2217).

Example E202

4-[2-(Cyclopropylmethoxy)-5-(difluoromethyl)phenyl]-N-[(1S*,3S*,4S*)-3-fluoro-4-(propanoylamino)cyclopentyl]-6-methyl-5H-pyrrolo[3,2-d]pyrimidine-7-carboxamide Starting from N-[(1S*,3S*,4S*)-3-amino-4-fluorocyclopentyl]-4-[2-(cyclopropylmethoxy)-5-(difluoromethyl)phenyl]-6-methyl-5H-pyrrolo[3,2-d]pyrimidine-7-carboxamide hydrochloride (example D.f70) and commercially available propionyl chloride the title compound is obtained as colorless solid.
HR-MS (ESI): m/z=530.2382 ([MH]$^+$, $C_{27}H_{31}F_3N_5O_3^+$, calc. 530.2374).

Example E203

4-[2-(cyclopropylmethoxy)-5-(difluoromethyl)phenyl]-N-{(1S*,3S*,4S*)-3-fluoro-4-[(methoxyacetyl)amino]cyclopentyl}-6-methyl-5H-pyrrolo[3,2-d]pyrimidine-7-carboxamide Starting from N-[(1S*,3S*,4S*)-3-amino-4-fluorocyclopentyl]-4-[2-(cyclopropylmethoxy)-5-(difluoromethyl)phenyl]-6-methyl-5H-pyrrolo[3,2-d]pyrimidine-7-carboxamide hydrochloride (example D.f70) and commercially available propionyl chloride the title compound is obtained as colorless solid.

HR-MS (ESI): m/z=546.2323 ([MH]$^+$, $C_{27}H_{31}F_3N_5O_4^+$, calc. 0.546.2323).

Example F1

4-[5-(Cyclopropylmethoxy)-1,3-benzodioxol-4-yl]-N-(1-glycoloylpiperidin-4-yl)-6-methyl-5H-pyrrolo[3,2-d]pyrimidine-7-carboxamide 4-[5-(Cyclopropylmethoxy)-1,3-benzodioxol-4-yl]-6-methyl-N-piperidin-4-yl-5H-pyrrolo[3,2-d]pyrimidine-7-carboxamide hydrochloride from example D.f1 (486 mg; 1.0 mmol) is dissolved in dry dichloromethane (5 mL) and DBU (2.5 mmol). Commercially available 2-chloro-2-oxoethyl acetate (1.1 mmol) is syringed into the reaction mixture at ice bath temperature. After addition stirring is continued at ambient temperature overnight. Methanol (1 mL) is added and stirring is continued for two hours. The volatiles are evaporated.
The residue is dissolved in methanol (5 mL), treated with 5M KOH (1.5 mmol) and stirred overnight at ambient temperature. The pH of the reaction mixture is adjusted to 6-7 by addition of 2M citric acid. The volatiles are evaporated. The residue is purified by reversed phase preparative HPLC. The collected product fraction is freeze-dried to yield the title compound as colorless solid.
MS (ESI): m/z=508 (MH$^+$, 100%).
$^1$H-NMR (300 MHz, DMSO-d$_6$): 12.00 (s, 1H, —NH); 8.93 (s, 1H); 8.76 (d, J=7.7, 1H, —NH); 7.00 (d, J=8.6, 1H); 6.56 (d, J=8.6, 1H); 6.00 (s, 2H); 4.50 (t, J=5.3, 1H, —OH); 4.25-4.03 (m, 2H); 4.12 (m, 2H); 3.76 (d, J=6.8, 2H); 3.67 (m, 1H); 3.19 (m, 1H); 3.02 (m, 1H); 2.77 (s, 3H); 1.97 (m, 2H); 1.54 (m, 1H); 1.42 (m, 1H); 0.88 (m, 1H); 0.31 (m, 2H); 0.13 (m, 2H).
The following compounds are prepared analogously to the procedure described in above example

Example F2

4-[5-(Cyclopropylmethoxy)-1,3-benzodioxol-4-yl]-N-{1-[(2S)-2-hydroxypropanoyl]piperidin-4-yl}-6-methyl-5H-pyrrolo[3,2-d]pyrimidine-7-carboxamide Starting from 4-[5-(cyclopropylmethoxy)-1,3-benzodioxol-4-yl]-6-methyl-N-piperidin-4-yl-5H-pyrrolo[3,2-d]pyrimidine-7-carboxamide hydrochloride (example D.f1) and commercially available (2S)-1-chloro-1-oxopropan-2-yl acetate the title compound is obtained as colorless solid.
MS (ESI): m/z=522 (MH$^+$, 100%).
$^1$H-NMR (300 MHz, DMSO-d$_6$): 12.00 (s, 1H, —NH); 8.93 (s, 1H); 8.76 (d, J=7.5, 1H, —NH); 7.01 (d, J=8.6, 1H); 6.56 (d, J=8.6, 1H); 6.00 (s, 2H); 4.86 (d, J=6.8, 1H, —OH); 4.46 (m, 1H); 4.28-4.07 (m, 2H); 3.95 (m, 1H); 3.76 (d, J=6.8, 2H); 3.26 (m, 1H); 2.99 (m, 1H); 2.77 (s, 3H); 1.98 (m, 2H); 1.54 (m, 1H); 1.42 (m, 1H); 1.21 (br.s, 3H); 0.88 (m, 1H); 0.31 (m, 2H); 0.13 (m, 2H).

Example F3

4-[5-(Cyclopropylmethoxy)-1,3-benzodioxol-4-yl]-N-[trans-4-(glycoloylamino)cyclohexyl]-6-methyl-5H-pyrrolo[3,2-d]pyrimidine-7-carboxamide Starting from N-(trans-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride (example D.f2) and commercially available 2-chloro-2-oxoethyl acetate the title compound is obtained as colorless solid.

MS (ESI): m/z=522 (MH$^+$, 100%).

$^1$H-NMR (300 MHz, DMSO-d$_6$): 11.97 (s, 1H, —NH); 8.94 (s, 1H); 8.60 (d, J=7.7, 1H, —NH); 7.47 (d, J=8.2, 1H, —NH); 7.00 (d, J=8.6, 1H); 6.56 (d, J=8.6, 1H); 6.00 (s, 2H); 5.40 (t, J=5.8, 1H, —OH); 3.79 (m, 1H & d, J=5.8, 2H); 3.76 (d, J=6.8, 2H); 3.68 (m, 1H); 2.76 (s, 3H); 2.00 (m, 2H); 1.83 (m, 2H); 1.44 (m, 4H); 0.88 (m, 1H); 0.30 (m, 2H); 0.12 (m, 2H).

Example F4

4-[5-(cyclopropylmethoxy)-1,3-benzodioxol-4-yl]-N-(trans-4-{[(2S)-2-hydroxypropanoyl]amino}cyclohexyl)-6-methyl-5H-pyrrolo[3,2-d]pyrimidine-7-carboxamide Starting from N-(trans-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride (example D.f2) and commercially available (2S)-1-chloro-1-oxopropan-2-yl acetate the title compound is obtained as colorless solid.

MS (ESI): m/z=536 (MH$^+$, 100%).

$^1$H-NMR (300 MHz, DMSO-d$_6$): 11.97 (s, 1H, —NH); 8.94 (s, 1H); 8.59 (d, J=7.7, 1H, —NH); 7.42 (d, J=8.2, 1H, —NH); 7.00 (d, J=8.6, 1H); 6.56 (d, J=8.6, 1H); 6.00 (s, 2H); 5.40 (d, J=5.1, 1H, —OH); 3.94 (m, 1H); 3.80 (m, 1H); 3.76 (d, J=6.8, 2H); 3.63 (m, 1H); 2.76 (s, 3H); 2.00 (m, 2H); 1.83 (m, 2H); 1.42 (m, 4H); 1.21 (d, J=6.8, 3H); 0.88 (m, 1H); 0.30 (m, 2H); 0.12 (m, 2H).

Example F5

4-[5-(Cyclopropylmethoxy)-1,3-benzodioxol-4-yl]-N-[cis-4-(glycoloylamino)cyclohexyl]-6-methyl-5H-pyrrolo[3,2-d]pyrimidine-7-carboxamide Starting from N-(cis-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride (example D.f3) and commercially available 2-chloro-2-oxoethyl acetate the title compound is obtained as colorless solid.

MS (ESI): m/z=522 (MH$^+$, 100%).

$^1$H-NMR (300 MHz, DMSO-d$_6$): 11.97 (s, 1H, —NH); 8.97 (s, 1H); 8.90 (d, J=7.5, 1H, —NH); 7.53 (d, J=7.9, 1H, —NH); 7.01 (d, J=8.6, 1H); 6.56 (d, J=8.6, 1H); 6.00 (s, 2H); 5.32 (t, J=5.8, 1H, —OH); 4.05 (m, 1H); 3.82 (d, J=5.8, 2H); 3.76 (m, 1H & d, J=6.8, 2H); 2.77 (s, 3H); 1.85-1.57 (m, 8H); 0.89 (m, 1H); 0.31 (m, 2H); 0.13 (m, 2H).

Example F6

4-[5-(Cyclopropylmethoxy)-1,3-benzodioxol-4-yl]-N-(cis-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[5-(cyclopropylmethoxy)-1,3-benzodioxol-4-yl]-6-methyl-5H-pyrrolo[3,2-d]pyrimidine-7-carboxamide hydrochloride (example D.f3) and commercially available (2S)-1-chloro-1-oxopropan-2-yl acetate the title compound is obtained as colorless solid.

MS (ESI): m/z=536 (MH$^+$, 100%).

$^1$H-NMR (300 MHz, DMSO-d$_6$): 11.98 (s, 1H, —NH); 8.97 (s, 1H); 8.89 (d, J=7.3, 1H, —NH); 7.48 (d, J=7.9, 1H, —NH); 7.00 (d, J=8.6, 1H); 6.56 (d, J=8.6, 1H); 6.00 (s, 2H); 5.36 (d, J=5.5, 1H, —OH); 4.05 (m, 1H); 3.98 (m, 1H); 3.76 (m, 1H & d, J=6.8, 2H); 2.77 (s, 3H); 1.83-1.57 (m, 8H); 1.22 (d, J=6.8, 3H); 0.89 (m, 1H); 0.31 (m, 2H); 0.13 (m, 2H).

Example F7

4-[5-(Cyclopropylmethoxy)-1,3-benzodioxol-4-yl]-N-[(3R)-1-glycoloylpyrrolidin-3-yl]-6-methyl-5H-pyrrolo[3,2-d]pyrimidine-7-carboxamide Starting from 4-[5-(cyclopropylmethoxy)-1,3-benzodioxol-4-yl]-6-methyl-N-[(3R)-pyrrolidin-3-yl]-5H-pyrrolo[3,2-d]pyrimidine-7-carboxamide hydrochloride (example D.f4) and commercially available 2-chloro-2-oxoethyl acetate the title compound is obtained as colorless solid.

MS (ESI): m/z=494 (MH$^+$, 100%).

$^1$H-NMR (400 MHz, DMSO-d$_6$): 12.03 (s, 1H, —NH); 8.93 (s, 1H); [8.87 (d, J=7.0), 8.84 (d, 6.7), 1H, —NH]; 7.00 (d, J=8.6, 1H); 6.56 (d, J=8.6, 1H); 6.00 (s, 2H); [4.60 (m), 4.49 (m), 1H]; 4.55 (t, J=5.6, 1H, —OH); [4.05 (d, J=5.6), 4.01 (d, J=5.6), 2H]; 3.79-3.69 (m, 1H), 3.76 (d, J=6.7, 2H); 3.61-3.45 (m, 2H); 3.40-3.27 (m, 1H); 2.77 (s, 3H); 2.33-2.16 (m, 1H); [2.04 (m), 1.92 (m), 1H]; 0.88 (m, 1H); 0.31 (m, 2H); 0.12 (m, 2H).

Example F8

4-[5-(Cyclopropylmethoxy)-1,3-benzodioxol-4-yl]-N-{(3R)-1-[(2S)-2-hydroxypropanoyl]pyrrolidin-3-yl}-6-methyl-5H-pyrrolo[3,2-d]pyrimidine-7-carboxamide Starting from 4-[5-(cyclopropylmethoxy)-1,3-benzodioxol-4-yl]-6-methyl-N-[(3R)-pyrrolidin-3-yl]-5H-pyrrolo[3,2-d]pyrimidine-7-carboxamide hydrochloride (example D.f4) and commercially available (2S)-1-chloro-1-oxopropan-2-yl acetate the title compound is obtained as colorless solid.

MS (ESI): m/z=508 (MH$^+$, 100%).

$^1$H-NMR (400 MHz, DMSO-d$_6$): 12.03 (s, 1H, —NH); [8.92 (s), 8.89 (s), 1H]; [8.88 (d, J=6.9), 8.87 (d, 6.6), 1H, —NH]; 7.00 (d, J=8.6, 1H); 6.56 (d, J=8.6, 1H); 6.00 (s, 2H); [4.91 (d, J=6.8), 4.84 (d, J=6.8), 1H, —OH]; [4.58 (m), 4.51 (m), 1H]; [4.33 (m), 4.25 (m), 1H]; [3.84 (m), 3.78 (m), 1H], 3.76 (d, J=6.6, 2H); 3.71-3.53 (m, 2H); 3.46 (m), 3.36 (m), 1H]; 2.77 (s, 3H); [2.27 (m), 2.20 (m), 1H]; [2.04 (m), 1.92 (m), 1H]; [1.23 (d, J=6.5), 1.20 (d, J=6.5), 3H]; 0.88 (m, 1H); 0.31 (m, 2H); 0.12 (m, 2H).

Example F9

4-[5-(Cyclopropylmethoxy)-1,3-benzodioxol-4-yl]-N-[(3R*,4R*)-1-glycoloyl-4-hydroxypyrrolidin-3-yl]-6-methyl-5H-pyrrolo[3,2-d]pyrimidine-7-carboxamide Starting from 4-[5-(cyclopropylmethoxy)-1,3-benzodioxol-4-yl]-N-[(3R*,4R*)-4-hydroxypyrrolidin-3-yl]-6-methyl-5H-pyrrolo[3,2-d]pyrimidine-7-carboxamide hydrochloride (example D.f5) and commercially available 2-chloro-2-oxoethyl acetate the title compound is obtained as colorless solid.

HR-MS (ESI): m/z=510.1963 ([MH]$^+$, $C_{26}H_{30}N_5O_7^+$, calc. 510.1983).

Example F10

Diastereomeric mixture of 4-[5-(Cyclopropyl-methoxy)-1,3-benzodioxol-4-yl]-N-{(3R,4R)-4-hydroxy-1-[(2S)-2-hydroxypropanoyl]pyrrolidin-3-yl}-6-methyl-5H-pyrrolo[3,2-d]pyrimidine-7-carboxamide and 4-[5-(cyclopropylmethoxy)-1,3-benzodioxol-4-yl]N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide Starting from 4-[5-(cyclopropylmethoxy)-1,3-benzodioxol-4-yl]-N-[(3R*,4R*)-4-hydroxypyrrolidin-3-yl]-6-methyl-5H-pyrrolo[3,2-d]pyrimidine-7-carboxamide hydrochloride (example D.f5) and commercially available (2S)-1-chloro-1-oxopropan-2-yl acetate the title compound is obtained as colorless solid.

HR-MS (ESI): m/z=524.2123 ([MH]$^+$, $C_{26}H_{30}N_5O_7^+$, calc. 524.2140).

Example F11

4-[2-(Cyclopropylmethoxy)-4-fluorophenyl]-N-(1-glycoloylpiperidin-4-yl)-6-methyl-5H-pyrrolo[3,2-d]pyrimidine-7-carboxamide Starting from 4-[2-(cyclopropylmethoxy)-4-fluorophenyl]-6-methyl-N-piperidin-4-yl-5H-pyrrolo[3,2-d]pyrimidine-7-carboxamide hydrochloride (example D.f6) and commercially available 2-chloro-2-oxoethyl acetate the title compound is obtained as colorless solid.

MS (ESI): m/z=482 (MH$^+$, 100%).

$^1$H-NMR (300 MHz, DMSO-d$_6$): 11.80 (s, 1H, —NH); 8.94 (s. 1H); 8.81 (d, J=7.7, 1H, —NH); 7.66 (dd, J=8.4, 6.9, 1H); 7.08 (dd, J=11.7, 2.4, 1H); 6.96 (ddd, J=8.4, 8.4, 2.4, 1H); 4.51 (t, J=5.3, 1H, —OH); 4.25-4.04 (m, 2H); 4.13 (dd, J=5.3, 4.9, 2H); 3.91 (d, J=6.9, 2H); 3.68 (m, 1H); 3.20 (m, 1H); 3.02 (m, 1H); 2.79 (s, 3H); 1.97 (m, 2H); 1.54 (m, 1H); 1.42 (m, 1H); 0.96 (m, 1H); 0.38 (m, 2H): 0.25 (m, 2H).

Example F12

4-[2-(Cyclopropylmethoxy)-4-fluorophenyl]-N-{1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-4-fluorophenyl]-6-methyl-N-piperidin-4-yl-5H-pyrrolo[3,2-d]pyrimidine-7-carboxamide hydrochloride (example D.f6) and commercially available (2S)-1-chloro-1-oxopropan-2-yl acetate the title compound is obtained as colorless solid.

MS (ESI): m/z=496 (MH$^+$, 100%).

$^1$H-NMR (300 MHz, DMSO-d$_6$): 11.80 (s, 1H, —NH); 8.94 (s. 1H); 8.81 (d, J=5.9, 1H, —NH); 7.65 (dd, J=8.4, 7.1, 1H); 7.08 (dd, J=11.5, 2.3, 1H); 6.96 (ddd, J=8.4, 8.4, 2.3, 1H); 4.88 (d, J=6.7, 1H, —OH); 4.47 (m, 1H); 4.28-4.09 (m, 2H); 3.96 (m, 1H); 3.91 (d, J=6.9, 2H); 3.27 (m, 1H); 3.00 (m, 1H); 2.79 (s, 3H); 1.97 (m, 2H); 1.53 (m, 1H); 1.41 (m, 1H); 1.21 (br.s, 3H); 0.96 (m, 1H); 0.38 (m, 2H); 0.25 (m, 2H).

Example F13

4-[2-(Cyclopropylmethoxy)-4-fluorophenyl]-N-[trans-4-(glycoloylamino)cyclohexyl]-6-methyl-5H-pyrrolo[3,2-d]pyrimidine-7-carboxamide Starting from N-(trans-4-aminocyclohexyl)-4-[2-(cyclopropylmethoxy)-4-fluorophenyl]-6-methyl-5H-pyrrolo[3,2-d]pyrimidine-7-carboxamide hydrochloride (example D.f7) and commercially available 2-chloro-2-oxoethyl acetate the title compound is obtained as colorless solid.

MS (ESI): m/z=496 (MH$^+$, 100%).

$^1$H-NMR (300 MHz, DMSO-d$_6$): 11.77 (s, 1H, —NH); 8.95 (s, 1H); 8.65 (d, J=7.9, 1H, —NH); 7.66 (dd, 8.4, 6.9, 1H); 7.48 (d, J=8.2, 1H, —NH); 7.08 (dd, 11.7, 2.4, 1H); 6.96 (ddd, 8.4, 8.4, 2.4, 1H); 5.40 (t, J=5.7, 1H, —OH); 3.91 (d, J=7.1, 2H); 3.79 (d, J=5.7, 2H & m, 1H); 3.68 (m, 1H); 2.78 (s, 3H); 2.01 (m, 2H); 1.83 (m, 2H); 1.44 (m, 4H); 0.96 (m, 1H); 0.38 (m, 2H); 0.25 (m, 2H).

Example F14

4-[2-(Cyclopropylmethoxy)-4-fluorophenyl]-N-(trans-4-{[(2S)-2-hydroxypropanoyl]amino}cyclohexyl)-6-methyl-5H-pyrrolo[3,2-d]pyrimidine-7-carboxamide Starting from N-(trans-4-aminocyclohexyl)-4-[2-(cyclopropylmethoxy)-4-fluorophenyl]-6-methyl-5H-pyrrolo[3,2-d]pyrimidine-7-carboxamide hydrochloride (example D.f7) and commercially available (2S)-1-chloro-1-oxopropan-2-yl acetate the title compound is obtained as colorless solid.

MS (ESI): m/z=510 (MH$^+$, 100%).

$^1$H-NMR (300 MHz, DMSO-d$_6$): 11.77 (s, 1H, —NH); 8.95 (s, 1H); 8.64 (d, J=7.7, 1H, —NH); 7.66 (dd, 8.4, 7.1, 1H); 7.42 (d, J=8.2, 1H, —NH); 7.08 (dd, 11.7, 2.4, 1H); 6.95 (ddd, 8.4, 8.4, 2.4, 1H); 5.40 (d, J=5.1, 1H, —OH); 3.94 (m, 1H); 3.91 (d, J=6.9, 2H); 3.81 (m, 1H); 3.63 (m, 1H); 2.78 (s, 3H); 1.99 (m, 2H); 1.82 (m, 2H); 1.42 (m, 4H); 1.21 (d, J=6.8, 3H); 0.96 (m, 1H); 0.38 (m, 2H); 0.25 (m, 2H).

Example F15

4-[2-(cyclopropylmethoxy)-4-fluorophenyl]-N-[cis-4-(glycoloylamino)cyclohexyl]-6-methyl-5H-pyrrolo[3,2-d]pyrimidine-7-carboxamide Starting from N-(cis-4-aminocyclohexyl)-4-[2-(cyclopropylmethoxy)-4-fluorophenyl]-6-methyl-5H-pyrrolo[3,2-d]pyrimidine-7-carboxamide hydrochloride (example D.f8) and commercially available 2-chloro-2-oxoethyl acetate the title compound is obtained as colorless solid.

MS (ESI): m/z=496 (MH$^+$, 100%).

$^1$H-NMR (300 MHz, DMSO-d$_6$): 11.78 (s, 1H, —NH); 8.98 (s, 1H); 8.96 (d, J=7.6, 1H, —NH); 7.66 (dd, 8.4, 6.9, 1H); 7.53 (d, J=7.7, 1H, —NH); 7.09 (dd, 11.7, 2.4, 1H); 6.96 (ddd, 8.4, 8.4, 2.4, 1H); 5.33 (t, J=5.8, 1H, —OH); 4.06 (m, 1H); 3.91 (d, J=6.9, 2H); 3.82 (d, J=5.8, 2H); 3.80 (m, 1H); 2.79 (s, 3H); 1.82-1.58 (m, 8H); 0.96 (m, 1H); 0.38 (m, 2H); 0.26 (m, 2H).

Example F16

4-[2-(Cyclopropylmethoxy)-4-fluorophenyl]-N-(cis-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[2-(cyclopropylmethoxy)-4-fluorophenyl]-6-methyl-5H-pyrrolo[3,2-d]

pyrimidine-7-carboxamide hydrochloride (example D.f8) and commercially available (2S)-1-chloro-1-oxopropan-2-yl acetate the title compound is obtained as colorless solid.

MS (ESI): m/z=510 (MH$^+$, 100%).

$^1$H-NMR (300 MHz, DMSO-d$_6$): 11.78 (s, 1H, —NH); 8.98 (s, 1H); 8.95 (d, J=7.3, 1H, —NH); 7.66 (dd, 8.4, 7.1, 1H); 7.48 (d, J=7.9, 1H, —NH); 7.09 (dd, 11.5, 2.4, 1H); 6.96 (ddd, 8.4, 8.4, 2.4, 1H); 5.37 (d, J=5.5, 1H, —OH); 4.06 (m, 1H); 3.99 (m, 1H); 3.92 (d, J=6.9, 2H); 3.74 (m, 1H); 2.79 (s, 3H); 1.83-1.56 (m, 8H); 1.22 (d, J=6.8, 3H); 0.96 (m, 1H); 0.38 (m, 2H); 0.25 (m, 2H).

Example F17

4-[2-(Cyclopropylmethoxy)-4-fluorophenyl]-N-[(3R)-1-(hydroxyacetyl)pyrrolidin-3-yl]-6-methyl-5H-pyrrolo[3,2-d]pyrimidine-7-carboxamide Starting from 4-[2-(cyclopropylmethoxy)-4-fluorophenyl]-6-methyl-N-[(3R)-pyrrolidin-3-yl]-5H-pyrrolo[3,2-d]pyrimidine-7-carboxamide hydrochloride (example D.f9) and commercially available 2-chloro-2-oxoethyl acetate the title compound is obtained as colorless solid.

MS (ESI): m/z=468 (MH$^+$, 100%).

$^1$H-NMR (300 MHz, DMSO-d$_6$): 11.83 (s, 1H, —NH); 8.94 (s, 1H); [8.93 (d, J=7.1), 8.90 (d, J=7.0), 1H, —NH]; 7.66 (dd, J=8.4, 7.1, 1H); 7.09 (dd, J=11.7, 2.4, 1H); 6.96 (ddd, J=8.4, 8.4, 2.4, 1H); [4.60 (m), 4.50 (m), 1H]; 4.56 (t, J=5.7, 1H, —OH); [4.06 (d, J=5.7), 4.01 (d, J=5.7), 2H]; 3.91 (d, J=6.9, 2H); 3.80-3.68 (m, 1H); 3.62-3.43 (m, 2H); 3.40-3.27 (m, 1H); 2.79 (s, 3H); 2.34-2.16 (m, 1H); [2.05 (m), 1.92 (m), 1H]; 0.95 (m, 1H); 0.38 (m, 2H); 0.25 (m, 2H).

Example F18

4-[2-(cyclopropylmethoxy)-4-fluorophenyl]-N-{(3R)-1-[(2S)-2-hydroxypropanoyl]pyrrolidin-3-yl}-6-methyl-5H-pyrrolo[3,2-d]pyrimidine-7-carboxamide Starting from 4-[2-(cyclopropylmethoxy)-4-fluorophenyl]-6-methyl-N-[(3R)-pyrrolidin-3-yl]-5H-pyrrolo[3,2-d]pyrimidine-7-carboxamide hydrochloride (example D.f9) and commercially available (2S)-1-chloro-1-oxopropan-2-yl acetate the title compound is obtained as colorless solid.

HR-MS (ESI): m/z=498.2129 ([MH]$^+$, C$_{25}$H$_{29}$FN$_5$O$_4^+$, calc. 498.2147).

Example F19

4-[2-(Cyclopropylmethoxy)-4-fluorophenyl]-N-[(3R*,4R*)-4-hydroxy-1-(hydroxyacetyl)pyrrolidin-3-yl]-6-methyl-5H-pyrrolo[3,2-d]pyrimidine-7-carboxamide Starting from 4-[2-(cyclopropylmethoxy)-4-fluorophenyl]-N-[(3R*,4R*)-4-hydroxypyrrolidin-3-yl]-6-methyl-5H-pyrrolo[3,2-d]pyrimidine-7-carboxamide hydrochloride (example D.f10) and commercially available 2-chloro-2-oxoethyl acetate the title compound is obtained as colorless solid.

MS (ESI): m/z=484 (MH$^+$, 100%).

$^1$H-NMR (300 MHz, DMSO-d$_6$): 11.75 (br.s, 1H, —NH); [8.93 (s), 8.92 (s), 1H]; [8.87 (d, J=7.1), 8.82 (d, J=6.8), 1H, —NH]; 7.65 (dd, J=8.4, 7.0, 1H); 7.09 (dd, J=11.5, 2.4, 1H); 6.96 (ddd, J=8.4, 8.4, 2.4, 1H); [5.57 (br. s), 5.51 (br. s), 1H, —OH]; 4.60 (m, 1H, —OH); [4.37 (m), 4.20 (m), 1H]; 4.28 (m, 1H); 4.05 (br.d, J~2.0, 2H); 3.91 (d, 6.9, 2H); 3.87-3.59 (m, 2H); 3.48-3.27 (m, 2H); 2.78 (s. 3H); 0.95 (m, 1H); 0.38 (m, 2H); 0.25 (m, 2H).

Example F20

Diastereomeric mixture of 4-[2-(Cyclopropylmethoxy)-4-fluorophenyl]-N{(3R,4R)-4-hydroxy-1-[(2S)-2-hydroxypropanoyl]pyrrolidin-3-yl}-6-methyl-5H-pyrrolo[3,2-d]pyrimidine-7-carboxamide and 4-[2-(Cyclopropylmethoxy)-4-fluorophenyl]-N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide Starting from 4-[2-(cyclopropylmethoxy)-4-fluorophenyl]-N-[(3R*,4R*)-4-hydroxypyrrolidin-3-yl]-6-methyl-5H-pyrrolo[3,2-d]pyrimidine-7-carboxamide hydrochloride (example D.f10) and commercially available (2S)-1-chloro-1-oxopropan-2-yl acetate the title compound is obtained as colorless solid.

HR-MS (ESI): m/z=482.2178 ([MH]$^+$, C$_{25}$H$_{29}$FN$_5$O$_4^+$, calc. 482.2198).

Example F21

4-[2-(Cyclopropylmethoxy)-4-fluorophenyl]-N-[(3S*,4S*)-3-hydroxy-1-(hydroxyacetyl)piperidin-4-yl]-6-methyl-5H-pyrrolo[3,2-d]pyrimidine-7-carboxamide Starting from 4-[2-(cyclopropylmethoxy)-4-fluorophenyl]-N-[(3R*,4S*)-3-hydroxypiperidin-4-yl]-6-methyl-5H-pyrrolo[3,2-d]pyrimidine-7-carboxamide hydrochloride (example D.f11) and commercially available 2-chloro-2-oxoethyl acetate the title compound is obtained as colorless solid.

HR-MS (ESI): m/z=498.2134 ([MH]$^+$, C$_{25}$H$_{28}$FN$_5$O$_5^+$, calc. 498.2147).

Example F22

Diastereomeric mixture of 4-[2-(Cyclopropylmethoxy)-4-fluorophenyl]-N{(3S,45)-3-hydroxy-1-[(25)-2-hydroxypropanoyl]piperidin-4-yl}-6-methyl-5H-pyrrolo[3,2-d]pyrimidine-7-carboxamide and 4-[2-(Cyclopropylmethoxy)-4-fluorophenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-4-fluorophenyl]-N-[(3R*,4S*)-3-hydroxypiperidin-4-yl]-6-methyl-5H-pyrrolo[3,2-d]pyrimidine-7-carboxamide hydrochloride (example D.f11) and commercially available (2S)-1-chloro-1-oxopropan-2-yl acetate the title compound is obtained as colorless solid.

HR-MS (ESI): m/z=512.2293 ([MH]$^+$, C$_{26}$H$_{31}$FN$_5$O$_5^+$, calc. 512.2304).

Example F23

4-(2-Cyclopropylmethoxy-5-fluoro-phenyl)-6-methyl-5H-pyrrolo[3,2-d]pyrimidine-7-carboxylic acid [1-(2-hydroxy-acetyl)-piperidin-4-yl]-amide Starting from 4-(2-cyclopropylmethoxy-5-fluoro-phenyl)-6-methyl-5H-pyrrolo[3,2-d]pyrimidine-7-carboxylic acid piperidin-4-ylamide hydrochloride (example D.f12) and commercially available 2-chloro-2-oxoethyl acetate the title compound is obtained as colorless solid.

MS (ESI): m/z=482 (MH⁺, 100%), 356, 302.

¹H-NMR (300 MHz, DMSO-d₆): 11.84 (br.s, 1H, —NH); 8.96 (s, 1H); 8.80 (d, J=7.7, 1H, —NH); 7.42 (dd, J=9.0, 3.2, 1H); 7.37 (ddd, J=9.1, 8.3, 3.2, 1H); 7.19 (dd, J=9.1, 4.4, 1H); 4.50 (br.s, 1H, —OH); 4.25-4.03 (m, 2H); 4.13 (br.s, 2H); 3.87 (d, J=6.9, 2H); 3.68 (m, 1H); 3.20 (m, 1H); 3.02 (m, 1H); 2.79 (s, 3H); 1.97 (m, 2H); 1.55 (m, 1H); 1.42 (m, 1H); 0.94 (m, 1H); 0.36 (m, 2H); 0.22 (m, 2H).

Example F24

4-(2-Cyclopropylmethoxy-5-fluoro-phenyl)-6-methyl-5H-pyrrolo[3,2-d]pyrimidine-7-carboxylic acid [1-((S)-2-hydroxy-propionyl)-piperidin-4-yl]-amide Starting from 4-(2-cyclopropylmethoxy-5-fluoro-phenyl)-6-methyl-5H-pyrrolo[3,2-d]pyrimidine-7-carboxylic acid piperidin-4-ylamide hydrochloride (example D.f12) and commercially available (2S)-1-chloro-1-oxopropan-2-yl acetate the title compound is obtained as colorless solid.

MS (ESI): m/z=496 (MH⁺, 100%), 356, 302.

¹H-NMR (300 MHz, DMSO-d₆): 11.84 (br.s, 1H, —NH); 8.97 (s, 1H); 8.80 (d, J=7.7, 1H, —NH); 7.42 (dd, J=9.0, 3.2, 1H); 7.37 (ddd, J=9.1, 8.3, 3.2, 1H); 7.19 (dd, J=9.1, 4.4, 1H); 5.01-4.58 (s, 1H, —OH); 4.28-4.07 (m, 2H); 3.95 (m, 1H); 3.87 (d, J=6.9, 2H); 3.29 (m, 1H); 3.01 (m, 1H); 2.79 (s, 3H); 1.98 (m, 2H); 1.54 (m, 1H); 1.42 (m, 1H); 1.22 (br.s, 3H); 0.94 (m, 1H); 0.36 (m, 2H); 0.22 (m, 2H).

Example F25

4-[2-(Cyclopropylmethoxy)-5-fluorophenyl]-N-[trans-4-(glycoloylamino)cyclohexyl]-6-methyl-5H-pyrrolo[3,2-d]pyrimidine-7-carboxamide Starting from N-(trans-4-aminocyclohexyl)-4-[2-(cyclopropylmethoxy)-5-fluorophenyl]-6-methyl-5H-pyrrolo[3,2-d]pyrimidine-7-carboxamide hydrochloride (example D.f13) and commercially available 2-chloro-2-oxoethyl acetate the title compound is obtained as colorless solid.

MS (ESI): m/z=496 (MH⁺, 100%).

¹H-NMR (300 MHz, DMSO-d₆): 11.81 (s, 1H, —NH); 8.97 (s, 1H); 8.64 (d, J=7.9, 1H, —NH); 7.47 (d, J=8.4, 1H, —NH); 7.42 (dd, J=8.9, 3.3, 1H); 7.36 (ddd, J=9.1, 8.2, 3.3, 1H); 7.18 (dd, J=9.1, 4.4, 1H); 5.40 (t, J=5.7, 1H, —OH); 3.87 (d, J=6.8, 2H); 3.82 (m, 1H); 3.79 (d, J=5.7, 2H); 3.68 (m, 1H); 2.79 (s, 3H); 2.01 (m, 2H); 1.83 (m, 2H); 1.44 (m, 4H); 0.94 (m, 1H); 0.36 (m, 2H); 0.22 (m, 2H).

Example F26

4-[2-(Cyclopropylmethoxy)-5-fluorophenyl]-N-(trans-4-{[(2S)-2-hydroxypropanoyl]amino}cyclohexyl)-6-methyl-5H-pyrrolo[3,2-d]pyrimidine-7-carboxamide Starting from N-(trans-4-aminocyclohexyl)-4-[2-(cyclopropylmethoxy)-5-fluorophenyl]-6-methyl-5H-pyrrolo[3,2-d]pyrimidine-7-carboxamide hydrochloride (example D.f13) and commercially available (2S)-1-chloro-1-oxopropan-2-yl acetate the title compound is obtained as colorless solid.

MS (ESI): m/z=510 (MH⁺, 100%).

¹H-NMR (300 MHz, DMSO-d₆): 11.81 (s, 1H, —NH); 8.97 (s, 1H); 8.64 (d, J=7.7, 1H, —NH); 7.42 (dd, J=8.9, 3.3, 1H & d, J=8.4, 1H, —NH); 7.36 (ddd, J=9.1, 8.4, 3.3, 1H); 7.18 (dd, J=9.1, 4.4, 1H); 5.40 (d, J=5.3, 1H, —OH); 3.94 (m, 1H); 3.87 (d, J=6.9, 2H); 3.82 (m, 1H); 3.63 (m, 1H); 2.78 (s, 3H); 2.01 (m, 2H); 1.82 (m, 2H); 1.43 (m, 4H); 1.21 (d, J=6.7, 3H); 0.94 (m, 1H); 0.36 (m, 2H); 0.22 (m, 2H).

Example F27

4-[2-(Cyclopropylmethoxy)-5-fluorophenyl]-N-(cis-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[2-(cyclopropylmethoxy)-5-fluorophenyl]-6-methyl-5H-pyrrolo[3,2-d]pyrimidine-7-carboxamide hydrochloride (example D.f14) and commercially available (2S)-1-chloro-1-oxopropan-2-yl acetate the title compound is obtained as colorless solid.

MS (ESI): m/z=510 (MH⁺, 100%).

¹H-NMR (300 MHz, DMSO-d₆): 11.82 (s, 1H, —NH); 9.00 (s, 1H); 8.94 (d, J=7.7, 1H, —NH); 7.48 (d, J=7.9, 1H, —NH); 7.43 (dd, J=9.1, 3.3, 1H); 7.38 (ddd, J=8.9, 8.4, 3.3, 1H); 7.19 (dd, J=8.9, 4.4, 1H); 5.37 (d, J=5.5, 1H, —OH); 4.05 (m, 1H); 3.99 (td, J=6.8, 5.5, 1H); 3.88 (d, J=6.8, 2H); 3.75 (m, 1H); 2.79 (s, 3H); 1.81-1.58 (m, 8H); 1.22 (d, J=6.8, 3H); 0.94 (m, 1H); 0.37 (m, 2H); 0.23 (m, 2H).

Example F28

4-[2-(Cyclopropylmethoxy)-5-fluorophenyl]-N-[(3R)-1-(hydroxyacetyl)pyrrolidin-3-yl]-6-methyl-5H-pyrrolo[3,2-d]pyrimidine-7-carboxamide Starting from 4-[2-(cyclopropylmethoxy)-5-fluorophenyl]-6-methyl-N-[(3R)-pyrrolidin-3-yl]-5H-pyrrolo[3,2-d]pyrimidine-7-carboxamide hydrochloride (example D.f15) and commercially available 2-chloro-2-oxoethyl acetate the title compound is obtained as colorless solid.

HR-MS (ESI): m/z=468.2039 ([MH]⁺, C₂₄H₂₆FN₅O₄⁺, calc. 468.2042).

Example F29

4-[2-(Cyclopropylmethoxy)-5-fluorophenyl]-N-{(3R)-1-[(2S)-2-hydroxypropanoyl]pyrrolidin-3-yl}-6-methyl-5H-pyrrolo[3,2-d]pyrimidine-7-carboxamide Starting from 4-[2-(cyclopropylmethoxy)-5-fluorophenyl]-6-methyl-N-[(3R)-pyrrolidin-3-yl]-5H-pyrrolo[3,2-d]pyrimidine-7-carboxamide hydrochloride (example D.f15) and commercially available (2S)-1-chloro-1-oxopropan-2-yl acetate the title compound is obtained as colorless solid.

HR-MS (ESI): m/z=482.2199 ([MH]⁺, C₂₄H₂₆FN₅O₄⁺, calc. 482.2198).

Example F30

4-[2-(Cyclopropylmethoxy)-5-fluorophenyl]-N-[(3R*,4R*)-3-hydroxy-1-(hydroxyacetyl)piperidin-4-yl]-6-methyl-5H-pyrrolo[3,2-d]pyrimidine-7-carboxamide Starting from 4-[2-(cyclopropylmethoxy)-5-fluorophenyl]-N-[(3R*,4R*)-3-hydroxypiperidin-4-yl]-6-methyl-5H-pyrrolo[3,2-d]pyrimidine-7-carboxamide hydrochloride (example D.f16) and commercially available 2-chloro-2-oxoethyl acetate the title compound is obtained as colorless solid.

HR-MS (ESI): m/z=498.2142 ([MH]$^+$, $C_{25}H_{29}FN_5O_5^+$, calc. 498.2147).

Example F31

Diastereomeric mixture of 4-[2-(cyclopropyl-methoxy)-5-fluorophenyl]-N{(3R,4R)-3-hydroxy-1-[(2S)-2-hydroxypropanoyl]piperidin-4-yl}-6-methyl-5H-pyrrolo[3,2-d]pyrimidine-7-carboxamide and 4-[2-(cyclopropylmethoxy)-5-fluorophenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-5-fluorophenyl]-N-[(3R*,4R*)-3-hydroxypiperidin-4-yl]-6-methyl-5H-pyrrolo[3,2-d]pyrimidine-7-carboxamide hydrochloride (example D.f16) and commercially available (2S)-1-chloro-1-oxopropan-2-yl acetate the title compound is obtained as colorless solid.

HR-MS (ESI): m/z=512.2298 ([MH]$^+$, $C_{26}H_{31}FN_5O_5^+$, calc. 512.2304).

Example F32

4-(2-Ethoxy-5-fluorophenyl)-N-[1-(hydroxyacetyp-piperidin-4-yl]-6-methyl-5H-pyrrolo[3,2-d]pyrimidine-7-carboxamide Starting from 4-(2-ethoxy-5-fluorophenyl)-6-methyl-N-(piperidin-4-yl)-5H-pyrrolo[3,2-d]pyrimidine-7-carboxamide hydrochloride (example D.f17) and commercially available 2-chloro-2-oxoethyl acetate the title compound is obtained as colorless solid.

MS (ESI): m/z=456 (MH$^+$, 100%).
$^1$H-NMR (300 MHz, DMSO-d$_6$): 11.87 (s, 1H, —NH); 8.95 (s, 1H); 8.79 (d, J=7.7, 1H, —NH); 7.42 (ddd, J=9.1, 8.9, 3.2, 1H); 7.38 (dd, J=8.3, 3.2, 1H); 7.22 (dd, J=9.1, 4.4, 1H); 4.50 (t, J=5.5, 1H, —OH); 4.23-4.06 (m, 2H); 4.13 (d, J=5.5, 2H); 4.08 (qu, J=6.9, 2H); 3.68 (m, 1H); 3.20 (m, 1H); 3.02 (m, 1H); 2.78 (s, 3H); 1.97 (m, 2H); 1.53 (m, 1H); 1.42 (m, 1H); 1.11 (t, J=6.9, 3H).

Example F33

4-(2-Ethoxy-5-fluorophenyl)-N-{1-[(2S)-2-hydroxypropanoyl]piperidin-4-yl}-6-methyl-5H-pyrrolo[3,2-d]pyrimidine-7-carboxamide Starting from 4-(2-ethoxy-5-fluorophenyl)-6-methyl-N-(piperidin-4-yl)-5H-pyrrolo[3,2-d]pyrimidine-7-carboxamide hydrochloride (example D.f17) and commercially available (2S)-1-chloro-1-oxopropan-2-yl acetate the title compound is obtained as colorless solid.

MS (ESI): m/z=470 (MH$^+$, 100%).
$^1$H-NMR (300 MHz, DMSO-d$_6$): 11.87 (s, 1H, —NH); 8.96 (s, 1H); 8.79 (d, J=6.7, 1H, —NH); 7.42 (ddd, J=9.1, 8.9, 3.3, 1H); 7.38 (dd, J=8.3, 3.3, 1H); 7.22 (dd, J=9.1, 4.4, 1H); 4.86 (d, J=6.7, 1H, —OH); 4.47 (m, 1H); 4.26-4.11 (m, 2H); 4.08 (qu, J=6.9, 2H); 3.95 (m, 1H); 3.27 (m, 1H); 3.00 (m, 1H); 2.79 (s, 3H); 1.98 (m, 2H); 1.53 (m, 1H); 1.41 (m, 1H); 1.21 (br.s, 3H); 1.11 (t, J=6.9, 3H).

Example F34

4-[2-(Cyclopropylmethoxy)-4-methoxyphenyl]-N-(1-glycoloylpiperidin-4-yl)-6-methyl-5H-pyrrolo[3,2-d]pyrimidine-7-carboxamide Starting from 4-[2-(cyclopropylmethoxy)-4-methoxyphenyl]-6-methyl-N-piperidin-4-yl-5H-pyrrolo[3,2-d]pyrimidine-7-carboxamide hydrochloride (example D.f18) and commercially available 2-chloro-2-oxoethyl acetate the title compound is obtained as colorless solid.

MS (ESI): m/z=494 (MH$^+$, 100%).
$^1$H-NMR (300 MHz, DMSO-d$_6$): 11.68 (s, 1H, —NH); 8.90 (s, 1H); 8.84 (d, J=7.7, 1H, —NH); 7.58 (d, J=8.4, 1H); 6.72 (dd, J=8.4, 2.2, 2H); 6.69 (d, J=2.2, 1H); 4.50 (t, J=5.5, 1H, —OH); 4.24-4.02 (m, 2H); 4.13 (m, 2H); 3.90 (d, J=6.9, 2H); 3.86 (s, 3H); 3.67 (m, 1H); 310 (m, 1H); 3.02 (m, 1H); 2.78 (s, 3H); 1.96 (m, 2H); 1.54 (m, 1H); 1.41 (m, 1H); 0.96 (m, 1H); 0.38 (m, 2H); 0.26 (m, 2H).

Example F35

4-[2-(Cyclopropylmethoxy)-4-methoxyphenyl]-N-{1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-4-methoxyphenyl]-6-methyl-N-piperidin-4-yl-5H-pyrrolo[3,2-d]pyrimidine-7-carboxamide (example D.f18) and commercially available (2S)-1-chloro-1-oxopropan-2-yl acetate the title compound is obtained as colorless solid.

MS (ESI): m/z=508 (MH$^+$, 100%).
$^1$H-NMR (300 MHz, DMSO-d$_6$): 11.68 (s, 1H, —NH); 8.91 (s, 1H); 8.84 (d, J=7.5, 1H, —NH); 7.59 (d, J=8.4, 1H); 6.79 (d, J=2.2, 1H); 6.72 (dd, J=8.4, 2.2, 1H); 4.86 (t, J=6.9, 1H, —OH); 4.46 (m, 1H); 4.28-4.06 (m, 2H); 3.96 (m, 1H); 3.90 (d, J=6.9, 2H); 3.86 (s, 3H); 3.26 (m, 1H); 3.00 (m, 1H); 2.78 (s, 3H); 1.97 (m, 2H); 1.53 (m, 1H); 1.41 (m, 1H); 1.21 (br.s, 3H); 0.96 (m, 1H); 0.38 (m, 2H); 0.26 (m, 2H).

Example F36

4-[2-(Cyclopropylmethoxy)-4-methoxyphenyl]-N-(trans-4-{[(2S)-2-hydroxypropanoyl]amino}cyclohexyl)-6-methyl-5H-pyrrolo[3,2-d]pyrimidine-7-carboxamide Starting from N-(trans-4-aminocyclohexyl)-4-[2-(cyclopropylmethoxy)-4-methoxyphenyl]-6-methyl-5H-pyrrolo[3,2-d]pyrimidine-7-carboxamide hydrochloride (example D.f19) and commercially available (2S)-1-chloro-1-oxopropan-2-yl acetate the title compound is obtained as colorless solid.

MS (ESI): m/z=522 (MH$^+$, 100%).
$^1$H-NMR (300 MHz, DMSO-d$_6$): 11.65 (s, 1H, —NH); 8.91 (s, 1H); 8.67 (d, J=7.9, 1H, —NH); 7.59 (d, J=8.4, 1H); 7.42 (d, J=8.4, 1H, —NH); 6.72 (dd, J=8.4, 2.2, 2H); 6.68 (d, J=2.2, 1H); 5.40 (d, J=5.3, 1H, —OH); 3.94 (m, 1H); 3.90 (d, J=6.9, 2H); 3.86 (s, 3H); 3.80 (m, 1H); 3.63 (m, 1H); 2.77 (s, 3H); 2.01 (m, 2H); 1.82 (m, 2H); 1.42 (m, 4H); 1.21 (d, J=6.8, 3H); 0.96 (m, 1H); 0.38 (m, 2H); 0.26 (m, 2H).

Example F37

4-[2-(Cyclopropylmethoxy)-4-methoxyphenyl]-N-[(3R)-1-glycoloylpyrrolidin-3-yl]-6-methyl-5H-pyrrolo[3,2-d]pyrimidine-7-carboxamide Starting from 4-[2-(cyclopropylmethoxy)-4-methoxyphenyl]-6-methyl-N-[(3R)-pyrrolidin-3-yl]-5H-pyrrolo[3,2-d]

pyrimidine-7-carboxamide hydrochloride (example D.f21) and commercially available 2-chloro-2-oxoethyl acetate the title compound is obtained as colorless solid.

MS (ESI): m/z=480 (MH⁺, 100%).

$^1$H-NMR (300 MHz, DMSO-d$_6$): 11.71 (br.s, 1H, —NH); [8.95 (d, J=7.6), 8.93 (d, J=7.6), 1H, —NH]; 8.90 (s, 1H); 7.59 (d, J=8.4, 1H); 6.72 (dd, J=8.4, 2.2, 1H); 6.69 (d, J=2.2, 1H); [4.59 (m), 4.49 (m), 1H]; 4.55 (t, J=5.8, 1H, —OH); [4.06 (d, J=5.8), 4.01 (d, J=5.8), 1H]; 3.90 (d, J=6.9, 2H); 3.86 (s, 3H); 3.79-3.68 (m, 1H); 3.62-3.43 (m, 1H); 3.39-3.27 (m, 1H); 2.78 (s, 3H); 2.34-2.15 (m 1H); 2.09-1.86 (m, 1H); 0.95 (m, 1H); 0.37 (m, 2H); 0.26 (m, 2H).

Example F38

4-[2-(Cyclopropylmethoxy)-4-methoxyphenyl]-N-{(3R)-1-[(2S)-2-hydroxypropanoyl]pyrrolidin-3-yl}-6-methyl-5H-pyrrolo[3,2-d]pyrimidine-7-carboxamide Starting from 4-[2-(cyclopropylmethoxy)-4-methoxyphenyl]-6-methyl-N-[(3R)-pyrrolidin-3-yl]-5H-pyrrolo[3,2-d]pyrimidine-7-carboxamide hydrochloride (example D.f21) and commercially available (2S)-1-chloro-1-oxopropan-2-yl acetate the title compound is obtained as colorless solid.

HR-MS (ESI): m/z=494.2402 ([MH]⁺, C$_{26}$H$_{32}$N$_5$O$_5^+$, calc. 494.2389).

Example F39

4-[2-(Cyclopropylmethoxy)-4-methoxyphenyl]-N-[(3R*,4R*)-1-glycoloyl-4-hydroxypyrrolidin-3-yl]-6-methyl-5H-pyrrolo[3,2-d]pyrimidine-7-carboxamide Starting from 4-[2-(cyclopropylmethoxy)-4-methoxyphenyl]-N-[(3R*,4R*)-4-hydroxypyrrolidin-3-yl]-6-methyl-5H-pyrrolo[3,2-d]pyrimidine-7-carboxamide hydrochloride (example D.f22) and commercially available 2-chloro-2-oxoethyl acetate the title compound is obtained as colorless solid.

MS (ESI): m/z=496 (MH⁺, 100%).

$^1$H-NMR (300 MHz, DMSO-d$_6$): 11.72 (br.s, 1H, —NH); [8.90 (d, J=7.1), 8.85 (d, J=6.6), 1H, —NH]; [8.89 (s), 8.88 (s), 1H]; 7.58 (d, J=8.4, 1H); 6.72 (dd, J=8.4, 2.2, 1H); 6.69 (d, J=2.2, 1H); [5.56 (d, J=4.0), 5.50 (d, J=4.2), 1H, —OH]; [4.63 (t, J=5.7), 4.60 (t, J=5.7), 1H, —OH]; [4.37 (m), 4.19 (m), 1H]; 4.28 (m, 1H); [4.05 (d, J=5.7), 4.04 (d, J=5.7), 2H]; 3.90 (d, J=6.9, 2H); 3.86 (s, 3H); 3.84-3.69 (m, 1H); 3.68-3.59 (m, 1H); 3.46-3.32 (m, 2H); 2.78 (s, 3H); 0.95 (m, 1H); 0.37 (m, 2H); 0.26 (m, 2H).

Example F40

Diastereomeric mixture of 4-[2-(cyclopropylmethoxy)-4-methoxyphenyl]-N{(3R,4R)-4-hydroxy-1-[(2S)-2-hydroxypropanoyl]pyrrolidin-3-yl}-6-methyl-5H-pyrrolo[3,2-d]pyrimidine-7-carboxamide and 4-[2-(cyclopropylmethoxy)-4-methoxyphenyl]-N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide Starting from 4-[2-(cyclopropylmethoxy)-4-methoxyphenyl]-N-[(3R*,4R*)-4-hydroxypyrrolidin-3-yl]-6-methyl-5H-pyrrolo[3,2-d]pyrimidine-7-carboxamide hydrochloride (example D.f22) and commercially available (2S)-1-chloro-1-oxopropan-2-yl acetate the title compound is obtained as colorless solid.

HR-MS (ESI): m/z=510.2352 ([MH]⁺, C$_{26}$H$_{32}$N$_5$O$_5^+$, calc. 510.2347).

Example F41

4-[2-(Cyclopropylmethoxy)-5-methoxyphenyl]-N-(1-glycoloylpiperidin-4-yl)-6-methyl-5H-pyrrolo[3,2-d]pyrimidine-7-carboxamide Starting from 4-[2-(cyclopropylmethoxy)-5-methoxyphenyl]-6-methyl-N-piperidin-4-yl-5H-pyrrolo[3,2-d]pyrimidine-7-carboxamide hydrochloride (example D.f23) and commercially available 2-chloro-2-oxoethyl acetate the title compound is obtained as colorless solid.

MS (ESI): m/z=494 (MH⁺, 100%).

$^1$H-NMR (300 MHz, DMSO-d$_6$): 11.77 (s, 1H, —NH); 8.95 (s, 1H); 8.82 (d, J=7.7, 1H, —NH); 7.17 (t, J=1.8, 1H); 7.11 (d, J=1.8, 2H); 4.50 (t, J=5.5, 1H, —OH); 4.24-4.04 (m, 2H); 4.13 (m, 2H); 3.82 (d, J=6.9, 2H); 3.77 (s, 3H); 3.68 (m, 1H); 3.19 (m, 1H); 3.02 (m, 1H); 2.79 (s, 3H); 1.97 (m, 2H); 1.55 (m, 1H); 1.42 (m, 1H); 0.92 (m, 1H); 0.34 (m, 2H); 0.19 (m, 2H).

Example F42

4-[2-(Cyclopropylmethoxy)-5-methoxyphenyl]-N-{1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-5-methoxyphenyl]-6-methyl-N-piperidin-4-yl-5H-pyrrolo[3,2-d]pyrimidine-7-carboxamide hydrochloride (example D.f23) and commercially available (2S)-1-chloro-1-oxopropan-2-yl acetate the title compound is obtained as colorless solid.

MS (ESI): m/z=494 (MH⁺, 100%).

$^1$H-NMR (300 MHz, DMSO-d$_6$): 11.77 (s, 1H, —NH); 8.96 (s, 1H); 8.82 (d, J=7.7, 1H, —NH); 7.17 (t, J=1.8, 1H); 7.11 (d, J=1.8, 2H); 4.86 (d, J=6.9, 1H, —OH); 4.47 (m, 1H); 4.27-4.06 (m, 2H); 3.95 (m, 1H); 3.82 (d, J=6.9, 2H); 3.77 (s, 3H); 3.27 (m, 1H); 3.00 (m, 1H); 2.79 (s, 3H); 1.99 (m, 2H); 1.63-1.31 (m, 2H); 1.22 (br.s, 3H); 0.92 (m, 1H); 0.34 (m, 2H); 0.19 (m, 2H).

Example F43

4-[2-(Cyclopropylmethoxy)-5-methoxyphenyl]-N-[trans-4-(glycoloylamino)cyclohexyl]-6-methyl-5H-pyrrolo[3,2-d]pyrimidine-7-carboxamide Starting from N-(trans-4-aminocyclohexyl)-4-[2-(cyclopropylmethoxy)-5-methoxyphenyl]-6-methyl-5H-pyrrolo[3,2-d]pyrimidine-7-carboxamide hydrochloride (example D.f24) and commercially available 2-chloro-2-oxoethyl acetate the title compound is obtained as colorless solid.

MS (ESI): m/z=508 (MH⁺, 100%).

$^1$H-NMR (300 MHz, DMSO-d$_6$): 11.74 (s, 1H, —NH); 8.96 (s, 1H); 8.65 (d, J=7.8, 1H, —NH); 7.47 (d, J=8.2, 1H, —NH); 7.17 (t, J=1.8, 1H); 7.10 (d, J=1.8, 2H); 5.50 (t, J=5.8, 1H, —OH); 3.82 (d, J=6.9, 2H); 3.79 (d, J=5.8, 2H); 3.77 (s, 3H & m, 1H); 3.69 (m, 1H); 2.78 (s, 3H); 2.01 (m, 2H); 1.83 (m, 2H); 1.44 (m, 4H); 0.92 (m, 1H); 0.34 (m, 2H); 0.19 (m, 2H).

Example F44

4-[2-(Cyclopropylmethoxy)-5-methoxyphenyl]-N-(trans-4-{[(2S)-2-hydroxypropanoyl]amino}cyclohexyl)-6-methyl-5H-pyrrolo[3,2-d]pyrimidine-7-carboxamide Starting from N-(trans-4-aminocyclohexyl)-4-[2-(cyclopropylmethoxy)-5-methoxyphenyl]-6-methyl-5H-pyrrolo[3,2-d]pyrimidine-7-carboxamide hydrochloride (example D.f24) and commercially available (2S)-1-chloro-1-oxopropan-2-yl acetate the title compound is obtained as colorless solid.

MS (ESI): m/z=522 (MH$^+$, 100%).

$^1$H-NMR (300 MHz, DMSO-d$_6$): 11.74 (s, 1H, —NH); 8.96 (s, 1H); 8.65 (d, J=7.9, 1H, —NH); 7.42 (d, J=8.2, 1H, —NH); 7.18 (t, J=1.8, 1H); 7.10 (d, J=1.8, 2H); 5.40 (d, J=5.1, 1H, —OH); 3.94 (m, 1H); 3.82 (d, J=6.9, 2H & m, 1H); 3.77 (s, 3H); 3.63 (m, 1H); 2.78 (s, 3H); 2.01 (m, 2H); 1.82 (m, 2H); 1.43 (m, 4H); 1.21 (d, J=6.8, 3H); 0.92 (m, 1H); 0.34 (m, 2H); 0.19 (m, 2H).

Example F45

4-[2-(Cyclopropylmethoxy)-5-methoxyphenyl]-N-[cis-4-(glycoloylamino)cyclohexyl]-6-methyl-5H-pyrrolo[3,2-d]pyrimidine-7-carboxamide Starting from N-(cis-4-aminocyclohexyl)-4-[2-(cyclopropylmethoxy)-5-methoxyphenyl]-6-methyl-5H-pyrrolo[3,2-d]pyrimidine-7-carboxamide hydrochloride (example D.f25) and commercially available 2-chloro-2-oxoethyl acetate the title compound is obtained as colorless solid.

HR-MS (ESI): m/z=508.2558 ([MH]$^+$, C$_{27}$H$_{34}$N$_5$O$_5^+$, calc. 508.2554).

Example F46

4-[2-(cyclopropylmethoxy)-5-methoxyphenyl]-N-(cis-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[2-(cyclopropylmethoxy)-5-methoxyphenyl]-6-methyl-5H-pyrrolo[3,2-d]pyrimidine-7-carboxamide hydrochloride (example D.f25) and commercially available (2S)-1-chloro-1-oxopropan-2-yl acetate the title compound is obtained as colorless solid.

HR-MS (ESI): m/z=522.2710 ([MH]$^+$, C$_{28}$H$_{36}$N$_5$O$_5^+$, calc. 522.2711).

Example F47

4-[2-(cyclopropylmethoxy)-5-methoxyphenyl]-N-[(3R)-1-glycoloylpyrrolidin-3-yl]-6-methyl-5H-pyrrolo[3,2-d]pyrimidine-7-carboxamide Starting from 4-[2-(cyclopropylmethoxy)-5-methoxyphenyl]-6-methyl-N-[(3R)-pyrrolidin-3-yl]-5H-pyrrolo[3,2-d]pyrimidine-7-carboxamide hydrochloride (example D.f26) and commercially available 2-chloro-2-oxoethyl acetate the title compound is obtained as colorless solid.

HR-MS (ESI): m/z=480.2243 ([MH]$^+$, C$_{25}$H$_{30}$N$_5$O$_5^+$, calc. 480.2241).

Example F48

4-[2-(cyclopropylmethoxy)-5-methoxyphenyl]-N-{(3R)-1-[(2S)-2-hydroxypropanoyl]pyrrolidin-3-yl}-6-methyl-5H-pyrrolo[3,2-d]pyrimidine-7-carboxamide Starting from 4-[2-(cyclopropylmethoxy)-5-methoxyphenyl]-6-methyl-N-[(3R)-pyrrolidin-3-yl]-5H-pyrrolo[3,2-d]pyrimidine-7-carboxamide hydrochloride (example D.f26) and commercially available (2S)-1-chloro-1-oxopropan-2-yl acetate the title compound is obtained as colorless solid.

HR-MS (ESI): m/z=494.2399 ([MH]$^+$, C$_{26}$H$_{32}$N$_5$O$_5^+$, calc. 494.2398).

Example F49

4-[2-(Cyclopropylmethoxy)-5-methoxyphenyl]-N-[(3R*,4R*)-3-hydroxy-1-(hydroxyacetyl)piperidin-4-yl]-6-methyl-5H-pyrrolo[3,2-d]pyrimidine-7-carboxamide Starting from 4-[2-(cyclopropylmethoxy)-5-methoxyphenyl]-N-[(3R*,4R*)-3-hydroxypiperidin-4-yl]-6-methyl-5H-pyrrolo[3,2-d]pyrimidine-7-carboxamide hydrochloride (example D.f27) and commercially available 2-chloro-2-oxoethyl acetate the title compound is obtained as colorless solid.

HR-MS (ESI): m/z=510.2349 ([MH]$^+$, C$_{26}$H$_{32}$N$_5$O$_6^+$, calc. 510.2347).

Example F50

Diastereomeric mixture of 4-[2-(Cyclopropylmethoxy)-5-methoxyphenyl]-N{(3R,4R)-3-hydroxy-1-[(2S)-2-hydroxypropanoyl]piperidin-4-yl}-6-methyl-5H-pyrrolo[3,2-d]pyrimidine-7-carboxamide and 4-[2-(Cyclopropylmethoxy)-5-methoxyphenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-5-methoxyphenyl]-N-[(3R*,4R*)-3-hydroxypiperidin-4-yl]-6-methyl-5H-pyrrolo[3,2-d]pyrimidine-7-carboxamide hydrochloride (example D.f27) and commercially available (2S)-1-chloro-1-oxopropan-2-yl acetate the title compound is obtained as colorless solid.

HR-MS (ESI): m/z=524.2495 ([MH]$^+$, C$_{27}$H$_{34}$N$_5$O$_6^+$, calc. 514.2504).

Example F51

4-[2-(Cyclopropylmethoxy)-5-methylphenyl]-N-[1-(hydroxyacetyppiperidin-4-yl]-6-methyl-5H-pyrrolo[3,2-d]pyrimidine-7-carboxamide Starting from 4-[2-(cyclopropylmethoxy)-5-methylphenyl]-6-methyl-N-(piperidin-4-yl)-5H-pyrrolo[3,2-d]pyrimidine-7-carboxamide hydrochloride (example D.f28) and commercially available 2-chloro-2-oxoethyl acetate the title compound is obtained as colorless solid.

MS (ESI): m/z=478 (MH⁺, 100%).
¹H-NMR (300 MHz, DMSO-d₆): 11.74 (br.s, 1H, —NH); 8.93 (s, 1H); 8.83 (d, J=7.7, 1H, —NH); 7.43 (d, J=1.8, 1H); 7.33 (dd, J=8.4, 1.8, 1H); 7.06 (d, J=8.4, 1H); 4.51 (t, J=5.3, 1H, —OH); 4.24-4.05 (m, 2H); 4.13 (m, 2H); 3.86 (d, J=6.9, 2H); 3.68 (m, 1H); 3.20 (m, 1H); 3.03 (m, 1H); 2.78 (s, 3H); 2.33 (s, 3H); 1.97 (m, 2H); 1.54 (m, 1H); 1.42 (m, 1H); 0.94 (m, 1H); 0.36 (m, 2H); 0.22 (m, 2H).

Example F52

4-[2-(Cyclopropylmethoxy)-5-methylphenyl]-N-{1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-5-methylphenyl]-6-methyl-N-(piperidin-4-yl)-5H-pyrrolo[3,2-d]pyrimidine-7-carboxamide hydrochloride (example D.f28) and commercially available (2S)-1-chloro-1-oxopropan-2-yl acetate the title compound is obtained as colorless solid.

MS (ESI): m/z=492 (MH⁺, 100%).
¹H-NMR (300 MHz, DMSO-d₆): 11.74 (br.s, 1H, —NH); 8.94 (s, 1H); 8.83 (d, J=7.7, 1H, —NH); 7.43 (d, J=1.8, 1H); 7.33 (dd, J=8.6, 1.8, 1H); 7.06 (d, J=8.6, 1H); 4.86 (d, J=6.9, 1H, —OH); 4.47 (m, 1H); 4.24-4.08 (m, 2H); 4.95 (m, 1H); 3.86 (d, J=6.8, 2H); 3.27 (m, 1H); 3.00 (m, 1H); 2.78 (s, 3H); 2.33 (s, 3H); 1.98 (m, 2H); 1.63-1.32 (m, 2H); 1.21 (br.s, 3H); 0.94 (m, 1H); 0.36 (m, 2H); 0.22 (m, 2H).

Example F53

4-[2-(Cyclopropylmethoxy)-5-methylphenyl]-N-{trans-4-[(hydroxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-5-methylphenyl]-6-methyl-5H-pyrrolo[3,2-d]pyrimidine-7-carboxamide hydrochloride (example D.f29) and commercially available 2-chloro-2-oxoethyl acetate the title compound is obtained as colorless solid.

MS (ESI): m/z=492 (MH⁺, 100%).
¹H-NMR (300 MHz, DMSO-d₆): 11.71 (s, 1H, —NH); 8.94 (s, 1H); 8.66 (d, J=7.7, 1H, —NH); 7.47 (d, J=8.4, 1H, —NH); 7.43 (d, J=2.1, 1H); 7.32 (dd, J=8.4, 2.1, 1H); 7.06 (d, J=8.4, 1H); 5.40 (t, J=5.9, 1H, —OH); 3.86 (d, J=6.8, 2H); 3.79 (d, J=5.9, 2H & m, 1H); 3.68 (m, 1H); 2.77 (s, 3H); 2.33 (s, 3H); 2.01 (m, 2H); 1.83 (m, 2H); 1.44 (m, 4H); 0.94 (m, 1H); 0.35 (m, 2H); 0.22 (m, 2H).

Example F54

4-[2-(Cyclopropylmethoxy)-5-methylphenyl]-N-(trans-4-{[(2S)-2-hydroxypropanoyl]amino}cyclohexyl)-6-methyl-5H-pyrrolo[3,2-d]pyrimidine-7-carboxamide Starting from N-(trans-4-aminocyclohexyl)-4-[2-(cyclopropylmethoxy)-5-methylphenyl]-6-methyl-5H-pyrrolo[3,2-d]pyrimidine-7-carboxamide hydrochloride (example D.f29) and commercially available (2S)-1-chloro-1-oxopropan-2-yl acetate the title compound is obtained as colorless solid.

MS (ESI): m/z=506 (MH⁺, 100%).
¹H-NMR (300 MHz, DMSO-d₆): 11.71 (s, 1H, —NH); 8.94 (s, 1H); 8.66 (d, J=7.7, 1H, —NH); 7.43 (d, J=2.0, 1H); 7.42 (d, J=7.8, 1H, —NH); 7.33 (dd, J=8.4, 2.0, 1H); 7.06 (d, J=8.4, 1H); 5.40 (d, J=5.3, 1H, —OH); 3.94 (m, 1H); 3.86 (d, J=6.8, 2H); 3.80 (m, 1H); 3.63 (m, 1H); 2.77 (s, 3H); 2.33 (s, 3H); 2.01 (m, 2H); 1.83 (m, 2H); 1.43 (m, 4H); 1.21 (d, J=6.8, 3H); 0.94 (m, 1H); 0.35 (m, 2H); 0.22 (m, 2H).

Example F55

4-[2-(Cyclopropylmethoxy)-5-methylphenyl]-N-{cis-4-[(hydroxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-5-methylphenyl]-6-methyl-5H-pyrrolo[3,2-d]pyrimidine-7-carboxamide hydrochloride (example D.f30) and commercially available 2-chloro-2-oxoethyl acetate the title compound is obtained as colorless solid.

MS (ESI): m/z=492 (MH⁺, 100%).
¹H-NMR (300 MHz, DMSO-d₆): 11.72 (s, 1H, —NH); 8.97 (s, 1H & d, J=7.5, 1H, —NH); 7.53 (d, J=7.7, 1H, —NH); 7.44 (d, J=2.0, 1H); 7.33 (dd, J=8.4, 2.0, 1H); 7.06 (d, J=8.4, 1H); 5.33 (t, J=5.8, 1H, —OH); 4.06 (m, 1H); 3.86 (d, J=6.9, 2H); 3.83 (d, J=5.8, 3H); 3.80 (m, 1H); 2.76 (s, 3H); 2.33 (s, 3H); 1.81-1.61 (m, 8H); 0.94 (m, 1H); 0.36 (m, 2H); 0.23 (m, 2H).

Example F56

4-[2-(Cyclopropylmethoxy)-5-methylphenyl]-N-(cis-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[2-(cyclopropylmethoxy)-5-methylphenyl]-6-methyl-5H-pyrrolo[3,2-d]pyrimidine-7-carboxamide hydrochloride (example D.f30) and commercially available (2S)-1-chloro-1-oxopropan-2-yl acetate the title compound is obtained as colorless solid.

MS (ESI): m/z=520 (MH⁺, 100%).
¹H-NMR (300 MHz, DMSO-d₆): 11.72 (s, 1H, —NH); 8.97 (s, 1H); 8.96 (d, J=6.4, 1H, —NH); 7.48 (d, J=7.9, 1H, —NH); 7.44 (d, J=1.8, 1H); 7.33 (dd, J=8.6, 1.8, 1H); 7.06 (d, J=8.6, 1H); 5.37 (d, J=5.5, 1H, —OH); 4.05 (m, 1H); 3.99 (m, 1H); 3.86 (d, J=6.9, 2H); 3.75 (m, 1H); 2.78 (s, 3H); 2.33 (s, 3H); 1.81-1.57 (m, 8H); 1.22 (d, J=6.8, 3H); 0.94 (m, 1H); 0.36 (m, 2H); 0.23 (m, 2H).

Example F57

4-[2-(Cyclopropylmethoxy)-5-(trifluoromethyl)phenyl]-N-[1-(hydroxyacetyl)piperidin-4-yl]-6-methyl-5H-pyrrolo[3,2-d]pyrimidine-7-carboxamide Starting from 4-[2-(cyclopropylmethoxy)-5-(trifluoromethyl)phenyl]-6-methyl-N-(piperidin-4-yl)-5H-pyrrolo[3,2-d]pyrimidine-7-carboxamide hydrochloride (example D.f31) and commercially available 2-chloro-2-oxoethyl acetate the title compound is obtained as colorless solid.

MS (ESI): m/z=532 (MH⁺, 100%).
¹H-NMR (300 MHz, DMSO-d₆): 11.90 (s, 1H, —NH); 8.99 (s, 1H); 8.80 (d, J=7.7, 1H, —NH); 7.91 (d, J=2.0, 1H); 7.89 (dd, J=8.8, 2.0, 1H); 7.38 (d, J=8.8, 1H); 4.51 (t, J=5.5, 1H, —OH); 4.25-4.06 (m, 2H); 4.13 (m, 2H); 4.00 (d, J=6.9, 2H); 3.69 (m, 1H); 3.20 (m, 1H); 3.03 (m, 1H); 2.79 (s, 3H); 1.97 (m, 2H); 1.55 (m, 1H); 1.43 (m, 1H); 0.98 (m, 1H); 0.39 (m, 2H); 0.27 (m, 2H).

Example F58

4-[2-(Cyclopropylmethoxy)-5-(trifluoromethyl)phenyl]-N-{1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-5-(trifluoromethyl)phenyl]-6-methyl-N-(piperidin-4-yl)-5H-pyrrolo[3,2-d]pyrimidine-7-carboxamide hydrochloride (example D.f31) and commercially available (2S)-1-chloro-1-oxopropan-2-yl acetate the title compound is obtained as colorless solid.

MS (ESI): m/z=546 (MH+, 100%).

$^1$H-NMR (300 MHz, DMSO-$d_6$): 11.90 (s, 1H, —NH); 8.99 (s, 1H); 8.80 (d, J=7.5, 1H, —NH); 7.91 (d, J=2.0, 1H); 7.89 (dd, J=8.8, 2.0, 1H); 7.38 (d, J=8.8, 1H); 4.87 (d, J=6.9, 1H, —OH); 4.47 (m, 1H); 4.28-4.07 (m, 2H); 3.99 (d, J=6.9, 2H); 3.93 (m, 1H); 3.28 (m, 1H); 3.01 (m, 1H); 2.80 (s, 3H); 1.98 (m, 2H); 1.64-1.31 (m, 2H); 1.22 (br.s, 3H); 0.98 (m, 1H); 0.39 (m, 2H); 0.27 (m, 2H).

Example F59

4-[2-(Cyclopropylmethoxy)-5-(trifluoromethyl)phenyl]-N-{trans-4-[(hydroxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride (example D.f32) and commercially available 2-chloro-2-oxoethyl acetate the title compound is obtained as colorless solid.

MS (ESI): m/z=546 (MH+, 100%).

$^1$H-NMR (300 MHz, DMSO-$d_6$): 11.87 (s, 1H, —NH); 8.99 (s, 1H); 8.63 (d, J=7.7, 1H, —NH); 7.91 (d, J=2.0, 1H); 7.89 (dd, J=8.8, 2.0, 1H); 7.48 (d, J=8.2, 1H, —NH); 7.38 (d, J=8.8, 1H); 5.40 (t, J=5.9, 1H, —OH); 3.99 (d, J=6.9, 2H); 3.82 (m, 1H); 3.79 (d, J=5.9, 2H); 3.69 (m, 1H); 2.79 (s, 3H); 2.02 (m, 2H); 1.83 (m, 2H); 1.44 (m, 4H); 0.98 (m, 1H); 0.39 (m, 2H); 0.27 (m, 2H).

Example F60

4-[2-(Cyclopropylmethoxy)-5-(trifluoromethyl)phenyl]-N-(trans-4-{[(2S)-2-hydroxypropanoyl]amino}cyclohexyl)-6-methyl-5H-pyrrolo[3,2-d]pyrimidine-7-carboxamide Starting from N-(trans-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride (example D.f32) and commercially available (2S)-1-chloro-1-oxopropan-2-yl acetate the title compound is obtained as colorless solid.

MS (ESI): m/z=560 (MH+, 100%).

$^1$H-NMR (300 MHz, DMSO-$d_6$): 11.87 (s, 1H, —NH); 8.99 (s, 1H); 8.64 (d, J=7.8, 1H, —NH); 7.91 (d, J=2.0, 1H); 7.89 (dd, J=8.8, 2.0, 1H); 7.42 (d, J=8.2, 1H, —NH); 7.38 (d, J=8.8, 1H); 5.40 (d, J=5.1, 1H, —OH); 4.00 (d, J=6.9, 2H); 3.94 (m, 1H); 3.81 (m, 1H); 3.63 (m, 1H); 2.79 (s, 3H); 2.02 (m, 2H); 1.83 (m, 2H); 1.43 (m, 4H); 1.21 (d, J=6.8, 3H); 0.98 (m, 1H); 0.39 (m, 2H); 0.27 (m, 2H).

Example F61

4-[2-(Cyclopropylmethoxy)-5-(trifluoromethyl)phenyl]-N-{cis-4-[(hydroxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride (example D.f33) and commercially available 2-chloro-2-oxoethyl acetate the title compound is obtained as colorless solid.

MS (ESI): m/z=546 (MH+, 100%).

$^1$H-NMR (400 MHz, DMSO-$d_6$): 11.91 (s, 1H, —NH); 9.03 (s, 1H); 8.96 (d, J=7.3, 1H, —NH); 7.91 (s, 1H); 7.90 (d, J=8.8, 1H); 7.58 (d, J=7.8, 1H, —NH); 7.39 (d, J=8.8, 1H); 5.37 (t, J=5.9, 1H, —OH); 4.07 (m, 1H); 4.00 (d, J=7.0, 2H); 3.83 (d, J=5.9, 2H); 3.80 (m, 1H); 2.80 (s, 3H); 1.83-1.59 (m, 8H); 0.98 (m, 1H); 0.40 (m, 2H); 0.28 (m, 2H).

Example F62

4-[2-(Cyclopropylmethoxy)-5-(trifluoromethyl)phenyl]-N-(cis-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[2-(cyclopropylmethoxy)-5-(trifluoromethyl)phenyl]-6-methyl-5H-pyrrolo[3,2-d]pyrimidine-7-carboxamide hydrochloride (example D.f33) and commercially available (2S)-1-chloro-1-oxopropan-2-yl acetate the title compound is obtained as colorless solid.

MS (ESI): m/z=560 (MH+, 100%).

$^1$H-NMR (400 MHz, DMSO-$d_6$): 11.91 (s, 1H, —NH); 9.03 (s, 1H); 8.95 (d, J=7.3, 1H, —NH); 7.91 (s, 1H); 7.90 (d, J=8.8, 1H); 7.52 (d, J=7.6, 1H, —NH); 7.39 (d, J=8.8, 1H); 5.40 (d, J=5.5, 1H, —OH); 4.06 (m, 1H); 4.00 (d, J=7.0, 2H & m, 1H); 3.75 (m, 1H); 2.80 (s, 3H); 1.83-1.57 (m, 8H); 1.22 (d, J=6.8, 3H); 0.98 (m, 1H); 0.40 (m, 2H); 0.28 (m, 2H).

Example F63

4-[2-Ethoxy-5-(trifluoromethyl)phenyl]-N-[1-(hydroxyacetyl)piperidin-4-yl]-6-methyl-5H-pyrrolo[3,2-d]pyrimidine-7-carboxamide Starting from 4-[2-ethoxy-5-(trifluoromethyl)phenyl]-6-methyl-N-(piperidin-4-yl)-5H-pyrrolo[3,2-d]pyrimidine-7-carboxamide hydrochloride (example D.f34) and commercially available 2-chloro-2-oxoethyl acetate the title compound is obtained as colorless solid.

MS (ESI): m/z=506 (MH+, 100%).

$^1$H-NMR (400 MHz, DMSO-$d_6$): 11.93 (br.s, 1H, —NH); 8.98 (s, 1H); 8.79 (d, J=7.7, 1H, —NH); 7.92 (d, J=2.2, 1H); 7.91 (dd, J=9.4, 2.2, 1H); 7.42 (d, J=9.4, 1H); 4.50 (t, J=5.4, 1H, —OH); 4.21 (qu, J=7.0, 2H); 4.18-4.07 (m, 4H); 3.68 (m, 1H); 3.20 (m, 1H); 3.03 (m, 1H); 2.79 (s, 3H); 1.97 (m, 2H); 1.55 (m, 1H); 1.42 (m, 1H); 1.16 (t, J=7.0, 3H).

Example F64

4-[2-Ethoxy-5-(trifluoromethyl)phenyl]-N-{1-[(2S)-2-hydroxypropanoyl]piperidin-4-yl}-6-methyl-5H-pyrrolo[3,2-d]pyrimidine-7-carboxamide Starting from 4-[2-ethoxy-5-(trifluoromethyl)phenyl]-6-methyl-N-(piperidin-4-yl)-5H-pyrrolo[3,2-d]pyrimidine-7-carboxamide hydrochloride (example D.f34) and commercially available (2S)-1-chloro-1-oxopropan-2-yl acetate the title compound is obtained as colorless solid.

MS (ESI): m/z=520 (MH+, 100%).

$^1$H-NMR (400 MHz, DMSO-d$_6$): 11.93 (br.s, 1H, —NH); 8.98 (s, 1H); 8.79 (d, J=7.8, 1H, —NH); 7.92 (d, J=2.2, 1H); 7.91 (dd, J=9.5, 2.2, 1H); 7.42 (d, J=9.5, 1H); 4.86 (d, J=6.6, 1H, —OH); 4.46 (m, 1H); 4.21 (qu, J=7.0, 2H); 4.18-4.09 (m, 2H); 3.95 (m, 1H); 3.28 (m, 1H); 3.00 (m, 1H); 2.79 (s, 3H); 1.98 (m, 2H); 1.54 (m, 1H); 1.42 (m, 1H); 1.21 (br.s, 3H); 1.16 (t, J=7.0, 3H).

Example F65

4-[2-(Cyclopropylmethoxy)-4-fluoro-5-methoxyphenyl]-N-(1-glycoloylpiperidin-4-yl)-6-methyl-5H-pyrrolo[3,2-d]pyrimidine-7-carboxamide Starting from 4-[2-(cyclopropylmethoxy)-4-fluoro-5-methoxyphenyl]-6-methyl-N-piperidin-4-yl-5H-pyrrolo[3,2-d]pyrimidine-7-carboxamide hydrochloride (example D.f35) and commercially available 2-chloro-2-oxoethyl acetate the title compound is obtained as colorless solid.

MS (ESI): m/z=512 (MH+, 100%).

$^1$H-NMR (300 MHz, DMSO-d$_6$): 11.77 (s, 1H, —NH); 8.96 (s, 1H); 8.81 (d, J=7.5, 1H, —NH); 7.39 (d, J=9.9, 1H); 7.18 (d, J=13.3, 1H); 4.50 (t, J=5.5, 1H, —OH); 4.24-4.04 (m, 2H); 4.13 (m, 2H); 3.84 (s, 3H & d, J=6.8, 2H); 3.68 (m, 1H); 3.20 (m, 1H); 3.02 (m, 1H); 2.79 (s, 3H); 1.97 (m, 2H); 1.54 (m, 1H); 1.42 (m, 1H); 0.93 (m, 1H); 0.36 (m, 2H); 0.21 (m, 2H).

Example F66

4-[2-(Cyclopropylmethoxy)-4-fluoro-5-methoxyphenyl]-N-{1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-4-fluoro-5-methoxyphenyl]-6-methyl-N-piperidin-4-yl-5H-pyrrolo[3,2-d]pyrimidine-7-carboxamide hydrochloride (example D.f35) and commercially available (2S)-1-chloro-1-oxopropan-2-yl acetate the title compound is obtained as colorless solid.

MS (ESI): m/z=526 (MH+, 100%).

$^1$H-NMR (300 MHz, DMSO-d$_6$): 11.75 (s, 1H, —NH); 8.96 (s, 1H); 8.81 (d, J=7.5, 1H, —NH); 7.39 (d, J=9.9, 1H); 7.18 (d, J=13.3, 1H); 4.86 (d, J=6.9, 1H, —OH); 4.47 (m, 1H); 4.27-4.06 (m, 2H); 3.95 (m, 1H); 3.84 (s, 3H & d, J=6.9, 2H); 3.28 (m, 1H); 3.00 (m, 1H); 2.79 (s, 3H); 1.98 (m, 2H); 1.53 (m, 1H); 1.42 (m, 1H); 1.21 (br.s, 3H); 0.93 (m, 1H); 0.36 (m, 2H); 0.21 (m, 2H).

Example F67

4-[2-(Cyclopropylmethoxy)-4-fluoro-5-methoxyphenyl]-N-[trans-4-(glycoloylamino)cyclohexyl]-6-methyl-5H-pyrrolo[3,2-d]pyrimidine-7-carboxamide Starting from N-(trans-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride (example D.f36) and commercially available 2-chloro-2-oxoethyl acetate the title compound is obtained as colorless solid.

MS (ESI): m/z=526 (MH+, 100%).

$^1$H-NMR (300 MHz, DMSO-d$_6$): 11.73 (s, 1H, —NH); 8.96 (s, 1H); 8.64 (s, J=7.7, 1H, —NH); 7.47 (d, J=8.2, 1H, —NH); 7.39 (d, J=9.9, 1H); 7.18 (d, J=13.3, 1H); 5.40 (t, J=5.8, 1H, —OH); 3.84 (s, 3H & d, J=6.8, 2H); 3.79 (d, J=5.8, 2H & m, 1H); 3.68 (m, 1H); 2.78 (s, 3H); 2.01 (m, 2H); 1.83 (m, 2H); 1.44 (m, 4H); 0.93 (m, 1H); 0.36 (m, 2H); 0.21 (m, 2H).

Example F68

4-[2-(Cyclopropylmethoxy)-4-fluoro-5-methoxyphenyl]-N-(trans-4-{[(2S)-2-hydroxypropanoyl]amino}cyclohexyl)-6-methyl-5H-pyrrolo[3,2-d]pyrimidine-7-carboxamide Starting from N-(trans-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride (example D.f36) and commercially available (2S)-1-chloro-1-oxopropan-2-yl acetate the title compound is obtained as colorless solid.

MS (ESI): m/z=540 (MH+, 100%).

$^1$H-NMR (300 MHz, DMSO-d$_6$): 11.73 (s, 1H, —NH); 8.96 (s, 1H); 8.64 (d, J=7.7, 1H, —NH); 7.42 (d, J=8.1, 1H, —NH); 7.39 (d, J=9.9, 1H); 7.18 (d, J=13.3, 1H); 5.40 (d, J=5.1, 1H, —OH); 3.94 (m, 1H); 3.84 (s, 3H & d, J=6.8, 2H); 3.79 (d, J=5.8, 2H & m, 1H); 3.63 (m, 1H); 2.78 (s, 3H); 2.01 (m, 2H); 1.82 (m, 2H); 1.43 (m, 4H); 1.21 (d, J=6.7, 3H); 0.93 (m, 1H); 0.36 (m, 2H); 0.21 (m, 2H).

Example F69

4-[2-(Cyclopropylmethoxy)-4-fluoro-5-methoxyphenyl]-N-[cis-4-(glycoloylamino)cyclohexyl]-6-methyl-5H-pyrrolo[3,2-d]pyrimidine-7-carboxamide Starting from N-(cis-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride (example D.f37) and commercially available 2-chloro-2-oxoethyl acetate the title compound is obtained as colorless solid.

MS (ESI): m/z=526 (MH+, 100%).

$^1$H-NMR (300 MHz, DMSO-d$_6$): 11.74 (s, 1H, —NH); 8.99 (s, 1H); 8.95 (d, J=7.5, 1H, —NH); 7.52 (d, J=7.7, 1H, —NH); 7.43 (d, J=9.9, 1H); 7.19 (d, J=13.3, 1H); 5.33 (t, J=5.1, 1H, —OH); 4.06 (m, 1H); 3.85 (s, 3H & d, J=6.9, 2H); 3.82 (d, J=5.1, 2H & m, 1H); 2.79 (s, 3H); 1.72 (m, 8H); 0.93 (m, 1H); 0.37 (m, 2H); 0.22 (m, 2H).

Example F70

4-[2-(Cyclopropylmethoxy)-4-fluoro-5-methoxyphenyl]-N-(cis-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[2-(cyclopropylmethoxy)-4-fluoro-5-methoxyphenyl]-6-methyl-5H-pyrrolo[3,2-d]pyrimidine-7-carboxamide hydrochloride (example D.f37) and commercially available (2S)-1-chloro-1-oxopropan-2-yl acetate the title compound is obtained as colorless solid.

MS (ESI): m/z=540 (MH$^+$, 100%).

$^1$H-NMR (300 MHz, DMSO-d$_6$): 11.74 (s, 1H, —NH); 8.99 (s, 1H); 8.94 (d, J=7.5, 1H, —NH); 7.47 (d, J=7.8, 1H, —NH); 7.40 (d, J=9.9, 1H); 7.18 (d, J=13.3, 1H); 5.36 (d, J=5.5, 1H, —OH); 4.04 (m, 1H); 3.99 (m, 1H); 3.85 (s, 3H & d, J=6.9, 2H); 3.75 (m, 1H); 2.79 (s, 3H); 1.71 (m, 8H); 1.22 (d, J=6.7, 3H); 0.93 (m, 1H); 0.36 (m, 2H); 0.21 (m, 2H).

Example F71

4-[2-(Cyclopropylmethoxy)-4-fluoro-5-methoxyphenyl]-N-[(3R*,4R*)-1-glycoloyl-3-hydroxypiperidin-4-yl]-6-methyl-5H-pyrrolo[3,2-d]pyrimidine-7-carboxamide Starting from 4-[2-(cyclopropylmethoxy)-4-fluoro-5-methoxyphenyl]-N-[(3R*,4R*)-3-hydroxypiperidin-4-yl]-6-methyl-5H-pyrrolo[3,2-d]pyrimidine-7-carboxamide hydrochloride (example D.f38) and commercially available 2-chloro-2-oxoethyl acetate the title compound is obtained as colorless solid.

HR-MS (ESI): m/z=528.2258 ([MH]$^+$, C$_{26}$H$_{31}$FN$_5$O$_6^+$, calc. 528.2253).

Example F72

Diastereomeric mixture of 4-[2-(Cyclopropylmethoxy)-4-fluoro-5-methoxyphenyl]-N-[(rac.-3R,4R)-3-hydroxy-1-[(2S)-2-hydroxypropanoyl]piperidin-4-yl]-6-methyl-5H-pyrrolo[3,2-d]pyrimidine-7-carboxamide and 4-[2-(Cyclopropylmethoxy)-4-fluoro-5-methoxyphenyl]-N-{(rac.-3S,4S)-3-hydroxy-1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-4-fluoro-5-methoxyphenyl]-N-[(3R*,4R*)-3-hydroxypiperidin-4-yl]-6-methyl-5H-pyrrolo[3,2-d]pyrimidine-7-carboxamide hydrochloride (example D.f38) and commercially available (2S)-1-chloro-1-oxopropan-2-yl acetate the title compound is obtained as colorless solid.

HR-MS (ESI): m/z=542.2410 ([MH]$^+$, C$_{27}$H$_{33}$FN$_5$O$_6^+$, calc. 542.2409).

Example F73

4-[2-(Cyclopropylmethoxy)-4-fluoro-5-methoxyphenyl]-N-[(3S*,4S*)-1-glycoloyl-4-hydroxypiperidin-3-yl]-6-methyl-5H-pyrrolo[3,2-d]pyrimidine-7-carboxamide Starting from 4-[2-(cyclopropylmethoxy)-4-fluoro-5-methoxyphenyl]-N-[(3S*,4S*)-4-hydroxypiperidin-3-yl]-6-methyl-5H-pyrrolo[3,2-d]pyrimidine-7-carboxamide hydrochloride (example D.f39) and commercially available 2-chloro-2-oxoethyl acetate the title compound is obtained as colorless solid.

HR-MS (ESI): m/z=528.2252 ([MH]$^+$, C$_{26}$H$_{31}$FN$_5$O$_6^+$, calc. 528.2253).

Example F74

Diastereomeric mixture of 4-[2-(Cyclopropylmethoxy)-4-fluoro-5-methoxyphenyl]-N-{(rac.-3S,4S)-4-hydroxy-1-[(2S)-2-hydroxypropanoyl]piperidin-3-yl}-6-methyl-5H-pyrrolo[3,2-d]pyrimidine-7-carboxamide and 4-[2-(Cyclopropylmethoxy)-4-fluoro-5-methoxyphenyl]-N-{(rac.-3R,4R)-4-hydroxy-1-[(2S)-2-hydroxypropanoyl]piperidin-3-yl}-6-methyl-5H-pyrrolo[3,2-d]pyrimidine-7-carboxamide Starting from 4-[2-(cyclopropylmethoxy)-4-fluoro-5-methoxyphenyl]-N-[(3S*,4S*)-4-hydroxypiperidin-3-yl]-6-methyl-5H-pyrrolo[3,2-d]pyrimidine-7-carboxamide hydrochloride (example D.f39) and commercially available (2S)-1-chloro-1-oxopropan-2-yl acetate the title compound is obtained as colorless solid.

HR-MS (ESI): m/z=542.2393 ([MH]$^+$, C$_{27}$H$_{33}$FN$_5$O$_6^+$, calc. 542.2409).

Example F75

4-[2-(Cyclopropylmethoxy)-4-fluoro-5-methylphenyl]-N-[1-(hydroxyacetyl)piperidin-4-yl]-6-methyl-5H-pyrrolo[3,2-d]pyrimidine-7-carboxamide Starting from 4-[2-(cyclopropylmethoxy)-4-fluoro-5-methylphenyl]-6-methyl-N-(piperidin-4-yl)-5H-pyrrolo[3,2-d]pyrimidine-7-carboxamide hydrochloride (example D.f40) and commercially available 2-chloro-2-oxoethyl acetate the title compound is obtained as colorless solid.

MS (ESI): m/z=496 (MH$^+$, 100%).

$^1$H-NMR (300 MHz, DMSO-d$_6$): 11.75 (s, 1H, —NH); 8.93 (s, 1H); 8.81 (d, J=7.7, 1H, —NH); 7.53 (d, J=9.0, 1H); 7.03 (d, J=12.0, 1H); 4.50 (t, J=5.5, 1H, —OH); 4.25-4.05 (m, 2H & m, 2H); 3.87 (d, J=6.9, 2H); 3.68 (m, 1H); 3.20 (m, 1H); 3.02 (m, 1H); 2.78 (s, 3H); 2.25 (d, J=1.3, 3H); 1.97 (m, 2H); 1.53 (m, 1H); 1.42 (m, 1H); 0.95 (m, 1H); 0.37 (m, 2H); 0.24 (m, 2H).

Example F76

4-[2-(Cyclopropylmethoxy)-4-fluoro-5-methylphenyl]-N-{1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-4-fluoro-5-methylphenyl]-6-methyl-N-(piperidin-4-yl)-5H-pyrrolo[3,2-d]pyrimidine-7-carboxamide hydrochloride (example D.f40) and commercially available (2S)-1-chloro-1-oxopropan-2-yl acetate the title compound is obtained as colorless solid.

MS (ESI): m/z=510 (MH$^+$, 100%).

$^1$H-NMR (300 MHz, DMSO-d$_6$): 11.75 (s, 1H, —NH); 8.93 (s, 1H); 8.81 (d, J=7.7, 1H, —NH); 7.54 (dd, J=9.1, 0.6, 1H); 7.03 (d, J=12.0, 1H); 4.86 (d, J=6.9, 1H, —OH); 4.46 (m, 1H); 4.27-4.07 (m, 2H); 3.95 (m, 1H); 3.87 (d, J=6.9, 2H); 317 (m, 1H); 3.00 (m, 1H); 2.78 (s, 3H); 2.25 (d, J=1.3, 3H);

1.98 (m, 2H); 1.62-1.31 (m, 2H); 1.22 (br.s, 3H); 0.95 (m, 1H); 0.37 (m, 2H); 0.24 (m, 2H).

Example F77

4-[2-(Cyclopropylmethoxy)-4-fluoro-5-methylphenyl]-N-{trans-4-[(hydroxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride (example D.f41) and commercially available 2-chloro-2-oxoethyl acetate the title compound is obtained as colorless solid.

MS (ESI): m/z=510 (MH$^+$, 100%).
$^1$H-NMR (300 MHz, DMSO-$d_6$): 11.72 (s, 1H, —NH); 8.93 (s, 1H); 8.65 (d, J=7.7, 1H, —NH); 7.53 (d, J=9.1, 1H); 7.47 (d, J=8.2, 1H, —NH); 7.03 (d, J=12.2, 1H); 5.40 (t, J=5.7, 1H, —OH); 3.87 (d, J=6.9, 2H); 3.79 (m, 1H & d, J=5.7, 2H); 3.68 (m, 1H); 2.77 (s, 3H); 2.25 (d, J=1.1, 3H); 2.01 (m, 2H); 1.82 (m, 2H); 1.44 (m, 4H); 0.95 (m, 1H); 0.37 (m, 2H); 0.24 (m, 2H).

Example F78

4-[2-(Cyclopropylmethoxy)-4-fluoro-5-methylphenyl]-N-(trans-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride (example D.f41) and commercially available (2S)-1-chloro-1-oxopropan-2-yl acetate the title compound is obtained as colorless solid.

MS (ESI): m/z=524 (MH$^+$, 100%).
$^1$H-NMR (300 MHz, DMSO-$d_6$): 11.72 (s, 1H, —NH); 8.94 (s, 1H); 8.65 (d, J=7.7, 1H, —NH); 7.54 (d, J=9.1, 1H); 7.42 (d, J=8.4, 1H, —NH); 7.03 (d, J=12.2, 1H); 5.40 (d, J=5.2, 1H, —OH); 3.94 (dt, J=6.8, 5.2, 2H); 3.87 (d, J=6.9, 2H); 3.80 (m, 1H); 3.63 (m, 1H); 2.77 (s, 3H); 2.25 (d, J=1.1, 3H); 2.01 (m, 2H); 1.82 (m, 2H); 1.42 (m, 4H); 1.21 (d, J=6.8, 3H); 0.95 (m, 1H); 0.37 (m, 2H); 0.24 (m, 2H).

Example F79

4-[2-(Cyclopropylmethoxy)-4-fluoro-5-methylphenyl]-N-{cis-4-[(hydroxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride (example D.f42) and commercially available 2-chloro-2-oxoethyl acetate the title compound is obtained as colorless solid.

MS (ESI): m/z=510 (MH$^+$, 100%).
$^1$H-NMR (300 MHz, DMSO-$d_6$): 11.73 (s, 1H, —NH); 8.97 (s, 1H); 8.96 (d, J=7.3, 1H, —NH); 7.54 (d, J=9.1, 1H & d, J=7.5, 1H, —NH); 7.04 (d, J=12.2, 1H); 5.33 (t, J=5.8, 1H, —OH); 4.06 (m, 1H); 3.88 (d, J=6.9, 2H); 3.82 (d, J=5.8, 2H); 3.80 (m, 1H); 2.78 (s, 3H); 2.25 (d, J=0.9, 3H); 1.81-1.59 (m, 8H); 0.95 (m, 1H); 0.37 (m, 2H); 0.24 (m, 2H).

Example F80

4-[2-(Cyclopropylmethoxy)-4-fluoro-5-methylphenyl]-N-(cis-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[2-(cyclopropylmethoxy)-4-fluoro-5-methylphenyl]-6-methyl-5H-pyrrolo[3,2-d]pyrimidine-7-carboxamide hydrochloride (example D.f42) and commercially available (2S)-1-chloro-1-oxopropan-2-yl acetate the title compound is obtained as colorless solid.

MS (ESI): m/z=524 (MH$^+$, 100%).
$^1$H-NMR (300 MHz, DMSO-$d_6$): 11.73 (s, 1H, —NH); 8.97 (s, 1H); 8.95 (d, J=7.8, 1H, —NH); 7.54 (d, J=9.1, 1H); 7.48 (d, J=7.8, 1H, —NH); 7.04 (d, J=12.2, 1H); 5.36 (d, J=5.5, 1H, —OH); 4.05 (m, 1H); 3.99 (dt, J=6.8, 5.5, 1H); 3.88 (d, J=6.9, 2H); 3.75 (m, 1H); 2.78 (s, 3H); 2.25 (d, J=0.9, 3H); 1.80-1.59 (m, 8H); 1.22 (d, J=6.8, 3H); 0.95 (m, 1H); 0.37 (m, 2H); 0.24 (m, 2H).

Example F81

4-[2-(Cyclopropylmethoxy)-4-fluoro-5-methylphenyl]-N-[(3R*,4R*)-3-hydroxy-1-(hydroxyacetyl)piperidin-4-yl]-6-methyl-5H-pyrrolo[3,2-d]pyrimidine-7-carboxamide Starting from 4-[2-(cyclopropylmethoxy)-4-fluoro-5-methylphenyl]-N-[(3R*,4R*)-3-hydroxypiperidin-4-yl]-6-methyl-5H-pyrrolo[3,2-d]pyrimidine-7-carboxamide hydrochloride (example D.f43) and commercially available 2-chloro-2-oxoethyl acetate the title compound is obtained as colorless solid.

HR-MS (ESI): m/z=512.2324 ([MH]$^+$, $C_{26}H_{31}FN_5O_5^+$, calc. 512.2304).

Example F82

Diastereomeric mixture of 4-[2-(Cyclopropylmethoxy)-4-fluoro-5-methylphenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide and 4-[2-(Cyclopropylmethoxy)-4-fluoro-5-methylphenyl]-N{(3S,4S)-3-hydroxy-1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-4-fluoro-5-methylphenyl]-N-[(3R*,4R*)-3-hydroxypiperidin-4-yl]-6-methyl-5H-pyrrolo[3,2-d]pyrimidine-7-carboxamide hydrochloride (example D.f43) and commercially available (2S)-1-chloro-1-oxopropan-2-yl acetate the title compound is obtained as colorless solid.

HR-MS (ESI): m/z=526.2470 ([MH]$^+$, $C_{27}H_{33}FN_5O_5^+$, calc. 526.2460).

Example F83

4-[2-(Cyclopropylmethoxy)-5-fluoro-4-methoxyphenyl]-N-(1-glycoloylpiperidin-4-yl)-6-methyl-5H-pyrrolo[3,2-d]pyrimidine-7-carboxamide Starting from 4-[2-(cyclopropylmethoxy)-5-fluoro-4-methoxyphenyl]-6-methyl-N-piperidin-4-yl-5H-pyrrolo[3,2-d]pyrimidine-7-carboxamide hydrochloride (example D.f44) and commercially available 2-chloro-2-oxoethyl acetate the title compound is obtained as colorless solid.

MS (ESI): m/z=512 (MH+, 100%).

$^1$H-NMR (300 MHz, DMSO-$d_6$): 11.73 (br.s, 1H, —NH); 8.92 (s, 1H); 8.82 (d, J=7.7, 1H, —NH); 7.47 (d, J=11.9, 1H); 6.92 (d, J=7.3, 1H); 4.50 (t, J=5.3, 1H, —OH); 4.22-4.06 (m, 2H & d, J=5.3, 2H); 3.97 (s, 3H); 3.94 (d, J=6.9, 2H); 3.68 (m, 1H); 3.19 (m, 1H); 3.02 (m, 1H); 2.79 (s, 3H); 1.96 (m, 2H); 1.54 (m, 1H); 1.41 (m, 1H); 0.96 (m, 1H); 0.38 (m, 2H); 0.25 (m, 2H).

Example F84

4-[2-(Cyclopropylmethoxy)-5-fluoro-4-methoxyphenyl]-N-{1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-5-fluoro-4-methoxyphenyl]-6-methyl-N-piperidin-4-yl-5H-pyrrolo[3,2-d]pyrimidine-7-carboxamide hydrochloride (example D.f44) and commercially available (2S)-1-chloro-1-oxopropan-2-yl acetate the title compound is obtained as colorless solid.

MS (ESI): m/z=526 (MH+, 100%).

$^1$H-NMR (300 MHz, DMSO-$d_6$): 11.73 (br.s, 1H, —NH); 8.92 (s, 1H); 8.82 (d, J=7.7, 1H, —NH); 7.47 (d, J=11.9, 1H); 6.92 (d, J=7.3, 1H); 4.86 (d, J=6.9, 1H, —OH); 4.46 (m, 1H); 4.28-4.07 (m, 2H); 3.97 (s, 3H); 3.94 (d, J=6.9, 2H); 3.30 (m, 1H); 3.00 (m, 1H); 2.79 (s, 3H); 1.98 (m, 2H); 1.53 (m, 1H); 1.41 (m, 1H); 1.21 (br.s, 3H); 0.96 (m, 1H); 0.38 (m, 2H); 0.25 (m, 2H).

Example F85

4-[2-(Cyclopropylmethoxy)-5-fluoro-4-methoxyphenyl]-N-[trans-4-(glycoloylamino)cyclohexyl]-6-methyl-5H-pyrrolo[3,2-d]pyrimidine-7-carboxamide Starting from N-(trans-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride (example D.f45) and commercially available 2-chloro-2-oxoethyl acetate the title compound is obtained as colorless solid.

MS (ESI): m/z=526 (MH+, 100%).

$^1$H-NMR (300 MHz, DMSO-$d_6$): 11.70 (s, 1H, —NH); 8.92 (s, 1H); 8.66 (d, J=7.7, 1H, —NH); 7.47 (d, J=8.2, 1H, —NH & d, J=11.7, 1H); 6.93 (d, J=7.3, 1H); 5.40 (t, J=5.8, 1H, —OH); 3.97 (s, 3H); 3.94 (d, J=6.9, 2H); 3.79 (m, 1H & d, J=5.8, 2H); 3.69 (m, 1H); 2.78 (s, 3H); 2.01 (m, 2H); 1.82 (m, 2H); 1.44 (m, 4H); 0.96 (m, 1H); 0.38 (m, 2H); 0.25 (m, 2H).

Example F86

4-[2-(Cyclopropylmethoxy)-5-fluoro-4-methoxyphenyl]-N-(trans-4-{[(2S)-2-hydroxypropanoyl]amino}cyclohexyl)-6-methyl-5H-pyrrolo[3,2-d]pyrimidine-7-carboxamide Starting from N-(trans-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride (example D.f45) and commercially available (2S)-1-chloro-1-oxopropan-2-yl acetate the title compound is obtained as colorless solid.

MS (ESI): m/z=540 (MH+, 100%).

$^1$H-NMR (300 MHz, DMSO-$d_6$): 11.70 (s, 1H, —NH); 8.92 (s, 1H); 8.65 (d, J=7.7, 1H, —NH); 7.47 (d, J=11.9, 1H); 7.42 (d, J=8.2, 1H, —NH); 6.92 (d, J=7.3, 1H); 5.40 (d, J=5.1, 1H, —OH); 3.97 (s, 3H); 3.94 (d, J=6.9, 2H & m, 1H); 3.80 (m, 1H); 3.63 (m, 1H); 2.78 (s, 3H); 2.00 (m, 2H); 1.82 (m, 2H); 1.42 (m, 4H); 1.21 (d, J=6.7, 3H); 0.96 (m, 1H); 0.38 (m, 2H); 0.25 (m, 2H).

Example F87

4-[2-(Cyclopropylmethoxy)-5-fluoro-4-methoxyphenyl]-N-[cis-4-(glycoloylamino)cyclohexyl]-6-methyl-5H-pyrrolo[3,2-d]pyrimidine-7-carboxamide Starting from N-(cis-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride (example D.f46) and commercially available 2-chloro-2-oxoethyl acetate the title compound is obtained as colorless solid.

MS (ESI): m/z=526 (MH+, 100%).

$^1$H-NMR (300 MHz, DMSO-$d_6$): 11.70 (s, 1H, —NH); 8.97 (d, J=7.7, 1H, —NH); 8.95 (s, 1H); 7.53 (d, J=7.8, 1H, —NH); 7.47 (d, J=11.9, 1H); 6.93 (d, J=7.3, 1H); 5.33 (t, J=5.8, 1H, —OH); 4.06 (m, 1H); 3.97 (s, 3H); 3.94 (d, J=7.1, 2H); 3.82 (d, J=5.8, 1H); 3.80 (m, 1H); 2.79 (s, 3H); 1.82-1.59 (m, 8H); 0.96 (m, 1H); 0.39 (m, 2H); 0.25 (m, 2H).

Example F88

4-[2-(Cyclopropylmethoxy)-5-fluoro-4-methoxyphenyl]-N-(cis-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[2-(cyclopropylmethoxy)-5-fluoro-4-methoxyphenyl]-6-methyl-5H-pyrrolo[3,2-d]pyrimidine-7-carboxamide hydrochloride (example D.f46) and commercially available (2S)-1-chloro-1-oxopropan-2-yl acetate the title compound is obtained as colorless solid.

MS (ESI): m/z=540 (MH+, 100%).

$^1$H-NMR (300 MHz, DMSO-$d_6$): 11.70 (s, 1H, —NH); 8.96 (s, 1H & d, J=7.3, 1H, —NH); 7.47 (d, J=11.9, 1H); 7.46 (d, J=7.7, 1H, —NH); 6.93 (d, J=7.3, 1H); 5.36 (d, J=5.5, 1H, —OH); 4.05 (m, 1H); 4.00 (m, 1H); 3.97 (s, 3H); 3.94 (d, J=6.9, 2H); 3.75 (m, 1H); 2.79 (s, 3H); 1.80-1.58 (m, 8H); 1.22 (d, J=6.8, 3H); 0.96 (m, 1H); 0.39 (m, 2H); 0.25 (m, 2H).

Example F89

4-[2-(cyclopropylmethoxy)-5-fluoro-4-methoxyphenyl]-N-[(3R*,4R*)-3-hydroxy-1-(hydroxyacetyl)piperidin-4-yl]-6-methyl-5H-pyrrolo[3,2-d]pyrimidine-7-carboxamide Starting from 4-[2-(cyclopropylmethoxy)-5-fluoro-4-methoxyphenyl]-N-[(3R*,4R*)-3-hydroxypiperidin-4-yl]-6-methyl-5H-pyrrolo[3,2-d]pyrimidine-7-carboxamide hydrochloride (example D.f47) and commercially available 2-chloro-2-oxoethyl acetate the title compound is obtained as colorless solid.

HR-MS (ESI): m/z=528.2267 ([MH]+, $C_{26}H_{31}FN_5O_6^+$, calc. 528.2253).

Example F90

Diastereomeric mixture of 4-[2-(Cyclopropylmethoxy)-5-fluoro-4-methoxyphenyl]-N-{(3R,4R)-3-hydroxy-1-[(2S)-2-hydroxypropanoyl]piperidin-4-yl}-6-methyl-5H-pyrrolo[3,2-d]pyrimidine-7-carboxamide and 4-[2-(Cyclopropylmethoxy)-5-fluoro-4-methoxyphenyl]-N-{(3S,4S)-3-hydroxy-1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-5-fluoro-4-methoxyphenyl]-N-[(3R*,4R*)-3-hydroxypiperidin-4-yl]-6-methyl-5H-pyrrolo[3,2-d]pyrimidine-7-carboxamide hydrochloride (example D.f47) and commercially available (2S)-1-chloro-1-oxopropan-2-yl acetate the title compound is obtained as colorless solid.
HR-MS (ESI): m/z=542.2406 ([MH]$^+$, $C_{27}H_{33}FN_5O_6^+$, calc. 542.2409).

Example F91

4-[2-(Cyclopropylmethoxy)-5-ethylphenyl]-N-[1-(hydroxyacetyl)piperidin-4-yl]-6-methyl-5H-pyrrolo[3,2-d]pyrimidine-7-carboxamide Starting from 4-[2-(cyclopropylmethoxy)-5-ethylphenyl]-6-methyl-N-(piperidin-4-yl)-5H-pyrrolo[3,2-d]pyrimidine-7-carboxamide hydrochloride (example D.f48) and commercially available 2-chloro-2-oxoethyl acetate the title compound is obtained as colorless solid.
MS (ESI): m/z=492 (MH$^+$, 100%).
$^1$H-NMR (300 MHz, DMSO-d$_6$): 11.76 (s, 1H, —NH); 8.94 (s, 1H); 8.83 (d, J=7.7, 1H, —NH); 7.45 (d, J=2.2, 1H); 7.36 (dd, J=8.4, 2.2, 1H); 7.08 (d, J=8.4, 1H); 4.49 (br.s, 1H, —OH); 4.24-4.03 (m, 2H); 4.13 (d, J=4.6, 2H); 3.87 (d, J=6.9, 2H); 3.68 (m, 1H); 3.22 (m, 1H); 3.03 (m, 1H); 2.78 (s, 3H); 2.64 (qu, J=7.5, 2H); 1.97 (m, 2H); 1.54 (m, 1H); 1.42 (m, 1H); 1.18 (t, J=7.5, 3H); 0.94 (m, 1H); 0.36 (m, 2H); 0.23 (m, 2H).

Example F92

4-[2-(Cyclopropylmethoxy)-5-ethylphenyl]-N-{1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-5-ethylphenyl]-6-methyl-N-(piperidin-4-yl)-5H-pyrrolo[3,2-d]pyrimidine-7-carboxamide hydrochloride (example D.f48) and commercially available (2S)-1-chloro-1-oxopropan-2-yl acetate the title compound is obtained as colorless solid.
MS (ESI): m/z=505 (MH$^+$, 100%).
$^1$H-NMR (300 MHz, DMSO-d$_6$): 11.75 (s, 1H, —NH); 8.95 (s, 1H); 8.83 (d, J=7.5, 1H, —NH); 7.45 (d, J=2.4, 1H); 7.36 (dd, J=8.6, 2.4, 1H); 7.08 (d, J=8.6, 1H); 4.86 (d, J=6.9, 1H, —OH); 4.47 (m, 1H); 4.25-4.11 (m, 2H); 3.95 (m, 1H); 3.87 (d, J=6.9, 2H); 3.27 (m, 1H); 3.00 (m, 1H); 2.78 (s, 3H); 2.64 (qu, J=7.6, 2H); 1.98 (m, 2H); 1.53 (m, 1H); 1.42 (m, 1H); 1.21 (br.s, 3H); 1.18 (t, J=7.6, 3H); 0.94 (m, 1H); 0.36 (m, 2H); 0.23 (m, 2H).

Example F93

4-[2-(Cyclopropylmethoxy)-5-ethylphenyl]-N-{trans-4-[(hydroxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-5-ethylphenyl]-6-methyl-5H-pyrrolo[3,2-d]pyrimidine-7-carboxamide hydrochloride (example D.f49) and commercially available 2-chloro-2-oxoethyl acetate the title compound is obtained as colorless solid.
MS (ESI): m/z=506 (MH$^+$, 100%).
$^1$H-NMR (300 MHz, DMSO-d$_6$): 11.72 (br.s, 1H, —NH); 8.95 (s, 1H); 8.66 (d, J=7.9, 1H, —NH); 7.48 (d, J=8.4, 1H, —NH); 7.45 (d, J=2.4, 1H); 7.35 (dd, J=8.6, 2.4, 1H); 7.08 (d, J=8.6, 1H); 5.40 (t, J=5.7, 1H, —OH); 3.87 (d, J=6.9, 2H); 3.79 (d, J=5.7, 2H & m, 1H); 3.68 (m, 1H); 2.77 (s, 3H); 2.64 (qu, J=7.5, 2H); 2.02 (m, 2H); 1.83 (m, 2H); 1.44 (m, 4H); 1.18 (t, J=7.5, 3H); 0.94 (m, 1H); 0.36 (m, 2H); 0.22 (m, 2H).

Example F94

4-[2-(Cyclopropylmethoxy)-5-ethylphenyl]-N-(trans-4-{[(2S)-2-hydroxypropanoyl]amino}cyclohexyl)-6-methyl-5H-pyrrolo[3,2-d]pyrimidine-7-carboxamide Starting from N-(trans-4-aminocyclohexyl)-4-[2-(cyclopropylmethoxy)-5-ethylphenyl]-6-methyl-5H-pyrrolo[3,2-d]pyrimidine-7-carboxamide hydrochloride (example D.f49) and commercially available (2S)-1-chloro-1-oxopropan-2-yl acetate the title compound is obtained as colorless solid.
MS (ESI): m/z=520 (MH$^+$, 100%).
$^1$H-NMR (300 MHz, DMSO-d$_6$): 11.72 (s, 1H, —NH); 8.95 (s, 1H); 8.66 (d, J=7.8, 1H, —NH); 7.45 (d, J=2.4, 1H); 7.42 (d, J=8.4, 1H, —NH); 7.36 (dd, J=8.6, 2.4, 1H); 7.08 (d, J=8.6, 1H); 5.40 (t, J=5.1, 1H, —OH); 3.94 (m, 1H); 3.86 (d, J=6.9, 2H); 3.82 (m, 1H); 3.63 (m, 1H); 2.77 (s, 3H); 2.64 (qu, J=7.5, 2H); 2.00 (m, 2H); 1.82 (m, 2H); 1.43 (m, 4H); 1.21 (d, J=6.8, 3H); 1.18 (t, J=7.5, 3H); 0.94 (m, 1H); 0.36 (m, 2H); 0.22 (m, 2H).

Example F95

4-[2-(Cyclopropylmethoxy)-5-ethylphenyl]-N-{cis-4-[(hydroxyacetyl)amino]cyclohexyl}-6-methyl-5H-pyrrolo[3,2-d]pyrimidine-7-carboxamide Starting from N-(cis-4-aminocyclohexyl)-4-[2-(cyclopropylmethoxy)-5-ethylphenyl]-6-methyl-5H-pyrrolo[3,2-d]pyrimidine-7-carboxamide hydrochloride (example D.f50) and commercially available 2-chloro-2-oxoethyl acetate the title compound is obtained as colorless solid.
MS (ESI): m/z=506 (MH$^+$, 100%).
$^1$H-NMR (300 MHz, DMSO-d$_6$): 11.73 (s, 1H, —NH); 8.98 (s, 1H); 8.97 (d, J=7.5, 1H, —NH); 7.53 (d, J=7.8, 1H, —NH); 7.45 (d, J=2.3, 1H); 7.36 (dd, J=8.6, 2.3, 1H); 7.08 (d, J=8.6, 1H); 5.33 (br.s, 1H, —OH); 4.06 (m, 1H); 3.87 (d, J=6.8, 2H); 3.83 (s, 2H); 3.80 (m, 1H); 2.78 (s, 3H); 2.64 (qu, J=7.5, 2H); 1.85-1.55 (m, 8H); 1.19 (t, J=7.6, 53H); 0.94 (m, 1H); 0.36 (m, 2H); 0.23 (m, 2H).

Example F96

4-[2-(Cyclopropylmethoxy)-5-ethylphenyl]-N-(cis-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[2-(cyclopropylmethoxy)-5-ethylphenyl]-6-methyl-5H-pyrrolo[3,2-d]pyrimidine-7-carboxamide hydrochloride (example D.f50) and commercially available (2S)-1-chloro-1-oxopropan-2-yl acetate the title compound is obtained as colorless solid.

MS (ESI): m/z=520 (MH⁺, 100%).
¹H-NMR (300 MHz, DMSO-d₆): 11.73 (s, 1H, —NH); 8.98 (s, 1H); 8.96 (d, J=7.5, 1H, —NH); 7.48 (d, J=7.8, 1H, —NH); 7.45 (d, J=2.2, 1H); 7.36 (dd, J=8.4, 2.2, 1H); 7.08 (d, J=8.4, 1H); 5.37 (d, J=5.3, 1H, —OH); 4.06 (m, 1H); 3.99 (m, 1H); 3.87 (d, J=6.8, 2H); 3.75 (m, 1H); 2.78 (s, 3H); 2.64 (qu, J=7.6, 2H); 1.83-1.56 (m, 8H); 1.21 (t, J=7.6, 3H); 1.17 (d, J=7.7, 1H); 0.94 (m, 1H); 0.36 (m, 2H); 0.23 (m, 2H).

Example F97

4-[2-(Cyclopropylmethoxy)-5-ethylphenyl]-N-[(3R*,4R*)-4-hydroxy-1-(hydroxyacetyl)pyrrolidin-3-yl]-6-methyl-5H-pyrrolo[3,2-d]pyrimidine-7-carboxamide Starting from 4-[2-(cyclopropylmethoxy)-5-ethylphenyl]-N-[(3R*,4R*)-4-hydroxypyrrolidin-3-yl]-6-methyl-5H-pyrrolo[3,2-d]pyrimidine-7-carboxamide hydrochloride (example D.f51) and commercially available 2-chloro-2-oxoethyl acetate the title compound is obtained as colorless solid.
MS (ESI): m/z=494 (MH⁺, 100%).
¹H-NMR (300 MHz, DMSO-d₆): 11.80 (s, 1H, —NH); 8.92 (s, 1H); [8.88 (d, J=7.1), 8.84 (d, J=6.6), 1H, —NH]; 7.44 (d, J=2.4, 1H); 7.36 (dd, J=8.4, 2.4, 1H); 7.08 (d, J=8.4, 1H); [5.57 (d, J=3.8), 5.51 (d, J=4.0), 1H, —OH]; [4.64 (t, J=5.6), 4.60 (t, J=5.6), 1H, —OH]; [4.38 (m), 4.20 (m, 1H]; 4.28 (m, 1H); [4.06 (br. s), 4.04 (br. s), 2H]; 3.86 (d, J=6.9, 2H); 3.84-3.60 (m, 2H); 3.46-3.27 (m, 2H); 2.78 (s, 3H); 2.63 (qu, J=7.5, 2H); 1.18 (t, J=7.5, 3H); 0.93 (m, 1H); 0.36 (m, 2H); 0.22 (m, 2H).

Example F98

Diastereomeric mixture of 4-[2-(cyclopropylmethoxy)-5-ethylphenyl]-N-{(3R,4R)-4-hydroxy-1-[(2S)-2-hydroxypropanoyl]pyrrolidin-3-yl}-6-methyl-5H-pyrrolo[3,2-d]pyrimidine-7-carboxamide and 4-[2-(cyclopropylmethoxy)-5-ethylphenyl]-N-{(3S,4S)-4-hydroxy-1-[(2S)-2-hydroxypropanoyl]pyrrolidin-3-yl}-6-methyl-5H-pyrrolo[3,2-d]pyrimidine-7-carboxamide Starting from 4-[2-(cyclopropylmethoxy)-5-ethylphenyl]-N-[(3R*,4R*)-4-hydroxypyrrolidin-3-yl]-6-methyl-5H-pyrrolo[3,2-d]pyrimidine-7-carboxamide hydrochloride (example D.f51) and commercially available (2S)-1-chloro-1-oxopropan-2-yl acetate the title compound is obtained as colorless solid.
HR-MS (ESI): m/z=508.2548 ([MH]⁺, $C_{27}H_{34}N_5O_5^+$, calc. 508.2554).

Example F99

4-[2-(Cyclopropylmethoxy)-5-(propan-2-yl)phenyl]-N-{1-[(2S)-2-hydroxypropanoyl]piperidin-4-yl}-6-methyl-5H-pyrrolo[3,2-d]pyrimidine-7-carboxamide Starting from 4-[2-(cyclopropylmethoxy)-5-(propan-2-yl)phenyl]-6-methyl-N-(piperidin-4-yl)-5H-pyrrolo[3,2-d]pyrimidine-7-carboxamide hydrochloride (example D.f52) and commercially available (2S)-1-chloro-1-oxopropan-2-yl acetate the title compound is obtained as colorless solid.
MS (ESI): m/z=520 (MH⁺, 100%).
¹H-NMR (300 MHz, DMSO-d₆): 11.76 (s, 1H, —NH); 8.95 (s, 1H); 8.83 (d, J=7.1, 1H, —NH); 7.46 (d, J=2.4, 1H); 7.39 (dd, J=8.6, 2.4, 1H); 7.08 (d; J=8.6, 1H); 4.86 (d, J=6.9, 1H, —OH); 4.47 (m, 1H); 4.27-4.08 (m, 2H); 3.95 (m, 1H); 3.87 (d, J=6.9, 2H); 3.27 (m, 1H); 3.09-2.87 (m, 1H & sept, J=6.9, 1H); 2.78 (s, 3H); 1.98 (m, 2H); 1.53 (m, 1H); 1.42 (m, 1H); 1.22 (d, J=6.9, 6H & br.s, 3H); 0.94 (m, 1H); 0.36 (m, 2H); 0.22 (m, 2H).

Example F100

4-[2-(Cyclopropylmethoxy)-5-(propan-2-yl)phenyl]-N-(trans-4-{[(2S)-2-hydroxypropanoyl]amino}cyclohexyl)-6-methyl-5H-pyrrolo[3,2-d]pyrimidine-7-carboxamide Starting from N-(trans-4-aminocyclohexyl)-4-[2-(cyclopropylmethoxy)-5-(propan-2-yl)phenyl]-6-methyl-5H-pyrrolo[3,2-d]pyrimidine-7-carboxamide hydrochloride (example D.f53) and commercially available (2S)-1-chloro-1-oxopropan-2-yl acetate the title compound is obtained as colorless solid.
MS (ESI): m/z=534 (MH⁺, 100%).
¹H-NMR (300 MHz, DMSO-d₆): 11.73 (s, 1H, —NH); 8.96 (s, 1H); 8.66 (d, J=7.7, 1H, —NH); 7.47 (d, J=2.4, 1H); 7.42 (d, J=7.9, 1H, —NH); 7.39 (dd, J=8.6, 2.4, 1H); 7.08 (d; J=8.6, 1H); 5.40 (d, J=5.3, 1H, —OH); 3.94 (td, J=6.8, 5.3, 1H); 3.87 (d, J=6.9, 2H); 3.81 (m, 1H); 3.64 (m, 1H); 2.94 (sept, J=6.9, 1H); 2.77 (s, 3H); 2.01 (m, 2H); 1.82 (m, 2H); 1.43 (m, 4H); 1.22 (d, J=6.9, 6H); 1.21 (d, J=6.8, 3H); 0.94 (m, 1H); 0.36 (m, 2H); 0.22 (m, 2H).

Example F101

4-[2-(Cyclopropylmethoxy)-5-(propan-2-yl)phenyl]-N-(cis-4-{[(2S)-2-hydroxypropanoyl]amino}cyclohexyl)-6-methyl-5H-pyrrolo[3,2-d]pyrimidine-7-carboxamide Starting from N-(cis-4-aminocyclohexyl)-4-[2-(cyclopropylmethoxy)-5-(propan-2-yl)phenyl]-6-methyl-5H-pyrrolo[3,2-d]pyrimidine-7-carboxamide hydrochloride (example D.f54) and commercially available (2S)-1-chloro-1-oxopropan-2-yl acetate the title compound is obtained as colorless solid.
MS (ESI): m/z=534 (MH⁺, 100%).
¹H-NMR (300 MHz, DMSO-d₆): 11.74 (s, 1H, —NH); 8.99 (s, 1H); 8.96 (d, J=7.5, 1H, —NH); 7.48 (d, J=7.7, 1H, —NH); 7.47 (d, J=2.4, 1H); 7.39 (dd, J=8.6, 2.4, 1H); 7.09 (d; J=8.6, 1H); 5.37 (d, J=5.4, 1H, —OH); 4.05 (m, 1H); 3.99 (td, J=6.8, 5.4, 1H); 3.87 (d, J=6.9, 2H); 3.75 (m, 1H); 2.95 (sept, J=6.9, 1H); 2.78 (s, 3H); 1.81-1.59 (m, 8H); 1.22 (d, J=6.9, 6H & d, J=6.9, 3H); 0.94 (m, 1H); 0.36 (m, 2H); 0.23 (m, 2H).

Example F102

4-[5-Acetyl-2-(cyclopropylmethoxy)phenyl]-N-[1-(hydroxyacetyl)piperidin-4-yl]-6-methyl-5H-pyrrolo[3,2-d]pyrimidine-7-carboxamide Starting from 4-[5-acetyl-2-(cyclopropylmethoxy)phenyl]-6-methyl-N-(piperidin-4-yl)-5H-pyrrolo[3,2-d]pyrimidine-7-carboxamide hydrochloride (example D.f55) and commercially available 2-chloro-2-oxoethyl acetate the title compound is obtained as colorless solid.
MS (ESI): m/z=506 (MH⁺, 100%).
¹H-NMR (400 MHz, DMSO-d₆): 11.88 (s, 1H, —NH); 8.99 (s, 1H); 8.82 (d, J=7.7, 1H, —NH); 8.21 (d, J=2.3, 1H); 8.15 (dd, J=8.8, 2.3, 1H); 7.30 (d, J=8.8, 1H); 4.51 (t, J=5.5, 1H, —OH); 4.24-4.06 (m, 4H); 4.01 (d, J=7.0, 2H); 3.68 (m, 1H); 3.20 (m, 1H); 3.03 (m, 1H); 2.79 (s, 3H); 2.58 (s, 3H); 1.97 (m, 2H); 1.55 (m, 1H); 1.44 (m, 1H); 0.99 (m, 1H); 0.39 (m, 2H); 0.28 (m, 2H).

Example F103

4-[5-Acetyl-2-(cyclopropylmethoxy)phenyl]-N-{1-[(2S)-2-hydroxypropanoyl]piperidin-4-yl}-6-methyl-5H-pyrrolo[3,2-d]pyrimidine-7-carboxamide Starting from 4-[5-acetyl-2-(cyclopropylmethoxy)phenyl]-6-methyl-N-(piperidin-4-yl)-5H-pyrrolo[3,2-d]pyrimidine-7-carboxamide hydrochloride (example D.f55) and commercially available (2S)-1-chloro-1-oxopropan-2-yl acetate the title compound is obtained as colorless solid.

MS (ESI): m/z=520 (MH$^+$, 100%).

$^1$H-NMR (400 MHz, DMSO-d$_6$): 11.88 (s, 1H, —NH); 9.00 (s, 1H); 8.81 (d, J=6.7, 1H, —NH); 8.21 (d, J=2.3, 1H); 8.15 (dd, J=8.8, 2.3, 1H); 7.30 (d, J=8.8, 1H); 4.47 (br.s, 1H, —OH); 4.27-4.10 (m, 2H); 4.01 (d, J=7.1, 2H); 3.95 (m, 1H); 3.27 (m, 1H); 3.00 (m, 1H); 2.79 (s, 3H); 2.58 (s, 3H); 1.99 (m, 2H); 1.55 (m, 1H); 1.41 (m, 1H); 1.21 (br.s, 3H); 0.99 (m, 1H); 0.39 (m, 2H); 0.28 (m, 2H).

Example F104

4-[5-Acetyl-2-(cyclopropylmethoxy)phenyl]-N-{trans-4-[(hydroxyacetyl)amino]cyclohexyl}-6-methyl-5H-pyrrolo[3,2-d]pyrimidine-7-carboxamide Starting from 4-[5-acetyl-2-(cyclopropylmethoxy)phenyl]-N-(trans-4-aminocyclohexyl)-6-methyl-S-1-pyrrolo[3,2-d]pyrimidine-7-carboxamide hydrochloride (example D.f56) and commercially available 2-chloro-2-oxoethyl acetate the title compound is obtained as colorless solid.

MS (ESI): m/z=520 (MH$^+$, 100%).

$^1$H-NMR (400 MHz, DMSO-d$_6$): 11.85 (s, 1H, —NH); 9.00 (s, 1H); 8.65 (d, J=7.7, 1H, —NH); 8.21 (d, J=2.3, 1H); 8.15 (dd, J=8.8, 2.3, 1H); 7.48 (d, J=8.3, 1H, —NH); 7.30 (d, J=8.8, 1H); 5.40 (t, J=5.8, 1H, —OH); 4.01 (d, J=7.0, 2H); 3.82 (m, 1H); 3.79 (d, J=5.8, 2H); 3.69 (m, 1H); 2.79 (s, 3H); 2.58 (s, 3H); 2.01 (m, 2H); 1.83 (m, 2H); 1.45 (m, 4H); 0.99 (m, 1H); 0.39 (m, 2H); 0.28 (m, 2H).

Example F105

4-[5-Acetyl-2-(cyclopropylmethoxy)phenyl]-N-(trans-4-{[(2S)-2-hydroxypropanoyl]amino}cyclohexyl)-6-methyl-5H-pyrrolo[3,2-d]pyrimidine-7-carboxamide Starting from 4-[5-acetyl-2-(cyclopropylmethoxy)phenyl]-N-(trans-4-aminocyclohexyl)-6-methyl-5H-pyrrolo[3,2-d]pyrimidine-7-carboxamide hydrochloride (example D.f56) and commercially available (2S)-1-chloro-1-oxopropan-2-yl acetate the title compound is obtained as colorless solid.

MS (ESI): m/z=534 (MH$^+$, 100%).

$^1$H-NMR (400 MHz, DMSO-d$_6$): 11.85 (s, 1H, —NH); 9.00 (s, 1H); 8.65 (d, J=7.7, 1H, —NH); 8.21 (d, J=2.2, 1H); 8.15 (dd, J=8.9, 2.2, 1H); 7.42 (d, J=8.3, 1H, —NH); 7.30 (d, J=8.9, 1H); 5.40 (d, J=5.1, 1H, —OH); 4.01 (d, J=7.0, 2H); 3.94 (td, J=6.8, 5.1, 1H); 3.82 (m, 1H); 3.64 (m, 1H); 2.78 (s, 3H); 2.58 (s, 3H); 2.01 (m, 2H); 1.84 (m, 2H); 1.44 (m, 4H); 1.21 (d, J=6.8, 3H); 0.99 (m, 1H); 0.39 (m, 2H); 0.27 (m, 2H).

Example F106

4-[2-(Cyclopropylmethoxy)-5-methylphenyl]-N-[1-(hydroxyacetyl)piperidin-4-yl]-2,6-dimethyl-5H-pyrrolo[3,2-d]pyrimidine-7-carboxamide Starting from 4-[2-(cyclopropylmethoxy)-5-methylphenyl]-2,6-dimethyl-N-(piperidin-4-yl)-5H-pyrrolo[3,2-d]pyrimidine-7-carboxamide hydrochloride (example D.f57) and commercially available 2-chloro-2-oxoethyl acetate the title compound is obtained as colorless solid.

MS (ESI): m/z=492 (MH$^+$, 100%)

$^1$H-NMR (300 MHz, DMSO-d$_6$): 11.60 (s, 1H, —NH); 9.05 (d, J=7.5, 1H, —NH); 7.39 (d, J=2.0, 1H); 7.31 (dd, J=8.6, 2.0, 1H); 7.04 (d, J=8.6, 1H); 4.52 (t, J=5.3, 1H, —OH); 4.24-4.04 (m, 2H); 4.13 (m, 2H); 3.85 (d, J=6.9, 2H); 3.67 (m, 1H); 3.24 (m, 1H); 3.12 (m, 1H); 2.75 (s, 3H); 2.72 (s, 3H); 2.32 (s, 3H); 1.96 (m, 2H); 1.69-1.36 (m, 2H); 0.93 (m, 1H); 0.35 (m, 2H); 0.22 (m, 2H).

Example F107

4-[2-(Cyclopropylmethoxy)-5-methylphenyl]-N-{1-[(2S)-2-hydroxypropanoyl]piperidin-4-yl}-2,6-dimethyl-5H-pyrrolo[3,2-d]pyrimidine-7-carboxamide Starting from 4-[2-(cyclopropylmethoxy)-5-methylphenyl]-2,6-dimethyl-N-(piperidin-4-yl)-5H-pyrrolo[3,2-d]pyrimidine-7-carboxamide hydrochloride (example D.f57) and commercially available (2S)-1-chloro-1-oxopropan-2-yl acetate the title compound is obtained as colorless solid.

MS (ESI): m/z=506 (MH$^+$, 100%)

$^1$H-NMR (300 MHz, DMSO-d$_6$): 11.58 (s, 1H, —NH); 9.05 (br.s, 1H, —NH); 7.39 (d, J=1.8, 1H); 7.31 (dd, J=8.4, 1.8, 1H); 7.04 (d, J=8.4, 1H); 4.86 (m, 1H, —OH); 4.47 (m, 1H); 4.21-3.99 (m, 2H); 3.99-3.80 (m, 1H); 3.84 (d, J=6.9, 2H); 3.43-3.24 (m, 1H); 3.24-2.98 (m, 1H); 2.75 (s, 3H); 2.72 (s, 3H); 2.33 (s, 3H); 2.05-1.89 (m, 2H); 1.63-1.36 (m, 2H); 1.21 (d, J=6.0, 3H); 0.93 (m, 1H); 0.35 (m, 2H); 0.22 (m, 2H).

Example F108

4-[2-(Cyclopropylmethoxy)-5-fluoro-4-methoxyphenyl]-N-{1-[(2S)-2-hydroxypropanoyl]piperidin-4-yl}-2,6-dimethyl-5H-pyrrolo[3,2-d]pyrimidine-7-carboxamide Starting from 4-[2-(cyclopropylmethoxy)-5-fluoro-4-methoxyphenyl]-2,6-dimethyl-N-(piperidin-4-yl)-5H-pyrrolo[3,2-d]pyrimidine-7-carboxamide hydrochloride (example D.f58) and commercially available (2S)-1-chloro-1-oxopropan-2-yl acetate the title compound is obtained as colorless solid.

MS (ESI): 540 (MH$^+$, 100%)

$^1$H-NMR (300 MHz, DMSO-d$_6$): 11.56 (s, 1H, —NH); 9.04 (m, 1H, —NH); 7.43 (d, J=11.9, 1H); 6.91 (d, J=7.3, 1H); 4.91-4.80 (m, 1H, —OH); 4.47 (m, 1H); 4.21-4.07 (m, 2H); 3.96 (s, 3H); 3.93 (d, J=6.9, 2H); 3.89 (m, 1H); 3.44-3.25 (m, 1H); 3.38-3.25 (m, 1H); 3.25-2.99 (m, 1H); 2.76 (s, 3H); 2.71 (s, 3H); 2.04-1.89 (m, 2H); 1.64-1.34 (m, 2H); 1.21 (d, J=6.2, 3H); 0.95 (m, 1H); 0.38 (m, 2H); 0.25 (m, 2H).

Example F109

4-[2-(Cyclopropylmethoxy)-4-fluoro-5-methoxyphenyl]-N-[1-(hydroxyacetyl)piperidin-4-yl]-2,6-dimethyl-5H-pyrrolo[3,2-d]pyrimidine-7-carboxamide Starting from 4-[2-(cyclopropylmethoxy)-4-fluoro-5-methoxyphenyl]-2,6-dimethyl-N-(piperidin-4-yl)-5H-pyrrolo[3,2-d]pyrimidine-7-carboxamide hydrochloride (example D.f59) and commercially 2-chloro-2-oxoethyl acetate the title compound is obtained as colorless solid.

MS (ESI): m/z=526 (MH+, 100%).

$^1$H-NMR (300 MHz, DMSO-d$_6$): 11.61 (s, 1H, —NH); 9.02 (d, J=7.7, 1H, —NH); 7.34 (d, J=9.9, 1H); 7.16 (d, J=13.3, 1H); 4.50 (t, J=5.5, 1H, —OH); 4.21-4.05 (m, 2H); 4.13 (s, 2H); 3.84 (s, 3H); 3.82 (d, J=6.8, 2H); 3.66 (m, 1H); 3.24 (m, 1H); 3.11 (m, 1H); 2.75 (s, 3H); 2.73 (s, 3H); 1.96 (m, 2H); 1.64-1.37 (m, 2H); 0.92 (m, 1H); 0.35 (m, 2H); 0.19 (m, 2H).

Example F110

4-[2-(Cyclopropylmethoxy)-4-fluoro-5-methoxyphenyl]-N-{1-[(2S)-2-hydroxypropanoyl]piperidin-4-yl}-2,6-dimethyl-5H-pyrrolo[3,2-d]pyrimidine-7-carboxamide Starting from 4-[2-(cyclopropylmethoxy)-4-fluoro-5-methoxyphenyl]-2,6-dimethyl-N-(piperidin-4-yl)-5H-pyrrolo[3,2-d]pyrimidine-7-carboxamide hydrochloride (example D.f59) and commercially 2-chloro-2-oxoethyl acetate the title compound is obtained as colorless solid.

MS (ESI): m/z=540 (MH+, 100%).

$^1$H-NMR (300 MHz, DMSO-d$_6$): 11.61 (s, 1H, —NH); 9.03 (br.s, 1H, —NH); 7.33 (d, J=9.9, 1H); 7.16 (d, J=13.5, 1H); 4.86 (br.s, 1H, —OH); 4.47 (m, 1H); 4.23-4.00 (m, 2H); 3.88 (m, 1H); 3.84 (s, 3H); 3.82 (d, J=6.8, 2H); 3.36 (m, 1H); 3.10 (m, 1H); 2.75 (s, 3H); 2.73 (s, 3H); 1.97 (m, 2H); 1.62-1.37 (m, 2H); 1.21 (d, J=6.0, 3H); 0.91 (m, 1H); 0.35 (m, 2H); 0.19 (m, 2H).

Example F111

4-[2-(Cyclopropylmethoxy)-4-fluoro-5-methoxyphenyl]-N-[(3R)-1-glycoloylpyrrolidin-3-yl]-6-methyl-5H-pyrrolo[3,2-d]pyrimidine-7-carboxamide MS (ESI): m/z=498 (MH+, 100%).

$^1$H-NMR (300 MHz, DMSO-d$_6$): 11.80 (s, 1H, —NH); 8.95 (s, 1H); [8.92 (d, J=7.3), 8.90 (d, J=7.9), 1H, —NH]; 7.93 (d, J=9.8, 1H); 7.18 (d, J=13.4, 1H); 4.67-4.46 (m, 1H); 4.56 T, J=5.7, 1H, —OH); [4.06 (d, J=5.7), 4.01 (d, J=5.7), 1H]; 3.85 (d, J=6.9, 2H & s, 3H); 3.81-3.69 (m, 1H); 3.64-3.46 (m, 2H); 3.38-3.31 (m, 1H); 2.79 (s, 3H); 2.35-2.17 (m, 1H); [2.05 (m), 1.93 (m), 1H]; 0.93 (m, 1H); 0.36 (m, 2H); 0.22 (m, 2H).

Example F112

4-[2-(Cyclopropylmethoxy)-4-fluoro-5-methoxyphenyl]-N-{(3R)-1-[(2S)-2-hydroxypropanoyl]pyrrolidin-3-yl}-6-methyl-5H-pyrrolo[3,2-d]pyrimidine-7-carboxamide MS (ESI): m/z=512 (MH+, 100%).

$^1$H-NMR (300 MHz, DMSO-d$_6$): 11.80 (s, 1H, —NH); [8.95 (s), 8.92 (s), 1H]; 8.92 (d, J=7.1, 1H, —NH); 7.39 (d, J=9.9, 1H); 7.18 (d, J=13.5, 1H); [4.91 (d, J=6.9), 4.84 (d, J=6.9), 1H, —OH]; [4.58 (m), 4.51 (m), 1H]; [4.33 (m), 4.26 (m), 1H]; 3.84 (d, J=6.6, 2H & s, 3H); 3.87-3.79 (m, 1H); 3.87-3.42 (m, 2H); 3.39-3.27 (m, 1H); 2.79 (s, 3H); 2.33-2.15 (m, 1H); [2.05 (m), 1.92 (m), 1H]; [1.23 (d, J=6.6), 1.20 (d, J=6.6), 3H]; 0.93 (m, 1H); 0.36 (m, 2H); 0.21 (m, 2H).

Example F113

4-[2-(Cyclopropylmethoxy)-4-fluoro-5-methoxyphenyl]-N-[(3R*,4R*)-1-glycoloyl-4-hydroxypyrrolidin-3-yl]-6-methyl-5H-pyrrolo[3,2-d]pyrimidine-7-carboxamide MS (ESI): m/z=514 (MH+, 100%).

$^1$H-NMR (300 MHz, DMSO-d$_6$): 11.81 (s, 1H, —NH); [8.94 (s), 8.93 (s), 1H]; [8.86 (d, J=7.3), 8.82 (d, J=6.6), 1H, —NH]; 7.39 (d, J=9.9, 1H); 7.18 (d, J=13.3, 1H); [5.57 (d, J=3.8), 5.50 (d, J=4.0), 1H, —OH]; [4.64 (t, J=5.7), 4.60 (t, J=5.7), 1H, —OH]; 4.41-4.17 (m, 2H); [4.06 (br. s), 4.04 (br. s), 2H]; 3.84 (d, J=6.8, 2H & s, 3H); 3.80-3.60 (m, 2H); 3.46-3.27 (m, 2H); 2.79 (s, 3H); 0.92 (m, 1H); 0.36 (m, 2H); 0.20 (m, 2H).

Example F114

4-[2-(Cyclopropylmethoxy)-4-fluoro-5-methoxyphenyl]-N-{(3R*,4R*)-4-hydroxy-1-[(2S)-2-hydroxypropanoyl]pyrrolidin-3-yl}-6-methyl-5H-pyrrolo[3,2-d]pyrimidine-7-carboxamide (mixture of diastereomers)

MS (ESI): m/z=528 (MH+, 100%).

1H-NMR (300 MHz, DMSO-d$_6$): 11.81 (s, 1H, —NH); [8.93 (s), 8.91 (s), 8.89 (s), 8.88 (s), 1H]; 8.87-8.82 (m, 1H, —NH); 7.39 (d, J=9.9, 1H); 7.18 (d, J=13.3, 1H); [5.57 (d, J=3.7), 5.55 (d, J=3.7), 5.50 (d, J=2.0), 5.49 (d, J=1.8), 1H, —OH]; [4.64 (t, J=5.7), 4.60 (t, J=5.7), 1H, —OH]; 4.41-4.17 (m, 2H); [4.97 (d, J=6.8), 4.95 (d, J=7.1), 4.89 (d, J=3.5), 4.87 (d, J=3.5), 1H, —OH]; 4.38-4.17 (m, 3H); 4.03-3.27 (m, 4H); 3.84 (d, J=6.9, 2H & s, 3H); 2.79 (s, 3H); 1.27-1.21 (m, 3H); 0.92 (m, 1H); 0.36 (m, 2H); 0.20 (m, 2H).

Example F115

4-[2-(Cyclopropylmethoxy)-5-fluoro-4-methoxyphenyl]-N-[(3R)-1-glycoloylpyrrolidin-3-yl]-6-methyl-5H-pyrrolo[3,2-d]pyrimidine-7-carboxamide MS (ESI): m/z=498 (MH+, 100%).

Example F116

4-[2-(Cyclopropylmethoxy)-5-fluoro-4-methoxyphenyl]-N-{(3R)-1-[(2S)-2-hydroxypropanoyl]pyrrolidin-3-yl}-6-methyl-5H-pyrrolo[3,2-d]pyrimidine-7-carboxamide MS (ESI): m/z=512 (MH+, 100%).

Example F117

4-[2-(Cyclopropylmethoxy)-5-fluoro-4-methoxyphenyl]-N-[(3R*,4R*)-1-glycoloyl-4-hydroxypyrrolidin-3-yl]-6-methyl-5H-pyrrolo[3,2-d]pyrimidine-7-carboxamide MS (ESI): m/z=514 (MH$^+$, 100%).

Example F118

4-[2-(Cyclopropylmethoxy)-5-fluoro-4-methoxyphenyl]-N-{(3R*,4R*)-4-hydroxy-1-[(2S)-2-hydroxypropanoyl]pyrrolidin-3-yl}-6-methyl-5H-pyrrolo[3,2-d]pyrimidine-7-carboxamide (mixture of diastereomeres)

MS (ESI): m/z=528 (MH$^+$, 100%).

Example F119

4-[2-(Cyclopropylmethoxy)-5-methoxyphenyl]-N-[(3R*,4R*)-1-glycoloyl-4-hydroxypyrrolidin-3-yl]-6-methyl-5H-pyrrolo[3,2-d]pyrimidine-7-carboxamide MS (ESI): m/z=496 (MH$^+$, 100%).

Example F120

4-[2-(Cyclopropylmethoxy)-5-methoxyphenyl]-N-{(31R*,4R*)-4-hydroxy-1-[(2S)-2-hydroxypropanoyl]pyrrolidin-3-yl}-6-methyl-5H-pyrrolo[3,2-d]pyrimidine-7-carboxamide (mixture of diastereomeres)

MS (ESI): m/z=510 (MH$^+$, 100%).

The following compounds in the table would fall within the scope of the genus of formula I as described in claim 1:

| | |
|---|---|
| P1 | N-(1-Acetylpiperidin-4-yl)-4-[2-(cyclopropylmethoxy)-5-(difluoromethyl)phenyl]-6-methyl-5H-pyrrolo[3,2-d]pyrimidine-7-carboxamide |
| P2 | 4-[2-(Cyclopropylmethoxy)-5-(difluoromethyl)phenyl]-6-methyl-N-(1-propionylpiperidin-4-yl)-5H-pyrrolo[3,2-d]pyrimidine-7-carboxamide |
| P3 | 4-[2-(Cyclopropylmethoxy)-5-(difluoromethyl)phenyl]-N-[1-(methoxyacetyl)piperidin-4-yl]-6-methyl-5H-pyrrolo[3,2-d]pyrimidine-7-carboxamide |
| P4 | 4-[2-(Cyclopropylmethoxy)-5-(difluoromethyl)phenyl]-N-(1-glycoloylpiperidin-4-yl)-6-methyl-5H-pyrrolo[3,2-d]pyrimidine-7-carboxamide |
| P5 | 4-[2-(Cyclopropylmethoxy)-5-(difluoromethyl)phenyl]-N-{1-[(2S)-2-hydroxypropanoyl]piperidin-4-yl}-6-methyl-5H-pyrrolo[3,2-d]pyrimidine-7-carboxamide |
| P6 | N-(trans-4-Acetamidocyclohexyl)-4-[2-(cyclopropylmethoxy)-5-(difluoromethyl)phenyl]-6-methyl-5H-pyrrolo[3,2-d]pyrimidine-7-carboxamide |
| P7 | 4-[2-(Cyclopropylmethoxy)-5-(difluoromethyl)phenyl]-6-methyl-N-[trans-4-(propionylamino)cyclohexyl]-5H-pyrrolo[3,2-d]pyrimidine-7-carboxamide |
| P8 | 4-[2-(Cyclopropylmethoxy)-5-(difluoromethyl)phenyl]-N-{trans-4-[(methoxyacetyl)amino]cyclohexyl}-6-methyl-5H-pyrrolo[3,2-d]pyrimidine-7-carboxamide |
| P9 | 4-[2-(Cyclopropylmethoxy)-5-(difluoromethyl)phenyl]-N-{trans-4-[(hydroxyacetyl)amino]cyclohexyl}-6-methyl-5H-pyrrolo[3,2-d]pyrimidine-7-carboxamide |
| P10 | 4-[2-(Cyclopropylmethoxy)-5-(difluoromethyl)phenyl]-N-(trans-4-{[(2S)-2-hydroxypropanoyl]amino}cyclohexyl)-6-methyl-5H-pyrrolo[3,2-d]pyrimidine-7-carboxamide |
| P11 | N-[cis-4-(Acetylamino)cyclohexyl]-4-[2-(cyclopropylmethoxy)-5-(difluoromethyl)phenyl]-6-methyl-5H-pyrrolo[3,2-d]pyrimidine-7-carboxamide |
| P12 | 4-[2-(Cyclopropylmethoxy)-5-(difluoromethyl)phenyl]-6-methyl-N-[cis-4-(propanoylamino)cyclohexyl]-5H-pyrrolo[3,2-d]pyrimidine-7-carboxamide |
| P13 | 4-[2-(Cyclopropylmethoxy)-5-(difluoromethyl)phenyl]-N-{cis-4-[(methoxyacetyl)amino]cyclohexyl}-6-methyl-5H-pyrrolo[3,2-d]pyrimidine-7-carboxamide |
| P14 | 4-[2-(Cyclopropylmethoxy)-5-(difluoromethyl)phenyl]-N-{cis-4-[(hydroxyacetyl)amino]cyclohexyl}-6-methyl-5H-pyrrolo[3,2-d]pyrimidine-7-carboxamide |
| P15 | 4-[2-(Cyclopropylmethoxy)-5-(difluoromethyl)phenyl]-N-(cis-4-{[(2S)-2-hydroxypropanoyl]amino}cyclohexyl)-6-methyl-5H-pyrrolo[3,2-d]pyrimidine-7-carboxamide |
| P16 | 4-[2-(Cyclopropylmethoxy)-5-(difluoromethyl)phenyl]-N-[(1R,3S)-3-hydroxycyclopentyl]-6-methyl-5H-pyrrolo[3,2-d]pyrimidine-7-carboxamide |
| P17 | 4-[2-(Cyclopropylmethoxy)-5-(difluoromethyl)phenyl]-N-[(1R,3R)-3-hydroxycyclopentyl]-6-methyl-5H-pyrrolo[3,2-d]pyrimidine-7-carboxamide |
| P18 | 4-[2-(Cyclopropylmethoxy)-5-(difluoromethyl)phenyl]-N-[(1S,3S)-3-hydroxycyclopentyl]-6-methyl-5H-pyrrolo[3,2-d]pyrimidine-7-carboxamide |
| P19 | 4-[2-(Cyclopropylmethoxy)-5-(difluoromethyl)phenyl]-N-[(1S,3R)-3-hydroxycyclopentyl]-6-methyl-5H-pyrrolo[3,2-d]pyrimidine-7-carboxamide |
| P20 | 4-[2-(Cyclopropylmethoxy)-5-(difluoromethyl)phenyl]-N-[(1R,2S)-2-hydroxycyclopentyl]-6-methyl-5H-pyrrolo[3,2-d]pyrimidine-7-carboxamide |
| P21 | 4-[2-(Cyclopropylmethoxy)-5-(difluoromethyl)phenyl]-N-[(1R,2R)-2-hydroxycyclopentyl]-6-methyl-5H-pyrrolo[3,2-d]pyrimidine-7-carboxamide |
| P22 | 4-[2-(Cyclopropylmethoxy)-5-(difluoromethyl)phenyl]-N-[(1S,2S)-2-hydroxycyclopentyl]-6-methyl-5H-pyrrolo[3,2-d]pyrimidine-7-carboxamide |
| P23 | 4-[2-(Cyclopropylmethoxy)-5-(difluoromethyl)phenyl]-N-[(1S,2R)-2-hydroxycyclopentyl]-6-methyl-5H-pyrrolo[3,2-d]pyrimidine-7-carboxamide |
| P24 | N-[(3S,5S)-1-Acetyl-5-methylpyrrolidin-3-yl]-4-[2-(cyclopropylmethoxy)-5-(difluoromethyl)phenyl]-6-methyl-5H-pyrrolo[3,2-d]pyrimidine-7-carboxamide |
| P25 | 4-[2-(Cyclopropylmethoxy)-5-(difluoromethyl)phenyl]-6-methyl-N-[(3S,5S)-5-methyl-1-propanoylpyrrolidin-3-yl]-5H-pyrrolo[3,2-d]pyrimidine-7-carboxamide |
| P26 | 4-[2-(Cyclopropylmethoxy)-5-(difluoromethyl)phenyl]-N-[(3S,5S)-1-(methoxyacetyl)-5-methylpyrrolidin-3-yl]-6-methyl-5H-pyrrolo[3,2-d]pyrimidine-7-carboxamide |
| P27 | 4-[2-(Cyclopropylmethoxy)-5-(difluoromethyl)phenyl]-N-[(3S,5S)-1-(hydroxyacetyl)-5-methylpyrrolidin-3-yl]-6-methyl-5H-pyrrolo[3,2-d]pyrimidine-7-carboxamide |
| P28 | 4-[2-(Cyclopropylmethoxy)-5-(difluoromethyl)phenyl]-N-{(3S,5S)-1-[(2S)-2-hydroxypropanoyl]-5-methylpyrrolidin-3-yl}-6-methyl-5H-pyrrolo[3,2-d]pyrimidine-7-carboxamide |

-continued

| | |
|---|---|
| P29 | N-[(3S,5R)-1-Acetyl-5-methylpyrrolidin-3-yl]-4-[2-(cyclopropylmethoxy)-5-(difluoromethyl)phenyl]-6-methyl-5H-pyrrolo[3,2-d]pyrimidine-7-carboxamide |
| P30 | 4-[2-(Cyclopropylmethoxy)-5-(difluoromethyl)phenyl]-6-methyl-N-[(3S,5R)-5-methyl-1-propanoylpyrrolidin-3-yl]-5H-pyrrolo[3,2-d]pyrimidine-7-carboxamide |
| P31 | 4-[2-(Cyclopropylmethoxy)-5-(difluoromethyl)phenyl]-N-[(3S,5R)-1-(methoxyacetyl)-5-methylpyrrolidin-3-yl]-6-methyl-5H-pyrrolo[3,2-d]pyrimidine-7-carboxamide |
| P32 | 4-[2-(Cyclopropylmethoxy)-5-(difluoromethyl)phenyl]-N-[(3S,5R)-1-(hydroxyacetyl)-5-methylpyrrolidin-3-yl]-6-methyl-5H-pyrrolo[3,2-d]pyrimidine-7-carboxamide |
| P33 | 4-[2-(Cyclopropylmethoxy)-5-(difluoromethyl)phenyl]-N-{(3S,5R)-1-[(2S)-2-hydroxy-propanoyl]-5-methylpyrrolidin-3-yl}-6-methyl-5H-pyrrolo[3,2-d]pyrimidine-7-carboxamide |
| P34 | N-[(3R,5R)-1-Acetyl-5-methylpyrrolidin-3-yl]-4-[2-(cyclopropylmethoxy)-5-(difluoromethyl)phenyl]-6-methyl-5H-pyrrolo[3,2-d]pyrimidine-7-carboxamide |
| P35 | 4-[2-(Cyclopropylmethoxy)-5-(difluoromethyl)phenyl]-6-methyl-N-[(3R,5R)-5-methyl-1-propanoylpyrrolidin-3-yl]-5H-pyrrolo[3,2-d]pyrimidine-7-carboxamide |
| P36 | 4-[2-(Cyclopropylmethoxy)-5-(difluoromethyl)phenyl]-N-[(3R,5R)-1-(methoxyacetyl)-5-methylpyrrolidin-3-yl]-6-methyl-5H-pyrrolo[3,2-d]pyrimidine-7-carboxamide |
| P37 | 4-[2-(Cyclopropylmethoxy)-5-(difluoromethyl)phenyl]-N-[(3R,5R)-1-(hydroxyacetyl)-5-methylpyrrolidin-3-yl]-6-methyl-5H-pyrrolo[3,2-d]pyrimidine-7-carboxamide |
| P38 | 4-[2-(Cyclopropylmethoxy)-5-(difluoromethyl)phenyl]-N-{(3R,5R)-1-[(2S)-2-hydroxy-propanoyl]-5-methylpyrrolidin-3-yl}-6-methyl-5H-pyrrolo[3,2-d]pyrimidine-7-carboxamide |
| P39 | N-[(3R,5S)-1-Acetyl-5-methylpyrrolidin-3-yl]-4-[2-(cyclopropylmethoxy)-5-(difluoromethyl)phenyl]-6-methyl-5H-pyrrolo[3,2-d]pyrimidine-7-carboxamide |
| P40 | 4-[2-(Cyclopropylmethoxy)-5-(difluoromethyl)phenyl]-6-methyl-N-[(3R,5S)-5-methyl-1-propanoylpyrrolidin-3-yl]-5H-pyrrolo[3,2-d]pyrimidine-7-carboxamide |
| P41 | 4-[2-(Cyclopropylmethoxy)-5-(difluoromethyl)phenyl]-N-[(3R,5S)-1-(methoxyacetyl)-5-methylpyrrolidin-3-yl]-6-methyl-5H-pyrrolo[3,2-d]pyrimidine-7-carboxamide |
| P42 | 4-[2-(Cyclopropylmethoxy)-5-(difluoromethyl)phenyl]-N-[(3R,5S)-1-(hydroxyacetyl)-5-methylpyrrolidin-3-yl]-6-methyl-5H-pyrrolo[3,2-d]pyrimidine-7-carboxamide |
| P43 | 4-[2-(Cyclopropylmethoxy)-5-(difluoromethyl)phenyl]-N-{(3R,5S)-1-[(2S)-2-hydroxy-propanoyl]-5-methylpyrrolidin-3-yl}-6-methyl-5H-pyrrolo[3,2-d]pyrimidine-7-carboxamide |
| P44 | N-[(3S,4S)-1-Acetyl-4-fluoropyrrolidin-3-yl]-4-[2-(cyclopropylmethoxy)-5-(difluoromethyl)phenyl]-6-methyl-5H-pyrrolo[3,2-d]pyrimidine-7-carboxamide |
| P45 | 4-[2-(Cyclopropylmethoxy)-5-(difluoromethyl)phenyl]-N-[(3S,4S)-4-fluoro-1-propanoylpyrrolidin-3-yl]-6-methyl-5H-pyrrolo[3,2-d]pyrimidine-7-carboxamide |
| P46 | 4-[2-(Cyclopropylmethoxy)-5-(difluoromethyl)phenyl]-N-[(3S,4S)-4-fluoro-1-(methoxyacetyl)pyrrolidin-3-yl]-6-methyl-5H-pyrrolo[3,2-d]pyrimidine-7-carboxamide |
| P47 | 4-[2-(Cyclopropylmethoxy)-5-(difluoromethyl)phenyl]-N-[(3S,4S)-4-fluoro-1-(hydroxyacetyl)pyrrolidin-3-yl]-6-methyl-5H-pyrrolo[3,2-d]pyrimidine-7-carboxamide |
| P48 | 4-[2-(Cyclopropylmethoxy)-5-(difluoromethyl)phenyl]-N-{(3S,4S)-4-fluoro-1-[(2S)-2-hydroxypropanoyl]pyrrolidin-3-yl}-6-methyl-5H-pyrrolo[3,2-d]pyrimidine-7-carboxamide |
| P49 | N-[(3R,4S)-1-Acetyl-4-fluoropyrrolidin-3-yl]-4-[2-(cyclopropylmethoxy)-5-(difluoromethyl)phenyl]-6-methyl-5H-pyrrolo[3,2-d]pyrimidine-7-carboxamide |
| P50 | 4-[2-(Cyclopropylmethoxy)-5-(difluoromethyl)phenyl]-N-[(3R,4S)-4-fluoro-1-propanoylpyrrolidin-3-yl]-6-methyl-5H-pyrrolo[3,2-d]pyrimidine-7-carboxamide |
| P51 | 4-[2-(Cyclopropylmethoxy)-5-(difluoromethyl)phenyl]-N-[(3R,4S)-4-fluoro-1-(methoxyacetyl)pyrrolidin-3-yl]-6-methyl-5H-pyrrolo[3,2-d]pyrimidine-7-carboxamide |
| P52 | 4-[2-(Cyclopropylmethoxy)-5-(difluoromethyl)phenyl]-N-[(3R,4S)-4-fluoro-1-(hydroxyacetyl)pyrrolidin-3-yl]-6-methyl-5H-pyrrolo[3,2-d]pyrimidine-7-carboxamide |
| P53 | 4-[2-(Cyclopropylmethoxy)-5-(difluoromethyl)phenyl]-N-{(3R,4S)-4-fluoro-1-[(2S)-2-hydroxypropanoyl]pyrrolidin-3-yl}-6-methyl-5H-pyrrolo[3,2-d]pyrimidine-7-carboxamide |
| P54 | N-[(3R,4R)-1-Acetyl-4-fluoropyrrolidin-3-yl]-4-[2-(cyclopropylmethoxy)-5-(difluoromethyl)phenyl]-6-methyl-5H-pyrrolo[3,2-d]pyrimidine-7-carboxamide |
| P55 | 4-[2-(Cyclopropylmethoxy)-5-(difluoromethyl)phenyl]-N-[(3R,4R)-4-fluoro-1-propanoylpyrrolidin-3-yl]-6-methyl-5H-pyrrolo[3,2-d]pyrimidine-7-carboxamide |
| P56 | 4-[2-(Cyclopropylmethoxy)-5-(difluoromethyl)phenyl]-N-[(3R,4R)-4-fluoro-1-(methoxyacetyl)pyrrolidin-3-yl]-6-methyl-5H-pyrrolo[3,2-d]pyrimidine-7-carboxamide |
| P57 | 4-[2-(Cyclopropylmethoxy)-5-(difluoromethyl)phenyl]-N-[(3R,4R)-4-fluoro-1-(hydroxyacetyl)pyrrolidin-3-yl]-6-methyl-5H-pyrrolo[3,2-d]pyrimidine-7-carboxamide |
| P58 | 4-[2-(Cyclopropylmethoxy)-5-(difluoromethyl)phenyl]-N-{(3R,4R)-4-fluoro-1-[(2S)-2-hydroxypropanoyl]pyrrolidin-3-yl}-6-methyl-5H-pyrrolo[3,2-d]pyrimidine-7-carboxamide |
| P59 | N-[(3S,4R)-1-Acetyl-4-fluoropyrrolidin-3-yl]-4-[2-(cyclopropylmethoxy)-5-(difluoromethyl)phenyl]-6-methyl-5H-pyrrolo[3,2-d]pyrimidine-7-carboxamide |
| P60 | 4-[2-(Cyclopropylmethoxy)-5-(difluoromethyl)phenyl]-N-[(3S,4R)-4-fluoro-1-propanoylpyrrolidin-3-yl]-6-methyl-5H-pyrrolo[3,2-d]pyrimidine-7-carboxamide |
| P61 | 4-[2-(Cyclopropylmethoxy)-5-(difluoromethyl)phenyl]-N-[(3S,4R)-4-fluoro-1-(methoxyacetyl)pyrrolidin-3-yl]-6-methyl-5H-pyrrolo[3,2-d]pyrimidine-7-carboxamide |
| P62 | 4-[2-(Cyclopropylmethoxy)-5-(difluoromethyl)phenyl]-N-[(3S,4RH-fluoro-1-(hydroxyacetyl)pyrrolidin-3-yl]-6-methyl-5H-pyrrolo[3,2-d]pyrimidine-7-carboxamide |
| P63 | 4-[2-(Cyclopropylmethoxy)-5-(difluoromethyl)phenyl]-N-{(3S,4R)-4-fluoro-1-[(2S)-2-hydroxypropanoyl]pyrrolidin-3-yl}-6-methyl-5H-pyrrolo[3,2-d]pyrimidine-7-carboxamide |
| P64 | N-[(3S*,4R*)-1-Acetyl-4-methylpyrrolidin-3-yl]-4-[2-(cyclopropylmethoxy)-5-(difluoromethyl)phenyl]-6-methyl-5H-pyrrolo[3,2-d]pyrimidine-7-carboxamide |
| P65 | 4-[2-(Cyclopropylmethoxy)-5-(difluoromethyl)phenyl]-6-methyl-N-[(3S*,4R*)-4-methyl-1-propanoylpyrrolidin-3-yl]-5H-pyrrolo[3,2-d]pyrimidine-7-carboxamide |
| P66 | 4-[2-(Cyclopropylmethoxy)-5-(difluoromethyl)phenyl]-N-[(3S*,4R*)-1-(methoxyacetyl)-4-methylpyrrolidin-3-yl]-6-methyl-5H-pyrrolo[3,2-d]pyrimidine-7-carboxamide |
| P67 | 4-[2-(Cyclopropylmethoxy)-5-(difluoromethyl)phenyl]-N-[(3S*,4R*)-1-(hydroxyacetyl)-4-methylpyrrolidin-3-yl]-6-methyl-5H-pyrrolo[3,2-d]pyrimidine-7-carboxamide |

-continued

| | |
|---|---|
| P68 | 4-[2-(Cyclopropylmethoxy)-5-(difluoromethyl)phenyl]-N-{(3S*,4R*)-1-[(2S)-2-hydroxypropanoyl]-4-methylpyrrolidin-3-yl}-6-methyl-5H-pyrrolo[3,2-d]pyrimidine-7-carboxamide |
| P69 | N-[(3S*,4S*)-1-Acetyl-4-methylpyrrolidin-3-yl]-4-[2-(cyclopropylmethoxy)-5-(difluoromethyl)phenyl]-6-methyl-5H-pyrrolo[3,2-d]pyrimidine-7-carboxamide |
| P70 | 4-[2-(Cyclopropylmethoxy)-5-(difluoromethyl)phenyl]-6-methyl-N-[(3S*,4S*)-4-methyl-1-propanoylpyrrolidin-3-yl]-5H-pyrrolo[3,2-d]pyrimidine-7-carboxamide |
| P71 | 4-[2-(Cyclopropylmethoxy)-5-(difluoromethyl)phenyl]-N-[(3S*,4S*)-1-(methoxyacetyl)-4-methylpyrrolidin-3-yl]-6-methyl-5H-pyrrolo[3,2-d]pyrimidine-7-carboxamide |
| P72 | 4-[2-(Cyclopropylmethoxy)-5-(difluoromethyl)phenyl]-N-[(3S*,4S*)-1-(hydroxyacetyl)-4-methylpyrrolidin-3-yl]-6-methyl-5H-pyrrolo[3,2-d]pyrimidine-7-carboxamide |
| P73 | 4-[2-(Cyclopropylmethoxy)-5-(difluoromethyl)phenyl]-N-{(3S*,4S*)-1-[(2S)-2-hydroxypropanoyl]-4-methylpyrrolidin-3-yl}-6-methyl-5H-pyrrolo[3,2-d]pyrimidine-7-carboxamide |
| P74 | N-[(3S*)-1-Acetyl-4,4-dimethylpyrrolidin-3-yl]-4-[2-(cyclopropylmethoxy)-5-(difluoromethyl)phenyl]-6-methyl-5H-pyrrolo[3,2-d]pyrimidine-7-carboxamide |
| P75 | 4-[2-(Cyclopropylmethoxy)-5-(difluoromethyl)phenyl]-N-[(3S*)-4,4-dimethyl-1-propanoylpyrrolidin-3-yl]-6-methyl-5H-pyrrolo[3,2-d]pyrimidine-7-carboxamide |
| P76 | 4-[2-(Cyclopropylmethoxy)-5-(difluoromethyl)phenyl]-N-[(3S*)-1-(methoxyacetyl)-4,4-dimethylpyrrolidin-3-yl]-6-methyl-5H-pyrrolo[3,2-d]pyrimidine-7-carboxamide |
| P77 | 4-[2-(Cyclopropylmethoxy)-5-(difluoromethyl)phenyl]-N-[(3S*)-1-(hydroxyacetyl)-4,4-dimethylpyrrolidin-3-yl]-6-methyl-5H-pyrrolo[3,2-d]pyrimidine-7-carboxamide |
| P78 | 4-[2-(Cyclopropylmethoxy)-5-(difluoromethyl)phenyl]-N-{(3S*)-1-[(2S)-2-hydroxypropanoyl]-4,4-dimethylpyrrolidin-3-yl}-6-methyl-5H-pyrrolo[3,2-d]pyrimidine-7-carboxamide |
| P79 | N-[(7S*)-5-Acetyl-5-azaspiro[2.4]hept-7-yl]-4-[2-(cyclopropylmethoxy)-5-(difluoromethyl)phenyl]-6-methyl-5H-pyrrolo[3,2-d]pyrimidine-7-carboxamide |
| P80 | 4-[2-(Cyclopropylmethoxy)-5-(difluoromethyl)phenyl]-6-methyl-N-[(7S*)-5-propanoyl-5-azaspiro[2.4]hept-7-yl]-5H-pyrrolo[3,2-d]pyrimidine-7-carboxamide |
| P81 | 4-[2-(Cyclopropylmethoxy)-5-(difluoromethyl)phenyl]-N-[(7S*)-5-(methoxyacetyl)-5-azaspiro[2.4]hept-7-yl]-6-methyl-5H-pyrrolo[3,2-d]pyrimidine-7-carboxamide |
| P82 | 4-[2-(Cyclopropylmethoxy)-5-(difluoromethyl)phenyl]-N-[(7S*)-5-(hydroxyacetyl)-5-azaspiro[2.4]hept-7-yl]-6-methyl-5H-pyrrolo[3,2-d]pyrimidine-7-carboxamide |
| P83 | 4-[2-(Cyclopropylmethoxy)-5-(difluoromethyl)phenyl]-N-{(7S*)-5-[(2S)-2-hydroxypropanoyl]-5-azaspiro[2.4]hept-7-yl}-6-methyl-5H-pyrrolo[3,2-d]pyrimidine-7-carboxamide |
| P84 | N-[(3R*)-1-Acetyl-4,4-difluoropyrrolidin-3-yl]-4-[2-(cyclopropylmethoxy)-5-(difluoromethyl)phenyl]-6-methyl-5H-pyrrolo[3,2-d]pyrimidine-7-carboxamide |
| P85 | 4-[2-(Cyclopropylmethoxy)-5-(difluoromethyl)phenyl]-N-[(3R*)-4,4-difluoro-1-propanoylpyrrolidin-3-yl]-6-methyl-5H-pyrrolo[3,2-d]pyrimidine-7-carboxamide |
| P86 | 4-[2-(Cyclopropylmethoxy)-5-(difluoromethyl)phenyl]-N-[(3R*)-4,4-difluoro-1-(methoxyacetyl)pyrrolidin-3-yl]-6-methyl-5H-pyrrolo[3,2-d]pyrimidine-7-carboxamide |
| P87 | 4-[2-(Cyclopropylmethoxy)-5-(difluoromethyl)phenyl]-N-[(3R*)-4,4-difluoro-1-(hydroxyacetyl)pyrrolidin-3-yl]-6-methyl-5H-pyrrolo[3,2-d]pyrimidine-7-carboxamide |
| P88 | 4-[2-(Cyclopropylmethoxy)-5-(difluoromethyl)phenyl]-N-{(3R*)-4,4-difluoro-1-[(2S)-2-hydroxypropanoyl]pyrrolidin-3-yl}-6-methyl-5H-pyrrolo[3,2-d]pyrimidine-7-carboxamide |
| P89 | N-[(1S*,3S*)-3-(Acetylamino)cyclopentyl]-4-[2-(cyclopropylmethoxy)-5-(difluoromethyl)phenyl]-6-methyl-5H-pyrrolo[3,2-d]pyrimidine-7-carboxamide |
| P90 | 4-[2-(Cyclopropylmethoxy)-5-(difluoromethyl)phenyl]-6-methyl-N-[(1S*,3S*)-3-(propanoylamino)cyclopentyl]-5H-pyrrolo[3,2-d]pyrimidine-7-carboxamide |
| P91 | 4-[2-(Cyclopropylmethoxy)-5-(difluoromethyl)phenyl]-N-{(1S*,3S*)-3-[(methoxyacetyl)amino]cyclopentyl}-6-methyl-5H-pyrrolo[3,2-d]pyrimidine-7-carboxamide |
| P92 | 4-[2-(Cyclopropylmethoxy)-5-(difluoromethyl)phenyl]-N-{(1S*,3S*)-3-[(hydroxyacetyl)amino]cyclopentyl}-6-methyl-5H-pyrrolo[3,2-d]pyrimidine-7-carboxamide |
| P93 | 4-[2-(Cyclopropylmethoxy)-5-(difluoromethyl)phenyl]-N-[(1S*,3S*)-3-{[(2S)-2-hydroxypropanoyl]amino}cyclopentyl]-6-methyl-5H-pyrrolo[3,2-d]pyrimidine-7-carboxamide |
| P94 | N-[(1S*,3R*)-3-(Acetylamino)cyclopentyl]-4-[2-(cyclopropylmethoxy)-5-(difluoromethyl)phenyl]-6-methyl-5H-pyrrolo[3,2-d]pyrimidine-7-carboxamide |
| P95 | 4-[2-(Cyclopropylmethoxy)-5-(difluoromethyl)phenyl]-6-methyl-N-[(1S*,3R*)-3-(propanoylamino)cyclopentyl]-5H-pyrrolo[3,2-d]pyrimidine-7-carboxamide |
| P96 | 4-[2-(Cyclopropylmethoxy)-5-(difluoromethyl)phenyl]-N-{(1S*,3R*)-3-[(methoxyacetyl)amino]cyclopentyl}-6-methyl-5H-pyrrolo[3,2-d]pyrimidine-7-carboxamide |
| P97 | 4-[2-(Cyclopropylmethoxy)-5-(difluoromethyl)phenyl]-N-{(1S*,3R*)-3-[(hydroxyacetyl)amino]cyclopentyl}-6-methyl-5H-pyrrolo[3,2-d]pyrimidine-7-carboxamide |
| P98 | 4-[2-(Cyclopropylmethoxy)-5-(difluoromethyl)phenyl]-N-[(1S*,3R*)-3-{[(2S)-2-hydroxypropanoyl]amino}cyclopentyl]-6-methyl-5H-pyrrolo[3,2-d]pyrimidine-7-carboxamide |
| P99 | N-[(1R*,2R*,4R*)-4-(Acetylamino)-2-fluorocyclopentyl]-4-[2-(cyclopropylmethoxy)-5-(difluoromethyl)phenyl]-6-methyl-5H-pyrrolo[3,2-d]pyrimidine-7-carboxamide |
| P100 | 4-[2-(Cyclopropylmethoxy)-5-(difluoromethyl)phenyl]-N-[(1R*,2R*,4R*)-2-fluoro-4-(propanoylamino)cyclopentyl]-6-methyl-5H-pyrrolo[3,2-d]pyrimidine-7-carboxamide |
| P101 | 4-[2-(Cyclopropylmethoxy)-5-(difluoromethyl)phenyl]-N-{(1R*,2R*,4R*)-2-fluoro-4-[(methoxyacetyl)amino]cyclopentyl}-6-methyl-5H-pyrrolo[3,2-d]pyrimidine-7-carboxamide |
| P102 | 4-[2-(Cyclopropylmethoxy)-5-(difluoromethyl)phenyl]-N-{(1R*,2R*,4R*)-2-fluoro-4-[(hydroxyacetyl)amino]cyclopentyl}-6-methyl-5H-pyrrolo[3,2-d]pyrimidine-7-carboxamide |
| P103 | 4-[2-(Cyclopropylmethoxy)-5-(difluoromethyl)phenyl]-N-[(1R*,2R*,4R*)-2-fluoro-4-{[(2S)-2-hydroxypropanoyl]amino}cyclopentyl]-6-methyl-5H-pyrrolo[3,2-d]pyrimidine-7-carboxamide |
| P104 | N-[(1R*,2R*,4S*)-4-(Acetylamino)-2-fluorocyclopentyl]-4-[2-(cyclopropylmethoxy)-5-(difluoromethyl)phenyl]-6-methyl-5H-pyrrolo[3,2-d]pyrimidine-7-carboxamide |
| P105 | 4-[2-(Cyclopropylmethoxy)-5-(difluoromethyl)phenyl]-N-[(1R*,2R*,4S*)-2-fluoro-4-(propanoylamino)cyclopentyl]-6-methyl-5H-pyrrolo[3,2-d]pyrimidine-7-carboxamide |
| P106 | 4-[2-(Cyclopropylmethoxy)-5-(difluoromethyl)phenyl]-N-{(1R*,2R*,4S*)-2-fluoro-4-[(methoxyacetyl)amino]cyclopentyl}-6-methyl-5H-pyrrolo[3,2-d]pyrimidine-7-carboxamide |

| | -continued |
|---|---|
| P107 | 4-[2-(Cyclopropylmethoxy)-5-(difluoromethyl)phenyl]-N-{(1R*,2R*,4S*)-2-fluoro-4-[(hydroxyacetyl)amino]cyclopentyl}-6-methyl-5H-pyrrolo[3,2-d]pyrimidine-7-carboxamide |
| P108 | 4-[2-(Cyclopropylmethoxy)-5-(difluoromethyl)phenyl]-N-[(1R*,2R*,4S*)-2-fluoro-4-{[(2S)-2-hydroxypropanoyl]amino}cyclopentyl]-6-methyl-5H-pyrrolo[3,2-d]pyrimidine-7-carboxamide |
| P109 | 4-[2-(Cyclopropylmethoxy)-5-(difluoromethyl)phenyl]-N-[(1R,2S)-2-hydroxycyclohexyl]-6-methyl-5H-pyrrolo[3,2-d]pyrimidine-7-carboxamide |
| P110 | 4-[2-(Cyclopropylmethoxy)-5-(difluoromethyl)phenyl]-N-[(1R,2R)-2-hydroxycyclohexyl]-6-methyl-5H-pyrrolo[3,2-d]pyrimidine-7-carboxamide |
| P111 | 4-[2-(Cyclopropylmethoxy)-5-(difluoromethyl)phenyl]-N-[(1S,2S)-2-hydroxycyclohexyl]-6-methyl-5H-pyrrolo[3,2-d]pyrimidine-7-carboxamide |
| P112 | 4-[2-(Cyclopropylmethoxy)-5-(difluoromethyl)phenyl]-N-[(1S,2R)-2-hydroxycyclohexyl]-6-methyl-5H-pyrrolo[3,2-d]pyrimidine-7-carboxamide |
| P113 | 4-[2-(Cyclopropylmethoxy)-5-(difluoromethyl)phenyl]-N-[(1S,3R)-3-hydroxycyclohexyl]-6-methyl-5H-pyrrolo[3,2-d]pyrimidine-7-carboxamide |
| P114 | 4-[2-(Cyclopropylmethoxy)-5-(difluoromethyl)phenyl]-N-[(1S,3S)-3-hydroxycyclohexyl]-6-methyl-5H-pyrrolo[3,2-d]pyrimidine-7-carboxamide |
| P115 | 4-[2-(Cyclopropylmethoxy)-5-(difluoromethyl)phenyl]-N-[(1R,3R)-3-hydroxycyclohexyl]-6-methyl-5H-pyrrolo[3,2-d]pyrimidine-7-carboxamide |
| P116 | 4-[2-(Cyclopropylmethoxy)-5-(difluoromethyl)phenyl]-N-[(1R,3S)-3-hydroxycyclohexyl]-6-methyl-5H-pyrrolo[3,2-d]pyrimidine-7-carboxamide |
| P117 | 4-[2-(Cyclopropylmethoxy)-5-(difluoromethyl)phenyl]-N-(trans-4-hydroxycyclohexyl)-6-methyl-5H-pyrrolo[3,2-d]pyrimidine-7-carboxamide |
| P118 | 4-[2-(Cyclopropylmethoxy)-5-(difluoromethyl)phenyl]-N-(cis-4-hydroxycyclohexyl)-6-methyl-5H-pyrrolo[3,2-d]pyrimidine-7-carboxamide |
| P119 | N-[(3S,4R)-1-Acetyl-3-fluoropiperidin-4-yl]-4-[2-(cyclopropylmethoxy)-5-(difluoromethyl)phenyl]-6-methyl-5H-pyrrolo[3,2-d]pyrimidine-7-carboxamide |
| P120 | 4-[2-(Cyclopropylmethoxy)-5-(difluoromethyl)phenyl]-N-[(3S,4R)-3-fluoro-1-propanoylpiperidin-4-yl]-6-methyl-5H-pyrrolo[3,2-d]pyrimidine-7-carboxamide |
| P121 | 4-[2-(Cyclopropylmethoxy)-5-(difluoromethyl)phenyl]-N-[(3S,4R)-3-fluoro-1-(methoxyacetyl)piperidin-4-yl]-6-methyl-5H-pyrrolo[3,2-d]pyrimidine-7-carboxamide |
| P122 | 4-[2-(Cyclopropylmethoxy)-5-(difluoromethyl)phenyl]-N-[(3S,4R)-3-fluoro-1-(hydroxyacetyl)piperidin-4-yl]-6-methyl-5H-pyrrolo[3,2-d]pyrimidine-7-carboxamide |
| P123 | 4-[2-(Cyclopropylmethoxy)-5-(difluoromethyl)phenyl]-N-{(3S,4R)-3-fluoro-1-[(2S)-2-hydroxypropanoyl]piperidin-4-yl}-6-methyl-5H-pyrrolo[3,2-d]pyrimidine-7-carboxamide |
| P124 | N-[(3R,4R)-1-Acetyl-3-fluoropiperidin-4-yl]-4-[2-(cyclopropylmethoxy)-5-(difluoromethyl)phenyl]-6-methyl-5H-pyrrolo[3,2-d]pyrimidine-7-carboxamide |
| P125 | 4-[2-(Cyclopropylmethoxy)-5-(difluoromethyl)phenyl]-N-[(3R,4R)-3-fluoro-1-propanoylpiperidin-4-yl]-6-methyl-5H-pyrrolo[3,2-d]pyrimidine-7-carboxamide |
| P126 | 4-[2-(Cyclopropylmethoxy)-5-(difluoromethyl)phenyl]-N-[(3R,4R)-3-fluoro-1-(methoxyacetyl)piperidin-4-yl]-6-methyl-5H-pyrrolo[3,2-d]pyrimidine-7-carboxamide |
| P127 | 4-[2-(Cyclopropylmethoxy)-5-(difluoromethyl)phenyl]-N-[(3R,4R)-3-fluoro-1-(hydroxyacetyl)piperidin-4-yl]-6-methyl-5H-pyrrolo[3,2-d]pyrimidine-7-carboxamide |
| P128 | 4-[2-(Cyclopropylmethoxy)-5-(difluoromethyl)phenyl]-N-{(3R,4R)-3-fluoro-1-[(2S)-2-hydroxypropanoyl]piperidin-4-yl}-6-methyl-5H-pyrrolo[3,2-d]pyrimidine-7-carboxamide |
| P129 | N-[(3S,4S)-1-Acetyl-3-fluoropiperidin-4-yl]-4-[2-(cyclopropylmethoxy)-5-(difluoromethyl)phenyl]-6-methyl-5H-pyrrolo[3,2-d]pyrimidine-7-carboxamide |
| P130 | 4-[2-(Cyclopropylmethoxy)-5-(difluoromethyl)phenyl]-N-[(3S,4S)-3-fluoro-1-propanoylpiperidin-4-yl]-6-methyl-5H-pyrrolo[3,2-d]pyrimidine-7-carboxamide |
| P131 | 4-[2-(Cyclopropylmethoxy)-5-(difluoromethyl)phenyl]-N-[(3S,4S)-3-fluoro-1-(methoxyacetyl)piperidin-4-yl]-6-methyl-5H-pyrrolo[3,2-d]pyrimidine-7-carboxamide |
| P132 | 4-[2-(Cyclopropylmethoxy)-5-(difluoromethyl)phenyl]-N-[(3S,4S)-3-fluoro-1-(hydroxyacetyl)piperidin-4-yl]-6-methyl-5H-pyrrolo[3,2-d]pyrimidine-7-carboxamide |
| P133 | 4-[2-(Cyclopropylmethoxy)-5-(difluoromethyl)phenyl]-N-{(3S,4S)-3-fluoro-1-[(2S)-2-hydroxypropanoyl]piperidin-4-yl}-6-methyl-5H-pyrrolo[3,2-d]pyrimidine-7-carboxamide |
| P134 | N-[(3R,4S)-1-Acetyl-3-fluoropiperidin-4-yl]-4-[2-(cyclopropylmethoxy)-5-(difluoromethyl)phenyl]-6-methyl-5H-pyrrolo[3,2-d]pyrimidine-7-carboxamide |
| P135 | 4-[2-(Cyclopropylmethoxy)-5-(difluoromethyl)phenyl]-N-[(3R,4S)-3-fluoro-1-propanoylpiperidin-4-yl]-6-methyl-5H-pyrrolo[3,2-d]pyrimidine-7-carboxamide |
| P136 | 4-[2-(Cyclopropylmethoxy)-5-(difluoromethyl)phenyl]-N-[(3R,4S)-3-fluoro-1-(methoxyacetyl)piperidin-4-yl]-6-methyl-5H-pyrrolo[3,2-d]pyrimidine-7-carboxamide |
| P137 | 4-[2-(Cyclopropylmethoxy)-5-(difluoromethyl)phenyl]-N-[(3R,4S)-3-fluoro-1-(hydroxyacetyl)piperidin-4-yl]-6-methyl-5H-pyrrolo[3,2-d]pyrimidine-7-carboxamide |
| P138 | 4-[2-(Cyclopropylmethoxy)-5-(difluoromethyl)phenyl]-N-{(3R,4S)-3-fluoro-1-[(2S)-2-hydroxypropanoyl]piperidin-4-yl}-6-methyl-5H-pyrrolo[3,2-d]pyrimidine-7-carboxamide |
| P139 | N-[(1R*,2R*,4R*)-4-(Acetylamino)-2-methylcyclohexyl]-4-[2-(cyclopropylmethoxy)-5-(difluoromethyl)phenyl]-6-methyl-5H-pyrrolo[3,2-d]pyrimidine-7-carboxamide |
| P140 | 4-[2-(Cyclopropylmethoxy)-5-(difluoromethyl)phenyl]-6-methyl-N-[(1R*,2R*,4R*)-2-methyl-4-(propanoylamino)cyclohexyl]-5H-pyrrolo[3,2-d]pyrimidine-7-carboxamide |
| P141 | 4-[2-(Cyclopropylmethoxy)-5-(difluoromethyl)phenyl]-N-{(1R*,2R*,4R*)-4-[(methoxy-acetyl)amino]-2-methylcyclohexyl}-6-methyl-5H-pyrrolo[3,2-d]pyrimidine-7-carboxamide |
| P142 | 4-[2-(Cyclopropylmethoxy)-5-(difluoromethyl)phenyl]-N-{(1R*,2R*,4R*)-4-[(hydroxy-acetyl)amino]-2-methylcyclohexyl}-6-methyl-5H-pyrrolo[3,2-d]pyrimidine-7-carboxamide |
| P143 | 4-[2-(Cyclopropylmethoxy)-5-(difluoromethyl)phenyl]-N-[(1R*,2R*,4R*)-4-{[(2S)-2-hydroxypropanoyl]amino}-2-methylcyclohexyl]-6-methyl-5H-pyrrolo[3,2-d]pyrimidine-7-carboxamide |
| P144 | N-[(1R*,2R*,4S*)-4-(acetylamino)-2-methylcyclohexyl]-4-[2-(cyclopropylmethoxy)-5-(difluoromethyl)phenyl]-6-methyl-5H-pyrrolo[3,2-d]pyrimidine-7-carboxamide |

| | |
|---|---|
| P145 | 4-[2-(Cyclopropylmethoxy)-5-(difluoromethyl)phenyl]-6-methyl-N-[(1R*,2R*,4S*)-2-methyl-4-(propanoylamino)cyclohexyl]-5H-pyrrolo[3,2-d]pyrimidine-7-carboxamide |
| P146 | 4-[2-(Cyclopropylmethoxy)-5-(difluoromethyl)phenyl]-N-{(1R*,2R*,4S*)-4-[(methoxyacetyl)amino]-2-methylcyclohexyl}-6-methyl-5H-pyrrolo[3,2-d]pyrimidine-7-carboxamide |
| P147 | 4-[2-(Cyclopropylmethoxy)-5-(difluoromethyl)phenyl]-N-{(1R*,2R*,4S*)-4-[(hydroxyacetyl)amino]-2-methylcyclohexyl}-6-methyl-5H-pyrrolo[3,2-d]pyrimidine-7-carboxamide |
| P148 | 4-[2-(Cyclopropylmethoxy)-5-(difluoromethyl)phenyl]-N-[(1R*,2R*,4S*)-4-{[(2S)-2-hydroxypropanoyl]amino}-2-methylcyclohexyl]-6-methyl-5H-pyrrolo[3,2-d]pyrimidine-7-carboxamide |
| P149 | N-[(1S*,2R*,4S*)-4-(acetylamino)-2-methylcyclohexyl]-4-[2-(cyclopropylmethoxy)-5-(difluoromethyl)phenyl]-6-methyl-5H-pyrrolo[3,2-d]pyrimidine-7-carboxamide |
| P150 | 4-[2-(Cyclopropylmethoxy)-5-(difluoromethyl)phenyl]-6-methyl-N-[(1S*,2R*,4S*)-2-methyl-4-(propanoylamino)cyclohexyl]-5H-pyrrolo[3,2-d]pyrimidine-7-carboxamide |
| P151 | 4-[2-(Cyclopropylmethoxy)-5-(difluoromethyl)phenyl]-N-{(1S*,2R*,4S*)-4-[(methoxyacetyl)amino]-2-methylcyclohexyl}-6-methyl-5H-pyrrolo[3,2-d]pyrimidine-7-carboxamide |
| P152 | 4-[2-(Cyclopropylmethoxy)-5-(difluoromethyl)phenyl]-N-{(1S*,2R*,4S*)-4-[(hydroxyacetyl)amino]-2-methylcyclohexyl}-6-methyl-5H-pyrrolo[3,2-d]pyrimidine-7-carboxamide |
| P153 | 4-[2-(Cyclopropylmethoxy)-5-(difluoromethyl)phenyl]-N-[(1S*,2R*,4S*)-4-{[(2S)-2-hydroxypropanoyl]amino}-2-methylcyclohexyl]-6-methyl-5H-pyrrolo[3,2-d]pyrimidine-7-carboxamide |
| P154 | N-[(1S*,2R*,4R*)-4-(Acetylamino)-2-methylcyclohexyl]-4-[2-(cyclopropylmethoxy)-5-(difluoromethyl)phenyl]-6-methyl-5H-pyrrolo[3,2-d]pyrimidine-7-carboxamide |
| P155 | 4-[2-(Cyclopropylmethoxy)-5-(difluoromethyl)phenyl]-6-methyl-N-[(1S*,2R*,4R*)-2-methyl-4-(propanoylamino)cyclohexyl]-5H-pyrrolo[3,2-d]pyrimidine-7-carboxamide |
| P156 | 4-[2-(Cyclopropylmethoxy)-5-(difluoromethyl)phenyl]-N-{(1S*,2R*,4R*)-4-[(methoxyacetyl)amino]-2-methylcyclohexyl}-6-methyl-5H-pyrrolo[3,2-d]pyrimidine-7-carboxamide |
| P157 | 4-[2-(Cyclopropylmethoxy)-5-(difluoromethyl)phenyl]-N-{(1S*,2R*,4R*)-4-[(hydroxyacetyl)amino]-2-methylcyclohexyl}-6-methyl-5H-pyrrolo[3,2-d]pyrimidine-7-carboxamide |
| P158 | 4-[2-(Cyclopropylmethoxy)-5-(difluoromethyl)phenyl]-N-[(1S*,2R*,4R*)-4-{[(2S)-2-hydroxypropanoyl]amino}-2-methylcyclohexyl]-6-methyl-5H-pyrrolo[3,2-d]pyrimidine-7-carboxamide |
| P159 | N-[(1R*,2R*,4R*)-4-(Acetylamino)-2-fluorocyclohexyl]-4-[2-(cyclopropylmethoxy)-5-(difluoromethyl)phenyl]-6-methyl-5H-pyrrolo[3,2-d]pyrimidine-7-carboxamide |
| P160 | 4-[2-(Cyclopropylmethoxy)-5-(difluoromethyl)phenyl]-N-[(1R*,2R*,4R*)-2-fluoro-4-(propanoylamino)cyclohexyl]-6-methyl-5H-pyrrolo[3,2-d]pyrimidine-7-carboxamide |
| P161 | 4-[2-(Cyclopropylmethoxy)-5-(difluoromethyl)phenyl]-N-{(1R*,2R*,4R*)-2-fluoro-4-[(methoxyacetyl)amino]cyclohexyl}-6-methyl-5H-pyrrolo[3,2-d]pyrimidine-7-carboxamide |
| P162 | 4-[2-(Cyclopropylmethoxy)-5-(difluoromethyl)phenyl]-N-{(1R*,2R*,4R*)-2-fluoro-4-[(hydroxyacetyl)amino]cyclohexyl}-6-methyl-5H-pyrrolo[3,2-d]pyrimidine-7-carboxamide |
| P163 | 4-[2-(Cyclopropylmethoxy)-5-(difluoromethyl)phenyl]-N-[(1R*,2R*,4R*)-2-fluoro-4-{[(2S)-2-hydroxypropanoyl]amino}cyclohexyl]-6-methyl-5H-pyrrolo[3,2-d]pyrimidine-7-carboxamide |
| P164 | N-[(1R*,2R*,4S*)-4-(Acetylamino)-2-fluorocyclohexyl]-4-[2-(cyclopropylmethoxy)-5-(difluoromethyl)phenyl]-6-methyl-5H-pyrrolo[3,2-d]pyrimidine-7-carboxamide |
| P165 | 4-[2-(Cyclopropylmethoxy)-5-(difluoromethyl)phenyl]-N-[(1R*,2R*,4S*)-2-fluoro-4-(propanoylamino)cyclohexyl]-6-methyl-5H-pyrrolo[3,2-d]pyrimidine-7-carboxamide |
| P166 | 4-[2-(Cyclopropylmethoxy)-5-(difluoromethyl)phenyl]-N-{(1R*,2R*,4S*)-2-fluoro-4-[(methoxyacetyl)amino]cyclohexyl}-6-methyl-5H-pyrrolo[3,2-d]pyrimidine-7-carboxamide |
| P167 | 4-[2-(Cyclopropylmethoxy)-5-(difluoromethyl)phenyl]-N-{(1R*,2R*,4S*)-2-fluoro-4-[(hydroxyacetyl)amino]cyclohexyl}-6-methyl-5H-pyrrolo[3,2-d]pyrimidine-7-carboxamide |
| P168 | 4-[2-(Cyclopropylmethoxy)-5-(difluoromethyl)phenyl]-N-[(1R*,2R*,4S*)-2-fluoro-4-{[(2S)-2-hydroxypropanoyl]amino}cyclohexyl]-6-methyl-5H-pyrrolo[3,2-d]pyrimidine-7-carboxamide |
| P169 | N-[(1S*,2R*,4S*)-4-(Acetylamino)-2-fluorocyclohexyl]-4-[2-(cyclopropylmethoxy)-5-(difluoromethyl)phenyl]-6-methyl-5H-pyrrolo[3,2-d]pyrimidine-7-carboxamide |
| P170 | 4-[2-(Cyclopropylmethoxy)-5-(difluoromethyl)phenyl]-N-[(1S*,2R*,4S*)-2-fluoro-4-(propanoylamino)cyclohexyl]-6-methyl-5H-pyrrolo[3,2-d]pyrimidine-7-carboxamide |
| P171 | 4-[2-(Cyclopropylmethoxy)-5-(difluoromethyl)phenyl]-N-{(1S*,2R*,4S*)-2-fluoro-4-[(methoxyacetyl)amino]cyclohexyl}-6-methyl-5H-pyrrolo[3,2-d]pyrimidine-7-carboxamide |
| P172 | 4-[2-(Cyclopropylmethoxy)-5-(difluoromethyl)phenyl]-N-{(1S*,2R*,4S*)-2-fluoro-4-[(hydroxyacetyl)amino]cyclohexyl}-6-methyl-5H-pyrrolo[3,2-d]pyrimidine-7-carboxamide |
| P173 | 4-[2-(Cyclopropylmethoxy)-5-(difluoromethyl)phenyl]-N-[(1S*,2R*,4S*)-2-fluoro-4-{[(2S)-2-hydroxypropanoyl]amino}cyclohexyl]-6-methyl-5H-pyrrolo[3,2-d]pyrimidine-7-carboxamide |
| P174 | N-[(1S*,2R*,4R*)-4-(Acetylamino)-2-fluorocyclohexyl]-4-[2-(cyclopropylmethoxy)-5-(difluoromethyl)phenyl]-6-methyl-5H-pyrrolo[3,2-d]pyrimidine-7-carboxamide |
| P175 | 4-[2-(Cyclopropylmethoxy)-5-(difluoromethyl)phenyl]-N-[(1S*,2R*,4R*)-2-fluoro-4-(propanoylamino)cyclohexyl]-6-methyl-5H-pyrrolo[3,2-d]pyrimidine-7-carboxamide |
| P176 | 4-[2-(Cyclopropylmethoxy)-5-(difluoromethyl)phenyl]-N-{(1S*,2R*,4R*)-2-fluoro-4-[(methoxyacetyl)amino]cyclohexyl}-6-methyl-5H-pyrrolo[3,2-d]pyrimidine-7-carboxamide |
| P177 | 4-[2-(Cyclopropylmethoxy)-5-(difluoromethyl)phenyl]-N-{(1S*,2R*,4R*)-2-fluoro-4-[(hydroxyacetyl)amino]cyclohexyl}-6-methyl-5H-pyrrolo[3,2-d]pyrimidine-7-carboxamide |
| P178 | 4-[2-(Cyclopropylmethoxy)-5-(difluoromethyl)phenyl]-N-[(1S*,2R*,4R*)-2-fluoro-4-{[(2S)-2-hydroxypropanoyl]amino}cyclohexyl]-6-methyl-5H-pyrrolo[3,2-d]pyrimidine-7-carboxamide |
| P179 | N-[(1S*,3R*,4S*)-4-(acetylamino)-3-methylcyclohexyl]-4-[2-(cyclopropylmethoxy)-5-(difluoromethyl)phenyl]-6-methyl-5H-pyrrolo[3,2-d]pyrimidine-7-carboxamide |
| P180 | 4-[2-(Cyclopropylmethoxy)-5-(difluoromethyl)phenyl]-6-methyl-N-[(1S*,3R*,4S*)-3-methyl-4-(propanoylamino)cyclohexyl]-5H-pyrrolo[3,2-d]pyrimidine-7-carboxamide |

-continued

| | |
|---|---|
| P181 | 4-[2-(Cyclopropylmethoxy)-5-(difluoromethyl)phenyl]-N-{(1S*,3R*,4S*)-4-[(methoxyacetyl)amino]-3-methylcyclohexyl}-6-methyl-5H-pyrrolo[3,2-d]pyrimidine-7-carboxamide |
| P182 | 4-[2-(Cyclopropylmethoxy)-5-(difluoromethyl)phenyl]-N-{(1S*,3R*,4S*)-4-[(hydroxyacetyl)amino]-3-methylcyclohexyl}-6-methyl-5H-pyrrolo[3,2-d]pyrimidine-7-carboxamide |
| P183 | 4-[2-(Cyclopropylmethoxy)-5-(difluoromethyl)phenyl]-N-[(1S*,3R*,4S*)-4-{[(2S)-2-hydroxypropanoyl]amino}-3-methylcyclohexyl]-6-methyl-5H-pyrrolo[3,2-d]pyrimidine-7-carboxamide |
| P184 | N-[(1S*,3R*,4R*)-4-(Acetylamino)-3-methylcyclohexyl]-4-[2-(cyclopropylmethoxy)-5-(difluoromethyl)phenyl]-6-methyl-5H-pyrrolo[3,2-d]pyrimidine-7-carboxamide |
| P185 | 4-[2-(Cyclopropylmethoxy)-5-(difluoromethyl)phenyl]-6-methyl-N-[(1S*,3R*,4R*)-3-methyl-4-(propanoylamino)cyclohexyl]-5H-pyrrolo[3,2-d]pyrimidine-7-carboxamide |
| P186 | 4-[2-(Cyclopropylmethoxy)-5-(difluoromethyl)phenyl]-N-{(1S*,3R*,4R*)-4-[(methoxyacetyl)amino]-3-methylcyclohexyl}-6-methyl-5H-pyrrolo[3,2-d]pyrimidine-7-carboxamide |
| P187 | 4-[2-(Cyclopropylmethoxy)-5-(difluoromethyl)phenyl]-N-{(1S*,3R*,4R*)-4-[(hydroxyacetyl)amino]-3-methylcyclohexyl}-6-methyl-5H-pyrrolo[3,2-d]pyrimidine-7-carboxamide |
| P188 | 4-[2-(Cyclopropylmethoxy)-5-(difluoromethyl)phenyl]-N-[(1S*,3R*,4R*)-4-{[(2S)-2-hydroxypropanoyl]amino}-3-methylcyclohexyl]-6-methyl-5H-pyrrolo[3,2-d]pyrimidine-7-carboxamide |
| P189 | N-[(1R*,3R*,4R*)-4-(acetylamino)-3-methylcyclohexyl]-4-[2-(cyclopropylmethoxy)-5-(difluoromethyl)phenyl]-6-methyl-5H-pyrrolo[3,2-d]pyrimidine-7-carboxamide |
| P190 | 4-[2-(Cyclopropylmethoxy)-5-(difluoromethyl)phenyl]-6-methyl-N-[(1R*,3R*,4R*)-3-methyl-4-(propanoylamino)cyclohexyl]-5H-pyrrolo[3,2-d]pyrimidine-7-carboxamide |
| P191 | 4-[2-(Cyclopropylmethoxy)-5-(difluoromethyl)phenyl]-N-{(1R*,3R*,4R*)-4-[(methoxyacetyl)amino]-3-methylcyclohexyl}-6-methyl-5H-pyrrolo[3,2-d]pyrimidine-7-carboxamide |
| P192 | 4-[2-(Cyclopropylmethoxy)-5-(difluoromethyl)phenyl]-N-{(1R*,3R*,4R*)-4-[(hydroxyacetyl)amino]-3-methylcyclohexyl}-6-methyl-5H-pyrrolo[3,2-d]pyrimidine-7-carboxamide |
| P193 | 4-[2-(Cyclopropylmethoxy)-5-(difluoromethyl)phenyl]-N-[(1R*,3R*,4R*)-4-{[(2S)-2-hydroxypropanoyl]amino}-3-methylcyclohexyl]-6-methyl-5H-pyrrolo[3,2-d]pyrimidine-7-carboxamide |
| P194 | N-[(1R*,3R*,4S*)-4-(Acetylamino)-3-methylcyclohexyl]-4-[2-(cyclopropylmethoxy)-5-(difluoromethyl)phenyl]-6-methyl-5H-pyrrolo[3,2-d]pyrimidine-7-carboxamide |
| P195 | 4-[2-(Cyclopropylmethoxy)-5-(difluoromethyl)phenyl]-6-methyl-N-[(1R*,3R*,4S*)-3-methyl-4-(propanoylamino)cyclohexyl]-5H-pyrrolo[3,2-d]pyrimidine-7-carboxamide |
| P196 | 4-[2-(Cyclopropylmethoxy)-5-(difluoromethyl)phenyl]-N-{(1R*,3R*,4S*)-4-[(methoxyacetyl)amino]-3-methylcyclohexyl}-6-methyl-5H-pyrrolo[3,2-d]pyrimidine-7-carboxamide |
| P197 | 4-[2-(Cyclopropylmethoxy)-5-(difluoromethyl)phenyl]-N-{(1R*,3R*,4S*)-4-[(hydroxyacetyl)amino]-3-methylcyclohexyl}-6-methyl-5H-pyrrolo[3,2-d]pyrimidine-7-carboxamide |
| P198 | 4-[2-(Cyclopropylmethoxy)-5-(difluoromethyl)phenyl]-N-[(1R*,3R*,4S*)-4-{[(2S)-2-hydroxypropanoyl]amino}-3-methylcyclohexyl]-6-methyl-5H-pyrrolo[3,2-d]pyrimidine-7-carboxamide |
| P199 | N-[(1S*,3R*,4S*)-4-(acetylamino)-3-fluorocyclohexyl]-4-[2-(cyclopropylmethoxy)-5-(difluoromethyl)phenyl]-6-methyl-5H-pyrrolo[3,2-d]pyrimidine-7-carboxamide |
| P200 | 4-[2-(Cyclopropylmethoxy)-5-(difluoromethyl)phenyl]-N-[(1S*,3R*,4S*)-3-fluoro-4-(propanoylamino)cyclohexyl]-6-methyl-5H-pyrrolo[3,2-d]pyrimidine-7-carboxamide |
| P201 | 4-[2-(Cyclopropylmethoxy)-5-(difluoromethyl)phenyl]-N-{(1S*,3R*,4S*)-3-fluoro-4-[(methoxyacetyl)amino]cyclohexyl}-6-methyl-5H-pyrrolo[3,2-d]pyrimidine-7-carboxamide |
| P202 | 4-[2-(Cyclopropylmethoxy)-5-(difluoromethyl)phenyl]-N-{(1S*,3R*,4S*)-3-fluoro-4-[(hydroxyacetyl)amino]cyclohexyl}-6-methyl-5H-pyrrolo[3,2-d]pyrimidine-7-carboxamide |
| P203 | 4-[2-(Cyclopropylmethoxy)-5-(difluoromethyl)phenyl]-N-[(1S*,3R*,4S*)-3-fluoro-4-{[(2S)-2-hydroxypropanoyl]amino}cyclohexyl]-6-methyl-5H-pyrrolo[3,2-d]pyrimidine-7-carboxamide |
| P204 | N-[(1S*,3R*,4R*)-4-(acetylamino)-3-fluorocyclohexyl]-4-[2-(cyclopropylmethoxy)-5-(difluoromethyl)phenyl]-6-methyl-5H-pyrrolo[3,2-d]pyrimidine-7-carboxamide |
| P205 | 4-[2-(Cyclopropylmethoxy)-5-(difluoromethyl)phenyl]-N-[(1S*,3R*,4R*)-3-fluoro-4-(propanoylamino)cyclohexyl]-6-methyl-5H-pyrrolo[3,2-d]pyrimidine-7-carboxamide |
| P206 | 4-[2-(Cyclopropylmethoxy)-5-(difluoromethyl)phenyl]-N-{(1S*,3R*,4R*)-3-fluoro-4-[(methoxyacetyl)amino]cyclohexyl}-6-methyl-5H-pyrrolo[3,2-d]pyrimidine-7-carboxamide |
| P207 | 4-[2-(Cyclopropylmethoxy)-5-(difluoromethyl)phenyl]-N-{(1S*,3R*,4R*)-3-fluoro-4-[(hydroxyacetyl)amino]cyclohexyl}-6-methyl-5H-pyrrolo[3,2-d]pyrimidine-7-carboxamide |
| P208 | 4-[2-(cyclopropylmethoxy)-5-(difluoromethyl)phenyl]-N-[(1S*,3R*,4R*)-3-fluoro-4-{[(2S)-2-hydroxypropanoyl]amino}cyclohexyl]-6-methyl-5H-pyrrolo[3,2-d]pyrimidine-7-carboxamide |
| P209 | N-[(1R*,3R*,4R*)-4-(Acetylamino)-3-fluorocyclohexyl]-4-[2-(cyclopropylmethoxy)-5-(difluoromethyl)phenyl]-6-methyl-5H-pyrrolo[3,2-d]pyrimidine-7-carboxamide |
| P210 | 4-[2-(Cyclopropylmethoxy)-5-(difluoromethyl)phenyl]-N-[(1R*,3R*,4R*)-3-fluoro-4-(propanoylamino)cyclohexyl]-6-methyl-5H-pyrrolo[3,2-d]pyrimidine-7-carboxamide |
| P211 | 4-[2-(Cyclopropylmethoxy)-5-(difluoromethyl)phenyl]-N-{(1R*,3R*,4R*)-3-fluoro-4-[(methoxyacetyl)amino]cyclohexyl}-6-methyl-5H-pyrrolo[3,2-d]pyrimidine-7-carboxamide |
| P212 | 4-[2-(Cyclopropylmethoxy)-5-(difluoromethyl)phenyl]-N-{(1R*,3R*,4R*)-3-fluoro-4-[(hydroxyacetyl)amino]cyclohexyl}-6-methyl-5H-pyrrolo[3,2-d]pyrimidine-7-carboxamide |
| P213 | 4-[2-(Cyclopropylmethoxy)-5-(difluoromethyl)phenyl]-N-[(1R*,3R*,4R*)-3-fluoro-4-{[(2S)-2-hydroxypropanoyl]amino}cyclohexyl]-6-methyl-5H-pyrrolo[3,2-d]pyrimidine-7-carboxamide |
| P214 | N-[(1R*,3R*,4S*)-4-(Acetylamino)-3-fluorocyclohexyl]-4-[2-(cyclopropylmethoxy)-5-(difluoromethyl)phenyl]-6-methyl-5H-pyrrolo[3,2-d]pyrimidine-7-carboxamide |
| P215 | 4-[2-(Cyclopropylmethoxy)-5-(difluoromethyl)phenyl]-N-[(1R*,3R*,4S*)-3-fluoro-4-(propanoylamino)cyclohexyl]-6-methyl-5H-pyrrolo[3,2-d]pyrimidine-7-carboxamide |
| P216 | 4-[2-(Cyclopropylmethoxy)-5-(difluoromethyl)phenyl]-N-{(1R*,3R*,4S*)-3-fluoro-4-[(methoxyacetyl)amino]cyclohexyl}-6-methyl-5H-pyrrolo[3,2-d]pyrimidine-7-carboxamide |

| | |
|---|---|
| P217 | 4-[2-(Cyclopropylmethoxy)-5-(difluoromethyl)phenyl]-N-{(1R*,3R*,4S*)-3-fluoro-4-[(hydroxyacetyl)amino]cyclohexyl}-6-methyl-5H-pyrrolo[3,2-d]pyrimidine-7-carboxamide |
| P218 | 4-[2-(Cyclopropylmethoxy)-5-(difluoromethyl)phenyl]-N-[(1R*,3R*,4S*)-3-fluoro-4-{[(2S)-2-hydroxypropanoyl]amino}cyclohexyl]-6-methyl-5H-pyrrolo[3,2-d]pyrimidine-7-carboxamide |
| P219 | 4-[2-(Cyclopropylmethoxy)-5-fluorophenyl]-N-[(1R,3S)-3-hydroxycyclopentyl]-6-methyl-5H-pyrrolo[3,2-d]pyrimidine-7-carboxamide |
| P220 | 4-[2-(Cyclopropylmethoxy)-5-fluorophenyl]-N-[(1R,3R)-3-hydroxycyclopentyl]-6-methyl-5H-pyrrolo[3,2-d]pyrimidine-7-carboxamide |
| P221 | 4-[2-(Cyclopropylmethoxy)-5-fluorophenyl]-N-[(1S,3S)-3-hydroxycyclopentyl]-6-methyl-5H-pyrrolo[3,2-d]pyrimidine-7-carboxamide |
| P222 | 4-[2-(Cyclopropylmethoxy)-5-fluorophenyl]-N-[(1S,3R)-3-hydroxycyclopentyl]-6-methyl-5H-pyrrolo[3,2-d]pyrimidine-7-carboxamide |
| P223 | 4-[2-(Cyclopropylmethoxy)-5-fluorophenyl]-N-[(1R,2S)-2-hydroxycyclopentyl]-6-methyl-5H-pyrrolo[3,2-d]pyrimidine-7-carboxamide |
| P224 | 4-[2-(Cyclopropylmethoxy)-5-fluorophenyl]-N-[(1R,2R)-2-hydroxycyclopentyl]-6-methyl-5H-pyrrolo[3,2-d]pyrimidine-7-carboxamide |
| P225 | 4-[2-(Cyclopropylmethoxy)-5-fluorophenyl]-N-[(1S,2S)-2-hydroxycyclopentyl]-6-methyl-5H-pyrrolo[3,2-d]pyrimidine-7-carboxamide |
| P226 | 4-[2-(Cyclopropylmethoxy)-5-fluorophenyl]-N-[(1S,2R)-2-hydroxycyclopentyl]-6-methyl-5H-pyrrolo[3,2-d]pyrimidine-7-carboxamide |
| P227 | N-[(3S,5S)-1-Acetyl-5-methylpyrrolidin-3-yl]-4-[2-(cyclopropylmethoxy)-5-fluorophenyl]-6-methyl-5H-pyrrolo[3,2-d]pyrimidine-7-carboxamide |
| P228 | 4-[2-(Cyclopropylmethoxy)-5-fluorophenyl]-6-methyl-N-[(3S,5S)-5-methyl-1-propanoylpyrrolidin-3-yl]-5H-pyrrolo[3,2-d]pyrimidine-7-carboxamide |
| P229 | 4-[2-(Cyclopropylmethoxy)-5-fluorophenyl]-N-[(3S,5S)-1-(methoxyacetyl)-5-methylpyrrolidin-3-yl]-6-methyl-5H-pyrrolo[3,2-d]pyrimidine-7-carboxamide |
| P230 | 4-[2-(Cyclopropylmethoxy)-5-fluorophenyl]-N-[(3S,5S)-1-(hydroxyacetyl)-5-methylpyrrolidin-3-yl]-6-methyl-5H-pyrrolo[3,2-d]pyrimidine-7-carboxamide |
| P231 | 4-[2-(Cyclopropylmethoxy)-5-fluorophenyl]-N-{(3S,5S)-1-[(2S)-2-hydroxypropanoyl]-5-methylpyrrolidin-3-yl}-6-methyl-5H-pyrrolo[3,2-d]pyrimidine-7-carboxamide |
| P232 | N-[(3S,5R)-1-Acetyl-5-methylpyrrolidin-3-yl]-4-[2-(cyclopropylmethoxy)-5-fluorophenyl]-6-methyl-5H-pyrrolo[3,2-d]pyrimidine-7-carboxamide |
| P233 | 4-[2-(Cyclopropylmethoxy)-5-fluorophenyl]-6-methyl-N-[(3S,5R)-5-methyl-1-propanoylpyrrolidin-3-yl]-5H-pyrrolo[3,2-d]pyrimidine-7-carboxamide |
| P234 | 4-[2-(Cyclopropylmethoxy)-5-fluorophenyl]-N-[(3S,5R)-1-(methoxyacetyl)-5-methylpyrrolidin-3-yl]-6-methyl-5H-pyrrolo[3,2-d]pyrimidine-7-carboxamide |
| P235 | 4-[2-(Cyclopropylmethoxy)-5-fluorophenyl]-N-[(3S,5R)-1-(hydroxyacetyl)-5-methylpyrrolidin-3-yl]-6-methyl-5H-pyrrolo[3,2-d]pyrimidine-7-carboxamide |
| P236 | 4-[2-(Cyclopropylmethoxy)-5-fluorophenyl]-N-{(3S,5R)-1-[(2S)-2-hydroxypropanoyl]-5-methylpyrrolidin-3-yl}-6-methyl-5H-pyrrolo[3,2-d]pyrimidine-7-carboxamide |
| P237 | N-[(3R,5R)-1-Acetyl-5-methylpyrrolidin-3-yl]-4-[2-(cyclopropylmethoxy)-5-fluorophenyl]-6-methyl-5H-pyrrolo[3,2-d]pyrimidine-7-carboxamide |
| P238 | 4-[2-(Cyclopropylmethoxy)-5-fluorophenyl]-6-methyl-N-[(3R,5R)-5-methyl-1-propanoylpyrrolidin-3-yl]-5H-pyrrolo[3,2-d]pyrimidine-7-carboxamide |
| P239 | 4-[2-(Cyclopropylmethoxy)-5-fluorophenyl]-N-[(3R,5R)-1-(methoxyacetyl)-5-methylpyrrolidin-3-yl]-6-methyl-5H-pyrrolo[3,2-d]pyrimidine-7-carboxamide |
| P240 | 4-[2-(Cyclopropylmethoxy)-5-fluorophenyl]-N-[(3R,5R)-1-(hydroxyacetyl)-5-methylpyrrolidin-3-yl]-6-methyl-5H-pyrrolo[3,2-d]pyrimidine-7-carboxamide |
| P241 | 4-[2-(Cyclopropylmethoxy)-5-fluorophenyl]-N-{(3R,5R)-1-[(2S)-2-hydroxypropanoyl]-5-methylpyrrolidin-3-yl}-6-methyl-5H-pyrrolo[3,2-d]pyrimidine-7-carboxamide |
| P242 | N-[(3R,5S)-1-Acetyl-5-methylpyrrolidin-3-yl]-4-[2-(cyclopropylmethoxy)-5-fluorophenyl]-6-methyl-5H-pyrrolo[3,2-d]pyrimidine-7-carboxamide |
| P243 | 4-[2-(Cyclopropylmethoxy)-5-fluorophenyl]-6-methyl-N-[(3R,5S)-5-methyl-1-propanoylpyrrolidin-3-yl]-5H-pyrrolo[3,2-d]pyrimidine-7-carboxamide |
| P244 | 4-[2-(Cyclopropylmethoxy)-5-fluorophenyl]-N-[(3R,5S)-1-(methoxyacetyl)-5-methylpyrrolidin-3-yl]-6-methyl-5H-pyrrolo[3,2-d]pyrimidine-7-carboxamide |
| P245 | 4-[2-(Cyclopropylmethoxy)-5-fluorophenyl]-N-[(3R,5S)-1-(hydroxyacetyl)-5-methylpyrrolidin-3-yl]-6-methyl-5H-pyrrolo[3,2-d]pyrimidine-7-carboxamide |
| P246 | 4-[2-(Cyclopropylmethoxy)-5-fluorophenyl]-N-{(3R,5S)-1-[(2S)-2-hydroxypropanoyl]-5-methylpyrrolidin-3-yl}-6-methyl-5H-pyrrolo[3,2-d]pyrimidine-7-carboxamide |
| P247 | N-[(3S,4S)-1-Acetyl-4-fluoropyrrolidin-3-yl]-4-[2-(cyclopropylmethoxy)-5-fluorophenyl]-6-methyl-5H-pyrrolo[3,2-d]pyrimidine-7-carboxamide |
| P248 | 4-[2-(Cyclopropylmethoxy)-5-fluorophenyl]-N-[(3S,4S)-4-fluoro-1-propanoylpyrrolidin-3-yl]-6-methyl-5H-pyrrolo[3,2-d]pyrimidine-7-carboxamide |
| P249 | 4-[2-(Cyclopropylmethoxy)-5-fluorophenyl]-N-[(3S,4S)-4-fluoro-1-(methoxyacetyl)pyrrolidin-3-yl]-6-methyl-5H-pyrrolo[3,2-d]pyrimidine-7-carboxamide |
| P250 | 4-[2-(Cyclopropylmethoxy)-5-fluorophenyl]-N-[(3S,4S)-4-fluoro-1-(hydroxyacetyl)pyrrolidin-3-yl]-6-methyl-5H-pyrrolo[3,2-d]pyrimidine-7-carboxamide |
| P251 | 4-[2-(Cyclopropylmethoxy)-5-fluorophenyl]-N-{(3S,4S)-4-fluoro-1-[(2S)-2-hydroxypropanoyl]pyrrolidin-3-yl}-6-methyl-5H-pyrrolo[3,2-d]pyrimidine-7-carboxamide |
| P252 | N-[(3R,4S)-1-Acetyl-4-fluoropyrrolidin-3-yl]-4-[2-(cyclopropylmethoxy)-5-fluorophenyl]-6-methyl-5H-pyrrolo[3,2-d]pyrimidine-7-carboxamide |
| P253 | 4-[2-(Cyclopropylmethoxy)-5-fluorophenyl]-N-[(3R,4S)-4-fluoro-1-propanoylpyrrolidin-3-yl]-6-methyl-5H-pyrrolo[3,2-d]pyrimidine-7-carboxamide |
| P254 | 4-[2-(Cyclopropylmethoxy)-5-fluorophenyl]-N-[(3R,4S)-4-fluoro-1-(methoxyacetyl)pyrrolidin-3-yl]-6-methyl-5H-pyrrolo[3,2-d]pyrimidine-7-carboxamide |
| P255 | 4-[2-(Cyclopropylmethoxy)-5-fluorophenyl]-N-[(3R,4S)-4-fluoro-1-(hydroxyacetyl)pyrrolidin-3-yl]-6-methyl-5H-pyrrolo[3,2-d]pyrimidine-7-carboxamide |

| | -continued |
|---|---|
| P256 | 4-[2-(Cyclopropylmethoxy)-5-fluorophenyl]-N-{(3R,4S)-4-fluoro-1-[(2S)-2-hydroxypropanoyl]pyrrolidin-3-yl}-6-methyl-5H-pyrrolo[3,2-d]pyrimidine-7-carboxamide |
| P257 | N-[(3R,4R)-1-Acetyl-4-fluoropyrrolidin-3-yl]-4-[2-(cyclopropylmethoxy)-5-fluorophenyl]-6-methyl-5H-pyrrolo[3,2-d]pyrimidine-7-carboxamide |
| P258 | 4-[2-(Cyclopropylmethoxy)-5-fluorophenyl]-N-[(3R,4R)-4-fluoro-1-propanoylpyrrolidin-3-yl]-6-methyl-5H-pyrrolo[3,2-d]pyrimidine-7-carboxamide |
| P259 | 4-[2-(Cyclopropylmethoxy)-5-fluorophenyl]-N-[(3R,4R)-4-fluoro-1-(methoxyacetyl)pyrrolidin-3-yl]-6-methyl-5H-pyrrolo[3,2-d]pyrimidine-7-carboxamide |
| P260 | 4-[2-(Cyclopropylmethoxy)-5-fluorophenyl]-N-[(3R,4R)-4-fluoro-1-(hydroxyacetyl)pyrrolidin-3-yl]-6-methyl-5H-pyrrolo[3,2-d]pyrimidine-7-carboxamide |
| P261 | 4-[2-(Cyclopropylmethoxy)-5-fluorophenyl]-N-{(3R,4R)-4-fluoro-1-[(2S)-2-hydroxypropanoyl]pyrrolidin-3-yl}-6-methyl-5H-pyrrolo[3,2-d]pyrimidine-7-carboxamide |
| P262 | N-[(3S,4R)-1-Acetyl-4-fluoropyrrolidin-3-yl]-4-[2-(cyclopropylmethoxy)-5-fluorophenyl]-6-methyl-5H-pyrrolo[3,2-d]pyrimidine-7-carboxamide |
| P263 | 4-[2-(Cyclopropylmethoxy)-5-fluorophenyl]-N-[(3S,4R)-4-fluoro-1-propanoylpyrrolidin-3-yl]-6-methyl-5H-pyrrolo[3,2-d]pyrimidine-7-carboxamide |
| P264 | 4-[2-(Cyclopropylmethoxy)-5-fluorophenyl]-N-[(3S,4R)-4-fluoro-1-(methoxyacetyl)pyrrolidin-3-yl]-6-methyl-5H-pyrrolo[3,2-d]pyrimidine-7-carboxamide |
| P265 | 4-[2-(Cyclopropylmethoxy)-5-fluorophenyl]-N-[(3S,4R)-4-fluoro-1-(hydroxyacetyl)pyrrolidin-3-yl]-6-methyl-5H-pyrrolo[3,2-d]pyrimidine-7-carboxamide |
| P266 | 4-[2-(Cyclopropylmethoxy)-5-fluorophenyl]-N-{(3S,4R)-4-fluoro-1-[(2S)-2-hydroxypropanoyl]pyrrolidin-3-yl}-6-methyl-5H-pyrrolo[3,2-d]pyrimidine-7-carboxamide |
| P267 | N-[(3S*,4R*)-1-Acetyl-4-methylpyrrolidin-3-yl]-4-[2-(cyclopropylmethoxy)-5-fluorophenyl]-6-methyl-5H-pyrrolo[3,2-d]pyrimidine-7-carboxamide |
| P268 | 4-[2-(Cyclopropylmethoxy)-5-fluorophenyl)phenyl]-6-methyl-N-[(3S*,4R*)-4-methyl-1-propanoylpyrrolidin-3-yl]-5H-pyrrolo[3,2-d]pyrimidine-7-carboxamide |
| P269 | 4-[2-(Cyclopropylmethoxy)-5-fluorophenyl]-N-[(3S*,4R*)-1-(methoxyacetyl)-4-methylpyrrolidin-3-yl]-6-methyl-5H-pyrrolo[3,2-d]pyrimidine-7-carboxamide |
| P270 | 4-[2-(Cyclopropylmethoxy)-5-fluorophenyl]-N-[(3S*,4R*)-1-(hydroxyacetyl)-4-methylpyrrolidin-3-yl]-6-methyl-5H-pyrrolo[3,2-d]pyrimidine-7-carboxamide |
| P271 | 4-[2-(Cyclopropylmethoxy)-5-fluorophenyl]-N-{(3S*,4R*)-1-[(2S)-2-hydroxypropanoyl]-4-methylpyrrolidin-3-yl}-6-methyl-5H-pyrrolo[3,2-d]pyrimidine-7-carboxamide |
| P272 | N-[(3S*,4S*)-1-Acetyl-4-methylpyrrolidin-3-yl]-4-[2-(cyclopropylmethoxy)-5-fluorophenyl]-6-methyl-5H-pyrrolo[3,2-d]pyrimidine-7-carboxamide |
| P273 | 4-[2-(Cyclopropylmethoxy)-5-fluorophenyl]-6-methyl-N-[(3S*,4S*)-4-methyl-1-propanoylpyrrolidin-3-yl]-5H-pyrrolo[3,2-d]pyrimidine-7-carboxamide |
| P274 | 4-[2-(Cyclopropylmethoxy)-5-fluorophenyl]-N-[(3S*,4S*)-1-(methoxyacetyl)-4-methylpyrrolidin-3-yl]-6-methyl-5H-pyrrolo[3,2-dlpyrimidine-7-carboxamide |
| P275 | 4-[2-(Cyclopropylmethoxy)-5-fluorophenyl]-N-[(3S*,4S*)-1-(hydroxyacetyl)-4-methylpyrrolidin-3-yl]-6-methyl-5H-pyrrolo[3,2-d]pyrimidine-7-carboxamide |
| P276 | 4-[2-(Cyclopropylmethoxy)-5-fluorophenyl]-N-{(3S*,4S*)-1-[(2S)-2-hydroxypropanoyl]-4-methylpyrrolidin-3-yl}-6-methyl-5H-pyrrolo[3,2-d]pyrimidine-7-carboxamide |
| P277 | N-[(3S*)-1-Acetyl-4,4-dimethylpyrrolidin-3-yl]-4-[2-(cyclopropylmethoxy)-5-fluorophenyl]-6-methyl-5H-pyrrolo[3,2-d]pyrimidine-7-carboxamide |
| P278 | 4-[2-(Cyclopropylmethoxy)-5-fluorophenyl]-N-[(3S*)-4,4-dimethyl-1-propanoylpyrrolidin-3-yl]-6-methyl-5H-pyrrolo[3,2-dlpyrimidine-7-carboxamide |
| P279 | 4-[2-(Cyclopropylmethoxy)-5-fluorophenyl]-N-[(3S*)-1-(methoxyacetyl)-4,4-dimethylpyrrolidin-3-yl]-6-methyl-5H-pyrrolo[3,2-d]pyrimidine-7-carboxamide |
| P280 | 4-[2-(Cyclopropylmethoxy)-5-fluorophenyl]-N-[(3S*)-1-(hydroxyacetyl)-4,4-dimethylpyrrolidin-3-yl]-6-methyl-5H-pyrrolo[3,2-d]pyrimidine-7-carboxamide |
| P281 | 4-[2-(Cyclopropylmethoxy)-5-fluorophenyl]-N-{(3S*)-1-[(2S)-2-hydroxypropanoyl]-4,4-dimethylpyrrolidin-3-yl}-6-methyl-5H-pyrrolo[3,2-d]pyrimidine-7-carboxamide |
| P282 | N-[(7S*)-5-Acetyl-5-azaspiro[2.4]hept-7-yl]-4-[2-(cyclopropylmethoxy)-5-fluorophenyl]-6-methyl-5H-pyrrolo[3,2-d]pyrimidine-7-carboxamide |
| P283 | 4-[2-(Cyclopropylmethoxy)-5-fluorophenyl]-6-methyl-N-[(7S*)-5-propanoyl-5-azaspiro[2.4]hept-7-yl]-5H-pyrrolo[3,2-d]pyrimidine-7-carboxamide |
| P284 | 4-[2-(Cyclopropylmethoxy)-5-fluorophenyl]-N-[(7S*)-5-(methoxyacetyl)-5-azaspiro[2.4]hept-7-yl]-6-methyl-5H-pyrrolo[3,2-d]pyrimidine-7-carboxamide |
| P285 | 4-[2-(Cyclopropylmethoxy)-5-fluorophenyl]-N-[(7S*)-5-(hydroxyacetyl)-5-azaspiro[2.4]hept-7-yl]-6-methyl-5H-pyrrolo[3,2-d]pyrimidine-7-carboxamide |
| P286 | 4-[2-(Cyclopropylmethoxy)-5-fluorophenyl]-N-{(7S*)-5-[(2S)-2-hydroxypropanoyl]-5-azaspiro[2.4]hept-7-yl}-6-methyl-5H-pyrrolo[3,2-d]pyrimidine-7-carboxamide |
| P287 | N-[(3R*)-1-Acetyl-4,4-difluoropyrrolidin-3-yl]-4-[2-(cyclopropylmethoxy)-5-fluorophenyl]-6-methyl-5H-pyrrolo[3,2-d]pyrimidine-7-carboxamide |
| P288 | 4-[2-(Cyclopropylmethoxy)-5-fluorophenyl]-N-[(3R*)-4,4-difluoro-1-propanoylpyrrolidin-3-yl]-6-methyl-5H-pyrrolo[3,2-d]pyrimidine-7-carboxamide |
| P289 | 4-[2-(Cyclopropylmethoxy)-5-fluorophenyl]-N-[(3R*)-4,4-difluoro-1-(methoxyacetyl)pyrrolidin-3-yl]-6-methyl-5H-pyrrolo[3,2-d]pyrimidine-7-carboxamide |
| P290 | 4-[2-(Cyclopropylmethoxy)-5-fluorophenyl]-N-[(3R*)-4,4-difluoro-1-(hydroxyacetyl)pyrrolidin-3-yl]-6-methyl-5H-pyrrolo[3,2-d]pyrimidine-7-carboxamide |
| P291 | 4-[2-(Cyclopropylmethoxy)-5-fluorophenyl]-N-{(3R*)-4,4-difluoro-1-[(2S)-2-hydroxypropanoyl]pyrrolidin-3-yl}-6-methyl-5H-pyrrolo[3,2-d]pyrimidine-7-carboxamide |
| P292 | N-[(1S*,3S*)-3-(Acetylamino)cyclopentyl]-4-[2-(cyclopropylmethoxy)-5-fluorophenyl]-6-methyl-5H-pyrrolo[3,2-d]pyrimidine-7-carboxamide |
| P293 | 4-[2-(Cyclopropylmethoxy)-5-fluorophenyl]-6-methyl-N-[(1S*,3S*)-3-(propanoylamino)cyclopentyl]-5H-pyrrolo[3,2-d]pyrimidine-7-carboxamide |
| P294 | 4-[2-(Cyclopropylmethoxy)-5-fluorophenyl]-N-{(1S*,3S*)-3-[(methoxyacetyl)amino]cyclopentyl}-6-methyl-5H-pyrrolo[3,2-d]pyrimidine-7-carboxamide |

| | -continued |
|---|---|
| P295 | 4-[2-(Cyclopropylmethoxy)-5-fluorophenyl]-N-{(1S*,3S*)-3-[(hydroxyacetyl)amino]cyclopentyl}-6-methyl-5H-pyrrolo[3,2-d]pyrimidine-7-carboxamide |
| P296 | 4-[2-(Cyclopropylmethoxy)-5-fluorophenyl]-N-[(1S*,3S*)-3-{[(2S)-2-hydroxypropanoyl]amino}cyclopentyl]-6-methyl-5H-pyrrolo[3,2-d]pyrimidine-7-carboxamide |
| P297 | N-[(1S*,3R*)-3-(Acetylamino)cyclopentyl]-4-[2-(cyclopropylmethoxy)-5-fluorophenyl]-6-methyl-5H-pyrrolo[3,2-d]pyrimidine-7-carboxamide |
| P298 | 4-[2-(Cyclopropylmethoxy)-5-fluorophenyl]-6-methyl-N-[(1S*,3R*)-3-(propanoylamino)cyclopentyl]-5H-pyrrolo[3,2-d]pyrimidine-7-carboxamide |
| P299 | 4-[2-(Cyclopropylmethoxy)-5-fluorophenyl]-N-{(1S*,3R*)-3-[(methoxyacetyl)amino]cyclopentyl}-6-methyl-5H-pyrrolo[3,2-d]pyrimidine-7-carboxamide |
| P300 | 4-[2-(Cyclopropylmethoxy)-5-fluorophenyl]-N-{(1S*,3R*)-3-[(hydroxyacetyl)amino]cyclopentyl}-6-methyl-5H-pyrrolo[3,2-d]pyrimidine-7-carboxamide |
| P301 | 4-[2-(Cyclopropylmethoxy)-5-fluorophenyl]-N-[(1S*,3R*)-3-{[(2S)-2-hydroxypropanoyl]amino}cyclopentyl]-6-methyl-5H-pyrrolo[3,2-d]pyrimidine-7-carboxamide |
| P302 | N-[(1R*,2R*,4R*)-4-(Acetylamino)-2-fluorocyclopentyl]-4-[2-(cyclopropylmethoxy)-5-fluorophenyl]-6-methyl-5H-pyrrolo[3,2-d]pyrimidine-7-carboxamide |
| P303 | 4-[2-(Cyclopropylmethoxy)-5-fluorophenyl]-N-[(1R*,2R*,4R*)-2-fluoro-4-(propanoylamino)cyclopentyl]-6-methyl-5H-pyrrolo[3,2-d]pyrimidine-7-carboxamide |
| P304 | 4-[2-(Cyclopropylmethoxy)-5-fluorophenyl]-N-{(1R*,2R*,4R*)-2-fluoro-4-[(methoxyacetyl)amino]cyclopentyl}-6-methyl-5H-pyrrolo[3,2-d]pyrimidine-7-carboxamide |
| P305 | 4-[2-(Cyclopropylmethoxy)-5-fluorophenyl]-N-{(1R*,2R*,4R*)-2-fluoro-4-[(hydroxyacetyl)amino]cyclopentyl}-6-methyl-5H-pyrrolo[3,2-d]pyrimidine-7-carboxamide |
| P306 | 4-[2-(Cyclopropylmethoxy)-5-fluorophenyl]-N-[(1R*,2R*,4R*)-2-fluoro-4-{[(2S)-2-hydroxypropanoyl]amino}cyclopentyl]-6-methyl-5H-pyrrolo[3,2-d]pyrimidine-7-carboxamide |
| P307 | N-[(1R*,2R*,4S*)-4-(Acetylamino)-2-fluorocyclopentyl]-4-[2-(cyclopropylmethoxy)-5-fluorophenyl]-6-methyl-5H-pyrrolo[3,2-d]pyrimidine-7-carboxamide |
| P308 | 4-[2-(Cyclopropylmethoxy)-5-fluorophenyl]-N-[(1R*,2R*,4S*)-2-fluoro-4-(propanoylamino)cyclopentyl]-6-methyl-5H-pyrrolo[3,2-d]pyrimidine-7-carboxamide |
| P309 | 4-[2-(Cyclopropylmethoxy)-5-fluorophenyl]-N-{(1R*,2R*,4S*)-2-fluoro-4-[(methoxyacetyl)amino]cyclopentyl}-6-methyl-5H-pyrrolo[3,2-d]pyrimidine-7-carboxamide |
| P310 | 4-[2-(Cyclopropylmethoxy)-5-fluorophenyl]-N-{(1R*,2R*,4S*)-2-fluoro-4-[(hydroxyacetyl)amino]cyclopentyl}-6-methyl-5H-pyrrolo[3,2-d]pyrimidine-7-carboxamide |
| P311 | 4-[2-(Cyclopropylmethoxy)-5-fluorophenyl]-N-[(1R*,2R*,4S*)-2-fluoro-4-{[(2S)-2-hydroxypropanoyl]amino}cyclopentyl]-6-methyl-5H-pyrrolo[3,2-d]pyrimidine-7-carboxamide |
| P312 | 4-[2-(Cyclopropylmethoxy)-5-fluorophenyl]-N-[(1R,2S)-2-hydroxycyclohexyl]-6-methyl-5H-pyrrolo[3,2-d]pyrimidine-7-carboxamide |
| P313 | 4-[2-(Cyclopropylmethoxy)-5-fluorophenyl]-N-[(1R,2R)-2-hydroxycyclohexyl]-6-methyl-5H-pyrrolo[3,2-d]pyrimidine-7-carboxamide |
| P314 | 4-[2-(Cyclopropylmethoxy)-5-fluorophenyl]-N-[(1S,2S)-2-hydroxycyclohexyl]-6-methyl-5H-pyrrolo[3,2-d]pyrimidine-7-carboxamide |
| P315 | 4-[2-(Cyclopropylmethoxy)-5-fluorophenyl]-N-[(1S,2R)-2-hydroxycyclohexyl]-6-methyl-5H-pyrrolo[3,2-d]pyrimidine-7-carboxamide |
| P316 | 4-[2-(Cyclopropylmethoxy)-5-fluorophenyl]-N-[(1S,3R)-3-hydroxycyclohexyl]-6-methyl-5H-pyrrolo[3,2-d]pyrimidine-7-carboxamide |
| P317 | 4-[2-(Cyclopropylmethoxy)-5-fluorophenyl]-N-[(1S,3S)-3-hydroxycyclohexyl]-6-methyl-5H-pyrrolo[3,2-d]pyrimidine-7-carboxamide |
| P318 | 4-[2-(Cyclopropylmethoxy)-5-fluorophenyl]-N-[(1R,3R)-3-hydroxycyclohexyl]-6-methyl-5H-pyrrolo[3,2-d]pyrimidine-7-carboxamide |
| P319 | 4-[2-(Cyclopropylmethoxy)-5-fluorophenyl]-N-[(1R,3S)-3-hydroxycyclohexyl]-6-methyl-5H-pyrrolo[3,2-d]pyrimidine-7-carboxamide |
| P320 | 4-[2-(Cyclopropylmethoxy)-5-fluorophenyl]-N-(trans-4-hydroxycyclohexyl)-6-methyl-5H-pyrrolo[3,2-d]pyrimidine-7-carboxamide |
| P321 | 4-[2-(Cyclopropylmethoxy)-5-fluorophenyl]-N-(cis-4-hydroxycyclohexyl)-6-methyl-5H-pyrrolo[3,2-d]pyrimidine-7-carboxamide |
| P322 | N-[(3S,4R)-1-Acetyl-3-fluoropiperidin-4-yl]-4-[2-(cyclopropylmethoxy)-5-fluorophenyl]-6-methyl-5H-pyrrolo[3,2-d]pyrimidine-7-carboxamide |
| P323 | 4-[2-(Cyclopropylmethoxy)-5-fluorophenyl]-N-[(3S,4R)-3-fluoro-1-propanoylpiperidin-4-yl]-6-methyl-5H-pyrrolo[3,2-d]pyrimidine-7-carboxamide |
| P324 | 4-[2-(Cyclopropylmethoxy)-5-fluorophenyl]-N-[(3S,4R)-3-fluoro-1-(methoxyacetyl)piperidin-4-yl]-6-methyl-5H-pyrrolo[3,2-d]pyrimidine-7-carboxamide |
| P325 | 4-[2-(Cyclopropylmethoxy)-5-fluorophenyl]-N-[(3S,4R)-3-fluoro-1-(hydroxyacetyl)piperidin-4-yl]-6-methyl-5H-pyrrolo[3,2-d]pyrimidine-7-carboxamide |
| P326 | 4-[2-(Cyclopropylmethoxy)-5-fluorophenyl]-N-{(3S,4R)-3-fluoro-1-[(2S)-2-hydroxypropanoyl]piperidin-4-yl}-6-methyl-5H-pyrrolo[3,2-d]pyrimidine-7-carboxamide |
| P327 | N-[(3R,4R)-1-Acetyl-3-fluoropiperidin-4-yl]-4-[2-(cyclopropylmethoxy)-5-fluorophenyl]-6-methyl-5H-pyrrolo[3,2-d]pyrimidine-7-carboxamide |
| P328 | 4-[2-(Cyclopropylmethoxy)-5-fluorophenyl]-N-[(3R,4R)-3-fluoro-1-propanoylpiperidin-4-yl]-6-methyl-5H-pyrrolo[3,2-d]pyrimidine-7-carboxamide |
| P329 | 4-[2-(Cyclopropylmethoxy)-5-fluorophenyl]-N-[(3R,4R)-3-fluoro-1-(methoxyacetyl)piperidin-4-yl]-6-methyl-5H-pyrrolo[3,2-dlpyrimidine-7-carboxamide |
| P330 | 4-[2-(Cyclopropylmethoxy)-5-fluorophenyl]-N-[(3R,4R)-3-fluoro-1-(hydroxyacetyl)piperidin-4-yl]-6-methyl-5H-pyrrolo[3,2-d]pyrimidine-7-carboxamide |
| P331 | 4-[2-(Cyclopropylmethoxy)-5-fluorophenyl]-N-{(3R,4R)-3-fluoro-1-[(2S)-2-hydroxypropanoyl]piperidin-4-yl}-6-methyl-5H-pyrrolo[3,2-d]pyrimidine-7-carboxamide |
| P332 | N-[(3S,4S)-1-Acetyl-3-fluoropiperidin-4-yl]-4-[2-(cyclopropylmethoxy)-5-fluorophenyl]-6-methyl-5H-pyrrolo[3,2-d]pyrimidine-7-carboxamide |

-continued

| | |
|---|---|
| P333 | 4-[2-(Cyclopropylmethoxy)-5-fluorophenyl]-N-[(3S,4S)-3-fluoro-1-propanoylpiperidin-4-yl]-6-methyl-5H-pyrrolo[3,2-d]pyrimidine-7-carboxamide |
| P334 | 4-[2-(Cyclopropylmethoxy)-5-fluorophenyl]-N-[(3S,4S)-3-fluoro-1-(methoxyacetyl)piperidin-4-yl]-6-methyl-5H-pyrrolo[3,2-d]pyrimidine-7-carboxamide |
| P335 | 4-[2-(Cyclopropylmethoxy)-5-fluorophenyl]-N-[(3S,4S)-3-fluoro-1-(hydroxyacetyl)piperidin-4-yl]-6-methyl-5H-pyrrolo[3,2-d]pyrimidine-7-carboxamide |
| P336 | 4-[2-(Cyclopropylmethoxy)-5-fluorophenyl]-N-{(3S,4S)-3-fluoro-1-[(2S)-2-hydroxypropanoyl]piperidin-4-yl}-6-methyl-5H-pyrrolo[3,2-d]pyrimidine-7-carboxamide |
| P337 | N-[(3R,4S)-1-Acetyl-3-fluoropiperidin-4-yl]-4-[2-(cyclopropylmethoxy)-5-fluorophenyl]-6-methyl-5H-pyrrolo[3,2-d]pyrimidine-7-carboxamide |
| P338 | 4-[2-(Cyclopropylmethoxy)-5-fluorophenyl]-N-[(3R,4S)-3-fluoro-1-propanoylpiperidin-4-yl]-6-methyl-5H-pyrrolo[3,2-d]pyrimidine-7-carboxamide |
| P339 | 4-[2-(Cyclopropylmethoxy)-5-fluorophenyl]-N-[(3R,4S)-3-fluoro-1-(methoxyacetyl)piperidin-4-yl]-6-methyl-5H-pyrrolo[3,2-d]pyrimidine-7-carboxamide |
| P340 | 4-[2-(Cyclopropylmethoxy)-5-fluorophenyl]-N-[(3R,4S)-3-fluoro-1-(hydroxyacetyl)piperidin-4-yl]-6-methyl-5H-pyrrolo[3,2-d]pyrimidine-7-carboxamide |
| P341 | 4-[2-(Cyclopropylmethoxy)-5-fluorophenyl]-N-{(3R,4S)-3-fluoro-1-[(2S)-2-hydroxypropanoyl]piperidin-4-yl}-6-methyl-5H-pyrrolo[3,2-d]pyrimidine-7-carboxamide |
| P342 | N-[(1R*,2R*,4R*)-4-(Acetylamino)-2-methylcyclohexyl]-4-[2-(cyclopropylmethoxy)-5-fluorophenyl]-6-methyl-5H-pyrrolo[3,2-d]pyrimidine-7-carboxamide |
| P343 | 4-[2-(Cyclopropylmethoxy)-5-fluorophenyl]-6-methyl-N-[(1R*,2R*,4R*)-2-methyl-4-(propanoylamino)cyclohexyl]-5H-pyrrolo[3,2-d]pyrimidine-7-carboxamide |
| P344 | 4-[2-(Cyclopropylmethoxy)-5-fluorophenyl]-N-[(1R*,2R*,4R*)-4-[(methoxyacetyl)amino]-2-methylcyclohexyl}-6-methyl-5H-pyrrolo[3,2-d]pyrimidine-7-carboxamide |
| P345 | 4-[2-(Cyclopropylmethoxy)-5-fluorophenyl]-N-[(1R*,2R*,4R*)-4-[(hydroxyacetyl)amino]-2-methylcyclohexyl}-6-methyl-5H-pyrrolo[3,2-d]pyrimidine-7-carboxamide |
| P346 | 4-[2-(Cyclopropylmethoxy)-5-fluorophenyl]-N-[(1R*,2R*,4R*)-4-{[(2S)-2-hydroxypropanoyl]amino}-2-methylcyclohexyl]-6-methyl-5H-pyrrolo[3,2-d]pyrimidine-7-carboxamide |
| P347 | N-[(1R*,2R*,4S*)-4-(acetylamino)-2-methylcyclohexyl]-4-[2-(cyclopropylmethoxy)-5-fluorophenyl]-6-methyl-5H-pyrrolo[3,2-d]pyrimidine-7-carboxamide |
| P348 | 4-[2-(Cyclopropylmethoxy)-5-fluorophenyl]-6-methyl-N-[(1R*,2R*,4S*)-2-methyl-4-(propanoylamino)cyclohexyl]-5H-pyrrolo[3,2-d]pyrimidine-7-carboxamide |
| P349 | 4-[2-(Cyclopropylmethoxy)-5-fluorophenyl]-N-[(1R*,2R*,4S*)-4-[(methoxyacetyl)amino]-2-methylcyclohexyl}-6-methyl-5H-pyrrolo[3,2-d]pyrimidine-7-carboxamide |
| P350 | 4-[2-(Cyclopropylmethoxy)-5-fluorophenyl]-N-[(1R*,2R*,4S*)-4-[(hydroxyacetyl)amino]-2-methylcyclohexyl}-6-methyl-5H-pyrrolo[3,2-d]pyrimidine-7-carboxamide |
| P351 | 4-[2-(Cyclopropylmethoxy)-5-fluorophenyl]-N-[(1R*,2R*,4S*)-4-{[(2S)-2-hydroxypropanoyl]amino}-2-methylcyclohexyl]-6-methyl-5H-pyrrolo[3,2-d]pyrimidine-7-carboxamide |
| P352 | N-[(1S*,2R*,4S*)-4-(acetylamino)-2-methylcyclohexyl]-4-[2-(cyclopropylmethoxy)-5-fluorophenyl]-6-methyl-5H-pyrrolo[3,2-d]pyrimidine-7-carboxamide |
| P353 | 4-[2-(Cyclopropylmethoxy)-5-fluorophenyl]-6-methyl-N-[(1S*,2R*,4S*)-2-methyl-4-(propanoylamino)cyclohexyl]-5H-pyrrolo[3,2-d]pyrimidine-7-carboxamide |
| P354 | 4-[2-(Cyclopropylmethoxy)-5-fluorophenyl]-N-{(1S*,2R*,4S*)-4-[(methoxyacetyl)amino]-2-methylcyclohexyl}-6-methyl-5H-pyrrolo[3,2-d]pyrimidine-7-carboxamide |
| P355 | 4-[2-(Cyclopropylmethoxy)-5-fluorophenyl]-N-{(1S*,2R*,4S*)-4-[(hydroxyacetyl)amino]-2-methylcyclohexyl}-6-methyl-5H-pyrrolo[3,2-d]pyrimidine-7-carboxamide |
| P356 | 4-[2-(Cyclopropylmethoxy)-5-fluorophenyl]-N-[(1S*,2R*,4S*)-4-{[(2S)-2-hydroxypropanoyl]amino}-2-methylcyclohexyl]-6-methyl-5H-pyrrolo[3,2-d]pyrimidine-7-carboxamide |
| P357 | N-[(1S*,2R*,4R*)-4-(Acetylamino)-2-methylcyclohexyl]-4-[2-(cyclopropylmethoxy)-5-fluorophenyl]-6-methyl-5H-pyrrolo[3,2-d]pyrimidine-7-carboxamide |
| P358 | 4-[2-(Cyclopropylmethoxy)-5-fluorophenyl]-6-methyl-N-[(1S*,2R*,4R*)-2-methyl-4-(propanoylamino)cyclohexyl]-5H-pyrrolo[3,2-d]pyrimidine-7-carboxamide |
| P359 | 4-[2-(Cyclopropylmethoxy)-5-fluorophenyl]-N-[(1S*,2R*,4R*)-4-[(methoxyacetyl)amino]-2-methylcyclohexyl}-6-methyl-5H-pyrrolo[3,2-d]pyrimidine-7-carboxamide |
| P360 | 4-[2-(Cyclopropylmethoxy)-5-fluorophenyl]-N-{(1S*,2R*,4R*)-4-[(hydroxyacetyl)amino]-2-methylcyclohexyl}-6-methyl-5H-pyrrolo[3,2-d]pyrimidine-7-carboxamide |
| P361 | 4-[2-(Cyclopropylmethoxy)-5-fluorophenyl]-N-[(1S*,2R*,4R*)-4-{[(2S)-2-hydroxypropanoyl]amino}-2-methylcyclohexyl]-6-methyl-5H-pyrrolo[3,2-d]pyrimidine-7-carboxamide |
| P362 | N-[(1R*,2R*,4R*)-4-(Acetylamino)-2-fluorocyclohexyl]-4-[2-(cyclopropylmethoxy)-5-fluorophenyl]-6-methyl-5H-pyrrolo[3,2-d]pyrimidine-7-carboxamide |
| P363 | 4-[2-(Cyclopropylmethoxy)-5-fluorophenyl]-N-[(1R*,2R*,4R*)-2-fluoro-4-(propanoylamino)cyclohexyl]-6-methyl-5H-pyrrolo[3,2-d]pyrimidine-7-carboxamide |
| P364 | 4-[2-(Cyclopropylmethoxy)-5-fluorophenyl]-N-{(1R*,2R*,4R*)-2-fluoro-4-[(methoxyacetyl)amino]cyclohexyl}-6-methyl-5H-pyrrolo[3,2-d]pyrimidine-7-carboxamide |
| P365 | 4-[2-(Cyclopropylmethoxy)-5-fluorophenyl]-N-{(1R*,2R*,4R*)-2-fluoro-4-[(hydroxyacetyl)amino]cyclohexyl}-6-methyl-5H-pyrrolo[3,2-d]pyrimidine-7-carboxamide |
| P366 | 4-[2-(Cyclopropylmethoxy)-5-fluorophenyl]-N-[(1R*,2R*,4R*)-2-fluoro-4-{[(2S)-2-hydroxypropanoyl]amino}cyclohexyl]-6-methyl-5H-pyrrolo[3,2-d]pyrimidine-7-carboxamide |
| P367 | N-[(1R*,2R*,4S*)-4-(Acetylamino)-2-fluorocyclohexyl]-4-[2-(cyclopropylmethoxy)-5-fluorophenyl]-6-methyl-5H-pyrrolo[3,2-d]pyrimidine-7-carboxamide |
| P368 | 4-[2-(Cyclopropylmethoxy)-5-fluorophenyl]-N-[(1R*,2R*,4S*)-2-fluoro-4-(propanoylamino)cyclohexyl]-6-methyl-5H-pyrrolo[3,2-d]pyrimidine-7-carboxamide |
| P369 | 4-[2-(Cyclopropylmethoxy)-5-fluorophenyl]-N-{(1R*,2R*,4S*)-2-fluoro-4-[(methoxyacetyl)amino]cyclohexyl}-6-methyl-5H-pyrrolo[3,2-d]pyrimidine-7-carboxamide |
| P370 | 4-[2-(Cyclopropylmethoxy)-5-fluorophenyl]-N-{(1R*,2R*,4S*)-2-fluoro-4-[(hydroxyacetyl)amino]cyclohexyl}-6-methyl-5H-pyrrolo[3,2-d]pyrimidine-7-carboxamide |
| P371 | 4-[2-(Cyclopropylmethoxy)-5-fluorophenyl]-N-[(1R*,2R*,4S*)-2-fluoro-4-{[(2S)-2-hydroxypropanoyl]amino}cyclohexyl]-6-methyl-5H-pyrrolo[3,2-d]pyrimidine-7-carboxamide |

| | |
|---|---|
| P372 | N-[(1S*,2R*,4S*)-4-(Acetylamino)-2-fluorocyclohexyl]-4-[2-(cyclopropylmethoxy)-5-fluorophenyl]-6-methyl-5H-pyrrolo[3,2-d]pyrimidine-7-carboxamide |
| P373 | 4-[2-(Cyclopropylmethoxy)-5-fluorophenyl]-N-[(1S*,2R*,4S*)-2-fluoro-4-(propanoylamino)cyclohexyl]-6-methyl-5H-pyrrolo[3,2-d]pyrimidine-7-carboxamide |
| P374 | 4-[2-(Cyclopropylmethoxy)-5-fluorophenyl]-N-{(1S*,2R*,4S*)-2-fluoro-4-[(methoxyacetyl)amino]cyclohexyl}-6-methyl-5H-pyrrolo[3,2-d]pyrimidine-7-carboxamide |
| P375 | 4-[2-(Cyclopropylmethoxy)-5-fluorophenyl]-N-{(1S*,2R*,4S*)-2-fluoro-4-[(hydroxyacetyl)amino]cyclohexyl}-6-methyl-5H-pyrrolo[3,2-d]pyrimidine-7-carboxamide |
| P376 | 4-[2-(Cyclopropylmethoxy)-5-fluorophenyl]-N-[(1S*,2R*,4S*)-2-fluoro-4-{[(2S)-2-hydroxypropanoyl]amino}cyclohexyl]-6-methyl-5H-pyrrolo[3,2-d]pyrimidine-7-carboxamide |
| P377 | N-[(1S*,2R*,4R*)-4-(Acetylamino)-2-fluorocyclohexyl]-4-[2-(cyclopropylmethoxy)-5-fluorophenyl]-6-methyl-5H-pyrrolo[3,2-d]pyrimidine-7-carboxamide |
| P378 | 4-[2-(Cyclopropylmethoxy)-5-fluorophenyl]-N-[(1S*,2R*,4R*)-2-fluoro-4-(propanoylamino)cyclohexyl]-6-methyl-5H-pyrrolo[3,2-d]pyrimidine-7-carboxamide |
| P379 | 4-[2-(Cyclopropylmethoxy)-5-fluorophenyl]-N-{(1S*,2R*,4R*)-2-fluoro-4-[(methoxyacetyl)amino]cyclohexyl}-6-methyl-5H-pyrrolo[3,2-d]pyrimidine-7-carboxamide |
| P380 | 4-[2-(Cyclopropylmethoxy)-5-fluorophenyl]-N-{(1S*,2R*,4R*)-2-fluoro-4-[(hydroxyacetyl)amino]cyclohexyl}-6-methyl-5H-pyrrolo[3,2-d]pyrimidine-7-carboxamide |
| P381 | 4-[2-(Cyclopropylmethoxy)-5-fluorophenyl]-N-[(1S*,2R*,4R*)-2-fluoro-4-{[(2S)-2-hydroxypropanoyl]amino}cyclohexyl]-6-methyl-5H-pyrrolo[3,2-d]pyrimidine-7-carboxamide |
| P382 | N-[(1S*,3R*,4S*)-4-(acetylamino)-3-methylcyclohexyl]-4-[2-(cyclopropylmethoxy)-5-fluorophenyl]-6-methyl-5H-pyrrolo[3,2-d]pyrimidine-7-carboxamide |
| P383 | 4-[2-(Cyclopropylmethoxy)-5-fluorophenyl]-6-methyl-N-[(1S*,3R*,4S*)-3-methyl-4-(propanoylamino)cyclohexyl]-5H-pyrrolo[3,2-d]pyrimidine-7-carboxamide |
| P384 | 4-[2-(Cyclopropylmethoxy)-5-fluorophenyl]-N-{(1S*,3R*,4S*)-4-[(methoxyacetyl)amino]-3-methylcyclohexyl}-6-methyl-5H-pyrrolo[3,2-d]pyrimidine-7-carboxamide |
| P385 | 4-[2-(Cyclopropylmethoxy)-5-fluorophenyl]-N-{(1S*,3R*,4S*)-4-[(hydroxyacetyl)amino]-3-methylcyclohexyl}-6-methyl-5H-pyrrolo[3,2-d]pyrimidine-7-carboxamide |
| P386 | 4-[2-(Cyclopropylmethoxy)-5-fluorophenyl]-N-[(1S*,3R*,4S*)-4-{[(2S)-2-hydroxypropanoyl]amino}-3-methylcyclohexyl]-6-methyl-5H-pyrrolo[3,2-d]pyrimidine-7-carboxamide |
| P387 | N-[(1S*,3R*,4R*)-4-(Acetylamino)-3-methylcyclohexyl]-4-[2-(cyclopropylmethoxy)-5-fluorophenyl]-6-methyl-5H-pyrrolo[3,2-d]pyrimidine-7-carboxamide |
| P388 | 4-[2-(Cyclopropylmethoxy)-5-fluorophenyl]-6-methyl-N-[(1S*,3R*,4R*)-3-methyl-4-(propanoylamino)cyclohexyl]-5H-pyrrolo[3,2-d]pyrimidine-7-carboxamide |
| P389 | 4-[2-(Cyclopropylmethoxy)-5-fluorophenyl]-N-[(1S*,3R*,4R*)-4-[(methoxyacetyl)amino]-3-methylcyclohexyl}-6-methyl-5H-pyrrolo[3,2-d]pyrimidine-7-carboxamide |
| P390 | 4-[2-(Cyclopropylmethoxy)-5-fluorophenyl]-N-{(1S*,3R*,4R*)-4-[(hydroxyacetyl)amino]-3-methylcyclohexyl}-6-methyl-5H-pyrrolo[3,2-d]pyrimidine-7-carboxamide |
| P391 | 4-[2-(Cyclopropylmethoxy)-5-fluorophenyl]-N-[(1S*,3R*,4R*)-4-{[(2S)-2-hydroxypropanoyl]amino}-3-methylcyclohexyl]-6-methyl-5H-pyrrolo[3,2-d]pyrimidine-7-carboxamide |
| P392 | N-[(1R*,3R*,4R*)-4-(acetylamino)-3-methylcyclohexyl]-4-[2-(cyclopropylmethoxy)-5-fluorophenyl]-6-methyl-5H-pyrrolo[3,2-d]pyrimidine-7-carboxamide |
| P393 | 4-[2-(Cyclopropylmethoxy)-5-fluorophenyl]-6-methyl-N-[(1R*,3R*,4R*)-3-methyl-4-(propanoylamino)cyclohexyl]-5H-pyrrolo[3,2-d]pyrimidine-7-carboxamide |
| P394 | 4-[2-(Cyclopropylmethoxy)-5-fluorophenyl]-N-[(1R*,3R*,4R*)-4-[(methoxyacetyl)amino]-3-methylcyclohexyl]-6-methyl-5H-pyrrolo[3,2-d]pyrimidine-7-carboxamide |
| P395 | 4-[2-(Cyclopropylmethoxy)-5-fluorophenyl]-N-[(1R*,3R*,4R*)-4-[(hydroxyacetyl)amino]-3-methylcyclohexyl]-6-methyl-5H-pyrrolo[3,2-d]pyrimidine-7-carboxamide |
| P396 | 4-[2-(Cyclopropylmethoxy)-5-fluorophenyl]-N-[(1R*,3R*,4R*)-4-{[(2S)-2-hydroxypropanoyl]amino}-3-methylcyclohexyl]-6-methyl-5H-pyrrolo[3,2-d]pyrimidine-7-carboxamide |
| P397 | N-[(1R*,3R*,4S*)-4-(Acetylamino)-3-methylcyclohexyl]-4-[2-(cyclopropylmethoxy)-5-fluorophenyl]-6-methyl-5H-pyrrolo[3,2-d]pyrimidine-7-carboxamide |
| P398 | 4-[2-(Cyclopropylmethoxy)-5-fluorophenyl]-6-methyl-N-[(1R*,3R*,4S*)-3-methyl-4-(propanoylamino)cyclohexyl]-5H-pyrrolo[3,2-d]pyrimidine-7-carboxamide |
| P399 | 4-[2-(Cyclopropylmethoxy)-5-fluorophenyl]-N-[(1R*,3R*,4S*)-4-[(methoxyacetyl)amino]-3-methylcyclohexyl]-6-methyl-5H-pyrrolo[3,2-d]pyrimidine-7-carboxamide |
| P400 | 4-[2-(Cyclopropylmethoxy)-5-fluorophenyl]-N-[(1R*,3R*,4S*)-4-[(hydroxyacetyl)amino]-3-methylcyclohexyl]-6-methyl-5H-pyrrolo[3,2-d]pyrimidine-7-carboxamide |
| P401 | 4-[2-(Cyclopropylmethoxy)-5-fluorophenyl]-N-[(1R*,3R*,4S*)-4-{[(2S)-2-hydroxypropanoyl]amino}-3-methylcyclohexyl]-6-methyl-5H-pyrrolo[3,2-d]pyrimidine-7-carboxamide |
| P402 | N-[(1S*,3R*,4S*)-4-(acetylamino)-3-fluorocyclohexyl]-4-[2-(cyclopropylmethoxy)-5-fluorophenyl]-6-methyl-5H-pyrrolo[3,2-d]pyrimidine-7-carboxamide |
| P403 | 4-[2-(Cyclopropylmethoxy)-5-fluorophenyl]-N-[(1S*,3R*,4S*)-3-fluoro-4-(propanoylamino)cyclohexyl]-6-methyl-5H-pyrrolo[3,2-d]pyrimidine-7-carboxamide |
| P404 | 4-[2-(Cyclopropylmethoxy)-5-fluorophenyl]-N-{(1S*,3R*,4S*)-3-fluoro-4-[(methoxyacetyl)amino]cyclohexyl}-6-methyl-5H-pyrrolo[3,2-d]pyrimidine-7-carboxamide |
| P405 | 4-[2-(Cyclopropylmethoxy)-5-fluorophenyl]-N-{(1S*,3R*,4S*)-3-fluoro-4-[(hydroxyacetyl)amino]cyclohexyl}-6-methyl-5H-pyrrolo[3,2-d]pyrimidine-7-carboxamide |
| P406 | 4-[2-(Cyclopropylmethoxy)-5-fluorophenyl]-N-[(1S*,3R*,4S*)-3-fluoro-4-{[(2S)-2-hydroxypropanoyl]amino}cyclohexyl]-6-methyl-5H-pyrrolo[3,2-d]pyrimidine-7-carboxamide |
| P407 | N-[(1S*,3R*,4R*)-4-(acetylamino)-3-fluorocyclohexyl]-4-[2-(cyclopropylmethoxy)-5-fluorophenyl]-6-methyl-5H-pyrrolo[3,2-d]pyrimidine-7-carboxamide |
| P408 | 4-[2-(Cyclopropylmethoxy)-5-fluorophenyl]-N-[(1S*,3R*,4R*)-3-fluoro-4-(propanoylamino)cyclohexyl]-6-methyl-5H-pyrrolo[3,2-d]pyrimidine-7-carboxamide |
| P409 | 4-[2-(Cyclopropylmethoxy)-5-fluorophenyl]-N-{(1S*,3R*,4R*)-3-fluoro-4-[(methoxyacetyl)amino]cyclohexyl}-6-methyl-5H-pyrrolo[3,2-d]pyrimidine-7-carboxamide |
| P410 | 4-[2-(Cyclopropylmethoxy)-5-fluorophenyl]-N-{(1S*,3R*,4R*)-3-fluoro-4-[(hydroxyacetyl)amino]cyclohexyl}-6-methyl-5H-pyrrolo[3,2-d]pyrimidine-7-carboxamide |

| | |
|---|---|
| P411 | 4-[2-(cyclopropylmethoxy)-5-fluorophenyl]-N-[(1S*,3R*,4R*)-3-fluoro-4-{[(2S)-2-hydroxypropanoyl]amino}cyclohexyl]-6-methyl-5H-pyrrolo[3,2-d]pyrimidine-7-carboxamide |
| P412 | N-[(1R*,3R*,4R*)-4-(Acetylamino)-3-fluorocyclohexyl]-4-[2-(cyclopropylmethoxy)-5-fluorophenyl]-6-methyl-5H-pyrrolo[3,2-d]pyrimidine-7-carboxamide |
| P413 | 4-[2-(Cyclopropylmethoxy)-5-fluorophenyl]-N-[(1R*,3R*,4R*)-3-fluoro-4-(propanoylamino)cyclohexyl]-6-methyl-5H-pyrrolo[3,2-d]pyrimidine-7-carboxamide |
| P414 | 4-[2-(Cyclopropylmethoxy)-5-fluorophenyl]-N-{(1R*,3R*,4R*)-3-fluoro-4-[(methoxyacetyl)amino]cyclohexyl}-6-methyl-5H-pyrrolo[3,2-d]pyrimidine-7-carboxamide |
| P415 | 4-[2-(Cyclopropylmethoxy)-5-fluorophenyl]-N-{(1R*,3R*,4R*)-3-fluoro-4-[(hydroxyacetyl)amino]cyclohexyl}-6-methyl-5H-pyrrolo[3,2-d]pyrimidine-7-carboxamide |
| P416 | 4-[2-(Cyclopropylmethoxy)-5-fluorophenyl]-N-[(1R*,3R*,4R*)-3-fluoro-4-{[(2S)-2-hydroxypropanoyl]amino}cyclohexyl]-6-methyl-5H-pyrrolo[3,2-d]pyrimidine-7-carboxamide |
| P417 | N-[(1R*,3R*,4S*)-4-(Acetylamino)-3-fluorocyclohexyl]-4-[2-(cyclopropylmethoxy)-5-fluorophenyl]-6-methyl-5H-pyrrolo[3,2-d]pyrimidine-7-carboxamide |
| P418 | 4-[2-(Cyclopropylmethoxy)-5-fluorophenyl]-N-[(1R*,3R*,4S*)-3-fluoro-4-(propanoylamino)cyclohexyl]-6-methyl-5H-pyrrolo[3,2-d]pyrimidine-7-carboxamide |
| P419 | 4-[2-(Cyclopropylmethoxy)-5-fluorophenyl]-N-{(1R*,3R*,4S*)-3-fluoro-4-[(methoxyacetyl)amino]cyclohexyl}-6-methyl-5H-pyrrolo[3,2-d]pyrimidine-7-carboxamide |
| P420 | 4-[2-(Cyclopropylmethoxy)-5-fluorophenyl]-N-{(1R*,3R*,4S*)-3-fluoro-4-[(hydroxyacetyl)amino]cyclohexyl}-6-methyl-5H-pyrrolo[3,2-d]pyrimidine-7-carboxamide |
| P421 | 4-[2-(Cyclopropylmethoxy)-5-fluorophenyl]-N-[(1R*,3R*,4S*)-3-fluoro-4-{[(2S)-2-hydroxypropanoyl]amino}cyclohexyl]-6-methyl-5H-pyrrolo[3,2-d]pyrimidine-7-carboxamide |
| P422 | 4-[2-(Cyclopropylmethoxy)-5-methylphenyl]-N-[(1R,3S)-3-hydroxycyclopentyl]-6-methyl-5H-pyrrolo[3,2-d]pyrimidine-7-carboxamide |
| P423 | 4-[2-(Cyclopropylmethoxy)-5-methylphenyl]-N-[(1R,3R)-3-hydroxycyclopentyl]-6-methyl-5H-pyrrolo[3,2-d]pyrimidine-7-carboxamide |
| P424 | 4-[2-(Cyclopropylmethoxy)-5-methylphenyl]-N-[(1S,3S)-3-hydroxycyclopentyl]-6-methyl-5H-pyrrolo[3,2-d]pyrimidine-7-carboxamide |
| P425 | 4-[2-(Cyclopropylmethoxy)-5-methylphenyl]-N-[(1S,3R)-3-hydroxycyclopentyl]-6-methyl-5H-pyrrolo[3,2-d]pyrimidine-7-carboxamide |
| P427 | N-[(3S,5S)-1-Acetyl-5-methylpyrrolidin-3-yl]-4-[2-(cyclopropylmethoxy)-5-methylphenyl]-6-methyl-5H-pyrrolo[3,2-d]pyrimidine-7-carboxamide |
| P428 | 4-[2-(Cyclopropylmethoxy)-5-methylphenyl]-6-methyl-N-[(3S,5S)-5-methyl-1-propanoylpyrrolidin-3-yl]-5H-pyrrolo[3,2-d]pyrimidine-7-carboxamide |
| P429 | 4-[2-(Cyclopropylmethoxy)-5-methylphenyl]-N-[(3S,5S)-1-(methoxyacetyl)-5-methylpyrrolidin-3-yl]-6-methyl-5H-pyrrolo[3,2-d]pyrimidine-7-carboxamide |
| P430 | 4-[2-(Cyclopropylmethoxy)-5-methylphenyl]-N-[(3S,5S)-1-(hydroxyacetyl)-5-methylpyrrolidin-3-yl]-6-methyl-5H-pyrrolo[3,2-d]pyrimidine-7-carboxamide |
| P431 | 4-[2-(Cyclopropylmethoxy)-5-methylphenyl]-N-{(3S,5S)-1-[(2S)-2-hydroxypropanoyl]-5-methylpyrrolidin-3-yl}-6-methyl-5H-pyrrolo[3,2-d]pyrimidine-7-carboxamide |
| P432 | N-[(3S,5R)-1-Acetyl-5-methylpyrrolidin-3-yl]-4-[2-(cyclopropylmethoxy)-5-methylphenyl]-6-methyl-5H-pyrrolo[3,2-d]pyrimidine-7-carboxamide |
| P433 | 4-[2-(Cyclopropylmethoxy)-5-methylphenyl]-6-methyl-N-[(3S,5R)-5-methyl-1-propanoylpyrrolidin-3-yl]-5H-pyrrolo[3,2-d]pyrimidine-7-carboxamide |
| P434 | 4-[2-(Cyclopropylmethoxy)-5-methylphenyl]-N-[(3S,5R)-1-(methoxyacetyl)-5-methylpyrrolidin-3-yl]-6-methyl-5H-pyrrolo[3,2-d]pyrimidine-7-carboxamide |
| P435 | 4-[2-(Cyclopropylmethoxy)-5-methylphenyl]-N-[(3S,5R)-1-(hydroxyacetyl)-5-methylpyrrolidin-3-yl]-6-methyl-5H-pyrrolo[3,2-d]pyrimidine-7-carboxamide |
| P436 | 4-[2-(Cyclopropylmethoxy)-5-methylphenyl]-N-{(3S,5R)-1-[(2S)-2-hydroxypropanoyl]-5-methylpyrrolidin-3-yl}-6-methyl-5H-pyrrolo[3,2-d]pyrimidine-7-carboxamide |
| P437 | N-[(3R,5R)-1-Acetyl-5-methylpyrrolidin-3-yl]-4-[2-(cyclopropylmethoxy)-5-methylphenyl]-6-methyl-5H-pyrrolo[3,2-d]pyrimidine-7-carboxamide |
| P438 | 4-[2-(Cyclopropylmethoxy)-5-methylphenyl]-6-methyl-N-[(3R,5R)-5-methyl-1-propanoylpyrrolidin-3-yl]-5H-pyrrolo[3,2-d]pyrimidine-7-carboxamide |
| P439 | 4-[2-(Cyclopropylmethoxy)-5-methylphenyl]-N-[(3R,5R)-1-(methoxyacetyl)-5-methylpyrrolidin-3-yl]-6-methyl-5H-pyrrolo[3,2-d]pyrimidine-7-carboxamide |
| P440 | 4-[2-(Cyclopropylmethoxy)-5-methylphenyl]-N-[(3R,5R)-1-(hydroxyacetyl)-5-methylpyrrolidin-3-yl]-6-methyl-5H-pyrrolo[3,2-d]pyrimidine-7-carboxamide |
| P441 | 4-[2-(Cyclopropylmethoxy)-5-methylphenyl]-N-{(3R,5R)-1-[(2S)-2-hydroxypropanoyl]-5-methylpyrrolidin-3-yl}-6-methyl-5H-pyrrolo[3,2-d]pyrimidine-7-carboxamide |
| P442 | N-[(3R,5S)-1-Acetyl-5-methylpyrrolidin-3-yl]-4-[2-(cyclopropylmethoxy)-5-methylphenyl]-6-methyl-5H-pyrrolo[3,2-d]pyrimidine-7-carboxamide |
| P443 | 4-[2-(Cyclopropylmethoxy)-5-methylphenyl]-6-methyl-N-[(3R,5S)-5-methyl-1-propanoylpyrrolidin-3-yl]-5H-pyrrolo[3,2-d]pyrimidine-7-carboxamide |
| P444 | 4-[2-(Cyclopropylmethoxy)-5-methylphenyl]-N-[(3R,5S)-1-(methoxyacetyl)-5-methylpyrrolidin-3-yl]-6-methyl-5H-pyrrolo[3,2-d]pyrimidine-7-carboxamide |
| P445 | 4-[2-(Cyclopropylmethoxy)-5-methylphenyl]-N-[(3R,5S)-1-(hydroxyacetyl)-5-methylpyrrolidin-3-yl]-6-methyl-5H-pyrrolo[3,2-d]pyrimidine-7-carboxamide |
| P446 | 4-[2-(Cyclopropylmethoxy)-5-methylphenyl]-N-{(3R,5S)-1-[(2S)-2-hydroxypropanoyl]-5-methylpyrrolidin-3-yl}-6-methyl-5H-pyrrolo[3,2-d]pyrimidine-7-carboxamide |
| P447 | N-[(3S,4S)-1-Acetyl-4-fluoropyrrolidin-3-yl]-4-[2-(cyclopropylmethoxy)-5-methylphenyl]-6-methyl-5H-pyrrolo[3,2-d]pyrimidine-7-carboxamide |
| P448 | 4-[2-(Cyclopropylmethoxy)-5-methylphenyl]-N-[(3S,4S)-4-fluoro-1-propanoylpyrrolidin-3-yl]-6-methyl-5H-pyrrolo[3,2-d]pyrimidine-7-carboxamide |
| P449 | 4-[2-(Cyclopropylmethoxy)-5-methylphenyl]-N-[(3S,4S)-4-fluoro-1-(methoxyacetyl)pyrrolidin-3-yl]-6-methyl-5H-pyrrolo[3,2-d]pyrimidine-7-carboxamide |
| P450 | 4-[2-(Cyclopropylmethoxy)-5-methylphenyl]-N-[(3S,4S)-4-fluoro-1-(hydroxyacetyl)pyrrolidin-3-yl]-6-methyl-5H-pyrrolo[3,2-d]pyrimidine-7-carboxamide |

| | |
|---|---|
| P451 | 4-[2-(Cyclopropylmethoxy)-5-methylphenyl]-N-{(3S,4S)-4-fluoro-1-[(2S)-2-hydroxypropanoyl]pyrrolidin-3-yl}-6-methyl-5H-pyrrolo[3,2-d]pyrimidine-7-carboxamide |
| P452 | N-[(3R,4S)-1-Acetyl-4-fluoropyrrolidin-3-yl]-4-[2-(cyclopropylmethoxy)-5-methylphenyl]-6-methyl-5H-pyrrolo[3,2-d]pyrimidine-7-carboxamide |
| P453 | 4-[2-(Cyclopropylmethoxy)-5-methylphenyl]-N-[(3R,4S)-4-fluoro-1-propanoylpyrrolidin-3-yl]-6-methyl-5H-pyrrolo[3,2-d]pyrimidine-7-carboxamide |
| P454 | 4-[2-(Cyclopropylmethoxy)-5-methylphenyl]-N-[(3R,4S)-4-fluoro-1-(methoxyacetyl)pyrrolidin-3-yl]-6-methyl-5H-pyrrolo[3,2-d]pyrimidine-7-carboxamide |
| P455 | 4-[2-(Cyclopropylmethoxy)-5-methylphenyl]-N-[(3R,4S)-4-fluoro-1-(hydroxyacetyl)pyrrolidin-3-yl]-6-methyl-5H-pyrrolo[3,2-d]pyrimidine-7-carboxamide |
| P456 | 4-[2-(Cyclopropylmethoxy)-5-methylphenyl]-N-{(3R,4S)-4-fluoro-1-[(2S)-2-hydroxypropanoyl]pyrrolidin-3-yl}-6-methyl-5H-pyrrolo[3,2-d]pyrimidine-7-carboxamide |
| P457 | N-[(3R,4R)-1-Acetyl-4-fluoropyrrolidin-3-yl]-4-[2-(cyclopropylmethoxy)-5-methylphenyl]-6-methyl-5H-pyrrolo[3,2-d]pyrimidine-7-carboxamide |
| P458 | 4-[2-(Cyclopropylmethoxy)-5-methylphenyl]-N-[(3R,4R)-4-fluoro-1-propanoylpyrrolidin-3-yl]-6-methyl-5H-pyrrolo[3,2-d]pyrimidine-7-carboxamide |
| P459 | 4-[2-(Cyclopropylmethoxy)-5-methylphenyl]-N-[(3R,4R)-4-fluoro-1-(methoxyacetyl)pyrrolidin-3-yl]-6-methyl-5H-pyrrolo[3,2-d]pyrimidine-7-carboxamide |
| P460 | 4-[2-(Cyclopropylmethoxy)-5-methylphenyl]-N-[(3R,4R)-4-fluoro-1-(hydroxyacetyl)pyrrolidin-3-yl]-6-methyl-5H-pyrrolo[3,2-d]pyrimidine-7-carboxamide |
| P461 | 4-[2-(Cyclopropylmethoxy)-5-methylphenyl]-N-[(3R,4R)-4-fluoro-1-[(2S)-2-hydroxypropanoyl]pyrrolidin-3-yl}-6-methyl-5H-pyrrolo[3,2-d]pyrimidine-7-carboxamide |
| P462 | N-[(3S,4R)-1-Acetyl-4-fluoropyrrolidin-3-yl]-4-[2-(cyclopropylmethoxy)-5-methylphenyl]-6-methyl-5H-pyrrolo[3,2-d]pyrimidine-7-carboxamide |
| P463 | 4-[2-(Cyclopropylmethoxy)-5-methylphenyl]-N-[(3S,4R)-4-fluoro-1-propanoylpyrrolidin-3-yl]-6-methyl-5H-pyrrolo[3,2-d]pyrimidine-7-carboxamide |
| P464 | 4-[2-(Cyclopropylmethoxy)-5-methylphenyl]-N-[(3S,4R)-4-fluoro-1-(methoxyacetyl)pyrrolidin-3-yl]-6-methyl-5H-pyrrolo[3,2-d]pyrimidine-7-carboxamide |
| P465 | 4-[2-(Cyclopropylmethoxy)-5-methylphenyl]-N-[(3S,4R)-4-fluoro-1-(hydroxyacetyl)pyrrolidin-3-yl]-6-methyl-5H-pyrrolo[3,2-d]pyrimidine-7-carboxamide |
| P466 | 4-[2-(Cyclopropylmethoxy)-5-methylphenyl]-N-{(3S,4R)-4-fluoro-1-[(2S)-2-hydroxypropanoyl]pyrrolidin-3-yl}-6-methyl-5H-pyrrolo[3,2-d]pyrimidine-7-carboxamide |
| P467 | N-[(3S*,4R*)-1-Acetyl-4-methylpyrrolidin-3-yl]-4-[2-(cyclopropylmethoxy)-5-methylphenyl]-6-methyl-5H-pyrrolo[3,2-d]pyrimidine-7-carboxamide |
| P468 | 4-[2-(Cyclopropylmethoxy)-5-methylphenyl]-6-methyl-N-[(3S*,4R*)-4-methyl-1-propanoylpyrrolidin-3-yl]-5H-pyrrolo[3,2-d]pyrimidine-7-carboxamide |
| P469 | 4-[2-(Cyclopropylmethoxy)-5-methylphenyl]-N-[(3S*,4R*)-1-(methoxyacetyl)-4-methylpyrrolidin-3-yl]-6-methyl-5H-pyrrolo[3,2-d]pyrimidine-7-carboxamide |
| P470 | 4-[2-(Cyclopropylmethoxy)-5-methylphenyl]-N-[(3S*,4R*)-1-(hydroxyacetyl)-4-methylpyrrolidin-3-yl]-6-methyl-5H-pyrrolo[3,2-d]pyrimidine-7-carboxamide |
| P471 | 4-[2-(Cyclopropylmethoxy)-5-methylphenyl]-N-{(3S*,4R*)-1-[(2S)-2-hydroxypropanoyl]-4-methylpyrrolidin-3-yl}-6-methyl-5H-pyrrolo[3,2-d]pyrimidine-7-carboxamide |
| P472 | N-[(3S*,4S*)-1-Acetyl-4-methylpyrrolidin-3-yl]-4-[2-(cyclopropylmethoxy)-5-methylphenyl]-6-methyl-5H-pyrrolo[3,2-d]pyrimidine-7-carboxamide |
| P473 | 4-[2-(Cyclopropylmethoxy)-5-methylphenyl]-6-methyl-N-[(3S*,4S*)-4-methyl-1-propanoylpyrrolidin-3-yl]-5H-pyrrolo[3,2-d]pyrimidine-7-carboxamide |
| P474 | 4-[2-(Cyclopropylmethoxy)-5-methylphenyl]-N-[(3S*,4S*)-1-(methoxyacetyl)-4-methylpyrrolidin-3-yl]-6-methyl-5H-pyrrolo[3,2-d]pyrimidine-7-carboxamide |
| P475 | 4-[2-(Cyclopropylmethoxy)-5-methylphenyl]-N-[(3S*,4S*)-1-(hydroxyacetyl)-4-methylpyrrolidin-3-yl]-6-methyl-5H-pyrrolo[3,2-d]pyrimidine-7-carboxamide |
| P476 | 4-[2-(Cyclopropylmethoxy)-5-methylphenyl]-N-{(3S*,4S*)-1-[(2S)-2-hydroxypropanoyl]-4-methylpyrrolidin-3-yl}-6-methyl-5H-pyrrolo[3,2-d]pyrimidine-7-carboxamide |
| P477 | N-[(3S*)-1-Acetyl-4,4-dimethylpyrrolidin-3-yl]-4-[2-(cyclopropylmethoxy)-5-methylphenyl]-6-methyl-5H-pyrrolo[3,2-d]pyrimidine-7-carboxamide |
| P478 | 4-[2-(Cyclopropylmethoxy)-5-methylphenyl]-N-[(3S*)-4,4-dimethyl-1-propanoylpyrrolidin-3-yl]-6-methyl-5H-pyrrolo[3,2-d]pyrimidine-7-carboxamide |
| P479 | 4-[2-(Cyclopropylmethoxy)-5-methylphenyl]-N-[(3S*)-1-(methoxyacetyl)-4,4-dimethylpyrrolidin-3-yl]-6-methyl-5H-pyrrolo[3,2-d]pyrimidine-7-carboxamide |
| P480 | 4-[2-(Cyclopropylmethoxy)-5-methylphenyl]-N-[(3S*)-1-(hydroxyacetyl)-4,4-dimethylpyrrolidin-3-yl]-6-methyl-5H-pyrrolo[3,2-d]pyrimidine-7-carboxamide |
| P481 | 4-[2-(Cyclopropylmethoxy)-5-methylphenyl]-N-{(3S*)-1-[(2S)-2-hydroxypropanoyl]-4,4-dimethylpyrrolidin-3-yl}-6-methyl-5H-pyrrolo[3,2-d]pyrimidine-7-carboxamide |
| P482 | N-[(7S*)-5-Acetyl-5-azaspiro[2.4]hept-7-yl]-4-[2-(cyclopropylmethoxy)-5-methylphenyl]-6-methyl-5H-pyrrolo[3,2-d]pyrimidine-7-carboxamide |
| P483 | 4-[2-(Cyclopropylmethoxy)-5-methylphenyl]-6-methyl-N-[(7S*)-5-propanoyl-5-azaspiro[2.4]hept-7-yl]-5H-pyrrolo[3,2-d]pyrimidine-7-carboxamide |
| P484 | 4-[2-(Cyclopropylmethoxy)-5-methylphenyl]-N-[(7S*)-5-(methoxyacetyl)-5-azaspiro[2.4]hept-7-yl]-6-methyl-5H-pyrrolo[3,2-d]pyrimidine-7-carboxamide |
| P485 | 4-[2-(Cyclopropylmethoxy)-5-methylphenyl]-N-[(7S)-5-(hydroxyacetyl)-5-azaspiro[2.4]hept-7-yl]-6-methyl-5H-pyrrolo[3,2-d]pyrimidine-7-carboxamide |
| P486 | 4-[2-(Cyclopropylmethoxy)-5-methylphenyl]-N-{(7S*)-5-[(2S)-2-hydroxypropanoyl]-5-azaspiro[2.4]hept-7-yl}-6-methyl-5H-pyrrolo[3,2-d]pyrimidine-7-carboxamide |
| P487 | N-[(3R*)-1-Acetyl-4,4-difluoropyrrolidin-3-yl]-4-[2-(cyclopropylmethoxy)-5-methylphenyl]-6-methyl-5H-pyrrolo[3,2-d]pyrimidine-7-carboxamide |
| P488 | 4-[2-(Cyclopropylmethoxy)-5-methylphenyl]-N-[(3R*)-4,4-difluoro-1-propanoylpyrrolidin-3-yl]-6-methyl-5H-pyrrolo[3,2-d]pyrimidine-7-carboxamide |
| P489 | 4-[2-(Cyclopropylmethoxy)-5-methylphenyl]-N-[(3R*)-4,4-difluoro-1-(methoxyacetyl)pyrrolidin-3-yl]-6-methyl-5H-pyrrolo[3,2-d]pyrimidine-7-carboxamide |

| | |
|---|---|
| P490 | 4-[2-(Cyclopropylmethoxy)-5-methylphenyl]-N-[(3R*)-4,4-difluoro-1-(hydroxyacetyl)pyrrolidin-3-yl]-6-methyl-5H-pyrrolo[3,2-d]pyrimidine-7-carboxamide |
| P491 | 4-[2-(Cyclopropylmethoxy)-5-methylphenyl]-N-{(3R*)-4,4-difluoro-1-[(2S)-2-hydroxypropanoyl]pyrrolidin-3-yl}-6-methyl-5H-pyrrolo[3,2-d]pyrimidine-7-carboxamide |
| P492 | N-[(1S*,3S*)-3-(Acetylamino)cyclopentyl]-4-[2-(cyclopropylmethoxy)-5-methylphenyl]-6-methyl-5H-pyrrolo[3,2-d]pyrimidine-7-carboxamide |
| P493 | 4-[2-(Cyclopropylmethoxy)-5-methylphenyl]-6-methyl-N-[(1S*,3S*)-3-(propanoylamino)cyclopentyl]-5H-pyrrolo[3,2-d]pyrimidine-7-carboxamide |
| P494 | 4-[2-(Cyclopropylmethoxy)-5-methylphenyl]-N-{(1S*,3S*)-3-[(methoxyacetyl)amino]cyclopentyl}-6-methyl-5H-pyrrolo[3,2-d]pyrimidine-7-carboxamide |
| P495 | 4-[2-(Cyclopropylmethoxy)-5-methylphenyl]-N-{(1S*,3S*)-3-[(hydroxyacetyl)amino]cyclopentyl}-6-methyl-5H-pyrrolo[3,2-d]pyrimidine-7-carboxamide |
| P496 | 4-[2-(Cyclopropylmethoxy)-5-methylphenyl]-N-[(1S*,3S*)-3-{[(2S)-2-hydroxypropanoyl]amino}cyclopentyl]-6-methyl-5H-pyrrolo[3,2-d]pyrimidine-7-carboxamide |
| P497 | N-[(1S*,3R*)-3-(Acetylamino)cyclopentyl]-4-[2-(cyclopropylmethoxy)-5-methylphenyl]-6-methyl-5H-pyrrolo[3,2-d]pyrimidine-7-carboxamide |
| P498 | 4-[2-(Cyclopropylmethoxy)-5-methylphenyl]-6-methyl-N-[(1S*,3R*)-3-(propanoylamino)cyclopentyl]-5H-pyrrolo[3,2-d]pyrimidine-7-carboxamide |
| P499 | 4-[2-(Cyclopropylmethoxy)-5-methylphenyl]-N-{(1S*,3R*)-3-[(methoxyacetyl)amino]cyclopentyl}-6-methyl-5H-pyrrolo[3,2-d]pyrimidine-7-carboxamide |
| P500 | 4-[2-(Cyclopropylmethoxy)-5-methylphenyl]-N-{(1S*,3R*)-3-[(hydroxyacetyl)amino]cyclopentyl}-6-methyl-5H-pyrrolo[3,2-d]pyrimidine-7-carboxamide |
| P501 | 4-[2-(Cyclopropylmethoxy)-5-methylphenyl]-N-[(1S*,3R*)-3-{[(2S)-2-hydroxypropanoyl]amino}cyclopentyl]-6-methyl-5H-pyrrolo[3,2-d]pyrimidine-7-carboxamide |
| P502 | N-[(1R*,2R*,4R*)-4-(Acetylamino)-2-fluorocyclopentyl]-4-[2-(cyclopropylmethoxy)-5-methylphenyl]-6-methyl-5H-pyrrolo[3,2-d]pyrimidine-7-carboxamide |
| P503 | 4-[2-(Cyclopropylmethoxy)-5-methylphenyl]-N-[(1R*,2R*,4R*)-2-fluoro-4-(propanoylamino)cyclopentyl]-6-methyl-5H-pyrrolo[3,2-d]pyrimidine-7-carboxamide |
| P504 | 4-[2-(Cyclopropylmethoxy)-5-methylphenyl]-N-{(1R*,2R*,4R*)-2-fluoro-4-[(methoxyacetyl)amino]cyclopentyl}-6-methyl-5H-pyrrolo[3,2-d]pyrimidine-7-carboxamide |
| P505 | 4-[2-(Cyclopropylmethoxy)-5-methylphenyl]-N-{(1R*,2R*,4R*)-2-fluoro-4-[(hydroxyacetyl)amino]cyclopentyl}-6-methyl-5H-pyrrolo[3,2-d]pyrimidine-7-carboxamide |
| P506 | 4-[2-(Cyclopropylmethoxy)-5-methylphenyl]-N-[(1R*,2R*,4R*)-2-fluoro-4-{[(2S)-2-hydroxypropanoyl]amino}cyclopentyl]-6-methyl-5H-pyrrolo[3,2-d]pyrimidine-7-carboxamide |
| P507 | N-[(1R*,2R*,4S*)-4-(Acetylamino)-2-fluorocyclopentyl]-4-[2-(cyclopropylmethoxy)-5-methylphenyl]-6-methyl-5H-pyrrolo[3,2-d]pyrimidine-7-carboxamide |
| P508 | 4-[2-(Cyclopropylmethoxy)-5-methylphenyl]-N-[(1R*,2R*,4S*)-2-fluoro-4-(propanoylamino)cyclopentyl]-6-methyl-5H-pyrrolo[3,2-d]pyrimidine-7-carboxamide |
| P509 | 4-[2-(Cyclopropylmethoxy)-5-methylphenyl]-N-{(1R*,2R*,4S*)-2-fluoro-4-[(methoxyacetyl)amino]cyclopentyl}-6-methyl-5H-pyrrolo[3,2-d]pyrimidine-7-carboxamide |
| P510 | 4-[2-(Cyclopropylmethoxy)-5-methylphenyl]-N-{(1R*,2R*,4S*)-2-fluoro-4-[(hydroxyacetyl)amino]cyclopentyl}-6-methyl-5H-pyrrolo[3,2-d]pyrimidine-7-carboxamide |
| P511 | 4-[2-(Cyclopropylmethoxy)-5-methylphenyl]-N-[(1R*,2R*,4S*)-2-fluoro-4-{[(2S)-2-hydroxypropanoyl]amino}cyclopentyl]-6-methyl-5H-pyrrolo[3,2-d]pyrimidine-7-carboxamide |
| P512 | 4-[2-(Cyclopropylmethoxy)-5-methylphenyl]-N-[(1R,2S)-2-hydroxycyclohexyl]-6-methyl-5H-pyrrolo[3,2-d]pyrimidine-7-carboxamide |
| P513 | 4-[2-(Cyclopropylmethoxy)-5-methylphenyl]-N-[(1R,2R)-2-hydroxycyclohexyl]-6-methyl-5H-pyrrolo[3,2-d]pyrimidine-7-carboxamide |
| P514 | 4-[2-(Cyclopropylmethoxy)-5-methylphenyl]-N-[(1S,2S)-2-hydroxycyclohexyl]-6-methyl-5H-pyrrolo[3,2-d]pyrimidine-7-carboxamide |
| P515 | 4-[2-(Cyclopropylmethoxy)-5-methylphenyl]-N-[(1S,2R)-2-hydroxycyclohexyl]-6-methyl-5H-pyrrolo[3,2-d]pyrimidine-7-carboxamide |
| P516 | 4-[2-(Cyclopropylmethoxy)-5-methylphenyl]-N-[(1S,3R)-3-hydroxycyclohexyl]-6-methyl-5H-pyrrolo[3,2-d]pyrimidine-7-carboxamide |
| P517 | 4-[2-(Cyclopropylmethoxy)-5-methylphenyl]-N-[(1S,3S)-3-hydroxycyclohexyl]-6-methyl-5H-pyrrolo[3,2-d]pyrimidine-7-carboxamide |
| P518 | 4-[2-(Cyclopropylmethoxy)-5-methylphenyl]-N-[(1R,3R)-3-hydroxycyclohexyl]-6-methyl-5H-pyrrolo[3,2-d]pyrimidine-7-carboxamide |
| P519 | 4-[2-(Cyclopropylmethoxy)-5-methylphenyl]-N-[(1R,3S)-3-hydroxycyclohexyl]-6-methyl-5H-pyrrolo[3,2-d]pyrimidine-7-carboxamide |
| P520 | 4-[2-(Cyclopropylmethoxy)-5-methylphenyl]-N-(trans-4-hydroxycyclohexyl)-6-methyl-5H-pyrrolo[3,2-d]pyrimidine-7-carboxamide |
| P521 | 4-[2-(Cyclopropylmethoxy)-5-methylphenyl]-N-(cis-4-hydroxycyclohexyl)-6-methyl-5H-pyrrolo[3,2-d]pyrimidine-7-carboxamide |
| P522 | N-[(3S,4R)-1-Acetyl-3-fluoropiperidin-4-yl]-4-[2-(cyclopropylmethoxy)-5-methylphenyl]-6-methyl-5H-pyrrolo[3,2-d]pyrimidine-7-carboxamide |
| P523 | 4-[2-(Cyclopropylmethoxy)-5-methylphenyl]-N-[(3S,4R)-3-fluoro-1-propanoylpiperidin-4-yl]-6-methyl-5H-pyrrolo[3,2-d]pyrimidine-7-carboxamide |
| P524 | 4-[2-(Cyclopropylmethoxy)-5-methylphenyl]-N-[(3S,4R)-3-fluoro-1-(methoxyacetyl)piperidin-4-yl]-6-methyl-5H-pyrrolo[3,2-d]pyrimidine-7-carboxamide |
| P525 | 4-[2-(Cyclopropylmethoxy)-5-methylphenyl]-N-[(3S,4R)-3-fluoro-1-(hydroxyacetyl)piperidin-4-yl]-6-methyl-5H-pyrrolo[3,2-d]pyrimidine-7-carboxamide |
| P526 | 4-[2-(Cyclopropylmethoxy)-5-methylphenyl]-N-{(3S,4R)-3-fluoro-1-[(2S)-2-hydroxypropanoyl]piperidin-4-yl}-6-methyl-5H-pyrrolo[3,2-d]pyrimidine-7-carboxamide |
| P527 | N-[(3R,4R)-1-Acetyl-3-fluoropiperidin-4-yl]-4-[2-(cyclopropylmethoxy)-5-methylphenyl]-6-methyl-5H-pyrrolo[3,2-d]pyrimidine-7-carboxamide |

| | |
|---|---|
| P528 | 4-[2-(Cyclopropylmethoxy)-5-methylphenyl]-N-[(3R,4R)-3-fluoro-1-propanoylpiperidin-4-yl]-6-methyl-5H-pyrrolo[3,2-d]pyrimidine-7-carboxamide |
| P529 | 4-[2-(Cyclopropylmethoxy)-5-methylphenyl]-N-[(3R,4R)-3-fluoro-1-(methoxyacetyl)piperidin-4-yl]-6-methyl-5H-pyrrolo[3,2-d]pyrimidine-7-carboxamide |
| P530 | 4-[2-(Cyclopropylmethoxy)-5-methylphenyl]-N-[(3R,4R)-3-fluoro-1-(hydroxyacetyl)piperidin-4-yl]-6-methyl-5H-pyrrolo[3,2-d]pyrimidine-7-carboxamide |
| P531 | 4-[2-(Cyclopropylmethoxy)-5-methylphenyl]-N-{(3R,4R)-3-fluoro-1-[(2S)-2-hydroxypropanoyl]piperidin-4-yl}-6-methyl-5H-pyrrolo[3,2-d]pyrimidine-7-carboxamide |
| P532 | N-[(3S,4S)-1-Acetyl-3-fluoropiperidin-4-yl]-4-[2-(cyclopropylmethoxy)-5-methylphenyl]-6-methyl-5H-pyrrolo[3,2-d]pyrimidine-7-carboxamide |
| P533 | 4-[2-(Cyclopropylmethoxy)-5-methylphenyl]-N-[(3S,4S)-3-fluoro-1-propanoylpiperidin-4-yl]-6-methyl-5H-pyrrolo[3,2-d]pyrimidine-7-carboxamide |
| P534 | 4-[2-(Cyclopropylmethoxy)-5-methylphenyl]-N-[(3S,4S)-3-fluoro-1-(methoxyacetyl)piperidin-4-yl]-6-methyl-5H-pyrrolo[3,2-d]pyrimidine-7-carboxamide |
| P535 | 4-[2-(Cyclopropylmethoxy)-5-methylphenyl]-N-[(3S,4S)-3-fluoro-1-(hydroxyacetyl)piperidin-4-yl]-6-methyl-5H-pyrrolo[3,2-d]pyrimidine-7-carboxamide |
| P536 | 4-[2-(Cyclopropylmethoxy)-5-methylphenyl]-N-{(3S,4S)-3-fluoro-1-[(2S)-2-hydroxypropanoyl]piperidin-4-yl}-6-methyl-5H-pyrrolo[3,2-d]pyrimidine-7-carboxamide |
| P537 | N-[(3R,4S)-1-Acetyl-3-fluoropiperidin-4-yl]-4-[2-(cyclopropylmethoxy)-5-methylphenyl]-6-methyl-5H-pyrrolo[3,2-d]pyrimidine-7-carboxamide |
| P538 | 4-[2-(Cyclopropylmethoxy)-5-methylphenyl]-N-[(3R,4S)-3-fluoro-1-propanoylpiperidin-4-yl]-6-methyl-5H-pyrrolo[3,2-d]pyrimidine-7-carboxamide |
| P539 | 4-[2-(Cyclopropylmethoxy)-5-methylphenyl]-N-[(3R,4S)-3-fluoro-1-(methoxyacetyl)piperidin-4-yl]-6-methyl-5H-pyrrolo[3,2-d]pyrimidine-7-carboxamide |
| P540 | 4-[2-(Cyclopropylmethoxy)-5-methylphenyl]-N-[(3R,4S)-3-fluoro-1-(hydroxyacetyl)piperidin-4-yl]-6-methyl-5H-pyrrolo[3,2-d]pyrimidine-7-carboxamide |
| P541 | 4-[2-(Cyclopropylmethoxy)-5-methylphenyl]-N-{(3R,4S)-3-fluoro-1-[(2S)-2-hydroxypropanoyl]piperidin-4-yl}-6-methyl-5H-pyrrolo[3,2-d]pyrimidine-7-carboxamide |
| P542 | N-[(1R*,2R*,4R*)-4-(Acetylamino)-2-methylcyclohexyl]-4-[2-(cyclopropylmethoxy)-5-methylphenyl]-6-methyl-5H-pyrrolo[3,2-d]pyrimidine-7-carboxamide |
| P543 | 4-[2-(Cyclopropylmethoxy)-5-methylphenyl]-6-methyl-N-[(1R*,2R*,4R*)-2-methyl-4-(propanoylamino)cyclohexyl]-5H-pyrrolo[3,2-d]pyrimidine-7-carboxamide |
| P544 | 4-[2-(Cyclopropylmethoxy)-5-methylphenyl]-N-{(1R*,2R*,4R*)-4-[(methoxyacetyl)amino]-2-methylcyclohexyl}-6-methyl-5H-pyrrolo[3,2-d]pyrimidine-7-carboxamide |
| P545 | 4-[2-(Cyclopropylmethoxy)-5-methylphenyl]-N-{(1R,2R,4R)-4-[(hydroxyacetyl)amino]-2-methylcyclohexyi}-6-methyl-5H-pyrrolo[3,2-d]pyrimidine-7-carboxamide |
| P546 | 4-[2-(Cyclopropylmethoxy)-5-methylphenyl]-N-[(1R*,2R*,4R*)-4-{[(2S)-2-hydroxypropanoyl]amino}-2-methylcyclohexyl]-6-methyl-5H-pyrrolo[3,2-d]pyrimidine-7-carboxamide |
| P547 | N-[(1R*,2R*,4S*)-4-(acetylamino)-2-methylcyclohexyl]-4-[2-(cyclopropylmethoxy)-5-methylphenyl]-6-methyl-5H-pyrrolo[3,2-d]pyrimidine-7-carboxamide |
| P548 | 4-[2-(Cyclopropylmethoxy)-5-methylphenyl]-6-methyl-N-[(1R*,2R*,4S*)-2-methyl-4-(propanoylamino)cyclohexyl]-5H-pyrrolo[3,2-d]pyrimidine-7-carboxamide |
| P549 | 4-[2-(Cyclopropylmethoxy)-5-methylphenyl]-N-{(1R*,2R*,4S*)-4-[(methoxyacetyl)amino]-2-methylcyclohexyl}-6-methyl-5H-pyrrolo[3,2-d]pyrimidine-7-carboxamide |
| P550 | 4-[2-(Cyclopropylmethoxy)-5-methylphenyl]-N-{(1R*,2R*,4S*)-4-[(hydroxyacetyl)amino]-2-methylcyclohexyl}-6-methyl-5H-pyrrolo[3,2-d]pyrimidine-7-carboxamide |
| P551 | 4-[2-(Cyclopropylmethoxy)-5-methylphenyl]-N-[(1R*,2R*,4S*)-4-{[(2S)-2-hydroxypropanoyl]amino}-2-methylcyclohexyl]-6-methyl-5H-pyrrolo[3,2-d]pyrimidine-7-carboxamide |
| P552 | N-[(1S*,2R*,4S*)-4-(acetylamino)-2-methylcyclohexyl]-4-[2-(cyclopropylmethoxy)-5-methylphenyl]-6-methyl-5H-pyrrolo[3,2-d]pyrimidine-7-carboxamide |
| P553 | 4-[2-(Cyclopropylmethoxy)-5-methylphenyl]-6-methyl-N-[(1S*,2R*,4S*)-2-methyl-4-(propanoylamino)cyclohexyl]-5H-pyrrolo[3,2-d]pyrimidine-7-carboxamide |
| P554 | 4-[2-(Cyclopropylmethoxy)-5-methylphenyl]-N-{(1S*,2R*,4S*)-4-[(methoxyacetyl)amino]-2-methylcyclohexyl}-6-methyl-5H-pyrrolo[3,2-d]pyrimidine-7-carboxamide |
| P555 | 4-[2-(Cyclopropylmethoxy)-5-methylphenyl]-N-{(1S*,2R*,4S*)-4-[(hydroxyacetyl)amino]-2-methylcyclohexyl}-6-methyl-5H-pyrrolo[3,2-d]pyrimidine-7-carboxamide |
| P556 | 4-[2-(Cyclopropylmethoxy)-5-methylphenyl]-N-[(1S*,2R*,4S*)-4-{[(2S)-2-hydroxypropanoyl]amino}-2-methylcyclohexyl]-6-methyl-5H-pyrrolo[3,2-d]pyrimidine-7-carboxamide |
| P557 | N-[(1S*,2R*,4R*)-4-(Acetylamino)-2-methylcyclohexyl]-4-[2-(cyclopropylmethoxy)-5-methylphenyl]-6-methyl-5H-pyrrolo[3,2-d]pyrimidine-7-carboxamide |
| P558 | 4-[2-(Cyclopropylmethoxy)-5-methylphenyl]-6-methyl-N-[(1S*,2R*,4R*)-2-methyl-4-(propanoylamino)cyclohexyl]-5H-pyrrolo[3,2-d]pyrimidine-7-carboxamide |
| P559 | 4-[2-(Cyclopropylmethoxy)-5-methylphenyl]-N-{(1S*,2R*,4R*)-4-[(methoxyacetyl)amino]-2-methylcyclohexyl}-6-methyl-5H-pyrrolo[3,2-d]pyrimidine-7-carboxamide |
| P560 | 4-[2-(Cyclopropylmethoxy)-5-methylphenyl]-N-{(1S*,2R*,4R*)-4-[(hydroxyacetyl)amino]-2-methylcyclohexyl}-6-methyl-5H-pyrrolo[3,2-d]pyrimidine-7-carboxamide |
| P561 | 4-[2-(Cyclopropylmethoxy)-5-methylphenyl]-N-[(1S*,2R*,4R*)-4-{[(2S)-2-hydroxypropanoyl]amino}-2-methylcyclohexyl]-6-methyl-5H-pyrrolo[3,2-d]pyrimidine-7-carboxamide |
| P562 | N-[(1R*,2R*,4R*)-4-(Acetylamino)-2-fluorocyclohexyl]-4-[2-(cyclopropylmethoxy)-5-methylphenyl]-6-methyl-5H-pyrrolo[3,2-d]pyrimidine-7-carboxamide |
| P563 | 4-[2-(Cyclopropylmethoxy)-5-methylphenyl]-N-[(1R*,2R*,4R*)-2-fluoro-4-(propanoylamino)cyclohexyl]-6-methyl-5H-pyrrolo[3,2-d]pyrimidine-7-carboxamide |
| P564 | 4-[2-(Cyclopropylmethoxy)-5-methylphenyl]-N-{(1R*,2R*,4R*)-2-fluoro-4-[(methoxyacetyl)amino]cyclohexyl}-6-methyl-5H-pyrrolo[3,2-d]pyrimidine-7-carboxamide |
| P565 | 4-[2-(Cyclopropylmethoxy)-5-methylphenyl]-N-{(1R*,2R*,4R*)-2-fluoro-4-[(hydroxyacetyl)amino]cyclohexyl}-6-methyl-5H-pyrrolo[3,2-d]pyrimidine-7-carboxamide |
| P566 | 4-[2-(Cyclopropylmethoxy)-5-methylphenyl]-N-[(1R*,2R*,4R*)-2-fluoro-4-{[(2S)-2-hydroxypropanoyl]amino}cyclohexyl]-6-methyl-5H-pyrrolo[3,2-d]pyrimidine-7-carboxamide |

-continued

| | |
|---|---|
| P567 | N-[(1R*,2R*,4S*)-4-(Acetylamino)-2-fluorocyclohexyl]-4-[2-(cyclopropylmethoxy)-5-methylphenyl]-6-methyl-5H-pyrrolo[3,2-d]pyrimidine-7-carboxamide |
| P568 | 4-[2-(Cyclopropylmethoxy)-5-methylphenyl]-N-[(1R*,2R*,4S*)-2-fluoro-4-(propanoylamino)cyclohexyl]-6-methyl-5H-pyrrolo[3,2-d]pyrimidine-7-carboxamide |
| P569 | 4-[2-(Cyclopropylmethoxy)-5-methylphenyl]-N-{(1R*,2R*,4S*)-2-fluoro-4-[(methoxyacetyl)amino]cyclohexyl}-6-methyl-5H-pyrrolo[3,2-d]pyrimidine-7-carboxamide |
| P570 | 4-[2-(Cyclopropylmethoxy)-5-methylphenyl]-N-{(1R*,2R*,4S*)-2-fluoro-4-[(hydroxyacetyl)amino]cyclohexyl}-6-methyl-5H-pyrrolo[3,2-d]pyrimidine-7-carboxamide |
| P571 | 4-[2-(Cyclopropylmethoxy)-5-methylphenyl]-N-[(1R*,2R*,4S*)-2-fluoro-4-{[(2S)-2-hydroxypropanoyl]amino}cyclohexyl]-6-methyl-5H-pyrrolo[3,2-d]pyrimidine-7-carboxamide |
| P572 | N-[(1S*,2R*,4S*)-4-(Acetylamino)-2-fluorocyclohexyl]-4-[2-(cyclopropylmethoxy)-5-methylphenyl]-6-methyl-5H-pyrrolo[3,2-d]pyrimidine-7-carboxamide |
| P573 | 4-[2-(Cyclopropylmethoxy)-5-methylphenyl]-N-[(1S*,2R*,4S*)-2-fluoro-4-(propanoylamino)cyclohexyl]-6-methyl-5H-pyrrolo[3,2-d]pyrimidine-7-carboxamide |
| P574 | 4-[2-(Cyclopropylmethoxy)-5-methylphenyl]-N-{(1S*,2R*,4S*)-2-fluoro-4-[(methoxyacetyl)amino]cyclohexyl}-6-methyl-5H-pyrrolo[3,2-d]pyrimidine-7-carboxamide |
| P575 | 4-[2-(Cyclopropylmethoxy)-5-methylphenyl]-N-{(1S*,2R*,4S*)-2-fluoro-4-[(hydroxyacetyl)amino]cyclohexyl}-6-methyl-5H-pyrrolo[3,2-d]pyrimidine-7-carboxamide |
| P576 | 4-[2-(Cyclopropylmethoxy)-5-methylphenyl]-N-[(1S*,2R*,4S*)-2-fluoro-4-{[(2S)-2-hydroxypropanoyl]amino}cyclohexyl]-6-methyl-5H-pyrrolo[3,2-d]pyrimidine-7-carboxamide |
| P577 | N-[(1S*,2R*,4R*)-4-(Acetylamino)-2-fluorocyclohexyl]-4-[2-(cyclopropylmethoxy)-5-methylphenyl]-6-methyl-5H-pyrrolo[3,2-d]pyrimidine-7-carboxamide |
| P578 | 4-[2-(Cyclopropylmethoxy)-5-methylphenyl]-N-[(1S*,2R*,4R*)-2-fluoro-4-(propanoylamino)cyclohexyl]-6-methyl-5H-pyrrolo[3,2-d]pyrimidine-7-carboxamide |
| P579 | 4-[2-(Cyclopropylmethoxy)-5-methylphenyl]-N-{(1S*,2R*,4R*)-2-fluoro-4-[(methoxyacetyl)amino]cyclohexyl}-6-methyl-5H-pyrrolo[3,2-d]pyrimidine-7-carboxamide |
| P580 | 4-[2-(Cyclopropylmethoxy)-5-methylphenyl]-N-{(1S*,2R*,4R*)-2-fluoro-4-[(hydroxyacetyl)amino]cyclohexyl}-6-methyl-5H-pyrrolo[3,2-d]pyrimidine-7-carboxamide |
| P581 | 4-[2-(Cyclopropylmethoxy)-5-methylphenyl]-N-[(1S*,2R*,4R*)-2-fluoro-4-{[(2S)-2-hydroxypropanoyl]amino}cyclohexyl]-6-methyl-5H-pyrrolo[3,2-d]pyrimidine-7-carboxamide |
| P582 | N-[(1S*,3R*,4S*)-4-(acetylamino)-3-methylcyclohexyl]-4-[2-(cyclopropylmethoxy)-5-methylphenyl]-6-methyl-5H-pyrrolo[3,2-d]pyrimidine-7-carboxamide |
| P583 | 4-[2-(Cyclopropylmethoxy)-5-methylphenyl]-6-methyl-N-[(1S*,3R*,4S*)-3-methyl-4-(propanoylamino)cyclohexyl]-5H-pyrrolo[3,2-d]pyrimidine-7-carboxamide |
| P584 | 4-[2-(Cyclopropylmethoxy)-5-methylphenyl]-N-{(1S*,3R*,4S*)-4-[(methoxyacetyl)amino]-3-methylcyclohexyl}-6-methyl-5H-pyrrolo[3,2-d]pyrimidine-7-carboxamide |
| P585 | 4-[2-(Cyclopropylmethoxy)-5-methylphenyl]-N-{(1S*,3R*,4S*)-4-[(hydroxyacetyl)amino]-3-methylcyclohexyl}-6-methyl-5H-pyrrolo[3,2-d]pyrimidine-7-carboxamide |
| P586 | 4-[2-(Cyclopropylmethoxy)-5-methylphenyl]-N-[(1S*,3R*,4S*)-4-{[(2S)-2-hydroxypropanoyl]amino}-3-methylcyclohexyl]-6-methyl-5H-pyrrolo[3,2-d]pyrimidine-7-carboxamide |
| P587 | N-[(1S*,3R*,4R*)-4-(Acetylamino)-3-methylcyclohexyl]-4-[2-(cyclopropylmethoxy)-5-methylphenyl]-6-methyl-5H-pyrrolo[3,2-d]pyrimidine-7-carboxamide |
| P588 | 4-[2-(Cyclopropylmethoxy)-5-methylphenyl]-6-methyl-N-[(1S*,3R*,4R*)-3-methyl-4-(propanoylamino)cyclohexyl]-5H-pyrrolo[3,2-d]pyrimidine-7-carboxamide |
| P589 | 4-[2-(Cyclopropylmethoxy)-5-methylphenyl]-N-{(1S*,3R*,4R*)-4-[(methoxyacetyl)amino]-3-methylcyclohexyl}-6-methyl-5H-pyrrolo[3,2-d]pyrimidine-7-carboxamide |
| P590 | 4-[2-(Cyclopropylmethoxy)-5-methylphenyl]-N-{(1S*,3R*,4R*)-4-[(hydroxyacetyl)amino]-3-methylcyclohexyl}-6-methyl-5H-pyrrolo[3,2-d]pyrimidine-7-carboxamide |
| P591 | 4-[2-(Cyclopropylmethoxy)-5-methylphenyl]-N-[(1S*,3R*,4R*)-4-{[(2S)-2-hydroxypropanoyl]amino}-3-methylcyclohexyl]-6-methyl-5H-pyrrolo[3,2-d]pyrimidine-7-carboxamide |
| P592 | N-[(1R*,3R*,4R*)-4-(acetylamino)-3-methylcyclohexyl]-4-[2-(cyclopropylmethoxy)-5-methylphenyl]-6-methyl-5H-pyrrolo[3,2-d]pyrimidine-7-carboxamide |
| P593 | 4-[2-(Cyclopropylmethoxy)-5-methylphenyl]-6-methyl-N-[(1R*,3R*,4R*)-3-methyl-4-(propanoylamino)cyclohexyl]-5H-pyrrolo[3,2-d]pyrimidine-7-carboxamide |
| P594 | 4-[2-(Cyclopropylmethoxy)-5-methylphenyl]-N-{(1R*,3R*,4R*)-4-[(methoxyacetyl)amino]-3-methylcyclohexyl}-6-methyl-5H-pyrrolo[3,2-d]pyrimidine-7-carboxamide |
| P595 | 4-[2-(Cyclopropylmethoxy)-5-methylphenyl]-N-{(1R*,3R*,4R*)-4-[(hydroxyacetyl)amino]-3-methylcyclohexyl}-6-methyl-5H-pyrrolo[3,2-d]pyrimidine-7-carboxamide |
| P596 | 4-[2-(Cyclopropylmethoxy)-5-methylphenyl]-N-[(1R*,3R*,4R*)-4-{[(2S)-2-hydroxypropanoyl]amino}-3-methylcyclohexyl]-6-methyl-5H-pyrrolo[3,2-d]pyrimidine-7-carboxamide |
| P597 | N-[(1R*,3R*,4S*)-4-(Acetylamino)-3-methylcyclohexyl]-4-[2-(cyclopropylmethoxy)-5-methylphenyl]-6-methyl-5H-pyrrolo[3,2-d]pyrimidine-7-carboxamide |
| P598 | 4-[2-(Cyclopropylmethoxy)-5-methylphenyl]-6-methyl-N-[(1R*,3R*,4S*)-3-methyl-4-(propanoylamino)cyclohexyl]-5H-pyrrolo[3,2-d]pyrimidine-7-carboxamide |
| P599 | 4-[2-(Cyclopropylmethoxy)-5-methylphenyl]-N-{(1R*,3R*,4S*)-4-[(methoxyacetyl)amino]-3-methylcyclohexyl}-6-methyl-5H-pyrrolo[3,2-d]pyrimidine-7-carboxamide |
| P600 | 4-[2-(Cyclopropylmethoxy)-5-methylphenyl]-N-{(1R*,3R*,4S*)-4-[(hydroxyacetyl)amino]-3-methylcyclohexyl}-6-methyl-5H-pyrrolo[3,2-d]pyrimidine-7-carboxamide |
| P601 | 4-[2-(Cyclopropylmethoxy)-5-methylphenyl]-N-[(1R*,3R*,4S*)-4-{[(2S)-2-hydroxypropanoyl]amino}-3-methylcyclohexyl]-6-methyl-5H-pyrrolo[3,2-d]pyrimidine-7-carboxamide |
| P602 | N-[(1S*,3R*,4S*)-4-(acetylamino)-3-fluorocyclohexyl]-4-[2-(cyclopropylmethoxy)-5-methylphenyl]-6-methyl-5H-pyrrolo[3,2-d]pyrimidine-7-carboxamide |
| P603 | 4-[2-(Cyclopropylmethoxy)-5-methylphenyl]-N-[(1S*,3R*,4S*)-3-fluoro-4-(propanoylamino)cyclohexyl]-6-methyl-5H-pyrrolo[3,2-d]pyrimidine-7-carboxamide |
| P604 | 4-[2-(Cyclopropylmethoxy)-5-methylphenyl]-N-{(1S*,3R*,4S*)-3-fluoro-4-[(methoxyacetyl)amino]cyclohexyl}-6-methyl-5H-pyrrolo[3,2-d]pyrimidine-7-carboxamide |
| P605 | 4-[2-(Cyclopropylmethoxy)-5-methylphenyl]-N-{(1S*,3R*,4S*)-3-fluoro-4-[(hydroxyacetyl)amino]cyclohexyl}-6-methyl-5H-pyrrolo[3,2-d]pyrimidine-7-carboxamide |

| | -continued |
|---|---|
| P606 | 4-[2-(Cyclopropylmethoxy)-5-methylphenyl]-N-[(1S*,3R*,4S*)-3-fluoro-4-{[(2S)-2-hydroxypropanoyl]amino}cyclohexyl]-6-methyl-5H-pyrrolo[3,2-d]pyrimidine-7-carboxamide |
| P607 | N-[(1S*,3R*,4R*)-4-(acetylamino)-3-fluorocyclohexyl]-4-[2-(cyclopropylmethoxy)-5-methylphenyl]-6-methyl-5H-pyrrolo[3,2-d]pyrimidine-7-carboxamide |
| P608 | 4-[2-(Cyclopropylmethoxy)-5-methylphenyl]-N-[(1S*,3R*,4R*)-3-fluoro-4-(propanoylamino)cyclohexyl]-6-methyl-5H-pyrrolo[3,2-d]pyrimidine-7-carboxamide |
| P609 | 4-[2-(Cyclopropylmethoxy)-5-methylphenyl]-N-{(1S*,3R*,4R*)-3-fluoro-4-[(methoxyacetyl)amino]cyclohexyl}-6-methyl-5H-pyrrolo[3,2-d]pyrimidine-7-carboxamide |
| P610 | 4-[2-(Cyclopropylmethoxy)-5-methylphenyl]-N-{(1S*,3R*,4R*)-3-fluoro-4-[(hydroxyacetyl)amino]cyclohexyl}-6-methyl-5H-pyrrolo[3,2-d]pyrimidine-7-carboxamide |
| P611 | 4-[2-(cyclopropylmethoxy)-5-methylphenyl]-N-[(1S*,3R*,4R*)-3-fluoro-4-{[(2S)-2-hydroxypropanoyl]amino}cyclohexyl]-6-methyl-5H-pyrrolo[3,2-d]pyrimidine-7-carboxamide |
| P612 | N-[(1R*,3R*,4R*)-4-(Acetylamino)-3-fluorocyclohexyl]-4-[2-(cyclopropylmethoxy)-5-methylphenyl]-6-methyl-5H-pyrrolo[3,2-d]pyrimidine-7-carboxamide |
| P613 | 4-[2-(Cyclopropylmethoxy)-5-methylphenyl]-N-[(1R*,3R*,4R*)-3-fluoro-4-(propanoylamino)cyclohexyl]-6-methyl-5H-pyrrolo[3,2-d]pyrimidine-7-carboxamide |
| P614 | 4-[2-(Cyclopropylmethoxy)-5-methylphenyl]-N-{(1R*,3R*,4R*)-3-fluoro-4-[(methoxyacetyl)amino]cyclohexyl}-6-methyl-5H-pyrrolo[3,2-d]pyrimidine-7-carboxamide |
| P615 | 4-[2-(Cyclopropylmethoxy)-5-methylphenyl]-N-{(1R*,3R*,4R*)-3-fluoro-4-[(hydroxyacetyl)amino]cyclohexyl}-6-methyl-5H-pyrrolo[3,2-d]pyrimidine-7-carboxamide |
| P616 | 4-[2-(Cyclopropylmethoxy)-5-methylphenyl]-N-[(1R*,3R*,4R*)-3-fluoro-4-{[(2S)-2-hydroxypropanoyl]amino}cyclohexyl]-6-methyl-5H-pyrrolo[3,2-d]pyrimidine-7-carboxamide |
| P617 | N-[(1R*,3R*,4S*)-4-(Acetylamino)-3-fluorocyclohexyl]-4-[2-(cyclopropylmethoxy)-5-methylphenyl]-6-methyl-5H-pyrrolo[3,2-d]pyrimidine-7-carboxamide |
| P618 | 4-[2-(Cyclopropylmethoxy)-5-methylphenyl]-N-[(1R*,3R*,4S*)-3-fluoro-4-(propanoylamino)cyclohexyl]-6-methyl-5H-pyrrolo[3,2-d]pyrimidine-7-carboxamide |
| P619 | 4-[2-(Cyclopropylmethoxy)-5-methylphenyl]-N-{(1R*,3R*,4S*)-3-fluoro-4-[(methoxyacetyl)amino]cyclohexyl}-6-methyl-5H-pyrrolo[3,2-d]pyrimidine-7-carboxamide |
| P620 | 4-[2-(Cyclopropylmethoxy)-5-methylphenyl]-N-{(1R*,3R*,4S*)-3-fluoro-4-[(hydroxyacetyl)amino]cyclohexyl}-6-methyl-5H-pyrrolo[3,2-d]pyrimidine-7-carboxamide |
| P621 | 4-[2-(Cyclopropylmethoxy)-5-methylphenyl]-N-[(1R*,3R*,4S*)-3-fluoro-4-{[(2S)-2-hydroxypropanoyl]amino}cyclohexyl]-6-methyl-5H-pyrrolo[3,2-d]pyrimidine-7-carboxamide |
| P622 | 4-[2-(Cyclopropylmethoxy)-5-(trifluoromethyl)phenyl]-N-[(1R,3S)-3-hydroxycyclopentyl]-6-methyl-5H-pyrrolo[3,2-d]pyrimidine-7-carboxamide |
| P623 | 4-[2-(Cyclopropylmethoxy)-5-(trifluoromethyl)phenyl]-N-[(1R,3R)-3-hydroxycyclopentyl]-6-methyl-5H-pyrrolo[3,2-d]pyrimidine-7-carboxamide |
| P624 | 4-[2-(Cyclopropylmethoxy)-5-(trifluoromethyl)phenyl]-N-[(1S,3S)-3-hydroxycyclopentyl]-6-methyl-5H-pyrrolo[3,2-d]pyrimidine-7-carboxamide |
| P625 | 4-[2-(Cyclopropylmethoxy)-5-(trifluoromethyl)phenyl]-N-[(1S,3R)-3-hydroxycyclopentyl]-6-methyl-5H-pyrrolo[3,2-d]pyrimidine-7-carboxamide |
| P627 | 4-[2-(Cyclopropylmethoxy)-5-(trifluoromethyl)phenyl]-N-[(1R,2S)-2-hydroxycyclopentyl]-6-methyl-5H-pyrrolo[3,2-d]pyrimidine-7-carboxamide |
| P628 | 4-[2-(Cyclopropylmethoxy)-5-(trifluoromethyl)phenyl]-N-[(1R,2R)-2-hydroxycyclopentyl]-6-methyl-5H-pyrrolo[3,2-d]pyrimidine-7-carboxamide |
| P629 | 4-[2-(Cyclopropylmethoxy)-5-(trifluoromethyl)phenyl]-N-[(1S,2S)-2-hydroxycyclopentyl]-6-methyl-5H-pyrrolo[3,2-d]pyrimidine-7-carboxamide |
| P630 | 4-[2-(Cyclopropylmethoxy)-5-(trifluoromethyl)phenyl]-N-[(1S,2R)-2-hydroxycyclopentyl]-6-methyl-5H-pyrrolo[3,2-d]pyrimidine-7-carboxamide |
| P631 | N-[(3S,5S)-1-Acetyl-5-methylpyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P632 | 4-[2-(Cyclopropylmethoxy)-5-(trifluoromethyl)phenyl]-6-methyl-N-[(3S,5S)-5-methyl-1-propanoylpyrrolidin-3-yl]-5H-pyrrolo[3,2-d]pyrimidine-7-carboxamide |
| P633 | 4-[2-(Cyclopropylmethoxy)-5-(trifluoromethyl)phenyl]-N-[(3S,5S)-1-(methoxyacetyl)-5-methylpyrrolidin-3-yl]-6-methyl-5H-pyrrolo[3,2-d]pyrimidine-7-carboxamide |
| P634 | 4-[2-(Cyclopropylmethoxy)-5-(trifluoromethyl)phenyl]-N-[(3S,5S)-1-(hydroxyacetyl)-5-methylpyrrolidin-3-yl]-6-methyl-5H-pyrrolo[3,2-d]pyrimidine-7-carboxamide |
| P635 | 4-[2-(Cyclopropylmethoxy)-5-(trifluoromethyl)phenyl]-N-{(3S,5S)-1-[(2S)-2-hydroxypropanoyl]-5-methylpyrrolidin-3-yl}-6-methyl-5H-pyrrolo[3,2-d]pyrimidine-7-carboxamide |
| P636 | N-[(3S,5R)-1-Acetyl-5-methylpyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P637 | 4-[2-(Cyclopropylmethoxy)-5-(trifluoromethyl)phenyl]-6-methyl-N-[(3S,5R)-5-methyl-1-propanoylpyrrolidin-3-yl]-5H-pyrrolo[3,2-d]pyrimidine-7-carboxamide |
| P638 | 4-[2-(Cyclopropylmethoxy)-5-(trifluoromethyl)phenyl]-N-[(3S,5R)-1-(methoxyacetyl)-5-methylpyrrolidin-3-yl]-6-methyl-5H-pyrrolo[3,2-d]pyrimidine-7-carboxamide |
| P639 | 4-[2-(Cyclopropylmethoxy)-5-(trifluoromethyl)phenyl]-N-[(3S,5R)-1-(hydroxyacetyl)-5-methylpyrrolidin-3-yl]-6-methyl-5H-pyrrolo[3,2-d]pyrimidine-7-carboxamide |
| P640 | 4-[2-(Cyclopropylmethoxy)-5-(trifluoromethyl)phenyl]-N-{(3S,5R)-1-[(2S)-2-hydroxypropanoyl]-5-methylpyrrolidin-3-yl}-6-methyl-5H-pyrrolo[3,2-d]pyrimidine-7-carboxamide |
| P641 | N-[(3R,5R)-1-Acetyl-5-methylpyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P642 | 4-[2-(Cyclopropylmethoxy)-5-(trifluoromethyl)phenyl]-6-methyl-N-[(3R,5R)-5-methyl-1-propanoylpyrrolidin-3-yl]-5H-pyrrolo[3,2-d]pyrimidine-7-carboxamide |
| P643 | 4-[2-(Cyclopropylmethoxy)-5-(trifluoromethyl)phenyl]-N-[(3R,5R)-1-(methoxyacetyl)-5-methylpyrrolidin-3-yl]-6-methyl-5H-pyrrolo[3,2-d]pyrimidine-7-carboxamide |
| P644 | 4-[2-(Cyclopropylmethoxy)-5-(trifluoromethyl)phenyl]-N-[(3R,5R)-1-(hydroxyacetyl)-5-methylpyrrolidin-3-yl]-6-methyl-5H-pyrrolo[3,2-d]pyrimidine-7-carboxamide |
| P645 | 4-[2-(Cyclopropylmethoxy)-5-(trifluoromethyl)phenyl]-N-{(3R,5R)-1-[(2S)-2-hydroxypropanoyl]-5-methylpyrrolidin-3-yl}-6-methyl-5H-pyrrolo[3,2-d]pyrimidine-7-carboxamide |

| | -continued |
|---|---|
| P646 | N-[(3R,5S)-1-Acetyl-5-methylpyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P647 | 4-[2-(Cyclopropylmethoxy)-5-(trifluoromethyl)phenyl]-6-methyl-N-[(3R,5S)-5-methyl-1-propanoylpyrrolidin-3-yl]-5H-pyrrolo[3,2-d]pyrimidine-7-carboxamide |
| P648 | 4-[2-(Cyclopropylmethoxy)-5-(trifluoromethyl)phenyl]-N-[(3R,5S)-1-(methoxyacetyl)-5-methylpyrrolidin-3-yl]-6-methyl-5H-pyrrolo[3,2-d]pyrimidine-7-carboxamide |
| P649 | 4-[2-(Cyclopropylmethoxy)-5-(trifluoromethyl)phenyl]-N-[(3R,5S)-1-(hydroxyacetyl)-5-methylpyrrolidin-3-yl]-6-methyl-5H-pyrrolo[3,2-d]pyrimidine-7-carboxamide |
| P650 | 4-[2-(Cyclopropylmethoxy)-5-(trifluoromethyl)phenyl]-N-{(3R,5S)-1-[(2S)-2-hydroxypropanoyl]-5-methylpyrrolidin-3-yl}-6-methyl-5H-pyrrolo[3,2-d]pyrimidine-7-carboxamide |
| P651 | N-[(3S,4S)-1-Acetyl-4-fluoropyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P652 | 4-[2-(Cyclopropylmethoxy)-5-(trifluoromethyl)phenyl]-N-[(3S,4S)-4-fluoro-1-propanoylpyrrolidin-3-yl]-6-methyl-5H-pyrrolo[3,2-d]pyrimidine-7-carboxamide |
| P653 | 4-[2-(Cyclopropylmethoxy)-5-(trifluoromethyl)phenyl]-N-[(3S,4S)-4-fluoro-1-(methoxyacetyl)pyrrolidin-3-yl]-6-methyl-5H-pyrrolo[3,2-d]pyrimidine-7-carboxamide |
| P654 | 4-[2-(Cyclopropylmethoxy)-5-(trifluoromethyl)phenyl]-N-[(3S,4S)-4-fluoro-1-(hydroxyacetyl)pyrrolidin-3-yl]-6-methyl-5H-pyrrolo[3,2-d]pyrimidine-7-carboxamide |
| P655 | 4-[2-(Cyclopropylmethoxy)-5-(trifluoromethyl)phenyl]-N-{(3S,4S)-4-fluoro-1-[(2S)-2-hydroxypropanoyl]pyrrolidin-3-yl}-6-methyl-5H-pyrrolo[3,2-d]pyrimidine-7-carboxamide |
| P656 | N-[(3R,4S)-1-Acetyl-4-fluoropyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P657 | 4-[2-(Cyclopropylmethoxy)-5-(trifluoromethyl)phenyl]-N-[(3R,4S)-4-fluoro-1-propanoylpyrrolidin-3-yl]-6-methyl-5H-pyrrolo[3,2-d]pyrimidine-7-carboxamide |
| P658 | 4-[2-(Cyclopropylmethoxy)-5-(trifluoromethyl)phenyl]-N-[(3R,4S)-4-fluoro-1-(methoxyacetyl)pyrrolidin-3-yl]-6-methyl-5H-pyrrolo[3,2-d]pyrimidine-7-carboxamide |
| P659 | 4-[2-(Cyclopropylmethoxy)-5-(trifluoromethyl)phenyl]-N-[(3R,4S)-4-fluoro-1-(hydroxyacetyl)pyrrolidin-3-yl]-6-methyl-5H-pyrrolo[3,2-d]pyrimidine-7-carboxamide |
| P660 | 4-[2-(Cyclopropylmethoxy)-5-(trifluoromethyl)phenyl]-N-{(3R,4S)-4-fluoro-1-[(2S)-2-hydroxypropanoyl]pyrrolidin-3-yl}-6-methyl-5H-pyrrolo[3,2-d]pyrimidine-7-carboxamide |
| P661 | N-[(3R,4R)-1-Acetyl-4-fluoropyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P662 | 4-[2-(Cyclopropylmethoxy)-5-(trifluoromethyl)phenyl]-N-[(3R,4R)-4-fluoro-1-propanoylpyrrolidin-3-yl]-6-methyl-5H-pyrrolo[3,2-d]pyrimidine-7-carboxamide |
| P663 | 4-[2-(Cyclopropylmethoxy)-5-(trifluoromethyl)phenyl]-N-[(3R,4R)-4-fluoro-1-(methoxyacetyl)pyrrolidin-3-yl]-6-methyl-5H-pyrrolo[3,2-d]pyrimidine-7-carboxamide |
| P664 | 4-[2-(Cyclopropylmethoxy)-5-(trifluoromethyl)phenyl]-N-[(3R,4R)-4-fluoro-1-(hydroxyacetyl)pyrrolidin-3-yl]-6-methyl-5H-pyrrolo[3,2-d]pyrimidine-7-carboxamide |
| P665 | 4-[2-(Cyclopropylmethoxy)-5-(trifluoromethyl)phenyl]-N-{(3R,4R)-4-fluoro-1-[(2S)-2-hydroxypropanoyl]pyrrolidin-3-yl}-6-methyl-5H-pyrrolo[3,2-d]pyrimidine-7-carboxamide |
| P666 | N-[(3S,4R)-1-Acetyl-4-fluoropyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P667 | 4-[2-(Cyclopropylmethoxy)-5-(trifluoromethyl)phenyl]-N-[(3S,4R)-4-fluoro-1-propanoylpyrrolidin-3-yl]-6-methyl-5H-pyrrolo[3,2-d]pyrimidine-7-carboxamide |
| P668 | 4-[2-(Cyclopropylmethoxy)-5-(trifluoromethyl)phenyl]-N-[(3S,4R)-4-fluoro-1-(methoxyacetyl)pyrrolidin-3-yl]-6-methyl-5H-pyrrolo[3,2-d]pyrimidine-7-carboxamide |
| P669 | 4-[2-(Cyclopropylmethoxy)-5-(trifluoromethyl)phenyl]-N-[(3S,4R)-4-fluoro-1-(hydroxyacetyl)pyrrolidin-3-yl]-6-methyl-5H-pyrrolo[3,2-d]pyrimidine-7-carboxamide |
| P670 | 4-[2-(Cyclopropylmethoxy)-5-(trifluoromethyl)phenyl]-N-{(3S,4R)-4-fluoro-1-[(2S)-2-hydroxypropanoyl]pyrrolidin-3-yl}-6-methyl-5H-pyrrolo[3,2-d]pyrimidine-7-carboxamide |
| P671 | N-[(3S*,4R*)-1-Acetyl-4-methylpyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P672 | 4-[2-(Cyclopropylmethoxy)-5-(trifluoromethyl)phenyl]-6-methyl-N-[(3S*,4R*)-4-methyl-1-propanoylpyrrolidin-3-yl]-5H-pyrrolo[3,2-d]pyrimidine-7-carboxamide |
| P673 | 4-[2-(Cyclopropylmethoxy)-5-(trifluoromethyl)phenyl]-N-[(3S*,4R*)-1-(methoxyacetyl)-4-methylpyrrolidin-3-yl]-6-methyl-5H-pyrrolo[3,2-d]pyrimidine-7-carboxamide |
| P674 | 4-[2-(Cyclopropylmethoxy)-5-(trifluoromethyl)phenyl]-N-[(3S*,4R*)-1-(hydroxyacetyl)-4-methylpyrrolidin-3-yl]-6-methyl-5H-pyrrolo[3,2-d]pyrimidine-7-carboxamide |
| P675 | 4-[2-(Cyclopropylmethoxy)-5-(trifluoromethyl)phenyl]-N-{(3S*,4R*)-1-[(2S)-2-hydroxypropanoyl]-4-methylpyrrolidin-3-yl}-6-methyl-5H-pyrrolo[3,2-d]pyrimidine-7-carboxamide |
| P676 | N-[(3S*,4S*)-1-Acetyl-4-methylpyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P677 | 4-[2-(Cyclopropylmethoxy)-5-(trifluoromethyl)phenyl]-6-methyl-N-[(3S*,4S*)-4-methyl-1-propanoylpyrrolidin-3-yl]-5H-pyrrolo[3,2-d]pyrimidine-7-carboxamide |
| P678 | 4-[2-(Cyclopropylmethoxy)-5-(trifluoromethyl)phenyl]-N-[(3S*,4S*)-1-(methoxyacetyl)-4-methylpyrrolidin-3-yl]-6-methyl-5H-pyrrolo[3,2-d]pyrimidine-7-carboxamide |
| P679 | 4-[2-(Cyclopropylmethoxy)-5-(trifluoromethyl)phenyl]-N-[(3S*,4S*)-1-(hydroxyacetyl)-4-methylpyrrolidin-3-yl]-6-methyl-5H-pyrrolo[3,2-d]pyrimidine-7-carboxamide |
| P680 | 4-[2-(Cyclopropylmethoxy)-5-(trifluoromethyl)phenyl]-N-{(3S*,4S*)-1-[(2S)-2-hydroxypropanoyl]-4-methylpyrrolidin-3-yl}-6-methyl-5H-pyrrolo[3,2-d]pyrimidine-7-carboxamide |
| P681 | N-[(3S*)-1-Acetyl-4,4-dimethylpyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P682 | 4-[2-(Cyclopropylmethoxy)-5-(trifluoromethyl)phenyl]-N-[(3S*)-4,4-dimethyl-1-propanoylpyrrolidin-3-yl]-6-methyl-5H-pyrrolo[3,2-d]pyrimidine-7-carboxamide |
| P683 | 4-[2-(Cyclopropylmethoxy)-5-(trifluoromethyl)phenyl]-N-[(3S*)-1-(methoxyacetyl)-4,4-dimethylpyrrolidin-3-yl]-6-methyl-5H-pyrrolo[3,2-d]pyrimidine-7-carboxamide |
| P684 | 4-[2-(Cyclopropylmethoxy)-5-(trifluoromethyl)phenyl]-N-[(3S*)-1-(hydroxyacetyl)-4,4-dimethylpyrrolidin-3-yl]-6-methyl-5H-pyrrolo[3,2-d]pyrimidine-7-carboxamide |

-continued

| | |
|---|---|
| P685 | 4-[2-(Cyclopropylmethoxy)-5-(trifluoromethyl)phenyl]-N-{(3S*)-1-[(2S)-2-hydroxypropanoyl]-4,4-dimethylpyrrolidin-3-yl}-6-methyl-5H-pyrrolo[3,2-d]pyrimidine-7-carboxamide |
| P686 | N-[(7S*)-5-Acetyl-5-azaspiro[2.4]hept-7-yl]-4-[2-(cyclopropylmethoxy)-5-(trifluoromethyl)phenyl]-6-methyl-5H-pyrrolo[3,2-d]pyrimidine-7-carboxamide |
| P687 | 4-[2-(Cyclopropylmethoxy)-5-(trifluoromethyl)phenyl]-6-methyl-N-[(7S*)-5-propanoyl-5-azaspiro[2.4]hept-7-yl]-5H-pyrrolo[3,2-d]pyrimidine-7-carboxamide |
| P688 | 4-[2-(Cyclopropylmethoxy)-5-(trifluoromethyl)phenyl]-N-[(7S*)-5-(methoxyacetyl)-5-azaspiro[2.4]hept-7-yl]-6-methyl-5H-pyrrolo[3,2-d]pyrimidine-7-carboxamide |
| P689 | 4-[2-(Cyclopropylmethoxy)-5-(trifluoromethyl)phenyl]-N-[(7S*)-5-(hydroxyacetyl)-5-azaspiro[2.4]hept-7-yl]-6-methyl-5H-pyrrolo[3,2-d]pyrimidine-7-carboxamide |
| P690 | 4-[2-(Cyclopropylmethoxy)-5-(trifluoromethyl)phenyl]-N-{(7S*)-5-[(2S)-2-hydroxypropanoyl]-5-azaspiro[2.4]hept-7-yl}-6-methyl-5H-pyrrolo[3,2-d]pyrimidine-7-carboxamide |
| P691 | N-[(3R*)-1-Acetyl-4,4-difluoropyrrolidin-3-yl]-4-[2-(cyclopropylmethoxy)-5-(trifluoromethyl)phenyl]-6-methyl-5H-pyrrolo[3,2-d]pyrimidine-7-carboxamide |
| P692 | 4-[2-(Cyclopropylmethoxy)-5-(trifluoromethyl)phenyl]-N-[(3R*)-4,4-difluoro-1-propanoylpyrrolidin-3-yl]-6-methyl-5H-pyrrolo[3,2-d]pyrimidine-7-carboxamide |
| P693 | 4-[2-(Cyclopropylmethoxy)-5-(trifluoromethyl)phenyl]-N-[(3R*)-4,4-difluoro-1-(methoxyacetyl)pyrrolidin-3-yl]-6-methyl-5H-pyrrolo[3,2-d]pyrimidine-7-carboxamide |
| P694 | 4-[2-(Cyclopropylmethoxy)-5-(trifluoromethyl)phenyl]-N-[(3R*)-4,4-difluoro-1-(hydroxyacetyl)pyrrolidin-3-yl]-6-methyl-5H-pyrrolo[3,2-d]pyrimidine-7-carboxamide |
| P695 | 4-[2-(Cyclopropylmethoxy)-5-(trifluoromethyl)phenyl]-N-{(3R*)-4,4-difluoro-1-[(2S)-2-hydroxypropanoyl]pyrrolidin-3-yl}-6-methyl-5H-pyrrolo[3,2-d]pyrimidine-7-carboxamide |
| P696 | N-[(1S*,3S*)-3-(Acetylamino)cyclopentyl]-4-[2-(cyclopropylmethoxy)-5-(trifluoromethyl)phenyl]-6-methyl-5H-pyrrolo[3,2-d]pyrimidine-7-carboxamide |
| P697 | 4-[2-(Cyclopropylmethoxy)-5-(trifluoromethyl)phenyl]-6-methyl-N-[(1S*,3S*)-3-(propanoylamino)cyclopentyl]-5H-pyrrolo[3,2-d]pyrimidine-7-carboxamide |
| P698 | 4-[2-(Cyclopropylmethoxy)-5-(trifluoromethyl)phenyl]-N-{(1S*,3S*)-3-[(methoxyacetyl)amino]cyclopentyl}-6-methyl-5H-pyrrolo[3,2-d]pyrimidine-7-carboxamide |
| P699 | 4-[2-(Cyclopropylmethoxy)-5-(trifluoromethyl)phenyl]-N-{(1S*,3S*)-3-[(hydroxyacetyl)amino]cyclopentyl}-6-methyl-5H-pyrrolo[3,2-d]pyrimidine-7-carboxamide |
| P700 | 4-[2-(Cyclopropylmethoxy)-5-(trifluoromethyl)phenyl]-N-[(1S*,3S*)-3-{[(2S)-2-hydroxypropanoyl]amino}cyclopentyl]-6-methyl-5H-pyrrolo[3,2-d]pyrimidine-7-carboxamide |
| P701 | N-[(1S*,3R*)-3-(Acetylamino)cyclopentyl]-4-[2-(cyclopropylmethoxy)-5-(trifluoromethyl)phenyl]-6-methyl-5H-pyrrolo[3,2-d]pyrimidine-7-carboxamide |
| P702 | 4-[2-(Cyclopropylmethoxy)-5-(trifluoromethyl)phenyl]-6-methyl-N-[(1S*,3R*)-3-(propanoylamino)cyclopentyl]-5H-pyrrolo[3,2-d]pyrimidine-7-carboxamide |
| P703 | 4-[2-(Cyclopropylmethoxy)-5-(trifluoromethyl)phenyl]-N-{(1S*,3R*)-3-[(methoxyacetyl)amino]cyclopentyl}-6-methyl-5H-pyrrolo[3,2-d]pyrimidine-7-carboxamide |
| P704 | 4-[2-(Cyclopropylmethoxy)-5-(trifluoromethyl)phenyl]-N-{(1S*,3R*)-3-[(hydroxyacetyl)amino]cyclopentyl}-6-methyl-5H-pyrrolo[3,2-d]pyrimidine-7-carboxamide |
| P705 | 4-[2-(Cyclopropylmethoxy)-5-(trifluoromethyl)phenyl]-N-[(1S*,3R*)-3-{[(2S)-2-hydroxypropanoyl]amino}cyclopentyl]-6-methyl-5H-pyrrolo[3,2-d]pyrimidine-7-carboxamide |
| P706 | N-[(1R*,2R*,4R*)-4-(Acetylamino)-2-fluorocyclopentyl]-4-[2-(cyclopropylmethoxy)-5-(trifluoromethyl)phenyl]-6-methyl-5H-pyrrolo[3,2-d]pyrimidine-7-carboxamide |
| P707 | 4-[2-(Cyclopropylmethoxy)-5-(trifluoromethyl)phenyl]-N-[(1R*,2R*,4R*)-2-fluoro-4-(propanoylamino)cyclopentyl]-6-methyl-5H-pyrrolo[3,2-d]pyrimidine-7-carboxamide |
| P708 | 4-[2-(Cyclopropylmethoxy)-5-(trifluoromethyl)phenyl]-N-{(1R*,2R*,4R*)-2-fluoro-4-[(methoxyacetyl)amino]cyclopentyl}-6-methyl-5H-pyrrolo[3,2-d]pyrimidine-7-carboxamide |
| P709 | 4-[2-(Cyclopropylmethoxy)-5-(trifluoromethyl)phenyl]-N-{(1R*,2R*,4R*)-2-fluoro-4-[(hydroxyacetyl)amino]cyclopentyl}-6-methyl-5H-pyrrolo[3,2-d]pyrimidine-7-carboxamide |
| P710 | 4-[2-(Cyclopropylmethoxy)-5-(trifluoromethyl)phenyl]-N-[(1R*,2R*,4R*)-2-fluoro-4-{[(2S)-2-hydroxypropanoyl]amino}cyclopentyl]-6-methyl-5H-pyrrolo[3,2-d]pyrimidine-7-carboxamide |
| P711 | N-[(1R*,2R*,4S*)-4-(Acetylamino)-2-fluorocyclopentyl]-4-[2-(cyclopropylmethoxy)-5-(trifluoromethyl)phenyl]-6-methyl-5H-pyrrolo[3,2-d]pyrimidine-7-carboxamide |
| P712 | 4-[2-(Cyclopropylmethoxy)-5-(trifluoromethyl)phenyl]-N-[(1R*,2R*,4S*)-2-fluoro-4-(propanoylamino)cyclopentyl]-6-methyl-5H-pyrrolo[3,2-d]pyrimidine-7-carboxamide |
| P713 | 4-[2-(Cyclopropylmethoxy)-5-(trifluoromethyl)phenyl]-N-{(1R*,2R*,4S*)-2-fluoro-4-[(methoxyacetyl)amino]cyclopentyl}-6-methyl-5H-pyrrolo[3,2-d]pyrimidine-7-carboxamide |
| P714 | 4-[2-(Cyclopropylmethoxy)-5-(trifluoromethyl)phenyl]-N-{(1R*,2R*,4S*)-2-fluoro-4-[(hydroxyacetyl)amino]cyclopentyl}-6-methyl-5H-pyrrolo[3,2-d]pyrimidine-7-carboxamide |
| P715 | 4-[2-(Cyclopropylmethoxy)-5-(trifluoromethyl)phenyl]-N-[(1R*,2R*,4S*)-2-fluoro-4-{[(2S)-2-hydroxypropanoyl]amino}cyclopentyl]-6-methyl-5H-pyrrolo[3,2-d]pyrimidine-7-carboxamide |
| P716 | 4-[2-(Cyclopropylmethoxy)-5-(trifluoromethyl)phenyl]-N-[(1R,2S)-2-hydroxycyclohexyl]-6-methyl-5H-pyrrolo[3,2-d]pyrimidine-7-carboxamide |
| P717 | 4-[2-(Cyclopropylmethoxy)-5-(trifluoromethyl)phenyl]-N-[(1R,2R)-2-hydroxycyclohexyl]-6-methyl-5H-pyrrolo[3,2-d]pyrimidine-7-carboxamide |
| P718 | 4-[2-(Cyclopropylmethoxy)-5-(trifluoromethyl)phenyl]-N-[(1S,2S)-2-hydroxycyclohexyl]-6-methyl-5H-pyrrolo[3,2-d]pyrimidine-7-carboxamide |
| P719 | 4-[2-(Cyclopropylmethoxy)-5-(trifluoromethyl)phenyl]-N-[(1S,2R)-2-hydroxycyclohexyl]-6-methyl-5H-pyrrolo[3,2-d]pyrimidine-7-carboxamide |
| P720 | 4-[2-(Cyclopropylmethoxy)-5-(trifluoromethyl)phenyl]-N-[(1S,3R)-3-hydroxycyclohexyl]-6-methyl-5H-pyrrolo[3,2-d]pyrimidine-7-carboxamide |
| P721 | 4-[2-(Cyclopropylmethoxy)-5-(trifluoromethyl)phenyl]-N-[(1S,3S)-3-hydroxycyclohexyl]-6-methyl-5H-pyrrolo[3,2-d]pyrimidine-7-carboxamide |
| P722 | 4-[2-(Cyclopropylmethoxy)-5-(trifluoromethyl)phenyl]-N-[(1R,3R)-3-hydroxycyclohexyl]-6-methyl-5H-pyrrolo[3,2-d]pyrimidine-7-carboxamide |

| | |
|---|---|
| P723 | 4-[2-(Cyclopropylmethoxy)-5-(trifluoromethyl)phenyl]-N-[(1R,3S)-3-hydroxycyclohexyl]-6-methyl-5H-pyrrolo[3,2-d]pyrimidine-7-carboxamide |
| P724 | 4-[2-(Cyclopropylmethoxy)-5-(trifluoromethyl)phenyl]-N-(trans-4-hydroxycyclohexyl)-6-methyl-5H-pyrrolo[3,2-d]pyrimidine-7-carboxamide |
| P725 | 4-[2-(Cyclopropylmethoxy)-5-(trifluoromethyl)phenyl]-N-(cis-4-hydroxycyclohexyl)-6-methyl-5H-pyrrolo[3,2-d]pyrimidine-7-carboxamide |
| P726 | N-[(3S,4R)-1-Acetyl-3-fluoropiperidin-4-yl]-4-[2-(cyclopropylmethoxy)-5-(trifluoromethyl)phenyl]-6-methyl-5H-pyrrolo[3,2-d]pyrimidine-7-carboxamide |
| P727 | 4-[2-(Cyclopropylmethoxy)-5-(trifluoromethyl)phenyl]-N-[(3S,4R)-3-fluoro-1-propanoylpiperidin-4-yl]-6-methyl-5H-pyrrolo[3,2-d]pyrimidine-7-carboxamide |
| P728 | 4-[2-(Cyclopropylmethoxy)-5-(trifluoromethyl)phenyl]-N-[(3S,4R)-3-fluoro-1-(methoxyacetyl)piperidin-4-yl]-6-methyl-5H-pyrrolo[3,2-d]pyrimidine-7-carboxamide |
| P729 | 4-[2-(Cyclopropylmethoxy)-5-(trifluoromethyl)phenyl]-N-[(3S,4R)-3-fluoro-1-(hydroxyacetyl)piperidin-4-yl]-6-methyl-5H-pyrrolo[3,2-d]pyrimidine-7-carboxamide |
| P730 | 4-[2-(Cyclopropylmethoxy)-5-(trifluoromethyl)phenyl]-N-{(3S,4R)-3-fluoro-1-[(2S)-2-hydroxypropanoyl]piperidin-4-yl}-6-methyl-5H-pyrrolo[3,2-d]pyrimidine-7-carboxamide |
| P731 | N-[(3R,4R)-1-Acetyl-3-fluoropiperidin-4-yl]-4-[2-(cyclopropylmethoxy)-5-(trifluoromethyl)phenyl]-6-methyl-5H-pyrrolo[3,2-d]pyrimidine-7-carboxamide |
| P732 | 4-[2-(Cyclopropylmethoxy)-5-(trifluoromethyl)phenyl]-N-[(3R,4R)-3-fluoro-1-propanoylpiperidin-4-yl]-6-methyl-5H-pyrrolo[3,2-d]pyrimidine-7-carboxamide |
| P733 | 4-[2-(Cyclopropylmethoxy)-5-(trifluoromethyl)phenyl]-N-[(3R,4R)-3-fluoro-1-(methoxyacetyl)piperidin-4-yl]-6-methyl-5H-pyrrolo[3,2-d]pyrimidine-7-carboxamide |
| P734 | 4-[2-(Cyclopropylmethoxy)-5-(trifluoromethyl)phenyl]-N-[(3R,4R)-3-fluoro-1-(hydroxyacetyl)piperidin-4-yl]-6-methyl-5H-pyrrolo[3,2-d]pyrimidine-7-carboxamide |
| P735 | 4-[2-(Cyclopropylmethoxy)-5-(trifluoromethyl)phenyl]-N-{(3R,4R)-3-fluoro-1-[(2S)-2-hydroxypropanoyl]piperidin-4-yl}-6-methyl-5H-pyrrolo[3,2-d]pyrimidine-7-carboxamide |
| P736 | N-[(3S,4S)-1-Acetyl-3-fluoropiperidin-4-yl]-4-[2-(cyclopropylmethoxy)-5-(trifluoromethyl)phenyl]-6-methyl-5H-pyrrolo[3,2-d]pyrimidine-7-carboxamide |
| P737 | 4-[2-(Cyclopropylmethoxy)-5-(trifluoromethyl)phenyl]-N-[(3S,4S)-3-fluoro-1-propanoylpiperidin-4-yl]-6-methyl-5H-pyrrolo[3,2-d]pyrimidine-7-carboxamide |
| P738 | 4-[2-(Cyclopropylmethoxy)-5-(trifluoromethyl)phenyl]-N-[(3S,4S)-3-fluoro-1-(methoxyacetyl)piperidin-4-yl]-6-methyl-5H-pyrrolo[3,2-d]pyrimidine-7-carboxamide |
| P739 | 4-[2-(Cyclopropylmethoxy)-5-(trifluoromethyl)phenyl]-N-[(3S,4S)-3-fluoro-1-(hydroxyacetyl)piperidin-4-yl]-6-methyl-5H-pyrrolo[3,2-d]pyrimidine-7-carboxamide |
| P740 | 4-[2-(Cyclopropylmethoxy)-5-(trifluoromethyl)phenyl]-N-{(3S,4S)-3-fluoro-1-[(2S)-2-hydroxypropanoyl]piperidin-4-yl}-6-methyl-5H-pyrrolo[3,2-d]pyrimidine-7-carboxamide |
| P741 | N-[(3R,4S)-1-Acetyl-3-fluoropiperidin-4-yl]-4-[2-(cyclopropylmethoxy)-5-(trifluoromethyl)phenyl]-6-methyl-5H-pyrrolo[3,2-d]pyrimidine-7-carboxamide |
| P742 | 4-[2-(Cyclopropylmethoxy)-5-(trifluoromethyl)phenyl]-N-[(3R,4S)-3-fluoro-1-propanoylpiperidin-4-yl]-6-methyl-5H-pyrrolo[3,2-d]pyrimidine-7-carboxamide |
| P743 | 4-[2-(Cyclopropylmethoxy)-5-(trifluoromethyl)phenyl]-N-[(3R,4S)-3-fluoro-1-(methoxyacetyl)piperidin-4-yl]-6-methyl-5H-pyrrolo[3,2-d]pyrimidine-7-carboxamide |
| P744 | 4-[2-(Cyclopropylmethoxy)-5-(trifluoromethyl)phenyl]-N-[(3R,4S)-3-fluoro-1-(hydroxyacetyl)piperidin-4-yl]-6-methyl-5H-pyrrolo[3,2-d]pyrimidine-7-carboxamide |
| P745 | 4-[2-(Cyclopropylmethoxy)-5-(trifluoromethyl)phenyl]-N-{(3R,4S)-3-fluoro-1-[(2S)-2-hydroxypropanoyl]piperidin-4-yl}-6-methyl-5H-pyrrolo[3,2-d]pyrimidine-7-carboxamide |
| P746 | N-[(1R*,2R*,4R*)-4-(Acetylamino)-2-methylcyclohexyl]-4-[2-(cyclopropylmethoxy)-5-(trifluoromethyl)phenyl]-6-methyl-5H-pyrrolo[3,2-d]pyrimidine-7-carboxamide |
| P747 | 4-[2-(Cyclopropylmethoxy)-5-(trifluoromethyl)phenyl]-6-methyl-N-[(1R*,2R*,4R*)-2-methyl-4-(propanoylamino)cyclohexyl]-5H-pyrrolo[3,2-d]pyrimidine-7-carboxamide |
| P748 | 4-[2-(Cyclopropylmethoxy)-5-(trifluoromethyl)phenyl]-N-{(1R*,2R*,4R*)-4-[(methoxyacetyl)amino]-2-methylcyclohexyl}-6-methyl-5H-pyrrolo[3,2-d]pyrimidine-7-carboxamide |
| P749 | 4-[2-(Cyclopropylmethoxy)-5-(trifluoromethyl)phenyl]-N-{(1R*,2R*,4R*)-4-[(hydroxyacetyl)amino]-2-methylcyclohexyl}-6-methyl-5H-pyrrolo[3,2-d]pyrimidine-7-carboxamide |
| P750 | 4-[2-(Cyclopropylmethoxy)-5-(trifluoromethyl)phenyl]-N-[(1R*,2R*,4R*)-4-{[(2S)-2-hydroxypropanoyl]amino}-2-methylcyclohexyl]-6-methyl-5H-pyrrolo[3,2-d]pyrimidine-7-carboxamide |
| P751 | N-[(1R*,2R*,4S*)-4-(acetylamino)-2-methylcyclohexyl]-4-[2-(cyclopropylmethoxy)-5-(trifluoromethyl)phenyl]-6-methyl-5H-pyrrolo[3,2-d]pyrimidine-7-carboxamide |
| P752 | 4-[2-(Cyclopropylmethoxy)-5-(trifluoromethyl)phenyl]-6-methyl-N-[(1R*,2R*,4S*)-2-methyl-4-(propanoylamino)cyclohexyl]-5H-pyrrolo[3,2-d]pyrimidine-7-carboxamide |
| P753 | 4-[2-(Cyclopropylmethoxy)-5-(trifluoromethyl)phenyl]-N-{(1R*,2R*,4S*)-4-[(methoxyacetyl)amino]-2-methylcyclohexyl}-6-methyl-5H-pyrrolo[3,2-d]pyrimidine-7-carboxamide |
| P754 | 4-[2-(Cyclopropylmethoxy)-5-(trifluoromethyl)phenyl]-N-{(1R*,2R*,4S*)-4-[(hydroxyacetyl)amino]-2-methylcyclohexyl}-6-methyl-5H-pyrrolo[3,2-d]pyrimidine-7-carboxamide |
| P755 | 4-[2-(Cyclopropylmethoxy)-5-(trifluoromethyl)phenyl]-N-[(1R*,2R*,4S*)-4-{[(2S)-2-hydroxypropanoyl]amino}-2-methylcyclohexyl]-6-methyl-5H-pyrrolo[3,2-d]pyrimidine-7-carboxamide |
| P756 | N-[(1S*,2R*,4S*)-4-(acetylamino)-2-methylcyclohexyl]-4-[2-(cyclopropylmethoxy)-5-(trifluoromethyl)phenyl]-6-methyl-5H-pyrrolo[3,2-d]pyrimidine-7-carboxamide |
| P757 | 4-[2-(Cyclopropylmethoxy)-5-(trifluoromethyl)phenyl]-6-methyl-N-[(1S*,2R*,4S*)-2-methyl-4-(propanoylamino)cyclohexyl]-5H-pyrrolo[3,2-d]pyrimidine-7-carboxamide |
| P758 | 4-[2-(Cyclopropylmethoxy)-5-(trifluoromethyl)phenyl]-N-{(1S*,2R*,4S*)-4-[(methoxyacetyl)amino]-2-methylcyclohexyl}-6-methyl-5H-pyrrolo[3,2-d]pyrimidine-7-carboxamide |
| P759 | 4-[2-(Cyclopropylmethoxy)-5-(trifluoromethyl)phenyl]-N-{(1S*,2R*,4S*)-4-[(hydroxyacetyl)amino]-2-methylcyclohexyl}-6-methyl-5H-pyrrolo[3,2-d]pyrimidine-7-carboxamide |
| P760 | 4-[2-(Cyclopropylmethoxy)-5-(trifluoromethyl)phenyl]-N-[(1S*,2R*,4S*)-4-{[(2S)-2-hydroxypropanoyl]amino}-2-methylcyclohexyl]-6-methyl-5H-pyrrolo[3,2-d]pyrimidine-7-carboxamide |

| | |
|---|---|
| P761 | N-[(1S*,2R*,4R*)-4-(Acetylamino)-2-methylcyclohexyl]-4-[2-(cyclopropylmethoxy)-5-(trifluoromethyl)phenyl]-6-methyl-5H-pyrrolo[3,2-d]pyrimidine-7-carboxamide |
| P762 | 4-[2-(Cyclopropylmethoxy)-5-(trifluoromethyl)phenyl]-6-methyl-N-[(1S*,2R*,4R*)-2-methyl-4-(propanoylamino)cyclohexyl]-5H-pyrrolo[3,2-d]pyrimidine-7-carboxamide |
| P763 | 4-[2-(Cyclopropylmethoxy)-5-(trifluoromethyl)phenyl]-N-{(1S*,2R*,4R*)-4-[(methoxyacetyl)amino]-2-methylcyclohexyl}-6-methyl-5H-pyrrolo[3,2-d]pyrimidine-7-carboxamide |
| P764 | 4-[2-(Cyclopropylmethoxy)-5-(trifluoromethyl)phenyl]-N-{(1S*,2R*,4R*)-4-[(hydroxyacetyl)amino]-2-methylcyclohexyl}-6-methyl-5H-pyrrolo[3,2-d]pyrimidine-7-carboxamide |
| P765 | 4-[2-(Cyclopropylmethoxy)-5-(trifluoromethyl)phenyl]-N-[(1S*,2R*,4R*)-4-{[(2S)-2-hydroxypropanoyl]amino}-2-methylcyclohexyl]-6-methyl-5H-pyrrolo[3,2-d]pyrimidine-7-carboxamide |
| P766 | N-[(1R*,2R*,4R*)-4-(Acetylamino)-2-fluorocyclohexyl]-4-[2-(cyclopropylmethoxy)-5-(trifluoromethyl)phenyl]-6-methyl-5H-pyrrolo[3,2-d]pyrimidine-7-carboxamide |
| P767 | 4-[2-(Cyclopropylmethoxy)-5-(trifluoromethyl)phenyl]-N-[(1R*,2R*,4R*)-2-fluoro-4-(propanoylamino)cyclohexyl]-6-methyl-5H-pyrrolo[3,2-d]pyrimidine-7-carboxamide |
| P768 | 4-[2-(Cyclopropylmethoxy)-5-(trifluoromethyl)phenyl]-N-{(1R*,2R*,4R*)-2-fluoro-4-[(methoxyacetyl)amino]cyclohexyl}-6-methyl-5H-pyrrolo[3,2-d]pyrimidine-7-carboxamide |
| P769 | 4-[2-(Cyclopropylmethoxy)-5-(trifluoromethyl)phenyl]-N-{(1R*,2R*,4R*)-2-fluoro-4-[(hydroxyacetyl)amino]cyclohexyl}-6-methyl-5H-pyrrolo[3,2-d]pyrimidine-7-carboxamide |
| P770 | 4-[2-(Cyclopropylmethoxy)-5-(trifluoromethyl)phenyl]-N-[(1R*,2R*,4R*)-2-fluoro-4-{[(2S)-2-hydroxypropanoyl]amino}cyclohexyl]-6-methyl-5H-pyrrolo[3,2-d]pyrimidine-7-carboxamide |
| P771 | N-[(1R*,2R*,4S*)-4-(Acetylamino)-2-fluorocyclohexyl]-4-[2-(cyclopropylmethoxy)-5-(trifluoromethyl)phenyl]-6-methyl-5H-pyrrolo[3,2-d]pyrimidine-7-carboxamide |
| P772 | 4-[2-(Cyclopropylmethoxy)-5-(trifluoromethyl)phenyl]-N-[(1R*,2R*,4S*)-2-fluoro-4-(propanoylamino)cyclohexyl]-6-methyl-5H-pyrrolo[3,2-d]pyrimidine-7-carboxamide |
| P773 | 4-[2-(Cyclopropylmethoxy)-5-(trifluoromethyl)phenyl]-N-{(1R*,2R*,4S*)-2-fluoro-4-[(methoxyacetyl)amino]cyclohexyl}-6-methyl-5H-pyrrolo[3,2-d]pyrimidine-7-carboxamide |
| P774 | 4-[2-(Cyclopropylmethoxy)-5-(trifluoromethyl)phenyl]-N-{(1R*,2R*,4S*)-2-fluoro-4-[(hydroxyacetyl)amino]cyclohexyl}-6-methyl-5H-pyrrolo[3,2-d]pyrimidine-7-carboxamide |
| P775 | 4-[2-(Cyclopropylmethoxy)-5-(trifluoromethyl)phenyl]-N-[(1R*,2R*,4S*)-2-fluoro-4-{[(2S)-2-hydroxypropanoyl]amino}cyclohexyl]-6-methyl-5H-pyrrolo[3,2-d]pyrimidine-7-carboxamide |
| P776 | N-[(1S*,2R*,4S*)-4-(Acetylamino)-2-fluorocyclohexyl]-4-[2-(cyclopropylmethoxy)-5-(trifluoromethyl)phenyl]-6-methyl-5H-pyrrolo[3,2-d]pyrimidine-7-carboxamide |
| P777 | 4-[2-(Cyclopropylmethoxy)-5-(trifluoromethyl)phenyl]-N-[(1S*,2R*,4S*)-2-fluoro-4-(propanoylamino)cyclohexyl]-6-methyl-5H-pyrrolo[3,2-d]pyrimidine-7-carboxamide |
| P778 | 4-[2-(Cyclopropylmethoxy)-5-(trifluoromethyl)phenyl]-N-{(1S*,2R*,4S*)-2-fluoro-4-[(methoxyacetyl)amino]cyclohexyl}-6-methyl-5H-pyrrolo[3,2-d]pyrimidine-7-carboxamide |
| P779 | 4-[2-(Cyclopropylmethoxy)-5-(trifluoromethyl)phenyl]-N-{(1S*,2R*,4S*)-2-fluoro-4-[(hydroxyacetyl)amino]cyclohexyl}-6-methyl-5H-pyrrolo[3,2-d]pyrimidine-7-carboxamide |
| P780 | 4-[2-(Cyclopropylmethoxy)-5-(trifluoromethyl)phenyl]-N-[(1S*,2R*,4S*)-2-fluoro-4-{[(2S)-2-hydroxypropanoyl]amino}cyclohexyl]-6-methyl-5H-pyrrolo[3,2-d]pyrimidine-7-carboxamide |
| P781 | N-[(1S*,2R*,4R*)-4-(Acetylamino)-2-fluorocyclohexyl]-4-[2-(cyclopropylmethoxy)-5-(trifluoromethyl)phenyl]-6-methyl-5H-pyrrolo[3,2-d]pyrimidine-7-carboxamide |
| P782 | 4-[2-(Cyclopropylmethoxy)-5-(trifluoromethyl)phenyl]-N-[(1S*,2R*,4R*)-2-fluoro-4-(propanoylamino)cyclohexyl]-6-methyl-5H-pyrrolo[3,2-d]pyrimidine-7-carboxamide |
| P783 | 4-[2-(Cyclopropylmethoxy)-5-(trifluoromethyl)phenyl]-N-{(1S*,2R*,4R*)-2-fluoro-4-[(methoxyacetyl)amino]cyclohexyl}-6-methyl-5H-pyrrolo[3,2-d]pyrimidine-7-carboxamide |
| P784 | 4-[2-(Cyclopropylmethoxy)-5-(trifluoromethyl)phenyl]-N-{(1S*,2R*,4R*)-2-fluoro-4-[(hydroxyacetyl)amino]cyclohexyl}-6-methyl-5H-pyrrolo[3,2-d]pyrimidine-7-carboxamide |
| P785 | 4-[2-(Cyclopropylmethoxy)-5-(trifluoromethyl)phenyl]-N-[(1S*,2R*,4R*)-2-fluoro-4-{[(2S)-2-hydroxypropanoyl]amino}cyclohexyl]-6-methyl-5H-pyrrolo[3,2-d]pyrimidine-7-carboxamide |
| P786 | N-[(1S*,3R*,4S*)-4-(acetylamino)-3-methylcyclohexyl]-4-[2-(cyclopropylmethoxy)-5-(trifluoromethyl)phenyl]-6-methyl-5H-pyrrolo[3,2-d]pyrimidine-7-carboxamide |
| P787 | 4-[2-(Cyclopropylmethoxy)-5-(trifluoromethyl)phenyl]-6-methyl-N-[(1S*,3R*,4S*)-3-methyl-4-(propanoylamino)cyclohexyl]-5H-pyrrolo[3,2-d]pyrimidine-7-carboxamide |
| P788 | 4-[2-(Cyclopropylmethoxy)-5-(trifluoromethyl)phenyl]-N-{(1S*,3R*,4S*)-4-[(methoxyacetyl)amino]-3-methylcyclohexyl}-6-methyl-5H-pyrrolo[3,2-d]pyrimidine-7-carboxamide |
| P789 | 4-[2-(Cyclopropylmethoxy)-5-(trifluoromethyl)phenyl]-N-{(1S*,3R*,4S*)-4-[(hydroxyacetyl)amino]-3-methylcyclohexyl}-6-methyl-5H-pyrrolo[3,2-d]pyrimidine-7-carboxamide |
| P790 | 4-[2-(Cyclopropylmethoxy)-5-(trifluoromethyl)phenyl]-N-[(1S*,3R*,4S*)-4-{[(2S)-2-hydroxypropanoyl]amino}-3-methylcyclohexyl]-6-methyl-5H-pyrrolo[3,2-d]pyrimidine-7-carboxamide |
| P791 | N-[(1S*,3R*,4R*)-4-(Acetylamino)-3-methylcyclohexyl]-4-[2-(cyclopropylmethoxy)-5-(trifluoromethyl)phenyl]-6-methyl-5H-pyrrolo[3,2-d]pyrimidine-7-carboxamide |
| P792 | 4-[2-(Cyclopropylmethoxy)-5-(trifluoromethyl)phenyl]-6-methyl-N-[(1S*,3R*,4R*)-3-methyl-4-(propanoylamino)cyclohexyl]-5H-pyrrolo[3,2-d]pyrimidine-7-carboxamide |
| P793 | 4-[2-(Cyclopropylmethoxy)-5-(trifluoromethyl)phenyl]-N-{(1S*,3R*,4R*)-4-[(methoxyacetyl)amino]-3-methylcyclohexyl}-6-methyl-5H-pyrrolo[3,2-d]pyrimidine-7-carboxamide |
| P794 | 4-[2-(Cyclopropylmethoxy)-5-(trifluoromethyl)phenyl]-N-{(1S*,3R*,4R*)-4-[(hydroxyacetyl)amino]-3-methylcyclohexyl}-6-methyl-5H-pyrrolo[3,2-d]pyrimidine-7-carboxamide |
| P795 | 4-[2-(Cyclopropylmethoxy)-5-(trifluoromethyl)phenyl]-N-[(1S*,3R*,4R*)-4-{[(2S)-2-hydroxypropanoyl]amino}-3-methylcyclohexyl]-6-methyl-5H-pyrrolo[3,2-d]pyrimidine-7-carboxamide |

| | |
|---|---|
| P796 | N-[(1R*,3R*,4R*)-4-(acetylamino)-3-methylcyclohexyl]-4-[2-(cyclopropylmethoxy)-5-(trifluoromethyl)phenyl]-6-methyl-5H-pyrrolo[3,2-d]pyrimidine-7-carboxamide |
| P797 | 4-[2-(Cyclopropylmethoxy)-5-(trifluoromethyl)phenyl]-6-methyl-N-[(1R*,3R*,4R*)-3-methyl-4-(propanoylamino)cyclohexyl]-5H-pyrrolo[3,2-d]pyrimidine-7-carboxamide |
| P798 | 4-[2-(Cyclopropylmethoxy)-5-(trifluoromethyl)phenyl]-N-{(1R*,3R*,4R*)-4-[(methoxyacetyl)amino]-3-methylcyclohexyl}-6-methyl-5H-pyrrolo[3,2-d]pyrimidine-7-carboxamide |
| P799 | 4-[2-(Cyclopropylmethoxy)-5-(trifluoromethyl)phenyl]-N-{(1R*,3R*,4R*)-4-[(hydroxyacetyl)amino]-3-methylcyclohexyl}-6-methyl-5H-pyrrolo[3,2-d]pyrimidine-7-carboxamide |
| P800 | 4-[2-(Cyclopropylmethoxy)-5-(trifluoromethyl)phenyl]-N-[(1R*,3R*,4R*)-4-{[(2S)-2-hydroxypropanoyl]amino}-3-methylcyclohexyl]-6-methyl-5H-pyrrolo[3,2-d]pyrimidine-7-carboxamide |
| P801 | N-[(1R*,3R*,4S*)-4-(Acetylamino)-3-methylcyclohexyl]-4-[2-(cyclopropylmethoxy)-5-(trifluoromethyl)phenyl]-6-methyl-5H-pyrrolo[3,2-d]pyrimidine-7-carboxamide |
| P802 | 4-[2-(Cyclopropylmethoxy)-5-(trifluoromethyl)phenyl]-6-methyl-N-[(1R*,3R*,4S*)-3-methyl-4-(propanoylamino)cyclohexyl]-5H-pyrrolo[3,2-d]pyrimidine-7-carboxamide |
| P803 | 4-[2-(Cyclopropylmethoxy)-5-(trifluoromethyl)phenyl]-N-{(1R*,3R*,4S*)-4-[(methoxyacetyl)amino]-3-methylcyclohexyl}-6-methyl-5H-pyrrolo[3,2-d]pyrimidine-7-carboxamide |
| P804 | 4-[2-(Cyclopropylmethoxy)-5-(trifluoromethyl)phenyl]-N-{(1R*,3R*,4S*)-4-[(hydroxyacetyl)amino]-3-methylcyclohexyl}-6-methyl-5H-pyrrolo[3,2-d]pyrimidine-7-carboxamide |
| P805 | 4-[2-(Cyclopropylmethoxy)-5-(trifluoromethyl)phenyl]-N-[(1R*,3R*,4S*)-4-{[(2S)-2-hydroxypropanoyl]amino}-3-methylcyclohexyl]-6-methyl-5H-pyrrolo[3,2-d]pyrimidine-7-carboxamide |
| P806 | N-[(1S*,3R*,4S*)-4-(acetylamino)-3-fluorocyclohexyl]-4-[2-(cyclopropylmethoxy)-5-(trifluoromethyl)phenyl]-6-methyl-5H-pyrrolo[3,2-d]pyrimidine-7-carboxamide |
| P807 | 4-[2-(Cyclopropylmethoxy)-5-(trifluoromethyl)phenyl]-N-[(1S*,3R*,4S*)-3-fluoro-4-(propanoylamino)cyclohexyl]-6-methyl-5H-pyrrolo[3,2-d]pyrimidine-7-carboxamide |
| P808 | 4-[2-(Cyclopropylmethoxy)-5-(trifluoromethyl)phenyl]-N-{(1S*,3R*,4S*)-3-fluoro-4-[(methoxyacetyl)amino]cyclohexyl}-6-methyl-5H-pyrrolo[3,2-d]pyrimidine-7-carboxamide |
| P809 | 4-[2-(Cyclopropylmethoxy)-5-(trifluoromethyl)phenyl]-N-{(1S*,3R*,4S*)-3-fluoro-4-[(hydroxyacetyl)amino]cyclohexyl}-6-methyl-5H-pyrrolo[3,2-d]pyrimidine-7-carboxamide |
| P810 | 4-[2-(Cyclopropylmethoxy)-5-(trifluoromethyl)phenyl]-N-[(1S*,3R*,4S*)-3-fluoro-4-{[(2S)-2-hydroxypropanoyl]amino}cyclohexyl]-6-methyl-5H-pyrrolo[3,2-d]pyrimidine-7-carboxamide |
| P811 | N-[(1S*,3R*,4R*)-4-(acetylamino)-3-fluorocyclohexyl]-4-[2-(cyclopropylmethoxy)-5-(trifluoromethyl)phenyl]-6-methyl-5H-pyrrolo[3,2-d]pyrimidine-7-carboxamide |
| P812 | 4-[2-(Cyclopropylmethoxy)-5-(trifluoromethyl)phenyl]-N-[(1S*,3R*,4R*)-3-fluoro-4-(propanoylamino)cyclohexyl]-6-methyl-5H-pyrrolo[3,2-d]pyrimidine-7-carboxamide |
| P813 | 4-[2-(Cyclopropylmethoxy)-5-(trifluoromethyl)phenyl]-N-{(1S*,3R*,4R*)-3-fluoro-4-[(methoxyacetyl)amino]cyclohexyl}-6-methyl-5H-pyrrolo[3,2-d]pyrimidine-7-carboxamide |
| P814 | 4-[2-(Cyclopropylmethoxy)-5-(trifluoromethyl)phenyl]-N-{(1S*,3R*,4R*)-3-fluoro-4-[(hydroxyacetyl)amino]cyclohexyl}-6-methyl-5H-pyrrolo[3,2-d]pyrimidine-7-carboxamide |
| P815 | 4-[2-(cyclopropylmethoxy)-5-(trifluoromethyl)phenyl]-N-[(1S*,3R*,4R*)-3-fluoro-4-{[(2S)-2-hydroxypropanoyl]amino}cyclohexyl]-6-methyl-5H-pyrrolo[3,2-d]pyrimidine-7-carboxamide |
| P816 | N-[(1R*,3R*,4R*)-4-(Acetylamino)-3-fluorocyclohexyl]-4-[2-(cyclopropylmethoxy)-5-(trifluoromethyl)phenyl]-6-methyl-5H-pyrrolo[3,2-d]pyrimidine-7-carboxamide |
| P817 | 4-[2-(Cyclopropylmethoxy)-5-(trifluoromethyl)phenyl]-N-[(1R*,3R*,4R*)-3-fluoro-4-(propanoylamino)cyclohexyl]-6-methyl-5H-pyrrolo[3,2-d]pyrimidine-7-carboxamide |
| P818 | 4-[2-(Cyclopropylmethoxy)-5-(trifluoromethyl)phenyl]-N-{(1R*,3R*,4R*)-3-fluoro-4-[(methoxyacetyl)amino]cyclohexyl}-6-methyl-5H-pyrrolo[3,2-d]pyrimidine-7-carboxamide |
| P819 | 4-[2-(Cyclopropylmethoxy)-5-(trifluoromethyl)phenyl]-N-{(1R*,3R*,4R*)-3-fluoro-4-[(hydroxyacetyl)amino]cyclohexyl}-6-methyl-5H-pyrrolo[3,2-d]pyrimidine-7-carboxamide |
| P820 | 4-[2-(Cyclopropylmethoxy)-5-(trifluoromethyl)phenyl]-N-[(1R*,3R*,4R*)-3-fluoro-4-{[(2S)-2-hydroxypropanoyl]amino}cyclohexyl]-6-methyl-5H-pyrrolo[3,2-d]pyrimidine-7-carboxamide |
| P821 | N-[(1R*,3R*,4S*)-4-(Acetylamino)-3-fluorocyclohexyl]-4-[2-(cyclopropylmethoxy)-5-(trifluoromethyl)phenyl]-6-methyl-5H-pyrrolo[3,2-d]pyrimidine-7-carboxamide |
| P822 | 4-[2-(Cyclopropylmethoxy)-5-(trifluoromethyl)phenyl]-N-[(1R*,3R*,4S*)-3-fluoro-4-(propanoylamino)cyclohexyl]-6-methyl-5H-pyrrolo[3,2-d]pyrimidine-7-carboxamide |
| P823 | 4-[2-(Cyclopropylmethoxy)-5-(trifluoromethyl)phenyl]-N-{(1R*,3R*,4S*)-3-fluoro-4-[(methoxyacetyl)amino]cyclohexyl}-6-methyl-5H-pyrrolo[3,2-d]pyrimidine-7-carboxamide |
| P824 | 4-[2-(Cyclopropylmethoxy)-5-(trifluoromethyl)phenyl]-N-{(1R*,3R*,4S*)-3-fluoro-4-[(hydroxyacetyl)amino]cyclohexyl}-6-methyl-5H-pyrrolo[3,2-d]pyrimidine-7-carboxamide |
| P825 | 4-[2-(Cyclopropylmethoxy)-5-(trifluoromethyl)phenyl]-N-[(1R*,3R*,4S*)-3-fluoro-4-{[(2S)-2-hydroxypropanoyl]amino}cyclohexyl]-6-methyl-5H-pyrrolo[3,2-d]pyrimidine-7-carboxamide |
| P826 | N-(1-Acetylpiperidin-4-yl)-4-[6-(cyclopropylmethoxy)-2-fluoro-3-methylphenyl]-6-methyl-5H-pyrrolo[3,2-d]pyrimidine-7-carboxamide |
| P827 | 4-[6-(Cyclopropylmethoxy)-2-fluoro-3-methylphenyl]-6-methyl-N-(1-propanoylpiperidin-4-yl)-5H-pyrrolo[3,2-d]pyrimidine-7-carboxamide |
| P828 | 4-[6-(Cyclopropylmethoxy)-2-fluoro-3-methylphenyl]-N-[1-(methoxyacetyl)piperidin-4-yl]-6-methyl-5H-pyrrolo[3,2-d]pyrimidine-7-carboxamide |
| P829 | 4-[6-(Cyclopropylmethoxy)-2-fluoro-3-methylphenyl]-N-[1-(hydroxyacetyl)piperidin-4-yl]-6-methyl-5H-pyrrolo[3,2-d]pyrimidine-7-carboxamide |
| P830 | 4-[6-(Cyclopropylmethoxy)-2-fluoro-3-methylphenyl]-N-{1-[(2S)-2-hydroxypropanoyl]piperidin-4-yl}-6-methyl-5H-pyrrolo[3,2-d]pyrimidine-7-carboxamide |
| P831 | N-[trans-4-(Acetylamino)cyclohexyl]-4-[6-(cyclopropylmethoxy)-2-fluoro-3-methylphenyl]-6-methyl-5H-pyrrolo[3,2-d]pyrimidine-7-carboxamide |

| | |
|---|---|
| P832 | 4-[6-(Cyclopropylmethoxy)-2-fluoro-3-methylphenyl]-6-methyl-N-[trans-4-(propanoylamino)cyclohexyl]-5H-pyrrolo[3,2-d]pyrimidine-7-carboxamide |
| P833 | 4-[6-(Cyclopropylmethoxy)-2-fluoro-3-methylphenyl]-N-{trans-4-[(methoxyacetyl)amino]cyclohexyl}-6-methyl-5H-pyrrolo[3,2-d]pyrimidine-7-carboxamide |
| P834 | 4-[6-(Cyclopropylmethoxy)-2-fluoro-3-methylphenyl]-N-{trans-4-[(hydroxyacetyl)amino]cyclohexyl}-6-methyl-5H-pyrrolo[3,2-d]pyrimidine-7-carboxamide |
| P835 | 4-[6-(Cyclopropylmethoxy)-2-fluoro-3-methylphenyl]-N-(trans-4-{[(2S)-2-hydroxy-propanoyl]amino}cyclohexyl)-6-methyl-5H-pyrrolo[3,2-d]pyrimidine-7-carboxamide |
| P836 | N-[cis-4-(Acetylamino)cyclohexyl]-4-[6-(cyclopropylmethoxy)-2-fluoro-3-methylphenyl]-6-methyl-5H-pyrrolo[3,2-d]pyrimidine-7-carboxamide |
| P837 | 4-[6-(Cyclopropylmethoxy)-2-fluoro-3-methylphenyl]-6-methyl-N-[cis-4-(propanoylamino)cyclohexyl]-5H-pyrrolo[3,2-d]pyrimidine-7-carboxamide |
| P838 | 4-[6-(Cyclopropylmethoxy)-2-fluoro-3-methylphenyl]-N-{cis-4-[(methoxyacetyl)amino]cyclohexyl}-6-methyl-5H-pyrrolo[3,2-d]pyrimidine-7-carboxamide |
| P839 | 4-[6-(Cyclopropylmethoxy)-2-fluoro-3-methylphenyl]-N-{cis-4-[(hydroxyacetyl)amino]cyclohexyl}-6-methyl-5H-pyrrolo[3,2-d]pyrimidine-7-carboxamide |
| P840 | 4-[6-(Cyclopropylmethoxy)-2-fluoro-3-methylphenyl]-N-(cis-4-{[(2S)-2-hydroxy-propanoyl]amino}cyclohexyl)-6-methyl-5H-pyrrolo[3,2-d]pyrimidine-7-carboxamide |
| P841 | 4-[6-(Cyclopropylmethoxy)-2-fluoro-3-methylphenyl]-N-[(1R,3S)-3-hydroxycyclopentyl]-6-methyl-5H-pyrrolo[3,2-d]pyrimidine-7-carboxamide |
| P842 | 4-[6-(Cyclopropylmethoxy)-2-fluoro-3-methylphenyl]-N-[(1R,3R)-3-hydroxycyclopentyl]-6-methyl-5H-pyrrolo[3,2-d]pyrimidine-7-carboxamide |
| P843 | 4-[6-(Cyclopropylmethoxy)-2-fluoro-3-methylphenyl]-N-[(1S,3S)-3-hydroxycyclopentyl]-6-methyl-5H-pyrrolo[3,2-d]pyrimidine-7-carboxamide |
| P844 | 4-[6-(Cyclopropylmethoxy)-2-fluoro-3-methylphenyl]-N-[(1S,3R)-3-hydroxycyclopentyl]-6-methyl-5H-pyrrolo[3,2-d]pyrimidine-7-carboxamide |
| P845 | 4-[6-(Cyclopropylmethoxy)-2-fluoro-3-methylphenyl]-N-[(1R,2S)-2-hydroxycyclopentyl]-6-methyl-5H-pyrrolo[3,2-d]pyrimidine-7-carboxamide |
| P846 | 4-[6-(Cyclopropylmethoxy)-2-fluoro-3-methylphenyl]-N-[(1R,2R)-2-hydroxycyclopentyl]-6-methyl-5H-pyrrolo[3,2-d]pyrimidine-7-carboxamide |
| P847 | 4-[6-(Cyclopropylmethoxy)-2-fluoro-3-methylphenyl]-N-[(1S,2S)-2-hydroxycyclopentyl]-6-methyl-5H-pyrrolo[3,2-d]pyrimidine-7-carboxamide |
| P848 | 4-[6-(Cyclopropylmethoxy)-2-fluoro-3-methylphenyl]-N-[(1S,2R)-2-hydroxycyclopentyl]-6-methyl-5H-pyrrolo[3,2-d]pyrimidine-7-carboxamide |
| P849 | N-[(3S,5S)-1-Acetyl-5-methylpyrrolidin-3-yl]-4-[6-(cyclopropylmethoxy)-2-fluoro-3-methylphenyl]-6-methyl-5H-pyrrolo[3,2-d]pyrimidine-7-carboxamide |
| P850 | 4-[6-(Cyclopropylmethoxy)-2-fluoro-3-methylphenyl]-6-methyl-N-[(3S,5S)-5-methyl-1-propanoylpyrrolidin-3-yl]-5H-pyrrolo[3,2-d]pyrimidine-7-carboxamide |
| P851 | 4-[6-(Cyclopropylmethoxy)-2-fluoro-3-methylphenyl]-N-[(3S,5S)-1-(methoxyacetyl)-5-methylpyrrolidin-3-yl]-6-methyl-5H-pyrrolo[3,2-d]pyrimidine-7-carboxamide |
| P852 | 4-[6-(Cyclopropylmethoxy)-2-fluoro-3-methylphenyl]-N-[(3S,5S)-1-(hydroxyacetyl)-5-methylpyrrolidin-3-yl]-6-methyl-5H-pyrrolo[3,2-d]pyrimidine-7-carboxamide |
| P853 | 4-[6-(Cyclopropylmethoxy)-2-fluoro-3-methylphenyl]-N-{(3S,5S)-1-[(2S)-2-hydroxy-propanoyl]-5-methylpyrrolidin-3-yl}-6-methyl-5H-pyrrolo[3,2-d]pyrimidine-7-carboxamide |
| P854 | N-[(3S,5R)-1-Acetyl-5-methylpyrrolidin-3-yl]-4-[6-(cyclopropylmethoxy)-2-fluoro-3-methylphenyl]-6-methyl-5H-pyrrolo[3,2-d]pyrimidine-7-carboxamide |
| P855 | 4-[6-(Cyclopropylmethoxy)-2-fluoro-3-methylphenyl]-6-methyl-N-[(3S,5R)-5-methyl-1-propanoylpyrrolidin-3-yl]-5H-pyrrolo[3,2-d]pyrimidine-7-carboxamide |
| P856 | 4-[6-(Cyclopropylmethoxy)-2-fluoro-3-methylphenyl]-N-[(3S,5R)-1-(methoxyacetyl)-5-methylpyrrolidin-3-yl]-6-methyl-5H-pyrrolo[3,2-d]pyrimidine-7-carboxamide |
| P857 | 4-[6-(Cyclopropylmethoxy)-2-fluoro-3-methylphenyl]-N-[(3S,5R)-1-(hydroxyacetyl)-5-methylpyrrolidin-3-yl]-6-methyl-5H-pyrrolo[3,2-d]pyrimidine-7-carboxamide |
| P858 | 4-[6-(Cyclopropylmethoxy)-2-fluoro-3-methylphenyl]-N-{(3S,5R)-1-[(2S)-2-hydroxy-propanoyl]-5-methylpyrrolidin-3-yl}-6-methyl-5H-pyrrolo[3,2-d]pyrimidine-7-carboxamide |
| P859 | N-[(3R,5R)-1-Acetyl-5-methylpyrrolidin-3-yl]-4-[6-(cyclopropylmethoxy)-2-fluoro-3-methylphenyl]-6-methyl-5H-pyrrolo[3,2-d]pyrimidine-7-carboxamide |
| P860 | 4-[6-(Cyclopropylmethoxy)-2-fluoro-3-methylphenyl]-6-methyl-N-[(3R,5R)-5-methyl-1-propanoylpyrrolidin-3-yl]-5H-pyrrolo[3,2-d]pyrimidine-7-carboxamide |
| P861 | 4-[6-(Cyclopropylmethoxy)-2-fluoro-3-methylphenyl]-N-[(3R,5R)-1-(methoxyacetyl)-5-methylpyrrolidin-3-yl]-6-methyl-5H-pyrrolo[3,2-d]pyrimidine-7-carboxamide |
| P862 | 4-[6-(Cyclopropylmethoxy)-2-fluoro-3-methylphenyl]-N-[(3R,5R)-1-(hydroxyacetyl)-5-methylpyrrolidin-3-yl]-6-methyl-5H-pyrrolo[3,2-d]pyrimidine-7-carboxamide |
| P863 | 4-[6-(Cyclopropylmethoxy)-2-fluoro-3-methylphenyl]-N-{(3R,5R)-1-[(2S)-2-hydroxy-propanoyl]-5-methylpyrrolidin-3-yl}-6-methyl-5H-pyrrolo[3,2-d]pyrimidine-7-carboxamide |
| P864 | N-[(3R,5S)-1-Acetyl-5-methylpyrrolidin-3-yl]-4-[6-(cyclopropylmethoxy)-2-fluoro-3-methylphenyl]-6-methyl-5H-pyrrolo[3,2-d]pyrimidine-7-carboxamide |
| P865 | 4-[6-(Cyclopropylmethoxy)-2-fluoro-3-methylphenyl]-6-methyl-N-[(3R,5S)-5-methyl-1-propanoylpyrrolidin-3-yl]-5H-pyrrolo[3,2-d]pyrimidine-7-carboxamide |
| P866 | 4-[6-(Cyclopropylmethoxy)-2-fluoro-3-methylphenyl]-N-[(3R,5S)-1-(methoxyacetyl)-5-methylpyrrolidin-3-yl]-6-methyl-5H-pyrrolo[3,2-d]pyrimidine-7-carboxamide |
| P867 | 4-[6-(Cyclopropylmethoxy)-2-fluoro-3-methylphenyl]-N-[(3R,5S)-1-(hydroxyacetyl)-5-methylpyrrolidin-3-yl]-6-methyl-5H-pyrrolo[3,2-d]pyrimidine-7-carboxamide |
| P868 | 4-[6-(Cyclopropylmethoxy)-2-fluoro-3-methylphenyl]-N-{(3R,5S)-1-[(2S)-2-hydroxy-propanoyl]-5-methylpyrrolidin-3-yl}-6-methyl-5H-pyrrolo[3,2-d]pyrimidine-7-carboxamide |
| P869 | N-[(3S,4S)-1-Acetyl-4-fluoropyrrolidin-3-yl]-4-[6-(cyclopropylmethoxy)-2-fluoro-3-methylphenyl]-6-methyl-5H-pyrrolo[3,2-d]pyrimidine-7-carboxamide |
| P870 | 4-[6-(Cyclopropylmethoxy)-2-fluoro-3-methylphenyl]-N-[(3S,4S)-4-fluoro-1-propanoylpyrrolidin-3-yl]-6-methyl-5H-pyrrolo[3,2-d]pyrimidine-7-carboxamide |

| | |
|---|---|
| P871 | 4-[6-(Cyclopropylmethoxy)-2-fluoro-3-methylphenyl]-N-[(3S,4S)-4-fluoro-1-(methoxyacetyl)pyrrolidin-3-yl]-6-methyl-5H-pyrrolo[3,2-d]pyrimidine-7-carboxamide |
| P872 | 4-[6-(Cyclopropylmethoxy)-2-fluoro-3-methylphenyl]-N-[(3S,4S)-4-fluoro-1-(hydroxyacetyl)pyrrolidin-3-yl]-6-methyl-5H-pyrrolo[3,2-d]pyrimidine-7-carboxamide |
| P873 | 4-[6-(Cyclopropylmethoxy)-2-fluoro-3-methylphenyl]-N-{(3S,4S)-4-fluoro-1-[(2S)-2-hydroxypropanoyl]pyrrolidin-3-yl}-6-methyl-5H-pyrrolo[3,2-d]pyrimidine-7-carboxamide |
| P874 | N-[(3R,4S)-1-Acetyl-4-fluoropyrrolidin-3-yl]-4-[6-(cyclopropylmethoxy)-2-fluoro-3-methylphenyl]-6-methyl-5H-pyrrolo[3,2-d]pyrimidine-7-carboxamide |
| P875 | 4-[6-(Cyclopropylmethoxy)-2-fluoro-3-methylphenyl]-N-[(3R,4S)-4-fluoro-1-propanoylpyrrolidin-3-yl]-6-methyl-5H-pyrrolo[3,2-d]pyrimidine-7-carboxamide |
| P876 | 4-[6-(Cyclopropylmethoxy)-2-fluoro-3-methylphenyl]-N-[(3R,4S)-4-fluoro-1-(methoxyacetyl)pyrrolidin-3-yl]-6-methyl-5H-pyrrolo[3,2-d]pyrimidine-7-carboxamide |
| P877 | 4-[6-(Cyclopropylmethoxy)-2-fluoro-3-methylphenyl]-N-[(3R,4S)-4-fluoro-1-(hydroxyacetyl)pyrrolidin-3-yl]-6-methyl-5H-pyrrolo[3,2-d]pyrimidine-7-carboxamide |
| P878 | 4-[6-(Cyclopropylmethoxy)-2-fluoro-3-methylphenyl]-N-{(3R,4S)-4-fluoro-1-[(2S)-2-hydroxypropanoyl]pyrrolidin-3-yl}-6-methyl-5H-pyrrolo[3,2-d]pyrimidine-7-carboxamide |
| P879 | N-[(3R,4R)-1-Acetyl-4-fluoropyrrolidin-3-yl]-4-[6-(cyclopropylmethoxy)-2-fluoro-3-methylphenyl]-6-methyl-5H-pyrrolo[3,2-d]pyrimidine-7-carboxamide |
| P880 | 4-[6-(Cyclopropylmethoxy)-2-fluoro-3-methylphenyl]-N-[(3R,4R)-4-fluoro-1-propanoylpyrrolidin-3-yl]-6-methyl-5H-pyrrolo[3,2-d]pyrimidine-7-carboxamide |
| P881 | 4-[6-(Cyclopropylmethoxy)-2-fluoro-3-methylphenyl]-N-[(3R,4R)-4-fluoro-1-(methoxyacetyl)pyrrolidin-3-yl]-6-methyl-5H-pyrrolo[3,2-d]pyrimidine-7-carboxamide |
| P882 | 4-[6-(Cyclopropylmethoxy)-2-fluoro-3-methylphenyl]-N-[(3R,4R)-4-fluoro-1-(hydroxyacetyl)pyrrolidin-3-yl]-6-methyl-5H-pyrrolo[3,2-d]pyrimidine-7-carboxamide |
| P883 | 4-[6-(Cyclopropylmethoxy)-2-fluoro-3-methylphenyl]-N-{(3R,4R)-4-fluoro-1-[(2S)-2-hydroxypropanoyl]pyrrolidin-3-yl}-6-methyl-5H-pyrrolo[3,2-d]pyrimidine-7-carboxamide |
| P884 | N-[(3S,4R)-1-Acetyl-4-fluoropyrrolidin-3-yl]-4-[6-(cyclopropylmethoxy)-2-fluoro-3-methylphenyl]-6-methyl-5H-pyrrolo[3,2-d]pyrimidine-7-carboxamide |
| P885 | 4-[6-(Cyclopropylmethoxy)-2-fluoro-3-methylphenyl]-N-[(3S,4R)-4-fluoro-1-propanoylpyrrolidin-3-yl]-6-methyl-5H-pyrrolo[3,2-d]pyrimidine-7-carboxamide |
| P886 | 4-[6-(Cyclopropylmethoxy)-2-fluoro-3-methylphenyl]-N-[(3S,4R)-4-fluoro-1-(methoxyacetyl)pyrrolidin-3-yl]-6-methyl-5H-pyrrolo[3,2-d]pyrimidine-7-carboxamide |
| P887 | 4-[6-(Cyclopropylmethoxy)-2-fluoro-3-methylphenyl]-N-[(3S,4R)-4-fluoro-1-(hydroxyacetyl)pyrrolidin-3-yl]-6-methyl-5H-pyrrolo[3,2-d]pyrimidine-7-carboxamide |
| P888 | 4-[6-(Cyclopropylmethoxy)-2-fluoro-3-methylphenyl]-N-{(3S,4R)-4-fluoro-1-[(2S)-2-hydroxypropanoyl]pyrrolidin-3-yl}-6-methyl-5H-pyrrolo[3,2-d]pyrimidine-7-carboxamide |
| P889 | N-[(3S*,4R*)-1-Acetyl-4-methylpyrrolidin-3-yl]-4-[6-(cyclopropylmethoxy)-2-fluoro-3-methylphenyl]-6-methyl-5H-pyrrolo[3,2-d]pyrimidine-7-carboxamide |
| P890 | 4-[6-(Cyclopropylmethoxy)-2-fluoro-3-methylphenyl]-6-methyl-N-[(3S*,4R*)-4-methyl-1-propanoylpyrrolidin-3-yl]-5H-pyrrolo[3,2-d]pyrimidine-7-carboxamide |
| P891 | 4-[6-(Cyclopropylmethoxy)-2-fluoro-3-methylphenyl]-N-[(3S*,4R*)-1-(methoxyacetyl)-4-methylpyrrolidin-3-yl]-6-methyl-5H-pyrrolo[3,2-d]pyrimidine-7-carboxamide |
| P892 | 4-[6-(Cyclopropylmethoxy)-2-fluoro-3-methylphenyl]-N-[(3S*,4R*)-1-(hydroxyacetyl)-4-methylpyrrolidin-3-yl]-6-methyl-5H-pyrrolo[3,2-d]pyrimidine-7-carboxamide |
| P893 | 4-[6-(Cyclopropylmethoxy)-2-fluoro-3-methylphenyl]-N-{(3S*,4R*)-1-[(2S)-2-hydroxy-propanoyl]-4-methylpyrrolidin-3-yl}-6-methyl-5H-pyrrolo[3,2-d]pyrimidine-7-carboxamide |
| P894 | N-[(3S*,4S*)-1-Acetyl-4-methylpyrrolidin-3-yl]-4-[6-(Cyclopropylmethoxy)-2-fluoro-3-methylphenyl]-6-methyl-5H-pyrrolo[3,2-d]pyrimidine-7-carboxamide |
| P895 | 4-[6-(Cyclopropylmethoxy)-2-fluoro-3-methylphenyl]-6-methyl-N-[(3S*,4S*)-4-methyl-1-propanoylpyrrolidin-3-yl]-5H-pyrrolo[3,2-d]pyrimidine-7-carboxamide |
| P896 | 4-[6-(Cyclopropylmethoxy)-2-fluoro-3-methylphenyl]-N-[(3S*,4S*)-1-(methoxyacetyl)-4-methylpyrrolidin-3-yl]-6-methyl-5H-pyrrolo[3,2-d]pyrimidine-7-carboxamide |
| P897 | 4-[6-(Cyclopropylmethoxy)-2-fluoro-3-methylphenyl]-N-[(3S*,4S*)-1-(hydroxyacetyl)-4-methylpyrrolidin-3-yl]-6-methyl-5H-pyrrolo[3,2-d]pyrimidine-7-carboxamide |
| P898 | 4-[6-(Cyclopropylmethoxy)-2-fluoro-3-methylphenyl]-N-{(3S*,4S*)-1-[(2S)-2-hydroxy-propanoyl]-4-methylpyrrolidin-3-yl}-6-methyl-5H-pyrrolo[3,2-d]pyrimidine-7-carboxamide |
| P899 | N-[(3S*)-1-Acetyl-4,4-dimethylpyrrolidin-3-yl]-4-[6-(Cyclopropylmethoxy)-2-fluoro-3-methylphenyl]-6-methyl-5H-pyrrolo[3,2-d]pyrimidine-7-carboxamide |
| P900 | 4-[6-(Cyclopropylmethoxy)-2-fluoro-3-methylphenyl]-N-[(3S*)-4,4-dimethyl-1-propanoylpyrrolidin-3-yl]-6-methyl-5H-pyrrolo[3,2-d]pyrimidine-7-carboxamide |
| P901 | 4-[6-(Cyclopropylmethoxy)-2-fluoro-3-methylphenyl]-N-[(3S*)-1-(methoxyacetyl)-4,4-dimethylpyrrolidin-3-yl]-6-methyl-5H-pyrrolo[3,2-d]pyrimidine-7-carboxamide |
| P902 | 4-[6-(Cyclopropylmethoxy)-2-fluoro-3-methylphenyl]-N-[(3S*)-1-(hydroxyacetyl)-4,4-dimethylpyrrolidin-3-yl]-6-methyl-5H-pyrrolo[3,2-d]pyrimidine-7-carboxamide |
| P903 | 4-[6-(Cyclopropylmethoxy)-2-fluoro-3-methylphenyl]-N-{(3S*)-1-[(2S)-2-hydroxypropanoyl]-4,4-dimethylpyrrolidin-3-yl}-6-methyl-5H-pyrrolo[3,2-d]pyrimidine-7-carboxamide |
| P904 | N-[(7S*)-5-Acetyl-5-azaspiro[2.4]hept-7-yl]-4-[6-(Cyclopropylmethoxy)-2-fluoro-3-methylphenyl]-6-methyl-5H-pyrrolo[3,2-d]pyrimidine-7-carboxamide |
| P905 | 4-[6-(Cyclopropylmethoxy)-2-fluoro-3-methylphenyl]-6-methyl-N-[(7S*)-5-propanoyl-5-azaspiro[2.4]hept-7-yl]-5H-pyrrolo[3,2-d]pyrimidine-7-carboxamide |
| P906 | 4-[6-(Cyclopropylmethoxy)-2-fluoro-3-methylphenyl]-N-[(7S*)-5-(methoxyacetyl)-5-azaspiro[2.4]hept-7-yl]-6-methyl-5H-pyrrolo[3,2-d]pyrimidine-7-carboxamide |
| P907 | 4-[6-(Cyclopropylmethoxy)-2-fluoro-3-methylphenyl]-N-[(7S)-5-(hydroxyacetyl)-5-azaspiro[2.4]hept-7-yl]-6-methyl-5H-pyrrolo[3,2-d]pyrimidine-7-carboxamide |
| P908 | 4-[6-(Cyclopropylmethoxy)-2-fluoro-3-methylphenyl]-N-{(7S*)-5-[(2S)-2-hydroxypropanoyl]-5-azaspiro[2.4]hept-7-yl}-6-methyl-5H-pyrrolo[3,2-d]pyrimidine-7-carboxamide |
| P909 | N-[(3R*)-1-Acetyl-4,4-difluoropyrrolidin-3-yl]-4-[6-(Cyclopropylmethoxy)-2-fluoro-3-methylphenyl]-6-methyl-5H-pyrrolo[3,2-d]pyrimidine-7-carboxamide |

| | |
|---|---|
| P910 | 4-[6-(Cyclopropylmethoxy)-2-fluoro-3-methylphenyl]-N-[(3R*)-4,4-difluoro-1-propanoylpyrrolidin-3-yl]-6-methyl-5H-pyrrolo[3,2-d]pyrimidine-7-carboxamide |
| P911 | 4-[6-(Cyclopropylmethoxy)-2-fluoro-3-methylphenyl]-N-[(3R*)-4,4-difluoro-1-(methoxyacetyl)pyrrolidin-3-yl]-6-methyl-5H-pyrrolo[3,2-d]pyrimidine-7-carboxamide |
| P912 | 4-[6-(Cyclopropylmethoxy)-2-fluoro-3-methylphenyl]-N-[(3R*)-4,4-difluoro-1-(hydroxyacetyl)pyrrolidin-3-yl]-6-methyl-5H-pyrrolo[3,2-d]pyrimidine-7-carboxamide |
| P913 | 4-[6-(Cyclopropylmethoxy)-2-fluoro-3-methylphenyl]-N-{(3R*)-4,4-difluoro-1-[(2S)-2-hydroxypropanoyl]pyrrolidin-3-yl}-6-methyl-5H-pyrrolo[3,2-d]pyrimidine-7-carboxamide |
| P914 | N-[(1S*,3S*)-3-(Acetylamino)cyclopentyl]-4-[6-(cyclopropylmethoxy)-2-fluoro-3-methylphenyl]-6-methyl-5H-pyrrolo[3,2-d]pyrimidine-7-carboxamide |
| P915 | 4-[6-(Cyclopropylmethoxy)-2-fluoro-3-methylphenyl]-6-methyl-N-[(1S*,3S*)-3-(propanoylamino)cyclopentyl]-5H-pyrrolo[3,2-d]pyrimidine-7-carboxamide |
| P916 | 4-[6-(Cyclopropylmethoxy)-2-fluoro-3-methylphenyl]-N-{(1S*,3S*)-3-[(methoxyacetyl)amino]cyclopentyl}-6-methyl-5H-pyrrolo[3,2-d]pyrimidine-7-carboxamide |
| P917 | 4-[6-(Cyclopropylmethoxy)-2-fluoro-3-methylphenyl]-N-{(1S*,3S*)-3-[(hydroxyacetyl)amino]cyclopentyl}-6-methyl-5H-pyrrolo[3,2-d]pyrimidine-7-carboxamide |
| P918 | 4-[6-(Cyclopropylmethoxy)-2-fluoro-3-methylphenyl]-N-[(1S*,3S*)-3-{[(2S)-2-hydroxypropanoyl]amino}cyclopentyl]-6-methyl-5H-pyrrolo[3,2-d]pyrimidine-7-carboxamide |
| P919 | N-[(1S*,3R*)-3-(Acetylamino)cyclopentyl]-4-[6-(Cyclopropylmethoxy)-2-fluoro-3-methylphenyl]-6-methyl-5H-pyrrolo[3,2-d]pyrimidine-7-carboxamide |
| P920 | 4-[6-(Cyclopropylmethoxy)-2-fluoro-3-methylphenyl]-6-methyl-N-[(1S*,3R*)-3-(propanoylamino)cyclopentyl]-5H-pyrrolo[3,2-d]pyrimidine-7-carboxamide |
| P921 | 4-[6-(Cyclopropylmethoxy)-2-fluoro-3-methylphenyl]-N-{(1S*,3R*)-3-[(methoxyacetyl)amino]cyclopentyl}-6-methyl-5H-pyrrolo[3,2-d]pyrimidine-7-carboxamide |
| P922 | 4-[6-(Cyclopropylmethoxy)-2-fluoro-3-methylphenyl]-N-{(1S*,3R*)-3-[(hydroxyacetyl)amino]cyclopentyl}-6-methyl-5H-pyrrolo[3,2-d]pyrimidine-7-carboxamide |
| P923 | 4-[6-(Cyclopropylmethoxy)-2-fluoro-3-methylphenyl]-N-[(1S*,3R*)-3-{[(2S)-2-hydroxypropanoyl]amino}cyclopentyl]-6-methyl-5H-pyrrolo[3,2-d]pyrimidine-7-carboxamide |
| P924 | N-[(1R*,2R*,4R*)-4-(Acetylamino)-2-fluorocyclopentyl]-4-[6-(Cyclopropylmethoxy)-2-fluoro-3-methylphenyl]-6-methyl-5H-pyrrolo[3,2-d]pyrimidine-7-carboxamide |
| P925 | 4-[6-(Cyclopropylmethoxy)-2-fluoro-3-methylphenyl]-N-[(1R*,2R*,4R*)-2-fluoro-4-(propanoylamino)cyclopentyl]-6-methyl-5H-pyrrolo[3,2-d]pyrimidine-7-carboxamide |
| P926 | 4-[6-(Cyclopropylmethoxy)-2-fluoro-3-methylphenyl]-N-{(1R*,2R*,4R*)-2-fluoro-4-[(methoxyacetyl)amino]cyclopentyl}-6-methyl-5H-pyrrolo[3,2-d]pyrimidine-7-carboxamide |
| P927 | 4-[6-(Cyclopropylmethoxy)-2-fluoro-3-methylphenyl]-N-{(1R*,2R*,4R*)-2-fluoro-4-[(hydroxyacetyl)amino]cyclopentyl}-6-methyl-5H-pyrrolo[3,2-d]pyrimidine-7-carboxamide |
| P928 | 4-[6-(Cyclopropylmethoxy)-2-fluoro-3-methylphenyl]-N-[(1R*,2R*,4R*)-2-fluoro-4-{[(2S)-2-hydroxypropanoyl]amino}cyclopentyl]-6-methyl-5H-pyrrolo[3,2-d]pyrimidine-7-carboxamide |
| P929 | N-[(1R*,2R*,4S*)-4-(Acetylamino)-2-fluorocyclopentyl]-4-[6-(cyclopropylmethoxy)-2-fluoro-3-methylphenyl]-6-methyl-5H-pyrrolo[3,2-d]pyrimidine-7-carboxamide |
| P930 | 4-[6-(Cyclopropylmethoxy)-2-fluoro-3-methylphenyl]-N-[(1R*,2R*,4S*)-2-fluoro-4-(propanoylamino)cyclopentyl]-6-methyl-5H-pyrrolo[3,2-d]pyrimidine-7-carboxamide |
| P931 | 4-[6-(Cyclopropylmethoxy)-2-fluoro-3-methylphenyl]-N-{(1R*,2R*,4S*)-2-fluoro-4-[(methoxyacetyl)amino]cyclopentyl}-6-methyl-5H-pyrrolo[3,2-d]pyrimidine-7-carboxamide |
| P932 | 4-[6-(Cyclopropylmethoxy)-2-fluoro-3-methylphenyl]-N-{(1R*,2R*,4S*)-2-fluoro-4-[(hydroxyacetyl)amino]cyclopentyl}-6-methyl-5H-pyrrolo[3,2-d]pyrimidine-7-carboxamide |
| P933 | 4-[6-(Cyclopropylmethoxy)-2-fluoro-3-methylphenyl]-N-[(1R*,2R*,4S*)-2-fluoro-4-{[(2S)-2-hydroxypropanoyl]amino}cyclopentyl]-6-methyl-5H-pyrrolo[3,2-d]pyrimidine-7-carboxamide |
| P934 | 4-[6-(Cyclopropylmethoxy)-2-fluoro-3-methylphenyl]-N-[(1R,2S)-2-hydroxycyclohexyl]-6-methyl-5H-pyrrolo[3,2-d]pyrimidine-7-carboxamide |
| P935 | 4-[6-(Cyclopropylmethoxy)-2-fluoro-3-methylphenyl]-N-[(1R,2R)-2-hydroxycyclohexyl]-6-methyl-5H-pyrrolo[3,2-d]pyrimidine-7-carboxamide |
| P926 | 4-[6-(Cyclopropylmethoxy)-2-fluoro-3-methylphenyl]-N-[(1S,2S)-2-hydroxycyclohexyl]-6-methyl-5H-pyrrolo[3,2-d]pyrimidine-7-carboxamide |
| P937 | 4-[6-(Cyclopropylmethoxy)-2-fluoro-3-methylphenyl]-N-[(1S,2R)-2-hydroxycyclohexyl]-6-methyl-5H-pyrrolo[3,2-d]pyrimidine-7-carboxamide |
| P938 | 4-[6-(Cyclopropylmethoxy)-2-fluoro-3-methylphenyl]-N-[(1S,3R)-3-hydroxycyclohexyl]-6-methyl-5H-pyrrolo[3,2-d]pyrimidine-7-carboxamide |
| P939 | 4-[6-(Cyclopropylmethoxy)-2-fluoro-3-methylphenyl]-N-[(1S,3S)-3-hydroxycyclohexyl]-6-methyl-5H-pyrrolo[3,2-d]pyrimidine-7-carboxamide |
| P940 | 4-[6-(Cyclopropylmethoxy)-2-fluoro-3-methylphenyl]-N-[(1R,3R)-3-hydroxycyclohexyl]-6-methyl-5H-pyrrolo[3,2-d]pyrimidine-7-carboxamide |
| P941 | 4-[6-(Cyclopropylmethoxy)-2-fluoro-3-methylphenyl]-N-[(1R,3S)-3-hydroxycyclohexyl]-6-methyl-5H-pyrrolo[3,2-d]pyrimidine-7-carboxamide |
| P942 | 4-[6-(Cyclopropylmethoxy)-2-fluoro-3-methylphenyl]-N-(trans-4-hydroxycyclohexyl)-6-methyl-5H-pyrrolo[3,2-d]pyrimidine-7-carboxamide |
| P943 | 4-[6-(Cyclopropylmethoxy)-2-fluoro-3-methylphenyl]-N-(cis-4-hydroxycyclohexyl)-6-methyl-5H-pyrrolo[3,2-d]pyrimidine-7-carboxamide |
| P944 | N-[(3S,4R)-1-Acetyl-3-fluoropiperidin-4-yl]-4-[6-(cyclopropylmethoxy)-2-fluoro-3-methylphenyl]-6-methyl-5H-pyrrolo[3,2-d]pyrimidine-7-carboxamide |
| P945 | 4-[6-(Cyclopropylmethoxy)-2-fluoro-3-methylphenyl]-N-[(3S,4R)-3-fluoro-1-propanoylpiperidin-4-yl]-6-methyl-5H-pyrrolo[3,2-d]pyrimidine-7-carboxamide |
| P946 | 4-[6-(Cyclopropylmethoxy)-2-fluoro-3-methylphenyl]-N-[(3S,4R)-3-fluoro-1-(methoxyacetyl)piperidin-4-yl]-6-methyl-5H-pyrrolo[3,2-d]pyrimidine-7-carboxamide |
| P947 | 4-[6-(Cyclopropylmethoxy)-2-fluoro-3-methylphenyl]-N-[(3S,4R)-3-fluoro-1-(hydroxyacetyl)piperidin-4-yl]-6-methyl-5H-pyrrolo[3,2-d]pyrimidine-7-carboxamide |

| | |
|---|---|
| P948 | 4-[6-(Cyclopropylmethoxy)-2-fluoro-3-methylphenyl]-N-{(3S,4R)-3-fluoro-1-[(2S)-2-hydroxypropanoyl]piperidin-4-yl}-6-methyl-5H-pyrrolo[3,2-d]pyrimidine-7-carboxamide |
| P949 | N-[(3R,4R)-1-Acetyl-3-fluoropiperidin-4-yl]-4-[6-(cyclopropylmethoxy)-2-fluoro-3-methylphenyl]-6-methyl-5H-pyrrolo[3,2-d]pyrimidine-7-carboxamide |
| P950 | 4-[6-(Cyclopropylmethoxy)-2-fluoro-3-methylphenyl]-N-[(3R,4R)-3-fluoro-1-propanoylpiperidin-4-yl]-6-methyl-5H-pyrrolo[3,2-d]pyrimidine-7-carboxamide |
| P951 | 4-[6-(Cyclopropylmethoxy)-2-fluoro-3-methylphenyl]-N-[(3R,4R)-3-fluoro-1-(methoxyacetyl)piperidin-4-yl]-6-methyl-5H-pyrrolo[3,2-d]pyrimidine-7-carboxamide |
| P952 | 4-[6-(Cyclopropylmethoxy)-2-fluoro-3-methylphenyl]-N-[(3R,4R)-3-fluoro-1-(hydroxyacetyl)piperidin-4-yl]-6-methyl-5H-pyrrolo[3,2-d]pyrimidine-7-carboxamide |
| P953 | 4-[6-(Cyclopropylmethoxy)-2-fluoro-3-methylphenyl]-N-{(3R,4R)-3-fluoro-1-[(2S)-2-hydroxypropanoyl]piperidin-4-yl}-6-methyl-5H-pyrrolo[3,2-d]pyrimidine-7-carboxamide |
| P954 | N-[(3S,4S)-1-Acetyl-3-fluoropiperidin-4-yl]-4-[6-(cyclopropylmethoxy)-2-fluoro-3-methylphenyl]-6-methyl-5H-pyrrolo[3,2-d]pyrimidine-7-carboxamide |
| P955 | 4-[6-(Cyclopropylmethoxy)-2-fluoro-3-methylphenyl]-N-[(3S,4S)-3-fluoro-1-propanoylpiperidin-4-yl]-6-methyl-5H-pyrrolo[3,2-d]pyrimidine-7-carboxamide |
| P956 | 4-[6-(Cyclopropylmethoxy)-2-fluoro-3-methylphenyl]-N-[(3S,4S)-3-fluoro-1-(methoxyacetyl)piperidin-4-yl]-6-methyl-5H-pyrrolo[3,2-d]pyrimidine-7-carboxamide |
| P957 | 4-[6-(Cyclopropylmethoxy)-2-fluoro-3-methylphenyl]-N-[(3S,4S)-3-fluoro-1-(hydroxyacetyl)piperidin-4-yl]-6-methyl-5H-pyrrolo[3,2-d]pyrimidine-7-carboxamide |
| P958 | 4-[6-(Cyclopropylmethoxy)-2-fluoro-3-methylphenyl]-N-{(3S,4S)-3-fluoro-1-[(2S)-2-hydroxypropanoyl]piperidin-4-yl}-6-methyl-5H-pyrrolo[3,2-d]pyrimidine-7-carboxamide |
| P959 | N-[(3R,4S)-1-Acetyl-3-fluoropiperidin-4-yl]-4-[6-(cyclopropylmethoxy)-2-fluoro-3-methylphenyl]-6-methyl-5H-pyrrolo[3,2-d]pyrimidine-7-carboxamide |
| P960 | 4-[6-(Cyclopropylmethoxy)-2-fluoro-3-methylphenyl]-N-[(3R,4S)-3-fluoro-1-propanoylpiperidin-4-yl]-6-methyl-5H-pyrrolo[3,2-d]pyrimidine-7-carboxamide |
| P961 | 4-[6-(Cyclopropylmethoxy)-2-fluoro-3-methylphenyl]-N-[(3R,4S)-3-fluoro-1-(methoxyacetyl)piperidin-4-yl]-6-methyl-5H-pyrrolo[3,2-d]pyrimidine-7-carboxamide |
| P962 | 4-[6-(Cyclopropylmethoxy)-2-fluoro-3-methylphenyl]-N-[(3R,4S)-3-fluoro-1-(hydroxyacetyl)piperidin-4-yl]-6-methyl-5H-pyrrolo[3,2-d]pyrimidine-7-carboxamide |
| P963 | 4-[6-(Cyclopropylmethoxy)-2-fluoro-3-methylphenyl]-N-{(3R,4S)-3-fluoro-1-[(2S)-2-hydroxypropanoyl]piperidin-4-yl}-6-methyl-5H-pyrrolo[3,2-d]pyrimidine-7-carboxamide |
| P964 | N-[(1R*,2R*,4R*)-4-(Acetylamino)-2-methylcyclohexyl]-4-[6-(Cyclopropylmethoxy)-2-fluoro-3-methylphenyl]-6-methyl-5H-pyrrolo[3,2-d]pyrimidine-7-carboxamide |
| P965 | 4-[6-(Cyclopropylmethoxy)-2-fluoro-3-methylphenyl]-6-methyl-N-[(1R*,2R*,4R*)-2-methyl-4-(propanoylamino)cyclohexyl]-5H-pyrrolo[3,2-d]pyrimidine-7-carboxamide |
| P966 | 4-[6-(Cyclopropylmethoxy)-2-fluoro-3-methylphenyl]-N-{(1R*,2R*,4R*)-4-[(methoxyacetyl)amino]-2-methylcyclohexyl}-6-methyl-5H-pyrrolo[3,2-d]pyrimidine-7-carboxamide |
| P967 | 4-[6-(Cyclopropylmethoxy)-2-fluoro-3-methylphenyl]-N-{(1R*,2R*,4R*)-4-[(hydroxyacetyl)amino]-2-methylcyclohexyl}-6-methyl-5H-pyrrolo[3,2-d]pyrimidine-7-carboxamide |
| P968 | 4-[6-(Cyclopropylmethoxy)-2-fluoro-3-methylphenyl]-N-[(1R*,2R*,4R*)-4-{[(2S)-2-hydroxypropanoyl]amino}-2-methylcyclohexyl]-6-methyl-5H-pyrrolo[3,2-d]pyrimidine-7-carboxamide |
| P969 | N-[(1R*,2R*,4S*)-4-(acetylamino)-2-methylcyclohexyl]-4-[6-(cyclopropylmethoxy)-2-fluoro-3-methylphenyl]-6-methyl-5H-pyrrolo[3,2-d]pyrimidine-7-carboxamide |
| P970 | 4-[6-(Cyclopropylmethoxy)-2-fluoro-3-methylphenyl]-6-methyl-N-[(1R*,2R*,4S*)-2-methyl-4-(propanoylamino)cyclohexyl]-5H-pyrrolo[3,2-d]pyrimidine-7-carboxamide |
| P971 | 4-[6-(Cyclopropylmethoxy)-2-fluoro-3-methylphenyl]-N-{(1R*,2R*,4S*)-4-[(methoxyacetyl)amino]-2-methylcyclohexyl}-6-methyl-5H-pyrrolo[3,2-d]pyrimidine-7-carboxamide |
| P972 | 4-[6-(Cyclopropylmethoxy)-2-fluoro-3-methylphenyl]-N-{(1R*,2R*,4S*)-4-[(hydroxyacetyl)amino]-2-methylcyclohexyl}-6-methyl-5H-pyrrolo[3,2-d]pyrimidine-7-carboxamide |
| P973 | 4-[6-(Cyclopropylmethoxy)-2-fluoro-3-methylphenyl]-N-[(1R*,2R*,4S*)-4-{[(2S)-2-hydroxypropanoyl]amino}-2-methylcyclohexyl]-6-methyl-5H-pyrrolo[3,2-d]pyrimidine-7-carboxamide |
| P974 | N-[(1S*,2R*,4S*)-4-(acetylamino)-2-methylcyclohexyl]-4-[6-(cyclopropylmethoxy)-2-fluoro-3-methylphenyl]-6-methyl-5H-pyrrolo[3,2-d]pyrimidine-7-carboxamide |
| P975 | 4-[6-(Cyclopropylmethoxy)-2-fluoro-3-methylphenyl]-6-methyl-N-[(1S*,2R*,4S*)-2-methyl-4-(propanoylamino)cyclohexyl]-5H-pyrrolo[3,2-d]pyrimidine-7-carboxamide |
| P976 | 4-[6-(Cyclopropylmethoxy)-2-fluoro-3-methylphenyl]-N-{(1S*,2R*,4S*)-4-[(methoxyacetyl)amino]-2-methylcyclohexyl}-6-methyl-5H-pyrrolo[3,2-d]pyrimidine-7-carboxamide |
| P977 | 4-[6-(Cyclopropylmethoxy)-2-fluoro-3-methylphenyl]-N-{(1S*,2R*,4S*)-4-[(hydroxyacetyl)amino]-2-methylcyclohexyl}-6-methyl-5H-pyrrolo[3,2-d]pyrimidine-7-carboxamide |
| P978 | 4-[6-(Cyclopropylmethoxy)-2-fluoro-3-methylphenyl]-N-[(1S*,2R*,4S*)-4-{[(2S)-2-hydroxypropanoyl]amino}-2-methylcyclohexyl]-6-methyl-5H-pyrrolo[3,2-d]pyrimidine-7-carboxamide |
| P979 | N-[(1S*,2R*,4R*)-4-(Acetylamino)-2-methylcyclohexyl]-4-[6-(cyclopropylmethoxy)-2-fluoro-3-methylphenyl]-6-methyl-5H-pyrrolo[3,2-d]pyrimidine-7-carboxamide |
| P980 | 4-[6-(Cyclopropylmethoxy)-2-fluoro-3-methylphenyl]-6-methyl-N-[(1S*,2R*,4R*)-2-methyl-4-(propanoylamino)cyclohexyl]-5H-pyrrolo[3,2-d]pyrimidine-7-carboxamide |
| P981 | 4-[6-(Cyclopropylmethoxy)-2-fluoro-3-methylphenyl]-N-{(1S*,2R*,4R*)-4-[(methoxyacetyl)amino]-2-methylcyclohexyl}-6-methyl-5H-pyrrolo[3,2-d]pyrimidine-7-carboxamide |
| P982 | 4-[6-(Cyclopropylmethoxy)-2-fluoro-3-methylphenyl]-N-{(1S*,2R*,4R*)-4-[(hydroxyacetyl)amino]-2-methylcyclohexyl}-6-methyl-5H-pyrrolo[3,2-d]pyrimidine-7-carboxamide |
| P983 | 4-[6-(Cyclopropylmethoxy)-2-fluoro-3-methylphenyl]-N-[(1S*,2R*,4R*)-4-{[(2S)-2-hydroxypropanoyl]amino}-2-methylcyclohexyl]-6-methyl-5H-pyrrolo[3,2-d]pyrimidine-7-carboxamide |
| P984 | N-[(1R*,2R*,4R*)-4-(Acetylamino)-2-fluorocyclohexyl]-4-[6-(cyclopropylmethoxy)-2-fluoro-3-methylphenyl]-6-methyl-5H-pyrrolo[3,2-d]pyrimidine-7-carboxamide |

-continued

| | |
|---|---|
| P985 | 4-[6-(Cyclopropylmethoxy)-2-fluoro-3-methylphenyl]-N-[(1R*,2R*,4R*)-2-fluoro-4-(propanoylamino)cyclohexyl]-6-methyl-5H-pyrrolo[3,2-d]pyrimidine-7-carboxamide |
| P986 | 4-[6-(Cyclopropylmethoxy)-2-fluoro-3-methylphenyl]-N-{(1R*,2R*,4R*)-2-fluoro-4-[(methoxyacetyl)amino]cyclohexyl}-6-methyl-5H-pyrrolo[3,2-d]pyrimidine-7-carboxamide |
| P987 | 4-[6-(Cyclopropylmethoxy)-2-fluoro-3-methylphenyl]-N-{(1R*,2R*,4R*)-2-fluoro-4-[(hydroxyacetyl)amino]cyclohexyl}-6-methyl-5H-pyrrolo[3,2-d]pyrimidine-7-carboxamide |
| P988 | 4-[6-(Cyclopropylmethoxy)-2-fluoro-3-methylphenyl]-N-[(1R*,2R*,4R*)-2-fluoro-4-{[(2S)-2-hydroxypropanoyl]amino}cyclohexyl]-6-methyl-5H-pyrrolo[3,2-d]pyrimidine-7-carboxamide |
| P989 | N-[(1R*,2R*,4S*)-4-(Acetylamino)-2-fluorocyclohexyl]-4-[6-(cyclopropylmethoxy)-2-fluoro-3-methylphenyl]-6-methyl-5H-pyrrolo[3,2-d]pyrimidine-7-carboxamide |
| P990 | 4-[6-(Cyclopropylmethoxy)-2-fluoro-3-methylphenyl]-N-[(1R*,2R*,4S*)-2-fluoro-4-(propanoylamino)cyclohexyl]-6-methyl-5H-pyrrolo[3,2-d]pyrimidine-7-carboxamide |
| P991 | 4-[6-(Cyclopropylmethoxy)-2-fluoro-3-methylphenyl]-N-{(1R*,2R*,4S*)-2-fluoro-4-[(methoxyacetyl)amino]cyclohexyl}-6-methyl-5H-pyrrolo[3,2-d]pyrimidine-7-carboxamide |
| P992 | 4-[6-(Cyclopropylmethoxy)-2-fluoro-3-methylphenyl]-N-{(1R*,2R*,4S*)-2-fluoro-4-[(hydroxyacetyl)amino]cyclohexyl}-6-methyl-5H-pyrrolo[3,2-d]pyrimidine-7-carboxamide |
| P993 | 4-[6-(Cyclopropylmethoxy)-2-fluoro-3-methylphenyl]-N-[(1R*,2R*,4S*)-2-fluoro-4-{[(2S)-2-hydroxypropanoyl]amino}cyclohexyl]-6-methyl-5H-pyrrolo[3,2-d]pyrimidine-7-carboxamide |
| P994 | N-[(1S*,2R*,4S*)-4-(Acetylamino)-2-fluorocyclohexyl]-4-[6-(Cyclopropylmethoxy)-2-fluoro-3-methylphenyl]-6-methyl-5H-pyrrolo[3,2-d]pyrimidine-7-carboxamide |
| P994 | 4-[6-(Cyclopropylmethoxy)-2-fluoro-3-methylphenyl]-N-[(1S*,2R*,4S*)-2-fluoro-4-(propanoylamino)cyclohexyl]-6-methyl-5H-pyrrolo[3,2-d]pyrimidine-7-carboxamide |
| P996 | 4-[6-(Cyclopropylmethoxy)-2-fluoro-3-methylphenyl]-N-{(1S*,2R*,4S*)-2-fluoro-4-[(methoxyacetyl)amino]cyclohexyl}-6-methyl-5H-pyrrolo[3,2-d]pyrimidine-7 -carboxamide |
| P997 | 4-[6-(Cyclopropylmethoxy)-2-fluoro-3-methylphenyl]-N-{(1S*,2R*,4S*)-2-fluoro-4-[(hydroxyacetyl)amino]cyclohexyl}-6-methyl-5H-pyrrolo[3,2-d]pyrimidine-7-carboxamide |
| P998 | 4-[6-(Cyclopropylmethoxy)-2-fluoro-3-methylphenyl]-N-[(1S*,2R*,4S*)-2-fluoro-4-{[(2S)-2-hydroxypropanoyl]amino}cyclohexyl]-6-methyl-5H-pyrrolo[3,2-d]pyrimidine-7-carboxamide |
| P999 | N-[(1S*,2R*,4R*)-4-(Acetylamino)-2-fluorocyclohexyl]-4-[6-(Cyclopropylmethoxy)-2-fluoro-3-methylphenyl]-6-methyl-5H-pyrrolo[3,2-d]pyrimidine-7-carboxamide |
| P1000 | 4-[6-(Cyclopropylmethoxy)-2-fluoro-3-methylphenyl]-N-[(1S*,2R*,4R*)-2-fluoro-4-(propanoylamino)cyclohexyl]-6-methyl-5H-pyrrolo[3,2-d]pyrimidine-7-carboxamide |
| P1001 | 4-[6-(Cyclopropylmethoxy)-2-fluoro-3-methylphenyl]-N-{(1S*,2R*,4R*)-2-fluoro-4-[(methoxyacetyl)amino]cyclohexyl}-6-methyl-5H-pyrrolo[3,2-d]pyrimidine-7-carboxamide |
| P1002 | 4-[6-(Cyclopropylmethoxy)-2-fluoro-3-methylphenyl]-N-{(1S*,2R*,4R*)-2-fluoro-4-[(hydroxyacetyl)amino]cyclohexyl}-6-methyl-5H-pyrrolo[3,2-d]pyrimidine-7-carboxamide |
| P1003 | 4-[6-(Cyclopropylmethoxy)-2-fluoro-3-methylphenyl]-N-[(1S*,2R*,4R*)-2-fluoro-4-{[(2S)-2-hydroxypropanoyl]amino}cyclohexyl]-6-methyl-5H-pyrrolo[3,2-d]pyrimidine-7-carboxamide |
| P1004 | N-[(1S*,3R*,4S*)-4-(acetylamino)-3-methylcyclohexyl]-4-[6-(Cyclopropylmethoxy)-2-fluoro-3-methylphenyl]-6-methyl-5H-pyrrolo[3,2-d]pyrimidine-7-carboxamide |
| P1005 | 4-[6-(Cyclopropylmethoxy)-2-fluoro-3-methylphenyl]-6-methyl-N-[(1S*,3R*,4S*)-3-methyl-4-(propanoylamino)cyclohexyl]-5H-pyrrolo[3,2-d]pyrimidine-7-carboxamide |
| P1006 | 4-[6-(Cyclopropylmethoxy)-2-fluoro-3-methylphenyl]-N-{(1S*,3R*,4S*)-4-[(methoxyacetyl)amino]-3-methylcyclohexyl}-6-methyl-5H-pyrrolo[3,2-d]pyrimidine-7-carboxamide |
| P1007 | 4-[6-(Cyclopropylmethoxy)-2-fluoro-3-methylphenyl]-N-{(1S*,3R*,4S*)-4-[(hydroxyacetyl)amino]-3-methylcyclohexyl}-6-methyl-5H-pyrrolo[3,2-d]pyrimidine-7-carboxamide |
| P1008 | 4-[6-(Cyclopropylmethoxy)-2-fluoro-3-methylphenyl]-N-[(1S*,3R*,4S*)-4-{[(2S)-2-hydroxypropanoyl]amino}-3-methylcyclohexyl]-6-methyl-5H-pyrrolo[3,2-d]pyrimidine-7-carboxamide |
| P1009 | N-[(1S*,3R*,4R*)-4-(Acetylamino)-3-methylcyclohexyl]-4-[6-(cyclopropylmethoxy)-2-fluoro-3-methylphenyl]-6-methyl-5H-pyrrolo[3,2-d]pyrimidine-7-carboxamide |
| P1010 | 4-[6-(Cyclopropylmethoxy)-2-fluoro-3-methylphenyl]-6-methyl-N-[(1S*,3R*,4R*)-3-methyl-4-(propanoylamino)cyclohexyl]-5H-pyrrolo[3,2-d]pyrimidine-7-carboxamide |
| P1011 | 4-[6-(Cyclopropylmethoxy)-2-fluoro-3-methylphenyl]-N-{(1S*,3R*,4R*)-4-[(methoxyacetyl)amino]-3-methylcyclohexyl}-6-methyl-5H-pyrrolo[3,2-d]pyrimidine-7-carboxamide |
| P1012 | 4-[6-(Cyclopropylmethoxy)-2-fluoro-3-methylphenyl]-N-{(1S*,3R*,4R*)-4-[(hydroxyacetyl)amino]-3-methylcyclohexyl}-6-methyl-5H-pyrrolo[3,2-d]pyrimidine-7-carboxamide |
| P1013 | 4-[6-(Cyclopropylmethoxy)-2-fluoro-3-methylphenyl]-N-[(1S*,3R*,4R*)-4-{[(2S)-2-hydroxypropanoyl]amino}-3-methylcyclohexyl]-6-methyl-5H-pyrrolo[3,2-d]pyrimidine-7-carboxamide |
| P1014 | N-[(1R*,3R*,4R*)-4-(acetylamino)-3-methylcyclohexyl]-4-[6-(cyclopropylmethoxy)-2-fluoro-3-methylphenyl]-6-methyl-5H-pyrrolo[3,2-d]pyrimidine-7-carboxamide |
| P1015 | 4-[6-(Cyclopropylmethoxy)-2-fluoro-3-methylphenyl]-6-methyl-N-[(1R*,3R*,4R*)-3-methyl-4-(propanoylamino)cyclohexyl]-5H-pyrrolo[3,2-d]pyrimidine-7-carboxamide |
| P1016 | 4-[6-(Cyclopropylmethoxy)-2-fluoro-3-methylphenyl]-N-{(1R*,3R*,4R*)-4-[(methoxyacetyl)amino]-3-methylcyclohexyl}-6-methyl-5H-pyrrolo[3,2-d]pyrimidine-7-carboxamide |
| P1017 | 4-[6-(Cyclopropylmethoxy)-2-fluoro-3-methylphenyl]-N-{(1R*,3R*,4R*)-4-[(hydroxyacetyl)amino]-3-methylcyclohexyl}-6-methyl-5H-pyrrolo[3,2-d]pyrimidine-7-carboxamide |
| P1018 | 4-[6-(Cyclopropylmethoxy)-2-fluoro-3-methylphenyl]-N-[(1R*,3R*,4R*)-4-{[(2S)-2-hydroxypropanoyl]amino}-3-methylcyclohexyl]-6-methyl-5H-pyrrolo[3,2-d]pyrimidine-7-carboxamide |
| P1019 | N-[(1R*,3R*,4S*)-4-(Acetylamino)-3-methylcyclohexyl]-4-[6-(Cyclopropylmethoxy)-2-fluoro-3-methylphenyl]-6-methyl-5H-pyrrolo[3,2-d]pyrimidine-7-carboxamide |

| | -continued |
|---|---|
| P1020 | 4-[6-(Cyclopropylmethoxy)-2-fluoro-3-methylphenyl]-6-methyl-N-[(1R*,3R*,4S*)-3-methyl-4-(propanoylamino)cyclohexyl]-5H-pyrrolo[3,2-d]pyrimidine-7-carboxamide |
| P1021 | 4-[6-(Cyclopropylmethoxy)-2-fluoro-3-methylphenyl]-N-{(1R*,3R*,4S*)-4-[(methoxyacetyl)amino]-3-methylcyclohexyl}-6-methyl-5H-pyrrolo[3,2-d]pyrimidine-7-carboxamide |
| P1022 | 4-[6-(Cyclopropylmethoxy)-2-fluoro-3-methylphenyl]-N-{(1R*,3R*,4S*)-4-[(hydroxyacetyl)amino]-3-methylcyclohexyl}-6-methyl-5H-pyrrolo[3,2-d]pyrimidine-7-carboxamide |
| P1023 | 4-[6-(Cyclopropylmethoxy)-2-fluoro-3-methylphenyl]-N-[(1R*,3R*,4S*)-4-{[(2S)-2-hydroxypropanoyl]amino}-3-methylcyclohexyl]-6-methyl-5H-pyrrolo[3,2-d]pyrimidine-7-carboxamide |
| P1024 | N-[(1S*,3R*,4S*)-4-(acetylamino)-3-fluorocyclohexyl]-4-[6-(Cyclopropylmethoxy)-2-fluoro-3-methylphenyl]-6-methyl-5H-pyrrolo[3,2-d]pyrimidine-7-carboxamide |
| P1025 | 4-[6-(Cyclopropylmethoxy)-2-fluoro-3-methylphenyl]-N-[(1S*,3R*,4S*)-3-fluoro-4-(propanoylamino)cyclohexyl]-6-methyl-5H-pyrrolo[3,2-d]pyrimidine-7-carboxamide |
| P1026 | 4-[6-(Cyclopropylmethoxy)-2-fluoro-3-methylphenyl]-N-{(1S*,3R*,4S*)-3-fluoro-4-[(methoxyacetyl)amino]cyclohexyl}-6-methyl-5H-pyrrolo[3,2-d]pyrimidine-7-carboxamide |
| P1027 | 4-[6-(Cyclopropylmethoxy)-2-fluoro-3-methylphenyl]-N-{(1S*,3R*,4S*)-3-fluoro-4-[(hydroxyacetyl)amino]cyclohexyl}-6-methyl-5H-pyrrolo[3,2-d]pyrimidine-7-carboxamide |
| P1028 | 4-[6-(Cyclopropylmethoxy)-2-fluoro-3-methylphenyl]-N-[(1S*,3R*,4S*)-3-fluoro-4-{[(2S)-2-hydroxypropanoyl]amino}cyclohexyl]-6-methyl-5H-pyrrolo[3,2-d]pyrimidine-7-carboxamide |
| P1029 | N-[(1S*,3R*,4R*)-4-(acetylamino)-3-fluorocyclohexyl]-4-[6-(cyclopropylmethoxy)-2-fluoro-3-methylphenyl]-6-methyl-5H-pyrrolo[3,2-d]pyrimidine-7-carboxamide |
| P1030 | 4-[6-(Cyclopropylmethoxy)-2-fluoro-3-methylphenyl]-N-[(1S*,3R*,4R*)-3-fluoro-4-(propanoylamino)cyclohexyl]-6-methyl-5H-pyrrolo[3,2-d]pyrimidine-7-carboxamide |
| P1031 | 4-[6-(Cyclopropylmethoxy)-2-fluoro-3-methylphenyl]-N-{(1S*,3R*,4R*)-3-fluoro-4-[(methoxyacetyl)amino]cyclohexyl}-6-methyl-5H-pyrrolo[3,2-d]pyrimidine-7-carboxamide |
| P1032 | 4-[6-(Cyclopropylmethoxy)-2-fluoro-3-methylphenyl]-N-{(1S*,3R*,4R*)-3-fluoro-4-[(hydroxyacetyl)amino]cyclohexyl}-6-methyl-5H-pyrrolo[3,2-d]pyrimidine-7-carboxamide |
| P1033 | 4-[6-(Cyclopropylmethoxy)-2-fluoro-3-methylphenyl]-N-[(1S*,3R*,4R*)-3-fluoro-4-{[(2S)-2-hydroxypropanoyl]amino}cyclohexyl]-6-methyl-5H-pyrrolo[3,2-d]pyrimidine-7-carboxamide |
| P1034 | N-[(1R*,3R*,4R*)-4-(Acetylamino)-3-fluorocyclohexyl]-4-[6-(Cyclopropylmethoxy)-2-fluoro-3-methylphenyl]-6-methyl-5H-pyrrolo[3,2-d]pyrimidine-7-carboxamide |
| P1035 | 4-[6-(Cyclopropylmethoxy)-2-fluoro-3-methylphenyl]-N-[(1R*,3R*,4R*)-3-fluoro-4-(propanoylamino)cyclohexyl]-6-methyl-5H-pyrrolo[3,2-d]pyrimidine-7-carboxamide |
| P1036 | 4-[6-(Cyclopropylmethoxy)-2-fluoro-3-methylphenyl]-N-{(1R*,3R*,4R*)-3-fluoro-4-[(methoxyacetyl)amino]cyclohexyl}-6-methyl-5H-pyrrolo[3,2-d]pyrimidine-7-carboxamide |
| P1037 | 4-[6-(Cyclopropylmethoxy)-2-fluoro-3-methylphenyl]-N-{(1R*,3R*,4R*)-3-fluoro-4-[(hydroxyacetyl)amino]cyclohexyl}-6-methyl-5H-pyrrolo[3,2-d]pyrimidine-7-carboxamide |
| P1038 | 4-[6-(Cyclopropylmethoxy)-2-fluoro-3-methylphenyl]-N-[(1R*,3R*,4R*)-3-fluoro-4-{[(2S)-2-hydroxypropanoyl]amino}cyclohexyl]-6-methyl-5H-pyrrolo[3,2-d]pyrimidine-7-carboxamide |
| P1039 | N-[(1R*,3R*,4S*)-4-(Acetylamino)-3-fluorocyclohexyl]-4-[6-(cyclopropylmethoxy)-2-fluoro-3-methylphenyl]-6-methyl-5H-pyrrolo[3,2-d]pyrimidine-7-carboxamide |
| P1040 | 4-[6-(Cyclopropylmethoxy)-2-fluoro-3-methylphenyl]-N-[(1R*,3R*,4S*)-3-fluoro-4-(propanoylamino)cyclohexyl]-6-methyl-5H-pyrrolo[3,2-d]pyrimidine-7-carboxamide |
| P1041 | 4-[6-(Cyclopropylmethoxy)-2-fluoro-3-methylphenyl]-N-{(1R*,3R*,4S*)-3-fluoro-4-[(methoxyacetyl)amino]cyclohexyl}-6-methyl-5H-pyrrolo[3,2-d]pyrimidine-7-carboxamide |
| P1042 | 4-[6-(Cyclopropylmethoxy)-2-fluoro-3-methylphenyl]-N-{(1R*,3R*,4S*)-3-fluoro-4-[(hydroxyacetyl)amino]cyclohexyl}-6-methyl-5H-pyrrolo[3,2-d]pyrimidine-7-carboxamide |
| P1043 | 4-[6-(Cyclopropylmethoxy)-2-fluoro-3-methylphenyl]-N-[(1R*,3R*,4S*)-3-fluoro-4-{[(2S)-2-hydroxypropanoyl]amino}cyclohexyl]-6-methyl-5H-pyrrolo[3,2-d]pyrimidine-7-carboxamide |
| P1044 | 4-[2-(cyclopropylmethoxy)-5-methylphenyl]-N-[(1R*,2S*)-2-fluorocyclopentyl]-6-methyl-5H-pyrrolo[3,2-d]pyrimidine-7-carboxamide |
| P1045 | 4-[2-(cyclopropylmethoxy)-5-methylphenyl]-N-[(1R*,2R*)-2-fluorocyclopentyl]-6-methyl-5H-pyrrolo[3,2-d]pyrimidine-7-carboxamide |
| P1046 | 4-[2-(cyclopropylmethoxy)-5-methylphenyl]-N-[(1R*,2S*)-2-fluorocyclohexyl]-6-methyl-5H-pyrrolo[3,2-d]pyrimidine-7-carboxamide |
| P1047 | 4-[2-(cyclopropylmethoxy)-5-methylphenyl]-N-[(1R*,2R*)-2-fluorocyclohexyl]-6-methyl-5H-pyrrolo[3,2-d]pyrimidine-7-carboxamide |
| P1048 | 4-[2-(cyclopropylmethoxy)-5-methylphenyl]-N-(trans-4-fluorocyclohexyl)-6-methyl-5H-pyrrolo[3,2-d]pyrimidine-7-carboxamide |
| P1049 | 4-[2-(cyclopropylmethoxy)-5-methylphenyl]-N-(cis-4-fluorocyclohexyl)-6-methyl-5H-pyrrolo[3,2-d]pyrimidine-7-carboxamide | a salt thereof, or a stereoisomer of the compound or a salt thereof.

The following compounds of the above table are prepared analogously to the procedure described in above example E1.

Example P1

N-(1-Acetylpiperidin-4-yl)-4-[2-(cyclopropylmethoxy)-5-(difluoromethyl)phenyl]-6-methyl-5H-pyrrolo[3,2-d]pyrimidine-7-carboxamide Starting from 4-[2-(cyclopropylmethoxy)-5-(difluoromethyl)phenyl]-6-methyl-N-(piperidin-4-yl)-5H-pyrrolo[3,2-d]pyrimidine-7-carboxamide hydrochloride (example D.f60) and commercially available acetyl chloride the title compound is obtained as colorless solid.
HR-MS (ESI): m/z=498.2303 ([MH]$^+$, $C_{26}H_{30}F_2N_5O_3^+$, calc. 498.2311).

Example P2

4-[2-(Cyclopropylmethoxy)-5-(difluoromethyl)phenyl]-6-methyl-N-(1-propanoylpiperidin-4-yl)-5H-pyrrolo[3,2-d]pyrimidine-7-carboxamide Starting from 4-[2-(cyclopropylmethoxy)-5-(difluoromethyl)phenyl]-6-methyl-N-(piperidin-4-yl)-5H-pyrrolo[3,2-d]pyrimidine-7-carboxamide hydrochloride (example D.f60) and commercially available propionyl chloride the title compound is obtained as colorless solid.
HR-MS (ESI): m/z=512.2453 ([MH]$^+$, $C_{27}H_{32}F_2N_5O_3^+$, calc. 512.2468).

Example P3

4-[2-(Cyclopropylmethoxy)-5-(difluoromethyl)phenyl]-N-[1-(methoxyacetyl)piperidin-4-yl]-6-methyl-5H-pyrrolo[3,2-d]pyrimidine-7-carboxamide Starting from 4-[2-(cyclopropylmethoxy)-5-(difluoromethyl)phenyl]-6-methyl-N-(piperidin-4-yl)-5H-pyrrolo[3,2-d]pyrimidine-7-carboxamide hydrochloride (example D.f60) and commercially available methoxy-acetyl chloride the title compound is obtained as colorless solid.
HR-MS (ESI): m/z=528.2394 ([MH]$^+$, $C_{27}H_{32}F_2N_5O_4^+$, calc. 528.2417).

Example P6

N-[trans-4-(Acetylamino)cyclohexyl]-4-[2-(cyclopropylmethoxy)-5-(difluoromethyl)phenyl]-6-methyl-5H-pyrrolo[3,2-d]pyrimidine-7-carboxamide Starting from N-(trans-4-aminocyclohexyl)-4-[2-(cyclopropylmethoxy)-5-(difluoromethyl)phenyl]-6-methyl-5H-pyrrolo[3,2-d]pyrimidine-7-carboxamide hydrochloride (example D.f61) and commercially available acetyl chloride the title compound is obtained as colorless solid.
HR-MS (ESI): m/z=512.2457 ([MH]$^+$, $C_{27}H_{32}F_2N_5O_3^+$, calc. 512.2468).

Example P7

4-[2-(Cyclopropylmethoxy)-5-(difluoromethyl)phenyl]-6-methyl-N-[trans-4-(propanoylamino)cyclohexyl]-5$^H$-pyrrolo[3,2-d]pyrimidine-7-carboxamide Starting from N-(trans-4-aminocyclohexyl)-4-[2-(cyclopropylmethoxy)-5-(difluoromethyl)phenyl]-6-methyl-5H-pyrrolo[3,2-d]pyrimidine-7-carboxamide hydrochloride (example D.f61) and commercially available propionyl chloride the title compound is obtained as colorless solid.
HR-MS (ESI): m/z=526.2621 ([MH]$^+$, $C_{28}H_{34}F_2N_5O_3^+$, calc. 526.2624).

Example P8

4-[2-(Cyclopropylmethoxy)-5-(difluoromethyl)phenyl]-N-{trans-4-[(methoxyacetyl)amino]cyclohexyl}-6-methyl-5H-pyrrolo[3,2-d]pyrimidine-7-carboxamide Starting from N-(trans-4-aminocyclohexyl)-4-[2-(cyclopropylmethoxy)-5-(difluoromethyl)phenyl]-6-methyl-5H-pyrrolo[3,2-d]pyrimidine-7-carboxamide hydrochloride (example D.f61) and commercially available methoxy-acetyl chloride the title compound is obtained as colorless solid.
HR-MS (ESI): m/z=542.2571 ([MH]$^+$, $C_{28}H_{34}F_2N_5O_4^+$, calc. 542.2573).

Example P24

N-[(3S,5S)-1-Acetyl-5-methylpyrrolidin-3-yl]-4-[2-(cyclopropylmethoxy)-5-(difluoromethyl)phenyl]-6-methyl-5H-pyrrolo[3,2-d]pyrimidine-7-carboxamide Starting from 4-[2-(cyclopropylmethoxy)-5-(difluoromethyl)phenyl]-6-methyl-N-[(3S*,5S*)-5-methylpyrrolidin-3-yl]-5H-pyrrolo[3,2-d]pyrimidine-7-carboxamide hydrochloride (example D.f66) and commercially available acetyl chloride the title compound is obtained as colorless solid.
HR-MS (ESI): m/z=498.2316 ([MH]$^+$, $C_{26}H_{30}F_2N_5O_3^+$, calc. 498.2311).

Example P25

4-[2-(Cyclopropylmethoxy)-5-(difluoromethyl)phenyl]-6-methyl-N-[(3S,5S)-5-methyl-1-propanoylpyrrolidin-3-yl]-5H-pyrrolo[3,2-d]pyrimidine-7-carboxamide Starting from 4-[2-(cyclopropylmethoxy)-5-(difluoromethyl)phenyl]-6-methyl-N-[(3S*,5S*)-5-methylpyrrolidin-3-yl]-5H-pyrrolo[3,2-d]pyrimidine-7-carboxamide hydrochloride (example D.f66) and commercially available propionyl chloride the title compound is obtained as colorless solid.
HR-MS (ESI): m/z=512.2466 ([MH]$^+$, $C_{27}H_{32}F_2N_5O_3^+$, calc. 512.2468).

Example P26

4-[2-(Cyclopropylmethoxy)-5-(difluoromethyl)phenyl]-N-[(3S,5S)-1-(methoxyacetyl)-5-methylpyrrolidin-3-yl]-6-methyl-5H-pyrrolo[3,2-d]pyrimidine-7-carboxamide Starting from 4-[2-(cyclopropylmethoxy)-5-(difluoromethyl)phenyl]-6-methyl-N-[(3S*,5S*)-5-methylpyrrolidin-3-yl]-5H-pyrrolo[3,2-d]pyrimidine-7-carboxamide hydrochloride (example D.f66) and commercially available methoxy-acetyl chloride the title compound is obtained as colorless solid.
HR-MS (ESI): m/z=528.2411 ([MH]$^+$, $C_{27}H_{31}F_2N_5O_4^+$, calc. 528.2417).

Example P89

N-[(1S,3S)-3-(Acetylamino)cyclopentyl]-4-[2-(cyclopropylmethoxy)-5-(difluoromethyl)phenyl]-6-methyl-5H-pyrrolo[3,2-d]pyrimidine-7-carboxamide Starting from N-[(1S,3S)-3-aminocyclopentyl]-4-[2-(cyclopropylmethoxy)-5-(difluoromethyl)phenyl]-6-methyl-5H-pyrrolo[3,2-d]pyrimidine-7-carboxamide hydrochloride (example D.f64) and commercially available acetyl chloride the title compound is obtained as colorless solid.

HR-MS (ESI): m/z=498.2305 ([MH]$^+$, $C_{26}H_{30}F_2N_5O_3^+$, calc. 498.2311).

Example P90

4-[2-(Cyclopropylmethoxy)-5-(difluoromethyl)phenyl]-6-methyl-N-[(1S,3S)-3-(propanoylamino)cyclopentyl]-5H-pyrrolo[3,2-d]pyrimidine-7-carboxamide Starting from N-[(1S,3S)-3-aminocyclopentyl]-4-[2-(cyclopropylmethoxy)-5-(difluoromethyl)phenyl]-6-methyl-5H-pyrrolo[3,2-d]pyrimidine-7-carboxamide hydrochloride (example D.f64) and commercially available propionyl chloride the title compound is obtained as colorless solid.

HR-MS (ESI): m/z=512.2474 ([MH]$^+$, $C_2H_{32}F_2N_5O_3^+$, calc. 512.2468).

Example P91

4-[2-(Cyclopropylmethoxy)-5-(difluoromethyl)phenyl]-N-{(1S,3S)-3-[(methoxyacetyl)amino]cyclopentyl}-6-methyl-5H-pyrrolo[3,2-d]pyrimidine-7-carboxamide Starting from N-[(1S,3S)-3-aminocyclopentyl]-4-[2-(cyclopropylmethoxy)-5-(difluoromethyl)phenyl]-6-methyl-5H-pyrrolo[3,2-d]pyrimidine-7-carboxamide hydrochloride (example D.f64) and commercially available methoxy-acetyl chloride the title compound is obtained as colorless solid.

HR-MS (ESI): m/z=528.2418 ([MH]$^+$, $C_{27}H_{32}F_2N_5O_4^+$, calc. 528.2417).

Example P99

N-[(1R*,2R*,4R*)-4-(Acetylamino)-2-fluorocyclopentyl]-4-[2-(cyclopropylmethoxy)-5-(difluoromethyl)phenyl]-6-methyl-5H-pyrrolo[3,2-d]pyrimidine-7-carboxamide Starting from N-[(1R*,2R*,4R*)-4-amino-2-fluorocyclopentyl]-4-[2-(cyclopropylmethoxy)-5-(difluoromethyl)phenyl]-6-methyl-5H-pyrrolo[3,2-d]pyrimidine-7-carboxamide (example D.f71) and commercially available acetyl chloride the title compound is obtained as colorless solid.

HR-MS (ESI): m/z=516.2221 ([MH]$^+$, $C_{26}H_{29}F_3N_5O_3^+$, calc. 516.2217).

Example P100

4-[2-(Cyclopropylmethoxy)-5-(difluoromethyl)phenyl]-N-[(1R*,2R*,4R*)-2-fluoro-4-(propanoylamino)cyclopentyl]-6-methyl-5H-pyrrolo[3,2-d]pyrimidine-7-carboxamide Starting from N-[(1R*,2R*,4R*)-4-amino-2-fluorocyclopentyl]-4-[2-(cyclopropylmethoxy)-5-(difluoromethyl)phenyl]-6-methyl-5H-pyrrolo[3,2-d]pyrimidine-7-carboxamide (example D.f71) and commercially available propionyl chloride the title compound is obtained as colorless solid.

HR-MS (ESI): m/z=530.2375 ([MH]$^+$, $C_{27}H_{31}F_3N_5O_3^+$, calc. 530.2374).

Example P101

4-[2-(Cyclopropylmethoxy)-5-(difluoromethyl)phenyl]-N-{(1R*,2R*,4R*)-2-fluoro-4-[(methoxyacetyl)amino]cyclopentyl}-6-methyl-5H-pyrrolo[3,2-d]pyrimidine-7-carboxamide Starting from N-[(1R*,2R*,4R*)-4-amino-2-fluorocyclopentyl]-4-[2-(cyclopropylmethoxy)-5-(difluoromethyl)phenyl]-6-methyl-5H-pyrrolo[3,2-d]pyrimidine-7-carboxamide (example D.f71) and commercially available methoxy-acetyl chloride the title compound is obtained as colorless solid.

HR-MS (ESI): m/z=546.2324 ([MH]$^+$, $C_{27}H_{31}F_3N_5O_4^+$, calc. 546.2323).

Example P139

N-[(1S*,2S*,4S*)-4-(Acetylamino)-2-methylcyclohexyl]-4-[2-(cyclopropylmethoxy)-5-(difluoromethyl)phenyl]-6-methyl-5H-pyrrolo[3,2-d]pyrimidine-7-carboxamide Starting from N-[(1S*,2S*,4S*)-4-amino-2-methylcyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f63) and commercially available acetyl chloride the title compound is obtained as colorless solid.

HR-MS (ESI): m/z=526.2625 ([MH]$^+$, $C_{28}H_{34}F_2N_5O_3^+$, calc. 526.2624).

Example P140

4-[2-(Cyclopropylmethoxy)-5-(difluoromethyl)phenyl]-6-methyl-N-[(1S*,2S*,4S*)-2-methyl-4-(propanoylamino)cyclohexyl]-5H-pyrrolo[3,2-d]pyrimidine-7-carboxamide Starting from N-[(1S*,2S*,4S*)-4-amino-2-methylcyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f63) and commercially available propionyl chloride the title compound is obtained as colorless solid.

HR-MS (ESI): m/z=540.2773 ([MH]$^+$, $C_{29}H_{36}F_2N_5O_3^+$, calc. 540.2781).

Example P141

4-[2-(Cyclopropylmethoxy)-5-(difluoromethyl)phenyl]-N-{(1S*,2S*,4S*)-4-[(methoxyacetyl)amino]-2-methylcyclohexyl}-6-methyl-5H-pyrrolo[3,2-d]pyrimidine-7-carboxamide Starting from N-[(1S*,2S*,4S*)-4-amino-2-methylcyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f63) and commercially available methoxy-acetyl chloride the title compound is obtained as colorless solid.

451

HR-MS (ESI): m/z=556.2726 ([MH]$^+$, $C_{29}H_{36}F_2N_5O_4^+$, calc. 556.2730).

Example P159

N-[(1R*,2R*,4R*)-4-(Acetylamino)-2-fluorocyclohexyl]-4-[2-(cyclopropylmethoxy)-5-(difluoromethyl)phenyl]-6-methyl-5H-pyrrolo[3,2-d]pyrimidine-7-carboxamide Starting from N-[(1R*,2R*,4R*)-4-amino-2-fluorocyclohexyl]-4-[2-(cyclopropylmethoxy)-5-(difluoromethyl)phenyl]-6-methyl-5H-pyrrolo[3,2-d]pyrimidine-7-carboxamide (example D.f67) and commercially available acetyl chloride the title compound is obtained as colorless solid.

HR-MS (ESI): m/z=530.2386 ([MH]$^+$, $C_{27}H_{31}F_3N_5O_3^+$, calc. 530.2374).

Example P160

4-[2-(Cyclopropylmethoxy)-5-(difluoromethyl)phenyl]-N-[(1R*,2R*,4R*)-2-fluoro-4-(propanoylamino)cyclohexyl]-6-methyl-5H-pyrrolo[3,2-d]pyrimidine-7-carboxamide Starting from N-[(1R*,2R*,4R*)-4-amino-2-fluorocyclohexyl]-4-[2-(cyclopropylmethoxy)-5-(difluoromethyl)phenyl]-6-methyl-5H-pyrrolo[3,2-d]pyrimidine-7-carboxamide (example D.f67) and commercially available propionyl chloride the title compound is obtained as colorless solid.

HR-MS (ESI): m/z=544.2539 ([MH]$^+$, $C_{28}H_{33}F_3N_5O_3^+$, calc. 544.2530).

Example P161

4-[2-(Cyclopropylmethoxy)-5-(difluoromethyl)phenyl]-N-{(1R*,2R*,4R*)-2-fluoro-4-[(methoxyacetyl)amino]cyclohexyl}-6-methyl-5H-pyrrolo[3,2-d]pyrimidine-7-carboxamide Starting from N-[(1R*,2R*,4R*)-4-amino-2-fluorocyclohexyl]-4-[2-(cyclopropylmethoxy)-5-(difluoromethyl)phenyl]-6-methyl-5H-pyrrolo[3,2-d]pyrimidine-7-carboxamide (example D.f67) and commercially available methoxy-acetyl chloride the title compound is obtained as colorless solid.

HR-MS (ESI): m/z=560.2487 ([MH]$^+$, $C_{28}H_{32}F_3N_5O_4^+$, calc. 560.2479).

Example P169

N-[(1S*,2R*,4S*)-4-(Acetylamino)-2-fluorocyclohexyl]-4-[2-(cyclopropylmethoxy)-5-(difluoromethyl)phenyl]-6-methyl-5H-pyrrolo[3,2-d]pyrimidine-7-carboxamide Starting from N-[(1S*,2R*,4S*)-4-amino-2-fluorocyclohexyl]-4-[2-(cyclopropylmethoxy)-5-(difluoromethyl)phenyl]-6-methyl-5H-pyrrolo[3,2-d]pyrimidine-7-carboxamide (example D.f73) and commercially available acetyl chloride the title compound is obtained as colorless solid.

HR-MS (ESI): m/z=530.2378 ([MH]$^+$, $C_{27}H_{31}F_3N_5O_3^+$, calc. 530.2374).

452

Example P170

4-[2-(Cyclopropylmethoxy)-5-(difluoromethyl)phenyl]-N-[(1S*,2R*,4S*)-2-fluoro-4-(propanoylamino)cyclohexyl]-6-methyl-5H-pyrrolo[3,2-d]pyrimidine-7-carboxamide Starting from N-[(1S*,2R*,4S*)-4-amino-2-fluorocyclohexyl]-4-[2-(cyclopropylmethoxy)-5-(difluoromethyl)phenyl]-6-methyl-5H-pyrrolo[3,2-d]pyrimidine-7-carboxamide (example D.f73) and commercially available propionyl chloride the title compound is obtained as colorless solid.

HR-MS (ESI): m/z=544.2528 ([MH]$^+$, $C_{28}H_{33}F_3N_5O_3^+$, calc. 544.2530).

Example P171

4-[2-(Cyclopropylmethoxy)-5-(difluoromethyl)phenyl]-N-{(1S*,2R*,4S*)-2-fluoro-4-[(methoxyacetyl)amino]cyclohexyl}-6-methyl-5H-pyrrolo[3,2-d]pyrimidine-7-carboxamide Starting from N-[(1S*,2R*,4S*)-4-amino-2-fluorocyclohexyl]-4-[2-(cyclopropylmethoxy)-5-(difluoromethyl)phenyl]-6-methyl-5H-pyrrolo[3,2-d]pyrimidine-7-carboxamide (example D.f73) and commercially available methoxy-acetyl chloride the title compound is obtained as colorless solid.

HR-MS (ESI): m/z=560.2479 ([MH]$^+$, $C_{28}H_{33}F_3N_5O_4^+$, calc. 560.2479).

Example P189

N-[(1S*,3S*,4S*)-4-(Acetylamino)-3-methylcyclohexyl]-4-[2-(cyclopropylmethoxy)-5-(difluoromethyl)phenyl]-6-methyl-5H-pyrrolo[3,2-d]pyrimidine-7-carboxamide Starting from N-[(1S*,3S*,4S*)-4-amino-3-methylcyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f65) and commercially available acetyl chloride the title compound is obtained as colorless solid.

HR-MS (ESI): m/z=540.2788 ([MH]$^+$, $C_{29}H_{36}F_2N_5O_3^+$, calc. 540.2781).

Example P190

4-[2-(Cyclopropylmethoxy)-5-(difluoromethyl)phenyl]-6-methyl-N-[(1S*,3S*,4S*)-3-methyl-4-(propanoylamino)cyclohexyl]-5H-pyrrolo[3,2-d]pyrimidine-7-carboxamide Starting from N-[(1S*,3S*,4S*)-4-amino-3-methylcyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f65) and commercially available propionyl chloride the title compound is obtained as colorless solid.

HR-MS (ESI): m/z=526.2615 ([MH]$^+$, $C_{28}H_{34}F_2N_5O_3^+$, calc. 526.2624).

Example P191

4-[2-(Cyclopropylmethoxy)-5-(difluoromethyl)phenyl]-N-{(1S*,3S*,4S*)-4-[(methoxyacetyl)amino]-3-methylcyclohexyl}-6-methyl-5H-pyrrolo[3,2-d]pyrimidine-7-carboxamide Starting from N-[(1S*,3S*,4S*)-4-amino-3-methylcyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f65) and commercially available methoxy-acetyl chloride the title compound is obtained as colorless solid.

HR-MS (ESI): m/z=556.2729 ([MH]$^+$, $C_{29}H_{36}F_2N_5O_4^+$, calc. 556.2730).

Example P199

N-[(1S*,3R*,4S*)-4-(Acetylamino)-3-fluorocyclohexyl]-4-[2-(cyclopropylmethoxy)-5-(difluoromethyl)phenyl]-6-methyl-5H-pyrrolo[3,2-d]pyrimidine-7-carboxamide Starting from N-[(1S*,3R*,4S*)-4-amino-3-fluorocyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f72) and commercially available acetyl chloride the title compound is obtained as colorless solid.

HR-MS (ESI): m/z=530.2381 ([MH]$^+$, $C_{27}H_{31}F_3N_5O_3^+$, calc. 530.2374).

Example P200

4-[2-(Cyclopropylmethoxy)-5-(difluoromethyl)phenyl]-N-[(1S*,3R*,4S*)-3-fluoro-4-(propanoylamino)cyclohexyl]-6-methyl-5H-pyrrolo[3,2-d]pyrimidine-7-carboxamide Starting from N-[(1S*,3R*,4S*)-4-amino-3-fluorocyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f72) and commercially available propionyl chloride the title compound is obtained as colorless solid.

HR-MS (ESI): m/z=544.2525 ([MH]$^+$, $C_{28}H_{33}F_3N_5O_3^+$, calc. 544.2530).

Example P201

4-[2-(Cyclopropylmethoxy)-5-(difluoromethyl)phenyl]-N-{(1S*,3R*,4S*)-3-fluoro-4-[(methoxyacetyl)amino]cyclohexyl}-6-methyl-5H-pyrrolo[3,2-d]pyrimidine-7-carboxamide Starting from N-[(1S*,3R*,4S*)-4-amino-3-fluorocyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f72) and commercially available methoxy-acetyl chloride the title compound is obtained as colorless solid.

HR-MS (ESI): m/z=560.2478 ([MH]$^+$, $C_{28}H_{33}F_3N_5O_4^+$, calc. 560.2479).

Example P209

N-[(1S*,3S*,4S*)-4-(Acetylamino)-3-fluorocyclohexyl]-4-[2-(cyclopropylmethoxy)-5-(difluoromethyl)phenyl]-6-methyl-5H-pyrrolo[3,2-d]pyrimidine-7-carboxamide Starting from N-[(1S*,3S*,4S*)-4-amino-3-fluorocyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f62) and commercially available acetyl chloride the title compound is obtained as colorless solid.

HR-MS (ESI): m/z=530.2359 ([MH]$^+$, $C_{27}H_{31}F_3N_5O_3^+$, calc. 530.2374).

Example P210

4-[2-(Cyclopropylmethoxy)-5-(difluoromethyl)phenyl]-N-[(1S*,3S*,4S*)-3-fluoro-4-(propanoylamino)cyclohexyl]-6-methyl-5H-pyrrolo[3,2-d]pyrimidine-7-carboxamide Starting from N-[(1S*,3S*,4S*)-4-amino-3-fluorocyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f62) and commercially available propionyl chloride the title compound is obtained as colorless solid.

HR-MS (ESI): m/z=544.2536 ([MH]$^+$, $C_{28}H_{33}F_3N_5O_3^+$, calc. 544.2530).

Example P211

4-[2-(Cyclopropylmethoxy)-5-(difluoromethyl)phenyl]-N-{(1S*,3S*,4S*)-3-fluoro-4-[(methoxyacetyl)amino]cyclohexyl}-6-methyl-5H-pyrrolo[3,2-d]pyrimidine-7-carboxamide Starting from N-[(1S*,3S*,4S*)-4-amino-3-fluorocyclohexyl]-4-[2-(cyclopropylmethoxy)-5-(difluoromethyl)phenyl]-6-methyl-5H-pyrrolo[3,2-d]pyrimidine-7-carboxamide hydrochloride (example D.f62) and commercially available methoxy-acetyl chloride the title compound is obtained as colorless solid.

HR-MS (ESI): m/z=560.2466 ([MH]$^+$, $C_{28}H_{33}F_3N_5O_4^+$, calc. 560.2479).

Commercial Utility

The compounds of formula (I), the salts thereof, and the stereoisomers of the compounds and the salts thereof are hereinafter referred to as the compounds of the present subject matter. In particular, the compounds of the present subject matter are pharmaceutically acceptable.

The compounds of the present subject matter have valuable pharmaceutical properties which make them commercially utilizable. In particular, as type 5 phosphodiesterase (PDE5) inhibitors, they are able to influence the physiological and pathophysiological function of various cells, e.g., but not limited to, smooth muscle cells, fibroblasts, myofibroblasts and platelets, which are involved in a great variety of physiological and pathophysiological mechanisms. In particular, the PDE5 inhibiting compounds of the present subject matter can effect relaxation of the vasculature, thus increasing blood flow, improve the spatial balance between blood perfusion and ventilation within the lung ("re-matching" effect) thereby reducing the amount of so-called low V/Q-areas [areas within the lung with high perfusion (Q) but no or reduced ventilation (V)] and high V/Q-areas (areas within the lung with low perfusion but high ventilation), induce neurogenesis, inhibit platelet function, such as aggregation, adhesion and mediator release and, thus, have an anti-inflammatory effect. The compounds of the present subject matter are distinguished by valuable and desirable properties, such as, for example, high efficacy, low toxicity, superior bioavailability in general (e.g. good enteral absorption), superior therapeutic window, superior pharmacokinetics (e.g. half-life), absence of significant side effects, and further beneficial effects related with their therapeutic and pharmaceutical suitability.

Accordingly, the present subject matter further relates to the compounds of the present subject matter for the treatment or prophylaxis of diseases, especially diseases alleviated by inhibition of the type 5 phosphodiesterase. In particular, the present subject matter relates to the compounds of the present subject matter for the treatment or prophylaxis of the following diseases: male and female sexual dysfunction, such as, but not limited to, male erectile dysfunction, premature ejaculation, Peyronie's disease; acute and chronic airway diseases, such as, but not limited to, COPD (chronic obstructive pulmonary disease), bronchitis, emphysema, pulmonary vascular remodeling, pulmonary hypertension, lung fibrosis, idiopathic pulmonary lung fibrosis (IPF), asthma, cystic fibrosis, bronchiectasis, bronchiolitis obliterans, connective tissue diseases, sarcoidosis, kyphoscoliosis, pneumoconiosis, amyotrophic lateral sclerosis, thoracoplasty, extrinsic allergic alveolitis; inflammatory diseases, such as, but not limited to, vasculature inflammation, acute respiratory distress syndrome, nephritis, mesangial glomerulonephritis, chronic inflammatory bowel disease, disseminated intravascular inflammation, allergic vasculitis, dermatoses (e.g., but not limited to, psoriasis, toxic and allergic contact eczema, atopic eczema, seborrhoeic eczema, Lichen simplex, sunburn, pruritus in the anogenital area, alopecia greata, hypertrophic scars, discoid lupus erythematosus, follicular and widespread pyodermias, endogenous and exogenous acne, acne rosacea), disorders of the arthritis type (e.g., but not limited to, rheumatoid arthritis, rheumatoid spondylitis, osteoarthritis), disorders of the immune system [e.g., but not limited to, AIDS (acquired immunodeficiency syndrome), multiple sclerosis], graft versus host reaction, allograft rejections, shock [e.g., but not limited to, septic shock, endotoxin shock, gram-negative sepsis shock, toxic shock syndrome and ARDS (adult respiratory distress syndrome)], gastrointestinal inflammations (e.g., but not limited to, Crohn's disease and ulcerative colitis); disorders which are based on allergic and/or chronic, immunological false reactions (e.g., but not limited to, allergic rhinitis, allergic sinusitis, chronic rhinitis, chronic sinusitis, allergic conjunctivitis, nasal polyps); pain, such as, but not limited to, inflammatory pain;

right-heart failure, right heart hypertrophy (cor pulmonale), hypertension, hypercholesterolemia, hypertriglyceridemia;

ischaemic diseases, such as, but not limited to, diabetes mellitus, stroke, coronary artery disease, angina (including, but not limited to, vasospastic angina), myocardial infarction, peripheral artery disease, cerebrovascular obstruction, sleep apnea, macular ischaemia, arterial and venous occlusion, congestive heart failure;

diabetic gastroparesis and diseases with symptoms of gastroparesis;

diseases or conditions in which it is desirable to suppress platelet function, for example, but not limited to, after stent implantations (e.g., but not limited to, coronary stenting), after bypass operations, in pulmonary hypertension, thrombotic diseases, post-angioplasty stenosis, coronary artery disease, infarction (e.g., but not limited to, myocardial infarction), instable angina pectoris, stroke, and arterial and venous occlusion diseases (e.g., but not limited to, claudicatio intermittens);

diseases or conditions with an impairment or dysfunction of cerebral vascular reactivity and/or neurovascular coupling, such as, but not limited to, arteriosclerotic dementia, multi-infarct dementia, cerebral senility;

diseases which are based on neuronal damage or degradation, such as but not limited to, stroke, spinal cord injury, brain injury, morbus parkinson, amyotrophic lateral sclerosis, morbus alzheimer, amyloidosis, prion diseases and neuropathy;

peripheral arterial diseases, chronic renal failure, chronic heart failure, sepsis, senile dementia (Alzheimer's disease), Creutzfeld-Jacob disease, septic encephalopathy, arteriosclerotic encephalopathy, diabetes associated encephalopathy, toxic encephalopathy, vascular and neuronal dementia, Huntington's disease, Parkinson's disease, multiple sclerosis and preeclampsia;

portal hypertension, liver cirrhosis, toxic liver damage (e.g., but not limited to, alcohol-induced liver damage), hepatitis, thrombosis of the portal vein, Budd-Chiari syndrome, malformation of liver veins, compression of liver veins (e.g., but without limitation, due to tumors), arteriovenous fistula, diseases associated with an enlarged spleen, schistosomiasis (bilharziosis), sarcoidosis and other granulomatous diseases, primary biliary cirrhosis, myeloproliferative disorders (e.g., but not limited to, chronic myeloid leukemia, osteomyelofibrosis), lymphatic systemic diseases, collagenosis (e.g., but not limited to, systemic lupus erythematodes, sclerodermia), morbus Osler (congenital arteriovenous malformations, inter alia in the liver), nodular regenerative hyperplasia, tricuspid insufficiency, pericarditis constrictiva, veno-occlusive disease (VOD), non-alcoholic steatohepatitis (NASH), liver fibrosis;

benign prostatic hyperplasia;

insufficient uteroplacental blood flow in pregnancies with fetal growth restriction;

insufficient brain skills, such as but not limited to, verbal attainment, attention, concentration, deductive thinking, central auditory processing, cognition, learning, vigilance, apprehension and reagibility;

Overactive Bladder; LUTS=lower urinary tract symptoms; Raynauds syndrome/phenomenon.

In this respect, the term "pulmonary hypertension" in particular embraces pulmonary arterial hypertension including primary pulmonary hypertension (e.g. sporadic or familial) and pulmonary arterial hypertension related, for example, but without limitation, to collagen vascular disease, congenital systemic-to-pulmonary shunts, portal hypertension, human immunodeficiency virus infection, drugs or toxins (e.g., but not limited to, anorexigens), persistent pulmonary hypertension of the newborn;

pulmonary venous hypertension due to, for example, but without limitation, left-sided atrial or ventricular heart disease, left-sided valvular heart disease, extrinsic compression of central pulmonary veins (e.g. fibrosing mediastinitis, adenopathy in relation to tumors), pulmonary veno-occlusive disease;

pulmonary hypertension associated with disorders of the respiratory system or hypoxemia including, for example, but without limitation, chronic obstructive pulmonary disease (COPD), interstitial lung disease, sleep-disordered breathing, alveolar hypoventilation disorders, chronic exposure to high altitude, neonatal lung disease, alveolar-capillary dysplasia;

pulmonary hypertension caused by chronic thrombotic or embolic diseases including thromboembolic obstruction of proximal pulmonary arteries and obstruction of distal pulmonary arteries, such as pulmonary embolism (due to thrombus, tumor, ova, parasites, or foreign material), in situ thrombosis and sickle-cell disease, in particular chronic thromboembolic pulmonary hypertension (CTEPH);

pulmonary hypertension caused by disorders directly affecting the pulmonary vasculature including inflammatory disorders (e.g., but not limited to, schistosomiasis, sarcoidosis) and pulmonary capillary hemangiomatosis.

Preferably, the present subject matter further relates to the compounds of the present subject matter for the treatment or prophylaxis of the following diseases, especially diseases alleviated by inhibition of the type 5 phosphodiesterase: acute and chronic airway diseases, such as pulmonary hypertension, in particular chronic thromboembolic pulmonary hypertension, lung fibrosis, sarcoidosis, asthma, bronchitis, emphysema and chronic obstructive pulmonary disease.

Beside the inhibition of type 5 phosphodiesterase some of the compounds of the present subject matter have also substantial activity in inhibition of type 4 phosphodiesterase and thus have valuable pharmaceutical properties, which make them commercially utilizable.

PDE4 inhibitors are thought to be useful in the treatment or prophylaxis of a variety of diseases and disorders. They are thought to be suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways, of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases.

Thus, PDE4 inhibitors are thought to be useful in the treatment or prophylaxis of a variety of diseases and disorders, such as for example:

acute and chronic airway diseases, such as, but not limited to, bronchitis, allergic bronchitis, asthma, emphysema, COPD (chronic obstructive pulmonary disease), sarcoidosis, pulmonary hypertension and lung fibrosis;

diseases which are based on allergic and/or chronic, immunological false reactions in the region of the upper airways (pharynx, nose) and the adjacent regions (paranasal sinuses, eyes), such as, but not limited to, allergic rhinitis/sinusitis, chronic rhinitis/sinusitis, allergic conjunctivitis and also nasal polyps;

dermatological diseases especially of proliferative, inflammatory and allergic type, such as, but not limited to psoriasis (vulgaris), toxic and allergic contact eczema, atopic dermatitis (eczema), seborrhoeic eczema, Lichen simplex, sunburn, pruritus in the anogenital area, alopecia greata, hypertrophic scars, discoid lupus erythematosus, follicular and widespread pyodermias, endogenous and exogenous acne, acne rosacea and other proliferative, inflammatory and allergic skin disorders;

diseases which are based on an excessive release of TNF and leukotrienes, such as, for example, diseases of the arthritis type like rheumatoid arthritis, rheumatoid spondylitis, osteoarthritis and other arthritic conditions;

fibrotic diseases, such as, but not limited to, cystic fibrosis, pulmonary fibrosis, hepatic fibrosis and renal fibrosis;

viral, alcoholic or drug-induced acute and fulminant hepatitis, hepatic steatosis (alcoholic and non-alcoholic steatiohepatitis);

diseases of the immune system, such as, but not limited to, AIDS, multiple sclerosis, graft versus host reaction, allograft rejections;

cachexia, cancer cachexia, AIDS cachexia;

types of shock, such as, but not limited to, septic shock, endotoxin shock, gram-negative sepsis, toxic shock syndrome and ARDS (adult respiratory distress syndrome);

diseases in the gastrointestinal region, such as Crohn's disease and ulcerative colitis;

diseases of the heart which can be treated by PDE inhibitors, such as cardiac insufficiency;

diseases which can be treated on account of the tissue-relaxant action of the PDE inhibitors, such as, for example, erectile dysfunction, colics of the kidneys and of the ureters in connection with kidney stones or oncolytic action (to treat preterm delivery); glomerulonephritis and other urinary tract infections;

diabetes insipidus, diabetes mellitus (type I and in particular type II); cancer (in particular lymphoid and myeloid leukaemia); osteoporosis;

conditions associated with cerebral metabolic inhibition, such as, but not limited to, cerebral senility, senile dementia (Alzheimer's disease), memory impairment associated with Parkinson's disease or multiinfarct dementia;

and also diseases of the central nervous system, such as, but not limited to, depressions, anxiety states, spinal cord injury, schizophrenia or arteriosclerotic dementia.

Preferably, inhibitors of the type 4 phosphodiesterase are used in the treatment or prophylaxis of the following diseases: acute and chronic airway diseases, such as bronchitis, allergic bronchitis, asthma, emphysema, COPD, pulmonary hypertension and lung fibrosis;

allergic rhinitis;

and dermatological diseases, such as psoriasis and atopic dermatitis (eczema); rheumatoid arthritis;

and inflammations in the gastrointestinal region, such as Crohn's disease and ulcerative colitis.

It is noteworthy that compounds of the present subject matter, which are inhibitors of type 5 phosphodiesterase (PDE5) as well as of type 4 phosphodiesterase (PDE4), mentioned herein as dual type 4/5 phosphodiesterase inhibitors, are thought to be useful in the treatment or prophylaxis of the above mentioned diseases like inhibitors of the type 5 phosphodiesterase and/or inhibitors of the type 4 phosphodiesterase. Dual type 4/5 phosphodiesterase inhibitors have the potential to be more effective in treatment of distinct disease identities than compounds inhibiting one of those two enzymes only, since inhibition of PDE4 and PDE5 might address divers and different pathophysiologies occurring within one disease as e.g. lung fibrosis. In respect to lung fibrosis it has been described that inhibitors of type 4 phosphodiesterase inhibit TGF-β induced transition of lung fibroblasts to myofibroblasts (Dunkern et al., Eur. J. Pharmacol., 572(1): 12-22, 2007), which is a hallmark of fibrosis progression. They have further been described to inhibit matrix metalloproteinase production from lung fibroblasts (Martin-Chouly C A et al., Life Sci. 75(7): 823-40, 2004) and to prevent chemotaxis of these cells (Kohyama T et al., Am. J.

Respir. Cell Mol. Biol., 26(6): 694-701, 2002), which are important pathophysiological aspects of lung fibrosis. In addition the selective type 4 phosphodiesterase inhibitor roflumilast have also been shown in-vivo in the bleomycin-induced lung fibrosis model in mice to inhibit fibrosis development (Cortijo J et al., Br. J. Pharmacol., 156(3): 534-44, 2009).

On the other hand it has been shown in respect to lung fibrosis that PDE5 inhibition by means of the selective PDE5 inhibitor sildenafil attenuates bleomycin-induced pulmonary fibrosis and pulmonary hypertension through inhibition of ROS generation and RhoA/Rho kinase activation (Hemnes A R, Zaiman A, Champion H C, Am. J. Physiol. Lung Cell. Mol. Physiol. 2008 January; 294(1):L24-33. Epub 2007 Oct. 26) and it has been shown in clinical human open-label trials that sildenafil improves lung hemodynamic (vascular resistance and ventilation/perfusion matching) and increases exercise tolerance in patients with pulmonary fibrosis (Ghofrani et al., Lancet 360, 895-900, 2002; Collard et al., Chest 131, 897-899, 2007).

As described above the present subject matter covers beside type 5 phosphodiesterase inhibitors also dual type 4/5 phosphodiesterase inhibitors. In connection with this application preferred dual type 4/5 phosphodiesterase inhibitors have a $-\log IC_{50}$ (mol/l)] higher than 6.0 for inhibition of PDE4 and a $-\log IC_{50}$ (mol/l) higher than 8.0 for inhibition of PDE5. More preferred dual type 4/5 phosphodiesterase inhibitors have a $-\log IC_{50}$ (mol/l) higher than 7.0 for inhibition of PDE4 and a $-\log IC_{50}$ (mol/l) higher than 8.0 for inhibition of PDE5.

Preferably, the present subject matter relates to the compounds of the present subject matter for use in the treatment or prophylaxis of the following diseases, particularly diseases alleviated by inhibition of the dual type 4/5 phosphodiesterase:
lung fibrosis such as idiopathic pulmonary fibrosis, pulmonary arterial hypertension respectively pulmonary hypertension, COPD, asthma, bronchitis, emphysema, nephritis such as proliferative glomerulonephritis, liver fibrosis, sarcoidosis, fibrotic conditions in general such as myelofibrosis, retroperitoneal fibrosis, endomyocardial fibrosis, mediastinal fibrosis, nephrogenic systemic fibrosis, hypertrophic scars and toxic liver damage.

The present subject matter also relates to the use of a compound of the present subject matter in the manufacture of a pharmaceutical composition inhibiting the type 5 phosphodiesterase, in particular a pharmaceutical composition for the treatment or prophylaxis of diseases alleviated by inhibition of the type 5 phosphodiesterase, preferably, a pharmaceutical composition for the treatment or prophylaxis of the diseases exemplified above.

The present subject matter also further relates to the use of a compound of the present subject matter in the manufacture of a pharmaceutical composition inhibiting the dual type 4/5 phosphodiesterase, in particular a pharmaceutical composition for the treatment or prophylaxis of diseases alleviated by inhibition of the dual type 4/5 phosphodiesterase, preferably, a pharmaceutical composition for the treatment or prophylaxis of the diseases exemplified above.

Preferably, the present subject matter relates to the use of a compound of the present subject matter in the manufacture of a pharmaceutical composition for the treatment or prophylaxis of an acute or chronic airway disease, such as, but not limited to, pulmonary hypertension, lung fibrosis, sarcoidosis, asthma, bronchitis, emphysema and chronic obstructive pulmonary disease.

Preferably, the present subject matter relates to the use of a compound of the present subject matter in the manufacture of a pharmaceutical composition for the treatment or prophylaxis of an acute or chronic airway disease, such as, but not limited to, pulmonary hypertension, pulmonary arterial hypertension, lung fibrosis, idiopathic pulmonary lung fibrosis, sarcoidosis, asthma, bronchitis, emphysema and chronic obstructive pulmonary disease.

In a particularly preferred embodiment of the present subject matter, the present subject matter relates to the use of a compound of the above examples in the manufacture of a pharmaceutical composition for the treatment or prophylaxis of an acute or chronic airway disease, such as, but not limited to, pulmonary hypertension, lung fibrosis, sarcoidosis, asthma, bronchitis, emphysema and chronic obstructive pulmonary disease.

In a particularly preferred embodiment of the present subject matter, the present subject matter relates to the use of a compound of the above examples in the manufacture of a pharmaceutical composition for the treatment or prophylaxis of an acute or chronic airway disease, such as, but not limited to, pulmonary hypertension, pulmonary arterial hypertension, lung fibrosis, idiopathic pulmonary lung fibrosis, sarcoidosis, asthma, bronchitis, emphysema and chronic obstructive pulmonary disease.

The present subject matter further relates to a method of treating or preventing a disease comprising administering to a patient in need thereof a therapeutically effective amount of at least one of the compounds of the present subject matter.

In particular, the present subject matter relates to a method of treating or preventing one of the above mentioned diseases comprising administering to a patient in need thereof a therapeutically effective amount of at least one of the compounds of the present subject matter.

Especially, the present subject matter relates to a method of treating or preventing a disease which is alleviated by inhibition of the type 5 phosphodiesterase comprising administering to a patient in need thereof a therapeutically effective amount of at least one of the compounds of the present subject matter.

The present subject matter further relates to a method of treating or preventing a disease which is alleviated by inhibition of the dual type 4/5 phosphodiesterase comprising administering to a patient in need thereof a therapeutically effective amount of at least one of the compounds of the present subject matter.

Preferably, the present subject matter relates to a method of treating or preventing of an acute or chronic airway disease, for example, but not limited to, pulmonary hypertension, lung fibrosis, sarcoidosis, asthma, bronchitis, emphysema and chronic obstructive pulmonary disease, comprising administering to a patient in need thereof a therapeutically effective amount of at least one of the compounds of the present subject matter.

Preferably, the present subject matter relates to a method of treating or preventing of an acute or chronic airway disease, for example, but not limited to, pulmonary hypertension, pulmonary arterial hypertension, lung fibrosis, idiopathic pulmonary lung fibrosis, sarcoidosis, asthma, bronchitis, emphysema and chronic obstructive pulmonary disease, comprising administering to a patient in need thereof a therapeutically effective amount of at least one of the compounds of the present subject matter.

In the above methods, the patient is preferably a mammal, more preferably a human. Furthermore, in the above methods, at least one of the compounds of the present subject matter can be used. Preferably, one or two of the compounds of the present subject matter are used, more preferably, one of the compounds of the present subject matter is used.

In a particularly preferred embodiment of the present subject matter, the above methods of treating or preventing one of the above mentioned diseases comprise administering to a patient in need thereof a therapeutically effective amount of one compound of the examples according to the present present subject matter.

The present subject matter furthermore relates to a pharmaceutical composition which comprises at least one of the compounds of the present subject matter together with at least one pharmaceutically acceptable auxiliary.

The present subject matter additionally relates to a pharmaceutical composition for the treatment or prophylaxis of an acute or chronic airway disease, in particular for the treatment or prophylaxis of pulmonary hypertension, lung fibrosis, sarcoidosis, asthma, bronchitis, emphysema and chronic obstructive pulmonary disease.

The present subject matter additionally relates to a pharmaceutical composition for the treatment or prophylaxis of an acute or chronic airway disease, in particular for the treatment or prophylaxis of pulmonary hypertension, pulmonary arterial hypertension, lung fibrosis, idiopathic pulmonary lung fibrosis, sarcoidosis, asthma, bronchitis, emphysema and chronic obstructive pulmonary disease.

Preferably, the pharmaceutical composition comprises one or two of the compounds of the present subject matter. More preferably, the pharmaceutical composition comprises one of the compounds of the present subject matter.

In a particularly preferred embodiment of the present subject matter, the pharmaceutical composition comprises a compound of the examples according to the present subject matter together with at least one pharmaceutically acceptable auxiliary.

The present subject matter additionally relates to a pharmaceutical composition comprising at least one of the compounds of the present subject matter, at least one pharmaceutically acceptable auxiliary and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides.

In this respect, the therapeutic agent includes the corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides in form of the free compounds, the pharmaceutically acceptable salts thereof, the pharmaceutically acceptable derivatives thereof (e.g., but not limited to, ester derivatives), the solvates thereof and the stereoisomers of the compounds, salts, derivatives and solvates.

Co-administration of at least one of the compounds of the present subject matter with at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides can take place in form of a fixed combination, a non-fixed combination or a kit of parts.

A "fixed combination" is defined as a combination wherein the compound of the present subject matter and the therapeutic agent intended for co-administration are present in one dosing unit or in a single entity. One example of a fixed combination is a pharmaceutical composition wherein the compound of the present subject matter and the therapeutic agent are present in admixture for simultaneous administration. Another example of a fixed combination is a pharmaceutical composition wherein the compound of the present subject matter and the therapeutic compound are present in one dosing unit without being in admixture.

A "non-fixed combination" or "kit of parts" is defined as a combination wherein the compound of the present subject matter and the therapeutic agent are present in more than one dosing unit. In a non-fixed combination or a kit of parts the compound of the present subject matter and the therapeutic agent are provided as separate formulations. They might be packaged and presented together as separate components of a combination pack for simultaneous, sequential or separate use in combination therapy. Simultaneous or sequential administration of the compound of the present subject matter and the therapeutic agent are preferred. In case of sequential or separate administration of the compound of the present subject matter and the therapeutic agent, the compound of the present subject matter can be administered before or after administration of the therapeutic agent.

In case of sequential or separate administration of the compound of the present subject matter and the therapeutic agent, the compound of the present subject matter can be administered before or after administration of the therapeutic agent.

Sequential administration encompasses a short time period between the administration of the compound of the present subject matter and the therapeutic agent or vice versa (for example, the time that is needed to swallow one tablet after the other).

Separate administration encompasses longer time periods between the administration of the compound of the present subject matter and the therapeutic agent. In a preferred embodiment of the present subject matter, the compound of the present subject matter is administered while the therapeutic agent (or vice versa) still has an therapeutic effect on the patient being treated.

The type of formulation of the compound of the present subject matter and the therapeutic agent of a non-fixed combination or a kit of parts can be identical, i.e. both, the compound of the present subject matter and the therapeutic agent are formulated, for example, as powder, solution or suspension suitable for inhalative administration, or can be different, i.e. suited for different administration forms, such as e.g. the compound of the present subject matter is formulated as powder, solution or suspension suitable for inhalative administration and the therapeutic agent is formulated as tablet or capsule for oral administration.

Accordingly, the present subject matter additionally relates to a pharmaceutical composition presented either as a fixed combination, a non-fixed combination or kit of parts comprising at least one of the compounds of the present subject matter, at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, and at least one pharmaceutically acceptable auxiliary.

Examples of corticosteroids include without limitation budesonide, fluticasone such as fluticasone propionate, beclometasone such as beclometasone dipropionate, triamcinolone such as triamcinolone acetonide, mometasone, and ciclesonide. Examples of anticholinergics include without limitation tiotropium such as tiotropium bromide, and ipratropium such as ipratropium bromide, aclinidinium such as aclinidinium bromide, glycopyrronium such as glycopyrronium bromide. Examples of beta-mimetics include without limitation indacaterol, formoterol such as formoterol fumarate, and salmeterol such as salmeterol xinafoate, salbutamol, milveterol, carmoterol. Examples of lung surfactants include without limitation lusupultide, poractant alfa, sinapultide, beractant, bovactant, colfosceril auch as colfosceril palmitate, surfactant-TA, and calfactant. Examples of endothelin antagonists include without limitation bosentan, ambrisentan, atrasentan, darusentan, clazosentan, avosentan and sitaxsentan such as sitaxsentan sodium. Examples of prostacyclins include without limitation iloprost such as iloprost tromethamine, epoprostenol such as epoprostenol sodium and treprostinil such as treprostinil sodium. Examples of calcium channel blockers include without limitation amlodipine such as amlodipine besylate and amlodipine maleate, nifedipine, diltiazem such as diltiazem hydrochloride, verapamil such as verapamil hydrochloride, and felodipine. Examples of beta-blockers include without limitation bisoprolol such as bisoprolol fumarate, nebivolol, metoprolol such as metoprolol succinate and metoprolol tartrate, carvedilol, atenolol and nadolol. Examples of type 4 phosphodiesterase inhibitors include without limitation roflumilast, roflumilast N-oxide, cilomilast, tetomilast, apremilast and oglemilast. Examples of antidepressants include without limitation bupropion such as bupropion hydrochloride. Examples of antibiotics include without limitation amoxicillin, ampicillin, levofloxacin, clarithromycin, ciprofloxacin such as ciprofloxacin hydrochloride, telithromycin and azithromycin. Examples of anticoagulants include without limitation clopidogrel, enoxaparin, cilostazol, nadroparin, warfarin and abciximab. Examples of diuretics include without limitation furosemide, bumetanide and torsemide. Examples of digitalis glycosides include without limitation digoxin and digitoxin. Examples of Guanyl-cyclase activator/stimulators include without limitation BAY63-2521 (Riociguat) and Ataciguat.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a corticosteroid and at least one pharmaceutically acceptable auxiliary. In a particularly alternative embodiment, the above-mentioned fixed combination, non-fixed combination or kit of parts comprise:
a compound of the present subject matter and budesonide,
a compound of the present subject matter and fluticasone,
a compound of the present subject matter and beclometasone,
a compound of the present subject matter and mometasone,
a compound of the present subject matter and triamcinolone acetonide, or
a compound of the present subject matter and ciclesonide,
and at least one pharmaceutically acceptable auxiliary.

In an alternative embodiment, the pharmaceutically acceptable derivative of fluticasone is fluticasone-17-propionate. In another alternative embodiment, the pharmaceutically acceptable derivative of beclometasone is beclometasone 17,21-dipropionate ester. In an alternative embodiment, the pharmaceutically acceptable derivative of mometasone is mometasone furoate.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an anticholinergic and at least one pharmaceutically acceptable auxiliary. In a particularly alternative embodiment, the above-mentioned fixed combination, non-fixed combination or kit of parts comprise:
a compound of the present subject matter and glycopyrronium bromide,
a compound of the present subject matter and aclidinium bromide,
a compound of the present subject matter and tiotropium bromide, or
a compound of the present subject matter and ipratropium bromide,
and at least one pharmaceutically acceptable auxiliary.

In an alternative embodiment, the stereoisomer of glycopyrronium bromide is (R,R)-glycopyrronium bromide. In an alternative embodiment, tiotropium bromide is used in form of its monohydrate.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a beta-mimetic and at least one pharmaceutically acceptable auxiliary. In a particularly alternative embodiment, the above-mentioned fixed combination, non-fixed combination or kit of parts comprise:
a compound of the present subject matter and salbutamol,
a compound of the present subject matter and milveterol,
a compound of the present subject matter and indacaterol,
a compound of the present subject matter and carmoterol,
a compound of the present subject matter and salmeterol,
a compound of the present subject matter and formoterol,
and at least one pharmaceutically acceptable auxiliary.

In an alternative embodiment, the pharmaceutically acceptable salt of salbutamol is salbutamol sulfate. In an alternative embodiment, the pharmaceutically acceptable salt of milveterol is milveterol hydrochloride. In an alternative embodiment, the pharmaceutically acceptable salt of carmoterol is carmoterol hydrochloride. In an alternative embodiment, the pharmaceutically acceptable salt of salmeterol is salmeterol xinafoate. In another alternative embodiment, the pharmaceutically acceptable salt of formoterol is formoterol hemifumarate monohydrate. In another alternative embodiment, the stereoisomer of formoterol is R,R-formoterol. In another alternative embodiment, the pharmaceutically acceptable salt of R,R-formoterol is R,R-formoterol L-tartrate.

Preferably the beta-mimetic is a long-acting beta-mimetic; particularly an alternative in this respect are those beta-mimetics having a therapeutic effect over a 12-24 hours period.

In an alternative embodiment, the above-mentioned fixed combination, non-fixed combination or kit of parts comprise a compound of the present subject matter (in particular the compound of the present subject matter is one of the examples of the present subject matter), a lung surfactant and at least one pharmaceutically acceptable auxiliary. In a particularly alternative embodiment, the above-mentioned fixed combination, non-fixed combination or kit of parts comprise:
a compound of the present subject matter and lusupultide,
a compound of the present subject matter and poracant alfa,
a compound of the present subject matter and sinapultide,
a compound of the present subject matter and beracant,
a compound of the present subject matter and bovacant,
a compound of the present subject matter and colfosceril palmitate, a compound of the present subject matter and surfactant-TA, or
a compound of the present subject matter and calfacant,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an endothelin antagonist and at least one pharmaceutically acceptable auxiliary. In a particularly alternative embodiment, the above-mentioned fixed combination, non-fixed combination or kit of parts comprise:
a compound of the present subject matter and bosentan,
a compound of the present subject matter and ambrisentan,
a compound of the present subject matter and atrasentan,
a compound of the present subject matter and darusentan,
a compound of the present subject matter and clazosentan, or
a compound of the present subject matter and avosentan,
and at least one pharmaceutically acceptable auxiliary.

In another alternative embodiment, bosentan is used in form of its monohydrate. In another alternative embodiment the pharmaceutically acceptable salt of clazosentan is the disodium salt of clazosentan. In another alternative embodiment the pharmaceutically acceptable salts of atrasentan are atrasentan hydrochloride or the sodium salt of atrasentan. In another alternative embodiment the R-enantiomer of atrasentan is used. In another alternative embodiment the S-enantiomer of darusentan is used.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a prostacyclin and at least one pharmaceutically acceptable auxiliary. In a particularly alternative embodiment, the above-mentioned fixed combination, non-fixed combination or kit of parts comprise:
a compound of the present subject matter and iloprost,
a compound of the present subject matter and epoprostenol,
a compound of the present subject matter and triprostinil,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a calcium channel blocker and at least one pharmaceutically acceptable auxiliary. In a particularly alternative embodiment, the above-mentioned fixed combination, non-fixed combination or kit of parts comprise:
a compound of the present subject matter and amlodipine,
a compound of the present subject matter and nifedipine,
a compound of the present subject matter and diltiazem,
a compound of the present subject matter and verapamil, or
a compound of the present subject matter and felodipine,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a beta-blocker and at least one pharmaceutically acceptable auxiliary. In a particularly alternative embodiment, the above-mentioned fixed combination, non-fixed combination or kit of parts comprise:
a compound of the present subject matter and bisoprolol,
a compound of the present subject matter and nebivolol,
a compound of the present subject matter and metoprolol,
a compound of the present subject matter and carvedilol,
a compound of the present subject matter and atenolol, or
a compound of the present subject matter and nadolol,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a type 4 phosphodiesterase inhibitor and at least one pharmaceutically acceptable auxiliary. In a particularly alternative embodiment, the above-mentioned fixed combination, non-fixed combination or kit of parts comprise:
a compound of the present subject matter and roflumilast,
a compound of the present subject matter and roflumilast N-oxide,
a compound of the present subject matter and cilomilast,
a compound of the present subject matter and tetomilast
a compound of the present subject matter and apremilast, or
a compound of the present subject matter and oglemilast,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an antidepressant and at least one pharmaceutically acceptable auxiliary. In a particularly alternative embodiment, the above-mentioned fixed combination, non-fixed combination or kit of parts comprise:
a compound of the present subject matter and bupropion,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an antibiotic and at least one pharmaceutically acceptable auxiliary. In a particularly alternative embodiment, the above-mentioned fixed combination, non-fixed combination or kit of parts comprise:
a compound of the present subject matter and amoxicillin,
a compound of the present subject matter and ampicillin,
a compound of the present subject matter and levofloxacin,
a compound of the present subject matter and clarithromycin,
a compound of the present subject matter and ciprofloxacin,
a compound of the present subject matter and telithromycin, or
a compound of the present subject matter and azithromycin,
and at least one pharmaceutically acceptable auxiliary.

In an alternative embodiment, amoxicillin is used in form of its trihydrate. In another alternative embodiment, ampicillin is used in form of its trihydrate. In another alternative embodiment, the pharmaceutically acceptable salt of ampicillin is ampicillin natrium. In another alternative embodiment levofloxacin is used in form of its hemi hydrate. In another alternative embodiment, the pharmaceutically acceptable salt of ciprofloxacin is ciprofloxacin hydrochloride monohydrate. In another alternative embodiment, azithromycin is used in form of its monohydrate.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an anticoagulant and at least one pharmaceutically acceptable auxiliary. In a particularly alternative embodiment, the above-mentioned fixed combination, non-fixed combination or kit of parts comprise:
a compound of the present subject matter and clopidogrel,
a compound of the present subject matter and enoxaparin,
a compound of the present subject matter and cilostazol,
a compound of the present subject matter and nadroparin,
a compound of the present subject matter and warfarin, or
a compound of the present subject matter and abciximab,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a diuretic and at least one pharmaceutically acceptable auxiliary. In a particularly alternative embodiment, the above-mentioned fixed combination, non-fixed combination or kit of parts comprise:
a compound of the present subject matter and furosemide,
a compound of the present subject matter and bumetanide, or
a compound of the present subject matter and torsemide,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a digitalis glycoside and at least one pharmaceutically acceptable auxiliary. In a particularly alternative embodiment, the above-mentioned fixed combination, non-fixed combination or kit of parts comprise:
a compound of the present subject matter and digoxin, or
a compound of the present subject matter and digitoxin,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a corticosteroid, a beta-mimetic and at least one pharmaceutically acceptable auxiliary. In a particularly alternative embodiment, the above-mentioned fixed combination, non-fixed combination or kit of parts comprise:
a compound of the present subject matter, budesonide and salbutamol,
a compound of the present subject matter, budesonide and milveterol,
a compound of the present subject matter, budesonide and indacaterol,
a compound of the present subject matter, budesonide and carmoterol,
a compound of the present subject matter, budesonide and salmeterol,
a compound of the present subject matter, budesonide and formoterol,
a compound of the present subject matter, fluticasone and salbutamol,
a compound of the present subject matter, fluticasone and milveterol,
a compound of the present subject matter, fluticasone and indacaterol,
a compound of the present subject matter, fluticasone and carmoterol,
a compound of the present subject matter, fluticasone and salmeterol,
a compound of the present subject matter, fluticasone and formoterol,
a compound of the present subject matter, beclometasone and salbutamol,
a compound of the present subject matter, beclometasone and milveterol,
a compound of the present subject matter, beclometasone and indacaterol,
a compound of the present subject matter, beclometasone and carmoterol,
a compound of the present subject matter, beclometasone and salmeterol,
a compound of the present subject matter, beclometasone and formoterol,
a compound of the present subject matter, mometasone and salbutamol,
a compound of the present subject matter, mometasone and milveterol,
a compound of the present subject matter, mometasone and indacaterol,
a compound of the present subject matter, mometasone and carmoterol,
a compound of the present subject matter, mometasone and salmeterol,
a compound of the present subject matter, mometasone and formoterol,
a compound of the present subject matter, triamcinolone acetonide and salbutamol,
a compound of the present subject matter, triamcinolone acetonide and milveterol,
a compound of the present subject matter, triamcinolone acetonide and indacaterol,
a compound of the present subject matter, triamcinolone acetonide and carmoterol,
a compound of the present subject matter, triamcinolone acetonide and salmeterol,
a compound of the present subject matter, triamcinolone acetonide and formoterol,
a compound of the present subject matter, ciclesonide and salbutamol,
a compound of the present subject matter, ciclesonide and milveterol,
a compound of the present subject matter, ciclesonide and indacaterol,
a compound of the present subject matter, ciclesonide and carmoterol,
a compound of the present subject matter, ciclesonide and salmeterol, or
a compound of the present subject matter, ciclesonide and formoterol,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a beta-mimetic, an anticholinergic and at least one pharmaceutically acceptable auxiliary. In a particularly alternative embodiment, the above-mentioned fixed combination, non-fixed combination or kit of parts comprise:
a compound of the present subject matter, salbutamol and glycopyrronium bromide,
a compound of the present subject matter, salbutamol and aclidinium bromide, a compound of the present subject matter, salbutamol and tiotropium bromide,
a compound of the present subject matter, salbutamol and ipratropium bromide,
a compound of the present subject matter, milveterol and glycopyrronium bromide,
a compound of the present subject matter, milveterol and aclidinium bromide,
a compound of the present subject matter, milveterol and tiotropium bromide,
a compound of the present subject matter, milveterol and ipratropium bromide,
a compound of the present subject matter, salmeterol and glycopyrronium bromide,
a compound of the present subject matter, salmeterol and aclidinium bromide,
a compound of the present subject matter, salmeterol and tiotropium bromide,
a compound of the present subject matter, salmeterol and ipratropium bromide,
a compound of the present subject matter, formoterol and glycopyrronium bromide,
a compound of the present subject matter, formoterol and aclidinium bromide,
a compound of the present subject matter, formoterol and tiotropium bromide,
a compound of the present subject matter, formoterol and ipratropium bromide,
a compound of the present subject matter, indacaterol and glycopyrronium bromide,
a compound of the present subject matter, indacaterol and aclidinium bromide,
a compound of the present subject matter, indacaterol and tiotropium bromide,
a compound of the present subject matter, indacaterol and ipratropium bromide,
a compound of the present subject matter, carmoterol and glycopyrronium bromide,
a compound of the present subject matter, carmoterol and aclidinium bromide,
a compound of the present subject matter, carmoterol and tiotropium bromide, or
a compound of the present subject matter, carmoterol and ipratropium bromide,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), a corticosteroid, an anticholinergic and at least one pharmaceutically acceptable auxiliary. In a particularly alternative embodiment, the above-mentioned fixed combination, non-fixed combination or kit of parts comprise:
a compound of the present subject matter, budesonide and glycopyrronium bromide,
a compound of the present subject matter, budesonide and aclidinium bromide,
a compound of the present subject matter, budesonide and tiotropium bromide,
a compound of the present subject matter, budesonide and ipratropium bromide,
a compound of the present subject matter, fluticasone and glycopyrronium bromide,
a compound of the present subject matter, fluticasone and aclidinium bromide,
a compound of the present subject matter, fluticasone and tiotropium bromide,
a compound of the present subject matter, fluticasone and ipratropium bromide,
a compound of the present subject matter, beclometasone and glycopyrronium bromide,
a compound of the present subject matter, beclometasone and aclidinium bromide,
a compound of the present subject matter, beclometasone and tiotropium bromide,
a compound of the present subject matter, beclometasone and ipratropium bromide,
a compound of the present subject matter, mometasone and glycopyrronium bromide,
a compound of the present subject matter, mometasone and aclidinium bromide,
a compound of the present subject matter, mometasone and tiotropium bromide,
a compound of the present subject matter, mometasone and ipratropium bromide,
a compound of the present subject matter, triamcinolone acetonide and glycopyrronium bromide,
a compound of the present subject matter, triamcinolone acetonide and aclidinium bromide,
a compound of the present subject matter, triamcinolone acetonide and tiotropium bromide,
a compound of the present subject matter, triamcinolone acetonide and ipratropium bromide,
a compound of the present subject matter, ciclesonide and glycopyrronium bromide,
a compound of the present subject matter, ciclesonide and aclidinium bromide,
a compound of the present subject matter, ciclesonide and tiotropium bromide, or
a compound of the present subject matter, ciclesonide and ipratropium bromide,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), an guanyl-cyclase activator/stimulator and at least one pharmaceutically acceptable auxiliary. In a particularly alternative embodiment, the above-mentioned fixed combination, non-fixed combination or kit of parts comprise:
a compound of the present subject matter and BAY63-2521 (Riociguat),
a compound of the present subject matter and Ataciguat,
and at least one pharmaceutically acceptable auxiliary.

In an alternative embodiment, the above-mentioned fixed combination, non-fixed combination or kit of parts comprise a compound of the present subject matter (in particular the compound of the present subject matter is one of the examples of the present subject matter or a pharmaceutically acceptable salt thereof), pirfenidone and at least one pharmaceutically acceptable auxiliary. In a particularly alternative embodiment, the above-mentioned fixed combination, non-fixed combination or kit of parts comprise:
a compound of the present subject matter and pirfenidone, and at least one pharmaceutically acceptable auxiliary.

The above mentioned compound of the present subject matter is preferably a compound according to the examples.

The present subject matter furthermore relates to pharmaceutical compositions according to the present subject matter, as defined above, inhibiting the type 5 phosphodiesterase, especially for the treatment or prophylaxis of diseases alleviated by inhibition of type 5 phosphodiesterase, in particular for the treatment or prophylaxis of the diseases exemplified above.

The present subject matter even furthermore relates to pharmaceutical compositions according to the present subject matter, as defined above, inhibiting the dual type 4/5 phosphodiesterase, especially for the treatment or prophylaxis of diseases alleviated by inhibition of dual type 4/5 phosphodiesterase, in particular for the treatment or prophylaxis of the diseases exemplified above.

The present subject matter also encompasses pharmaceutical compositions according to the present subject matter, as defined above, for the treatment or prophylaxis of the following diseases: acute and chronic airway diseases, such as pulmonary hypertension, lung fibrosis, asthma, bronchitis, emphysema and chronic obstructive pulmonary disease.

The pharmaceutical compositions according to the present subject matter preferably contain the compound or compounds of the present subject matter in a total amount of from 0.1 to 99.9 wt %, more preferably 5 to 95 wt %, in particular 20 to 80 wt %. In case at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides is present in the pharmaceutical compositions of the present subject matter, the total amount of said therapeutic agent or therapeutic agents in the pharmaceutical compositions is preferably in the range of from 0.1 to 99.9 wt %, more preferably 5 to 95 wt %, in particular 20 to 80 wt %, under the provision that the total amount of the compound or compounds of the present subject matter and the therapeutic agent or therapeutic agents is less than 100 wt %. Preferably, the at least one compound of the present subject matter and the at least one therapeutic agent are present in the pharmaceutical composition in a weight ratio of from 1000:1 to 1:1000, more preferably 500:1 to 1:500.

As pharmaceutically acceptable auxiliaries, any auxiliaries known to be suitable for preparing pharmaceutical compositions can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

The pharmaceutical compositions can be formulated, for example, into tablets, coated tablets (dragees), pills, cachets, capsules (caplets), granules, powders, suppositories, solutions (e.g., but not limited to, sterile solutions), emulsions, suspensions, ointments, creams, lotions, pastes, oils, gels, sprays and patches (e.g., but not limited to, transdermal therapeutic systems). Additionally, the pharmaceutical compositions can be prepared as e.g. liposome delivery systems, systems in which the compound of the present subject matter is coupled to monoclonal antibodies and systems in which the compound of the present subject matter is coupled to polymers (e.g., but not limited to, soluble or biodegradable polymers).

In case of pharmaceutical compositions comprising at least one of the compounds of the present subject matter and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, the compound of the present subject matter and the therapeutic agent may be formulated together into the same dosage form (e.g., but not limited to, tablets), separately into the same dosage form (e.g., but not limited to, tablets), or into different dosage forms (without limitation e.g. the compound of the present subject matter may be formulated as tablet and the therapeutic agent may be formulated as powder, solution or suspension).

The pharmaceutical compositions can be manufactured in a manner known to a person skilled in the art, e.g. by dissolving, mixing, granulating, dragee-making, levigating, emulsifying, encapsulating, entrapping or lyophilizing processes.

The selected formulation depends inter alia on the route of administering the pharmaceutical composition. The pharmaceutical compositions of the present subject matter can be administered by any suitable route, for example, by the oral, sublingual, buccal, intravenous, intraarterial, intramuscular, subcutaneous, intracutaneous, topical, transdermal, intranasal, intraocular, intraperitoneal, intrasternal, intracoronary, transurethral, rectal or vaginal route, by inhalation or by insufflation. Oral administration is preferred.

In case of pharmaceutical compositions comprising at least one of the compounds of the present subject matter and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, the compound of the present subject matter and the therapeutic agent may be administered by the same route, e.g., without limitation, orally, or by different routes, e.g., without limitation, the compound of the present subject matter can be administered orally and the therapeutic agent can be administered by inhalation or instillation.

Tablets, coated tablets (dragees), pills, cachets, capsules (caplets), granules, solutions, emulsions and suspensions are e.g. suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g. pH conditions) or by coupling the compound of the present subject matter to a biodegradable polymer.

Administration by inhalation or instillation is preferably made by using an aerosol. The aerosol is a liquid-gaseous dispersion, a solid-gaseous dispersion or a mixed liquid/solid-gaseous dispersion.

The aerosol may be generated by means of aerosol-producing devices such as dry powder inhalers (DPIs), pressurized metered dose inhalers (PMDIs) and nebulizers. Depending on the kind of the compound of the present subject matter, and optionally the therapeutic agent, to be administered, the aerosol-producing device can contain the compound and, optionally, the therapeutic agent in form of a powder, a solution or a dispersion. The powder may contain, for example, one or more of the following auxiliaries: carriers, stabilizers and fillers. The solution may contain in addition to the solvent, for example, one or more of the following auxiliaries: propellants, solubilizers (co-solvents), surfactants, stabilizers, buffers, tonicity adjusting agents, preservatives and flavorings. The dispersion may contain in addition to the dispersant, for example, one or more of the following auxiliaries: propellants, surfactants, stabilizers, buffers, preservatives and flavorings. Examples of carriers include, but are not limited to, saccharides, e.g. lactose and glucose. Examples of propellants include, but are not limited to, fluorohydrocarbons, e.g. 1,1,1,2-tetrafluoroethane and 1,1,1,2,3,3,3-heptafluoropropane.

The particle size of the aerosol particles (solid, liquid or solid/liquid particles) is preferably less than 100 μm, more preferably it is in the range of from 0.5 to 10 μm, in particular in the range of from 2 to 6 μm (D50 value, measured by laser diffraction).

Specific aerosol-producing devices which may be used for inhaled administration include, but are not limited to, Cyclohaler®, Diskhaler®, Rotadisk®, Turbohaler®, Autohaler®, Turbohaler®, Novolizer®, Easyhaler®, Aerolizer®, Jethaler®, Diskus®, Ultrahaler® and Mystic® inhalers. The aerosol-producing devices may be combined with spacers or expanders, e.g. Aerochamber®, Nebulator®, Volumatic® and Rondo®, for improving inhalation efficiency.

In case of topical administration, suitable pharmaceutical formulations are, for example, ointments, creams, lotions, pastes, gels, powders, solutions, emulsions, suspensions, oils, sprays and patches (e.g., but not limited to, transdermal therapeutic systems).

For parenteral modes of administration such as, for example, intravenous, intraarterial, intramuscular, subcutaneous, intracutaneous, intraperitoneal and intrasternal administration, preferably solutions (e.g., but not limited to, sterile solutions, isotonic solutions) are used. They are preferably administered by injection or infusion techniques.

In case of intranasal administration, for example, sprays and solutions to be applied in drop form are preferred formulations.

For intraocular administration, solutions to be applied in drop form, gels and ointments are exemplified formulations.

Generally, the pharmaceutical compositions according to the present subject matter can be administered such that the dose of the compound of the present subject matter is in the range customary for type 5 phosphodiesterase inhibitors or dual type 4/5 phosphodiesterase inhibitors. In particular, a dose in the range of from 0.01 to 4000 mg of the compound of the present subject matter per day is preferred. In this respect, it is to be noted that the dose is dependent, for example, on the specific compound used, the species treated, age, body weight, general health, sex and diet of the subject treated, mode and time of administration, rate of excretion, severity of the disease to be treated and drug combination. In case the pharmaceutical composition of the present subject matter comprises at least one of the compounds of the present subject matter and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, the same dose ranges apply to the therapeutic agent.

The pharmaceutical compositions according to the present subject matter can be administered in a single dose per day or in multiple subdoses, for example, 2 to 4 doses per day. A single dose unit of the pharmaceutical composition can contain e.g. from 0.01 mg to 4000 mg, preferably 0.1 mg to 2000 mg, more preferably 0.5 to 1000 mg, most preferably 1 to 500 mg, of the compound of the present subject matter. In case the pharmaceutical composition of the present subject matter comprises at least one of the compounds of the present subject matter and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, a single dose unit of the pharmaceutical composition can contain e.g. from 0.01 mg to 4000 mg, preferably 0.1 mg to 2000 mg, more preferably 0.5 to 1000 mg, most preferably 1 to 500 mg, of the therapeutic agent. Furthermore, the pharmaceutical composition can be adapted to weekly, monthly or even more infrequent administration, for example by using an implant, e.g. a subcutaneous or intramuscular implant, by using the compound of the present subject matter in form of a sparingly soluble salt or by using the compound of the present subject matter coupled to a polymer. Administration of the pharmaceutical composition in a single dose per day is preferred.

In case the pharmaceutical composition of the present subject matter comprises at least one of the compounds of the present subject matter and at least one therapeutic agent selected from the group consisting of corticosteroids, anticholinergics, beta-mimetics, lung surfactants, endothelin antagonists, prostacyclins, calcium channel blockers, beta-blockers, type 4 phosphodiesterase inhibitors, guanyl-cyclase activators/stimulators, pirfenidone, antidepressants, antibiotics, anticoagulants, diuretics and digitalis glycosides, administration of the compound of the present subject matter and administration of the therapeutic agent can be made simultaneously or sequentially. In case of sequential administration, the compound of the present subject matter can be administered before or after administration of the therapeutic agent.

Biological Investigations

Method for Measuring Inhibition of the Type 5 Phosphodiesterase (PDE5) Activity:

As a source for human PDE5, platelets are used. For that purpose, 150 ml fresh blood from human donors anticoagulated with citrate [final concentration 0.3% (w/v)] is centrifuged at 200 g for 10 min to obtain the so-called platelet-rich-plasma (PRP) as a supernatant. 1/10 volume of ACD solution (85 mM $Na_3$-citrate, 111 mM D-glucose, 71 mM citric acid, pH 4.4) is added to 9/10 volume of PRP. After centrifugation (1,400 g, 10 min) the cell pellet is resuspended in 3 ml homogenization buffer (NaCl 140 mM, KCl 3.8 mM, EGTA (ethylene glycol tetraacetic acid) 1 mM, $MgCl_2$ 1 mM, Tris-HCl 20 mM, beta-mercaptoethanol 1 mM, pH 8.2) plus protease-inhibitor mix giving rise to the final concentrations of 0.5 mM Pefablock (Roche), 10 μM Leupeptin, 5 μM Trypsininhibitor, 2 mM Benzamidin and 10 μM Pepstatin A. The suspension is sonified and thereafter centrifuged for 15 min at 10,000 g. The resulting supernatant (platelet lysate) is used for enzymatic testings.

PDE5A1 activity is inhibited by the compounds of the present subject matter in a modified SPA (scintillation proximity assay) test, supplied by Amersham Biosciences (see procedural instructions "phosphodiesterase [3H]cAMP SPA enzyme assay, code TRKQ 7090"), carried out in 96-well microtitre plates (MTP's). The test volume is 100 μl and contains 20 mM Tris buffer (pH 7.4), 0.1 mg of BSA (bovine serum albumin)/ml, 5 mM $Mg^{2+}$, 1 μM motapizone, 10 nM PDE2 inhibitor 2-(3,4-dimethoxybenzyl)-7-[(1R,2R)-2-hydroxy-1-(2-phenylethyl)propyl]-5-methylimidazo[5,1-f][1,2,4]triazin-4(3H)-one, 0.5 μM cGMP (cyclic guanosine monophosphate) (including about 50,000 cpm of [3H]cGMP as a tracer), 1 µl of the respective compound dilution in dimethylsulfoxide (DMSO) and sufficient PDE5-containing platelet lysat (10,000×g supernatant, see above) to ensure that 10-20 wt % of the cGMP is converted under the said experimental conditions. The final concentration of DMSO in the assay (1% v/v) does not substantially affect the activity of the PDE investigated. After a preincubation of 5 min at 37° C., the reaction is started by adding the substrate (cGMP) and the assay is incubated for a further 15 min; after that, it is stopped by adding SPA beads (50 µl). In accordance with the manufacturer's instructions, the SPA beads had previously been resuspended in water, but are then diluted 1:3 (v/v) in water; the diluted solution also contains 3 mM 8-methoxymethyl-3-isobutyl-1-methylxanthine (IBMX) to ensure a complete PDE activity stop. After the beads have been sedimented (>30 min), the MTP's are analyzed in commercially available luminescence detection devices. The corresponding $IC_{50}$ values of the compounds for the inhibition of PDE activity are determined from the concentration-effect curves by means of non-linear regression.

For the following compounds PDE5A1 inhibitory values [measured as $-\log IC_{50}$ (mol/l)] between 8.0 and 9.0 have been determined. The numbers of the compounds correspond to the numbers of the examples.

Compounds: E28, E31-E33, E36, E39, E45-E54, E80, E154, E156, E158, E162, E177, E192-E194, F17, F19-F23, F27-F33, F97-F98, F119-F120, P3, P24-P26.

For the following compounds PDE5A1 inhibitory values [measured as $-\log IC_{50}$ (mol/l)] higher than 9.0 have been determined. The numbers of the compounds correspond to the numbers of the examples.

Compounds: E1-E27, E29-E30, E34-E35, E37-E38, E40-E44, E55-E79, E81-E153, E155, E157, E159-E161, E163-E176, E178-E191, E-195-E203, F1-F16, F18, F24-F26, F34-F74, F76-F96, F99-F118, P1-P2, P6-P8, P89-P91, P139-P141, P159-P161, P169-P171, P189-P191, P199-201, P209-P211.

Method for Measuring Inhibition of the Type 4 Phosphodiesterase (PDE4) Activity:

The PDE4B1 (GB no. L20966) was a gift of Prof. M. Conti (Stanford University, USA). It was amplified from the original plasmid (pCMV5) via PCR with primers Rb18 (5'-CAGACATCCTAAGAGGGGAT-3') and Rb10 (5'-AGAGGGGGATTATGTATCCAC-3') and cloned into the pCRBac vector (Invitrogen, Groningen, NL).

The recombinant baculovirus was prepared by means of homologous recombination in SF9 insect cells. The expression plasmids were cotransfected with Baculo-Gold DNA (Pharmingen, Hamburg) using a standard protocol (Pharmingen, Hamburg). Wt virus-free recombinant virus supernatants were selected using plaque assay methods. After that, high-titre virus supernatants were prepared by amplifying 3 times. PDE4B1 was expressed in SF21 cells by infecting $2\times10^6$ cells/ml with an MOI (multiplicity of infection) between 1 and 10 in the serum-free medium Insect Express Sf9-S2 (PAA, Pasching, Austria). The cells were cultured at 28° C. for 48-72 hours, after which they were pelleted for 5-10 min at 1000×g and 4° C.

The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 10 mM (3-mercaptoethanol, 2 mM benzamidine, 0.4 mM Pefablock, 10 µM leupeptin, 10 µM pepstatin A, 5 µM trypsin inhibitor) and disrupted by ultrasonication. The homogenate was then centrifuged for 10 min at 1000×g and the supernatant was stored at −80° C. until subsequent use (see below). The protein content was determined by the Bradford method (BioRad, Munich) using BSA as the standard.

PDE4B1 activity was inhibited by the compounds according to the present subject matter in a modified SPA (scintillation proximity assay) test, supplied by Amersham Biosciences (see procedural instructions "phosphodiesterase [3H]cAMP SPA enzyme assay, code TRKQ 7090"), carried out in 96-well microtitre plates (MTP's). The test volume is 100 µl and contains 20 mM Tris buffer (pH 7.4), 0.1 mg/ml of BSA, 5 mM $Mg^{2+}$, 0.5 µM cAMP (including about 50,000 cpm of [3H]cAMP), 1 µl of the respective substance dilution in DMSO and sufficient recombinant PDE (1000×g supernatant, see above) to ensure that 10-20% of the cAMP is converted under the said experimental conditions. The final concentration of DMSO in the assays (1% v/v) does not substantially affect the activity of the PDE investigated. After a preincubation of 5 min at 37° C., the reaction is started by adding the substrate (cAMP) and the assays are incubated for a further 15 min; after that, they are stopped by adding SPA beads (50 µl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding $IC_{50}$ values of the compounds for the inhibition of PDE4B1 activity are determined from the concentration-effect curves by means of non-linear regression.

For the following compounds PDE4B1 inhibitory values [measured as $-\log IC_{50}$ (mol/l)] between 6.0 and 7.0 have been determined. The numbers of the compounds correspond to the numbers of the examples.

Compounds: E37-E40, E45, E66-E74, E96, E145-E147, E151-E157, E159-E160, E169-E171, E177-E178, F23-F24, F27, F41-F46, F58, F97, F99-F101, F106.

For the following compounds PDE4B1 inhibitory values [measured as $-\log IC_{50}$ (mol/l)] higher than 7.0 have been determined. The numbers of the compounds correspond to the numbers of the examples.

Compounds: E41-E44, E81-E95, E97-E98, E148-E150, E176, E-195-E203, F25-F26, F51-F57, F59-F62, F93-F96, P1-P3, P6-P8, P24-P26, P89-P91, P99-P101, P139-P141, P159-P161, P169-P171, P189-P191, P199-201, P209-P211.

Animal Pharmacological Testing of PDE5 Inhibitory Action of Compounds

Nitric oxide regulates smooth muscle tone by elevation of cGMP via activation of guanylate cyclase and subsequent activation of cyclic GMP-dependent protein kinase. The amplitude and duration of the cGMP signal in smooth muscle is largely regulated by cGMP-specific cyclic nucleotide phosphodiesterase 5 (PDE5). Therefore, inhibition of PDE5 or activation of guanylate cyclase causes altered arterial blood pressure response, which is more pronounced under conditions of acute arterial hypertension, which can be easily induced by continuous intravenous (i.v.) phenylephrine(PE)-infusion. The aim of the study was to evaluate the effects of the selective PDE5 inhibitors described in this present subject matter on phenylephrine-induced acute arterial hypertension and sodiumnitroprusside (SNP) induced blood pressure response in anaesthetised male Sprague Dawley rats.

Method

The test compound (suspended in a 4% w/v aqueous methylcellulose solution either 3 or 10 mg/kg) or placebo (i.e. 4% aqueous methylcellulose solution) is administered orally to conscious Sprague Dawley rats 90 min prior to SNP administration. 40 min later, rats are anaesthetised by intramuscular administration of 80 mg/kg ketamine-HCl+4 mg/kg xylazin-HCl and ventilated with ~1.5% isoflurane in a mixture of ambient air and 40% oxygen. Catheters for i.v. PE- and SNP-administration and recording of mean arterial blood pressure (MAP) are inserted. One hour after compound or placebo administration, a continuous i.v. (V. femoralis) PE-infusion (3 µg/kg/min at an infusion rate of 0.06 ml/min) is started and maintained till the end of the experiment. 30 min after start of the PE-infusion, an i.v.-bolus of the NO-donor sodium nitroprusside (SNP, 30 µg/kg at a volume of 1.0 ml/kg) is administered. To assess the effect of test compounds (PDE5 inhibitory activity) in comparison to placebo, MAP response is analysed. MAP prior to SNP-administration and area under the curve of MAP within 180 s following SNP-administration, corrected for initial MAP (corr. $AUC_{MAP\ 0-180s}$) is used, to describe altered arterial vascular response and thus in vivo PDE5-inhibitory activity. The efficacy (% change vs. control) achievable in this model is approximately between −11% and −40% effect for the examples E1, E94, E102, E131, F24, F65, F69, F84 and F112.

Animal Pharmacological Testing of PDE4 Inhibitory Action of Compounds

The PDE4 inhibitory activity of compounds is well described to result in anti-inflammatory effects. Therefore compounds of the present subject matter have been tested for inhibition of lipopolysaccharide induced tumor necrosis factor α (TNFα) release in male Sprague Daley rats. The inhibition of LPS-induced TNFα production obtained by testing of compounds in this model is between 7% and 99% for the examples E84, E86, E87, E89, E93, E94, E95, F12, F53, F55, F56, P7, P8, P89, P90, P140, P141, P160, P161, P170, P171, P189-P191, P199-P201, P210 and P211.

Method

Compounds were administered at different doses to male Sprague Daley rats (n=6-8 animals per dose group). A LPS and placebo treated control group (n=6 to 8 animals) was enclosed.

Compound and placebo were administered per os (p.o.) by gavage (administration volume: 10 ml/kg) one hour before LPS challenge.

LPS was injected intravenously (i.v.) at a dose of 1 mg/kg (administration volume: 10 ml/kg). 1.5 h after LPS-challenge animals were sacrificed by i.v. injection of sodium pentobarbital (120 mg/kg). Heparinized blood was obtained by heart puncture. Blood was centrifuged (21,000×g, 4° C., 15 min), and plasma samples were kept frozen at −80° C. until determination of TNFα levels by ELISA.

The invention claimed is:

1. A method for treating idiopathic pulmonary lung fibrosis in a patient, comprising administering to said patient a therapeutically effective amount of a compound of formula (I)

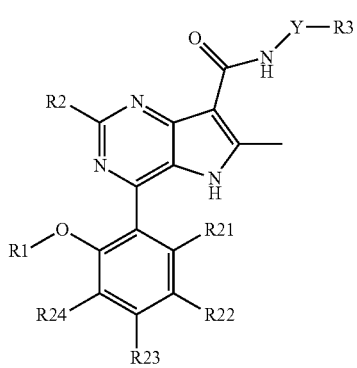

wherein
R1 is —CH$_2$-3-4C-cycloalkyl,
R2 is hydrogen,
R21 is hydrogen,
R22 is hydrogen, halogen, 1-4C-alkyl, 1-4C-alkoxy, —C(O)-1-4C-alkyl or 1-4C-fluoroalkyl,
or R21 and R22 combine to form a group —O—CH$_2$—O—,
R23 is hydrogen, halogen, 1-4C-alkoxy,
R24 is hydrogen,
Y is —(CH$_2$)$_n$—,
n is 0,
R3 is a cyclohexyl or cyclopentyl group substituted by R6 and optionally substituted by R61,
R6 is —NH—C(O)—R7,
R61 is halogen or 1-4C-alkyl,
R7 is 1-4C-alkyl, which is optionally substituted by R71, or R7 is 1-4C-alkoxy,
R71 is 1-4C-alkoxy,
or a salt thereof, a stereoisomer of the compound or a salt of the stereoisomer.

2. A method for treating idiopathic pulmonary lung fibrosis in a patient, comprising administering to said patient a therapeutically effective amount of a compound of formula (I)

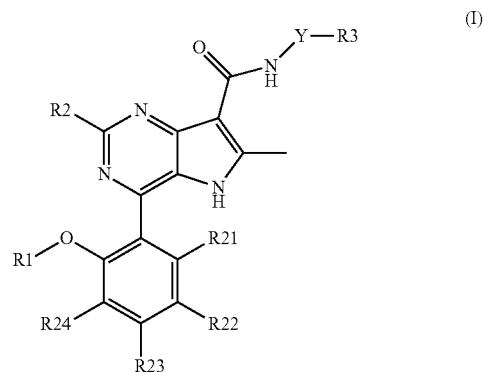

wherein
R1 is —CH$_2$-3-4C-cycloalkyl,
R2 is hydrogen,
R21 is hydrogen,
R22 is difluoromethyl or trifluoromethyl,
R23 is hydrogen,
R24 is hydrogen,
Y is —(CH$_2$)$_n$—,
n is 0,
R3 is a cyclohexyl group substituted by R6 and optionally substituted by R61,
R6 is —NH—C(O)—R7,
R61 is fluoro or methyl,
R7 is methyl or ethyl, which are optionally substituted by R71,
R71 is methoxy or hydroxy,
or a salt thereof, a stereoisomer of the compound or a salt of the stereoisomer.

3. The method of treating idiopathic pulmonary lung fibrosis in a patient according to claim 2, comprising administering to said patient a therapeutically effective amount of a compound of formula I, wherein
R1 is —CH$_2$-3-4C-cycloalkyl,
R2 is hydrogen,
R21 is hydrogen,
R22 is difluoromethyl,
R23 is hydrogen,
R24 is hydrogen,
Y is —(CH$_2$)n-, n is 0, R3 is a cyclohexyl group substituted by R6 and optionally substituted by R61, R6 is —NH—C(O)—R7, R61 is fluoro or methyl, R7 is methyl or ethyl, which are optionally substituted by R71, R71 is methoxy or hydroxy, or a salt thereof, a stereoisomer of the compound or a salt of the stereoisomer.

4. The method of treating idiopathic pulmonary lung fibrosis in a patient according to claim 1, comprising administering to said patient a therapeutically effective amount of a compound which is selected from the group consisting of N-(trans-4-acetamidocyclohexyl)-4-[5-(cyclopropylmethoxy)-1,3-benzodioxol-4-yl]-6-methyl-5H-pyrrolo[3,2-d]pyrimidine-7-carboxamide; 4-[5-(Cyclopropylmethoxy)-1,3-benzodioxol-4-yl]-6-methyl-N-[trans-4-(propionylamino)cyclohexyl]-5H-pyrrolo[3,2-d]pyrimidine-7-carboxamide; 4-[5-(Cyclopropylmethoxy)-1,3-benzodioxol-4-yl]-N-{trans-4-[(methoxyacetyl)amino]cyclohexyl}-6-methyl-5H-pyrrolo[3,2-d]pyrimidine-7-carboxamide; Ethyl {trans-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; N-(cis-4-acetamidocyclohexyl)-4-[5-(cyclopropylmethoxy)-1,3-benzodioxol-4-yl]-6-methyl-5H-pyrrolo[3,2-d]pyrimidine-7-carboxamide; 4-[5-(Cyclopropylmethoxy)-1,3-benzodioxol-4-yl]-6-methyl-N-[cis-4-(propionylamino)cyclohexyl]-5H-pyrrolo[3,2-d]pyrimidine-7-carboxamide; 4-[5-(Cyclopropylmethoxy)-1,3-benzodioxol-4-yl]-N-{cis-4-[(methoxyacetyl)amino]cyclohexyl}-6-methyl-5H-pyrrolo[3,2-d]pyrimidine-7-carboxamide; Ethyl {cis-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; N-(trans-4-acetamidocyclohexyl)-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-6-methyl-N-[trans-4-(propionylamino)cyclohexyl]-5H-pyrrolo[3,2-d]pyrimidine-7-carboxamide; 4-[2-(Cyclopropylmethoxy)-4-fluorophenyl]-N-{trans-4-[(methoxyacetyl)amino]cyclohexyl}-6-methyl-5H-pyrrolo[3,2-d]pyrimidine-7-carboxamide; N-(cis-4-acetamidocyclohexyl)-4-[2-(cyclopropylmethoxy)-4-fluorophenyl]-6-methyl-5H-pyrrolo[3,2-d]pyrimidine-7-carboxamide; 4-[2-(Cyclopropylmethoxy)-4-fluorophenyl]-6-methyl-N-[cis-4-(propionylamino)cyclohexyl]-5H-pyrrolo[3,2-d]pyrimidine-7-carboxamide; 4-[2-(Cyclopropylmethoxy)-4-fluorophenyl]-N-{cis-4-[(methoxyacetyl)amino]cyclohexyl}-6-methyl-5H-pyrrolo[3,2-d]pyrimidine-7-carboxamide; N-(trans-4-acetamidocyclohexyl)-4-[2-(cyclopropylmethoxy)-5-fluorophenyl]-6-methyl-5H-pyrrolo[3,2-d]pyrimidine-7-carboxamide; 4-[2-(Cyclopropylmethoxy)-5-fluorophenyl]-6-methyl-N-[trans-4-(propionylamino)cyclohexyl]-5H-pyrrolo[3,2-d]pyrimidine-7-carboxamide; 4-[2-(Cyclopropylmethoxy)-5-fluorophenyl]-N-{trans-4-[(methoxyacetyl)amino]cyclohexyl}-6-methyl-5H-pyrrolo[3,2-d]pyrimidine-7-carboxamide; Ethyl {trans-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate; N-(cis-4-acetamidocyclohexyl)-4-[2-(cyclopropylmethoxy)-5-fluorophenyl]-6-methyl-5H-pyrrolo[3,2-d]pyrimidine-7-carboxamide; N-(trans-4-acetamidocyclohexyl)-4-[2-(cyclopropylmethoxy)-4-methoxyphenyl]-6-methyl-5H-pyrrolo[3,2-d]pyrimidine-7-carboxamide; N-(cis-4-acetamidocyclohexyl)-4-[2-(cyclopropylmethoxy)-4-methoxyphenyl]-6-methyl-5H-pyrrolo[3,2-d]pyrimidine-7-carboxamide; N-(trans-4-acetamidocyclohexyl)-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-6-methyl-N-[trans-4-(propionylamino)cyclohexyl]-5H-pyrrolo[3,2-d]pyrimidine-7-carboxamide; 4-[2-(Cyclopropylmethoxy)-5-methoxyphenyl]-N-{trans-4-[(methoxyacetyl)amino]cyclohexyl}-6-methyl-5H-pyrrolo[3,2-d]pyrimidine-7-carboxamide; N-(cis-4-acetamidocyclohexyl)-4-[2-(cyclopropylmethoxy)-5-methoxyphenyl]-6-methyl-5H-pyrrolo[3,2-d]pyrimidine-7-carboxamide; 4-[2-(Cyclopropylmethoxy)-5-methoxyphenyl]-6-methyl-N-[cis-4-(propionylamino)cyclohexyl]-5H-pyrrolo[3,2-d]pyrimidine-7-carboxamide; 4-[2-(Cyclopropylmethoxy)-5-methoxyphenyl]-N-{cis-4-[(methoxyacetyl)amino]cyclohexyl}-6-methyl-5H-pyrrolo[3,2-d]pyrimidine-7-carboxamide; N-[trans-4-(acetylamino)cyclohexyl]-4-[2-(cyclopropylmethoxy)-5-methylphenyl]-6-methyl-5H-pyrrolo[3,2-d]pyrimidine-7-carboxamide; 4-[2-(Cyclopropylmethoxy)-5-methylphenyl]-6-methyl-N-[trans-4-(propanoylamino)cyclohexyl]-5H-pyrrolo[3,2-d]pyrimidine-7-carboxamide; 4-[2-(Cyclopropylmethoxy)-5-methylphenyl]-N-{trans-4-[(methoxyacetyl)amino]cyclohexyl}-6-methyl-5H-pyrrolo[3,2-d]pyrimidine-7-carboxamide; N-[cis-4-(acetylamino)cyclohexyl]-4-[2-(cyclopropylmethoxy)-5-methylphenyl]-6-methyl-5H-pyrrolo[3,2-d]pyrimidine-7-carboxamide; 4-[2-(Cyclopropylmethoxy)-5-methyl phenyl]-6-methyl-N-[cis-4-(propanoylamino)cyclohexyl]-5H-pyrrolo[3,2-d]pyrimidine-7-carboxamide; 4-[2-(Cyclopropylmethoxy)-5-methyl phenyl]-N-{cis-4-[(methoxyacetyl)amino]cyclohexyl}-6-methyl-5H-pyrrolo[3,2-d]pyrimidine-7-carboxamide; N-[trans-4-(acetylamino)cyclohexyl]-4-[2-(cyclopropylmethoxy)-5-(trifluoromethyl)phenyl]-6-methyl-5H-pyrrolo[3,2-d]pyrimidine-7-carboxamide; 4-[2-(cyclopropylmethoxy)-5-(trifluoromethyl)phenyl]-6-methyl-N-[trans-4-(propanoylamino)cyclohexyl]-5H-pyrrolo[3,2-d]pyrimidine-7-carboxamide; 4-[2-(Cyclopropylmethoxy)-5-(trifluoromethyl)phenyl]-N-{trans-4-[(methoxyacetyl)amino]cyclohexyl}-6-methyl-5H-pyrrolo[3,2-d]pyrimidine-7-carboxamide; N-[cis-4-(acetylamino)cyclohexyl]-4-[2-(cyclopropylmethoxy)-5-(trifluoromethyl)phenyl]-6-methyl-5H-pyrrolo[3,2-d]pyrimidine-7-carboxamide; 4-[2-(Cyclopropylmethoxy)-5-(trifluoromethyl)phenyl]-6-methyl-N-[cis-4-(propanoylamino)cyclohexyl]-5H-pyrrolo[3,2-d]pyrimidine-7-carboxamide; 4-[2-(Cyclopropylmethoxy)-5-(trifluoromethyl)phenyl]-N-{cis-4-[(methoxyacetyl)amino]cyclohexyl}-6-methyl-5H-pyrrolo[3,2-d]pyrimidine-7-carboxamide; N-(trans-4-Acetamidocyclohexyl)-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-6-methyl-N-[trans-4-(propionylamino)cyclohexyl]-5H- pyrrolo[3,2-d]pyrimidine-7-carboxamide; 4-[2-(Cyclopropylmethoxy)-4-fluoro-5-methoxyphenyl]-N-{trans-4-[(methoxyacetyl)amino]cyclohexyl}-6-methyl-5H-pyrrolo[3,2-d]pyrimidine-7-carboxamide; Ethyl {trans-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate; N-(cis-4-Acetamidocyclohexyl)-4-[2-(cyclopropylmethoxy)-4-fluoro-5-methoxyphenyl]-6-methyl-5H-pyrrolo[3,2-d]pyrimidine-7-carboxamide; 4-[2-(Cyclopropylmethoxy)-4-fluoro-5-methoxyphenyl]-6-methy-N-[cis-4-(propionylamino)cyclohexyl]-5H-pyrrolo[3,2-d]pyrimidine-7-carboxamide; 4-[2-(Cyclopropylmethoxy)-4-fluoro-5-methoxyphenyl]-N-{cis-4-[(methoxyacetyl)amino]cyclohexyl}-6-methyl-5H-pyrrolo[3,2-d]pyrimidine-7-carboxamide; N-[trans-4-(Acetylamino)cyclohexyl]-4-[2-(cyclopropylmethoxy)-4-fluoro-5-methylphenyl]-6-methyl-5H-pyrrolo[3,2-d]pyrimidine-7-carboxamide; 4-[2-(Cyclopropylmethoxy)-4-fluoro-5-methylphenyl]-6-methyl-N-[trans-4-(propanoylamino)cyclohexyl]-5H-pyrrolo[3,2-d]pyrimidine-7-carboxamide; 4-[2-(Cyclopropylmethoxy)-4-fluoro-5-methylphenyl]-N-{trans-4-[(methoxyacetyl)amino]cyclohexyl}-6-methyl-5H-pyrrolo[3,2-d]pyrimidine-7-carboxamide; N-[cis-4-(Acetylamino)cyclohexyl]-4-[2-(cyclopropylmethoxy)-4-fluoro-5-methylphenyl]-6-methyl-5H-pyrrolo[3,2-d]pyrimidine-7-carboxamide; 4-[2-(Cyclopropylmethoxy)-4-fluoro-5-methylphenyl]-6-methyl-N-[cis-4-(propanoylamino)cyclohexyl]-5H-pyrrolo[3,2-d]pyrimidine-7-carboxamide; 4-[2-(Cyclopropylmethoxy)-4-fluoro-5-methylphenyl]-N-{cis-4-[(methoxyacetyl)amino]cyclohexyl}-6-methyl-5H-pyrrolo[3,2-d]pyrimidine-7-carboxamide; N-(trans-4-Acetamidocyclohexyl)-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-6-methyl-N-[trans-4-(propionylamino)cyclohexyl]-5H-pyrrolo[3,2-d]pyrimidine-7-carboxamide; 4-[2-(Cyclopropylmethoxy)-5-fluoro-4-methoxyphenyl]-N-{trans-4-[(methoxyacetyl)amino]cyclohexyl}-6-methyl-5H-pyrrolo[3,2-d]pyrimidine-7-carboxamide; N-(cis-4-Acetamidocyclohexyl)-4-[2-(cyclopropylmethoxy)-5-fluoro-4-methoxyphenyl]-6-methyl-5H-pyrrolo[3,2-d]pyrimidine-7-carboxamide; 4-[2-(Cyclopropylmethoxy)-5-fluoro-4-methoxyphenyl]-6-methyl-N-[cis-4-(propionylamino)cyclohexyl]-5H-pyrrolo[3,2-d]pyrimidine-7-carboxamide; 4-[2-(Cyclopropylmethoxy)-5-fluoro-4-methoxyphenyl]-N-{cis-4-[(methoxyacetyl)amino]cyclohexyl}-6-methyl-5H-pyrrolo[3,2-d]pyrimidine-7-carboxamide; Ethyl {cis-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate; N-[trans-4-(Acetylamino)cyclohexyl]-4-[2-(cyclopropylmethoxy)-5-ethylphenyl]-6-methyl-5H-pyrrolo[3,2-d]pyrimidine-7-carboxamide; 4-[2-(Cyclopropylmethoxy)-5-ethylphenyl]-6-methyl-N-[trans-4-(propanoylamino)cyclohexyl]-5H-pyrrolo[3,2-d]pyrimidine-7-carboxamide; 4-[2-(Cyclopropylmethoxy)-5-ethylphenyl]-N-{trans-4-[(methoxyacetyl)amino]cyclohexyl}-6-methyl-5H-pyrrolo[3,2-d]pyrimidine-7-carboxamide; N-[cis-4-(Acetylamino)cyclohexyl]-4-[2-(cyclopropylmethoxy)-5-ethylphenyl]-6-methyl-5H-pyrrolo[3,2-d]pyrimidine-7-carboxamide; 4-[2-(Cyclopropylmethoxy)-5-ethylphenyl]-6-methyl-N-[cis-4-(propanoylamino)cyclohexyl]-5H-pyrrolo[3,2-d]pyrimidine-7-carboxamide; 4-[2-(Cyclopropylmethoxy)-5-ethylphenyl]-N-{cis-4-[(methoxyacetyl)amino]cyclohexyl}-6-methyl-5H-pyrrolo[3,2-d]pyrimidine-7-carboxamide; N-[trans-4-(Acetylamino)cyclohexyl]-4-[2-(cyclopropylmethoxy)-5-(propan-2-yl)phenyl]-6-methyl-5H-pyrrolo[3,2-d]pyrimidine-7-carboxamide; 4-[2-(Cyclopropylmethoxy)-5-(propan-2-yl)phenyl]-N-{trans-4-[(methoxyacetyl)amino]cyclohexyl}-6-methyl-5H-pyrrolo[3,2-d]pyrimidine-7-carboxamide; N-[cis-4-(Acetylamino)cyclohexyl]-4-[2-(cyclopropylmethoxy)-5-(propan-2-yl)phenyl]-6-methyl-5H-pyrrolo[3,2-d]pyrimidine-7-carboxamide; 4-[2-(Cyclopropylmethoxy)-5-(propan-2-yl)phenyl]-N-{cis-4-[(methoxyacetyl)amino]cyclohexyl}-6-methyl-5H-pyrrolo[3,2-d]pyrimidine-7-carboxamide; N-[trans-4-(Acetylamino)cyclohexyl]-4-[5-acetyl-2-(cyclopropylmethoxy)phenyl]-6-methyl-5H-pyrrolo[3,2-d]pyrimidine-7-carboxamide; 4-[5-Acetyl-2-(cyclopropylmethoxy)phenyl]-6-methyl-N-[trans-4-(propanoylamino)cyclohexyl]-5H-pyrrolo[3,2-d]pyrimidine-7-carboxamide; 4-[5-Acetyl-2-(cyclopropylmethoxy)phenyl]-N-{trans-4-[(methoxyacetyl)amino]cyclohexyl}-6-methyl-5H-pyrrolo[3,2-d]pyrimidine-7-carboxamide; tert-Butyl {trans-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; tert-Butyl {cis-4-[({4-[5-(cyclopropylmethoxy)-1,3-benzodioxol-4-yl]-6-methyl-5H-pyrrolo[3,2-d]pyrimidin-7-yl}carbonyl)amino]cyclohexyl}carbamate; tert-Butyl {trans-4-[({4-[2-(cyclopropylmethoxy)-4-fluorophenyl]-6-methyl-5H-pyrrolo[3,2-d]pyrimidin-7-yl}carbonyl)amino]cyclohexyl}carbamate; tert-butyl {cis-4-[({4-[2-(cyclopropylmethoxy)-4-fluorophenyl]-6-methyl-5H-pyrrolo[3,2-d]pyrimidin-7-yl}carbonyl)amino]cyclohexyl}carbamate; tert-Butyl {trans-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-fluorophenyl]-6-methyl-5H-pyrrolo[3,2-d]pyrimidin-7-yl}carbonyl)amino]cyclohexyl}carbamate; tert-Butyl {trans-4-[({4-[2-(cyclopropylmethoxy)-4-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-4-methoxyphenyl]-6-methyl-5H-pyrrolo[3,2-d]pyrimidin-7-yl}carbonyl)amino]cyclohexyl}carbamate; tert-Butyl {trans-4-[({4-[2-(cyclopropylmethoxy)-5-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-methoxyphenyl]-6-methyl-5H-pyrrolo[3,2-d]pyrimidin-7-yl}carbonyl)amino]cyclohexyl}carbamate; tert-Butyl {trans-4-[({4-[2-(cyclopropylmethoxy)-5-methylphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-methylphenyl]-6-methyl-5H-pyrrolo[3,2-d]pyrimidine-7-yl}carbonyl)amino]cyclohexyl}carbamate; tert-Butyl {trans-4-[({4-[2-(cyclopropylmethoxy)-5-(trifluoromethyl)phenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-(trifluoromethyl)phenyl]-

6-methyl-5H-pyrrolo[3,2-d]pyrimidin-7-yl}carbonyl)amino]cyclohexyl}carbamate; tert-Butyl {trans-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-4-fluoro-5-methoxyphenyl]-6-methyl-5H-pyrrolo[3,2-d]pyrimidin-7-yl}carbonyl)amino]cyclohexyl}carbamate; tert-Butyl {trans-4-[({4-[2-(cyclopropylmethoxy)-4-fluoro-5-methylphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-4-fluoro-5-methylphenyl]-6-methyl-5H-pyrrolo[3,2-d]pyrimidin-7-yl}carbonyl)amino]cyclohexyl}carbamate; tert-Butyl {trans-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-fluoro-4-methoxyphenyl]-6-methyl-5H-pyrrolo[3,2-d]pyrimidin-7-yl}carbonyl)amino]cyclohexyl}carbamate; tert-Butyl {trans-4-[({4-[2-(cyclopropylmethoxy)-5-ethylphenyl]-6-methyl-5H-pyrrolo[3,2-d]pyrimidin-7-yl}carbonyl)amino]cyclohexyl}carbamate; tert-butyl {cis-4-[({4-[2-(cyclopropylmethoxy)-5-ethylphenyl]-6-methyl-5H-pyrrolo[3,2-d]pyrimidin-7-yl}carbonyl)amino]cyclohexyl}carbamate; tert-Butyl {trans-4-[({4-[2-(cyclopropylmethoxy)-5-(propan-2-yl)phenyl]-6-methyl-5H-pyrrolo[3,2-d]pyrimidin-7-yl}carbonyl)amino]cyclohexyl}carbamate; tert-Butyl {cis-4-[({4-[2-(cyclopropylmethoxy)-5-(propan-2-yl)phenyl]-6-methyl-5H-pyrrolo[3,2-d]pyrimidin-7-yl}carbonyl)amino]cyclohexyl}carbamate; tert-Butyl {trans-4-[({4-[2-(cyclopropylmethoxy)-5-(2-methyl-1,3-dioxolan-2-yl)phenyl]-6-methyl-5H-pyrrolo[3,2-d]pyrimidin-7-yl}carbonyl)amino]cyclohexyl}carbamate; N-[trans-4-(Acetylamino)cyclohexyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-[trans-4-(propanoylamino)cyclohexyl]-5H-pyrrolo[3,2-d]pyrimidine-7-carboxamide; 4-[2-(Cyclopropylmethoxy)-5-(difluoromethyl)phenyl]-N-{trans-4-[(methoxyacetyl)amino]cyclohexyl}-6-methyl-5H-pyrrolo[3,2-d]pyrimidine-7-carboxamide; 4-[2-(Cyclopropylmethoxy)-5-(difluoromethyl)phenyl]-6-methyl-N-[(1S,3S)-3-(propanoylamino)cyclopentyl]-5H-pyrrolo[3,2-d]pyrimidine-7-carboxamide; 4-[2-(Cyclopropylmethoxy)-5-(difluoromethyl)phenyl]-N-{(1S,3S)-3-[(methoxyacetyl)amino]cyclopentyl}-6-methyl-5H-pyrrolo[3,2-d]pyrimidine-7-carboxamide; N-[(1R*,2R*,4R*)-4-(Acetylamino)-2-fluorocyclopentyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-N-[(1R*,2R*,4R*)-2-fluoro-4-(propanoylamino)cyclopentyl]-6-methyl-5H-pyrrolo[3,2-d]pyrimidine-7-carboxamide; 4-[2-(Cyclopropylmethoxy)-5-(difluoromethyl)phenyl]-N-{(1R*,2R*,4R*)-2-fluoro-4-[(methoxyacetyl)amino]cyclopentyl}6-methyl-5H-pyrrolo[3,2-d]pyrimidine-7-carboxamide; N-[(1S,2S*,4S*)-4-(Acetylamino)-2-methylcyclohexyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-[(1S*,2S*,4S*)-2-methyl-4-(propanoylamino)cyclohexyl]-5H-pyrrolo[3,2-d]pyrimidine-7-carboxamide; 4-[2-(Cyclopropylmethoxy)-5-(difluoromethyl)phenyl]-N-{(1S*,2S*,4S*)-4-[(methoxyacetyl)amino]-2-methylcyclohexyl}-6-methyl-5H-pyrrolo[3,2-d]pyrimidine-7-carboxamide; N-[(1R*,2R*,4R*)-4-(Acetylamino)-2-fluorocyclohexyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-N-[(1R*,2R*,4R*)-2-fluoro-4-(propanoylamino)cyclohexyl]-6-methyl-5H-pyrrolo[3,2-d]pyrimidine-7-carboxamide; 4-[2-(Cyclopropylmethoxy)-5-(difluoromethyl)phenyl]-N-{(1R*,2R*,4R*)-2-fluoro-4-[(methoxyacetyl)amino]cyclohexyl}-6-methy-5H-pyrrolo[3,2-d]pyrimidine-7-carboxamide; N-[(1S*,3S*,4S*)-4-(Acetylamino)-3-methylcyclohexyl]-4-[2-(cyclopropylmethoxy)-5-(difluoromethyl)phenyl]-6-methy-5H-pyrrolo[3,2-d]pyrimidine-7-carboxamide; 4-[2-(Cyclopropylmethoxy)-5-(difluoromethyl)phenyl]-6-methyl-N-[(1S*,3S*,4S*)-3-methyl-4-(propanoylamino)cyclohexyl]-5H-pyrrolo[3,2-d]pyrimidine-7-carboxamide; 4-[2-(Cyclopropylmethoxy)-5-(difluoromethyl)phenyl]-N-{(1S*,3S*,4S*)-4-[(methoxyacetyl)amino]-3-methylcyclohexyl}-6-methyl-5H-pyrrolo[3,2-d]pyrimidine-7-carboxamide; N-[(1S*,2S*,4S*)-4-(Acetylamino)-3-fluorocyclohexyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-N-[(1S*,3S*,4S*)-3-fluoro-4-(propanoylamino)cyclohexyl]-6-methyl-5H-pyrrolo[3,2-d]pyrimidine-7-carboxamide; 4-[2-(Cyclopropylmethoxy)-5-(difluoromethyl)phenyl]-N-{(1S*,3S*,4S*)-3-fluoro-4-[(methoxyacetyl)amino]cyclohexyl}-6-methyl-5H-pyrrolo[3,2-d]pyrimidine-7-carboxamide; N-[(1R*,3S*,4S*)-3-(Acetylamino)-4-methylcyclopentyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-[(1R*,3S*,4S*)-3-methyl-4-(propanoylamino)cyclopentyl]-5H-pyrrolo[3,2-d]pyrimidine-7-carboxamide; 4-[2-(Cyclopropylmethoxy)-5-(difluoromethyl)phenyl]-N-{(1R*,3S*,4S*)-3-[(methoxyacetyl)amino]-4-methylcyclopentyl}-6-methyl-5H-pyrrolo[3,2-d]pyrimidine-7-carboxamide; N-[(1R*,2R*,4S*)-4-(acetylamino)-2-methylcyclopentyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-6-methyl-N-[(1R*,2R*,4S*)-2-methyl-4-(propanoylamino)cyclopentyl]-5H-pyrrolo[3,2-d]pyrimidine-7-carboxamide; 4-[2-(Cyclopropylmethoxy)-5-(difluoromethyl)phenyl]-N-{(1R*,2R*,4S*)-4-[(methoxyacetyl)amino]-2-methylcyclopentyl}-6-methyl-5H-pyrrolo[3,2-d]pyrimidine-7-carboxamide; N-[(1S*,3S*,4S*)-3-(Acetylamino)-4-fluorocyclopentyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-N-[(1S*,3S*,4S*)-3-fluoro-4-(propanoylamino)cyclopentyl]-6-methyl-5H-pyrrolo[3,2-d]pyrimidine-7-carboxamide; 4-[2-(cyclopropylmethoxy)-5-(difluoromethyl)phenyl]-N-{(1S*,3S*,4S*)-3-fluoro-4-[(methoxyacetyl)amino]cyclopentyl}-6-methyl-5H-pyrrolo[3,2-d]pyrimidine-7-carboxamide; N-[(1S*, 2R*,4S*)-4-(Acetylamino)-2-fluorocyclohexyl]-4-[2-(cyclopropylmethoxy)-5-(difluoromethyl)phenyl]-6-methyl-5H-pyrrolo[3,2-d]pyrimidine-7-carboxamide; 4-[2-(Cyclopropylmethoxy)-5-(difluoromethyl)phenyl]-N-[(1S*,2R*,4S*)-2-fluoro-4-(propanoylamino)cyclohexyl]-6-methyl-5H-pyrrolo[3,2-d]pyrimidine-7-carboxamide; 4-[2-(Cyclopropylmethoxy)-5-(difluoromethyl)phenyl]-N-{(1S*,2R*,4S*)-2-fluoro-4-[(methoxyacetyl)amino]cyclohexyl}-6-methyl-5H-pyrrolo[3,2-d]pyrimidine-7-carboxamide;

salts of these compounds, stereoisomers of these compounds, and salts of the stereoisomers of these compounds.

5. The method of treating idiopathic pulmonary lung fibrosis in a patient according to claim 2, comprising administering a therapeutically effective amount of a compound selected from the group consisting of 4-[2-(Cyclopropylmethoxy)-5-(trifluoromethyl)phenyl]-N-{trans-4-[(hydroxyacetyl)amino]cyclohexyl}-6-methyl-5H-pyrrolo[3,2-d]pyrimidine-7-carboxamide; 4-[2-(Cyclopropylmethoxy)-5-(trifluoromethyl)phenyl]-N-(trans-4-{[(2S)-2-hydroxypropanoyl]amino}cyclohexyl)-6-methyl-5H-pyrrolo[3,2-d]pyrimidine-7-carboxamide; 4-[2-(Cyclopropylmethoxy)-5-(trifluoromethyl)phenyl]-N-{cis-4-[(hydroxyacetyl)amino]cyclohexyl}-6-methyl-5H-pyrrolo[3,2-d]pyrimidine-7-carboxamide; 4-[2-(Cyclopropylmethoxy)-5-(trifluoromethyl)phenyl]-N-(cis-4-{[(2S)-2-hydroxypropanoyl]amino}cyclohexyl)-6-methyl-5H-pyrrolo[3,2-d]pyrimidine-7-carboxamide;

salts of these compounds, stereoisomers of these compounds, and salts of the stereoisomers of these compounds.

6. The method of treating idiopathic pulmonary lung fibrosis in a patient according to claim 1, comprising administering a therapeutically effective amount of a compound selected from the group consisting of 4-[2-(cyclopropylmethoxy)-5-(trifluoromethyl)phenyl]-6-methyl-N-[trans-4-(propanoylamino)cyclohexyl]-5H-pyrrolo[3,2-d]pyrimidine-7-carboxamide, a salt thereof, a stereoisomer of the compound and a salt of the stereoisomer.

7. The method of treating idiopathic pulmonary lung fibrosis in a patient according to claim 1, comprising administering a therapeutically effective amount of a compound selected from the group consisting of 4-[2-(Cyclopropylmethoxy)-5-(difluoromethyl)phenyl]-6-methyl-N-[trans-4-(propanoylamino)cyclohexyl]-5H-pyrrolo[3,2-d]pyrimidine-7-carboxamide, a salt thereof, a stereoisomer of the compound and a salt of the stereoisomer.

8. The method of treating idiopathic pulmonary lung fibrosis in a patient according to claim 1, comprising administering a therapeutically effective amount of a compound selected from the group consisting of 4-[2-(Cyclopropylmethoxy)-5-(difluoromethyl)phenyl]-N-{trans-4-[(methoxyacetyl)amino]cyclohexyl}-6-methyl-5H-pyrrolo[3,2-d]pyrimidine-7-carboxamide, a salt thereof, a stereoisomer of the compound and a salt of the stereoisomer.

9. The method of treating idiopathic pulmonary lung fibrosis in a patient according to claim 1, comprising administering a therapeutically effective amount of a compound selected from the group consisting of 4-[2-(Cyclopropylmethoxy)-5-(difluoromethyl)phenyl]-N-[(1R*,2R*,4R*)-2-fluoro-4-(propanoylamino)cyclohexyl]-6-methyl-5H-pyrrolo[3,2-d]pyrimidine-7-carboxamide, a salt thereof, a stereoisomer of the compound and a salt of the stereoisomer.

10. The method of treating idiopathic pulmonary lung fibrosis in a patient according to claim 1, comprising administering a therapeutically effective amount of a compound selected from the group consisting of 4-[2-(Cyclopropylmethoxy)-5-(difluoromethyl)phenyl]-N-{(1R*,2R*,4R*)-2-fluoro-4-[(methoxyacetyl)amino]cyclohexyl}-6-methyl-5H-pyrrolo[3,2-d]pyrimidine-7-carboxamide, a salt thereof, a stereoisomer of the compound and a salt of the stereoisomer.

* * * * *